(12) United States Patent
Adams et al.

(10) Patent No.: US 10,975,056 B2
(45) Date of Patent: Apr. 13, 2021

(54) SUBSTITUTED PYRIDINES AS INHIBITORS OF DNMT1

(71) Applicants: GlaxoSmithKline Intellectual Property Development Limited, Middlesex (GB); Cancer Research Technology Ltd., London (GB)

(72) Inventors: Nicholas David Adams, Collegeville, PA (US); Andrew B. Benowitz, Collegeville, PA (US); María Lourdes Rueda Benede, Collegeville, PA (US); Karen Anderson Evans, Collegeville, PA (US); David T Fosbenner, Collegeville, PA (US); Bryan Wayne King, Collegeville, PA (US); Mei Li, Collegeville, PA (US); Juan Ignacio Luengo, Collegeville, PA (US); William Henry Miller, Collegeville, PA (US); Alexander Joseph Reif, Collegeville, PA (US); Stuart Paul Romeril, Collegeville, PA (US); Stanley J. Schmidt, Collegeville, PA (US); Roger J. Butlin, Manchester (GB); Kristin M. Goldberg, Manchester (GB); Allan M. Jordan, Manchester (GB); Christopher S. Kershaw, Manchester (GB); Ali Raoof, Manchester (GB); Bohdan Waszkowycz, Manchester (GB)

(73) Assignees: GlaxoSmithKline Intellectual Property Development Limited, Middlesex (GB); Cancer Research Technology Ltd., London (GB)

(*) Notice: Subject to any disclaimer, the term of this patent is extended or adjusted under 35 U.S.C. 154(b) by 0 days.

(21) Appl. No.: 16/309,121

(22) PCT Filed: Jun. 13, 2017

(86) PCT No.: PCT/IB2017/053511
§ 371 (c)(1),
(2) Date: Dec. 12, 2018

(87) PCT Pub. No.: WO2017/216727
PCT Pub. Date: Dec. 21, 2017

(65) Prior Publication Data
US 2019/0194166 A1    Jun. 27, 2019

Related U.S. Application Data

(60) Provisional application No. 62/412,343, filed on Oct. 25, 2016, provisional application No. 62/393,256, (Continued)

(51) Int. Cl.
C07D 401/12    (2006.01)
C07D 401/04    (2006.01)
(Continued)

(52) U.S. Cl.
CPC ............ *C07D 401/12* (2013.01); *A61P 35/00* (2018.01); *A61P 37/00* (2018.01); *C07D 213/73* (2013.01);
(Continued)

(58) Field of Classification Search
CPC .. C07D 401/12; C07D 401/04; C07D 401/14; C07D 213/73; C07D 213/74;
(Continued)

(56) References Cited

U.S. PATENT DOCUMENTS

2003/0166554 A1    9/2003    Cohen et al.
2004/0097560 A1    5/2004    Warshakoon et al.
(Continued)

FOREIGN PATENT DOCUMENTS

AU    2011253934 A1    1/2012
EP       526877 A2    2/1993
(Continued)

OTHER PUBLICATIONS

Buira, et al. "DNA Methylation Regulates Adenosine $A_{2A}$ Receptor Cell Surface Expression Levels". *Journal of Neurochemistry*, 112(5): 1273-1285 (Feb. 2, 2010).
(Continued)

*Primary Examiner* — Timothy R Rozof
(74) *Attorney, Agent, or Firm* — James K. Leonard; Duke M. Fitch; Edward R. Gimmi

(57) ABSTRACT

The invention is directed to substituted pyridine derivatives. Specifically, the invention is directed to compounds according to Formula (Iar):

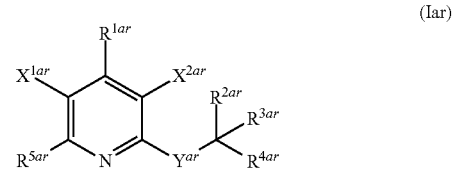

wherein $Y^{ar}$, $X^{1ar}$, $X^{2ar}$, $R^{1ar}$, $R^{2ar}$, $R^{3ar}$, $R^{4ar}$ and $R^{5ar}$ are as defined herein; or a pharmaceutically acceptable salt or prodrug thereof.

The compounds of the invention are selective inhibitors of DNMT1 and can be useful in the treatment of cancer, pre-cancerous syndromes, beta hemoglobinopathy disorders, sickle cell disease, sickle cell anemia, and beta thalassemia, and diseases associated with DNMT1 inhibition. Accordingly, the invention is further directed to pharmaceutical compositions comprising a compound of the invention. The invention is still further directed to methods of inhibiting DNMT1 activity and treatment of disorders associated (Continued)

therewith using a compound of the invention or a pharmaceutical composition comprising a compound of the invention.

21 Claims, 4 Drawing Sheets

Related U.S. Application Data filed on Sep. 12, 2016, provisional application No. 62/349,227, filed on Jun. 13, 2016.

(51) Int. Cl.

| | | |
|---|---|---|
| *C07D 213/73* | (2006.01) | |
| *C07D 213/74* | (2006.01) | |
| *C07D 413/14* | (2006.01) | |
| *C07D 417/12* | (2006.01) | |
| *A61P 37/00* | (2006.01) | |
| *A61P 35/00* | (2006.01) | |
| *C07D 401/14* | (2006.01) | |

(52) U.S. Cl.
CPC ......... *C07D 213/74* (2013.01); *C07D 401/04* (2013.01); *C07D 401/14* (2013.01); *C07D 413/14* (2013.01); *C07D 417/12* (2013.01)

(58) Field of Classification Search
CPC ..... C07D 413/14; C07D 417/12; A61P 37/00; A61P 35/00
See application file for complete search history.

(56) References Cited

U.S. PATENT DOCUMENTS

| | | | |
|---|---|---|---|
| 2006/0128755 A1 | 6/2006 | Nakagawa et al. | |
| 2006/0264432 A1 | 11/2006 | Rosentreter et al. | |
| 2009/0011994 A1 | 1/2009 | Stein et al. | |
| 2010/0160326 A1 | 6/2010 | Kimura et al. | |
| 2011/0152235 A1 | 6/2011 | Baldino et al. | |
| 2011/0152273 A1 | 6/2011 | Arikawa et al. | |
| 2012/0184572 A1 | 7/2012 | Song et al. | |
| 2012/0238557 A1 | 9/2012 | Masui et al. | |
| 2012/0316182 A1 | 12/2012 | Whitten et al. | |
| 2014/0357594 A1* | 12/2014 | Hendrickson | C07D 473/34 514/45 |

FOREIGN PATENT DOCUMENTS

| | | |
|---|---|---|
| KR | 2011/0027314 A | 3/2011 |
| WO | WO 9422853 A1 | 10/1994 |
| WO | WO 9724122 A1 | 7/1997 |
| WO | WO 9724124 A1 | 7/1997 |
| WO | WO 200144172 A1 | 6/2001 |
| WO | WO 200208203 A2 | 1/2002 |
| WO | WO 200270485 A1 | 9/2002 |
| WO | WO 2004002943 A1 | 1/2004 |
| WO | WO 2004020445 A2 | 3/2004 |
| WO | WO 2004052816 A1 | 6/2004 |
| WO | WO 2004054987 A1 | 7/2004 |
| WO | WO 2004092196 A2 | 10/2004 |
| WO | WO 2005030129 A2 | 4/2005 |
| WO | WO 2006044823 A2 | 4/2006 |
| WO | WO 2006045459 A1 | 5/2006 |
| WO | WO 2007025709 A2 | 3/2007 |
| WO | WO 2007089336 A2 | 8/2007 |
| WO | WO 2008093075 A2 | 8/2008 |
| WO | WO 2009034433 A2 | 3/2009 |
| WO | WO 2009047798 A2 | 4/2009 |
| WO | WO 2009087212 A2 | 7/2009 |
| WO | WO 2010001169 A2 | 1/2010 |
| WO | WO 2010020810 A1 | 2/2010 |
| WO | WO 2010048149 A2 | 4/2010 |
| WO | WO 2010080537 A1 | 7/2010 |
| WO | WO 2010088518 A2 | 8/2010 |
| WO | WO 2011076419 A1 | 6/2011 |
| WO | WO 2011103289 A2 | 8/2011 |
| WO | WO 2011150156 A2 | 12/2011 |
| WO | WO 2012040636 A2 | 3/2012 |
| WO | WO 2012099807 A1 | 7/2012 |
| WO | WO 2013019621 A1 | 2/2013 |
| WO | WO 2013019635 A1 | 2/2013 |
| WO | WO 2013178816 A1 | 12/2013 |
| WO | WO 2014052699 A1 | 4/2014 |
| WO | WO 2015110963 A1 | 7/2015 |
| WO | WO 2015110999 A1 | 7/2015 |

OTHER PUBLICATIONS

Database Registry, Chemical Abstracts Services, CAS Registry No. 1925135-75-6 (Entered STN: Jun. 5, 2016); 1925122-94-6 (Entered STN: Jun. 5, 2016); 1871466-28-2 (Entered STN: Feb. 22, 2016); 1808535-11-6 (Entered STN: Sep. 29, 2015); 1486351-30-7 (Entered STN: Dec. 3, 2013); 1406215-97-1 (Entered STN: Nov. 25, 2012); 1395049-40-7 (Entered STN: Sep. 20, 2012); 1315280-96-6 (Entered STN: Aug. 5, 2011); 1309132-69-1 (Entered STN: Jun. 13, 2011); 1307877-18-4 (Entered STN: Jun. 8, 2011).

Akpan I, Banzon V, Ibanez V, Vaitkus K, DeSimone J, Lavelle D. Decitabine increases fetal hemoglobin in Papio anubis by increasing +|− Globin Gene Transcription, Experimental Hematology, 38:989-93 (2010).

Chin J, Singh M, Banzon V, Vaitkus K, Ibanez V, Kouznetsova T, et al. Transcriptional activation of the +|−globin gene in baboons treated with decitabine and in cultured erythroid progenitor cells involves different mechanisms, Experimental Hematology, 37:1131-42 (2009).

Dover GJ, Charache SH, Boyer SH, Talbot J, Smith KD. 5-Azacytidine increases fetal hemoglobin production in a patient with sickle cell disease, Progress in Clinical and Biological Research, 134:475-88 (1983).

Ley TJ, DeSimone J, Noguchi CT, Turner PH, Schechter AN, Heller P, et al. 5-Azacytidine increases +|−globin synthesis and reduces the proportion of dense cells in patients with sickle cell anemia, Blood, 62:370-80 (1983).

Lowrey CH, Nienhuis AW. Brief report: Treatment with azacitidine of patients with end-stage +|− thalassemia, N Engl J Med., 329:845-8 (1993).

Mabaera R, Richardson CA, Johnson K, Hsu M, Fiering S, Lowrey CH. Developmental- and differentiation-specific patterns of human +|− and +|−globin promoter DNA methylation, Blood, .2007;110:1343-52 (2007).

Pop R, Shearstone JR, Shen Q, Liu Y, Hallstrom K, Koulnis M, et al. A key commitment step in erythropoiesis is synchronized with the cell cycle clock through mutual inhibition between PU.1 and S-phase progression, PLoS, 8(9):e1000484 (2010).

Saunthararajah Y, Hillery CA, Lavelle D, Molokie R, Dorn L, Bressler L, et al. Effects of 5-aza-2GÇ|−deoxycytidine on fetal hemoglobin levels, red cell adhesion, and hematopoietic differentiation in patients with sickle cell disease. Blood, 102:3865-70 (2003).

Shearstone JR, Pop R, Bock C, Boyle P, Meissner A, Socolovsky M. Global DNA demethylation during mouse erythropoiesis in vivo., Science, 334:799-802 (2011).

Ting et al. ,Genes Dev., 20:3215-3231 (2006).

National Center for Biotechnology Information. PubChem Compound Database; CID=1897590, https://pubchem.ncbi.nlm.nih.gov/compound/1897590, Jul. 13, 2005.

National Center for Biotechnology Information. PubChem Compound Database; CID=1897591, https://pubchem.ncbi.nlm.nih.gov/compound/1897591, Jul. 13, 2005.

National Center for Biotechnology Information. PubChem Compound Database; CID=1897592, https://pubchem.ncbi.nlm.nih.gov/compound/1897592, Jul. 13, 2005.

National Center for Biotechnology Information. PubChem Compound Database; CID=1897593, https://pubchem.ncbi.nlm.nih.gov/compound/1897593, Jul. 13, 2005.

(56) References Cited

OTHER PUBLICATIONS

National Center for Biotechnology Information. PubChem Compound Database; CID=1959999, https://pubchem.ncbi.nlm.nih.gov/compound/1959999, Jul. 13, 2005.

National Center for Biotechnology Information. PubChem Compound Database; CID=1960000, https://pubchem.ncbi.nlm.nih.gov/compound/1960000, Jul. 13, 2005.

National Center for Biotechnology Information. PubChem Compound Database; CID=1960001, https://pubchem.ncbi.nlm.nih.gov/compound/1960001, Jul. 13, 2005.

National Center for Biotechnology Information. PubChem Compound Database; CID=1960002, https://pubchem.ncbi.nlm.nih.gov/compound/1960002, Jul. 13, 2005.

National Center for Biotechnology Information. PubChem Compound Database; CID=53452988, https://pubchem.ncbi.nlm.nih.gov/compound/53452988, Oct. 30, 2011.

* cited by examiner

SUBSTITUTED PYRIDINES AS INHIBITORS OF DNMT1

This application is a 371 of International Application No. PCT/IB2017/053511, filed 13 Jun. 2017, which claims priority to U.S. Provisional 62/349,227, filed 13 Jun. 2016, U.S. Provisional 62/393,256, filed 12 Sep. 2016, and U.S. Provisional 62/412,343, filed 25 Oct. 2016.

FIELD OF THE INVENTION

The present invention relates to substituted pyridine derivatives that are selective inhibitors of the activity of DNA methyltransferase) (DNMT1). The present invention also relates to pharmaceutical compositions comprising such compounds and methods of using such compounds in the treatment of cancer, pre-cancerous syndromes, beta hemoglobinopathy disorders, sickle cell disease, sickle cell anaemia, and beta thalassemia, and other diseases associated with DNMT1 inhibition.

BACKGROUND OF THE INVENTION

Epigenetics is a way to turn genes on and off independent of the underlaying DNA sequence. DNA methylation occurring in gene promotors is an example of a repressive epigenetic mark resulting in chromatin compaction and gene silencing. DNA methylation is mediated by the DNA methyltransferase (DNMT) family of proteins which is comprised of four family members. Three of the family members, DNMT1, DNMT3A and DNMT3B, contain DNA methyltransferase activity. These three members are responsible for establishing the de novo DNA methylation pattern, while DNMT1 is primarily responsible for maintaining the methylation pattern in daughter strands following DNA replication.

In cancer, DNA methylation patterns become aberrant resulting in global hypomethylation and localized hypermethylation within promoter regions. This can result in downstream silencing of tumor suppressor genes (Ting et al. Genes Dev. 2006; 20:3215-3231). Additionally, silencing of DNMT1 results in DNA demethylation and reexpression of tumor suppressor genes resulting in tumor growth inhibition (Zhou et al. Oncol. Lett. 2014; 5: 2130-2134).

DNA methylation inhibitors (termed DNA hypomethylating agents) are clinically validated anti-cancer therapies utilized for the treatment of MDS, AML and CMML. While these agents are available, there is still significant opportunity for improvement regarding toxicity, utility in solid tumors and oral bioavailability. Hence, a novel DNMT inhibitor would be of interest for the treatment of cancer and/or any disease or condition mediated by DNA methylation. Of particular interest to this invention, is specifically targeting DNMT1 to prevent propagation of abnormal methylation patterns (such as those that occur in cancer) to daughter strands during replication.

US 2008/0132525 and WO 2006/078752 describe inhibitors of DNA methyltransferase. CA 2030875 describes methods and probes for detecting nucleoside transporter and method for producing the probes.

Hemoglobinopathies

Hemoglobin disorders, such as sickle cell anemia and beta-thalassaemia, represent the most common heritable blood diseases in the world. Sickle cell anemia and beta-thalassemia are characterized by disorders of hemoglobin, which is the oxygen carrying protein complex in red blood cells. Structurally, hemoglobin is normally composed of two pairs of proteins plus four molecules of heme. Adults and children older than about four months, express a form of hemoglobin referred to as adult hemoglobin, which predominantly consists of two alpha-globin proteins paired with two beta-globin proteins plus four molecules of heme. However, fetuses and infants typically express mostly fetal hemoglobin, which is composed of two alpha-globin proteins paired with two gamma-globin proteins plus four molecules of heme. Note that there are two forms of gamma-globin, termed G-gamma and A-gamma, that are encoded by two different genes (HBG1 and HBG2) but that are functionally equivalent to a large degree; fetal hemoglobin refers to any combination of a pair of G-gamma and/or A-gamma plus a pair of alpha-globin proteins plus four molecules of heme.

In sickle cell anemia, the gene encoding for beta-globin contains a mutation which results in an abnormal hemoglobin structure and causes red blood cells to adopt a characteristic sickle shape under certain conditions. This sickle shape leads to reduced red cell plasticity, longer capillary transit times, and frequent vaso-occlusive processes that can damage tissues and result in patient morbidity. In contrast, beta-thalassemia is characterized by inadequate beta-globin production to combine with normally produced alpha-globin. The resulting accumulation of alpha globin is toxic to red blood cell precursors, and results in ineffective erythropoiesis and extensive red blood cell hemolysis.

There is currently no approved pharmacologic treatment to cure sickle cell anemia or beta-thalassemia. However, increases in the number of red blood cells that produce fetal hemoglobin, combined with overall increases in the level of fetal hemoglobin per red blood cell have been proven to provide clinical benefit in sickle cell anemia and sickle cell disease patients by reducing the frequency of acute vaso-occlusive crises. Additionally, although not clinically proven, the disease biology of beta-thalassemia suggests that increasing fetal hemoglobin production to high levels may be a viable strategy for the therapy of this disease as well.

The object of this therapeutic approach, the de-repression of the silenced HBG1 and HBG2 genes, may be targeted through intervention in an epigenetic process in erythropoiesis. Changes in DNA methylation are key determining events in the course of hematopoiesis, marking differentiation milestones that result in commitments to various cell lineages. During erythropoiesis, a rapid decrease in global DNA methylation demarks a commitment point toward the expression of erythroid specific regulators GATA1 and KLF1, and suppression of hematopoietic progenitor regulators GATA2 and PU.1 (1, 2). For erythroid progenitor cells in adult bone marrow, DNA in the promoter region of the beta-globin HBB gene becomes unmethylated, corresponding to high level expression of beta-globin protein. In contrast, promoters of the HBG1 and HBG2 loci are highly methylated, resulting in greatly diminished expression of gamma-globin proteins (3). Although DNA methyltransferases DNMT1, DNMT3A, and DNMT3B are each expressed in erythroid progenitors, the relatively greater expression of DNMT1, particularly in the final stages of erythroid differentiation suggests that it plays a dominant role in globin gene regulation (2). 5-azacytidine and 5-aza-2'-deoxycytidine (decitabine) are pan-DNMT inhibitors that are known inducers of fetal hemoglobin in erythroid progenitor cells. In erythroid cell culture and in an in vivo model of fetal hemoglobin induction (4, 5), treatment with these agents causes decreased methylation of CpG sites in the HBG promoters with corresponding increases in the gamma globin protein expression. Moreover, in a limited set of clinical studies, both agents caused increases in fetal hemoglobin in patients with sickle cell anemia, sickle cell disease and beta-thalassemia (6-9). While effective at inducing fetal hemoglobin, these agents have not been widely used to treat sickle cell anemia, sickle cell disease, or beta-thalassemia due to concerns over long-term safety, dose-limiting toxicities, and an unsuitable dosing route.

REFERENCES (1) Pop R, Shearstone J R, Shen Q, Liu Y, Hallstrom K, Koulnis M, et al. A key commitment step in erythropoiesis is synchronized with the cell cycle clock through mutual inhibition between PU.1 and S-phase progression. 2010; 8.
(2) Shearstone J R, Pop R, Bock C, Boyle P, Meissner A, Socolovsky M. Global DNA demethylation during mouse erythropoiesis in vivo. 2011; 334:799-802.
(3) Mabaera R, Richardson C A, Johnson K, Hsu M, Fiering S, Lowrey C H. Developmental- and differentiation-specific patterns of human +|- and +|-globin promoter DNA methylation. 2007; 110:1343-52.
(4) Chin J, Singh M, Banzon V, Vaitkus K, Ibanez V, Kouznetsova T, et al. Transcriptional activation of the +|-globin gene in baboons treated with decitabine and in cultured erythroid progenitor cells involves different mechanisms. 2009; 37:1131-42.
(5) Akpan I, Banzon V, Ibanez V, Vaitkus K, DeSimone J, Lavelle D. Decitabine increases fetal hemoglobin in Papio anubis by increasing +|-globin gene transcription. 2010; 38:989-93.
(6) Dover G J, Charache S H, Boyer S H, Talbot J, Smith K D. 5-Azacytidine increases fetal hemoglobin production in a patient with sickle cell disease. 1983; 134:475-88.
(7) Saunthararajah Y, Hillery C A, Lavelle D, Molokie R, Dorn L, Bressler L, et al. Effects of 5-aza-2GÇ|-deoxycytidine on fetal hemoglobin levels, red cell adhesion, and hematopoietic differentiation in patients with sickle cell disease. 2003; 102:3865-70.
(8) Ley T J, DeSimone J, Noguchi C T, Turner P H, Schechter A N, Heller P, et al. 5-Azacytidine increases +|-globin synthesis and reduces the proportion of dense cells in patients with sickle cell anemia. 1983; 62:370-80.
(9) Lowrey C H, Nienhuis A W. Brief report: Treatment with azacitidine of patients with end-stage +|-thalassemia. 1993; 329:845-8.

It is an object of the present invention to provide novel compounds that are selective inhibitors of DNMT1.

It is also an object of this invention to provide compounds which increase the production of gamma globin, and thereby also increase the production of fetal hemoglobin in human erythroid cells. The compounds of this invention may therefore be useful to treat sickle cell anemia and sickle cell disease. Beta-thalassemia may also be ameliorated by treatment with these compounds.

It is also an object of the present invention to provide pharmaceutical compositions that comprise a pharmaceutical excipient and compounds of Formula (I).

It is also an object of the present invention to provide a method for treating cancer, pre-cancerous syndromes, beta hemoglobinopathies, such as sickle cell disease, sickle cell anaemia, and beta thalassemia, that comprises administering novel selective inhibitors of DNMT1 activity.

SUMMARY OF THE INVENTION

The invention is directed to substituted pyridine derivatives. Specifically, the invention is directed to compounds according to Formula (Iar):

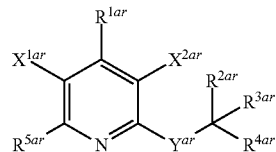

wherein $Y^{ar}$, $X^{1ar}$, $X^{2ar}$, $R^{1ar}$, $R^{2ar}$, $R^{3ar}$, $R^{4ar}$ and $R^{5ar}$ are as defined below; or a pharmaceutically acceptable salt or prodrug thereof.

The present invention also relates to the discovery that the compounds of Formula (I) are active as inhibitors of DNMT1, and selective against DNMT3A and DNMT3B.

This invention also relates to a method of treating cancer, which comprises administering to a subject in need thereof an effective amount of a DNMT1 inhibiting compound of Formula (I); or a pharmaceutically acceptable salt thereof.

This invention also relates to a method of treating pre-cancerous syndromes, which comprises administering to a subject in need thereof an effective amount of a DNMT1 inhibiting compound of Formula (I); or a pharmaceutically acceptable salt thereof.

This invention also relates to a method of treating beta hemoglobinopathies, which comprises administering to a subject in need thereof an effective amount of a DNMT1 inhibiting compound of Formula (I); or a pharmaceutically acceptable salt thereof.

This invention also relates to a method of treating sickle cell disease, which comprises administering to a subject in need thereof an effective amount of a DNMT1 inhibiting compound of Formula (I); or a pharmaceutically acceptable salt thereof.

This invention also relates to a method of treating sickle cell anemia, which comprises administering to a subject in need thereof an effective amount of a DNMT1 inhibiting compound of Formula (I); or a pharmaceutically acceptable salt thereof.

This invention also relates to a method of treating beta thalassemia, which comprises administering to a subject in need thereof an effective amount of a DNMT1 inhibiting compound of Formula (I); or a pharmaceutically acceptable salt thereof.

The invention also relates to a compound of Formula (I) or a pharmaceutically acceptable salt thereof for use in therapy.

The invention also relates to a compound of Formula (I) or a pharmaceutically acceptable salt thereof for use in the treatment of cancer.

The invention also relates to a compound of Formula (I) or a pharmaceutically acceptable salt thereof for use in the treatment of pre-cancerous syndromes.

The invention also relates to a compound of Formula (I) or a pharmaceutically acceptable salt thereof for use in the treatment of beta hemoglobinopathies.

The invention also relates to a compound of Formula (I) or a pharmaceutically acceptable salt thereof for use in the treatment of sickle cell disease.

The invention also relates to a compound of Formula (I) or a pharmaceutically acceptable salt thereof for use in the treatment of sickle cell anemia.

The invention also relates to a compound of Formula (I) or a pharmaceutically acceptable salt thereof for use in the treatment of beta thalassemia.

The invention also relates to the use of a compound of Formula (I) or a pharmaceutically acceptable salt thereof in the manufacture of a medicament for the treatment of cancer.

The invention also relates to the use of a compound of Formula (I) or a pharmaceutically acceptable salt thereof in the manufacture of a medicament for the treatment of pre-cancerous syndromes.

The invention also relates to the use of a compound of Formula (I) or a pharmaceutically acceptable salt thereof in the manufacture of a medicament for the treatment of beta hemoglobinopathies.

The invention also relates to the use of a compound of Formula (I) or a pharmaceutically acceptable salt thereof in the manufacture of a medicament for the treatment of sickle cell disease.

The invention also relates to the use of a compound of Formula (I) or a pharmaceutically acceptable salt thereof in the manufacture of a medicament for the treatment of sickle cell anemia.

The invention also relates to the use of a compound of Formula (I) or a pharmaceutically acceptable salt thereof in the manufacture of a medicament for the treatment of beta thalassemia.

Included in the present invention are pharmaceutical compositions that comprise a pharmaceutical carrier and a compound of Formula (I) or a pharmaceutically acceptable salt thereof.

The invention also relates to a pharmaceutical composition as defined above for use in therapy.

Also included in the present invention are methods of co-administering the presently invented DNMT1 inhibiting compounds with a further anti-neoplastic agent or agents.

Also included in the present invention are methods of co-administering the presently invented DNMT1 inhibiting compounds with a further fetal hemoglobin inducing agent or agents.

Also included in the present invention are methods of co-administering the presently invented DNMT1 inhibiting compounds with a further agent or agents that lessens the severity of beta hemoglobinopathies.

Also included in the present invention are methods of co-administering the presently invented DNMT1 inhibiting compounds with a further agent or agents that lessens the severity of sickle cell anemia.

Also included in the present invention are methods of co-administering the presently invented DNMT1 inhibiting compounds with a further agent or agents that lessens the severity of sickle cell disease.

Also included in the present invention are methods of co-administering the presently invented DNMT1 inhibiting compounds with a further agent or agents that lessens the severity of beta thalassemia.

The invention also relates to a combination for use in therapy which comprises a therapeutically effective amount of (i) a compound of Formula (I) or a pharmaceutically acceptable salt thereof; and (ii) at least one anti-neoplastic agent.

The invention also relates to a combination for use in therapy which comprises a therapeutically effective amount of (i) a compound of Formula (I) or a pharmaceutically acceptable salt thereof; and (ii) at least one further fetal hemoglobin inducing agent.

The invention also relates to a combination for use in therapy which comprises a therapeutically effective amount of (i) a compound of Formula (I) or a pharmaceutically acceptable salt thereof; and (ii) at least one further agent that lessens the severity of beta hemoglobinopathies.

The invention also relates to a combination for use in therapy which comprises a therapeutically effective amount of (i) a compound of Formula (I) or a pharmaceutically acceptable salt thereof; and (ii) at least one further agent that lessens the severity of sickle cell anemia.

The invention also relates to a combination for use in therapy which comprises a therapeutically effective amount of (i) a compound of Formula (I) or a pharmaceutically acceptable salt thereof; and (ii) at least one further agent that lessens the severity of sickle cell disease.

The invention also relates to a combination for use in therapy which comprises a therapeutically effective amount of (i) a compound of Formula (I) or a pharmaceutically acceptable salt thereof; and (ii) at least one further agent that lessens the severity of beta thalassemia.

DETAILED DESCRIPTION OF THE INVENTION

Figure 1A:
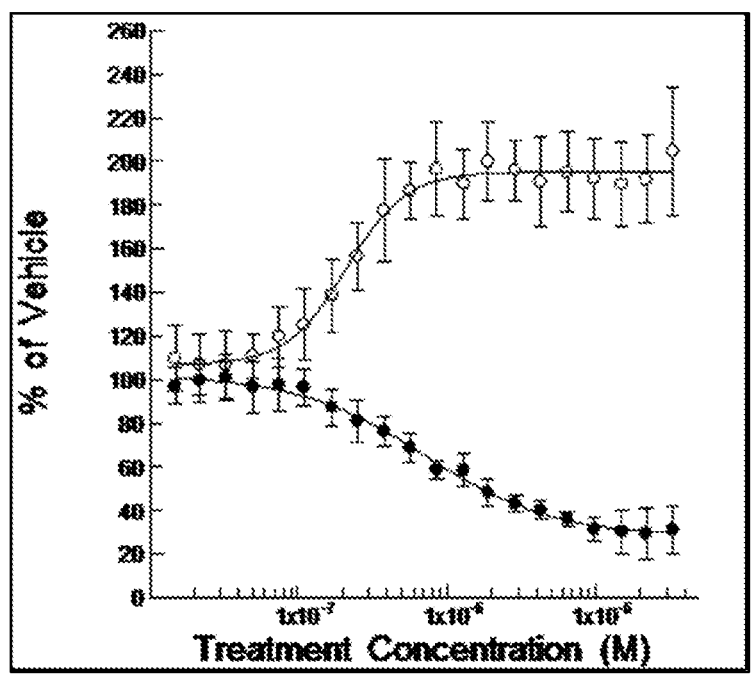
FIG. 1A depicts the effect of Compound A on erythroid progenitor cells (EPCs). Representative results (n=3 studies each) of 5 day treatment with Compound A on fetal hemoglobin (HbF) ELISA (open circles), and cell growth assay (closed circles).

This invention relates to compounds of Formula (Iar) and to the use of compounds of Formula (Iar) in the methods of the invention:

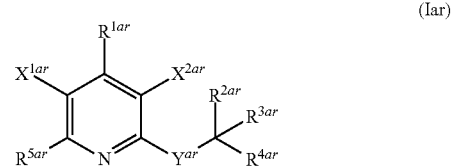

(Iar)

wherein:
$X^{1ar}$ and $X^{2ar}$ are independently selected from:
hydrogen,
cyano,
fluoro,
chloro,
bromo,
iodo, C$_{1-6}$alkyl,
R$^e$,
—OC$_{1-6}$alkyl,
—OR$^e$,
cycloalkyl,
cycloalkyl substituted from 1 to 4 times by R$^d$,
heterocycloalkyl,
heterocycloalkyl substituted from 1 to 4 times by R$^d$,
—SH, and
—SR$^a$;

Y$^{ar}$ is selected from: S, NH, NR$^z$, O, S(O) and S(O)$_2$;

R$^{1ar}$ is selected from:
amino,
—NHR$^a$,
—NR$^b$R$^c$,
cyano,
fluoro,
chloro,
bromo,
iodo,
C$_{1-6}$alkyl,
R$^e$,
—OC$_{1-6}$alkyl,
—OR$^e$,
cycloalkyl,
cycloalkyl substituted from 1 to 4 times by R$^d$,
heterocycloalkyl,
heterocycloalkyl substituted from 1 to 4 times by R$^d$,
aryl,
aryl substituted from 1 to 4 times by R$^d$,
heteroaryl,
heteroaryl substituted from 1 to 4 times by R$^d$,
—SH, and
—SR$^a$;

R$^{2ar}$ is selected from:
hydrogen,
C$_{1-6}$alkyl,
R$^e$,
cycloalkyl,
cycloalkyl substituted from 1 to 4 times by R$^d$,
heterocycloalkyl,
heterocycloalkyl substituted from 1 to 4 times by R$^d$,
—C(O)OR$^a$,
—C(O)NHR$^a$, and
—C(O)NR$^b$R$^c$;

R$^{3ar}$ is selected from:
hydrogen,
aryl,
aryl substituted from 1 to 4 times by R$^d$,
heteroaryl, and
heteroaryl substituted from 1 to 4 times by R$^d$;

R$^{4ar}$ is selected from:
hydrogen,
C$_{1-6}$alkyl,
R$^e$,
cycloalkyl,
cycloalkyl substituted from 1 to 4 times by R$^d$,
heterocycloalkyl,
heterocycloalkyl substituted from 1 to 4 times by R$^d$,
—C(O)OR$^a$,
—C(O)NHR$^a$, and
—C(O)NR$^b$R$^c$;

R$^{5ar}$ is selected from:
amino,
—NHR$^a$,
—NR$^b$R$^c$,
aryl,
aryl substituted from 1 to 4 times by R$^d$,
—OC$_{1-6}$alkyl,
—OR$^e$,
—Oaryl,
—Oaryl substituted from 1 to 4 times by R$^d$,
—Oheteroaryl,
—Oheteroaryl substituted from 1 to 4 times by R$^d$,
—SH, and
—SR$^a$;

where:
each R$^a$ is independently selected from
C$_{1-6}$alkyl,
R$^e$,
aryl,
aryl substituted from 1 to 4 times by R$^d$,
heteroaryl,
heteroaryl substituted from 1 to 4 times by R$^d$
cycloalkyl,
cycloalkyl substituted from 1 to 4 times by R$^d$,
heterocycloalkyl, and
heterocycloalkyl substituted from 1 to 4 times by R$^d$;

R$^b$ and R$^c$ are independently selected from:
C$_{1-6}$alkyl,
R$^e$,
aryl,
aryl substituted from 1 to 4 times by R$^d$,
heteroaryl,
heteroaryl substituted from 1 to 4 times by R$^d$;
cycloalkyl,
cycloalkyl substituted from 1 to 4 times by R$^d$,
heterocycloalkyl, and
heterocycloalkyl substituted from 1 to 4 times by R$^d$,
or
R$^b$ and R$^c$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
C$_{1-6}$alkyl,
R$^e$,
aryl,
aryl substituted from 1 to 4 times by R$^d$,
cycloalkyl,
cycloalkyl substituted from 1 to 4 times by R$^d$,
heterocycloalkyl, and
heterocycloalkyl substituted from 1 to 4 times by R$^d$,
C$_{1-4}$alkoxy,
C$_{1-4}$alkoxy substituted with from 1 to 6 substituents independently selected from: fluoro, oxo, —OH, —COOH, —NH$_2$, and —CN,
—CN,
oxo,
—OH,
—COOH,
—NO$_2$,
—NH$_2$,
—N(H)C$_{1-4}$alkyl,
—N(H)R$^e$,
—N(C$_{1-4}$alkyl)$_2$,
—NR$^e$R$^e$,
SO$_2$NH$_2$, SO$_2$CH$_2$CH$_3$, and
SO$_2$CH$_3$;
each R$^d$ is independently selected from:
fluoro,
chloro,
bromo,
iodo,
C$_{1-6}$alkyl,
R$^e$,
heteroaryl,
heteroaryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
cycloalkyl,
cycloalkyl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
aryl,
aryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
C$_{1-4}$alkoxy,
C$_{1-4}$alkoxy substituted from 1 to 4 times by fluoro,
—Oaryl,
—Oaryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)H,
—C(O)R$^{zz}$,
—C(O)aryl,
—C(O)aryl substituted from 1 to 4 times by R$^{zz}$,
—C(O)heteroaryl,
—C(O)heteroaryl substituted from 1 to 4 times by R$^{zz}$,
—OC(O)H,
—CO(O)R$^{zz}$,
—OC(O)aryl,
—CO(O)aryl substituted from 1 to 4 times by R$^{zz}$,
—OC(O)heteroaryl,
—OC(O)heteroaryl substituted from 1 to 4 times by R$^{zz}$,
mercapto,
—SR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)H,
—S(O)R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$H,
—S(O)$_2$R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NHS(O)$_2$H,
—NHS(O)$_2$R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NHC(O)H,
—NHC(O)R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)NH$_2$,
—C(O)NHR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)OH,
—C(O)OR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
oxo,
hydroxy,
amino,
—NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NR$^{x1}$R$^{x2}$, where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, nitro, cyano,

—NHC(O)NH$_2$,

—NHC(O)NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHC(O)NR$^{x1}$R$^{x2}$, where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, each $R^e$ is independently selected from:

$C_{1-6}$alkyl substituted with from 1 to 9 substituents independently selected from:

fluoro,
chloro,
bromo,
iodo,
$C_{1-6}$alkyl,
—OC$_{1-6}$alkyl,
—OC$_{1-6}$alkyl substituted with from 1 to 6 substituents independently selected from: fluoro, oxo, —OH, —COOH, —NH$_2$, and —CN,
mercapto,
—SR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)H,
—S(O)R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$H,
—S(O)$_2$R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
oxo,
hydroxy,
amino,
—NHR$^{xx}$,
where $R^{xx}$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OR$^{xy}$, —COOH, —CN, —OC$_{1-5}$alkyl, —OC$_{1-5}$alkyl substituted from 1 to 6 times by fluoro and —NR$^{xy}$R$^{xz}$, where $R^{xy}$ and $R^{xz}$ are independently selected from: hydrogen, aryl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH, —NR$^{x1}$R$^{x2}$, where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 Substituents independently selected from: fluoro, oxo, —OH, —COOH, —NH$_2$, and —CN, guanidino,

—C(O)OH,

—C(O)OR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—C(O)NH$_2$,

—C(O)NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)NR$^{x1}$R$^{x2}$, where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 Substituents independently selected from: fluoro, oxo, —OH, —COOH, —NH$_2$, and —CN, aryl, aryl substituted from 1 to 4 times by $R^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —Oaryl, —Oaryl substituted from 1 to 4 times by $R^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, heteroaryl, heteroaryl substituted from 1 to 4 times by $R^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —Oheteroaryl, —Oheteroaryl substituted from 1 to 4 times by $R^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
cycloalkyl,
cycloalkyl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN,
—NHS(O)$_2$H,
—NHS(O)$_2$R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NHC(O)NHR$^{xp}$,
  where R$^{xp}$ is selected from heteroaryl, cycloalkyl, heterocyloalkyl, and C$_{1-6}$alkyl substituted with from 1 to 4 substituents independently selected from: —COOH, —NH$_2$, and —CN,
—NHC(O)NR$^{x3}$R$^{x4}$,
  where R$^{x3}$ and R$^{x4}$ are each independently selected from heteroaryl, cycloalkyl, heterocyloalkyl, and C$_{1-6}$alkyl substituted with from 1 to 6 Substituents independently selected from: —COOH, —NH$_2$, and —CN,
nitro, and
cyano;
each R$^f$ is independently C$_{1-6}$alkyl optionally substituted from 1 to 6 times by R$^e$;
each R$^g$ is independently aryl optionally substituted from 1 to 5 times by R$^x$,
  where R$^x$ is independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
each R$^h$ is independently heteroaryl optionally substituted from 1 to 5 times by R$^x$,
  where R$^x$ is independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, and R$^z$ is selected from
  C$_{1-6}$alkyl,
  R$^e$,
  cycloalkyl,
  cycloalkyl substituted from 1 to 4 times by R$^d$,
  heterocycloalkyl, and
  heterocycloalkyl substituted from 1 to 4 times by R$^d$;
R$^{zz}$ is selected from
  C$_{1-6}$alkyl, and
  R$^e$;
provided that:
  at least one of R$^{2ar}$, R$^{3ar}$ and R$^{4ar}$, is hydrogen,
  R$^{2ar}$, R$^{3ar}$ and R$^{4ar}$ are not all hydrogen, and
  X$^{1ar}$ and X$^{2ar}$ are not both hydrogen;
or a pharmaceutically acceptable salt or prodrug thereof.

Suitably in the compounds of Formula (Iar) R$^{2ar}$ is —C(O)NH$_2$.

Suitably in the compounds of Formula (Iar) R$^{3ar}$ is aryl optionally substituted from 1 to 4 times by R$^d$.

Included in the compounds of the invention and used in the methods of the invention are compounds of Formula (I):

$$\underset{\text{(I)}}{\begin{array}{c}\text{structure with pyridine ring bearing } X^1, R^1, X^2, R^5, N, Y, R^2, R^3, R^4\end{array}}$$

wherein:
X$^1$ and X$^2$ are independently selected from:
  hydrogen,
  cyano,
  fluoro,
  chloro,
  bromo,
  iodo,
  C$_{1-6}$alkyl,
  R$^e$,
  —OC$_{1-6}$alkyl,
  —OR$^e$,
  cycloalkyl,
  cycloalkyl substituted from 1 to 4 times by R$^d$,
  heterocycloalkyl,
  heterocycloalkyl substituted from 1 to 4 times by R$^d$,
  —SH, and
  —SR$^a$;
Y is selected from: S, NH, NR$^z$, O, S(O) and S(O)$_2$;
R$^1$ is selected from:
  amino,
  —NHR$^a$,
  —NR$^b$R$^c$,
  cyano,
  fluoro,
  chloro,
  bromo,
  iodo,
  C$_{1-6}$alkyl,
  R$^e$,
  —OC$_{1-6}$alkyl,
  —OR$^e$,
  cycloalkyl,
  cycloalkyl substituted from 1 to 4 times by R$^d$,
  heterocycloalkyl,
  heterocycloalkyl substituted from 1 to 4 times by R$^d$, —SH, and
—SR$^a$;
R$^2$ is selected from:
hydrogen,
C$_{1-6}$alkyl,
R$^e$,
cycloalkyl,
cycloalkyl substituted from 1 to 4 times by R$^d$,
heterocycloalkyl,
heterocycloalkyl substituted from 1 to 4 times by R$^d$,
—C(O)OR$^a$,
—C(O)NHR$^a$, and
—C(O)NR$^b$R$^c$;
R$^3$ is selected from:
hydrogen,
aryl,
aryl substituted from 1 to 4 times by R$^d$,
heteroaryl, and
heteroaryl substituted from 1 to 4 times by R$^d$;
R$^4$ is selected from:
hydrogen,
C$_{1-6}$alkyl,
R$^e$,
cycloalkyl,
cycloalkyl substituted from 1 to 4 times by R$^d$,
heterocycloalkyl,
heterocycloalkyl substituted from 1 to 4 times by R$^d$,
—C(O)OR$^a$,
—C(O)NHR$^a$, and
—C(O)NR$^b$R$^c$;
R$^5$ is selected from:
amino,
—NHR$^a$,
—NR$^b$R$^c$,
aryl,
aryl substituted from 1 to 4 times by R$^d$,
—OC$_{1-6}$alkyl,
—OR$^e$,
—Oaryl,
—Oaryl substituted from 1 to 4 times by R$^d$,
—Oheteroaryl,
—Oheteroaryl substituted from 1 to 4 times by R$^d$,
—SH, and
—SR$^a$;
where:
each R$^a$ is independently selected from
C$_{1-6}$alkyl,
R$^e$,
aryl,
aryl substituted from 1 to 4 times by R$^d$,
heteroaryl,
heteroaryl substituted from 1 to 4 times by R$^d$
cycloalkyl,
cycloalkyl substituted from 1 to 4 times by R$^d$,
heterocycloalkyl, and
heterocycloalkyl substituted from 1 to 4 times by R$^d$;
R$^b$ and R$^c$ are independently selected from:
C$_{1-6}$alkyl,
R$^e$,
aryl,
aryl substituted from 1 to 4 times by R$^d$,
heteroaryl,
heteroaryl substituted from 1 to 4 times by R$^d$;
cycloalkyl,
cycloalkyl substituted from 1 to 4 times by R$^d$,
heterocycloalkyl, and
heterocycloalkyl substituted from 1 to 4 times by R$^d$,
or
R$^b$ and R$^c$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
C$_{1-6}$alkyl,
R$^e$,
aryl,
aryl substituted from 1 to 4 times by R$^d$,
cycloalkyl,
cycloalkyl substituted from 1 to 4 times by R$^d$,
heterocycloalkyl, and
heterocycloalkyl substituted from 1 to 4 times by R$^d$,
C$_{1-4}$alkoxy,
C$_{1-4}$alkoxy substituted with from 1 to 6 substituents independently selected from: fluoro, oxo, —OH, —COOH, —NH$_2$, and —CN,
—CN,
oxo,
—OH,
—COOH,
—NO$_2$,
—NH$_2$,
—N(H)C$_{1-4}$alkyl,
—N(H)R$^e$,
—N(C$_{1-4}$alkyl)$_2$,
—NR$^e$R$^e$,
SO$_2$NH$_2$,
SO$_2$CH$_2$CH$_3$, and
SO$_2$CH$_3$;
each R$^d$ is independently selected from:
fluoro,
chloro,
bromo,
iodo,
C$_{1-6}$alkyl,
R$^e$,
heteroaryl,
heteroaryl substituted from 1 to 4 times by R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
cycloalkyl,
cycloalkyl substituted from 1 to 4 times by R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
aryl,
aryl substituted from 1 to 4 times by R$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, $C_{1-4}$alkoxy, $C_{1-4}$alkoxy substituted from 1 to 4 times by fluoro, —Oaryl, —Oaryl substituted from 1 to 4 times by $R^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—C(O)H,

—C(O)R$^{zz}$,

—C(O)aryl,

—C(O)aryl substituted from 1 to 4 times by R$^{zz}$,

—C(O)heteroaryl,

—C(O)heteroaryl substituted from 1 to 4 times by R$^{zz}$,

—OC(O)H,

—CO(O)R$^{zz}$,

—OC(O)aryl,

—CO(O)aryl substituted from 1 to 4 times by R$^{zz}$,

—OC(O)heteroaryl,

—OC(O)heteroaryl substituted from 1 to 4 times by R$^{zz}$, mercapto,

—SR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—S(O)H,

—S(O)R$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—S(O)$_2$H,

—S(O)$_2$R$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—S(O)$_2$NH$_2$,

—S(O)$_2$NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$NR$^{x1}$R$^{x2}$, where R$^{x1}$ and R$^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—NHS(O)$_2$H,

—NHS(O)$_2$R$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—NHC(O)H,

—NHC(O)R$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—C(O)NH$_2$,

—C(O)NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)NR$^{x1}$R$^{x2}$, where R$^{x1}$ and R$^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—C(O)OH,

—C(O)OR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, oxo, hydroxy, amino, —NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NR$^{x1}$R$^{x2}$, where R$^{x1}$ and R$^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, nitro, cyano,

—NHC(O)NH$_2$,

—NHC(O)NHR$^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHC(O)NR$^{x1}$R$^{x2}$, where R$^{x1}$ and R$^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, each R$^e$ is independently selected from:

$C_{1-6}$alkyl substituted with from 1 to 9 substituents independently selected from:

fluoro, chloro,
bromo,
iodo,
$C_{1-6}$alkyl,
—$OC_{1-6}$alkyl,
—$OC_{1-6}$alkyl substituted with from 1 to 6 substituents independently selected from: fluoro, oxo, —OH, —COOH, —$NH_2$, and —CN,
mercapto,
—$SR^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—S(O)H,
—S(O)$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—$S(O)_2$H,
—$S(O)_2R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
oxo,
hydroxy,
amino,
—$NHR^{xx}$,
  where $R^{xx}$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —$OR^{xy}$, —COOH, —CN, —$OC_{1-5}$alkyl, —$OC_{1-5}$alkyl substituted from 1 to 6 times by fluoro and —$NR^{xy}R^{xz}$, where $R^{xy}$ and $R^{xz}$ are independently selected from: hydrogen, aryl, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro and —COOH,
—$NR^{x1}R^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 Substituents independently selected from: fluoro, oxo, —OH, —COOH, —$NH_2$, and —CN,
guanidino,
—C(O)OH,
—C(O)$OR^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—C(O)$NH_2$,
—C(O)$NHR^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—C(O)$NR^{x1}R^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 Substituents independently selected from: fluoro, oxo, —OH, —COOH, —$NH_2$, and —CN,
aryl,
aryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—Oaryl,
—Oaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
heteroaryl,
heteroaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—Oheteroaryl,
—Oheteroaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
cycloalkyl,
cycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
heterocycloalkyl,
heterocycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—$S(O)_2NH_2$,
—$S(O)_2NHR^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—$S(O)_2NR^{x1}R^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 Substituents independently selected from: fluoro, oxo, —OH, —COOH, —$NH_2$, and —CN, —NHS(O)$_2$H,
—NHS(O)$_2$R$^x$,
   where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NHC(O)NHR$^{xp}$,
   where R$^{xp}$ is selected from heteroaryl, cycloalkyl, heterocyloalkyl, and C$_{1-6}$alkyl substituted with from 1 to 4 substituents independently selected from: —COOH, —NH$_2$, and —CN,
—NHC(O)NR$^{x3}$R$^{x4}$,
   where R$^{x3}$ and R$^{x4}$ are each independently selected from heteroaryl, cycloalkyl, heterocyloalkyl, and C$_{1-6}$alkyl substituted with from 1 to 6 Substituents independently selected from: —COOH, —NH$_2$, and —CN,
nitro, and
cyano;
each R$^f$ is independently C$_{1-6}$alkyl optionally substituted from 1 to 6 times by R$^e$;
each R$^g$ is independently aryl optionally substituted from 1 to 5 times by R$^x$,
   where R$^x$ is independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
each R$^h$ is independently heteroaryl optionally substituted from 1 to 5 times by R$^x$,
   where R$^x$ is independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, and
R$^z$ is selected from
   C$_{1-6}$alkyl,
   R$^e$,
   cycloalkyl,
   cycloalkyl substituted from 1 to 4 times by R$^d$,
   heterocycloalkyl, and
   heterocycloalkyl substituted from 1 to 4 times by R$^d$;
R$^{zz}$ is selected from
   C$_{1-6}$alkyl, and
   R$^e$;
provided that:
   at least one of R$^2$, R$^3$ and R$^4$, is hydrogen,
   R$^2$, R$^3$ and R$^4$ are not all hydrogen, and
   X$^1$ and X$^2$ are not both hydrogen;
or a pharmaceutically acceptable salt or prodrug thereof.

Included in the compounds of the invention and used in the methods of the invention are compounds of Formula (II):

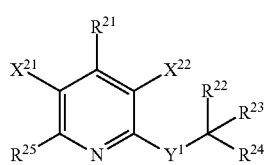

(II)

wherein:
X$^{21}$ and X$^{22}$ are independently selected from:
   hydrogen,
   cyano,
   fluoro,
   chloro,
   bromo,
   iodo,
   C$_{1-6}$alkyl,
   R$^e$,
   —OC$_{1-6}$alkyl,
   —OR$^e$,
   cycloalkyl,
   heterocycloalkyl, and
   —SH;
Y$^1$ is selected from: S, NH, NR$^z$, S(O) and S(O)$_2$;
R$^{21}$ is selected from:
   amino,
   cyano,
   fluoro,
   chloro,
   bromo,
   iodo,
   C$_{1-6}$alkyl,
   R$^e$,
   —OC$_{1-6}$alkyl,
   —OR$^e$,
   —NHR$^a$,
   —NR$^b$R$^c$,
   cycloalkyl,
   cycloalkyl substituted with from 1 to 4 times by R$^d$,
   heterocycloalkyl,
   —SH, and
   —SR$^a$;
R$^{22}$ is selected from:
   hydrogen,
   C$_{1-6}$alkyl,
   R$^e$,
   cycloalkyl,
   cycloalkyl substituted from 1 to 4 times by R$^d$,
   heterocycloalkyl,
   heterocycloalkyl substituted from 1 to 4 times by R$^d$,
   —C(O)OR$^a$, and
   —C(O)NHR$^a$;
R$^{23}$ is selected from:
   hydrogen,
   aryl,
   aryl substituted from 1 to 4 times by R$^d$,
   heteroaryl, and
   heteroaryl substituted from 1 to 4 times by R$^d$;
R$^{24}$ is selected from:
   hydrogen,
   C$_{1-6}$alkyl,
   R$^e$,
   cycloalkyl,
   cycloalkyl substituted from 1 to 4 times by R$^d$,
   heterocycloalkyl,
   heterocycloalkyl substituted from 1 to 4 times by R$^d$,
   —C(O)OR$^a$, and
   —C(O)NHR$^a$;
R$^{25}$ is selected from:
   amino,
   —NHR$^a$,
   —NR$^b$R$^c$,
   aryl,
   aryl substituted from 1 to 4 times by R$^d$,
   —OC$_{1-6}$alkyl,
   —OR$^e$,
   —Oaryl,
   —Oheteroaryl,
   —SH, and
   —SR$^a$;

where:
  each $R^a$ is independently selected from
    $C_{1-6}$alkyl,
    $R^e$,
    aryl,
    aryl substituted from 1 to 4 times by $R^d$,
    heteroaryl,
    heteroaryl substituted from 1 to 4 times by $R^d$
    cycloalkyl,
    cycloalkyl substituted from 1 to 4 times by $R^d$,
    heterocycloalkyl, and
    heterocycloalkyl substituted from 1 to 4 times by $R^d$;
  $R^b$ and $R^c$ are independently selected from:
    $C_{1-6}$alkyl,
    $R^e$,
    aryl,
    aryl substituted from 1 to 4 times by $R^d$,
    heteroaryl,
    heteroaryl substituted from 1 to 4 times by $R^d$;
    cycloalkyl,
    cycloalkyl substituted from 1 to 4 times by $R^d$,
    heterocycloalkyl, and
    heterocycloalkyl substituted from 1 to 4 times by $R^d$,
    or
  $R^b$ and $R^c$ are taken together with the nitrogen to which they are attached, and optionally from 1 to 3 additional heteroatoms, to form a heterocycloalkyl, which is optionally substituted with from 1 to 5 substituents independently selected from:
    fluoro,
    chloro,
    bromo,
    iodo,
    $C_{1-6}$alkyl,
    $R^e$,
    aryl,
    aryl substituted from 1 to 4 times by $R^d$,
    cycloalkyl,
    cycloalkyl substituted from 1 to 4 times by $R^d$,
    heterocycloalkyl, and
    heterocycloalkyl substituted from 1 to 4 times by $R^d$,
    $C_{1-4}$alkoxy,
    $C_{1-4}$alkoxy substituted with from 1 to 6 substituents independently selected from: fluoro, oxo, —OH, —COOH, —NH$_2$, and —CN,
    —CN,
    oxo,
    —OH,
    —COOH,
    —NO$_2$,
    —NH$_2$,
    —N(H)C$_{1-4}$alkyl,
    —N(H)R$^e$,
    —N(C$_{1-4}$alkyl)$_2$,
    SO$_2$NH$_2$,
    SO$_2$CH$_2$CH$_3$, and
    SO$_2$CH$_3$;
  each $R^d$ is independently selected from:
    fluoro,
    chloro,
    bromo,
    iodo,
    $C_{1-6}$alkyl,
    $R^e$,
    heteroaryl,
    heteroaryl substituted from 1 to 4 times by $R^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    cycloalkyl,
    cycloalkyl substituted from 1 to 4 times by $R^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    heterocycloalkyl,
    heterocycloalkyl substituted from 1 to 4 times by $R^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    aryl,
    aryl substituted from 1 to 4 times by $R^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    $C_{1-4}$alkoxy,
    $C_{1-4}$alkoxy substituted from 1 to 4 times by fluoro,
    —Oaryl,
    —Oaryl substituted from 1 to 4 times by $R^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    —C(O)H,
    —C(O)R$^{zz}$,
    —C(O)aryl,
    —C(O)aryl substituted from 1 to 4 times by $R^{zz}$,
    —C(O)heteroaryl,
    —C(O)heteroaryl substituted from 1 to 4 times by $R^{zz}$,
    —OC(O)H,
    —CO(O)R$^{zz}$,
    —OC(O)aryl,
    —CO(O)aryl substituted from 1 to 4 times by $R^{zz}$,
    —OC(O)heteroaryl,
    —OC(O)heteroaryl substituted from 1 to 4 times by $R^{zz}$,
    mercapto,
    —SR$^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    —S(O)H,
    —S(O)R$^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
    —S(O)$_2$H,
    —S(O)$_2$R$^x$,
      where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,

—S(O)$_2$NH$_2$,

—S(O)$_2$NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —S(O)$_2$NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—NHS(O)$_2$H,

—NHS(O)$_2$R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—NHC(O)H,

—NHC(O)R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—C(O)NH$_2$,

—C(O)NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —C(O)NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—C(O)OH,

—C(O)OR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, oxo, hydroxy, amino, —NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, nitro, cyano,

—NHC(O)NH$_2$,

—NHC(O)NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —NHC(O)NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, each R$^e$ is independently selected from:

C$_{1-6}$alkyl substituted with from 1 to 9 substituents independently selected from:
fluoro,
chloro,
bromo,
iodo,
C$_{1-6}$alkyl,
—OC$_{1-6}$alkyl,
—OC$_{1-6}$alkyl substituted with from 1 to 6 substituents independently selected from: fluoro, oxo, —OH, —COOH, —NH$_2$, and —CN,
mercapto,
—SR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)H,
—S(O)R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$H,
—S(O)$_2$R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
oxo,
hydroxy,
amino,
—NHR$^{xx}$,
where R$^{xx}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OR$^{xy}$, —COOH, —CN, —OC$_{1-5}$alkyl, —OC$_{1-5}$alkyl substituted from 1 to 6 times by fluoro and —NR$^{xy}$R$^{xz}$, where R$^{xy}$ and R$^{xz}$ are independently selected from: hydrogen, aryl, C$_{1-5}$alkyl and C$_{1-5}$alkyl substituted with from 1 to 4 substituents independently selected from:

fluoro, oxo, —OH, —OC$_{1-5}$alkyl, —OC$_{1-5}$alkyl substituted from 1 to 6 times by fluoro and —COOH, —NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN, guanidino,

—C(O)OH,

—C(O)OR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—C(O)NH$_2$,

—C(O)NHR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —C(O)NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN, aryl, aryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —Oaryl, —Oaryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, heteroaryl, heteroaryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —Oheteroaryl, —Oheteroaryl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, cycloalkyl, cycloalkyl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, heterocycloalkyl, heterocycloalkyl substituted from 1 to 4 times by R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—S(O)$_2$NH$_2$,

—S(O)$_2$NHR$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —S(O)$_2$NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN,

—NHS(O)$_2$H,

—NHS(O)$_2$R$^x$,
  where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —NHC(O)NHR$^{xp}$,
  where R$^{xp}$ is selected from heteroaryl, cycloalkyl, heterocyloalkyl, and C$_{1-6}$alkyl substituted with from 1 to 4 substituents independently selected from: —COOH, —NH$_2$, and —CN, —NHC(O)NR$^{x3}$R$^{x4}$,
  where R$^{x3}$ and R$^{x4}$ are each independently selected from heteroaryl, cycloalkyl, heterocyloalkyl, and C$_{1-6}$alkyl substituted with from 1 to 6 Substituents independently selected from: —COOH, —NH$_2$, and —CN, nitro, and cyano;

each R$^f$ is independently C$_{1-6}$alkyl optionally substituted from 1 to 6 times by R$^e$;

each R$^g$ is independently aryl optionally substituted from 1 to 5 times by R$^x$,
  where R$^x$ is independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, each R$^h$ is independently heteroaryl optionally substituted from 1 to 5 times by R$^x$,
  where R$^x$ is independently selected from aryl, heteroaryl, cycloalkyl, heterocyloalkyl, C$_{1-6}$alkyl, and C$_{1-6}$alkyl substituted with from 1 to 6 substituents Independently selected from: fluoro, oxo, —OH, —COOH, —NH$_2$, and —CN, and R$^z$ is selected from
  C$_{1-6}$alkyl,
  R$^e$,
  cycloalkyl,
  cycloalkyl substituted from 1 to 4 times by R$^d$,
  heterocycloalkyl, and
  heterocycloalkyl substituted from 1 to 4 times by R$^d$;

$R^{zz}$ is selected from
  $C_{1-6}$alkyl, and
  $R^e$;
provided that:
  at least one of $R^{22}$, $R^{23}$ and $R^{24}$, is hydrogen,
  $R^{22}$, $R^{23}$ and $R^{24}$ are not all hydrogen, and
  $X^{21}$ and $X^{22}$ are not both hydrogen;
or a pharmaceutically acceptable salt or prodrug thereof.

Included in the compounds of the invention and used in the methods of the invention are compounds of Formula (III):

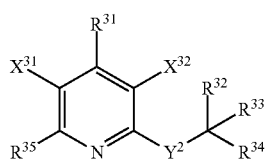

wherein:
$X^{31}$ and $X^{32}$ are independently selected from:
  hydrogen,
  cyano,
  fluoro,
  chloro,
  bromo,
  iodo,
  $C_{1-6}$alkyl,
  —$OC_{1-6}$alkyl,
  cycloalkyl, and
  —SH;
$Y^2$ is selected from: S, NH, $NR^z$ and S(O);
$R^{31}$ is selected from:
  $C_{1-6}$alkyl,
  $R^{e1}$,
  —$OC_{1-6}$alkyl,
  —$OR^{e1}$,
  —$NHR^{a1}$,
  —$NR^{b1}R^{c1}$,
  cycloalkyl,
  cycloalkyl substituted from 1 to 4 times by $R^{d1}$,
  —SH, and
  —$SR^{a1}$;
$R^{32}$ is selected from:
  hydrogen,
  $C_{1-6}$alkyl,
  $R^{e1}$,
  cycloalkyl,
  cycloalkyl substituted from 1 to 4 times by $R^{d1}$,
  heterocycloalkyl, and
  heterocycloalkyl substituted from 1 to 4 times by $R^{d1}$;
$R^{33}$ is selected from:
  hydrogen,
  aryl,
  aryl substituted from 1 to 4 times by $R^{d1}$,
  heteroaryl, and
  heteroaryl substituted from 1 to 4 times by $R^{d1}$;
$R^{34}$ is selected from:
  hydrogen,
  $C_{1-6}$alkyl,
  $R^{e1}$,
  cycloalkyl,
  cycloalkyl substituted from 1 to 4 times by $R^{d1}$,
  heterocycloalkyl, and
  heterocycloalkyl substituted from 1 to 4 times by $R^{d1}$;
$R^{35}$ is selected from:
  amino,
  —$NHR^{a1}$,
  —$NR^{b1}R^{c1}$,
  aryl,
  aryl substituted from 1 to 4 times by $R^{d1}$,
  —$OC_{1-6}$alkyl,
  —$OR^{e1}$,
  —SH, and
  —$SR^{a1}$;
where:
  each $R^{a1}$ is independently selected from
    $C_{1-6}$alkyl,
    $R^{e1}$,
    aryl,
    heteroaryl,
    cycloalkyl, and
    heterocycloalkyl;
  $R^{b1}$ and $R^{c1}$ are independently selected from:
    $C_{1-6}$alkyl,
    $R^{e1}$,
    aryl,
    aryl substituted from 1 to 4 times by $R^{d1}$,
    heteroaryl,
    heteroaryl substituted from 1 to 4 times by $R^{d1}$;
    cycloalkyl,
    cycloalkyl substituted from 1 to 4 times by $R^{d1}$,
    heterocycloalkyl, and
    heterocycloalkyl substituted from 1 to 4 times by $R^{d1}$, or
  $R^{b1}$ and $R^{c1}$ are taken together with the nitrogen to which they are attached, and optionally from 1 to 3 additional heteroatoms, to form a heterocycloalkyl, which is optionally substituted with from 1 to 5 substituents independently selected from:
    fluoro,
    chloro,
    bromo,
    iodo,
    $C_{1-6}$alkyl,
    $R^{e1}$,
    aryl,
    aryl substituted from 1 to 4 times by $R^{d1}$,
    cycloalkyl,
    cycloalkyl substituted from 1 to 4 times by $R^{d1}$,
    heterocycloalkyl, and
    heterocycloalkyl substituted from 1 to 4 times by $R^{d1}$,
    $C_{1-4}$alkoxy,
    $C_{1-4}$alkoxy substituted with from 1 to 6 substituents independently selected from: fluoro, oxo, —OH, —COOH, —$NH_2$, and —CN,
    —CN,
    oxo,
    —OH,
    —COOH,
    —$NO_2$,
    —$NH_2$,
    —N(H)$C_{1-4}$alkyl,
    —N(H)$R^{e1}$,
    —N($C_{1-4}$alkyl)$_2$,
    $SO_2NH_2$,
    $SO_2CH_2CH_3$, and
    $SO_2CH_3$;
  each $R^{d1}$ is independently selected from:
    fluoro,
    chloro,
    bromo,
    iodo, C$_{1-6}$alkyl,
R$^{e1}$,
heteroaryl,
heteroaryl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
cycloalkyl,
cycloalkyl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
heterocycloalkyl,
heterocycloalkyl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
aryl,
aryl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
C$_{1-4}$alkoxy,
C$_{1-4}$alkoxy substituted from 1 to 4 times by fluoro,
—Oaryl,
—C(O)H,
—C(O)R$^{zz}$,
—C(O)aryl,
—C(O)heteroaryl,
—OC(O)H,
—CO(O)R$^{zz}$,
—OC(O)aryl,
—OC(O)heteroaryl,
mercapto,
—SR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—S(O)H,
—S(O)R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—S(O)$_2$H,
—S(O)$_2$R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—S(O)$_2$NH$_2$,
—S(O)$_2$NHR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—NHS(O)$_2$H,
—NHS(O)$_2$R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—NHC(O)H,
—NHC(O)R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—C(O)NH$_2$,
—C(O)NHR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—C(O)OH,
—C(O)OR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
oxo,
hydroxy,
amino,
—NHR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
nitro,
cyano,
—NHC(O)NH$_2$, and
—NHC(O)NHR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro;
each R$^{e1}$ is independently selected from:
  C$_{1-6}$alkyl substituted with from 1 to 9 substituents independently selected from:
    fluoro,
    chloro,
    bromo,
    iodo,
    C$_{1-6}$alkyl,
    —OC$_{1-6}$alkyl,
    —OC$_{1-6}$alkyl substituted with from 1 to 6 substituents independently selected from: fluoro, oxo, —OH, —COOH, —NH$_2$, and —CN,
    mercapto,
    —SR$^{xa}$,
      where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
    —S(O)H,
    —S(O)R$^{xa}$,
      where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
    —S(O)$_2$H,
    —S(O)$_2$R$^{xa}$, where $R^{xa}$ is selected from aryl, heteroaryl, cycloalkyl, heterocyloalkyl, $C_{1-6}$alkyl, and $C_{1-6}$alkyl substituted from 1 to 6 times by fluoro, oxo,
hydroxy,
amino,
—$NHR^{xx}$,
  where $R^{xx}$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —$OR^{xy}$, —COOH, —CN, —$OC_{1-5}$alkyl, —$OC_{1-5}$alkyl substituted from 1 to 6 times by fluoro and —$NR^{xy}R^{xz}$, where $R^{xy}$ and $R^{xz}$ are independently selected from: hydrogen, aryl, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro and —COOH,
—$NR^{x1x}R^{x2x}$,
  where $R^{x1x}$ and $R^{x2x}$ are each independently selected from $C_{1-4}$alkyl, and $C_{1-4}$alkyl substituted with from 1 to 4 substituents independently selected from: fluoro, oxo, and —OH,
guanidino,
—C(O)OH,
—C(O)$OR^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—C(O)$NHR^{xa}$,
  where $R^{xa}$ is selected from aryl, heteroaryl, cycloalkyl, and heterocyloalkyl,
aryl,
aryl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—Oaryl,
—Oaryl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
heteroaryl,
heteroaryl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—Oheteroaryl,
—Oheteroaryl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
cycloalkyl,
cycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
heterocycloalkyl,
heterocycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—$S(O)_2NH_2$,
—$S(O)_2NHR^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—$NHS(O)_2H$,
—$NHS(O)_2R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—$NHC(O)NHR^{xa}$,
  where $R^{xa}$ is selected from heteroaryl, cycloalkyl, and heterocyloalkyl,
nitro, and
cyano;

each $R^f$ is independently $C_{1-6}$alkyl optionally substituted from 1 to 6 times by $R^{e1}$;
each $R^g$ is independently aryl optionally substituted from 1 to 5 times by $R^x$,
  where $R^x$ is independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
each $R^h$ is independently heteroaryl optionally substituted from 1 to 5 times by $R^x$,
  where $R^x$ is independently selected from aryl, heteroaryl, cycloalkyl, heterocyloalkyl, $C_{1-6}$alkyl, and $C_{1-6}$alkyl substituted with from 1 to 6 substituents Independently selected from: fluoro, oxo, —OH, —COOH, —$NH_2$, and —CN, and
$R^z$ is selected from
  $C_{1-6}$alkyl,
  $R^{e1}$,
  cycloalkyl,
  cycloalkyl substituted from 1 to 4 times by $R^{d1}$,
  heterocycloalkyl, and
  heterocycloalkyl substituted from 1 to 4 times by $R^{d1}$;
$R^{zz}$ is selected from
  $C_{1-6}$alkyl, and
  $R^{e1}$;
provided that:
  at least one of $R^{32}$, $R^{33}$ and $R^{34}$, is hydrogen,
  $R^{32}$, $R^{33}$ and $R^{34}$ are not all hydrogen, and
  $X^{31}$ and $X^{32}$ are not both hydrogen;
or a pharmaceutically acceptable salt or prodrug thereof.

Suitably in the compounds of Formula (III), neither $X^{31}$ nor $X^{32}$ are hydrogen.

Included in the compounds of the invention and used in the methods of the invention are compounds of Formula (IVar):

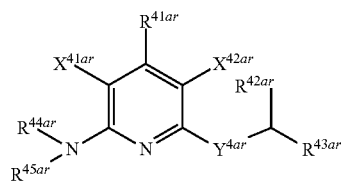

(IVar)

wherein:
X$^{41ar}$ and X$^{42ar}$ are independently selected from: —CN, fluoro, chloro, bromo and iodo;
Y$^{4ar}$ is selected from: S and NH;
R$^{41ar}$ is selected from:
  C$_{1-6}$alkyl,
  C$_{1-6}$alkyl substituted with from 1 to 9 substituents independently selected from: fluoro, chloro, bromo, iodo, oxo, C$_{1-4}$alkyloxy, —OH, —COOH, —NH$_2$ —N(H)C$_{1-4}$alkyl, —N(C$_{1-4}$alkyl)$_2$ and —CN,
  C$_{1-4}$alkyloxy,
  C$_{1-4}$alkyloxy substituted from 1 to 4 times by fluoro,
  —N(H)C$_{1-4}$alkyl,
  —N(C$_{1-4}$alkyl)$_2$,
  —SC$_{1-4}$alkyl,
  aryl,
  aryl substituted with from 1 to 4 substituents independently selected from:
    fluoro,
    chloro,
    bromo,
    iodo,
    C$_{1-6}$alkyl,
    C$_{1-6}$alkyl substituted with from 1 to 9 substituents independently selected from: fluoro, chloro, bromo, iodo, oxo, —OH, —NH$_2$ and —CN,
    C$_{1-4}$alkoxy,
    —CN,
    oxo,
    —OH,
    —NO$_2$, and
    —NH$_2$,
  heteroaryl,
  heteroaryl substituted with from 1 to 4 substituents independently selected from:
    fluoro,
    chloro,
    bromo,
    iodo,
    C$_{1-6}$alkyl,
    C$_{1-6}$alkyl substituted with from 1 to 9 substituents independently selected from: fluoro, chloro, bromo, iodo, oxo, —OH, —NH$_2$ and —CN,
    C$_{1-4}$alkoxy,
    —CN,
    oxo,
    —OH,
    —NO$_2$, and
    —NH$_2$,
  cycloalkyl,
  cycloalkyl substituted with from 1 to 4 substituents independently selected from:
    fluoro,
    chloro,
    bromo,
    iodo,
    C$_{1-6}$alkyl,
    C$_{1-6}$alkyl substituted with from 1 to 9 substituents independently selected from: fluoro, chloro, bromo, iodo, oxo, —OH, —NH$_2$ and —CN,
    C$_{1-4}$alkoxy,
    —CN,
    oxo,
    —OH,
    —NO$_2$, and
    —NH$_2$;
R$^{42ar}$ is selected from:
  hydrogen,
  C$_{1-6}$alkyl,
  C$_{1-6}$alkyl substituted with from 1 to 9 substituents independently selected from: fluoro, chloro, bromo, iodo, oxo, —OH, —NH$_2$, —N(H)C$_{1-4}$alkyl, —N(C$_{1-4}$alkyl)$_2$, and —CN,
  heterocycloalkyl, and
  heterocycloalkyl substituted with from 1 to 4 substituents independently selected from:
    fluoro,
    chloro,
    bromo,
    iodo,
    C$_{1-6}$alkyl,
    C$_{1-6}$alkyl substituted with from 1 to 9 substituents independently selected from: fluoro, chloro, bromo, iodo, oxo, —OH, —NH$_2$ and —CN,
    —NHC(O)H,
    —NHC(O)R$^{xa1}$,
      where R$^{xa1}$ is selected from aryl, heteroaryl, cycloalkyl, heterocycloalkyl, C$_{1-6}$alkyl, and C$_{1-6}$alkyl substituted from 1 to 6 times by fluoro,
    C$_{1-4}$alkoxy,
    —CN,
    oxo,
    —OH,
    —NO$_2$, and
    —NH$_2$;
R$^{43ar}$ is selected from:
  hydrogen,
  C$_{1-6}$alkyl,
  aryl,
  aryl substituted with from 1 to 4 substituents independently selected from:
    fluoro,
    chloro,
    bromo,
    iodo,
    C$_{1-6}$alkyl,
    C$_{1-6}$alkyl substituted with from 1 to 9 substituents independently selected from: fluoro, chloro, bromo, iodo, oxo, —CN, —OR$^{49}$ and —NR$^{46}$R$^{47}$,
      where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH, C$_{1-4}$alkoxy,
—CN,
oxo,
—OH,
—S(O)$_2$NH$_2$,
—S(O)$_2$NHCH$_3$,
—NO$_2$, and
—NH$_2$,
heteroaryl, and
heteroaryl substituted with from 1 to 4 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —CN, —OR$^{49}$ and —NR$^{46}$R$^{47}$, where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
C$_{1-4}$alkoxy,
—CN,
oxo,
—OH,
—S(O)$_2$NH$_2$,
—S(O)$_2$NHCH$_3$,
—NO$_2$, and
—NH$_2$; and
R$^{44ar}$ and R$^{45ar}$ are independently selected from:
hydrogen,
C$_{1-6}$alkyl,
C$_{1-6}$alkyl substituted with from 1 to 9 substituents independently selected from: fluoro, chloro, bromo, iodo, heterocycloalkyl, C$_{1-4}$alkoxy, oxo, —OH, —NH$_2$ and —CN,
heterocycloalkyl, and
heterocycloalkyl substituted with from 1 to 5 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —OH, —NH$_2$ and —CN,
aryl,
C$_{1-4}$alkoxy,
—CN,
oxo,
—OH,
—COOH,
—NO$_2$,
—NH$_2$, and
SO$_2$NH$_2$, or R$^{44ar}$ and R$^{45ar}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
aryl,
cycloalkyl,
heterocycloalkyl,
heterocycloalkyl substituted with from 1 to 9 substituents independently selected from: C$_{1-6}$alkyl, —C$_{1-6}$alkylOH, fluoro, —C$_{1-6}$alkylNH$_2$, chloro, bromo, iodo, oxo, —OH, —NH$_2$ and —CN,
C$_{1-4}$alkoxy,
C$_{1-4}$alkoxy substituted with from 1 to 4 substituents independently selected from: fluoro, oxo, —OH, —COOH, —NH$_2$, and —CN,
—CN,
oxo,
—OH,
—COOH,
—NO$_2$,
—NH$_2$,
—N(H)C$_{1-4}$alkyl,
—N(H)C$_{1-6}$alkyl substituted with from 1 to 9 substituents independently selected from: fluoro, chloro, bromo, iodo, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
—N(C$_{1-4}$alkyl)$_2$,
SO$_2$NH$_2$,
SO$_2$CH$_2$CH$_3$, and
SO$_2$CH$_3$;
provided that:
R$^{42ar}$ and R$^{43ar}$ are not both hydrogen;
or a pharmaceutically acceptable salt or prodrug thereof.
Suitably in the compounds of Formula (IVar) neither R$^{44ar}$ nor R$^{45ar}$ is hydrogen.
Suitably in the compounds of Formula (IVar) R$^{42ar}$ is —C(O)NH$_2$.
Suitably in the compounds of Formula (IVar) R$^{43ar}$ is aryl substituted with from 1 to 4 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —CN, —OR$^{49}$ and —NR$^{46}$R$^{47}$, where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

Included in the compounds of the invention and used in the methods of the invention are compounds of Formula (IV):

$$\text{(IV)}$$

wherein:

X$^{41}$ and X$^{42}$ are independently selected from: —CN, fluoro, chloro, bromo and iodo;

Y$^4$ is selected from: S and NH;

R$^{41}$ is selected from:
- C$_{1-6}$alkyl,
- C$_{1-6}$alkyl substituted with from 1 to 9 substituents independently selected from: fluoro, chloro, bromo, iodo, oxo, C$_{1-4}$alkyloxy, —OH, —COOH, —NH$_2$ —N(H)C$_{1-4}$alkyl, —N(C$_{1-4}$alkyl)$_2$ and —CN,
- C$_{1-4}$alkyloxy,
- C$_{1-4}$alkyloxy substituted from 1 to 4 times by fluoro,
- —N(H)C$_{1-4}$alkyl,
- —N(C$_{1-4}$alkyl)$_2$,
- —SC$_{1-4}$alkyl,
- cycloalkyl,
- cycloalkyl substituted with from 1 to 4 substituents independently selected from:
  - fluoro,
  - chloro,
  - bromo,
  - iodo,
  - C$_{1-6}$alkyl,
  - C$_{1-6}$alkyl substituted with from 1 to 9 substituents independently selected from: fluoro, chloro, bromo, iodo, oxo, —OH, —NH$_2$ and —CN,
  - C$_{1-4}$alkoxy,
  - —CN,
  - oxo,
  - —OH,
  - —NO$_2$, and
  - —NH$_2$;

R$^{42}$ is selected from:
- hydrogen,
- C$_{1-6}$alkyl,
- C$_{1-6}$alkyl substituted with from 1 to 9 substituents independently selected from: fluoro, chloro, bromo, iodo, oxo, —OH, —NH$_2$, —N(H)C$_{1-4}$alkyl, —N(C$_{1-4}$alkyl)$_2$, and —CN,
- heterocycloalkyl, and
- heterocycloalkyl substituted with from 1 to 4 substituents independently selected from:
  - fluoro,
  - chloro,
  - bromo,
  - iodo,
  - C$_{1-6}$alkyl,
  - C$_{1-6}$alkyl substituted with from 1 to 9 substituents independently selected from: fluoro, chloro, bromo, iodo, oxo, —OH, —NH$_2$ and —CN,
  - —NHC(O)H,
  - —NHC(O)R$^{xa1}$,
  where R$^{xa1}$ is selected from aryl, heteroaryl, cycloalkyl, heterocyloalkyl, C$_{1-6}$alkyl, and C$_{1-6}$alkyl substituted from 1 to 6 times by fluoro,
  - C$_{1-4}$alkoxy,
  - —CN,
  - oxo,
  - —OH,
  - —NO$_2$, and
  - —NH$_2$;

R$^{43}$ is selected from:
- hydrogen,
- C$_{1-6}$alkyl,
- aryl,
- aryl substituted with from 1 to 4 substituents independently selected from:
  - fluoro,
  - chloro,
  - bromo,
  - iodo,
  - C$_{1-6}$alkyl,
  - C$_{1-6}$alkyl substituted with from 1 to 9 substituents independently selected from: fluoro, chloro, bromo, iodo, oxo, —CN, —OR$^{49}$ and —NR$^{46}$R$^{47}$, where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
  - C$_{1-4}$alkoxy,
  - —CN,
  - oxo,
  - —OH,
  - —S(O)$_2$NH$_2$,
  - —S(O)$_2$NHCH$_3$,
  - —NO$_2$, and
  - —NH$_2$,
- heteroaryl, and
- heteroaryl substituted with from 1 to 4 substituents independently selected from:
  - fluoro,
  - chloro,
  - bromo,
  - iodo,
  - C$_{1-6}$alkyl,
  - C$_{1-6}$alkyl substituted with from 1 to 9 substituents independently selected from: fluoro, chloro, bromo, iodo, oxo, —CN, —OR$^{49}$ and —NR$^{46}$R$^{47}$, where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, $C_{1-5}$alkyl and $C_{1-5}$alkyl substituted with from 1 to 4 substituents independently selected from: fluoro, oxo, —OH, —O$C_{1-5}$alkyl, —O$C_{1-5}$alkyl substituted from 1 to 6 times by fluoro and —COOH,
$C_{1-4}$alkoxy,
—CN,
oxo,
—OH,
—S(O)$_2$NH$_2$,
—S(O)$_2$NHCH$_3$,
—NO$_2$, and
—NH$_2$; and $R^{44}$ and $R^{45}$ are independently selected from:
hydrogen,
$C_{1-6}$alkyl,
$C_{1-6}$alkyl substituted with from 1 to 9 substituents independently selected from: fluoro, chloro, bromo, iodo, heterocycloalkyl, $C_{1-4}$alkoxy, oxo, —OH, —NH$_2$ and —CN,
heterocycloalkyl, and
heterocycloalkyl substituted with from 1 to 5 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN,
aryl,
$C_{1-4}$alkoxy,
—CN,
oxo,
—OH,
—COOH,
—NO$_2$,
—NH$_2$, and
SO$_2$NH$_2$, or $R^{44}$ and $R^{45}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, $C_{1-4}$alkoxy, oxo, phenyl, cycloalkyl, heterocycloalkyl, methylheterocycloalkyl, —OH, —NH$_2$, —N(H)$C_{1-4}$alkyl, —N($C_{1-4}$alkyl)$_2$, and —CN,
aryl,
cycloalkyl,
heterocycloalkyl,
heterocycloalkyl substituted with from 1 to 9 substituents independently selected from: $C_{1-6}$alkyl, —$C_{1-6}$alkylOH, fluoro, —$C_{1-6}$alkylNH$_2$, chloro, bromo, iodo, oxo, —OH, —NH$_2$ and —CN,
$C_{1-4}$alkoxy,
$C_{1-4}$alkoxy substituted with from 1 to 4 substituents independently selected from: fluoro, oxo, —OH, —COOH, —NH$_2$, and —CN,
—CN,
oxo,
—OH,
—COOH,
—NO$_2$,
—NH$_2$,
—N(H)$C_{1-4}$alkyl,
—N(H)$C_{1-6}$alkyl substituted with from 1 to 9 substituents independently selected from: fluoro, chloro, bromo, iodo, $C_{1-4}$alkoxy, oxo, phenyl, cycloalkyl, heterocycloalkyl, methylheterocycloalkyl, —OH, —NH$_2$, —N(H)$C_{1-4}$alkyl, —N($C_{1-4}$alkyl)$_2$, and —CN,
—N($C_{1-4}$alkyl)$_2$,
SO$_2$NH$_2$,
SO$_2$CH$_2$CH$_3$, and
SO$_2$CH$_3$;
provided that:
$R^{42}$ and $R^{43}$ are not both hydrogen;
or a pharmaceutically acceptable salt or prodrug thereof.

Suitably in the compounds of Formula (IV) neither $R^{44}$ nor $R^{45}$ is hydrogen.

This invention relates to novel compounds of Formula (IVaar) and to the use of compounds of Formula (IVaar) in the methods of the invention:

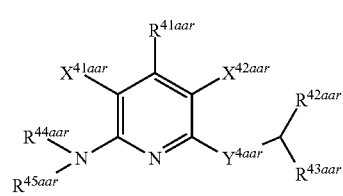

(IVaar)

wherein:
$X^{41aar}$ and $X^{42aar}$ are independently selected from: —CN, fluoro, chloro, bromo and iodo;
$Y^{4aar}$ is selected from: S and NH;
$R^{41aar}$ is selected from:
$C_{1-6}$alkyl,
$C_{1-6}$alkyl substituted with from 1 to 9 substituents independently selected from: fluoro, chloro, bromo, iodo, oxo, $C_{1-4}$alkyloxy, —OH, —COOH, —NH$_2$ —N(H)$C_{1-4}$alkyl, —N($C_{1-4}$alkyl)$_2$ and —CN,
$C_{1-4}$alkyloxy,
$C_{1-4}$alkyloxy substituted from 1 to 4 times by fluoro,
—N(H)$C_{1-4}$alkyl,
—N($C_{1-4}$alkyl)$_2$,
—S$C_{1-4}$alkyl,
aryl,
aryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN, $C_{1-4}$alkoxy,
—CN,
oxo,
—OH,
—NO$_2$, and
—NH$_2$,
heteroaryl,
heteroaryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN,
$C_{1-4}$alkoxy,
—CN,
oxo,
—OH,
—NO$_2$, and
—NH$_2$,
cycloalkyl,
cycloalkyl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN,
$C_{1-4}$alkoxy,
—CN,
oxo,
—OH,
—NO$_2$, and
—NH$_2$;
$R^{42aar}$ selected from:
hydrogen,
$C_{1-6}$alkyl,
$C_{1-6}$alkyl substituted with from 1 to 9 substituents independently selected from: fluoro, chloro, bromo, iodo, oxo, —OH, —NH$_2$, —N(H)C$_{1-4}$alkyl, —N(C$_{1-4}$alkyl)$_2$, and —CN,
heterocycloalkyl, and
heterocycloalkyl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN,
—NHC(O)H,
—NHC(O)R$^{xa1}$,
where R$^{xa1}$ is selected from aryl, heteroaryl, cycloalkyl, heterocycloalkyl, $C_{1-6}$alkyl, and $C_{1-6}$alkyl substituted from 1 to 6 times by fluoro,
$C_{1-4}$alkoxy,
—CN,
oxo,
—OH,
—NO$_2$, and
—NH$_2$;
$R^{43aar}$ selected from:
hydrogen,
$C_{1-6}$alkyl,
aryl,
aryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —CN, —OR$^{49}$ and —NR$^{46}$R$^{47}$, where R$^{46}$ and R$^{47}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
$C_{1-4}$alkoxy,
—CN,
oxo,
—OH,
—S(O)$_2$NH$_2$,
—S(O)$_2$NHCH$_3$,
—NO$_2$, and
—NH$_2$,
heteroaryl, and
heteroaryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —CN, —OR$^{49}$ and —NR$^{46}$R$^{47}$, where R$^{46}$ and R$^{47}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
$C_{1-4}$alkoxy,
—CN,
oxo,
—OH,
—S(O)$_2$NH$_2$,
—S(O)$_2$NHCH$_3$, —NO$_2$, and
—NH$_2$; and
R$^{44aar}$ and R$^{45aar}$ are independently selected from:
hydrogen,
C$_{1-6}$alkyl,
C$_{1-6}$alkyl substituted with from 1 to 9 substituents independently selected from: fluoro, chloro, bromo, iodo, heterocycloalkyl, C$_{1-4}$alkoxy, oxo, —OH, —NH$_2$ and —CN,
heterocycloalkyl, and
heterocycloalkyl substituted with from 1 to 5 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —OH, —NH$_2$ and —CN,
aryl,
C$_{1-4}$alkoxy,
C$_{1-4}$alkoxy substituted with from 1 to 4 substituents independently selected from: fluoro, oxo, —OH, —COOH, —NH$_2$, and —CN,
—CN,
oxo,
—OH,
—COOH,
—NO$_2$,
—NH$_2$, and
SO$_2$NH$_2$, or
R$^{44aar}$ and R$^{45aar}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
aryl,
cycloalkyl,
heterocycloalkyl,
heterocycloalkyl substituted with from 1 to 9 substituents independently selected from: C$_{1-6}$alkyl, —C$_{1-6}$alkylOH, fluoro, —C$_{1-6}$alkylNH$_2$, chloro, bromo, iodo, oxo, —OH, —NH$_2$ and —CN,
C$_{1-4}$alkoxy,
—CN,
oxo,
—OH,
—COOH,
—NO$_2$,
—NH$_2$,
—N(H)C$_{1-4}$alkyl,
—N(H)C$_{1-6}$alkyl substituted with from 1 to 9 substituents independently selected from: fluoro, chloro, bromo, iodo, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
—N(C$_{1-4}$alkyl)$_2$,
SO$_2$NH$_2$,
SO$_2$CH$_2$CH$_3$, and
SO$_2$CH$_3$;
provided that:
R$^{42aar}$ and R$^{43aar}$ are not both hydrogen, and
R$^{44aar}$ and R$^{45aar}$ are not both hydrogen;
or a pharmaceutically acceptable salt or prodrug thereof.

Suitably in the compounds of Formula (IVaar) neither R$^{44aar}$ nor R$^{45aar}$ is hydrogen.

Suitably in the compounds of Formula (IVaar) R$^{42aar}$ is —C(O)NH$_2$.

Suitably in the compounds of Formula (IVaar) R$^{43aar}$ is aryl substituted with from 1 to 4 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —CN, —OR$^{49}$ and —NR$^{46}$R$^{47}$,
where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (IVa) and to the use of compounds of Formula (IVa) in the methods of the invention:

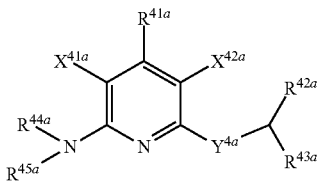

(IVa)

wherein:
X$^{41a}$ and X$^{42a}$ are independently selected from: —CN, fluoro, chloro, bromo and iodo;
Y$^{4a}$ is selected from: S and NH;
R$^{41a}$ is selected from:
C$_{1-6}$alkyl,
C$_{1-6}$alkyl substituted with from 1 to 9 substituents independently selected from: fluoro, chloro, bromo, iodo, oxo, C$_{1-4}$alkyloxy, —OH, —COOH, —NH$_2$ —N(H)C$_{1-4}$alkyl, —N(C$_{1-4}$alkyl)$_2$ and —CN,
C$_{1-4}$alkyloxy,
C$_{1-4}$alkyloxy substituted from 1 to 4 times by fluoro,
—N(H)C$_{1-4}$alkyl,
—N(C$_{1-4}$alkyl)$_2$,
—SC$_{1-4}$alkyl,
cycloalkyl, cycloalkyl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —$NH_2$ and —CN,
$C_{1-4}$alkoxy,
—CN,
oxo,
—OH,
—$NO_2$, and
—$NH_2$;

$R^{42a}$ is selected from:
hydrogen,
$C_{1-6}$alkyl,
$C_{1-6}$alkyl substituted with from 1 to 9 substituents independently selected from: fluoro, chloro, bromo, iodo, oxo, —OH, —$NH_2$, —N(H)$C_{1-4}$alkyl, —N($C_{1-4}$alkyl)$_2$, and —CN,
heterocycloalkyl, and
heterocycloalkyl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —$NH_2$ and —CN,
—NHC(O)H,
—NHC(O)$R^{xa1}$,
where $R^{xa1}$ is selected from aryl, heteroaryl, cycloalkyl, heterocyloalkyl, $C_{1-6}$alkyl, and $C_{1-6}$alkyl substituted from 1 to 6 times by fluoro,
$C_{1-4}$alkoxy,
—CN,
oxo,
—OH,
—$NO_2$, and
—$NH_2$;

$R^{43a}$ is selected from:
hydrogen,
$C_{1-6}$alkyl,
aryl,
aryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —CN, —$OR^{49}$ and —$NR^{46}R^{47}$, where $R^{46}$ and $R^{47}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —O$C_{1-5}$alkyl, —O$C_{1-5}$alkyl substituted from 1 to 6 times by fluoro, —COOH and —$NR^{48}R^{49}$, where $R^{48}$ and $R^{49}$ are independently selected from: hydrogen, phenyl, $C_{1-5}$alkyl and $C_{1-5}$alkyl substituted with from 1 to 4 substituents independently selected from: fluoro, oxo, —OH, —O$C_{1-5}$alkyl, —O$C_{1-5}$alkyl substituted from 1 to 6 times by fluoro and —COOH,
$C_{1-4}$alkoxy,
—CN,
oxo,
—OH,
—S(O)$_2$NH$_2$,
—S(O)$_2$NHCH$_3$,
—$NO_2$, and
—$NH_2$,
heteroaryl, and
heteroaryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —CN, —$OR^{49}$ and —$NR^{46}R^{47}$, where $R^{46}$ and $R^{47}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —O$C_{1-5}$alkyl, —O$C_{1-5}$alkyl substituted from 1 to 6 times by fluoro, —COOH and —$NR^{48}R^{49}$, where $R^{48}$ and $R^{49}$ are independently selected from: hydrogen, phenyl, $C_{1-5}$alkyl and $C_{1-5}$alkyl substituted with from 1 to 4 substituents independently selected from: fluoro, oxo, —OH, —O$C_{1-5}$alkyl, —O$C_{1-5}$alkyl substituted from 1 to 6 times by fluoro and —COOH,
$C_{1-4}$alkoxy,
—CN,
oxo,
—OH,
—S(O)$_2$NH$_2$,
—S(O)$_2$NHCH$_3$,
—$NO_2$, and
—$NH_2$; and $R^{44a}$ and $R^{45a}$ are independently selected from:
hydrogen,
$C_{1-6}$alkyl,
$C_{1-6}$alkyl substituted with from 1 to 9 substituents independently selected from: fluoro, chloro, bromo, iodo, heterocycloalkyl, $C_{1-4}$alkoxy, oxo, —OH, —$NH_2$ and —CN,
heterocycloalkyl, and
heterocycloalkyl substituted with from 1 to 5 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —$NH_2$ and —CN,
aryl,
$C_{1-4}$alkoxy, $C_{1-4}$alkoxy substituted with from 1 to 4 substituents independently selected from: fluoro, oxo, —OH, —COOH, —NH$_2$, and —CN,
—CN,
oxo,
—OH,
—COOH,
—NO$_2$,
—NH$_2$, and
SO$_2$NH$_2$, or $R^{44a}$ and $R^{45a}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, $C_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
aryl,
cycloalkyl,
heterocycloalkyl,
heterocycloalkyl substituted with from 1 to 9 substituents independently selected from: $C_{1-6}$alkyl, —C$_{1-6}$alkylOH, fluoro, —C$_{1-6}$alkylNH$_2$, chloro, bromo, iodo, oxo, —OH, —NH$_2$ and —CN,
$C_{1-4}$alkoxy,
—CN,
oxo,
—OH,
—COOH,
—NO$_2$,
—NH$_2$,
—N(H)C$_{1-4}$alkyl,
—N(H)C$_{1-6}$alkyl substituted with from 1 to 9 substituents independently selected from: fluoro, chloro, bromo, iodo, $C_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
—N(C$_{1-4}$alkyl)$_2$,
SO$_2$NH$_2$,
SO$_2$CH$_2$CH$_3$, and
SO$_2$CH$_3$;
provided that:
$R^{42a}$ and $R^{43a}$ are not both hydrogen, and
$R^{44a}$ and $R^{45a}$ are not both hydrogen;
or a pharmaceutically acceptable salt or prodrug thereof.

Suitably in the compounds of Formula (IVa) neither $R^{44a}$ nor $R^{45a}$ is hydrogen.

Included in the compounds of the invention and used in the methods of the invention are compounds of Formula (V):

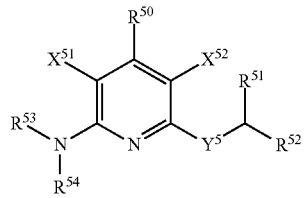

(V)

wherein:
$X^{51}$ and $X^{52}$ are independently selected from: —CN, fluoro and chloro;
$Y^5$ is selected from: S and NH;
$R^{50}$ is selected from:
$C_{1-6}$alkyl,
$C_{1-6}$alkyl substituted with from 1 to 9 substituents independently selected from: fluoro and chloro,
—N(H)C$_{1-4}$alkyl,
—N(C$_{1-4}$alkyl)$_2$,
—SC$_{1-4}$alkyl,
$C_{1-4}$alkyloxy,
cycloalkyl,
cycloalkyl substituted with from 1 to 5 substituents independently selected from:
fluoro,
chloro,
—OH,
$C_{1-6}$alkyl, and
$C_{1-6}$alkyl substituted with from 1 to 9 substituents independently selected from: fluoro and chloro;
$R^{51}$ is selected from:
hydrogen,
$C_{1-6}$alkyl,
—C(O)NHR$^{55}$, where $R^{55}$ is selected from: hydrogen, $C_{1-6}$alkyl, $C_{1-6}$alkyl substituted with from 1 to 9 substituents independently selected from: fluoro and chloro,
heterocycloalkyl, and
heterocycloalkyl substituted with from 1 to 4 substituents independently selected from:
fluoro,
chloro,
$C_{1-6}$alkyl,
$C_{1-6}$alkyl substituted with from 1 to 6 substituents independently selected from: fluoro, chloro, bromo, oxo, —OH, —NH$_2$ and —CN,
—NHC(O)H,
—NHC(O)R$^{xa2}$,
where $R^{xa2}$ is selected from aryl, heteroaryl, cycloalkyl, heterocyloalkyl, $C_{1-6}$alkyl, and $C_{1-6}$alkyl substituted from 1 to 6 times by fluoro,
$C_{1-4}$alkoxy,
—CN,
oxo,
—OH, and
—NH$_2$;
$R^{52}$ is selected from:
hydrogen,
$C_{1-6}$alkyl,
aryl,
aryl substituted with from 1 to 4 substituents independently selected from:
fluoro,
chloro, $C_{1-6}$alkyl,
$C_{1-6}$alkyl substituted with from 1 to 9 substituents independently selected from: fluoro, chloro, bromo, iodo, oxo, —CN, —OR$^{59}$ and —NR$^{56}$R$^{57}$, where R$^{56}$ and R$^{57}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
oxo,
—CN,
—S(O)$_2$NH$_2$,
—S(O)$_2$NHCH$_3$,
—OH;
heteroaryl, and
heteroaryl substituted with from 1 to 4 substituents independently selected from:
fluoro,
chloro,
$C_{1-6}$alkyl,
$C_{1-6}$alkyl substituted with from 1 to 9 substituents independently selected from: fluoro, chloro, bromo, iodo, oxo, —CN, —OR$^{59}$ and —NR$^{56}$R$^{57}$, where R$^{56}$ and R$^{57}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-6}$alkyl, —OC$_{1-5}$alkyl substituted from 1 to 6 times by fluoro and —COOH,
oxo,
—S(O)$_2$NH$_2$,
—S(O)$_2$NHCH$_3$,
—OH; and
R$^{53}$ and R$^{54}$ are independently selected from:
hydrogen,
$C_{1-6}$alkyl,
$C_{1-6}$alkyl substituted with from 1 to 6 substituents independently selected from: fluoro, chloro, oxo, heterocycloalkyl, $C_{1-4}$alkoxy, —OH and —NH$_2$,
heterocycloalkyl, and
heterocycloalkyl substituted with from 1 to 5 substituents independently selected from:
fluoro,
chloro,
$C_{1-6}$alkyl,
$C_{1-6}$alkyl substituted with from 1 to 9 substituents independently selected from: fluoro and chloro,
$C_{1-4}$alkoxy, and
—OH, or
R$^{53}$ and R$^{54}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
$C_{1-6}$alkyl,
$C_{1-6}$alkyl substituted with from 1 to 9 substituents independently selected from: fluoro, chloro, $C_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
heterocycloalkyl,
heterocycloalkyl substituted with from 1 to 9 substituents independently selected from: $C_{1-6}$alkyl, —C$_{1-6}$alkylOH, fluoro, —C$_{1-6}$alkylNH$_2$, chloro, oxo and —OH,
$C_{1-4}$alkoxy,
$C_{1-4}$alkoxy substituted with from 1 to 4 substituents independently selected from: fluoro, oxo, —OH, —COOH, —NH$_2$, and —CN,
—CN,
oxo,
—OH,
—COOH,
—NH$_2$,
—N(H)C$_{1-4}$alkyl,
—N(H)C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, and
—N(C$_{1-4}$alkyl)$_2$;
provided that:
R$^{51}$ and R$^{52}$ are not both hydrogen;
or a pharmaceutically acceptable salt or prodrug thereof.
Suitably in the compounds of Formula (V) neither R$^{53}$ nor R$^{54}$ is hydrogen.
This invention relates to novel compounds of Formula (Vaar) and to the use of compounds of Formula (Vaar) in the methods of the invention:

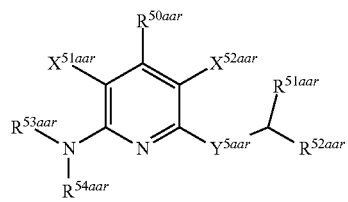

(Vaar)

wherein:
X$^{51aar}$ and X$^{52aar}$ are independently selected from: —CN, fluoro and chloro;
Y$^{5aar}$ is selected from: S and NH;
R$^{50aar}$ is selected from:
$C_{1-6}$alkyl,
$C_{1-6}$alkyl substituted with from 1 to 9 substituents independently selected from: fluoro and chloro,
—N(H)C$_{1-4}$alkyl,
—N(C$_{1-4}$alkyl)$_2$,
—SC$_{1-4}$alkyl,
$C_{1-4}$alkyloxy,
aryl,
alkyl substituted with from one to five substituents independently selected from:

fluoro,
chloro,
—OH,
$C_{1-6}$alkyl, and
$C_{1-6}$alkyl substituted with from 1 to 9 substituents independently selected from: fluoro and chloro,
heteroaryl,
heteroalkyl substituted with from one to five substituents independently selected from:
fluoro,
chloro,
—OH,
$C_{1-6}$alkyl, and
$C_{1-6}$alkyl substituted with from 1 to 9 substituents independently selected from: fluoro and chloro,
cycloalkyl,
cycloalkyl substituted with from one to five substituents independently selected from:
fluoro,
chloro,
—OH,
$C_{1-6}$alkyl, and
$C_{1-6}$alkyl substituted with from 1 to 9 substituents independently selected from: fluoro and chloro;
$R^{51aar}$ is selected from:
hydrogen,
$C_{1-6}$alkyl,
—C(O)NHR$^{55}$, where R$^{55}$ is selected from: hydrogen, $C_{1-6}$alkyl, $C_{1-6}$alkyl substituted with from 1 to 9 substituents independently selected from: fluoro and chloro,
heterocycloalkyl, and
heterocycloalkyl substituted with from 1 to 4 substituents independently selected from:
fluoro,
chloro,
$C_{1-6}$alkyl,
$C_{1-6}$alkyl substituted with from 1 to 6 substituents independently selected from: fluoro, chloro, bromo, oxo, —OH, —NH$_2$ and —CN,
—NHC(O)H,
—NHC(O)R$^{xa2}$,
where R$^{xa2}$ is selected from aryl, heteroaryl, cycloalkyl, heterocyloalkyl, $C_{1-6}$alkyl, and $C_{1-6}$alkyl substituted from 1 to 6 times by fluoro,
$C_{1-4}$alkoxy,
—CN,
oxo,
—OH, and
—NH$_2$;
$R^{52aar}$ is selected from:
hydrogen,
$C_{1-6}$alkyl,
aryl,
aryl substituted with from 1 to 4 substituents independently selected from:
fluoro,
chloro,
$C_{1-6}$alkyl,
$C_{1-6}$alkyl substituted with from 1 to 9 substituents independently selected from: fluoro, chloro, bromo, iodo, oxo, —CN, —OR$^{59}$ and —NR$^{56}$R$^{57}$, where R$^{56}$ and R$^{57}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
oxo,
—CN,
—S(O)$_2$NH$_2$,
—S(O)$_2$NHCH$_3$,
—OH,
heteroaryl, and
heteroaryl substituted with from 1 to 4 substituents independently selected from:
fluoro,
chloro,
$C_{1-6}$alkyl,
$C_{1-6}$alkyl substituted with from 1 to 9 substituents independently selected from: fluoro, chloro, bromo, iodo, oxo, —CN, —OR$^{59}$ and —NR$^{56}$R$^{57}$, where R$^{56}$ and R$^{57}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
oxo,
—S(O)$_2$NH$_2$,
—S(O)$_2$NHCH$_3$,
—OH; and
$R^{53aar}$ and $R^{54aar}$ are independently selected from:
hydrogen,
$C_{1-6}$alkyl,
$C_{1-6}$alkyl substituted with from 1 to 6 substituents independently selected from: fluoro, chloro, oxo, heterocycloalkyl, $C_{1-4}$alkoxy, —OH and —NH$_2$,
heterocycloalkyl, and
heterocycloalkyl substituted with from 1 to 5 substituents independently selected from:
fluoro,
chloro,
$C_{1-6}$alkyl,
$C_{1-6}$alkyl substituted with from 1 to 9 substituents independently selected from: fluoro and chloro,
$C_{1-4}$alkoxy, and
—OH, or
$R^{53aar}$ and $R^{54aar}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
$C_{1-6}$alkyl,
$C_{1-6}$alkyl substituted with from 1 to 9 substituents independently selected from: fluoro, chloro, $C_{1-4}$alkoxy, oxo, phenyl, cycloalkyl, heterocycloalkyl, methylheterocycloalkyl, —OH, —NH$_2$,
—N(H)C$_{1-4}$alkyl, —N(C$_{1-4}$alkyl)$_2$, and —CN,
heterocycloalkyl,
heterocycloalkyl substituted with from 1 to 9 substituents independently selected from: C$_{1-6}$alkyl, —C$_{1-6}$alkylOH, fluoro, —C$_{1-6}$alkylNH$_2$, chloro, oxo and —OH,
C$_{1-4}$alkoxy,
C$_{1-4}$alkoxy substituted with from 1 to 4 substituents independently selected from: fluoro, oxo, —OH, —COOH, —NH$_2$, and —CN,
—CN,
oxo,
—OH,
—COOH,
—NH$_2$,
—N(H)C$_{1-4}$alkyl,
—N(H)C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, and
—N(C$_{1-4}$alkyl)$_2$;
provided that:
R$^{51aar}$ and R$^{52aar}$ are not both hydrogen, and
R$^{53aar}$ and R$^{54aar}$ are not both hydrogen;
or a pharmaceutically acceptable salt or prodrug thereof.

Suitably in the compounds of Formula (Vaar) neither R$^{53aar}$ nor R$^{54aar}$ is hydrogen.

Suitably in the compounds of Formula (Vaar) R$^{51aar}$ is —C(O)NH$_2$.

Suitably in the compounds of Formula (Vaar) R$^{52aar}$ is aryl substituted with from 1 to 4 substituents independently selected from:
fluoro,
chloro,
C$_{1-6}$alkyl,
C$_{1-6}$alkyl substituted with from 1 to 9 substituents independently selected from: fluoro, chloro, bromo, iodo, oxo, —CN, —OR$^{59}$ and —NR$^{56}$R$^{57}$,
where R$^{56}$ and R$^{57}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (Va) and to the use of compounds of Formula (Va) in the methods of the invention:

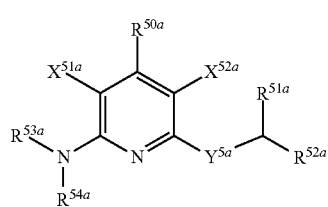

(Va)

wherein:
X$^{51a}$ and X$^{52a}$ are independently selected from: —CN, fluoro and chloro;
Y$^{5a}$ is selected from: S and NH;
R$^{50a}$ is selected from:
C$_{1-6}$alkyl,
C$_{1-6}$alkyl substituted with from 1 to 9 substituents independently selected from: fluoro and chloro,
—N(H)C$_{1-4}$alkyl,
—N(C$_{1-4}$alkyl)$_2$,
—SC$_{1-4}$alkyl,
C$_{1-4}$alkyloxy,
cycloalkyl,
cycloalkyl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro;
R$^{51a}$ is selected from:
hydrogen,
C$_{1-6}$alkyl,
—C(O)NHR$^{55}$, where R$^{55}$ is selected from: hydrogen, C$_{1-6}$alkyl, C$_{1-6}$alkyl substituted with from 1 to 9 substituents independently selected from: fluoro and chloro,
heterocycloalkyl, and
heterocycloalkyl substituted with from 1 to 4 substituents independently selected from:
fluoro,
chloro,
C$_{1-6}$alkyl,
C$_{1-6}$alkyl substituted with from 1 to 6 substituents independently selected from: fluoro, chloro, bromo, oxo, —OH, —NH$_2$ and —CN,
—NHC(O)H,
—NHC(O)R$^{xa2}$,
where R$^{xa2}$ is selected from aryl, heteroaryl, cycloalkyl, heterocyloalkyl, C$_{1-6}$alkyl, and C$_{1-6}$alkyl substituted from 1 to 6 times by fluoro,
C$_{1-4}$alkoxy,
—CN,
oxo,
—OH, and
—NH$_2$;
R$^{52a}$ is selected from:
hydrogen,
C$_{1-6}$alkyl,
aryl,
aryl substituted with from 1 to 4 substituents independently selected from:
fluoro,
chloro,
C$_{1-6}$alkyl,
C$_{1-6}$alkyl substituted with from 1 to 9 substituents independently selected from: fluoro, chloro, bromo, iodo, oxo, —CN, —OR$^{59}$ and —NR$^{56}$R$^{57}$,
where R$^{56}$ and R$^{57}$ are independently selected from: hydrogen, —S(O)$_2$CH$_3$, C$_{1-6}$alkyl and C$_{1-6}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and NR$^{58}$R$^{59}$, where R$^{58}$ and R$^{59}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH, oxo,
—CN,
—S(O)$_2$NH$_2$,
—S(O)$_2$NHCH$_3$,
—OH, heteroaryl, and
heteroaryl substituted with from 1 to 4 substituents independently selected from:
fluoro,
chloro,
C$_{1-6}$alkyl,
C$_{1-6}$alkyl substituted with from 1 to 9 substituents independently selected from: fluoro, chloro, bromo, iodo, oxo, —CN, —OR$^{59}$ and —NR$^{56}$R$^{57}$, where R$^{56}$ and R$^{57}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH, oxo,
—S(O)$_2$NH$_2$,
—S(O)$_2$NHCH$_3$,
—OH; and R$^{53a}$ and R$^{54a}$ are independently selected from:
hydrogen,
C$_{1-6}$alkyl,
C$_{1-6}$alkyl substituted with from 1 to 6 substituents independently selected from: fluoro, chloro, oxo, heterocycloalkyl, C$_{1-4}$alkoxy, —OH and —NH$_2$,
heterocycloalkyl, and
heterocycloalkyl substituted with from 1 to 5 substituents independently selected from:
fluoro,
chloro,
C$_{1-6}$alkyl,
C$_{1-6}$alkyl substituted with from 1 to 9 substituents independently selected from: fluoro and chloro,
C$_{1-4}$alkoxy, and
—OH, or R$^{53a}$ and R$^{54a}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
C$_{1-6}$alkyl,
C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, heterocycloalkyl,
heterocycloalkyl substituted with from 1 to 9 substituents independently selected from: C$_{1-6}$alkyl, —C$_{1-6}$alkylOH, fluoro, —C$_{1-6}$alkylNH$_2$, chloro, oxo and —OH,
C$_{1-4}$alkoxy,
C$_{1-4}$alkoxy substituted with from 1 to 4 substituents independently selected from: fluoro, oxo, —OH, —COOH, —NH$_2$, and —CN,
—CN,
oxo,
—OH,
—COOH,
—NH$_2$,
—N(H)C$_{1-4}$alkyl,
—N(H)C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, and
—N(C$_{1-4}$alkyl)$_2$;

provided that:
R$^{51a}$ and R$^{52a}$ are not both hydrogen, and
R$^{53a}$ and R$^{54a}$ are not both hydrogen;

or a pharmaceutically acceptable salt or prodrug thereof.

Suitably in the compounds of Formula (Va) neither R$^{53a}$ nor R$^{54a}$ is hydrogen.

Included in the compounds of the invention and used in the methods of the invention are compounds of Formula (VI):

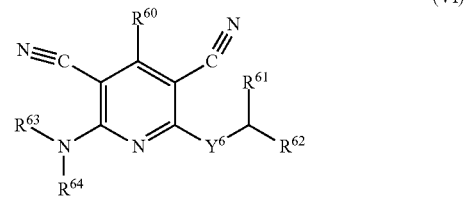

(VI)

wherein:
Y$^6$ is selected from: S and NH;
R$^{60}$ is selected from:
C$_{1-3}$alkyl,
C$_{1-3}$alkyl substituted with from 1 to 6 substituents independently selected from: fluoro and chloro,
—N(H)C$_{1-3}$alkyl,
—N(C$_{1-3}$alkyl)$_2$,
—SC$_{1-4}$alkyl,
C$_{1-3}$alkyloxy,
cycloalkyl,
cycloalkyl substituted with from one to 3 substituents independently selected from:
fluoro,
chloro,
—OH, and
C$_{1-3}$alkyl;

R$^{61}$ is selected from:
hydrogen,
—C(O)NH$_2$,
heterocycloalkyl, and
heterocycloalkyl substituted with from 1 to 4 substituents independently selected from:

oxo,
C$_{1-4}$alkyl substituted with from 1 to 4 substituents independently selected from: fluoro, oxo, and —NH$_2$,
—NHC(O)H, and
—NHC(O)R$^{xa3}$,
where R$^{xa3}$ is selected from C$_{1-6}$alkyl, and C$_{1-6}$alkyl substituted from 1 to 6 times by fluoro;
R$^{62}$ is selected from:
hydrogen,
C$_{1-3}$alkyl,
aryl,
aryl substituted with from 1 to 4 substituents independently selected from:
fluoro,
chloro,
C$_{1-6}$alkyl,
C$_{1-6}$alkyl substituted with from 1 to 5 substituents independently selected from: fluoro, chloro, bromo, iodo, oxo, —CN, —OR$^{69}$ and —NR$^{66}$R$^{67}$,
where R$^{66}$ and R$^{67}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where R$^{68}$ and R$^{69}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
—S(O)$_2$NH$_2$, and
—S(O)$_2$NHCH$_3$,
hetroaryl, and
hetroaryl substituted with from 1 to 4 substituents independently selected from:
fluoro,
chloro,
C$_{1-6}$alkyl,
C$_{1-6}$alkyl substituted with from 1 to 5 substituents independently selected from: fluoro, chloro, bromo, iodo, oxo, —CN, —OR$^{69}$ and —NR$^{66}$R$^{67}$,
where R$^{66}$ and R$^{67}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where R$^{68}$ and R$^{69}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—S(O)$_2$NH$_2$, and
—S(O)$_2$NHCH$_3$; and
R$^{63}$ and R$^{64}$ are independently selected from:
hydrogen,
C$_{1-4}$alkyl,
C$_{1-4}$alkyl substituted with from 1 to 6 substituents independently selected from: fluoro, heterocycloalkyl, oxo, —NH$_2$, C$_{1-4}$alkoxy, and —OH,
heterocycloalkyl, and
heterocycloalkyl substituted with from 1 to 5 substituents independently selected from:
fluoro,
chloro,
—OH, and
C$_{1-6}$alkyl, or
R$^{63}$ and R$^{64}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
C$_{1-6}$alkyl,
C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
heterocycloalkyl,
heterocycloalkyl substituted with from 1 to 9 substituents independently selected from: C$_{1-6}$alkyl, —C$_{1-6}$alkylOH, fluoro, chloro, oxo and —OH,
C$_{1-4}$alkoxy,
C$_{1-4}$alkoxy substituted with from 1 to 4 substituents independently selected from: fluoro, oxo, —OH, —COOH, —NH$_2$, and —CN,
oxo,
—NH$_2$,
—N(H)C$_{1-4}$alkyl,
—N(H)C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, and
—N(C$_{1-4}$alkyl)$_2$;
provided that:
R$^{61}$ and R$^{62}$ are not both hydrogen;
or a pharmaceutically acceptable salt or prodrug thereof.
Suitably in the compounds of Formula (VI) neither R$^{63}$ nor R$^{64}$ is hydrogen.
This invention relates to novel compounds of Formula (VIaar) and to the use of compounds of Formula (VIaar) in the methods of the invention:

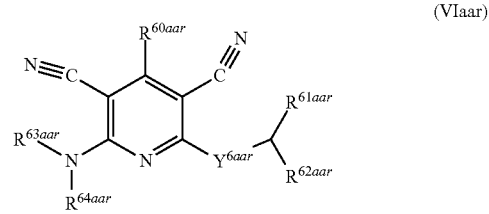

(VIaar)

wherein:
Y$^{6aar}$ is selected from: S and NH;
R$^{60aar}$ is selected from:
C$_{1-3}$alkyl,
C$_{1-3}$alkyl substituted with from 1 to 6 substituents independently selected from: fluoro and chloro,
—N(H)C$_{1-3}$alkyl,
—N(C$_{1-3}$alkyl)$_2$,
—SC$_{1-4}$alkyl,
C$_{1-3}$alkyloxy, aryl,
aryl substituted with from one to 3 substituents independently selected from:
   fluoro,
   chloro,
   —OH, and
   $C_{1-3}$alkyl,
heteroaryl,
heteroaryl substituted with from one to 3 substituents independently selected from:
   fluoro,
   chloro,
   —OH, and
   $C_{1-3}$alkyl,
cycloalkyl,
cycloalkyl substituted with from one to 3 substituents independently selected from:
   fluoro,
   chloro,
   —OH, and
   $C_{1-3}$alkyl;
$R^{61aar}$ is selected from:
   hydrogen,
   —C(O)NH$_2$,
   heterocycloalkyl, and
   heterocycloalkyl substituted with from 1 to 4 substituents independently selected from:
      oxo,
      $C_{1-4}$alkyl substituted with from 1 to 4 substituents independently selected from: fluoro, oxo, and —NH$_2$,
      —NHC(O)H, and
      —NHC(O)$R^{xa3}$,
         where $R^{xa3}$ is selected from $C_{1-6}$alkyl, and $C_{1-6}$alkyl substituted from 1 to 6 times by fluoro;
$R^{62aar}$ is selected from:
   hydrogen,
   $C_{1-3}$alkyl,
   aryl,
   aryl substituted with from 1 to 4 substituents independently selected from:
      fluoro,
      chloro,
      $C_{1-6}$alkyl,
      $C_{1-6}$alkyl substituted with from 1 to 5 substituents independently selected from: fluoro, chloro, bromo, iodo, oxo, —CN, —OR$^{69}$ and —NR$^{66}$R$^{67}$, where R$^{66}$ and R$^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where R$^{68}$ and R$^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
      —CN,
      —S(O)$_2$NH$_2$, and
      —S(O)$_2$NHCH$_3$,
   hetroaryl, and
   hetroaryl substituted with from 1 to 4 substituents independently selected from:
      fluoro,
      chloro,
      $C_{1-6}$alkyl,
      $C_{1-6}$alkyl substituted with from 1 to 5 substituents independently selected from: fluoro, chloro, bromo, iodo, oxo, —CN, —OR$^{69}$ and —NR$^{66}$R$^{67}$, where R$^{66}$ and R$^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where R$^{68}$ and R$^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
      —S(O)$_2$NH$_2$, and
      —S(O)$_2$NHCH$_3$;
$R^{63aar}$ and $R^{64aar}$ are independently selected from:
   hydrogen,
   $C_{1-4}$alkyl,
   $C_{1-4}$alkyl substituted with from 1 to 6 substituents independently selected from: fluoro, heterocycloalkyl, oxo, —NH$_2$, $C_{1-4}$alkoxy, and —OH,
   heterocycloalkyl, and
   heterocycloalkyl substituted with from 1 to 5 substituents independently selected from:
      fluoro,
      chloro,
      —OH, and
      $C_{1-6}$alkyl, or
$R^{63aar}$ and $R^{64aar}$ are taken together with the nitrogen to which they are attached, and optionally from 1 to 3 additional heteroatoms, to form a heterocycloalkyl, which is optionally substituted with from 1 to 5 substituents independently selected from:
   fluoro,
   chloro,
   $C_{1-6}$alkyl,
   $C_{1-6}$alkyl substituted with from 1 to 9 substituents independently selected from: fluoro, chloro, $C_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
   heterocycloalkyl,
   heterocycloalkyl substituted with from 1 to 9 substituents independently selected from: $C_{1-6}$alkyl, —C$_{1-6}$alkylOH, fluoro, chloro, oxo and —OH,
   $C_{1-4}$alkoxy,
   $C_{1-4}$alkoxy substituted with from 1 to 4 substituents independently selected from: fluoro, oxo, —OH, —COOH, —NH$_2$, and —CN,
   oxo,
   —NH$_2$,
   —N(H)C$_{1-4}$alkyl,
   —N(H)C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, and
   —N(C$_{1-4}$alkyl)$_2$;
provided that:
$R^{61aar}$ and $R^{62aar}$ are not both hydrogen, and
$R^{63aar}$ and $R^{64aar}$ are not both hydrogen;

or a pharmaceutically acceptable salt or prodrug thereof.

Suitably in the compounds of Formula (VIaar) neither $R^{63aar}$ nor $R^{64aar}$ is hydrogen.

Suitably in the compounds of Formula (VIaar) $R^{61aar}$ is —C(O)NH$_2$.

Suitably in the compounds of Formula (VIaar) $R^{62aar}$ is aryl substituted with from 1 to 4 substituents independently selected from:
fluoro,
chloro,
$C_{1-6}$alkyl,
$C_{1-6}$alkyl substituted with from 1 to 5 substituents independently selected from: fluoro, chloro, bromo, iodo, oxo, —CN, —OR$^{69}$ and —NR$^{66}$R$^{67}$,
where $R^{66}$ and $R^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where $R^{68}$ and $R^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (VIa) and to the use of compounds of Formula (VIa) in the methods of the invention:

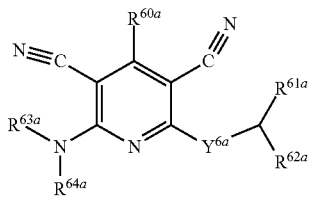

(VIa)

wherein:
$Y^{6a}$ is selected from: S and NH;
$R^{69a}$ is selected from:
$C_{1-3}$alkyl,
$C_{1-3}$alkyl substituted with from 1 to 6 substituents independently selected from: fluoro and chloro,
—N(H)C$_{1-3}$alkyl,
—N(C$_{1-3}$alkyl)$_2$,
—SC$_{1-4}$alkyl,
$C_{1-3}$alkyloxy,
cycloalkyl,
cycloalkyl substituted with from one to 3 substituents independently selected from:
fluoro,
chloro,
—OH, and
$C_{1-3}$alkyl;
$R^{61a}$ is selected from:
hydrogen,
—C(O)NH$_2$,
heterocycloalkyl, and
heterocycloalkyl substituted with from 1 to 4 substituents independently selected from:
oxo,
$C_{1-4}$alkyl substituted with from 1 to 4 substituents independently selected from: fluoro, oxo, and —NH$_2$,
—NHC(O)H, and
—NHC(O)R$^{xa3}$,
where $R^{xa3}$ is selected from $C_{1-6}$alkyl, and $C_{1-6}$alkyl substituted from 1 to 6 times by fluoro;
$R^{62a}$ is selected from:
hydrogen,
$C_{1-3}$alkyl,
aryl,
aryl substituted with from 1 to 4 substituents independently selected from:
fluoro,
chloro,
$C_{1-6}$alkyl,
$C_{1-6}$alkyl substituted with from 1 to 5 substituents independently selected from: fluoro, chloro, bromo, iodo, oxo, —CN, —OR$^{69}$ and —NR$^{66}$R$^{67}$,
where $R^{66}$ and $R^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where $R^{68}$ and $R^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
—S(O)$_2$NH$_2$, and
—S(O)$_2$NHCH$_3$,
hetroaryl, and
hetroaryl substituted with from 1 to 4 substituents independently selected from:
fluoro,
chloro,
$C_{1-6}$alkyl,
$C_{1-6}$alkyl substituted with from 1 to 5 substituents independently selected from: fluoro, chloro, bromo, iodo, oxo, —CN, —OR$^{69}$ and —NR$^{66}$R$^{67}$,
where $R^{66}$ and $R^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where $R^{68}$ and $R^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—S(O)$_2$NH$_2$, and
—S(O)$_2$NHCH$_3$;
$R^{63a}$ and $R^{64a}$ are independently selected from:
hydrogen,
$C_{1-4}$alkyl,
$C_{1-4}$alkyl substituted with from 1 to 6 substituents independently selected from: fluoro, heterocycloalkyl, oxo, —NH$_2$, $C_{1-4}$alkoxy, and —OH,
heterocycloalkyl, and
heterocycloalkyl substituted with from 1 to 5 substituents independently selected from:
fluoro,
chloro, —OH, and
C$_{1-6}$alkyl, or
R$^{63a}$ and R$^{64a}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
C$_{1-6}$alkyl,
C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN,
heterocycloalkyl,
heterocycloalkyl substituted with from 1 to 9 substituents independently selected from: C$_{1-6}$alkyl, —C$_{1-6}$alkylOH, fluoro, chloro, oxo and —OH,
C$_{1-4}$alkoxy,
C$_{1-4}$alkoxy substituted with from 1 to 4 substituents independently selected from: fluoro, oxo, —OH, —COOH, —NH$_2$, and —CN,
oxo,
—NH$_2$,
—N(H)C$_{1-4}$alkyl,
—N(H)C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-4}$alkyl, —N(C$_{1-4}$alkyl)$_2$, and —CN, and
—N(C$_{1-4}$alkyl)$_2$;
provided that:
R$^{61a}$ and R$^{62a}$ are not both hydrogen, and
R$^{63a}$ and R$^{64a}$ are not both hydrogen;
or a pharmaceutically acceptable salt or prodrug thereof.

Suitably in the compounds of Formula (VIa) neither R$^{63a}$ nor R$^{64a}$ is hydrogen.

Included in the compounds of the invention and used in the methods of the invention are compounds of Formula (VII):

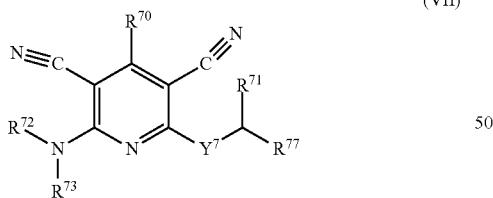

(VII)

wherein:
Y$^7$ is selected from: S and NH;
R$^{70}$ is selected from:
ethyl,
—CH$_2$CF$_3$,
—NCH$_3$,
—SCH$_3$,
ethoxy, and
cyclopropyl;
R$^{71}$ is selected from:
hydrogen,
—C(O)NH$_2$,
heterocycloalkyl, and heterocycloalkyl substituted by oxo, —C(O)CH$_3$ or —NHC(O)CH$_3$;
R$^{77}$ is selected from:
hydrogen,
C$_{1-3}$alkyl, and
aryl,
aryl substituted with from 1 to 4 substituents independently selected from:
fluoro,
chloro,
C$_{1-6}$alkyl,
C$_{1-6}$alkyl substituted with from 1 to 3 substituents independently selected from: fluoro, chloro, bromo, iodo, oxo, —CN, —OR$^{79}$ and —NR$^{76}$R$^{77}$, where R$^{76}$ and R$^{77}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78}$R$^{79}$, where R$^{78}$ and R$^{79}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
S(O)$_2$NH$_2$, and
—S(O)$_2$NHCH$_3$,
pyridinyl,
thiazolyl, and
thiazolyl substituted by —C(O)CH$_3$ or —NHC(O)CH$_3$;
R$^{72}$ and R$^{73}$ are independently selected from:
hydrogen,
C$_{1-3}$alkyl,
C$_{1-3}$alkyl substituted with from 1 to 3 substituents independently selected from: —OH, oxo, —NH$_2$, morpholino and methoxy,
5-oxa-2azaspiro[3.4]octanyl, and
8-azabicyclo[3.2.1]octanyl, or
R$^{72}$ and R$^{73}$ are taken together with the nitrogen to which they are attached, and optionally from 1 to 3 additional heteroatoms, to form a heterocycloalkyl selected from:
pyrrolidinyl,
piperidinyl,
1,4diazepanyl,
piperazinyl,
2,9-diazaspiro[5.5]undecanyl,
2,8-diazaspiro[4.5]decanyl,
hexahydro-1H-pyrrolo[1,2a][1,4]diazepinyl,
morpholinyl,
1-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
1,8-diazaspiro[4.5]decanyl, and
5-oxa-2-azaspiro[3.4]octanyl,
all of which are optionally substituted with from 1 to 5 substituents independently selected from:
fluoro,
oxo,
—OH,
—CH$_3$, —CH₂OH,
methoxy,
—CH₂CH₃,
—C(O)CH₃,
—CH₂CH₂OH,
—CH₂CH₂CH₃,
—CH₂CH₂OCH₃,
—CH₂CH(OH)CH₃,
—CH₂C(O)OCH₃,
—C(O)CH(CH₃)₂,
—CH₂CH₂N(CH₃)₂,
—CH₂CH₂CH₂N(CH₃)₂,
—OCH₂CH₂NH₂,
—NH₂,
—NHCH₃,
—N(CH₃)₂,
—NHC(O)—CNH₂(CH₃)₂,
—NHC(O)CH₂NH₂,
—NHC(O)CHCH₃NH₂,
—NHC(O)—CNH₂(CH₃)₂,
—NHC(O)aminotetrahydropyranyl,
—CH₂NH₂,
—CH₂CH₂NH₂,
—CH₂CH₂CH₂NH₂,
—CH₂N(CH₃)₂,
—C(O)aminooxetanyl,
—S(O)₂CH₂CH₃,
—S(O)₂CH₃,
benzoyl,
3-pyrrolidinylpropyl,
cyclopropylmethyl,
piperidinyl,
morpholinyl,
morpholinylmethyl,
methylpiperazinylmethyl,
pyrrolidinyl,
pyrrolidinylmethyl,
piperazinylmethyl,
oxoimidazolidinyl, and
2-hydroxyethylpiperidinyl;
provided that:
$R^{71}$ and $R^{77}$ are not both hydrogen;
or a pharmaceutically acceptable salt or prodrug thereof.

Suitably in the compounds of Formula (VII) neither $R^{72}$ nor $R^{73}$ is hydrogen.

This invention relates to novel compounds of Formula (VIIaar) and to the use of compounds of Formula (VIIaar) in the methods of the invention:

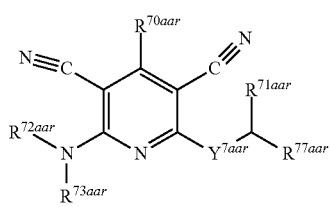

(VIIaar)

wherein:
$Y^{7aar}$ is selected from: S and NH;
$R^{70aar}$ is selected from:
ethyl,
—CH₂CF₃,
—NCH₃,
—SCH₃,
ethoxy,
methoxy,
phenyl,
furanyl, and
cyclopropyl;
$R^{71aar}$ is selected from:
hydrogen,
—C(O)NH₂,
heterocycloalkyl, and
heterocycloalkyl substituted by oxo, —C(O)CH₃ or —NHC(O)CH₃;
$R^{77aar}$ is selected from:
hydrogen,
$C_{1-3}$alkyl, and
aryl,
aryl substituted with from 1 to 4 substituents independently selected from:
fluoro,
chloro,
$C_{1-6}$alkyl,
$C_{1-6}$alkyl substituted with from 1 to 3 substituents independently selected from: fluoro, chloro, bromo, iodo, oxo, —CN, —OR$^{79a}$ and —NR$^{76a}$R$^{77a}$,
where $R^{76a}$ and $R^{77a}$ are independently selected from: hydrogen, —S(O)₂CH₃, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a}$R$^{79a}$, where $R^{78a}$ and $R^{79a}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
S(O)₂NH₂, and
—S(O)₂NHCH₃,
pyridinyl,
thiazolyl, and
thiazolyl substituted by —C(O)CH₃ or —NHC(O)CH₃;
$R^{72aar}$ and $R^{73aar}$ are independently selected from:
hydrogen,
$C_{1-3}$alkyl,
$C_{1-3}$alkyl substituted with from 1 to 3 substituents independently selected from: —OH, oxo, —NH₂, morpholino and methoxy,
5-oxa-2azaspiro[3.4]octanyl, and
8-azabicyclo[3.2.1]octanyl, or
$R^{72aar}$ and $R^{73aar}$ are taken together with the nitrogen to which they are attached, and optionally from 1 to 3 additional heteroatoms, to form a heterocycloalkyl selected from:
pyrrolidinyl,
piperidinyl,
1,4diazepanyl,
piperazinyl,
2,9-diazaspiro[5.5]undecanyl,
2,8-diazaspiro[4.5]decanyl,
hexahydro-1H-pyrrolo[1,2a][1,4]diazepinyl,
morpholinyl,
1-oxa-6-azaspiro[3.4]octanyl,
1,7-diazaspiro[3.5]nonanyl,
2,7-diazaspiro[3.5]nonanyl, 2,6-diazaspiro[3.4]octanyl,
azetidinyl,
1,8-diazaspiro[4.5]decanyl, and
5-oxa-2-azaspiro[3.4]octanyl,
all of which are optionally substituted with from 1 to 5 substituents independently selected from:
fluoro,
oxo,
—OH,
—CH$_3$,
—CH$_2$OH,
methoxy,
—CH$_2$CH$_3$,
—C(O)CH$_3$,
—CH$_2$CH$_2$OH,
—CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$CH$_2$CH$_2$N(CH$_3$)$_2$,
—OCH$_2$CH$_2$NH$_2$,
—OCH$_2$CH$_2$OH,
—NH$_2$,
—NHCH$_3$,
—N(CH$_3$)$_2$,
—NHC(O)—CNH$_2$(CH$_3$)$_2$,
—NHC(O)CH$_2$NH$_2$,
—NHC(O)CHCH$_3$NH$_2$,
—NHC(O)—CNH$_2$(CH$_3$)$_2$,
—NHC(O)aminotetrahydropyranyl,
—CH$_2$NH$_2$,
—CH$_2$CH$_2$NH$_2$,
—CH$_2$CH$_2$CH$_2$NH$_2$,
—CH$_2$N(CH$_3$)$_2$,
—C(O)aminooxetanyl,
—C(O)aminotetrahydropyranyl,
—S(O)$_2$CH$_2$CH$_3$,
—S(O)$_2$CH$_3$,
benzoyl,
3-pyrrolidinylpropyl,
cyclopropylmethyl,
piperidinyl,
morpholinyl,
morpholinylmethyl,
methylpiperazinylmethyl,
methylpiperazinyl,
pyrrolidinyl,
pyrrolidinylmethyl,
piperazinylmethyl,
oxoimidazolidinyl, and
2-hydroxyethylpiperidinyl;
provided that:
$R^{72aar}$ and $R^{73aar}$ are not both hydrogen, and
$R^{71aar}$ and $R^{77aar}$ are not both hydrogen;
or a pharmaceutically acceptable salt or prodrug thereof.
Suitably in the compounds of Formula (VIIaar) neither $R^{72aar}$ nor $R^{73aar}$ is hydrogen.
Suitably in the compounds of Formula (VIIaar) $R^{71aar}$ is —C(O)NH$_2$.
Suitably in the compounds of Formula (VIIaar) $R^{77aar}$ is aryl substituted with from 1 to 4 substituents independently selected from:
fluoro,
chloro,
C$_{1-6}$alkyl,
C$_{1-6}$alkyl substituted with from 1 to 3 substituents independently selected from: fluoro, chloro, bromo, iodo, oxo, —CN, —OR$^{79a}$ and —NR$^{76a}$R$^{77a}$,
where R$^{76a}$ and R$^{77a}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a}$R$^{79a}$, where R$^{78a}$ and R$^{79a}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (VIIa) and to the use of compounds of Formula (VIIa) in the methods of the invention:

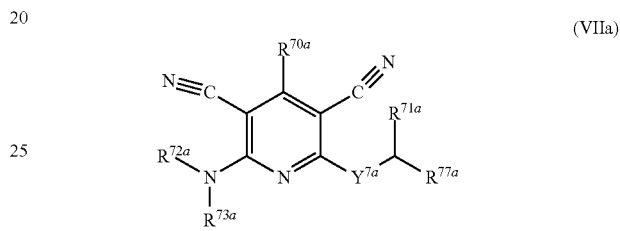

(VIIa)

wherein:
$Y^{7a}$ is selected from: S and NH;
$R^{70a}$ is selected from:
ethyl,
—CH$_2$CF$_3$,
—NCH$_3$,
—SCH$_3$,
ethoxy, and
cyclopropyl;
$R^{71a}$ is selected from:
hydrogen,
—C(O)NH$_2$,
heterocycloalkyl, and
heterocycloalkyl substituted by oxo, —C(O)CH$_3$ or —NHC(O)CH$_3$;
$R^{77a}$ is selected from:
hydrogen,
C$_{1-3}$alkyl, and
aryl,
aryl substituted with from 1 to 4 substituents independently selected from:
fluoro,
chloro,
C$_{1-6}$alkyl,
C$_{1-6}$alkyl substituted with from 1 to 3 substituents independently selected from: fluoro, chloro, bromo, iodo, oxo, —CN, —OR$^{79a}$ and —NR$^{76a}$R$^{77a}$,
where R$^{76a}$ and R$^{77a}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a}$R$^{79a}$, where R$^{78a}$ and R$^{79a}$ are independently selected from: hydrogen, phenyl, C$_{1-5}$alkyl and C$_{1-5}$alkyl substituted with from 1 to 4 substituents independently selected from:

fluoro, oxo, —OH, —OC$_{1-5}$alkyl, —OC$_{1-5}$alkyl substituted from 1 to 6 times by fluoro and
—COOH,
—CN,
S(O)$_2$NH$_2$, and
—S(O)$_2$NHCH$_3$,
pyridinyl,
thiazolyl, and
thiazolyl substituted by —C(O)CH$_3$ or —NHC(O)CH$_3$;
R$^{72a}$ and R$^{73a}$ are independently selected from:
hydrogen,
C$_{1-3}$alkyl,
C$_{1-3}$alkyl substituted with from 1 to 3 substituents independently selected from: —OH, oxo, —NH$_2$, morpholino and methoxy,
5-oxa-2azaspiro[3.4]octanyl, and
8-azabicyclo[3.2.1]octanyl, or
R$^{72a}$ and R$^{73a}$ are taken together with the nitrogen to which they are attached, and optionally from 1 to 3 additional heteroatoms, to form a heterocycloalkyl selected from:
pyrrolidinyl,
piperidinyl,
1,4diazepanyl,
piperazinyl
2,9-diazaspiro[5.5]undecanyl,
2,8-diazaspiro[4.5]decanyl,
hexahydro-1H-pyrrolo[1,2a][1,4]diazepinyl,
morpholinyl,
1-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
1,8-diazaspiro[4.5]decanyl, and
5-oxa-2-azaspiro[3.4]octanyl,
all of which are optionally substituted with from 1 to 5 substituents independently selected from:
fluoro,
oxo,
—OH,
—CH$_3$,
—CH$_2$OH,
methoxy,
—CH$_2$CH$_3$,
—C(O)CH$_3$,
—CH$_2$CH$_2$OH,
—CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$CH$_2$CH$_2$N(CH$_3$)$_2$,
—OCH$_2$CH$_2$NH$_2$,
—NH$_2$,
—NHCH$_3$,
—N(CH$_3$)$_2$,
—NHC(O)—CNH$_2$(CH$_3$)$_2$,
—NHC(O)CH$_2$NH$_2$,
—NHC(O)CHCH$_3$NH$_2$,
—NHC(O)—CNH$_2$(CH$_3$)$_2$,
—NHC(O)aminotetrahydropyranyl,
—CH$_2$NH$_2$,
—CH$_2$CH$_2$NH$_2$,
—CH$_2$CH$_2$CH$_2$NH$_2$,
—CH$_2$N(CH$_3$)$_2$,
—C(O)aminooxetanyl,
—S(O)$_2$CH$_2$CH$_3$,
—S(O)$_2$CH$_3$,
benzoyl,
3-pyrrolidinylpropyl,
cyclopropylmethyl,
piperidinyl,
morpholinyl,
morpholinylmethyl,
methylpiperazinylmethyl,
pyrrolidinyl,
pyrrolidinylmethyl,
piperazinylmethyl,
oxoimidazolidinyl, and
2-hydroxyethylpiperidinyl;
provided that:
R$^{72a}$ and R$^{73a}$ are not both hydrogen, and
R$^{71a}$ and R$^{77a}$ are not both hydrogen;
or a pharmaceutically acceptable salt or prodrug thereof.
Suitably in the compounds of Formula (VIIa) neither R$^{72a}$ nor R$^{73a}$ is hydrogen.

Included in the compounds of the invention and used in the methods of the invention are compounds of Formula (VIII):

(VIII)

wherein:
Y$^8$ is selected from: S and NH;
R$^{80}$ is selected from:
ethyl,
—CH$_2$CF$_3$,
—NCH$_3$,
—SCH$_3$,
ethoxy, and
cyclopropyl;
R$^{81}$ is selected from:
hydrogen,
—C(O)NH$_2$,
heterocycloalkyl, and
heterocycloalkyl substituted by oxo, —C(O)CH$_3$ or —NHC(O)CH$_3$;
R$^{87}$ is selected from:
hydrogen,
CH$_3$,
phenyl,
phenyl substituted with from 1 to 4 substituents independently selected from:
fluoro,
chloro,
C$_{1-6}$alkyl,
C$_{1-6}$alkyl substituted with from 1 to 3 substituents independently selected from: fluoro, chloro, bromo, iodo, oxo, —CN, —OR$^{89}$ and —NR$^{86}$R$^{87}$, where R$^{86}$ and R$^{87}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{88}$R$^{89}$, where R$^{88}$ and R$^{89}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
S(O)$_2$NH$_2$, and
—S(O)$_2$NHCH$_3$,
pyridinyl,
thiazolyl, and
thiazolyl substituted by —C(O)CH$_3$ or —NHC(O)CH$_3$;
R$^{82}$ and R$^{83}$ are independently selected from:
hydrogen,
C$_{1-3}$alkyl,
C$_{1-3}$alkyl substituted with from 1 to 3 substituents independently selected from: —OH, oxo, —NH$_2$, morpholino and methoxy,
5-oxa-2azaspiro[3.4]octanyl, and
8-azabicyclo[3.2.1]octanyl, or
R$^{82}$ and R$^{83}$ are taken together with the nitrogen to which they are attached, and optionally from 1 to 3 additional heteroatoms, to form a heterocycloalkyl selected from:
pyrrolidinyl,
piperidinyl,
1,4diazepanyl,
piperazinyl,
2,9-diazaspiro[5.5]undecanyl,
2,8-diazaspiro[4.5]decanyl,
hexahydro-1H-pyrrolo[1,2a][1,4]diazepinyl,
morpholinyl,
1-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
1,8-diazaspiro[4.5]decanyl, and
5-oxa-2-azaspiro[3.4]octanyl,
all of which are optionally substituted with from 1 to 5 substituents independently selected from:
fluoro,
oxo,
—OH,
—CH$_3$,
—CH$_2$OH,
methoxy,
—CH$_2$CH$_3$,
—C(O)CH$_3$,
—CH$_2$CH$_2$OH,
—CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$CH$_2$CH$_2$N(CH$_3$)$_2$,
—OCH$_2$CH$_2$NH$_2$,
—NH$_2$,
—NHCH$_3$,
—N(CH$_3$)$_2$,
—NHC(O)—CNH$_2$(CH$_3$)$_2$,
—NHC(O)CH$_2$NH$_2$,
—NHC(O)CHCH$_3$NH$_2$,
—NHC(O)—CNH$_2$(CH$_3$)$_2$,
—NHC(O)aminotetrahydropyranyl,
—CH$_2$NH$_2$,
—CH$_2$CH$_2$NH$_2$,
—CH$_2$CH$_2$CH$_2$NH$_2$,
—CH$_2$N(CH$_3$)$_2$,
—C(O)aminooxetanyl,
—S(O)$_2$CH$_2$CH$_3$,
—S(O)$_2$CH$_3$,
benzoyl,
3-pyrrolidinylpropyl,
cyclopropylmethyl,
piperidinyl,
morpholinyl,
morpholinylmethyl,
methylpiperazinylmethyl,
pyrrolidinyl,
pyrrolidinylmethyl,
piperazinylmethyl,
oxoimidazolidinyl, and
2-hydroxyethylpiperidinyl;
provided that:
R$^{81}$ and R$^{87}$ are not both hydrogen;
or a pharmaceutically acceptable salt or prodrug thereof.
Suitably in the compounds of Formula (VIII) neither R$^{82a}$ nor R$^{83a}$ is hydrogen.
This invention relates to novel compounds of Formula (VIIIaar) and to the use of compounds of Formula (VIIIaar) in the methods of the invention:

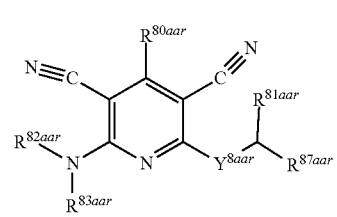

(VIIIaar)

wherein:
Y$^{8aar}$ is selected from: S and NH;
R$^{80aar}$ is selected from:
ethyl,
—CH$_2$CF$_3$,
—NCH$_3$,
—SCH$_3$,
ethoxy,
methoxy,
phenyl,
furanyl, and
cyclopropyl;
R$^{81aar}$ is selected from:
hydrogen,
—C(O)NH$_2$,
heterocycloalkyl, and
heterocycloalkyl substituted by oxo, —C(O)CH$_3$ or —NHC(O)CH$_3$;
R$^{87aar}$ is selected from:
hydrogen,
CH$_3$,
phenyl,
phenyl substituted with from 1 to 4 substituents independently selected from:

fluoro,
chloro,
$C_{1-6}$alkyl,
$C_{1-6}$alkyl substituted with from 1 to 3 substituents independently selected from: fluoro, chloro, bromo, iodo, oxo, —CN, —OR$^{89}$ and —NR$^{86}$R$^{87}$,
  where R$^{86}$ and R$^{87}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{88}$R$^{89}$, where R$^{88}$ and R$^{89}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
—S(O)$_2$NH$_2$, and
—S(O)$_2$NHCH$_3$,
pyridinyl,
thiazolyl, and
thiazolyl substituted by —C(O)CH$_3$ or —NHC(O)CH$_3$;
R$^{82aar}$ and R$^{83aar}$ are independently selected from:
hydrogen,
$C_{1-3}$alkyl,
$C_{1-3}$alkyl substituted with from 1 to 3 substituents independently selected from: —OH, oxo, —NH$_2$, morpholino and methoxy,
5-oxa-2azaspiro[3.4]octanyl, and
8-azabicyclo[3.2.1]octanyl, or
R$^{82aar}$ and R$^{83aar}$ are taken together with the nitrogen to which they are attached, and optionally from 1 to 3 additional heteroatoms, to form a heterocycloalkyl selected from:
pyrrolidinyl,
piperidinyl,
1,4diazepanyl,
piperazinyl,
2,9-diazaspiro[5.5]undecanyl,
2,8-diazaspiro[4.5]decanyl,
hexahydro-1H-pyrrolo[1,2a][1,4]diazepinyl,
morpholinyl,
1-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
1,8-diazaspiro[4.5]decanyl, and
5-oxa-2-azaspiro[3.4]octanyl,
all of which are optionally substituted with from 1 to 5 substituents independently selected from:
fluoro,
oxo,
—OH,
—CH$_3$,
—CH$_2$OH,
methoxy,
—CH$_2$CH$_3$,
—C(O)CH$_3$,
—CH$_2$CH$_2$OH,
—CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$CH$_2$CH$_2$N(CH$_3$)$_2$,
—OCH$_2$CH$_2$NH$_2$,
—OCH$_2$CH$_2$OH,
—NH$_2$,
—NHCH$_3$,
—N(CH$_3$)$_2$,
—NHC(O)—CNH$_2$(CH$_3$)$_2$,
—NHC(O)CH$_2$NH$_2$,
—NHC(O)CHCH$_3$NH$_2$,
—NHC(O)—CNH$_2$(CH$_3$)$_2$,
—NHC(O)aminotetrahydropyranyl,
—CH$_2$NH$_2$,
—CH$_2$CH$_2$NH$_2$,
—CH$_2$CH$_2$CH$_2$NH$_2$,
—CH$_2$N(CH$_3$)$_2$,
—C(O)aminooxetanyl,
—C(O)aminotetrahydropyranyl,
—S(O)$_2$CH$_2$CH$_3$,
—S(O)$_2$CH$_3$,
benzoyl,
3-pyrrolidinylpropyl,
cyclopropylmethyl,
piperidinyl,
morpholinyl,
morpholinylmethyl,
methylpiperazinylmethyl,
methylpiperazinyl,
pyrrolidinyl,
pyrrolidinylmethyl,
piperazinylmethyl,
oxoimidazolidinyl, and
2-hydroxyethylpiperidinyl;
provided that:
R$^{81aar}$ and R$^{87aar}$ are not both hydrogen, and
R$^{82aar}$ and R$^{83aar}$ are not both hydrogen;
or a pharmaceutically acceptable salt or prodrug thereof.

Suitably in the compounds of Formula (VIIIaar) neither R$^{82aar}$ nor R$^{83aar}$ is hydrogen.

Suitably in the compounds of Formula (VIIIaar) R$^{81aar}$ is —C(O)NH$_2$.

Suitably in the compounds of Formula (VIIIaar) R$^{87aar}$ is phenyl substituted with from 1 to 4 substituents independently selected from:
fluoro,
chloro,
$C_{1-6}$alkyl,
$C_{1-6}$alkyl substituted with from 1 to 3 substituents independently selected from: fluoro, chloro, bromo, iodo, oxo, —CN, —OR$^{89}$ and —NR$^{86}$R$^{87}$,
  where R$^{86}$ and R$^{87}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{88}$R$^{89}$, where R$^{88}$ and R$^{89}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (VIIIa) and to the use of compounds of Formula (VIIIa) in the methods of the invention:

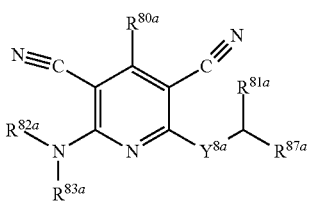

(VIIIa)

wherein:
$Y^{8a}$ is selected from: S and NH;
$R^{80a}$ is selected from:
  ethyl,
  —$CH_2CF_3$,
  —$NCH_3$,
  —$SCH_3$,
  ethoxy, and
  cyclopropyl;
$R^{81a}$ is selected from:
  hydrogen,
  —$C(O)NH_2$,
  heterocycloalkyl, and
  heterocycloalkyl substituted by oxo, —$C(O)CH_3$ or —$NHC(O)CH_3$;
$R^{87a}$ is selected from:
  hydrogen,
  $CH_3$,
  phenyl,
  phenyl substituted with from 1 to 4 substituents independently selected from:
    fluoro,
    chloro,
    $C_{1-6}$alkyl,
    $C_{1-6}$alkyl substituted with from 1 to 3 substituents independently selected from: fluoro, chloro, bromo, iodo, oxo, —CN, —$OR^{89}$ and —$NR^{86}R^{87}$, where $R^{86}$ and $R^{87}$ are independently selected from: hydrogen, —$S(O)_2CH_3$, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro, —COOH and —$NR^{88}R^{89}$, where $R^{88}$ and $R^{89}$ are independently selected from: hydrogen, phenyl, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro and —COOH,
    —CN,
    —$S(O)_2NH_2$, and
    —$S(O)_2NHCH_3$,
  pyridinyl,
  thiazolyl, and
  thiazolyl substituted by —$C(O)CH_3$ or —NHC(O)$CH_3$;
$R^{82a}$ and $R^{83a}$ are independently selected from:
  hydrogen,
  $C_{1-3}$alkyl,
  $C_{1-3}$alkyl substituted with from 1 to 3 substituents independently selected from: —OH, oxo, —$NH_2$, morpholino and methoxy,
  5-oxa-2azaspiro[3.4]octanyl, and
  8-azabicyclo[3.2.1]octanyl, or $R^{82a}$ and $R^{83a}$ are taken together with the nitrogen to which they are attached, and optionally from 1 to 3 additional heteroatoms, to form a heterocycloalkyl selected from:
  pyrrolidinyl,
  piperidinyl,
  1,4diazepanyl,
  piperazinyl,
  2,9-diazaspiro[5.5]undecanyl,
  2,8-diazaspiro[4.5]decanyl,
  hexahydro-1H-pyrrolo[1,2a][1,4]diazepinyl,
  morpholinyl,
  1-oxa-6-azaspiro[3.4]octanyl,
  1,7-diazaspiro[3.5]nonanyl,
  2,7-diazaspiro[3.5]nonanyl,
  2,6-diazaspiro[3.4]octanyl,
  azetidinyl,
  1,8-diazaspiro[4.5]decanyl, and
  5-oxa-2-azaspiro[3.4]octanyl,
  all of which are optionally substituted with from 1 to 5 substituents independently selected from:
    fluoro,
    oxo,
    —OH,
    —$CH_3$,
    —$CH_2OH$,
    methoxy,
    —$CH_2CH_3$,
    —$C(O)CH_3$,
    —$CH_2CH_2OH$,
    —$CH_2CH_2CH_3$,
    —$CH_2CH_2OCH_3$,
    —$CH_2CH(OH)CH_3$,
    —$CH_2C(O)OCH_3$,
    —$C(O)CH(CH_3)_2$,
    —$CH_2CH_2N(CH_3)_2$,
    —$CH_2CH_2CH_2N(CH_3)_2$,
    —$OCH_2CH_2NH_2$,
    —$NH_2$,
    —$NHCH_3$,
    —$N(CH_3)_2$,
    —NHC(O)—$CNH_2(CH_3)_2$,
    —NHC(O)$CH_2NH_2$,
    —NHC(O)$CHCH_3NH_2$,
    —NHC(O)—$CNH_2(CH_3)_2$,
    —NHC(O)aminotetrahydropyranyl,
    —$CH_2NH_2$,
    —$CH_2CH_2NH_2$,
    —$CH_2CH_2CH_2NH_2$,
    —$CH_2N(CH_3)_2$,
    —C(O)aminooxetanyl,
    —$S(O)_2CH_2CH_3$,
    —$S(O)_2CH_3$,
    benzoyl,
    3-pyrrolidinylpropyl,
    cyclopropylmethyl,
    piperidinyl,
    morpholinyl,
    morpholinylmethyl,
    methylpiperazinylmethyl,
    pyrrolidinyl,
    pyrrolidinylmethyl,
    piperazinylmethyl,
    oxoimidazolidinyl, and
    2-hydroxyethylpiperidinyl;

provided that:
R$^{81a}$ and R$^{87a}$ are not both hydrogen, and
R$^{82a}$ and R$^{83a}$ are not both hydrogen;
or a pharmaceutically acceptable salt or prodrug thereof.

Suitably in the compounds of Formula (VIIIa) neither R$^{82a}$ nor R$^{83a}$ is hydrogen.

This invention relates to novel compounds of Formula (Q) and to the use of compounds of Formula (Q) in the methods of the invention:

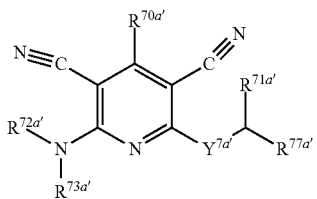

(Q)

wherein:
Y$^{7a'}$ is selected from: S and NH;
R$^{70a'}$ is selected from:
  ethyl,
  —CH$_2$CF$_3$, and
  cyclopropyl;
R$^{71a'}$ is selected from:
  hydrogen,
  CH$_3$,
  phenyl,
  phenyl substituted with chloro, and
  pyridine,
R$^{77a'}$ is selected from:
  —C(O)NH$_2$, and
  aryl,
  aryl substituted with from 1 to 4 substituents independently selected from:
    fluoro,
    chloro,
    C$_{1-6}$alkyl,
    C$_{1-6}$alkyl substituted with from 1 to 3 substituents independently selected from: fluoro, chloro, bromo, iodo, oxo, —CN, —OR$^{79a'}$ and —NR$^{76a'}$R$^{77a'}$,
      where R$^{76a'}$ and R$^{77a'}$ are independently selected form: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a'}$R$^{79a'}$, where R$^{78a'}$ and R$^{79a'}$ are independently selected form: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
    S(O)$_2$NH$_2$,
    —S(O)$_2$NHCH$_3$, and
R$^{72a'}$ and R$^{73a'}$ are independently selected from:
  hydrogen,
  C$_{1-3}$alkyl,
  C$_{1-3}$alkyl substituted with from 1 to 3 substituents independently selected from: morpholino and methoxy,
  5-oxa-2azaspiro[3.4]octan, and
  8-azabicyclo[3.2.1]octan, or
R$^{72a'}$ and R$^{73a'}$ are taken together with the nitrogen to which they are attached, and optionally from 1 to 3 additional heteroatoms, to form a heterocycloalkyl selected from:
  pyrrolidinyl,
  piperidinyl,
  1,4diazepan
  piperazinyl,
  2,9-diazaspiro[5.5]undecan,
  2,8-diazaspiro[4.5]decan,
  octahydro-1H-pyrrolo[1,2a][1,4]diazepin,
  morpholin,
  1-oxa-6-azaspiro[3.4]octan,
  1,7-diazaspiro[3.5]nonan,
  2,7-diazaspiro[3.5]nonan,
  2,6-diazaspiro[3.4]octan,
  azetidin,
  1,8-diazaspiro[4.5]decan, and
  5-oxa-2-azaspiro[3.4]octan,
  all of which are optionally substituted with from 1 to 5 substituents independently selected from:
    fluoro,
    oxo,
    —OH,
    —CH$_3$,
    —CH$_2$OH,
    methoxy,
    —CH$_2$CH$_3$,
    —C(O)CH$_3$,
    —CH$_2$CH$_2$OH,
    —CH$_2$CH$_2$CH$_3$,
    —CH$_2$CH$_2$OCH$_3$,
    —CH$_2$CH(OH)CH$_3$,
    —CH$_2$C(O)OCH$_3$,
    —C(O)CH(CH$_3$)$_2$,
    —CH$_2$CH$_2$N(CH$_3$)$_2$,
    —CH$_2$CH$_2$CH$_2$N(CH$_3$)$_2$,
    —NH$_2$,
    —NHCH$_3$,
    —N(CH$_3$)$_2$,
    —CH$_2$NH$_2$,
    —CH$_2$CH$_2$NH$_2$,
    —CH$_2$CH$_2$CH$_2$NH$_2$,
    —CH$_2$N(CH$_3$)$_2$,
    —S(O)$_2$CH$_2$CH$_3$,
    —S(O)$_2$CH$_3$,
    benzoyl,
    3-pyrrolidinylpropyl,
    2-cyclopropylmethyl,
    piperidinyl,
    morpholinyl,
    morpholinylmethyl,
    methylpiperazinylmethyl,
    pyrrolidinyl,
    pyrrolidinylmethyl,
    piperazinylmethyl,
    oxoimidazolidinyl, and
    2-hydroxyethylpiperidinyl;
provided that:
R$^{72a'}$ and R$^{73a'}$ are not both hydrogen;
or a pharmaceutically acceptable salts thereof.

Suitably in the compounds of Formula (Q) neither R$^{72a'}$ nor R$^{73a'}$ is hydrogen.

This invention relates to novel compounds of Formula (T) and to the use of compounds of Formula (T) in the methods of the invention:

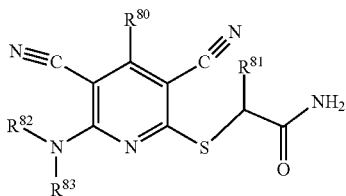

(T)

wherein:
R[80] is selected from:
  ethyl,
  —CH$_2$CF$_3$, and
  cyclopropyl;
R[81] is selected from:
  phenyl, and
  phenyl substituted with chloro or fluoro, and
R[72a′] and R[73a′] are independently selected from:
  C$_{1-3}$alkyl,
  C$_{1-3}$alkyl substituted with from 1 to 3 substituents independently selected from: oxo, and NH$_2$, or
R[72a′] and R[73a′] are taken together with the nitrogen to which they are attached, and optionally from 1 to 3 additional heteroatoms, to form a heterocycloalkyl selected from:
  pyrrolidinyl,
  piperidinyl,
  1,4diazepan,
  piperazinyl,
  2,9-diazaspiro[5.5]undecan,
  2,8-diazaspiro[4.5]decan,
  octahydro-1H-pyrrolo[1,2a][1,4]diazepin,
  morpholin,
  1-oxa-6-azaspiro[3.4]octan,
  1,7-diazaspiro[3.5]nonan,
  2,7-diazaspiro[3.5]nonan,
  2,6-diazaspiro[3.4]octan,
  azetidin,
  1,8-diazaspiro[4.5]decan, and
  5-oxa-2-azaspiro[3.4]octan,
  all of which are optionally substituted with from 1 to 5 substituents independently selected from:
    fluoro,
    oxo,
    —OH,
    —CH$_3$,
    —CH$_2$OH,
    methoxy,
    —CH$_2$CH$_3$,
    —C(O)CH$_3$,
    —CH$_2$CH$_2$OH,
    —CH$_2$CH$_2$CH$_3$,
    —CH$_2$CH$_2$OCH$_3$,
    —CH$_2$CH(OH)CH$_3$,
    —CH$_2$C(O)OCH$_3$,
    —C(O)CH(CH$_3$)$_2$,
    —CH$_2$CH$_2$N(CH$_3$)$_2$,
    —CH$_2$CH$_2$CH$_2$N(CH$_3$)$_2$,
    —NH$_2$,
    —NHCH$_3$,
    —N(CH$_3$)$_2$,
    —NHCH$_2$C(CH$_3$)$_3$,
    —N(CH$_3$)cyclobutane,
    —CH$_2$NH$_2$,
    —CH$_2$CH$_2$NH$_2$,
    —CH$_2$CH$_2$CH$_2$NH$_2$,
    —CH$_2$N(CH$_3$)$_2$,
    —S(O)$_2$CH$_2$CH$_3$,
    —S(O)$_2$CH$_3$,
    benzoyl,
    3-pyrrolidinylpropyl,
    2-cyclopropylmethyl,
    piperidinyl,
    morpholinyl,
    morpholinylmethyl,
    methylpiperazinylmethyl,
    pyrrolidinyl,
    pyrrolidinylmethyl,
    piperazinylmethyl,
    oxoimidazolidinyl, and
    2-hydroxyethylpiperidinyl;
or a pharmaceutically acceptable salt or prodrug thereof.

Suitably in the compounds of Formula (T), the compounds are in the form of a phosphate prodrug.

This invention relates to novel compounds of Formula (Ta) and to the use of compounds of Formula (Ta) in the methods of the invention:

(Ta)

wherein:
R[80a] is selected from:
  ethyl,
  —CH$_2$CF$_3$, and
  cyclopropyl;
R[81a] is selected from:
  phenyl, and
  phenyl substituted with chloro or fluoro, and
R[82a] and R[83a] are taken together with the nitrogen to which they are attached, and optionally from 1 to 3 additional heteroatoms, to form a heterocycloalkyl selected from:
  pyrrolidinyl,
  piperidinyl,
  1,4diazepan,
  piperazinyl,
  2,9-diazaspiro[5.5]undecan,
  2,8-diazaspiro[4.5]decan,
  octahydro-1H-pyrrolo[1,2a][1,4]diazepin,
  morpholin,
  1-oxa-6-azaspiro[3.4]octan,
  1,7-diazaspiro[3.5]nonan,
  2,7-diazaspiro[3.5]nonan,
  2,6-diazaspiro[3.4]octan,
  azetidin,
  1,8-diazaspiro[4.5]decan, and
  5-oxa-2-azaspiro[3.4]octan,
  all of which are optionally substituted with from 1 to 5 substituents independently selected from:
    fluoro,
    oxo,
    —OH,
    —CH$_3$, —CH$_2$OH,
methoxy,
—CH$_2$CH$_3$,
—C(O)CH$_3$,
—CH$_2$CH$_2$OH,
—CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$CH$_2$CH$_2$N(CH$_3$)$_2$,
—NH$_2$,
—NHCH$_3$,
—N(CH$_3$)$_2$,
—NHCH$_2$C(CH$_3$)$_3$,
—N(CH$_3$)cyclobutane,
—CH$_2$NH$_2$,
—CH$_2$CH$_2$NH$_2$,
—CH$_2$CH$_2$CH$_2$NH$_2$,
—CH$_2$N(CH$_3$)$_2$,
—S(O)$_2$CH$_2$CH$_3$,
—S(O)$_2$CH$_3$,
benzoyl,
3-pyrrolidinylpropyl,
2-cyclopropylmethyl,
piperidinyl,
morpholinyl,
morpholinylmethyl,
methylpiperazinylmethyl,
pyrrolidinyl,
pyrrolidinylmethyl,
piperazinylmethyl,
oxoimidazolidinyl, and
2-hydroxyethylpiperidinyl;
or a pharmaceutically acceptable salt or prodrug thereof.

Suitably in the compounds of Formula (Ta), the compounds are in the form of a phosphate prodrug.

This invention relates to novel compounds of Formula (S) and to the use of compounds of Formula (S) in the methods of the invention:

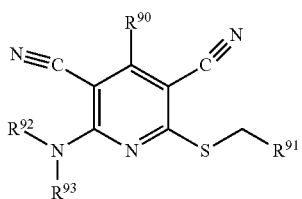

(S)

wherein:
$R^{90}$ is selected from:
ethyl,
—CH$_2$CF$_3$, and
cyclopropyl;
$R^{91}$ is selected from:
phenyl, and
phenyl substituted with from 1 to 2 substituents independently selected from:
fluoro,
chloro,
C$_{1-4}$alkoxy,
C$_{1-4}$alkoxy substituted with from 1 to 3 substituents independently selected from: fluoro, chloro, oxo, —OH, —NH$_2$, —NHCH$_3$, and N(CH$_3$)$_2$,
C$_{1-6}$alkyl,
C$_{1-6}$alkyl substituted with from 1 to 3 substituents independently selected from: fluoro, chloro, bromo, iodo, oxo, —S(O)$_2$CH$_3$, —CN, —OR$^{79a'}$ and —NR$^{76a'}$R$^{77a'}$,
wherein R$^{76a'}$ and R$^{77a'}$ are independently selected form: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a'}$R$^{79a'}$, where R$^{78a'}$ and R$^{79a'}$ are independently selected form: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—N(CH$_3$)S(O)$_2$CFH$_2$,
—N(CH$_3$)S(O)$_2$CF$_2$H,
—N(CH$_3$)S(O)$_2$CF$_3$,
—OS(O)$_2$CH$_3$,
—S(O)$_2$NH$_2$, and
—S(O)$_2$NHCH$_3$, and
$R^{92}$ and $R^{93}$ are independently selected from:
C$_{1-3}$alkyl,
C$_{1-3}$alkyl substituted with from 1 to 3 substituents independently selected from: oxo, —N(CH$_2$CH$_3$)$_3$, —CH$_2$CH$_2$piperidinyl, and NH$_2$, or
$R^{92}$ and $R^{93}$ are taken together with the nitrogen to which they are attached, and optionally from 1 to 3 additional heteroatoms, to form a heterocycloalkyl selected from:
pyrrolidinyl,
piperidinyl,
1,4diazepan,
piperazinyl,
2,9-diazaspiro[5.5]undecan,
2,8-diazaspiro[4.5]decan,
octahydro-1H-pyrrolo[1,2a][1,4]diazepin,
morpholin,
1-oxa-6-azaspiro[3.4]octan,
1,7-diazaspiro[3.5]nonan,
2,7-diazaspiro[3.5]nonan,
2,6-diazaspiro[3.4]octan,
azetidin,
1,8-diazaspiro[4.5]decan, and
5-oxa-2-azaspiro[3.4]octan,
all of which are optionally substituted with from 1 to 5 substituents independently selected from:
fluoro,
oxo,
—OH,
—CH$_3$,
—CH$_2$OH,
methoxy,
—CH$_2$CH$_3$,
—C(O)CH$_3$,
—CH$_2$CH$_2$OH, —CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$N(CH$_3$)$_2$,
—CH$_2$CH$_2$CH$_2$N(CH$_3$)$_2$,
—NH$_2$,
—NHCH$_3$,
—N(CH$_3$)$_2$,
—NHCH$_2$C(CH$_3$)$_3$,
—NHCH(CH$_3$)$_2$,
—NHC(O)CH(CH$_3$)(NH$_2$),
—NHC(O)C(CH$_3$)$_3$,
—N(CH$_3$)cyclobutane,
—CH$_2$NH$_2$,
—CH$_2$pyrrolidinyl,
—CH$_2$CH$_2$NH$_2$,
—CH$_2$CH$_2$CH$_2$NH$_2$,
—CH$_2$N(CH$_3$)$_2$,
—S(O)$_2$CH$_2$CH$_3$,
—S(O)$_2$CH$_3$,
benzoyl,
3-pyrrolidinylpropyl,
2-cyclopropylmethyl,
piperidinyl,
morpholinyl,
morpholinylmethyl,
methylpiperazinylmethyl,
pyrrolidinyl,
pyrrolidinylmethyl,
piperazinylmethyl,
oxoimidazolidinyl, and
2-hydroxyethylpiperidinyl;
or a pharmaceutically acceptable salt or prodrug thereof.

Suitably in the compounds of Formula (S), the compounds are in the form of a phosphate prodrug.

This invention relates to novel compounds of Formula (Sa) and to the use of compounds of Formula (Sa) in the methods of the invention:

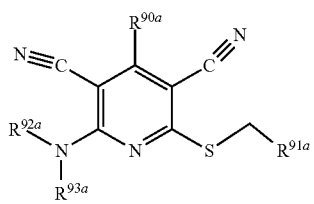

(Sa)

wherein:
R$^{90a}$ is selected from:
ethyl,
—CH$_2$CF$_3$, and
cyclopropyl;
R$^{91a}$ is selected from:
phenyl, and
phenyl substituted with from 1 to 2 substituents independently selected from:
fluoro,
chloro,
C$_{1-4}$alkoxy,
C$_{1-4}$alkoxy substituted with from 1 to 3 substituents independently selected from: fluoro, chloro, oxo, —OH, —NH$_2$, —NHCH$_3$, and —N(CH$_b$)2,
C$_{1-6}$alkyl,
C$_{1-6}$alkyl substituted with from 1 to 3 substituents independently selected from: fluoro, chloro, bromo, iodo, oxo, —S(O)$_2$CH$_3$, —CN, —OR$^{79a'}$ and —NR$^{76a'}$R$^{77a'}$,
where R$^{76a'}$ and R$^{77a'}$ are independently selected form: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a'}$R$^{79a'}$, where R$^{78a'}$ and R$^{79a'}$ are independently selected form: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—N(CH$_3$)S(O)$_2$CFH$_2$,
—N(CH$_3$)S(O)$_2$CF$_2$H,
—N(CH$_3$)S(O)$_2$CF$_3$,
—OS(O)$_2$CH$_3$,
—S(O)$_2$NH$_2$, and
—S(O)$_2$NHCH$_3$, and
R$^{92a}$ and R$^{93a}$ are independently selected from:
C$_{1-3}$alkyl,
C$_{1-3}$alkyl substituted with from 1 to 3 substituents independently selected from: oxo, —N(CH$_2$CH$_3$)$_3$, —CH$_2$CH$_2$piperidinyl, and NH$_2$, or
R$^{92a}$ and R$^{93a}$ are taken together with the nitrogen to which they are attached, and optionally from 1 to 3 additional heteroatoms, to form a heterocycloalkyl selected from:
pyrrolidinyl,
piperidinyl,
1,4diazepan,
piperazinyl,
2,9-diazaspiro[5.5]undecan,
2,8-diazaspiro[4.5]decan,
octahydro-1H-pyrrolo[1,2a][1,4]diazepin,
morpholin,
1-oxa-6-azaspiro[3.4]octan,
1,7-diazaspiro[3.5]nonan,
2,7-diazaspiro[3.5]nonan,
2,6-diazaspiro[3.4]octan,
azetidin,
1,8-diazaspiro[4.5]decan, and
5-oxa-2-azaspiro[3.4]octan,
all of which are optionally substituted with from 1 to 5 substituents independently selected from:
fluoro,
oxo,
—OH,
—CH$_3$,
—CH$_2$OH,
methoxy,
—CH$_2$CH$_3$,
—C(O)CH$_3$,
—CH$_2$CH$_2$OH, —CH$_2$CH$_2$CH$_3$,
—CH$_2$CH$_2$OCH$_3$,
—CH$_2$CH(OH)CH$_3$,
—CH$_2$C(O)OCH$_3$,
—C(O)CH(CH$_3$)$_2$,
—CH$_2$CH$_2$N(CH$_3$)$_2$,
—CH$_2$N(CH$_3$)$_2$,
—CH$_2$CH$_2$CH$_2$N(CH$_3$)$_2$,
—NH$_2$,
—NHCH$_3$,
—N(CH$_3$)$_2$,
—NHCH$_2$C(CH$_3$)$_3$,
—NHCH(CH$_3$)$_2$,
—NHC(O)CH(CH$_3$)(NH$_2$),
—NHC(O)C(CH$_3$)$_3$,
—N(CH$_3$)cyclobutane,
—CH$_2$NH$_2$,
—CH$_2$pyrrolidinyl,
—CH$_2$CH$_2$NH$_2$,
—CH$_2$CH$_2$CH$_2$NH$_2$,
—CH$_2$N(CH$_3$)$_2$,
—S(O)$_2$CH$_2$CH$_3$,
—S(O)$_2$CH$_3$,
benzoyl,
3-pyrrolidinylpropyl,
2-cyclopropylmethyl,
piperidinyl,
morpholinyl,
morpholinylmethyl,
methylpiperazinylmethyl,
pyrrolidinyl,
pyrrolidinylmethyl,
piperazinylmethyl,
oxoimidazolidinyl, and
2-hydroxyethylpiperidinyl;
or a pharmaceutically acceptable salt or prodrug thereof.

Suitably in the compounds of Formula (Sa), the compounds are in the form of a phosphate prodrug.

Primary Amide

This invention relates to compounds of Formula (Ibr) and to the use of compounds of Formula (Ibr) in the methods of the invention:

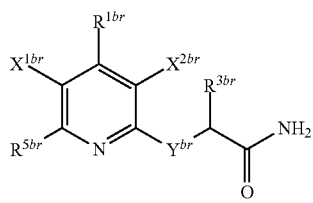

(Ibr)

wherein:
X$^{1br}$ and X$^{2br}$ are independently selected from:
hydrogen,
—CN,
fluoro,
chloro,
bromo,
iodo,
C$_{1-6}$alkyl,
R$^e$,
—OC$_{1-6}$alkyl,
—OR$^e$,
cycloalkyl,
cycloalkyl substituted from 1 to 4 times by R$^d$,
heterocycloalkyl,
heterocycloalkyl substituted from 1 to 4 times by R$^d$,
—SH, and
—SR$^a$;
Y$^{br}$ is selected from: S, NH, NR$^z$, O, S(O), and S(O)$_2$;
R$^{1br}$ is selected from:
—NH$_2$,
—NHR$^a$,
—NR$^b$R$^c$,
—CN,
fluoro,
chloro,
bromo,
iodo,
C$_{1-6}$alkyl,
R$^e$,
—OC$_{1-6}$alkyl,
—OR$^e$,
cycloalkyl,
cycloalkyl substituted from 1 to 4 times by R$^d$,
heterocycloalkyl,
heterocycloalkyl substituted from 1 to 4 times by R$^d$,
aryl,
aryl substituted from 1 to 4 times by R$^d$,
heteroaryl,
heteroaryl substituted from 1 to 4 times by R$^d$,
—SH, and
—SR$^a$;
R$^{3br}$ is selected from:
hydrogen,
C$_{1-6}$alkyl,
R$^e$,
heterocycloalkyl,
heterocycloalkyl substituted from 1 to 4 times by R$^d$,
aryl,
aryl substituted from 1 to 4 times by R$^d$,
heteroaryl, and
heteroaryl substituted from 1 to 4 times by R$^d$; and
R$^{5br}$ is selected from:
—NH$_2$,
—NHR$^a$,
—NR$^b$R$^c$,
aryl,
aryl substituted from 1 to 4 times by R$^d$,
—C$_{1-6}$alkyl,
—OC$_{1-6}$alkyl,
—OR$^e$,
—Oaryl,
—Oaryl substituted from 1 to 4 times by R$^d$,
—Oheteroaryl,
—Oheteroaryl substituted from 1 to 4 times by R$^d$,
—SH, and
—SR$^a$;
where:
each R$^a$ is independently selected from
C$_{1-6}$alkyl,
R$^e$,
aryl,
aryl substituted from 1 to 4 times by R$^d$,
heteroaryl,
heteroaryl substituted from 1 to 4 times by R$^d$
cycloalkyl,
cycloalkyl substituted from 1 to 4 times by R$^d$,
heterocycloalkyl, and
heterocycloalkyl substituted from 1 to 4 times by R$^d$;

$R^b$ and $R^c$ are independently selected from:
    $C_{1-6}$alkyl,
    $R^e$,
    aryl,
    aryl substituted from 1 to 4 times by $R^d$,
    heteroaryl,
    heteroaryl substituted from 1 to 4 times by $R^d$;
    cycloalkyl,
    cycloalkyl substituted from 1 to 4 times by $R^d$,
    heterocycloalkyl, and
    heterocycloalkyl substituted from 1 to 4 times by $R^d$,
    or
$R^b$ and $R^c$ are taken together with the nitrogen to which they are attached, and optionally from 1 to 3 additional heteroatoms independently selected from O, N, and S, to form a heterocycloalkyl, which is optionally substituted with from 1 to 5 substituents independently selected from:
    fluoro,
    chloro,
    bromo,
    iodo,
    $C_{1-6}$alkyl,
    $R^e$,
    —$OR^e$,
    aryl,
    aryl substituted from 1 to 4 times by $R^d$,
    cycloalkyl,
    cycloalkyl substituted from 1 to 4 times by $R^d$,
    heterocycloalkyl, and
    heterocycloalkyl substituted from 1 to 4 times by $R^d$,
    $C_{1-4}$alkoxy,
    —CN,
    oxo,
    —OH,
    —COOH,
    —$NO_2$,
    —$NH_2$,
    —$N(H)C_{1-5}$alkyl,
    —$N(H)R^e$,
    —$N(C_{1-5}$alkyl$)_2$,
    —$NR^eR^e$,
    —$N(R^e)C_{1-5}$alkyl,
    —$ONHC(NH)NH_2$,
    —Oheterocycloalkyl,
    —NHcycloalkyl,
    —$N(C_{1-5}$alkyl)cycloalkyl,
    —NHheterocycloalkyl,
    —$N(C_{1-5}$alkyl)heterocycloalkyl,
    —$S(O)_2C_{1-4}$alkyl,
    —$SO_2NH_2$,
    —$S(O)_2$phenyl,
    benzoyl,
    2-methylcyclopropyl,
    imidazolyl,
    (methoxypyridinylmethyl)amino,
    (methylcyclopropylmethyl)amino,
    (fluorophenylmethyl)amino,
    (methyloxetanylmethyl)amino, and
    (methylcyclobutylmethyl)amino,
each $R^d$ is independently selected from:
    fluoro,
    chloro,
    bromo,
    iodo,
    $C_{1-6}$alkyl,
    $R^e$,
    heteroaryl,
    heteroaryl substituted from 1 to 4 times by $R^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    cycloalkyl,
    cycloalkyl substituted from 1 to 4 times by $R^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    heterocycloalkyl,
    heterocycloalkyl substituted from 1 to 4 times by $R^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    aryl,
    aryl substituted from 1 to 4 times by $R^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    $C_{1-4}$alkoxy,
    $C_{1-4}$alkoxy substituted from 1 to 4 times by fluoro,
    —Oaryl,
    —Oaryl substituted from 1 to 4 times by $R^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    —$OR^e$,
    —C(O)H,
    —$C(O)R^{zz}$,
    —C(O)aryl,
    —C(O)aryl substituted from 1 to 4 times by $R^{zz}$,
    —C(O)heteroaryl,
    —C(O)heteroaryl substituted from 1 to 4 times by $R^{zz}$,
    —OC(O)H,
    —$CO(O)R^{zz}$,
    —OC(O)aryl,
    —CO(O)aryl substituted from 1 to 4 times by $R^{zz}$,
    —OC(O)heteroaryl,
    —OC(O)heteroaryl substituted from 1 to 4 times by $R^{zz}$,
    —SH,
    —$SR^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    —S(O)H,
    —$S(O)R^x$,
        where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
    —$S(O)_2H$,
    —$S(O)_2R^x$, where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$NH$_2$,
—S(O)$_2$NHR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$NR$^{x1}$R$^{x2}$,
where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —P(O)(CH$_3$)$_2$,
—NHS(O)$_2$H,
—NHS(O)$_2$R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHC(O)H,
—NHC(O)R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)NH$_2$,
—C(O)NHR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)NR$^{x1}$R$^{x2}$,
where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)OH,
—C(O)OR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, oxo,
—OH,
—NH$_2$,
—NHR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NR$^{x1}$R$^{x2}$,
where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NH$_2$,
—CN,
—NHC(O)NH$_2$,
—NHC(O)NHR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHC(O)NR$^{x1}$R$^{x2}$,
where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, each $R^e$ is independently selected from:
$C_{1-6}$alkyl substituted with from 1 to 9 substituents independently selected from:
fluoro,
chloro,
bromo,
iodo,
—OC$_{1-6}$alkyl,
—OC$_{1-6}$alkyl substituted with from 1 to 6 substituents independently selected from: fluoro, oxo, —OH, —COOH, —NH$_2$, and —CN, —OC(O)C$_{1-6}$alkyl,
—OC(O)C$_{1-6}$alkyl substituted with from 1 to 6 substituents independently selected from: fluoro, oxo, —OH, —COOH, —NH$_2$, and —CN, —ONHC(NH)NH$_2$,
—OP(O)(OH)$_2$,
—SH,
—SR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)H,
—S(O)R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$H,
—S(O)$_2$R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, oxo,
—OH,
—NH$_2$,
—NHR$^{xx}$,
where $R^{xx}$ is selected from aryl, heteroaryl, cycloalkyl, cycloalkyl substituted with $C_{1-4}$alkoxy, $C_{1-4}$alkoxy substituted with from 1 to 6 substituents independently selected from:

fluoro, triazolyl, cyclopropyl, oxo, —OR$^{xy}$, —COOH, —CN, and —NR$^{xy}$R$^{xz}$, where R$^{xy}$ and R$^{xz}$ are Independently selected from: hydrogen, aryl, C$_{1-5}$alkyl heterocyloalkyl, C$_{1-6}$alkyl, and C$_{1-6}$alkyl substituted with from 1 to 6 substituents independently selected from: fluoro, oxo, —OR$^{xy}$, —COOH, —CN, and —NR$^{xy}$R$^{xz}$, where R$^{xy}$ and R$^{xz}$ are Independently selected from: hydrogen, aryl, C$_{1-5}$alkyl and C$_{1-5}$alkyl substituted with from 1 to 4 substituents independently selected from: fluoro, triazolyl, cyclopropyl, oxo, —OH, —OC$_{1-5}$alkyl, —OC$_{1-5}$alkyl substituted from 1 to 6 times by fluoro and —COOH, —NR$^{x1}$R$^{x2}$,
  where R$^{x1}$ and R$^{x2}$ are each independently selected from aryl, heteroaryl, cycloalkyl, heterocyloalkyl, C$_{1-4}$alkoxy, C$_{1-6}$alkyl, and C$_{1-6}$alkyl substituted with from 1 to 6 substituents independently selected from: fluoro, C$_{1-4}$alkoxy, triazolyl, cyclopropyl, oxo, —OH, —COOH,
  —NH$_2$, and —CN,
guanidino,
—C(O)OH,
—C(O)OR$^{x}$,
  where R$^{x}$ is selected from aryl, heteroaryl, cycloalkyl, heterocycloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)NH$_2$,
—C(O)NHR$^{x}$,
  where R$^{x}$ is selected from aryl, heteroaryl, —OH, C$_{1-4}$alkoxy, cycloalkyl, cycloalkyl substituted with HO—(C$_{1-4}$alkyl)-, heterocyloalkyl, heterocyloalkyl substituted with HO —(C$_{1-4}$alkyl)-, C$_{1-6}$alkyl, and C$_{1-6}$alkyl substituted with from 1 to 6 substituents independently selected from: fluoro, oxo, —OH, —COOH, heteroaryl, —NH$_2$, and —CN,
—C(O)NR$^{x1}$R$^{x2}$,
  where R$^{x1}$ and R$^{x2}$ are each independently selected from aryl, heteroaryl, cycloalkyl, cycloalkyl substituted with HO—(C$_{1-4}$alkyl)-, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
  or R$^{x1}$ and R$^{x2}$ taken together with the nitrogen to which they are attached, and optionally from 1 to 3 additional heteroatoms independently selected from O, N, and S, to form a heterocycloalkyl, which is optionally substituted with from 1 to 5 substituents independently selected from fluoro, oxo, —OH, HO—(C$_{1-4}$alkyl)-, —COOH, —NH$_2$, and —CN,
aryl,
aryl substituted from 1 to 4 times by R$^{x}$,
  where R$^{x}$ is selected from fluoro, chloro, bromo, iodo, aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, —N(CH$_3$)$_2$, —NHC(O)C$_{1-4}$alkyl, and —CN,
—Oaryl,
—Oaryl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, —N(CH$_3$)$_2$, and —CN,
heteroaryl,
heteroaryl substituted from 1 to 4 times by R$^{x}$,
  where R$^{x}$ selected from aryl, heteroaryl, cycloalkyl, heterocyloalkyl, C$_{1-4}$alkoxy, C$_{1-6}$alkyl, and C$_{1-6}$alkyl substituted with from 1 to 6 substituents independently selected from: fluoro, oxo, —OH, —COOH, —NH$_2$, and —CN,
—Oheteroaryl,
—Oheteroaryl substituted from 1 to 4 times by R$^{x}$,
  where R$^{x}$ selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, —N(CH$_3$)$_2$, and —CN,
cycloalkyl,
cycloalkyl substituted from 1 to 4 times by R$^{x}$,
  where R$^{x}$ selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, —N(CH$_3$)$_2$, and —CN,
heterocycloalkyl,
heterocycloalkyl substituted from 1 to 4 times by R$^{x}$,
  where R$^{x}$ selected from oxo, —OH, —N(C$_{1-4}$alkyl)$_2$, aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, —N(CH$_3$)$_2$, and —CN,
—S(O)$_2$NH$_2$,
—S(O)$_2$NHR$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN,
—NHS(O)$_2$H,
—NHS(O)$_2$R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—OC(O)NH$_2$,
—NHC(O)R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN —NHC(O)NHR$^{xp}$,
  where R$^{xp}$ is selected from heteroaryl, cycloalkyl, heterocyloalkyl, and C$_{1-6}$alkyl substituted with from 1 to 4 substituents independently selected from: —COOH, —NH$_2$, and —CN,
—NHC(O)NR$^{x3}$R$^{x4}$,
  where R$^{x3}$ and R$^{x4}$ are each independently selected from heteroaryl, cycloalkyl, heterocyloalkyl, and C$_{1-6}$alkyl substituted with from 1 to 6 Substituents independently selected from: —COOH, —NH$_2$, and —CN,
—NHC(O)C(O)NH$_2$,
—NO$_2$, and
—CN; and
R$^z$ is selected from
  C$_{1-6}$alkyl,
  R$^e$,
  cycloalkyl,
  cycloalkyl substituted from 1 to 4 times by R$^d$,
  heterocycloalkyl, and
  heterocycloalkyl substituted from 1 to 4 times by R$^d$;
R$^{zz}$ is selected from
  C$_{1-6}$alkyl, and
  R$^e$;
provided that:
  X$^{1br}$ and X$^{2br}$ are not both hydrogen;
or a pharmaceutically acceptable salt or prodrug thereof.

Suitably in the compounds of Formula (Ibr) R$^{3br}$ is aryl optionally substituted from 1 to 4 times by R$^d$.

Suitably in the compounds of Formula (Ibr) neither X$^{1br}$ nor X$^{2br}$ are hydrogen.

Suitably in the compounds of Formula (Ibr), the compounds are in the form of a phosphate prodrug.

Suitably in the compounds of Formula (Ibr), the compounds are in the form of a —C(O)CH(NH$_2$)CH(CH$_3$)$_2$ prodrug.

Included in the compounds of the invention and used in the methods of the invention are compounds of Formula (IIbr):

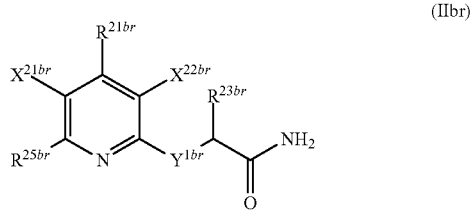

(IIbr)

wherein:
  X$^{21br}$ and X$^{22br}$ are independently selected from:
    hydrogen,
    cyano,
    fluoro,
    chloro,
    bromo,
    iodo,
    C$_{1-6}$alkyl,
    R$^e$,
    —OC$_{1-6}$alkyl,
    —OR$^e$,
    cycloalkyl,
    heterocycloalkyl, and
    —SH;
  Y$^{1br}$ is selected from: S, NH, and NR$^z$;
  R$^{21br}$ is selected from:
    amino,
    cyano,
    fluoro,
    chloro,
    bromo,
    iodo,
    C$_{1-6}$alkyl,
    R$^e$,
    —OC$_{1-6}$alkyl,
    —NHR$^a$,
    —NR$^b$R$^c$,
    cycloalkyl,
    cycloalkyl substituted with from 1 to 4 times by R$^d$,
    heterocycloalkyl,
    heterocycloalkyl substituted from 1 to 4 times by R$^d$,
    aryl,
    aryl substituted from 1 to 4 times by R$^d$,
    heteroaryl,
    —OR$^e$,
    heteroaryl substituted from 1 to 4 times by R$^d$,
    —SH, and
    —SR$^a$;
  R$^{23br}$ is selected from:
    C$_{1-6}$alkyl,
    C$_{1-6}$alkyl substituted with from 1 to 9 substituents independently selected from: fluoro, chloro, C$_{1-4}$alkoxy, oxo, phenyl, cycloalkyl, heterocycloalkyl, —OH, —NH$_2$, —N(H)C$_{1-4}$alkyl, —N(C$_{1-4}$alkyl)$_2$, and —CN,
    heterocycloalkyl,
    aryl,
    aryl substituted from 1 to 4 times by R$^d$,
    heteroaryl, and
    heteroaryl substituted from 1 to 4 times by R$^d$; and
  R$^{25br}$ is selected from:
    amino,
    —NHR$^a$,
    —NR$^b$R$^c$,
    aryl,
    aryl substituted from 1 to 4 times by R$^d$,
    —OC$_{1-6}$alkyl,
    —OR$^e$,
    —Oaryl,
    —Oheteroaryl,
    —SH, and
    —SR$^a$;
where:
  each R$^a$ is independently selected from
    C$_{1-6}$alkyl,
    R$^e$,
    aryl,
    aryl substituted from 1 to 4 times by R$^d$,
    heteroaryl,
    heteroaryl substituted from 1 to 4 times by R$^d$
    cycloalkyl,
    cycloalkyl substituted from 1 to 4 times by R$^d$,
    heterocycloalkyl, and
    heterocycloalkyl substituted from 1 to 4 times by R$^d$;
  R$^b$ and R$^c$ are independently selected from:
    C$_{1-6}$alkyl,
    R$^e$,
    aryl,
    aryl substituted from 1 to 4 times by R$^d$,
    heteroaryl,
    heteroaryl substituted from 1 to 4 times by R$^d$;
    cycloalkyl, cycloalkyl substituted from 1 to 4 times by $R^d$,
heterocycloalkyl, and
heterocycloalkyl substituted from 1 to 4 times by $R^d$,
or
$R^b$ and $R^c$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
$C_{1-6}$alkyl,
$R^e$,
—$OR^e$,
aryl,
aryl substituted from 1 to 4 times by $R^d$,
cycloalkyl,
cycloalkyl substituted from 1 to 4 times by $R^d$,
heterocycloalkyl, and
heterocycloalkyl substituted from 1 to 4 times by $R^d$,
$C_{1-4}$alkoxy,
$C_{1-4}$alkoxy substituted with from 1 to 6 substituents independently selected from: fluoro, oxo, —OH, —COOH, —$NH_2$, and —CN,
—CN,
oxo,
—OH,
—COOH,
—$NO_2$,
—$NH_2$,
—N(H)$C_{1-4}$alkyl,
—N(H)$R^e$,
—N($C_{1-4}$alkyl)$_2$,
—ONHC(NH)$NH_2$,
—Oheterocycloalkyl,
—NHcycloalkyl,
—NHheterocycloalkyl,
—S(O)$_2$CH$_2$CH$_3$,
—S(O)$_2$CH$_2$CH$_2$CH$_3$,
—SO$_2$NH$_2$,
—S(O)$_2$phenyl,
—S(O)$_2$CH$_3$,
benzoyl,
benzylamino,
3-pyrrolidinylpropyl,
2-cyclopropylmethyl,
cyclobutylamino,
cyclobutyl-N(CH$_3$)—,
piperidinyl,
imidazolyl,
morpholinyl,
morpholinylmethyl,
methylpiperazinylmethyl,
methyl piperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;
each $R^d$ is independently selected from:
fluoro,
chloro,
bromo,
iodo,
$C_{1-6}$alkyl,
$R^e$,
heteroaryl,
heteroaryl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
cycloalkyl,
cycloalkyl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
heterocycloalkyl,
heterocycloalkyl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
aryl,
aryl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
$C_{1-4}$alkoxy,
$C_{1-4}$alkoxy substituted from 1 to 4 times by fluoro,
—Oaryl,
—Oaryl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—C(O)H,
—C(O)$R^{zz}$,
—C(O)aryl,
—C(O)aryl substituted from 1 to 4 times by $R^{zz}$,
—C(O)heteroaryl,
—C(O)heteroaryl substituted from 1 to 4 times by $R^{zz}$,
—OC(O)H,
—CO(O)$R^{zz}$,
—OC(O)aryl,
—CO(O)aryl substituted from 1 to 4 times by $R^{zz}$,
—OC(O)heteroaryl,
—OC(O)heteroaryl substituted from 1 to 4 times by $R^{zz}$,
mercapto,
—$SR^x$, where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—S(O)H,

—S(O)R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—S(O)$_2$H,

—S(O)$_2$R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—S(O)$_2$NH$_2$,

—S(O)$_2$NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —S(O)$_2$NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—P(O)(CH$_3$)$_2$,

—NHS(O)$_2$H,

—NHS(O)$_2$R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—NHC(O)H,

—NHC(O)R$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—C(O)NH$_2$,

—C(O)NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —C(O)NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

—C(O)OH,

—C(O)OR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, oxo, hydroxy, amino, —NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, nitro, cyano,

—NHC(O)NH$_2$,

—NHC(O)NHR$^x$,
where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, —NHC(O)NR$^{x1}$R$^{x2}$,
where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, each R$^e$ is independently selected from:

C$_{1-6}$alkyl substituted with from 1 to 9 substituents independently selected from:

fluoro, chloro, bromo, iodo,

C$_{1-6}$alkyl,

—OC$_{1-6}$alkyl,

—OC$_{1-6}$alkyl substituted with from 1 to 6 substituents independently selected from: fluoro, oxo, —OH, —COOH, —NH$_2$, and —CN, mercapto, —SR$^x$,
where R$^x$ is selected from aryl, heteroaryl, cycloalkyl, heterocycloalkyl, C$_{1-6}$alkyl, and C$_{1-6}$alkyl substituted with from 1 to 6 substituents independently selected from: fluoro, oxo, —OH, —COOH, —NH$_2$, and —CN,

—S(O)H,

—S(O)R$^x$,
where R$^x$ is selected from aryl, heteroaryl, cycloalkyl, heterocycloalkyl, C$_{1-6}$alkyl, and C$_{1-6}$alkyl substituted with from 1 to 6 substituents independently selected from: fluoro, oxo, —OH, —COOH, —NH$_2$, and —CN,

—S(O)$_2$H,

—S(O)$_2$R$^x$,
where R$^x$ is selected from aryl, heteroaryl, cycloalkyl, heterocycloalkyl, C$_{1-6}$alkyl, and C$_{1-6}$alkyl substituted with from 1 to 6 substituents independently selected from: fluoro, oxo, —OH, —COOH, —NH$_2$, and —CN, oxo,
hydroxy,
amino,
—NHR$^{xx}$,
  where R$^{xx}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OR$^{xy}$, —COOH, —CN, —OC$_{1-5}$alkyl, —OC$_{1-5}$alkyl substituted from 1 to 6 times by fluoro and NR$^{xy}$R$^{xz}$, where R$^{xy}$ and R$^{xz}$ are independently selected from: hydrogen, aryl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN,
guanidino,
—C(O)OH,
—C(O)OR$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)NH$_2$,
—C(O)NHR$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—C(O)NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN,
aryl,
aryl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—Oaryl,
—Oaryl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
heteroaryl,
heteroaryl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—Oheteroaryl,
—Oheteroaryl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
cycloalkyl,
cycloalkyl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 Substituents independently selected from: fluoro, oxo, —OH, —COOH, —NH$_2$, and —CN,
—NHS(O)$_2$H,
—NHS(O)$_2$R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NHC(O)NHR$^{xp}$,
  where R$^{xp}$ is selected from heteroaryl, cycloalkyl, heterocyloalkyl, and C$_{1-6}$alkyl substituted with from 1 to 4 substituents independently selected from: —COOH, —NH$_2$, and —CN,
—NHC(O)NR$^{x3}$R$^{x4}$,
  where R$^{x3}$ and R$^{x4}$ are each independently selected from heteroaryl, cycloalkyl, heterocyloalkyl, and C$_{1-6}$alkyl substituted with from 1 to 6 Substituents independently selected from: —COOH, —NH$_2$, and —CN,
nitro, and
cyano; and
R$^{z}$ is selected from
  C$_{1-6}$alkyl,
  R$^{e}$,
  cycloalkyl,
  cycloalkyl substituted from 1 to 4 times by R$^{d}$,
  heterocycloalkyl, and
  heterocycloalkyl substituted from 1 to 4 times by R$^{d}$;
R$^{zz}$ is selected from
  C$_{1-6}$alkyl, and
  R$^{e}$;

provided that:
X$^{21br}$ and X$^{22br}$ are not both hydrogen;
or a pharmaceutically acceptable salt or prodrug thereof.

Suitably in the compounds of Formula (IIbr) R$^{23br}$ is aryl optionally substituted from 1 to 4 times by R$^d$.

Suitably in the compounds of Formula (IIbr) neither X$^{21br}$ nor X$^{22br}$ are hydrogen.

Suitably in the compounds of Formula (IIbr), the compounds are in the form of a phosphate prodrug.

Suitably in the compounds of Formula (IIbr), the compounds are in the form of a —C(O)CH(NH$_2$)CH(CH$_3$)$_2$ prodrug.

Included in the compounds of the invention and used in the methods of the invention are compounds of Formula (IIIbr):

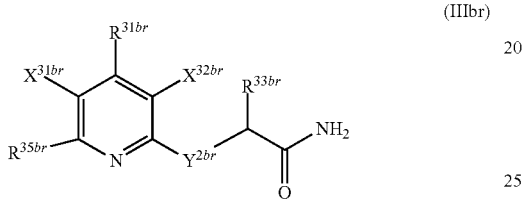
(IIIbr)

wherein:
X$^{31br}$ and X$^{32br}$ are independently selected from:
  hydrogen,
  cyano,
  fluoro,
  chloro,
  bromo,
  iodo,
  C$_{1-6}$alkyl,
  —OC$_{1-6}$alkyl,
  cycloalkyl, and
  —SH;
Y$^{2br}$ is selected from: S, NH, and NR$^z$;
R$^{31br}$ is selected from:
  C$_{1-6}$alkyl,
  R$^{e1}$,
  —OC$_{1-6}$alkyl,
  —OR$^{e1}$,
  —NHR$^{a1}$,
  —NR$^{b1}$R$^{c1}$,
  cycloalkyl,
  cycloalkyl substituted from 1 to 4 times by R$^{d1}$,
  heterocycloalkyl,
  heterocycloalkyl substituted from 1 to 4 times by R$^{d1}$,
  aryl,
  aryl substituted from 1 to 4 times by R$^{d1}$,
  heteroaryl,
  heteroaryl substituted from 1 to 4 times by R$^{d1}$,
  —SH, and
  —SR$^{a1}$;
R$^{33br}$ is selected from:
  C$_{1-6}$alkyl,
  heterocycloalkyl,
  aryl,
  aryl substituted from 1 to 4 times by R$^{d1}$,
  heteroaryl, and
  heteroaryl substituted from 1 to 4 times by Rd$^1$; and
R$^{35br}$ is selected from:
  amino,
  —NHR$^{a1}$,
  —NR$^{b1}$R$^{c1}$,
  aryl,
  aryl substituted from 1 to 4 times by R$^{d1}$,
  —OC$_{1-6}$alkyl,
  —OR$^{e1}$,
  —SH, and
  —SR$^{a1}$;
where:
  each R$^{a1}$ is independently selected from
    C$_{1-6}$alkyl,
    R$^{e1}$,
    aryl,
    heteroaryl,
    cycloalkyl, and
    heterocycloalkyl;
  R$^{b1}$ and R$^{c1}$ are independently selected from:
    C$_{1-6}$alkyl,
    R$^{e1}$,
    —OR$^{e1}$,
    aryl,
    aryl substituted from 1 to 4 times by R$^{d1}$,
    heteroaryl,
    heteroaryl substituted from 1 to 4 times by R$^{d1}$;
    cycloalkyl,
    cycloalkyl substituted from 1 to 4 times by R$^{d1}$,
    heterocycloalkyl, and
    heterocycloalkyl substituted from 1 to 4 times by R$^{d1}$, or
  R$^{b1}$ and R$^{c1}$ are taken together with the nitrogen to which they are attached, and optionally from 1 to 3 additional heteroatoms, to form a heterocycloalkyl, which is optionally substituted with from 1 to 5 substituents independently selected from:
    fluoro,
    chloro,
    bromo,
    iodo,
    C$_{1-6}$alkyl,
    R$^{e1}$,
    aryl,
    aryl substituted from 1 to 4 times by R$^{d1}$,
    cycloalkyl,
    cycloalkyl substituted from 1 to 4 times by R$^{d1}$,
    heterocycloalkyl, and
    heterocycloalkyl substituted from 1 to 4 times by R$^{d1}$,
    C$_{1-4}$alkoxy,
    C$_{1-4}$alkoxy substituted with from 1 to 6 substituents independently selected from: fluoro, oxo, —OH, —COOH, —NH$_2$, and —CN,
    —CN,
    oxo,
    —OH,
    —COOH,
    —NO$_2$,
    —NH$_2$,
    —N(H)C$_{1-4}$alkyl,
    —N(H)R$^{e1}$,
    —N(C$_{1-4}$alkyl)$_2$,
    —ONHC(NH)NH$_2$,
    —Oheterocycloalkyl,
    —NHcycloalkyl,
    —NHheterocycloalkyl,
    —S(O)$_2$CH$_2$CH$_3$,
    —S(O)$_2$CH$_2$CH$_2$CH$_3$,
    —SO$_2$NH$_2$,
    —S(O)$_2$phenyl,
    —S(O)$_2$CH$_3$, benzoyl,
benzylamino,
3-pyrrolidinylpropyl,
2-cyclopropyl methyl,
cyclobutylamino,
cyclobutyl-N(CH$_3$)—,
piperidinyl,
imidazolyl,
morpholinyl,
morpholinylmethyl,
methylpiperazinylmethyl,
methyl piperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;

each $R^{d1}$ is independently selected from:
fluoro,
chloro,
bromo,
iodo,
$C_{1-6}$alkyl,
$R^{e1}$,
heteroaryl,
heteroaryl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
cycloalkyl,
cycloalkyl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
heterocycloalkyl,
heterocycloalkyl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
aryl,
aryl substituted from 1 to 4 times by $R^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
$C_{1-4}$alkoxy,
$C_{1-4}$alkoxy substituted from 1 to 4 times by fluoro,
—Oaryl,
—C(O)H,
—C(O)R$^{zz}$,
—C(O)aryl,
—C(O)heteroaryl,
—OC(O)H,
—CO(O)R$^{zz}$,
—OC(O)aryl,
—OC(O)heteroaryl,
mercapto,
—SR$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)H,
—S(O)R$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)$_2$H,
—S(O)$_2$R$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)$_2$NH$_2$,
—S(O)$_2$NHR$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—P(O)(CH$_3$)$_2$,
—NHS(O)$_2$H,
—NHS(O)$_2$R$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—NHC(O)H,
—NHC(O)R$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—C(O)NH$_2$,
—C(O)NHR$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—C(O)OH,
—C(O)OR$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
oxo,
hydroxy,
amino,
—NHR$^{xa}$,
  where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
nitro,
cyano,
—NHC(O)NH$_2$, and
—NHC(O)NHR$^{xa}$, where $R^{xa}$ is selected from aryl, heteroaryl, cycloalkyl, heterocyloalkyl, $C_{1-6}$alkyl, and $C_{1-6}$alkyl substituted from 1 to 6 times by fluoro;

each $R^{e1}$ is independently selected from:
$C_{1-6}$alkyl substituted with from 1 to 9 substituents independently selected from:
fluoro,
chloro,
bromo,
iodo,
$C_{1-6}$alkyl,
—$OC_{1-6}$alkyl,
—$OC_{1-6}$alkyl substituted with from 1 to 6 substituents independently selected from: fluoro, oxo, —OH, —COOH, —$NH_2$, and —CN,
mercapto,
—$SR^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)H,
—S(O)$R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)$_2$H,
—S(O)$_2R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
oxo,
hydroxy,
amino,
—$NHR^{xx}$,
where $R^{xx}$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —$OR^{xy}$, —COOH, —CN, —$OC_{1-5}$alkyl, —$OC_{1-5}$alkyl substituted from 1 to 6 times by fluoro and —$NR^{xy}R^{xz}$, where $R^{xy}$ and $R^{xz}$ are independently selected from: hydrogen, aryl, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro and —COOH,
—$NR^{x1x}R^{x2x}$,
where $R^{x1x}$ and $R^{x2x}$ are each independently selected from $C_{1-4}$alkyl, and $C_{1-4}$alkyl substituted with from 1 to 4 substituents independently selected from: fluoro, oxo, and —OH,
guanidino,
—C(O)OH,
—C(O)$OR^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—C(O)$NHR^{xa}$,
where $R^{xa}$ is selected from aryl, heteroaryl, cycloalkyl, and heterocyloalkyl, aryl,
aryl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—Oaryl,
—Oaryl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
heteroaryl,
heteroaryl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—Oheteroaryl,
—Oheteroaryl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
cycloalkyl,
cycloalkyl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
heterocycloalkyl,
heterocycloalkyl substituted from 1 to 4 times by $R^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —$NH_2$, and —CN,
—S(O)$_2NH_2$,
—S(O)$_2NHR^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—NHS(O)$_2$H,
—NHS(O)$_2R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
—NHC(O)$NHR^{xa}$,
where $R^{xa}$ is selected from heteroaryl, cycloalkyl, and heterocyloalkyl,
nitro, and
cyano; and $R^z$ is selected from
$C_{1-6}$alkyl,
$R^{e1}$,
cycloalkyl,
cycloalkyl substituted from 1 to 4 times by $R^{d1}$,
heterocycloalkyl, and
heterocycloalkyl substituted from 1 to 4 times by $R^{d1}$;

$R^{zz}$ is selected from
$C_{1-6}$alkyl, and
$R^{e1}$;

provided that:

$X^{31br}$ and $X^{32br}$ are not both hydrogen;

or a pharmaceutically acceptable salt or prodrug thereof.

Suitably in the compounds of Formula (IIIbr), neither $X^{31br}$ nor $X^{32br}$ are hydrogen.

Suitably in the compounds of Formula (IIIbr) $R^{33br}$ is aryl optionally substituted from 1 to 4 times by $R^{d1}$.

Suitably in the compounds of Formula (IIIbr), the compounds are in the form of a phosphate prodrug.

Suitably in the compounds of Formula (IIIbr), the compounds are in the form of a —C(O)CH(NH$_2$)CH(CH$_3$)$_2$ prodrug.

This invention relates to novel compounds of Formula (IVbbr) and to the use of compounds of Formula (IVbbr) in the methods of the invention:

(IVbbr)

wherein:
- $X^{41bbr}$ and $X^{42bbr}$ are independently selected from: —CN, methyl, fluoro, chloro, bromo and iodo;
- $Y^{4bbr}$ is selected from: S and NH;
- $R^{41bbr}$ is selected from:
  - $C_{1-6}$alkyl,
  - $C_{1-6}$alkyl substituted with from 1 to 9 substituents independently selected from: fluoro, chloro, bromo, iodo, oxo, $C_{1-4}$alkyloxy, —OH, —COOH, —NH$_2$ —N(H)C$_{1-4}$alkyl, —N(C$_{1-4}$alkyl)$_2$ and —CN,
  - $C_{1-4}$alkyloxy,
  - $C_{1-4}$alkyloxy substituted from 1 to 4 times by fluoro,
  - —N(H)C$_{1-4}$alkyl,
  - —N(C$_{1-4}$alkyl)$_2$,
  - —SC$_{1-4}$alkyl,
  - aryl,
  - aryl substituted with from 1 to 4 substituents independently selected from:
    - fluoro,
    - chloro,
    - bromo,
    - iodo,
    - $C_{1-6}$alkyl,
    - $C_{1-6}$alkyl substituted with from 1 to 9 substituents independently selected from: fluoro, chloro, bromo, iodo, oxo, —OH, —NH$_2$ and —CN,
    - $C_{1-4}$alkoxy,
    - —CN,
    - oxo,
    - —OH,
    - —NO$_2$, and
    - —NH$_2$,
  - heteroaryl,
  - heteroaryl substituted with from 1 to 4 substituents independently selected from:
    - fluoro,
    - chloro,
    - bromo,
    - iodo,
    - $C_{1-6}$alkyl,
    - $C_{1-6}$alkyl substituted with from 1 to 9 substituents independently selected from: fluoro, chloro, bromo, iodo, oxo, —OH, —NH$_2$ and —CN,
    - $C_{1-4}$alkoxy,
    - —CN,
    - oxo,
    - —OH,
    - —NO$_2$, and
    - —NH$_2$,
  - cycloalkyl,
  - cycloalkyl substituted with from 1 to 4 substituents independently selected from:
    - fluoro,
    - chloro,
    - bromo,
    - iodo,
    - $C_{1-6}$alkyl,
    - $C_{1-6}$alkyl substituted with from 1 to 9 substituents independently selected from: fluoro, chloro, bromo, iodo, oxo, —OH, —NH$_2$ and —CN,
    - $C_{1-4}$alkoxy,
    - —CN,
    - oxo,
    - —OH,
    - —NO$_2$, and
    - —NH$_2$;
- $R^{43bbr}$ is selected from:
  - $C_{1-4}$alkyl,
  - phenyl,
  - phenyl substituted with 1 or 2 substituents independently selected from: fluoro, —CH$_3$, —CF$_3$, chloro, —C(O)phenyl, pyrrolidinyl, —P(O)(CH$_3$)$_2$, —C(O)NH$_2$, —S(O)$_2$NHCH$_3$, —OCH$_2$CH$_2$N(CH$_3$)$_2$ and CH$_2$C(O)NH$_2$,
  - thienyl,
  - piperidinyl,
  - pyridine, and
  - pyridine substituted with 1 or 2 substituents independently selected from: fluoro, —CH$_3$, —CF$_3$, and —OCH$_3$;
- $R^{44bbr}$ and $R^{45bbr}$ are independently selected from:
  - hydrogen,
  - $C_{1-6}$alkyl,
  - $C_{1-6}$alkyl substituted with from 1 to 9 substituents independently selected from: phenyl, morpholino, triazolyl, imidazolyl, pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)C(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
  - where said phenyl, morpholino, triazolyl, imidazolyl, azepinyl, azetidinyl, pyrrolidinyl, piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and CH$_2$NH$_2$,
cycloalkyl,
cycloalkyl substituted with from one to five substituents independently selected from:
 fluoro,
 chloro,
 —OH,
 C$_{1-6}$alkyl, and
 C$_{1-6}$alkyl substituted with from 1 to 9 substituents independently selected from: fluoro and chloro;
heterocycloalkyl, and
heterocycloalkyl substituted with from 1 to 5 substituents independently selected from:
 fluoro,
 chloro,
 bromo,
 iodo,
 C$_{1-6}$alkyl,
 C$_{1-6}$alkyl substituted with from 1 to 9 substituents independently selected from: fluoro, chloro, bromo, iodo, oxo, —OH, —NH$_2$ and —CN,
 aryl,
 C$_{1-4}$alkoxy,
 C$_{1-4}$alkoxy substituted with from 1 to 4 substituents independently selected from: fluoro, oxo, —OH, —COOH, —NH$_2$, and —CN,
 —CN,
 oxo,
 —OH,
 —COOH,
 —NO$_2$,
 —NH$_2$, and
 SO$_2$NH$_2$, or
R$^{44bbr}$ and R$^{45bbr}$ are taken together with the nitrogen to which they are attached, and optionally from 1 to 3 additional heteroatoms independently selected from O, N, and S, to form a heterocycloalkyl, which is optionally substituted with from 1 to 5 substituents independently selected from:
 fluoro,
 chloro,
 bromo,
 iodo,
 C$_{1-6}$alkyl,
 C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl-, —OH, —NH$_2$, —N(H)C$_{1-5}$alkyl, aminoheterocycloalkyl-, —N(C$_{1-5}$alkyl)$_2$, —CN, —N(C$_{1-4}$alkyl)(CH$_2$OCH$_3$), and —NHC$_{1-4}$alkyl substituted by one or two substituents independently selected from oxo, NH$_2$, and —OH,
 aryl,
 cycloalkyl,
 heterocycloalkyl,
 heterocycloalkyl substituted with from 1 to 9 substituents independently selected from: C$_{1-6}$alkyl, —C$_{1-6}$alkylOH, fluoro, —C$_{1-6}$alkylNH$_2$, chloro, bromo, iodo, oxo, —OH, —NH$_2$ and —CN,
 C$_{1-4}$alkoxy,
 C$_{1-4}$alkoxy substituted with from 1 to 4 substituents independently selected from: fluoro, oxo, —OH, —COOH, —NH$_2$, and —CN,
 —CN,
 oxo,
 —OH,
 —OP(O)(OH)$_2$,
 —COOH,
 —CONH$_2$,
 —NO$_2$,
 —NH$_2$,
 —N(H)C$_{1-5}$alkyl,
 —N(H)C$_{1-6}$alkyl substituted with from 1 to 9 substituents independently selected from: fluoro, chloro, bromo, iodo, C$_{1-4}$alkoxy, oxo, phenyl, cycloalkyl, aminoC$_{1-4}$alkoxy, heterocycloalkyl, methylheterocycloalkyl-, —OH, —NH$_2$, —N(H)C$_{1-4}$alkyl, —N(C$_{1-4}$alkyl)$_2$, and —CN,
 —Ooxetanyl,
 —ONHC(NH)NH$_2$,
 —NHcyclopropyl,
 —NHoxetanyl,
 —N(C$_{1-5}$alkyl)$_2$,
 —S(O)$_2$CH$_2$CH$_3$,
 S(O)$_2$CH$_2$CH$_2$CH$_3$,
 —S(O)$_2$CH$_3$,
 —SO$_2$NH$_2$,
 —S(O)$_2$phenyl,
 benzoyl,
 benzylamino,
 -propylpyrrolidinyl,
 -methylcyclopropyl,
 cyclobutylamino,
 cyclobutyl-N(CH$_3$)—,
 piperidinyl,
 imidazolyl,
 morpholinyl,
 morpholinylmethyl,
 methylpiperazinylmethyl,
 methyl piperazinyl,
 pyrrolidinyl,
 pyrrolidinylmethyl,
 (methoxypyridinylmethyl)amino,
 methylpyrrolidinyl,
 difluoropyrrolidinyl,
 dimethylpyrrolidinyl,
 (methylcyclopropylmethyl)amino,
 hydroxymethylpyrrolidinyl,
 fluoropyrrolidinyl,
 fluorophenylmethylamino,
 piperazinylmethyl,
 oxazolidinyl,
 (methyloxetanmethyl)amino,
 (methylcyclobutylmethyl)amino,
 oxoimidazolidinyl, and
 2-hydroxyethylpiperidinyl;
provided that:
 X$^{41bbr}$ and X$^{42bbr}$ are not both hydrogen, and
 R$^{44bbr}$ and R$^{45bbr}$ are not both hydrogen;
or a pharmaceutically acceptable salt or prodrug thereof.

Suitably in the compounds of Formula (IVbbr) neither R$^{44bbr}$ nor R$^{45bbr}$ is hydrogen.

Suitably in the compounds of Formula (IVbbr) R$^{43br}$ is phenyl.

Suitably in the compounds of Formula (IVbbr) neither X$^{41bbr}$ nor X$^{42bbr}$ are hydrogen.

Suitably in the compounds of Formula (IVbbr), the compounds are in the form of a phosphate prodrug.

Suitably in the compounds of Formula (IVbbr), the compounds are in the form of a —C(O)CH(NH$_2$)CH(CH$_3$)$_2$ prodrug.

This invention relates to novel compounds of Formula (Vbbr) and to the use of compounds of Formula (Vbbr) in the methods of the invention:

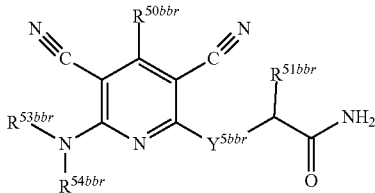

(Vbbr)

wherein:
Y$^{5bbr}$ is selected from: S and NH;
R$^{50bbr}$ is selected from:
C$_{1-6}$alkyl,
C$_{1-6}$alkyl substituted with from 1 to 9 substituents independently selected from: fluoro and chloro,
—N(H)C$_{1-4}$alkyl,
—N(C$_{1-4}$alkyl)$_2$,
—SC$_{1-4}$alkyl,
C$_{1-4}$alkyloxy,
aryl,
alkyl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro,
heteroaryl,
heteroalkyl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro,
cycloalkyl,
cycloalkyl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro;
R$^{51bbr}$ is selected from:
—CH$_3$,
phenyl,
phenyl substituted with 1 or 2 substituents independently selected from: fluoro, —CH$_3$, —CF$_3$, chloro, —C(O)phenyl, pyrrolidinyl, —C(O)NH$_2$, —S(O)$_2$NHCH$_3$, —OCH$_2$CH$_2$N(CH$_3$)$_2$ and —CH$_2$C(O)NH$_2$,
thienyl,
piperidinyl,
pyridine, and
pyridine substituted with 1 or 2 substituents independently selected from: fluoro, —CH$_3$, —CF$_3$, and —OCH$_3$;

R$^{53bbr}$ and R$^{54bbr}$ are independently selected from:
hydrogen,
C$_{1-6}$alkyl,
C$_{1-6}$alkyl substituted with from 1 to 9 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cycloalkyl,
cycloalkyl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro;
heterocycloalkyl, and
heterocycloalkyl substituted with from 1 to 5 substituents independently selected from:
fluoro,
chloro,
C$_{1-6}$alkyl,
C$_{1-6}$alkyl substituted with from 1 to 9 substituents independently selected from: fluoro and chloro,
C$_{1-4}$alkoxy, and
—OH, or
R$^{53bbr}$ and R$^{54bbr}$ are taken together with the nitrogen to which they are attached, and optionally from 1 to 3 additional heteroatoms independently selected from O, N, and S, to form a heterocycloalkyl, to form a heterocycloalkyl, which is optionally substituted with from 1 to 5 substituents independently selected from:
fluoro,
chloro,
C$_{1-6}$alkyl,
C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-5}$alkyl, aminoheterocycloalkyl, —N(C$_{1-5}$alkyl)$_2$, —CN, —N(C$_{1-4}$alkyl)(CH$_2$OCH$_3$), and —NHC$_{1-4}$alkyl substituted by one or two substituents independently selected from oxo, NH$_2$, and —OH, heterocycloalkyl,
heterocycloalkyl substituted with from 1 to 9 substituents independently selected from: $C_{1-6}$alkyl, —$C_{1-6}$alkylOH, fluoro, —$C_{1-6}$alkylNH$_2$, chloro, oxo and —OH,
$C_{1-4}$alkoxy,
$C_{1-4}$alkoxy substituted with from 1 to 4 substituents Independently selected from: fluoro, oxo, —OH, —COOH, —NH$_2$, and —CN,
—CN,
oxo,
—OH,
—OP(O)(OH)$_2$,
—COOH,
—CONH$_2$,
—NH$_2$,
—N(H)$C_{1-4}$alkyl,
—N(H)$C_{1-6}$alkyl substituted with from 1 to 9 substituents independently selected from: fluoro, chloro, $C_{1-4}$alkoxy, oxo, phenyl, cycloalkyl, amino$C_{1-4}$alkoxy, heterocycloalkyl, methylheterocycloalkyl, —OH, —NH$_2$, —N(H)$C_{1-4}$alkyl, —N($C_{1-4}$alkyl)$_2$, and —CN,
—Ooxetanyl,
—ONHC(NH)NH$_2$,
—NHcyclopropyl,
—NHoxetanyl,
—N($C_{1-4}$alkyl)$_2$,
—S(O)$_2$CH$_2$CH$_3$,
S(O)$_2$CH$_2$CH$_2$CH$_3$,
—S(O)$_2$CH$_3$,
—S(O)$_2$phenyl,
benzoyl,
benzylamino,
-propylpyrrolidinyl,
-methylcyclopropyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyll
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
fluorophenylmethylamino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
$R^{53bbr}$ and $R^{54bbr}$ are not both hydrogen;
or a pharmaceutically acceptable salt or prodrug thereof.
Suitably in the compounds of Formula (Vbbr) neither $R^{53bbr}$ nor $R^{54bbr}$ is hydrogen.
Suitably in the compounds of Formula (Vbbr) $R^{51bbr}$ is phenyl.

Suitably in the compounds of Formula (Vbbr), the compounds are in the form of a phosphate prodrug.
Suitably in the compounds of Formula (Vbbr), the compounds are in the form of a —C(O)CH(NH$_2$)CH(CH$_3$)$_2$ prodrug.
This invention relates to novel compounds of Formula (VIbbr) and to the use of compounds of Formula (VIbbr) in the methods of the invention:

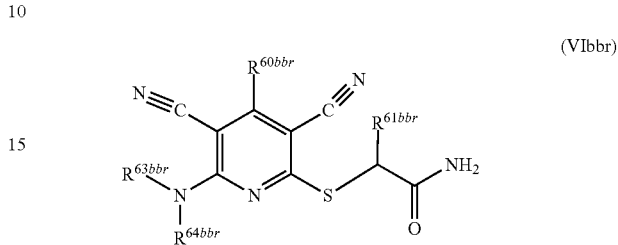

(VIbbr)

wherein:
$R^{60bbr}$ is selected from:
$C_{1-3}$alkyl,
$C_{1-3}$alkyl substituted with from 1 to 6 substituents independently selected from: fluoro and chloro,
—N(H)$C_{1-3}$alkyl,
—N($C_{1-3}$alkyl)$_2$,
—S$C_{1-4}$alkyl,
$C_{1-3}$alkyloxy,
aryl,
aryl substituted with from one to 3 substituents independently selected from:
fluoro,
chloro,
—OH, and
$C_{1-3}$alkyl,
heteroaryl,
heteroaryl substituted with from one to 3 substituents independently selected from:
fluoro,
chloro,
—OH, and
$C_{1-3}$alkyl,
cycloalkyl,
cycloalkyl substituted with from one to three substituents independently selected from:
fluoro,
chloro,
—OH, and
$C_{1-3}$alkyl;
$R^{61bbr}$ is selected from:
—CH$_3$,
phenyl,
phenyl substituted with 1 or 2 substituents independently selected from: fluoro, —CH$_3$, —CF$_3$, chloro, —C(O)phenyl, pyrrolidinyl, —C(O)NH$_2$, —S(O)$_2$NHCH$_3$, —OCH$_2$CH$_2$N(CH$_3$)$_2$ and —CH$_2$C(O)NH$_2$,
thienyl,
piperidinyl,
pyridine, and
pyridine substituted with 1 or 2 substituents independently selected from: fluoro, —CH$_3$, —CF$_3$, and —OCH$_3$;
$R^{63bbr}$ and $R^{64bbr}$ are independently selected from:
hydrogen,
$C_{1-4}$alkyl, C$_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
 where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cycloalkyl,
cycloalkyl substituted with from 1 to 5 substituents independently selected from:
 fluoro,
 chloro,
 —OH, and
 C$_{1-6}$alkyl,
heterocycloalkyl, and
heterocycloalkyl substituted with from 1 to 5 substituents independently selected from:
 fluoro,
 chloro,
 —OH, and
 C$_{1-6}$alkyl, or
R$^{63bbr}$ and R$^{64bbr}$ are taken together with the nitrogen to which they are attached, and optionally from 1 to 3 additional heteroatoms independently selected from O, N, and S, to form a heterocycloalkyl, to form a heterocycloalkyl, which is optionally substituted with from 1 to 5 substituents independently selected from:
 fluoro,
 chloro,
 —OH,
 —OP(O)(OH)$_2$,
 —CN,
 C$_{1-6}$alkyl,
 C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl, —OH, —NH$_2$, —N(H)C$_{1-5}$alkyl, aminoheterocycloalkyl, —N(C$_{1-5}$alkyl)$_2$, —CN, —N(C$_{1-4}$alkyl)(CH$_2$OCH$_3$), and —NHC$_{1-4}$alkyl substituted by one or two substituents independently selected from oxo, NH$_2$, and —OH,
 heterocycloalkyl,
 heterocycloalkyl substituted with from 1 to 9 substituents independently selected from: C$_{1-6}$alkyl, —C$_{1-6}$alkylOH, fluoro, chloro, oxo and —OH,
 C$_{1-4}$alkoxy,
 C$_{1-4}$alkoxy substituted with from 1 to 4 substituents independently selected from: fluoro, oxo, —OH, —COOH, —NH$_2$, and —CN,
 oxo,
 —NH$_2$,
 —N(H)C$_{1-6}$alkyl,
 —N(H)C$_{1-6}$alkyl substituted with from 1 to 9 substituents independently selected from: fluoro, chloro, C$_{1-4}$alkoxy, oxo, phenyl, cycloalkyl, aminoC$_{1-4}$alkoxy, heterocycloalkyl, methylheterocycloalkyl, —OH, —NH$_2$, —N(H)C$_{1-4}$alkyl, —N(C$_{1-4}$alkyl)$_2$, and —CN,
 —ONHC(NH)NH$_2$,
 —Ooxetanyl,
 —ONHC(NH)NH$_2$,
 —NHcyclopropyl,
 —NHoxetanyl,
 —N(C$_{1-4}$alkyl)$_2$,
 —S(O)$_2$CH$_2$CH$_3$,
 S(O)$_2$CH$_2$CH$_2$CH$_3$,
 —S(O)$_2$CH$_3$,
 —S(O)$_2$phenyl,
 benzoyl,
 benzylamino,
 -propylpyrrolidinyl,
 -methylcyclopropyl,
 cyclobutylamino,
 cyclobutyl-N(CH$_3$)—,
 piperidinyl,
 imidazolyl,
 morpholinyl,
 morpholinylmethyl,
 methylpiperazinylmethyl,
 methyl piperazinyl,
 pyrrolidinyl,
 pyrrolidinylmethyl,
 (methoxypyridinylmethyl)amino,
 methylpyrrolidinyl,
 difluoropyrrolidinyl,
 dimethylpyrrolidinyl,
 (methylcyclopropylmethyl)amino,
 hydroxymethylpyrrolidinyl,
 fluoropyrrolidinyl,
 (fluorophenylmethyl)amino,
 piperazinylmethyl,
 oxazolidinyl,
 (methyloxetanylmethyl)amino,
 (methylcyclobutylmethyl)amino,
 oxoimidazolidinyl, and
 2-hydroxyethylpiperidinyl;
provided that:
 R$^{63bbr}$ and R$^{64bbr}$ are not both hydrogen;
or a pharmaceutically acceptable salt or prodrug thereof.

Suitably in the compounds of Formula (VIbbr) neither R$^{63bbr}$ nor R$^{64bbr}$ is hydrogen.

Suitably in the compounds of Formula (VIbbr) R$^{61bbr}$ is phenyl.

Suitably in the compounds of Formula (VIbbr), the compounds are in the form of a phosphate prodrug.

Suitably in the compounds of Formula (VIbbr), the compounds are in the form of a —C(O)CH(NH$_2$)CH(CH$_3$)$_2$ prodrug.

This invention relates to novel compounds of Formula (VIIbbr) and to the use of compounds of Formula (VIIbbr) in the methods of the invention:

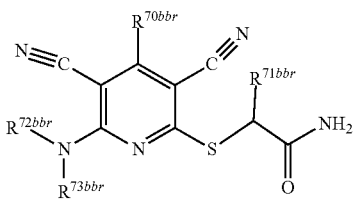

(VIIbbr)

wherein:
R$^{70bbr}$ is selected from:
ethyl,
ethyl substituted from 1 to 4 times by fluoro,
—NCH$_3$,
—SCH$_3$,
ethoxy,
methoxy,
propoxy,
phenyl,
furanyl,
cyclopropyl, and
cyclopropyl substituted once or twice by fluoro;
R$^{71bbr}$ is selected from:
phenyl,
phenyl substituted with 1 or 2 substituents independently selected from: fluoro, —CH$_3$, —CF$_3$, chloro, —C(O)phenyl, pyrrolidinyl, —C(O)NH$_2$, —S(O)$_2$NHCH$_3$, —OCH$_2$CH$_2$N(CH$_3$)$_2$ and CH$_2$C(O)NH$_2$,
thienyl,
piperidinyl,
pyridine, and
pyridine substituted with 1 or 2 substituents independently selected from: fluoro, —CH$_3$, —CF$_3$, and —OCH$_3$; and
R$^{72bbr}$ and R$^{73bbr}$ are independently selected from:
hydrogen,
C$_{1-4}$alkyl,
C$_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and CH$_2$NH$_2$,
cyclobutyl,
aminocyclobutyl,
tetrahydrofuran,
5-oxa-2azaspiro[3.4]octan, and
8-azabicyclo[3.2.1]octan, or
R$^{72bbr}$ and R$^{73bbr}$ are taken together with the nitrogen to which they are attached, and optionally from 1 to 3 additional heteroatoms, to form a heterocycloalkyl selected from:
pyrrolidinyl,
pyrrolo[3,4-c]pyrazolyl,
piperidinyl,
1,4diazepanyl,
piperazinyl,
6,7-dihydro-triazolo[4,5-c]pyridinyl,
2,9-diazaspiro[5.5]undecanyl,
2,8-diazaspiro[4.5]decanyl,
octahydro-1H-pyrrolo[1,2a][1,4]diazepinyl,
oxa-diazaspiro[4.5]decanyl,
oxazolyl,
morpholinyl,
1-oxa-6-azaspiro[3.4]octanyl,
2-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
hexahydropyrrolo[3,4-b]oxazinyl,
dihydronaphthyridinyl,
diazabicycloheptanyl,
1,8-diazaspiro[4.5]decanyl, and
5-oxa-2-azaspiro[3.4]octanyl,
all of which are optionally substituted with from 1 to 5 substituents independently selected from:
fluoro,
chloro,
oxo,
—OH,
—CN,
—CH$_3$,
—CH$_2$OH,
methoxy,
—CH$_2$CH$_3$,
—C(O)CH$_3$,
—C(O)NH$_2$,
—OCH$_2$CH$_2$OH,
—OCH$_2$CH$_2$NH$_2$,
—ONHC(NH)NH$_2$,
—OC(O)NH$_2$,
—Ooxetanyl,
—CH$_2$CH$_2$OH,
—CH$_2$CH$_2$CH$_2$OH,
—CH$_2$CH$_2$CH$_3$,
—CH$_2$CH$_2$OCH$_3$,
—CH$_2$CH(OH)CH$_3$,
—CH$_2$CH(OH)CH$_2$OH,
—CH$_2$C(O)OCH$_3$,
—CH$_2$C(O)NH$_2$,
—C(O)CH(CH$_3$)$_2$,
—CH$_2$CH$_2$N(CH$_3$)$_2$,
—CH$_2$CH$_2$NHCH$_2$CH$_3$,
—CH$_2$CH$_2$CH$_2$N(CH$_3$)$_2$,
—CH$_2$CH$_2$NHCH$_2$C(CH$_3$)$_3$,
—CH$_2$CH$_2$N(CH$_3$)CH$_2$OCH$_3$,
—C(CH$_3$)$_2$CH$_2$OH,
—CH$_2$C(CH$_3$)$_2$OH,
—CH$_2$C(CH$_3$)$_2$OCH$_3$,
—C(O)CH$_2$OH, —CH$_2$isothiazolyl,
—CH$_2$thiazolyl,
—CH$_2$pyrazolyl,
—CH$_2$imidazolyl,
—CH$_2$pyridinyl,
—CH$_2$oxazolyl,
—CH$_2$pyrrolyl,
—CH$_2$isoxazoly,
—CH$_2$furanyl,
—CH$_2$CH$_2$morpholinyl,
—CH$_2$CH$_2$pyrrolidinyl,
—CH$_2$CH$_2$pyrrolidinylCH$_3$,
—CH$_2$CH$_2$CH$_2$pyrrolidinyl,
—C(O)phenyl,
—C(O)C(tetrahydropyranyl)NH$_2$,
—NH$_2$,
—NHCH$_3$,
—N(CH$_3$)$_2$,
—NHC(O)CH$_3$,
—NHCH$_2$CHF$_2$,
—NHCH$_2$C(CH$_3$)$_3$,
—NHCH$_2$CH(CH$_3$)$_2$,
—NHCH$_2$CH$_2$OCH$_3$,
—NHCH$_2$CH$_2$OH,
—NHCH$_2$CH$_2$NH$_2$,
—NHCH$_2$C(O)OH,
—NHC(O)CH$_2$NH$_2$,
—NHC(O)CH$_2$CH$_2$CH$_2$NH$_2$,
—NHCH$_2$C(O)NH$_2$,
—NHCH$_2$C(OH)(CH$_3$)$_2$,
—NHC(O)CH(CH$_3$)NH$_2$,
—NHC(O)OCH(CH$_3$)NH$_2$,
—NHC(O)CH(CH$_3$)$_2$,
—NHC(O)C(CH$_3$)$_2$NH$_2$,
—NHC(O)CH$_2$OH,
—NHC(O)CH(CH$_2$OH)NH$_2$,
—NHC(O)(oxetanyl)NH$_2$,
—NHC(O)OC(CH$_3$)$_3$,
—NHC(CH$_3$)$_2$C(O)OCH$_3$,
—NHcyclopropyl,
—NHoxetanyl,
—CH$_2$NH$_2$,
—CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$CH$_3$,
benzoyl,
benzylamino,
3-pyrrolidinylpropyl,
2-cyclopropylmethyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;
provided that:
$R^{72bbr}$ and $R^{73bbr}$ are not both hydrogen,
or a pharmaceutically acceptable salt or prodrug thereof.

Suitably in the compounds of Formula (VIIbbr) neither $R^{72bbr}$ nor $R^{73bbr}$ is hydrogen.

Suitably in the compounds of Formula (VIIbbr) $R^{71bbr}$ is phenyl.

Suitably in the compounds of Formula (VIIbbr), the compounds are in the form of a phosphate prodrug.

Suitably in the compounds of Formula (VIIbbr), the compounds are in the form of a —C(O)CH(NH$_2$)CH(CH$_3$)$_2$ prodrug.

This invention relates to novel compounds of Formula (Qb) and to the use of compounds of Formula (Qb) in the methods of the invention:

(Qb)

wherein:
$R^{70a''}$ is selected from:
  ethyl,
  —OCH$_3$,
  —CH$_2$CF$_3$, and
  cyclopropyl;
$R^{71a''}$ is selected from:
  phenyl,
  phenyl substituted with 1 or 2 substituents independently selected from: fluoro, —CH$_3$, —CF$_3$, and chloro,
  pyridine, and
  pyridine substituted with 1 or 2 substituents independently selected from: fluoro, —CH$_3$, —CF$_3$, and —OCH$_3$; and
$R^{72a''}$ and $R^{73a''}$ are independently selected from:
  hydrogen,
  C$_{1-4}$alkyl,
  C$_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH₂CH₃)₂, —NCH(CH₂OH)₂,
—N(CH₂CH₂OH)₂, —NHCH₂CH₂OH,
—NHCH₂CH₂NH₂, —N(CH₃)CH₂(CH₃)₂CH₂OH,
—NHCH₂CH₃, —NHCH₂CH₂OCH₃, —N(CH₃)CH₂CH₂OH, —NHC(O)C(O)NH₂, —N(CH₃)CH₂CH₂CH₂OH, —N(CH₃)CH₂CH(OH)CH₂OH,
—N(CH₃)CH₂CH₂NH₂, oxo, —NHCH₂C(CH₃)₂CH₂OH, —OH, —NH₂, —NHCH₃,
—NHCH₂CH₂OH, —N(CH₃)₂, —N(CH₃)CH₂CH₃, —NHOC(CH₃)₂NH₂, —N(CH₃)CH₂cyclopropyl, —NHCH₂cyclopropyl,
—NHoxetanyl, —NCH₂CH₂triazole, piperazinyl, piperidinyl, pyrazolyl, azepinyl, azetidinyl, methoxy, and cyclopropylamino,
  where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH₂, —N(CH₃)₂, hydroxymethyl, oxo, —OH, and —CH₂NH₂,
cyclobutyl,
aminocyclobutyl,
tetrahydrofuran,
5-oxa-2azaspiro[3.4]octan, and
8-azabicyclo[3.2.1]octan, or
$R^{72a''}$ and $R^{73a''}$ are taken together with the nitrogen to which they are
attached, and optionally from 1 to 3 additional heteroatoms independently
selected from O, N, and S, to form a heterocycloalkyl
  selected from:
  pyrrolidinyl,
  pyrrolo[3,4-c]pyrazolyl,
  piperidinyl,
  1,4diazepanyl,
  piperazinyl,
  6,7-dihydro-triazolo[4,5-c]pyridinyl,
  2,9-diazaspiro[5.5]undecanyl,
  2,8-diazaspiro[4.5]decanyl,
  octahydro-1H-pyrrolo[1,2a][1,4]diazepinyl,
  oxa-diazaspiro[4.5]decanyl,
  oxazolyl,
  morpholinyl,
  1-oxa-6-azaspiro[3.4]octanyl,
  2-oxa-6-azaspiro[3.4]octanyl,
  1,7-diazaspiro[3.5]nonanyl,
  2,7-diazaspiro[3.5]nonanyl,
  2,6-diazaspiro[3.4]octanyl,
  azetidinyl,
  hexahydropyrrolo[3,4-b]oxazinyl,
  dihydronaphthyridinyl,
  diazabicycloheptanyl,
  1,8-diazaspiro[4.5]decanyl, and
  5-oxa-2-azaspiro[3.4]octanyl,
  all of which are optionally substituted with from 1 to 5 substituents independently selected from:
    fluoro,
    chloro,
    oxo,
    —OH,
    —OP(O)(OH)₂,
    —CN,
    —CH₃,
    —CH₂OH,
    methoxy,
    —CH₂CH₃,
    —C(O)CH₃,
    —C(O)NH₂,
    —OCH₂CH₂OH,
    —OCH₂CH₂NH₂,
    —ONHC(NH)NH₂,
    —OC(O)NH₂,
    —Ooxetanyl,
    —CH₂CH₂OH,
    —CH₂CH₂CH₂OH,
    —CH₂CH₂CH₃,
    —CH₂CH₂OCH₃,
    —CH₂CH(OH)CH₃,
    —CH₂CH(OH)CH₂OH,
    —CH₂C(O)OCH₃,
    —CH₂C(O)NH₂,
    —C(O)CH(CH₃)₂,
    —CH₂CH₂N(CH₃)₂,
    —CH₂CH₂NHCH₂CH₃,
    —CH₂CH₂CH₂N(CH₃)₂,
    —CH₂CH₂NHCH₂C(CH₃)₃,
    —CH₂CH₂N(CH₃)CH₂OCH₃,
    —C(CH₃)₂CH₂OH,
    —CH₂C(CH₃)₂OH,
    —CH₂C(CH₃)₂OCH₃,
    —C(O)CH₂OH,
    —CH₂isothiazolyl,
    —CH₂thiazolyl,
    —CH₂pyrazolyl,
    —CH₂imidazolyl,
    —CH₂pyridinyl,
    —CH₂oxazolyl,
    —CH₂pyrrolyl,
    —CH₂isoxazoly,
    —CH₂furanyl,
    —CH₂CH₂morpholinyl,
    —CH₂CH₂pyrrolidinyl,
    —CH₂CH₂pyrrolidinylCH₃,
    —CH₂CH₂CH₂pyrrolidinyl,
    —C(O)phenyl,
    —C(O)C(tetrahydropyranyl)NH₂,
    —NH₂,
    —NHCH₃,
    —N(CH₃)₂,
    —NHC(O)CH₃,
    —NHCH₂CHF₂,
    —NHCH₂C(CH₃)₃,
    —NHCH₂CH(CH₃)₂,
    —NHCH₂CH₂OCH₃,
    —NHCH₂CH₂OH,
    —NHCH₂CH₂NH₂,
    —NHCH₂C(O)OH,
    —NHC(O)CH₂NH₂,
    —NHC(O)CH₂CH₂CH₂NH₂,
    —NHCH₂C(O)NH₂,
    —NHCH₂C(OH)(CH₃)₂,
    —NHC(O)CH(CH₃)NH₂,
    —NHC(O)OCH(CH₃)NH₂,
    —NHC(O)CH(CH₃)₂,
    —NHC(O)C(CH₃)₂NH₂,
    —NHC(O)CH₂OH,
    —NHC(O)CH(CH₂OH)NH₂,
    —NHC(O)(oxetanyl)NH₂,
    —NHC(O)OC(CH₃)₃,
    —NHC(CH₃)₂C(O)OCH₃,
    —NHcyclopropyl,
    —NHoxetanyl,
    —CH₂NH₂, —CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
-propylpyrrolidinyl,
-methylcyclopropyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
(fluorophenylmethyl)amino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
R$^{72a''}$ and R$^{73a''}$ are not both hydrogen;
or a pharmaceutically acceptable salt or prodrug thereof.

Suitably in the compounds of Formula (Qb) neither R$^{72a''}$ nor R$^{73a''}$ is hydrogen.

Suitably in the compounds of Formula (Qb) R$^{71a''}$ is phenyl.

Suitably in the compounds of Formula (Qb), the compounds are in the form of a phosphate prodrug.

Suitably in the compounds of Formula (Qb), the compounds are in the form of a —C(O)CH(NH$_2$)CH(CH$_3$)$_2$ prodrug.

This invention relates to novel compounds of Formula (Qb1) and to the use of compounds of Formula (Qb1) in the methods of the invention:

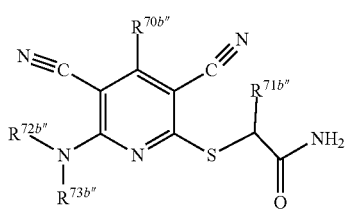

(Qb1)

wherein:
R$^{70b''}$ is selected from:
ethyl,
—OCH$_3$,
—CH$_2$CF$_3$, and
cyclopropyl;
R$^{71b''}$ is selected from:
phenyl,
phenyl substituted with 1 or 2 substituents independently selected from: fluoro, —CH$_3$, —CF$_3$, and chloro,
pyridine, and
pyridine substituted with 1 or 2 substituents independently selected from: fluoro, —CH$_3$, —CF$_3$, and —OCH$_3$; and
R$^{72b''}$ and R$^{73b''}$ are independently selected from:
C$_{1-4}$alkyl,
C$_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and CH$_2$NH$_2$,
cyclobutyl,
aminocyclobutyl,
tetrahydrofuran,
5-oxa-2azaspiro[3.4]octan, and
8-azabicyclo[3.2.1]octan, or
R$^{72b''}$ and R$^{73b''}$ are taken together with the nitrogen to which they are attached, and optionally from 1 to 3 additional heteroatoms, to form a heterocycloalkyl selected from:
pyrrolidinyl,
pyrrolo[3,4-c]pyrazolyl,
piperidinyl,
1,4diazepanyl,
piperazinyl,
6,7-dihydro-triazolo[4,5-c]pyridinyl,
2,9-diazaspiro[5.5]undecanyl,
2,8-diazaspiro[4.5]decanyl,
octahydro-1H-pyrrolo[1,2a][1,4]diazepinyl,
oxa-diazaspiro[4.5]decanyl,
oxazolyl,
morpholinyl,
1-oxa-6-azaspiro[3.4]octanyl,
2-oxa-6-azaspiro[3.4]octanyl, 1,7-diazaspiro[3.5]nonanyl,
2,7-diazaspiro[3.5]nonanyl,
2,6-diazaspiro[3.4]octanyl,
azetidinyl,
hexahydropyrrolo[3,4-b]oxazinyl,
dihydronaphthyridinyl,
diazabicycloheptanyl,
1,8-diazaspiro[4.5]decanyl, and
5-oxa-2-azaspiro[3.4]octanyl,
all of which are optionally substituted with from 1 to 5 substituents independently selected from:
fluoro,
chloro,
oxo,
—OH,
—CN,
—CH$_3$,
—CH$_2$OH,
methoxy,
—CH$_2$CH$_3$,
—C(O)CH$_3$,
—C(O)NH$_2$,
—OCH$_2$CH$_2$OH,
—OCH$_2$CH$_2$NH$_2$,
—ONHC(NH)NH$_2$,
—OC(O)NH$_2$,
—Ooxetanyl,
—CH$_2$CH$_2$OH,
—CH$_2$CH$_2$CH$_2$OH,
—CH$_2$CH$_2$CH$_3$,
—CH$_2$CH$_2$OCH$_3$,
—CH$_2$CH(OH)CH$_3$,
—CH$_2$CH(OH)CH$_2$OH,
—CH$_2$C(O)OCH$_3$,
—CH$_2$C(O)NH$_2$,
—C(O)CH(CH$_3$)$_2$,
—CH$_2$CH$_2$N(CH$_3$)$_2$,
—CH$_2$CH$_2$NHCH$_2$CH$_3$,
—CH$_2$CH$_2$CH$_2$N(CH$_3$)$_2$,
—CH$_2$CH$_2$NHCH$_2$C(CH$_3$)$_3$,
—CH$_2$CH$_2$N(CH$_3$)CH$_2$OCH$_3$,
—C(CH$_3$)$_2$CH$_2$OH,
—CH$_2$C(CH$_3$)$_2$OH,
—CH$_2$C(CH$_3$)$_2$OCH$_3$,
—C(O)CH$_2$OH,
—CH$_2$isothiazolyl,
—CH$_2$thiazolyl,
—CH$_2$pyrazolyl,
—CH$_2$imidazolyl,
—CH$_2$pyridinyl,
—CH$_2$oxazolyl,
—CH$_2$pyrrolyl,
—CH$_2$isoxazoly,
—CH$_2$furanyl,
—CH$_2$CH$_2$morpholinyl,
—CH$_2$CH$_2$pyrrolidinyl,
—CH$_2$CH$_2$pyrrolidinylCH$_3$,
—CH$_2$CH$_2$CH$_2$pyrrolidinyl,
—C(O)phenyl,
—C(O)C(tetrahydropyranyl)NH$_2$,
—NH$_2$,
—NHCH$_3$,
—N(CH$_3$)$_2$,
—NHC(O)CH$_3$,
—NHCH$_2$CHF$_2$,
—NHCH$_2$C(CH$_3$)$_3$,
—NHCH$_2$CH(CH$_3$)$_2$,
—NHCH$_2$CH$_2$OCH$_3$,
—NHCH$_2$CH$_2$OH,
—NHCH$_2$CH$_2$NH$_2$,
—NHCH$_2$C(O)OH,
—NHC(O)CH$_2$NH$_2$,
—NHC(O)CH$_2$CH$_2$CH$_2$NH$_2$,
—NHCH$_2$C(O)NH$_2$,
—NHCH$_2$C(OH)(CH$_3$)$_2$,
—NHC(O)CH(CH$_3$)NH$_2$,
—NHC(O)OCH(CH$_3$)NH$_2$,
—NHC(O)CH(CH$_3$)$_2$,
—NHC(O)C(CH$_3$)$_2$NH$_2$,
—NHC(O)CH$_2$OH,
—NHC(O)CH(CH$_2$OH)NH$_2$,
—NHC(O)(oxetanyl)NH$_2$,
—NHC(O)OC(CH$_3$)$_3$,
—NHC(CH$_3$)$_2$C(O)OCH$_3$,
—NHcyclopropyl,
—NHoxetanyl,
—CH$_2$NH$_2$,
—CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
3-pyrrolidinylpropyl,
2-cyclopropylmethyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;
provided that:
$R^{72b''}$ and $R^{73b''}$ are not both unsubstituted alkyl;
or a pharmaceutically acceptable salt or prodrug thereof.
Suitably in the compounds of Formula (Qb1) $R^{71b''}$ is phenyl.

Suitably in the compounds of Formula (Qb1), the compounds are in the form of a phosphate prodrug.

Suitably in the compounds of Formula (Qb1), the compounds are in the form of a —C(O)CH(NH$_2$)CH(CH$_3$)$_2$ prodrug.

This invention relates to novel compounds of Formula (Qb2) and to the use of compounds of Formula (Qb2) in the methods of the invention:

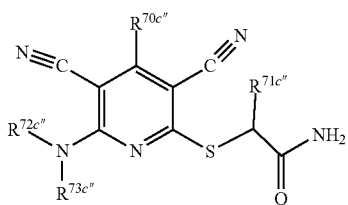

(Qb2)

wherein:

$R^{70c''}$ is selected from:
  ethyl,
  —OCH$_3$,
  —CH$_2$CF$_3$, and
  cyclopropyl;

$R^{71c''}$ is selected from:
  phenyl,
  phenyl substituted with 1 or 2 substituents independently selected from: fluoro, —CH$_3$, —CF$_3$, and chloro,
  pyridine, and
  pyridine substituted with 1 or 2 substituents independently selected from: fluoro, —CH$_3$, —CF$_3$, and —OCH$_3$; and $R^{72c''}$ and $R^{73c''}$ are are taken together with the nitrogen to which they are attached, and optionally from 1 to 3 additional heteroatoms, to form a heterocycloalkyl selected from:
  pyrrolidinyl,
  pyrrolo[3,4-c]pyrazolyl,
  piperidinyl,
  1,4diazepanyl,
  piperazinyl,
  6,7-dihydro-triazolo[4,5-c]pyridinyl,
  2,9-diazaspiro[5.5]undecanyl,
  2,8-diazaspiro[4.5]decanyl,
  octahydro-1H-pyrrolo[1,2a][1,4]diazepinyl,
  oxa-diazaspiro[4.5]decanyl,
  oxazolyl,
  morpholinyl,
  1-oxa-6-azaspiro[3.4]octanyl,
  2-oxa-6-azaspiro[3.4]octanyl,
  1,7-diazaspiro[3.5]nonanyl,
  2,7-diazaspiro[3.5]nonanyl,
  2,6-diazaspiro[3.4]octanyl,
  azetidinyl,
  hexahydropyrrolo[3,4-b]oxazinyl,
  dihydronaphthyridinyl,
  diazabicycloheptanyl,
  1,8-diazaspiro[4.5]decanyl, and
  5-oxa-2-azaspiro[3.4]octanyl,
  all of which are optionally substituted with from 1 to 5 substituents independently selected from:
    fluoro,
    chloro,
    oxo,
    —OH,
    —CN,
    —CH$_3$,
    —CH$_2$OH,
    methoxy,
    —CH$_2$CH$_3$,
    —C(O)CH$_3$,
    —C(O)NH$_2$,
    —OCH$_2$CH$_2$OH,
    —OCH$_2$CH$_2$NH$_2$,
    —ONHC(NH)NH$_2$,
    —OC(O)NH$_2$,
    —Ooxetanyl,
    —CH$_2$CH$_2$OH,
    —CH$_2$CH$_2$CH$_2$OH,
    —CH$_2$CH$_2$CH$_3$,
    —CH$_2$CH$_2$OCH$_3$,
    —CH$_2$CH(OH)CH$_3$,
    —CH$_2$CH(OH)CH$_2$OH,
    —CH$_2$C(O)OCH$_3$,
    —CH$_2$C(O)NH$_2$,
    —C(O)CH(CH$_3$)$_2$,
    —CH$_2$CH$_2$N(CH$_3$)$_2$,
    —CH$_2$CH$_2$NHCH$_2$CH$_3$,
    —CH$_2$CH$_2$CH$_2$N(CH$_3$)$_2$,
    —CH$_2$CH$_2$NHCH$_2$C(CH$_3$)$_3$,
    —CH$_2$CH$_2$N(CH$_3$)CH$_2$OCH$_3$,
    —C(CH$_3$)$_2$CH$_2$OH,
    —CH$_2$C(CH$_3$)$_2$OH,
    —CH$_2$C(CH$_3$)$_2$OCH$_3$,
    —C(O)CH$_2$OH,
    —CH$_2$isothiazolyl,
    —CH$_2$thiazolyl,
    —CH$_2$pyrazolyl,
    —CH$_2$imidazolyl,
    —CH$_2$pyridinyl,
    —CH$_2$oxazolyl,
    —CH$_2$pyrrolyl,
    —CH$_2$isoxazoly,
    —CH$_2$furanyl,
    —CH$_2$CH$_2$morpholinyl,
    —CH$_2$CH$_2$pyrrolidinyl,
    —CH$_2$CH$_2$pyrrolidinylCH$_3$,
    —CH$_2$CH$_2$CH$_2$pyrrolidinyl,
    —C(O)phenyl,
    —C(O)C(tetrahydropyranyl)NH$_2$,
    —NH$_2$,
    —NHCH$_3$,
    —N(CH$_3$)$_2$,
    —NHC(O)CH$_3$,
    —NHCH$_2$CHF$_2$,
    —NHCH$_2$C(CH$_3$)$_3$,
    —NHCH$_2$CH(CH$_3$)$_2$,
    —NHCH$_2$CH$_2$OCH$_3$,
    —NHCH$_2$CH$_2$OH,
    —NHCH$_2$CH$_2$NH$_2$,
    —NHCH$_2$C(O)OH,
    —NHC(O)CH$_2$NH$_2$,
    —NHC(O)CH$_2$CH$_2$CH$_2$NH$_2$,
    —NHCH$_2$C(O)NH$_2$,
    —NHCH$_2$C(OH)(CH$_3$)$_2$,
    —NHC(O)CH(CH$_3$)NH$_2$,
    —NHC(O)OCH(CH$_3$)NH$_2$,
    —NHC(O)CH(CH$_3$)$_2$,
    —NHC(O)C(CH$_3$)$_2$NH$_2$,
    —NHC(O)CH$_2$OH,
    —NHC(O)CH(CH$_2$OH)NH$_2$, —NHC(O)(oxetanyl)NH$_2$,
—NHC(O)OC(CH$_3$)$_3$,
—NHC(CH$_3$)$_2$C(O)OCH$_3$,
—NHcyclopropyl,
—NHoxetanyl,
—CH$_2$NH$_2$,
—CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
3-pyrrolidinylpropyl,
2-cyclopropylmethyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;

or a pharmaceutically acceptable salt or prodrug thereof.

Suitably in the compounds of Formula (Qb2) $R^{71c''}$ is phenyl.

Suitably in the compounds of Formula (Qb2), the compounds are in the form of a phosphate prodrug.

Suitably in the compounds of Formula (Qb2), the compounds are in the form of a —C(O)CH(NH$_2$)CH(CH$_3$)$_2$ prodrug.

Non Primary Amide:

This invention relates to compounds of Formula (Icr) and to the use of compounds of Formula (Icr) in the methods of the invention:

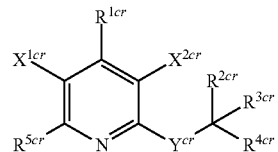

(Icr)

wherein:
$X^{1cr}$ and $X^{2cr}$ are independently selected from:
  hydrogen,
  cyano,
  fluoro,
  chloro,
  bromo,
  iodo,
  $C_{1-6}$alkyl,
  $R^e$,
  —O$C_{1-6}$alkyl,
  —O$R^e$,
  cycloalkyl,
  cycloalkyl substituted from 1 to 4 times by $R^d$,
  heterocycle,
  heterocycle substituted from 1 to 4 times by $R^d$,
  —SH, and
  —S$R^a$;
$Y^{cr}$ is selected from: S, NH, N$R^z$, O, S(O) and S(O)$_2$;
$R^{1cr}$ is selected from:
  amino,
  —NH$R^a$,
  —N$R^b R^c$,
  cyano,
  fluoro,
  chloro,
  bromo,
  iodo,
  $C_{1-6}$alkyl,
  $R^e$,
  —O$C_{1-6}$alkyl,
  —O$R^e$,
  cycloalkyl,
  cycloalkyl substituted from 1 to 4 times by $R^d$,
  heterocycle,
  heterocycle substituted from 1 to 4 times by $R^d$,
  aryl,
  aryl substituted from 1 to 4 times by $R^d$,
  heteroaryl,
  heteroaryl substituted from 1 to 4 times by $R^d$,
  —SH, and
  —S$R^a$;
$R^{2cr}$ is selected from:
  hydrogen,
  $C_{1-6}$alkyl, and
  $C_{1-6}$alkyl substituted with from 1 to 6 substituents independently selected from: halogen, —OH, —COOH;
$R^{3cr}$ is selected from:
  aryl,
  aryl substituted from 1 to 4 times by $R^d$,
  heteroaryl, and
  heteroaryl substituted from 1 to 4 times by $R^d$;
$R^{4cr}$ is selected from:
  hydrogen,
  $C_{1-6}$alkyl, and $C_{1-6}$alkyl substituted with from 1 to 6 substituents independently selected from: halogen, —OH, —COOH;

$R^{5cr}$ is selected from:
  amino,
  —NHR$^a$,
  —NR$^b$R$^c$,
  aryl,
  aryl substituted from 1 to 4 times by R$^d$,
  —C$_{1-6}$alkyl,
  —OC$_{1-6}$alkyl,
  —OR$^e$,
  —Oaryl,
  —Oaryl substituted from 1 to 4 times by R$^d$,
  —Oheteroaryl,
  —Oheteroaryl substituted from 1 to 4 times by R$^d$,
  —SH, and
  —SR$^a$;
where:
  each R$^a$ is independently selected from
    C$_{1-6}$alkyl,
    R$^e$,
    aryl,
    aryl substituted from 1 to 4 times by R$^d$,
    heteroaryl,
    heteroaryl substituted from 1 to 4 times by R$^d$
    cycloalkyl,
    cycloalkyl substituted from 1 to 4 times by R$^d$,
    heterocycloalkyl, and
    heterocycloalkyl substituted from 1 to 4 times by R$^d$;
  R$^b$ and R$^c$ are independently selected from:
    C$_{1-6}$alkyl,
    R$^e$,
    aryl,
    aryl substituted from 1 to 4 times by R$^d$,
    heteroaryl,
    heteroaryl substituted from 1 to 4 times by R$^d$;
    cycloalkyl,
    cycloalkyl substituted from 1 to 4 times by R$^d$,
    heterocycloalkyl, and
    heterocycloalkyl substituted from 1 to 4 times by R$^d$,
    or
  R$^b$ and R$^c$ are taken together with the nitrogen to which they are attached, and optionally from 1 to 3 additional heteroatoms independently selected from O, N, and S, to form a heterocycloalkyl, which is optionally substituted with from 1 to 5 substituents independently selected from:
    fluoro,
    chloro,
    bromo,
    iodo,
    C$_{1-6}$alkyl,
    R$^e$,
    —OR$^e$,
    aryl,
    aryl substituted from 1 to 4 times by R$^d$,
    heteroaryl,
    heteroaryl substituted from 1 to 4 times by R$^d$,
    cycloalkyl,
    cycloalkyl substituted from 1 to 4 times by R$^d$,
    heterocycloalkyl, and
    heterocycloalkyl substituted from 1 to 4 times by R$^d$,
    C$_{1-4}$alkoxy,
    —CN,
    oxo,
    —OH,
    —COOH,
    —NO$_2$,
    —NH$_2$,
    —N(H)C$_{1-5}$alkyl,
    —N(H)R$^e$,
    —N(C$_{1-5}$alkyl)$_2$,
    —NR$^e$R$^e$,
    —N(R$^e$)C$_{1-5}$alkyl,
    —ONHC(NH)NH$_2$,
    —Oheterocycloalkyl,
    —NHcycloalkyl,
    —N(C$_{1-5}$alkyl)cycloalkyl,
    —NHheterocycloalkyl,
    —N(C$_{1-5}$alkyl)heterocycloalkyl,
    —S(O)$_2$C$_{1-4}$alkyl,
    —SO$_2$NH$_2$
    —S(O)$_2$phenyl,
    benzoyl,
    2-methylcyclopropyl,
    imidazolyl,
    (methoxypyridinylmethyl)amino,
    (methylcyclopropylmethyl)amino,
    (fluorophenylmethyl)amino,
    (methyloxetanylmethyl)amino, and
    (methylcyclobutylmethyl)amino;
  each R$^d$ is independently selected from:
    fluoro,
    chloro,
    bromo,
    iodo,
    C$_{1-6}$alkyl,
    R$^e$,
    heteroaryl,
    heteroaryl substituted from 1 to 4 times by R$^x$,
      where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    cycloalkyl,
    cycloalkyl substituted from 1 to 4 times by R$^x$,
      where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    heterocycloalkyl,
    heterocycloalkyl substituted from 1 to 4 times by R$^x$,
      where R$^x$ is selected from aryl, heteroaryl, cycloalkyl, heterocyloalkyl, fluoro, oxo, C$_{1-6}$alkyl, and C$_{1-6}$alkyl substituted
        with from 1 to 6 substituents independently selected from: fluoro, oxo, —OH, —COOH, —NH$_2$, and —CN,
    aryl,
    aryl substituted from 1 to 4 times by R$^x$,
      where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    C$_{1-4}$alkoxy,
    C$_{1-4}$alkoxy substituted with from 1 to 4 substituents independently selected from: fluoro, oxo, —OH, —COOH, —NH$_2$, —NHC$_{1-4}$alkyl, —N(C$_{1-4}$alkyl)$_2$ and —CN, —Oaryl,
—Oaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—OR$^e$,
—C(O)H,
—C(O)R$^{zz}$,
—C(O)aryl,
—C(O)aryl substituted from 1 to 4 times by $R^{zz}$,
—C(O)heteroaryl,
—C(O)heteroaryl substituted from 1 to 4 times by $R^{zz}$,
—OC(O)H,
—CO(O)R$^{zz}$,
—OC(O)aryl,
—CO(O)aryl substituted from 1 to 4 times by $R^{zz}$,
—OC(O)heteroaryl,
—OC(O)heteroaryl substituted from 1 to 4 times by $R^{zz}$,
mercapto,
—SR$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)H,
—S(O)R$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$H,
—S(O)$_2$R$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—OS(O)$_2$R$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—P(O)(CH$_3$)$_2$,
—NHS(O)$_2$H,
—NHS(O)$_2$R$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—NHC(O)H,
—NHC(O)R$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—C(O)NH$_2$,
—C(O)NHR$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—C(O)NR$^{x1}$R$^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—C(O)OH,
—C(O)OR$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
oxo,
hydroxy,
amino,
—NHR$^x$,
  where $R^x$ is selected from aryl, heteroaryl, cycloalkyl, heterocyloalkyl, $C_{1-6}$alkyl, $C_{1-6}$alkyl substituted with from 1 to 6 substituents independently selected from: fluoro, oxo, —OH, —COOH, —NH$_2$, and —CN, $C_{1-6}$alkoxy, and $C_{1-6}$alkoxy substituted with from 1 to 6 substituents Independently selected from: fluoro, oxo, —OH, —COOH, —NH$_2$, and CN
—NR$^{x1}$R$^{x2}$,
  where $R^{x1}$ and $R^{x2}$ are each independently selected from aryl, heteroaryl, cycloalkyl, heterocyloalkyl, —S(O)$_2$C$_{1-6}$alkyl, —S(O)$_2$C$_{1-6}$alkyl substituted with from 1 to 6 substituents independently selected from: fluoro, oxo, —OH, —COOH, —NH$_2$, and —CN, $C_{1-6}$alkyl, and $C_{1-6}$alkyl substituted with from 1 to 6 substituents independently selected from: fluoro, oxo, —OH, —COOH, —NH$_2$, and —CN,
boronic acid,
nitro,
cyano,
—NHC(O)NH$_2$,
—NHC(O)NHR$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHC(O)NR$^{x1}$R$^{x2}$,
  where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN, each R$^e$ is independently selected from:
  C$_{1-6}$alkyl substituted with from 1 to 9 substituents independently selected from:
    fluoro,
    chloro,
    bromo,
    iodo,
    —OC$_{1-6}$alkyl,
    —OC$_{1-6}$alkyl substituted with from 1 to 6 substituents independently selected from: fluoro, oxo, —OH, —COOH, —NH$_2$, and —CN,
    —OC(O)C$_{1-6}$alkyl,
    —OC(O)C$_{1-6}$alkyl substituted with from 1 to 6 substituents independently selected from: fluoro, oxo, —OH, —COOH, —NH$_2$, and —CN,
    —ONHC(NH)NH$_2$,
    —OP(O)(OH)$_2$,
    mercapto,
    —SR$^x$,
      where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    —S(O)H,
    —S(O)R$^x$,
      where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    —S(O)$_2$H,
    —S(O)$_2$R$^x$,
      where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    oxo,
    hydroxy,
    amino,
    —NHR$^{xx}$,
      where R$^{xx}$ is selected from aryl, heteroaryl, cycloalkyl, cycloalkyl substituted with C$_{1-4}$alkoxy, C$_{1-4}$alkoxy substituted with from 1 to 6 substituents independently selected from: fluoro, triazolyl, cyclopropyl, oxo, —OR$^{xy}$, —COOH, —CN, and —NR$^{xy}$R$^{xz}$, where R$^{xy}$ and R$^{xz}$ are Independently selected from: hydrogen, aryl, C$_{1-5}$alkyl heterocyloalkyl, C$_{1-6}$alkyl, and C$_{1-6}$alkyl substituted with from 1 to 6 substituents independently selected from: fluoro, oxo, —OR$^{xy}$, —COOH, —CN, and —NR$^{xy}$R$^{xz}$, where R$^{xy}$ and R$^{xz}$ are Independently selected from: hydrogen, aryl, C$_{1-5}$alkyl and C$_{1-5}$alkyl substituted with from 1 to 4 substituents independently selected from: fluoro, triazolyl, cyclopropyl, oxo, —OH,
    —OC$_{1-5}$alkyl, —OC$_{1-5}$alkyl substituted from 1 to 6 times by fluoro and —COOH,
    —NR$^{x1}$R$^{x2}$,
      where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
  guanidino,
  —C(O)OH,
  —C(O)OR$^x$,
    where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
  —C(O)NH$_2$,
  —C(O)NHR$^x$,
    where R$^x$ is selected from aryl, heteroaryl, —OH, C$_{1-4}$alkoxy, cycloalkyl, cycloalkyl substituted with HO—(C$_{1-4}$alkyl)-, heterocyloalkyl, heterocyloalkyl substituted with HO—(C$_{1-4}$alkyl)-, C$_{1-6}$alkyl, and C$_{1-6}$alkyl substituted with from 1 to 6 substituents independently selected from: fluoro, oxo, —OH, —COOH, heteroaryl, —NH$_2$, and —CN,
  —C(O)NR$^{x1}$R$^{x2}$,
    where R$^{x1}$ and R$^{x2}$ are each independently selected from aryl, heteroaryl, cycloalkyl, cycloalkyl substituted with HO—(C$_{1-4}$alkyl)-, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
    or R$^{x1}$ and R$^{x2}$ taken together with the nitrogen to which they are attached, and optionally from 1 to 3 additional heteroatoms independently selected from O, N, and S, to form a heterocycloalkyl, which is optionally substituted with from 1 to 5 substituents independently selected from fluoro, oxo, —OH, HO—(C$_{1-4}$alkyl)-, —COOH, —NH$_2$, and —CN,
  aryl,
  aryl substituted from 1 to 4 times by R$^x$,
    where R$^x$ is selected from fluoro, chloro, bromo, iodo, aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, —N(CH$_3$)$_2$, —NHC(O)C$_{1-4}$alkyl, and —CN,
  —Oaryl,
  —Oaryl substituted from 1 to 4 times by R$^x$,
    where R$^x$ selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
  heteroaryl,
  heteroaryl substituted from 1 to 4 times by R$^x$,
    where R$^x$ selected from aryl, heteroaryl, cycloalkyl, heterocyloalkyl, C$_{1-4}$alkoxy C$_{1-6}$alkyl, and C$_{1-6}$alkyl substituted with from 1 to 6 substituents independently selected from: fluoro, oxo, —OH, —COOH, —NH$_2$, and —CN,
  —Oheteroaryl,
  —Oheteroaryl substituted from 1 to 4 times by R$^x$, where $R^x$ selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
cycloalkyl,
cycloalkyl substituted from 1 to 4 times by $R^x$,
where $R^x$ selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by $R^x$,
where $R^x$ selected from oxo, —OH, —N(C$_{1-4}$alkyl)$_2$, aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, —N(CH$_3$)$_2$, and —CN,
—S(O)$_2$NH$_2$,
—S(O)$_2$NHR$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—NHS(O)$_2$H,
—NHS(O)$_2$R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—OC(O)NH$_2$,
—NHC(O)R$^x$,
where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN
—NHC(O)NHR$^{xp}$,
where $R^{xp}$ is selected from heteroaryl, cycloalkyl, heterocyloalkyl, and $C_{1-6}$alkyl substituted with from 1 to 4 substituents independently selected from: —COOH, —NH$_2$, and —CN,
—NHC(O)NR$^{x3}$R$^{x4}$,
where $R^{x3}$ and $R^{x4}$ are each independently selected from heteroaryl, cycloalkyl, heterocyloalkyl, and $C_{1-6}$alkyl substituted with from 1 to 6 substituents independently selected from: —COOH, —NH$_2$, and —CN,
—NHC(O)C(O)NH$_2$,
—NO$_2$, and
—CN; and
$R^z$ is selected from
$C_{1-6}$alkyl,
$R^e$,
cycloalkyl,
cycloalkyl substituted from 1 to 4 times by $R^d$,
heterocycloalkyl, and
heterocycloalkyl substituted from 1 to 4 times by $R^d$; and
$R^{zz}$ is selected from
$C_{1-6}$alkyl, and
$R^e$;
provided that:
$X^{1cr}$ and $X^{2cr}$ are not both hydrogen;
or a pharmaceutically acceptable salt or prodrug thereof.

Suitably in the compounds of Formula (Icr) neither $X^{1cr}$ nor $X^{2cr}$ are hydrogen.

Suitably in the compounds of Formula (Icr), the compounds are in the form of a phosphate prodrug.

Suitably in the compounds of Formula (Icr), the compounds are in the form of a —C(O)CH(NH$_2$)CH(CH$_3$)$_2$ prodrug.

Included in the compounds of the invention and used in the methods of the invention are compounds of Formula (IIcr):

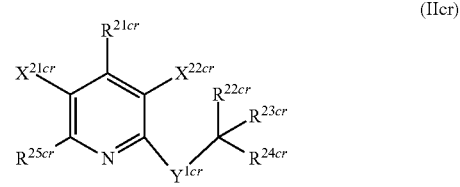

(IIcr)

wherein:
$X^{21cr}$ and $X^{22cr}$ are independently selected from:
hydrogen,
cyano,
fluoro,
chloro,
bromo,
iodo,
$C_{1-6}$alkyl,
$R^e$,
—OC$_{1-6}$alkyl,
—OR$^e$,
cycloalkyl,
heterocycle, and
—SH;
$Y^{1cr}$ is selected from: S, NH, and NR$^z$;
$R^{21cr}$ is selected from:
amino,
cyano,
fluoro,
chloro,
bromo,
iodo,
$C_{1-6}$alkyl,
$R^e$,
—OC$_{1-6}$alkyl,
—OR$^e$,
—NHR$^a$,
—NR$^b$R$^c$,
aryl,
aryl substituted from 1 to 4 times by $R^d$,
heteroaryl,
heteroaryl substituted from 1 to 4 times by $R^d$,
cycloalkyl,
cycloalkyl substituted with from 1 to 4 times by $R^d$,
heterocycle, heterocycle substituted with from 1 to 4 times by $R^d$,
—SH, and
—$SR^a$;

$R^{22cr}$ is selected from:
hydrogen,
$C_{1-6}$alkyl, and
$C_{1-6}$alkyl substituted with from 1 to 6 substituents independently selected from: fluoro, chloro, and bromo;

$R^{23cr}$ is selected from:
aryl,
aryl substituted from 1 to 4 times by $R^d$,
heteroaryl, and
heteroaryl substituted from 1 to 4 times by $R^d$;

$R^{24cr}$ is selected from:
hydrogen,
$C_{1-6}$alkyl, and
$C_{1-6}$alkyl substituted with from 1 to 6 substituents independently selected from: fluoro, chloro, and bromo;

$R^{25cr}$ is selected from:
amino,
—$NHR^a$,
—$NR^bR^c$,
aryl,
aryl substituted from 1 to 4 times by $R^d$,
—$OC_{1-6}$alkyl,
—Oaryl,
—Oheteroaryl,
—SH, and
—$SR^a$;

where:
each $R^a$ is independently selected from
$C_{1-6}$alkyl,
$R^e$,
aryl,
aryl substituted from 1 to 4 times by $R^d$,
heteroaryl,
heteroaryl substituted from 1 to 4 times by $R^d$
cycloalkyl,
—$OR^e$,
cycloalkyl substituted from 1 to 4 times by $R^d$,
heterocycloalkyl, and
heterocycloalkyl substituted from 1 to 4 times by $R^d$;

$R^b$ and $R^c$ are independently selected from:
$C_{1-6}$alkyl,
$R^e$,
aryl,
aryl substituted from 1 to 4 times by $R^d$,
heteroaryl,
heteroaryl substituted from 1 to 4 times by $R^d$;
cycloalkyl,
cycloalkyl substituted from 1 to 4 times by $R^d$,
heterocycloalkyl, and
heterocycloalkyl substituted from 1 to 4 times by $R^d$, or $R^b$ and $R^c$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
$C_{1-6}$alkyl,
$R^e$, —$OR^e$,
aryl,
aryl substituted from 1 to 4 times by $R^d$,
heteroaryl,
heteroaryl substituted from 1 to 4 times by $R^d$,
cycloalkyl,
cycloalkyl substituted from 1 to 4 times by $R^d$,
heterocycloalkyl, and
heterocycloalkyl substituted from 1 to 4 times by $R^d$,
$C_{1-4}$alkoxy,
$C_{1-4}$alkoxy substituted with from 1 to 6 substituents independently selected from: fluoro, oxo, —OH, —COOH, —$NH_2$, and —CN,
—CN,
oxo,
—OH,
—COOH,
—$NO_2$,
—$NH_2$,
—$N(H)C_{1-4}$alkyl,
—$N(H)R^e$,
—$N(C_{1-4}$alkyl$)_2$,
—$ONHC(NH)NH_2$,
—Oheterocycloalkyl,
—NHcycloalkyl,
—NHheterocycloalkyl,
—$S(O)_2CH_2CH_3$,
—$S(O)_2CH_2CH_2CH_3$,
—$S(O)_2$phenyl,
—$S(O)_2CH_3$,
benzoyl,
benzylamino,
3-pyrrolidinylpropyl,
2-cyclopropylmethyl,
cyclobutylamino,
cyclobutyl-$N(CH_3)$—,
piperidinyl,
imidazolyl,
morpholinyl,
morpholinylmethyl,
methylpiperazinylmethyl,
methyl piperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;

each $R^d$ is independently selected from:
fluoro,
chloro,
bromo,
iodo,
$C_{1-6}$alkyl,
$R^e$,
heteroaryl, heteroaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, cycloalkyl,
cycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, heterocycloalkyl,
heterocycloalkyl substituted from 1 to 4 times by $R^x$,
  where $R^x$ is selected from aryl, heteroaryl, cycloalkyl, heterocyloalkyl, fluoro, oxo, $C_{1-6}$alkyl, and $C_{1-6}$alkyl substituted
    with from 1 to 6 substituents independently selected from: fluoro, oxo, —OH, —COOH, —NH$_2$, and —CN, aryl,
aryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, $C_{1-4}$alkoxy,
$C_{1-4}$alkoxy substituted with from 1 to 4 substituents independently selected
  from: fluoro, oxo, —OH, —COOH, —NH$_2$, and —CN, —Oaryl,
—Oaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)H,
—C(O)$R^{zz}$,
—C(O)aryl,
—C(O)aryl substituted from 1 to 4 times by $R^{zz}$,
—C(O)heteroaryl,
—C(O)heteroaryl substituted from 1 to 4 times by $R^{zz}$,
—OC(O)H,
—CO(O)$R^{zz}$,
—OC(O)aryl,
—CO(O)aryl substituted from 1 to 4 times by $R^{zz}$,
—OC(O)heteroaryl,
—OC(O)heteroaryl substituted from 1 to 4 times by $R^{zz}$,
mercapto,
—S$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)H,
—S(O)$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$H,
—S(O)$_2$$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —OS(O)$_2$$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$NH$_2$,
—S(O)$_2$NH$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —S(O)$_2$N$R^{x1}R^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHS(O)$_2$H,
—NHS(O)$_2$$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —NHC(O)H,
—NHC(O)$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)NH$_2$,
—C(O)NH$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)N$R^{x1}R^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, —C(O)OH,
—C(O)O$R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN, oxo,
hydroxy,
amino, —NHR$^x$,
　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NR$^{x1}$R$^{x2}$,
　where R$^{x1}$ and R$^{x2}$ are each independently selected from aryl, heteroaryl, cycloalkyl, heterocyloalkyl, —S(O)$_2$C$_{1-6}$alkyl, —S(O)$_2$C$_{1-6}$alkyl substituted with from 1 to 6 substituents independently selected from: fluoro, oxo, —OH, —COOH, —NH$_2$, and
　—CN, C$_{1-6}$alkyl, and C$_{1-6}$alkyl substituted with from 1 to 6 substituents independently selected from: fluoro, oxo, —OH, —COOH, —NH$_2$, and —CN,
boronic acid,
nitro,
cyano,
—NHC(O)NH$_2$,
—NHC(O)NHR$^x$,
　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—NHC(O)NR$^{x1}$R$^{x2}$,
　where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
each R$^e$ is independently selected from:
　C$_{1-6}$alkyl substituted with from 1 to 9 substituents independently selected from:
　fluoro,
　chloro,
　bromo,
　iodo,
　C$_{1-6}$alkyl,
　—OC$_{1-6}$alkyl,
　—OC$_{1-6}$alkyl substituted with from 1 to 6 substituents independently selected from: fluoro, oxo, —OH, —COOH, —NH$_2$, and —CN,
　mercapto,
　—SR$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　—S(O)H,
　—S(O)R$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　—S(O)$_2$H,
　—S(O)$_2$R$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　oxo,
　hydroxy,
　amino,
　—NHR$^{xx}$,
　　where R$^{xx}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OR$^{xy}$, —COOH, —CN, —OC$_{1-5}$alkyl, —OC$_{1-5}$alkyl substituted from 1 to 6 times by fluoro and —NR$^{xy}$R$^{xz}$, where R$^{xy}$ and R$^{xz}$ are independently selected from: hydrogen, aryl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
　—NR$^{x1}$R$^{x2}$,
　　where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　guanidino,
　—C(O)OH,
　—C(O)OR$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　—C(O)NH$_2$,
　—C(O)NHR$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　—C(O)NR$^{x1}$R$^{x2}$,
　　where R$^{x1}$ and R$^{x2}$ are each independently selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　aryl,
　aryl substituted from 1 to 4 times by R$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　—Oaryl,
　—Oaryl substituted from 1 to 4 times by R$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
　heteroaryl,
　heteroaryl substituted from 1 to 4 times by R$^x$,
　　where R$^x$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,

147

—Oheteroaryl,
—Oheteroaryl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
cycloalkyl,
cycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by $R^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
  where $R^{x1}$ and $R^{x2}$ are each independently selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—NHS(O)$_2$H,
—NHS(O)$_2$R$^x$,
  where $R^x$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OH, —COOH, —NH$_2$, and —CN,
—NHC(O)NHR$^{xp}$,
  where $R^{xp}$ is selected from heteroaryl, cycloalkyl, heterocyloalkyl, and $C_{1-6}$alkyl substituted with from 1 to 4 substituents independently selected from: —COOH, —NH$_2$, and —CN,
—NHC(O)NR$^{x3}$R$^{x4}$,
  where $R^{x3}$ and $R^{x4}$ are each independently selected from heteroaryl, cycloalkyl, heterocyloalkyl, and $C_{1-6}$alkyl substituted with from 1 to 6 substituents independently selected from: —COOH, —NH$_2$, and —CN,
nitro, and
cyano;
$R^z$ is selected from
  $C_{1-6}$alkyl,
  $R^e$,
  cycloalkyl,
  cycloalkyl substituted from 1 to 4 times by $R^d$,
  heterocycloalkyl, and
  heterocycloalkyl substituted from 1 to 4 times by $R^d$;
$R^{zz}$ is selected from
  $C_{1-6}$alkyl, and
  $R^e$;

148 provided that:
  $X^{21cr}$ and $X^{22cr}$ are not both hydrogen;
or a pharmaceutically acceptable salt or prodrug thereof.

Suitably in the compounds of Formula (IIcr) neither $X^{21cr}$ nor $X^{22cr}$ are hydrogen.

Suitably in the compounds of Formula (IIcr), the compounds are in the form of a phosphate prodrug.

Suitably in the compounds of Formula (IIcr), the compounds are in the form of a —C(O)CH(NH$_2$)CH(CH$_3$)$_2$ prodrug.

Included in the compounds of the invention and used in the methods of the invention are compounds of Formula (IIIcr):

(IIIcr)

wherein:
  $X^{31cr}$ and $X^{32cr}$ are independently selected from:
    hydrogen,
    cyano,
    fluoro,
    chloro,
    bromo,
    iodo,
    $C_{1-6}$alkyl,
    —OC$_{1-6}$alkyl,
    cycloalkyl, and
    —SH;
  $Y^{2cr}$ is selected from: S, NH, and NR$^z$;
  $R^{31cr}$ is selected from:
    $C_{1-6}$alkyl,
    $R^e$,
    —OC$_{1-6}$alkyl,
    —OR$^{e1}$,
    —NHR$^{a1}$,
    —NR$^{b1}$R$^{c1}$,
    aryl,
    aryl substituted from 1 to 4 times by $R^{d1}$,
    heteroaryl,
    heteroaryl substituted from 1 to 4 times by $R^{d1}$,
    cycloalkyl,
    cycloalkyl substituted from 1 to 4 times by $R^{d1}$,
    heterocycloalkyl,
    heterocycloalkyl substituted from 1 to 4 times by $R^{d1}$,
    —SH, and
    —SR$^{a1}$;
  $R^{32cr}$ is selected from:
    hydrogen,
    $C_{1-3}$alkyl, and
    $C_{1-3}$alkyl substituted from 1 to 4 times by fluoro;
  $R^{33cr}$ is selected from:
    aryl,
    aryl substituted from 1 to 4 times by $R^{d1}$,
    heteroaryl, and
    heteroaryl substituted from 1 to 4 times by $R^{d1}$;
  $R^{34cr}$ is selected from:
    hydrogen,
    $C_{1-3}$alkyl, and
    $C_{1-3}$alkyl substituted from 1 to 4 times by fluoro;

$R^{35cr}$ is selected from:
amino,
—NH$R^{a1}$,
—N$R^{b1}R^{c1}$,
aryl,
aryl substituted from 1 to 4 times by $R^{d1}$,
—O$C_{1-6}$alkyl,
—O$R^{e1}$,
—SH, and
—S$R^{a1}$;
where:
each $R^{a1}$ is independently selected from
$C_{1-6}$alkyl,
$R^{e1}$,
aryl,
heteroaryl,
cycloalkyl,
heterocycloalkyl, and
heterocycloalkyl substituted from 1 to 4 times by $R^{d1}$;
$R^{b1}$ and $R^{c1}$ are independently selected from:
$C_{1-6}$alkyl,
$R^{e1}$,
—O$R^{e1}$,
aryl,
aryl substituted from 1 to 4 times by $R^{d1}$,
heteroaryl,
heteroaryl substituted from 1 to 4 times by $R^{d1}$;
cycloalkyl,
cycloalkyl substituted from 1 to 4 times by $R^{d1}$,
heterocycloalkyl, and
heterocycloalkyl substituted from 1 to 4 times by $R^{d1}$, or
$R^{b1}$ and $R^{c1}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
bromo,
iodo,
$C_{1-6}$alkyl,
$R^{e1}$,
aryl,
aryl substituted from 1 to 4 times by $R^{d1}$,
cycloalkyl,
cycloalkyl substituted from 1 to 4 times by $R^{d1}$,
heterocycloalkyl, and
heterocycloalkyl substituted from 1 to 4 times by $R^{d1}$,
$C_{1-4}$alkoxy,
$C_{1-4}$alkoxy substituted with from 1 to 6 substituents independently selected from: fluoro, oxo, —OH, —COOH, —NH$_2$, and —CN,
—CN,
oxo,
—OH,
—COOH,
—NO$_2$,
—NH$_2$,
—N(H)$C_{1-4}$alkyl,
—N(H)$R^{e1}$,
—N($C_{1-4}$alkyl)$_2$,
—ONHC(NH)NH$_2$,
—Oheterocycloalkyl,
—NHcycloalkyl,
—NHheterocycloalkyl,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
3-pyrrolidinylpropyl,
2-cyclopropyl methyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;
each $R^{d1}$ is independently selected from:
fluoro,
chloro,
bromo,
iodo,
$C_{1-6}$alkyl,
$R^{e1}$,
heteroaryl,
heteroaryl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
cycloalkyl,
cycloalkyl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro,
heterocycloalkyl,
heterocycloalkyl substituted from 1 to 4 times by $R^x$,
where $R^x$ is selected from: fluoro, oxo, $C_{1-6}$alkyl, and $C_{1-6}$alkyl
substituted with from 1 to 6 substituents independently selected
from: fluoro, oxo, —OH, —COOH, —NH$_2$, and —CN,
aryl,
aryl substituted from 1 to 4 times by $R^{xa}$,
where $R^{xa}$ is selected from aryl, heteroaryl, cycloalkyl, heterocyloalkyl, $C_{1-6}$alkyl, and $C_{1-6}$alkyl substituted from 1 to 6 times by fluoro, $C_{1-4}$alkoxy,
$C_{1-4}$alkoxy substituted with from 1 to 4 substituents independently selected from: fluoro and —NH$_2$,
—Oaryl,
—C(O)H,
—C(O)R$^{zz}$,
—C(O)aryl,
—C(O)heteroaryl,
—OC(O)H,
—CO(O)R$^{zz}$,
—OC(O)aryl,
—OC(O)heteroaryl,
mercapto,
—SR$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)H,
—S(O)R$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)$_2$H,
—S(O)$_2$R$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—OS(O)$_2$R$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—S(O)$_2$NH$_2$,
—S(O)$_2$NHR$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—NHS(O)$_2$H,
—NHS(O)$_2$R$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—NHC(O)H,
—NHC(O)R$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—C(O)NH$_2$,
—C(O)NHR$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
—C(O)OH,
—C(O)OR$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
oxo,
hydroxy,
amino,
—NR$^{x1a}$R$^{x2a}$,
 where R$^{x1a}$ and R$^{x2a}$ are each independently selected from —S(O)$_2$C$_{1-6}$alkyl, and $C_{1-6}$alkyl,
—NHR$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
nitro,
cyano,
boronic acid,
—NHC(O)NH$_2$, and
—NHC(O)NHR$^{xa}$,
 where R$^{xa}$ is selected from aryl, heteroaryl, cycloalkyl, heterocyloalkyl, $C_{1-6}$alkyl, and $C_{1-6}$alkyl substituted from 1 to 6 times by fluoro;
each R$^{e1}$ is independently selected from:
 $C_{1-6}$alkyl substituted with from 1 to 9 substituents independently selected from:
 fluoro,
 chloro,
 bromo,
 iodo,
 $C_{1-6}$alkyl,
 —OC$_{1-6}$alkyl,
 —OC$_{1-6}$alkyl substituted with from 1 to 6 substituents independently selected from: fluoro, oxo, —OH, —COOH, —NH$_2$, and —CN,
 mercapto,
 —SR$^{xa}$,
  where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
 —S(O)H,
 —S(O)R$^{xa}$,
  where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
 —S(O)$_2$H,
 —S(O)$_2$R$^{xa}$,
  where R$^{xa}$ is selected from aryl, heteroaryl, cycloalkyl, heterocyloalkyl, $C_{1-6}$alkyl, and $C_{1-6}$alkyl substituted from 1 to 6 times by fluoro,
 oxo,
 hydroxy,
 amino,
 —NHR$^{xx}$,
  where R$^{xx}$ is selected from aryl, heteroaryl, cycloalkyl, heterocyloalkyl, $C_{1-6}$alkyl, and $C_{1-6}$alkyl substituted with from 1 to 6 substituents independently selected from: fluoro, oxo, —OR$^{xy}$, —COOH, —CN, —OC$_{1-5}$alkyl, —OC$_{1-5}$alkyl substituted from 1 to 6 times by fluoro and —NR$^{xy}$R$^{xz}$, where R$^{xy}$ and R$^{xz}$ are independently selected from: hydrogen, aryl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
 —NR$^{x1x}$R$^{x2x}$,
  where R$^{x1x}$ and R$^{x2x}$ are each independently selected from $C_{1-4}$alkyl, and $C_{1-4}$alkyl substituted with from 1 to 4 substituents independently selected from: fluoro, oxo, and —OH,
guanidino,
—C(O)OH,
—C(O)OR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—C(O)NHR$^{xa}$,
  where R$^{xa}$ is selected from aryl, heteroaryl, cycloalkyl, and heterocyloalkyl,
aryl,
aryl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—Oaryl,
—Oaryl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
heteroaryl,
heteroaryl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—Oheteroaryl,
—Oheteroaryl substituted from 1 to 4 times by R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
cycloalkyl,
cycloalkyl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
heterocycloalkyl,
heterocycloalkyl substituted from 1 to 4 times by R$^{x}$,
  where R$^{x}$ is selected from aryl, heteroaryl, cycloalkyl, heterocyloalkyl, C$_{1-6}$alkyl, and C$_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—NHS(O)$_2$H,
—NHS(O)$_2$R$^{xa}$,
  where R$^{xa}$ is selected from aryl, heteroaryl, cycloalkyl, heterocyloalkyl, C$_{1-6}$alkyl, and C$_{1-6}$alkyl substituted from 1 to 6 times by fluoro,
—NHC(O)NHR$^{xa}$,
  where R$^{xa}$ is selected from heteroaryl, cycloalkyl, and heterocyloalkyl,
nitro, and
cyano;
R$^{z}$ is selected from
  C$_{1-6}$alkyl,
  R$^{e1}$,
  cycloalkyl,
  cycloalkyl substituted from 1 to 4 times by R$^{d1}$,
  heterocycloalkyl, and
  heterocycloalkyl substituted from 1 to 4 times by R$^{d1}$;
R$^{zz}$ is selected from
  C$_{1-6}$alkyl, and
  R$^{e1}$;
provided that:
  X$^{31cr}$ and X$^{32cr}$ are not both hydrogen;
or a pharmaceutically acceptable salt or prodrug thereof.

Suitably in the compounds of Formula (IIIcr), neither X$^{31cr}$ nor X$^{32cr}$ are hydrogen.

Suitably in the compounds of Formula (IIIcr), the compounds are in the form of a phosphate prodrug.

Suitably in the compounds of Formula (IIIcr), the compounds are in the form of a —C(O)CH(NH$_2$)CH(CH$_3$)$_2$ prodrug.

This invention relates to novel compounds of Formula (IVccr) and to the use of compounds of Formula (IVccr) in the methods of the invention:

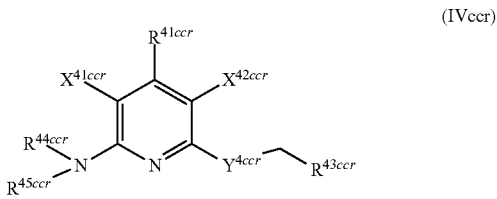

(IVccr)

wherein:
X$^{41ccr}$ and X$^{42ccr}$ are independently selected from: —CN, methyl, fluoro, chloro, bromo and iodo;
Y$^{4ccr}$ is selected from: S and NH;
R$^{41ccr}$ is selected from:
  C$_{1-6}$alkyl,
  C$_{1-6}$alkyl substituted with from 1 to 9 substituents independently selected from: fluoro, chloro, bromo, iodo, oxo, C$_{1-4}$alkyloxy, —OH, —COOH, —NH$_2$ —N(H)C$_{1-4}$alkyl, —N(C$_{1-4}$alkyl)$_2$ and —CN,
  C$_{1-4}$alkyloxy,
  C$_{1-4}$alkyloxy substituted from 1 to 4 times by fluoro,
  —N(H)C$_{1-4}$alkyl,
  —N(C$_{1-4}$alkyl)$_2$,
  —SC$_{1-4}$alkyl,
  aryl,
  aryl substituted with from 1 to 4 substituents independently selected from:
    fluoro,
    chloro,
    bromo,
    iodo,
    C$_{1-6}$alkyl,
    C$_{1-6}$alkyl substituted with from 1 to 9 substituents independently selected from: fluoro, chloro, bromo, iodo, oxo, —OH, —NH$_2$ and —CN,
    C$_{1-4}$alkoxy,
    —CN,
    oxo, —OH,
—NO$_2$, and
—NH$_2$,
heteroaryl,
heteroaryl substituted with from 1 to 4 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —OH, —NH$_2$ and —CN,
C$_{1-4}$alkoxy,
—CN,
oxo,
—OH,
—NO$_2$, and
—NH$_2$,
cycloalkyl,
cycloalkyl substituted with from 1 to 4 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —OH, —NH$_2$ and —CN,
C$_{1-4}$alkoxy,
—CN,
oxo,
—OH,
—NO$_2$, and
—NH$_2$;
R$^{43ccr}$ is selected from:
aryl,
aryl substituted with from 1 to 4 substituents independently selected from:
fluoro,
chloro,
bromo,
iodo,
C$_{1-4}$alkoxy,
C$_{1-4}$alkoxy substituted with from 1 to 3 substituents independently selected from: fluoro, chloro, oxo, —OH, —NH$_2$, —NHCH$_3$, and N(CH$_3$)$_2$,
C$_{1-6}$alkyl,
C$_{1-6}$alkyl substituted with from 1 to 9 substituents independently selected from: fluoro, chloro, bromo, iodo, oxo, —S(O)$_2$C$_{1-4}$alkyl, —CN, —OR$^{49}$ and —NR$^{46}$R$^{47}$,
where R$^{46}$ and R$^{47}$ are independently selected from: hydrogen, —S(O)$_2$CH$_3$, pyrazole, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—CN,
oxo,
—OH,
heterocycloalkyl,
heterocycloalkyl independently substituted once or twice with a substituent selected from: fluoro and oxo,
—N(CH$_3$)S(O)$_2$CFH$_2$,
—N(CH$_3$)S(O)$_2$CF$_2$H,
—N(CH$_3$)S(O)$_2$CF$_3$,
—OS(O)$_2$CH$_3$,
—S(O)$_2$NH$_2$,
—S(O)$_2$NHCH$_3$,
—NR$^{80a'}$R$^{81a'}$ where R$^{80a'}$ and R$^{81a'}$ are independently selected form: hydrogen, —S(O)$_2$CH$_3$, phenyl, C$_{1-5}$alkyl and C$_{1-5}$alkyl substituted with from 1 to 4 substituents independently selected from: fluoro, oxo, —OH, —NH$_2$, —OC$_{1-5}$alkyl, —OC$_{1-5}$alkyl substituted from 1 to 6 times by fluoro and —COOH,
boronic acid,
—NO$_2$, and
—NH$_2$,
heteroaryl, and
heteroaryl substituted with from 1 to 4 substituents independently selected from:
fluoro,
chloro,
bromo,
iodo,
C$_{1-6}$alkyl,
C$_{1-6}$alkyl substituted with from 1 to 9 substituents independently selected from: fluoro, chloro, bromo, iodo, oxo, —CN, —OR$^{49}$ and —NR$^{46}$R$^{47}$,
where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
C$_{1-4}$alkoxy,
—CN,
oxo,
—OH,
—S(O)$_2$NH$_2$,
—S(O)$_2$NHCH$_3$,
—NO$_2$, and
—NH$_2$; and
R$^{44ccr}$ and R$^{45ccr}$ are independently selected from:
hydrogen,
C$_{1-6}$alkyl,
C$_{1-6}$alkyl substituted with from 1 to 9 substituents independently selected from: phenyl, morpholino, triazolyl, imidazolyl, pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)C(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino, where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and CH$_2$NH$_2$, cycloalkyl,
cycloalkyl substituted with from one to five substituents independently selected from:
   fluoro,
   chloro,
   —OH,
   C$_{1-6}$alkyl, and
   C$_{1-6}$alkyl substituted with from 1 to 9 substituents independently selected from: fluoro and chloro;
heterocycloalkyl, and
heterocycloalkyl substituted with from 1 to 5 substituents independently selected from:
   fluoro,
   chloro,
   bromo,
   iodo,
   C$_{1-6}$alkyl,
   C$_{1-6}$alkyl substituted with from 1 to 9 substituents independently selected from: fluoro, chloro, bromo, iodo, oxo, —OH, —NH$_2$ and —CN,
   aryl,
   C$_{1-4}$alkoxy,
   C$_{1-4}$alkoxy substituted with from 1 to 4 substituents independently selected from: fluoro, oxo, —OH, —COOH, —NH$_2$, and —CN,
   —CN,
   oxo,
   —OH,
   —COOH,
   —NO$_2$,
   —NH$_2$, and
   SO$_2$NH$_2$, or R$^{44ccr}$ and R$^{45ccr}$ are taken together with the nitrogen to which they are attached, and optionally from 1 to 3 additional heteroatoms independently selected from O, N, and S, to form a heterocycloalkyl, which is optionally substituted with from 1 to 5 substituents independently selected from:
   fluoro,
   chloro,
   bromo,
   iodo,
   C$_{1-6}$alkyl,
   C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl-, —OH, —NH$_2$, —N(H)C$_{1-5}$alkyl, aminoheterocycloalkyl-, —N(C$_{1-5}$alkyl)$_2$, —CN, —N(C$_{1-4}$alkyl)(CH$_2$OCH$_3$), and —NHC$_{1-4}$alkyl substituted by one or two substituents independently selected from oxo, NH$_2$, and —OH,
   aryl,
   cycloalkyl,
   heterocycloalkyl,
   heterocycloalkyl substituted with from 1 to 9 substituents independently selected from: C$_{1-6}$alkyl, —C$_{1-6}$alkylOH, fluoro, —C$_{1-6}$alkylNH$_2$, chloro, bromo, iodo, oxo, —OH, —NH$_2$ and —CN,
   C$_{1-4}$alkoxy,
   C$_{1-4}$alkoxy substituted with from 1 to 4 substituents independently selected from: fluoro, oxo, —OH, —COOH, —NH$_2$, and —CN,
   —CN,
   oxo,
   —OH,
   —OP(O)(OH)$_2$,
   —COOH,
   —NO$_2$,
   —NH$_2$,
   —N(H)C$_{1-5}$alkyl,
   —N(H)C$_{1-6}$alkyl substituted with from 1 to 9 substituents independently selected from: fluoro, chloro, bromo, iodo, C$_{1-4}$alkoxy, oxo, phenyl, cycloalkyl, aminoC$_{1-4}$alkoxy, heterocycloalkyl, methylheterocycloalkyl, —OH, —NH$_2$, —N(H)C$_{1-4}$alkyl, —N(C$_{1-4}$alkyl)$_2$, and —CN,
   —Ooxetanyl,
   —ONHC(NH)NH$_2$,
   —NHcyclopropyl,
   —NHoxetanyl,
   —N(C$_{1-5}$alkyl)$_2$,
   —S(O)$_2$CH$_2$CH$_3$,
   S(O)$_2$CH$_2$CH$_2$CH$_3$,
   —S(O)$_2$CH$_3$,
   —SO$_2$NH$_2$,
   —S(O)$_2$phenyl,
   benzoyl,
   benzylamino,
   -propylpyrrolidinyl,
   -methylcyclopropyl,
   cyclobutylamino,
   cyclobutyl-N(CH$_3$)—,
   piperidinyl,
   imidazolyl,
   morpholinyl,
   morpholinylmethyl,
   methylpiperazinylmethyl,
   methylpiperazinyl,
   pyrrolidinyl,
   pyrrolidinylmethyl,
   (methoxypyridinylmethyl)amino,
   methylpyrrolidinyl,
   difluoropyrrolidinyl,
   dimethylpyrrolidinyl,
   (methylcyclopropylmethyl)amino,
   hydroxymethylpyrrolidinyl,
   fluoropyrrolidinyl,
   fluorophenylmethylamino,
   piperazinlymethyl,
   oxazolidinyl,
   (methyloxetanmethyl)amino,
   (methylcyclobutylmethyl)amino,
   oxoimidazolidinyl, and
   2-hydroxyethylpiperidinyl;

provided that:
R$^{44ccr}$ and R$^{45ccr}$ are not both hydrogen;
or a pharmaceutically acceptable salt or prodrug thereof.

Suitably in the compounds of Formula (IVccr), the compounds are in the form of a phosphate prodrug.

Suitably in the compounds of Formula (IVccr), the compounds are in the form of a —C(O)CH(NH$_2$)CH(CH$_3$)$_2$ prodrug.

Suitably in the compounds of Formula (IVccr) neither R$^{44ccr}$ nor R$^{45ccr}$ is hydrogen.

Suitably in the compounds of Formula (IVccr) R$^{43ccr}$ is aryl substituted with from 1 to 4 substituents independently selected from:
fluoro,
chloro,
bromo,
iodo,
heterocycloalkyl,
heterocycloalkyl independently substituted once or twice a substituent selected from: fluoro and oxo,
—OS(O)$_2$CH$_3$,
—N(CH$_3$)S(O)$_2$CH$_3$,
C$_{1-6}$alkyl substituted with from 1 to 9 substituents independently selected from: fluoro, chloro, bromo, iodo, oxo, —S(O)$_2$C$_{1-4}$alkyl, —CN, —OR$^{49}$ and —NR$^{46}$R$^{47}$,
where R$^{46}$ and R$^{47}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{48}$R$^{49}$, where R$^{48}$ and R$^{49}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (Vccr) and to the use of compounds of Formula (Vccr) in the methods of the invention:

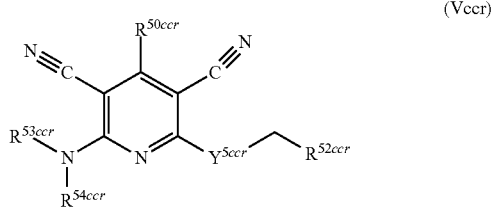

(Vccr)

wherein:
Y$^{5ccr}$ is selected from: S and NH;
R$^{50ccr}$ is selected from:
C$_{1-6}$alkyl,
C$_{1-6}$alkyl substituted with from 1 to 9 substituents independently selected from: fluoro and chloro,
—N(H)C$_{1-4}$alkyl,
—N(C$_{1-4}$alkyl)$_2$,
—SC$_{1-4}$alkyl,
C$_{1-4}$alkyloxy,
aryl,
aryl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro,
heteroaryl,
heteroaryl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro,
cycloalkyl,
cycloalkyl substituted with from one to five substituents independently selected from:
fluoro,
chloro,
—OH,
C$_{1-6}$alkyl, and
C$_{1-6}$alkyl substituted with from 1 to 9 substituents independently selected from: fluoro and chloro;
R$^{52ccr}$ is selected from:
aryl,
aryl substituted with from 1 to 4 substituents independently selected from:
fluoro,
chloro,
C$_{1-4}$alkoxy,
C$_{1-4}$alkoxy substituted with from 1 to 3 substituents independently selected from: fluoro, chloro, oxo, —OH, —NH$_2$, —NHCH$_3$, and —N(CH$_3$)$_2$,
C$_{1-6}$alkyl,
C$_{1-6}$alkyl substituted with from 1 to 9 substituents independently selected from: fluoro, chloro, bromo, iodo, oxo, —S(O)$_2$CH$_3$, —CN, —OR$^{59}$ and —NR$^{56}$R$^{57}$,
where R$^{56}$ and R$^{57}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where R$^{58}$ and R$^{59}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
oxo,
—CN,
tetrahydroisothiazolyl,
tetrahydroisothiazolyl substituted twice by oxo, tetrahydro-1,2-thiazinyl,
tetrahydro-1,2-thiazinyl substituted twice by oxo,
—N(CH$_3$)S(O)$_2$CH$_3$,
—N(CH$_3$)S(O)$_2$CFH$_2$,
—N(CH$_3$)S(O)$_2$CF$_2$H,
—N(CH$_3$)S(O)$_2$CF$_3$,
—OS(O)$_2$CH$_3$,
—S(O)$_2$NH$_2$,
—S(O)$_2$NHCH$_3$,
—NR$^{80a'}$R$^{81a'}$ where R$^{80a'}$ and R$^{81a'}$ are independently selected form: hydrogen, —S(O)$_2$CH$_3$, phenyl, C$_{1-5}$alkyl and C$_{1-5}$alkyl substituted with from 1 to 4 substituents independently selected from: fluoro, oxo, —OH, —NH$_2$, —OC$_{1-5}$alkyl, —$OC_{1-5}$alkyl substituted from 1 to 6 times by fluoro and —COOH, and
—OH;
heteroaryl, and
heteroaryl substituted with from 1 to 4 substituents independently selected from:
fluoro,
chloro,
$C_{1-6}$alkyl,
$C_{1-6}$alkyl substituted with from 1 to 9 substituents independently selected from: fluoro, chloro, bromo, iodo, oxo, —CN, —$OR^{59}$ and —$NR^{56}R^{57}$, where $R^{56}$ and $R^{57}$ are independently selected from: hydrogen, —$S(O)_2CH_3$, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro, —COOH and —$NR^{58}R^{59}$, where $R^{58}$ and $R^{59}$ are independently selected from: hydrogen, phenyl, $C_{1-5}$alkyl and $C_{1-5}$alkyl substituted with from 1 to 4 substituents independently selected from: fluoro, oxo, —OH, —$OC_{1-5}$alkyl, —$OC_{1-5}$alkyl substituted from 1 to 6 times by fluoro and —COOH,
oxo,
—$S(O)_2NH_2$,
—$S(O)_2NHCH_3$,
—OH; and
$R^{53ccr}$ and $R^{54ccr}$ are independently selected from:
hydrogen,
$C_{1-6}$alkyl,
$C_{1-6}$alkyl substituted with from 1 to 9 substituents independently selected from: phenyl, morpholino, triazolyl, imidazolyl, —$CH_2CH_2$pyrrolidinyl, —$OC(O)NH_2$, —$OCH_2CH_2NH_2$, —$ONHC(NH_2)NH_2$, —$NHCH_2C(CH_3)_3$, —$NOCH_3$, —NHOH, —$NHCH_2CH_2F$, —$N(CH_3)CH_2CH_2OCH_3$, —$N(CH_2CH_3)_2$, —$NCH(CH_2OH)_2$, —$N(CH_2CH_2OH)_2$, —$NHCH_2CH_2OH$, —$NHCH_2CH_2NH_2$, —$N(CH_3)CH_2(CH_3)_2CH_2OH$, —$NHCH_2CH_3$, —$NHCH_2CH_2OCH_3$, —$N(CH_3)CH_2CH_2OH$, —$NHC(O)C(O)NH_2$, —$N(CH_3)CH_2CH_2CH_2OH$, —$N(CH_3)CH_2CH(OH)CH_2OH$, —$N(CH_3)CH_2CH_2NH_2$, oxo, —$NHCH_2C(CH_3)_2CH_2OH$, —OH, —$NH_2$, —$NHCH_3$, —$NHCH_2CH_2CH_2OH$, —$N(CH_3)_2$, —$N(CH_3)CH_2CH_3$, —$NHOC(CH_3)_2NH_2$, —$N(CH_3)CH_2$cyclopropyl, —$NHCH_2$cyclopropyl, —NHoxetanyl, —$NCH_2CH_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —$NH_2$, —$N(CH_3)_2$, hydroxymethyl, oxo, —OH, and —$CH_2NH_2$,
cycloalkyl,
cycloalkyl substituted with from one to five substituents independently selected from:
fluoro,
chloro,
—OH,
$C_{1-6}$alkyl, and
$C_{1-6}$alkyl substituted with from 1 to 9 substituents independently selected from: fluoro and chloro;

heterocycloalkyl, and
heterocycloalkyl substituted with from 1 to 5 substituents independently selected from:
fluoro,
chloro,
$C_{1-6}$alkyl,
$C_{1-6}$alkyl substituted with from 1 to 9 substituents independently selected from: fluoro and chloro,
$C_{1-4}$alkoxy, and
—OH, or
$R^{53ccr}$ and $R^{54ccr}$ are taken together with the nitrogen to which they are attached, and optionally from 1 to 3 additional heteroatoms, to form a heterocycloalkyl, which is optionally substituted with from 1 to 5 substituents independently selected from:
fluoro,
chloro,
$C_{1-6}$alkyl,
$C_{1-6}$alkyl substituted with from 1 to 9 substituents independently selected from: fluoro, chloro, $C_{1-4}$alkoxy, oxo, phenyl, cycloalkyl, heterocycloalkyl, methylheterocycloalkyl, —OH, —$NH_2$, —$N(H)C_{1-5}$alkyl, aminoheterocycloalkyl, —$N(C_{1-5}$alkyl$)_2$, —CN, —$N(C_{1-4}$alkyl$)(CH_2OCH_3)$, and —$NHC_{1-4}$alkyl substituted by one or two substituents independently selected from oxo, $NH_2$, and —OH,
heterocycloalkyl,
heterocycloalkyl substituted with from 1 to 9 substituents independently selected from: $C_{1-6}$alkyl, —$C_{1-6}$alkylOH, fluoro, —$C_{1-6}$alkyl$NH_2$, chloro, oxo and —OH,
$C_{1-4}$alkoxy,
$C_{1-4}$alkoxy substituted with from 1 to 4 substituents independently selected from: fluoro, oxo, —OH, —COOH, —$NH_2$, and —CN,
—CN,
oxo,
—OH,
—$OP(O)(OH)_2$,
—COOH,
—$CONH_2$,
—$NH_2$,
—$N(H)C_{1-4}$alkyl,
—$N(H)C_{1-6}$alkyl substituted with from 1 to 9 substituents independently selected from: fluoro, chloro, $C_{1-4}$alkoxy, oxo, phenyl, cycloalkyl, amino$C_{1-4}$alkoxy, heterocycloalkyl, methylheterocycloalkyl, —OH, —$NH_2$, —$N(H)C_{1-4}$alkyl, —$N(C_{1-4}$alkyl$)_2$, and —CN,
—Ooxetanyl,
—$ONHC(NH)NH_2$,
—NHcyclopropyl,
—NHoxetanyl,
—$N(C_{1-4}$alkyl$)_2$,
—$S(O)_2CH_2CH_3$,
$S(O)_2CH_2CH_3$,
—$S(O)_2CH_3$,
—$S(O)_2$phenyl,
benzoyl,
benzylamino,
-propylpyrrolidinyl,
-methylcyclopropyl,
cyclobutylamino,
cyclobutyl-$N(CH_3)$—,
piperidinyl,
imidazolyl, morpholinyl,
morpholinylmethyl,
methylpiperazinylmethyl,
methylpiperazinlyl
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
fluorophenylmethylamino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
$R^{53ccr}$ and $R^{54ccr}$ are not both hydrogen;
or a pharmaceutically acceptable salt or prodrug thereof.

Suitably in the compounds of Formula (Vccr), the compounds are in the form of a phosphate prodrug.

Suitably in the compounds of Formula (Vccr), the compounds are in the form of a —C(O)CH(NH$_2$)CH(CH$_3$)$_2$ prodrug.

Suitably in the compounds of Formula (Vccr) neither $R^{53ccr}$ nor $R^{54ccr}$ is hydrogen.

Suitably in the compounds of Formula (Vccr) $R^{52ccr}$ is aryl substituted with from 1 to 4 substituents independently selected from:
fluoro,
chloro,
tetrahydrothiazolyl,
tetrahydrothiazolyl substituted twice by oxo,
tetrahydrothiazinyl,
tetrahydrothiazinyl substituted twice by oxo,
—N(CH$_3$)S(O)$_2$CH$_3$,
—OS(O)$_2$CH$_3$,
$C_{1-6}$alkyl,
$C_{1-6}$alkyl substituted with from 1 to 9 substituents independently selected from: fluoro, chloro, bromo, iodo, oxo, —S(O)$_2$CH$_3$, —CN, —OR$^{59}$ and —NR$^{56}$R$^{57}$,
where $R^{56}$ and $R^{57}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{58}$R$^{59}$, where $R^{58}$ and $R^{59}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (VIccr) and to the use of compounds of Formula (VIccr) in the methods of the invention:

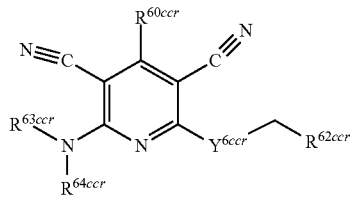

(VIccr)

wherein:
$Y^{6ccr}$ is selected from: S and NH;
$R^{60ccr}$ is selected from:
$C_{1-3}$alkyl,
$C_{1-3}$alkyl substituted with from 1 to 6 substituents independently selected from: fluoro and chloro,
—N(H)C$_{1-3}$alkyl,
—N(C$_{1-3}$alkyl)$_2$,
—SC$_{1-4}$alkyl,
$C_{1-3}$alkyloxy,
aryl,
aryl substituted with from one to 3 substituents independently selected from:
fluoro,
chloro,
—OH, and
$C_{1-3}$alkyl,
heteroaryl,
heteroaryl substituted with from one to 3 substituents independently selected from:
fluoro,
chloro,
—OH, and
$C_{1-3}$alkyl,
cycloalkyl,
cycloalkyl substituted with from one to 3 substituents independently selected from:
fluoro,
chloro,
—OH, and
$C_{1-3}$alkyl;
$R^{62ccr}$ is selected from:
phenyl,
phenyl substituted with from 1 to 4 substituents independently selected from:
fluoro,
chloro,
—CN,
oxo,
$C_{1-4}$alkoxy,
$C_{1-4}$alkoxy substituted with from 1 to 3 substituents independently selected from: fluoro, chloro, oxo, —OH, —NH$_2$, —NHCH$_3$, and —N(CH$_3$)$_2$,
$C_{1-6}$alkyl,
$C_{1-6}$alkyl substituted with from 1 to 5 substituents independently selected from: fluoro, chloro, bromo, iodo, oxo, —S(O)$_2$CH$_3$, —CN, —OR$^{69}$ and —NR$^{66}$R$^{67}$,
where $R^{66}$ and $R^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where $R^{68}$ and $R^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH, tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—N(CH$_3$)S(O)$_2$CFH$_2$,
—N(CH$_3$)S(O)$_2$CF$_2$H,
—N(CH$_3$)S(O)$_2$CF$_3$,
—OS(O)$_2$CH$_3$,
—S(O)$_2$NH$_2$,
—S(O)$_2$NHCH$_3$, and
—NR$^{80a'}$R$^{81a'}$ where R$^{80a'}$ and R$^{81a'}$ are independently selected form: hydrogen, —S(O)$_2$CH$_3$, phenyl, $C_{1-5}$alkyl and $C_{1-5}$alkyl substituted with from 1 to 4 substituents independently selected from: fluoro, oxo, —OH, —NH$_2$, —OC$_{1-5}$alkyl, —OC$_{1-5}$alkyl substituted from 1 to 6 times by fluoro and —COOH, hetroaryl, and
hetroaryl substituted with from 1 to 4 substituents independently selected from:
fluoro,
chloro,
$C_{1-6}$alkyl,
$C_{1-6}$alkyl substituted with from 1 to 5 substituents independently selected from: fluoro, chloro, bromo, iodo, oxo, —S(O)$_2$CH$_3$, —CN, —OR$^{69}$ and —NR$^{66}$R$^{67}$,
where R$^{66}$ and R$^{67}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where R$^{68}$ and R$^{69}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
—S(O)$_2$NH$_2$, and
—S(O)$_2$NHCH$_3$; and R$^{63ccr}$ and R$^{64ccr}$ are independently selected from:
hydrogen,
$C_{1-4}$alkyl,
$C_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cycloalkyl,
cycloalkyl substituted with from 1 to 5 substituents independently selected from:
fluoro,
chloro,
—OH, and
$C_{1-6}$alkyl,
heterocycloalkyl, and
heterocycloalkyl substituted with from 1 to 5 substituents independently selected from:
fluoro,
chloro,
—OH, and
$C_{1-6}$alkyl, or
R$^{63ccr}$ and R$^{64ccr}$ are taken together with the nitrogen to which they are attached, and optionally from 1 to 3 additional heteroatoms independently selected from O, N, and S, to form a heterocycloalkyl, to form a heterocycloalkyl, which is optionally substituted with from 1 to 5 substituents independently selected from:
fluoro,
chloro,
—OH,
—OP(O)(OH)$_2$,
—CN,
$C_{1-6}$alkyl,
$C_{1-6}$alkyl substituted with from 1 to 9 substituents independently selected from: fluoro, chloro, $C_{1-4}$alkoxy, oxo, phenyl, cycloalkyl, heterocycloalkyl, methylheterocycloalkyl, —OH, —NH$_2$, —N(H)C$_{1-6}$alkyl, aminoheterocycloalkyl, —N(C$_{1-6}$alkyl)$_2$, —CN, —N(C$_{1-4}$alkyl)(CH$_2$OCH$_3$), and —NHC$_{1-4}$alkyl substituted by one or two substituents independently selected from oxo, NH$_2$, and —OH,
heterocycloalkyl,
heterocycloalkyl substituted with from 1 to 9 substituents independently selected from: $C_{1-6}$alkyl, —C$_{1-6}$alkylOH, fluoro, chloro, oxo and —OH,
$C_{1-4}$alkoxy,
$C_{1-4}$alkoxy substituted with from 1 to 4 substituents independently selected from: fluoro, oxo, —OH, —COOH, —NH$_2$, and —CN,
oxo,
—NH$_2$,
—N(H)C$_{1-4}$alkyl,
—N(H)C$_{1-6}$alkyl substituted with from 1 to 9 substituents independently selected from: fluoro, chloro, C$_{1-4}$alkoxy, oxo, phenyl, cycloalkyl, aminoC$_{1-4}$alkoxy, heterocycloalkyl, methylheterocycloalkyl, —OH, —NH$_2$, —N(H)C$_{1-4}$alkyl, —N(C$_{1-4}$alkyl)$_2$, and —CN,
—ONHC(NH)NH$_2$,
—Ooxetanyl,
—ONHC(NH)NH$_2$, —NHcyclopropyl,
—NHoxetanyl,
—N(C$_{1-4}$alkyl)$_2$,
—S(O)$_2$CH$_2$CH$_3$,
S(O)$_2$CH$_2$CH$_2$CH$_3$,
—S(O)$_2$CH$_3$,
—S(O)$_2$phenyl,
benzoyl,
benzylamino,
-propylpyrrolidinyl,
-methylcyclopropyl,
cyclobutylamino,
cyclobutyl-N(CH$_3$)—,
piperidinyl,
imidazolyl,
morpholinyl,
morpholinylmethyl,
methylpiperazinylmethyl,
methyl piperazinyl,
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
(fluorophenylmethyl)amino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
$R^{63ccr}$ and $R^{64ccr}$ are not both hydrogen;
or a pharmaceutically acceptable salt or prodrug thereof.

Suitably in the compounds of Formula (VIccr), the compounds are in the form of a phosphate prodrug.

Suitably in the compounds of Formula (VIccr), the compounds are in the form of a —C(O)CH(NH$_2$)CH(CH$_3$)$_2$ prodrug.

Suitably in the compounds of Formula (VIccr) neither $R^{63ccr}$ nor $R^{64ccr}$ is hydrogen.

Suitably in the compounds of Formula (VIccr) $R^{62ccr}$ is phenyl substituted with from 1 to 4 substituents independently selected from:
fluoro,
chloro,
tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—OS(O)$_2$CH$_3$,
C$_{1-6}$alkyl,
C$_{1-6}$alkyl substituted with from 1 to 5 substituents independently selected from: fluoro, chloro, bromo, iodo, oxo, —S(O)$_2$CH$_3$, —CN, —OR$^{69}$ and —NR$^{66}$R$^{67}$, where R$^{66}$ and R$^{67}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{68}$R$^{69}$, where R$^{68}$ and R$^{69}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (VIIccr) and to the use of compounds of Formula (VIIccr) in the methods of the invention:

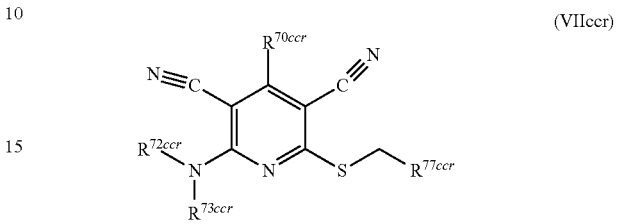

(VIIccr)

wherein:
$R^{70ccr}$ is selected from:
ethyl,
ethyl substituted from 1 to 4 times by fluoro,
—NCH$_3$,
—SCH$_3$,
ethoxy,
methoxy,
phenyl,
furanyl,
cyclopropyl,
cyclopropyl substituted once or twice by fluoro;
$R^{77ccr}$ is selected from:
phenyl,
phenyl substituted with from 1 to 4 substituents independently selected from:
fluoro,
chloro,
—CN,
oxo,
C$_{1-4}$alkoxy,
C$_{1-4}$alkoxy substituted with from 1 to 3 substituents independently selected from: fluoro, chloro, oxo, —OH, —NH$_2$, —NHCH$_3$, and —N(CH$_3$)$_2$,
C$_{1-6}$alkyl,
C$_{1-6}$alkyl substituted with from 1 to 3 substituents independently selected from: fluoro, chloro, bromo, iodo, oxo, —S(O)$_2$CH$_3$, —CN, —OR$^{79a}$ and —NR$^{76a}$R$^{77a}$,
where R$^{76a}$ and R$^{77a}$ are independently selected from: hydrogen, —S(O)$_2$CH$_3$, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a}$R$^{79a}$, where R$^{78a}$ and R$^{79a}$ are independently selected from: hydrogen, phenyl, C$_{1-5}$alkyl and C$_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—N(CH$_3$)S(O)$_2$CFH$_2$, —N(CH$_3$)S(O)$_2$CF$_2$H,
—N(CH$_3$)S(O)$_2$CF$_3$,
—OS(O)$_2$CH$_3$,
—S(O)$_2$NH$_2$,
—S(O)$_2$NHCH$_3$, and
—NR$^{80a'}$R$^{81a'}$ where R$^{80a'}$ and R$^{81a'}$ are independently selected form: hydrogen, —S(O)$_2$CH$_3$, phenyl, C$_{1-5}$alkyl and C$_{1-5}$alkyl substituted with from 1 to 4 substituents independently selected from: fluoro, oxo, —OH, —NH$_2$, —OC$_{1-5}$alkyl, —OC$_{1-5}$alkyl substituted from 1 to 6 times by fluoro and —COOH,
dihydropyridinyl,
oxo-dihydropyridinyl,
tetrahydroisoquinolinyl,
tetrahydroisoquinolinyl substituted by —C(O)CH$_3$,
thiazolyl, and
thiazolyl substituted by a substituent selected from: —C(O)CH$_3$ and —NHC(O)CH$_3$;
R$^{72ccr}$ and R$^{73ccr}$ are independently selected from:
hydrogen,
C$_{1-4}$alkyl,
C$_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cyclobutyl,
aminocyclobutyl,
tetrahydrofuran,
5-oxa-2azaspiro[3.4]octan, and
8-azabicyclo[3.2.1]octan, or
R$^{72ccr}$ and R$^{73ccr}$ are taken together with the nitrogen to which they are attached, and optionally from 1 to 3 additional heteroatoms independently selected from O, N, and S, to form a heterocycloalkyl, to form a heterocycloalkyl selected from:
pyrrolidinyl,
pyrrolo[3,4-c]pyrazolyl,
piperidinyl,
1,4diazepanyl,
piperazinyl,
6,7-dihydro-triazolo[4,5-c]pyridinyl,
2,9-diazaspiro[5.5]undecanyl,
2,8-diazaspiro[4.5]decanyl,
octahydro-1H-pyrrolo[1,2a][1,4]diazepinyl,
oxa-diazaspiro[4.5]decanyl,
oxazolyl,
morpholinyl,
1-oxa-6-azaspiro[3.4]octanyl,
2-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
hexahydropyrrolo[3,4-b]oxazinyl,
dihydronaphthyridinyl,
diazabicycloheptanyl,
1,8-diazaspiro[4.5]decanyl, and
5-oxa-2-azaspiro[3.4]octanyl,
all of which are optionally substituted with from 1 to 5 substituents independently selected from:
fluoro,
chloro,
oxo,
—OH,
—OP(O)(OH)$_2$,
—CN,
—CH$_3$,
—CH$_2$OH,
methoxy,
—CH$_2$CH$_3$,
—C(O)CH$_3$,
—C(O)NH$_2$,
—OCH$_2$CH$_2$OH,
—OCH$_2$CH$_2$NH$_2$,
—ONHC(NH)NH$_2$,
—OC(O)NH$_2$,
—Ooxetanyl,
—CH$_2$CH$_2$OH,
—CH$_2$CH$_2$CH$_2$OH,
—CH$_2$CH$_2$CH$_3$,
—CH$_2$CH$_2$OCH$_3$,
—CH$_2$CH(OH)CH$_3$,
—CH$_2$CH(OH)CH$_2$OH,
—CH$_2$C(O)OCH$_3$,
—CH$_2$C(O)NH$_2$,
—C(O)CH(CH$_3$)$_2$,
—CH$_2$CH$_2$N(CH$_3$)$_2$,
—CH$_2$CH$_2$NHCH$_2$CH$_3$,
—CH$_2$CH$_2$CH$_2$N(CH$_3$)$_2$,
—CH$_2$CH$_2$NHCH$_2$C(CH$_3$)$_3$,
—CH$_2$CH$_2$N(CH$_3$)CH$_2$OCH$_3$,
—C(CH$_3$)$_2$CH$_2$OH,
—CH$_2$C(CH$_3$)$_2$OH,
—CH$_2$C(CH$_3$)$_2$OCH$_3$,
—C(O)CH$_2$OH,
—CH$_2$isothiazolyl,
—CH$_2$thiazolyl,
—CH$_2$pyrazolyl,
—CH$_2$imidazolyl,
—CH$_2$pyridinyl,
—CH$_2$oxazolyl,
—CH$_2$pyrrolyl,
—CH$_2$pyrrolidinyl,
—CH$_2$isoxazoly,
—CH$_2$furanyl,
—CH$_2$CH$_2$morpholinyl,
—CH$_2$CH$_2$pyrrolidinyl,
—CH$_2$CH$_2$pyrrolidinylCH$_3$,
—CH$_2$CH$_2$CH$_2$pyrrolidinyl,
—C(O)phenyl, —C(O)C(tetrahydropyranyl)NH$_2$,
—NH$_2$,
—NHCH$_3$,
—N(CH$_3$)$_2$,
—NHC(O)CH$_3$,
—NHCH(CH$_3$)$_2$,
—NHCH$_2$CHF$_2$,
—NHCH$_2$C(CH$_3$)$_3$,
—NHCH$_2$CH(CH$_3$)$_2$,
—NHCH$_2$CH$_2$OCH$_3$,
—NHCH$_2$CH$_2$OH,
—NHCH$_2$CH$_2$NH$_2$,
—NHCH$_2$C(O)OH,
—NHC(O)CH$_2$NH$_2$,
—NHC(O)CH$_2$CH$_2$CH$_2$NH$_2$,
—NHCH$_2$C(O)NH$_2$,
—NHCH$_2$C(OH)(CH$_3$)$_2$,
—NHC(O)CH(CH$_3$)NH$_2$,
—NHC(O)OCH(CH$_3$)NH$_2$,
—NHC(O)CH(CH$_3$)$_2$,
—NHC(O)C(CH$_3$)$_3$,
—NHC(O)C(CH$_3$)$_2$NH$_2$,
—NHC(O)CH$_2$OH,
—NHC(O)CH(CH$_2$OH)NH$_2$,
—NHC(O)(oxetanyl)NH$_2$,
—NHC(O)OC(CH$_3$)$_3$,
—NHC(CH$_3$)$_2$C(O)OCH$_3$,
—NHcyclopropyl,
—NHoxetanyl,
—CH$_2$NH$_2$,
—CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
-propylpyrrolidinyl,
-methylcyclopropyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
(fluorophenylmethyl)amino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
$R^{72ccr}$ and $R^{73ccr}$ are not both hydrogen;
or a pharmaceutically acceptable salt or prodrug thereof.

Suitably in the compounds of Formula (VIIccr), the compounds are in the form of a phosphate prodrug.

Suitably in the compounds of Formula (VIIccr), the compounds are in the form of a —C(O)CH(NH$_2$)CH(CH$_3$)$_2$ prodrug.

Suitably in the compounds of Formula (VIIccr) neither $R^{72ccr}$ nor $R^{73ccr}$ is hydrogen.

Suitably in the compounds of Formula (VIIccr) $R^{77ccr}$ is phenyl substituted with from 1 to 4 substituents independently selected from:
fluoro,
chloro,
—CN,
oxo,
$C_{1-4}$alkoxy,
$C_{1-4}$alkoxy substituted with from 1 to 3 substituents independently selected from: fluoro, chloro, oxo, —OH, —NH$_2$, —NHCH$_3$, and —N(CH$_3$)$_2$,
tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—OS(O)$_2$CH$_3$,
$C_{1-6}$alkyl,
$C_{1-6}$alkyl substituted with from 1 to 3 substituents independently selected from: fluoro, chloro, bromo, iodo, oxo, —S(O)$_2$CH$_3$, —CN, —OR$^{79a}$ and —NR$^{76a}$R$^{77a}$, where R$^{76a}$ and R$^{77a}$ are independently selected from: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a}$R$^{79a}$, where R$^{78a}$ and R$^{79a}$ are independently selected from: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH.

This invention relates to novel compounds of Formula (Qc) and to the use of compounds of Formula (Qc) in the methods of the invention:

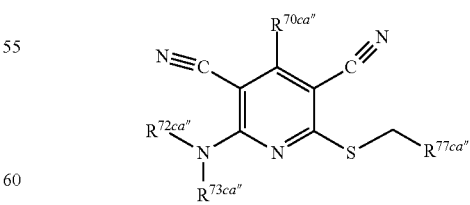

(Qc)

wherein:
$R^{70ca''}$ is selected from:
ethyl,
—OCH$_3$,
—CH$_2$CF$_3$, and cyclopropyl;
$R^{77ca''}$ is selected from:
  phenyl,
  phenyl substituted with from 1 to 4 substituents independently selected from:
    fluoro,
    chloro,
    —CN,
    oxo,
    $C_{1-4}$alkoxy,
    $C_{1-4}$alkoxy substituted with from 1 to 3 substituents independently selected from: fluoro, chloro, oxo, —OH, —NH$_2$, —NHCH$_3$, and —N(CH$_3$)$_2$,
    $C_{1-6}$alkyl,
    $C_{1-6}$alkyl substituted with from 1 to 3 substituents independently selected from: fluoro, chloro, bromo, iodo, oxo, —S(O)$_2$CH$_3$, —CN, —OR$^{79a}$ and —NR$^{76a'}$R$^{77a'}$,
      where $R^{76a}$ and $R^{77a}$ are independently selected form: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a'}$R$^{79a'}$, where $R^{78a'}$ and $R^{79a'}$ are independently selected form: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
    tetrahydroisothiazolyl,
    tetrahydroisothiazolyl substituted twice by oxo,
    tetrahydro-1,2-thiazinyl,
    tetrahydro-1,2-thiazinyl substituted twice by oxo,
    —N(CH$_3$)S(O)$_2$CFH$_2$,
    —N(CH$_3$)S(O)$_2$CF$_2$H,
    —N(CH$_3$)S(O)$_2$CF$_3$,
    —OS(O)$_2$CH$_3$,
    —S(O)$_2$NH$_2$,
    —S(O)$_2$NHCH$_3$, and
    —NR$^{80a'}$R$^{81a'}$ where $R^{80a'}$ and $R^{81a'}$ are independently selected
      form: hydrogen, —S(O)$_2$CH$_3$, phenyl, $C_{1-5}$alkyl and $C_{1-5}$alkyl substituted with from 1 to 4 substituents independently selected from: fluoro, oxo, —OH,
      —NH$_2$, —OC$_{1-5}$alkyl, —OC$_{1-5}$alkyl substituted from 1 to 6
      times by fluoro and —COOH, and
$R^{72ca''}$ and $R^{73ca''}$ selected from:
  hydrogen,
  $C_{1-4}$alkyl,
  $C_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
    where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and CH$_2$NH$_2$,
  cyclobutyl,
  aminocyclobutyl,
  tetrahydrofuran,
  5-oxa-2azaspiro[3.4]octan, and
  8-azabicyclo[3.2.1]octan, or
$R^{72a''}$ and $R^{73a''}$ are taken together with the nitrogen to which they are attached, and optionally from 1 to 3 additional heteroatoms independently selected from O, N, and S, to form a heterocycloalkyl selected from:
  pyrrolidinyl,
  pyrrolo[3,4-c]pyrazolyl,
  piperidinyl,
  1,4diazepanyl,
  piperazinyl,
  6,7-dihydro-triazolo[4,5-c]pyridinyl,
  2,9-diazaspiro[5.5]undecanyl,
  2,8-diazaspiro[4.5]decanyl,
  octahydro-1H-pyrrolo[1,2a][1,4]diazepinyl,
  oxa-diazaspiro[4.5]decanyl,
  oxazolyl,
  morpholinyl,
  1-oxa-6-azaspiro[3.4]octanyl,
  2-oxa-6-azaspiro[3.4]octanyl,
  1,7-diazaspiro[3.5]nonanyl,
  2,7-diazaspiro[3.5]nonanyl,
  2,6-diazaspiro[3.4]octanyl,
  azetidinyl,
  hexahydropyrrolo[3,4-b]oxazinyl,
  dihydronaphthyridinyl,
  diazabicycloheptanyl,
  1,8-diazaspiro[4.5]decanyl, and
  5-oxa-2-azaspiro[3.4]octanyl,
  all of which are optionally substituted with from 1 to 5 substituents independently selected from:
    fluoro,
    chloro,
    oxo,
    —OH,
    —OP(O)(OH)$_2$,
    —CN,
    —CH$_3$,
    —CH$_2$OH,
    methoxy,
    —CH$_2$CH$_3$,
    —C(O)CH$_3$,
    —C(O)NH$_2$,
    —OCH$_2$CH$_2$OH,
    —OCH$_2$CH$_2$NH$_2$,
    —ONHC(NH)NH$_2$,
    —OC(O)NH$_2$,
    —Ooxetanyl,
    —CH$_2$CH$_2$OH,
    —CH$_2$CH$_2$CH$_2$OH, —CH₂CH₂CH₃,
—CH₂CH₂OCH₃,
—CH₂CH(OH)CH₃,
—CH₂CH(OH)CH₂OH,
—CH₂C(O)OCH₃,
—CH₂C(O)NH₂,
—C(O)CH(CH₃)₂,
—CH₂CH₂N(CH₃)₂,
—CH₂CH₂NHCH₂CH₃,
—CH₂CH₂CH₂N(CH₃)₂,
—CH₂CH₂NHCH₂C(CH₃)₃,
—CH₂CH₂N(CH₃)CH₂OCH₃,
—C(CH₃)₂CH₂OH,
—CH₂C(CH₃)₂OH,
—CH₂C(CH₃)₂OCH₃,
—C(O)CH₂OH,
—CH₂isothiazolyl,
—CH₂thiazolyl,
—CH₂pyrazolyl,
—CH₂imidazolyl,
—CH₂pyridinyl,
—CH₂oxazolyl,
—CH₂pyrrolyl,
—CH₂pyrrolidinyl,
—CH₂isoxazoly,
—CH₂furanyl,
—CH₂CH₂morpholinyl,
—CH₂CH₂pyrrolidinyl,
—CH₂CH₂pyrrolidinylCH₃,
—CH₂CH₂CH₂pyrrolidinyl,
—C(O)phenyl,
—C(O)C(tetrahydropyranyl)NH₂,
—NH₂,
—NHCH₃,
—N(CH₃)₂,
—NHC(O)CH₃,
—NHCH(CH₃)₂,
—NHCH₂CHF₂,
—NHCH₂C(CH₃)₃,
—NHCH₂CH(CH₃)₂,
—NHCH₂CH₂OCH₃,
—NHCH₂CH₂OH,
—NHCH₂CH₂NH₂,
—NHCH₂C(O)OH,
—NHC(O)CH₂NH₂,
—NHC(O)CH₂CH₂CH₂NH₂,
—NHCH₂C(O)NH₂,
—NHCH₂C(OH)(CH₃)₂,
—NHC(O)CH(CH₃)NH₂,
—NHC(O)OCH(CH₃)NH₂,
—NHC(O)CH(CH₃)₂,
—NHC(O)C(CH₃)₃,
—NHC(O)C(CH₃)₂NH₂,
—NHC(O)CH₂OH,
—NHC(O)CH(CH₂OH)NH₂,
—NHC(O)(oxetanyl)NH₂,
—NHC(O)OC(CH₃)₃,
—NHC(CH₃)₂C(O)OCH₃,
—NHcyclopropyl,
—NHoxetanyl,
—CH₂NH₂,
—CH₂CH₂NH₂,
—CH₂CH₂CH₂NH₂,
—CH₂NHCH₂C(CH₃)₃,
—CH₂NHC(O)C(CH₃)₃,
—CH₂NHC(O)CH₂NH₂,
—CH₂NHC(O)CH₂OH,
—CH₂N(CH₃)₂,
—CH₂NHCH₃,
—CH₂N(CH₂CH₃)₂,
—CH₂CH₂N(CH₃)₂,
—S(O)₂CH₂CH₃,
—S(O)₂CH₂CH₂CH₃,
—S(O)₂phenyl,
—S(O)₂CH₃,
benzoyl,
benzylamino,
-propylpyrrolidinyl,
-methylcyclopropyl,
cyclobutylamino,
cyclobutyl-N(CH₃)—,
piperidinyl,
imidazolyl,
morpholinyl,
morpholinylmethyl,
methylpiperazinylmethyl,
methylpiperazinyl,
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
(fluorophenylmethyl)amino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
$R^{72a''}$ and $R^{73a''}$ are not both hydrogen;
or a pharmaceutically acceptable salt or prodrug thereof.

Suitably in the compounds of Formula (Qc), the compounds are in the form of a phosphate prodrug.

Suitably in the compounds of Formula (Qc), the compounds are in the form of a —C(O)CH(NH₂)CH(CH₃)₂ prodrug.

Suitably in the compounds of Formula (Qc) neither $R^{72a''}$ nor $R^{73a''}$ is hydrogen.

This invention relates to novel compounds of Formula (Qc1) and to the use of compounds of Formula (Qc1) in the methods of the invention:

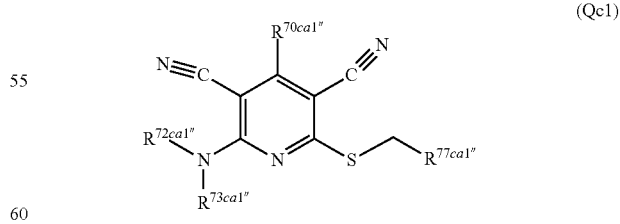

(Qc1)

wherein:
$R^{70ca1''}$ is selected from:
ethyl,
—OCH₃,
—CH₂CF₃, and
cyclopropyl;

$R^{77ca1''}$ is selected from:
 phenyl,
 phenyl substituted with from 1 to 4 substituents independently selected from:
  fluoro,
  chloro,
  —CN,
  oxo,
  $C_{1-4}$alkoxy,
  $C_{1-4}$alkoxy substituted with from 1 to 3 substituents independently selected from: fluoro, chloro, oxo, —OH, —NH$_2$, —NHCH$_3$, and —N(CH$_3$)$_2$,
  $C_{1-6}$alkyl,
  $C_{1-6}$alkyl substituted with from 1 to 3 substituents independently selected from: fluoro, chloro, bromo, iodo, oxo, —S(O)$_2$CH$_3$, —CN, —OR$^{79a}$ and —NR$^{76a'}$R$^{77a'}$,
   where $R^{76a}$ and $R^{77a}$ are independently selected form: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a'}$R$^{79a'}$, where $R^{78a'}$ and $R^{79a'}$ are independently selected form: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
  tetrahydroisothiazolyl,
  tetrahydroisothiazolyl substituted twice by oxo,
  tetrahydro-1,2-thiazinyl,
  tetrahydro-1,2-thiazinyl substituted twice by oxo,
  —OS(O)$_2$CH$_3$,
  —N(CH$_3$)S(O)$_2$CH$_3$,
  —N(CH$_3$)S(O)$_2$CFH$_2$,
  —N(CH$_3$)S(O)$_2$CF$_2$H,
  —N(CH$_3$)S(O)$_2$CF$_3$,
  —S(O)$_2$NH$_2$,
  —S(O)$_2$NHCH$_3$, and
  —NR$^{80a'}$R$^{81a'}$ where $R^{80a'}$ and $R^{81a'}$ are independently selected form: hydrogen, —S(O)$_2$CH$_3$, phenyl, $C_{1-5}$alkyl and $C_{1-5}$alkyl substituted with from 1 to 4 substituents independently selected from: fluoro, oxo, —OH, —NH$_2$, —OC$_{1-5}$alkyl, —OC$_{1-5}$alkyl substituted from 1 to 6 times by fluoro and —COOH, and
$R^{72ca1''}$ and $R^{73ca1''}$ are independently selected from:
 $C_{1-4}$alkyl,
 $C_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
  where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
 cyclobutyl,
 aminocyclobutyl,
 tetrahydrofuran,
 5-oxa-2azaspiro[3.4]octan, and
 8-azabicyclo[3.2.1]octan, or
$R^{72ca1''}$ and $R^{73ca1''}$ are taken together with the nitrogen to which they are attached, and optionally from 1 to 3 additional heteroatoms, to form a heterocycloalkyl selected from:
 pyrrolidinyl,
 pyrrolo[3,4-c]pyrazolyl,
 piperidinyl,
 1,4diazepanyl,
 piperazinyl,
 6,7-dihydro-triazolo[4,5-c]pyridinyl,
 2,9-diazaspiro[5.5]undecanyl,
 2,8-diazaspiro[4.5]decanyl,
 octahydro-1H-pyrrolo[1,2a][1,4]diazepinyl,
 oxa-diazaspiro[4.5]decanyl,
 oxazolyl,
 morpholinyl,
 1-oxa-6-azaspiro[3.4]octanyl,
 2-oxa-6-azaspiro[3.4]octanyl,
 1,7-diazaspiro[3.5]nonanyl,
 2,7-diazaspiro[3.5]nonanyl,
 2,6-diazaspiro[3.4]octanyl,
 azetidinyl,
 hexahydropyrrolo[3,4-b]oxazinyl,
 dihydronaphthyridinyl,
 diazabicycloheptanyl,
 1,8-diazaspiro[4.5]decanyl, and
 5-oxa-2-azaspiro[3.4]octanyl,
 all of which are optionally substituted with from 1 to 5 substituents independently selected from:
  fluoro,
  chloro,
  oxo,
  —OH,
  —CN,
  —CH$_3$,
  —CH$_2$OH,
  methoxy,
  —CH$_2$CH$_3$,
  —C(O)CH$_3$,
  —C(O)NH$_2$,
  —OCH$_2$CH$_2$OH,
  —OCH$_2$CH$_2$NH$_2$,
  —ONHC(NH)NH$_2$,
  —OC(O)NH$_2$,
  —Ooxetanyl,
  —CH$_2$CH$_2$OH,
  —CH$_2$CH$_2$CH$_2$OH,
  —CH$_2$CH$_2$CH$_3$,
  —CH$_2$CH$_2$OH,
  —CH$_2$CH(OH)CH$_3$,
  —CH$_2$CH(OH)CH$_2$OH,
  —CH$_2$C(O)OCH$_3$, —CH₂C(O)NH₂,
—C(O)CH(CH₃)₂,
—CH₂CH₂N(CH₃)₂,
—CH₂CH₂NHCH₂CH₃,
—CH₂CH₂CH₂N(CH₃)₂,
—CH₂CH₂NHCH₂C(CH₃)₃,
—CH₂CH₂N(CH₃)CH₂OCH₃,
—C(CH₃)₂CH₂OH,
—CH₂C(CH₃)₂OH,
—CH₂C(CH₃)₂OCH₃,
—C(O)CH₂OH,
—CH₂isothiazolyl,
—CH₂thiazolyl,
—CH₂pyrazolyl,
—CH₂imidazolyl,
—CH₂pyridinyl,
—CH₂oxazolyl,
—CH₂pyrrolyl,
—CH₂pyrrolidinyl,
—CH₂isoxazoly,
—CH₂furanyl,
—CH₂CH₂morpholinyl,
—CH₂CH₂pyrrolidinyl,
—CH₂CH₂pyrrolidinylCH₃,
—CH₂CH₂CH₂pyrrolidinyl,
—C(O)phenyl,
—C(O)C(tetrahydropyranyl)NH₂,
—NH₂,
—NHCH₃,
—N(CH₃)₂,
—NHC(O)CH₃,
—NHCH(CH₃)₂,
—NHCH₂CHF₂,
—NHCH₂C(CH₃)₃,
—NHCH₂CH(CH₃)₂,
—NHCH₂CH₂OCH₃,
—NHCH₂CH₂OH,
—NHCH₂CH₂NH₂,
—NHCH₂C(O)OH,
—NHC(O)CH₂NH₂,
—NHC(O)CH₂CH₂CH₂NH₂,
—NHCH₂C(O)NH₂,
—NHCH₂C(OH)(CH₃)₂,
—NHC(O)CH(CH₃)NH₂,
—NHC(O)OCH(CH₃)NH₂,
—NHC(O)CH(CH₃)₂,
—NHC(O)C(CH₃)₃,
—NHC(O)C(CH₃)₂NH₂,
—NHC(O)CH₂OH,
—NHC(O)CH(CH₂OH)NH₂,
—NHC(O)(oxetanyl)NH₂,
—NHC(O)OC(CH₃)₃,
—NHC(CH₃)₂C(O)OCH₃,
—NHcyclopropyl,
—NHoxetanyl,
—CH₂NH₂,
—CH₂CH₂NH₂,
—CH₂CH₂CH₂NH₂,
—CH₂NHCH₂C(CH₃)₃,
—CH₂NHC(O)C(CH₃)₃,
—CH₂NHC(O)CH₂NH₂,
—CH₂NHC(O)CH₂OH,
—CH₂N(CH₃)₂,
—CH₂NHCH₃,
—CH₂N(CH₂CH₃)₂,
—CH₂CH₂N(CH₃)₂,
—S(O)₂CH₂CH₃,
—S(O)₂CH₂CH₂CH₃,
—S(O)₂phenyl,
—S(O)₂CH₃,
benzoyl,
benzylamino,
3-pyrrolidinylpropyl,
2-cyclopropylmethyl,
cyclobutylamino,
cyclobutyl-N(CH₃)—,
piperidinyl,
imidazolyl,
morpholinyl,
morpholinylmethyl,
methylpiperazinylmethyl,
methylpiperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;
provided that:
$R^{72ca1''}$ and $R^{73ca1''}$ are not both unsubstituted alkyl;
or a pharmaceutically acceptable salt or prodrug thereof.

Suitably in the compounds of Formula (Qc1), the compounds are in the form of a phosphate prodrug.

Suitably in the compounds of Formula (Qc1), the compounds are in the form of a —C(O)CH(NH₂)CH(CH₃)₂ prodrug.

This invention relates to novel compounds of Formula (Qc2) and to the use of compounds of Formula (Qc2) in the methods of the invention:

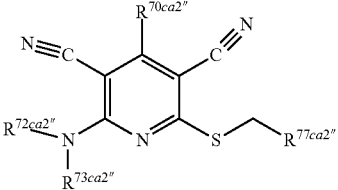

(Qc2)

wherein:
$R^{70ca2''}$ is selected from:
ethyl,
—OCH₃,
—CH₂CF₃, and
cyclopropyl;
$R^{77ca2''}$ is selected from:
phenyl,
phenyl substituted with from 1 to 4 substituents independently selected from:
fluoro,
chloro,
—CN, oxo,
$C_{1-4}$alkoxy,
$C_{1-4}$alkoxy substituted with from 1 to 3 substituents independently selected from: fluoro, chloro, oxo, —OH, —NH$_2$, —NHCH$_3$, and —N(CH$_3$)$_2$,
$C_{1-6}$alkyl,
$C_{1-6}$alkyl substituted with from 1 to 3 substituents independently selected from: fluoro, chloro, bromo, iodo, oxo, —S(O)$_2$CH$_3$, —CN, —OR$^{79a'}$ and —NR$^{76a'}$R$^{77a'}$,
 where R$^{76a'}$ and R$^{77a'}$ are independently selected form: hydrogen, —S(O)$_2$CH$_3$, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro, —COOH and —NR$^{78a'}$R$^{79a'}$, where R$^{78a'}$ and R$^{79a'}$ are independently selected form: hydrogen, phenyl, $C_{1-5}$alkyl and $C_{1-5}$alkyl substituted with from 1 to 4 substituents independently selected from: fluoro, oxo, —OH, —OC$_{1-5}$alkyl, —OC$_{1-5}$alkyl substituted from 1 to 6 times by fluoro and —COOH,
tetrahydroisothiazolyl,
tetrahydroisothiazolyl substituted twice by oxo,
tetrahydro-1,2-thiazinyl,
tetrahydro-1,2-thiazinyl substituted twice by oxo,
—N(CH$_3$)S(O)$_2$CH$_3$,
—N(CH$_3$)S(O)$_2$CFH$_2$,
—N(CH$_3$)S(O)$_2$CF$_2$H,
—N(CH$_3$)S(O)$_2$CF$_3$,
—OS(O)$_2$CH$_3$,
—S(O)$_2$NH$_2$,
—S(O)$_2$NHCH$_3$, and
—NR$^{80a'}$R$^{81a'}$ where R$^{80a'}$ and R$^{81a'}$ are independently selected form: hydrogen, —S(O)$_2$CH$_3$, phenyl, $C_{1-5}$alkyl and $C_{1-5}$alkyl substituted with from 1 to 4 substituents independently selected from: fluoro, oxo, —OH, —NH$_2$, —OC$_{1-5}$alkyl, —OC$_{1-5}$alkyl substituted from 1 to 6 times by fluoro and —COOH, and
R$^{72ca2''}$ and R$^{73ca2''}$ are taken together with the nitrogen to which they are attached, and optionally from 1 to 3 additional heteroatoms, to form a heterocycloalkyl selected from:
pyrrolidinyl,
pyrrolo[3,4-c]pyrazolyl,
piperidinyl,
1,4diazepanyl,
piperazinyl,
6,7-dihydro-triazolo[4,5-c]pyridinyl,
2,9-diazaspiro[5.5]undecanyl,
2,8-diazaspiro[4.5]decanyl,
octahydro-1H-pyrrolo[1,2a][1,4]diazepinyl,
oxa-diazaspiro[4.5]decanyl,
oxazolyl,
morpholinyl,
1-oxa-6-azaspiro[3.4]octanyl,
2-oxa-6-azaspiro[3.4]octanyl,
1,7-diazaspiro[3.5]nonanyl,
2,7-diazaspiro[3.5]nonanyl,
2,6-diazaspiro[3.4]octanyl,
azetidinyl,
hexahydropyrrolo[3,4-b]oxazinyl,
dihydronaphthyridinyl,
diazabicycloheptanyl,
1,8-diazaspiro[4.5]decanyl, and
5-oxa-2-azaspiro[3.4]octanyl,
all of which are optionally substituted with from 1 to 5 substituents independently selected from:
fluoro,
chloro,
oxo,
—OH,
—CN,
—CH$_3$,
—CH$_2$OH,
methoxy,
—CH$_2$CH$_3$,
—C(O)CH$_3$,
—C(O)NH$_2$,
—OCH$_2$CH$_2$OH,
—OCH$_2$CH$_2$NH$_2$,
—ONHC(NH)NH$_2$,
—OC(O)NH$_2$,
—Ooxetanyl,
—CH$_2$CH$_2$OH,
—CH$_2$CH$_2$CH$_2$OH,
—CH$_2$CH$_2$CH$_3$,
—CH$_2$CH$_2$OCH$_3$,
—CH$_2$CH(OH)CH$_3$,
—CH$_2$CH(OH)CH$_2$OH,
—CH$_2$C(O)OCH$_3$,
—CH$_2$C(O)NH$_2$,
—C(O)CH(CH$_3$)$_2$,
—CH$_2$CH$_2$N(CH$_3$)$_2$,
—CH$_2$CH$_2$NHCH$_2$CH$_3$,
—CH$_2$CH$_2$CH$_2$N(CH$_3$)$_2$,
—CH$_2$CH$_2$NHCH$_2$C(CH$_3$)$_3$,
—CH$_2$CH$_2$N(CH$_3$)CH$_2$OCH$_3$,
—C(CH$_3$)$_2$CH$_2$OH,
—CH$_2$C(CH$_3$)$_2$OH,
—CH$_2$C(CH$_3$)$_2$OCH$_3$,
—C(O)CH$_2$OH,
—CH$_2$isothiazolyl,
—CH$_2$thiazolyl,
—CH$_2$pyrazolyl,
—CH$_2$imidazolyl,
—CH$_2$pyridinyl,
—CH$_2$oxazolyl,
—CH$_2$pyrrolyl,
—CH$_2$pyrrolidinyl,
—CH$_2$isoxazoly,
—CH$_2$furanyl,
—CH$_2$CH$_2$morpholinyl,
—CH$_2$CH$_2$pyrrolidinyl,
—CH$_2$CH$_2$pyrrolidinylCH$_3$,
—CH$_2$CH$_2$CH$_2$pyrrolidinyl,
—C(O)phenyl,
—C(O)C(tetrahydropyranyl)NH$_2$,
—NH$_2$,
—NHCH$_3$,
—N(CH$_3$)$_2$,
—NHC(O)CH$_3$,
—NHCH(CH$_3$)$_2$,
—NHCH$_2$CHF$_2$,
—NHCH$_2$C(CH$_3$)$_3$,
—NHCH$_2$CH(CH$_3$)$_2$,
—NHCH$_2$CH$_2$OCH$_3$,
—NHCH$_2$CH$_2$OH,
—NHCH$_2$CH$_2$NH$_2$,
—NHCH$_2$C(O)OH,
—NHC(O)CH$_2$NH$_2$,
—NHC(O)CH$_2$CH$_2$CH$_2$NH$_2$, —NHCH$_2$C(O)NH$_2$,
—NHCH$_2$C(OH)(CH$_3$)$_2$,
—NHC(O)CH(CH$_3$)NH$_2$,
—NHC(O)OCH(CH$_3$)NH$_2$,
—NHC(O)CH(CH$_3$)$_2$,
—NHC(O)C(CH$_3$)$_3$,
—NHC(O)C(CH$_3$)$_2$NH$_2$,
—NHC(O)CH$_2$OH,
—NHC(O)CH(CH$_2$OH)NH$_2$,
—NHC(O)(oxetanyl)NH$_2$,
—NHC(O)OC(CH$_3$)$_3$,
—NHC(CH$_3$)$_2$C(O)OCH$_3$,
—NHcyclopropyl,
—NHoxetanyl,
—CH$_2$NH$_2$,
—CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
3-pyrrolidinylpropyl,
2-cyclopropylmethyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
methoxypyridinylmethylamino,
methylpyrrolidinyl,
difluoropyrrolidinyl,
dimethylpyrrolidinyl,
methylcyclopropylmethylamino,
hydroxymethylpyrrolidinyl,
fluoropyrrolidinyl,
fluorophenylmethylamino,
piperazinylmethyl,
oxazolidinyl,
methyloxetanmethylamino,
methylcyclobutylmethylamino,
oxoimidazolidinyl, and
2-hydroxyethylpiperidinyl;
or a pharmaceutically acceptable salt or prodrug thereof.

Suitably in the compounds of Formula (Qc2), the compounds are in the form of a phosphate prodrug.

Suitably in the compounds of Formula (Qc2), the compounds are in the form of a —C(O)CH(NH$_2$)CH(CH$_3$)$_2$ prodrug.

In an embodiment, $X^{51a}$ is selected from: —CN, fluoro and chloro. In an embodiment, $X^{52a}$ is selected from: —CN, fluoro and chloro. In an embodiment, $X^{51a}$ is —CN. In an embodiment, $X^{52a}$ is —CN.

In an embodiment, $Y^{5a}$ is selected from: S and NH. In an embodiment, $Y^{5a}$ is S.

In an embodiment, $Y^{5bbr}$ is S.

In an embodiment, $R^{50a}$ is selected from: $C_{1-6}$alkyl, $C_{1-6}$alkyl substituted with from 1 to 9 substituents independently selected from: fluoro and chloro, and cycloalkyl. In an embodiment, $R^{50a}$ is selected from ethyl, cyclopropyl and 2,2,2,trifluoroethyl. In an embodiment, $R^{50a}$ is ethyl.

In an embodiment, $R^{50bbr}$ is selected from: $C_{1-6}$alkyl, $C_{1-6}$alkyl substituted with from 1 to 9 substituents independently selected from: fluoro and chloro, and cycloalkyl. In an embodiment, $R^{50bbr}$ is selected from ethyl, cyclopropyl and 2,2,2,trifluoroethyl. In an embodiment, $R^{50bbr}$ is ethyl.

In an embodiment, $R^{50aar}$ is selected from: phenyl, furanyl, $C_{1-6}$alkyl, $C_{1-6}$alkyl substituted with from 1 to 9 substituents independently selected from: fluoro and chloro, and cycloalkyl. In an embodiment, $R^{50aar}$ is selected from phenyl, furanyl, ethyl, cyclopropyl and 2,2,2,trifluoroethyl. In an embodiment, $R^{50aar}$ is ethyl. In an embodiment, $R^{50aar}$ is phenyl. In an embodiment, $R^{50aar}$ is furanyl.

In an embodiment $R^{51a}$ is selected from: hydrogen, $C_{1-6}$alkyl, aryl, chlorophenyl and heteroaryl. In an embodiment $R^{51a}$ is selected from: hydrogen, methyl, phenyl, chlorophenyl and pyridine. In an embodiment $R^{51a}$ is phenyl. In an embodiment $R^{51a}$ is hydrogen.

In an embodiment $R^{51bbr}$ is selected from: hydrogen, $C_{1-6}$alkyl, aryl, chlorophenyl and heteroaryl. In an embodiment $R^{51bbr}$ is selected from: hydrogen, methyl, phenyl, chlorophenyl, piperidinyl and pyridinyl. In an embodiment $R^{51bbr}$ is phenyl. In an embodiment $R^{51bbr}$ is pyridinyl.

In an embodiment $R^{52a}$ is selected from: —C(O)NH$_2$ and -phenylCH$_2$NHC(O)CH$_3$. In an embodiment $R^{52a}$ is —C(O)NH$_2$. In an embodiment $R^{52a}$ is -phenylCH$_2$NHC(O)CH$_3$.

In an embodiment $R^{53a}$ and $R^{54a}$ are independently selected from: hydrogen, methyl, morpholinethyl, methoxyethyl, oxaazaspiro[3.4]octan, 5-oxa-2-azaspiro[3.4]octan, aminoethyl, amino-2-oxoethyl and hydroxyethyl.

In an embodiment $R^{53a}$ and $R^{54a}$ are taken together with the nitrogen to which they are attached to form: pyrrolidinyl, hydroxypyrrolidinyl, piperidinyl, hydroxypiperidinyl, 1,4-diazepanyl, methyl-1,4-diazepanyl, methoxyethyl-1,4-diazepanyl, hydroxypropyl-1,4-diazepanyl, methyl-1,4-diazepanacetate, (methyl)oxo-1,4-diazepanyl, (methyl)oxopiperazinyl, propylpiperazinyl, aminopyrrolidinyl, oxo-1,4-diazepanyl, piperidinylpiperazinyl, hydroxymethylpiperazinyl, oxopiperazinyl, morpholinpiperidinyl, hydroxyethyl 1,4diazepanyl, dimethylaminopropylpiperazinyl, pyrrolidinpiperidinyl, piperidinpiperidinyl, pyrrolidinpropyl-1,4-diazepanyl, methylpiperazinyl, dimethylaminopiperidinyl, dimethylpiperazinyl, dimethylmorpholinyl, (aminomethyl)hydroxypiperidinyl, aminopiperidinyl, methylaminopiperidinyl, piperazinyl, aminoethylpiperazinyl, ethylpiperazinyl, morpholinmethylpiperidinyl, aminopropylpiperazinyl, methylpiperazinmethylpiperidinyl, pyrrolidinmethylpiperidinyl, methylpiperazinpiperidinyl, ethyl1,4diazepanyl, imidazolidinpiperidinyl, oxoimidazolidinpiperidinyl, propyl1,4-diazepanyl, azetidinyl, methoxyazetidinyl, acetylpiperazinyl, hydroxyethylpiperazinyl, morpholinyl, 2-methylpropanoylpiperazinyl, ethanesulfonylpiperazinyl, methanesulfonylpiperazinyl, benzoylpiperazinyl, oxopiperidinyl, hydroxyethylpiperidinpiperidinyl, hydroxymethylmorpholinyl or difluoropiperidinyl, In an embodiment $R^{53}$ and $R^{54}$ are taken together with the nitrogen to which they are attached to form: diazaspiroundecanyl, 2,9-diazaspiro[5.5]undecanyl, diazaspirodecanyl, 2,8-diazaspiro[4.5]decanyl, hexahydropyrrolo-1,4-diazepanyl, methyl-2,9-diazaspiro[5.5]undecanyl, cyclopropylmethyl-2,9-diazaspiro[5.5]undecanyl, oxaazaspirooctanyl, oxaazaspiro[3.4]octanyl, diazaspirononanyl, diazaspiro[3.5]nonanyl, 1,7-diazaspiro[3.5]nonanyl, 2,7-diazaspiro[3.5]nonanyl, diazaspirooctanyl, diazaspiro[3.4]octanyl, 2,6-diazaspiro[3.4]octanyl, methanesulfonyl-1,8-diazaspiro[4.5]decanyl, azabicyclooctanyl, 8-azabicyclo[3.2.1]octanyl, 4-amino-4-methylpiperidin-1-yl, $NH_2CH_2C(O)NH$-piperidinyl, $NH_2CH(CH_3)C(O)NH$-piperidinyl, 3-aminooxetane-3-carbonyl)piperazinyl, 4-amino-(piperidin-4-yl)tetrahydro-2H-pyran-4-carboxamide, 4-amino-(piperazin-4-yl)tetrahydro-2H-pyran-4-carboxamide, hydroxyethyl-1,4-diazepanyl, aminopiperidinyl, hydroxyazetidinyl, hydroxypyrrolidinyl or hydroxyethoxypiperidinyl.

In an embodiment $R^{53bbr}$ and $R^{54bbr}$ are independently selected from: hydrogen, methyl, morpholinethyl, methoxyethyl, oxaazaspiro[3.4]octan, 5-oxa-2-azaspiro[3.4]octan, aminoethyl, amino-2-oxoethyl and hydroxyethyl.

In an embodiment $R^{53bbr}$ and $R^{54bbr}$ are taken together with the nitrogen to which they are attached to form: pyrrolidinyl, hydroxypyrrolidinyl, piperidinyl, hydroxypiperidinyl, 1,4-diazepanyl, methyl-1,4-diazepanyl, methoxyethyl-1,4-diazepanyl, hydroxypropyl-1,4-diazepanyl, methyl-1,4-diazepanacetate, (methyl)oxo-1,4-diazepanyl, (methyl)oxopiperazinyl, propylpiperazinyl, aminopyrrolidinyl, oxo-1,4-diazepanyl, piperidinylpiperazinyl, hydroxymethylpiperazinyl, oxopiperazinyl, morpholinpiperidinyl, hydroxyethyl 1,4diazepanyl, dimethylaminopropylpiperazinyl, pyrrolidinpiperidinyl, piperidinpiperidinyl, pyrrolidinpropyl-1,4-diazepanyl, methylpiperazinyl, dimethylaminopiperidinyl, dimethylpiperazinyl, dimethylmorpholinyl, (aminomethyl)hydroxypiperidinyl, aminopiperidinyl, methylaminopiperidinyl, piperazinyl, aminoethylpiperazinyl, ethylpiperazinyl, morpholinmethylpiperidinyl, aminopropylpiperazinyl, methylpiperazinmethylpiperidinyl, pyrrolidinmethylpiperidinyl, methylpiperazinpiperidinyl, ethyl1,4diazepanyl, imidazolidinpiperidinyl, oxoimidazolidinpiperidinyl, propy-l1,4-diazepanyl, azetidinyl, methoxyazetidinyl, acetylpiperazinyl, hydroxyethylpiperazinyl, morpholinyl, 2-methylpropanoylpiperazinyl, ethanesulfonylpiperazinyl, methanesulfonylpiperazinyl, benzoylpiperazinyl, oxopiperidinyl, hydroxyethylpiperidinpiperidinyl, hydroxymethylmorpholinyl or difluoropiperidinyl, In an embodiment $R^{53bbr}$ and $R^{54bbr}$ are taken together with the nitrogen to which they are attached to form: diazaspiroundecanyl, 2,9-diazaspiro[5.5]undecanyl, diazaspirodecanyl, 2,8-diazaspiro[4.5]decanyl, hexahydropyrrolo-1,4-diazepanyl, methyl-2,9-diazaspiro[5.5]undecanyl, cyclopropylmethyl-2,9-diazaspiro[5.5]undecanyl, oxaazaspirooctanyl, oxaazaspiro[3.4]octanyl, diazaspirononanyl, diazaspiro[3.5]nonanyl, 1,7-diazaspiro[3.5]nonanyl, 2,7-diazaspiro[3.5]nonanyl, diazaspirooctanyl, diazaspiro[3.4]octanyl, 2,6-diazaspiro[3.4]octanyl, methanesulfonyl-1,8-diazaspiro[4.5]decanyl, azabicyclooctanyl, 8-azabicyclo[3.2.1]octanyl, 4-amino-4-methylpiperidin-1-yl, $NH_2CH_2C(O)NH$-piperidinyl, $NH_2CH(CH_3)C(O)NH$-piperidinyl, 3-aminooxetane-3-carbonyl)piperazinyl, 4-amino-(piperidin-4-yl)tetrahydro-2H-pyran-4-carboxamide, 4-amino-(piperazin-4-yl)tetrahydro-2H-pyran-4-carboxamide, hydroxyethyl-1,4-diazepanyl, aminopiperidinyl, hydroxyazetidinyl, hydroxypyrrolidinyl or hydroxyethoxypiperidinyl.

In an embodiment, $X^{41ccr}$ is selected from: —CN, fluoro and chloro. In an embodiment, $X^{42ccr}$ is selected from: —CN, fluoro and chloro. In an embodiment, $X^{41ccr}$ is —CN. In an embodiment, $X^{42ccr}$ is —CN.

In an embodiment, $Y^{4ccr}$ is selected from: S and NH. In an embodiment, $Y^{4ccr}$ is S.

In an embodiment, $R^{41ccr}$ is selected from: $C_{1-6}$alkyl, $C_{1-6}$alkyl substituted with from 1 to 9 substituents independently selected from: fluoro and chloro, and cycloalkyl. In an embodiment, $R^{41ccr}$ is selected from ethyl, cyclopropyl and 2,2,2,trifluoroethyl. In an embodiment, $R^{41ccr}$ is ethyl.

In an embodiment, $R^{43ccr}$ is selected from: phenyl, phenyl substituted with 1 or 2 substituents independently selected form: $—OS(O)_2CH_3$, $—N(CH_3)S(O)_2CH_3$, $—CH_2NHC(O)CH_3$, $—CH_2NHC(O)CH_2NH_2$, $—CH_2NHC(O)CH_3$, tetrahydrothiazolyl, tetrehydrothiazolyl substituted once or twice by oxo, tetrahydrothiazinyl, tetrahydrothiazinyl substituted once or twice by oxo, and $—CH_2S(O)_2CH_3$, In an embodiment $R^{44ccr}$ and $R^{45ccr}$ are independently selected from: hydrogen, methyl, and $C_{1-6}$alkyl substituted with from 1 to 9 substituents independently selected from: $—N(CH_2CH_3)_2$, and $—NHOC(CH_3)_2NH_2$.

In an embodiment $R^{44ccr}$ and $R^{45ccr}$ are taken together with the nitrogen to which they are attached to form: piperidinyl, piperidinyl substituted by one or two substituents independently selected from: amino, $—NHCH(CH_3)$, pyrrolidinyl, $—NHC(O)C(CH_3)_3$, $—NH(O)CH(CH_3)(NH_2)$, fluoro, chloro, and $CH_2N(CH_3)_2$, morpholinyl, morpholinyl substituted by $CH_2$pyrrolidinyl, 1,4diazepanyl, and methyl1,4diazepanyl.

In an embodiment, $X^{41bbr}$ is selected from: —CN, fluoro and chloro. In an embodiment, $X^{42bbr}$ is selected from: —CN, fluoro and chloro. In an embodiment, $X^{41bbr}$ is —CN. In an embodiment, $X^{42bbr}$ is —CN.

In an embodiment, $Y^{4bbr}$ is selected from: S and NH. In an embodiment, $Y^{4bbr}$ is S.

In an embodiment, $R^{41bbr}$ is selected from: $C_{1-6}$alkyl, $C_{1-6}$alkyl substituted with from 1 to 9 substituents independently selected from: fluoro and chloro, and cycloalkyl. In an embodiment, $R^{41bbr}$ is selected from ethyl, cyclopropyl and 2,2,2,trifluoroethyl. In an embodiment, $R^{41bbr}$ is ethyl.

In an embodiment, $R^{43bbr}$ is selected from: phenyl, and phenyl substituted with 1 or 2 substituents independently selected form: fluoro and chloro.

In an embodiment $R^{44bbr}$ and $R^{45bbr}$ are independently selected from: methyl, and $—CH_2C(O)NH_2$.

In an embodiment $R^{44bbr}$ and $R^{45bbr}$ are taken together with the nitrogen to which they are attached to form: piperidinyl, piperidinyl substituted by one or two substituents independently selected from: amino, $—NHCH_2C(CH_3)_3$, flouro, chloro, and $—N(CH_3)$cyclobutyl, pyrrolidinyl, and pyrrolidinyl substituted by hydroxy.

Included in the compounds of Formula (I) and in the methods of the invention are:
2-[(6-amino-3,5-dicyano-4-ethylpyridin-2-yl)sulfanyl]-2-phenylacetamide;
(R)-[(6-amino-3,5-dicyano-4-ethylpyridin-2-yl)sulfanyl]-2-phenylacetamide;
2-{[3,5-dicyano-6-(dimethylamino)-4-ethylpyridin-2-yl]sulfanyl}-2-phenylacetamide;
2-((3,5-dicyano-4-cyclopropyl-6-(1,4-diazepan-1-yl)pyridin-2-yl)thio)-2-phenylacetamide;
2-{[3,5-dicyano-4-cyclopropyl-6-(4-ethyl-1,4-diazepan-1-yl)pyridin-2-yl]sulfanyl}-2-phenylacetamide;
2-((3,5-dicyano-4-ethyl-6-(4-propyl-1,4-diazepan-1-yl)pyridin-2-yl)thio)-2-phenylacetamide;
2-{[3,5-dicyano-4-ethyl-6-(4-ethyl-1,4-diazepan-1-yl)pyridin-2-yl]sulfanyl}-2-phenylacetamide;
2-{[3,5-dicyano-4-ethyl-6-(5-oxo-1,4-diazepan-1-yl)pyridin-2-yl]sulfanyl}-2-phenylacetamide;

2-((3,5-dicyano-4-cyclopropyl-6-morpholinopyridin-2-yl)thio)-2-(pyridin-4-yl)acetamide;
2-{[3,5-dicyano-4-ethyl-6-(4-methyl-3-oxopiperazin-1-yl)pyridin-2-yl]sulfanyl}-2-(pyridin-4-yl)acetamide;
2-[(3,5-dicyano-4-ethyl-6-{methyl[2-(morpholin-4-yl)ethyl]amino}pyridin-2-yl)sulfanyl]-2-phenylacetamide;
2-{[3,5-dicyano-4-ethyl-6-(4-propylpiperazin-1-yl)pyridin-2-yl]sulfanyl}-2-phenylacetamide;
2-({3,5-dicyano-4-ethyl-6-[4-(piperidin-4-yl)piperazin-1-yl]pyridin-2-yl}sulfanyl)-2-phenylacetamide;
2-({3,5-dicyano-4-cyclopropyl-6-[3-(hydroxymethyl)piperazin-1-yl]pyridin-2-yl}sulfanyl)-2-phenylacetamide;
2-{[3,5-dicyano-4-cyclopropyl-6-(3-oxopiperazin-1-yl)pyridin-2-yl]sulfanyl}-2-phenylacetamide;
2-({3,5-dicyano-4-cyclopropyl-6-[4-(morpholin-4-yl)piperidin-1-yl]pyridin-2-yl}sulfanyl)-2-phenylacetamide;
2-((3,5-dicyano-4-ethyl-6-(2,8-diazaspiro[4.5]decan-8-yl)pyridin-2-yl)thio)-2-phenylacetamide; 2,2,2-trifluoroacetic acid;
2-((3,5-Dicyano-4-cyclopropyl-6-(3-(dimethylamino)piperidin-1-yl)pyridin-2-yl)thio)-2-phenylacetamide;
2-((3,5-Dicyano-4-cyclopropyl-6-(3-methylpiperazin-1-yl)pyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
2-((3,5-Dicyano-4-cyclopropyl-6-(2,6-dimethylmorpholino)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((6-(4-(Aminomethyl)-4-hydroxypiperidin-1-yl)-3,5-dicyano-4-cyclopropylpyridin-2-yl)thio)-2-phenylacetamide;
2-((3,5-dicyano-4-cyclopropyl-6-(3-(methylamino)piperidin-1-yl)pyridin-2-yl)thio)-2-phenylacetamide;
2-((6-(3-aminopiperidin-1-yl)-3,5-dicyano-4-cyclopropylpyridin-2-yl)thio)-2-phenylacetamide;
2-((3,5-Dicyano-4-cyclopropyl-6-(dimethylamino)pyridin-2-yl)thio)-2-(pyridin-4-yl)acetamide;
2-((3,5-dicyano-6-(dimethylamino)-4-ethylpyridin-2-yl)thio)-2-(pyridin-4-yl)acetamide;
2-((6-(4-aminopiperidin-1-yl)-3,5-dicyano-4-cyclopropylpyridin-2-yl)thio)-2-phenylacetamide;
2-((3,5-dicyano-4-cyclopropyl-6-(4-(dimethylamino)piperidin-1-yl)pyridin-2-yl)thio)-2-phenylacetamide;
2-((3,5-dicyano-4-cyclopropyl-6-(piperazin-1-yl)pyridin-2-yl)thio)-2-(pyridin-4-yl)acetamide;
2-((3,5-dicyano-4-cyclopropyl-6-(1,4-diazepan-1-yl)pyridin-2-yl)thio)-2-(pyridin-4-yl)acetamide;
2-((3,5-dicyano-4-cyclopropyl-6-((R)-3-hydroxypiperidin-1-yl)pyridin-2-yl)thio)-2-phenylacetamide;
2-(3,5-dicyano-4-cyclopropyl-6-((S)-3-hydroxypiperidin-1-yl)pyridin-2-ylthio)-2-phenylacetamide;
2-((3,5-Dicyano-4-cyclopropyl-6-((S)-3-hydroxypyrrolidin-1-yl)pyridin-2-yl)thio)-2-(pyridin-4-yl)acetamide;
2-((3,5-Dicyano-4-ethyl-6-(4-ethylpiperazin-1-yl)pyridin-2-yl)thio)-2-phenylacetamide;
2-((3,5-Dicyano-4-ethyl-6-(1-oxa-6-azaspiro[3.4]octan-6-yl)pyridin-2-yl)thio)-2-phenylacetamide;
2-((6-(4-(3-aminopropyl)piperazin-1-yl)-3,5-dicyano-4-ethylpyridin-2-yl)thio)-2-phenylacetamide;
2-((3,5-Dicyano-4-ethyl-6-(1,7-diazaspiro[3.5]nonan-1-yl)pyridin-2-yl)thio)-2-phenylacetamide trifluoroacetate;
2-((3,5-Dicyano-4-cyclopropyl-6-(4-(pyrrolidin-1-ylmethyl)piperidin-1-yl)pyridin-2-yl)thio)-2-phenylacetamide;
2-((3,5-Dicyano-4-cyclopropyl-6-(4-(4-methylpiperazin-1-yl)piperidin-1-yl)pyridin-2-yl)thio)-2-phenylacetamide;
(R)-2-((3,5-dicyano-6-(1,4-diazepan-1-yl)-4-ethylpyridin-2-yl)amino)-2-phenylacetamide;
2-((3,5-Dicyano-4-cyclopropyl-6-(4-(pyrrolidin-1-yl)piperidin-1-yl)pyridin-2-yl)thio)-2-phenylacetamide trifluoroacetate;
2-((3,5-Dicyano-4-ethyl-6-(2,7-diazaspiro[3.5]nonan-7-yl)pyridin-2-yl)thio)-2-phenylacetamide;
2-((3,5-Dicyano-4-ethyl-6-(2,6-diazaspiro[3.4]octan-6-yl)pyridin-2-yl)thio)-2-phenylacetamide;
2-((3,5-dicyano-4-cyclopropyl-6-(1,4-diazepan-1-yl)pyridin-2-yl)thio)propanamide;
2-((3,5-Dicyano-4-ethyl-6-(4-(2-oxoimidazolidin-1-yl)piperidin-1-yl)pyridin-2-yl)thio)-2-phenylacetamide;
2-((3,5-Dicyano-4-ethyl-6-(4-hydroxypiperidin-1-yl)pyridin-2-yl)thio)-2-phenylacetamide;
2-((3,5-Dicyano-4-ethyl-6-((S)-3-hydroxypyrrolidin-1-yl)pyridin-2-yl)thio)-2-phenylacetamide;
2-((3,5-Dicyano-4-ethyl-6-(3-oxopiperazin-1-yl)pyridin-2-yl)thio)-2-phenylacetamide;
2-[(6-amino-3,5-dicyano-4-cyclopropyl-2-pyridyl)sulfanyl]-2-phenyl-acetamide;
2-((3,5-Dicyano-4-ethyl-6-(methylamino)pyridin-2-yl)thio)-2-phenylacetamide;
2-((3,5-Dicyano-4-ethyl-6-((2-methoxyethyl)(methyl)amino)pyridin-2-yl)thio)-2-phenylacetamide;
2-((3,5-Dicyano-4-ethyl-6-(3-methoxyazetidin-1-yl)pyridin-2-yl)thio)-2-phenylacetamide;
2-((3,5-Dicyano-4-ethyl-6-(piperazin-1-yl)pyridin-2-yl)thio)-2-phenylacetamide;
2-((3,5-Dicyano-4-ethyl-6-(4-methyl-1,4-diazepan-1-yl)pyridin-2-yl)thio)-2-phenylacetamide;
2-((3,5-Dicyano-4-ethyl-6-morpholinopyridin-2-yl)thio)-2-phenylacetamide;
2-[[6-(azetidin-1-yl)-3,5-dicyano-4-ethyl-2-pyridyl]sulfanyl]-2-phenyl-acetamide;
2-((3,5-dicyano-4-ethyl-6-(4-oxopiperidin-1-yl)pyridin-2-yl)thio)-2-phenylacetamide;
2-((3,5-dicyano-4-ethyl-6-(1'-(2-hydroxyethyl)-[4,4'-bipiperidin]-1-yl)pyridin-2-yl)thio)-2-phenylacetamide;
2-((3,5-Dicyano-6-((3S,5R)-3,5-dimethylpiperazin-1-yl)-4-ethylpyridin-2-yl)thio)-2-phenylacetamide;
2-((6-(8-azabicyclo[3.2.1]octan-3-yl(methyl)amino)-3,5-dicyano-4-ethylpyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
(R)-2-((3,5-dicyano-6-(dimethylamino)-4-ethylpyridin-2-yl)thio)-2-phenylacetamide;
(R)-2-[(3,5-Dicyano-4-ethyl-6-morpholino-2-pyridyl)sulfanyl]-2-phenyl-acetamide;
N-(4-((3,5-Dicyano-4-ethyl-6-(4-(pyrrolidin-1-yl)piperidin-1-yl)pyridin-2-ylthio)methyl)benzyl)acetamide trifluoroacetate;
2-{[3,5-dicyano-4-ethyl-6-(5-methyl-1,4-diazepan-1-yl)pyridin-2-yl]sulfanyl}-2-phenylacetamide;
2-(4-(Aminomethyl)benzylthio)-4-ethyl-6-(4-(pyrrolidin-1-yl)piperidin-1-yl)pyridine-3,5-dicarbonitrile;
tert-Butyl 4-(((3,5-dicyano-4-ethyl-6-(4-methyl-1,4-diazepan-1-yl)pyridin-2-yl)thio)methyl)benzylcarbamate;
4-(((3,5-Dicyano-4-ethyl-6-(4-methyl-1,4-diazepan-1-yl)pyridin-2-yl)thio)methyl)benzamide;
2-((4-(Aminomethyl)benzyl)thio)-4-ethyl-6-(4-methyl-1,4-diazepan-1-yl)pyridine-3,5-dicarbonitrile, 2Hydrochloride;
2-(4-(((3,5-Dicyano-4-ethyl-6-(4-methyl-1,4-diazepan-1-yl)pyridin-2-yl)thio)methyl)phenyl)acetic acid;
4-(((3,5-Dicyano-4-ethyl-6-(4-methyl-1,4-diazepan-1-yl)pyridin-2-yl)thio)methyl)benzoic acid;

2-(Dimethylamino)-4-ethyl-6-(((6-oxo-1,6-dihydropyridin-3-yl)methyl)thio)pyridine-3,5-dicarbonitrile;

N-(4-(((3,5-Dicyano-4-ethyl-6-(4-methyl-1,4-diazepan-1-yl)pyridin-2-yl)thio)methyl)thiazol-2-yl)acetamide;

4-(((3,5-Dicyano-4-ethyl-6-(4-methyl-1,4-diazepan-1-yl)pyridin-2-yl)thio)methyl)benzenesulfonamide;

N-(4-(((3,5-Dicyano-4-ethyl-6-(4-methyl-1,4-diazepan-1-yl)pyridin-2-yl)thio)methyl)benzyl)acetamide;

tert-Butyl(2-((4-(((3,5-dicyano-4-ethyl-6-(4-methyl-1,4-diazepan-1-yl)pyridin-2-yl)thio)methyl)benzyl)amino)-2-oxoethyl)carbamate;

N-(4-(((3,5-Dicyano-4-ethyl-6-(4-methyl-1,4-diazepan-1-yl)pyridin-2-yl)thio)methyl)benzyl)methanesulfonamide;

2-Amino-N-(4-(((3,5-dicyano-4-ethyl-6-(4-methyl-1,4-diazepan-1-yl)pyridin-2-yl)thio)methyl)benzyl)acetamide;

2-(4-Aminopiperidin-1-yl)-6-(benzylthio)-4-ethylpyridine-3,5-dicarbonitrile;

4-(((3,5-Dicyano-4-ethyl-6-(4-methyl-1,4-diazepan-1-yl)pyridin-2-yl)thio)methyl)benzyl acetate;

2-(4-(((3,5-Dicyano-4-ethyl-6-(4-methyl-1,4-diazepan-1-yl)pyridin-2-yl)thio)methyl)phenyl acetamide;

2-(4-(((3,5-Dicyano-4-ethyl-6-(4-methyl-1,4-diazepan-1-yl)pyridin-2-yl)thio)methyl)phenyl)-N-methylacetamide;

4-Ethyl-2-((4-(hydroxymethyl)benzyl)thio)-6-(4-methyl-1,4-diazepan-1-yl)pyridine-3,5-dicarbonitrile;

N-(4-(((3,5-Dicyano-4-ethyl-6-(4-methyl-1,4-diazepan-1-yl)pyridin-2-yl)thio)methyl)benzyl)-2-hydroxyacetamide;

N-(4-(((3,5-Dicyano-4-ethyl-6-(4-methyl-1,4-diazepan-1-yl)pyridin-2-yl)thio)methyl)benzyl)propionamide;

N-(4-(((3,5-Dicyano-4-ethyl-6-(4-methyl-1,4-diazepan-1-yl)pyridin-2-yl)thio)methyl)benzyl)isobutyramide;

N-(4-(((3,5-Dicyano-4-ethyl-6-(4-methyl-1,4-diazepan-1-yl)pyridin-2-yl)thio)methyl)benzyl)-3-methylbutanamide;

4-Ethyl-2-((4-(((2-hydroxyethyl)amino)methyl)benzyl)thio)-6-(4-methyl-1,4-diazepan-1-yl)pyridine-3,5-dicarbonitrile;

N-(4-(((3,5-Dicyano-6-(4-methyl-1,4-diazepan-1-yl)-4-(methylamino)pyridin-2-yl)thio)methyl)benzyl)acetamide;

2-(((2-Acetyl-1,2,3,4-tetrahydroisoquinolin-6-yl)methyl)thio)-6-(dimethylamino)-4-ethylpyridine-3,5-dicarbonitrile;

2-((4-Cyanobenzyl)thio)-4-ethyl-6-(4-methyl-1,4-diazepan-1-yl)pyridine-3,5-dicarbonitrile;

2-Amino-N-(1-(6-(benzylthio)-3,5-dicyano-4-ethylpyridin-2-yl)piperidin-4-yl)acetamide, Trifluoroacetic acid salt;

2-Amino-N-(1-(6-(benzylthio)-3,5-dicyano-4-ethylpyridin-2-yl)piperidin-4-yl)-2-methylpropanamide, Formic acid salt;

3-Amino-N-(4-(((3,5-dicyano-4-ethyl-6-(4-methyl-1,4-diazepan-1-yl)pyridin-2-yl)thio)methyl)benzyl)propanamide;

(S)-2-Amino-N-(4-(((3,5-dicyano-4-ethyl-6-(4-methyl-1,4-diazepan-1-yl)pyridin-2-yl)thio)methyl)benzyl)propanamide;

(R)-2-Amino-N-(4-(((3,5-dicyano-4-ethyl-6-(4-methyl-1,4-diazepan-1-yl)pyridin-2-yl)thio)methyl)benzyl)propanamide;

1-(4-(((3,5-Dicyano-4-ethyl-6-(4-methyl-1,4-diazepan-1-yl)pyridin-2-yl)thio)methyl)benzyl)-3-ethylurea;

1-(4-(((3,5-Dicyano-4-ethyl-6-(4-methyl-1,4-diazepan-1-yl)pyridin-2-yl)thio)methyl)benzyl)-3-phenylurea;

N-(4-(((3,5-Dicyano-6-(4-methyl-1,4-diazepan-1-yl)-4-(methylthio)pyridin-2-yl)thio)methyl)benzyl)acetamide;

(E)-3-(4-(((3,5-Dicyano-6-(dimethylamino)-4-ethylpyridin-2-yl)thio)methyl)phenyl)acrylic acid, Trifluoroacetic acid salt;

N-(4-(((3,5-Dicyano-4-ethyl-6-((2-hydroxyethyl)(methyl)amino)pyridin-2-yl)thio)methyl)benzyl)acetamide;

4-(((3,5-Dicyano-4-ethyl-6-(4-methyl-1,4-diazepan-1-yl)pyridin-2-yl)thio)methyl)-N-methylbenzenesulfonamide;

N-(4-(((3,5-Dicyano-4-ethoxy-6-(4-methyl-1,4-diazepan-1-yl)pyridin-2-yl)thio)methyl)benzyl)acetamide;

2-({3,5-Dicyano-4-ethyl-6-[4-(2-methoxyethyl)-1,4-diazepan-1-yl]pyridin-2-yl}sulfanyl)-2-phenylacetamide;

2-((3,5-dicyano-4-ethyl-6-(4-(2-hydroxpropyl)-1,4-diazepan-1-yl)pyridin-2-yl)thio)-2-phenylacetamide;

Methyl 2-[4-(6-{[carbamoyl(phenyl)methyl]sulfanyl}-3,5-dicyano-4-ethylpyridin-2-yl)-1,4-diazepan-1-yl]acetate;

2-{[3,5-Dicyano-4-cyclopropyl-6-(4-methyl-5-oxo-1,4-diazepan-1-yl)pyridin-2-yl]sulfanyl}-2-phenylacetamide;

2-{[3,5-Dicyano-4-cyclopropyl-6-(5-oxo-1,4-diazepan-1-yl)pyridin-2-yl]sulfanyl}-2-phenylacetamide;

2-{[3,5-Dicyano-4-ethyl-6-(4-methyl-5-oxo-1,4-diazepan-1-yl)pyridin-2-yl]sulfanyl}-2-phenylacetamide;

2-{[3,5-Dicyano-6-(1,4-diazepan-1-yl)-4-ethylpyridin-2-yl]sulfanyl}-2-phenylacetamide;

2-({3,5-Dicyano-6-[4-(2-hydroxyethyl)-1,4-diazepan-1-yl]-4-(2,2,2-trifluoroethyl)pyridin-2-yl}sulfanyl)-2-phenylacetamide;

(2R)-2-({3,5-Dicyano-4-ethyl-6-[4-(2-hydroxyethyl)-1,4-diazepan-1-yl]pyridin-2-yl}amino)-2-phenylacetamide;

2-({6-[(3S)-3-Aminopyrrolidin-1-yl]-3,5-dicyano-4-cyclopropylpyridin-2-yl}sulfanyl)-2-phenylacetamide;

2-((3,5-Dicyano-4-ethyl-6-(2,9-diazaspiro[5.5]undecan-9-yl)pyridin-2-yl)thio)-2-phenylacetamide;

2-((3,5-Dicyano-4-ethyl-6-(hexahydro-1H-pyrrolo[1,2-a][1,4]diazepin-2(3H)-yl)pyridin-2-yl)thio)-2-phenylacetamide;

2-((3,5-Dicyano-4-ethyl-6-(2-methyl-2,9-diazaspiro[5.5]undecan-9-yl)pyridin-2-yl)thio)-2-phenylacetamide;

2-((3,5-Dicyano-6-(2-(cyclopropylmethyl)-2,9-diazaspiro[5.5]undecan-9-yl)-4-ethylpyridin-2-yl)thio)-2-phenylacetamide hydrochloride;

2-((3,5-Dicyano-6-(4-(3-(dimethylamino)propyl)piperazin-1-yl)-4-ethylpyridin-2-yl)thio)-2-phenylacetamide;

2-((3,5-Dicyano-4-ethyl-6-(4-(pyrrolidin-3-yl)piperidin-1-yl)pyridin-2-yl)thio)-2-phenylacetamide; 2,2,2-trifluoroacetic acid;

2-((6-([4,4'-Bipiperidin]-1-yl)-3,5-dicyano-4-ethylpyridin-2-yl)thio)-2-phenylacetamide; 2,2,2-trifluoroacetic acid;

2-((6-(4-(2-Aminoethyl)piperazin-1-yl)-3,5-dicyano-4-ethylpyridin-2-yl)thio)-2-phenylacetamide;

2-((6-(4-(3-Aminopropyl)piperazin-1-yl)-3,5-dicyano-4-cyclopropylpyridin-2-yl)thio)-2-phenylacetamide;

2-((3,5-Dicyano-4-cyclopropyl-6-(4-((4-methylpiperazin-1-yl)methyl)piperidin-1-yl)pyridin-2-yl)thio)-2-phenylacetamide trifluoroacetate;

2-((6-(4-Acetylpiperazin-1-yl)-3,5-dicyano-4-ethylpyridin-2-yl)thio)-2-phenylacetamide;

2-((3,5-Dicyano-4-cyclopropyl-6-(dimethylamino)pyridin-2-yl)thio)-2-phenylacetamide;

2-(4-Chlorophenyl)-2-((3,5-dicyano-6-(dimethylamino)-4-ethylpyridin-2-yl)thio)acetamide;

2-((3,5-Dicyano-4-ethyl-6-(4-(2-hydroxyethyl)piperazin-1-yl)pyridin-2-yl)thio)-2-phenylacetamide;

2-[(3,5-Dicyano-4-cyclopropyl-6-morpholino-2-pyridyl)sulfanyl]-2-phenyl-acetamide;

2-((6-(4-Benzoylpiperazin-1-yl)-3,5-dicyano-4-ethylpyridin-2-yl)thio)-2-phenylacetamide;

2-((3,5-Dicyano-4-ethyl-6-((5S,6S)-6-hydroxy-1-(methyl-sulfonyl)-1,8-diazaspiro[4.5]decan-8-yl)pyridin-2-yl)thio)-2-phenylacetamide;
2-((3,5-Dicyano-6-(4,4-difluoropiperidin-1-yl)-4-ethylpyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide;
2-((6-(4-amino-4-methylpiperidin-1-yl)-3,5-dicyano-4-ethylpyridin-2-yl)thio)-2-phenylacetamide;
2-amino-N-(1-(6-((2-amino-2-oxo-1-phenylethyl)thio)-3,5-dicyano-4-ethylpyridin-2-yl)piperidin-4-yl)acetamide 2,2,2-trifluoroacetate;
(2S)-2-amino-N-(1-(6-((2-amino-2-oxo-1-phenylethyl)thio)-3,5-dicyano-4-ethylpyridin-2-yl)piperidin-4-yl)propanamide 2,2,2-trifluoroacetate;
2-((6-(4-(3-aminooxetane-3-carbonyl)piperazin-1-yl)-3,5-dicyano-4-ethylpyridin-2-yl)thio)-2-phenylacetamide formate;
4-amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide 2,2,2-trifluoroacetate;
2-((6-(4-(4-aminotetrahydro-2H-pyran-4-carbonyl)piperazin-1-yl)-3,5-dicyano-4-ethylpyridin-2-yl)thio)-2-phenylacetamide 2,2,2-trifluoroacetate;
2-((3,5-dicyano-6-(4-(2-hydroxyethyl)-1,4-diazepan-1-yl)-4-methoxypyridin-2-yl)thio)-2-phenylacetamide;
2-((6-(4-aminopiperidin-1-yl)-3,5-dicyano-4-ethylpyridin-2-yl)thio)-2-phenylacetamide;
2-((6-((2-aminoethyl)(methyl)amino)-3,5-dicyano-4-ethylpyridin-2-yl)thio)-2-phenylacetamide 2,2,2-trifluoroacetate;
2-((6-((2-amino-2-oxoethyl)(methyl)amino)-3,5-dicyano-4-ethylpyridin-2-yl)thio)-2-phenylacetamide;
2-((3,5-dicyano-4-ethyl-6-(3-hydroxyazetidin-1-yl)pyridin-2-yl)thio)-2-phenylacetamide;
2-((3,5-dicyano-4-ethyl-6-((2-hydroxyethyl)(methyl)amino)pyridin-2-yl)thio)-2-phenylacetamide;
2-amino-N-(1-(6-((2-amino-2-oxo-1-phenylethyl)thio)-3,5-dicyano-4-ethylpyridin-2-yl)piperidin-4-yl)-2-methylpropanamide;
2-((6-(4-(2-aminoethoxy)piperidin-1-yl)-3,5-dicyano-4-ethylpyridin-2-yl)thio)-2-phenylacetamide 2,2,2-trifluoroacetate;
2-((3,5-dicyano-4-ethyl-6-(3-hydroxypyrrolidin-1-yl)pyridin-2-yl)thio)-2-phenylacetamide;
2-((3,5-dicyano-4-ethyl-6-(4-(2-hydroxyethoxy)piperidin-1-yl)pyridin-2-yl)thio)-2-phenylacetamide;
N-(4-(((6-(4-aminopiperidin-1-yl)-3,5-dicyano-4-ethylpyridin-2-yl)thio)methyl)benzyl)acetamide 2,2,2-trifluoroacetate; and
2-((3,5-dicyano-6-(dimethylamino)-4-ethylpyridin-2-yl)thio)-2-(piperidin-4-yl)acetamide;
or a pharmaceutically acceptable salt or prodrug thereof.
Included prodrugs of Formula (I) of the invention are:
1-(6-((2-amino-2-oxo-1-phenylethyl)thio)-3,5-dicyano-4-ethylpyridin-2-yl)pyrrolidin-3-yl dihydrogen phosphate;
2-((6-((2-amino-2-oxo-1-phenylethyl)thio)-3,5-dicyano-4-ethylpyridin-2-yl)(methyl)amino)ethyl dihydrogen phosphate;
1-(6-((2-amino-2-oxo-1-phenylethyl)thio)-3,5-dicyano-4-ethylpyridin-2-yl)azetidin-3-yl dihydrogen phosphate;
(2S)-2-((1-(6-((2-amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-amino-2-oxo-1-phenylethyl)thio)-3,5-dicyano-4-ethylpyridin-2-yl)piperidin-4-yl)oxy)ethyl dihydrogen phosphate;

1-(6-((2-amino-2-oxo-1-phenylethyl)thio)-3,5-dicyano-4-ethylpyridin-2-yl)piperidin-4-yl dihydrogen phosphate;
or a pharmaceutically acceptable salt thereof.
Suitably, the presently invented novel compounds of Formula (IVa) are selected from:
2-{[3,5-dicyano-6-(dimethylamino)-4-ethylpyridin-2-yl]sulfanyl}-2-phenylacetamide;
2-((3,5-dicyano-4-cyclopropyl-6-(1,4-diazepan-1-yl)pyridin-2-yl)thio)-2-phenylacetamide;
2-{[3,5-dicyano-4-cyclopropyl-6-(4-ethyl-1,4-diazepan-1-yl)pyridin-2-yl]sulfanyl}-2-phenylacetamide;
2-((3,5-dicyano-4-ethyl-6-(4-propyl-1,4-diazepan-1-yl)pyridin-2-yl)thio)-2-phenylacetamide;
2-{[3,5-dicyano-4-ethyl-6-(4-ethyl-1,4-diazepan-1-yl)pyridin-2-yl]sulfanyl}-2-phenylacetamide;
2-{[3,5-dicyano-4-ethyl-6-(5-oxo-1,4-diazepan-1-yl)pyridin-2-yl]sulfanyl}-2-phenylacetamide;
2-((3,5-dicyano-4-cyclopropyl-6-morpholinopyridin-2-yl)thio)-2-(pyridin-4-yl)acetamide;
2-{[3,5-dicyano-4-ethyl-6-(4-methyl-3-oxopiperazin-1-yl)pyridin-2-yl]sulfanyl}-2-(pyridin-4-yl)acetamide;
2-[(3,5-dicyano-4-ethyl-6-{methyl[2-(morpholin-4-yl)ethyl]amino}pyridin-2-yl)sulfanyl]-2-phenylacetamide;
2-{[3,5-dicyano-4-ethyl-6-(4-propylpiperazin-1-yl)pyridin-2-yl]sulfanyl}-2-phenylacetamide;
2-({3,5-dicyano-4-ethyl-6-[4-(piperidin-4-yl)piperazin-1-yl]pyridin-2-yl}sulfanyl)-2-phenylacetamide;
2-({3,5-dicyano-4-cyclopropyl-6-[3-(hydroxymethyl)piperazin-1-yl]pyridin-2-yl}sulfanyl)-2-phenylacetamide;
2-{[3,5-dicyano-4-cyclopropyl-6-(3-oxopiperazin-1-yl)pyridin-2-yl]sulfanyl}-2-phenylacetamide;
2-({3,5-dicyano-4-cyclopropyl-6-[4-(morpholin-4-yl)piperidin-1-yl]pyridin-2-yl}sulfanyl)-2-phenylacetamide;
2-((3,5-dicyano-4-ethyl-6-(2,8-diazaspiro[4.5]decan-8-yl)pyridin-2-yl)thio)-2-phenylacetamide; 2,2,2-trifluoroacetic acid;
2-((3,5-Dicyano-4-cyclopropyl-6-(3-(dimethylamino)piperidin-1-yl)pyridin-2-yl)thio)-2-phenylacetamide;
2-((3,5-Dicyano-4-cyclopropyl-6-(3-methylpiperazin-1-yl)pyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
2-((3,5-Dicyano-4-cyclopropyl-6-(2,6-dimethylmorpholino)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((6-(4-(Aminomethyl)-4-hydroxypiperidin-1-yl)-3,5-dicyano-4-cyclopropylpyridin-2-yl)thio)-2-phenylacetamide;
2-((3,5-dicyano-4-cyclopropyl-6-(3-(methylamino)piperidin-1-yl)pyridin-2-yl)thio)-2-phenylacetamide;
2-((6-(3-aminopiperidin-1-yl)-3,5-dicyano-4-cyclopropylpyridin-2-yl)thio)-2-phenylacetamide;
2-((3,5-dicyano-4-cyclopropyl-6-(dimethylamino)pyridin-2-yl)thio)-2-(pyridin-4-yl)acetamide;
2-((3,5-dicyano-6-(dimethylamino)-4-ethylpyridin-2-yl)thio)-2-(pyridin-4-yl)acetamide;
2-((6-(4-aminopiperidin-1-yl)-3,5-dicyano-4-cyclopropylpyridin-2-yl)thio)-2-phenylacetamide;
2-((3,5-dicyano-4-cyclopropyl-6-(4-(dimethylamino)piperidin-1-yl)pyridin-2-yl)thio)-2-phenylacetamide;
2-((3,5-dicyano-4-cyclopropyl-6-(piperazin-1-yl)pyridin-2-yl)thio)-2-(pyridin-4-yl)acetamide;
2-((3,5-dicyano-4-cyclopropyl-6-(1,4-diazepan-1-yl)pyridin-2-yl)thio)-2-(pyridin-4-yl)acetamide;
2-((3,5-dicyano-4-cyclopropyl-6-((R)-3-hydroxypiperidin-1-yl)pyridin-2-yl)thio)-2-phenylacetamide;

2-(3,5-dicyano-4-cyclopropyl-6-((S)-3-hydroxypiperidin-1-yl)pyridin-2-ylthio)-2-phenylacetamide;

2-((3,5-dicyano-4-cyclopropyl-6-((S)-3-hydroxypyrrolidin-1-yl)pyridin-2-yl)thio)-2-(pyridin-4-yl)acetamide;

2-((3,5-dicyano-4-ethyl-6-(4-ethylpiperazin-1-yl)pyridin-2-yl)thio)-2-phenylacetamide;

2-((3,5-Dicyano-4-ethyl-6-(1-oxa-6-azaspiro[3.4]octan-6-yl)pyridin-2-yl)thio)-2-phenylacetamide;

2-((6-(4-(3-aminopropyl)piperazin-1-yl)-3,5-dicyano-4-ethylpyridin-2-yl)thio)-2-phenylacetamide;

2-((3,5-Dicyano-4-ethyl-6-(1,7-diazaspiro[3.5]nonan-1-yl)pyridin-2-yl)thio)-2-phenylacetamide trifluoroacetate;

2-((3,5-Dicyano-4-cyclopropyl-6-(4-(pyrrolidin-1-ylmethyl)piperidin-1-yl)pyridin-2-yl)thio)-2-phenylacetamide;

2-((3,5-Dicyano-4-cyclopropyl-6-(4-(4-methylpiperazin-1-yl)piperidin-1-yl)pyridin-2-yl)thio)-2-phenylacetamide;

(R)-2-((3,5-dicyano-6-(1,4-diazepan-1-yl)-4-ethylpyridin-2-yl)amino)-2-phenylacetamide;

2-((3,5-Dicyano-4-cyclopropyl-6-(4-(pyrrolidin-1-yl)piperidin-1-yl)pyridin-2-yl)thio)-2-phenylacetamide trifluoroacetate;

2-((3,5-Dicyano-4-ethyl-6-(2,7-diazaspiro[3.5]nonan-7-yl)pyridin-2-yl)thio)-2-phenylacetamide;

2-((3,5-Dicyano-4-ethyl-6-(2,6-diazaspiro[3.4]octan-6-yl)pyridin-2-yl)thio)-2-phenylacetamide;

2-((3,5-dicyano-4-cyclopropyl-6-(1,4-diazepan-1-yl)pyridin-2-yl)thio)propanamide;

2-((3,5-Dicyano-4-ethyl-6-(4-(2-oxoimidazolidin-1-yl)piperidin-1-yl)pyridin-2-yl)thio)-2-phenylacetamide;

2-((3,5-Dicyano-4-ethyl-6-(4-hydroxypiperidin-1-yl)pyridin-2-yl)thio)-2-phenylacetamide;

2-((3,5-Dicyano-4-ethyl-6-((S)-3-hydroxypyrrolidin-1-yl)pyridin-2-yl)thio)-2-phenylacetamide;

2-((3,5-Dicyano-4-ethyl-6-(3-oxopiperazin-1-yl)pyridin-2-yl)thio)-2-phenylacetamide;

2-((3,5-Dicyano-4-ethyl-6-((2-methoxyethyl)(methyl)amino)pyridin-2-yl)thio)-2-phenylacetamide;

2-((3,5-Dicyano-4-ethyl-6-(3-methoxyazetidin-1-yl)pyridin-2-yl)thio)-2-phenylacetamide;

2-((3,5-Dicyano-4-ethyl-6-(piperazin-1-yl)pyridin-2-yl)thio)-2-phenylacetamide;

2-((3,5-Dicyano-4-ethyl-6-(4-methyl-1,4-diazepan-1-yl)pyridin-2-yl)thio)-2-phenylacetamide;

2-((3,5-Dicyano-4-ethyl-6-morpholinopyridin-2-yl)thio)-2-phenylacetamide;

2-[[6-(azetidin-1-yl)-3,5-dicyano-4-ethyl-2-pyridyl]sulfanyl]-2-phenyl-acetamide;

2-((3,5-dicyano-4-ethyl-6-(4-oxopiperidin-1-yl)pyridin-2-yl)thio)-2-phenylacetamide;

2-((3,5-dicyano-4-ethyl-6-(1'-(2-hydroxyethyl)-[4,4'-bipiperidin]-1-yl)pyridin-2-yl)thio)-2-phenylacetamide;

2-((3,5-Dicyano-6-((3S,5R)-3,5-dimethylpiperazin-1-yl)-4-ethylpyridin-2-yl)thio)-2-phenylacetamide;

2-((6-(8-azabicyclo[3.2.1]octan-3-yl(methyl)amino)-3,5-dicyano-4-ethylpyridin-2-yl)thio)-2-phenylacetamide;

2-((3,5-Dicyano-4-cyclopropyl-6-(2-(hydroxymethyl)morpholino)pyridin-2-yl)thio)-2-phenylacetamide;

(R)-2-((3,5-dicyano-6-(dimethylamino)-4-ethylpyridin-2-yl)thio)-2-phenylacetamide;

(R)-2-[(3,5-Dicyano-4-ethyl-6-morpholino-2-pyridyl)sulfanyl]-2-phenyl-acetamide;

N-(4-((3,5-Dicyano-4-ethyl-6-(4-(pyrrolidin-1-yl)piperidin-1-yl)pyridin-2-ylthio)methyl)benzyl)acetamide trifluoroacetate;

2-{[3,5-dicyano-4-ethyl-6-(5-methyl-1,4-diazepan-1-yl)pyridin-2-yl]sulfanyl}-2-phenylacetamide;

2-(4-(Aminomethyl)benzylthio)-4-ethyl-6-(4-(pyrrolidin-1-yl)piperidin-1-yl)pyridine-3,5-dicarbonitrile;

tert-Butyl 4-(((3,5-dicyano-4-ethyl-6-(4-methyl-1,4-diazepan-1-yl)pyridin-2-yl)thio)methyl)benzylcarbamate;

4-(((3,5-Dicyano-4-ethyl-6-(4-methyl-1,4-diazepan-1-yl)pyridin-2-yl)thio)methyl)benzamide;

2-((4-(Aminomethyl)benzyl)thio)-4-ethyl-6-(4-methyl-1,4-diazepan-1-yl)pyridine-3,5-dicarbonitrile, 2Hydrochloride;

2-(4-(((3,5-Dicyano-4-ethyl-6-(4-methyl-1,4-diazepan-1-yl)pyridin-2-yl)thio)methyl)phenyl)acetic acid;

4-(((3,5-Dicyano-4-ethyl-6-(4-methyl-1,4-diazepan-1-yl)pyridin-2-yl)thio)methyl)benzoic acid;

2-(Dimethylamino)-4-ethyl-6-(((6-oxo-1,6-dihydropyridin-3-yl)methyl)thio)pyridine-3,5-dicarbonitrile;

N-(4-(((3,5-Dicyano-4-ethyl-6-(4-methyl-1,4-diazepan-1-yl)pyridin-2-yl)thio)methyl)thiazol-2-yl)acetamide;

4-(((3,5-Dicyano-4-ethyl-6-(4-methyl-1,4-diazepan-1-yl)pyridin-2-yl)thio)methyl)benzenesulfonamide;

N-(4-(((3,5-Dicyano-4-ethyl-6-(4-methyl-1,4-diazepan-1-yl)pyridin-2-yl)thio)methyl)benzyl)acetamide;

tert-Butyl(2-((4-(((3,5-dicyano-4-ethyl-6-(4-methyl-1,4-diazepan-1-yl)pyridin-2-yl)thio)methyl)benzyl)amino)-2-oxoethyl)carbamate;

N-(4-(((3,5-Dicyano-4-ethyl-6-(4-methyl-1,4-diazepan-1-yl)pyridin-2-yl)thio)methyl)benzyl)methanesulfonamide;

2-Amino-N-(4-(((3,5-dicyano-4-ethyl-6-(4-methyl-1,4-diazepan-1-yl)pyridin-2-yl)thio)methyl)benzyl)acetamide;

2-(4-Aminopiperidin-1-yl)-6-(benzylthio)-4-ethylpyridine-3,5-dicarbonitrile;

4-(((3,5-Dicyano-4-ethyl-6-(4-methyl-1,4-diazepan-1-yl)pyridin-2-yl)thio)methyl)benzyl acetate;

2-(4-(((3,5-Dicyano-4-ethyl-6-(4-methyl-1,4-diazepan-1-yl)pyridin-2-yl)thio)methyl)phenyl acetamide;

2-(4-(((3,5-Dicyano-4-ethyl-6-(4-methyl-1,4-diazepan-1-yl)pyridin-2-yl)thio)methyl)phenyl)-N-methylacetamide;

4-Ethyl-2-((4-(hydroxymethyl)benzyl)thio)-6-(4-methyl-1,4-diazepan-1-yl)pyridine-3,5-dicarbonitrile;

N-(4-(((3,5-Dicyano-4-ethyl-6-(4-methyl-1,4-diazepan-1-yl)pyridin-2-yl)thio)methyl)benzyl)-2-hydroxyacetamide;

N-(4-(((3,5-Dicyano-4-ethyl-6-(4-methyl-1,4-diazepan-1-yl)pyridin-2-yl)thio)methyl)benzyl)propionamide;

N-(4-(((3,5-Dicyano-4-ethyl-6-(4-methyl-1,4-diazepan-1-yl)pyridin-2-yl)thio)methyl)benzyl)isobutyramide;

N-(4-(((3,5-Dicyano-4-ethyl-6-(4-methyl-1,4-diazepan-1-yl)pyridin-2-yl)thio)methyl)benzyl)-3-methylbutanamide;

4-Ethyl-2-((4-(((2-hydroxyethyl)amino)methyl)benzyl)thio)-6-(4-methyl-1,4-diazepan-1-yl)pyridine-3,5-dicarbonitrile;

N-(4-(((3,5-Dicyano-6-(4-methyl-1,4-diazepan-1-yl)-4-(methylamino)pyridin-2-yl)thio)methyl)benzyl)acetamide;

2-(((2-Acetyl-1,2,3,4-tetrahydroisoquinolin-6-yl)methyl)thio)-6-(dimethylamino)-4-ethylpyridine-3,5-dicarbonitrile;

2-((4-Cyanobenzyl)thio)-4-ethyl-6-(4-methyl-1,4-diazepan-1-yl)pyridine-3,5-dicarbonitrile;

2-Amino-N-(1-(6-(benzylthio)-3,5-dicyano-4-ethylpyridin-2-yl)piperidin-4-yl)acetamide, Trifluoroacetic acid salt;

2-Amino-N-(1-(6-(benzylthio)-3,5-dicyano-4-ethylpyridin-2-yl)piperidin-4-yl)-2-methylpropanamide, Formic acid salt;

3-Amino-N-(4-(((3,5-dicyano-4-ethyl-6-(4-methyl-1,4-diazepan-1-yl)pyridin-2-yl)thio)methyl)benzyl)propanamide;

(S)-2-Amino-N-(4-(((3,5-dicyano-4-ethyl-6-(4-methyl-1,4-diazepan-1-yl)pyridin-2-yl)thio)methyl)benzyl)propanamide;
(R)-2-Amino-N-(4-(((3,5-dicyano-4-ethyl-6-(4-methyl-1,4-diazepan-1-yl)pyridin-2-yl)thio)methyl)benzyl)propanamide;
1-(4-(((3,5-Dicyano-4-ethyl-6-(4-methyl-1,4-diazepan-1-yl)pyridin-2-yl)thio)methyl)benzyl)-3-ethylurea;
1-(4-(((3,5-Dicyano-4-ethyl-6-(4-methyl-1,4-diazepan-1-yl)pyridin-2-yl)thio)methyl)benzyl)-3-phenylurea;
N-(4-(((3,5-Dicyano-6-(4-methyl-1,4-diazepan-1-yl)-4-(methylthio)pyridin-2-yl)thio)methyl)benzyl)acetamide;
(E)-3-(4-(((3,5-Dicyano-6-(dimethylamino)-4-ethylpyridin-2-yl)thio)methyl)phenyl)acrylic acid, Trifluoroacetic acid salt;
N-(4-(((3,5-Dicyano-4-ethyl-6-((2-hydroxyethyl)(methyl)amino)pyridin-2-yl)thio)methyl)benzyl)acetamide;
4-(((3,5-Dicyano-4-ethyl-6-(4-methyl-1,4-diazepan-1-yl)pyridin-2-yl)thio)methyl)-N-methylbenzenesulfonamide;
N-(4-(((3,5-Dicyano-4-ethoxy-6-(4-methyl-1,4-diazepan-1-yl)pyridin-2-yl)thio)methyl)benzyl)acetamide;
2-({3,5-Dicyano-4-ethyl-6-[4-(2-methoxyethyl)-1,4-diazepan-1-yl]pyridin-2-yl}sulfanyl)-2-phenylacetamide;
2-((3,5-dicyano-4-ethyl-6-(4-(2-hydroxpropyl)-1,4-diazepan-1-yl)pyridin-2-yl)thio)-2-phenylacetamide;
Methyl 2-[4-(6-{[carbamoyl(phenyl)methyl]sulfanyl}-3,5-dicyano-4-ethylpyridin-2-yl)-1,4-diazepan-1-yl]acetate;
2-{[3,5-Dicyano-4-cyclopropyl-6-(4-methyl-5-oxo-1,4-diazepan-1-yl)pyridin-2-yl]sulfanyl}-2-phenylacetamide;
2-{[3,5-Dicyano-4-cyclopropyl-6-(5-oxo-1,4-diazepan-1-yl)pyridin-2-yl]sulfanyl}-2-phenylacetamide;
2-{[3,5-Dicyano-4-ethyl-6-(4-methyl-5-oxo-1,4-diazepan-1-yl)pyridin-2-yl]sulfanyl}-2-phenylacetamide;
2-{[3,5-Dicyano-6-(1,4-diazepan-1-yl)-4-ethylpyridin-2-yl]sulfanyl}-2-phenylacetamide;
2-({3,5-Dicyano-6-[4-(2-hydroxyethyl)-1,4-diazepan-1-yl]-4-(2,2,2-trifluoroethyl)pyridin-2-yl}sulfanyl)-2-phenylacetamide;
(2R)-2-({3,5-Dicyano-4-ethyl-6-[4-(2-hydroxyethyl)-1,4-dlaze pan-1-yl]pyridin-2-yl}amino)-2-phenylacetamide;
2-({6-[(3S)-3-Aminopyrrolidin-1-yl]-3,5-dicyano-4-cyclopropylpyridin-2-yl}sulfanyl)-2-phenylacetamide;
2-((3,5-Dicyano-4-ethyl-6-(2,9-diazaspiro[5.5]undecan-9-yl)pyridin-2-yl)thio)-2-phenylacetamide;
2-((3,5-Dicyano-4-ethyl-6-(hexahydro-1H-pyrrolo[1,2-a][1,4]diazepin-2(3H)-yl)pyridin-2-yl)thio)-2-phenylacetamide;
2-((3,5-Dicyano-4-ethyl-6-(2-methyl-2,9-diazaspiro[5.5]undecan-9-yl)pyridin-2-yl)thio)-2-phenylacetamide;
2-((3,5-Dicyano-6-(2-(cyclopropylmethyl)-2,9-diazaspiro[5.5]undecan-9-yl)-4-ethylpyridin-2-yl)thio)-2-phenylacetamide hydrochloride;
2-((3,5-Dicyano-6-(4-(3-(dimethylamino)propyl)piperazin-1-yl)-4-ethylpyridin-2-yl)thio)-2-phenylacetamide;
2-((3,5-Dicyano-4-ethyl-6-(4-(pyrrolidin-3-yl)piperidin-1-yl)pyridin-2-yl)thio)-2-phenylacetamide; 2,2,2-trifluoroacetic acid;
2-((6-([4,4'-Bipiperidin]-1-yl)-3,5-dicyano-4-ethylpyridin-2-yl)thio)-2-phenylacetamide; 2,2,2-trifluoroacetic acid;
2-((6-(4-(2-Aminoethyl)piperazin-1-yl)-3,5-dicyano-4-ethylpyridin-2-yl)thio)-2-phenylacetamide;
2-((6-(4-(3-Aminopropyl)piperazin-1-yl)-3,5-dicyano-4-cyclopropylpyridin-2-yl)thio)-2-phenylacetamide;
2-((3,5-Dicyano-4-cyclopropyl-6-(4-((4-methylpiperazin-1-yl)methyl)piperidin-1-yl)pyridin-2-yl)thio)-2-phenylacetamide trifluoroacetate;
2-((6-(4-Acetylpiperazin-1-yl)-3,5-dicyano-4-ethylpyridin-2-yl)thio)-2-phenylacetamide;
2-((3,5-Dicyano-4-cyclopropyl-6-(dimethylamino)pyridin-2-yl)thio)-2-phenylacetamide;
2-(4-Chlorophenyl)-2-((3,5-dicyano-6-(dimethylamino)-4-ethylpyridin-2-yl)thio)acetamide;
2-((3,5-Dicyano-4-ethyl-6-(4-(2-hydroxyethyl)piperazin-1-yl)pyridin-2-yl)thio)-2-phenylacetamide;
2-[(3,5-Dicyano-4-cyclopropyl-6-morpholino-2-pyridyl)sulfanyl]-2-phenyl-acetamide;
2-((6-(4-Benzoylpiperazin-1-yl)-3,5-dicyano-4-ethylpyridin-2-yl)thio)-2-phenylacetamide;
2-((3,5-Dicyano-4-ethyl-6-((5S,6S)-6-hydroxy-1-(methylsulfonyl)-1,8-diazaspiro[4.5]decan-8-yl)pyridin-2-yl)thio)-2-phenylacetamide;
2-((3,5-Dicyano-6-(4,4-difluoropiperidin-1-yl)-4-ethylpyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide;
2-((6-(4-amino-4-methylpiperidin-1-yl)-3,5-dicyano-4-ethylpyridin-2-yl)thio)-2-phenylacetamide;
2-amino-N-(1-(6-((2-amino-2-oxo-1-phenylethyl)thio)-3,5-dicyano-4-ethylpyridin-2-yl)piperidin-4-yl)acetamide 2,2,2-trifluoroacetate;
(2S)-2-amino-N-(1-(6-((2-amino-2-oxo-1-phenylethyl)thio)-3,5-dicyano-4-ethylpyridin-2-yl)piperidin-4-yl)propanamide 2,2,2-trifluoroacetate;
2-((6-(4-(3-aminooxetane-3-carbonyl)piperazin-1-yl)-3,5-dicyano-4-ethylpyridin-2-yl)thio)-2-phenylacetamide formate;
4-amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide 2,2,2-trifluoroacetate;
2-((6-(4-(4-aminotetrahydro-2H-pyran-4-carbonyl)piperazin-1-yl)-3,5-dicyano-4-ethylpyridin-2-yl)thio)-2-phenylacetamide 2,2,2-trifluoroacetate;
2-((3,5-dicyano-6-(4-(2-hydroxyethyl)-1,4-diazepan-1-yl)-4-methoxypyridin-2-yl)thio)-2-phenylacetamide;
2-((6-(4-aminopiperidin-1-yl)-3,5-dicyano-4-ethylpyridin-2-yl)thio)-2-phenylacetamide;
2-((6-((2-aminoethyl)(methyl)amino)-3,5-dicyano-4-ethylpyridin-2-yl)thio)-2-phenylacetamide 2,2,2-trifluoroacetate;
2-((6-((2-amino-2-oxoethyl)(methyl)amino)-3,5-dicyano-4-ethylpyridin-2-yl)thio)-2-phenylacetamide;
2-((3,5-dicyano-4-ethyl-6-(3-hydroxyazetidin-1-yl)pyridin-2-yl)thio)-2-phenylacetamide;
2-((3,5-dicyano-4-ethyl-6-((2-hydroxyethyl)(methyl)amino)pyridin-2-yl)thio)-2-phenylacetamide;
2-amino-N-(1-(6-((2-amino-2-oxo-1-phenylethyl)thio)-3,5-dicyano-4-ethylpyridin-2-yl)piperidin-4-yl)-2-methylpropanamide;
2-((6-(4-(2-aminoethoxy)piperidin-1-yl)-3,5-dicyano-4-ethylpyridin-2-yl)thio)-2-phenylacetamide 2,2,2-trifluoroacetate;
2-((3,5-dicyano-4-ethyl-6-(3-hydroxpyrrolidin-1-yl)pyridin-2-yl)thio)-2-phenylacetamide;
2-((3,5-dicyano-4-ethyl-6-(4-(2-hydroxyethoxy)piperidin-1-yl)pyridin-2-yl)thio)-2-phenylacetamide;
N-(4-(((6-(4-aminopiperidin-1-yl)-3,5-dicyano-4-ethylpyridin-2-yl)thio)methyl)benzyl)acetamide 2,2,2-trifluoroacetate; and
2-((3,5-dicyano-6-(dimethylamino)-4-ethylpyridin-2-yl)thio)-2-(piperidin-4-yl)acetamide;
or a pharmaceutically acceptable salt or prodrug thereof.
Included prodrugs of Formula (IVa) of the invention are:

1-(6-((2-amino-2-oxo-1-phenylethyl)thio)-3,5-dicyano-4-ethylpyridin-2-yl)pyrrolidin-3-yl dihydrogen phosphate;
2-((6-((2-amino-2-oxo-1-phenylethyl)thio)-3,5-dicyano-4-ethylpyridin-2-yl)(methyl)amino)ethyl dihydrogen phosphate;
1-(6-((2-amino-2-oxo-1-phenylethyl)thio)-3,5-dicyano-4-ethylpyridin-2-yl)azetidin-3-yl dihydrogen phosphate;
(2S)-2-((1-(6-((2-amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-amino-2-oxo-1-phenylethyl)thio)-3,5-dicyano-4-ethylpyridin-2-yl)piperidin-4-yl)oxy)ethyl dihydrogen phosphate;
1-(6-((2-amino-2-oxo-1-phenylethyl)thio)-3,5-dicyano-4-ethylpyridin-2-yl)piperidin-4-yl dihydrogen phosphate;
or a pharmaceutically acceptable salt thereof.

Primary Amide:

Included in the compounds of Formula (Ibr) and in the methods of the invention are:

2-[(6-amino-3,5-dicyano-4-ethylpyridin-2-yl)sulfanyl]-2-phenylacetamide;
(R)-[(6-amino-3,5-dicyano-4-ethylpyridin-2-yl)sulfanyl]-2-phenylacetamide;
2-{[3,5-dicyano-6-(dimethylamino)-4-ethylpyridin-2-yl]sulfanyl}-2-phenylacetamide;
2-((3,5-dicyano-4-cyclopropyl-6-(1,4-diazepan-1-yl)pyridin-2-yl)thio)-2-phenylacetamide;
2-{[3,5-dicyano-4-cyclopropyl-6-(4-ethyl-1,4-diazepan-1-yl)pyridin-2-yl]sulfanyl}-2-phenylacetamide;
2-((3,5-dicyano-4-ethyl-6-(4-propyl-1,4-diazepan-1-yl)pyridin-2-yl)thio)-2-phenylacetamide;
2-{[3,5-dicyano-4-ethyl-6-(4-ethyl-1,4-diazepan-1-yl)pyridin-2-yl]sulfanyl}-2-phenylacetamide;
2-{[3,5-dicyano-4-ethyl-6-(5-oxo-1,4-diazepan-1-yl)pyridin-2-yl]sulfanyl}-2-phenylacetamide;
2-((3,5-dicyano-4-cyclopropyl-6-morpholinopyridin-2-yl)thio)-2-(pyridin-4-yl)acetamide;
2-{[3,5-dicyano-4-ethyl-6-(4-methyl-3-oxopiperazin-1-yl)pyridin-2-yl]sulfanyl}-2-(pyridin-4-yl)acetamide;
2-[(3,5-dicyano-4-ethyl-6-{methyl[2-(morpholin-4-yl)ethyl]amino}pyridin-2-yl)sulfanyl]-2-phenylacetamide;
2-{[3,5-dicyano-4-ethyl-6-(4-propylpiperazin-1-yl)pyridin-2-yl]sulfanyl}-2-phenylacetamide;
2-({3,5-dicyano-4-ethyl-6-[4-(piperidin-4-yl)piperazin-1-yl]pyridin-2-yl}sulfanyl)-2-phenylacetamide;
2-({3,5-dicyano-4-cyclopropyl-6-[3-(hydroxymethyl)piperazin-1-yl]pyridin-2-yl}sulfanyl)-2-phenylacetamide;
2-{[3,5-dicyano-4-cyclopropyl-6-(3-oxopiperazin-1-yl)pyridin-2-yl]sulfanyl}-2-phenylacetamide;
2-({3,5-dicyano-4-cyclopropyl-6-[4-(morpholin-4-yl)piperidin-1-yl]pyridin-2-yl}sulfanyl)-2-phenylacetamide;
2-((3,5-dicyano-4-ethyl-6-(2,8-diazaspiro[4.5]decan-8-yl)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((3,5-Dicyano-4-cyclopropyl-6-(3-methylpiperazin-1-yl)pyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
2-((3,5-Dicyano-4-cyclopropyl-6-(2,6-dimethylmorpholino)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((6-(4-(Aminomethyl)-4-hydroxypiperidin-1-yl)-3,5-dicyano-4-cyclopropylpyridin-2-yl)thio)-2-phenylacetamide;
2-((3,5-dicyano-4-cyclopropyl-6-(3-(methylamino)piperidin-1-yl)pyridin-2-yl)thio)-2-phenylacetamide;
2-((6-(3-aminopiperidin-1-yl)-3,5-dicyano-4-cyclopropylpyridin-2-yl)thio)-2-phenylacetamide;
2-((3,5-dicyano-4-cyclopropyl-6-(dimethylamino)pyridin-2-yl)thio)-2-(pyridin-4-yl)acetamide;
2-((3,5-dicyano-6-(dimethylamino)-4-ethylpyridin-2-yl)thio)-2-(pyridin-4-yl)acetamide;
2-((6-(4-aminopiperidin-1-yl)-3,5-dicyano-4-cyclopropylpyridin-2-yl)thio)-2-phenylacetamide;
2-((3,5-dicyano-4-cyclopropyl-6-(4-(dimethylamino)piperidin-1-yl)pyridin-2-yl)thio)-2-phenylacetamide;
2-((3,5-dicyano-4-cyclopropyl-6-(piperazin-1-yl)pyridin-2-yl)thio)-2-(pyridin-4-yl)acetamide;
2-((3,5-dicyano-4-cyclopropyl-6-(1,4-diazepan-1-yl)pyridin-2-yl)thio)-2-(pyridin-4-yl)acetamide;
2-((3,5-dicyano-4-cyclopropyl-6-((R)-3-hydroxypiperidin-1-yl)pyridin-2-yl)thio)-2-phenylacetamide;
2-(3,5-dicyano-4-cyclopropyl-6-((S)-3-hydroxypiperidin-1-yl)pyridin-2-ylthio)-2-phenylacetamide;
2-((3,5-dicyano-4-cyclopropyl-6-((S)-3-hydroxypyrrolidin-1-yl)pyridin-2-yl)thio)-2-(pyridin-4-yl)acetamide;
2-((3,5-dicyano-4-ethyl-6-(4-ethylpiperazin-1-yl)pyridin-2-yl)thio)-2-phenylacetamide;
2-((3,5-Dicyano-4-ethyl-6-(1-oxa-6-azaspiro[3.4]octan-6-yl)pyridin-2-yl)thio)-2-phenylacetamide;
2-((6-(4-(3-aminopropyl)piperazin-1-yl)-3,5-dicyano-4-ethylpyridin-2-yl)thio)-2-phenylacetamide;
2-((3,5-Dicyano-4-ethyl-6-(1,7-diazaspiro[3.5]nonan-1-yl)pyridin-2-yl)thio)-2-phenylacetamide;
2-((3,5-Dicyano-4-cyclopropyl-6-(4-(pyrrolidin-1-ylmethyl)piperidin-1-yl)pyridin-2-yl)thio)-2-phenylacetamide;
2-((3,5-Dicyano-4-cyclopropyl-6-(4-(4-methylpiperazin-1-yl)piperidin-1-yl)pyridin-2-yl)thio)-2-phenylacetamide;
(R)-2-((3,5-dicyano-6-(1,4-diazepan-1-yl)-4-ethylpyridin-2-yl)amino)-2-phenylacetamide;
2-((3,5-Dicyano-4-cyclopropyl-6-(4-(pyrrolidin-1-yl)piperidin-1-yl)pyridin-2-yl)thio)-2-phenylacetamide;
2-((3,5-Dicyano-4-ethyl-6-(2,7-diazaspiro[3.5]nonan-7-yl)pyridin-2-yl)thio)-2-phenylacetamide;
2-((3,5-Dicyano-4-ethyl-6-(2,6-diazaspiro[3.4]octan-6-yl)pyridin-2-yl)thio)-2-phenylacetamide;
2-((3,5-dicyano-4-cyclopropyl-6-(1,4-diazepan-1-yl)pyridin-2-yl)thio)propanamide;
2-((3,5-Dicyano-4-ethyl-6-(4-(2-oxoimidazolidin-1-yl)piperidin-1-yl)pyridin-2-yl)thio)-2-phenylacetamide;
2-((3,5-Dicyano-4-ethyl-6-(4-hydroxypiperidin-1-yl)pyridin-2-yl)thio)-2-phenylacetamide;
2-((3,5-Dicyano-4-ethyl-6-((S)-3-hydroxypyrrolidin-1-yl)pyridin-2-yl)thio)-2-phenylacetamide;
2-((3,5-Dicyano-4-ethyl-6-(3-oxopiperazin-1-yl)pyridin-2-yl)thio)-2-phenylacetamide;
2-[(6-amino-3,5-dicyano-4-cyclopropyl-2-pyridyl)sulfanyl]-2-phenyl-acetamide;
2-((3,5-Dicyano-4-ethyl-6-(methylamino)pyridin-2-yl)thio)-2-phenylacetamide;
2-((3,5-Dicyano-4-ethyl-6-((2-methoxyethyl)(methyl)amino)pyridin-2-yl)thio)-2-phenylacetamide;
2-((3,5-Dicyano-4-ethyl-6-(3-methoxyazetidin-1-yl)pyridin-2-yl)thio)-2-phenylacetamide;
2-((3,5-Dicyano-4-ethyl-6-(piperazin-1-yl)pyridin-2-yl)thio)-2-phenylacetamide;
2-((3,5-Dicyano-4-ethyl-6-(4-methyl-1,4-diazepan-1-yl)pyridin-2-yl)thio)-2-phenylacetamide;
2-((3,5-Dicyano-4-ethyl-6-morpholinopyridin-2-yl)thio)-2-phenylacetamide;

2-[[6-(azetidin-1-yl)-3,5-dicyano-4-ethyl-2-pyridyl]sulfanyl]-2-phenyl-acetamide;
2-((3,5-dicyano-4-ethyl-6-(4-oxopiperidin-1-yl)pyridin-2-yl)thio)-2-phenylacetamide;
2-((3,5-dicyano-4-ethyl-6-(1'-(2-hydroxyethyl)-[4,4'-bipiperidin]-1-yl)pyridin-2-yl)thio)-2-phenylacetamide;
2-((3,5-Dicyano-6-((3S,5R)-3,5-dimethylpiperazin-1-yl)-4-ethylpyridin-2-yl)thio)-2-phenylacetamide;
2-((6-(8-azabicyclo[3.2.1]octan-3-yl(methyl)amino)-3,5-dicyano-4-ethylpyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
(R)-2-((3,5-dicyano-6-(dimethylamino)-4-ethylpyridin-2-yl)thio)-2-phenylacetamide;
(R)-2-[(3,5-Dicyano-4-ethyl-6-morpholino-2-pyridyl)sulfanyl]-2-phenyl-acetamide;
2-{[3,5-dicyano-4-ethyl-6-(5-methyl-1,4-diazepan-1-yl)pyridin-2-yl]sulfanyl}-2-phenylacetamide;
2-({3,5-Dicyano-4-ethyl-6-[4-(2-methoxyethyl)-1,4-diazepan-1-yl]pyridin-2-yl}sulfanyl)-2-phenylacetamide;
2-((3,5-dicyano-4-ethyl-6-(4-(2-hydroxpropyl)-1,4-diazepan-1-yl)pyridin-2-yl)thio)-2-phenylacetamide;
Methyl 2-[4-(6-{[carbamoyl(phenyl)methyl]sulfanyl}-3,5-dicyano-4-ethylpyridin-2-yl)-1,4-diazepan-1-yl]acetate;
2-{[3,5-Dicyano-4-cyclopropyl-6-(4-methyl-5-oxo-1,4-diazepan-1-yl)pyridin-2-yl]sulfanyl}-2-phenylacetamide;
2-{[3,5-Dicyano-4-cyclopropyl-6-(5-oxo-1,4-diazepan-1-yl)pyridin-2-yl]sulfanyl}-2-phenylacetamide;
2-{[3,5-Dicyano-4-ethyl-6-(4-methyl-5-oxo-1,4-diazepan-1-yl)pyridin-2-yl]sulfanyl}-2-phenylacetamide;
2-{[3,5-Dicyano-6-(1,4-diazepan-1-yl)-4-ethylpyridin-2-yl]sulfanyl}-2-phenylacetamide;
2-({3,5-Dicyano-6-[4-(2-hydroxyethyl)-1,4-diazepan-1-yl]-4-(2,2,2-trifluoroethyl)pyridin-2-yl}sulfanyl)-2-phenylacetamide;
(2R)-2-({3,5-Dicyano-4-ethyl-6-[4-(2-hydroxyethyl)-1,4-diazepan-1-yl]pyridin-2-yl}amino)-2-phenylacetamide;
2-({6-[(3S)-3-Aminopyrrolidin-1-yl]-3,5-dicyano-4-cyclopropylpyridin-2-yl}sulfanyl)-2-phenylacetamide;
2-((3,5-Dicyano-4-ethyl-6-(2,9-diazaspiro[5.5]undecan-9-yl)pyridin-2-yl)thio)-2-phenylacetamide;
2-((3,5-Dicyano-4-ethyl-6-(hexahydro-1H-pyrrolo[1,2-a][1,4]diazepin-2(3H)-yl)pyridin-2-yl)thio)-2-phenylacetamide;
2-((3,5-Dicyano-4-ethyl-6-(2-methyl-2,9-diazaspiro[5.5]undecan-9-yl)pyridin-2-yl)thio)-2-phenylacetamide;
2-((3,5-Dicyano-6-(2-(cyclopropylmethyl)-2,9-diazaspiro[5.5]undecan-9-yl)-4-ethylpyridin-2-yl)thio)-2-phenylacetamide;
2-((3,5-Dicyano-6-(4-(3-(dimethylamino)propyl)piperazin-1-yl)-4-ethylpyridin-2-yl)thio)-2-phenylacetamide;
2-((3,5-Dicyano-4-ethyl-6-(4-(pyrrolidin-3-yl)piperidin-1-yl)pyridin-2-yl)thio)-2-phenylacetamide;
2-((6-([4,4'-Bipiperidin]-1-yl)-3,5-dicyano-4-ethylpyridin-2-yl)thio)-2-phenylacetamide;
2-((6-(4-(2-Aminoethyl)piperazin-1-yl)-3,5-dicyano-4-ethylpyridin-2-yl)thio)-2-phenylacetamide;
2-((6-(4-(3-Aminopropyl)piperazin-1-yl)-3,5-dicyano-4-cyclopropylpyridin-2-yl)thio)-2-phenylacetamide;
2-((3,5-Dicyano-4-cyclopropyl-6-(4-((4-methylpiperazin-1-yl)methyl)piperidin-1-yl)pyridin-2-yl)thio)-2-phenylacetamide;
2-((6-(4-Acetylpiperazin-1-yl)-3,5-dicyano-4-ethylpyridin-2-yl)thio)-2-phenylacetamide;
2-((3,5-Dicyano-4-cyclopropyl-6-(dimethylamino)pyridin-2-yl)thio)-2-phenylacetamide;
2-(4-Chlorophenyl)-2-((3,5-dicyano-6-(dimethylamino)-4-ethylpyridin-2-yl)thio)acetamide;
2-((3,5-Dicyano-4-ethyl-6-(4-(2-hydroxyethyl)piperazin-1-yl)pyridin-2-yl)thio)-2-phenylacetamide;
2-[(3,5-Dicyano-4-cyclopropyl-6-morpholino-2-pyridyl)sulfanyl]-2-phenyl-acetamide;
2-((6-(4-Benzoylpiperazin-1-yl)-3,5-dicyano-4-ethylpyridin-2-yl)thio)-2-phenylacetamide;
2-((3,5-Dicyano-4-ethyl-6-((5S,6S)-6-hydroxy-1-(methylsulfonyl)-1,8-diazaspiro[4.5]decan-8-yl)pyridin-2-yl)thio)-2-phenylacetamide;
2-((3,5-Dicyano-6-(4,4-difluoropiperidin-1-yl)-4-ethylpyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide;
2-((3,5-dicyano-4-(furan-2-yl)-6-(4-methyl-1,4-diazepan-1-yl)pyridin-2-yl)thio)-2-phenylacetamide;
2-((6-(4-Amino-4-methylpiperidin-1-yl)-3,5-dicyano-4-ethylpyridin-2-yl)thio)-2-phenylacetamide;
2-Amino-N-(1-(6-((2-amino-2-oxo-1-phenylethyl)thio)-3,5-dicyano-4-ethylpyridin-2-yl)piperidin-4-yl)acetamide;
(2S)-2-Amino-N-(1-(6-((2-amino-2-oxo-1-phenylethyl)thio)-3,5-dicyano-4-ethylpyridin-2-yl)piperidin-4-yl)propanamide;
2-((6-(4-(3-Aminooxetane-3-carbonyl)piperazin-1-yl)-3,5-dicyano-4-ethylpyridin-2-yl)thio)-2-phenylacetamide;
4-Amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide;
2-((6-(4-(4-Aminotetrahydro-2H-pyran-4-carbonyl)piperazin-1-yl)-3,5-dicyano-4-ethylpyridin-2-yl)thio)-2-phenylacetamide;
2-((3,5-Dicyano-6-(4-(2-hydroxyethyl)-1,4-diazepan-1-yl)-4-methoxypyridin-2-yl)thio)-2-phenylacetamide;
2-((6-(4-Aminopiperidin-1-yl)-3,5-dicyano-4-ethylpyridin-2-yl)thio)-2-phenylacetamide;
2-((6-((2-Aminoethyl)(methyl)amino)-3,5-dicyano-4-ethylpyridin-2-yl)thio)-2-phenylacetamide;
2-((6-((2-Amino-2-oxoethyl)(methyl)amino)-3,5-dicyano-4-ethylpyridin-2-yl)thio)-2-phenylacetamide;
2-((3,5-Dicyano-4-ethyl-6-(3-hydroxyazetidin-1-yl)pyridin-2-yl)thio)-2-phenylacetamide;
2-(3,5-Dicyano-4-ethyl-6-((2-hydroxyethyl)(methyl)amino)pyridin-2-ylthio)-2-phenylacetamide;
2-Amino-N-(1-(6-((2-amino-2-oxo-1-phenylethyl)thio)-3,5-dicyano-4-ethylpyridin-2-yl)piperidin-4-yl)-2-methylpropanamide;
2-((6-(4-(2-Aminoethoxy)piperidin-1-yl)-3,5-dicyano-4-ethylpyridin-2-yl)thio)-2-phenylacetamide;
1-(6-((2-Amino-2-oxo-1-phenylethyl)thio)-3,5-dicyano-4-ethylpyridin-2-yl)pyrrolidin-3-yl dihydrogen phosphate;
2-((6-((2-Amino-2-oxo-1-phenylethyl)thio)-3,5-dicyano-4-ethylpyridin-2-yl)(methyl)amino)ethyl dihydrogen phosphate;
1-(6-((2-Amino-2-oxo-1-phenylethyl)thio)-3,5-dicyano-4-ethylpyridin-2-yl)azetidin-3-yl dihydrogen phosphate;
(2S)-2-((1-(6-((2-Amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-Amino-2-oxo-1-phenylethyl)thio)-3,5-dicyano-4-ethylpyridin-2-yl)piperidin-4-yl)oxy)ethyl dihydrogen phosphate;
1-(6-((2-Amino-2-oxo-1-phenylethyl)thio)-3,5-dicyano-4-ethylpyridin-2-yl)piperidin-4-yl dihydrogen phosphate;
2-((3,5-Dicyano-6-(dimethylamino)-4-ethylpyridin-2-yl)thio)-2-(piperidin-4-yl)acetamide; yl)acetamide;

2-((3,5-Dicyano-4-ethyl-6-(4-(propylsulfonyl)piperazin-1-yl)pyridin-2-yl)thio)-2-phenylacetamide;
2-((3,5-Dicyano-4-ethyl-6-(4-(phenylsulfonyl)piperazin-1-yl)pyridin-2-yl)thio)-2-phenylacetamide;
2-((3,5-Dicyano-4-ethyl-6-((R)-3-hydroxypyrrolidin-1-yl)pyridin-2-yl)thio)-2-phenylacetamide;
2-((3,5-Dicyano-4-ethyl-6-(2-oxa-6-azaspiro[3.4]octan-6-yl)pyridin-2-yl)thio)-2-phenylacetamide;
(R)-2-((3,5-Dicyano-4-ethyl-6-(4-ethyl-1,4-diazepan-1-yl)pyridin-2-yl)amino)-2-phenylacetamide;
(R)-2-((3,5-Dicyano-4-ethyl-6-(4-(3-(pyrrolidin-1-yl)propyl)-1,4-diazepan-1-yl)pyridin-2-yl)amino)-2-phenylacetamide;
2-(3,5-Dicyano-4-cyclopropyl-6-(3-hydroxypiperidin-1-yl)pyridin-2-ylthio)-2-phenylacetamide;
2-((3,5-Dichloro-4-ethyl-6-(4-methyl-1,4-diazepan-1-yl)pyridin-2-yl)thio)-2-phenylacetamide;
2-((3,5-Dicyano-6-(1,1-dioxidothiomorpholino)-4-ethylpyridin-2-yl)thio)-2-phenylacetamide;
2-((3,5-Dicyano-4-ethyl-6-(methyl(2-(piperazin-1-yl)ethyl)amino)pyridin-2-yl)thio)-2-phenylacetamide;
(R)-2-((3,5-Dicyano-4-ethyl-6-((S)-3-hydroxypyrrolidin-1-yl)pyridin-2-yl)thio)-2-phenylacetamide;
2-((6-((2-(4-(Aminomethyl)-4-hydroxypiperidin-1-yl)ethyl)(methyl)amino)-3,5-dicyano-4-ethylpyridin-2-yl)thio)-2-phenylacetamide;
2-((4-Cyano-3-(1,4-diazepan-1-yl)-6,7-dihydro-5H-cyclopenta[c]pyridin-1-yl)thio)-2-phenylacetamide;
2-((6-(4-(1H-Imidazol-1-yl)piperidin-1-yl)-3,5-dicyano-4-ethylpyridin-2-yl)thio)-2-phenylacetamide;
2-((3,5-Dicyano-4-ethyl-6-(4-(pyridin-4-ylmethyl)piperazin-1-yl)pyridin-2-yl)thio)-2-phenylacetamide;
2-((3,5-Dicyano-6-(2-(dimethylamino)ethoxy)-4-ethylpyridin-2-yl)thio)-2-phenylacetamide;
2-((1-(6-((2-Amino-2-oxo-1-phenylethyl)thio)-3,5-dicyano-4-cyclopropylpyridin-2-yl)piperidin-3-yl)amino)acetic acid;
2-((3,5-Dicyano-4-ethyl-6-(4-(oxazol-2-ylmethyl)piperazin-1-yl)pyridin-2-yl)thio)-2-phenylacetamide;
2-((6-(4-((1H-Pyrrol-2-yl) methyl) piperazin-1-yl)-3,5-dicyano-4-ethylpyridin-2-yl)thio)-2-phenylacetamide;
2-((3,5-Dicyano-6-(3,4-dihydro-2,7-naphthyridin-2 (1H)-yl)-4-ethylpyridin-2-yl)thio)-2-phenylacetamide;
2-((3,5-Dicyano-4-ethyl-6-((S)-3-hydroxypyrrolidin-1-yl)pyridin-2-yl)thio)-2-(pyridin-2-yl)acetamide;
2-((6-(4-((1H-Pyrrol-3-yl)methyl)piperazin-1-yl)-3,5-dicyano-4-ethylpyridin-2-yl)thio)-2-phenylacetamide;
2-((3,5-Dicyano-4-ethyl-6-(4-(isoxazol-3-ylmethyl)piperazin-1-yl)pyridin-2-yl)thio)-2-phenylacetamide;
2-((3,5-Dicyano-4-ethyl-6-(4-(oxazol-5-ylmethyl)piperazin-1-yl)pyridin-2-yl)thio)-2-phenylacetamide;
2-((3,5-Dicyano-4-ethyl-6-(4-(isoxazol-4-ylmethyl)piperazin-1-yl)pyridin-2-yl)thio)-2-phenylacetamide;
3-Amino-N-(1-(6-((2-amino-2-oxo-1-phenylethyl)thio)-3,5-dicyano-4-ethylpyridin-2-yl)piperidin-4-yl)oxetane-3-carboxamide;
2-((6-(4-((1H-Pyrazol-4-yl)methyl)piperazin-1-yl)-3,5-dicyano-4-ethylpyridin-2-yl)thio)-2-phenylacetamide;
2-((6-(4-((1H-Imidazol-5-yl)methyl)piperazin-1-yl)-3,5-dicyano-4-ethylpyridin-2-yl)thio)-2-phenylacetamide;
2-((3,5-Dicyano-4-ethyl-6-(4-(1-hydroxy-2-methylpropan-2-yl)piperazin-1-yl)pyridin-2-yl)thio)-2-phenylacetamide;
2-((6-(4-((1H-Imidazol-2-yl)methyl)piperazin-1-yl)-3,5-dicyano-4-ethylpyridin-2-yl)thio)-2-phenylacetamide;
2-((3,5-Dicyano-6-(dimethylamino)-4-methoxypyridin-2-yl)thio)-2-phenylacetamide;
2-((3,5-Dicyano-6-(dimethylamino)-4-ethoxypyridin-2-yl)thio)-2-phenylacetamide;
2-((3,5-Dicyano-4-ethoxy-6-(4-(2-hydroxyethyl)-1,4-diazepan-1-yl) pyridin-2-yl)thio)-2-phenylacetamide;
2-((3,5-Dicyano-4-ethyl-6-(4-(2-hydroxy-2-methylpropyl)-1,4-diazepan-1-yl)pyridin-2-yl)thio)-2-phenylacetamide;
2-((3,5-Dicyano-4-ethyl-6-(4-(thiazol-5-ylmethyl)piperazin-1-yl)pyridin-2-yl)thio)-2-phenylacetamide;
2-((3,5-Dicyano-4-ethyl-6-(piperazin-1-yl)pyridin-2-yl)thio)-2-(4-fluorophenyl)acetamide;
2-((3,5-Dicyano-4-ethyl-6-(4-(isothiazol-4-ylmethyl)piperazin-1-yl)pyridin-2-yl)thio)-2-phenylacetamide;
2-((3,5-Dicyano-6-(dimethylamino)-4-ethylpyridin-2-yl)thio)-2-(4-fluorophenyl)acetamide;
2-((3,5-Dicyano-6-(dimethylamino)-4-ethylpyridin-2-yl)thio)-2-(5-fluoropyridin-2-yl)acetamide;
2-((3,5-Dicyano-4-ethyl-6-(4-(furan-3-ylmethyl)piperazin-1-yl)pyridin-2-yl)thio)-2-phenylacetamide;
2-((3,5-Dicyano-4-ethyl-6-((2-morpholinoethyl)thio)pyridin-2-yl)thio)-2-phenylacetamide;
2-((3,5-Dicyano-6-(4-methyl-1,4-diazepan-1-yl)-4-(methylthio)pyridin-2-yl)thio)-2-phenylacetamide;
2-((3,5-Dichloro-4-ethyl-6-(4-(2-hydroxyethyl)-1,4-diazepan-1-yl)pyridin-2-yl)thio)-2-phenylacetamide; p 2-((3, 5-Dicyano-4-ethyl-6-(hexahydropyrrolo[3,4-b][1,4]oxazin-6(2H)-yl)pyridin-2-yl)thio)-2-phenylacetamide;
2-((3,5-Dicyano-4-ethyl-6-(4-methyl-1,4-diazepan-1-yl)pyridin-2-yl)thio)-2-(5-methylpyridin-2-yl)acetamide;
2-((3,5-Dicyano-4-ethyl-6-(4-methyl-1,4-diazepan-1-yl)pyridin-2-yl)thio)-2-(6-fluoropyridin-2-yl)acetamide;
2-((3,5-Dicyano-6-(4-(dimethylamino)piperidin-1-yl)-4-ethylpyridin-2-yl)thio)-2-(4-fluorophenyl)acetamide;
2-((3,5-Dicyano-4-ethyl-6-(4-methyl-1,4-diazepan-1-yl)pyridin-2-yl)thio)-2-(4-methylpyridin-2-yl)acetamide;
2-((3,5-Dicyano-4-ethyl-6-(4-methyl-1,4-diazepan-1-yl)pyridin-2-yl)thio)-2-(3-methoxypyridin-2-yl)acetamide;
2-((3,5-Dicyano-6-(4-(dimethylamino)piperidin-1-yl)-4-ethylpyridin-2-yl)thio)-2-(2,4-difluorophenyl)acetamide;
2-((3,5-Dicyano-4-ethyl-6-(4-(pyrrolidin-1-yl)piperidin-1-yl)pyridin-2-yl)thio)-2-(5-fluoropyridin-2-yl)acetamide;
2-((3,5-Dicyano-4-ethoxy-6-(4-(2-hydroxyethyl)-1,4-diazepan-1-yl)pyridin-2-yl)thio)propanamide;
2-((3,5-Dicyano-6-(4-(2-hydroxyethyl)-1,4-diazepan-1-yl)-4-propoxpyridin-2-yl)thio)-2-phenylacetamide;
2-((3,5-Dicyano-4-ethyl-6-(4-methyl-1,4-diazepan-1-yl)pyridin-2-yl)thio)-2-(4-methoxypyridin-2-yl)acetamide;
2-((3,5-Dicyano-4-ethyl-6-(2-methyl-2,8-diazaspiro[4.5]decan-8-yl)pyridin-2-yl)thio)-2-phenylacetamide;
2-((3,5-Dicyano-6-(4-(dimethylamino)piperidin-1-yl)-4-ethylpyridin-2-yl)thio)-2-(3,4-difluorophenyl)acetamide;
1-(6-((2-Amino-2-oxo-1-phenylethyl)thio)-3,5-dicyano-4-ethylpyridin-2-yl)piperidine-4-carboxamide;
2-((3,5-Dicyano-6-((2-(dimethylamino)ethyl)thio)-4-ethylpyridin-2-yl)thio)-2-phenylacetamide;
2-((3,5-Dicyano-6-((3S,4R)-3,4-dihydroxypyrrolidin-1-yl)-4-ethylpyridin-2-yl)thio)-2-phenylacetamide;
2-((3,5-Dicyano-4-ethyl-6-(4-methyl-1,4-diazepan-1-yl)pyridin-2-yl)thio)-2-(3-fluoropyridin-2-yl)acetamide;
2-((3,5-Dicyano-4-ethyl-6-(4-methyl-1,4-diazepan-1-yl)pyridin-2-yl)thio)-2-(5-methoxypyridin-2-yl)acetamide;
2-((3,5-Dicyano-4-ethyl-6-(4-(1-hydroxy-2-methylpropan-2-yl)piperazin-1-yl)pyridin-2-yl)thio)-2-(4-fluorophenyl)acetamide;
2-((3,5-Dicyano-4-ethyl-6-(4-methyl-1,4-diazepan-1-yl)pyridin-2-yl)thio)-2-(3-(trifluoromethyl)phenyl)acetamide;

2-((3,5-Dicyano-4-ethyl-6-(4-(2-hydroxyethoxy)piperidin-1-yl)pyridin-2-yl)thio)-2-phenylacetamide;
2-((3,5-Dicyano-4-ethyl-6-(4-methyl-1,4-diazepan-1-yl)pyridin-2-yl)thio)-2-(2-fluoropyridin-3-yl)acetamide;
2-((3,5-Dicyano-4-ethyl-6-(4-methyl-1,4-diazepan-1-yl)pyridin-2-yl)thio)-2-(6-fluoropyridin-3-yl)acetamide;
3-((6-(2-Amino-2-oxo-1-phenylethylthio)-3,5-dicyano-4-ethylpyridin-2-yl)(methyl)amino)propanamide;
2-((3,5-Dicyano-4-ethyl-6-(4-(oxetan-3-yloxy)piperidin-1-yl)pyridin-2-yl)thio)-2-phenylacetamide;
2-((3,5-Dicyano-6-(4-((2,2-difluoroethyl) amino)-4-methylpiperidin-1-yl)-4-ethylpyridin-2-yl)thio)-2-phenylacetamide;
2-((3,5-Dicyano-4-ethyl-6-(4-methyl-1,4-diazepan-1-yl)pyridin-2-yl)thio)-2-(4-(trifluoromethyl)phenyl)acetamide;
2-((6-(4-Aminopiperazin-1-yl)-3,5-dicyano-4-ethylpyridin-2-yl)thio)-2-phenylacetamide;
2-((6-((2-Amino-2-oxoethyl)thio)-3,5-dicyano-4-ethylpyridin-2-yl)thio)-2-phenylacetamide;
2-((3,5-Dicyano-4-ethyl-6-(pyrrolo[3,4-c]pyrazol-5(1H,4H,6H)-yl)pyridin-2-yl)thio)-2-phenylacetamide;
2-((3,5-Dicyano-6-(dimethylamino)-4-ethylpyridin-2-yl)thio)-2-(5-methoxypyridin-2-yl)acetamide;
2-((3,5-Dicyano-6-(dimethylamino)-4-ethylpyridin-2-yl)thio)-2-(5-methylpyridin-2-yl)acetamide;
2-((3,5-Dicyano-4-ethyl-6-(4-methyl-1,4-diazepan-1-yl)pyridin-2-yl)thio)-2-(2-fluoropyridin-4-yl)acetamide;
2-((3,5-Dicyano-4-ethyl-6-(4-hydroxy-4-(hydroxymethyl)piperidin-1-yl)pyridin-2-yl)thio)-2-phenylacetamide;
2-((3,5-Dicyano-4-ethyl-6-(2-oxo-3-oxa-1,8-diazaspiro[4.5]decan-8-yl)pyridin-2-yl)thio)-2-phenylacetamide;
2-((6-(4-Amino-4-(hydroxymethyl)piperidin-1-yl)-3,5-dicyano-4-ethylpyridin-2-yl)thio)-2-phenylacetamide;
2-((6-(4-(Aminomethyl)-4-hydroxypiperidin-1-yl)-3,5-dicyano-4-ethylpyridin-2-yl)thio)-2-phenylacetamide;
2-(3-Benzoylphenyl)-2-((3,5-dicyano-4-ethyl-6-(4-(2-hydroxyethyl)-1,4-diazepan-1-yl)pyridin-2-yl)thio)acetamide;
2-(4-Benzoylphenyl)-2-((3,5-dicyano-4-ethyl-6-(4-(2-hydroxyethyl)-1,4-diazepan-1-yl)pyridin-2-yl)thio)acetamide;
2-((3,5-Dicyano-4-ethyl-6-(4-methyl-1,4-diazepan-1-yl)pyridin-2-yl)thio)-2-(2-methylpyridin-4-yl)acetamide;
2-((3,5-Dicyano-4-ethyl-6-(4-methyl-1,4-diazepan-1-yl)pyridin-2-yl)thio)-2-(3-(pyrrolidin-1-yl)phenyl)acetamide;
2-((3,5-Dicyano-4-ethyl-6-(4-methyl-1,4-diazepan-1-yl)pyridin-2-yl)thio)-2-(3-fluoropyridin-4-yl)acetamide;
2-((3,5-Dicyano-4-ethyl-6-(4-methyl-1,4-diazepan-1-yl)pyridin-2-yl)thio)-2-(2,5-difluoropyridin-4-yl)acetamide;
2-((3,5-Dicyano-6-(4-(2,5-dioxoimidazolidin-1-yl)piperidin-1-yl)-4-ethylpyridin-2-yl)thio)-2-phenylacetamide;
4-Amino-1-(6-((2-amino-2-oxo-1-phenylethyl)thio)-3,5-dicyano-4-ethylpyridin-2-yl) piperidine-4-carboxamide;
2-((3,5-Dicyano-6-(4-(2,5-dioxopyrrolidin-1-yl)piperidin-1-yl)-4-ethylpyridin-2-yl)thio)-2-phenylacetamide;
2-((3,5-dicyano-4-ethyl-6-(4-methyl-1,4-diazepan-1-yl)pyridin-2-yl)thio)-2-phenylacetamide (isomer 1);
2-((3,5-dicyano-4-ethyl-6-(4-methyl-1,4-diazepan-1-yl)pyridin-2-yl)thio)-2-phenylacetamide (Isomer 2);
2-((3,5-Dicyano-4-ethyl-6-(2-oxo-1-oxa-3,8-diazaspiro[4.5]decan-8-yl)pyridin-2-yl)thio)-2-phenylacetamide;
1-(6-((2-Amino-2-oxo-1-phenylethyl)thio)-3,5-dicyano-4-ethylpyridin-2-yl)-4-hydroxy piperidine-4-carboxamide;
1-(6-((2-Amino-2-oxo-1-phenylethyl)thio)-3,5-dicyano-4-ethylpyridin-2-yl)azetidin-3-yl carbamate;
2-((3,5-Dicyano-6-(4-(2,4-dioxooxazolidin-3-yl)piperidin-1-yl)-4-ethylpyridin-2-yl)thio)-2-phenylacetamide;
3-((6-((2-Amino-2-oxo-1-phenylethyl)thio)-3,5-dicyano-4-ethylpyridin-2-yl)(methyl)amino)-2-hydroxy-2-methyl-propanamide;
2-((3,5-Dicyano-4-ethyl-6-(3-(hydroxymethyl)azetidin-1-yl)pyridin-2-yl)thio)-2-phenylacetamide;
2-(3,5-Dicyano-4-ethyl-6-(piperazin-1-yl)pyridin-2-ylthio)-2-(thiophen-3-yl)acetamide;
2-((3,5-Dicyano-4-ethyl-6-(4-methyl-1,4-diazepan-1-yl)pyridin-2-yl)thio)-2-(5-methylpyridin-3-yl)acetamide;
2-((6-(4-(3-Amino-2-oxopyrrolidin-1-yl)piperidin-1-yl)-3,5-dicyano-4-ethylpyridin-2-yl)thio)-2-phenylacetamide;
1-(6-((2-Amino-2-oxo-1-phenylethyl)thio)-3,5-dicyano-4-ethylpyridin-2-yl)piperidin-4-yl (2S)-2-amino-3-methylbutanoate;
2-((6-((2-Amino-2-oxo-1-phenylethyl)thio)-3,5-dicyano-4-ethylpyridin-2-yl) (methyl) amino)ethyl (2S)-2-amino-3-methylbutanoate;
2,2'-((3,5-Dicyano-4-ethylpyridine-2,6-diyl)bis(sulfanediyl))bis(2-phenylacetamide);
(2S)-(1-(6-((2-Amino-2-oxo-1-phenylethyl)thio)-3,5-dicyano-4 ethylpyridin-2-yl)azetidin-3-yl)methyl 2-amino-3-methylbutanoate;
2-((6-(3-Aminoazetidin-1-yl)-3,5-dicyano-4-ethylpyridin-2-yl)thio)-2-phenylacetamide;
2-((3,5-Dicyano-4-ethyl-6-methylpyridin-2-yl)thio)-2-phenylacetamide;
N-(1-(6-((2-Amino-2-oxo-1-phenylethyl)thio)-3,5-dicyano-4-ethylpyridin-2-yl)piperidin-4-yl)-2-hydroxyacetamide;
N-(1-(6-((2-Amino-2-oxo-1-phenylethyl)thio)-3,5-dicyano-4-ethylpyridin-2-yl)azetidin-3-yl)-2-hydroxyacetamide;
2-((3-Cyano-4-ethyl-5-methyl-6-(piperazin-1-yl)pyridin-2-yl)thio)-2-phenylacetamide;
2-((3,5-Dicyano-4-ethyl-6-(5-methyl-2,5-diazabicyclo[2.2.1]heptan-2-yl)pyridin-2-yl)thio)-2-phenylacetamide;
2-((3,5-Dicyano-4-ethyl-6-(4-(2-(pyrrolidin-1-yl)ethyl)piperazin-1-yl)pyridin-2-yl)thio)-2-phenylacetamide;
2-((3,5-Dicyano-6-(dimethylamino)-4-ethylpyridin-2-yl)thio)-2-phenylacetamide-2-d;
(R)-2-((3,5-Dicyano-6-(dimethylamino)-4-ethylpyridin-2-yl)thio)-2-phenylacetamide-2-d;
2-((6-(4-(4-Bromobenzoyl)piperazin-1-yl)-3,5-dicyano-4-ethylpyridin-2-yl)thio)-2-phenylacetamide;
2-((3,5-Dicyano-4-ethyl-6-(4-(2-hydroxyethyl)-1,4-diazepan-1-yl)pyridin-2-yl)thio)-2-phenylacetamide;
2-((3,5-Dicyano-6-(4-cyanopiperidin-1-yl)-4-ethylpyridin-2-yl)thio)-2-phenylacetamide;
(S)-2-((3,5-Dicyano-4-ethyl-6-((S)-3-hydroxypyrrolidin-1-yl)pyridin-2-yl)thio)-2-phenylacetamide;
2-((6-(4-Amino-4-methylpiperidin-1-yl)-3,5-dicyano-4-cyclopropylpyridin-2-yl)thio)-2-phenylacetamide;
2-((3,5-Dicyano-4-ethyl-6-((S)-3-hydroxypyrrolidin-1-yl)pyridin-2-yl)thio)-2-(pyridin-2-yl)acetamide;
2-((3,5-Dichloro-4-ethyl-6-(piperazin-1-yl)pyridin-2-yl)thio)-2-phenylacetamide;
tert-Butyl (1-(6-((2-amino-2-oxo-1-phenylethyl)thio)-3,5-dicyano-4-ethylpyridin-2-yl)piperidin-4-yl)carbamate;
2-((6-(3-(2-Amino-2-oxoethyl)azetidin-1-yl)-3,5-dicyano-4-ethylpyridin-2-yl)thio)-2-phenylacetamide;
(2R)-1-(6-((2-Amino-2-oxo-1-phenylethyl)thio)-3,5-dicyano-4-ethylpyridin-2-yl)azetidin-3-yl 2-amino-3-methylbutanoate;
2-((3,5-Dicyano-4-ethyl-6-(methyl((5-oxo-4,5-dihydro-1H-1,2,4-triazol-3-yl)methyl)amino)pyridin-2-yl)thio)-2-phenylacetamide;

2-((6-(((4H-1,2,4-Triazol-3-yl)methyl)(methyl)amino)-3,5-dicyano-4-ethylpyridin-2-yl)thio)-2-phenylacetamide;
2-((3,5-Dicyano-4-ethoxy-6-methylpyridin-2-yl)thio)-2-phenylacetamide;
2-((3,5-Dicyano-4,6-diethylpyridin-2-yl)thio)-2-phenylacetamide;
2-((6-((2-(4H-1,2,4-Triazol-4-yl)ethyl)(methyl)amino)-3,5-dicyano-4-ethylpyridin-2-yl)thio)-2-phenylacetamide;
2-((6-(((1H-Pyrazol-3-yl)methyl)(methyl)amino)-3,5-dicyano-4-ethylpyridin-2-yl)thio)-2-phenylacetamide;
2-((3,5-Dicyano-6-(6,7-dihydro-1H-[1,2,3]triazolo[4,5-c]pyridin-5(4H)-yl)-4-ethylpyridin-2-yl)thio)-2-phenylacetamide;
2-((6-(((1H-Imidazol-2-yl)methyl)(methyl)amino)-3,5-dicyano-4-ethylpyridin-2-yl)thio)-2-phenylacetamide;
2-((6-(((1H-Imidazol-5-yl)methyl)(methyl)amino)-3,5-dicyano-4-ethylpyridin-2-yl)thio)-2-phenylacetamide;
(2R)-2-Amino-N-(1-(6-((2-amino-2-oxo-1-phenylethyl)thio)-3,5-dicyano-4-ethylpyridin-2-yl)piperidin-4-yl)propanamide;
4-(2-Amino-1-((3,5-dicyano-4-ethyl-6-(4-methyl-1,4-diazepan-1-yl)pyridin-2-yl)thio)-2-oxoethyl)benzamide;
2-((3,5-Dicyano-4-cyclopropyl-6-(3-hydroxypyrrolidin-1-yl)pyridin-2-yl)thio)-2-phenylacetamide;
2-((3,5-Dicyano-4-ethyl-6-(3-hydroxypyrrolidin-1-yl)pyridin-2-yl)thio)-2-phenylacetamide;
(2R)-2-Amino-N-(1-(6-((2-amino-2-oxo-1-phenylethyl)thio)-3,5-dicyano-4-cyclopropyl pyridin-2-yl)piperidin-4-yl)propanamide;
2-((6-((2-Aminoethyl)(methyl)amino)-3,5-dicyano-4-cyclopropylpyridin-2-yl)thio)-2-phenylacetamide;
2-Amino-N-(1-(6-((2-amino-2-oxo-1-phenylethyl)thio)-3,5-dicyano-4-cyclopropylpyridin-2-yl)piperidin-4-yl)-2-methylpropanamide;
4-(2-Amino-1-((3,5-dicyano-6-(dimethylamino)-4-ethylpyridin-2-yl)thio)-2-oxoethyl)benzamide;
2-(6-(4-Aminopiperidin-1-yl)-3-cyano-4-ethyl-5-methylpyridin-2-ylthio)-2-phenylacetamide;
2-((3,5-Dicyano-4-ethyl-6-(4-methyl-1,4-diazepan-1-yl)pyridin-2-yl)thio)-2-(4-(N-methylsulfamoyl)phenyl)acetamide;
2-((3,5-Dicyano-4-ethyl-6-(6-fluoro-1,4-diazepan-1-yl)pyridin-2-yl)thio)-2-phenylacetamide;
2-((6-(4-Amino-3,3-difluoropiperidin-1-yl)-3,5-dicyano-4-ethylpyridin-2-yl)thio)-2-phenylacetamide;
tert-Butyl (1-(6-((2-amino-2-oxo-1-phenylethyl)thio)-3,5-dicyano-4-ethylpyridin-2-yl)-3,3-difluoropiperidin-4-yl)carbamate;
2-((3,5-Dicyano-4-cyclopropyl-6-((2-hydroxyethyl)(methyl)amino)pyridin-2-yl)thio)-2-phenylacetamide;
2-((3,5-Dicyano-4-cyclopropyl-6-(3-hydroxyazetidin-1-yl)pyridin-2-yl)thio)-2-phenylacetamide;
1-(6-((2-Amino-2-oxo-1-phenylethyl)thio)-3,5-dicyano-4-ethylpyridin-2-yl)pyrrolidine-3-carboxamide;
2-((6-((3-Aminopropyl) (methyl) amino)-3,5-dicyano-4-cyclopropylpyridin-2-yl) thio)-2-phenylacetamide;
2-((3,5-Dicyano-4-cyclopropyl-6-((2-(3-hydroxyazetidin-1-yl)-2-oxoethyl)(methyl)amino) pyridin-2-yl)thio)-2-phenylacetamide;
2-((6-(4-((2-Aminoethyl)amino)piperidin-1-yl)-3,5-dicyano-4-ethylpyridin-2-yl)thio)-2-phenylacetamide;
2-((6-((2-Amino-2-oxoethyl)(methyl)amino)-3,5-dicyano-4-cyclopropylpyridin-2-yl)thio)-2-phenylacetamide;
2-((6-((2-Amino-2-oxo-1-phenylethyl)thio)-3,5-dicyano-4-cyclopropylpyridin-2-yl)(methyl)amino)ethyl carbamate;
(2R)-2-Amino-N-(1-(6-((2-amino-2-oxo-1-phenylethyl)thio)-3,5-dicyano-4-ethylpyridin-2-yl)piperidin-4-yl)-3-hydroxypropanamide;
(2S)-2-Amino-N-(1-(6-((2-amino-2-oxo-1-phenylethyl)thio)-3,5-dicyano-4-ethylpyridin-2-yl) piperidin-4-yl)-3-hydroxypropanamide;
2-(4-(2-Amino-2-oxoethyl)phenyl)-2-(3,5-dicyano-4-ethyl-6-(4-methyl-1,4-diazepan-1-yl)pyridin-2-ylthio)acetamide;
2-(4-(2-Amino-2-oxoethyl)phenyl)-2-(3,5-dicyano-6-(dimethylamino)-4-ethylpyridin-2-ylthio)acetamide;
2-((3,5-Dicyano-6-(dimethylamino)-4-ethylpyridin-2-yl)thio)-2-(4-(N-methylsulfamoyl)phenyl)acetamide;
2-((3,5-Dicyano-6-(dimethylamino-$d_6$)-4-ethylpyridin-2-yl)thio)-2-phenylacetamide;
(R)-2-((3,5-Dicyano-4-ethyl-6-(4-(pyrrolidin-1-yl)piperidin-1-yl)pyridin-2-yl)thio)-2-phenylacetamide;
(R)-2-((3,5-Dicyano-6-(4-(dimethylamino)piperidin-1-yl)-4-ethylpyridin-2-yl)thio)-2-phenylacetamide;
2-(3,5-dicyano-6-(dimethylamino)-4-ethylpyridin-2-yl-thio)-2-(3-(2-(dimethylamino)ethoxy)phenyl)acetamide;
2-((3,5-Dicyano-4-ethyl-6-(4-(neopentylamino)piperidin-1-yl)pyridin-2-yl)thio)-2-(4-fluorophenyl)acetamide;
2-((3,5-dicyano-4-ethyl-6-(3-fluoro-4-A(neopentylamino) piperidin-1-yl)pyridin-2-yl)thio)-2-phenylacetamide;
2-((6-(4-aminopiperidin-1-yl)-3,5-dicyano-4-ethylpyridin-2-yl)thio)-2-(4-(trifluoromethyl)phenyl)acetamide;
2-((3,5-Dicyano-4-ethyl-6-(4-(pyrrolidin-1-yl)piperidin-1-yl)pyridin-2-yl)thio)-2-phenylacetamide;
(R)-2-((6-(4-aminopiperidin-1-yl)-3,5-dicyano-4-ethylpyridin-2-yl)thio)-2-phenylacetamide;
2-((6-((2-amino-2-oxoethyl)(methyl)amino)-3,5-dicyano-4-ethylpyridin-2-yl)thio)-2-phenylacetamide; (single enantiomer)
(3S)-1-(6-((2-amino-2-oxo-1-phenylethyl)thio)-3,5-dicyano-4-ethylpyridin-2-yl)
Pyrrolidin-3-yl dihydrogen phosphate;
(3R)-1-(6-((2-amino-2-oxo-1-phenylethyl)thio)-3,5-dicyano-4-ethylpyridin-2-yl)pyrrolidin-3-yl dihydrogen phosphate;
(S)-1-(6-(((S)-2-amino-2-oxo-1-phenylethyl)thio)-3,5-dicyano-4-ethylpyridin-2-yl)pyrrolidin-3-yl dihydrogen phosphate;
(S)-1-(6-(((R)-2-amino-2-oxo-1-phenylethyl)thio)-3,5-dicyano-4-ethylpyridin-2-yl) pyrrolidin-3-yl dihydrogen phosphate;
2-((3,5-Dicyano-6-(dimethylamino)-4-ethylpyridin-2-yl)thio)-2-(3-(dimethylphosphoryl)phenyl)acetamide;
2-((3,5-Dicyano-4-ethyl-6-((S)-3-hydroxypyrrolidin-1-yl)pyridin-2-yl)thio)-2-(3-(dimethylphosphoryl)phenyl)acetamide;
(R)-2-((6-((2-amino-2-oxo-1-phenylethyl)thio)-3,5-dicyano-4-ethylpyridin-2-yl)(methyl)amino)ethyl dihydrogen phosphate;
(R)-2-((3,5-dicyano-4-ethyl-6-((S)-3-hydroxypyrrolidin-1-yl)pyridin-2-yl)thio)-2-(4-methoxyphenyl)acetamide;
(R)-2-(4-chlorophenyl)-2-((3,5-dicyano-4-ethyl-6-((S)-3-hydroxypyrrolidin-1-yl)pyridin-2-yl)thio)acetamide;
(R)-2-((3,5-dicyano-4-ethyl-6-((S)-3-hydroxpyrrolidin-1-yl)pyridin-2-yl)thio)-2-(4-fluoro phenyl)acetamide;
(S)-1-(6-(((R)-2-amino-1-(4-fluorophenyl)-2-oxoethyl)thio)-3,5-dicyano-4-ethylpyridin-2-yl)pyrrolidin-3-yl dihydrogen phosphate;
2-((3,5-dicyano-4-ethyl-6-((S)-3-hydroxypyrrolidin-1-yl)pyridin-2-yl)thio)-2-(4-fluorophenyl) acetamide;
2-((3,5-dicyano-4-ethyl-6-((S)-3-hydroxypyrrolidin-1-yl)pyridin-2-yl)thio)-2-(2,6-difluorophenyl) acetamide;

2-((3,5-dicyano-4-ethyl-6-((S)-3-hydroxypyrrolidin-1-yl)pyridin-2-yl)thio)-2-(2,3-difluorophenyl) acetamide;

2-((3,5-dicyano-4-ethyl-6-((S)-3-hydroxypyrrolidin-1-yl)pyridin-2-yl)thio)-2-(2,4-difluorophenyl) acetamide;

2-((3,5-dicyano-4-ethyl-6-(4-((S)-2-(hydroxymethyl)pyrrolidin-1-yl)piperidin-1-yl)pyridin-2-yl)thio)-2-phenylacetamide;

2-((3,5-dicyano-4-ethyl-6-(4-((2-hydroxyethyl)(methyl)amino)piperidin-1-yl)pyridin-2-yl)thio)-2-phenylacetamide;

2-((3,5-dicyano-4-ethyl-6-(4-((2-hydroxy-2-methylpropyl)(methyl)amino)piperidin-1-yl)pyridin-2-yl)thio)-2-phenylacetamide;

2-((3,5-dicyano-4-ethyl-6-(4-(pyrrolidin-1-ylmethyl)piperidin-1-yl)pyridin-2-yl)thio)-2-phenylacetamide;

2-((3,5-dicyano-4-ethyl-6-(4-((2-methoxy-2-methylpropyl)amino)piperidin-1-yl)pyridin-2-yl)thio)-2-phenylacetamide;

2-((3,5-dicyano-4-ethyl-6-(4-((2-hydroxy-2-methylpropyl)amino)piperidin-1-yl)pyridin-2-yl)thio)-2-phenylacetamide;

2-((3,5-dicyano-6-(4-(cyclobutylamino)piperidin-1-yl)-4-ethylpyridin-2-yl)thio)-2-phenylacetamide;

2-((3,5-dicyano-4-ethyl-6-(4-(((3-methyloxetan-3-yl)methyl)amino)piperidin-1-yl)pyridin-2-yl)thio)-2-phenylacetamide;

2-((3,5-dicyano-4-ethyl-6-(4-(4-methylpiperazin-1-yl)piperidin-1-yl)pyridin-2-yl)thio)-2-phenylacetamide;

2-((3,5-dicyano-4-ethyl-6-(4-((R)-2-methylpyrrolidin-1-yl)piperidin-1-yl)pyridin-2-yl)thio)-2-phenylacetamide;

2-((3,5-dicyano-6-(4-((2R,5S)-2,5-dimethylpyrrolidin-1-yl)piperidin-1-yl)-4-ethylpyridin-2-yl)thio)-2-phenylacetamide;

2-((3,5-dicyano-4-ethyl-6-(4-((S)-2-methylpyrrolidin-1-yl)piperidin-1-yl)pyridin-2-yl)thio)-2-phenylacetamide;

2-((3,5-dicyano-6-(4-(cyclobutyl(methyl)amino)piperidin-1-yl)-4-ethylpyridin-2-yl)thio)-2-phenylacetamide;

2-(6-(4-(benzylamino)piperidin-1-yl)-3,5-dicyano-4-ethylpyridin-2-ylthio)-2-phenylacetamide;

2-((3,5-dicyano-4-ethyl-6-(4-(((6-methoxypyridin-2-yl)methyl)amino)piperidin-1-yl)pyridin-2-yl)thio)-2-phenylacetamide;

2-((3,5-dicyano-4-ethyl-6-(4-((S)-3-fluoropyrrolidin-1-yl)piperidin-1-yl)pyridin-2-yl)thio)-2-phenylacetamide;

2-((3,5-dicyano-4-ethyl-6-(methyl(2-((R)-2-methylpyrrolidin-1-yl)ethyl)amino)pyridin-2-yl)thio)-2-phenylacetamide;

2-((3,5-dicyano-4-ethyl-6-(4-((R)-3-fluoropyrrolidin-1-yl)piperidin-1-yl)pyridin-2-yl)thio)-2-phenylacetamide;

2-((3,5-dicyano-6-(4-((2S,5S)-2,5-dimethylpyrrolidin-1-yl)piperidin-1-yl)-4-ethylpyridin-2-yl)thio)-2-phenylacetamide;

2-((3,5-dicyano-4-ethyl-6-(methyl(2-((S)-2-methylpyrrolidin-1-yl)ethyl)amino)pyridin-2-yl)thio)-2-phenylacetamide;

2-((3,5-dicyano-4-ethyl-6-(4-((R)-2-(hydroxymethyl)pyrrolidin-1-yl)piperidin-1-yl)pyridin-2-yl)thio)-2-phenylacetamide;

2-((3,5-dicyano-6-(4-(dimethylamino)piperidin-1-yl)-4-ethylpyridin-2-yl)thio)-2-(4-fluorophenyl)acetamide;

2-((3,5-dicyano-4-ethyl-6-(4-(((1-methylcyclobutyl)methyl)amino)piperidin-1-yl)pyridin-2-yl)thio)-2-phenylacetamide;

2-((3,5-dicyano-4-ethyl-6-(4-(((6-methoxypyridin-3-yl)methyl)amino)piperidin-1-yl)pyridin-2-yl)thio)-2-phenylacetamide;

2-(3,5-dicyano-4-ethyl-6-((2-(ethylamino)ethyl)(methyl)amino)pyridin-2-ylthio)-2-phenylacetamide;

2-((3,5-dicyano-4-ethyl-6-(4-((4-methylpiperazin-1-yl)methyl)piperidin-1-yl)pyridin-2-yl)thio)-2-phenylacetamide;

2-((3,5-dicyano-4-ethyl-6-(methyl(2-(methylamino)ethyl)amino)pyridin-2-yl)thio)-2-phenylacetamide;

2-((3,5-dicyano-6-(4-((2R,5R)-2,5-dimethylpyrrolidin-1-yl)piperidin-1-yl)-4-ethylpyridin-2-yl)thio)-2-phenylacetamide;

2-((3,5-dicyano-4-ethyl-6-(4-(((1-methylcyclopropyl)methyl)amino)piperidin-1-yl)pyridin-2-yl)thio)-2-phenylacetamide;

2-((3,5-dicyano-4-ethyl-6-(4-((4-fluorobenzyl)amino)piperidin-1-yl)pyridin-2-yl)thio)-2-phenylacetamide;

2-((3,5-dicyano-4-ethyl-6-((2-((S)-2-(hydroxymethyl)pyrrolidin-1-yl)ethyl)(methyl)amino)pyridin-2-yl)thio)-2-phenylacetamide;

2-(3,5-dicyano-6-((2-((2S,5R)-2,5-dimethylpyrrolidin-1-yl)ethyl)(methyl)amino)-4-ethylpyridin-2-ylthio)-2-phenylacetamide;

2-((6-((2-(azepan-1-yl)ethyl)(methyl)amino)-3,5-dicyano-4-ethylpyridin-2-yl)thio)-2-phenylacetamide;

2-((3,5-dicyano-4-ethyl-6-(methyl(2-(piperidin-1-yl)ethyl)amino)pyridin-2-yl)thio)-2-phenylacetamide;

2-((3,5-dicyano-4-ethyl-6-((2-((R)-2-(hydroxymethyl)pyrrolidin-1-yl)ethyl)(methyl)amino)pyridin-2-yl)thio)-2-phenylacetamide;

2-(3,5-dicyano-4-ethyl-6-((2-(ethyl(methyl)amino)ethyl)(methyl)amino)pyridin-2-ylthio)-2-phenylacetamide;

2-((3,5-dicyano-6-((2-((2R,5R)-2,5-dimethylpyrrolidin-1-yl)ethyl)(methyl)amino)-4-ethylpyridin-2-yl)thio)-2-phenylacetamide;

2-(3,5-dicyano-4-ethyl-6-((2-((S)-3-hydroxypyrrolidin-1-yl)ethyl)(methyl)amino)pyridin-2-ylthio)-2-phenylacetamide;

methyl 2-((1-(6-((2-amino-2-oxo-1-phenylethyl)thio)-3,5-dicyano-4-ethylpyridin-2-yl)piperidin-4-yl)amino)-2-methylpropanoate;

2-((3,5-dicyano-4-ethyl-6-(methyl(2-(neopentylamino)ethyl)amino)pyridin-2-yl)thio)-2-phenylacetamide;

2-(3,5-dicyano-4-ethyl-6-(methyl(2-(1-methylcyclopropylamino)ethyl)amino)pyridin-2-ylthio)-2-phenylacetamide;

2-((3,5-dicyano-6-((2-((2S,5S)-2,5-dimethylpyrrolidin-1-yl)ethyl)(methyl)amino)-4-ethylpyridin-2-yl)thio)-2-phenylacetamide;

2-((3,5-dicyano-4-ethyl-6-((2-((2-methoxyethyl)amino)ethyl)(methyl)amino)pyridin-2-yl)thio)-2-phenylacetamide;

2-((3,5-dicyano-4-ethyl-6-(4-((2-methoxy-2-methylpropyl)(methyl)amino)piperidin-1-yl)pyridin-2-yl)thio)-2-phenylacetamide;

2-((3,5-dicyano-6-((2-(dimethylamino)ethyl)(methyl)amino)-4-ethylpyridin-2-yl)thio)-2-phenylacetamide;

2-(3,5-dicyano-4-ethyl-6-((2-((R)-3-hydroxypyrrolidin-1-yl)ethyl)(methyl)amino)pyridin-2-ylthio)-2-phenylacetamide;

2-((3,5-dicyano-4-ethyl-6-((2-((2-fluoroethyl)amino)ethyl)(methyl)amino)pyridin-2-yl)thio)-2-phenylacetamide;

2-((3,5-dicyano-6-(4-(3,3-difluoropyrrolidin-1-yl)piperidin-1-yl)-4-ethylpyridin-2-yl)thio)-2-phenylacetamide;

2-((1-(6-((2-amino-2-oxo-1-phenylethyl)thio)-3,5-dicyano-4-ethylpyridin-2-yl)piperidin-4-yl)amino)acetic acid;

2-((6-((3-aminocyclobutyl)(methyl)amino)-3,5-dicyano-4-ethylpyridin-2-yl)thio)-2-phenylacetamide;

(R)-2-(3,5-dicyano-4-ethyl-6-(methyl((R)-tetrahydrofuran-3-yl)amino)pyridin-2-ylthio)-2-phenylacetamide;
(S)-2-(3,5-dicyano-4-ethyl-6-(methyl((R)-tetrahydrofuran-3-yl)amino)pyridin-2-ylthio)-2-phenylacetamide;
2-((3,5-dicyano-4-ethyl-6-(4-morpholinopiperidin-1-yl)pyridin-2-yl)thio)-2-phenylacetamide;
2-((3,5-dicyano-4-ethyl-6-(4-(2-hydroxyethyl)-3-oxopiperazin-1-yl)pyridin-2-yl)thio)-2-phenylacetamide;
2-((3,5-dicyano-4-ethyl-6-(4-(pyrrolidin-1-yl)piperidin-1-yl)pyridin-2-yl)thio)-2-(4-fluorophenyl)acetamide;
(R)-2-((6-((3S,4R)-4-amino-3-fluoropiperidin-1-yl)-3,5-dicyano-4-ethylpyridin-2-yl)thio)-2-phenylacetamide;
2-((3,5-dicyano-4-ethyl-6-(3-fluoro-4-(methylamino)piperidin-1-yl)pyridin-2-yl)thio)-2-phenylacetamide;
rel-2-((6-(trans)-4-amino-3-fluoropiperidin-1-yl)-3,5-dicyano-4-ethylpyridin-2-yl)thio)-2-phenylacetamide;
(R)-2-((6-((3R,4S)-4-amino-3-fluoropiperidin-1-yl)-3,5-dicyano-4-ethylpyridin-2-yl)thio)-2-phenylacetamide;
2-((3,5-dicyano-4-ethyl-6-(3-fluoro-4-((2-methoxyethyl)amino)piperidin-1-yl)pyridin-2-yl)thio)-2-phenylacetamide;
2-((3,5-dicyano-4-ethyl-6-(methyl(2-(pyrrolidin-1-yl)ethyl)amino)pyridin-2-yl)thio)-2-phenylacetamide;
2-((3,5-dicyano-6-(3-((dimethylamino)methyl)pyrrolidin-1-yl)-4-ethylpyridin-2-yl)thio)-2-phenylacetamide;
2-((3,5-dicyano-4-ethyl-6-(4-((2-hydroxy-2-methylpropyl)amino)piperidin-1-yl)pyridin-2-yl)thio)-2-(4-fluorophenyl)acetamide;
(R)-2-((6-((3S,4R)-4-amino-3-hydroxypiperidin-1-yl)-3,5-dicyano-4-ethylpyridin-2-yl)thio)-2-phenylacetamide;
2-((3,5-dicyano-6-((2-(diethylamino)ethyl)(methyl)amino)-4-ethylpyridin-2-yl)thio)-2-phenylacetamide;
2-((3,5-dicyano-6-((2-((R)-3-(dimethylamino)pyrrolidin-1-yl)ethyl)(methyl)amino)-4-ethylpyridin-2-yl)thio)-2-phenylacetamide;
2-((3,5-dicyano-6-((2-((S)-3-(dimethylamino)pyrrolidin-1-yl)ethyl)(methyl)amino)-4-ethylpyridin-2-yl)thio)-2-phenylacetamide;
(R)-2-((6-((3R,4R)-4-amino-3-fluoropiperidin-1-yl)-3,5-dicyano-4-ethylpyridin-2-yl)thio)-2-phenylacetamide;
(R)-2-((6-((3S,4S)-4-amino-3-fluoropiperidin-1-yl)-3,5-dicyano-4-ethylpyridin-2-yl)thio)-2-phenylacetamide;
2-((3,5-dicyano-4-ethyl-6-(3-(methylamino)pyrrolidin-1-yl)pyridin-2-yl)thio)-2-phenylacetamide;
2-((6-(4-aminopiperidin-1-yl)-3,5-dicyano-4-ethylpyridin-2-yl)thio)-2-(4-fluorophenyl)acetamide;
(R)-2-((6-((3R,4R)-4-amino-3-hydroxypiperidin-1-yl)-3,5-dicyano-4-ethylpyridin-2-yl)thio)-2-phenylacetamide;
2-((6-((R)-3-aminopyrrolidin-1-yl)-3,5-dicyano-4-ethylpyridin-2-yl)thio)-2-phenylacetamide;
2-((6-(3-(aminomethyl)pyrrolidin-1-yl)-3,5-dicyano-4-ethylpyridin-2-yl)thio)-2-phenylacetamide;
2-((3,5-dicyano-4-ethyl-6-(4-(methylamino)piperidin-1-yl)pyridin-2-yl)thio)-2-(4-fluorophenyl)acetamide;
2-((3,5-dicyano-6-(4-(cyclopropylamino)-3-fluoropiperidin-1-yl)-4-ethylpyridin-2-yl)thio)-2-phenylacetamide;
2-((4-((S)-3-aminopyrrolidin-1-yl)-3,5-dicyano-4-ethylpyridin-2-yl)thio)-2-phenylacetamide;
2-((6-((2-((R)-3-aminopyrrolidin-1-yl)ethyl)(methyl)amino)-3,5-dicyano-4-ethylpyridin-2-yl)thio)-2-phenylacetamide;
3,5-dicyano-6-((R)-3-(dimethylamino)pyrrolidin-1-yl)-4-ethylpyridin-2-yl)thio)-2-(4-fluorophenyl)acetamide;
(S)-2-((6-((3S,4R)-4-amino-3-fluoropiperidin-1-yl)-3,5-dicyano-4-ethylpyridin-2-yl)thio)-2-phenylacetamide;
2-((3,5-dicyano-4-ethyl-6-(4-(neopentylamino)piperidin-1-yl)pyridin-2-yl)thio)-2-(4-(trifluoromethyl)phenyl)acetamide;
tert-butyl ((3S,4R)-1-(6-(((R)-2-amino-2-oxo-1-phenylethyl)thio)-3,5-dicyano-4-ethylpyridin-2-yl)-3-hydroxypiperidin-4-yl)carbamate;
rel-tert-butyl (cis)-1-(6-((2-amino-2-oxo-1-phenylethyl)thio)-3,5-dicyano-4-ethylpyridin-2-yl)-3-fluoropiperidin-4-yl)carbamate;
2-((6-((2-((S)-3-aminopyrrolidin-1-yl)ethyl)(methyl)amino)-3,5-dicyano-4-ethylpyridin-2-yl)thio)-2-phenylacetamide;
2-((3,5-dicyano-6-((R)-3-(dimethylamino)pyrrolidin-1-yl)-4-ethylpyridin-2-yl)thio)-2-phenylacetamide;
tert-butyl ((3R,4S)-1-(6-(((R)-2-amino-2-oxo-1-phenylethyl)thio)-3,5-dicyano-4-ethylpyridin-2-yl)-3-hydroxypiperidin-4-yl)carbamate;
rel-tert-butyl (cis)-1-(6-((2-amino-2-oxo-1-phenylethyl)thio)-3,5-dicyano-4-ethylpyridin-2-yl)-3-fluoropiperidin-4-yl)carbamate;
2-((3,5-dicyano-6-((S)-3-(dimethylamino)pyrrolidin-1-yl)-4-ethylpyridin-2-yl)thio)-2-phenylacetamide;
(S)-2-((6-((3R,4S)-4-amino-3-fluoropiperidin-1-yl)-3,5-dicyano-4-ethylpyridin-2-yl)thio)-2-phenylacetamide;
2-((3,5-dicyano-4-ethyl-6-((S)-3-((2-hydroxy-2-methylpropyl)amino)pyrrolidin-1-yl)pyridin-2-yl)thio)-2-phenylacetamide;
tert-butyl ((3R,4R)-1-(6-(((R)-2-amino-2-oxo-1-phenylethyl)thio)-3,5-dicyano-4-ethylpyridin-2-yl)-3-hydroxypiperidin-4-yl)carbamate;
2-((3,5-dicyano-6-((S)-3-(dimethylamino)pyrrolidin-1-yl)-4-ethylpyridin-2-yl)thio)-2-(4-fluorophenyl)acetamide;
rel-2-((6-cis-4-amino-3-fluoropiperidin-1-yl)-3,5-dicyano-4-ethylpyridin-2-yl)thio)-2-phenylacetamide;
2-((3,5-dicyano-4-ethyl-6-(4-(methylamino)piperidin-1-yl)pyridin-2-yl)thio)-2-phenylacetamide;
2-((3,5-dicyano-6-(4-(dimethylamino)piperidin-1-yl)-4-ethylpyridin-2-yl)thio)-2-phenylacetamide;
2-((3,5-dicyano-4-ethyl-6-(4-(ethyl(methyl)amino)piperidin-1-yl)pyridin-2-yl)thio)-2-phenylacetamide;
2-((3,5-dicyano-4-ethyl-6-(4-(neopentylamino)piperidin-1-yl)pyridin-2-yl)thio)-2-phenylacetamide;
2-((3,5-dicyano-4-ethyl-6-(4-(methyl(neopentyl)amino)piperidin-1-yl)pyridin-2-yl)thio)-2-phenylacetamide;
2-((3,5-dicyano-6-(4-(cyclopropylamino)piperidin-1-yl)-4-ethylpyridin-2-yl)thio)-2-phenylacetamide;
2-((3,5-dicyano-4-ethyl-6-(4-((2-methoxyethyl)amino)piperidin-1-yl)pyridin-2-yl)thio)-2-phenylacetamide;
2-((3,5-dicyano-6-(4-((2,2-difluoroethyl)amino)piperidin-1-yl)-4-ethylpyridin-2-yl)thio)-2-phenylacetamide;
2-((3,5-dicyano-4-ethyl-6-((R)-2-((neopentylamino)methyl)morpholino)pyridin-2-yl)thio)-2-phenylacetamide;
2-((3,5-dicyano-6-(2-((dimethylamino)methyl)morpholino)-4-ethylpyridin-2-yl)thio)-2-phenylacetamide;
2-((3,5-dicyano-6-(2-((diethylamino)methyl)morpholino)-4-ethylpyridin-2-yl)thio)-2-phenylacetamide;
2-((3,5-dicyano-4-ethyl-6-(2-(pyrrolidin-1-ylmethyl)morpholino)pyridin-2-yl)thio)-2-phenylacetamide;
(R)-2-((6-((R)-2-(aminomethyl)morpholino)-3,5-dicyano-4-ethylpyridin-2-yl)thio)-2-phenylacetamide;
2-((6-(2-(aminomethyl)morpholino)-3,5-dicyano-4-ethylpyridin-2-yl)thio)-2-phenylacetamide;
2-((3,5-dicyano-4-ethyl-6-(2-((methylamino)methyl)morpholino)pyridin-2-yl)thio)-2-phenylacetamide;
2-((6-((R)-2-(aminomethyl)morpholino)-3,5-dicyano-4-ethylpyridin-2-yl)thio)-2-phenylacetamide;

2-((3,5-dicyano-6-(3-((dimethylamino)methyl)piperidin-1-yl)-4-ethylpyridin-2-yl)thio)-2-phenylacetamide;
2-((3,5-dicyano-4-ethyl-6-(3-((methylamino)methyl)piperidin-1-yl)pyridin-2-yl)thio)-2-phenylacetamide;
2-((3,5-dicyano-4-ethyl-6-((S)-2-((neopentylamino)methyl)morpholino)pyridin-2-yl)thio)-2-phenylacetamide;
2-((3,5-dicyano-4-ethyl-6-((S)-3-((neopentylamino)methyl)piperidin-1-yl)pyridin-2-yl)thio)-2-phenylacetamide;
2-amino-N-(((2S)-4-(6-((2-amino-2-oxo-1-phenylethyl)thio)-3,5-dicyano-4-ethylpyridin-2-yl)morpholin-2-yl)methyl)-2-methylpropanamide;
2-((4-((S)-3-(aminomethyl)piperidin-1-yl)-3,5-dicyano-4-ethylpyridin-2-yl)thio)-2-phenylacetamide;
2-((3,5-dicyano-6-((R)-2-((diethylamino)methyl)morpholino)-4-ethylpyridin-2-yl)thio)-2-phenylacetamide;
2-amino-N-(((2R)-4-(6-((2-amino-2-oxo-1-phenylethyl)thio)-3,5-dicyano-4-ethylpyridin-2-yl)morpholin-2-yl)methyl)-2-methylpropanamide;
2-(6-(4-aminopiperidin-1-yl)-3,5-dicyano-4-ethylpyridin-2-yl)thio)-2-(3-fluoropyridin-2-yl)acetamide;
2-((6-((S)-2-(aminomethyl)morpholino)-3,5-dicyano-4-ethylpyridin-2-yl)thio)-2-phenylacetamide;
2-amino-N-(((3S)-1-(6-((2-amino-2-oxo-1-phenylethyl)thio)-3,5-dicyano-4-ethylpyridin-2-yl)piperidin-3-yl)methyl)-2-methylpropanamide;
2-amino-N-(((3S)-1-(6-((2-amino-2-oxo-1-phenylethyl)thio)-3,5-dicyano-4-ethylpyridin-2-yl)piperidin-3-yl)methyl)acetamide;
2-amino-N-(((2R)-4-(6-((2-amino-2-oxo-1-phenylethyl)thio)-3,5-dicyano-4-ethylpyridin-2-yl)morpholin-2-yl)methyl)acetamide;
2-((6-((R)-3-(aminomethyl)piperidin-1-yl)-3,5-dicyano-4-ethylpyridin-2-yl)thio)-2-(4-fluorophenyl)acetamide;
2-((3,5-dicyano-4-ethyl-6-((R)-3-((neopentylamino)methyl)piperidin-1-yl)pyridin-2-yl)thio)-2-(4-fluorophenyl)acetamide;
2-amino-N-(((2S)-4-(6-((2-amino-2-oxo-1-phenylethyl)thio)-3,5-dicyano-4-ethylpyridin-2-yl)morpholin-2-yl)methyl)acetamide;
N—(((R)-4-(6-(((R)-2-amino-2-oxo-1-phenylethyl)thio)-3,5-dicyano-4-ethylpyridin-2-yl)morpholin-2-yl)methyl)-2-hydroxyacetamide;
(S)-2-((6-(4-aminopiperidin-1-yl)-3,5-dicyano-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(2-hydroxyethyl)-N-methylacetamide;
2-((3,5-dicyano-4-ethyl-6-((S)-3-(methylamino)piperidin-1-yl)pyridin-2-yl)thio)-2-phenylacetamide;
2-((6-(4-amino-4-methylpiperidin-1-yl)-3,5-dicyano-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)-N-methylacetamide;
2-amino-N-(1-(6-((2-amino-2-oxo-1-phenylethyl)thio)-3,5-dicyano-4-cyclopropylpyridin-2-yl)azetidin-3-yl)acetamide;
(2S)-2-amino-N-(1-(6-((2-amino-2-oxo-1-phenylethyl)thio)-3,5-dicyano-4-cyclopropylpyridin-2-yl)azetidin-3-yl)-3-hydroxypropanamide;
2-((6-((S)-3-aminopiperidin-1-yl)-3,5-dicyano-4-ethylpyridin-2-yl)thio)-2-phenylacetamide;
2-((3,5-dicyano-4-ethyl-6-((2-((R)-3-hydroxypyrrolidin-1-yl)-2-oxoethyl)(methyl)amino)pyridin-2-yl)thio)-2-phenylacetamide;

(2R)-2-amino-N-(1-(6-((2-amino-2-oxo-1-phenylethyl)thio)-3,5-dicyano-4-cyclopropylpyridin-2-yl)azetidin-3-yl)-3-hydroxypropanamide;
2-((6-((2-amino-2-oxo-1-phenylethyl)thio)-3,5-dicyano-4-ethylpyridin-2-yl)(methyl)amino)-N-(3-hydroxy-2,2-dimethylpropyl)-N-methylacetamide;
2-((3,5-dicyano-4-ethyl-6-((2-((S)-3-hydroxpyrrolidin-1-yl)-2-oxoethyl)(methyl)amino)pyridin-2-yl)thio)-2-phenylacetamide;
2-((6-(4-amino-4-methylpiperidin-1-yl)-3,5-dicyano-4-ethylpyridin-2-yl)thio)-2-phenylacetamide;
2-((6-(4-(aminomethyl)-4-fluoropiperidin-1-yl)-3,5-dicyano-4-ethylpyridin-2-yl)thio)-2-phenylacetamide hydrochloride;
2-((6-((2-amino-2-oxo-1-phenylethyl)thio)-3,5-dicyano-4-cyclopropylpyridin-2-yl)(methyl)amino)-N-(2-aminoethyl)acetamide hydrochloride;
2-((3,5-dicyano-4-ethyl-6-(methyl(2-oxo-2-(pyrrolidin-1-yl)ethyl)amino)pyridin-2-yl)thio)-2-phenylacetamide;
2-((3,5-dicyano-4-ethyl-6-((2-(4-hydroxypiperidin-1-yl)-2-oxoethyl)(methyl)amino)pyridin-2-yl)thio)-2-phenylacetamide;
2-((3,5-dicyano-4-ethyl-6-(methyl(2-oxo-2-(piperazin-1-yl)ethyl)amino)pyridin-2-yl)thio)-2-phenylacetamide;
2-((3,5-dicyano-4-ethyl-6-(methyl(2-morpholino-2-oxoethyl)amino)pyridin-2-yl)thio)-2-phenylacetamide;
(R)-2-((6-((S)-3-(aminomethyl)-3-hydroxypyrrolidin-1-yl)-3,5-dicyano-4-ethylpyridin-2-yl)thio)-2-phenylacetamide;
2-((3,5-dicyano-4-ethyl-6-((S)-3-(guanidinooxy)pyrrolidin-1-yl)pyridin-2-yl)thio)-2-phenylacetamide;
2-amino-N-(2-((6-((2-amino-2-oxo-1-phenylethyl)thio)-3,5-dicyano-4-ethylpyridin-2-yl)(methyl)amino)ethyl)-2-methylpropanamide;
2-((6-((2-(2-aminoethoxy)ethyl)(methyl)amino)-3,5-dicyano-4-ethylpyridin-2-yl)thio)-2-phenylacetamide;
4-amino-N-(1-(6-((2-amino-2-oxo-1-phenylethyl)thio)-3,5-dicyano-4-ethylpyridin-2-yl)piperidin-4-yl)butanamide;
2-((6-((2-amino-2-oxo-1-phenylethyl)thio)-3,5-dicyano-4-ethylpyridin-2-yl)(methyl)amino)-N-(2-aminoethyl)acetamide;
2-((6-((2-(azetidin-1-yl)-2-oxoethyl)(methyl)amino)-3,5-dicyano-4-ethylpyridin-2-yl)thio)-2-phenylacetamide;
2-((6-((R)-3-(aminomethyl)-3-fluoropyrrolidin-1-yl)-3,5-dicyano-4-ethylpyridin-2-yl)thio)-2-phenylacetamide;
2-((3,5-dicyano-4-ethyl-6-((2-(3-hydroxyazetidin-1-yl)-2-oxoethyl)(methyl)amino)pyridin-2-yl)thio)-2-phenylacetamide;
2-((3,5-dicyano-4-ethyl-6-(4-(guanidinooxy)piperidin-1-yl)pyridin-2-yl)thio)-2-phenylacetamide;
2-((6-(3-aminoazetidin-1-yl)-3,5-dicyano-4-ethylpyridin-2-yl)thio)-2-phenylacetamide; (single stereoisomer)
2-((3,5-dicyano-4-ethyl-6-((R)-3-(methylamino)piperidin-1-yl)pyridin-2-yl)thio)-2-phenylacetamide;
2-((3,5-dicyano-4-ethyl-6-((2-((3R,4S)-3-hydroxy-4-(hydroxymethyl)pyrrolidin-1-yl)-2-oxoethyl)(methyl)amino)pyridin-2-yl)thio)-2-phenylacetamide;
(R)-2-((6-((S)-3-(aminomethyl)-3-fluoropyrrolidin-1-yl)-3,5-dicyano-4-ethylpyridin-2-yl)thio)-2-phenylacetamide;
2-((6-((2-amino-2-oxo-1-phenylethyl)thio)-3,5-dicyano-4-cyclopropylpyridin-2-yl)(methyl)amino)-N-(1,3-dihydroxypropan-2-yl)acetamide;
2-((3,5-dicyano-4-ethyl-6-((S)-3-(oxetan-3-ylamino)piperidin-1-yl)pyridin-2-yl)thio)-2-phenylacetamide;
2-((6-((2-amino-2-oxo-1-phenylethyl)thio)-3,5-dicyano-4-cyclopropylpyridin-2-yl)(methyl)amino)-N,N-bis(2-hydroxyethyl)acetamide;

2-amino-N-(1-(6-((2-amino-2-oxo-1-phenylethyl)thio)-3,5-dicyano-4-cyclopropylpyridin-2-yl)piperidin-4-yl)acetamide;
2-((3,5-dicyano-4-ethyl-6-(4-((2-hydroxyethyl)amino)-4-methylpiperidin-1-yl)pyridin-2-yl)thio)-2-phenylacetamide;
2-((3,5-dicyano-4-ethyl-6-((2-(guanidinooxy)ethyl)(methyl)amino)pyridin-2-yl)thio)-2-phenylacetamide;
2-((6-(4-((2-aminoethyl)amino)piperidin-1-yl)-3,5-dicyano-4-ethylpyridin-2-yl)thio)-2-phenylacetamide;
2-((3,5-dicyano-4-ethyl-6-((2-((S)-2-(hydroxymethyl)morpholino)-2-oxoethyl)(methyl)amino)pyridin-2-yl)thio)-2-phenylacetamide;
2-((3,5-dicyano-6-((2-((cis-3,4-dihydroxypyrrolidin-1-yl)-2-oxoethyl)(methyl)amino)-4-ethylpyridin-2-yl)thio)-2-phenylacetamide;
2-((3,5-dicyano-4-ethyl-6-((2-((S)-3-(hydroxymethyl)pyrrolidin-1-yl)-2-oxoethyl)(methyl)amino)pyridin-2-yl)thio)-2-phenylacetamide;
2-((3,5-dicyano-4-ethyl-6-((2-((3S,4S)-3-hydroxy-4-(hydroxymethyl)pyrrolidin-1-yl)-2-oxoethyl)(methyl)amino)pyridin-2-yl)thio)-2-phenylacetamide;
2-((3,5-dicyano-4-ethyl-6-((S)-3-(neopentylamino)piperidin-1-yl)pyridin-2-yl)thio)-2-phenylacetamide;
2-((3,5-dicyano-4-ethyl-6-((2-((R)-3-(hydroxymethyl)pyrrolidin-1-yl)-2-oxoethyl)(methyl)amino)pyridin-2-yl)thio)-2-phenylacetamide;
2-((3,5-dicyano-6-((2-((3R,4R)-3,4-dihydroxypyrrolidin-1-yl)-2-oxoethyl)(methyl)amino)-4-ethylpyridin-2-yl)thio)-2-phenylacetamide;
(R)-2-((3,5-dicyano-4-ethyl-6-((S)-3-hydroxy-3-(hydroxymethyl)pyrrolidin-1-yl)pyridin-2-yl)thio)-2-phenylacetamide;
(2S)-2-amino-N-(1-(6-((2-amino-2-oxo-1-phenylethyl)thio)-3,5-dicyano-4-cyclopropylpyridin-2-yl)piperidin-4-yl)propanamide;
2-((6-(4-(2-aminoethoxy)piperidin-1-yl)-3,5-dicyano-4-cyclopropylpyridin-2-yl)thio)-2-phenylacetamide;
2-((3,5-dicyano-4-cyclopropyl-6-(4-((2-hydroxyethyl)amino)piperidin-1-yl)pyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(1,3-dihydroxypropan-2-yl)acetamide;
2-((3,5-dicyano-6-((2-((3R,5S)-3,5-dihydroxypiperidin-1-yl)-2-oxoethyl)(methyl)amino)-4-ethylpyridin-2-yl)thio)-2-phenylacetamide;
2-((3,5-dicyano-6-((2-((3S,4S)-3,4-dihydroxypyrrolidin-1-yl)-2-oxoethyl)(methyl)amino)-4-ethylpyridin-2-yl)thio)-2-phenylacetamide;
2-((3,5-dicyano-4-ethyl-6-(4-((2-hydroxyethyl)amino)-4-(hydroxymethyl)piperidin-1-yl)pyridin-2-yl)thio)-2-phenylacetamide;
2-((3,5-dicyano-4-ethyl-6-((2-((R)-2-(hydroxymethyl)morpholino)-2-oxoethyl)(methyl)amino)pyridin-2-yl)thio)-2-phenylacetamide;
2-((6-((2-amino-2-oxo-1-phenylethyl)thio)-3,5-dicyano-4-ethylpyridin-2-yl)(methyl)amino)-N-methoxyacetamide;
2-((3,5-dicyano-4-ethyl-6-((2-((3R,4R)-3-hydroxy-4-(hydroxymethyl)pyrrolidin-1-yl)-2-oxoethyl)(methyl)amino)pyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(3-hydroxypropyl)-N-methylacetamide;
2-((6-((2-amino-2-oxo-1-phenylethyl)thio)-3,5-dicyano-4-ethylpyridin-2-yl)(methyl)amino)-N-((R)-2,3-dihydroxypropyl)acetamide;
2-((6-(4-((2-amino-2-oxoethyl)amino)piperidin-1-yl)-3,5-dicyano-4-cyclopropylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N,N-bis(2-hydroxyethyl)acetamide;
2-((6-((2-amino-2-oxo-1-phenylethyl)thio)-3,5-dicyano-4-ethylpyridin-2-yl)(methyl)amino)-N-(2-hydroxyethyl)acetamide;
2-((6-((3-aminopropyl)(methyl)amino)-3,5-dicyano-4-ethylpyridin-2-yl)thio)-2-phenylacetamide;
2-((6-(3-(aminomethyl)azetidin-1-yl)-3,5-dicyano-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)acetamide;
(R)-2-((3,5-dicyano-4-ethyl-6-((S)-3-hydroxypyrrolidin-1-yl)pyridin-2-yl)thio)-2-(2,4-difluorophenyl)acetamide;
2-((6-((2-amino-2-oxo-1-phenylethyl)thio)-3,5-dicyano-4-ethylpyridin-2-yl)(methyl)amino)-N-(3-(hydroxymethyl)oxetan-3-yl)acetamide;
2-((3,5-dicyano-4-ethyl-6-(3-(guanidinooxy)azetidin-1-yl)pyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(3-hydroxypropyl)acetamide;
2-((3,5-dicyano-6-(4-(2,3-dihydroxypropyl)-1,4-diazepan-1-yl)-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-hydroxyacetamide;
3-amino-N-(1-(6-((2-amino-2-oxo-1-phenylethyl)thio)-3,5-dicyano-4-cyclopropylpyridin-2-yl)azetidin-3-yl)oxetane-3-carboxamide;
2-((3,5-dicyano-4-ethyl-6-((S)-3-hydroxypyrrolidin-1-yl)pyridin-2-yl)thio)-2-(2-fluorophenyl)acetamide;
2-((3,5-dicyano-6-((S)-3-(cyclopropylamino)piperidin-1-yl)-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(3-hydroxy-2,2-dimethylpropyl)acetamide;
N-(2-(4H-1,2,4-triazol-4-yl)ethyl)-2-((6-((2-amino-2-oxo-1-phenylethyl)thio)-3,5-dicyano-4-ethylpyridin-2-yl)(methyl)amino)acetamide;
N1-(2-((6-((2-amino-2-oxo-1-phenylethyl)thio)-3,5-dicyano-4-ethylpyridin-2-yl)(methyl)amino)ethyl)oxalamide;
2-((6-(3-(aminomethyl)-3-fluoroazetidin-1-yl)-3,5-dicyano-4-ethylpyridin-2-yl)thio)-2-phenylacetamide;
(R)-2-((3,5-dicyano-4-ethyl-6-((R)-3-hydroxy-3-(hydroxymethyl)pyrrolidin-1-yl)pyridin-2-yl)thio)-2-phenylacetamide;
2-((3,5-dicyano-6-((S)-3-((2,2-difluoroethyl)amino)piperidin-1-yl)-4-ethylpyridin-2-yl)thio)-2-phenylacetamide;
2-((6-((R)-3-aminopiperidin-1-yl)-3,5-dicyano-4-ethylpyridin-2-yl)thio)-2-phenylacetamide;
2-((6-(4-aminopiperidin-1-yl)-3,5-dicyano-4-methoxypyridin-2-yl)thio)-2-phenylacetamide;
2-((3,5-dicyano-4-ethyl-6-((S)-4-hydroxyisoxazolidin-2-yl)pyridin-2-yl)thio)-2-phenylacetamide;
(R)-2-((3,5-dicyano-4-ethyl-6-((3-hydroxpropyl)(methyl)amino)pyridin-2-yl)thio)-2-phenylacetamide;
2-((3,5-dicyano-6-((S)-3-hydroxpyrrolidin-1-yl)-4-methoxypyridin-2-yl)thio)-2-phenylacetamide;
2-((3,5-dicyano-4-ethyl-6-(4-(3-methoxyazetidin-1-yl)piperidin-1-yl)pyridin-2-yl)thio)-2-phenylacetamide;

2-((3,5-dicyano-4-ethyl-6-(4-(3-methoxyazetidin-1-yl)piperidin-1-yl)pyridin-2-yl)thio)-2-(4-fluorophenyl)acetamide;

(R)-2-((3,5-dicyano-4-ethyl-6-((2-hydroxyethyl)(methyl)amino)pyridin-2-yl)thio)-2-phenylacetamide;

(R)-2-((6-((R)-3-(aminomethyl)-3-hydroxypyrrolidin-1-yl)-3,5-dicyano-4-ethylpyridin-2-yl)thio)-2-phenylacetamide;

2-((3,5-Dicyano-6-(4-(cyclobutyl(methyl)amino)piperidin-1-yl)-4-ethylpyridin-2-yl)thio)-2-(4-fluorophenyl)acetamide; and 2-((3,5-dicyano-4-ethyl-6-(methyl(1-methylpyrrolidin-3-yl)amino)pyridin-2-yl)thio)-2-phenylacetamide;

or a pharmaceutically acceptable salt or prodrug thereof.

Suitably, presently invented novel compounds of Formula (IVbbr) are selected from:

2-{[3,5-dicyano-6-(dimethylamino)-4-ethylpyridin-2-yl]sulfanyl}-2-phenylacetamide;

2-((3,5-dicyano-4-cyclopropyl-6-(1,4-diazepan-1-yl)pyridin-2-yl)thio)-2-phenylacetamide;

2-{[3,5-dicyano-4-cyclopropyl-6-(4-ethyl-1,4-diazepan-1-yl)pyridin-2-yl]sulfanyl}-2-phenylacetamide;

2-((3,5-dicyano-4-ethyl-6-(4-propyl-1,4-diazepan-1-yl)pyridin-2-yl)thio)-2-phenylacetamide;

2-{[3,5-dicyano-4-ethyl-6-(4-ethyl-1,4-diazepan-1-yl)pyridin-2-yl]sulfanyl}-2-phenylacetamide;

2-{[3,5-dicyano-4-ethyl-6-(5-oxo-1,4-diazepan-1-yl)pyridin-2-yl]sulfanyl}-2-phenylacetamide;

2-((3,5-dicyano-4-cyclopropyl-6-morpholinopyridin-2-yl)thio)-2-(pyridin-4-yl)acetamide;

2-{[3,5-dicyano-4-ethyl-6-(4-methyl-3-oxopiperazin-1-yl)pyridin-2-yl]sulfanyl}-2-(pyridin-4-yl)acetamide;

2-[(3,5-dicyano-4-ethyl-6-{methyl[2-(morpholin-4-yl)ethyl]amino}pyridin-2-yl)sulfanyl]-2-phenylacetamide;

2-{[3,5-dicyano-4-ethyl-6-(4-propylpiperazin-1-yl)pyridin-2-yl]sulfanyl}-2-phenylacetamide;

2-({3,5-dicyano-4-ethyl-6-[4-(piperidin-4-yl)piperazin-1-yl]pyridin-2-yl}sulfanyl)-2-phenylacetamide;

2-({3,5-dicyano-4-cyclopropyl-6-[3-(hydroxymethyl)piperazin-1-yl]pyridin-2-yl}sulfanyl)-2-phenylacetamide;

2-{[3,5-dicyano-4-cyclopropyl-6-(3-oxopiperazin-1-yl)pyridin-2-yl]sulfanyl}-2-phenylacetamide;

2-({3,5-dicyano-4-cyclopropyl-6-[4-(morpholin-4-yl)piperidin-1-yl]pyridin-2-yl}sulfanyl)-2-phenylacetamide;

2-((3,5-dicyano-4-ethyl-6-(2,8-diazaspiro[4.5]decan-8-yl)pyridin-2-yl)thio)-2-phenylacetamide;

2-((3,5-Dicyano-4-cyclopropyl-6-(3-(dimethylamino)piperidin-1-yl)pyridin-2-yl)thio)-2-phenylacetamide;

2-((3,5-Dicyano-4-cyclopropyl-6-(3-methylpiperazin-1-yl)pyridin-2-yl)thio)-2-phenylacetamide;

2-((3,5-Dicyano-4-cyclopropyl-6-(2-(hydroxmethyl)morpholino)pyridin-2-yl)thio)-2-phenylacetamide;

2-((3,5-Dicyano-4-cyclopropyl-6-(2,6-dimethylmorpholino)pyridin-2-yl)thio)-2-phenylacetamide;

2-((3,5-Dicyano-4-cyclopropyl-6-(3-(dimethylamino)piperidin-1-yl)pyridin-2-yl)thio)-2-phenylacetamide;

2-((6-(4-(Aminomethyl)-4-hydroxypiperidin-1-yl)-3,5-dicyano-4-cyclopropylpyridin-2-yl)thio)-2-phenylacetamide;

2-((3,5-dicyano-4-cyclopropyl-6-(3-(methylamino)piperidin-1-yl)pyridin-2-yl)thio)-2-phenylacetamide;

2-((6-(3-aminopiperidin-1-yl)-3,5-dicyano-4-cyclopropylpyridin-2-yl)thio)-2-phenylacetamide;

2-((3,5-dicyano-4-cyclopropyl-6-(dimethylamino)pyridin-2-yl)thio)-2-(pyridin-4-yl)acetamide;

2-((3,5-dicyano-6-(dimethylamino)-4-ethylpyridin-2-yl)thio)-2-(pyridin-4-yl)acetamide;

2-((6-(4-aminopiperidin-1-yl)-3,5-dicyano-4-cyclopropylpyridin-2-yl)thio)-2-phenylacetamide;

2-((3,5-dicyano-4-cyclopropyl-6-(4-(dimethylamino)piperidin-1-yl)pyridin-2-yl)thio)-2-phenylacetamide;

2-((3,5-dicyano-4-cyclopropyl-6-(piperazin-1-yl)pyridin-2-yl)thio)-2-(pyridin-4-yl)acetamide;

2-((3,5-dicyano-4-cyclopropyl-6-(1,4-diazepan-1-yl)pyridin-2-yl)thio)-2-(pyridin-4-yl)acetamide;

2-((3,5-dicyano-4-cyclopropyl-6-((R)-3-hydroxypiperidin-1-yl)pyridin-2-yl)thio)-2-phenylacetamide;

2-(3,5-dicyano-4-cyclopropyl-6-((S)-3-hydroxypiperidin-1-yl)pyridin-2-ylthio)-2-phenylacetamide;

2-((3,5-dicyano-4-cyclopropyl-6-((S)-3-hydroxypyrrolidin-1-yl)pyridin-2-yl)thio)-2-(pyridin-4-yl)acetamide;

2-((3,5-dicyano-4-ethyl-6-(4-ethylpiperazin-1-yl)pyridin-2-yl)thio)-2-phenylacetamide;

2-((3,5-Dicyano-4-ethyl-6-(1-oxa-6-azaspiro[3.4]octan-6-yl)pyridin-2-yl)thio)-2-phenylacetamide;

2-((6-(4-(3-aminopropyl)piperazin-1-yl)-3,5-dicyano-4-ethylpyridin-2-yl)thio)-2-phenylacetamide;

2-((3,5-Dicyano-4-ethyl-6-(1,7-diazaspiro[3.5]nonan-1-yl)pyridin-2-yl)thio)-2-phenylacetamide;

2-((3,5-Dicyano-4-cyclopropyl-6-(4-(pyrrolidin-1-ylmethyl)piperidin-1-yl) pyridin-2-yl)thio)-2-phenylacetamide;

2-((3,5-Dicyano-4-cyclopropyl-6-(4-(4-methylpiperazin-1-yl)piperidin-1-yl)pyridin-2-yl)thio)-2-phenylacetamide;

(R)-2-((3,5-dicyano-6-(1,4-diazepan-1-yl)-4-ethylpyridin-2-yl)amino)-2-phenylacetamide;

2-((3,5-Dicyano-4-cyclopropyl-6-(4-(pyrrolidin-1-yl)piperidin-1-yl)pyridin-2-yl)thio)-2-phenylacetamide;

2-((3,5-Dicyano-4-ethyl-6-(2,7-diazaspiro[3.5]nonan-7-yl)pyridin-2-yl)thio)-2-phenylacetamide;

2-((3,5-Dicyano-4-ethyl-6-(2,6-diazaspiro[3.4]octan-6-yl)pyridin-2-yl)thio)-2-phenylacetamide;

2-((3,5-dicyano-4-cyclopropyl-6-(1,4-diazepan-1-yl)pyridin-2-yl)thio)propanamide;

2-((3,5-Dicyano-4-ethyl-6-(4-(2-oxoimidazolidin-1-yl)piperidin-1-yl)pyridin-2-yl)thio)-2-phenylacetamide;

2-((3,5-Dicyano-4-ethyl-6-(4-hydroxypiperidin-1-yl)pyridin-2-yl)thio)-2-phenylacetamide;

2-((3,5-Dicyano-4-ethyl-6-((S)-3-hydroxypyrrolidin-1-yl)pyridin-2-yl)thio)-2-phenylacetamide;

2-((3,5-Dicyano-4-ethyl-6-(3-oxopiperazin-1-yl)pyridin-2-yl)thio)-2-phenylacetamide;

2-((3,5-Dicyano-4-ethyl-6-((2-methoxyethyl)(methyl)amino)pyridin-2-yl)thio)-2-phenylacetamide;

2-((3,5-Dicyano-4-ethyl-6-(3-methoxyazetidin-1-yl)pyridin-2-yl)thio)-2-phenylacetamide;

2-((3,5-Dicyano-4-ethyl-6-(piperazin-1-yl)pyridin-2-yl)thio)-2-phenylacetamide;

2-((3,5-Dicyano-4-ethyl-6-(4-methyl-1,4-diazepan-1-yl)pyridin-2-yl)thio)-2-phenylacetamide;

2-((3,5-Dicyano-4-ethyl-6-morpholinopyridin-2-yl)thio)-2-phenylacetamide;

2-[[6-(azetidin-1-yl)-3,5-dicyano-4-ethyl-2-pyridyl]sulfanyl]-2-phenyl-acetamide;

2-((3,5-Dicyano-4-ethyl-6-(4-oxopiperidin-1-yl)pyridin-2-yl)thio)-2-phenylacetamide;

2-((3,5-dicyano-4-ethyl-6-(1'-(2-hydroxyethyl)-[4,4'-bipiperidin]-1-yl)pyridin-2-yl)thio)-2-phenylacetamide;

2-((3,5-Dicyano-6-((3S,5R)-3,5-dimethylpiperazin-1-yl)-4-ethylpyridin-2-yl)thio)-2-phenylacetamide;

2-((6-(8-azabicyclo[3.2.1]octan-3-yl(methyl)amino)-3,5-dicyano-4-ethylpyridin-2-yl)thio)-2-phenylacetamide;

2-((3,5-Dicyano-4-cyclopropyl-6-(2-(hydroxymethyl)morpholino)pyridin-2-yl)thio)-2-phenylacetamide;

(R)-2-((3,5-dicyano-6-(dimethylamino)-4-ethylpyridin-2-yl)thio)-2-phenylacetamide;
(R)-2-[(3,5-Dicyano-4-ethyl-6-morpholino-2-pyridyl)sulfanyl]-2-phenyl-acetamide;
2-{[3,5-dicyano-4-ethyl-6-(5-methyl-1,4-diazepan-1-yl)pyridin-2-yl]sulfanyl}-2-phenylacetamide;
2-({3,5-Dicyano-4-ethyl-6-[4-(2-methoxyethyl)-1,4-diazepan-1-yl]pyridin-2-yl}sulfanyl)-2-phenylacetamide;
2-((3,5-dicyano-4-ethyl-6-(4-(2-hydroxypropyl)-1,4-diazepan-1-yl)pyridin-2-yl)thio)-2-phenylacetamide;
Methyl 2-[4-(6-{[carbamoyl(phenyl)methyl]sulfanyl}-3,5-dicyano-4-ethylpyridin-2-yl)-1,4-diazepan-1-yl]acetate;
2-{[3,5-Dicyano-4-cyclopropyl-6-(4-methyl-5-oxo-1,4-diazepan-1-yl)pyridin-2-yl]sulfanyl}-2-phenylacetamide;
2-{[3,5-Dicyano-4-cyclopropyl-6-(5-oxo-1,4-diazepan-1-yl)pyridin-2-yl]sulfanyl}-2-phenylacetamide;
2-{[3,5-Dicyano-4-ethyl-6-(4-methyl-5-oxo-1,4-diazepan-1-yl)pyridin-2-yl]sulfanyl}-2-phenylacetamide;
2-{[3,5-Dicyano-6-(1,4-diazepan-1-yl)-4-ethylpyridin-2-yl]sulfanyl}-2-phenylacetamide;
2-({3,5-Dicyano-6-[4-(2-hydroxyethyl)-1,4-diazepan-1-yl]-4-(2,2,2-trifluoroethyl)pyridin-2-yl}sulfanyl)-2-phenylacetamide;
(2R)-2-({3,5-Dicyano-4-ethyl-6-[4-(2-hydroxyethyl)-1,4-diazepan-1-yl]pyridin-2-yl}amino)-2-phenylacetamide;
2-({6-[(3S)-3-Aminopyrrolidin-1-yl]-3,5-dicyano-4-cyclopropylpyridin-2-yl}sulfanyl)-2-phenylacetamide;
2-((3,5-Dicyano-4-ethyl-6-(2,9-diazaspiro[5.5]undecan-9-yl)pyridin-2-yl)thio)-2-phenylacetamide;
2-((3,5-Dicyano-4-ethyl-6-(hexahydro-1H-pyrrolo[1,2-a][1,4]diazepin-2(3H)-yl)pyridin-2-yl)thio)-2-phenylacetamide;
2-((3,5-Dicyano-4-ethyl-6-(2-methyl-2,9-diazaspiro[5.5]undecan-9-yl)pyridin-2-yl)thio)-2-phenylacetamide;
2-((3,5-Dicyano-6-(2-(cyclopropylmethyl)-2,9-diazaspiro[5.5]undecan-9-yl)-4-ethylpyridin-2-yl)thio)-2-phenylacetamide;
2-((3,5-Dicyano-6-(4-(3-(dimethylamino)propyl)piperazin-1-yl)-4-ethylpyridin-2-yl)thio)-2-phenylacetamide;
2-((3,5-Dicyano-4-ethyl-6-(4-(pyrrolidin-3-yl)piperidin-1-yl)pyridin-2-yl)thio)-2-phenylacetamide;
2-((6-([4,4'-Bipiperidin]-1-yl)-3,5-dicyano-4-ethylpyridin-2-yl)thio)-2-phenylacetamide;
2-((6-(4-(2-Aminoethyl)piperazin-1-yl)-3,5-dicyano-4-ethylpyridin-2-yl)thio)-2-phenylacetamide;
2-((6-(4-(3-Aminopropyl)piperazin-1-yl)-3,5-dicyano-4-cyclopropylpyridin-2-yl)thio)-2-phenylacetamide;
2-((3,5-Dicyano-4-cyclopropyl-6-(4-((4-methylpiperazin-1-yl)methyl)piperidin-1-yl)pyridin-2-yl)thio)-2-phenylacetamide;
2-((6-(4-Acetylpiperazin-1-yl)-3,5-dicyano-4-ethylpyridin-2-yl)thio)-2-phenylacetamide;
2-((3,5-Dicyano-4-cyclopropyl-6-(dimethylamino)pyridin-2-yl)thio)-2-phenylacetamide;
2-(4-Chlorophenyl)-2-((3,5-dicyano-6-(dimethylamino)-4-ethylpyridin-2-yl)thio)acetamide;
2-((3,5-Dicyano-4-ethyl-6-(4-(2-hydroxyethyl)piperazin-1-yl)pyridin-2-yl)thio)-2-phenylacetamide;
2-[(3,5-Dicyano-4-cyclopropyl-6-morpholino-2-pyridyl)sulfanyl]-2-phenyl-acetamide;
2-(6-(4-Benzoylpiperazin-1-yl)-3,5-dicyano-4-ethylpyridin-2-yl)thio)-2-phenylacetamide;
2-((3,5-Dicyano-4-ethyl-6-((5S,6S)-6-hydroxy-1-(methylsulfonyl)-1,8-diazaspiro[4.5]decan-8-yl)pyridin-2-yl)thio)-2-phenylacetamide;
2-((3,5-Dicyano-6-(4,4-difluoropiperidin-1-yl)-4-ethylpyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide;
2-((3,5-dicyano-4-(furan-2-yl)-6-(4-methyl-1,4-diazepan-1-yl)pyridin-2-yl)thio)-2-phenylacetamide;
2-((6-(4-Amino-4-methylpiperidin-1-yl)-3,5-dicyano-4-ethylpyridin-2-yl)thio)-2-phenylacetamide;
2-Amino-N-(1-(6-((2-amino-2-oxo-1-phenylethyl)thio)-3,5-dicyano-4-ethylpyridin-2-yl)piperidin-4-yl)acetamide;
(2S)-2-Amino-N-(1-(6-((2-amino-2-oxo-1-phenylethyl)thio)-3,5-dicyano-4-ethylpyridin-2-yl)piperidin-4-yl)propanamide;
2-((6-(4-(3-Aminooxetane-3-carbonyl)piperazin-1-yl)-3,5-dicyano-4-ethylpyridin-2-yl)thio)-2-phenylacetamide;
4-Amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide;
2-((6-(4-(4-Aminotetrahydro-2H-pyran-4-carbonyl)piperazin-1-yl)-3,5-dicyano-4-ethylpyridin-2-yl)thio)-2-phenylacetamide;
2-((3,5-Dicyano-6-(4-(2-hydroxyethyl)-1,4-diazepan-1-yl)-4-methoxypyridin-2-yl)thio)-2-phenylacetamide;
2-((6-(4-Aminopiperidin-1-yl)-3,5-dicyano-4-ethylpyridin-2-yl)thio)-2-phenylacetamide;
2-((6-((2-Aminoethyl)(methyl)amino)-3,5-dicyano-4-ethylpyridin-2-yl)thio)-2-phenylacetamide;
2-((6-((2-Amino-2-oxoethyl)(methyl)amino)-3,5-dicyano-4-ethylpyridin-2-yl)thio)-2-phenylacetamide;
2-((3,5-Dicyano-4-ethyl-6-(3-hydroxyazetidin-1-yl)pyridin-2-yl)thio)-2-phenylacetamide;
2-(3,5-Dicyano-4-ethyl-6-((2-hydroxyethyl)(methyl)amino)pyridin-2-ylthio)-2-phenylacetamide;
2-Amino-N-(1-(6-((2-amino-2-oxo-1-phenylethyl)thio)-3,5-dicyano-4-ethylpyridin-2-yl)piperidin-4-yl)-2-methylpropanamide;
2-((6-(4-(2-Aminoethoxy)piperidin-1-yl)-3,5-dicyano-4-ethylpyridin-2-yl)thio)-2-phenylacetamide;
1-(6-((2-Amino-2-oxo-1-phenylethyl)thio)-3,5-dicyano-4-ethylpyridin-2-yl)pyrrolidin-3-yl dihydrogen phosphate;
2-((6-((2-Amino-2-oxo-1-phenylethyl)thio)-3,5-dicyano-4-ethylpyridin-2-yl)(methyl)amino)ethyl dihydrogen phosphate;
1-(6-((2-Amino-2-oxo-1-phenylethyl)thio)-3,5-dicyano-4-ethylpyridin-2-yl)azetidin-3-yl dihydrogen phosphate;
(2S)-2-((1-(6-((2-Amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-Amino-2-oxo-1-phenylethyl)thio)-3,5-dicyano-4-ethylpyridin-2-yl)piperidin-4-yl)oxy)ethyl dihydrogen phosphate;
1-(6-((2-Amino-2-oxo-1-phenylethyl)thio)-3,5-dicyano-4-ethylpyridin-2-yl)piperidin-4-yl dihydrogen phosphate;
2-((3,5-Dicyano-6-(dimethylamino)-4-ethylpyridin-2-yl)thio)-2-(piperidin-4-yl)acetamide;
2-((3,5-Dicyano-4-ethyl-6-(4-(propylsulfonyl)piperazin-1-yl)pyridin-2-yl)thio)-2-phenylacetamide;
2-((3,5-Dicyano-4-ethyl-6-(4-(phenylsulfonyl)piperazin-1-yl)pyridin-2-yl)thio)-2-phenylacetamide;
2-((3,5-Dicyano-4-ethyl-6-((R)-3-hydroxpyrrolidin-1-yl)pyridin-2-yl)thio)-2-phenylacetamide;
2-((3,5-Dicyano-4-ethyl-6-(2-oxa-6-azaspiro[3.4]octan-6-yl)pyridin-2-yl)thio)-2-phenylacetamide;
(R)-2-((3,5-Dicyano-4-ethyl-6-(4-ethyl-1,4-diazepan-1-yl)pyridin-2-yl)amino)-2-phenylacetamide;
(R)-2-((3,5-Dicyano-4-ethyl-6-(4-(3-(pyrrolidin-1-yl)propyl)-1,4-diazepan-1-yl)pyridin-2-yl)amino)-2-phenylacetamide;

2-(3,5-Dicyano-4-cyclopropyl-6-(3-hydroxypiperidin-1-yl)pyridin-2-ylthio)-2-phenylacetamide;
2-((3,5-Dichloro-4-ethyl-6-(4-methyl-1,4-diazepan-1-yl)pyridin-2-yl)thio)-2-phenylacetamide;
2-((3,5-Dicyano-6-(1,1-dioxidothiomorpholino)-4-ethylpyridin-2-yl)thio)-2-phenylacetamide;
2-((3,5-Dicyano-4-ethyl-6-(methyl(2-(piperazin-1-yl)ethyl)amino)pyridin-2-yl)thio)-2-phenylacetamide;
(R)-2-((3,5-Dicyano-4-ethyl-6-((S)-3-hydroxypyrrolidin-1-yl)pyridin-2-yl)thio)-2-phenylacetamide;
2-((6-((2-(4-(Aminomethyl)-4-hydroxypiperidin-1-yl)ethyl)(methyl)amino)-3,5-dicyano-4-ethylpyridin-2-yl)thio)-2-phenylacetamide;
2-((4-Cyano-3-(1,4-diazepan-1-yl)-6,7-dihydro-5H-cyclopenta[c]pyridin-1-yl)thio)-2-phenylacetamide;
2-((6-(4-(1H-Imidazol-1-yl)piperidin-1-yl)-3,5-dicyano-4-ethylpyridin-2-yl)thio)-2-phenylacetamide;
2-((3,5-Dicyano-4-ethyl-6-(4-(pyridin-4-ylmethyl)piperazin-1-yl)pyridin-2-yl)thio)-2-phenylacetamide;
2-((3,5-Dicyano-6-(2-(dimethylamino)ethoxy)-4-ethylpyridin-2-yl)thio)-2-phenylacetamide;
2-((1-(6-((2-Amino-2-oxo-1-phenylethyl)thio)-3,5-dicyano-4-cyclopropylpyridin-2-yl)piperidin-3-yl)amino)acetic acid;
2-((3,5-Dicyano-4-ethyl-6-(4-(oxazol-2-ylmethyl)piperazin-1-yl)pyridin-2-yl)thio)-2-phenylacetamide;
2-((6-(4-((1H-Pyrrol-2-yl) methyl) piperazin-1-yl)-3,5-dicyano-4-ethylpyridin-2-yl)thio)-2-phenylacetamide;
2-((3,5-Dicyano-6-(3,4-dihydro-2,7-naphthyridin-2 (1H)-yl)-4-ethylpyridin-2-yl)thio)-2-phenylacetamide;
2-((3,5-Dicyano-4-ethyl-6-((S)-3-hydroxypyrrolidin-1-yl)pyridin-2-yl)thio)-2-(pyridin-3-yl)acetamide;
2-((6-(4-((1H-Pyrrol-3-yl)methyl)piperazin-1-yl)-3,5-dicyano-4-ethylpyridin-2-yl)thio)-2-phenylacetamide;
2-((3,5-Dicyano-4-ethyl-6-(4-(isoxazol-3-ylmethyl)piperazin-1-yl)pyridin-2-yl)thio)-2-phenylacetamide;
2-((3,5-Dicyano-4-ethyl-6-(4-(oxazol-5-ylmethyl)piperazin-1-yl)pyridin-2-yl)thio)-2-phenylacetamide;
2-((3,5-Dicyano-4-ethyl-6-(4-(isoxazol-4-ylmethyl)piperazin-1-yl)pyridin-2-yl)thio)-2-phenylacetamide;
3-Amino-N-(1-(6-((2-amino-2-oxo-1-phenylethyl)thio)-3,5-dicyano-4-ethylpyridin-2-yl)piperidin-4-yl)oxetane-3-carboxamide;
2-((6-(4-((1H-Pyrazol-4-yl)methyl)piperazin-1-yl)-3,5-dicyano-4-ethylpyridin-2-yl)thio)-2-phenylacetamide;
2-((6-(4-((1H-Imidazol-5-yl)methyl)piperazin-1-yl)-3,5-dicyano-4-ethylpyridin-2-yl)thio)-2-phenylacetamide;
2-((3,5-Dicyano-4-ethyl-6-(4-(1-hydroxy-2-methylpropan-2-yl)piperazin-1-yl)pyridin-2-yl)thio)-2-phenylacetamide;
2-((6-(4-((1H-Imidazol-2-yl)methyl)piperazin-1-yl)-3,5-dicyano-4-ethylpyridin-2-yl)thio)-2-phenylacetamide;
2-((3,5-Dicyano-6-(dimethylamino)-4-methoxypyridin-2-yl)thio)-2-phenylacetamide;
2-((3,5-Dicyano-6-(dimethylamino)-4-ethoxypyridin-2-yl)thio)-2-phenylacetamide;
2-((3,5-Dicyano-4-ethoxy-6-(4-(2-hydroxyethyl)-1,4-diazepan-1-yl) pyridin-2-yl)thio)-2-phenylacetamide;
2-((3,5-Dicyano-4-ethyl-6-(4-(2-hydroxy-2-methylpropyl)-1,4-diazepan-1-yl)pyridin-2-yl)thio)-2-phenylacetamide;
2-((3,5-Dicyano-4-ethyl-6-(4-(thiazol-5-ylmethyl)piperazin-1-yl)pyridin-2-yl)thio)-2-phenylacetamide;
2-((3,5-Dicyano-4-ethyl-6-(piperazin-1-yl)pyridin-2-yl)thio)-2-(4-fluorophenyl)acetamide;
2-((3,5-Dicyano-4-ethyl-6-(4-(isothiazol-4-ylmethyl)piperazin-1-yl)pyridin-2-yl)thio)-2-phenylacetamide;
2-((3,5-Dicyano-6-(dimethylamino)-4-ethylpyridin-2-yl)thio)-2-(4-fluorophenyl)acetamide;
2-((3,5-Dicyano-6-(dimethylamino)-4-ethylpyridin-2-yl)thio)-2-(5-fluoropyridin-2-yl)acetamide;
2-((3,5-Dicyano-4-ethyl-6-(4-(furan-3-ylmethyl)piperazin-1-yl)pyridin-2-yl)thio)-2-phenylacetamide;
2-((3,5-Dicyano-4-ethyl-6-((2-morpholinoethyl)thio)pyridin-2-yl)thio)-2-phenylacetamide;
2-((3,5-Dicyano-6-(4-methyl-1,4-diazepan-1-yl)-4-(methylthio)pyridin-2-yl)thio)-2-phenylacetamide;
2-((3,5-Dichloro-4-ethyl-6-(4-(2-hydroxyethyl)-1,4-diazepan-1-yl)pyridin-2-yl)thio)-2-phenylacetamide;
2-((3,5-Dicyano-4-ethyl-6-(hexahydropyrrolo[3,4-b][1,4]oxazin-6(2H)-yl)pyridin-2-yl)thio)-2-phenylacetamide;
2-((3,5-Dicyano-4-ethyl-6-(4-methyl-1,4-diazepan-1-yl)pyridin-2-yl)thio)-2-(5-methylpyridin-2-yl)acetamide;
2-((3,5-Dicyano-4-ethyl-6-(4-methyl-1,4-diazepan-1-yl)pyridin-2-yl)thio)-2-(6-fluoropyridin-2-yl)acetamide;
2-((3,5-Dicyano-6-(4-(dimethylamino)piperidin-1-yl)-4-ethylpyridin-2-yl)thio)-2-(4-fluorophenyl)acetamide;
2-((3,5-Dicyano-4-ethyl-6-(4-methyl-1,4-diazepan-1-yl)pyridin-2-yl)thio)-2-(4-methylpyridin-2-yl)acetamide;
2-((3,5-Dicyano-4-ethyl-6-(4-methyl-1,4-diazepan-1-yl)pyridin-2-yl)thio)-2-(3-methoxypyridin-2-yl)acetamide;
2-((3,5-Dicyano-6-(4-(dimethylamino)piperidin-1-yl)-4-ethylpyridin-2-yl)thio)-2-(2,4-difluorophenyl)acetamide;
2-((3,5-Dicyano-4-ethyl-6-(4-(pyrrolidin-1-yl)piperidin-1-yl)pyridin-2-yl)thio)-2-(5-fluoropyridin-2-yl)acetamide;
2-((3,5-Dicyano-4-ethoxy-6-(4-(2-hydroxyethyl)-1,4-diazepan-1-yl)pyridin-2-yl)thio)propanamide;
2-((3,5-Dicyano-6-(4-(2-hydroxyethyl)-1,4-diazepan-1-yl)-4-propoxypyridin-2-yl)thio)-2-phenylacetamide;
2-((3,5-Dicyano-4-ethyl-6-(4-methyl-1,4-diazepan-1-yl)pyridin-2-yl)thio)-2-(4-methoxypyridin-2-yl)acetamide;
2-((3,5-Dicyano-4-ethyl-6-(2-methyl-2,8-diazaspiro[4.5]decan-8-yl)pyridin-2-yl)thio)-2-phenylacetamide;
2-((3,5-Dicyano-6-(4-(dimethylamino)piperidin-1-yl)-4-ethylpyridin-2-yl)thio)-2-(3,4-difluorophenyl)acetamide;
1-(6-((2-Amino-2-oxo-1-phenylethyl)thio)-3,5-dicyano-4-ethylpyridin-2-yl)piperidine-4-carboxamide;
2-((3,5-Dicyano-6-((2-(dimethylamino)ethyl)thio)-4-ethylpyridin-2-yl)thio)-2-phenylacetamide;
2-((3,5-Dicyano-6-((3S,4R)-3,4-dihydroxypyrrolidin-1-yl)-4-ethylpyridin-2-yl)thio)-2-phenylacetamide;
2-((3,5-Dicyano-4-ethyl-6-(4-methyl-1,4-diazepan-1-yl)pyridin-2-yl)thio)-2-(3-fluoropyridin-2-yl)acetamide;
2-((3,5-Dicyano-4-ethyl-6-(4-methyl-1,4-diazepan-1-yl)pyridin-2-yl)thio)-2-(5-methoxypyridin-2-yl)acetamide;
2-((3,5-Dicyano-4-ethyl-6-(4-(1-hydroxy-2-methylpropan-2-yl)piperazin-1-yl)pyridin-2-yl)thio)-2-(4-fluorophenyl)acetamide;
2-((3,5-Dicyano-4-ethyl-6-(4-methyl-1,4-diazepan-1-yl)pyridin-2-yl)thio)-2-(3-(trifluoromethyl)phenyl)acetamide;
2-((3,5-Dicyano-4-ethyl-6-(4-(2-hydroxyethoxy)piperidin-1-yl)pyridin-2-yl)thio)-2-phenylacetamide;
2-((3,5-Dicyano-4-ethyl-6-(4-methyl-1,4-diazepan-1-yl)pyridin-2-yl)thio)-2-(2-fluoropyridin-3-yl)acetamide;
2-((3,5-Dicyano-4-ethyl-6-(4-methyl-1,4-diazepan-1-yl)pyridin-2-yl)thio)-2-(6-fluoropyridin-3-yl)acetamide;
3-((6-(2-Amino-2-oxo-1-phenylethylthio)-3,5-dicyano-4-ethylpyridin-2-yl)(methyl)amino)propanamide;
2-((3,5-Dicyano-4-ethyl-6-(4-(oxetan-3-yloxy)piperidin-1-yl)pyridin-2-yl)thio)-2-phenylacetamide;
2-((3,5-Dicyano-6-(4-((2,2-difluoroethyl) amino)-4-methylpiperidin-1-yl)-4-ethylpyridin-2-yl)thio)-2-phenylacetamide;

2-((3,5-Dicyano-4-ethyl-6-(4-methyl-1,4-diazepan-1-yl)pyridin-2-yl)thio)-2-(4-(trifluoromethyl)phenyl)acetamide;
2-((6-(4-Aminopiperazin-1-yl)-3,5-dicyano-4-ethylpyridin-2-yl)thio)-2-phenylacetamide;
2-((6-((2-Amino-2-oxoethyl)thio)-3,5-dicyano-4-ethylpyridin-2-yl)thio)-2-phenylacetamide;
2-((3,5-Dicyano-4-ethyl-6-(pyrrolo[3,4-c]pyrazol-5(1H,4H,6H)-yl)pyridin-2-yl)thio)-2-phenylacetamide;
2-((3,5-Dicyano-6-(dimethylamino)-4-ethylpyridin-2-yl)thio)-2-(5-methoxypyridin-2-yl)acetamide;
2-((3,5-Dicyano-6-(dimethylamino)-4-ethylpyridin-2-yl)thio)-2-(5-methylpyridin-2-yl)acetamide;
2-((3,5-Dicyano-4-ethyl-6-(4-methyl-1,4-diazepan-1-yl)pyridin-2-yl)thio)-2-(2-fluoropyridin-4-yl)acetamide;
2-((3,5-Dicyano-4-ethyl-6-(4-hydroxy-4-(hydroxymethyl)piperidin-1-yl)pyridin-2-yl)thio)-2-phenylacetamide;
2-((3,5-Dicyano-4-ethyl-6-(2-oxo-3-oxa-1,8-diazaspiro[4.5]decan-8-yl)pyridin-2-yl)thio)-2-phenylacetamide;
2-((6-(4-Amino-4-(hydroxymethyl)piperidin-1-yl)-3,5-dicyano-4-ethylpyridin-2-yl)thio)-2-phenylacetamide;
2-((6-(4-(Aminomethyl)-4-hydroxypiperidin-1-yl)-3,5-dicyano-4-ethylpyridin-2-yl)thio)-2-phenylacetamide;
2-(3-Benzoylphenyl)-2-((3,5-dicyano-4-ethyl-6-(4-(2-hydroxyethyl)-1,4-diazepan-1-yl)pyridin-2-yl)thio)acetamide;
2-(4-Benzoylphenyl)-2-((3,5-dicyano-4-ethyl-6-(4-(2-hydroxyethyl)-1,4-diazepan-1-yl)pyridin-2-yl)thio)acetamide;
2-((3,5-Dicyano-4-ethyl-6-(4-methyl-1,4-diazepan-1-yl)pyridin-2-yl)thio)-2-(2-methylpyridin-4-yl)acetamide;
2-((3,5-Dicyano-4-ethyl-6-(4-methyl-1,4-diazepan-1-yl)pyridin-2-yl)thio)-2-(3-(pyrrolidin-1-yl)phenyl)acetamide;
2-((3,5-Dicyano-4-ethyl-6-(4-methyl-1,4-diazepan-1-yl)pyridin-2-yl)thio)-2-(3-fluoropyridin-4-yl)acetamide;
2-((3,5-Dicyano-4-ethyl-6-(4-methyl-1,4-diazepan-1-yl)pyridin-2-yl)thio)-2-(2,5-difluoropyridin-4-yl)acetamide;
2-((3,5-Dicyano-6-(4-(2,5-dioxoimidazolidin-1-yl)piperidin-1-yl)-4-ethylpyridin-2-yl)thio)-2-phenylacetamide;
4-Amino-1-(6-((2-amino-2-oxo-1-phenylethyl)thio)-3,5-dicyano-4-ethylpyridin-2-yl) piperidine-4-carboxamide;
2-((3,5-Dicyano-6-(4-(2,5-dioxopyrrolidin-1-yl)piperidin-1-yl)-4-ethylpyridin-2-yl)thio)-2-phenylacetamide;
2-((3,5-dicyano-4-ethyl-6-(4-methyl-1,4-diazepan-1-yl)pyridin-2-yl)thio)-2-phenylacetamide (isomer 1);
2-((3,5-Dicyano-4-ethyl-6-(4-methyl-1,4-diazepan-1-yl)pyridin-2-yl)thio)-2-phenylacetamide (Isomer 2);
2-((3,5-Dicyano-4-ethyl-6-(2-oxo-1-oxa-3,8-diazaspiro[4.5]decan-8-yl)pyridin-2-yl)thio)-2-phenylacetamide;
1-(6-((2-Amino-2-oxo-1-phenylethyl)thio)-3,5-dicyano-4-ethylpyridin-2-yl)-4-hydroxy piperidine-4-carboxamide;
1-(6-((2-Amino-2-oxo-1-phenylethyl)thio)-3,5-dicyano-4-ethylpyridin-2-yl)azetidin-3-yl carbamate;
2-((3,5-Dicyano-6-(4-(2,4-dioxooxazolidin-3-yl)piperidin-1-yl)-4-ethylpyridin-2-yl)thio)-2-phenylacetamide;
3-((6-((2-Amino-2-oxo-1-phenylethyl)thio)-3,5-dicyano-4-ethylpyridin-2-yl)(methyl)amino)-2-hydroxy-2-methylpropanamide;
2-((3,5-Dicyano-4-ethyl-6-(3-(hydroxymethyl)azetidin-1-yl)pyridin-2-yl)thio)-2-phenylacetamide;
2-(3,5-Dicyano-4-ethyl-6-(piperazin-1-yl)pyridin-2-ylthio)-2-(thiophen-3-yl)acetamide;
2-((3,5-Dicyano-4-ethyl-6-(4-methyl-1,4-diazepan-1-yl)pyridin-2-yl)thio)-2-(5-methylpyridin-3-yl)acetamide;
2-((6-(4-(3-Amino-2-oxopyrrolidin-1-yl)piperidin-1-yl)-3,5-dicyano-4-ethylpyridin-2-yl)thio)-2-phenylacetamide;
1-(6-((2-Amino-2-oxo-1-phenylethyl)thio)-3,5-dicyano-4-ethylpyridin-2-yl)piperidin-4-yl (2S)-2-amino-3-methylbutanoate;
2-((6-((2-Amino-2-oxo-1-phenylethyl)thio)-3,5-dicyano-4-ethylpyridin-2-yl) (methyl) amino)ethyl (2S)-2-amino-3-methylbutanoate;
2,2'-((3,5-Dicyano-4-ethylpyridine-2,6-diyl)bis(sulfanediyl))bis(2-phenylacetamide)
(2S)-(1-(6-((2-Amino-2-oxo-1-phenylethyl)thio)-3,5-dicyano-4 ethylpyridin-2-yl)azetidin-3-yl)methyl 2-amino-3-methylbutanoate;
2-((6-(3-Aminoazetidin-1-yl)-3,5-dicyano-4-ethylpyridin-2-yl)thio)-2-phenylacetamide;
2-((3,5-Dicyano-4-ethyl-6-methylpyridin-2-yl)thio)-2-phenylacetamide;
N-(1-(6-((2-Amino-2-oxo-1-phenylethyl)thio)-3,5-dicyano-4-ethylpyridin-2-yl)piperidin-4-yl)-2-hydroxyacetamide;
N-(1-(6-((2-Amino-2-oxo-1-phenylethyl)thio)-3,5-dicyano-4-ethylpyridin-2-yl)azetidin-3-yl)-2-hydroxyacetamide;
2-((3-Cyano-4-ethyl-5-methyl-6-(piperazin-1-yl)pyridin-2-yl)thio)-2-phenylacetamide;
2-((3,5-Dicyano-4-ethyl-6-(5-methyl-2,5-diazabicyclo[2.2.1]heptan-2-yl)pyridin-2-yl)thio)-2-phenylacetamide;
2-((3,5-Dicyano-4-ethyl-6-(4-(2-(pyrrolidin-1-yl)ethyl)piperazin-1-yl)pyridin-2-yl)thio)-2-phenylacetamide;
2-((3,5-Dicyano-6-(dimethylamino)-4-ethylpyridin-2-yl)thio)-2-phenylacetamide-2-d;
(R)-2-((3,5-Dicyano-6-(dimethylamino)-4-ethylpyridin-2-yl)thio)-2-phenylacetamide-2-d;
2-((6-(4-(4-Bromobenzoyl)piperazin-1-yl)-3,5-dicyano-4-ethylpyridin-2-yl)thio)-2-phenylacetamide;
2-((3,5-Dicyano-4-ethyl-6-(4-(2-hydroxyethyl)-1,4-diazepan-1-yl)pyridin-2-yl)thio)-2-phenylacetamide;
2-((3,5-Dicyano-6-(4-cyanopiperidin-1-yl)-4-ethylpyridin-2-yl)thio)-2-phenylacetamide;
(S)-2-((3,5-Dicyano-4-ethyl-6-((S)-3-hydroxypyrrolidin-1-yl)pyridin-2-yl)thio)-2-phenylacetamide;
2-((6-(4-Amino-4-methylpiperidin-1-yl)-3,5-dicyano-4-cyclopropylpyridin-2-yl)thio)-2-phenylacetamide;
2-((3,5-Dicyano-4-ethyl-6-((S)-3-hydroxypyrrolidin-1-yl)pyridin-2-yl)thio)-2-(pyridin-2-yl)acetamide;
2-((3,5-Dichloro-4-ethyl-6-(piperazin-1-yl)pyridin-2-yl)thio)-2-phenylacetamide;
tert-Butyl (1-(6-((2-amino-2-oxo-1-phenylethyl)thio)-3,5-dicyano-4-ethylpyridin-2-yl)piperidin-4-yl)carbamate;
2-((6-(3-(2-Amino-2-oxoethyl)azetidin-1-yl)-3,5-dicyano-4-ethylpyridin-2-yl)thio)-2-phenylacetamide;
(2R)-1-(6-((2-Amino-2-oxo-1-phenylethyl)thio)-3,5-dicyano-4-ethylpyridin-2-yl)azetidin-3-yl 2-amino-3-methylbutanoate;
2-((3,5-Dicyano-4-ethyl-6-(methyl((5-oxo-4,5-dihydro-1H-1,2,4-triazol-3-yl)methyl)amino)pyridin-2-yl)thio)-2-phenylacetamide;
2-((6-(((4H-1,2,4-Triazol-3-yl)methyl)(methyl)amino)-3,5-dicyano-4-ethylpyridin-2-yl)thio)-2-phenylacetamide;
2-((3,5-Dicyano-4-ethoxy-6-methylpyridin-2-yl)thio)-2-phenylacetamide;
2-((3,5-Dicyano-4,6-diethylpyridin-2-yl)thio)-2-phenylacetamide;
2-((6-((2-(4H-1,2,4-Triazol-4-yl)ethyl)(methyl)amino)-3,5-dicyano-4-ethylpyridin-2-yl)thio)-2-phenylacetamide;
2-((6-(((1H-Pyrazol-3-yl)methyl)(methyl)amino)-3,5-dicyano-4-ethylpyridin-2-yl)thio)-2-phenylacetamide;
2-((3,5-Dicyano-6-(6,7-dihydro-1H-[1,2,3]triazolo[4,5-c]pyridin-5(4H)-yl)-4-ethylpyridin-2-yl)thio)-2-phenylacetamide;

2-((6-(((1H-Imidazol-2-yl)methyl)(methyl)amino)-3,5-di-cyano-4-ethylpyridin-2-yl)thio)-2-phenylacetamide;
2-((6-(((1H-Imidazol-5-yl)methyl)(methyl)amino)-3,5-di-cyano-4-ethylpyridin-2-yl)thio)-2-phenylacetamide;
(2R)-2-Amino-N-(1-(6-((2-amino-2-oxo-1-phenylethyl)thio)-3,5-dicyano-4-ethylpyridin-2-yl)piperidin-4-yl)propanamide;
4-(2-Amino-1-((3,5-dicyano-4-ethyl-6-(4-methyl-1,4-diazepan-1-yl)pyridin-2-yl)thio)-2-oxoethyl)benzamide;
2-((3,5-Dicyano-4-cyclopropyl-6-(3-hydroxypyrrolidin-1-yl)pyridin-2-yl)thio)-2-phenylacetamide;
2-((3,5-Dicyano-4-ethyl-6-(3-hydroxpyrrolidin-1-yl)pyridin-2-yl)thio)-2-phenylacetamide;
(2R)-2-Amino-N-(1-(6-((2-amino-2-oxo-1-phenylethyl)thio)-3,5-dicyano-4-cyclopropylpyridin-2-yl)piperidin-4-yl)propanamide;
2-((6-((2-Aminoethyl)(methyl)amino)-3,5-dicyano-4-cyclopropylpyridin-2-yl)thio)-2-phenylacetamide;
2-Amino-N-(1-(6-((2-amino-2-oxo-1-phenylethyl)thio)-3,5-dicyano-4-cyclopropylpyridin-2-yl)piperidin-4-yl)-2-methylpropanamide;
4-(2-Amino-1-((3,5-dicyano-6-(dimethylamino)-4-ethylpyridin-2-yl)thio)-2-oxoethyl)benzamide;
2-(6-(4-Aminopiperidin-1-yl)-3-cyano-4-ethyl-5-methylpyridin-2-ylthio)-2-phenylacetamide;
2-((3,5-Dicyano-4-ethyl-6-(4-methyl-1,4-diazepan-1-yl)pyridin-2-yl)thio)-2-(4-(N-methylsulfamoyl)phenyl)acetamide;
2-((3,5-Dicyano-4-ethyl-6-(6-fluoro-1,4-diazepan-1-yl)pyridin-2-yl)thio)-2-phenylacetamide;
2-((6-(4-Amino-3,3-difluoropiperidin-1-yl)-3,5-dicyano-4-ethylpyridin-2-yl)thio)-2-phenylacetamide;
tert-Butyl (1-(6-((2-amino-2-oxo-1-phenylethyl)thio)-3,5-dicyano-4-ethylpyridin-2-yl)-3,3-difluoropiperidin-4-yl)carbamate;
2-((3,5-Dicyano-4-cyclopropyl-6-((2-hydroxyethyl)(methyl)amino)pyridin-2-yl)thio)-2-phenylacetamide;
2-((3,5-Dicyano-4-cyclopropyl-6-(3-hydroxyazetidin-1-yl)pyridin-2-yl)thio)-2-phenylacetamide;
1-(6-((2-Amino-2-oxo-1-phenylethyl)thio)-3,5-dicyano-4-ethylpyridin-2-yl)pyrrolidine-3-carboxamide;
2-((6-((3-Aminopropyl) (methyl) amino)-3,5-dicyano-4-cyclopropylpyridin-2-yl) thio)-2-phenylacetamide;
2-((3,5-Dicyano-4-cyclopropyl-6-((2-(3-hydroxyazetidin-1-yl)-2-oxoethyl)(methyl)amino) pyridin-2-yl)thio)-2-phenylacetamide;
2-((6-(4-((2-Amino-2-oxoethyl)amino)piperidin-1-yl)-3,5-dicyano-4-ethylpyridin-2-yl)thio)-2-phenylacetamide;
2-((6-((2-Aminoethyl)(methyl)amino)-3,5-dicyano-4-cyclopropylpyridin-2-yl)thio)-2-phenylacetamide;
2-((6-((2-Amino-2-oxo-1-phenylethyl)thio)-3,5-dicyano-4-cyclopropylpyridin-2-yl)(methyl)amino)ethyl carbamate;
(2R)-2-Amino-N-(1-(6-((2-amino-2-oxo-1-phenylethyl)thio)-3,5-dicyano-4-ethylpyridin-2-yl)piperidin-4-yl)-3-hydroxypropanamide;
(2S)-2-Amino-N-(1-(6-((2-amino-2-oxo-1-phenylethyl)thio)-3,5-dicyano-4-ethylpyridin-2-yl) piperidin-4-yl)-3-hydroxypropanamide;
2-(4-(2-Amino-2-oxoethyl)phenyl)-2-(3,5-dicyano-4-ethyl-6-(4-methyl-1,4-diazepan-1-yl)pyridin-2-ylthio)acetamide;
2-(4-(2-Amino-2-oxoethyl)phenyl)-2-(3,5-dicyano-6-(dimethylamino)-4-ethylpyridin-2-ylthio)acetamide;
2-((3,5-Dicyano-6-(dimethylamino)-4-ethylpyridin-2-yl)thio)-2-(4-(N-methylsulfamoyl)phenyl)acetamide;
2-((3,5-Dicyano-6-(dimethylamino-d$_6$)-4-ethylpyridin-2-yl)thio)-2-phenylacetamide;
(R)-2-((3,5-Dicyano-4-ethyl-6-(4-(pyrrolidin-1-yl)piperidin-1-yl)pyridin-2-yl)thio)-2-phenylacetamide;
(R)-2-((3,5-Dicyano-6-(4-(dimethylamino)piperidin-1-yl)-4-ethylpyridin-2-yl)thio)-2-phenylacetamide;
2-(3,5-dicyano-6-(dimethylamino)-4-ethylpyridin-2-ylthio)-2-(3-(2-(dimethylamino)ethoxy)phenyl)acetamide;
2-((3,5-Dicyano-4-ethyl-6-(4-(neopentylamino)piperidin-1-yl)pyridin-2-yl)thio)-2-(4-fluorophenyl)acetamide;
2-((3,5-dicyano-4-ethyl-6-(3-fluoro-4-A(neopentylamino)piperidin-1-yl)pyridin-2-yl)thio)-2-phenylacetamide;
2-((6-(4-aminopiperidin-1-yl)-3,5-dicyano-4-ethylpyridin-2-yl)thio)-2-(4-(trifluoromethyl)phenyl)acetamide;
2-((3,5-Dicyano-4-ethyl-6-(4-(pyrrolidin-1-yl)piperidin-1-yl)pyridin-2-yl)thio)-2-phenylacetamide;
(R)-2-((6-(4-aminopiperidin-1-yl)-3,5-dicyano-4-ethylpyridin-2-yl)thio)-2-phenylacetamide;
2-((6-((2-amino-2-oxoethyl)(methyl)amino)-3,5-dicyano-4-ethylpyridin-2-yl)thio)-2-phenylacetamide; (single enantiomer)
(3S)-1-(6-((2-amino-2-oxo-1-phenylethyl)thio)-3,5-dicyano-4-ethylpyridin-2-yl)
Pyrrolidin-3-yl dihydrogen phosphate;
(3R)-1-(6-((2-amino-2-oxo-1-phenylethyl)thio)-3,5-dicyano-4-ethylpyridin-2-yl)pyrrolidin-3-yl dihydrogen phosphate;
(S)-1-(6-(((S)-2-amino-2-oxo-1-phenylethyl)thio)-3,5-dicyano-4-ethylpyridin-2-yl)pyrrolidin-3-yl dihydrogen phosphate;
(S)-1-(6-(((R)-2-amino-2-oxo-1-phenylethyl)thio)-3,5-dicyano-4-ethylpyridin-2-yl) pyrrolidin-3-yl dihydrogen phosphate;
2-((3,5-Dicyano-6-(dimethylamino)-4-ethylpyridin-2-yl)thio)-2-(3-(dimethylphosphoryl)phenyl)acetamide;
2-((3,5-Dicyano-4-ethyl-6-((S)-3-hydroxpyrrolidin-1-yl)pyridin-2-yl)thio)-2-(3-(dimethylphosphoryl)phenyl)acetamide;
(R)-2-((6-((2-amino-2-oxo-1-phenylethyl)thio)-3,5-dicyano-4-ethylpyridin-2-yl)(methyl)amino)ethyl dihydrogen phosphate;
(R)-2-((3,5-dicyano-4-ethyl-6-((S)-3-hydroxypyrrolidin-1-yl)pyridin-2-yl)thio)-2-(4-methoxyphenyl)acetamide;
(R)-2-(4-chlorophenyl)-2-((3,5-dicyano-4-ethyl-6-((S)-3-hydroxypyrrolidin-1-yl)pyridin-2-yl)thio)acetamide;
(R)-2-((3,5-dicyano-4-ethyl-6-((S)-3-hydroxpyrrolidin-1-yl)pyridin-2-yl)thio)-2-(4-fluoro phenyl)acetamide;
(S)-1-(6-(((R)-2-amino-1-(4-fluorophenyl)-2-oxoethyl) thio)-3,5-dicyano-4-ethylpyridin-2-yl)pyrrolidin-3-yl dihydrogen phosphate;
2-((3,5-dicyano-4-ethyl-6-((S)-3-hydroxypyrrolidin-1-yl) pyridin-2-yl) thio)-2-(4-fluorophenyl) acetamide;
2-((3,5-dicyano-4-ethyl-6-((S)-3-hydroxypyrrolidin-1-yl) pyridin-2-yl) thio)-2-(2,6-difluorophenyl) acetamide;
2-((3,5-dicyano-4-ethyl-6-((S)-3-hydroxypyrrolidin-1-yl) pyridin-2-yl) thio)-2-(2,3-difluorophenyl) acetamide;
2-((3,5-dicyano-4-ethyl-6-((S)-3-hydroxypyrrolidin-1-yl) pyridin-2-yl) thio)-2-(2,4-difluorophenyl) acetamide;
2-((3,5-dicyano-4-ethyl-6-(4-((S)-2-(hydroxymethyl)pyrrolidin-1-yl)piperidin-1-yl)pyridin-2-yl)thio)-2-phenylacetamide;
2-((3,5-dicyano-4-ethyl-6-(4-((2-hydroxyethyl)(methyl) amino)piperidin-1-yl)pyridin-2-yl)thio)-2-phenylacetamide;
2-((3,5-dicyano-4-ethyl-6-(4-((2-hydroxy-2-methylpropyl) (methyl)amino)piperidin-1-yl)pyridin-2-yl)thio)-2-phenylacetamide;
2-((3,5-dicyano-4-ethyl-6-(4-(pyrrolidin-1-ylmethyl)piperidin-1-yl)pyridin-2-yl)thio)-2-phenylacetamide;

2-((3,5-dicyano-4-ethyl-6-(4-((2-methoxy-2-methylpropyl)amino)piperidin-1-yl)pyridin-2-yl)thio)-2-phenylacetamide;

2-((3,5-dicyano-4-ethyl-6-(4-((2-hydroxy-2-methylpropyl)amino)piperidin-1-yl)pyridin-2-yl)thio)-2-phenylacetamide;

2-((3,5-dicyano-6-(4-(cyclobutylamino)piperidin-1-yl)-4-ethylpyridin-2-yl)thio)-2-phenylacetamide;

2-((3,5-dicyano-4-ethyl-6-(4-(((3-methyloxetan-3-yl)methyl)amino)piperidin-1-yl)pyridin-2-yl)thio)-2-phenylacetamide;

2-((3,5-dicyano-4-ethyl-6-(4-(4-methylpiperazin-1-yl)piperidin-1-yl)pyridin-2-yl)thio)-2-phenylacetamide;

2-((3,5-dicyano-4-ethyl-6-(4-((R)-2-methylpyrrolidin-1-yl)piperidin-1-yl)pyridin-2-yl)thio)-2-phenylacetamide;

2-((3,5-dicyano-6-(4-((2R,5S)-2,5-dimethylpyrrolidin-1-yl)piperidin-1-yl)-4-ethylpyridin-2-yl)thio)-2-phenylacetamide;

2-((3,5-dicyano-4-ethyl-6-(4-((S)-2-methylpyrrolidin-1-yl)piperidin-1-yl)pyridin-2-yl)thio)-2-phenylacetamide;

2-((3,5-dicyano-6-(4-(cyclobutyl(methyl)amino)piperidin-1-yl)-4-ethylpyridin-2-yl)thio)-2-phenylacetamide;

2-(6-(4-(benzylamino)piperidin-1-yl)-3,5-dicyano-4-ethylpyridin-2-ylthio)-2-phenylacetamide;

2-((3,5-dicyano-4-ethyl-6-(4-(((6-methoxypyridin-2-yl)methyl)amino)piperidin-1-yl)pyridin-2-yl)thio)-2-phenylacetamide;

2-((3,5-dicyano-4-ethyl-6-(4-((S)-3-fluoropyrrolidin-1-yl)piperidin-1-yl)pyridin-2-yl)thio)-2-phenylacetamide;

2-((3,5-dicyano-4-ethyl-6-(methyl(2-((R)-2-methylpyrrolidin-1-yl)ethyl)amino)pyridin-2-yl)thio)-2-phenylacetamide;

2-((3,5-dicyano-4-ethyl-6-(4-((R)-3-fluoropyrrolidin-1-yl)piperidin-1-yl)pyridin-2-yl)thio)-2-phenylacetamide;

2-((3,5-dicyano-6-(4-((2S,5S)-2,5-dimethylpyrrolidin-1-yl)piperidin-1-yl)-4-ethylpyridin-2-yl)thio)-2-phenylacetamide;

2-((3,5-dicyano-4-ethyl-6-(methyl(2-((S)-2-methylpyrrolidin-1-yl)ethyl)amino)pyridin-2-yl)thio)-2-phenylacetamide;

2-((3,5-dicyano-4-ethyl-6-(4-((R)-2-(hydroxymethyl)pyrrolidin-1-yl)piperidin-1-yl)pyridin-2-yl)thio)-2-phenylacetamide;

2-((3,5-dicyano-6-(4-(dimethylamino)piperidin-1-yl)-4-ethylpyridin-2-yl)thio)-2-(4-fluorophenyl)acetamide;

2-((3,5-dicyano-4-ethyl-6-(4-(((1-methylcyclobutyl)methyl)amino)piperidin-1-yl)pyridin-2-yl)thio)-2-phenylacetamide;

2-((3,5-dicyano-4-ethyl-6-(4-(((6-methoxypyridin-3-yl)methyl)amino)piperidin-1-yl)pyridin-2-yl)thio)-2-phenylacetamide;

2-(3,5-dicyano-4-ethyl-6-((2-(ethylamino)ethyl)(methyl)amino)pyridin-2-ylthio)-2-phenylacetamide;

2-((3,5-dicyano-4-ethyl-6-(4-((4-methylpiperazin-1-yl)methyl)piperidin-1-yl)pyridin-2-yl)thio)-2-phenylacetamide;

2-((3,5-dicyano-4-ethyl-6-(methyl(2-(methylamino)ethyl)amino)pyridin-2-yl)thio)-2-phenylacetamide;

2-((3,5-dicyano-6-(4-((2R,5R)-2,5-dimethylpyrrolidin-1-yl)piperidin-1-yl)-4-ethylpyridin-2-yl)thio)-2-phenylacetamide;

2-((3,5-dicyano-4-ethyl-6-(4-(((1-methylcyclopropyl)methyl)amino)piperidin-1-yl)pyridin-2-yl)thio)-2-phenylacetamide;

2-((3,5-dicyano-4-ethyl-6-(4-((4-fluorobenzyl)amino)piperidin-1-yl)pyridin-2-yl)thio)-2-phenylacetamide;

2-((3,5-dicyano-4-ethyl-6-((2-((S)-2-(hydroxymethyl)pyrrolidin-1-yl)ethyl)(methyl)amino)pyridin-2-yl)thio)-2-phenylacetamide;

2-(3,5-dicyano-6-((2-((2S,5R)-2,5-dimethylpyrrolidin-1-yl)ethyl)(methyl)amino)-4-ethylpyridin-2-ylthio)-2-phenylacetamide;

2-((6-((2-(azepan-1-yl)ethyl)(methyl)amino)-3,5-dicyano-4-ethylpyridin-2-yl)thio)-2-phenylacetamide;

2-((3,5-dicyano-4-ethyl-6-(methyl(2-(piperidin-1-yl)ethyl)amino)pyridin-2-yl)thio)-2-phenylacetamide;

2-((3,5-dicyano-4-ethyl-6-((2-((R)-2-(hydroxymethyl)pyrrolidin-1-yl)ethyl)(methyl)amino)pyridin-2-yl)thio)-2-phenylacetamide;

2-(3,5-dicyano-4-ethyl-6-((2-(ethyl(methyl)amino)ethyl)(methyl)amino)pyridin-2-ylthio)-2-phenylacetamide;

2-((3,5-dicyano-6-((2-((2R,5R)-2,5-dimethylpyrrolidin-1-yl)ethyl)(methyl)amino)-4-ethylpyridin-2-yl)thio)-2-phenylacetamide;

2-(3,5-dicyano-4-ethyl-6-((2-((S)-3-hydroxypyrrolidin-1-yl)ethyl)(methyl)amino)pyridin-2-ylthio)-2-phenylacetamide;

methyl 2-((1-(6-((2-amino-2-oxo-1-phenylethyl)thio)-3,5-dicyano-4-ethylpyridin-2-yl)piperidin-4-yl)amino)-2-methylpropanoate;

2-((3,5-dicyano-4-ethyl-6-(methyl(2-(neopentylamino)ethyl)amino)pyridin-2-yl)thio)-2-phenylacetamide;

2-(3,5-dicyano-4-ethyl-6-(methyl(2-(1-methylcyclopropylamino)ethyl)amino)pyridin-2-ylthio)-2-phenylacetamide;

2-((3,5-dicyano-6-((2-((2S,5S)-2,5-dimethylpyrrolidin-1-yl)ethyl)(methyl)amino)-4-ethylpyridin-2-yl)thio)-2-phenylacetamide;

2-((3,5-dicyano-4-ethyl-6-((2-((2-methoxyethyl)amino)ethyl)(methyl)amino)pyridin-2-yl)thio)-2-phenylacetamide;

2-((3,5-dicyano-4-ethyl-6-(4-((2-methoxy-2-methylpropyl)(methyl)amino)piperidin-1-yl)pyridin-2-yl)thio)-2-phenylacetamide;

2-((3,5-dicyano-6-((2-(dimethylamino)ethyl)(methyl)amino)-4-ethylpyridin-2-yl)thio)-2-phenylacetamide;

2-(3,5-dicyano-4-ethyl-6-((2-((R)-3-hydroxypyrrolidin-1-yl)ethyl)(methyl)amino)pyridin-2-ylthio)-2-phenylacetamide;

2-((3,5-dicyano-4-ethyl-6-((2-((2-fluoroethyl)amino)ethyl)(methyl)amino)pyridin-2-yl)thio)-2-phenylacetamide;

2-((3,5-dicyano-6-(4-(3,3-difluoropyrrolidin-1-yl)piperidin-1-yl)-4-ethylpyridin-2-yl)thio)-2-phenylacetamide;

2-((1-(6-((2-amino-2-oxo-1-phenylethyl)thio)-3,5-dicyano-4-ethylpyridin-2-yl)piperidin-4-yl)amino)acetic acid;

2-((6-((3-aminocyclobutyl)(methyl)amino)-3,5-dicyano-4-ethylpyridin-2-yl)thio)-2-phenylacetamide;

(R)-2-(3,5-dicyano-4-ethyl-6-(methyl((R)-tetrahydrofuran-3-yl)amino)pyridin-2-ylthio)-2-phenylacetamide;

(S)-2-(3,5-dicyano-4-ethyl-6-(methyl((R)-tetrahydrofuran-3-yl)amino)pyridin-2-ylthio)-2-phenylacetamide;

2-((3,5-dicyano-4-ethyl-6-(4-morpholinopiperidin-1-yl)pyridin-2-yl)thio)-2-phenylacetamide;

2-((3,5-dicyano-4-ethyl-6-(4-(2-hydroxyethyl)-3-oxopiperazin-1-yl)pyridin-2-yl)thio)-2-phenylacetamide;

2-((3,5-dicyano-4-ethyl-6-(4-(pyrrolidin-1-yl)piperidin-1-yl)pyridin-2-yl)thio)-2-(4-fluorophenyl)acetamide;

(R)-2-((6-((3S,4R)-4-amino-3-fluoropiperidin-1-yl)-3,5-dicyano-4-ethylpyridin-2-yl)thio)-2-phenylacetamide;

2-((3,5-dicyano-4-ethyl-6-(3-fluoro-4-(methylamino)piperidin-1-yl)pyridin-2-yl)thio)-2-phenylacetamide;

rel-2-((6-(trans)-4-amino-3-fluoropiperidin-1-yl)-3,5-dicyano-4-ethylpyridin-2-yl)thio)-2-phenylacetamide;

(R)-2-((6-((3R,4S)-4-amino-3-fluoropiperidin-1-yl)-3,5-dicyano-4-ethylpyridin-2-yl)thio)-2-phenylacetamide;
2-((3,5-dicyano-4-ethyl-6-(3-fluoro-4-((2-methoxyethyl)amino)piperidin-1-yl)pyridin-2-yl)thio)-2-phenylacetamide;
2-((3,5-dicyano-4-ethyl-6-(methyl(2-(pyrrolidin-1-yl)ethyl)amino)pyridin-2-yl)thio)-2-phenylacetamide;
2-((3,5-dicyano-6-(3-((dimethylamino)methyl)pyrrolidin-1-yl)-4-ethylpyridin-2-yl)thio)-2-phenylacetamide;
2-((3,5-dicyano-4-ethyl-6-(4-((2-hydroxy-2-methylpropyl)amino)piperidin-1-yl)pyridin-2-yl)thio)-2-(4-fluorophenyl)acetamide;
(R)-2-((6-((3S,4R)-4-amino-3-hydroxypiperidin-1-yl)-3,5-dicyano-4-ethylpyridin-2-yl)thio)-2-phenylacetamide;
2-((3,5-dicyano-6-((2-(diethylamino)ethyl)(methyl)amino)-4-ethylpyridin-2-yl)thio)-2-phenylacetamide;
2-((3,5-dicyano-6-((2-((R)-3-(dimethylamino)pyrrolidin-1-yl)ethyl)(methyl)amino)-4-ethylpyridin-2-yl)thio)-2-phenylacetamide;
2-((3,5-dicyano-6-((2-((S)-3-(dimethylamino)pyrrolidin-1-yl)ethyl)(methyl)amino)-4-ethylpyridin-2-yl)thio)-2-phenylacetamide;
(R)-2-((6-((3R,4R)-4-amino-3-fluoropiperidin-1-yl)-3,5-dicyano-4-ethylpyridin-2-yl)thio)-2-phenylacetamide;
(R)-2-((6-((3S,4S)-4-amino-3-fluoropiperidin-1-yl)-3,5-dicyano-4-ethylpyridin-2-yl)thio)-2-phenylacetamide;
2-((3,5-dicyano-4-ethyl-6-(3-(methylamino)pyrrolidin-1-yl)pyridin-2-yl)thio)-2-phenylacetamide;
2-((6-(4-aminopiperidin-1-yl)-3,5-dicyano-4-ethylpyridin-2-yl)thio)-2-(4-fluorophenyl)acetamide;
(R)-2-((6-((3R,4R)-4-amino-3-hydroxypiperidin-1-yl)-3,5-dicyano-4-ethylpyridin-2-yl)thio)-2-phenylacetamide;
2-((6-((R)-3-aminopyrrolidin-1-yl)-3,5-dicyano-4-ethylpyridin-2-yl)thio)-2-phenylacetamide;
2-((6-(3-(aminomethyl)pyrrolidin-1-yl)-3,5-dicyano-4-ethylpyridin-2-yl)thio)-2-phenylacetamide;
2-((3,5-dicyano-4-ethyl-6-(4-(methylamino)piperidin-1-yl)pyridin-2-yl)thio)-2-(4-fluorophenyl)acetamide;
2-((3,5-dicyano-6-(4-(cyclopropylamino)-3-fluoropiperidin-1-yl)-4-ethylpyridin-2-yl)thio)-2-phenylacetamide;
2-((4-((S)-3-aminopyrrolidin-1-yl)-3,5-dicyano-4-ethylpyridin-2-yl)thio)-2-phenylacetamide;
2-((6-((2-((R)-3-aminopyrrolidin-1-yl)ethyl)(methyl)amino)-3,5-dicyano-4-ethylpyridin-2-yl)thio)-2-phenylacetamide;
3,5-dicyano-6-((R)-3-(dimethylamino)pyrrolidin-1-yl)-4-ethylpyridin-2-yl)thio)-2-(4-fluorophenyl)acetamide;
(S)-2-((6-((3S,4R)-4-amino-3-fluoropiperidin-1-yl)-3,5-dicyano-4-ethylpyridin-2-yl)thio)-2-phenylacetamide;
2-((3,5-dicyano-4-ethyl-6-(4-(neopentylamino)piperidin-1-yl)pyridin-2-yl)thio)-2-(4-(trifluoromethyl)phenyl)acetamide;
tert-butyl ((3S,4R)-1-(6-(((R)-2-amino-2-oxo-1-phenylethyl)thio)-3,5-dicyano-4-ethylpyridin-2-yl)-3-hydroxypiperidin-4-yl)carbamate;
rel-tert-butyl (cis)-1-(6-((2-amino-2-oxo-1-phenylethyl)thio)-3,5-dicyano-4-ethylpyridin-2-yl)-3-fluoropiperidin-4-yl)carbamate;
2-((6-((2-((S)-3-aminopyrrolidin-1-yl)ethyl)(methyl)amino)-3,5-dicyano-4-ethylpyridin-2-yl)thio)-2-phenylacetamide;
2-((3,5-dicyano-6-((R)-3-(dimethylamino)pyrrolidin-1-yl)-4-ethylpyridin-2-yl)thio)-2-phenylacetamide;
tert-butyl ((3R,4S)-1-(6-(((R)-2-amino-2-oxo-1-phenylethyl)thio)-3,5-dicyano-4-ethylpyridin-2-yl)-3-hydroxypiperidin-4-yl)carbamate;
rel-tert-butyl (cis)-1-(6-((2-amino-2-oxo-1-phenylethyl)thio)-3,5-dicyano-4-ethylpyridin-2-yl)-3-fluoropiperidin-4-yl)carbamate;
2-((3,5-dicyano-6-((S)-3-(dimethylamino)pyrrolidin-1-yl)-4-ethylpyridin-2-yl)thio)-2-phenylacetamide;
(S)-2-((6-((3R,4S)-4-amino-3-fluoropiperidin-1-yl)-3,5-dicyano-4-ethylpyridin-2-yl)thio)-2-phenylacetamide;
2-((3,5-dicyano-4-ethyl-6-((S)-3-((2-hydroxy-2-methylpropyl)amino)pyrrolidin-1-yl)pyridin-2-yl)thio)-2-phenylacetamide;
tert-butyl ((3R,4R)-1-(6-(((R)-2-amino-2-oxo-1-phenylethyl)thio)-3,5-dicyano-4-ethylpyridin-2-yl)-3-hydroxypiperidin-4-yl)carbamate;
2-((3,5-dicyano-6-((S)-3-(dimethylamino)pyrrolidin-1-yl)-4-ethylpyridin-2-yl)thio)-2-(4-fluorophenyl)acetamide;
rel-2-((6-cis-4-amino-3-fluoropiperidin-1-yl)-3,5-dicyano-4-ethylpyridin-2-yl)thio)-2-phenylacetamide;
2-((3,5-dicyano-4-ethyl-6-(4-(methylamino)piperidin-1-yl)pyridin-2-yl)thio)-2-phenylacetamide;
2-((3,5-dicyano-6-(4-(dimethylamino)piperidin-1-yl)-4-ethylpyridin-2-yl)thio)-2-phenylacetamide;
2-((3,5-dicyano-4-ethyl-6-(4-(ethyl(methyl)amino)piperidin-1-yl)pyridin-2-yl)thio)-2-phenylacetamide;
2-((3,5-dicyano-4-ethyl-6-(4-(neopentylamino)piperidin-1-yl)pyridin-2-yl)thio)-2-phenylacetamide;
2-((3,5-dicyano-4-ethyl-6-(4-(methyl(neopentyl)amino)piperidin-1-yl)pyridin-2-yl)thio)-2-phenylacetamide;
2-((3,5-dicyano-6-(4-(cyclopropylamino)piperidin-1-yl)-4-ethylpyridin-2-yl)thio)-2-phenylacetamide;
2-((3,5-dicyano-4-ethyl-6-(4-((2-methoxyethyl)amino)piperidin-1-yl)pyridin-2-yl)thio)-2-phenylacetamide;
2-((3,5-dicyano-6-(4-((2,2-difluoroethyl)amino)piperidin-1-yl)-4-ethylpyridin-2-yl)thio)-2-phenylacetamide;
2-((3,5-dicyano-4-ethyl-6-((R)-2-((neopentylamino)methyl)morpholino)pyridin-2-yl)thio)-2-phenylacetamide;
2-((3,5-dicyano-6-(2-((dimethylamino)methyl)morpholino)-4-ethylpyridin-2-yl)thio)-2-phenylacetamide;
2-((3,5-dicyano-6-(2-((diethylamino)methyl)morpholino)-4-ethylpyridin-2-yl)thio)-2-phenylacetamide;
2-((3,5-dicyano-4-ethyl-6-(2-(pyrrolidin-1-ylmethyl)morpholino)pyridin-2-yl)thio)-2-phenylacetamide;
(R)-2-((6-((R)-2-(aminomethyl)morpholino)-3,5-dicyano-4-ethylpyridin-2-yl)thio)-2-phenylacetamide;
2-((6-(2-(aminomethyl)morpholino)-3,5-dicyano-4-ethylpyridin-2-yl)thio)-2-phenylacetamide;
2-((3,5-dicyano-4-ethyl-6-(2-((methylamino)methyl)morpholino)pyridin-2-yl)thio)-2-phenylacetamide;
2-((6-((R)-2-(aminomethyl)morpholino)-3,5-dicyano-4-ethylpyridin-2-yl)thio)-2-phenylacetamide;
2-((3,5-dicyano-6-(3-((dimethylamino)methyl)piperidin-1-yl)-4-ethylpyridin-2-yl)thio)-2-phenylacetamide;
2-((3,5-dicyano-4-ethyl-6-(3-((methylamino)methyl)piperidin-1-yl)pyridin-2-yl)thio)-2-phenylacetamide;
2-((3,5-dicyano-4-ethyl-6-((S)-2-((neopentylamino)methyl)morpholino)pyridin-2-yl)thio)-2-phenylacetamide;
2-((3,5-dicyano-4-ethyl-6-((S)-3-((neopentylamino)methyl)piperidin-1-yl)pyridin-2-yl)thio)-2-phenylacetamide;
2-amino-N-(((2S)-4-(6-((2-amino-2-oxo-1-phenylethyl)thio)-3,5-dicyano-4-ethylpyridin-2-yl)morpholin-2-yl)methyl)-2-methylpropanamide;
2-((4-((S)-3-(aminomethyl)piperidin-1-yl)-3,5-dicyano-4-ethylpyridin-2-yl)thio)-2-phenylacetamide;
2-((3,5-dicyano-6-((R)-2-((diethylamino)methyl)morpholino)-4-ethylpyridin-2-yl)thio)-2-phenylacetamide;
2-amino-N-(((2R)-4-(6-((2-amino-2-oxo-1-phenylethyl)thio)-3,5-dicyano-4-ethylpyridin-2-yl)morpholin-2-yl)methyl)-2-methylpropanamide;

2-((6-(4-aminopiperidin-1-yl)-3,5-dicyano-4-ethylpyridin-2-yl)thio)-2-(3-fluoropyridin-2-yl)acetamide;

2-((6-((S)-2-(aminomethyl) morpholino)-3,5-dicyano-4-ethylpyridin-2-yl)thio)-2-phenylacetamide;

2-amino-N-(((3S)-1-(6-((2-amino-2-oxo-1-phenylethyl)thio)-3,5-dicyano-4-ethylpyridin-2-yl)piperidin-3-yl)methyl)-2-methylpropanamide;

2-amino-N-(((3S)-1-(6-((2-amino-2-oxo-1-phenylethyl)thio)-3,5-dicyano-4-ethylpyridin-2-yl)piperidin-3-yl)methyl)acetamide;

2-amino-N-(((2R)-4-(6-((2-amino-2-oxo-1-phenylethyl)thio)-3,5-dicyano-4-ethylpyridin-2-yl)morpholin-2-yl)methyl)acetamide;

2-((6-((R)-3-(aminomethyl)piperidin-1-yl)-3,5-dicyano-4-ethylpyridin-2-yl)thio)-2-(4-fluorophenyl)acetamide;

2-((3,5-dicyano-4-ethyl-6-((R)-3-((neopentylamino)methyl)piperidin-1-yl)pyridin-2-yl)thio)-2-(4-fluorophenyl)acetamide;

2-amino-N-(((2S)-4-(6-((2-amino-2-oxo-1-phenylethyl)thio)-3,5-dicyano-4-ethylpyridin-2-yl)morpholin-2-yl)methyl)acetamide;

N-(((R)-4-(6-(((R)-2-amino-2-oxo-1-phenylethyl)thio)-3,5-dicyano-4-ethylpyridin-2-yl)morpholin-2-yl)methyl)-2-hydroxyacetamide;

(S)-2-((6-(4-aminopiperidin-1-yl)-3,5-dicyano-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(2-hydroxyethyl)-N-methylacetamide;

2-((3,5-dicyano-4-ethyl-6-((S)-3-(methylamino)piperidin-1-yl)pyridin-2-yl)thio)-2-phenylacetamide;

2-((6-(4-amino-4-methylpiperidin-1-yl)-3,5-dicyano-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)-N-methylacetamide;

2-amino-N-(1-(6-((2-amino-2-oxo-1-phenylethyl)thio)-3,5-dicyano-4-cyclopropylpyridin-2-yl)azetidin-3-yl)acetamide;

(2S)-2-amino-N-(1-(6-((2-amino-2-oxo-1-phenylethyl)thio)-3,5-dicyano-4-cyclopropylpyridin-2-yl)azetidin-3-yl)-3-hydroxypropanamide;

2-((6-((S)-3-aminopiperidin-1-yl)-3,5-dicyano-4-ethylpyridin-2-yl)thio)-2-phenylacetamide;

2-((3,5-dicyano-4-ethyl-6-((2-((R)-3-hydroxypyrrolidin-1-yl)-2-oxoethyl)(methyl)amino)pyridin-2-yl)thio)-2-phenylacetamide;

(2R)-2-amino-N-(1-(6-((2-amino-2-oxo-1-phenylethyl)thio)-3,5-dicyano-4-cyclopropylpyridin-2-yl)azetidin-3-yl)-3-hydroxypropanamide;

2-((6-((2-amino-2-oxo-1-phenylethyl)thio)-3,5-dicyano-4-ethylpyridin-2-yl)(methyl)amino)-N-(3-hydroxy-2,2-dimethylpropyl)-N-methylacetamide;

2-((3,5-dicyano-4-ethyl-6-((2-((S)-3-hydroxpyrrolidin-1-yl)-2-oxoethyl)(methyl)amino)pyridin-2-yl)thio)-2-phenylacetamide;

2-((6-(4-amino-4-methylpiperidin-1-yl)-3,5-dicyano-4-ethylpyridin-2-yl)thio)-2-phenylacetamide;

2-((6-(4-(aminomethyl)-4-fluoropiperidin-1-yl)-3,5-dicyano-4-ethylpyridin-2-yl)thio)-2-phenylacetamide hydrochloride;

2-((6-((2-amino-2-oxo-1-phenylethyl)thio)-3,5-dicyano-4-cyclopropylpyridin-2-yl)(methyl)amino)-N-(2-aminoethyl)acetamide hydrochloride;

2-((3,5-dicyano-4-ethyl-6-(methyl(2-oxo-2-(pyrrolidin-1-yl)ethyl)amino)pyridin-2-yl)thio)-2-phenylacetamide;

2-((3,5-dicyano-4-ethyl-6-((2-(4-hydroxypiperidin-1-yl)-2-oxoethyl)(methyl)amino)pyridin-2-yl)thio)-2-phenylacetamide;

2-((3,5-dicyano-4-ethyl-6-(methyl(2-oxo-2-(piperazin-1-yl)ethyl)amino)pyridin-2-yl)thio)-2-phenylacetamide;

2-((3,5-dicyano-4-ethyl-6-(methyl(2-morpholino-2-oxoethyl)amino)pyridin-2-yl)thio)-2-phenylacetamide;

(R)-2-((6-((S)-3-(aminomethyl)-3-hydroxypyrrolidin-1-yl)-3,5-dicyano-4-ethylpyridin-2-yl)thio)-2-phenylacetamide;

2-((3,5-dicyano-4-ethyl-6-((S)-3-(guanidinooxy)pyrrolidin-1-yl)pyridin-2-yl)thio)-2-phenylacetamide;

2-amino-N-(2-((6-((2-amino-2-oxo-1-phenylethyl)thio)-3,5-dicyano-4-ethylpyridin-2-yl)(methyl)amino)ethyl)-2-methylpropanamide;

2-((6-((2-(2-aminoethoxy)ethyl)(methyl)amino)-3,5-dicyano-4-ethylpyridin-2-yl)thio)-2-phenylacetamide;

4-amino-N-(1-(6-((2-amino-2-oxo-1-phenylethyl)thio)-3,5-dicyano-4-ethylpyridin-2-yl)piperidin-4-yl)butanamide;

2-((6-((2-amino-2-oxo-1-phenylethyl)thio)-3,5-dicyano-4-ethylpyridin-2-yl)(methyl)amino)-N-(2-aminoethyl)acetamide;

2-((6-((2-(azetidin-1-yl)-2-oxoethyl)(methyl)amino)-3,5-dicyano-4-ethylpyridin-2-yl)thio)-2-phenylacetamide;

2-((6-((R)-3-(aminomethyl)-3-fluoropyrrolidin-1-yl)-3,5-dicyano-4-ethylpyridin-2-yl)thio)-2-phenylacetamide;

2-((3,5-dicyano-4-ethyl-6-((2-(3-hydroxyazetidin-1-yl)-2-oxoethyl)(methyl)amino)pyridin-2-yl)thio)-2-phenylacetamide;

2-((3,5-dicyano-4-ethyl-6-(4-(guanidinooxy)piperidin-1-yl)pyridin-2-yl)thio)-2-phenylacetamide;

2-((6-(3-aminoazetidin-1-yl)-3,5-dicyano-4-ethylpyridin-2-yl)thio)-2-phenylacetamide; (single stereoisomer)

2-((3,5-dicyano-4-ethyl-6-((R)-3-(methylamino)piperidin-1-yl)pyridin-2-yl)thio)-2-phenylacetamide;

2-((3,5-dicyano-4-ethyl-6-((2-((3R,4S)-3-hydroxy-4-(hydroxymethyl)pyrrolidin-1-yl)-2-oxoethyl)(methyl)amino)pyridin-2-yl)thio)-2-phenylacetamide;

(R)-2-((4-((S)-3-(aminomethyl)-3-fluoropyrrolidin-1-yl)-3,5-dicyano-4-ethylpyridin-2-yl)thio)-2-phenylacetamide;

2-((6-((2-amino-2-oxo-1-phenylethyl)thio)-3,5-dicyano-4-cyclopropylpyridin-2-yl)(methyl)amino)-N-(1,3-dihydroxypropan-2-yl)acetamide;

2-((3,5-dicyano-4-ethyl-6-((S)-3-(oxetan-3-ylamino)piperidin-1-yl)pyridin-2-yl)thio)-2-phenylacetamide;

2-((6-((2-amino-2-oxo-1-phenylethyl)thio)-3,5-dicyano-4-cyclopropylpyridin-2-yl)(methyl)amino)-N,N-bis(2-hydroxyethyl)acetamide;

2-amino-N-(1-(6-((2-amino-2-oxo-1-phenylethyl)thio)-3,5-dicyano-4-cyclopropylpyridin-2-yl)piperidin-4-yl)acetamide;

2-((3,5-dicyano-4-ethyl-6-(4-((2-hydroxyethyl)amino)-4-methylpiperidin-1-yl)pyridin-2-yl)thio)-2-phenylacetamide;

2-((3,5-dicyano-4-ethyl-6-((2-(guanidinooxy)ethyl)(methyl)amino)pyridin-2-yl)thio)-2-phenylacetamide;

2-((6-(4-((2-aminoethyl)amino)piperidin-1-yl)-3,5-dicyano-4-ethylpyridin-2-yl)thio)-2-phenylacetamide;

2-((3,5-dicyano-4-ethyl-6-((2-((S)-2-(hydroxymethyl)morpholino)-2-oxoethyl)(methyl)amino)pyridin-2-yl)thio)-2-phenylacetamide;

2-((3,5-dicyano-6-((2-((cis)-3,4-dihydroxypyrrolidin-1-yl)-2-oxoethyl)(methyl)amino)-4-ethylpyridin-2-yl)thio)-2-phenylacetamide;

2-((3,5-dicyano-4-ethyl-6-((2-((S)-3-(hydroxymethyl)pyrrolidin-1-yl)-2-oxoethyl)(methyl)amino)pyridin-2-yl)thio)-2-phenylacetamide;

2-((3,5-dicyano-4-ethyl-6-((2-((3S,4S)-3-hydroxy-4-(hydroxymethyl)pyrrolidin-1-yl)-2-oxoethyl)(methyl)amino)pyridin-2-yl)thio)-2-phenylacetamide;

2-((3,5-dicyano-4-ethyl-6-((S)-3-(neopentylamino)piperidin-1-yl)pyridin-2-yl)thio)-2-phenylacetamide;

2-((3,5-dicyano-4-ethyl-6-((2-((R)-3-(hydroxymethyl)pyrrolidin-1-yl)-2-oxoethyl)(methyl)amino)pyridin-2-yl)thio)-2-phenylacetamide;

2-((3,5-dicyano-6-((2-((3R,4R)-3,4-dihydroxypyrrolidin-1-yl)-2-oxoethyl)(methyl)amino)-4-ethylpyridin-2-yl)thio)-2-phenylacetamide;

(R)-2-((3,5-dicyano-4-ethyl-6-((S)-3-hydroxy-3-(hydroxymethyl)pyrrolidin-1-yl)pyridin-2-yl)thio)-2-phenylacetamide; p (2S)-2-amino-N-(1-(6-((2-amino-2-oxo-1-phenylethyl)thio)-3,5-dicyano-4-cyclopropylpyridin-2-yl)piperidin-4-yl)propanamide;

2-((6-(4-(2-aminoethoxy)piperidin-1-yl)-3,5-dicyano-4-cyclopropylpyridin-2-yl)thio)-2-phenylacetamide;

2-((3,5-dicyano-4-cyclopropyl-6-(4-((2-hydroxyethyl)amino)piperidin-1-yl)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(1,3-dihydroxypropan-2-yl)acetamide;

2-((3,5-dicyano-6-((2-((3R,5S)-3,5-dihydroxypiperidin-1-yl)-2-oxoethyl)(methyl)amino)-4-ethylpyridin-2-yl)thio)-2-phenylacetamide;

2-((3,5-dicyano-6-((2-((3S,4S)-3,4-dihydroxypyrrolidin-1-yl)-2-oxoethyl)(methyl)amino)-4-ethylpyridin-2-yl)thio)-2-phenylacetamide;

2-((3,5-dicyano-4-ethyl-6-(4-((2-hydroxyethyl)amino)-4-(hydroxymethyl)piperidin-1-yl)pyridin-2-yl)thio)-2-phenylacetamide;

2-((3,5-dicyano-4-ethyl-6-((2-((R)-2-(hydroxymethyl)morpholino)-2-oxoethyl)(methyl)amino)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-methoxyacetamide;

2-((3,5-dicyano-4-ethyl-6-((2-((3R,4R)-3-hydroxy-4-(hydroxymethyl)pyrrolidin-1-yl)-2-oxoethyl)(methyl)amino)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(3-hydroxypropyl)-N-methylacetamide;

2-((6-((2-amino-2-oxo-1-phenylethyl)thio)-3,5-dicyano-4-ethylpyridin-2-yl)(methyl)amino)-N-((R)-2,3-dihydroxypropyl)acetamide;

2-((6-(4-((2-amino-2-oxoethyl)amino)piperidin-1-yl)-3,5-dicyano-4-cyclopropylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N,N-bis(2-hydroxyethyl)acetamide;

2-((6-((2-amino-2-oxo-1-phenylethyl)thio)-3,5-dicyano-4-ethylpyridin-2-yl)(methyl)amino)-N-(2-hydroxyethyl)acetamide;

2-((6-((3-aminopropyl)(methyl)amino)-3,5-dicyano-4-ethylpyridin-2-yl)thio)-2-phenylacetamide;

2-((6-(3-(aminomethyl)azetidin-1-yl)-3,5-dicyano-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)acetamide;

(R)-2-((3,5-dicyano-4-ethyl-6-((S)-3-hydroxypyrrolidin-1-yl)pyridin-2-yl)thio)-2-(2,4-difluorophenyl)acetamide;

2-((6-((2-amino-2-oxo-1-phenylethyl)thio)-3,5-dicyano-4-ethylpyridin-2-yl)(methyl)amino)-N-(3-(hydroxymethyl)oxetan-3-yl)acetamide;

2-((3,5-dicyano-4-ethyl-6-(3-(guanidinooxy)azetidin-1-yl)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(3-hydroxypropyl)acetamide;

2-((3,5-dicyano-6-(4-(2,3-dihydroxypropyl)-1,4-diazepan-1-yl)-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-hydroxyacetamide;

3-amino-N-(1-(6-((2-amino-2-oxo-1-phenylethyl)thio)-3,5-dicyano-4-cyclopropylpyridin-2-yl)azetidin-3-yl)oxetane-3-carboxamide;

2-((3,5-dicyano-4-ethyl-6-((S)-3-hydroxypyrrolidin-1-yl)pyridin-2-yl)thio)-2-(2-fluorophenyl)acetamide;

2-((3,5-dicyano-6-((S)-3-(cyclopropylamino)piperidin-1-yl)-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(3-hydroxy-2,2-dimethylpropyl)acetamide;

N-(2-(4H-1,2,4-triazol-4-yl)ethyl)-2-((6-((2-amino-2-oxo-1-phenylethyl)thio)-3,5-dicyano-4-ethylpyridin-2-yl)(methyl)amino)acetamide;

N1-(2-((6-((2-amino-2-oxo-1-phenylethyl)thio)-3,5-dicyano-4-ethylpyridin-2-yl)(methyl)amino)ethyl)oxalamide;

2-((6-(3-(aminomethyl)-3-fluoroazetidin-1-yl)-3,5-dicyano-4-ethylpyridin-2-yl)thio)-2-phenylacetamide;

(R)-2-((3,5-dicyano-4-ethyl-6-((R)-3-hydroxy-3-(hydroxymethyl)pyrrolidin-1-yl)pyridin-2-yl)thio)-2-phenylacetamide;

2-((3,5-dicyano-6-((S)-3-((2,2-difluoroethyl)amino)piperidin-1-yl)-4-ethylpyridin-2-yl)thio)-2-phenylacetamide;

2-((6-((R)-3-aminopiperidin-1-yl)-3,5-dicyano-4-ethylpyridin-2-yl)thio)-2-phenylacetamide;

2-((6-(4-aminopiperidin-1-yl)-3,5-dicyano-4-methoxypyridin-2-yl)thio)-2-phenylacetamide;

2-((3,5-dicyano-4-ethyl-6-((S)-4-hydroxyisoxazolidin-2-yl)pyridin-2-yl)thio)-2-phenylacetamide;

(R)-2-((3,5-dicyano-4-ethyl-6-((3-hydroxpropyl)(methyl)amino)pyridin-2-yl)thio)-2-phenylacetamide;

2-((3,5-dicyano-6-((S)-3-hydroxpyrrolidin-1-yl)-4-methoxypyridin-2-yl)thio)-2-phenylacetamide;

2-((3,5-dicyano-4-ethyl-6-(4-(3-methoxyazetidin-1-yl)piperidin-1-yl)pyridin-2-yl)thio)-2-phenylacetamide; and 2-((3,5-dicyano-4-ethyl-6-(4-(3-methoxyazetidin-1-yl)piperidin-1-yl)pyridin-2-yl)thio)-2-(4-fluorophenyl)acetamide;

or a pharmaceutically acceptable salt or prodrug thereof.

Suitably, presently invented novel compounds of Formula (IVbbr) are selected from:

2-{[3,5-dicyano-6-(dimethylamino)-4-ethylpyridin-2-yl]sulfanyl}-2-phenylacetamide;

2-((6-((2-Amino-2-oxoethyl)(methyl)amino)-3,5-dicyano-4-ethylpyridin-2-yl)thio)-2-phenylacetamide;

(R)-2-((3,5-Dicyano-4-ethyl-6-((S)-3-hydroxypyrrolidin-1-yl)pyridin-2-yl)thio)-2-phenylacetamide;

2-((6-(4-Aminopiperidin-1-yl)-3,5-dicyano-4-ethylpyridin-2-yl)thio)-2-phenylacetamide;

2-((6-(4-aminopiperidin-1-yl)-3,5-dicyano-4-ethylpyridin-2-yl)thio)-2-(4-fluorophenyl)acetamide;

2-((3,5-dicyano-6-(4-(cyclobutyl(methyl)amino)piperidin-1-yl)-4-ethylpyridin-2-yl)thio)-2-phenylacetamide;

2-((3,5-dicyano-4-ethyl-6-(3-fluoro-4-A(neopentylamino)piperidin-1-yl)pyridin-2-yl)thio)-2-phenylacetamide;

(R)-2-((3,5-dicyano-4-ethyl-6-((2-hydroxyethyl)(methyl) amino)pyridin-2-yl)thio)-2-phenylacetamide;
2-((3,5-Dicyano-6-(4-(cyclobutyl(methyl)amino)piperidin-1-yl)-4-ethylpyridin-2-yl)thio)-2-(4-fluorophenyl)acetamide; and
2-((3,5-dicyano-4-ethyl-6-(methyl(1-methylpyrrolidin-3-yl) amino)pyridin-2-yl)thio)-2-phenylacetamide;

or a pharmaceutically acceptable salt or prodrug thereof.

Suitably, presently invented novel compounds of Formula (IVbbr) are selected from:
(R)-2-((3,5-dicyano-4-ethyl-6-((2-hydroxyethyl)(methyl) amino)pyridin-2-yl)thio)-2-phenylacetamide;
2-((3,5-Dicyano-6-(4-(cyclobutyl(methyl)amino)piperidin-1-yl)-4-ethylpyridin-2-yl)thio)-2-(4-fluorophenyl)acetamide; and
2-((3,5-dicyano-4-ethyl-6-(methyl(1-methylpyrrolidin-3-yl) amino)pyridin-2-yl)thio)-2-phenylacetamide;

or a pharmaceutically acceptable salt or prodrug thereof.

Suitably, presently invented novel compounds of Formula (Vbbr) are selected from:
2-((3,5-dicyano-4-cyclopropyl-6-(1,4-diazepan-1-yl)pyridin-2-yl)thio)-2-phenylacetamide;
2-{[3,5-dicyano-4-cyclopropyl-6-(4-ethyl-1,4-diazepan-1-yl)pyridin-2-yl]sulfanyl}-2-phenylacetamide;
2-((3,5-dicyano-4-ethyl-6-(4-propyl-1,4-diazepan-1-yl) pyridin-2-yl)thio)-2-phenylacetamide;
2-{[3,5-dicyano-4-ethyl-6-(4-ethyl-1,4-diazepan-1-yl)pyridin-2-yl]sulfanyl}-2-phenylacetamide;
2-{[3,5-dicyano-4-ethyl-6-(5-oxo-1,4-diazepan-1-yl)pyridin-2-yl]sulfanyl}-2-phenylacetamide;
2-((3,5-dicyano-4-cyclopropyl-6-morpholinopyridin-2-yl) thio)-2-(pyridin-4-yl)acetamide;
2-{[3,5-dicyano-4-ethyl-6-(4-methyl-3-oxopiperazin-1-yl) pyridin-2-yl]sulfanyl}-2-(pyridin-4-yl)acetamide;
2-[(3,5-dicyano-4-ethyl-6-{methyl[2-(morpholin-4-yl) ethyl]amino}pyridin-2-yl)sulfanyl]-2-phenylacetamide;
2-{[3,5-dicyano-4-ethyl-6-(4-propylpiperazin-1-yl)pyridin-2-yl]sulfanyl}-2-phenylacetamide;
2-({3,5-dicyano-4-ethyl-6-[4-(piperidin-4-yl)piperazin-1-yl]pyridin-2-yl}sulfanyl)-2-phenylacetamide;
2-({3,5-dicyano-4-cyclopropyl-6-[3-(hydroxymethyl)piperazin-1-yl]pyridin-2-yl}sulfanyl)-2-phenylacetamide;
2-{[3,5-dicyano-4-cyclopropyl-6-(3-oxopiperazin-1-yl) pyridin-2-yl]sulfanyl}-2-phenylacetamide;
2-({3,5-dicyano-4-cyclopropyl-6-[4-(morpholin-4-yl)piperidin-1-yl]pyridin-2-yl}sulfanyl)-2-phenylacetamide;
2-((3,5-dicyano-4-ethyl-6-(2,8-diazaspiro[4.5]decan-8-yl) pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((3,5-Dicyano-4-cyclopropyl-6-(3-methylpiperazin-1-yl) pyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
2-((3,5-Dicyano-4-cyclopropyl-6-(2,6-dimethylmorpholino)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((6-(4-(Aminomethyl)-4-hydroxypiperidin-1-yl)-3,5-dicyano-4-cyclopropylpyridin-2-yl)thio)-2-phenylacetamide;
2-((3,5-dicyano-4-cyclopropyl-6-(3-(methylamino)piperidin-1-yl)pyridin-2-yl)thio)-2-phenylacetamide;
2-((6-(3-aminopiperidin-1-yl)-3,5-dicyano-4-cyclopropylpyridin-2-yl)thio)-2-phenylacetamide;
2-((6-(4-aminopiperidin-1-yl)-3,5-dicyano-4-cyclopropylpyridin-2-yl)thio)-2-phenylacetamide;
2-((3,5-dicyano-4-cyclopropyl-6-(4-(dimethylamino)piperidin-1-yl)pyridin-2-yl)thio)-2-phenylacetamide;
2-((3,5-dicyano-4-cyclopropyl-6-(piperazin-1-yl)pyridin-2-yl)thio)-2-(pyridin-4-yl)acetamide;
2-((3,5-dicyano-4-cyclopropyl-6-(1,4-diazepan-1-yl)pyridin-2-yl)thio)-2-(pyridin-4-yl)acetamide;
2-((3,5-dicyano-4-cyclopropyl-6-((R)-3-hydroxypiperidin-1-yl)pyridin-2-yl)thio)-2-phenylacetamide;
2-(3,5-dicyano-4-cyclopropyl-6-((S)-3-hydroxypiperidin-1-yl)pyridin-2-ylthio)-2-phenylacetamide;
2-((3,5-dicyano-4-cyclopropyl-6-((S)-3-hydroxypyrrolidin-1-yl)pyridin-2-yl)thio)-2-(pyridin-4-yl)acetamide;
2-((3,5-dicyano-4-ethyl-6-(4-ethylpiperazin-1-yl)pyridin-2-yl)thio)-2-phenylacetamide;
2-((3,5-Dicyano-4-ethyl-6-(1-oxa-6-azaspiro[3.4]octan-6-yl)pyridin-2-yl)thio)-2-phenylacetamide;
2-((6-(4-(3-aminopropyl)piperazin-1-yl)-3,5-dicyano-4-ethylpyridin-2-yl)thio)-2-phenylacetamide;
2-((3,5-Dicyano-4-ethyl-6-(1,7-diazaspiro[3.5]nonan-1-yl) pyridin-2-yl)thio)-2-phenylacetamide;
2-((3,5-Dicyano-4-cyclopropyl-6-(4-(pyrrolidin-1-ylmethyl)piperidin-1-yl)pyridin-2-yl)thio)-2-phenylacetamide;
2-((3,5-Dicyano-4-cyclopropyl-6-(4-(4-methylpiperazin-1-yl)piperidin-1-yl)pyridin-2-yl)thio)-2-phenylacetamide;
(R)-2-((3,5-dicyano-6-(1,4-diazepan-1-yl)-4-ethylpyridin-2-yl)amino)-2-phenylacetamide;
2-((3,5-Dicyano-4-cyclopropyl-6-(4-(pyrrolidin-1-yl)piperidin-1-yl)pyridin-2-yl)thio)-2-phenylacetamide;
2-((3,5-Dicyano-4-ethyl-6-(2,7-diazaspiro[3.5]nonan-7-yl) pyridin-2-yl)thio)-2-phenylacetamide;
2-((3,5-Dicyano-4-ethyl-6-(2,6-diazaspiro[3.4]octan-6-yl) pyridin-2-yl)thio)-2-phenylacetamide;
2-((3,5-dicyano-4-cyclopropyl-6-(1,4-diazepan-1-yl)pyridin-2-yl)thio)propanamide;
2-((3,5-Dicyano-4-ethyl-6-(4-(2-oxoimidazolidin-1-yl)piperidin-1-yl)pyridin-2-yl)thio)-2-phenylacetamide;
2-((3,5-Dicyano-4-ethyl-6-(4-hydroxypiperidin-1-yl)pyridin-2-yl)thio)-2-phenylacetamide;
2-((3,5-Dicyano-4-ethyl-6-((S)-3-hydroxypyrrolidin-1-yl) pyridin-2-yl)thio)-2-phenylacetamide;
2-((3,5-Dicyano-4-ethyl-6-(3-oxopiperazin-1-yl)pyridin-2-yl)thio)-2-phenylacetamide;
2-((3,5-Dicyano-4-ethyl-6-((2-methoxyethyl)(methyl) amino)pyridin-2-yl)thio)-2-phenylacetamide;
2-((3,5-Dicyano-4-ethyl-6-(3-methoxyazetidin-1-yl)pyridin-2-yl)thio)-2-phenylacetamide;
2-((3,5-Dicyano-4-ethyl-6-(piperazin-1-yl)pyridin-2-yl) thio)-2-phenylacetamide;
2-((3,5-Dicyano-4-ethyl-6-(4-methyl-1,4-diazepan-1-yl) pyridin-2-yl)thio)-2-phenylacetamide;
2-((3,5-Dicyano-4-ethyl-6-morpholinopyridin-2-yl)thio)-2-phenylacetamide;
2-[[6-(azetidin-1-yl)-3,5-dicyano-4-ethyl-2-pyridyl]sulfanyl]-2-phenyl-acetamide;
2-((3,5-dicyano-4-ethyl-6-(4-oxopiperidin-1-yl)pyridin-2-yl)thio)-2-phenylacetamide;
2-((3,5-Dicyano-4-ethyl-6-(1'-(2-hydroxyethyl)-[4,4'-bipiperidin]-1-yl)pyridin-2-yl)thio)-2-phenylacetamide;
2-((3,5-Dicyano-6-((3S,5R)-3,5-dimethylpiperazin-1-yl)-4-ethylpyridin-2-yl)thio)-2-phenylacetamide;
2-((6-(8-azabicyclo[3.2.1]octan-3-yl(methyl)amino)-3,5-dicyano-4-ethylpyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
(R)-2-[(3,5-Dicyano-4-ethyl-6-morpholino-2-pyridyl)sulfanyl]-2-phenyl-acetamide;

N-(4-((3,5-Dicyano-4-ethyl-6-(4-(pyrrolidin-1-yl)piperidin-1-yl)pyridin-2-ylthio)methyl)benzyl)acetamide trifluoroacetate;
2-{[3,5-dicyano-4-ethyl-6-(5-methyl-1,4-diazepan-1-yl)pyridin-2-yl]sulfanyl}-2-phenylacetamide;
2-({3,5-Dicyano-4-ethyl-6-[4-(2-methoxyethyl)-1,4-diazepan-1-yl]pyridin-2-yl}sulfanyl)-2-phenylacetamide;
2-((3,5-dicyano-4-ethyl-6-(4-(2-hydroxypropyl)-1,4-diazepan-1-yl)pyridin-2-yl)thio)-2-phenylacetamide;
Methyl 2-[4-(6-{[carbamoyl(phenyl)methyl]sulfanyl}-3,5-dicyano-4-ethylpyridin-2-yl)-1,4-diazepan-1-yl]acetate;
2-{[3,5-Dicyano-4-cyclopropyl-6-(4-methyl-5-oxo-1,4-diazepan-1-yl)pyridin-2-yl]sulfanyl}-2-phenylacetamide;
2-{[3,5-Dicyano-4-cyclopropyl-6-(5-oxo-1,4-diazepan-1-yl)pyridin-2-yl]sulfanyl}-2-phenylacetamide;
2-{[3,5-Dicyano-4-ethyl-6-(4-methyl-5-oxo-1,4-diazepan-1-yl)pyridin-2-yl]sulfanyl}-2-phenylacetamide;
2-{[3,5-Dicyano-6-(1,4-diazepan-1-yl)-4-ethylpyridin-2-yl]sulfanyl}-2-phenylacetamide;
2-({3,5-Dicyano-6-[4-(2-hydroxyethyl)-1,4-diazepan-1-yl]-4-(2,2,2-trifluoroethyl)pyridin-2-yl}sulfanyl)-2-phenylacetamide;
(2R)-2-({3,5-Dicyano-4-ethyl-6-[4-(2-hydroxyethyl)-1,4-diazepan-1-yl]pyridin-2-yl}amino)-2-phenylacetamide;
2-({6-[(3S)-3-Aminopyrrolidin-1-yl]-3,5-dicyano-4-cyclopropylpyridin-2-yl}sulfanyl)-2-phenylacetamide;
2-((3,5-Dicyano-4-ethyl-6-(2,9-diazaspiro[5.5]undecan-9-yl)pyridin-2-yl)thio)-2-phenylacetamide;
2-((3,5-Dicyano-4-ethyl-6-(hexahydro-1H-pyrrolo[1,2-a][1,4]diazepin-2(3H)-yl)pyridin-2-yl)thio)-2-phenylacetamide;
2-((3,5-Dicyano-4-ethyl-6-(2-methyl-2,9-diazaspiro[5.5]undecan-9-yl)pyridin-2-yl)thio)-2-phenylacetamide;
2-((3,5-Dicyano-6-(2-(cyclopropylmethyl)-2,9-diazaspiro[5.5]undecan-9-yl)-4-ethylpyridin-2-yl)thio)-2-phenylacetamide hydrochloride;
2-((3,5-Dicyano-6-(4-(3-(dimethylamino)propyl)piperazin-1-yl)-4-ethylpyridin-2-yl)thio)-2-phenylacetamide;
2-((3,5-Dicyano-4-ethyl-6-(4-(pyrrolidin-3-yl)piperidin-1-yl)pyridin-2-yl)thio)-2-phenylacetamide; 2,2,2-trifluoroacetic acid;
2-((6-([4,4'-Bipiperidin]-1-yl)-3,5-dicyano-4-ethylpyridin-2-yl)thio)-2-phenylacetamide;
2-((6-(4-(2-Aminoethyl)piperazin-1-yl)-3,5-dicyano-4-ethylpyridin-2-yl)thio)-2-phenylacetamide;
2-((6-(4-(3-Aminopropyl)piperazin-1-yl)-3,5-dicyano-4-cyclopropylpyridin-2-yl)thio)-2-phenylacetamide;
2-((3,5-Dicyano-4-cyclopropyl-6-(4-((4-methylpiperazin-1-yl)methyl)piperidin-1-yl)pyridin-2-yl)thio)-2-phenylacetamide;
2-((6-(4-Acetylpiperazin-1-yl)-3,5-dicyano-4-ethylpyridin-2-yl)thio)-2-phenylacetamide;
2-((3,5-Dicyano-4-ethyl-6-(4-(2-hydroxyethyl)piperazin-1-yl)pyridin-2-yl)thio)-2-phenylacetamide;
2-[(3,5-Dicyano-4-cyclopropyl-6-morpholino-2-pyridyl)sulfanyl]-2-phenyl-acetamide;
2-((6-(4-Benzoylpiperazin-1-yl)-3,5-dicyano-4-ethylpyridin-2-yl)thio)-2-phenylacetamide;
2-((3,5-Dicyano-4-ethyl-6-((5S,6S)-6-hydroxy-1-(methylsulfonyl)-1,8-diazaspiro[4.5]decan-8-yl)pyridin-2-yl)thio)-2-phenylacetamide;
2-((3,5-Dicyano-6-(4,4-difluoropiperidin-1-yl)-4-ethylpyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide;
2-((3,5-dicyano-4-(furan-2-yl)-6-(4-methyl-1,4-diazepan-1-yl)pyridin-2-yl)thio)-2-phenylacetamide;
2-((6-(4-amino-4-methylpiperidin-1-yl)-3,5-dicyano-4-ethylpyridin-2-yl)thio)-2-phenylacetamide;
2-amino-N-(1-(6-((2-amino-2-oxo-1-phenylethyl)thio)-3,5-dicyano-4-ethylpyridin-2-yl)piperidin-4-yl)acetamide;
(2S)-2-amino-N-(1-(6-((2-amino-2-oxo-1-phenylethyl)thio)-3,5-dicyano-4-ethylpyridin-2-yl)piperidin-4-yl)propanamide;
2-((6-(4-(3-aminooxetane-3-carbonyl)piperazin-1-yl)-3,5-dicyano-4-ethylpyridin-2-yl)thio)-2-phenylacetamide;
4-amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide;
2-((6-(4-(4-aminotetrahydro-2H-pyran-4-carbonyl)piperazin-1-yl)-3,5-dicyano-4-ethylpyridin-2-yl)thio)-2-phenylacetamide; p 2-((3,5-dicyano-6-(4-(2-hydroxyethyl)-1,4-diazepan-1-yl)-4-methoxypyridin-2-yl)thio)-2-phenylacetamide;
2-((6-(4-aminopiperidin-1-yl)-3,5-dicyano-4-ethylpyridin-2-yl)thio)-2-phenylacetamide;
2-((6-((2-aminoethyl)(methyl)amino)-3,5-dicyano-4-ethylpyridin-2-yl)thio)-2-phenylacetamide;
2-((6-((2-amino-2-oxoethyl)(methyl)amino)-3,5-dicyano-4-ethylpyridin-2-yl)thio)-2-phenylacetamide;
2-((3,5-dicyano-4-ethyl-6-(3-hydroxyazetidin-1-yl)pyridin-2-yl)thio)-2-phenylacetamide;
2-((3,5-dicyano-4-ethyl-6-((2-hydroxyethyl)(methyl)amino)pyridin-2-yl)thio)-2-phenylacetamide;
2-amino-N-(1-(6-((2-amino-2-oxo-1-phenylethyl)thio)-3,5-dicyano-4-ethylpyridin-2-yl)piperidin-4-yl)-2-methylpropanamide;
2-((6-(4-(2-aminoethoxy)piperidin-1-yl)-3,5-dicyano-4-ethylpyridin-2-yl)thio)-2-phenylacetamide;
2-((3,5-dicyano-4-ethyl-6-(3-hydroxypyrrolidin-1-yl)pyridin-2-yl)thio)-2-phenylacetamide;
2-((3,5-dicyano-4-ethyl-6-(4-(2-hydroxyethoxy)piperidin-1-yl)pyridin-2-yl)thio)-2-phenylacetamide;
or a pharmaceutically acceptable salt or prodrug thereof.
Included prodrugs of Formula (Vbbr) of the invention are:
1-(6-((2-amino-2-oxo-1-phenylethyl)thio)-3,5-dicyano-4-ethylpyridin-2-yl)pyrrolidin-3-yl dihydrogen phosphate;
2-((6-((2-amino-2-oxo-1-phenylethyl)thio)-3,5-dicyano-4-ethylpyridin-2-yl)(methyl)amino)ethyl dihydrogen phosphate;
1-(6-((2-amino-2-oxo-1-phenylethyl)thio)-3,5-dicyano-4-ethylpyridin-2-yl)azetidin-3-yl dihydrogen phosphate;
(2S)-2-((1-(6-((2-amino-2-oxo-1-phenylethyl)thio)-3,5-dicyano-4-ethylpyridin-2-yl)piperidin-4-yl)oxy)ethyl 2-amino-3-methylbutanoate;
(S)-1-(6-(((S)-2-amino-2-oxo-1-phenylethyl)thio)-3,5-dicyano-4-ethylpyridin-2-yl)pyrrolidin-3-yl dihydrogen phosphate;
2-((1-(6-((2-amino-2-oxo-1-phenylethyl)thio)-3,5-dicyano-4-ethylpyridin-2-yl)piperidin-4-yl)oxy)ethyl dihydrogen phosphate; and
1-(6-((2-amino-2-oxo-1-phenylethyl)thio)-3,5-dicyano-4-ethylpyridin-2-yl)piperidin-4-yl dihydrogen phosphate;
or a pharmaceutically acceptable salt thereof.
Non Primary Amide:
Suitably, presently invented novel compounds of Formula (Icr) are selected from:
2-amino-N-(1-(3,5-dicyano-4-ethyl-6-((4-(N-methylmethylsulfonamido)benzyl)thio)pyridin-2-yl)piperidin-4-yl)-2-methylpropanamide;
(R)-2-amino-N-(1-(3,5-dicyano-4-ethyl-6-((4-(N-methylmethylsulfonamido)benzyl)thio)pyridin-2-yl)piperidin-4-yl)propanamide;

N-(4-(((3,5-dicyano-4-ethyl-6-(methyl(2-(piperidin-1-yl)
   ethyl)amino)pyridin-2-yl)thio)methyl)phenyl)-N-methyl-
   methanesulfonamide;
N-(4-(((6-(4-Aminopiperidin-1-yl))-3,5-dicyano-4-eth-
   ylpyridin-2-yl)thio)methyl)benzyl)acetamide;
2-(4-aminopiperidin-1-yl)-6-((4-(1,1-dioxidoisothiazolidin-
   2-yl)benzyl)thio)-4-ethylpyridine-3,5-dicarbonitrile;
2-(4-aminopiperidin-1-yl)-6-((4-(1,1-dioxido-1,2-thiazinan-
   2-yl)benzyl)thio)-4-ethylpyridine-3,5-dicarbonitrile;
2-(4-aminopiperidin-1-yl)-4-ethyl-6-((4-((methylsulfonyl)
   methyl)benzyl)thio)pyridine-3,5-dicarbonitrile;
4-(((6-(4-aminopiperidin-1-yl)-3,5-dicyano-4-ethylpyridin-
   2-yl)thio)methyl)phenyl methanesulfonate;
N-(4-(((3,5-dicyano-4-ethyl-6-(4-(isopropylamino)piperi-
   din-1-yl)pyridin-2-yl)thio)methyl)phenyl)-N-methyl-
   methanesulfonamide;
N-(4-(((6-(4-aminopiperidin-1-yl)-3,5-dicyano-4-ethylpyri-
   din-2-yl)thio)methyl)phenyl)-N-methylmethanesulfona-
   mide;
N-(4-((3,5-Dicyano-4-ethyl-6-(4-(pyrrolidin-1-yl)piperidin-
   1-yl)pyridin-2-ylthio)methyl)benzyl)acetamide;
2-amino-N-(4-(((3,5-dicyano-6-((2-(diethylamino)ethyl)
   (methyl)amino)-4-ethylpyridin-2-yl)thio)methyl)benzyl)
   acetamide;
rel-2-amino-N-(4-(((6-(cis-4-amino-3-fluoropiperidin-1-
   yl)-3,5-dicyano-4-ethylpyridin-2-yl)thio)methyl)benzyl)
   acetamide;
N-(4-(((3,5-dicyano-4-ethyl-6-(2-(pyrrolidin-1-ylmethyl)
   morpholino)pyridin-2-yl)thio)methyl)phenyl)-N-methyl-
   methanesulfonamide;
N-(4-(((3,5-Dicyano-4-ethyl-6-(4-methyl-1,4-diazepan-1-
   yl)pyridin-2-yl)thio)methyl)benzyl)acetamide; and
N-(4-(((3,5-dicyano-6-(3-((dimethylamino)methyl)piperi-
   din-1-yl)-4-ethylpyridin-2-yl)thio)methyl)phenyl)-N-
   methylmethanesulfonamide;
or a pharmaceutically acceptable salt or prodrug thereof.
Suitably, presently invented novel compounds of Formula
(Icr) are selected from:
N-(4-((3,5-Dicyano-4-ethyl-6-(4-(pyrrolidin-1-yl)piperidin-
   1-yl)pyridin-2-ylthio)methyl)benzyl)acetamide;
2-(4-(Aminomethyl)benzylthio)-4-ethyl-6-(4-(pyrrolidin-1-
   yl)piperidin-1-yl)pyridine-3,5-dicarbonitrile;
tert-Butyl 4-(((3,5-dicyano-4-ethyl-6-(4-methyl-1,4-diaz-
   epan-1-yl)pyridin-2-yl)thio)methyl)benzylcarbamate;
4-(((3,5-Dicyano-4-ethyl-6-(4-methyl-1,4-diazepan-1-yl)
   pyridin-2-yl)thio)methyl)benzamide;
2-((4-(Aminomethyl)benzyl)thio)-4-ethyl-6-(4-methyl-1,4-
   diazepan-1-yl)pyridine-3,5-dicarbonitrile;
2-(4-(((3,5-Dicyano-4-ethyl-6-(4-methyl-1,4-diazepan-1-yl)
   pyridin-2-yl)thio)methyl)phenyl)acetic acid;
4-(((3,5-Dicyano-4-ethyl-6-(4-methyl-1,4-diazepan-1-yl)
   pyridin-2-yl)thio)methyl)benzoic acid;
2-(Dimethylamino)-4-ethyl-6-(((6-oxo-1,6-dihydropyridin-
   3-yl)methyl)thio)pyridine-3,5-dicarbonitrile;
N-(4-(((3,5-Dicyano-4-ethyl-6-(4-methyl-1,4-diazepan-1-
   yl)pyridin-2-yl)thio)methyl)thiazol-2-yl)acetamide;
4-(((3,5-Dicyano-4-ethyl-6-(4-methyl-1,4-diazepan-1-yl)
   pyridin-2-yl)thio)methyl)benzenesulfonamide;
N-(4-(((3,5-Dicyano-4-ethyl-6-(4-methyl-1,4-diazepan-1-
   yl)pyridin-2-yl)thio)methyl)benzyl)acetamide;
tert-Butyl (2-((4-(((3,5-dicyano-4-ethyl-6-(4-methyl-1,4-di-
   azepan-1-yl)pyridin-2-yl)thio)methyl)benzyl)amino)-2-
   oxoethyl)carbamate;
N-(4-(((3,5-Dicyano-4-ethyl-6-(4-methyl-1,4-diazepan-1-
   yl)pyridin-2-yl)thio)methyl)benzyl)methanesulfonamide;
2-Amino-N-(4-(((3,5-Dicyano-4-ethyl-6-(4-methyl-1,4-di-
   azepan-1-yl)pyridin-2-yl)thio)methyl)benzyl)acetamide;
2-(4-Aminopiperidin-1-yl)-6-(benzylthio)-4-ethylpyridine-
   3,5-dicarbonitrile;
4-(((3,5-Dicyano-4-ethyl-6-(4-methyl-1,4-diazepan-1-yl)
   pyridin-2-yl)thio)methyl)benzyl acetate;
2-(4-(((3,5-Dicyano-4-ethyl-6-(4-methyl-1,4-diazepan-1-yl)
   pyridin-2-yl)thio)methyl)phenyl acetamide;
2-(4-(((3,5-Dicyano-4-ethyl-6-(4-methyl-1,4-diazepan-1-yl)
   pyridin-2-yl)thio)methyl)phenyl)-N-methylacetamide;
4-Ethyl-2-((4-(hydroxymethyl)benzyl)thio)-6-(4-methyl-1,
   4-diazepan-1-yl)pyridine-3,5-dicarbonitrile;
N-(4-(((3,5-Dicyano-4-ethyl-6-(4-methyl-1,4-diazepan-1-
   yl)pyridin-2-yl)thio)methyl)benzyl)-2-hydroxyacet-
   amide;
Example 87N-(4-(((3,5-Dicyano-4-ethyl-6-(4-methyl-1,4-
   diazepan-1-yl)pyridin-2-yl)thio) methyl)benzyl)propio-
   namide;
N-(4-(((3,5-Dicyano-4-ethyl-6-(4-methyl-1,4-diazepan-1-
   yl)pyridin-2-yl)thio)methyl)benzyl)isobutyramide;
N-(4-(((3,5-Dicyano-4-ethyl-6-(4-methyl-1,4-diazepan-1-
   yl)pyridin-2-yl)thio)methyl)benzyl)-3-methylbutana-
   mide;
4-Ethyl-2-((4-(((2-hydroxyethyl)amino)methyl)benzyl)
   thio)-6-(4-methyl-1,4-diazepan-1-yl)pyridine-3,5-dicar-
   bonitrile;
N-(4-(((3,5-Dicyano-6-(4-methyl-1,4-diazepan-1-yl)-4-
   (methylamino)pyridin-2-yl)thio)methyl)benzyl)acet-
   amide;
2-(((2-Acetyl-1,2,3,4-tetrahydroisoquinolin-6-yl)methyl)
   thio)-6-(dimethylamino)-4-ethylpyridine-3,5-dicarboni-
   trile;
2-((4-Cyanobenzyl)thio)-4-ethyl-6-(4-methyl-1,4-diazepan-
   1-yl)pyridine-3,5-dicarbonitrile;
2-Amino-N-(1-(6-(benzylthio)-3,5-dicyano-4-ethylpyridin-
   2-yl)piperidin-4-yl)acetamide;
2-Amino-N-(1-(6-(benzylthio)-3,5-dicyano-4-ethylpyridin-
   2-yl)piperidin-4-yl)-2-methylpropanamide;
3-Amino-N-(4-(((3,5-dicyano-4-ethyl-6-(4-methyl-1,4-di-
   azepan-1-yl)pyridin-2-yl)thio)methyl)benzyl)propana-
   mide;
(S)-2-Amino-N-(4-(((3,5-dicyano-4-ethyl-6-(4-methyl-1,4-
   diazepan-1-yl)pyridin-2-yl)thio)methyl)benzyl)propana-
   mide;
(R)-2-Amino-N-(4-(((3,5-dicyano-4-ethyl-6-(4-methyl-1,4-
   diazepan-1-yl)pyridin-2-yl)thio)methyl)benzyl)propana-
   mide;
1-(4-(((3,5-Dicyano-4-ethyl-6-(4-methyl-1,4-diazepan-1-yl)
   pyridin-2-yl)thio)methyl)benzyl)-3-ethylurea;
1-(4-(((3,5-Dicyano-4-ethyl-6-(4-methyl-1,4-diazepan-1-yl)
   pyridin-2-yl)thio)methyl)benzyl)-3-phenylurea;
N-(4-(((3,5-Dicyano-6-(4-methyl-1,4-diazepan-1-yl)-4-
   (methylthio)pyridin-2-yl)thio)methyl)benzyl)acetamide;
(E)-3-(4-(((3,5-Dicyano-6-(dimethylamino)-4-ethylpyridin-
   2-yl)thio)methyl)phenyl)acrylic acid;
N-(4-(((3,5-Dicyano-4-ethyl-6-((2-hydroxyethyl)(methyl)
   amino)pyridin-2-yl)thio)methyl)benzyl)acetamide;
4-(((3,5-Dicyano-4-ethyl-6-(4-methyl-1,4-diazepan-1-yl)
   pyridin-2-yl)thio)methyl)-N-methylbenzenesulfonamide;
N-(4-(((3,5-Dicyano-4-ethoxy-6-(4-methyl-1,4-diazepan-1-
   yl)pyridin-2-yl)thio)methyl)benzyl)acetamide;
N-(4-(((6-(4-Aminopiperidin-1-yl)-3,5-dicyano-4-eth-
   ylpyridin-2-yl)thio)methyl)benzyl)acetamide;
(S)-2-((1-(6-((4-(Acetamidomethyl)benzyl)thio)-3,5-di-
   cyano-4-ethylpyridin-2-yl)piperidin-4-yl)oxy)ethyl
   2-amino-3-methylbutanoate;
(S)-2-((6-((4-(Acetamidomethyl)benzyl)thio)-3,5-dicyano-
   4-ethylpyridin-2-yl)(methyl)amino)ethyl 2-amino-3-
   methylbutanoate;

2-Amino-N-(4-(((3,5-dicyano-6-(dimethylamino)-4-ethylpyridin-2-yl)thio)methyl)benzyl)acetamide;
4-Ethyl-2-(4-methyl-1,4-diazepan-1-yl)-6-((4-((2-oxopyrrolidin-1-yl)methyl)benzyl)thio)pyridine-3,5-dicarbonitrile;
2-((4-(Aminomethyl)benzyl)thio)-6-(dimethylamino)-4-ethylpyridine-3,5-dicarbonitrile;
N-(4-(((3,5-Dicyano-6-(dimethylamino)-4-ethylpyridin-2-yl)thio) methyl) phenyl) acetamide;
N-(4-(((3,5-Dicyano-6-(dimethylamino)-4-ethylpyridin-2-yl)thio)methyl)benzyl)-2-hydroxyacetamide;
3-Amino-N-(4-(((3,5-dicyano-6-(dimethylamino)-4-ethylpyridin-2-yl)thio)methyl)benzyl)propanamide;
(S)-1-(6-((4-(Acetamidomethyl)benzyl)thio)-3,5-dicyano-4-ethylpyridin-2-yl)azetidin-3-yl 2-amino-3-methylbutanoate;
N-(4-(((3,5-Dicyano-4-ethyl-6-methylpyridin-2-yl)thio)methyl)benzyl)acetamide;
2-(4-(((3,5-Dicyano-6-(dimethylamino)-4-ethylpyridin-2-yl)thio)methyl)-1H-pyrazol-1-yl)acetamide;
N-(4-(((3,5-Dicyano-6-(dimethylamino)-4-ethylpyridin-2-yl)thio)methyl)phenyl) methanesulfonamide;
(S)-1-(6-((4-(Acetamidomethyl)benzyl)thio)-3,5-dicyano-4-ethylpyridin-2-yl)piperidin-4-yl 2-amino-3-methylbutanoate;
N-(1-(6-((4-(Acetamidomethyl)benzyl)thio)-3,5-dicyano-4-ethylpyridin-2-yl)piperidin-4-yl)acetamide;
2-(4-(((3,5-Dicyano-6-(dimethylamino)-4-ethylpyridin-2-yl)thio)methyl)phenyl)-N-(2-hydroxyethyl)acetamide;
4-(((3,5-Dicyano-6-(dimethylamino)-4-ethylpyridin-2-yl)thio) methyl)-N-(2-hydroxyethyl)benzamide;
2-((4-(1H-Imidazol-1-yl)benzyl)thio)-4-ethyl-6-(4-methyl-1,4-diazepan-1-yl)pyridine-3,5-dicarbonitrile;
2-((4-Cyano-3-methylbenzyl)thio)-4-ethyl-6-(4-methyl-1,4-diazepan-1-yl)pyridine-3,5-dicarbonitrile;
tert-Butyl(4-(((3,5-dicyano-4-ethyl-6-(4-methyl-1,4-diazepan-1-yl)pyridin-2-yl)thio)methyl)phenyl)carbamate;
2-((4-Aminobenzyl)thio)-4-ethyl-6-(4-methyl-1,4-diazepan-1-yl)pyridine-3,5-dicarbonitrile;
N-(4-(((3,5-Dicyano-4-ethyl-6-(4-methyl-1,4-diazepan-1-yl)pyridin-2-yl)thio)methyl)phenyl)acetamide;
N-(4-(((3,5-Dicyano-4-ethyl-6-(4-methyl-1,4-diazepan-1-yl)pyridin-2-yl)thio)methyl)phenyl) methanesulfonamide;
2-(((6-Aminopyridin-3-yl)methyl)thio)-4-ethyl-6-(4-methyl-1,4-diazepan-1-yl)pyridine-3,5-dicarbonitrile;
N-(4-(((3,5-Dicyano-4-ethyl-6-(4-methyl-1,4-diazepan-1-yl)pyridin-2-yl)thio)methyl)phenyl)-2-hydroxyacetamide;
2-Amino-N-(4-(((3,5-dicyano-4-ethyl-6-(4-methyl-1,4-diazepan-1-yl)pyridin-2-yl)thio)methyl)phenyl)acetamide;
N-(4-(((3,5-Dicyano-4-ethyl-6-(3-oxopiperazin-1-yl)pyridin-2-yl)thio) methyl) benzyl) acetamide;
N-(4-(((3,5-Dicyano-4-ethyl-6-(3-hydroxypyrrolidin-1-yl)pyridin-2-yl)thio)methyl)benzyl)acetamide;
N-(4-(1-(3,5-Dicyano-6-(4-(dimethylamino)piperidin-1-yl)-4-ethylpyridin-2-ylthio)propyl)benzyl)acetamide;
N-(5-(((3,5-dicyano-4-ethyl-6-(4-methyl-1,4-diazepan-1-yl)pyridin-2-yl)thio)methyl)pyridin-2-yl)methanesulfonamide;
2-(6-(4-(Acetamidomethyl)benzylthio)-3,5-dicyano-4-ethylpyridin-2-ylthio)-2-phenylacetamide;
4-Ethyl-2-((4-(pyridin-3-yl)benzyl)thio)-6-(4-(pyrrolidin-1-yl)piperidin-1-yl)pyridine-3,5-dicarbonitrile;
4-Ethyl-2-((4-(pyridin-4-yl)benzyl)thio)-6-(4-(pyrrolidin-1-yl)piperidin-1-yl)pyridine-3,5-dicarbonitrile;
2-Amino-N-(1-(3,5-dicyano-4-ethyl-6-((4-sulfamoylbenzyl)thio)pyridin-2-yl)piperidin-4-yl)acetamide;
2-(4-(((3,5-Dicyano-4-ethyl-6-(4-methyl-1,4-diazepan-1-yl)pyridin-2-yl)thio)methyl)phenyl)-N-(2-hydroxyethyl)acetamide;
2-(((1H-Indol-5-yl)methyl)thio)-4-ethyl-6-(4-(pyrrolidin-1-yl)piperidin-1-yl)pyridine-3,5-dicarbonitrile;
4-(((6-(4-Aminopiperidin-1-yl)-3,5-dicyano-4-ethylpyridin-2-yl)thio)methyl) benzenesulfonamide;
2-((Benzo[d][1,3]dioxol-5-ylmethyl)thio)-4-ethyl-6-(4-methyl-1,4-diazepan-1-yl)pyridine-3,5-dicarbonitrile;
2-(((3,3-Dimethoxy-2-oxoindolin-5-yl)methyl)thio)-4-ethyl-6-(4-methyl-1,4-diazepan-1-yl)pyridine-3,5-dicarbonitrile;
2-(((2,3-Dioxoindolin-5-yl)methyl)thio)-4-ethyl-6-(4-methyl-1,4-diazepan-1-yl)pyridine-3,5-dicarbonitrile;
N-(4-(((6-(((4H-1,2,4-Triazol-3-yl)methyl)(methyl)amino)-3,5-dicyano-4-ethylpyridin-2-yl)thio)methyl)benzyl)acetamide;
4-Ethyl-2-((4-(pyridin-2-yl)benzyl)thio)-6-(4-(pyrrolidin-1-yl)piperidin-1-yl)pyridine-3,5-dicarbonitrile;
N-(4-(((3,5-Dicyano-4-ethyl-6-(4-methyl-1,4-diazepan-1-yl)pyridin-2-yl)thio)methyl)phenyl)-N-methylacetamide;
N-(4-(((3,5-Dicyano-4-ethyl-6-(4-methyl-1,4-diazepan-1-yl)pyridin-2-yl) thio)methyl)phenyl)-N-methylmethanesulfonamide;
4-((3,5-Dicyano-4-ethyl-6-(4-methyl-1,4-diazepan-1-yl)pyridin-2-ylthio)methyl)phenylboronic acid;
N-(4-(((3,5-Dicyano-4-ethyl-6-(4-methyl-1,4-diazepan-1-yl)pyridin-2-yl)thio)methyl)benzyl)-2-(methylamino)acetamide;
2-((4-Amino-3-fluorobenzyl)thio)-4-ethyl-6-(4-methyl-1,4-diazepan-1-yl)pyridine-3,5-dicarbonitrile;
N-(4-(((3,5-Dicyano-4-ethyl-6-(4-methyl-1,4-diazepan-1-yl)pyridin-2-yl)thio)methyl)-2-fluorophenyl)methanesulfonamide;
N-(4-(((3,5-Dicyano-4-ethyl-6-(4-methyl-1,4-diazepan-1-yl)pyridin-2-yl) thio)methyl)-2-fluorophenyl)acetamide;
2-(4-Aminopiperidin-1-yl)-4-ethyl-6-(((1-(2-hydroxyethyl)-1H-pyrazol-4-yl)methyl)thio)pyridine-3,5-dicarbonitrile;
N-(4-(((3,5-Dicyano-4-ethyl-6-(3-hydroxypyrrolidin-1-yl)pyridin-2-yl)thio)methyl)benzyl)-2-hydroxyacetamide;
N-(4-(((6-((2-Amino-2-oxoethyl)(methyl) amino)-3,5-dicyano-4-ethylpyridin-2-yl) thio) methyl) benzyl)-2-hydroxyacetamide;
2-(4-(2-(Dimethylamino)ethoxy)benzylthio)-4-ethyl-6-(4-methyl-1,4-diazepan-1-yl)pyridine-3,5-dicarbonitrile;
4-Ethyl-2-(4-methyl-1,4-diazepan-1-yl)-6-((4-(methylsulfonyl)benzyl)thio)pyridine-3,5-dicarbonitrile;
2-(4-Aminopiperidin-1-yl)-6-(((1-(2,3-dihydroxypropyl)-1H-pyrazol-4-yl)methyl)thio)-4-ethylpyridine-3,5-dicarbonitrile;
4-Ethyl-2-(4-methyl-1,4-diazepan-1-yl)-6-((4-(4-methylpiperazin-1-yl)benzyl)thio)pyridine-3,5-dicarbonitrile;
4-Ethyl-2-(4-methyl-1,4-diazepan-1-yl)-6-((4-(((2-oxopyrrolidin-3-yl)amino)methyl)benzyl)thio)pyridine-3,5-dicarbonitrile;
2-(((1H-Benzo[d]imidazol-5-yl)methyl)thio)-4-ethyl-6-(4-methyl-1,4-diazepan-1-yl)pyridine-3,5-dicarbonitrile;
4-Ethyl-2-(4-methyl-1,4-diazepan-1-yl)-6-(4-(methylsulfonylmethyl)benzylthio)pyridine-3,5-dicarbonitrile;
2-{[3,5-dicyano-6-(dimethylamino)-4-ethylpyridin-2-yl]sulfanyl}-2-phenylacetamide;
N-(4-(((3,5-dicyano-4-ethyl-6-(methyl(2-(neopentylamino)ethyl)amino)pyridin-2-yl)thio)methyl)phenyl)-N-methylmethanesulfonamide;

N-(4-(((3,5-dicyano-4-ethyl-6-((2-((2-methoxyethyl) (methyl)amino)ethyl)(methyl)amino)pyridin-2-yl)thio) methyl)phenyl)-N-methylmethanesulfonamide;
N-(4-(((3,5-dicyano-4-ethyl-6-(methyl(2-(methylamino) ethyl)amino)pyridin-2-yl)thio)methyl)phenyl)-N-methyl- methanesulfonamide;
N-(4-(((3,5-dicyano-4-ethyl-6-((2-((2-methoxyethyl)amino) ethyl)(methyl)amino)pyridin-2-yl)thio)methyl)phenyl)- N-methylmethanesulfonamide;
N-(4-(((3,5-dicyano-4-ethyl-6-(methyl(2-((1-methylcyclo- propyl)amino)ethyl)amino)pyridin-2-yl)thio)methyl)phe- nyl)-N-methylmethanesulfonamide;
N-(4-(((3,5-dicyano-6-((2-(dimethylamino)ethyl)(methyl) amino)-4-ethylpyridin-2-yl)thio)methyl)phenyl)-N-meth- ylmethanesulfonamide;
N-(4-(((6-((2-aminoethyl)(methyl)amino)-3,5-dicyano-4- ethylpyridin-2-yl)thio)methyl)phenyl)-N-methylmeth- anesulfonamide;
2-(4-aminopiperidin-1-yl)-4-ethyl-6-((4-((methylsulfonyl) methyl)benzyl)thio)pyridine-3,5-dicarbonitrile;
N-(4-(((3,5-dicyano-4-ethyl-6-((2-((2-fluoroethyl)amino) ethyl)(methyl)amino)pyridin-2-yl)thio)methyl)phenyl)- N-methylmethanesulfonamide;
2-amino-N-(4-(((3,5-dicyano-6-((2-(diethylamino)ethyl) (methyl)amino)-4-ethylpyridin-2-yl)thio)methyl)benzyl) acetamide;
4-(((3,5-dicyano-4-ethyl-6-(4-methyl-1,4-diazepan-1-yl) pyridin-2-yl)thio)methyl)-N-(1H-pyrazol-4-yl)benz- amide;
rel-2-amino-N-(4-(((6-(cis-4-amino-3-fluoropiperidin-1- yl)-3,5-dicyano-4-ethylpyridin-2-yl)thio)methyl)benzyl) acetamide;
N-(4-(((3,5-dicyano-4-ethyl-6-(4-(isopropylamino)piperi- din-1-yl)pyridin-2-yl)thio)methyl)phenyl)-N-methyl- methanesulfonamide;
N-(4-(((3,5-dicyano-4-ethyl-6-(4-((2-methoxyethyl)amino) piperidin-1-yl)pyridin-2-yl)thio)methyl)phenyl)-N-meth- ylmethanesulfonamide;
N-(4-(((3,5-dicyano-4-ethyl-6-(4-(neopentylamino)piperi- din-1-yl)pyridin-2-yl)thio)methyl)phenyl)-N-methyl- methanesulfonamide;
N-(4-(((3,5-dicyano-4-ethyl-6-(methyl(2-(pyrrolidin-1-yl) ethyl)amino)pyridin-2-yl)thio)methyl)phenyl)-N-methyl- methanesulfonamide;
N-(4-(((3,5-dicyano-6-(2-((dimethylamino)methyl)mor- pholino)-4-ethylpyridin-2-yl)thio)methyl)phenyl)-N- methylmethanesulfonamide;
2-amino-N-(1-(3,5-dicyano-4-ethyl-6-((4-(N-methylmeth- ylsulfonamido)benzyl)thio)pyridin-2-yl)piperidin-4-yl)- 2-methylpropanamide;
N-(4-(((3,5-dicyano-6-(4-(cyclopropylamino)piperidin-1- yl)-4-ethylpyridin-2-yl)thio)methyl)phenyl)-N-methyl- methanesulfonamide;
N-(4-(((3,5-dicyano-4-ethyl-6-(2-(pyrrolidin-1-ylmethyl) morpholino)pyridin-2-yl)thio)methyl)phenyl)-N-methyl- methanesulfonamide;
N-(4-(((3,5-dicyano-4-ethyl-6-(methyl(2-(piperidin-1-yl) ethyl)amino)pyridin-2-yl)thio)methyl)phenyl)-N-methyl- methanesulfonamide;
N-(4-(((3,5-dicyano-6-((2-(diethylamino)ethyl)(methyl) amino)-4-ethylpyridin-2-yl)thio)methyl)phenyl)-N-meth- ylmethanesulfonamide;
N-(4-(((3,5-dicyano-6-(2-((diethylamino)methyl)mor- pholino)-4-ethylpyridin-2-yl)thio)methyl)phenyl)-N- methylmethanesulfonamide;
N-(4-(((3,5-dicyano-4-ethyl-6-(4-(pyrrolidin-1-yl)piperi- din-1-yl)pyridin-2-yl)thio)methyl)phenyl)-N-methyl- methanesulfonamide;
(R)-2-amino-N-(1-(3,5-dicyano-4-ethyl-6-((4-(N-methylm- ethylsulfonamido)benzyl)thio)pyridin-2-yl)piperidin-4- yl)propanamide;
(S)-2-amino-N-(1-(3,5-dicyano-4-ethyl-6-((4-(N-methylm- ethylsulfonamido)benzyl)thio)pyridin-2-yl)piperidin-4- yl)propanamide;
N-(4-(((6-(4-aminopiperidin-1-yl)-3,5-dicyano-4-ethylpyri- din-2-yl)thio)methyl)phenyl)-N-methylmethanesulfona- mide;
2-amino-N-(1-(3,5-dicyano-4-ethyl-6-((4-(N-methylmeth- ylsulfonamido)benzyl)thio)pyridin-2-yl)piperidin-4-yl) acetamide;
N-(4-(((6-(2-(aminomethyl)morpholino)-3,5-dicyano-4-eth- ylpyridin-2-yl)thio)methyl)phenyl)-N-methylmethane- sulfonamide;
N-(4-(((3,5-dicyano-4-ethyl-6-(4-methyl-1,4-diazepan-1-yl) pyridin-2-yl)thio)methyl)phenyl)-1-fluoro-N-methyl- methanesulfonamide;
N-(4-(((3,5-dicyano-4-ethyl-6-(2-((methylamino)methyl) morpholino)pyridin-2-yl)thio)methyl)phenyl)-N-methyl- methanesulfonamide;
N-(4-(((3,5-dicyano-6-(3-((dimethylamino)methyl)piperi- din-1-yl)-4-ethylpyridin-2-yl)thio)methyl)phenyl)-N- methylmethanesulfonamide;
2-(4-aminopiperidin-1-yl)-6-((4-(1,1-dioxidoisothiazolidin- 2-yl)benzyl)thio)-4-ethylpyridine-3,5-dicarbonitrile;
2-(4-aminopiperidin-1-yl)-6-((4-(1,1-dioxido-1,2-thiazinan- 2-yl)benzyl)thio)-4-ethylpyridine-3,5-dicarbonitrile;
N-(4-(((3,5-dicyano-4-ethyl-6-(4-methyl-1,4-diazepan-1-yl) pyridin-2-yl)thio)methyl)phenyl)-1,1-difluoro-N-methyl- methanesulfonamide;
2-((4-(1,1-dioxidoisothiazolidin-2-yl)benzyl)thio)-4-ethyl- 6-(4-(neopentylamino)piperidin-1-yl)pyridine-3,5-dicar- bonitrile;
2-((4-(1,1-dioxido-1,2-thiazinan-2-yl)benzyl)thio)-4-ethyl- 6-(4-(neopentylamino)piperidin-1-yl)pyridine-3,5-dicar- bonitrile;
4-(((6-(4-aminopiperidin-1-yl)-3,5-dicyano-4-ethylpyridin- 2-yl)thio)methyl)phenyl methanesulfonate;
(R)-2-amino-N-((1-(3,5-dicyano-4-ethyl-6-((4-(N-methyl- methylsulfonamido)benzyl)thio)pyridin-2-yl)pyrrolidin- 3-yl)methyl)acetamide;
(S)-2-amino-N-((1-(3,5-dicyano-4-ethyl-6-((4-(N-methylm- ethylsulfonamido)benzyl)thio)pyridin-2-yl)pyrrolidin-3- yl)methyl)acetamide;
N-(4-(1-((6-(4-aminopiperidin-1-yl)-3,5-dicyano-4-eth- ylpyridin-2-yl)thio)ethyl)phenyl)-N-methylmethane- sulfonamide;
N-(4-(((6-(4-aminopiperidin-1-yl)-3,5-dicyano-4-methoxy- pyridin-2-yl)thio)methyl)phenyl)-N-methylmethane- sulfonamide; and
N-(4-(((3,5-dicyano-4-ethyl-6-(4-((2-hydroxyethyl)amino) piperidin-1-yl)pyridin-2-yl)thio)methyl)phenyl)-N-meth- ylmethanesulfonamide;
or a pharmaceutically acceptable salt or prodrug thereof.

The skilled artisan will appreciate that pharmaceutically acceptable salts, of the compounds according to Formula (I) may be prepared. Indeed, in certain embodiments of the invention pharmaceutically acceptable salts of the compounds according to Formula (I) may be preferred over the respective free or unsalted compound. Accordingly, the invention is further directed to pharmaceutically acceptable salts, of the compounds according to Formula (I). The invention is further directed to free or unsalted compounds of Formula (I).

The pharmaceutically acceptable salts of the compounds of the invention are readily prepared by those of skill in the art.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compounds according to Formula (I) may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula (I), or in any chemical structure illustrated herein, is not specified the structure is intended to encompass all individual stereoisomers and all mixtures thereof. Thus, compounds according to Formula (I) containing one or more chiral centers may be used as racemic mixtures, enantiomerically enriched mixtures, or as enantiomerically pure individual stereoisomers.

The compounds according to Formula (I) and pharmaceutically acceptable salts thereof may contain isotopically-labelled compounds, which are identical to those recited in Formula (I) and following, but for the fact that one or more atoms are replaced by an atom having an atomic mass or mass number different from the atomic mass or mass number usually found in nature. Examples of such isotopes include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Isotopically-labelled compounds, for example those into which radioactive isotopes such as $^{3}H$ or $^{14}C$ are incorporated, are useful in drug and/or substrate tissue distribution assays. Tritium, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), both are useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds can generally be prepared by substituting a readily available isotopically labelled reagent for a non-isotopically labelled reagent.

The compounds according to Formula (I) may also contain double bonds or other centers of geometric asymmetry. Where the stereochemistry of a center of geometric asymmetry present in Formula (I), or in any chemical structure illustrated herein, is not specified, the structure is intended to encompass the trans (E) geometric isomer, the cis (Z) geometric isomer, and all mixtures thereof. Likewise, all tautomeric forms are also included in Formula (I) whether such tautomers exist in equilibrium or predominately in one form.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism ("polymorphs"). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may exist in solvated and unsolvated forms. As used herein, the term "solvate" refers to a complex of variable stoichiometry formed by a solute (in this invention, a compound of Formula (I) or a salt) and a solvent. Such solvents, for the purpose of the invention, may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice structures incorporated with water molecules are typically referred to as "hydrates". Hydrates include stoichiometric hydrates as well as compositions containing variable amounts of water.

It is also noted that the compounds of Formula (I) may form tautomers. 'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention.

While aspects for each variable have generally been listed above separately for each variable this invention includes those compounds in which several or each aspect in Formula (I) is selected from each of the aspects listed above. Therefore, this invention is intended to include all combinations of aspects for each variable.

Definitions

It will be appreciated that the following definitions apply to each of the aforementioned formulae and to all instances of these terms, unless the context dictates otherwise.

"Alkyl" refers to a hydrocarbon chain having the specified number of "member atoms". For example, $C_1$-$C_6$ alkyl refers to an alkyl group having from 1 to 6 member atoms. Alkyl groups may be saturated, unsaturated, straight or branched. Representative branched alkyl groups have one, two, or three branches. Alkyl includes but is not limited to: methyl, ethyl, ethylenyl, propyl (n-propyl and isopropyl), butenyl, butyl (n-butyl, isobutyl, and t-butyl), pentyl and hexyl.

"Alkoxy" refers to an —O-alkyl group wherein "alkyl" is as defined herein. For example, $C_1$-$C_4$alkoxy refers to an alkoxy group having from 1 to 4 carbon member atoms. Examples of such groups include but is not limited to: methoxy, ethoxy, propoxy, butoxy, and t-butoxy.

"Aryl" refers to an aromatic hydrocarbon ring system. Aryl groups are monocyclic, bicyclic, and tricyclic ring systems having a total of five to fourteen ring member atoms, wherein at least one ring system is aromatic and wherein each ring in the system contains 3 to 7 member atoms, such as but no limited to: phenyl, dihydroindene, naphthalene, tetrahydronaphthalene and biphenyl. Suitably aryl is phenyl.

"Cycloalkyl", unless otherwise defined, refers to a saturated or unsaturated non aromatic hydrocarbon ring or rings having from three to seven carbon atoms. Cycloalkyl groups are monocyclic or spiro ring systems. For example, $C_3$-$C_7$ cycloalkyl refers to a cycloalkyl group having from 3 to 7 member atoms. Examples of cycloalkyl as used herein include but is not limited to: cyclopropyl, cyclobutyl, cyclopentyl, cyclohexyl, cyclobutenyl, cyclopentenyl, cyclohexenyl, spiro heptanyl and cycloheptyl. Suitably cycloalkyl is selected from: cyclopropyl, cyclopentyl and cyclohexyl.

"Heteroaryl" refers to a monocyclic aromatic 4 to 8 member ring containing from 1 to 7 carbon atoms and containing from 1 to 4 heteroatoms independently selected from nitrogen, oxygen and sulfur, provided that when the number of carbon atoms is 3, the aromatic ring contains at least two heteroatoms, or to such aromatic ring is fused one or more rings, such as heteroaryl rings, aryl rings, heterocyclic rings, or cycloalkyl rings. Heteroaryl groups containing more than one heteroatom may contain different heteroatoms. Heteroaryl includes but is not limited to: benzoimidazolyl, benzothiazolyl, benzothiophenyl, benzopyrazinyl, benzotriazolyl, benzotriazinyl, benzo[1,4]dioxanyl, benzofuranyl, 9H-a-carbolinyl, cinnolinyl, furanyl, imidazolyl, oxazoly, indazolyl, indolizinyl, indolyl, isoindolyl, isothiazolyl, isoquinolinyl, isoxazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyrazolopyrimidinyl, pyrazolopyridinyl, pyrrolizinyl, pyridazyl, pyrazinyl, pyrimidyl, quinoxalinyl, quinazolinyl, quinolinyl, quinolizinyl, thienyl, thiophenyl, triazolyl, triazinyl, tetrazolopyrimidinyl, triazolopyrimidinyl, tetrazolyl, thiadiazolyl, thiazolyl and thiazolidinyl. Suitably heteroaryl is selected from: furanyl, pyrazolyl, pyrrolyl, imidazolyl, isoxazolyl, isothiazolyl, oxazolyl, triazolyl, thiazolyl and thienyl. Suitably heteroaryl is a pyridyl group or an imidazolyl group. Suitably heteroaryl is a pyridyl.

"Heterocyclic" or "heterocycloalkyl", as used herein, unless otherwise defined, refers to a saturated or unsaturated non-aromatic ring containing 4 to 12 member atoms, of which 1 to 11 are carbon atoms and from 1 to 6 are heteroatoms independently selected from nitrogen, oxygen and sulfur. Heterocycloalkyl groups containing more than one heteroatom may contain different heteroatoms. Such ring may be optionally fused to one or more other "heterocyclic" rings, aryl rings, heteroaryl rings, or cycloalkyl rings. Such rings may be bridged bicyclic or spiro. Examples of "heterocyclic" groups include, but are not limited to: 1,4diazepanyl, azetidinyl, oxetanyl, 1,4-dioxanyl, 1,3-dioxanyl, pyrrolidinyl, pyrrolidin-2-onyl, piperidinyl, piperazinyl, piperazinyl-2,5-dionyl, morpholinyl, dihydropyranyl, dihydrocinnolinyl, dihydropyridinyl, tetrahydropyranyl, 2,3-dihydrofuranyl, 2,3-dihydrobenzofuranyl, dihydroisoxazolyl, tetrahydrooxazolyl, tetrahydrofuranyl, tetrahydrothiazolyl, tetrahydrothiazinyl, tetrahydrothiopyranyl, tetrahydrothiophenyl, dihydroquinoxalinyl, tetrahydroquinoxalinyl, tetrahydroisoquinolinyl, tetrahydropyridinyl, tetrahydrocarbolinyl, 2,9-diazaspiro[5.5]undecanyl, 1,8-diazaspiro[4.5]decanyl, 2,8-diazaspiro[4.5]decanyl, hexahydropyrrolo-1,4-diazepanyl, 1-oxa-6-azaspiro[3.4]octanyl, 5-oxa-2-azaspiro[3.4]octanyl, 1,7-diazaspiro[3.5]nonanyl, 2,7-diazaspiro[3.5]nonanyl, 2,6-diazaspiro[3.4]octanyl, 1,8-diazaspiro[4.5]decanyl and 8-azabicyclo[3.2.1]octanyl. Suitably heterocyclic is selected from: 1,4-diazepanyl, azetidinyl, oxetanyl, pyrrolidinyl, dihydropyridinyl, piperidinyl, piperazinyl, morpholinyl, tetrahydroisoquinolinyl, tetrahydropyranyl, 2,9-diazaspiro[5.5]undecanyl, 1,8-diazaspiro[4.5]decanyl, 2,8-diazaspiro[4.5]decanyl, hexahydropyrrolo-1,4-diazepanyl, 1-oxa6-azaspiro[3.4]octanyl, 5-oxa-2-azaspiro[3.4]octanyl, 1,7-diazaspiro[3.5]nonanyl, 2,7-diazaspiro[3.5]nonanyl, 2,6-diazaspiro[3.4]octanyl, 1,8-diazaspiro[4.5]decanyl and 8-azabicyclo[3.2.1]octanyl.

"Heteroatom" refers to a nitrogen, sulphur or oxygen atom.

"Halogen" and "halo" refers to a fluorine, chlorine, bromine, or iodine atom.

As used herein, the term "mercapto" refers to the group —SH.

As used herein, the term "oxo" refers to the group =O.

As used herein, the term "hydroxy" refers to the group —OH.

As used herein, the term "amino" refers to the group —NH$_2$.

As used herein, the term "aminocarbonyl" refers to the group —C(O)NH$_2$.

As used herein, the term "guanidino" refers to the group —NHC(=NH)NH$_2$.

As used herein, the term "carboxy" refers to the group —C(O)OH.

As used herein, the term "cyano" refers to the group —CN.

As used herein, the term "prodrug" refers to a compound that is metabolized in the body to produce a biologically active compound. This more biologically active compound is referred to herein as an "active compound". An example of a prodrug of the invention is the compound of Example 151. An example of the corresponding active compound is the compound of Example 147.

As used herein, the term "active compound" refers to a compound inhibits the activity of DNMT1, suitably a compound that is a selective inhibitor of DNMT1.

As used herein, the term "selective", when referring to chemical compounds, suitably the active compounds of the present invention, means the compounds exhibit an IC50 over 30 times more active, suitably over 50 times more active, suitably over 100 times more active as an inhibitor against DNMT1, than DNMT3A or DNMT3B in the Breaklight Assay described herein or a similar assay.

As used herein, the term "Compound A" refers to: 2-{[3,5-dicyano-6-(dimethylamino)-4-ethylpyridin-2-yl]sulfanyl}-2-phenylacetamide, the compound of Example 3.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
Ac$_2$O (acetic anhydride);
A-CN (acetonitrile);
AIBN (azobis(isobutyronitrile));
BINAP (2,2'-bis(diphenylphosphino)-1,1'-binaphthyl);
BMS (borane-dimethyl sulphide complex);
Bn (benzyl);
Boc (tert-Butoxycarbonyl);
Boc$_2$O (di-tert-butyl dicarbonate);
BOP (Benzotriazole-1-yl-oxy-tris-(dimethylamino)-phosphonium hexafluorophosphate);
CAN (cerric ammonium nitrate);
Cbz (benzyloxycarbonyl);
CSI (chlorosulfonyl isocyanate);
CSF (cesium fluoride);
DABCO (1,4-Diazabicyclo[2.2.2]octane);
DAST (Diethylamino)sulfur trifluoride);
DBU (1,8-Diazabicyclo[5.4.0]undec-7-ene);
DCC (Dicyclohexyl Carbodiimide);
DCE (1,2-dichloroethane);
DCM (dichloromethane);
DDQ (2,3-Dichloro-5,6-dicyano-1,4-benzoquinone);
ATP (adenosine triphosphate);
Bis-pinacolatodiboron (4,4,4',4',5,5,5',5'-Octamethyl-2,2'-bi-1,3,2-dioxaborolane);
BSA (bovine serum albumin);
C18 (refers to 18-carbon alkyl groups on silicon in HPLC stationary phase)
CH$_3$—CN (acetonitrile) Cy (cyclohexyl);
DCM (dichloromethane);
DIEA (diisopropylethylamine);
DIPEA (Hunig's base, N-ethyl-N-(1-methylethyl)-2-propanamine);
Dioxane (1,4-dioxane);
DMAP (4-dimethylaminopyridine);
DME (1,2-dimethoxyethane);
DMEDA (N,N'-dimethylethylenediamine);
DMF (N,N-dimethylformamide);
DMSO (dimethylsulfoxide);
DPPA (diphenyl phosphoryl azide);
EDC (N-(3-dimethylaminopropyl)-N'ethylcarbodiimide) hydrochloride salt;
EDTA (ethylenediaminetetraacetic acid);
EtOAc (ethyl acetate);
EtOH (ethanol);
Et$_2$O (diethyl ether);
HEPES (4-(2-hydroxyethyl)-1-piperazinyl ethane sulfonic acid);
HATU (O-(7-Azabenzotriazol-1-yl)-N,N,N',N'-tetramethyluronium hexafluorophosphate);
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
Hunig's Base (N,N-Diisopropylethylamine);
IPA (isopropyl alcohol);
Indoline (2,3-dihydro-1H-indole);
KHMDS (potassium hexamethyldisilazide);
LAH (lithium aluminum hydride);
LDA (lithium diisopropylamide);
LHMDS (lithium hexamethyldisilazide);
MeOH (methanol);
MTBE (methyl tert-butyl ether);
mcM (micromolar);
mCPBA (m-chloroperbezoic acid);
NaHMDS (sodium hexamethyldisilazide);
NCS (N-chlorosuccinimide);
NBS (N-bromosuccinimide);
PE (petroleum ether);
Pd$_2$(dba)$_3$ (Tris(dibenzylideneacetone)dipalladium(0);
Pd(dppf)Cl$_2$.DCM Complex ([1,1'-Bis(diphenylphosphino) ferrocene]dichloropalladium(II).dichloromethane complex);
PyBOP (benzotriazol-1-yl-oxytripyrrolidinophosphonium hexafluorophosphate);
PyBrOP (bromotripyrrolidinophosphonium hexafluorophosphate);
RPHPLC (reverse phase high pressure liquid chromatography);
RT (room temperature);
Sat. (saturated);
SFC (supercritical fluid chromatography);
SGC (silica gel chromatography);
SM (starting material);
TLC (thin layer chromatography);
TEA (triethylamine);
TEMPO (2,2,6,6-Tetramethylpiperidinyl 1-oxyl, free radical);
TFA (trifluoroacetic acid);

THF (tetrahydrofuran); and
Ts-Cl (p-toluenesulfonyl chloride).

All references to ether are to diethyl ether and brine refers to a saturated aqueous solution of NaCl.

Compound Preparation

The compounds according to Formula (I) are prepared using conventional organic synthetic methods. Suitable synthetic routes are depicted below in the following general reaction schemes. All of the starting materials are commercially available or are readily prepared from commercially available starting materials by those of skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Organic Synthesis* (4th ed.), John Wiley & Sons, NY (2006). In some instances, a substituent may be specifically selected to be reactive under the reaction conditions used. Under these circumstances, the reaction conditions convert the selected substituent into another substituent that is either useful as an intermediate compound or is a desired substituent in a target compound.

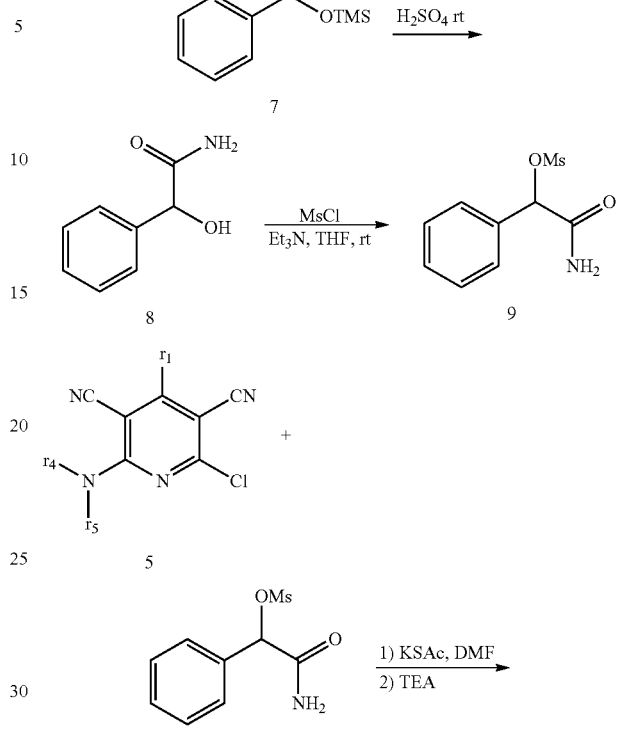

In some cases intermediate of formula 13, is used to obtain intermediate of formula 4, as shown in Scheme 2, and used in subsequent steps as shown in Scheme 1 and Scheme 2.

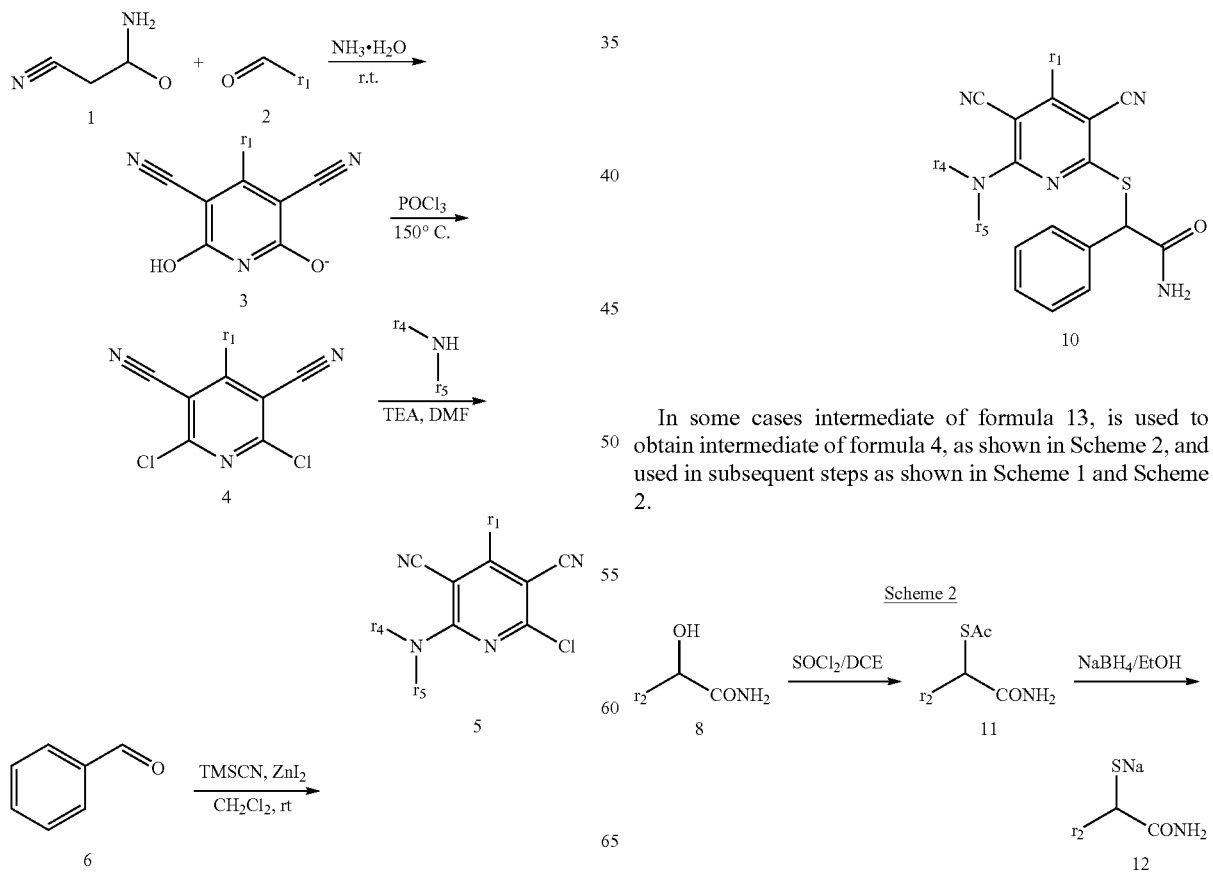

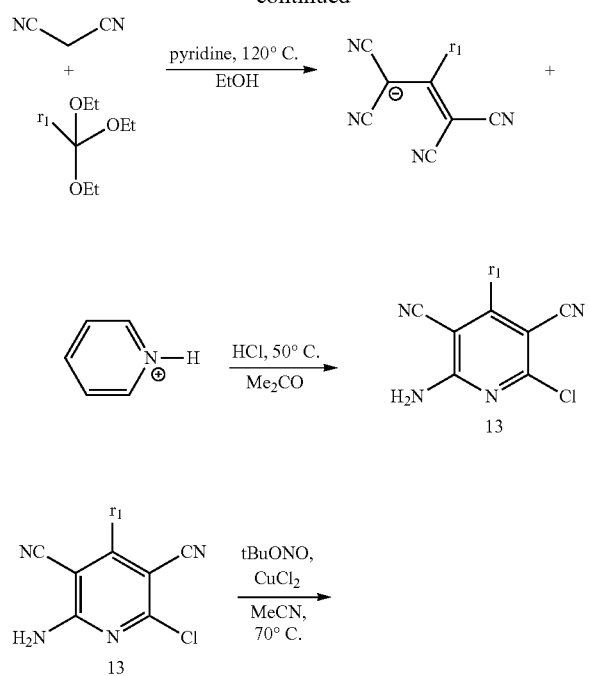

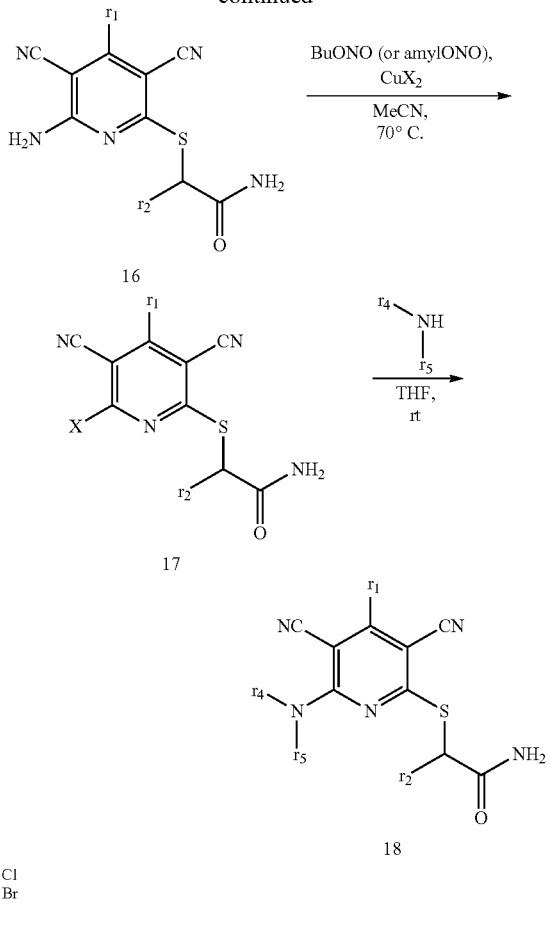

In other cases intermediate of formula 13 is used to obtain compound of formula 16, which is used in subsequent steps to give compounds of formula 18 as described in Scheme 3.

Scheme 3

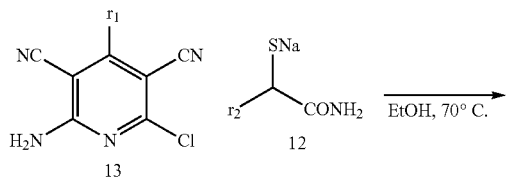

In some cases compounds of formula 19 and 20 are used to give the compounds of formula 21 as described in Scheme 4.

Scheme 4

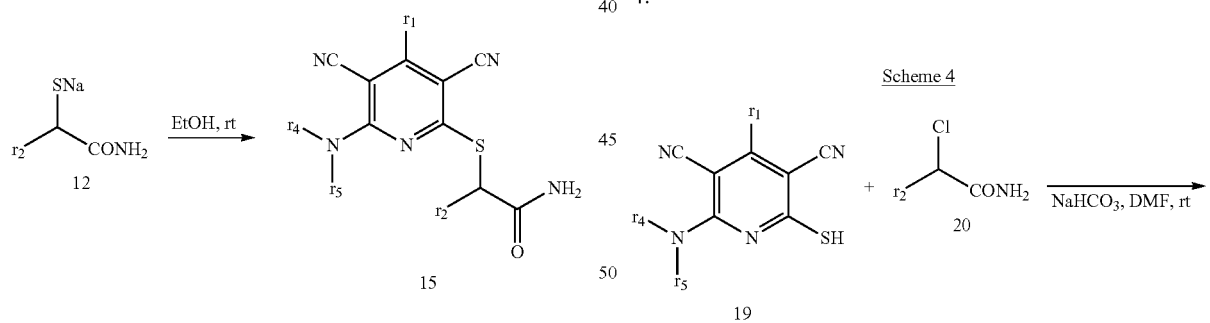

Compounds of formula 24 are prepared by the synthetic route shown in Scheme 5. Intermediates of formula 22 are commercially available compounds, that could be or could not be single enantiomers. When compounds of formula 22 are single enantiomers, so are the corresponding compounds of formula 23 and formula 24.

used as in Scheme 7. Intermediates of formula 27 are commercially available or are synthesized using conventional organic synthesis procedures that can be reproduced by any skilled artisan.

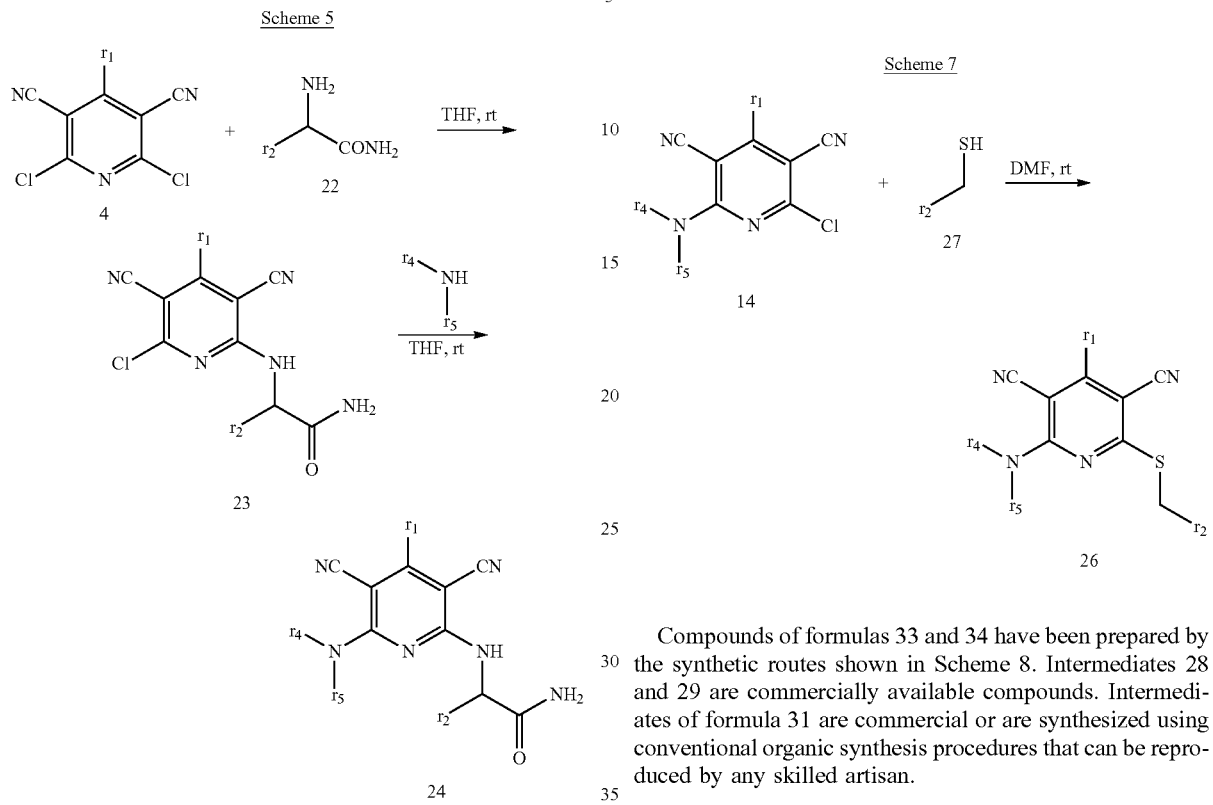

For compounds of formula 26, intermediate of formula 14 and intermediate of formula 25 have been used as shown in Scheme 6. Intermediates of formula 25 are commercially available or are synthesized using conventional organic synthesis procedures that can be reproduced by any skilled artisan.

Compounds of formulas 33 and 34 have been prepared by the synthetic routes shown in Scheme 8. Intermediates 28 and 29 are commercially available compounds. Intermediates of formula 31 are commercial or are synthesized using conventional organic synthesis procedures that can be reproduced by any skilled artisan.

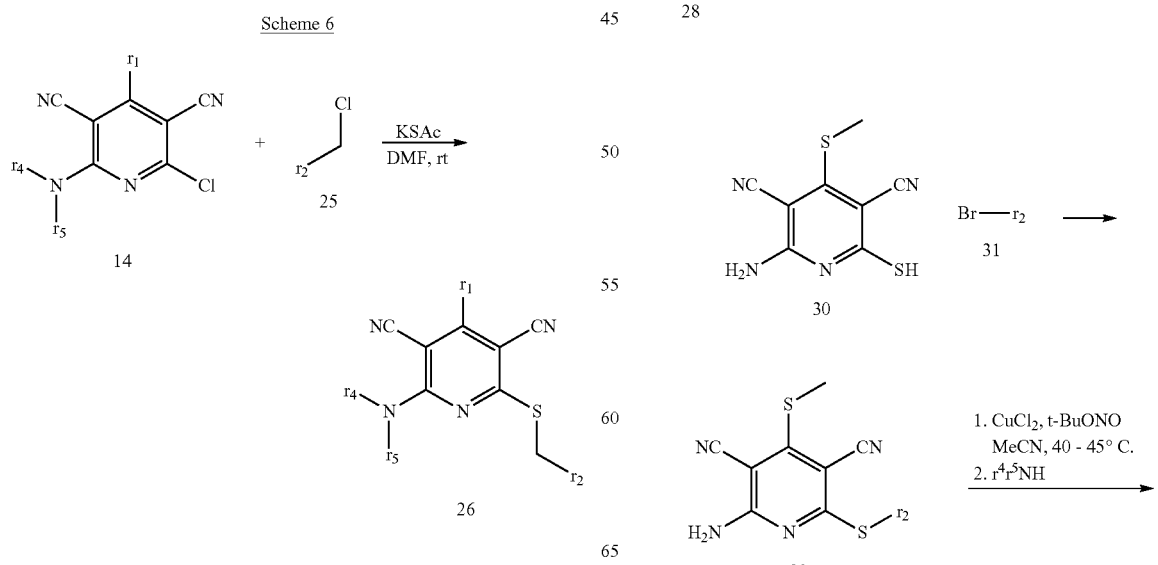

Alternatively for compounds of formula 26, intermediate of formula 14 and intermediate of formula 27 have been -continued

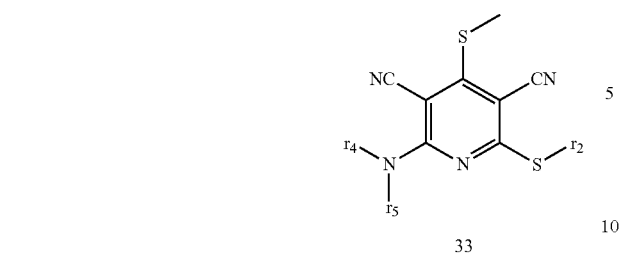
33

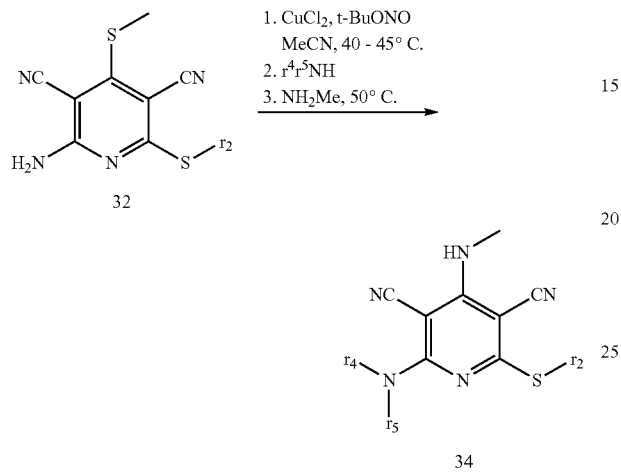

Compounds of formula 40 have been prepared by the synthetic routes shown in Scheme 9. Intermediates 35 and 36 are commercially available compounds. Intermediates of formula 31 are commercial or are synthesized using conventional organic synthesis procedures that can be reproduced by any skilled artisan.

Scheme 9

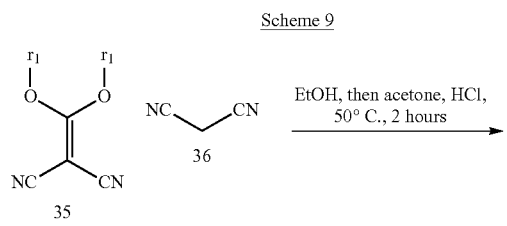

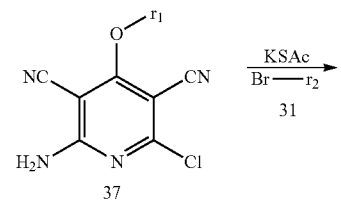
37

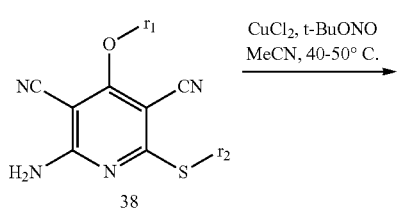
38

-continued

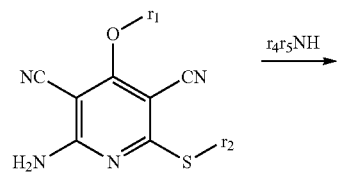
39

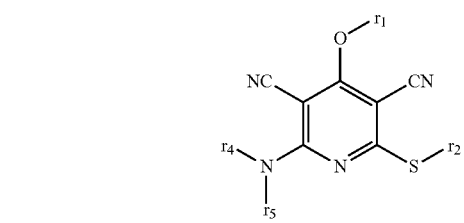
40

Compounds of formula 43 have been prepared by the synthetic routes shown in Scheme 10. Intermediate 41 is commercial.

Scheme 10

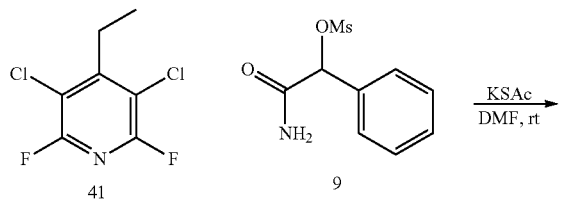

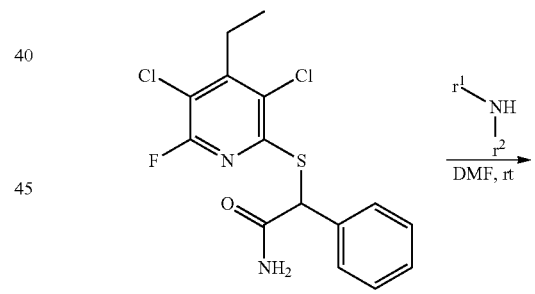
42

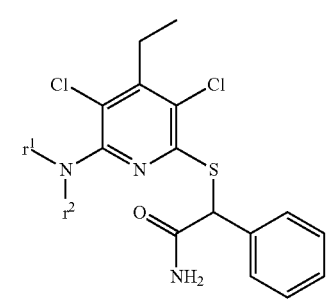
43

Compounds of formula 48 have been prepared by the synthetic routes shown in scheme 11. Intermediates 1 and 44 are commercially available.

Scheme 11
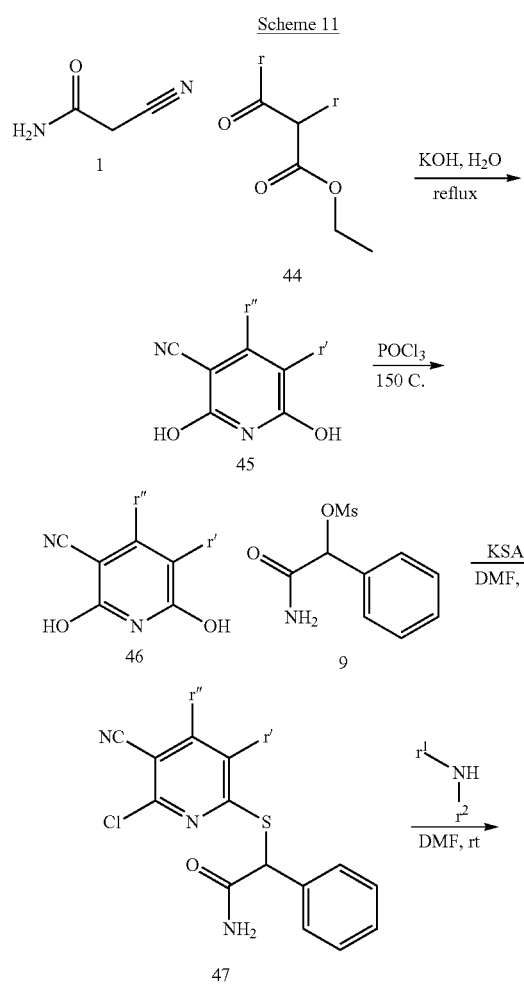
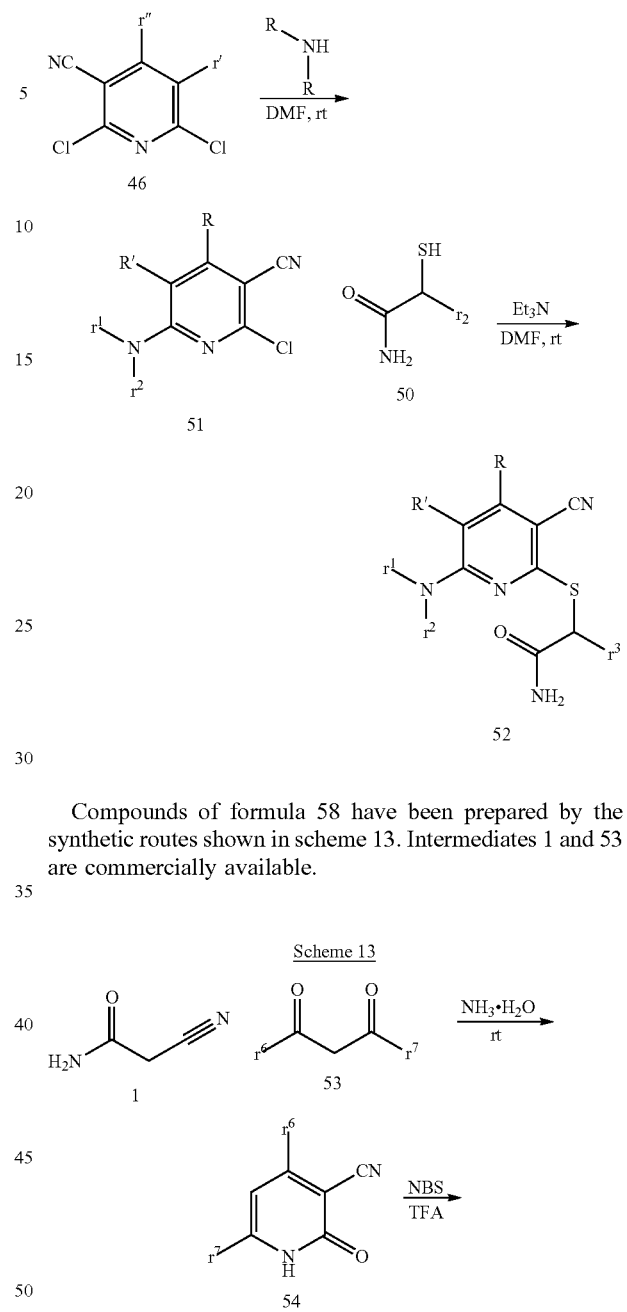
Compounds of formula 52 have been prepared by the synthetic routes shown in scheme 12. Intermediate 49 is commercial and intermediate 46 is shown above in scheme 11.
Scheme 12
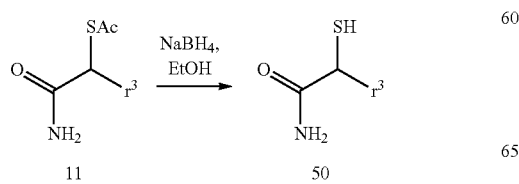
Compounds of formula 58 have been prepared by the synthetic routes shown in scheme 13. Intermediates 1 and 53 are commercially available.
Scheme 13
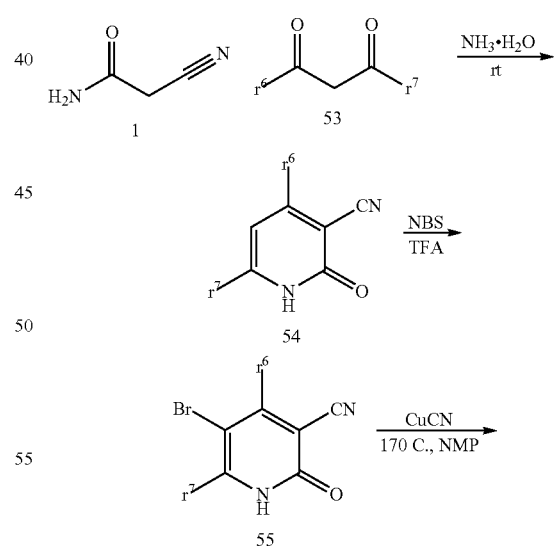

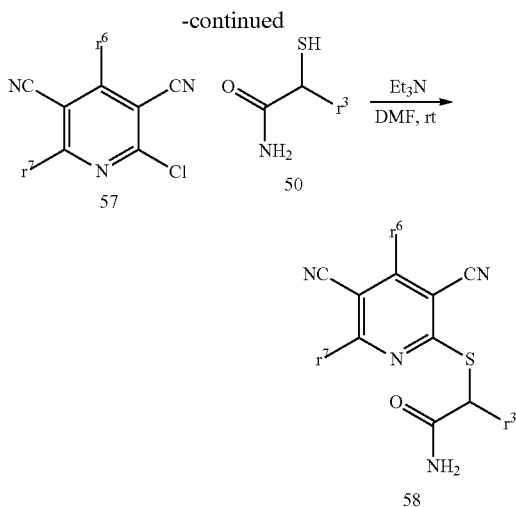

Methods of Use

The compounds according to Formula (I) and pharmaceutically acceptable salts thereof are selective inhibitors of DNMT1. These compounds are potentially useful in the treatment of conditions that respond to the selective inhibition of DNMT1. These include but are not limited to, cancer and pre-cancerous syndromes and beta hemoglobinopathies such as sickle cell disease, sickle cell anemia, and beta thalassemia. Accordingly, in another aspect the invention is directed to methods of treating such conditions.

Suitably, the present invention relates to a method for treating breast cancer, including inflammatory breast cancer, ductal carcinoma, and lobular carcinoma.

Suitably the present invention relates to a method for treating colon cancer.

Suitably the present invention relates to a method for treating pancreatic cancer, including insulinomas, adenocarcinoma, ductal adenocarcinoma, adenosquamous carcinoma, acinar cell carcinoma, and glucagonoma.

Suitably the present invention relates to a method for treating skin cancer, including melanoma, including metastatic melanoma.

Suitably the present invention relates to a method for treating lung cancer including small cell lung cancer, non-small cell lung cancer, squamous cell carcinoma, adenocarcinoma, and large cell carcinoma.

Suitably the present invention relates to a method for treating cancers selected from the group consisting of: cancers of the lung, bone, pancreas, skin, head, neck, uterus, ovaries, stomach, colon, breast, esophagus, small intestine, bowel, endocrine system, thyroid glad, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary -CNS lymphoma; neoplasms of the -CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; and Hodgkin's Disease.

Suitably the present invention relates to a method for treating cancers selected from the group consisting of brain (gliomas), glioblastomas, astrocytomas, glioblastoma multiforme, Bannayan-Zonana syndrome, Cowden disease, Lhermitte-Duclos disease, Wilms tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), neuroendocrine cancers and testicular cancer.

Suitably the present invention relates to a method for treating pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

In some embodiments, the compounds of the invention can be used to overcome T-cell tolerance.

In some embodiments, the compounds of the invention can be used to treat diabetic nephropathy, diabetes, podocyte injury, atherosclerosis, psoriasis, idiopathic pulmonary fibrosis, scleroderma, liver cirrhosis, rheumatoid arthritis, and Alzheimer's disease.

Compounds of the invention can also be used to increase or enhance an immune response, including increasing the immune response to an antigen; to improve immunization, including increasing vaccine efficacy; and to increase inflammation. In some embodiments, the compounds of the invention can be used to enhance the immune response to vaccines including, but not limited, *Listeria* vaccines, oncolytic viral vaccines, and cancer vaccines such as GV AX® (granulocyte-macrophage colony-stimulating factor (GM-CF) gene-transfected tumor cell vaccine).

Further diseases and disorders treatable with compounds of the invention include, but are not limited to, treating beta hemoglobinopathies, such as sickle cell disease, sickle cell anemia, and beta thalassemia.

The methods of treatment of the invention comprise administering an effective amount of a compound according to Formula (I) or a pharmaceutically acceptable salt, thereof to a patient in need thereof.

By the term "treating" and derivatives thereof as used herein, in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The term "treating" and derivatives thereof refers to therapeutic therapy. Therapeutic therapy is appropriate to alleviate symptoms or to treat at early signs of disease or its progression.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

Prophylactic therapy is appropriate when a subject has, for example, a strong family history of cancer or is otherwise considered at high risk for developing cancer, or when a subject has been exposed to a carcinogen or when the subject has a strong family history of a beta-hemoglobinopathy such as sickle cell disease, sickle cell anemia, or beta-thalassemia.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "patient" or "subject" refers to a human or other mammal. Suitably the patient or subject is a human.

The compounds of Formula (I) or pharmaceutically acceptable salts thereof may be administered by any suitable route of administration, including systemic administration. Systemic administration includes oral administration and parenteral administration. Parenteral administration refers to routes of administration other than enteral, transdermal, or by inhalation, and is typically by injection or infusion. Parenteral administration includes intravenous, intramuscular, and subcutaneous injection or infusion.

The compounds of Formula (I) or pharmaceutically acceptable salts thereof may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 1-500 mg once daily or BID per person.

Additionally, the compounds of Formula (I) or pharmaceutically acceptable salts thereof may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, include the preparation of phosphates, amides, ethers, esters, thioesters, carbonates, and carbamate. Where a —COOH or —OH group is present, pharmaceutically acceptable esters can be employed, for example methyl, ethyl, and the like for —COOH, and acetate maleate and the like for —OH, and those esters known in the art for modifying solubility or hydrolysis characteristics.

Accordingly, the invention is further directed to prodrugs of the compounds according to Formula (I). Suitably, the prodrug is a dihydrogen phosphate. Suitably, the prodrug is a 2-amino-3-methylbutanoate.

Included in the prodrugs of Formula (I) are:
1-(6-((2-amino-2-oxo-1-phenylethyl)thio)-3,5-dicyano-4-ethylpyridin-2-yl)pyrrolidin-3-yl dihydrogen phosphate;
2-((6-((2-amino-2-oxo-1-phenylethyl)thio)-3,5-dicyano-4-ethylpyridin-2-yl)(methyl)amino)ethyl dihydrogen phosphate;
1-(6-((2-amino-2-oxo-1-phenylethyl)thio)-3,5-dicyano-4-ethylpyridin-2-yl)azetidin-3-yl dihydrogen phosphate;
(2S)-2-((1-(6-((2-amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-amino-2-oxo-1-phenylethyl)thio)-3,5-dicyano-4-ethylpyridin-2-yl)piperidin-4-yl)oxy)ethyl dihydrogen phosphate; and
1-(6-((2-amino-2-oxo-1-phenylethyl)thio)-3,5-dicyano-4-ethylpyridin-2-yl)piperidin-4-yl dihydrogen phosphate;
a pharmaceutically acceptable salt thereof.

Prodrugs of the compounds of the invention are readily prepared by those of skill in the art.

The compounds of Formula (I) and pharmaceutically acceptable salts thereof may be co-administered with at least one other active agent known to be useful in the treatment of cancer or pre-cancerous syndromes.

By the term "co-administration" as used herein is meant either simultaneous administration or any manner of separate sequential administration of an inhibitor of the activity of DMNT1, as described herein, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Examples of a further active ingredient or ingredients (anti-neoplastic agent) for use in combination or co-administered with the presently invented combinations are indicated below. This list is non-limiting. Additional anti-neoplastic agents are contemplated for use with the presently invented compounds.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active ingredient or ingredients (anti-neoplastic agent) for use in combination or co-administered with the presently invented combinations are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian and breast cancer in the United States.

Docetaxel, (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R-(R*,R*)-2,3-dihydroxybutanedioate (1:2)(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as Bi-CNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids, leading to cell death. Examples of antibiotic anti-neoplastic agents include, but are not limited to, actinomycins such as dactinomycin, anthrocyclins such as daunorubicin and doxorubicin; and bleomycins. Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below. Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, including the racemic mixture (R,S) form as well as the R and S enantiomers:

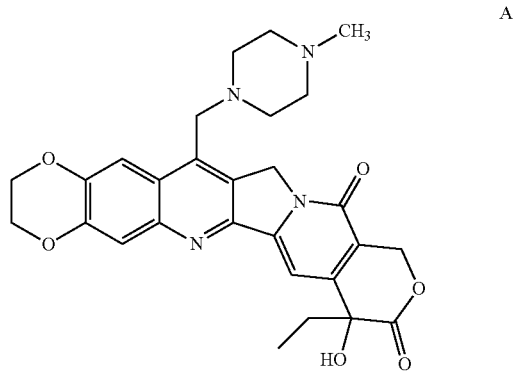 [SMILES: CCC1(O)C(=O)OCc2c1cc1n(c2=O)Cc2c-1nc1cc3c(cc1c2CN1CCN(C)CC1)OCCO3]

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; and 5,491,237.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Suitably, the pharmaceutically active compounds of the invention are used in combination with a VEGFR inhibitor, suitably 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt thereof, which is disclosed and claimed in in International Application No. PCT/US01/49367, having an International filing date of Dec. 19, 2001, International Publication Number WO02/059110 and an International Publication date of Aug. 1, 2002, the entire disclosure of which is hereby incorporated by reference, and which is the compound of Example 69. 5-[[4-[(2,3-dimethyl-2H-indazol-6-yl)methylamino]-2-pyrimidinyl]amino]-2-methylbenzenesulfonamide can be prepared as described in International Application No. PCT/US01/49367.

Suitably, 5-[[4-[(2,3-dimethyl-2H-indazol-6-yl)methylamino]-2-pyrimidinyl]amino]-2-methylbenzenesulfonamide is in the form of a monohydrochloride salt. This salt form can be prepared by one of skill in the art from the description in International Application No. PCT/US01/49367, having an International filing date of Dec. 19, 2001.

5-[[4-[(2,3-dimethyl-2H-indazol-6-yl)methylamino]-2-pyrimidinyl]amino]-2-methylbenzenesulfonamide is sold commercially as the monohydrochloride salt and is known by the generic name pazopanib and the trade name Votrient®.

Pazopanib is implicated in the treatment of cancer and ocular diseases/angiogenesis. Suitably the present invention relates to the treatment of cancer and ocular diseases/angiogenesis, suitably age-related macular degeneration, which method comprises the administration of a compound of Formula (I) alone or in combination with pazopanib.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, PDK1 and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; Pearce, L. R et al. Nature Reviews Molecular Cell Biology (2010) 11, 9-22. and Martinez-Iacaci, L., et al, Int. J. Cancer (2000), 88(1), 44-52.

Suitably, the pharmaceutically active compounds of the invention are used in combination with a MEK inhibitor. Suitably, N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, which is disclosed and claimed in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference. N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, can be prepared as described in United States Patent Publication No. US 2006/0014768, Published Jan. 19, 2006, the entire disclosure of which is hereby incorporated by reference.

Suitably, the pharmaceutically active compounds of the invention are used in combination with a B-Raf inhibitor. Suitably, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed, in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4-yl]-2-fluorophenyl}-2,6-difluorobenzenesulfonamide can be prepared as described in International Application No. PCT/US2009/042682.

Suitably, the pharmaceutically active compounds of the invention are used in combination with an Akt inhibitor. Suitably, N-{(1S)-2-amino-1-[(3,4-difluorophenyl)methyl]ethyl}-5-chloro-4-(4-chloro-1-methyl-1H-pyrazol-5-yl)-2-furancarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3,4-difluorophenyl)methyl]ethyl}-5-chloro-4-(4-chloro-1-methyl-1H-pyrazol-5-yl)-2-furancarboxamide is the compound of example 224 and can be prepared as described in International Application No. PCT/US2008/053269.

Suitably, the pharmaceutically active compounds of the invention are used in combination with an Akt inhibitor. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3-fluorophenyl)methyl]ethyl}-5-chloro-4-(4-chloro-1-methyl-1H-pyrazol-5-yl)-2-thiophenecarboxamide is the compound of example 96 and can be prepared as described in International Application No. PCT/US2008/053269. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Inhibitors of Phosphotidylinositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha, beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of Formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat Acad. Sci. U.S.A.* 97(18): 10014-10019 (2000)), and are included as cell cycle signaling inhibitors. Histone deacetylase (HDAC) inhibitors are implicated in the transcriptional activation of p21WAF1/CIP1 (Vigushin et al., *Anticancer Drugs*, 13(1): 1-13 (January 2002)), and are suitable cell cycle signaling inhibitors for use in combination herein.

Examples of Such HDAC Inhibitors Include:

1. Vorinostat, including pharmaceutically acceptable salts thereof. Marks et al., *Nature Biotechnology* 25, 84 to 90 (2007); Stenger, *Community Oncology* 4, 384-386 (2007).

Vorinostat has the following chemical structure and name:

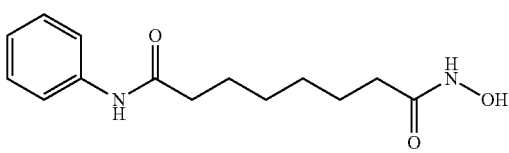 [SMILES: O=C(CCCCCCC(=O)Nc1ccccc1)NO]

N-hydroxy-N-phenyl-octanediamide

2. Romidepsin, including pharmaceutically acceptable salts thereof. Vinodhkumar et al., *Biomedicine & Pharmacotherapy* 62 (2008) 85-93.

Romidepsin, has the following chemical structure and name:

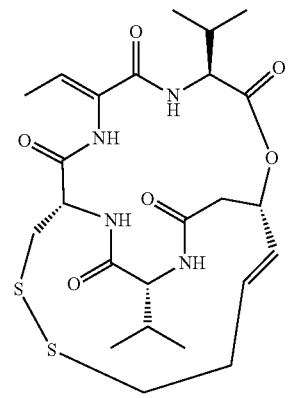 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. *Drugs of the Future* 32(4): 315-322 (2007).

Panobinostat, has the following chemical structure and name:

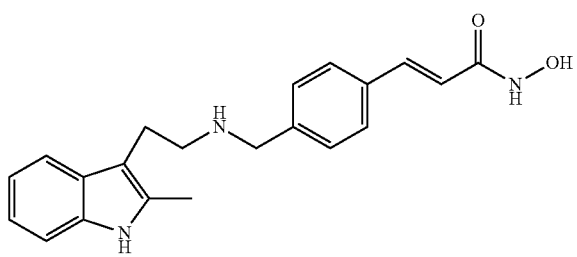 [SMILES: Cc1[nH]c2ccccc2c1CCNCc1ccc(/C=C/C(=O)NO)cc1]

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).

Valproic acid, has the following chemical structure and name:

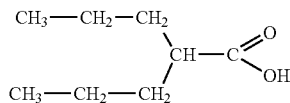

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

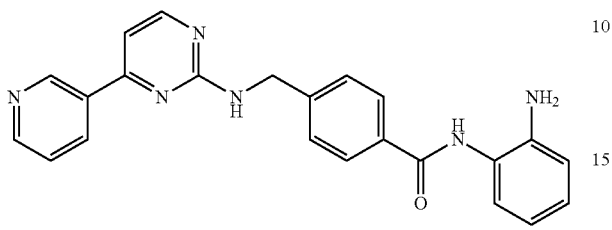

N-(2-Aminophenyl)-4-[[(4-pyridin-3-ylpyrimidin-2-yl)amino]methyl] benzamide

Further examples of such HDAC inhibitors are included in Bertrand European Journal of Medicinal Chemistry 45, (2010) 2095-2116, particularly the compounds of table 3 therein as indicated below.

| Hydroxamic acids | |
|---|---|
| 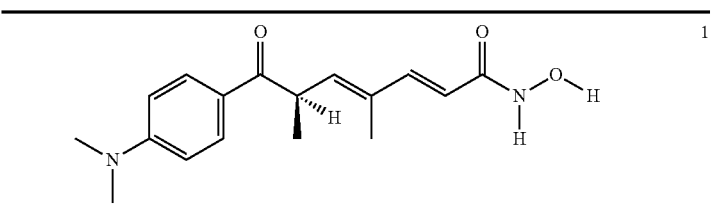 Trichostatine A (TSA), | 1 |
| 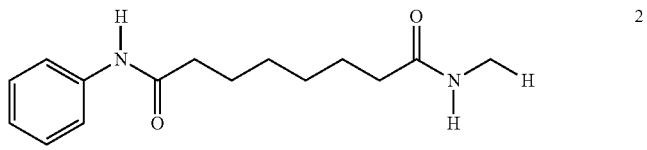 SAHA, | 2 |
| 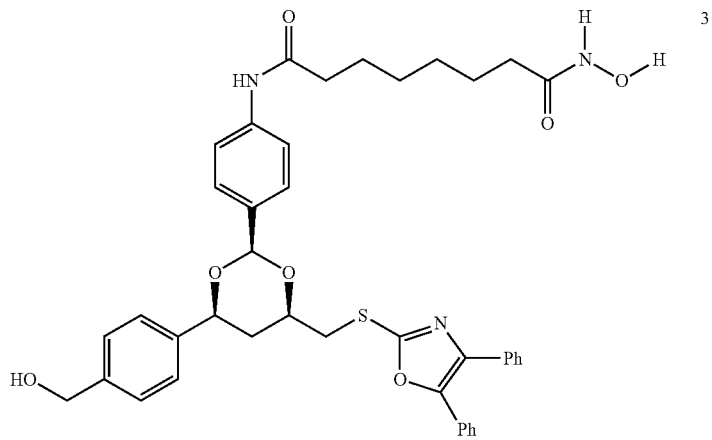 Tubacin, | 3 |

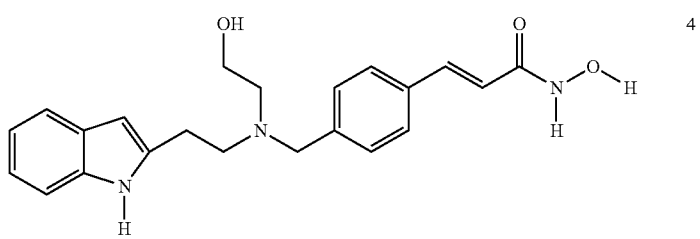
LAQ824,
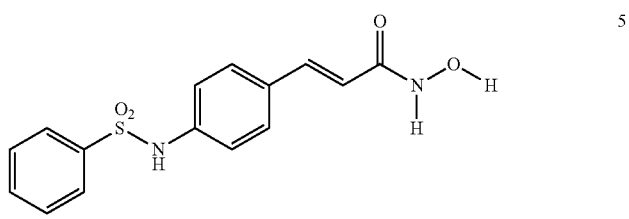
Sulfonamide,
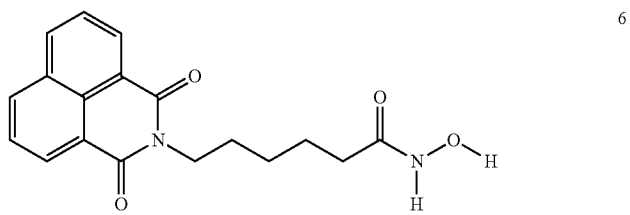
Scriptaid,
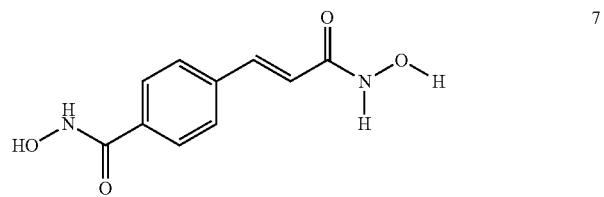
CBHA,
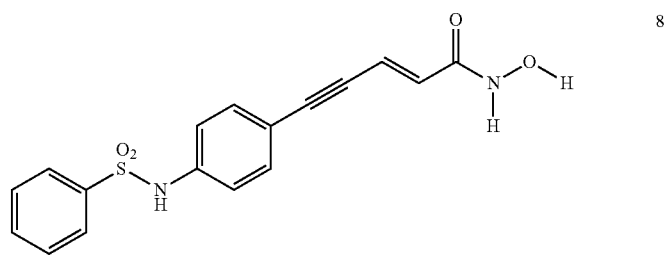
Oxamflatin,

| Cyclic tetrapeptides |
|---|
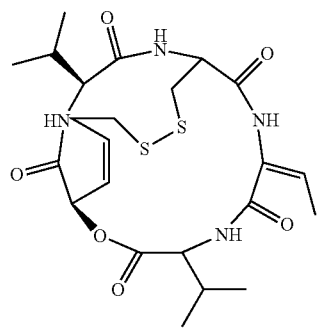 [SMILES: C/C=C1/NC(=O)C2CSSCC/C=C\[C@@H](OC(=O)C(C(C)C)NC1=O)C(=O)N[C@@H](C(C)C)C(=O)N2]
FK228,
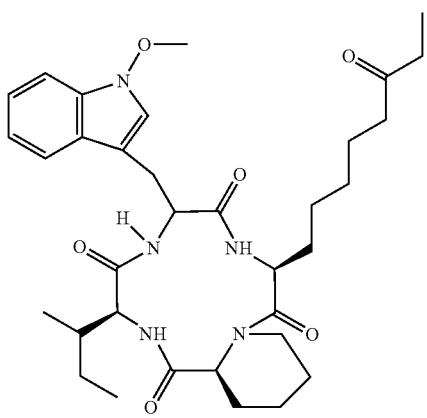 [SMILES: CCC(=O)CCCCC[C@@H]1NC(=O)C(Cc2cn(OC)c3ccccc23)NC(=O)[C@H](C(C)CC)NC(=O)[C@@H]2CCCCN2C1=O]
Apicidin,
| Short chain carboxylic acids |
|---|
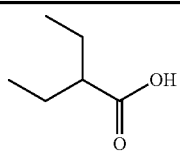
Valproic acid,
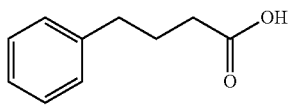 [SMILES: O=C(O)CCCc1ccccc1]
Phenylbutyric acid,
| Benzamides |
|---|
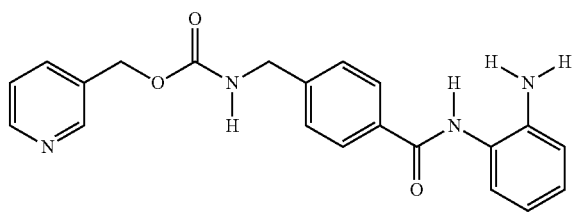 [SMILES: Nc1ccccc1NC(=O)c1ccc(CNC(=O)OCc2cccnc2)cc1]
MS-275,

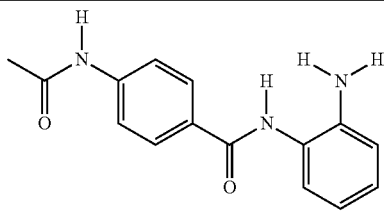

CI-994,

Keto derivatives

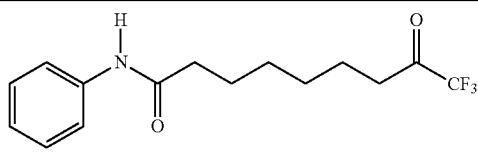

Trifluorométhyl cétone,

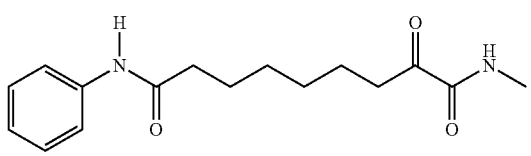 [SMILES: CNC(=O)C(=O)CCCCCCC(=O)Nc1ccccc1]

alpha-cétoamide,

Proteasome inhibitors are drugs that block the action of proteasomes, cellular complexes that break down proteins, like the p53 protein. Several proteasome inhibitors are marketed or are being studied in the treatment of cancer. Suitable proteasome inhibitors for use in combination herein include:
1. Bortezomib (Velcade®), including pharmaceutically acceptable salts thereof. Adams J, Kauffman M (2004), *Cancer Invest* 22 (2): 304-11.
Bortezomib has the following chemical structure and name.

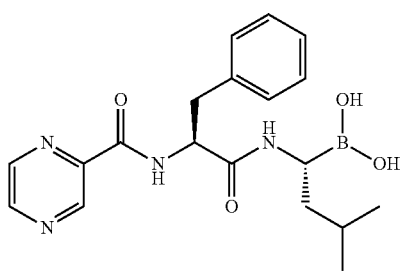 [SMILES: CC(C)C[C@H](NC(=O)[C@H](Cc1ccccc1)NC(=O)c1cnccn1)B(O)O]

[(1R)-3-methyl-1-({(2S)-3-phenyl-2-[(pyrazin-2-ylcarbonyl)amino]propanoyl}amino)butyl]boronic acid 2. Disulfiram, including pharmaceutically acceptable salts thereof. Bouma et al. (1998). *J. Antimicrob. Chemother.* 42 (6): 817-20.

Disulfiram has the following chemical structure and name.

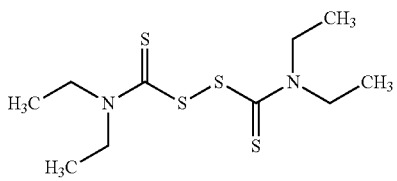 [SMILES: CCN(CC)C(=S)SSC(=S)N(CC)CC]

1,1',1'',1'''-[disulfanediylbis(carbonothioylnitrilo)]
tetraethane

3. Epigallocatechin gallate (EGCG), including pharmaceutically acceptable salts thereof. Williamson et al., (December 2006), *The Journal of Allergy and Clinical Immunology* 118 (6): 1369-74.

Epigallocatechin gallate has the following chemical structure and name.

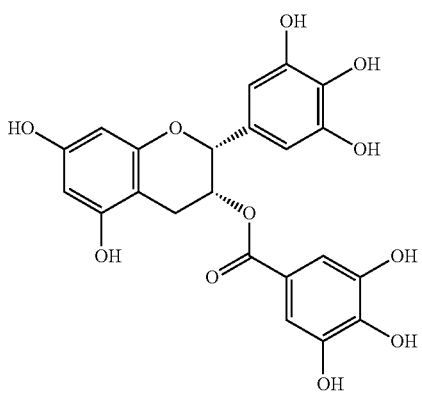 [SMILES: O=C(O[C@@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)chroman-3-yl]3,4,5-trihydroxybenzoate 4. Salinosporamide A, including pharmaceutically acceptable salts thereof. Feling et at, (2003), *Angew. Chem. Int. Ed. Engl.* 42 (3): 355-7.

Salinosporamide A has the following chemical structure and name.

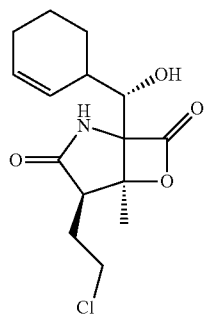 [SMILES: C[C@@]12OC(=O)C1([C@@H](O)C1C=CCCC1)NC(=O)[C@@H]2CCCl]

(4R,5S)-4-(2-chloroethyl)-1-((1S)-cyclohex-2-enyl(hydroxy)methyl)-5-methyl-6-oxa-2-azabicyclo3.2.0 heptane-3,7-dione 5. Carfilzomib, including pharmaceutically acceptable salts thereof. Kuhn D J, et al, Blood, 2007, 110:3281-3290.

Carfilzomib has the following chemical structure and name.

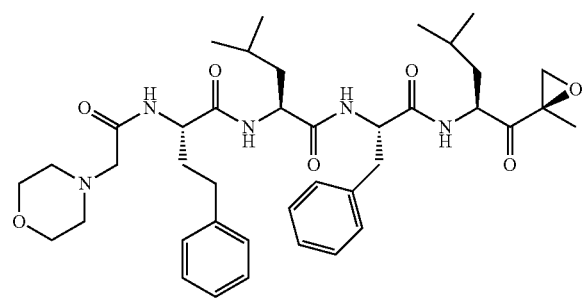 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

(S)-4-methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide The 70 kilodalton heat shock proteins (Hsp70s) and 90 kilodalton heat shock proteins (Hsp90s) are a family of ubiquitously expressed heat shock proteins. Hsp70s and Hsp90s are over expressed certain cancer types. Several Hsp70s and Hsp90s inhibitors are being studied in the treatment of cancer. Suitable Hsp70s and Hsp90s inhibitors for use in combination herein include:

1. 17-AAG(Geldanamycin), including pharmaceutically acceptable salts thereof. Jia W et al. Blood. 2003 Sep. 1; 102(5):1824-32.

17-AAG(Geldanamycin) has the following chemical structure and name.

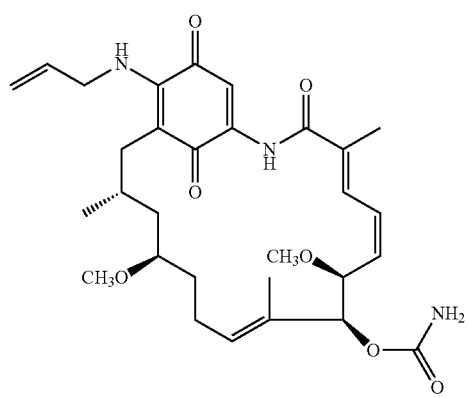

17-(Allylamino)-17-demethoxygeldanamycin

2. Radicicol, including pharmaceutically acceptable salts thereof. (Lee et al., Mol Cell Endocrinol. 2002, 188, 47-54)

Radicicol has the following chemical structure and name.

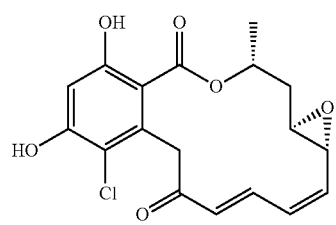

(1aR,2Z,4E,14R,15aR)-8-chloro-9,11-dihydroxy-14-methyl-15,15a-dihydro-1aH-benzo[c]oxireno[2,3-k][1]oxacyclotetradecine-6,12(7H,14H)-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.

D. A. Tennant et. al., Nature Reviews, 2010, 267.

P. Leder, et. al., Cancer Cell, 2006, 9, 425.

High levels of fatty acid synthase (FAS) have been found in cancer precursor lesions. Pharmacological inhibition of FAS affects the expression of key oncogenes involved in both cancer development and maintenance. Alli et al. *Oncogene* (2005) 24, 39-46. doi:10.1038

Inhibitors of cancer metabolism, including inhibitors of LDH-A and inhibitors of fatty acid biosynthesis (or FAS inhibitors), are suitable for use in combination with the compounds of this invention.

Additional examples of a further active ingredient or ingredients (anti-neoplastic agent) for use in combination or co-administered with the presently invented CD73 inhibiting compounds are anti-PD-L1 agents.

Anti-PD-L1 antibodies and methods of making the same are known in the art.

Such antibodies to PD-L1 may be polyclonal or monoclonal, and/or recombinant, and/or humanized.

Exemplary PD-L1 antibodies are disclosed in:
U.S. Pat. No. 8,217,149; Ser. No. 12/633,339;
U.S. Pat. No. 8,383,796; Ser. No. 13/091,936;
U.S. Pat. No. 8,552,154; Ser. No. 13/120,406;
US patent publication No. 20110280877; Ser. No. 13/068,337;
US Patent Publication No. 20130309250; Ser. No. 13/892,671;
WO2013019906;
WO2013079174;
U.S. application Ser. No. 13/511,538 (filed Aug. 7, 2012), which is the US National Phase of International Application No. PCT/US10/58007 (filed 2010);
and
U.S. application Ser. No. 13/478,511 (filed May 23, 2012).

Additional exemplary antibodies to PD-L1 (also referred to as CD274 or B7-H1) and methods for use are disclosed in U.S. Pat. No. 7,943,743; US20130034559, WO2014055897, U.S. Pat. Nos. 8,168,179; and 7,595,048. PD-L1 antibodies are in development as immuno-modulatory agents for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149.

In another embodiment, the antibody to PD-L1 is an antibody disclosed in U.S. application Ser. No. 13/511,538. In another embodiment, the anti-PD-L1 antibody comprises the CDRs of an antibody disclosed in U.S. application Ser. No. 13/511,538.

In another embodiment, the antibody to PD-L1 is an antibody disclosed in application Ser. No. 13/478,511. In another embodiment, the anti-PD-L1 antibody comprises the CDRs of an antibody disclosed in U.S. application Ser. No. 13/478,511.

In one embodiment, the anti-PD-L1 antibody is BMS-936559 (MDX-1105). In another embodiment, the anti-PD-L1 antibody is MPDL3280A (RG7446). In another embodiment, the anti-PD-L1 antibody is MED14736.

Additional examples of a further active ingredient or ingredients (anti-neoplastic agent) for use in combination or co-administered with the presently invented CD73 inhibiting compounds are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the vario us aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 6; nivolumab, a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MED14736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of P13k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of a further active ingredient or ingredients (anti-neoplastic agent) for use in combination or co-administered with the presently invented CD73 inhibiting compounds are immuno-modulators.

As used herein "immuno-modulators" refer to any substance including monoclonal antibodies that affects the immune system. The ICOS binding proteins of the present invention can be considered immune-modulators. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, OX-40 antibodies, PD-L1 antibodies, LAG3 antibodies, TIM-3 antibodies, 41BB antibodies and GITR antibodies.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

CD134, also known as ANTIBODIES TO OX40, is a member of the TNFR-superfamily of receptors which is not constitutively expressed on resting nave T cells, unlike CD28. ANTIBODIES TO OX40 is a secondary costimulatory molecule, expressed after 24 to 72 hours following activation; its ligand, ANTIBODIES TO OX40L, is also not expressed on resting antigen presenting cells, but is following their activation. Expression of ANTIBODIES TO OX40 is dependent on full activation of the T cell; without CD28, expression of ANTIBODIES TO OX40 is delayed and of fourfold lower levels. OX-40 antibodies, OX-40 fusion proteins and methods of using them are disclosed in U.S. Pat. Nos. 7,504,101; 7,758,852; 7,858,765; 7,550,140; 7,960,515; WO2012027328; WO2013028231.

Additional examples of a further active ingredient or ingredients (anti-neoplastic agent) for use in combination or co-administered with the presently invented CD73 inhibiting compounds are Toll-like Receptor 4 (TLR4) antagonists.

Aminoalkyl glucosaminide phosphates (AGPs) are known to be useful as vaccine adjuvants and immunostimulatory agents for stimulating cytokine production, activating macrophages, promoting innate immune response, and augmenting antibody production in immunized animals. Aminoalkyl glucosaminide phosphates (AGPs) are synthetic ligands of the Toll-like Receptor 4 (TLR4). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. Nos. 7,129,219, 6,525,028 and 6,911,434. Certain AGPs act as agonists of TLR4, while others are recognized as TLR4 antagonists.

Additional examples of a further active ingredient or ingredients (anti-neoplastic agent) for use in combination or co-administered with the presently invented CD73 inhibiting compounds are antibodies to ICOS.

CDRs for murine antibodies to human ICOS having agonist activity are shown in PCT/EP2012/055735 (WO 2012/131004). Antibodies to ICOS are also disclosed in WO 2008/137915, WO 2010/056804, EP 1374902, EP1374901, and EP1125585.

Additional examples of a further active ingredient or ingredients (anti-neoplastic agent) for use in combination or co-administered with the presently invented compound of Formula (I) are STING modulating compounds, CD39 inhibitors and A2a and A2a adenosine antagonists.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; proteasome inhibitors; and inhibitors of cancer metabolism.

The compounds of Formula (I) and pharmaceutically acceptable salts thereof may be co-administered with at least one other active agent known to be useful for treating beta hemoglobinopathies, such as sickle cell disease, sickle cell anemia, and beta thalassemia.

Examples of a further active ingredient or ingredients for use in combination or co-administered with the presently invented combinations is hydroxyurea.

Compositions

The pharmaceutically active compounds within the scope of this invention are useful as selective DNMT1 inhibitors in mammals, particularly humans, in need thereof.

The present invention provides a pharmaceutical composition containing a pharmaceutically acceptable excipient and an effective amount of a compound of Formula (I) as described above or a pharmaceutically acceptable salt thereof.

The present invention provides a process for preparing a pharmaceutical composition containing a pharmaceutically acceptable excipient and an effective amount of a compound of Formula (I) as described above or a pharmaceutically acceptable salt thereof, which process comprises bringing the compound of Formula (I) or a pharmaceutically acceptable salt thereof into association with a pharmaceutically acceptable excipient.

The present invention therefore provides a method of treating cancer, pre-cancerous syndromes and other conditions requiring DNMT1 inhibition, which comprises administering an effective amount of a compound of Formula (I) or a pharmaceutically acceptable salt thereof. The compounds of Formula (I) also provide for a method of treating the above indicated disease states because of their demonstrated ability to act as DNMT1 inhibitors. The drug may be administered to a patient in need thereof by any conventional route of administration, including, but not limited to, intravenous, intramuscular, oral, topical, subcutaneous, intradermal, intraocular and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical compositions are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-500 mg/kg of active compound, preferably 0.01-100 mg/kg. When treating a human patient in need of a DNMT1 inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.5 to 3500 mg of active compound. Suitably oral dosage units for human administration preferably contain from 0.5 to 1,000 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular DMNT1 inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing DNMT1 inhibitory activity in mammals, including humans, comprises administering to a subject in need of such activity an effective DNMT1 inhibiting amount of a pharmaceutically active compound of the present invention.

The invention also provides for the use of a compound of Formula (I) or a pharmaceutically acceptable salt thereof in the manufacture of a medicament for use as a DNMT1 inhibitor.

The invention also provides a compound of Formula (I) or a pharmaceutically acceptable salt thereof for use in therapy.

The invention also provides a compound of Formula (I) or a pharmaceutically acceptable salt thereof for use in treating cancer and pre-cancerous syndromes.

The invention also provides the use of a compound of Formula (I) or a pharmaceutically acceptable salt thereof in the manufacture of a medicament for treating cancer and pre-cancerous syndromes.

The invention also provides a compound of Formula (I) or a pharmaceutically acceptable salt thereof for use in treating a beta-hemoglobinopathy such as sickle cell disease, sickle cell anemia, or beta-thalassemia.

The invention also provides the use of a compound of Formula (I) or a pharmaceutically acceptable salt thereof in the manufacture of a medicament for treating a beta-hemoglobinopathy such as sickle cell disease, sickle cell anemia, or beta-thalassemia.

The invention also provides for a pharmaceutical composition for use as a DNMT1 inhibitor which comprises a compound of Formula (I) or a pharmaceutically acceptable salt thereof and a pharmaceutically acceptable carrier.

The invention also provides for a pharmaceutical composition for use in the treatment of cancer which comprises a compound of Formula (I) or a pharmaceutically acceptable salt thereof and a pharmaceutically acceptable carrier.

In addition, the pharmaceutically active compounds of the present invention can be co-administered with further active ingredients, such as other compounds known to treat cancer, or compounds known to have utility when used in combination with a DNMT1 inhibitor.

The invention also provides a pharmaceutical composition comprising from 0.5 to 1,000 mg of a compound of Formula (I) or pharmaceutically acceptable salt thereof and from 0.5 to 1,000 mg of a pharmaceutically acceptable excipient.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

The following Examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Example 1

2-[(6-amino-3,5-dicyano-4-ethylpyridin-2-yl)sulfanyl]-2-phenylacetamide

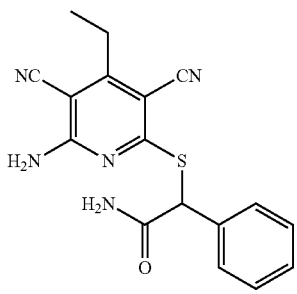 [SMILES: CCc1c(C#N)c(N)nc(SC(C(N)=O)c2ccccc2)c1C#N]

This compound was purchased from a commercial source; CAS 184530-72-1. This compound may also be prepared according to the method of V. D. Dyachenko, S. G. Krivokolysko, V. P. Litvinov, Chemistry of Heterocyclic Compounds, Vol. 32, No. 8, 1996.

Example 2

(R)-[(6-amino-3,5-dicyano-4-ethylpyridin-2-yl)sulfanyl]-2-phenylacetamide

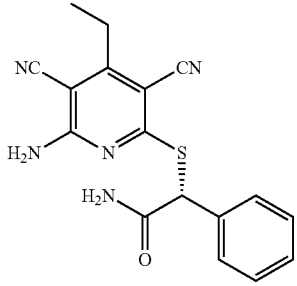 [SMILES: CCc1c(C#N)c(N)nc(S[C@@H](C(N)=O)c2ccccc2)c1C#N]

Racemic 2-[(6-amino-3,5-dicyano-4-ethylpyridin-2-yl)sulfanyl]-2-phenylacetamide (39 mg) was dissolved in 4 mg portions in 1000 volumes using 1.30 mL of boiling methanol with sonication, followed by 1.30 mL of ethanol, followed by 1.30 mL of n-heptane for each 4 mg. Carried out about 10 chiral preps at 4 mg each (4 mL each). The sample was resolved by chiral HPLC using a Chiralpack, IC, 5 microns, (21 mm×250 mm) eluting with 70:30 n-heptane:methanol (20 mL/min). Collected a total of about 300 mL of product solution which was concentrated to near dryness and then the product was dried at 40° C. under high vacuum to afford (R)-2-[(3,5-dicyano-4-ethyl-6-morpholino-2-pyridyl)sulfanyl]-2-phenyl-acetamide (18 mg) as a white solid. LCMS m/z=338.3 [M+H]$^+$. 98% ee chiral purity. Optical Rotation: −336 degrees (C=0.1, DMSO-$d_6$, 23° C.). $^1$H NMR (DMSO-$d_6$) δ ppm 7.91 (br. s., 2H), 7.75 (s, 1H), 7.59 (d, J=6.8 Hz, 2H), 7.27-7.40 (m, 4H), 5.56 (s, 1H), 2.69 (q, J=7.4 Hz, 2H), 1.18 (t, J=7.6 Hz, 3H).

Example 3

2-{[3,5-dicyano-6-(dimethylamino)-4-ethylpyridin-2-yl]sulfanyl}-2-phenylacetamide

Step 1: Ammonium 3,5-dicyano-4-ethyl-6-hydroxypyridin-2-olate

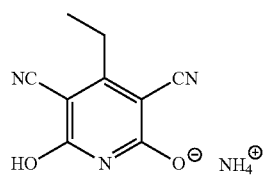

To a solution of 2-cyanoacetamide (28.6 g, 0.34 mol) in water (190 mL) was added ammonium hydroxide (25%, aqueous, 10 mL) and propionaldehyde (10 g, 0.17 mol). Then the reaction solution was stirred at room temperature overnight. The solid was filtered and washed with cold methanol, then dried under reduced pressure to give ammonium 3,5-dicyano-4-ethyl-6-hydroxypyridin-2-olate (12 g, 34.3%) as a white solid. LCMS m/z=187.9 [M]$^−$.

Step 2: 2,6-dichloro-4-ethylpyridine-3,5-dicarbonitrile

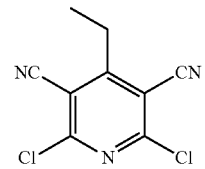

Ammonium 3,5-dicyano-4-ethyl-6-hydroxypyridin-2-olate (12 g, 58.2 mmol) was added slowly to POCl$_3$ (100 mL) in a sealed tube. The mixture was stirred at 150° C. for 15 hours. The solvent was removed under reduced pressure. The residue was poured into ice-water. The solid was filtered and dried to give 2,6-dichloro-4-ethylpyridine-3,5-dicarbonitrile (10.8 g, 83%) as a light yellow solid. $^1$H NMR (400 MHz, CDCl$_3$) δ ppm 3.13 (d, J=7.7 Hz, 2H), 1.42 (t, J=7.7 Hz, 3H).

Step 3: 2-Chloro-6-(dimethylamino)-4-ethylpyridine-3,5-dicarbonitrile

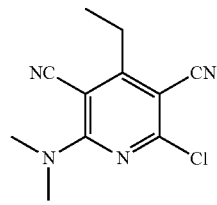 [SMILES: CCc1c(C#N)c(Cl)nc(N(C)C)c1C#N]

To a solution of 2,6-dichloro-4-ethylpyridine-3,5-dicarbonitrile (1 g, 4.44 mmol) in N,N-dimethylformamide (10 mL) was added dimethylamine (2 M in tetrahydrofuran, 2.2 mL, 4.44 mmol) and triethylamine (0.62 mL, 4.44 mmol). The reaction was stirred at room temperature for 5 minutes. Water was added to the reaction. The solid was filtered and purified by flash column chromatography eluted by petroleum ether:ethyl acetate=3:1 to give 2-chloro-6-(dimethylamino)-4-ethylpyridine-3,5-dicarbonitrile (900 mg, 87%). LCMS m/z=234.9 [M+H]⁺.

Step 4: 2-hydroxy-2-phenylacetamide

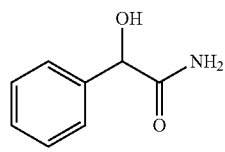 [SMILES: NC(=O)C(O)c1ccccc1]

To a solution of 2-hydroxy-2-phenylacetic acid (20 g, 0.13 mol) in MeOH (140 mL) was added CH₃COCl (27.9 g, 0.36 mol) dropwise. Then the solution was stirred at room temperature for 20 hours. The resulting solution was concentrated to give solid which was dissolved in MeOH (60 mL). NH₃.H₂O (140 mL) was added. The mixture was stirred at 4° C. for 18 hours. The mixture was concentrated to give 2-hydroxy-2-phenylacetamide (20 g, 100% yield) as a white solid. LCMS m/z=152.0 [M+H]⁺.

Step 5: 2-amino-2-oxo-1-phenylethyl methanesulfonate

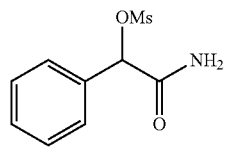 [SMILES: CS(=O)(=O)OC(C(N)=O)c1ccccc1]

To a solution of 2-hydroxy-2-phenylacetamide (20 g, 0.13 mmol) in CH₃—CN (400 mL) was added triethylamine (36 mL, 0.26 mmol) and MsCl (18.2 g, 0.16 mol). Then the mixture was stirred at 40° C. for 6 hours. The solvent was removed and the residue was resolved with DCM and H₂O, the organic layer was washed with brine, dried and concentrated to give 2-amino-2-oxo-1-phenylethyl methanesulfonate (15 g) as a white solid. LCMS m/z=247 [M+Na]⁺.

Step 6: 2-{[3,5-dicyano-6-(dimethylamino)-4-ethylpyridin-2-yl]sulfanyl}-2-phenylacetamide

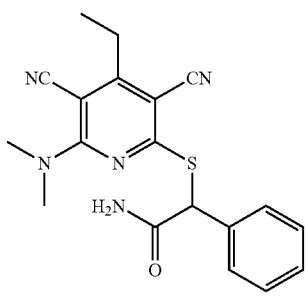 [SMILES: CCc1c(C#N)c(SC(C(N)=O)c2ccccc2)nc(N(C)C)c1C#N]

A solution of 2-chloro-6-(dimethylamino)-4-ethylpyridine-3,5-dicarbonitrile (450 mg, 1.92 mmol) and KSAc (263 mg, 2.31 mmol) in N,N-dimethylformamide (20 mL) was stirred at room temperature for 30 minutes then 2-amino-2-oxo-1-phenylethyl methanesulfonate (528 mg, 1.06 mmol) and triethylamine (0.53 mL, 3.84 mmol) were added to the solution. The mixture was stirred at room temperature overnight then diluted with water (20 mL). The precipitated solid was collected by filtration and purified by silica gel column chromatography (eluted by DCM:MeOH=20:1) to give 2-{[3,5-dicyano-6-(dimethylamino)-4-ethylpyridin-2-yl]sulfanyl}-2-phenylacetamide (400 mg, 57%). LCMS m/z=365.9 [M+H]⁺. ¹H NMR (400 MHz, CDCl₃) δ ppm 7.47-7.43 (m, 2H), 7.42-7.34 (m, 3H), 6.55 (b r s, 1H), 5.60 (br s, 1H), 5.43 (s, 1H), 3.40 (s, 6H), 2.92 (q, J=7.6 Hz, 2H), 1.32 (t, J=7.6 Hz, 3H).

Example 4

2-((3,5-dicyano-4-cyclopropyl-6-(1,4-diazepan-1-yl)pyridin-2-yl)thio)-2-phenylacetamide Step 1: Ammonium 3,5-dicyano-4-cyclopropyl-6-hydroxypyridin-2-olate

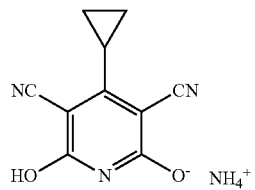 [SMILES: N#Cc1c([O-])nc(O)c(C#N)c1C1CC1 ; [NH4+]]

To a mixture of cyclopropanecarbaldehyde (47.3 g, 562 mmol) in H₂O (320 mL) was added NH₃.H₂O (16 mL) and 2-cyanoacetamide (20 g, 285 mmol). The mixture was stirred at room temperature overnight. The solid was filtered and washed with cold MeOH to give ammonium 3,5-dicyano-4-cyclopropyl-6-hydroxypyridin-2-olate as a white solid (20 g, 32%). LCMS m/z=199.9 [M]⁻.

Step 2: 2,6-Dichloro-4-cyclopropylpyridine-3,5-dicarbonitrile

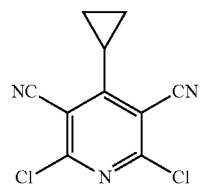 [SMILES: N#Cc1c(Cl)nc(Cl)c(C#N)c1C1CC1]

Ammonium 3,5-dicyano-4-cyclopropyl-6-hydroxypyridin-2-olate (20 g, 91.7 mmol) was added to POCl₃ (500 mL), then the mixture was stirred at 150° C. in a sealed tube overnight. The solvent was removed under vacuo. The residue was poured into ice-water. The solid formed was filtered, washed with water, dried to give 2,6-dichloro-4-cyclopropylpyridine-3,5-dicarbonitrile (21 g) as a yellow solid. ¹H NMR (400 MHz, CDCl₃) δ ppm 2.36-2.27 (m, 1H), 1.51-1.44 (m, 4H).

Step 3: tert-butyl 4-(6-chloro-3,5-dicyano-4-cyclopropylpyridin-2-yl)-1,4-diazepane-1-carboxylate

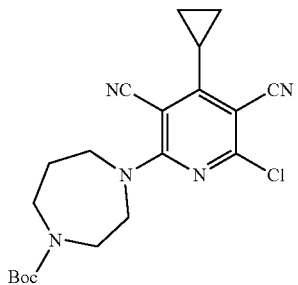 [SMILES: CC(C)(C)OC(=O)N1CCCN(c2nc(Cl)c(C#N)c(C3CC3)c2C#N)CC1]

To a solution of 2,6-dichloro-4-cyclopropylpyridine-3,5-dicarbonitrile (2.37 g, 10 mmol) in N,N-dimethylformamide (50 mL) was added tert-butyl 1,4-diazepane-1-carboxylate (2 g, 10 mmol) and triethylamine (1.4 mL, 10 mmol). Then the mixture was stirred at room temperature for 5 minutes. Water was added to the reaction, extracted with ethyl acetate. The organic layer was washed with water and brine, dried, concentrated and purified by flash column chromatography (eluted by petroleum ether:ethyl acetate=5:1) to give tert-butyl 4-(6-chloro-3,5-dicyano-4-cyclopropylpyridin-2-yl)-1,4-diazepane-1-carboxylate (3.4 g, 85%) as a white solid. LCMS m/z=424.0 [M+H]$^+$.

Step 4: tert-butyl 4-(6-((2-amino-2-oxo-1-phenylethyl)thio)-3,5-dicyano-4-cyclopropylpyridin-2-yl)-1,4-diazepane-1-carboxylate

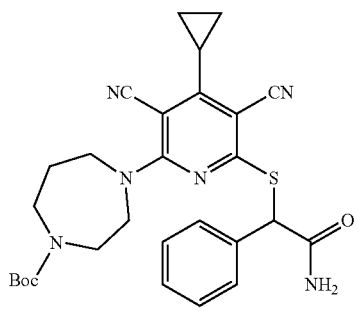 [SMILES: CC(C)(C)OC(=O)N1CCCN(c2nc(SC(C(N)=O)c3ccccc3)c(C#N)c(C3CC3)c2C#N)CC1]

tert-Butyl 4-(6-chloro-3,5-dicyano-4-cyclopropylpyridin-2-yl)-1,4-diazepane-1-carboxylate (600 mg, 1.5 mmol) and KSAc (205 mg, 1.8 mmol) in N,N-dimethylformamide (15 mL) were stirred at room temperature for 30 minutes. 2-Amino-2-oxo-1-phenylethyl methanesulfonate (synthesis described in example 3 step 5, 377 mg, 1.6 mmol) was added followed by triethylamine (0.42 mL, 3 mmol), then the mixture was stirred at room temperature for 2 hours. Water was added, the solid was stirred, filtered and purified by flash column chromatography (eluted by petroleum ether:ethyl acetate=2:3) to give tert-butyl 4-(6-((2-amino-2-oxo-1-phenylethyl)thio)-3,5-dicyano-4-cyclopropylpyridin-2-yl)-1,4-diazepane-1-carboxylate (300 mg, 38%) as white solid. LCMS m/z=533.0 [M+H]$^+$.

Step 5: 2-((3,5-dicyano-4-cyclopropyl-6-(1,4-diazepan-1-yl)pyridin-2-yl)thio)-2-phenylacetamide

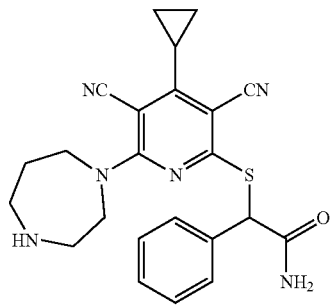

To a solution of tert-butyl 4-(6-((2-amino-2-oxo-1-phenylethyl)thio)-3,5-dicyano-4-cyclopropylpyridin-2-yl)-1,4-diazepane-1-carboxylate (300 mg, 0.56 mmol) in DCM (10 mL) was added trifluoroacetic acid (1 mL). The reaction solution was stirred at room temperature overnight. The solvent was washed with saturated aqueous NaHCO$_3$ solution and brine, concentrated and purified by flash column chromatography (eluted by DCM:MeOH=10:1) to give 2-((3,5-dicyano-4-cyclopropyl-6-(1,4-diazepan-1-yl)pyridin-2-yl)thio)-2-phenylacetamide (170 mg, 70%) as a white solid. LCMS m/z=433.0 [M+H]$^+$. $^1$H NMR (400 MHz, CDCl$_3$) δ ppm 7.46-7.33 (m, 5H), 6.66 (br s, 1H), 5.78 (br s, 1H), 5.34 (s, 1H), 4.10-3.88 (m, 4H), 3.19 (t, J=5.3 Hz, 2H), 2.99-2.91 (m, 2H), 2.12-1.94 (m, 4H), 1.33-1.24 (m, 2H), 1.15-1.06 (m, 2H).

Example 5

2-{[3,5-dicyano-4-cyclopropyl-6-(4-ethyl-1,4-diazepan-1-yl)pyridin-2-yl]sulfanyl}-2-phenylacetamide

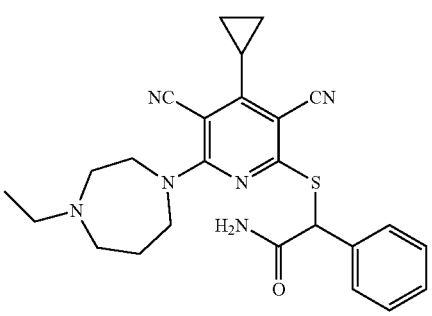 [SMILES: CCN1CCCN(c2nc(SC(C(N)=O)c3ccccc3)c(C#N)c(C3CC3)c2C#N)CC1]

To a solution of 2-((3,5-dicyano-4-cyclopropyl-6-(1,4-diazepan-1-yl)pyridin-2-yl)thio)-2-phenylacetamide (synthesis described in example 4, step 5, 120 mg, 0.28 mmol) in DCM (5 mL) was added CH$_3$CHO (37 mg, 0.84 mmol) and NaBH(OAc)$_3$ (119 mg, 0.56 mmol). The reaction was stirred at room temperature overnight. The resulting solution was washed with saturated aqueous NaHCO$_3$ solution, water and brine. The solvent was removed and the residue was purified by flash column chromatography (eluted by DCM:MeOH=10:1) to give 2-{[3,5-dicyano-4-cyclopropyl-6-(4-ethyl-1,4-diazepan-1-yl)pyridin-2-yl]sulfanyl}-2-phenylacetamide (17 mg, 13%) as a white solid. LCMS m/z=460.8 [M+H]$^+$. $^1$H NMR (400 MHz, CDCl$_3$) δ ppm 7.48-7.31 (m, 5H), 6.64 (br s, 1H), 5.91 (br s, 1H), 5.36 (s, 1H), 4.08-3.84 (m, 4H), 2.97-2.83 (m, 2H), 2.75-2.58 (m, 4H), 2.15-2.01 (m, 3H), 1.31-1.24 (m, 2H), 1.15-1.04 (m, 5H).

Example 6

2-((3,5-dicyano-4-ethyl-6-(4-propyl-1,4-diazepan-1-yl)pyridin-2-yl)thio)-2-phenylacetamide Step 1: 2-[(6-bromo-3,5-dicyano-4-ethyl-2-pyridyl)sulfanyl]-2-phenyl-acetamide

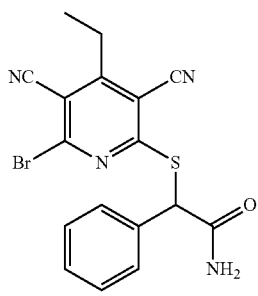 [SMILES: CCc1c(C#N)c(Br)nc(SC(C(N)=O)c2ccccc2)c1C#N]

A stirred suspension of 2-[(6-amino-3,5-dicyano-4-ethyl-2-pyridyl)sulfanyl]-2-phenyl-acetamide (synthesis described in example 2, 150 mg, 0.44 mmol) in dry acetonitrile (8 mL) was treated with copper(II) bromide (168 mg, 0.75 mmol) and tert-butylnitrite (0.09 mL, 0.78 mmol) then heated at 70° C. for 15 minutes under an atmosphere of nitrogen. The product mixture was cooled to ambient temperature, dry loaded onto SiO$_2$ (1 g) and chromatographed on SiO$_2$ (4 g RediSep cartridge) eluting with 20-100% EtOAc/isohexane to give 2-[(6-bromo-3,5-dicyano-4-ethyl-2-pyridyl)sulfanyl]-2-phenyl-acetamide (55 mg, 31% yield) as an off-white solid. LCMS m/z=401.0 [M–H]$^-$.

Step 2: 2-((3,5-dicyano-4-ethyl-6-(4-propyl-1,4-diazepan-1-yl)pyridin-2-yl)thio)-2-phenylacetamide

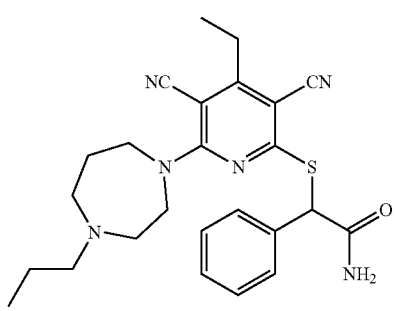 [SMILES: CCCN1CCCN(c2nc(SC(C(N)=O)c3ccccc3)c(C#N)c(CC)c2C#N)CC1]

A solution of 2-[(6-bromo-3,5-dicyano-4-ethyl-2-pyridyl)sulfanyl]-2-phenyl-acetamide (31 mg, 0.08 mmol) in tetrahydrofuran (1 mL) was treated with 1-propyl-1,4-diazepane (0.03 mL, 0.19 mmol) and stirred at room temperature for 2 hours. The product mixture was concentrated and loaded onto SiO$_2$ (0.9 g) and chromatographed on SiO$_2$ (4 g RediSep cartridge, eluting with 0-10% MeOH, 0-0.1% NH$_3$/CH$_2$Cl$_2$) and triturated with diethyl ether to afford 2-[[3,5-dicyano-4-ethyl-6-(4-propyl-1,4-diazepan-1-yl)-2-pyridyl]sulfanyl]-2-phenyl-acetamide (27 mg, 76% yield) as a white solid. LCMS m/z=461.2 [M–H]$^-$. $^1$H NMR (300 MHz, DMSO-d$_6$) δ ppm 7.92 (s, 1H), 7.54-7.45 (m, 2H), 7.43-7.30 (m, 4H), 5.51 (s, 1H), 3.89 (br s, 4H), 2.77 (q, J=7.4 Hz, 4H), 2.68-2.53 (m, 2H), 2.47-2.17 (m, 2H), 1.91 (br s, 2H), 1.42 (br s, 2H), 1.20 (t, J=7.5 Hz, 3H), 0.83 (br t, J=7.3 Hz, 3H).

Example 7

2-{[3,5-dicyano-4-ethyl-6-(4-ethyl-1,4-diazepan-1-yl)pyridin-2-yl]sulfanyl}-2-phenylacetamide

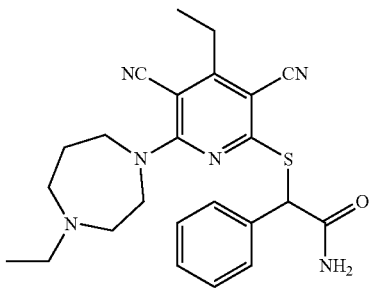 [SMILES: CCc1c(C#N)c(SC(C(N)=O)c2ccccc2)nc(N2CCCN(CC)CC2)c1C#N]

A solution of 2-[(6-bromo-3,5-dicyano-4-ethyl-2-pyridyl)sulfanyl]-2-phenyl-acetamide (synthesis described in example 6, step 1, 32 mg, 0.08 mmol) in tetrahydrofuran (1 mL) was treated with N-ethylhomopiperazinyl (0.03 mL, 0.20 mmol) and stirred at ambient temperature for 2 hours. The product mixture was loaded onto SiO$_2$ (0.9 g) and chromatographed on SiO$_2$ (4 g RediSep cartridge eluting with 0-10% MeOH, 0-0.1% NH$_3$/CH$_2$Cl$_2$) to furnish 2-[[3,5-dicyano-4-ethyl-6-(4-ethyl-1,4-diazepan-1-yl)-2-pyridyl]sulfanyl]-2-phenyl-acetamide (33 mg, 94% yield) as a white solid. LCMS m/z=447.2 [M–H]$^-$. $^1$H NMR (300 MHz, DMSO-d$_6$) δ ppm 7.93 (s, 1H), 7.54-7.42 (m, 2H), 7.47-7.30 (m, 4H), 5.51 (s, 1H), 4.09-3.79 (m, 4H), 3.02-2.64 (m, 8H), 2.02 (br s, 2H), 1.22 (t, J=7.5 Hz, 3H), 1.08 (br t, J=6.8 Hz, 3H).

Example 8

2-{[3,5-dicyano-4-ethyl-6-(5-oxo-1,4-diazepan-1-yl)pyridin-2-yl]sulfanyl}-2-phenylacetamide Step 1: Chloro-4-ethyl-6-(5-oxo-1,4-diazepan-1-yl)pyridine-3,5-dicarbonitrile

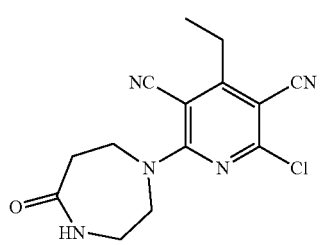 [SMILES: CCc1c(C#N)c(Cl)nc(N2CCNC(=O)CC2)c1C#N]

To a stirred solution of 2,6-dichloro-4-ethylpyridine-3,5-dicarbonitrile (synthesis described in example 3, step 2, 225 mg, 1 mmol) and triethylamine (202 mg, 2 mmol) in dichloromethane (10 mL) was added 1,4-diazepan-5-one (114 mg, 1 mmol) dropwise. The resulting solution was stirred at room temperature overnight. The reaction was quenched with HCl solution (6N), then extracted with dichloromethane (40 mL). The organic layer was washed with brine (30 mL) then dried over anhydrous sodium sulfate, filtered, and concentrated under reduced pressure. The residue was purified by silica gel chromatograph (petroleum ether/ethyl acetate=5:1) to afford chloro-4-ethyl-6-(5-oxo-1,4-diazepan-1-yl)pyridine-3,5-dicarbonitrile (150 mg, 50%). LCMS m/z=304 [M+H]⁺.

Step 2: 2-{[3,5-dicyano-4-ethyl-6-(5-oxo-1,4-diazepan-1-Opyridin-2-yl]sulfanyl}-2-phenylacetamide

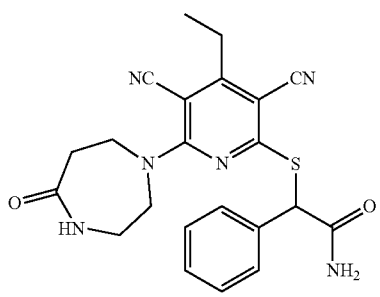 [SMILES: CCc1c(C#N)c(SC(C(N)=O)c2ccccc2)nc(N2CCNC(=O)CC2)c1C#N]

To a stirred solution of potassium thioacetate (114 mg, 1.0 mmol) in N,N-dimethylformamide (20 mL) was added dropwise a solution of chloro-4-ethyl-6-(5-oxo-1,4-diazepan-1-yl)pyridine-3,5-dicarbonitrile (150 mg, 0.5 mmol) in N,N-dimethylformamide (5 mL) at 0° C. The resulting solution was stirred at ambient temperature for 2 hours followed by the addition of potassium carbonate (138 mg, 1.0 mmol) and 2-amino-2-oxo-1-phenylethyl methanesulfonate (synthesis described in example 3 step 5, 344 mg, 3.0 mmol). The resulting mixture was stirred at room temperature overnight. The reaction was quenched with HCl solution (1N, 60 mL), then extracted with ethyl acetate (40 mL). The organic layer was washed with brine (30 mL) and concentrated to dryness. The residue was purified by prep-HPLC to give 2-{[3,5-dicyano-4-ethyl-6-(5-oxo-1,4-diazepan-1-yl)pyridin-2-yl]sulfanyl}-2-phenylacetamide (85 mg) as a white solid. LCMS m/z=435 [M+H]⁺. ¹H NMR (400 MHz, DMSO-d₆) δ ppm 1.23 (m, 3H), 2.68 (s, 2H), 2.79 (m, 2H), 3.35 (s, 2H), 4.00 (s, 4H), 5.53 (s, 1H), 7.40 (m, 3H), 7.51 (m, 2H), 7.74 (s, 1H), 7.93 (s, 1H).

Example 9

2-((3,5-dicyano-4-cyclopropyl-6-morpholinopyridin-2-yl)thio)-2-(pyridin-4-yl)acetamide Step 1: 2-(pyridin-4-yl)-2-((trimethylsilyl)oxy)acetonitrile

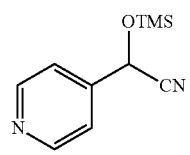

A mixture of isonicotinaldehyde (3.5 g, 32.7 mmol), TMS-CN (163.3 mmol) in CHCl₃ (50 mL) was stirred at 50° C. for 12 hours. The resulting mixture was concentrated. The residue was purified by silica gel column eluting with petroleum ether/ethyl acetate=20/1 to give 2-(pyridin-4-yl)-2-((trimethylsilyl)oxy)acetonitrile (1.8 g, 22% yield) as colorless oil. LCMS m/z=207 [M+H]⁺.

Step 2: 2-hydroxy-2-(pyridin-4-yl)acetamide

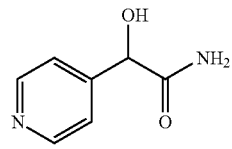 [SMILES: NC(=O)C(O)c1ccncc1]

To a stirring solution of conc. H₂SO₄ (90%, 10 mL) was added 2-(pyridin-4-yl)-2-((trimethylsilyl)oxy)acetonitrile (1.8 g, 8.72 mmol). The resulting mixture was stirred at room temperature for 5 hours. then poured into ice water, and made basic by NH₃.H₂O to pH 9. The solution was concentrated, the residue was purified by silica gel column eluting with CH₂Cl₂/MeOH (30/1) to give 2-hydroxy-2-(pyridin-4-yl)acetamide(900 mg, 53% yield) as a white solid. LCMS m/z=153 [M+H]⁺.

Step 3: 2-amino-2-oxo-1-(pyridin-4-yl)ethyl methanesulfonate

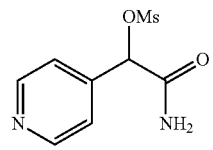 [SMILES: CS(=O)(=O)OC(C(N)=O)c1ccncc1]

To a stirring mixture of 2-hydroxy-2-(pyridin-4-yl)acetamide (900 mg, 5.91 mmol) Et₃N (1.79 g, 17.7 mmol) in tetrahydrofuran (25 mL) was added MsCl (745 mg, 6.5 mmol) at 0° C. The resulting mixture was stirred at room temperature for 2 hours. The reaction mixture was concentrated. The residue was purified by silica gel column eluting with CH₂Cl₂/MeOH (70/10) to give 2-amino-2-oxo-1-(pyridin-4-yl)ethyl methanesulfonate (800 mg, 59% yield) as brown oil. LCMS m/z=231 [M+H]⁺.

Step 4: 2-chloro-4-cyclopropyl-6-morpholinopyridine-3,5-dicarbonitrile

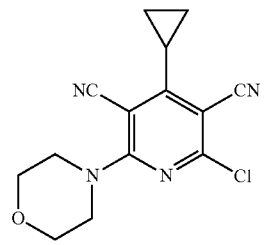 [SMILES: N#Cc1c(Cl)nc(N2CCOCC2)c(C#N)c1C1CC1]

To a solution of 2,6-dichloro-4-cyclopropylpyridine-3,5-dicarbonitrile (10 g, 42.2 mmol) in N,N-dimethylformamide (200 mL) was added morpholine (3.7 g, 42.2 mmol) and triethylamine (4.3 g, 42.2 mmol). the reaction solution was stirred at room temperature for 5 minutes. Water was added to the reaction, and the resulting solid was filtered, washed with water and dried to give 2-chloro-4-cyclopropyl-6-morpholinopyridine-3,5-dicarbonitrile as a yellow solid (9.3 g, 77% yield). LCMS m/z=289 [M+H]⁺.

Step 5: 2-((3,5-dicyano-4-cyclopropyl-6-morpholinopyridin-2-yl)thio)-2-(pyridin-4-yl)acetamide

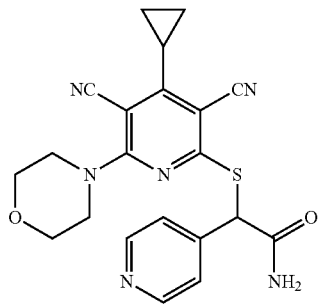 [SMILES: N#Cc1c(SC(C(N)=O)c2ccncc2)nc(N2CCOCC2)c(C#N)c1C1CC1]

A mixture of 2-chloro-4-cyclopropyl-6-morpholinopyridine-3,5-dicarbonitrile (200 mg, 0.69 mmol), KSAc (788 mg, 0.69 mmol) in N,N-dimethylformamide (8 mL) was stirred at room temperature for 30 minutes. Then 2-amino-2-oxo-1-(pyridin-4-yl)ethyl methanesulfonate (191 mg, 0.83 mmol) and triethylamine (209 mg, 202 mmol) were added. The resulting mixture was stirred at room temperature for 12 hours. The reaction mixture was poured into water (50 mL), then extracted with EtOAc (50 mL×2). The combined organic layers were dried, concentrated and the residue was purified by silica gel column eluting with CH$_2$Cl$_2$/MeOH (50/1) to give 2-((3,5-dicyano-4-cyclopropyl-6-morpholinopyridin-2-yl)thio)-2-(pyridin-4-yl)acetamide (100 mg, 34% yield) as a white solid. LCMS m/z=421 [M+H]⁺. ¹H NMR (400 MHz, DMSO) δ ppm 8.58 (dd, J=4.6, 1.4 Hz, 2H), 8.04 (br s, 1H), 7.55-7.45 (m, 3H), 5.57 (s, 1H), 3.80 (m, 4H), 3.71-3.56 (m, 4H), 2.16-2.08 (m, 1H), 1.16-1.07 (m, 2H), 1.02-0.93 (m, 2H).

Example 10

2-{[3,5-dicyano-4-ethyl-6-(4-methyl-3-oxopiperazin-1-yl)pyridin-2-yl]sulfanyl}-2-(pyridin-4-yl)acetamide Step 1: 2-chloro-4-ethyl-6-(4-methyl-3-oxopiperazin-1-yl)pyridine-3,5-dicarbonitrile

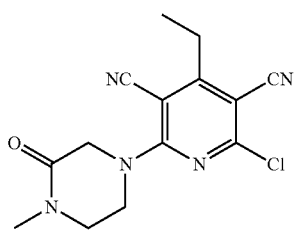 [SMILES: CCc1c(C#N)c(Cl)nc(N2CCN(C)C(=O)C2)c1C#N]

A solution of 2,6-dichloro-4-ethylpyridine-3,5-dicarbonitrile (synthesis described in example 3 step 2, 226 mg, 1.000 mmol), 1-methylpiperazin-2-one (114 mg, 1.000 mmol) and triethylamine (0.167 mL, 1.200 mmol) in N,N-dimethylformamide (8 mL) was stirred at room temperature for 30 minutes. The reaction mixture was poured into water (50 mL), and extracted with ethyl acetate (50 mL×2), the combined organic layers were dried, concentrated to give desired product (270 mg, 89% yield) as a white solid. LCMS m/z=304.0 [M+H]⁺.

Step 2: 2-{[3,5-dicyano-4-ethyl-6-(4-methyl-3-oxopiperazin-1-yl)pyridin-2-yl]sulfanyl}-2-(pyridin-4-yl)acetamide

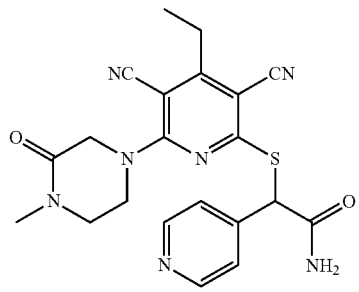 [SMILES: CCc1c(C#N)c(SC(C(N)=O)c2ccncc2)nc(N2CCN(C)C(=O)C2)c1C#N]

A solution of potassium thioacetate (122 mg, 1.067 mmol), 2-chloro-4-ethyl-6-(4-methyl-3-oxopiperazin-1-yl)pyridine-3,5-dicarbonitrile (synthesis described in example 9 step 3, 270 mg, 0.889 mmol) in N,N-dimethylformamide (10 mL) was stirred at room temperature for 30 minutes, then 2-amino-2-oxo-1-(pyridin-4-yl)ethyl methanesulfonate (246 mg, 1.067 mmol) and triethylamine (0.248 mL, 1.778 mmol) was added to the solution. The reaction mixture was stirred at room temperature for 12 hours. The reaction mixture was poured into water (50 mL), and extracted with ethyl acetate (50 mL×2), the combined organic layers were dried, concentrated, the residue was purified by silica gel column eluting with DCM/MeOH (30/1) to give 2-{[3,5-dicyano-4-ethyl-6-(4-methyl-3-oxopiperazin-1-yl)pyridin-2-yl]sulfanyl}-2-(pyridin-4-yl)acetamide (50 mg, 13% yield) as a white solid. LCMS m/z=435.8 [M+H]⁺. ¹H NMR (400 MHz, CDCl$_3$) δ ppm 8.64 (d, J=3.8 Hz, 2H), 7.47 (d, J=5.3 Hz, 2H), 7.25 (br s, 1H), 6.14 (br s, 1H), 5.50 (s, 1H), 4.43 (dd, J=56.9, 17.3 Hz, 2H), 4.26-4.17 (m, 1H), 4.18-4.08 (m, 1H), 3.58-3.47 (m, 2H), 3.03 (s, 3H), 2.96 (q, J=7.6 Hz, 2H), 1.34 (t, J=7.6 Hz, 3H).

Example 11

2-[(3,5-dicyano-4-ethyl-6-{methyl[2-(morpholin-4-yl)ethyl]amino}pyridin-2-yl)sulfanyl]-2-phenylacetamide Step 1: 2-chloro-4-ethyl-6-(methyl(2-morpholinoethyl)amino)pyridine-3,5-dicarbonitrile

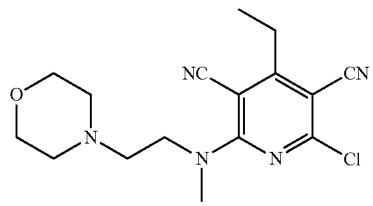 [SMILES: CCc1c(C#N)c(Cl)nc(N(C)CCN2CCOCC2)c1C#N]

303

To a solution of 2,6-dichloro-4-ethylpyridine-3,5-dicarbonitrile (synthesis described in example 3 step 2, 300 mg, 1.327 mmol) and N-methyl-2-morpholinoethanamine (191 mg, 1.327 mmol) in N,N-dimethylformamide (15 mL) was added Et₃N (0.185 mL, 1.327 mmol) at room temperature and the resulting mixture was stirred at room temperature for 1 hour. The reaction mixture was poured into water (50 mL) and extracted with ethyl acetate (50 mL×2), the combined organic layers were dried and concentrated to give desired product (320 mg, 72% yield) as a pale solid. LCMS m/z=334 [M+H]⁺.

Step 2: 2-[(3,5-dicyano-4-ethyl-6-{methyl[2-(morpholin-4-yl)ethyl]amino}pyridin-2-yl)sulfanyl]-2-phenylacetamide

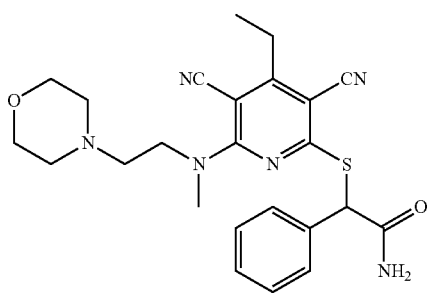 [SMILES: CCc1c(C#N)c(SC(C(N)=O)c2ccccc2)nc(N(C)CCN2CCOCC2)c1C#N]

A solution of potassium thioacetate (82 mg, 0.719 mmol), 2-chloro-4-ethyl-6-(methyl(2-morpholinoethyl)amino)pyridine-3,5-dicarbonitrile (200 mg, 0.599 mmol) in N,N-dimethylformamide (10 mL) was stirred at room temperature for 30 minutes, then 2-amino-2-oxo-1-phenylethyl methanesulfonate (synthesis described in example 3 step 5, 165 mg, 0.719 mmol) and triethylamine (0.167 mL, 1.198 mmol) was added to the solution. The reaction mixture was stirred at room temperature for 12 hours. The reaction mixture was poured into water (50 mL), and extracted with ethyl acetate (50 mL×2), the combined organic layers were dried, concentrated, the residue was purified by silica gel column eluting with DCM/MeOH (30/1) to give 2-[(3,5-dicyano-4-ethyl-6-{methyl[2-(morpholin-4-yl)ethyl]amino}pyridin-2-yl)sulfanyl]-2-phenylacetamide (75 mg, 27% yield) as a white solid. LCMS m/z=465.0 [M+H]⁺. ¹H NMR (400 MHz, CDCl₃) δ ppm 7.48-7.32 (m, 5H), 6.98 (br s, 1H), 5.84 (br s, 1H), 5.41 (s, 1H), 4.20-4.06 (m, 1H), 3.78-3.60 (m, 5H), 3.45 (s, 3H), 2.91 (q, J=7.6 Hz, 2H), 2.80-2.65 (m, 2H), 2.62-2.45 (m, 4H), 1.32 (t, J=7.6 Hz, 3H).

304

Example 12

2-{[3,5-dicyano-4-ethyl-6-(4-propylpiperazin-1-yl)pyridin-2-yl]sulfanyl}-2-phenylacetamide Step 1: 2-chloro-4-ethyl-6-(4-propylpiperazin-1-yl)pyridine-3,5-dicarbonitrile

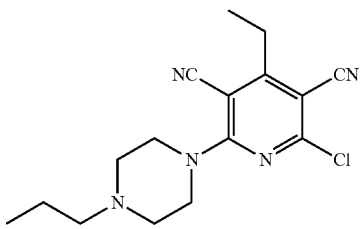 [SMILES: CCCN1CCN(c2nc(Cl)c(C#N)c(CC)c2C#N)CC1]

A mixture of 2,6-dichloro-4-ethylpyridine-3,5-dicarbonitrile (synthesis described in example 3 step 2, 300 mg, 1.32 mmol), 1-propylpiperazinyl hydrochloride (217.8 mg, 1.32 mmol) and Et₃N (133.3 mg, 1.32 mmol) in N,N-dimethylformamide (10 mL) was stirred at room temperature for 1 hour. The resulting mixture was poured into water (50 mL), then extracted with EtOAc (50 mL×2), the combined organic layer was dried and concentrated to give 2-chloro-4-ethyl-6-(4-propylpiperazin-1-yl)pyridine-3,5-dicarbonitrile (310 mg, 74%) as a brown oil. LCMS m/z=318.0 [M+H]⁺.

Step 2: 2-{[3,5-dicyano-4-ethyl-6-(4-propylpiperazin-1-yl)pyridin-2-yl]sulfanyl}-2-phenylacetamide

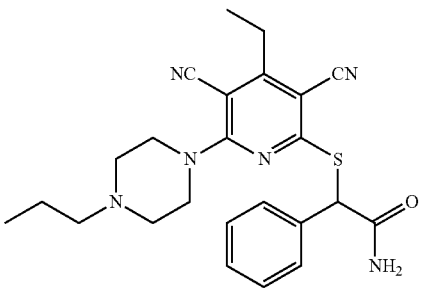 [SMILES: CCCN1CCN(c2nc(SC(C(N)=O)c3ccccc3)c(C#N)c(CC)c2C#N)CC1]

A solution of 2-chloro-4-ethyl-6-(4-propylpiperazin-1-yl)pyridine-3,5-dicarbonitrile (310 mg, 0.97 mmol) and KSAc (134 mg, 1.17 mmol) in N,N-dimethylformamide (10 mL) was stirred at room temperature for 30 minutes then 2-amino-2-oxo-1-phenylethyl methanesulfonate (synthesis described in example 3 step 5, 268 mg, 0.97 mmol) and Et₃N (196 mg, 1.94 mmol) in N,N-dimethylformamide were added. The mixture was stirred at room temperature for 12 hours. The reaction mixture was poured into water (50 mL), then extracted with EtOAc (50 mL×2), the combined organic layer was dried and concentrated. The residue was purified by silica gel column chromatography (CH₂Cl₂: MeOH 20:1) to give 2-{[3,5-dicyano-4-ethyl-6-(4-propylpiperazin-1-yl)pyridin-2-yl]sulfanyl}-2-phenylacetamide (100 mg, 23%) as a white solid. LCMS m/z=488.8 [M+H]⁺. ¹H NMR (400 MHz, CDCl₃) δ ppm 7.48-7.42 (m, 2H), 7.41-7.35 (m, 3H), 6.51 (br s, 1H), 5.68 (br s, 1H), 5.36 (s, 1H), 4.04-3.91 (m, 4H), 2.91 (q, J=7.6 Hz, 2H), 2.65-2.50

(m, 4H), 2.41-2.31 (m, 2H), 1.61-1.47 (m, 2H), 1.32 (t, J=7.6 Hz, 3H), 0.93 (t, J=7.4 Hz, 3H).

Example 13

2-({3,5-dicyano-4-ethyl-6-[4-(piperidin-4-yl)piperazin-1-yl]pyridin-2-yl}sulfanyl)-2-phenylacetamide

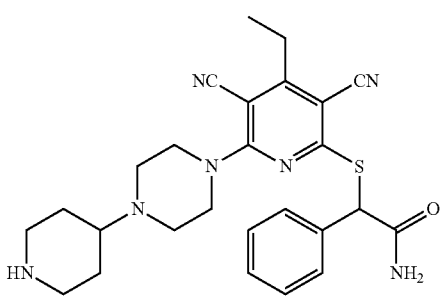 [SMILES: CCc1c(C#N)c(SC(C(N)=O)c2ccccc2)nc(N2CCN(C3CCNCC3)CC2)c1C#N]

To a mixture of 2-[(6-bromo-3,5-dicyano-4-ethyl-2-pyridyl)sulfanyl]-2-phenyl-acetamide (synthesis described in example 6 step 1, 28 mg, 0.0700 mmol) and tert-butyl 4-piperazin-1-ylpiperidinyl-1-carboxylate (20.68 mg, 0.0800 mmol) in tetrahydrofuran (2 mL) was added triethylamine (19.4 µL, 0.1400 mmol). The mixture was stirred for 6 hours. Additional tert-butyl 4-piperazin-1-ylpiperidinyl-1-carboxylate (4.6 mg. 0.25 eq.) and Et₃N (9.7 µL, 1 eq.) added and the mixture stirred for a further 16 hours. The mixture was diluted with EtOAc (20 mL), washed with water (3×20 mL), brine (25 mL), filtered through a hydrophobic frit and the solvent removed under reduced pressure. The residue was dissolved in DCM and chromatographed on SiO₂ (4 g RediSep cartridge) using 0-10% MeOH in DCM as eluent to afford 25 mg of a colorless residue. The residue was dissolved in DCM (2 mL) and trifluoroacetic acid (0.5 mL, 6.73 mmol) was added. The mixture was stirred at room temperature for 1 hour, the solvent removed under reduced pressure, the residue triturated with Et₂O and dried in vacuo at 50° C. to afford an off-white powder, which was dissolved in DMSO and purified by prep HPLC to afford 2-[[3,5-dicyano-4-ethyl-6-[4-(4-piperidyl)piperazin-1-yl]-2-pyridyl]sulfanyl]-2-phenyl-acetamide (12 mg, 0.0245 mmol, 35%) as a white powder. LCMS m/z=488.3 [M−H]⁻. ¹H NMR (300 MHz, DMSO-d₆) δ ppm 8.37 (s, 1H), 7.94 (s, 1H), 7.52 (d, J=6.7 Hz, 2H), 7.45-7.29 (m, 4H), 5.53 (s, 1H), 3.90-3.82 (m, 4H), 3.18-3.04 (m, 2H), 2.96-2.61 (m, 6H), 2.61-2.53 (m, 2H), 2.48-2.16 (m, 1H), 1.81 (br d, J=12.4 Hz, 2H), 1.54 (br s, 2H), 1.20 (t, J=7.6 Hz, 3H).

Example 14

2-({3,5-dicyano-4-cyclopropyl-6-[3-(hydroxymethyl)piperazin-1-yl]pyridin-2-yl}sulfanyl)-2-phenylacetamide Step 1: 4-(6-chloro-3,5-dicyano-4-cyclopropylpyridin-2-yl)-2-(hydroxymethyl)piperazinyl-1-carboxylate

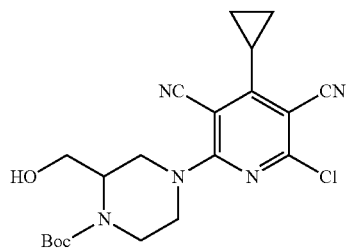 [SMILES: CC(C)(C)OC(=O)N1CCN(c2nc(Cl)c(C#N)c(C3CC3)c2C#N)CC1CO]

To a solution of 2,6-dichloro-4-cyclopropylpyridine-3,5-dicarbonitrile (synthesis described in example 4 step 2, 238 mg, 1 mmol) in N,N-dimethylformamide (8 mL) at room temperature was added tert-butyl 2-(hydroxymethyl)piperazinyl-1-carboxylate (216 mg, 1 mmol), followed by Et₃N (101 mg, 1 mmol). The mixture was stirred at room temperature for 1 hour. The reaction mixture was poured into water (50 mL) and extracted with EtOAc (50 mL×2). The combined organic layers were dried and concentrated, and the residue was purified by silica gel column eluting with CH₂Cl₂:MeOH 50:1 to give 4-(6-chloro-3,5-dicyano-4-cyclopropylpyridin-2-yl)-2-(hydroxymethyl)piperazinyl-1-carboxylate (260 mg, 82%) as a brown oil. LCMS m/z=318.0 [M+H-Boc]⁺.

Step 2: tert-Butyl 4-(6-((2-amino-2-oxo-1-phenylethyl)thio)-3,5-dicyano-4-cyclopropylpyridin-2-yl)-2-(hydroxymethyl)piperazinyl-1-carboxylate

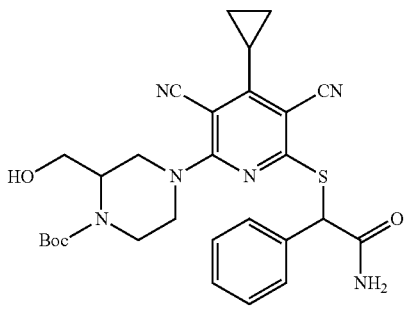 [SMILES: CC(C)(C)OC(=O)N1CCN(c2nc(SC(C(N)=O)c3ccccc3)c(C#N)c(C3CC3)c2C#N)CC1CO]

A solution of tert-Butyl 4-(6-chloro-3,5-dicyano-4-cyclopropylpyridin-2-yl)-2-(hydroxymethyl)piperazinyl-1-carboxylate (260 mg, 0.62 mmol) and KSAc (85 mg, 0.74 mmol) in N,N-dimethylformamide (10 mL) was stirred at room temperature for 30 minutes then 2-amino-2-oxo-1-phenylethyl methanesulfonate (synthesis described in example 3 step 5, 170 mg, 0.74 mmol) and Et₃N (125 mg, 1.24 mmol) were added to the solution. The mixture was stirred at room temperature for 12 hours then poured into water (50 mL), and extracted with EtOAc (50 mL×2). The combined organic layers were dried, concentrated and purified by silica gel column chromatography (CH$_2$Cl$_2$:MeOH 40:1) to give tert-Butyl 4-(6-((2-amino-2-oxo-1-phenylethyl)thio)-3,5-dicyano-4-cyclopropylpyridin-2-yl)-2-(hydroxymethyl)piperazinyl-1-carboxylate (280 mg, 82%) as a white solid. LCMS m/z=570.7 [M+Na]$^+$.

Step 3: 2-({3,5-dicyano-4-cyclopropyl-6-[3-(hydroxymethyl)piperazin-1-yl]pyridin-2-yl}sulfanyl)-2-phenylacetamide

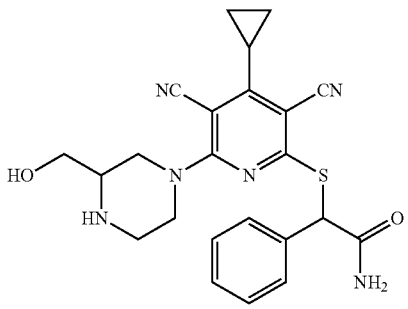 [SMILES: N#Cc1c(SC(C(N)=O)c2ccccc2)nc(N2CCNC(CO)C2)c(C#N)c1C1CC1]

To a solution of tert-Butyl 4-(6-((2-amino-2-oxo-1-phenylethyl)thio)-3,5-dicyano-4-cyclopropylpyridin-2-yl)-2-(hydroxymethyl)piperazinyl-1-carboxylate (280 mg, 0.61 mmol) in DCM (10 mL) at room temperature was added trifluoroacetic acid (3 mL). The mixture was stirred at room temperature for 12 hours then concentrated under vacuum, basified with sat. NaHCO$_3$ solution and extracted with DCM (50 mL×2). The combined organic layers were dried concentrated and purified by silica gel column chromatography (CH$_2$Cl$_2$:MeOH 30:1) to give 2-({3,5-dicyano-4-cyclopropyl-6-[3-(hydroxymethyl)piperazin-1-yl]pyridin-2-yl}sulfanyl)-2-phenylacetamide (90 mg, 32%) as a white solid. LCMS m/z=448.8 [M+H]$^+$. $^1$H NMR (400 MHz, CD$_3$OD) δ ppm 7.60-7.50 (m, 2H), 7.50-7.31 (m, 3H), 5.54 (s, 1H), 4.69-4.44 (m, 2H), 3.72-3.55 (m, 2H), 3.32-3.25 (m, 1H), 3.21-2.89 (m, 4H), 2.20-2.10 (m, 1H), 1.28-1.20 (m, 2H), 1.15-1.05 (m, 2H).

Example 15

2-{[3,5-dicyano-4-cyclopropyl-6-(3-oxopiperazin-1-yl)pyridin-2-yl]sulfanyl}-2-phenylacetamide Step 1: 2-Chloro-4-cyclopropyl-6-(3-oxopiperazin-1-yl)pyridine-3,5-dicarbonitrile

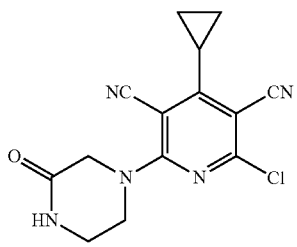 [SMILES: N#Cc1c(Cl)nc(N2CCNC(=O)C2)c(C#N)c1C1CC1]

To a solution of 2,6-dichloro-4-cyclopropylpyridine-3,5-dicarbonitrile (synthesis described in example 4 step 2, 237 mg, 1 mmol) in N,N-dimethylformamide (10 mL) at room temperature was added piperazin-2-one (100 mg, 1 mmol), followed by Et$_3$N (0.14 mL, 1 mmol). The mixture was stirred at room temperature for 5 minutes, then diluted with water and extracted with EtOAc. The combined organic layers were washed with water and brine, dried and concentrated to give 2-chloro-4-cyclopropyl-6-(3-oxopiperazin-1-yl)pyridine-3,5-dicarbonitrile (290 mg, 96%). LCMS m/z=301.9 [M+H]$^+$.

Step 2: 2-{[3,5-dicyano-4-cyclopropyl-6-(3-oxopiperazin-1-yl)pyridin-2-yl]sulfanyl}-2-phenylacetamide

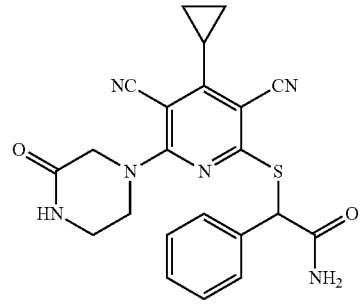 [SMILES: N#Cc1c(SC(C(N)=O)c2ccccc2)nc(N2CCNC(=O)C2)c(C#N)c1C1CC1]

A solution of 2-chloro-4-cyclopropyl-6-(3-oxopiperazin-1-yl)pyridine-3,5-dicarbonitrile (290 mg, 0.96 mmol) and KSAc (132 mg, 1.16 mmol) in N,N-dimethylformamide (10 mL) was stirred at room temperature for 30 minutes then 2-amino-2-oxo-1-phenylethyl methanesulfonate (synthesis described in example 3 step 5, 265 mg, 1.16 mmol) and Et$_3$N (0.27 mL, 1.92 mmol) were added to the solution. The mixture was stirred at room temperature overnight then diluted with water (20 mL). The precipitated solid was collected by filtration and purified by silica gel column chromatography (MeOH:DCM=10:1) to give 2-{[3,5-dicyano-4-cyclopropyl-6-(3-oxopiperazin-1-yl)pyridin-2-yl]sulfanyl}-2-phenylacetamide (48 mg, 12%). LCMS m/z=432.8 [M+H]$^+$. $^1$H NMR (400 MHz, CD$_3$OD) δ ppm 7.56 (d, J=6.8 Hz, 2H), 7.45-7.35 (m, 3H), 5.57 (s, 1H), 4.48 (q, J=17.8 Hz, 2H), 4.21-4.04 (m, 2H), 3.50 (t, J=5.2 Hz, 2H), 2.21-2.11 (m, 1H), 1.30-1.22 (m, 2H), 1.14-1.06 (m, 2H).

Example 16

2-({3,5-dicyano-4-cyclopropyl-6-[4-(morpholin-4-yl)piperidin-1-yl]pyridin-2-yl}sulfanyl-2-phenylacetamide Step 1: 2-chloro-4-cyclopropyl-6-(4-morpholinopiperidin-1-yl)pyridine-3,5-dicarbonitrile

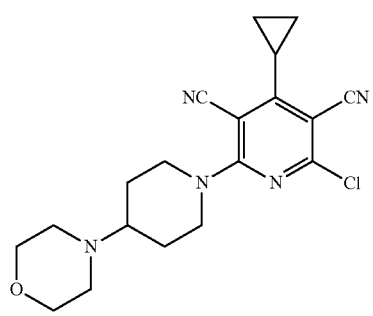 [SMILES: N#Cc1c(Cl)nc(N2CCC(N3CCOCC3)CC2)c(C#N)c1C1CC1]

A mixture of 2,6-dichloro-4-cyclopropylpyridine-3,5-dicarbonitrile (synthesis described in example 4 step 2, 238 mg, 1 mmol) 4-(piperidin-4-yl)morpholine dihydrochloride (115 mg, 1 mmol) and Et$_3$N (303 mg, 3 mmol) in N,N-dimethylformamide (8 mL) at was stirred at room temperature for 30 minutes. The reaction mixture was poured into water (50 mL) and extracted with EtOAc (50 mL×2). The combined organic layers were dried and concentrated to give 2-chloro-4-cyclopropyl-6-(4-morpholinopiperidin-1-yl)pyridine-3,5-dicarbonitrile (320 mg, 86%) as a brown solid. LCMS m/z=372.1 [M+H]$^+$.

Step 2: 2-({3,5-dicyano-4-cyclopropyl-6-[4-(morpholin-4-yl)piperidin-1-yl]pyridin-2-yl}sulfanyl)-2-phenylacetamide

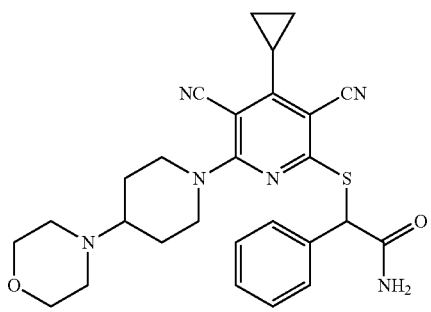 [SMILES: N#Cc1c(SC(C(N)=O)c2ccccc2)nc(N2CCC(N3CCOCC3)CC2)c(C#N)c1C1CC1]

A solution of 2-chloro-4-cyclopropyl-6-(4-morpholinopiperidin-1-yl)pyridine-3,5-dicarbonitrile (320 mg, 0.86 mmol) and KSAc (117 mg, 1.03 mmol) in N,N-dimethylformamide (10 mL) was stirred at room temperature for 30 minutes then 2-amino-2-oxo-1-phenylethyl methanesulfonate (synthesis described in example 3 step 5, 236 mg, 1.03 mmol) and Et$_3$N (174 mg, 1.72 mmol) were added. The resulting mixture was stirred at room temperature for 12 hours. The mixture was poured into water (50 mL), and extracted with EtOAc (50 mL×2). The combined organic layers were dried concentrated, and the residue was purified by silica gel column chromatography (CH$_2$Cl$_2$:MeOH=50:1) to give 2-({3,5-dicyano-4-cyclopropyl-6-[4-(morpholin-4-yl)piperidin-1-yl]pyridin-2-yl}sulfanyl)-2-phenylacetamide (130 mg, 30%) as a white solid. LCMS m/z=502.8 [M+H]$^+$. $^1$H NMR (400 MHz, CDCl$_3$) δ ppm 7.50-7.43 (m, 2H), 7.43-7.35 (m, 3H), 6.57 (br s, 1H), 5.68 (br s, 1H), 5.37 (s, 1H), 4.65 (d, J=14.1 Hz, 2H), 3.82-3.70 (m, 4H), 3.19 (t, J=12.7 Hz, 2H), 2.66-2.45 (m, 5H), 2.13-2.02 (m, 3H), 1.70-1.59 (m, 2H), 1.32-1.27 (m, 2H), 1.19-1.14 (m, 2H).

Example 17

2-((3,5-dicyano-4-ethyl-6-(2,8-diazaspiro[4.5]decan-8-yl)pyridin-2-yl)thio)-2-phenylacetamide; 2,2,2-trifluoroacetic acid

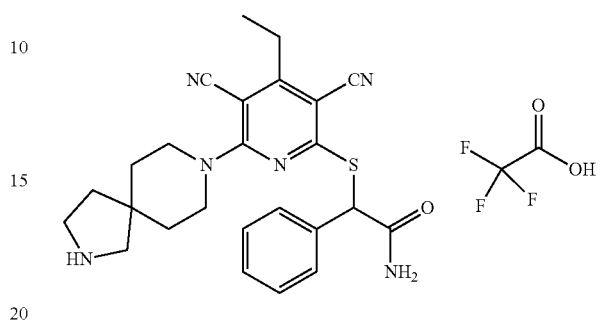

To a mixture of 2-[(6-bromo-3,5-dicyano-4-ethyl-2-pyridyl)sulfanyl]-2-phenyl-acetamide (synthesis described in example 6 step 1, 30 mg, 0.07 mmol) and tert-butyl 2,8-diazaspiro[4.5]decane-2-carboxylate hydrochloride (23 mg, 0.08 mmol) in tetrahydrofuran (2 mL) was added triethylamine (0.03 mL, 0.25 mmol). The reaction mixture was stirred for 1 hour. The mixture was diluted with EtOAc (20 mL), washed with water (3×20 mL), saturated sodium chloride (25 mL), filtered through a hydrophobic frit and the solvent was removed under reduced pressure. The crude product was chromatographed on SiO$_2$ (4 g RediSep cartridge) using 0-10% MeOH in CH$_2$Cl$_2$ as eluent. The resulting residue was dissolved in CH$_2$Cl$_2$ (2 mL) followed by the addition of trifluoroacetic acid (0.5 mL, 6.73 mmol) and the subsequent mixture was stirred at ambient temperature for 1 hour. The solvent was removed under reduced pressure and the product was triturated with diethyl ether, dried in vacuo at 50° C. to afford 2-[[3,5-dicyano-6-(2,8-diazaspiro[4.5]decan-8-yl)-4-ethyl-2-pyridyl]sulfanyl]-2-phenyl-acetamide; 2,2,2-trifluoroacetic acid (38 mg, 88% yield) as a white solid. LCMS m/z=459.3 [M–H]$^-$. 1H NMR (300 MHz, DMSO-d$_6$) δ ppm 8.79 (br s, 2H), 7.92 (s, 1H), 7.57-7.47 (m, 2H), 7.44-7.30 (m, 4H), 5.53 (s, 1H), 4.30-3.98 (m, 2H), 3.91-3.60 (m, 2H), 3.43-3.12 (m, 4H), 2.78 (q, J=7.5 Hz, 2H), 2.11-1.81 (m, 6H), 1.22 (t, J=7.6 Hz, 3H).

Example 18

2-((3,5-Dicyano-4-cyclopropyl-6-(3-(dimethylamino)piperidin-1-yl)pyridin-2-yl)thio)-2-phenylacetamide Step 1: tert-butyl 3-(dimethylamino)piperidinyl-1-carboxylate

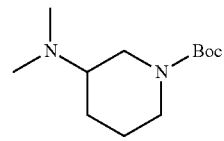 [SMILES: CN(C)C1CCCN(C(=O)OC(C)(C)C)C1]

To a solution of tert-butyl 3-oxopiperidinyl-1-carboxylate (500 mg, 2.5 mmol) in dichloromethane (10 mL) was added a solution of dimethylamine in tetrahydrofuran (3.8 mL, 2

M, 7.5 mmol). After stirring at room temperature for 5 minutes, NaBH(OAc)₃ (1.06 g, 5 mmol) was added to the mixture. The mixture was stirred at room temperature overnight then concentrated under vacuum and purified by silica gel column chromatography (CH₂Cl₂:MeOH=10:1) to give tert-butyl 3-(dimethylamino)piperidinyl-1-carboxylate (500 mg, 88%) as a white solid. LCMS m/z=229.0 [M+H]⁺.

Step 2: N,N-dimethylpiperidin-3-amine

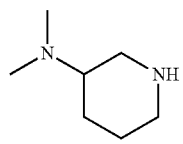

To a solution of tert-butyl 3-(dimethylamino)piperidinyl-1-carboxylate (500 mg, 2.19 mmol) in dichloromethane (4 mL) was added trifluoroacetic acid (4 mL). The mixture was stirred at room temperature overnight then concentrated under vacuum, basified with saturated aqueous NaHCO₃ solution and extracted with dichloromethane. The combined organic layers were concentrated under vacuum to give N,N-dimethylpiperidin-3-amine (250 mg). LCMS m/z=129.1 [M+H]⁺.

Step 3: 2-Chloro-4-cyclopropyl-6-(3-(dimethylamino)piperidin-1-yl)pyridine-3,5-dicarbonitrile

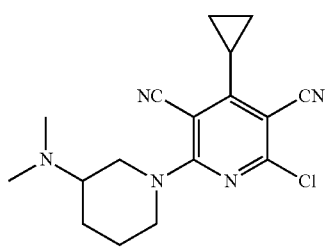 [SMILES: CN(C)C1CCCN(c2nc(Cl)c(C#N)c(C3CC3)c2C#N)C1]

To a solution of 2,6-dichloro-4-cyclopropylpyridine-3,5-dicarbonitrile (synthesis described in example 4 step 2, 236 mg, 1 mmol) in N,N-dimethylformamide (10 mL) at room temperature was added N,N-dimethylpiperidin-3-amine (128 mg, 1 mmol), followed by triethylamine (0.14 mL 1 mmol). The mixture was stirred at room temperature for 5 minutes, then diluted with water. The precipitated solid was collected by filtration and purified by silica gel column chromatography (CH₂Cl₂:ethyl acetate=1:1) to give 2-chloro-4-cyclopropyl-6-(3-(dimethylamino)piperidin-1-yl)pyridine-3,5-dicarbonitrile (190 mg, 58%). LCMS m/z=329.8 [M+H]⁺.

Step 4: 2-((3,5-Dicyano-4-cyclopropyl-6-(3-(dimethylamino)piperidin-1-yl)pyridin-2-yl)thio)-2-phenylacetamide

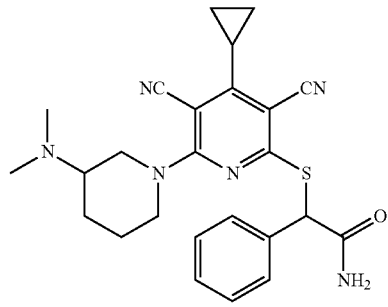 [SMILES: CN(C)C1CCCN(c2nc(SC(C(N)=O)c3ccccc3)c(C#N)c(C3CC3)c2C#N)C1]

A solution of 2-chloro-4-cyclopropyl-6-(3-(dimethylamino)piperidin-1-yl)pyridine-3,5-dicarbonitrile (190 mg, 0.58 mmol) and KSAc (80 mg, 0.7 mmol) in N,N-dimethylformamide (6 mL) was stirred at room temperature for 30 minutes then 2-amino-2-oxo-1-phenylethyl methanesulfonate (synthesis described in example 3 step 5, 159 mg, 0.7 mmol) and triethylamine (0.16 mL, 1.16 mmol) were. The mixture was stirred at room temperature overnight then diluted with water. The precipitated solid was collected by filtration and purified by silica gel column chromatography (dichloromethane:methanol=20:1) to give 2-((3,5-dicyano-4-cyclopropyl-6-(3-(dimethylamino)piperidin-1-yl)pyridin-2-yl)thio)-2-phenylacetamide (132 mg, 49%). LCMS m/z=460.9 [M+H]⁺. ¹H NMR (400 MHz, CDCl₃) δ ppm 7.49-7.44 (m, 2H), 7.40-7.34 (m, 3H), 5.54 (s, 1H), 5.42 (s, 1H), 4.89-4.76 (m, 1H), 4.55 (d, J=13.6 Hz, 1H), 3.16-3.06 (m, 1H), 3.00-2.92 (m, 1H), 2.75-2.64 (m, 1H), 2.41 (s, 6H), 2.12-2.03 (m, 2H), 2.00-1.93 (m, 1H), 1.68-1.45 (m, 3H), 1.30-1.24 (m, 2H), 1.19-1.07 (m, 2H).

Example 19

2-((3,5-Dicyano-4-cyclopropyl-6-(3-methylpiperazin-1-yl)pyridin-2-yl)thio)-2-phenylacetamide Step 1: 4-(6-chloro-3,5-dicyano-4-cyclopropylpyridin-2-yl)-2-methylpiperazinyl-1-carboxylate

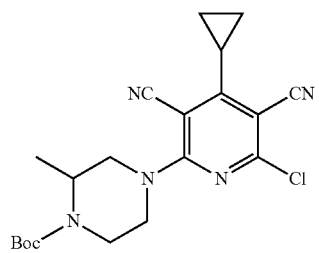 [SMILES: CC1CN(c2nc(Cl)c(C#N)c(C3CC3)c2C#N)CCN1C(=O)OC(C)(C)C]

To a solution of 2,6-dichloro-4-cyclopropylpyridine-3,5-dicarbonitrile (synthesis described in example 4 step 2, 236 mg, 1 mmol) in N,N-dimethylformamide (10 mL) was added tert-butyl 2-methylpiperazinyl-1-carboxylate (200 mg, 1 mmol), followed by triethylamine (0.14 mL,1 mmol). The mixture was stirred at room temperature for 5 minutes, then diluted with water. The precipitated solid was collected by filtration and dried in an oven to give 4-(6-chloro-3,5-dicyano-4-cyclopropylpyridin-2-yl)-2-methylpiperazinyl-1-carboxylate (330 mg, 82%). LCMS m/z=301.9 [M+H-Boc]+.

Step 2: tert-Butyl 4-(6-((2-amino-2-oxo-1-phenylethyl)thio)-3,5-dicyano-4-cyclopropylpyridin-2-yl)-2-methylpiperazinyl-1-carboxylate

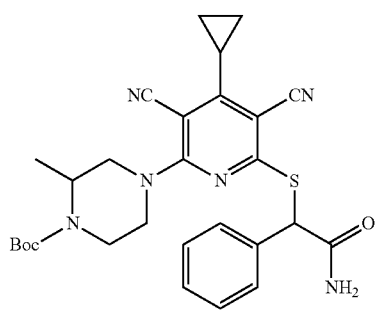 [SMILES: CC1CN(c2nc(SC(C(N)=O)c3ccccc3)c(C#N)c(C3CC3)c2C#N)CCN1C(=O)OC(C)(C)C]

A solution of tert-butyl 4-(6-chloro-3,5-dicyano-4-cyclopropylpyridin-2-yl)-2-methylpiperazinyl-1-carboxylate (330 mg, 0.82 mmol) and KSAc (113 mg, 0.99 mmol) in N,N-dimethylformamide (9 mL) was stirred at room temperature for 30 minutes then 2-amino-2-oxo-1-phenylethyl methanesulfonate (synthesis described in example 3 step 5, 226 mg, 0.99 mmol) and triethylamine (0.23 mL, 1.64 mmol) were added to the solution. The mixture was stirred at room temperature overnight then diluted with water. The precipitated solid was collected by filtration and purified by silica gel column chromatography (dichloromethane:methanol=20:1) to give tert-butyl 4-(6-((2-amino-2-oxo-1-phenylethyl)thio)-3,5-dicyano-4-cyclopropylpyridin-2-yl)-2-methylpiperazinyl-1-carboxylate (280 mg, 64%). $^1$H NMR (400 MHz, CDCl$_3$) δ ppm 7.49-7.45 (m, 2H), 7.44-7.36 (m, 3H), 6.58-6.48 (m, 1H), 5.62 (br s, 1H), 5.40-5.35 (m, 1H), 4.49-4.27 (m, 3H), 4.03-3.95 (m, 1H), 3.62-3.53 (m, 1H), 3.43-3.27 (m, 2H), 2.16-2.08 (m, 1H), 1.50 (s, 9H), 1.35-1.28 (m, 2H), 1.27-1.22 (m, 3H), 1.21-1.11 (m, 2H).

Step 3: 2-((3,5-Dicyano-4-cyclopropyl-6-(3-methylpiperazin-1-yl)pyridin-2-yl)thio)-2-phenylacetamide

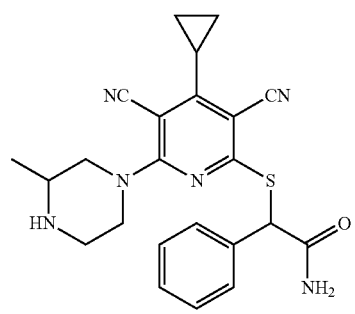 [SMILES: CC1CN(c2nc(SC(C(N)=O)c3ccccc3)c(C#N)c(C3CC3)c2C#N)CCN1]

To a solution of tert-Butyl 4-(6-((2-amino-2-oxo-1-phenylethyl)thio)-3,5-dicyano-4-cyclopropylpyridin-2-yl)-2-methylpiperazinyl-1-carboxylate (280 mg, 0.53 mmol) in dichloromethane (5 mL) at room temperature was added trifluoroacetic acid (4 mL). The mixture was stirred at room temperature overnight then concentrated under vacuum, basified with sat. NaHCO$_3$ solution, and extracted with dichloromethane (20 mL×3). The combined organic layers were concentrated under vacuum, and purified by silica gel column chromatography (dichloromethane:methanol=20:1) to give 2-((3,5-dicyano-4-cyclopropyl-6-(3-methylpiperazin-1-yl)pyridin-2-yl)thio)-2-phenylacetamide (194.5 mg, 86%). LCMS m/z=432.8 [M+H]+. $^1$H NMR (400 MHz, CDCl$_3$) δ ppm 7.48-7.42 (m, 2H), 7.41-7.31 (m, 3H), 6.53 (s, 1H), 5.82-5.72 (m, 1H), 5.34 (s, 1H), 4.58-4.46 (m, 2H), 3.26-3.12 (m, 2H), 2.99-2.78 (m, 3H), 2.15-2.03 (m, 2H), 1.33-1.24 (m, 2H), 1.20-1.09 (m, 5H).

Example 20

2-((3,5-Dicyano-4-cyclopropyl6-(2-(hydroxymethyl)morpholino)pyridin-2-yl)thio)-2-phenylacetamide Step 1: 2-Chloro-4-cyclopropyl-6-(3,5-dimethylpiperazin-1-yl)pyridine-3,5-dicarbonitrile

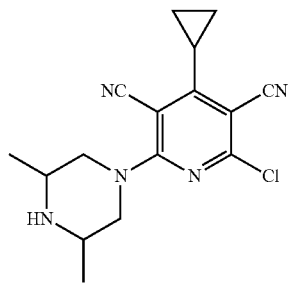 [SMILES: CC1CN(c2nc(Cl)c(C#N)c(C3CC3)c2C#N)CC(C)N1]

To a solution of 2,6-dichloro-4-cyclopropylpyridine-3,5-dicarbonitrile (synthesis described in example 4 step 2, 237 mg, 1 mmol) in N,N-dimethylformamide (10 mL) was added 2,6-dimethylpiperazinyl (114 mg, 1 mmol), followed by triethylamine (0.14 mL, 1 mmol). The mixture was stirred at room temperature for 5 minutes, then diluted with water. The precipitated solid was collected by filtration and dried in an oven to give 2-chloro-4-cyclopropyl-6-(3,5-dimethylpiperazin-1-yl)pyridine-3,5-dicarbonitrile (280 mg, 89%) as a white solid. LCMS m/z=316.0 [M+H]+.

Step 2: 2-((3,5-Dicyano-4-cyclopropyl-6-(2-(hydroxymethyl)morpholino)pyridin-2-yl)thio)-2-phenylacetamide

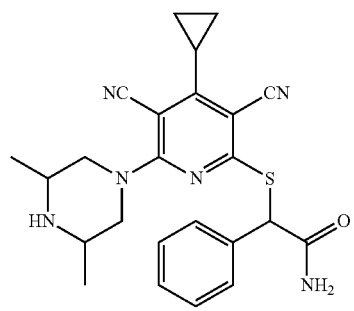

A solution of 2-chloro-4-cyclopropyl-6-(3,5-dimethylpiperazin-1-yl)pyridine-3,5-dicarbonitrile (280 mg, 0.89 mmol) and KSAc (122 mg, 1.07 mmol) in N,N-dimethylformamide (9 mL) was stirred at room temperature for 30 minutes then 2-amino-2-oxo-1-phenylethyl methanesulfonate (synthesis described in example 3 step 5, 245 mg, 1.07 mmol) and triethylamine (0.25 mL, 1.78 mmol) were added to the solution. The mixture was stirred at room temperature overnight then diluted with water. The precipitated solid was collected by filtration and purified by silica gel column chromatography (CH$_2$Cl$_2$:MeOH 10:1) to give 2-((3,5-dicyano-4-cyclopropyl-6-(2-(hydroxymethyl)morpholino)pyridin-2-yl)thio)-2-phenylacetamide (43 mg, 11%) as a gray solid. LCMS m/z=446.6 [M+H]$^+$. $^1$H NMR (400 MHz, CDCl$_3$) δ ppm 7.49-7.42 (m, 2H), 7.41-7.32 (m, 3H), 6.55 (br s, 1H), 5.65 (br s, 1H), 5.34 (s, 1H), 4.61-4.49 (m, 2H), 3.10-2.75 (m, 4H), 2.12-2.04 (m, 1H), 1.37-1.18 (m, 8H), 1.18-1.11 (m, 2H). 1H not observed.

Example 21

2-((3,5-Dicyano-4-cyclopropyl-6-(2,6-dimethylmorpholino)pyridin-2-yl)thio)-2-phenylacetamide Step 1: 2-Chloro-4-cyclopropyl-6-(2,6-dimethylmorpholino)pyridine-3,5-dicarbonitrile

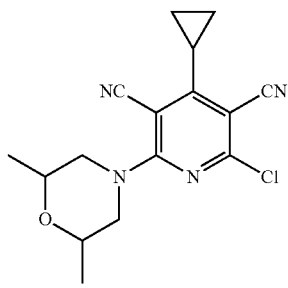 [SMILES: CC1CN(c2nc(Cl)c(C#N)c(C3CC3)c2C#N)CC(C)O1]

A mixture of 2,6-dichloro-4-cyclopropylpyridine-3,5-dicarbonitrile (synthesis described in example 4 step 2, 238 mg, 1 mmol) 2,6-dimethylmorpholine (115 mg, 1 mmol), and triethylamine (101 mg, 1 mmol) N,N-dimethylformamide (8 mL) was stirred at room temperature for 30 minutes. The reaction was poured into water (50 mL) and extracted with ethyl acetate (50 mL×2). The combined organic layers were dried and concentrated under vacuum to give 2-chloro-4-cyclopropyl-6-(2,6-dimethylmorpholino)pyridine-3,5-dicarbonitrile (280 mg, 89%) as a white solid. LCMS m/z=317.0 [M+H]$^+$.

Step 2: 2-((3,5-Dicyano-4-cyclopropyl-6-(2,6-dimethylmorpholino)pyridin-2-yl)thio)-2-phenylacetamide

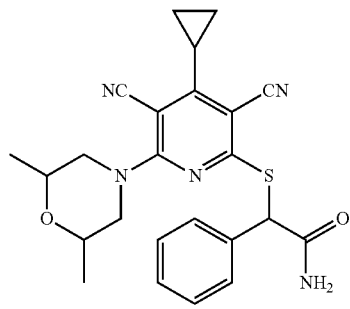 [SMILES: CC1CN(c2nc(SC(C(N)=O)c3ccccc3)c(C#N)c(C3CC3)c2C#N)CC(C)O1]

A solution of 2-chloro-4-cyclopropyl-6-(2,6-dimethylmorpholino)pyridine-3,5-dicarbonitrile (280 mg, 0.88 mmol) and KSAc (121 mg, 1.06 mmol) in N,N-dimethylformamide (10 mL) was stirred at room temperature for 30 minutes then 2-amino-2-oxo-1-phenylethyl methanesulfonate (synthesis described in example 3 step 5, 242 mg, 1.06 mmol) and triethylamine (178 mg, 1.76 mmol) were added to the solution. The mixture was stirred at room temperature for 12 hours then diluted with water (50 mL), and extracted with ethyl acetate (50 mL×2). The combined organic layers were, concentrated under vacuum, and purified by silica gel column chromatography (CH$_2$Cl$_2$:MeOH 50:1) to give 2-((3,5-dicyano-4-cyclopropyl-6-(2,6-dimethylmorpholino)pyridin-2-yl)thio)-2-phenylacetamide (120 mg, 30%) as a white solid. LCMS m/z=447.8 [M+H]$^+$. $^1$H NMR (400 MHz, CDCl$_3$) δ ppm 7.49-7.42 (m, 2H), 7.42-7.33 (m, 3H), 6.51 (br s, 1H), 5.52 (br s, 1H), 5.31 (s, 1H), 4.56-4.45 (m, 2H), 3.75-3.60 (m, 2H), 2.94-2.81 (m, 2H), 2.14-2.04 (m, 1H), 1.36-1.22 (m, 8H), 1.18-1.12 (m, 2H).

Example 22

2-((3,5-Dicyano-4-cyclopropyl-6-(3-(dimethylamino)piperidin-1-yl)pyridin-2-yl)thio)-2-phenylacetamide Step 1: 2-Chloro-4-cyclopropyl-6-(4-methyl-3-oxopiperazin-1-yl)pyridine-3,5-dicarbonitrile

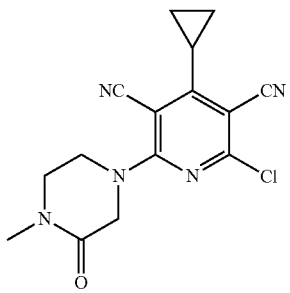 [SMILES: CN1CCN(c2nc(Cl)c(C#N)c(C3CC3)c2C#N)CC1=O]

A solution of 2,6-dichloro-4-cyclopropylpyridine-3,5-dicarbonitrile (synthesis described in example 4 step 2, 238 mg, 1 mmol) 1-methylpiperazin-2-one (114 mg, 1 mmol), and triethylamine (121 mg, 1.2 mmol) in N,N-dimethylformamide (8 mL) was stirred at room temperature for 30 minutes, then diluted with water (50 mL) and extracted with ethyl acetate (50 mL×2). The combined organic layers were dried and concentrated under vacuum to give 2-chloro-4-cyclopropyl-6-(4-methyl-3-oxopiperazin-1-yl)pyridine-3,5-dicarbonitrile (260 mg, 83%) as a brown solid. LCMS m/z=315.8 [M+H]$^+$.

Step 2: 2-((3,5-Dicyano-4-cyclopropyl-6-(3-(dimethylamino)piperidin-1-yl)pyridin-2-yl)thio)-2-phenylacetamide

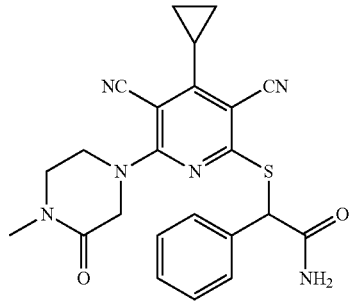 [SMILES: CN1CCN(c2nc(SC(C(N)=O)c3ccccc3)c(C#N)c(C3CC3)c2C#N)CC1=O]

A solution of 2-Chloro-4-cyclopropyl-6-(4-methyl-3-oxopiperazin-1-yl)pyridine-3,5-dicarbonitrile (260 mg, 0.82 mmol) and KSAc (122 mg, 1.07 mmol) in N,N-dimethylformamide (6 mL) was stirred at room temperature for 30 minutes then 2-amino-2-oxo-1-phenylethyl methanesulfonate (synthesis described in example 3 step 5, 244 mg, 1.07 mmol) and triethylamine (166 mg, 1.64 mmol) were added to the solution. The mixture was stirred at room temperature for 12 hours then diluted with water (50 mL), and extracted with ethyl acetate (50 mL×2). The combined organic layers were dried, concentrated under vacuum, and purified by silica gel column chromatography (CH$_2$Cl$_2$:MeOH 40:1) to give 2-((3,5-dicyano-4-cyclopropyl-6-(3-(dimethylamino)piperidin-1-yl)pyridin-2-yl)thio)-2-phenylacetamide (110 mg, 30%) as a white solid. LCMS m/z=446.8 [M+H]$^+$. $^1$H NMR (400 MHz, CDCl$_3$) δ ppm 7.53-7.44 (m, 2H), 7.44-7.33 (m, 3H), 6.87 (br s, 1H), 5.76 (br s, 1H), 5.41 (s, 1H), 4.52 (d, J=17.4 Hz, 1H), 4.34 (d, J=17.4 Hz, 1H), 4.25-4.15 (m, 1H), 4.12-3.99 (m, 1H), 3.50 (s, 2H), 3.03 (s, 3H), 2.15-2.06 (m, 1H), 1.36-1.27 (m, 2H), 1.23-1.12 (m, 2H).

Example 23

2-((6-(4-(Aminomethyl)-4-hydroxypiperidin-1-yl)-3,5-dicyano-4-cyclopropylpyridin-2-yl)thio-2-phenylacetamide Step 1: 4-(Aminomethyl)-1-benzylpiperidin-4-ol

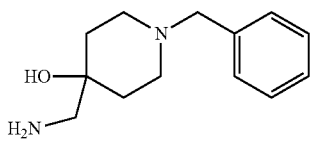

To a pre-cooled solution (20° C.) of 1-benzylpiperidin-4-one (1.0 g, 5.3 mmol) and triethylamine (0.15 mL 1.1 mmol) was added TMS-CN (0.63 g, 6.4 mmol). The mixture was stirred at room temperature for 3 hours then cautiously added to a mixture of LiAlH$_4$ (0.23 g, 6.1 mmol) in tetrahydrofuran (50 mL). The mixture was refluxed for 1.5 hours then cooled to room temperature, quenched with water (0.23 mL), followed by NaOH solution (1N, 0.23 mL) and water (0.46 mL). The mixture was stirred overnight then filtered and the filtrate was concentrated under vacuum to give 4-(aminomethyl)-1-benzylpiperidin-4-ol (1.2 g). LCMS m/z=221.0 [M+H]$^+$.

Step 2: tert-Butyl ((1-benzyl-4-hydroxypiperidin-4-yl)methyl)carbamate

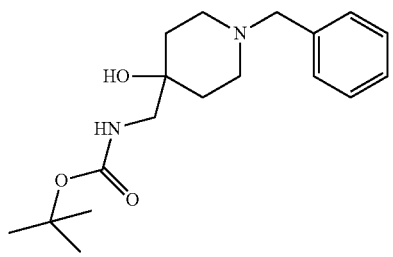 [SMILES: CC(C)(C)OC(=O)NCC1(O)CCN(Cc2ccccc2)CC1]

To a solution of 4-(aminomethyl)-1-benzylpiperidin-4-ol (1.2 g, crude) in dichloromethane (25 mL) was added (Boc)$_2$O (1.4 g, 6.4 mmol). The mixture was stirred at room temperature overnight then concentrated under vacuum and purified by silica gel column chromatography (petroleum ether:ethyl acetate (2:1) to give to give tert-butyl ((1-benzyl-4-hydroxypiperidin-4-yl)methyl)carbamate (1.2 g, 71%). $^1$H NMR (400 MHz, CDCl$_3$) δ ppm 7.38-7.31 (m, 4H), 7.28-7.24 (m, 1H), 4.92 (br s, 1H), 3.56 (s, 2H), 3.20-3.10 (m, 2H), 2.69-2.57 (m, 2H), 2.49-2.29 (m, 3H), 1.72-1.57 (m, 4H), 1.46 (s, 9H).

Step 3: tert-Butyl ((4-hydroxypiperidin-4-yl)methyl)carbamate

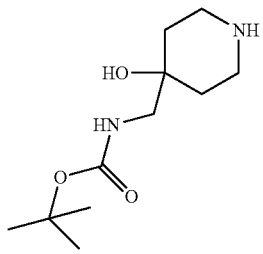 [SMILES: CC(C)(C)OC(=O)NCC1(O)CCNCC1]

To a solution of tert-butyl ((1-benzyl-4-hydroxypiperidin-4-yl)methyl)carbamate (800 mg, 2.5 mmol) in ethanol (25 mL) were added hydrazine hydrate (0.25 mL, 5 mmol) and Pd/C (280 mg). The mixture was refluxed for 3 hours. The mixture was filtered through Celite® and the filtrate was concentrated under vacuum and purified by silica gel column chromatography (CH$_2$Cl$_2$:MeOH 20:1) to give to give tert-butyl ((4-hydroxypiperidin-4-yl)methyl)carbamate (400 mg, 70%). $^1$H NMR (400 MHz, CDCl$_3$) δ ppm 5.08 (br s, 1H), 3.17-3.08 (m, 2H), 3.01-2.92 (m, 2H), 2.90-2.82 (m, 2H), 2.45 (br s, 2H), 1.61-1.50 (m, 4H), 1.45 (s, 9H).

Step 4: tert-Butyl ((1-(6-((2-amino-2-oxo-1-phenyl-ethyl)thio)-3,5-dicyano-4-cyclopropylpyridin-2-yl)-4-hydroxypiperidin-4-yl)methyl)carbamate

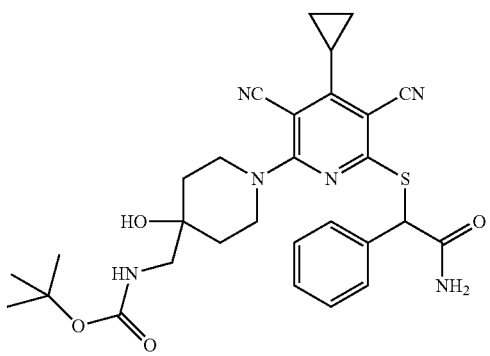 [SMILES: CC(C)(C)OC(=O)NCC1(O)CCN(c2nc(SC(C(N)=O)c3ccccc3)c(C#N)c(C3CC3)c2C#N)CC1]

To a solution of 2,6-dichloro-4-cyclopropylpyridine-3,5-dicarbonitrile (synthesis described in example 4 step 2, 237 mg, 1 mmol) in N,N-dimethylformamide (10 mL) was added tert-butyl ((4-hydroxypiperidin-4-yl)methyl)carbamate (230 mg, 1 mmol), followed by Et$_3$N (0.14 mL 1 mmol). The mixture was stirred at room temperature for 5 minutes, then diluted with water. The precipitated solid was collected by filtration and purified by silica gel column chromatography (DCM:ethyl acetate 1:1) to afford 300 mg of a residue. A solution the residue and KSAc (96 mg, 0.84 mmol) in N,N-dimethylformamide (7 mL) was stirred at room temperature for 30 minutes then 2-amino-2-oxo-1-phenylethyl methanesulfonate (synthesis described in example 3 step 5, 191 mg, 0.84 mmol) and Et$_3$N (0.19 mL, 1.4 mmol) were added to the solution. The mixture was stirred at room temperature overnight then diluted with water. The precipitated solid was collected by filtration and purified by silica gel column chromatography (CH$_2$Cl$_2$:MeOH 20:1) to give tert-butyl ((1-(6-((2-amino-2-oxo-1-phenylethyl)thio)-3,5-dicyano-4-cyclopropylpyridin-2-yl)-4-hydroxypiperidin-4-yl)methyl)carbamate (233 mg) as a yellow solid. LCMS m/z=562.8 [M+H]$^+$.

Step 5: 2-((6-(4-(Aminomethyl)-4-hydroxypiperidin-1-yl)-3,5-dicyano-4-cyclopropylpyridin-2-yl)thio)-2-phenylacetamide

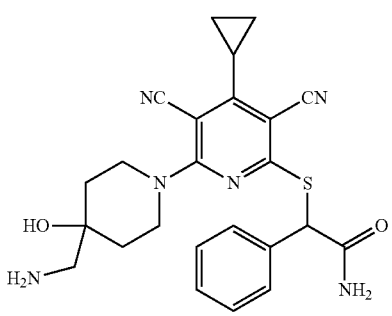 [SMILES: N#Cc1c(SC(C(N)=O)c2ccccc2)nc(N2CCC(O)(CN)CC2)c(C#N)c1C1CC1]

To a solution of tert-butyl ((1-(6-((2-amino-2-oxo-1-phenylethyl)thio)-3,5-dicyano-4-cyclopropylpyridin-2-yl)-4-hydroxypiperidin-4-yl)methyl)carbamate (233 mg, 0.41 mmol) in dichloromethane (4 mL) at room temperature was added trifluoroacetic acid (3 mL). The mixture was stirred at room temperature overnight then concentrated under vacuum, basified with saturated aqueous NaHCO$_3$ solution, and extracted with dichloromethane (20 mL×3). The combined organic layers were concentrated under vacuum, and purified by silica gel column chromatography (DCM:MeOH 10:1) to give 2-((6-(4-(Aminomethyl)-4-hydroxypiperidin-1-yl)-3,5-dicyano-4-cyclopropylpyridin-2-yl)thio)-2-phenylacetamide (62.2 mg, 33%). LCMS m/z=462.7 [M+H]$^+$. $^1$H NMR (400 MHz, CD$_3$OD) δ ppm 7.54 (d, J=6.8 Hz, 2H), 7.44-7.35 (m, 3H), 5.51 (s, 1H), 4.44 (dd, J=17.5, 14.3 Hz, 2H), 3.56 (dd, J=24.0, 10.7 Hz, 2H), 2.63 (s, 2H), 2.17-2.07 (m, 1H), 1.77-1.60 (m, 4H), 1.27-1.20 (m, 2H), 1.11-1.05 (m, 2H). 5H not observed.

Example 24

2-((3,5-dicyano-4-cyclopropyl-6-(3-(methylamino)piperidin-1-yl)pyridin-2-yl)thio)-2-phenylacetamide

Step 1: 1-benzyl-N-methylpiperidin-3-amine

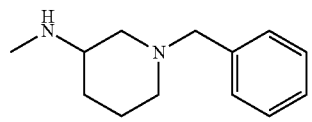

To a solution of 1-benzylpiperidin-3-one (1.0 g, 5.3 mmol) in dichloromethane (25 mL) was added a solution of methylamine in tetrahydrofuran (5.3 mL, 2 M, 10.6 mmol). The mixture was stirred at room temperature for 5 minutes then NaBH(OAc)$_3$ (2.2 g, 10.6 mmol) was added to the solution. The mixture was stirred at room temperature overnight then washed with saturated aqueous NaHCO$_3$ solution, dried and concentrated under vacuum to give 1-benzyl-N-methylpiperidin-3-amine (1.0 g, crude). LCMS m/z=205.1 [M+H]$^+$.

Step 2: tert-butyl (1-benzylpiperidin-3-yl)(methyl)carbamate

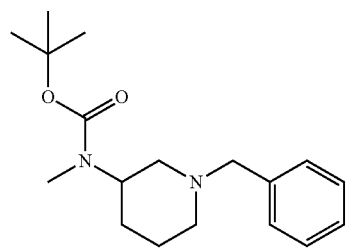 [SMILES: CN(C(=O)OC(C)(C)C)C1CCCN(Cc2ccccc2)C1]

To a solution of 1-benzyl-N-methylpiperidin-3-amine (1.0 g) and triethylamine (1.36 mL, 9.8 mmol) in dichloromethane (25 mL) was added (Boc)$_2$O (1.26 g, 5.9 mmol). The mixture was stirred at room temperature overnight then concentrated under vacuum and purified by silica gel column chromatography (petroleum ether:ethyl acetate 4:1) to give to give tert-butyl (1-benzylpiperidin-3-yl)(methyl)carbamate (1.3 g). LCMS m/z=305.0 [M+H]$^+$.

Step 3: tert-butyl (1-(6-chloro-3,5-dicyano-4-cyclopropylpyridin-2-yl)piperidin-3-yl)(methyl)carbamate

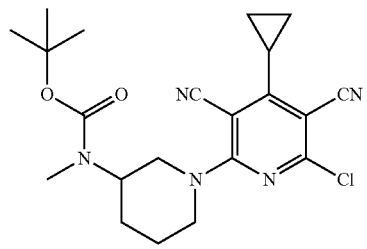 [SMILES: CN(C(=O)OC(C)(C)C)C1CCCN(c2nc(Cl)c(C#N)c(C3CC3)c2C#N)C1]

To a solution of tert-butyl ((1-benzyl-4-hydroxypiperidin-4-yl)methyl)carbamate (1.3 g, 4.3 mmol) in methanol (20 mL) was added Pd/C (130 mg). The mixture was stirred at room temperature under H₂ atmosphere (1 atm) overnight then filtered. The filtrate was concentrated under vacuum to give to give crude tert-butyl methyl(piperidin-3-yl)carbamate as a residue. To a solution of 2,6-dichloro-4-cyclopropylpyridine-3,5-dicarbonitrile (synthesis described in example 4 step 2, 236 mg, 1 mmol) in N,N-dimethylformamide (10 mL) was added tert-butyl methyl(piperidin-3-yl) carbamate (214 mg of crude residue above), followed by triethylamine (0.14 mL 1 mmol). The mixture was stirred at room temperature for 5 minutes, then diluted with water. The precipitated solid was collected by filtration and purified by silica gel column chromatography (dichloromethane:ethyl acetate 1:1) to give tert-butyl (1-(6-chloro-3,5-dicyano-4-cyclopropylpyridin-2-yl)piperidin-3-yl)(methyl)carbamate (320 mg, 77%). LCMS m/z=315.8 [M+H-Boc]⁺.

Step 4: tert-butyl (1-(6-((2-amino-2-oxo-1-phenylethyl)thio)-3,5-dicyano-4-cyclopropylpyridin-2-yl)piperidin-3-yl)(methyl)carbamate

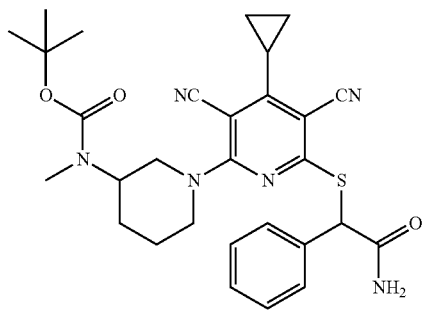 [SMILES: CN(C(=O)OC(C)(C)C)C1CCCN(c2nc(SC(C(N)=O)c3ccccc3)c(C#N)c(C3CC3)c2C#N)C1]

A solution of tert-butyl (1-(6-chloro-3,5-dicyano-4-cyclopropylpyridin-2-yl)piperidin-3-yl)(methyl)carbamate (320 mg, 0.77 mmol) and KSAc (106 mg, 0.93 mmol) in N,N-dimethylformamide (8 mL) was stirred at room temperature for 30 minutes then 2-amino-2-oxo-1-phenylethyl methanesulfonate (synthesis described in example 3 step 5, 212 mg, 0.93 mmol) and triethylamine (0.21 mL, 1.54 mmol) were added to the solution. The mixture was stirred at room temperature overnight then diluted with water. The precipitated solid was collected by filtration and purified by silica gel column chromatography (dichloromethane:methanol 20:1) to give tert-butyl (1-(6-((2-amino-2-oxo-1-phenylethyl)thio)-3,5-dicyano-4-cyclopropylpyridin-2-yl)piperidin-3-yl)(methyl)carbamate (250 mg, 60%). LCMS m/z=446.8 [M+H-Boc]⁺.

Step 5: 2-((3,5-dicyano-4-cyclopropyl-6-(3-(methylamino)piperidin-1-yl)pyridin-2-yl)thio)-2-phenylacetamide

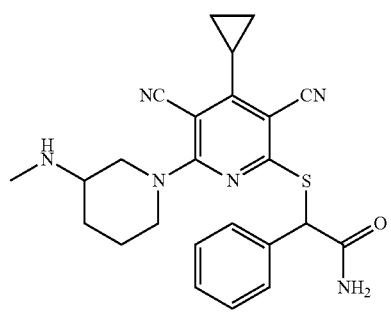 [SMILES: CNC1CCCN(c2nc(SC(C(N)=O)c3ccccc3)c(C#N)c(C3CC3)c2C#N)C1]

To a solution of tert-butyl (1-(6-((2-amino-2-oxo-1-phenylethyl)thio)-3,5-dicyano-4-cyclopropylpyridin-2-yl)piperidin-3-yl)(methyl)carbamate (250 mg, 0.46 mmol) in DCM (5 mL) was added trifluoroacetic acid (3 mL). The mixture was stirred at room temperature overnight then concentrated under vacuum, basified with saturated aqueous NaHCO₃ solution, and extracted with DCM. The organic layer was concentrated under vacuum, and purified by silica gel column chromatography (DCM:MeOH 20:1) to give 2-((3,5-dicyano-4-cyclopropyl-6-(3-(methylamino)piperidin-1-yl)pyridin-2-yl)thio)-2-phenylacetamide (180 mg, 88%). LCMS m/z=446.7 [M+H]⁺. ¹H NMR (400 MHz, CD₃OD) δ ppm 7.48-7.42 (m, 2H), 7.36-7.26 (m, 3H), 5.45 (s, 1H), 4.54-4.45 (m, 1H), 4.41-4.27 (m, 1H), 3.19-3.11 (m, 1H), 3.02-2.93 (m, 1H), 2.72-2.60 (m, 1H), 2.41 (d, J=5.6 Hz, 3H), 2.11-2.01 (m, 2H), 1.87-1.78 (m, 1H), 1.65-1.52 (m, 1H), 1.42-1.31 (m, 1H), 1.19-1.11 (m, 2H), 1.05-0.94 (m, 2H). 3H not observed.

Example 25

2-((6-(3-aminopiperidin-1-yl)-3,5-dicyano-4-cyclopropylpyridin-2-yl)thio)-2-phenylacetamide Step 1: tert-butyl (1-(6-((2-amino-2-oxo-1-phenylethyl)thio)-3,5-dicyano-4-cyclopropylpyridin-2-yl)piperidin-3-yl)carbamate

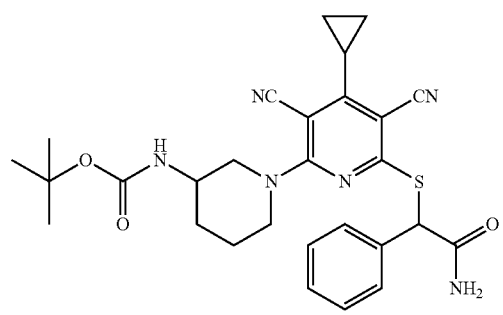 [SMILES: CC(C)(C)OC(=O)NC1CCCN(c2nc(SC(C(N)=O)c3ccccc3)c(C#N)c(C3CC3)c2C#N)C1]

323

To a solution of 2,6-dichloro-4-cyclopropylpyridine-3,5-dicarbonitrile (synthesis described in example 4 step 2, 236 mg, 1 mmol) in N,N-dimethylformamide (10 mL) was added tert-butyl piperidin-3-ylcarbamate (200 mg, 1 mmol) and triethylamine (0.14 mL, 1 mmol). The mixture was stirred at room temperature for 5 minutes. Water was added to the reaction and the resulting mixture filtered to afford a crude solid. A solution of the crude solid (401 mg) and KSAc (137 mg, 1.2 mmol) in N,N-dimethylformamide (10 mL) was stirred at room temperature for 30 minutes. Then 2-amino-2-oxo-1-phenylethyl methanesulfonate (synthesis described in example 3 step 5, 275 mg, 1.2 mmol) and triethylamine (0.28 mL, 2 mmol) were added to the reaction. The resulting solution was stirred at room temperature overnight. Water was added to the reaction. The solid was filtered and purified by flash column chromatography (dichloromethane: ethyl acetate 1:1) to give tert-butyl (1-(6-((2-amino-2-oxo-1-phenylethyl)thio)-3,5-dicyano-4-cyclopropylpyridin-2-yl)piperidin-3-yl)carbamate (230 mg, 43%). LCMS m/z=554.8 [M+Na]+.

Step 2: 2-((6-(3-aminopiperidin-1-yl)-3,5-dicyano-4-cyclopropylpyridin-2-yl)thio)-2-phenylacetamide

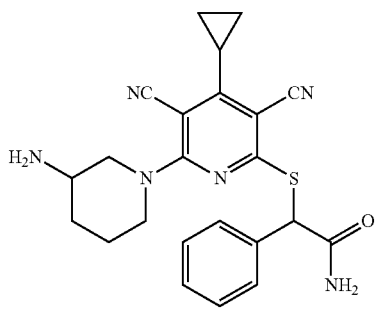 [SMILES: N#Cc1c(SC(C(N)=O)c2ccccc2)nc(N2CCCC(N)C2)c(C#N)c1C1CC1]

To a solution of tert-butyl (1-(6-((2-amino-2-oxo-1-phenylethyl)thio)-3,5-dicyano-4-cyclopropylpyridin-2-yl)piperidin-3-yl)carbamate (230 mg, 0.43 mL), in dichloromethane (4 mL) was added trifluoroacetic acid (4 mL). the reaction was stirred at room temperature overnight. The resulting solution was concentrated and neutralized with saturated aqueous NaHCO$_3$ solution, extracted with dichloromethane, the organic layer was washed with brine, concentrated and purified by flash column chromatography (eluted by DCM:MeOH 10:1) to give 2-((6-(3-aminopiperidin-1-yl)-3,5-dicyano-4-cyclopropylpyridin-2-yl)thio)-2-phenylacetamide (180.5 mg, 92%). LCMS m/z=432.7 [M+H]+. $^1$H NMR (400 MHz, CD$_3$OD) δ ppm 7.55 (d, J=7.0 Hz, 2H), 7.45-7.35 (m, 3H), 5.50 (d, J=6.4 Hz, 1H), 4.61-4.47 (m, 1H), 4.46-4.38 (m, 1H), 3.31-3.23 (m, 1H), 3.07-2.84 (m, 2H), 2.18-2.03 (m, 2H), 1.94-1.85 (m, 1H), 1.73-1.60 (m, 1H), 1.52-1.41 (m, 1H), 1.28-1.20 (m, 2H), 1.15-1.04 (m, 2H). 4H not observed.

324

Example 26

2-((3,5-dicyano-4-cyclopropyl-6-(dimethylamino)pyridin-2-yl)thio)-2-(pyridin-4-yl)acetamide Step 1: 2-chloro-4-cyclopropyl-6-(dimethylamino)pyridine-3,5-dicarbonitrile

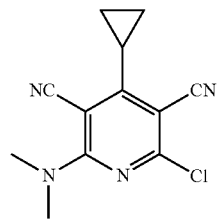 [SMILES: CN(C)c1nc(Cl)c(C#N)c(C2CC2)c1C#N]

To a solution of 2,6-dichloro-4-cyclopropylpyridine-3,5-dicarbonitrile (synthesis described in example 4 step 2, 4.8 g, 20.3 mmol) in N,N-dimethylformamide (100 mL) was added dimethylamine (2 M in tetrahydrofuran, 10 mL, 20.3 mmol) and triethylamine (2.8 mL, 20.3 mmol). The reaction was stirred at room temperature for 5 minutes. Water was added to the reaction. The solid was filtered and washed with water and dried to give 2-chloro-4-cyclopropyl-6-(dimethylamino)pyridine-3,5-dicarbonitrile (4.6 g, 92%) as a pink solid. LCMS m/z=246.9 [M+H]+.

Step 2: 2-((3,5-dicyano-4-cyclopropyl-6-(dimethylamino)pyridin-2-yl)thio)-2-(pyridin-4-yl)acetamide

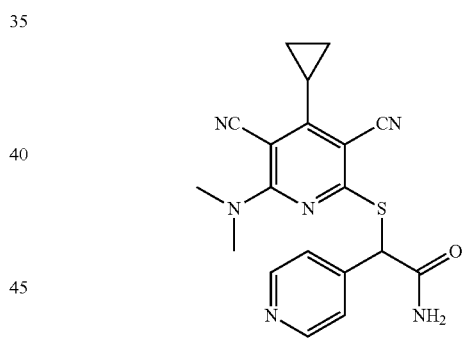

A mixture of 2-chloro-4-cyclopropyl-6-(dimethylamino)pyridine-3,5-dicarbonitrile (400 mg, 1.62 mL), KSAc (221 mg, 1.94 mmol) in N,N-dimethylformamide (10 mL) was stirred at room temperature for 30 minutes. Then 2-amino-2-oxo-1-(pyridin-4-yl)ethyl methanesulfonate (synthesis described in example 9 step 3, 448 mg, 1.94 mmol), Et$_3$N (327 mg, 3.24 mmol) was added. The resulting mixture was stirred at room temperature for 12 hours. The reaction mixture was poured into water (50 mL), and extracted with ethyl acetate (50 mL×2). The combined organic layers was dried and concentrated. The residue was purified by silica gel column eluting with dichloromethane/methanol (60/1) to give 2-((3,5-dicyano-4-cyclopropyl-6-(dimethylamino)pyridin-2-yl)thio)-2-(pyridin-4-yl)acetamide (220 mg, 36% yield) as a white solid. LCMS m/z=378.9 [M+H]+. $^1$H NMR (400 MHz, DMSO) δ ppm 8.57 (d, J=4.9 Hz, 2H), 8.07 (s, 1H), 7.53 (d, J=4.9 Hz, 2H), 7.49 (s, 1H), 5.65 (s, 1H), 3.27 (s, 6H), 2.15-2.03 (m, 1H), 1.19-1.08 (m, 2H), 0.98-0.88 (m, 2H).

Example 27

2-((3,5-dicyano-6-(dimethylamino)-4-ethylpyridin-2-yl)thio)-2-(pyridin-4-yl)acetamide 2-((3,5-dicyano-6-(dimethylamino)-4-ethylpyridin-2-yl)thio)-2-(pyridin-4-yl)acetamide

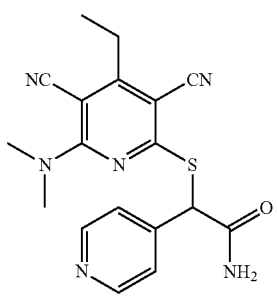 [SMILES: CCc1c(C#N)c(SC(C(N)=O)c2ccncc2)nc(N(C)C)c1C#N]

A mixture of 2-chloro-6-(dimethylamino)-4-ethylpyridine-3,5-dicarbonitrile (synthesis described in example 3 step 3, 234.7 mg, 1 mmol), KSAc (137 mg, 1.2 mmol) in N,N-dimethylformamide (10 mL) was stirred at room temperature for 30 minutes. then 2-amino-2-oxo-1-(pyridin-4-yl)ethyl methanesulfonate (synthesis described in example 9 step 3, 276 mg, 1.2 mmol) triethylamine (202 mg, 20 mmol) was added. The resulting mixture was stirred at room temperature for 12 hours. The reaction mixture was poured into water (50 mL), and extracted with ethyl acetate (50 mL×2). The combined organic layers was dried and concentrated. The residue was purified by silica gel column eluting with dichloromethane:methanol 40:1 to give 2-((3,5-dicyano-6-(dimethylamino)-4-ethylpyridin-2-yl)thio)-2-(pyridin-4-yl)acetamide (120 mg, 33% yield) as a white solid. LCMS m/z=366.9 [M+H]$^+$. $^1$H NMR (400 MHz, DMSO) δ ppm 8.57 (dd, J=4.5, 1.5 Hz, 2H), 8.07 (br s, 1H), 7.53 (dd, J=4.5, 1.5 Hz, 2H), 7.49 (br s, 1H), 5.66 (s, 1H), 3.30 (s, 6H), 2.75 (q, J=7.5 Hz, 2H), 1.20 (t, J=7.6 Hz, 3H).

Example 28

2-((6-(4-aminopiperidin-1-yl)-3,5-dicyano-4-cyclopropylpyridin-2-yl)thio)-2-phenylacetamide Step 1: tert-butyl (1-(6-chloro-3,5-dicyano-4-cyclopropylpyridin-2-yl)piperidin-4-yl)carbamate

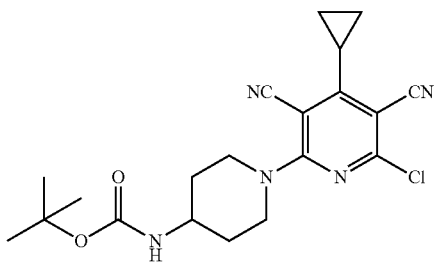 [SMILES: CC(C)(C)OC(=O)NC1CCN(c2nc(Cl)c(C#N)c(C3CC3)c2C#N)CC1]

To a solution of 2,6-dichloro-4-cyclopropylpyridine-3,5-dicarbonitrile (synthesis described in example 4 step 2, 236 mg, 1 mmol) in N,N-dimethylformamide (10 mL) was added tert-butyl piperidin-4-ylcarbamate (200 mg, 1 mmol) and triethylamine (0.14 mL, 1 mmol). The mixture was stirred at room temperature for 5 minutes. water was added to the reaction. The solid was filtered and dried to give tert-butyl (1-(6-chloro-3,5-dicyano-4-cyclopropylpyridin-2-yl)piperidin-4-yl)carbamate (390 mg, 97%). LCMS m/z=423.7 [M+Na]$^+$.

Step 2: tert-butyl (1-(6-((2-amino-2-oxo-1-phenylethyl)thio)-3,5-dicyano-4-cyclopropylpyridin-2-yl)piperidin-4-yl)carbamate

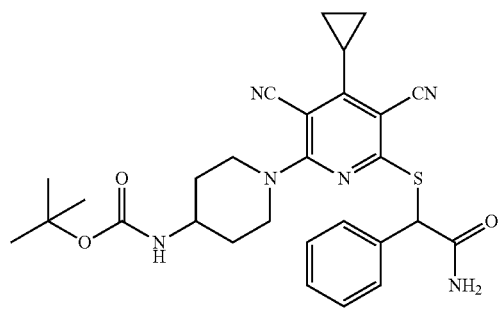 [SMILES: CC(C)(C)OC(=O)NC1CCN(c2nc(SC(C(N)=O)c3ccccc3)c(C#N)c(C3CC3)c2C#N)CC1]

To a solution of 2-amino-2-oxo-1-phenylethyl methanesulfonate (synthesis described in example 3 step 5, 390 mg, 0.97 mmol) in N,N-dimethylformamide (10 mL) was added KSAc (133 mg, 117 mmol). The reaction was stirred at room temperature for 30 minutes, then tert-butyl (1-(6-chloro-3,5-dicyano-4-cyclopropylpyridin-2-yl)piperidin-4-yl)carbamate (267 mg, 1.17 mmol) and triethylamine (0.27 mL, 1.94 mmol) were added to the reaction. The reaction was stirred at room temperature overnight. Water was added to the reaction, the solid was filtered and purified by flash column chromatography (eluted by DCM:MeOH=20:1) to give tert-butyl (1-(6-((2-amino-2-oxo-1-phenylethyl)thio)-3,5-dicyano-4-cyclopropylpyridin-2-yl)piperidin-4-yl)carbamate (36 mg). LCMS m/z=476.7 [M+H-isobutylene]$^+$ (major), 554.7 [M+Na]$^+$ (minor).

Step 3: 2-((6-(4-aminopiperidin-1-yl)-3,5-dicyano-4-cyclopropylpyridin-2-yl)thio)-2-phenylacetamide

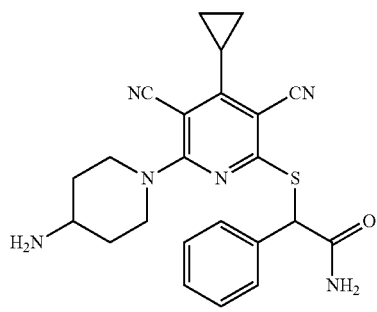 [SMILES: N#Cc1c(SC(C(N)=O)c2ccccc2)nc(N2CCC(N)CC2)c(C#N)c1C1CC1]

A mixture of tert-butyl (1-(6-((2-amino-2-oxo-1-phenylethyl)thio)-3,5-dicyano-4-cyclopropylpyridin-2-yl)piperidin-4-yl)carbamate (360 mg, 0.68 mmol), in DCM (7 mL) was added trifluoroacetic acid (4 mL). The reaction was stirred at room temperature overnight. The solvent was removed and the residue was neutralized by saturated aqueous NaHCO₃ solution and extracted with DCM. The organic layer was concentrated and purified by flash column chromatography (eluted by DCM:MeOH=10:1) to give (200 mg, 68%). LCMS m/z=432.8 [M+H]⁺. ¹H NMR (400 MHz, CDCl₃) δ ppm 7.48-7.42 (m, 2H), 7.41-7.32 (m, 3H), 6.54 (br s, 1H), 5.75 (br s, 1H), 5.35 (s, 1H), 4.57-4.46 (m, 2H), 3.30-3.19 (m, 2H), 3.10-3.00 (m, 1H), 2.12-2.04 (m, 1H), 2.04-1.94 (m, 2H), 1.79 (br s, 2H), 1.52-1.39 (m, 2H), 1.33-1.24 (m, 2H), 1.18-1.11 (m, 2H).

Example 29

2-((3,5-dicyano-4-cyclopropyl-6-(4-(dimethylamino) piperidin-1-yl)pyridin-2-yl)thio)-2-phenylacetamide Step 1: 2-chloro-4-cyclopropyl-6-(4-(dimethylamino)piperidin-1-yl)pyridine-3,5-dicarbonitrile

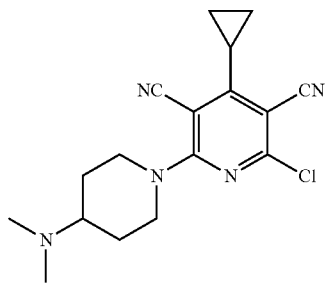 [SMILES: CN(C)C1CCN(c2nc(Cl)c(C#N)c(C3CC3)c2C#N)CC1]

To a solution of 2,6-dichloro-4-cyclopropylpyridine-3,5-dicarbonitrile (synthesis described in example 4 step 2, 200 mg, 0.85 mmol) in N,N-dimethylformamide (9 mL) was added N,N-dimethylpiperidin-4-amine (108 mg, 0.85 mmol) and triethylamine (0.12 mL, 0.85 mmol). The mixture was stirred at room temperature for 5 minutes. Water was added to the reaction. The solid was filtered and dried to give 2-chloro-4-cyclopropyl-6-(4-(dimethylamino)piperidin-1-yl)pyridine-3,5-dicarbonitrile (210 mg, 75% yield). LCMS m/z=330.3 [M+H]⁺.

Step 2: 2-((3,5-dicyano-4-cyclopropyl-6-(4-(dimethylamino)piperidin-1-yl)pyridin-2-yl)thio)-2-phenylacetamide

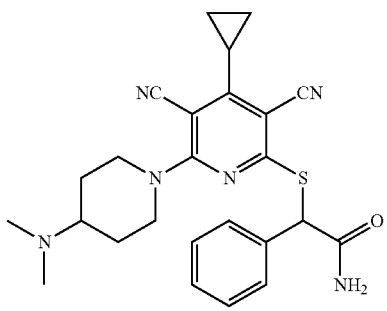 [SMILES: CN(C)C1CCN(c2nc(SC(C(N)=O)c3ccccc3)c(C#N)c(C3CC3)c2C#N)CC1]

A solution of 2-chloro-4-cyclopropyl-6-(4-(dimethylamino)piperidin-1-yl)pyridine-3,5-dicarbonitrile (210 mg, 0.64 mmol) and KSAc (88 mg, 0.77 mmol) in N,N-dimethylformamide (7 mL) was stirred at room temperature for 30 minutes. 2-Amino-2-oxo-1-phenylethyl methanesulfonate (synthesis described in example 3 step 5, 176 mg, 0.77 mmol) and triethylamine (0.81 mL, 1.28 mmol) were added to the reaction. The mixture was stirred at room temperature overnight. Water was added to the reaction, the solid was filtered and purified by flash column chromatography (eluted by DCM:MeOH=20:1) to give 2-((3,5-dicyano-4-cyclopropyl-6-(4-(dimethylamino)piperidin-1-yl)pyridin-2-yl)thio)-2-phenylacetamide (180 mg, 61% yield). LCMS m/z=460.9 [M+H]⁺. ¹H NMR (400 MHz, CDCl₃) δ ppm 7.50-7.45 (m, 2H), 7.44-7.35 (m, 3H), 6.54 (br s, 1H), 5.57 (br s, 1H), 5.39 (s, 1H), 4.69-4.62 (m, 2H), 3.19 (t, J=12.6 Hz, 2H), 2.52-2.43 (m, 1H), 2.36 (s, 6H), 2.14-2.01 (m, 3H), 1.65-1.58 (m, 2H), 1.34-1.27 (m, 2H), 1.20-1.13 (m, 2H).

Example 30

2-((3,5-dicyano-4-cyclopropyl-6-(piperazin-1-yl) pyridin-2-yl)thio)-2-(pyridin-4-yl)acetamide Step 1: tert-butyl 4-(6-chloro-3,5-dicyano-4-cyclopropylpyridin-2-yl)piperazinyl-1-carboxylate

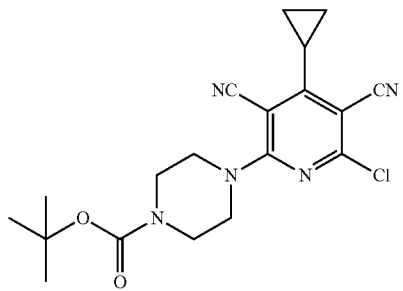 [SMILES: CC(C)(C)OC(=O)N1CCN(c2nc(Cl)c(C#N)c(C3CC3)c2C#N)CC1]

A mixture of 2,6-dichloro-4-cyclopropylpyridine-3,5-dicarbonitrile (synthesis described in example 4 step 2, 1.0 g, 4.2 mmol), tert-butyl piperazinyl-1-carboxylate (782 mg, 4.2 mmol), and Et₃N (424 mg, 1.2 mmol) in N,N-dimethylformamide (20 mL) was stirred at room temperature for 30 minutes. The reaction mixture was poured into water (100 mL) and extracted with EtOAc (100 mL×2). The combined organic layers were dried, and concentrated to give tert-butyl 4-(6-chloro-3,5-dicyano-4-cyclopropylpyridin-2-yl)piperazinyl-1-carboxylate (1.3 g, 80%) as a white solid. LCMS m/z=288.0 [M+H-Boc]⁺.

Step 2: tert-butyl 4-(6-((2-amino-2-oxo-1-(pyridin-4-yl)ethyl)thio)-3,5-dicyano-4-cyclopropylpyridin-2-yl)piperazinyl-1-carboxylate

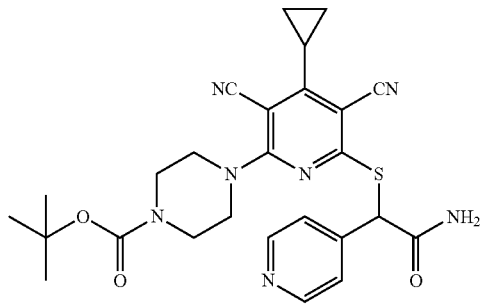 [SMILES: CC(C)(C)OC(=O)N1CCN(c2nc(SC(C(N)=O)c3ccncc3)c(C#N)c(C3CC3)c2C#N)CC1]

329

A solution of tert-butyl 4-(6-chloro-3,5-dicyano-4-cyclopropylpyridin-2-yl)piperazinyl-1-carboxylate (400 mg, 1.03 mmol) and potassium thioacetate (142 mg, 1.24 mmol) in N,N-dimethylformamide (10 mL) was stirred at room temperature for 30 minutes, then 2-amino-2-oxo-1-(pyridin-4-yl)ethyl methanesulfonate (synthesis described in example 9 step 3, 285 mg, 1.24 mmol) and Et₃N (208 mg, 2.06 mmol) were added to the reaction. The mixture was stirred at room temperature for 12 hours, then poured into water (50 mL), and extracted with EtOAc (50 mL×2). The combined organic layers were dried and concentrated. The remaining residue was purified by silica gel column chromatography (MeOH:CH₂Cl₂ 1:70) to give tert-butyl 4-(6-((2-amino-2-oxo-1-(pyridin-4-yl)ethyl)thio)-3,5-dicyano-4-cyclopropylpyridin-2-yl)piperazinyl-1-carboxylate (380 mg, 71%) as a white solid. LCMS m/z=519.9 [M+H]⁺.

Step 3: 2-((3,5-dicyano-4-cyclopropyl-6-(piperazin-1-yl)pyridin-2-yl)thio)-2-(pyridin-4-yl)acetamide

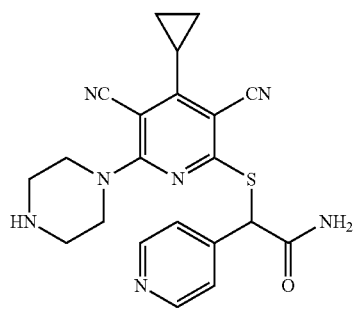 [SMILES: N#Cc1c(SC(C(N)=O)c2ccncc2)nc(N2CCNCC2)c(C#N)c1C1CC1]

A mixture of tert-butyl 4-(6-((2-amino-2-oxo-1-(pyridin-4-yl)ethyl)thio)-3,5-dicyano-4-cyclopropylpyridin-2-yl)piperazinyl-1-carboxylate (5) (380 mg, 0.73 mmol) and trifluoroacetic acid (2 mL) in dichloromethane (8 mL) was stirred at room temperature for 12 hours. After the reaction mixture was concentrated, the remaining residue was poured into water (50 mL), made basic with NaHCO₃ solution, and extracted with dichloromethane (50 mL×2). The combined organic layers were dried and concentrated. The remaining residue was purified by silica gel column chromatography (MeOH:DCM 1:30) to give 2-((3,5-dicyano-4-cyclopropyl-6-(piperazin-1-yl)pyridin-2-yl)thio)-2-(pyridin-4-yl)acetamide (110 mg, 36%) as a white solid. LCMS m/z=442.0 [M+Na]⁺. ¹H NMR (400 MHz, DMSO) δ ppm 8.57 (d, J=5.3 Hz, 2H), 8.09 (br s, 1H), 7.60-7.42 (m, 3H), 5.59 (s, 1H), 3.81-3.65 (m, 4H), 3.34 (br s, 1H), 2.89-2.68 (m, 4H), 2.19-2.04 (m, 1H), 1.18-1.07 (m, 2H), 1.00-0.93 (m, 2H).

330

Example 31

2-((3,5-dicyano-4-cyclopropyl-6-(1,4-diazepan-1-yl)pyridin-2-yl)thio)-2-(pyridin-4-yl)acetamide Step 1: tert-butyl 4-(6-((2-amino-2-oxo-1-(pyridin-4-yl)ethyl)thio)-3,5-dicyano-4-cyclopropylpyridin-2-yl)-1,4-diazepane-1-carboxylate

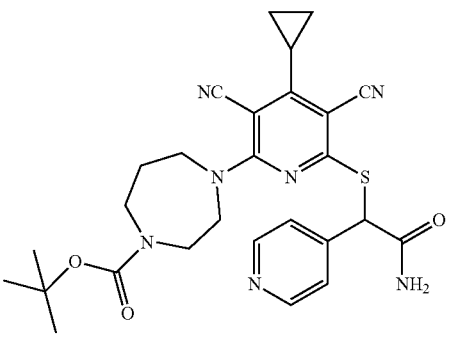 [SMILES: CC(C)(C)OC(=O)N1CCCN(c2nc(SC(C(N)=O)c3ccncc3)c(C#N)c(C3CC3)c2C#N)CC1]

A mixture of tert-butyl 4-(6-chloro-3,5-dicyano-4-cyclopropylpyridin-2-yl)-1,4-diazepane-1-carboxylate (synthesis described in example 4 step 3, 402 mg, 1.0 mmol) and potassium thioacetate (137 mg, 1.2 mmol) in N,N-dimethylformamide (10 mL) was stirred at room temperature for 30 minutes, then 2-amino-2-oxo-1-(pyridin-4-yl)ethyl methanesulfonate (synthesis described in example 9 step 3, 345 mg, 1.5 mmol) and Et₃N (202 mg, 2.0 mmol) were added to the reaction. The mixture was stirred at room temperature for 12 hours, then poured into water (50 mL) and extracted with ethyl acetate (50 mL×2). The combined organic layers were dried and concentrated. The remaining residue was purified by silica gel column chromatography (MeOH:CH₂Cl₂ 1:80) to give tert-butyl 4-(6-((2-amino-2-oxo-1-(pyridin-4-yl)ethyl)thio)-3,5-dicyano-4-cyclopropylpyridin-2-yl)-1,4-diazepane-1-carboxylate (380 mg, 71%) as a brown solid. LCMS m/z=533.9 [M+H]⁺.

Step 2: 2-((3,5-dicyano-4-cyclopropyl-6-(1,4-diazepan-1-yl)pyridin-2-yl)thio)-2-(pyridin-4-yl)acetamide

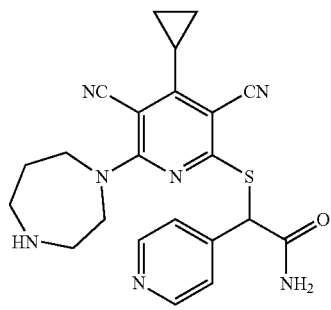 [SMILES: N#Cc1c(SC(C(N)=O)c2ccncc2)nc(N2CCCNCC2)c(C#N)c1C1CC1]

A mixture of tert-butyl 4-(6-((2-amino-2-oxo-1-(pyridin-4-yl)ethyl)thio)-3,5-dicyano-4-cyclopropylpyridin-2-yl)-1,4-diazepane-1-carboxylate (380 mg, 0.71 mmol) and trifluoroacetic acid (2 mL) in dichloromethane (10 mL) was stirred at room temperature for 12 hours. After the reaction mixture was concentrated, the remaining residue was poured into water (50 mL), made basic with NaHCO₃ solution, and extracted with dichloromethane (50 mL×2). The combined organic layers were dried and concentrated. The remaining residue was purified by silica gel column chromatography (MeOH:DCM 1:30) to give 2-((3,5-dicyano-4-cyclopropyl-6-(1,4-diazepan-1-yl)pyridin-2-yl)thio)-2-(pyridin-4-yl)acetamide (120 mg, 40%) as a white solid. LCMS m/z=433.9 [M+H]⁺. ¹H NMR (400 MHz, DMSO-d₆) δ ppm 8.58 (d, J=5.6 Hz, 2H), 8.10 (br s, 1H), 7.55-7.47 (m, 3H), 5.56 (s, 1H), 3.92-3.75 (m, 4H), 3.33 (br s, 1H), 2.98-2.84 (m, 2H), 2.80-2.73 (m, 2H), 2.15-2.07 (m, 1H), 1.85-1.70 (m, 2H), 1.18-1.09 (m, 2H), 0.98-0.92 (m, 2H).

Example 32

2-((3,5-dicyano-4-cyclopropyl-6-((R)-3-hydroxypiperidin-1-yl)pyridin-2-yl)thio)-2-phenylacetamide Step 1: (R)-2-chloro-4-cyclopropyl-6-(3-hydroxypiperidin-1-yl)pyridine-3,5-dicarbonitrile

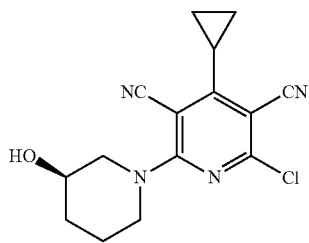 [SMILES: N#Cc1c(Cl)nc(N2CCC[C@@H](O)C2)c(C#N)c1C1CC1]

To a solution of 2,6-dichloro-4-cyclopropylpyridine-3,5-dicarbonitrile (synthesis described in example 4 step 2, 237 mg, 0.995 mmol) in N,N-dimethylformamide (10 mL) were added (R)-piperidin-3-ol (101 mg, 0.995 mmol) and Et₃N (0.139 mL, 0.995 mmol). The reaction mixture was stirred at 25° C. overnight. After diluting the reaction with water, the precipitated solid was collected by filtration and dried in an oven to give (R)-2-chloro-4-cyclopropyl-6-(3-hydroxypiperidin-1-yl)pyridine-3,5-dicarbonitrile (275 mg, 91%). LCMS m/z=303.1 [M+H]⁺.

Step 2: 2-((3,5-dicyano-4-cyclopropyl-6-((R)-3-hydroxypiperidin-1-yl)pyridin-2-yl)thio)-2-phenylacetamide

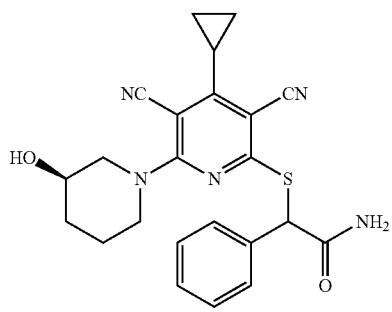 [SMILES: N#Cc1c(SC(C(N)=O)c2ccccc2)nc(N2CCC[C@@H](O)C2)c(C#N)c1C1CC1]

A solution of (R)-2-chloro-4-cyclopropyl-6-(3-hydroxypiperidin-1-yl)pyridine-3,5-dicarbonitrile (275 mg, 0.908 mmol) and potassium thioacetate (124 mg, 1.09 mmol) in N,N-dimethylformamide (8 mL) was stirred at room temperature for 30 minutes. Triethylamine (0.253 mL, 1.817 mmol) and 2-amino-2-oxo-1-phenylethyl methanesulfonate (synthesis described in example 3 step 5, 250 mg, 1.09 mmol) were then added and the reaction mixture stirred at 25° C. overnight. After diluting the reaction with water, the precipitated solid was collected by filtration and purified by silica gel column chromatography (MeOH:DCM 1:20) to give 2-((3,5-dicyano-4-cyclopropyl-6-((R)-3-hydroxypiperidin-1-yl)pyridin-2-yl)thio)-2-phenylacetamide (80 mg, 20%). LCMS m/z=434.2 [M+H]⁺. ¹H NMR (400 MHz, CDCl₃) δ ppm 7.52-7.43 (m, 2H), 7.43-7.32 (m, 3H), 6.93-6.79 (m, 1H), 5.83-5.68 (m, 1H), 5.28-5.20 (m, 1H), 4.65-4.44 (m, 1H), 4.05-3.98 (m, 0.5H), 3.94-3.87 (m, 1.5H), 3.81-3.75 (m, 0.5H), 3.66-3.55 (m, 0.5H), 3.48-3.38 (m, 0.5H), 3.07-2.99 (m, 0.5H), 2.29 (br s, 1H), 2.12-1.89 (m, 3H), 1.78-1.48 (m, 2H), 1.34-1.23 (m, 2H), 1.20-1.08 (m, 2H).

Example 33

2-(3,5-dicyano-4-cyclopropyl-6-((S)-3-hydroxypiperidin-1-yl)pyridin-2-ylthio)-2-phenylacetamide Step 1: (S)-2-chloro-4-cyclopropyl-6-(3-hydroxypiperidin-1-yl)pyridine-3,5-dicarbonitrile

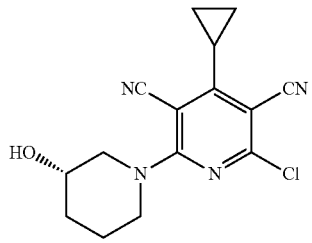 [SMILES: N#Cc1c(Cl)nc(N2CCC[C@H](O)C2)c(C#N)c1C1CC1]

To a solution of 2,6-dichloro-4-cyclopropylpyridine-3,5-dicarbonitrile (synthesis described in example 4 step 2, 237 mg, 0.995 mmol), in N,N-dimethylformamide (10 mL) were added (S)-piperidin-3-ol (101 mg, 0.995 mmol) and triethylamine (0.139 mL, 0.995 mmol). The reaction mixture was stirred at 25° C. overnight. After diluting the reaction with water, the precipitated solid was collected by filtration and dried to give (S)-2-chloro-4-cyclopropyl-6-(3-hydroxypiperidin-1-yl)pyridine-3,5-dicarbonitrile (275 mg, 91%). LCMS m/z=303.1 [M+H]⁺.

Step 2: 2-(3,5-dicyano-4-cyclopropyl-6-((S)-3-hydroxypiperidin-1-yl)pyridin-2-ylthio)-2-phenylacetamide

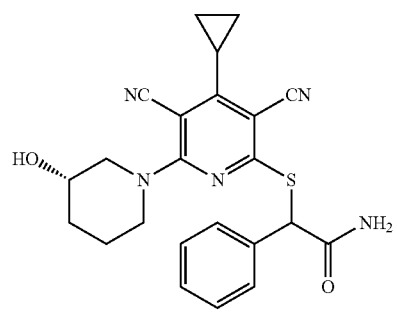 [SMILES: N#Cc1c(SC(C(N)=O)c2ccccc2)nc(N2CCC[C@H](O)C2)c(C#N)c1C1CC1]

A solution of (S)-2-chloro-4-cyclopropyl-6-(3-hydroxpiperidin-1-yl)pyridine-3,5-dicarbonitrile (275 mg, 0.908 mmol) and potassium thioacetate (124 mg, 1.09 mmol) in N,N-dimethylformamide (8 mL) was stirred at room temperature for 30 minutes. Triethylamine (0.253 mL, 1.817 mmol) and 2-amino-2-oxo-1-phenylethyl methanesulfonate (synthesis described in example 3 step 5, 250 mg, 1.09 mmol) were then added and the reaction mixture stirred at 25° C. overnight. After diluting the reaction with water, the precipitated solid was collected by filtration and purified by silica gel column chromatography (MeOH:DCM 1:20) to give 2-(3,5-dicyano-4-cyclopropyl-6-((S)-3-hydroxypiperidin-1-yl)pyridin-2-ylthio)-2-phenylacetamide (110 mg, 28%). LCMS m/z=434.1 [M+H]$^+$. $^1$H NMR (400 MHz, CDCl$_3$) δ ppm 7.50-7.43 (m, 2H), 7.42-7.34 (m, 3H), 6.92-6.79 (m, 1H), 5.77-5.64 (m, 1H), 5.28-5.21 (m, 1H), 4.63-4.46 (m, 1H), 4.05-3.98 (m, 0.5H), 3.95-3.88 (m, 1.5H), 3.81-3.75 (m, 0.5H), 3.65-3.56 (m, 0.5H), 3.49-3.39 (m, 0.5H), 3.07-2.99 (m, 0.5H), 2.12-2.03 (m, 2H), 2.00-1.88 (m, 2H), 1.79-1.54 (m, 2H), 1.32-1.24 (m, 2H), 1.20-1.08 (m, 2H).

Example 34

2-((3,5-dicyano-4-cyclopropyl-6-((S)-3-hydroxypyrrolidin-1-yl)pyridin-2-yl)thio)-2-(pyridin-4-yl)acetamide

Step 1: (S)-2-chloro-4-cyclopropyl-6-(3-hydroxypyrrolidin-1-yl)pyridine-3,5-dicarbonitrile

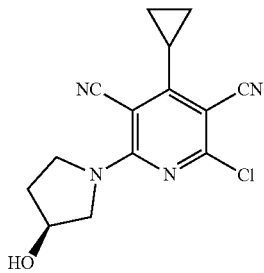 [SMILES: N#Cc1c(Cl)nc(N2CC[C@H](O)C2)c(C#N)c1C1CC1]

A mixture of 2,6-dichloro-4-cyclopropylpyridine-3,5-dicarbonitrile (synthesis described in example 4 step 2, 400 mg, 1.68 mmol), (S)-pyrrolidin-3-ol (146 mg, 1.68 mmol), and triethylamine (170 mg, 1.68 mmol) in N,N-dimethylformamide (10 mL) was stirred at room temperature for 30 minutes. The reaction mixture was poured into water (50 mL) and extracted with EtOAc (50 mL×2). The combined organic layers were dried and concentrated. The remaining residue was purified by silica gel column chromatography (MeOH:CH$_2$Cl$_2$ 1:80) to give (S)-2-chloro-4-cyclopropyl-6-(3-hydroxypyrrolidin-1-yl)pyridine-3,5-dicarbonitrile (320 mg, 66%) as a white solid. LCMS m/z=288.9 [M+H]$^+$.

Step 2: 2-((3,5-dicyano-4-cyclopropyl-6-((S)-3-hydroxypyrrolidin-1-yl)pyridin-2-yl)thio)-2-(pyridin-4-yl)acetamide

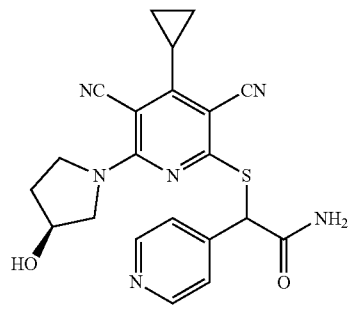 [SMILES: N#Cc1c(SC(C(N)=O)c2ccncc2)nc(N2CC[C@H](O)C2)c(C#N)c1C1CC1]

A solution of (S)-2-chloro-4-cyclopropyl-6-(3-hydroxypyrrolidin-1-yl)pyridine-3,5-dicarbonitrile (320 mg, 1.11 mmol) and potassium thioacetate (152 mg, 1.33 mmol) in N,N-dimethylformamide (10 mL) was stirred at room temperature for 30 minutes, then 2-amino-2-oxo-1-(pyridin-4-yl)ethyl methanesulfonate (synthesis described in example 3 step 5, 306 mg, 1.33 mmol) and Et$_3$N (224 mg, 2.22 mmol) were added to the reaction. The mixture was stirred at room temperature for 12 hours, then poured into water (50 mL), and extracted with EtOAc (50 mL×2). The combined organic layers were dried and concentrated. The remaining residue was purified by silica gel column chromatography (MeOH:CH$_2$Cl$_2$ 1:40) to give 2-((3,5-dicyano-4-cyclopropyl-6-((S)-3-hydroxypyrrolidin-1-yl)pyridin-2-yl)thio)-2-(pyridin-4-yl)acetamide (180 mg, 38%) as a white solid. LCMS m/z=420.8 [M+H]$^+$. $^1$H NMR (400 MHz, CD$_3$OD) δ ppm 8.57 (d, J=5.1 Hz, 2H), 7.63 (d, J=5.6 Hz, 2H), 5.70 (s, 1H), 4.53 (s, 1H), 4.10-3.72 (m, 4H), 2.16-2.02 (m, 3H), 1.27-1.18 (m, 2H), 1.12-1.00 (m, 2H). 3H not observed.

Example 35

2-((3,5-dicyano-4-ethyl-6-(4-ethylpiperazin-1-yl)pyridin-2-yl)thio)-2-phenylacetamide

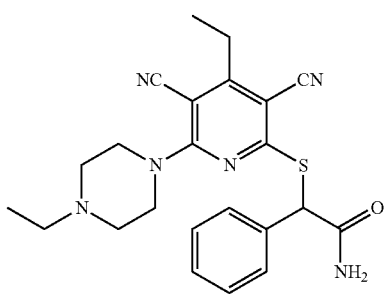 [SMILES: CCc1c(C#N)c(SC(C(N)=O)c2ccccc2)nc(N2CCN(CC)CC2)c1C#N]

A solution of 2-[(6-bromo-3,5-dicyano-4-ethyl-2-pyridyl)sulfanyl]-2-phenyl-acetamide (synthesis described in example 6 step 1, 16 mg, 0.04 mmol) in tetrahydrofuran (1 mL) was treated with 1-ethylpiperazinyl (0.011 mL, 0.089 mmol) and stirred at room temperature for 16 hours. The reaction mixture was dry loaded onto SiO$_2$ (0.9 g) and purified by silica gel chromatography (4 g RediSep cartridge; 0-10% MeOH, 0-1% NH$_3$/CH$_2$Cl$_2$) to give 2-[[3,5-dicyano-4-ethyl-6-(4-ethylpiperazin-1-yl)-2-pyridyl]sulfanyl]-2-phenyl-acetamide (14 mg, 81%), as a white solid. LCMS m/z=435 [M+H]⁺. ¹H NMR (300 MHz, DMSO-d₆) δ ppm 7.92 (s, 1H), 7.52 (br d, J=6.9 Hz, 2H), 7.46-7.29 (m, 4H), 5.53 (s, 1H), 3.37-3.30 (m, 4H), 2.84-2.54 (m, 2H), 2.48-2.32 (m, 6H), 1.20 (t, J=7.6 Hz, 3H), 1.04 (t, J=7.1 Hz, 3H).

Example 36

2-((3,5-Dicyano-4-ethyl-6-(1-oxa-6-azaspiro[3.4]octan-6-yl)pyridin-2-yl)thio)-2-phenylacetamide Step 1: Benzyl 3-hydroxypyrrolidinyl-1-carboxylate

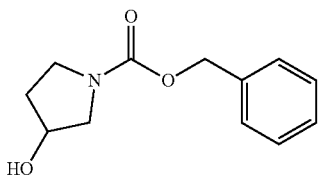 [SMILES: O=C(OCc1ccccc1)N1CCC(O)C1]

To a solution of pyrrolidin-3-ol (10.45 g, 120.1 mmol) in dichloromethane (300 mL) was added benzyl chloroformate (24.6 g, 144 mmol) and triethylamine (24.3 g, 240.2 mmol). The resulting solution was stirred at room temperature for 12 hours. After concentrating the reaction, the remaining material was partitioned between ethyl acetate (100 mL) and water (60 mL). The layers were separated. The organic layer was washed with water (60 mL), aqueous saturated sodium chloride solution (60 mL), dried and concentrated. The residue was purified by silica gel column chromatography (petroleum ether:ethyl acetate 2:1) to give benzyl 3-hydroxypyrrolidinyl-1-carboxylate (15.2 g, 57%) as a colorless gum. LCMS m/z=222.1 [M+H]⁺.

Step 2: Benzyl 3-oxopyrrolidinyl-1-carboxylate

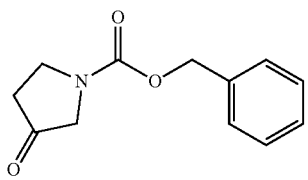 [SMILES: O=C1CCN(C(=O)OCc2ccccc2)C1]

A mixture of benzyl 3-hydroxypyrrolidinyl-1-carboxylate (14 g, 63.3 mmol) and IBX (21.3 g, 76 mmol) in acetonitrile (200 mL) was stirred at 70° C. for 2 hours. The mixture was filtered and the filtrate concentrated. The remaining residue was purified by silica gel column chromatography (petroleum ether:ethyl acetate 1:1) to give benzyl 3-oxopyrrolidinyl-1-carboxylate (11 g, 79%) as a colorless oil. ¹H NMR (400 MHz, DMSO-d₆) δ ppm 7.46-7.25 (m, 5H), 5.13 (s, 2H), 3.83-3.64 (m, 4H), 2.57 (s, 2H).

Step 3: Benzyl 1-oxa-6-azaspiro[3.4]octane-6-carboxylate

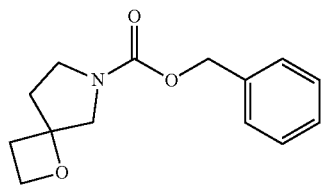 [SMILES: O=C(OCc1ccccc1)N1CCC2(CCO2)C1]

To a solution of trimethylsulfoxonium iodide (25.86 g, 117.5 mmol) in tert-butanol (78 mL) was added potassium tert-butanolate (11.6 g, 103.4 mmol). The mixture was stirred at 50° C. for 1 hour and then benzyl 3-oxopyrrolidinyl-1-carboxylate (10.3 g, 47 mmol) was added. The mixture was stirred at 50° C. for an additional 48 hours. The reaction was quenched with saturated ammonium chloride solution (200 mL) and extracted with ethyl acetate (50 mL×3). The combined organic layers were washed with saturated sodium chloride solution (100 mL), dried, and concentrated. The remaining residue was purified by silica gel column chromatography (petroleum ether:ethyl acetate 3:1) to give benzyl 1-oxa-6-azaspiro[3.4]octane-6-carboxylate (1.5 g, 12%) as a light yellow oil. LCMS m/z=248.0 [M+H]⁺.

Step 4: 1-Oxa-6-azaspiro[3.4]octane

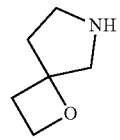

A mixture of benzyl 1-oxa-6-azaspiro[3.4]octane-6-carboxylate (1 g, 4 mmol) and 10% palladium on carbon (100 mg) in methanol (20 mL) was stirred at room temperature under a hydrogen atmosphere for 12 hours. The mixture was filtered and the filtrate concentrated. The remaining residue was purified by silica gel column chromatography (dichloromethane:methanol 20:1) to give 1-oxa-6-azaspiro[3.4]octane (700 mg, crude) as a colorless oil. LCMS m/z=114.0 [M+H]⁺.

Step 5: 2-Chloro-4-ethyl-6-(1-oxa-6-azaspiro[3.4]octan-6-yl)pyridine-3,5-dicarbonitrile

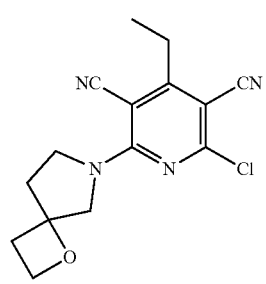 [SMILES: CCc1c(C#N)c(Cl)nc(N2CCC3(CCO3)C2)c1C#N]

To a solution of 2,6-dichloro-4-ethylpyridine-3,5-dicarbonitrile (678 mg, 3.01 mmol) in dichloromethane (20 mL) was added 1-oxa-6-azaspiro[3.4]octane (340 mg, 3.01 mmol) followed by triethylamine (303 mg, 3.01 mmol). The solution was stirred at room temperature for 12 hours. The reaction was partitioned between dichloromethane (40 mL) and water (30 mL). The layers were separated. The organic layer was washed with brine (30 mL), dried, and concentrated to afford 2-chloro-4-ethyl-6-(1-oxa-6-azaspiro[3.4]octan-6-yl)pyridine-3,5-dicarbonitrile (910 mg, crude) as a brown oil. LCMS m/z=303.0 [M+H]⁺.

Step 6: 4-Ethyl-2-mercapto-6-(1-oxa-6-azaspiro[3.4]octan-6-yl)pyridine-3,5-dicarbonitrile

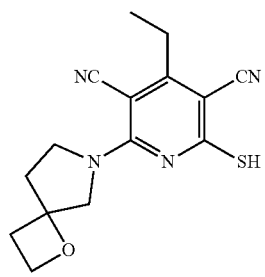 [SMILES: CCc1c(C#N)c(S)nc(N2CCC3(CCO3)C2)c1C#N]

A mixture of 2-chloro-4-ethyl-6-(1-oxa-6-azaspiro[3.4]octan-6-yl)pyridine-3,5-dicarbonitrile (synthesis described in example 3 step 2, 910 mg, 3.01 mmol) and potassium thioacetate (514 mg, 4.51 mmol) in N,N-dimethylformamide (10 mL) was stirred at room temperature for 1.5 hours and used directly in the next step. LCMS m/z=300.8 [M+H]⁺

Step 7: 2-((3,5-Dicyano-4-ethyl-6-(1-oxa-6-azaspiro[3.4]octan-6-yl)pyridin-2-yl)thio)-2-phenylacetamide

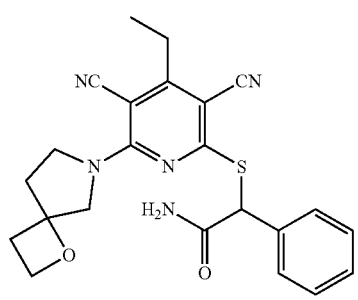 [SMILES: CCc1c(C#N)c(SC(C(N)=O)c2ccccc2)nc(N2CCC3(CCO3)C2)c1C#N]

To the above mixture was added potassium carbonate (826 mg, 6.00 mmol) and the reaction allowed to stir at room temperature for 1 hour, then 2-amino-2-oxo-1-phenylethyl methanesulfonate (synthesis described in example 3 step 5, 825 mg, 3.60 mmol) was added. The resulting mixture was stirred at room temperature for an additional 12 hours then was concentrated. The residue was purified by silica gel column chromatography (CH₂Cl₂:Methanol 30:1) to provide 2-((3,5-dicyano-4-ethyl-6-(1-oxa-6-azaspiro[3.4]octan-6-yl)pyridin-2-yl)thio)-2-phenylacetamide (107 mg, 8%) as a pale solid. LCMS m/z=433.8 [M+H]⁺. ¹H NMR (400 MHz, DMSO-d₆) δ ppm 1.21 (t, J=7.6 Hz, 3H), 2.17-2.06 (m, 1H), 2.41-2.33 (m, 1H), 2.85-2.63 (m, 4H), 4.05-3.71 (m, 3H), 4.13 (dd, J=28.3, 12.7 Hz, 1H), 4.52-4.40 (m, 2H), 5.61 (d, J=4.9 Hz, 1H), 7.45-7.31 (m, 4H), 7.54 (d, J=7.5 Hz, 2H), 7.93 (d, J=6.6 Hz, 1H).

Example 37

2-((6-(4-(3-aminopropyl)piperazin-1-yl)-3,5-dicyano-4-ethylpyridin-2-yl)thio)-2-phenylacetamide Step 1: tert-butyl (3-(4-benzylpiperazin-1-yl)propyl)carbamate

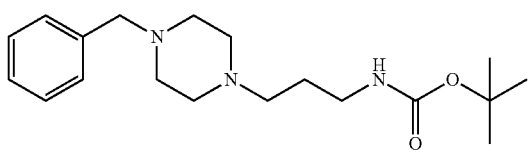 [SMILES: CC(C)(C)OC(=O)NCCCN1CCN(Cc2ccccc2)CC1]

To a solution of 1-benzylpiperazinyl (500 mg, 2.84 mmol) in CH₃—CN (30 mL) was added tert-butyl (3-bromopropyl)carbamate (1.0 g, 4.26 mmol) and K₂CO₃ (784 mg, 5.68 mmol). After the reaction was heated at 70° C. for 12 hours, the mixture was concentrated and the remaining material purified by silica gel column chromatography (CH₂Cl₂:methanol 10:1) to give tert-butyl (3-(4-benzylpiperazin-1-yl)propyl)carbamate (900 mg, 95%). LCMS m/z=334 [M+H].

Step 2: tert-butyl (3-(piperazin-1-yl)propyl)carbamate

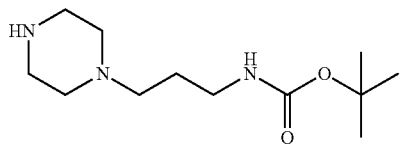 [SMILES: CC(C)(C)OC(=O)NCCCN1CCNCC1]

A mixture of tert-butyl (3-(4-benzylpiperazin-1-yl)propyl)carbamate (900 mg, 2.7 mmol) and palladium on carbon (90 mg) in methanol (30 mL) was stirred at room temperature under a hydrogen atmosphere overnight. The reaction mixture was filtered, the filtrate concentrated, and the remaining residue purified by silica gel column chromatography (CH₂Cl₂:methanol 5:1) to give tert-butyl (3-(piperazin-1-yl)propyl)carbamate (460 mg, 70% yield). LCMS m/z=244 [M+H]⁺.

Step 3: tert-butyl (3-(4-(6-chloro-3,5-dicyano-4-ethylpyridin-2-yl)piperazin-1-yl)propyl)carbamate

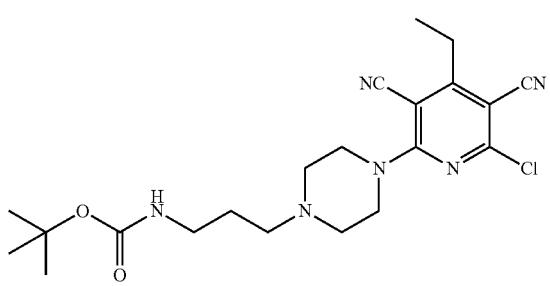 [SMILES: CCc1c(C#N)c(Cl)nc(N2CCN(CCCNC(=O)OC(C)(C)C)CC2)c1C#N]

To a solution of 2,6-dichloro-4-ethylpyridine-3,5-dicarbonitrile (synthesis described in example 3 step 2, 426 mg, 1.89 mmol) in N,N-dimethylformamide (10 mL) was added tert-butyl (3-(piperazin-1-yl)propyl)carbamate (460 mg, 1.89 mmol) and triethylamine (0.26 mL, 1.89 mmol). The reaction mixture was stirred at room temperature for 5 minutes, then was partitioned between ethyl acetate and water. The layers were separated. The organic layer was washed with water, brine, dried, and concentrated. The remaining residue was purified by silica gel column chromatography (petroleum ether:ethyl acetate 40:60) to give tert-butyl (3-(4-(6-chloro-3,5-dicyano-4-ethylpyridin-2-yl)piperazin-1-yl)propyl)carbamate (600 mg, 74%). LCMS m/z=433 [M+H]$^+$.

Step 4: tert-butyl (3-(4-(6-((2-amino-2-oxo-1-phenylethyl)thio)-3,5-dicyano-4-ethylpyridin-2-yl)piperazin-1-yl)propyl)carbamate

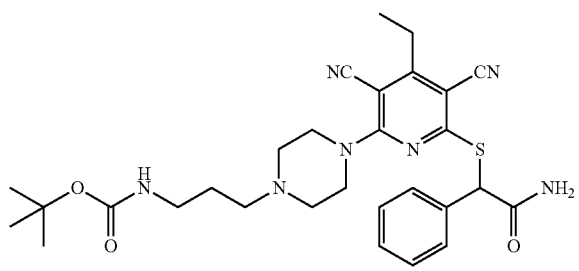 [SMILES: CCc1c(C#N)c(SC(C(N)=O)c2ccccc2)nc(N2CCN(CCCNC(=O)OC(C)(C)C)CC2)c1C#N]

To a solution of tert-butyl (3-(4-(6-chloro-3,5-dicyano-4-ethylpyridin-2-yl)piperazin-1-yl)propyl)carbamate (300 mg, 0.69 mmol) in N,N-dimethylformamide (7 mL) was added potassium thioacetate (95 mg, 0.83 mmol). The reaction was stirred at room temperature for 30 minutes, then 2-amino-2-oxo-1-phenylethyl methanesulfonate (synthesis described in example 3 step 5, 191 mg, 0.83 mmol) and triethylamine (0.19 mL, 1.38 mmol) were added to the reaction. The mixture was stirred at room temperature overnight. After the addition of water to the reaction, the precipitated solid was collected by filtration and was purified by silica gel column chromatography (CH$_2$Cl$_2$:methanol 20:1) to give tert-butyl (3-(4-(6-((2-amino-2-oxo-1-phenylethyl)thio)-3,5-dicyano-4-ethylpyridin-2-yl)piperazin-1-yl)propyl)carbamate (280 mg, 72%) as yellow solid. LCMS m/z=564 [M+H]$^+$.

Step 5: 2-((6-(4-(3-aminopropyl)piperazin-1-yl)-3,5-dicyano-4-ethylpyridin-2-yl)thio)-2-phenylacetamide

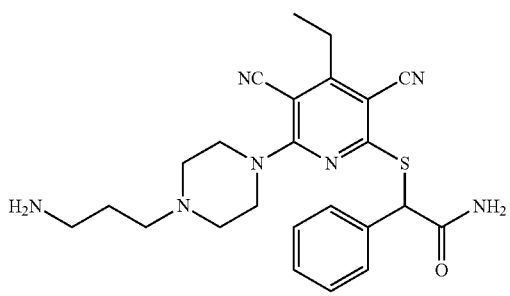 [SMILES: CCc1c(C#N)c(SC(C(N)=O)c2ccccc2)nc(N2CCN(CCCN)CC2)c1C#N]

A solution of tert-butyl (3-(4-(6-((2-amino-2-oxo-1-phenylethyl)thio)-3,5-dicyano-4-ethylpyridin-2-yl)piperazin-1-yl)propyl)carbamate (280 mg, 0.50 mmol) and trifluoroacetic acid (3 mL) in dichloromethane (5 mL) was stirred at room temperature overnight. The solvent was removed, the remaining material neutralized with saturated aqueous NaHCO$_3$ solution, and extracted with dichloromethane. The organic layer was washed with aqueous saturated sodium chloride solution and concentrated. The crude material was purified by silica gel column chromatography (CH$_2$Cl$_2$:methanol 5:1) to give 2-((6-(4-(3-aminopropyl)piperazin-1-yl)-3,5-dicyano-4-ethylpyridin-2-yl)thio)-2-phenylacetamide (91 mg, 39%) as a white solid. LCMS m/z=464 [M+H]$^+$. $^1$H NMR (400 MHz, CD$_3$OD) δ ppm 7.55 (d, J=6.7 Hz, 2H), 7.45-7.36 (m, 3H), 5.49 (s, 1H), 4.05-3.94 (m, 4H), 3.09 (t, J=7.1 Hz, 2H), 2.92 (q, J=7.6 Hz, 2H), 2.68-2.53 (m, 6H), 1.94-1.85 (m, 2H), 1.32 (t, J=7.6 Hz, 3H). 4H not observed.

Example 38

2-((3,5-Dicyano-4-ethyl-6-(1,7-diazaspiro[3.5] nonan-1-yl)pyridin-2-yl)thio)-2-phenylacetamide trifluoroacetate Step 1: tert-Butyl 4-methylenepiperidinyl-1-carboxylate

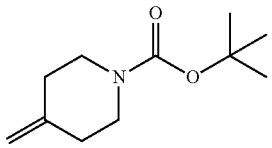

To a solution of methyltriphenylphosphonium bromide (9.5 g, 26.7 mmol) in tetrahydrofuran (30 mL) was added sodium hydride (60%, 1.07 g, 26.7 mmol) followed by the addition of dimethyl sulfoxide (33 mL). The resulting mixture was stirred at ambient temperature for 10 minutes and then treated with a solution of tert-butyl 4-oxopiperidinyl-1-carboxylate (5 g, 25 mmol) in tetrahydrofuran (20 mL) dropwise. The resulting mixture was stirred at ambient temperature for 30 minutes and then diluted with ethyl acetate (60 mL). The mixture washed with water (60 mL) and brine (60 mL), dried over sodium sulfate and concentrated under reduced pressure. The residue was purified with chromatography (petroleum ether:ethyl acetate=30:1) to afford the title compound (4 g, 80%) as a yellow oil. $^1$H NMR (400 MHz, chloroform-d) δ ppm 1.48 (s, 9H), 2.23-2.14 (m, 4H), 3.47-3.38 (m, 4H), 4.75 (s, 2H).

Step 2: tert-Butyl 1,7-diazaspiro[3.5]nonane-7-carboxylate

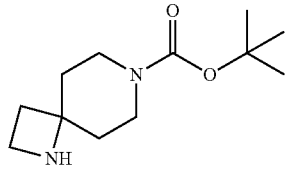 [SMILES: CC(C)(C)OC(=O)N1CCC2(CCN2)CC1]

To a solution of tert-butyl 4-methylenepiperidinyl-1-carboxylate (4 g, 20 mmol) in dichloromethane (50 mL) was added sulfurisocyanatidic chloride (3.4 g, 24 mmol) at 0° C. The resultant mixture was stirred at ambient temperature overnight and then diluted with diethyl ether (100 mL) and cooled to 0° C. The mixture was treated with a solution of sodium thiosulfate (9.5 g, 60 mmol) and potassium hydroxide (2.24 g, 40 mmol) in water (50 mL) at 0° C. The resultant mixture was stirred at 0° C. for 3 hours and extracted with ethyl acetate (2×50 mL). The organic phase was dried anhydrous sodium sulfate and concentrated under reduced pressure to give a yellow oil (4.1 g crude). The oil was dissolved in tetrahydrofuran (30 mL) and borane-dimethyl sulfide complex (2 M, 15 mL, 30 mmol) was added. The resultant mixture as stirred at 70° C. overnight. The mixture was cooled to ambient temperature and concentrated under reduced pressure to give the title compound (4.5 g, crude) as a yellow oil which was used in the next step without further purification. LCMS m/z=227.1 [M+H]$^+$.

Step 3: tert-Butyl 1-(6-chloro-3,5-dicyano-4-ethylpyridin-2-yl)-1,7-diazaspiro[3.5]nonane-7-carboxylate

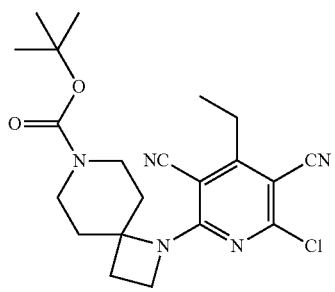 [SMILES: CCc1c(C#N)c(Cl)nc(N2CCC23CCN(C(=O)OC(C)(C)C)CC3)c1C#N]

tert-Butyl 1,7-diazaspiro[3.5]nonane-7-carboxylate (1.5 g, crude) and 2,6-dichloro-4-ethylpyridine-3,5-dicarbonitrile (synthesis described in example 3 step 2, 1 g, 4.5 mmol) were dissolved in tetrahydrofuran (20 mL) and triethylamine (1.14 g, 11.25 mmol) was added at 0° C. The resultant mixture was stirred at ambient temperature for 2 hours and then diluted with ethyl acetate (60 mL). The mixture was washed with water (40 mL) and brine (40 mL), dried over anhydrous sodium sulfate and concentrated under reduced pressure to afford the title compound (2.1 g, crude) as a yellow oil which was used in the next step without further purification. LCMS m/z=437.8 [M+Na]$^+$.

Step 4: tert-Butyl 1-(6-((2-amino-2-oxo-1-phenylethyl)thio)-3,5-dicyano-4-ethylpyridin-2-yl)-1,7-diazaspiro[3.5]nonane-7-carboxylate

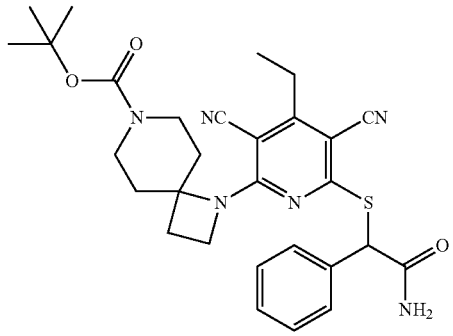 [SMILES: CCc1c(C#N)c(SC(C(N)=O)c2ccccc2)nc(N2CCC23CCN(C(=O)OC(C)(C)C)CC3)c1C#N]

To a solution of tert-butyl 1-(6-chloro-3,5-dicyano-4-ethylpyridin-2-yl)-1,7-diazaspiro[3.5]nonane-7-carboxylate (2.1 g, crude) in anhydrous N,N-dimethylformamide (30 mL) was added potassium thioacetate (0.7 g, 6 mmol). The resultant mixture was stirred at room temperature for 3 hours and then potassium carbonate (1.65 g, 12 mmol) was added and the reaction stirred for 2 hours at room temperature. Then 2-amino-2-oxo-1-phenylethyl methanesulfonate (synthesis described in example 3 step 5, 2.75 g, 12 mmol) was added and the resultant mixture was stirred at room temperature overnight, then diluted with ethyl acetate (80 mL), washed with water (60 mL) and brine (60 mL). The organic phase was dried over anhydrous sodium sulfate and concentrated under reduced pressure. The residue was purified by column chromatography (petroleum ether:ethyl acetate=1:1-1:2) to give the title compound (1 g, crude). LCMS m/z=546.8 [M+H]$^+$.

Step 5: 2-((3,5-Dicyano-4-ethyl-6-(1,7-diazaspiro[3.5]nonan-1-yl)pyridin-2-yl)thio)-2-phenylacetamide trifluoroacetate

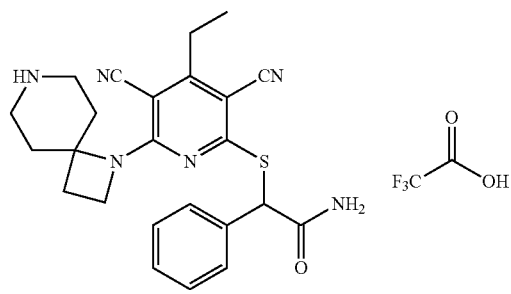 [SMILES: CCc1c(C#N)c(SC(C(N)=O)c2ccccc2)nc(N2CCC23CCNCC3)c1C#N ; O=C(O)C(F)(F)F]

To a solution of tert-butyl 1-(6-((2-amino-2-oxo-1-phenylethyl)thio)-3,5-dicyano-4-ethylpyridin-2-yl)-1,7-diazaspiro[3.5]nonane-7-carboxylate (0.9 g, crude) in 1,4-dioxane (20 mL) was bubbled in HCl(g) at 0° C. for 10 minutes. The resultant mixture was concentrated under reduced pressure and the residue was purified with prep-HPLC to give the title compound (120 mg, 15%) as a white solid. LCMS m/z=447.1 [M+H]$^+$. $^1$H NMR (400 MHz, DMSO-d$_6$) δ ppm 1.2 (t, J=6 Hz, 3H), 2.36-2.18 (m, 4H), 2.70 (q, J=6 Hz, 2H), 3.18-3.12 (m, 2H), 3.54-3.46 (m, 4H), 3.65-3.57 (m, 2H), 5.55-5.44 (m, 2H), 7.53-7.35 (m, 4H), 7.95-7.88 (m, 1H), 8.71-8.59 (br, 2H).

Example 39

2-((3,5-Dicyano-4-cyclopropyl-6-(4-(pyrrolidin-1-ylmethyl)piperidin-1-yl)pyridin-2-yl)thio)-2-phenylacetamide Step 1: tert-Butyl 4-(pyrrolidin-1-ylmethyl)piperidinyl-1-carboxylate

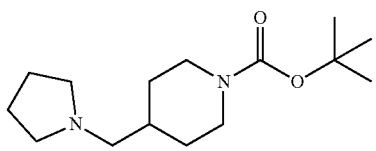 [SMILES: CC(C)(C)OC(=O)N1CCC(CN2CCCC2)CC1]

To a solution of tert-butyl 4-formylpiperidinyl-1-carboxylate (1 g, 4.69 mmol) and pyrrolidinyl (0.3 g, 4.22 mmol) in dichloromethane (20 mL) was added 2 drops of acetic acid. The mixture was stirred for one hour and then sodium triacetoxyborohydride (1 g, 4.7 mmol) was added. The mixture was stirred for one hour, and was then washed with aqueous sodium hydroxide (2 M, 2×50 mL) and aqueous HCl (2 M, 2×50 mL), dried over anhydrous sodium sulfate, filtered, and concentrated to afford the title compound (1 g, 80% yield). LCMS m/z=269 [M+H]+.

Step 2: 4-(Pyrrolidin-1-ylmethyl)piperidinyl hydrochloride

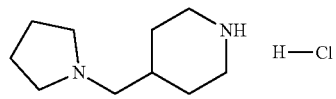

To a solution of hydrochloric acid in dioxane (4 M, 20 mL, 80 mmol) was added tert-butyl 4-(pyrrolidin-1-ylmethyl)piperidinyl-1-carboxylate (1 g, 3.73 mmol). The mixture was stirred for 2 hours and the resulting solid was collected by filtration, washed with ethyl acetate, and dried to give the crude title compound (0.8 g, >100% crude yield). LCMS m/z=169 [M+H]+.

Step 3: 2-Chloro-4-cyclopropyl-6-(4-(pyrrolidin-1-ylmethyl)piperidin-1-yl)pyridine-3,5-dicarbonitrile

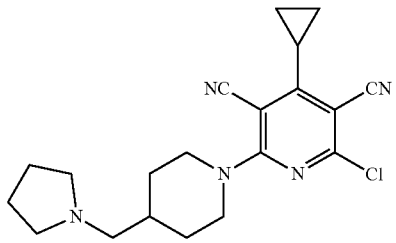 [SMILES: N#Cc1c(Cl)nc(N2CCC(CN3CCCC3)CC2)c(C#N)c1C1CC1]

To a solution of 2,6-dichloro-4-cyclopropylpyridine-3,5-dicarbonitrile (synthesis described in example 4 step 2, 500 mg, 2.1 mmol) and 4-(pyrrolidin-1-ylmethyl)piperidinyl hydrochloride (500 mg, 2.4 mmol) in dichloromethane (20 mL) was added triethylamine (750 mg, 7.5 mmol). The mixture was stirred for one hour, and was then washed with brine (2×100 mL), dried over anhydrous sodium sulfate, and concentrated. The residue was then purified by silica gel chromatography eluting with ethyl acetate:petroleum ether (1:3) to afford the title compound (750 mg, 96% yield). LCMS m/z=370 [M+H]+.

Step 4: 4-Cyclopropyl-2-mercapto-6-(4-(pyrrolidin-1-ylmethyl)piperidin-1-yl)pyridine-3,5-dicarbonitrile

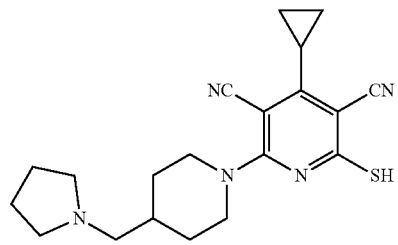

To a solution of 2-chloro-4-cyclopropyl-6-(4-(pyrrolidin-1-ylmethyl)piperidin-1-yl) pyridine-3,5-dicarbonitrile (750 mg, 2.0 mmol) in N,N-dimethylformamide (20 mL) was added potassium thioacetate (250 mg, 2.2 mmol). The mixture was stirred for two hours and was then diluted with ethyl acetate (200 mL), washed with brine (2×100 mL), dried over anhydrous sodium sulfate and concentrated to give the crude title compound (700 mg, 95% crude yield). LCMS m/z=368 [M+H]+.

Step 5: 2-((3,5-Dicyano-4-cyclopropyl-6-(4-(pyrrolidin-1-ylmethyl)piperidin-1-yl)pyridin-2-yl)thio)-2-phenylacetamide

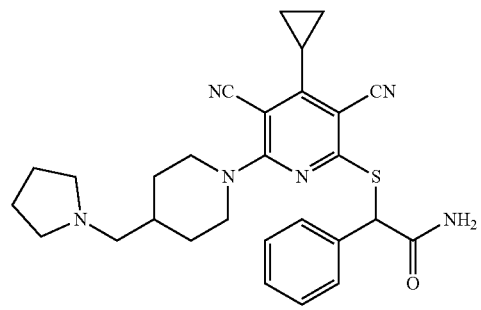 [SMILES: N#Cc1c(SC(C(N)=O)c2ccccc2)nc(N2CCC(CN3CCCC3)CC2)c(C#N)c1C1CC1]

To a solution of 4-cyclopropyl-2-mercapto-6-(4-(pyrrolidin-1-ylmethyl)piperidin-1-yl)pyridine-3,5-dicarbonitrile (700 mg, 1.9 mmol) in N,N-dimethylformamide (50 mL) was added 2-amino-2-oxo-1-phenylethyl methanesulfonate (synthesis described in example 3 step 5, 500 mg, 2.2 mmol) and potassium carbonate (300 mg, 2.2 mmol). The reaction mixture was stirred overnight at ambient temperature. The mixture was diluted with ethyl acetate (200 mL) and washed with brine (2×100 mL), dried over anhydrous sodium sulfate and concentrated. The residue was purified by prep-HPLC to give the title compound (15 mg, 1.5% yield). LCMS m/z=501 [M+H]⁺. ¹H NMR (400 MHz, DMSO-d₆) δ ppm 7.92 (s, 1H), 7.52 (d, J=7.0 Hz, 2H), 7.41-7.34 (m, 3H), 5.53 (s, 1H), 4.53 (t, J=12.2 Hz, 2H), 3.60 (br s, 3H), 3.17-3.10 (m, 3H), 3.04 (br s, 2H), 2.18-1.99 (m, 4H), 1.93-1.86 (m, 3H), 1.34-1.22 (m, 3H), 1.18-1.09 (m, 2H), 0.98 (dt, J=10.2, 5.2 Hz, 2H).

Example 40

2-((3,5-Dicyano-4-cyclopropyl-6-(4-(4-methylpiperazin-1-yl)piperidin-1-yl)pyridin-2-yl)thio)-2-phenylacetamide

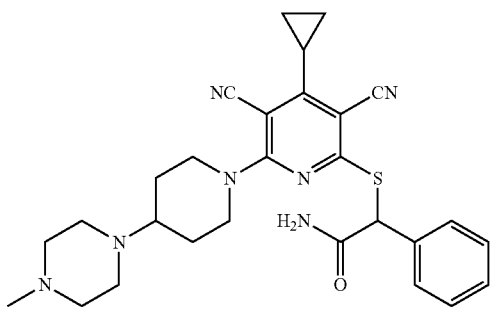 [SMILES: CN1CCN(C2CCN(c3nc(SC(C(N)=O)c4ccccc4)c(C#N)c(C4CC4)c3C#N)CC2)CC1]

To a solution of 2,6-dichloro-4-cyclopropylpyridine-3,5-dicarbonitrile (synthesis described in example 4 step 2, 300 mg, 1.26 mmol) and 1-methyl-4-(piperidin-4-yl)piperazinyl hydrochloride (243 mg, 1.10 mmol) in dichloromethane (50 mL) was added triethylamine (300 mg, 2.75 mmol). The mixture was stirred for one hour and then concentrated. To a solution of the residue in N,N-dimethylformamide (50 mL) was added potassium thioacetate (144 mg, 1.26 mmol), and the mixture was stirred overnight. To the mixture was added potassium carbonate (500 mg, 3.62 mmol) and 2-amino-2-oxo-1-phenylethyl methanesulfonate (synthesis described in example 3 step 5, 1 g, 4.46 mmol). The reaction was stirred at ambient temperature overnight and was then diluted with water (30 mL). The resulting solid was collected by filtration, and was then purified by prep-HPLC to give the title compound (200 mg, 37% yield). LCMS m/z=516 [M+H]⁺. ¹H NMR (400 MHz, DMSO-d₆) δ ppm 7.94 (s, 1H), 7.53 (d, J=7.1 Hz, 2H), 7.43-7.30 (m, 4H), 5.54 (s, 1H), 4.61 (s, 4H), 3.36-2.98 (m, 8H), 2.83 (s, 3H), 2.08-1.95 (m, 4H), 1.54 (dd, J=24.5, 11.2 Hz, 2H), 1.14 (dt, J=8.6, 3.1 Hz, 2H), 1.04-0.92 (m, 2H).

Example 41

(R)-2-((3,5-dicyano-6-(1,4-diazepan-1-yl)-4-ethylpyridin-2-yl)amino)-2-phenylacetamide Step 1: (R)-2-((6-chloro-3,5-dicyano-4-ethylpyridin-2-yl)amino)-2-phenylacetamide

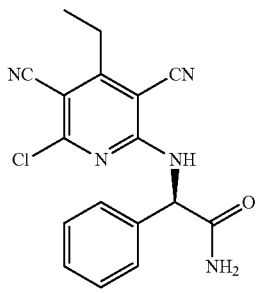 [SMILES: CCc1c(C#N)c(Cl)nc(N[C@@H](C(N)=O)c2ccccc2)c1C#N]

A stirred solution of 2,6-dichloro-4-ethylpyridine-3,5-dicarbonitrile (synthesis described in example 3 step 2, 148.5 mg, 0.657 mmol) dissolved in tetrahydrofuran (10 mL) was treated with (R)-2-amino-2-phenylacetamide (118 mg, 0.788 mmol) in one portion at 20° C. After 2 hours, the mixture was diluted with EtOAc (50 mL), washed with water (3×50 mL), brine, dried, then concentrated to provide (R)-2-((6-chloro-3,5-dicyano-4-ethylpyridin-2-yl)amino)-2-phenylacetamide (177 mg, 0.521 mmol, 79% yield) as a light yellow solid. LCMS m/z=340 [M+H]⁺.

Step 2: (R)-2-((3,5-dicyano-6-(1,4-diazepan-1-yl)-4-ethylpyridin-2-yl)amino)-2-phenylacetamide

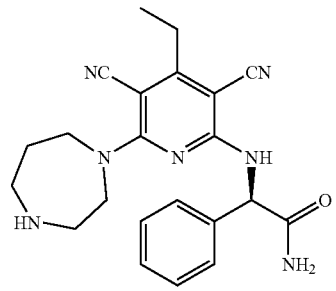 [SMILES: CCc1c(C#N)c(N[C@@H](C(N)=O)c2ccccc2)nc(N2CCCNCC2)c1C#N]

A solution of (R)-2-((6-chloro-3,5-dicyano-4-ethylpyridin-2-yl)amino)-2-phenylacetamide (39 mg, 0.115 mmol) in tetrahydrofuran (5 mL) was treated with a solution of 1,4-diazepane (184 mg, 1.836 mmol) in tetrahydrofuran (5 mL) in one portion at room temperature. The resulting suspension was stirred at room temperature for 1 hour, then the reaction mixture was diluted with ethyl acetate (20 mL), washed with water (2×20 mL), brine, then dried over sodium sulfate to provide the crude product. This material was purified on a 24 g Analogix column that had been preconditioned with dichloromethane, then eluted with 100% DCM (4 minutes) followed by a gradient from 0-100% (methanol containing 10% ammonium hydroxide)/dichloromethane over 25 minutes. The desired fractions were combined, concentrated in vacuo, then dried under vacuum to provide (R)-2-((3,5-dicyano-6-(1,4-diazepan-1-yl)-4-ethylpyridin- 2-yl)amino)-2-phenylacetamide (23 mg, 0.057 mmol, 50% yield) as a white solid. LCMS m/z=404 [M+H]+. 1H NMR (400 MHz, DMSO-d6): δ ppm 7.83 (s, 1H), 7.49-7.42 (m, 3H), 7.38-7.31 (m, 2H), 7.31-7.25 (m, 1H), 7.07 (d, J=6.1 Hz, 1H), 5.42 (d, J=6.1 Hz, 1H), 3.86-3.61 (m, 5H), 2.90-2.79 (m, 1H), 2.71 (q, J=7.7 Hz, 3H), 2.61 (t, J=5.7 Hz, 2H), 1.72 (dd, J=13.3, 7.5 Hz, 1H), 1.65-1.55 (m, 1H), 1.20 (t, J=7.6 Hz, 3H).

Example 42

2-((3,5-Dicyano-4-cyclopropyl-6-(4-(pyrrolidin-1-yl)piperidin-1-yl)pyridin-2-yl)thio)-2-phenylacetamide trifluoroacetate

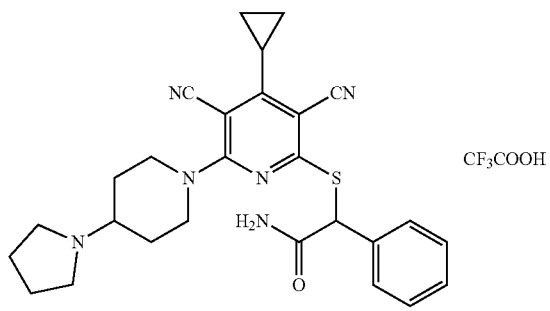 [SMILES: N#Cc1c(SC(C(N)=O)c2ccccc2)nc(N2CCC(N3CCCC3)CC2)c(C#N)c1C1CC1 ; "CF3COOH"]

To a solution of 2,6-dichloro-4-cyclopropylpyridine-3,5-dicarbonitrile (synthesis described in example 4 step 2, 500 mg, 2.10 mmol) and 4-(pyrrolidin-1-yl)piperidinyl (325 mg, 2.11 mmol) in dichloromethane (50 mL) was added triethylamine (230 mg, 2.28 mmol). The reaction was stirred at room temperature until LCMS showed the product. The mixture was concentrated to give a light yellow solid which was dissolved in N,N-dimethylformamide (50 mL) and potassium thioacetate (144 mg, 1.26 mmol) was added. The mixture was stirred at 25° C. for six hours and then potassium carbonate (500 mg, 3.60 mmol) and 2-amino-2-oxo-1-phenylethyl methanesulfonate (synthesis described in example 3 step 5, 1.0 g, 4.36 mmol) were added. The mixture was stirred overnight at room temperature. The mixture was diluted with water (30 mL) and extracted with ethyl acetate (30 mL). The organic phase was concentrated, and the residue was purified by prep-HPLC to give the title compound (120 mg, 22% yield). LCMS m/z=487 [M+H]+. 1H NMR (400 MHz, CDCl3) δ ppm 12.25 (s, 1H), 7.54-7.45 (m, 2H), 7.44-7.34 (m, 3H), 6.95 (s, 1H), 6.88 (s, 1H), 5.30 (s, 1H), 4.72 (t, J=12.3 Hz, 2H), 3.92 (d, J=38.7 Hz, 2H), 3.32 (t, J=13.1 Hz, 1H), 3.12 (s, 1H), 3.06-2.94 (m, 1H), 2.84 (s, 4H), 2.24-2.12 (m, 6H), 1.92 (d, J=8.3 Hz, 1H), 1.36-1.14 (m, 4H).

Example 43

2-((3,5-Dicyano-4-ethyl-6-(2,7-diazaspiro[3.5]nonan-7-yl)pyridin-2-yl)thio)-2-phenylacetamide Step 1: tert-Butyl 7-(6-chloro-3,5-dicyano-4-ethylpyridin-2-yl)-2,7-diazaspiro[3.5]nonane-2-carboxylate

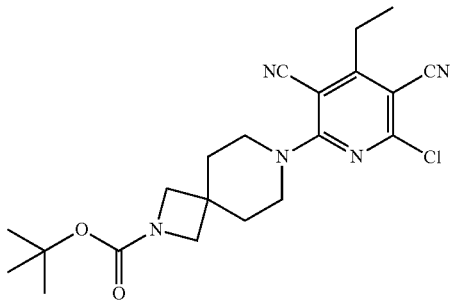 [SMILES: CCc1c(C#N)c(Cl)nc(N2CCC3(CC2)CN(C(=O)OC(C)(C)C)C3)c1C#N]

To a solution of 2,6-dichloro-4-ethylpyridine-3,5-dicarbonitrile (synthesis described in example 3 step 2, 452 mg, 2 mmol) in dichloromethane (20 mL) was added tert-butyl 2,7-diazaspiro[3.5]nonane-2-carboxylate (452 mg, 2 mmol) followed by triethylamine (202 mg, 2 mmol). The reaction was stirred for 12 hours and was diluted with dichloromethane (40 mL) and washed with water (25 mL) and brine (25 mL). The organic layer was dried over sodium sulfate, and concentrated to afford the crude title compound (820 mg) as a yellow solid. LCMS m/z=438 [M+Na]+.

Step 2: tert-Butyl 7-(3,5-dicyano-4-ethyl-6-mercaptopyridin-2-yl)-2,7-diazaspiro[3.5]nonane-2-carboxylate

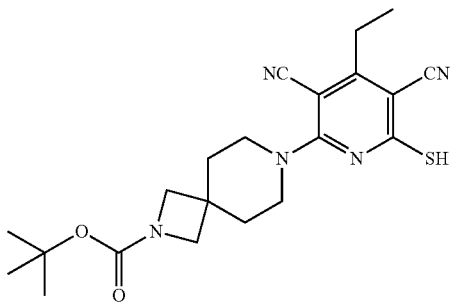 [SMILES: CCc1c(C#N)c(S)nc(N2CCC3(CC2)CN(C(=O)OC(C)(C)C)C3)c1C#N]

To a solution of crude tert-butyl 7-(6-chloro-3,5-dicyano-4-ethylpyridin-2-yl)-2,7-diazaspiro[3.5]nonane-2-carboxylate (820 mg, assumed 1.97 mmol) in N,N-dimethylformamide (8 mL) was added potassium thioacetate (271 mg, 2.36 mmol). The resulting mixture was stirred at ambient temperature for 2 hours. The mixture was then diluted with water (25 mL) and extracted with ethyl acetate (40 mL). The organic phase was washed with brine (25 mL), dried, and concentrated to afford the crude title compound (890 mg) as a brown oil. LCMS m/z=414 [M+H]+.

Step 3: tert-Butyl 7-(6-((2-amino-2-oxo-1-phenyl-ethyl)thio)-3,5-dicyano-4-ethylpyridin-2-yl)-2,7-diazaspiro[3.5]nonane-2-carboxylate

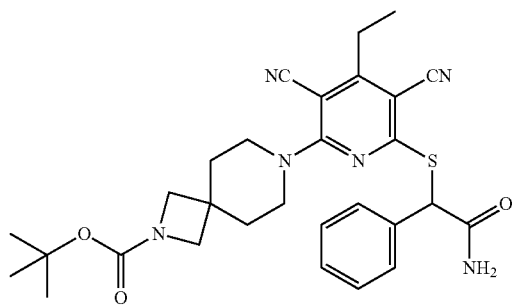 [SMILES: CCc1c(C#N)c(SC(C(N)=O)c2ccccc2)nc(N2CCC3(CC2)CN(C(=O)OC(C)(C)C)C3)c1C#N]

To a solution of crude tert-butyl 7-(3,5-dicyano-4-ethyl-6-mercaptopyridin-2-yl)-2,7-diazaspiro[3.5]nonane-2-carboxylate (890 mg) in N,N-dimethylformamide (6 mL) was added potassium carbonate (594 mg, 4.3 mmol). The mixture was stirred at ambient temperature for one hour followed by the addition of 2-amino-2-oxo-1-phenylethyl methanesulfonate (synthesis described in example 3 step 5, 741 mg, 3.23 mmol). The resulting mixture was stirred at ambient temperature for 12 hours. The mixture was then diluted with ethyl acetate (60 mL), washed with water (30 mL) and brine (30 mL), dried, and concentrated. The residue was purified by silica gel chromatography eluting with petroleum ether-ethyl acetate (2:1) to give the title compound (600 mg, 55% yield over 3 steps) as a brown solid. LCMS m/z=547 [M+H]$^+$.

Step 4: 2-((3,5-Dicyano-4-ethyl-6-(2,7-diazaspiro[3.5]nonan-7-yl)pyridin-2-yl)thio)-2-phenylacetamide

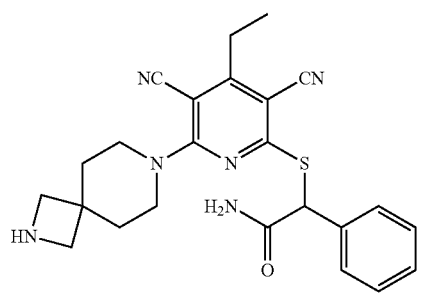 [SMILES: CCc1c(C#N)c(SC(C(N)=O)c2ccccc2)nc(N2CCC3(CC2)CNC3)c1C#N]

To a solution of tert-butyl 7-(6-((2-amino-2-oxo-1-phenylethyl)thio)-3,5-dicyano-4-ethylpyridin-2-yl)-2,7-diazaspiro[3.5]nonane-2-carboxylate (600 mg, 1.1 mmol) in dichloromethane (20 mL) was added trifluoroacetic acid (2 mL). The resulting solution was stirred at ambient temperature for 5 hours and concentrated under reduced pressure. The residue was diluted with ethyl acetate (60 mL) and was washed with aqueous sodium bicarbonate (40 mL), dried, and concentrated under reduced pressure. The residue was purified by silica gel chromatography eluting with dichloromethane-methanol (10:1) to give a solid that was washed with diethyl ether and dried to afford the title compound (90.8 mg, 18% yield) as a light yellow solid. LCMS m/z=447 [M+H]$^+$. $^1$H NMR (400 MHz, DMSO-d$_6$) δ ppm 9.09 (br s, 2H), 7.99 (s, 1H), 7.53 (d, J=7.1 Hz, 2H), 7.45-7.26 (m, 4H), 5.55 (s, 1H), 3.81 (t, J=5.3 Hz, 4H), 3.77 (s, 4H), 2.76 (q, J=7.5 Hz, 2H), 1.97-1.82 (m, 4H), 1.21 (t, J=7.6 Hz, 3H).

Example 44

2-((3,5-Dicyano-4-ethyl-6-(2,6-diazaspiro[3.4]octan-6-yl)pyridin-2-yl)thio)-2-phenylacetamide Step 1: tert-Butyl-6-(6-chloro-3,5-dicyano-4-ethylpyridin-2-yl)-2,6-diazaspiro[3.4]octane-2-carboxylate

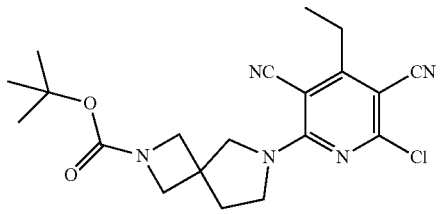 [SMILES: CCc1c(C#N)c(Cl)nc(N2CCC3(CN(C(=O)OC(C)(C)C)C3)C2)c1C#N]

To a solution of 2,6-dichloro-4-ethylpyridine-3,5-dicarbonitrile (synthesis described in example 3 step 2, 900 mg, 4 mmol) and tert-butyl 2,6-diazaspiro[3.4]octane-2-carboxylate (840 mg, 4 mmol) in dichloromethane (100 mL) was added triethylamine (400 mg, 4 mmol). The reaction was stirred for 30 minutes, was then washed with brine (2×100 mL), and the organic phase was dried over sodium sulfate and concentrated. The residue was purified by silica gel chromatography eluting with petroleum ether-ethyl acetate (3:1) to give the title compound (1.3 g, 81% yield). LCMS m/z=346 [M+H-isobutylene]$^+$.

Step 2: tert-Butyl 6-(3,5-dicyano-4-ethyl-6-mercaptopyridin-2-yl)-2,6-diazaspiro[3.4]octane-2 carboxylate

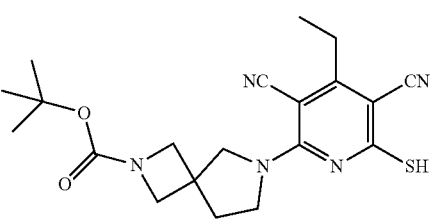 [SMILES: CCc1c(C#N)c(S)nc(N2CCC3(CN(C(=O)OC(C)(C)C)C3)C2)c1C#N]

To a solution of tert-butyl 6-(6-chloro-3,5-dicyano-4-ethylpyridin-2-yl)-2,6-diazaspiro[3.4]octane-2-carboxylate (1.3 g, 3.2 mmol) in N,N-dimethylformamide (20 mL) was added potassium thioacetate (554 mg, 4.8 mmol). The reaction was stirred for 3 hours, and the mixture was then diluted with ethyl acetate (200 mL) and washed with brine (2×100 mL). The organic phase was concentrated to afford the crude title compound (1 g, 78% crude yield). LCMS m/z=344 [M+H-isobutylene]$^+$.

351

Step 3: tert-Butyl 6-(6-((2-amino-2-oxo-1-phenyl-ethyl)thio)-3,5-dicyano-4-ethylpyridin-2-yl)-2,6-diazaspiro[3.4]octane-2-carboxylate

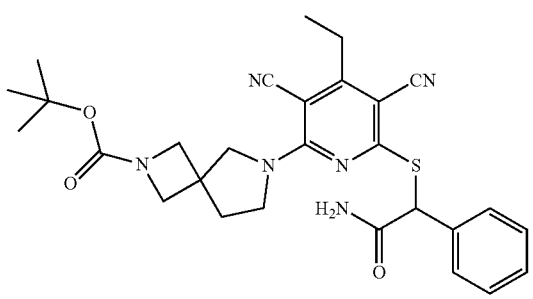 [SMILES: CCc1c(C#N)c(SC(C(N)=O)c2ccccc2)nc(N2CCC3(CN(C(=O)OC(C)(C)C)C3)C2)c1C#N]

To a solution of crude tert-butyl 6-(3,5-dicyano-4-ethyl-6-mercaptopyridin-2-yl)-2,6-diazaspiro[3.4]octane-2-carboxylate (1 g, assumed 2.5 mmol) in N,N-dimethylformamide (100 mL) was added 2-amino-2-oxo-1-phenylethyl methanesulfonate (synthesis described in example 3 step 5, 0.572 g, 2.5 mmol) and potassium carbonate (1.0 g, 7.2 mmol). The reaction was stirred overnight, and was then diluted with ethyl acetate (200 mL) and washed with brine (2×100 mL). The organic phase was dried over sodium sulfate, filtered, and concentrated to afford the crude title compound (0.8 g, 60% crude yield). LCMS m/z=477 [M+H-isobutylene]+.

Step 4: 2-((3,5-Dicyano-4-ethyl-6-(2,6-diazaspiro[3.4]octan-6-yl)pyridin-2-yl)thio)-2-phenylacetamide

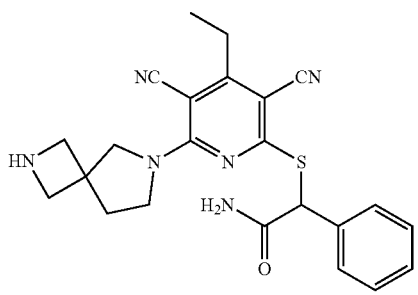 [SMILES: CCc1c(C#N)c(SC(C(N)=O)c2ccccc2)nc(N2CCC3(CNC3)C2)c1C#N]

To a solution of crude tert-butyl 6-(6-((2-amino-2-oxo-1-phenylethyl)thio)-3,5-dicyano-4-ethylpyridin-2-yl)-2,6-diazaspiro[3.4]octane-2-carboxylate (0.8 g, assumed 1.5 mmol) in dichloromethane (10 mL) was added trifluoroacetic acid (2 mL). The reaction was stirred overnight, and was then concentrated. The residue was purified by prep-HPLC to give the title compound (520 mg, 80% yield). LCMS m/z=433 [M+H]+. 1H NMR (400 MHz, DMSO-d6) δ ppm 8.48 (s, 1H), 8.08 (s, 1H), 7.54 (d, J=7.3 Hz, 2H), 7.42-7.31 (m, 4H), 5.63 (s, 1H), 4.22-3.77 (m, 8H), 2.75 (q, J=7.4 Hz, 2H), 2.26 (s, 2H), 1.29-1.10 (m, 3H).

352

Example 46

2-((3,5-dicyano-4-cyclopropyl-6-(1,4-diazepan-1-yl)pyridin-2-yl)thio)propanamide Step 1: tert-Butyl 4-(6-((1-amino-1-oxopropan-2-yl)thio)-3,5-dicyano-4-cyclopropylpyridin-2-yl)-1,4-diazepane-1-carboxylate

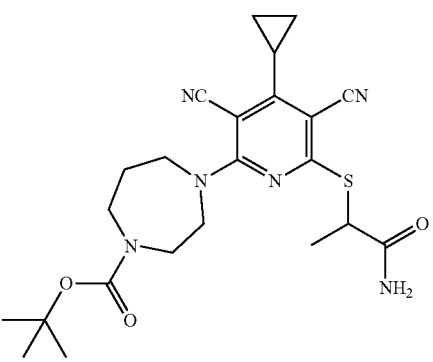 [SMILES: CC(Sc1nc(N2CCCN(C(=O)OC(C)(C)C)CC2)c(C#N)c(C2CC2)c1C#N)C(N)=O]

A mixture of tert-butyl 4-(6-chloro-3,5-dicyano-4-cyclopropylpyridin-2-yl)-1,4-diazepane-1-carboxylate (synthesis described in example 4 step 3, 300 mg, 0.74 mmol), KSAc (93 mg, 0.81 mmol) in N,N-dimethylformamide (8 mL) was stirred at room temperature for 30 minutes, then 2-bromopropanamide (136 mg, 0.89 mmol) was added. The resulting mixture was stirred at room temperature for 12 hours. The reaction mixture was poured into water (50 mL), then extracted with ethyl acetate (2×50 mL). The combined organic layer was dried, concentrated, and the residue was purified by silica gel chromatography using CH2Cl2:MeOH (100:1) to give the title compound (290 mg, 83% yield) as a white solid. LCMS m/z=371.0 [M+H-Boc]+.

Step 2: 2-((3,5-Dicyano-4-cyclopropyl-6-(1,4-diazepan-1-yl)pyridin-2-yl)thio)propanamide

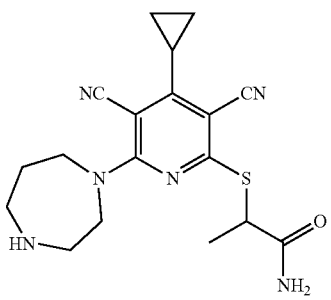 [SMILES: CC(Sc1nc(N2CCCNCC2)c(C#N)c(C2CC2)c1C#N)C(N)=O]

A mixture of tert-butyl 4-(6-((1-amino-1-oxopropan-2-yl)thio)-3,5-dicyano-4-cyclopropylpyridin-2-yl)-1,4-diazepane-1-carboxylate (synthesis described in example 6 step 1, 260 mg, 0.55 mmol) and trifluoroacetic acid (1 mL) in CH2Cl2 (6 mL) was stirred at room temperature for 12 hours. The resulting mixture was concentrated. The residue was poured into water (50 mL) and made basic by the addition of aqueous NaHCO3, then extracted with CH2Cl2 (2×50 mL). The combined organic layers were dried and concentrated. The residue was purified by silica gel chromatography eluting with CH₂Cl₂:MeOH (30:1) to give the title compound (80 mg, 39% yield) as a white solid. LCMS m/z=371 [M+H]⁺. ¹H NMR (400 MHz, CDCl₃) δ ppm 6.44 (br s, 1H), 5.35 (br s, 1H), 4.22 (q, J=7.6 Hz, 1H), 4.06-3.97 (m, 1H), 3.97-3.87 (m, 3H), 3.16-3.10 (m, 2H), 2.97-2.85 (m, 2H), 2.10-2.02 (m, 1H), 2.01-1.94 (m, 2H), 1.86 (br s, 2H), 1.64 (d, J=7.6 Hz, 3H), 1.35-1.23 (m, 2H), 1.15-1.05 (m, 2H).

Example 47

2-((3,5-Dicyano-4-ethyl-6-(4-(2-oxoimidazolidin-1-yl)piperidin-1-yl)pyridin-2-yl)thio)-2-phenylacetamide

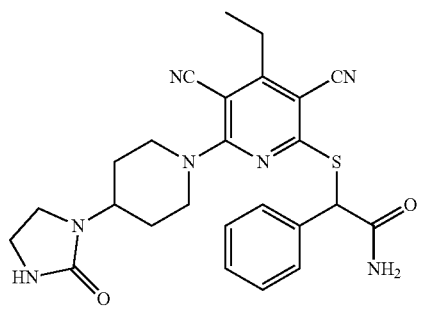 [SMILES: CCc1c(C#N)c(SC(C(N)=O)c2ccccc2)nc(N2CCC(N3CCNC3=O)CC2)c1C#N]

A solution of 2-((6-bromo-3,5-dicyano-4-ethylpyridin-2-yl)thio)-2-phenylacetamide (synthesis described in example 6 step 1, 15 mg, 0.04 mmol) in tetrahydrofuran (1 mL) was treated with 1-(piperidin-4-yl)imidazolidin-2-one hydrochloride (12 mg, 0.06 mmol) and triethylamine (0.013 mL, 0.09 mmol) and stirred at ambient temperature for 72 hours. The product mixture was dry loaded onto SiO₂ (0.9 g) and chromatographed on SiO₂ (4 g RediSep cartridge, eluting with 0-15% MeOH/CH₂Cl₂) to give the title compound (15 mg, 82% yield) as an off-white solid. LCMS m/z=490 [M+H]⁺. ¹H NMR (300 MHz, DMSO-d₆) δ ppm 7.93 (br s, 1H), 7.52 (br d, J=6.8 Hz, 2H), 7.46-7.30 (m, 4H), 6.32 (s, 1H), 5.54 (s, 1H), 4.67 (br d, J=12.9 Hz, 2H), 3.93-3.64 (m, 2H), 3.30-3.06 (m, 7H), 2.76 (q, J=7.0 Hz, 2H), 1.82-1.50 (m, 2H), 1.19 (t, J=7.5 Hz, 3H).

Example 48

2-((3,5-Dicyano-4-ethyl-6-(4-hydroxypiperidin-1-yl)pyridin-2-yl)thio)-2-phenylacetamide

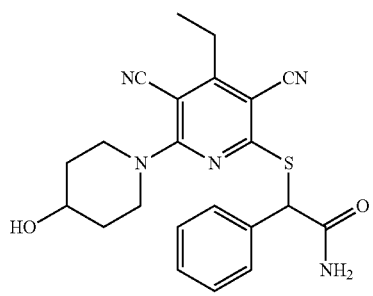 [SMILES: CCc1c(C#N)c(SC(C(N)=O)c2ccccc2)nc(N2CCC(O)CC2)c1C#N]

A solution of 2-((6-bromo-3,5-dicyano-4-ethylpyridin-2-yl)thio)-2-phenylacetamide (synthesis described in example 6 step 1, 16 mg, 0.04 mmol) in tetrahydrofuran (1 mL) was treated with 4-hydroxypiperidinyl (14 mg, 0.14 mmol) and stirred at ambient temperature for 3 hours. The reaction was then loaded onto SiO₂ (0.9 g) and chromatographed on SiO₂ (4 g RediSep cartridge, eluting with 0-15% MeOH/CH₂Cl₂) to give the title compound (15 mg, 88% yield) as a white solid. LCMS m/z=420 [M−H]⁻. ¹H NMR (300 MHz, DMSO-d₆) δ ppm 7.92 (s, 1H), 7.57-7.46 (m, 2H), 7.44-7.28 (m, 4H), 5.53 (s, 1H), 4.85 (d, J=4.1 Hz, 1H), 4.24-4.05 (m, 2H), 3.91-3.70 (m, 1H), 3.65-3.47 (m, 2H), 2.75 (q, J=7.4 Hz, 2H), 1.84 (br s, 2H), 1.61-1.34 (m, 2H), 1.20 (t, J=7.6 Hz, 3H).

Example 49

2-((3,5-Dicyano-4-ethyl-6-((S)-3-hydroxypyrrolidin-1-yl)pyridin-2-yl)thio)-2-phenylacetamide

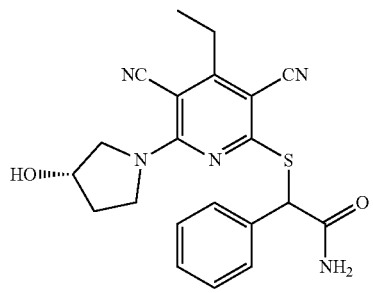 [SMILES: CCc1c(C#N)c(SC(C(N)=O)c2ccccc2)nc(N2CC[C@H](O)C2)c1C#N]

A solution of 2-((6-bromo-3,5-dicyano-4-ethylpyridin-2-yl)thio)-2-phenylacetamide (synthesis described in example 6 step 1, 17 mg, 0.04 mmol) in tetrahydrofuran (1 mL) was treated with (S)-3-pyrrolidinol (0.009 mL, 0.11 mmol) and stirred at ambient temperature for 3 hours. The reaction was then loaded onto SiO₂ (0.9 g) and chromatographed on SiO₂ (4 g RediSep cartridge, eluting with 0-15% MeOH/CH₂Cl₂) to give the title compound (12 mg, 70% yield) as a white solid. LCMS m/z=408 [M+H]⁺. ¹H NMR (300 MHz, DMSO-d₆) δ ppm 7.91 (br s, 1H), 7.52 (br d, J=7.2 Hz, 2H), 7.44-7.26 (m, 4H), 5.61 (s, 1H), 5.15 (br s, 1H), 4.42 (br s, 1H), 3.90 (br s, 2H), 3.85-3.64 (m, 2H), 2.89-2.56 (m, 2H), 1.95 (br s, 2H), 1.20 (br t, J=7.3 Hz, 3H).

Example 50

2-((3,5-Dicyano-4-ethyl-6-(3-oxopiperazin-1-yl)pyridin-2-yl)thio)-2-phenylacetamide Step 1: 2-Chloro-4-ethyl-6-(3-oxopiperazin-1-yl)pyridine-3,5-dicarbonitrile

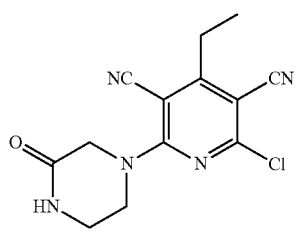 [SMILES: CCc1c(C#N)c(Cl)nc(N2CCNC(=O)C2)c1C#N]

To a solution of 2,6-dichloro-4-ethylpyridine-3,5-dicarbonitrile (synthesis described in example 3 step 2, 2.26 g, 10.00 mmol) in dichloromethane (30 mL) was added piperazin-2-one (1.001 g, 10.00 mmol) and triethylamine (1.012 g, 10.00 mmol). The mixture was stirred at 25° C. for 12 hours. The reaction mixture was diluted with dichloromethane (30 mL), washed with water (30 mL) and brine (30 mL), dried, and concentrated to give the title compound (2.4 g, 83% yield) as a light yellow solid. LCMS m/z=290 [M+H]$^+$.

Step 2: 4-Ethyl-2-mercapto-6-(3-oxopiperazin-1-yl)pyridine-3,5-dicarbonitrile

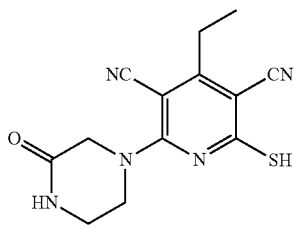 [SMILES: CCc1c(C#N)c(S)nc(N2CCNC(=O)C2)c1C#N]

To a solution of 2-chloro-4-ethyl-6-(3-oxopiperazin-1-yl)pyridine-3,5-dicarbonitrile (290 mg, 1.001 mmol) in N,N-dimethylformamide (5 mL) was added potassium thioacetate (229 mg, 2.002 mmol). The mixture was stirred at room temperature for 12 hours, diluted with ethyl acetate (60 mL), and washed with saturated aqueous ammonium chloride solution (60 mL). The organic phase was washed with brine (60 mL), dried, and concentrated to give crude 4-ethyl-2-mercapto-6-(3-oxopiperazin-1-yl)pyridine-3,5-dicarbonitrile (300 mg) as a brown solid. LCMS m/z=288 [M+H]$^+$.

Step 3: 2-((3,5-Dicyano-4-ethyl-6-(3-oxopiperazin-1-yl)pyridin-2-yl)thio)-2-phenylacetamide

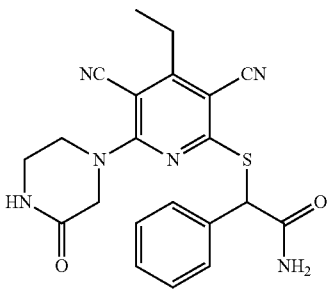 [SMILES: CCc1c(C#N)c(SC(C(N)=O)c2ccccc2)nc(N2CCNC(=O)C2)c1C#N]

To a solution of crude 4-ethyl-2-mercapto-6-(3-oxopiperazin-1-yl)pyridine-3,5-dicarbonitrile (300 mg, 1.044 mmol) in N,N-dimethylformamide (6 mL) was added potassium carbonate (synthesis described in example 3 step 5, 289 mg, 2.088 mmol). The mixture was stirred at room temperature for 2 hours, and 2-amino-2-oxo-1-phenylethyl methanesulfonate (synthesis described in example 3 step 5, 287 mg, 1.253 mmol) was then added. The mixture was stirred at room temperature for 12 hours. The reaction solution was diluted with ethyl acetate (60 mL), washed with water (60 mL) and brine (60 mL), dried, concentrated and purified by prep-HPLC to give 2-((3,5-dicyano-4-ethyl-6-(3-oxopiperazin-1-yl)pyridin-2-yl)thio)-2-phenylacetamide (35 mg, 8% yield) as a light brown solid. LCMS m/z=421.0 [M+H]$^+$. $^1$H NMR (400 MHz, DMSO-d$_6$) 8.30 (s, 1H), 7.95 (s, 1H), 7.54 (d, J=7.1 Hz, 2H), 7.46-7.24 (m, 4H), 5.57 (s, 1H), 4.39 (s, 2H), 4.07-3.97 (m, 2H), 2.78 (dd, J=8 Hz, 7.5 Hz, 2H), 1.22 (t, J=7.5 Hz, 3H).

Example 51

2-[(6-amino-3,5-dicyano-4-cyclopropyl-2-pyridyl)sulfanyl]-2-phenyl-acetamide

Step 1: 2-Amino-4-cyclopropyl-6-mercaptopyridine-3,5-dicarbonitrile; 4-methylmorpholine

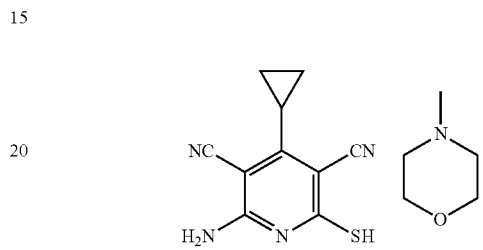

2-Cyanothioacetamide (860 mg, 8.56 mmol), N-methylmorpholine (2.2 mL, 20 mmol) and cyclopropane carboxaldehyde (0.32 mL, 4.28 mmol) were mixed and dissolved in ethanol (10 mL). The resulting solution was stirred at ambient temperature for 16 hours. The precipitate formed was washed with ethanol and dried under reduced pressure to furnish the title compound (322 mg, 24% yield) as a cream colored solid. LCMS m/z=217 [M+H]$^+$.

Step 2: 2-((6-Amino-3,5-dicyano-4-cyclopropylpyridin-2-yl)thio)-2-phenylacetamide

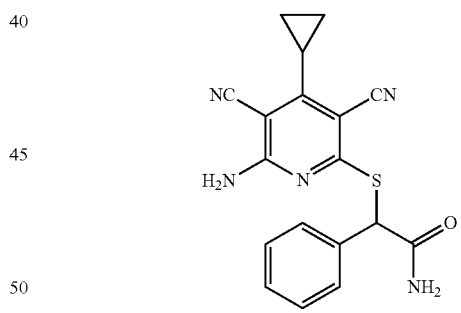

2-Amino-4-cyclopropyl-6-mercaptopyridine-3,5-dicarbonitrile; 4-methylmorpholine, (316 mg, 1 mmol) and 2-chloro-2-phenyl-acetamide (174 mg, 1.02 mmol) were dissolved in N,N-dimethylformamide (10 mL) and the reaction mixture was allowed to stir at ambient temperature for 16 hours. The mixture was diluted with EtOAc (50 mL) and washed with water (3×10 mL), saturated sodium chloride (10 mL) and then water (10 mL). The organic layer was dried over anhydrous sodium sulfate and concentrated under reduced pressure. The crude product was purified by preparative HPLC to furnish the title compound (7 mg, 2% yield) as a white solid. LCMS m/z=348 [M−H]$^−$. $^1$H NMR (300 MHz, DMSO-d$_6$) δ ppm 7.80 (br s, 2H), 7.73 (s, 1H), 7.58 (dd, J=1.6, 7.9 Hz, 2H), 7.39-7.26 (m, 4H), 5.54 (s, 1H), 2.15-2.00 (m, 1H), 1.25-0.95 (m, 4H).

Example 52

2-((3,5-Dicyano-4-ethyl-6-(methylamino)pyridin-2-yl)thio)-2-phenylacetamide

Step 1: 2-((6-Chloro-3,5-dicyano-4-ethylpyridin-2-yl)thio)-2-phenylacetamide

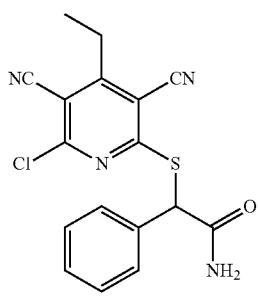

A stirred suspension of 2-((6-amino-3,5-dicyano-4-ethylpyridin-2-yl)thio)-2-phenylacetamide (synthesis described in example 1, 74 mg, 0.22 mmol) in dry acetonitrile (10 mL) was treated with copper(II) chloride (52 mg, 0.39 mmol) and isoamyl nitrite (0.052 mL, 0.39 mmol) then heated to 70° C. for 45 minutes under an atmosphere of nitrogen gas. More copper(II) chloride (52 mg, 0.39 mmol) and isoamyl nitrite (0.052 mL, 0.39 mmol) were then added. After 40 minutes a third series of additions was made: copper(II) chloride (52 mg, 0.39 mmol) then isoamyl nitrite (0.052 mL, 0.39 mmol). After 1 hour the reaction mixture was evaporated to dryness under vacuum to give the crude title compound that was used without further purification. LCMS m/z=355 [M−H]−.

Step 2: 2-((3,5-Dicyano-4-ethyl-6-(methylamino)pyridin-2-yl)thio)-2-phenylacetamide

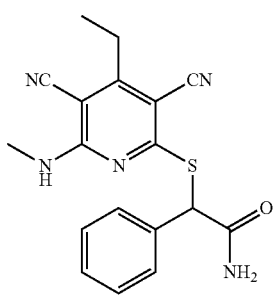 [SMILES: CCc1c(C#N)c(NC)nc(SC(C(N)=O)c2ccccc2)c1C#N]

A solution of crude 2-((6-chloro-3,5-dicyano-4-ethylpyridin-2-yl)thio)-2-phenylacetamide, (39.25 mg, 0.11 mmol) in tetrahydrofuran (3 mL) and ethanol (1.5 mL) was treated with methylamine solution (2 M in tetrahydrofuran, 0.44 mL, 0.88 mmol) then heated at 65° C. After 45 minutes more methylamine solution (2 M in tetrahydrofuran, 0.11 mL, 0.22 mmol) was added and heating was continued another 45 minutes. The reaction mixture was then allowed to cool and was loaded onto SiO$_2$ (1 g). Chromatography on SiO$_2$ (12 g RediSep cartridge, eluting with 0-10% MeOH/CH$_2$Cl$_2$) furnished 14 mg material that was then dissolved in DMSO (0.4 mL), diluted with 50% CH$_3$—CN/H$_2$O (0.4 mL), and the resulting solid was collected and washed with 50% CH$_3$—CN/H$_2$O (5 mL) to give the title compound (7 mg), as an off-white solid. LCMS m/z=350 [M−H]−. $^1$H NMR (300 MHz, DMSO-d$_6$) δ ppm 8.08 (br d, J=4.3 Hz, 1H), 7.91 (br s, 1H), 7.64-7.46 (m, 2H), 7.45-7.29 (m, 4H), 5.64 (s, 1H), 2.99 (br d, J=4.5 Hz, 3H), 2.69 (d, J=7.4 Hz, 2H), 1.17 (t, J=7.5 Hz, 3H).

Example 53

2-((3,5-Dicyano-4-ethyl-6-((2-methoxyethyl)(methyl)amino)pyridin-2-yl)thio)-2-phenylacetamide

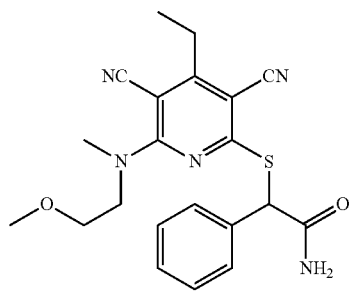 [SMILES: CCc1c(C#N)c(SC(C(N)=O)c2ccccc2)nc(N(C)CCOC)c1C#N]

A solution of 2-((6-bromo-3,5-dicyano-4-ethylpyridin-2-yl)thio)-2-phenylacetamide (synthesis described in example 6 step 1, 20 mg, 0.05 mmol) in tetrahydrofuran (1 mL) was treated with (2-methoxyethyl)-methylamine (0.012 mL, 0.11 mmol) at ambient temperature for 18 hours, loaded onto SiO$_2$ (4 g) and chromatographed on SiO$_2$ (4 g RediSep cartridge, eluting with 0-5% MeOH/CH$_2$Cl$_2$) to furnish the title compound (16 mg, 78% yield), as a white solid. LCMS m/z=410 [M+H]+. $^1$H NMR (300 MHz, DMSO-d$_6$) δ ppm 7.90 (s, 1H), 7.55-7.45 (m, 2H), 7.43-7.30 (m, 4H), 5.53 (s, 1H), 4.00 (s, 1H), 3.93 (s, 1H), 3.56 (t, J=5.2 Hz, 2H), 3.37 (s, 3H), 3.26 (s, 3H), 2.76 (q, J=7.5 Hz, 2H), 1.20 (t, J=7.6 Hz, 3H).

Example 54

2-((3,5-Dicyano-4-ethyl-6-(3-methoxyazetidin-1-yl)pyridin-2-yl)thio)-2-phenylacetamide

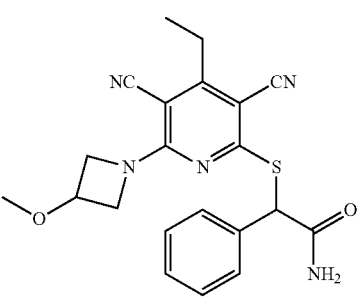 [SMILES: CCc1c(C#N)c(SC(C(N)=O)c2ccccc2)nc(N2CC(OC)C2)c1C#N]

A solution of 2-[(6-bromo-3,5-dicyano-4-ethyl-2-pyridyl)sulfanyl]-2-phenyl-acetamide (synthesis described in example 6 step 1, 20 mg, 0.05 mmol) in tetrahydrofuran (1 mL) was treated with 3-methoxyazetidine hydrochloride (16 mg, 0.13 mmol) and triethylamine (0.02 mL, 0.13 mmol). The resultant solution was stirred at ambient temperature for 45 minutes, dry loaded onto SiO$_2$ (0.9 g) and chromatographed on SiO₂ (4 g RediSep cartridge) eluting with 0-5% MeOH/CH₂Cl₂ to give 2-[[3,5-dicyano-4-ethyl-6-(3-methoxyazetidin-1-yl)-2-pyridyl]sulfanyl]-2-phenyl-acetamide (20 mg, 100% yield) as a white solid. LCMS m/z=408 [M+H]⁺. ¹H NMR (300 MHz, DMSO-d₆) δ ppm 7.86 (s, 1H), 7.57-7.46 (m, 2H), 7.44-7.28 (m, 4H), 5.55 (s, 1H), 4.60 (br s, 2H), 4.39-4.09 (m, 3H), 3.28 (br s, 3H), 2.69 (q, J=7.5 Hz, 2H), 1.19 (t, J=7.5 Hz, 3H).

Example 55

2-((3,5-Dicyano-4-ethyl-6-(piperazin-1-yl)pyridin-2-yl)thio)-2-phenylacetamide

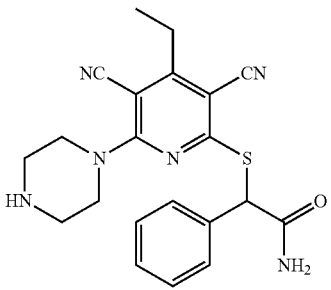 [SMILES: CCc1c(C#N)c(SC(C(N)=O)c2ccccc2)nc(N2CCNCC2)c1C#N]

A solution of 2-[(6-bromo-3,5-dicyano-4-ethyl-2-pyridyl)sulfanyl]-2-phenyl-acetamide (synthesis described in example 6 step 1, 137 mg, 0.34 mmol) in tetrahydrofuran (5 mL) was treated with a solution of piperazinyl (350 mg, 4.06 mmol) in tetrahydrofuran (5 mL) warmed to dissolve then re-cooled all at once at ambient temperature. The resultant suspension was stirred for 20 minutes. The product mixture was diluted with EtOAc (80 mL), washed with water (3×50 mL), saturated sodium chloride and dried through a hydrophobic frit to give 2-[(3,5-dicyano-4-ethyl-6-piperazin-1-yl)-2-pyridyl)sulfanyl]-2-phenyl-acetamide (123 mg, 88% yield) as an off-white solid. LCMS m/z=407 [M+H]⁺. ¹H NMR (300 MHz, DMSO-d₆) δ ppm 7.91 (s, 1H), 7.62-7.46 (m, 2H), 7.44-7.30 (m, 4H), 5.52 (s, 1H), 3.79 (br s, 4H), 3.43-3.37 (m, 1H), 2.88-2.67 (m, 6H), 1.20 (t, J=7.5 Hz, 3H).

Example 56

2-((3,5-Dicyano-4-ethyl-6-(4-methyl-1,4-diazepan-1-yl)pyridin-2-yl)thio)-2-phenylacetamide

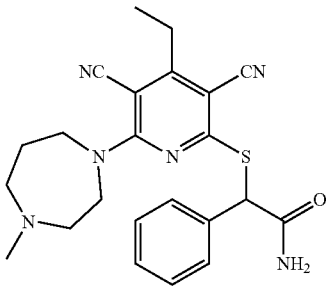 [SMILES: CCc1c(C#N)c(SC(C(N)=O)c2ccccc2)nc(N2CCCN(C)CC2)c1C#N]

A solution of 2-[(6-bromo-3,5-dicyano-4-ethyl-2-pyridyl)sulfanyl]-2-phenyl-acetamide (synthesis described in example 6 step 1, 467 mg, 1.16 mmol) in tetrahydrofuran (25 mL) was treated with N-methylhomopiperazinyl (0.36 mL, 2.91 mmol) and stirred at ambient temperature for 1.5 hours under an atmosphere of nitrogen. The product mixture was dry loaded onto SiO₂ (2 g) and chromatographed on SiO₂ (12 g RediSep cartridge, eluting with 0-10% MeOH, 0-1% NH₃/CH₂Cl₂) to afford 2-[[3,5-dicyano-4-ethyl-6-(4-methyl-1,4-diazepan-1-yl)-2-pyridyl]sulfanyl]-2-phenyl-acetamide (445 mg, 88% yield), as a white solid. LCMS m/z=435 [M+H]⁺. ¹H NMR (300 MHz, DMSO-d₆) δ ppm 7.91 (s, 1H), 7.54-7.45 (m, 2H), 7.43-7.29 (m, 4H), 5.51 (s, 1H), 4.01-3.79 (m, 4H), 2.84-2.55 (m, 6H), 2.26 (s, 3H), 2.08-1.79 (m, 2H), 1.21 (t, J=7.6 Hz, 3H).

Example 57

2-((3,5-Dicyano-4-ethyl-6-morpholinopyridin-2-yl)thio)-2-phenylacetamide

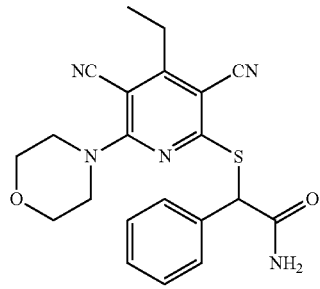 [SMILES: CCc1c(C#N)c(SC(C(N)=O)c2ccccc2)nc(N2CCOCC2)c1C#N]

A solution of 2-[(6-bromo-3,5-dicyano-4-ethyl-2-pyridyl)sulfanyl]-2-phenyl-acetamide (synthesis described in example 6 step 1, 28 mg, 0.07 mmol) in tetrahydrofuran (1 mL) and ethanol (0.5 mL) was treated with morpholine (0.009 mL, 0.1 mmol) with stirring at ambient temperature for 1 hour. The product mixture was dry loaded onto SiO₂ (0.8 g). Chromatography on SiO₂ (4 g RediSep cartridge, eluting with 0-5% MeOH/CH₂Cl₂) followed by trituration with diethyl ether afforded 2-[(3,5-dicyano-4-ethyl-6-morpholino-2-pyridyl)sulfanyl]-2-phenyl-acetamide (19 mg, 0.0466 mmol, 67% yield), as a white solid. LCMS m/z=408 [M+H]⁺. ¹H NMR (300 MHz, DMSO-d₆) δ ppm 7.90 (br s, 1H), 7.65-7.46 (m, 2H), 7.46-7.31 (m, 4H), 5.76-5.49 (m, 1H), 3.99-3.78 (m, 4H), 3.77-3.39 (m, 4H), 2.76 (q, J=7.3 Hz, 2H), 1.21 (t, J=7.6 Hz, 3H).

Example 58

2-[[6-(azetidin-1-yl)-3,5-dicyano-4-ethyl-2-pyridyl]sulfanyl]-2-phenyl-acetamide

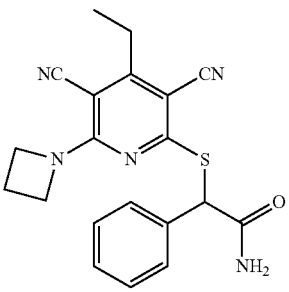 [SMILES: CCc1c(C#N)c(SC(C(N)=O)c2ccccc2)nc(N2CCC2)c1C#N]

A solution of 2-[(6-bromo-3,5-dicyano-4-ethyl-2-pyridyl)sulfanyl]-2-phenyl-acetamide (synthesis described in example 6 step 1, 23 mg, 0.06 mmol) in tetrahydrofuran (1 mL) was treated with azetidine hydrochloride (11.8 mg, 0.13 mmol) and triethylamine (0.02 mL, 0.15 mmol). The resultant solution was stirred at ambient temperature for 16 hours, dry loaded onto SiO$_2$ (0.9 g) and chromatographed on SiO$_2$ (4 g RediSep cartridge, eluting with 0-5% MeOH/CH$_2$Cl$_2$) to afford 2-[[6-(azetidin-1-yl)-3,5-dicyano-4-ethyl-2-pyridyl]sulfanyl]-2-phenyl-acetamide (19 mg, 0.0503 mmol, 86% yield) as a white solid. LCMS m/z=376 [M−H]$^-$. 1H NMR (300 MHz, DMSO-d$_6$) δ ppm 7.86 (s, 1H), 7.55-7.39 (m, 2H), 7.39-7.25 (m, 4H), 5.55 (s, 1H), 4.56-4.28 (m, 4H), 2.68 (q, J=7.5 Hz, 2H), 2.47-2.26 (m, 2H), 1.17 (t, J=7.6 Hz, 3H).

Example 59

2-((3,5-dicyano-4-ethyl-6-(4-oxopiperidin-1-yl)pyridin-2-yl)thio)-2-phenylacetamide

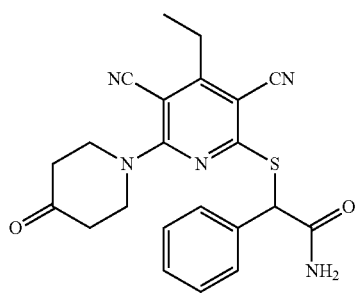 [SMILES: CCc1c(C#N)c(SC(C(N)=O)c2ccccc2)nc(N2CCC(=O)CC2)c1C#N]

A solution of 2-[(6-bromo-3,5-dicyano-4-ethyl-2-pyridyl)sulfanyl]-2-phenyl-acetamide (synthesis described in example 6 step 1, 20 mg, 0.05 mmol) in tetrahydrofuran (1 mL) was treated with 4-piperidinone hydrochloride hydrate (11 mg, 0.07 mmol) and triethylamine (0.017 mL, 0.12 mmol) then stirred at ambient temperature for 72 hours. The product mixture was dry loaded onto SiO$_2$ (0.9 g) and chromatographed on SiO$_2$ (4 g RediSep cartridge, eluting with 0-15% MeOH/CH$_2$Cl$_2$) to give 2-((3,5-dicyano-4-ethyl-6-(4-oxopiperidin-1-yl)pyridin-2-yl)thio)-2-phenylacetamide (15 mg, 0.0358 mmol, 73%) as a white solid. LCMS m/z=418 [M−H]$^-$. $^1$H NMR (300 MHz, CD$_3$OD with a drop of CDCl$_3$) δ ppm 7.55-7.41 (m, 4H), 7.41-7.31 (m, 3H), 5.40 (s, 1H), 3.99-3.80 (m, 4H), 2.88 (q, J=7.6 Hz, 2H), 1.95-1.77 (m, 4H), 1.30 (t, J=7.6 Hz, 3H).

Example 60

2-((3,5-dicyano-4-ethyl-6-(1'-(2-hydroxyethyl)-[4,4'-bipiperidin]-1-yl)pyridin-2-yl)thio)-2-phenylacetamide

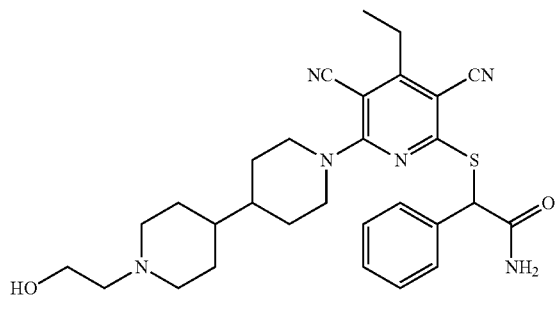 [SMILES: CCc1c(C#N)c(SC(C(N)=O)c2ccccc2)nc(N2CCC(C3CCN(CCO)CC3)CC2)c1C#N]

To a mixture of 2-[(6-bromo-3,5-dicyano-4-ethyl-2-pyridyl)sulfanyl]-2-phenyl-acetamide (synthesis described in example 6 step 1, 25 mg, 0.06 mmol) and 2-[4-(4-piperidyl)-1-piperidyl]ethanol dihydrochloride (20 mg, 0.07 mmol) in tetrahydrofuran (2 mL) was added triethylamine (0.035 mL, 0.25 mmol). The reaction mixture was stirred for 90 hours. The product mixture was diluted with EtOAc (20 mL), washed with water (3×20 mL), brine (25 mL), filtered through a hydrophobic frit and the solvent was removed under reduced pressure. The residue was dissolved in DMSO and purified by preparative HPLC to furnish 2-[[3,5-dicyano-4-ethyl-6-[4-[1-(2-hydroxyethyl)-4-piperidyl]-1-piperidyl]-2-pyridyl]sulfanyl]-2-phenyl-acetamide (10 mg, 30% yield) as a white powder. LCMS m/z=531 [M−H]$^-$. $^1$H NMR (300 MHz, DMSO-d$_6$) δ ppm 8.22 (s, 1H), 7.92 (s, 1H), 7.57-7.46 (m, 2H), 7.44-7.28 (m, 4H), 5.53 (s, 1H), 4.62 (br d, J=11.6 Hz, 2H), 3.74 (br s, 4H), 3.53 (br t, J=6.1 Hz, 2H), 3.31-2.94 (m, 3H), 2.75 (q, J=7.3 Hz, 2H), 2.48-2.36 (m, 1H), 2.27 (br s, 1H), 2.07 (br t, J=11.0 Hz, 2H), 1.80 (br d, J=11.5 Hz, 2H), 1.67 (br d, J=12.2 Hz, 2H), 1.41 (br s, 1H), 1.25-1.15 (m, 5H).

Example 61

2-((3,5-Dicyano-6-((3S,5R)-3,5-dimethylpiperazin-1-yl)-4-ethylpyridin-2-yl)thio)-2-phenylacetamide

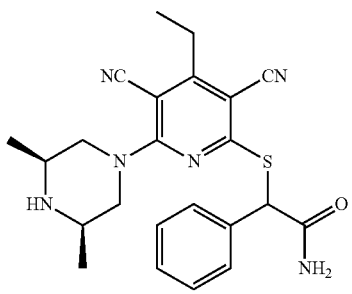 [SMILES: CCc1c(C#N)c(SC(C(N)=O)c2ccccc2)nc(N2C[C@@H](C)N[C@@H](C)C2)c1C#N]

To a mixture of 2-[(6-bromo-3,5-dicyano-4-ethyl-2-pyridyl)sulfanyl]-2-phenyl-acetamide (synthesis described in example 6 step 1, 30 mg, 0.07 mmol) and triethylamine (0.02 mL, 0.15 mmol) in tetrahydrofuran (2 mL) was added cis-2,6-dimethylpiperazinyl (9 mg, 0.08 mmol). The reaction mixture was allowed to stir for 1.5 hours. The product mixture was diluted with EtOAc (20 mL), washed with water (3×20 mL), saturated sodium chloride (25 mL), filtered through a hydrophobic frit and the solvent was removed under reduced pressure. The resulting solid was triturated with diethyl ether and dried in vacuo at 50° C. to give 2-[[3,5-dicyano-6-[(3R,5S)-3,5-dimethylpiperazin-1-yl]-4-ethyl-2-pyridyl]sulfanyl]-2-phenyl-acetamide (27 mg, 83% yield), as a white solid. LCMS m/z=433 [M–H]$^-$. $^1$H NMR (300 MHz, DMSO-d$_6$) δ ppm 7.94 (s, 1H), 7.58-7.46 (m, 2H), 7.44-7.31 (m, 4H), 5.50 (s, 1H), 4.46 (br d, J=12.4 Hz, 2H), 2.75 (q, J=7.4 Hz, 4H), 2.67-2.53 (m, 3H), 1.20 (t, J=7.8 Hz, 3H), 1.10-0.96 (m, 6H).

Example 62

2-((6-(8-azabicyclo[3.2.1]octan-3-yl(methyl)amino)-3,5-dicyano-4-ethylpyridin-2-yl)thio)-2-phenylacetamide Step 1: (1R,3r,5S)-tert-butyl 3-(((benzyloxy)carbonyl)amino)-8-azabicyclo[3.2.1]octane-8-carboxylate

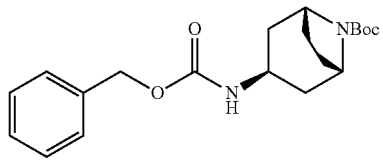 [SMILES: CC(C)(C)OC(=O)N1[C@@H]2CC[C@H]1C[C@@H](NC(=O)OCc1ccccc1)C2]

(1R,3r,5S)-tert-butyl 3-amino-8-azabicyclo[3.2.1]octane-8-carboxylate (1 g, 4.42 mmol) was dissolved in dichloromethane (15 mL) and triethylamine (1.23 mL, 8.84 mmol) was added. The solution was cooled to 0° C. and benzyl chloroformate (0.662 mL, 4.64 mmol) was added dropwise. The reaction was allowed to warm to room temperature overnight. The solvent was evaporated and the remaining material purified by silica gel column chromatography (10-75% ethyl acetate-hexane) to obtain (1R,3r,5S)-tert-butyl 3-(((benzyloxy)carbonyl)amino)-8-azabicyclo[3.2.1]octane-8-carboxylate (1.3 g, 82%). LCMS m/z=383 [M+Na]$^+$.

Step 2: (1R,3r,5S)-tert-butyl 3-(((benzyloxy)carbonyl)(methyl)amino)-8-azabicyclo[3.2.1]octane-8-carboxylate

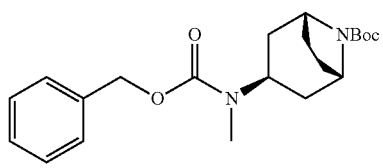 [SMILES: CN(C(=O)OCc1ccccc1)[C@H]1C[C@H]2CC[C@@H](C1)N2C(=O)OC(C)(C)C]

(1R,3r,5S)-tert-butyl 3-(((benzyloxy)carbonyl)amino)-8-azabicyclo[3.2.1]octane-8-carboxylate (700 mg, 1.94 mmol) was dissolved in tetrahydrofuran (15 mL) and N,N-dimethylformamide (5 mL) then sodium hydride (51.5 mg, 2.039 mmol) was added. The solution was stirred 15 minutes. The effervescence stopped and methyl iodide (0.158 mL, 2.52 mmol) was added dropwise. The reaction was allowed to stir at 25° C. for 2 hours. The solvents were evaporated and the crude dissolved in ethyl acetate, washed with water and dried over sodium sulfate. The crude compound was purified by silica gel chromatography (10-75% ethyl acetate-hexane) to give (1R,3r,5S)-tert-butyl 3-(((benzyloxy)carbonyl)(methyl)amino)-8-azabicyclo[3.2.1]octane-8-carboxylate (600 mg, 83%). LCMS m/z=397 [M+Na]$^+$.

Step 3: (1R,3r,5S)-tert-butyl 3-(methylamino)-8-azabicyclo[3.2.1]octane-8-carboxylate

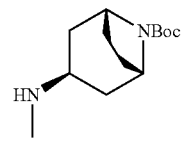

(1R,3r,5S)-tert-butyl 3-(((benzyloxy)carbonyl)(methyl)amino)-8-azabicyclo[3.2.1]octane-8-carboxylate (350 mg, 0.935 mmol) was dissolved in ethanol (20 mL) and 10% Pd/C (5 mg) was added and the reaction mixture exposed to hydrogen at 30 psi for 3 hours. The mixture was filtered and the filtrate concentrated to give (1R,3r,5S)-tert-butyl 3-(methylamino)-8-azabicyclo[3.2.1]octane-8-carboxylate (215 mg, 96%). LCMS m/z=241 [M+H]$^+$.

Step 4: tert-butyl 3-((6-chloro-3,5-dicyano-4-ethylpyridin-2-yl)(methyl)amino)-8-azabicyclo[3.2.1]octane-8-carboxylate

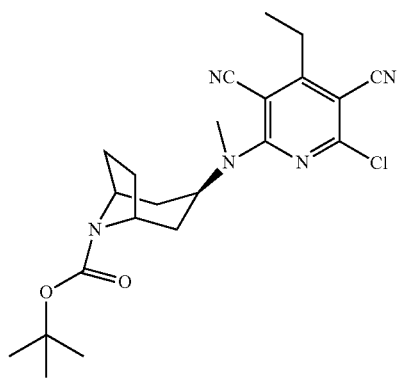

2,6-Dichloro-4-ethylpyridine-3,5-dicarbonitrile (synthesis described in example 3 step 2, 200 mg, 0.885 mmol) was dissolved in tetrahydrofuran (20 mL) and tert-butyl 3-(methylamino)-8-azabicyclo[3.2.1]octane-8-carboxylate (213 mg, 0.885 mmol) was added followed by of diisopropylethylamine (0.308 mL, 1.77 mmol). The solution was stirred for 4 hours at 40° C. The reaction was concentrated, the residue taken up in water, and the insoluble solid collected by filtration (135 mg of desired product). The filtrate was concentrated to give a solid that was purified by silica gel column chromatography (20-75% ethyl acetate-hexane) to afford another 115 mg of desired product. The two amounts were combined to provide tert-butyl 3-((6-chloro-3,5-dicyano-4-ethylpyridin-2-yl)(methyl)amino)-8-azabicyclo[3.2.1]octane-8-carboxylate (250 mg, 66%). LCMS m/z=452 [M+Na]$^+$.

Step 5: S-(2-Amino-2-oxo-1-phenylethyl) ethanethioate

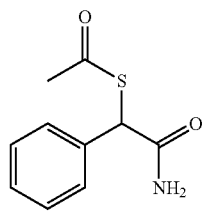

To a solution of 2-chloro-2-phenyl-acetamide (6 g, 35 mmol) in acetone (120 mL) was added potassium thioacetate (4.08 g, 36 mmol) and the reaction was stirred and heated at reflux under an atmosphere of nitrogen for 2 hours. The mixture was cooled and the solvent was removed under reduced pressure. The resulting solid was partitioned between water (200 mL) and EtOAc (200 mL), filtered and the phases separated. The organic phase was washed with brine (200 mL), filtered through a hydrophobic frit and the solvent removed under reduced pressure. The resulting solid was triturated with diethyl ether, filtered, washed with minimal diethyl ether and air dried to afford S-(2-amino-2-oxo-1-phenyl-ethyl)ethanethioate (2.8 g, 38% yield) as a beige powder. LCMS m/z=208.0 [M−H]⁻.

Step 6: 2-((6-(8-azabicyclo[3.2.1]octan-3-yl(methyl) amino)-3,5-dicyano-4-ethylpyridin-2-yl)thio)-2-phenylacetamide

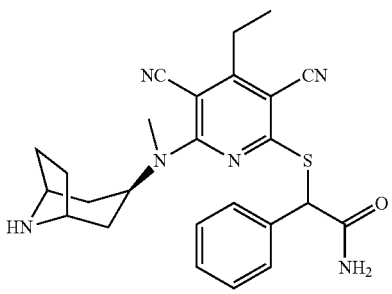

S-(2-amino-2-oxo-1-phenylethyl) ethanethioate (synthesis described in example 3 step 5, 120 mg, 0.575 mmol) was dissolved in ethanol (10 mL) and NaBH₄ (27.2 mg, 0.719 mmol) was added. The solution was stirred for 6 minutes at 70° C. The reaction was cooled and a solution of tert-butyl 3-((6-chloro-3,5-dicyano-4-ethylpyridin-2-yl)(methyl)amino)-8-azabicyclo[3.2.1]octane-8-carboxylate (206 mg, 0.479 mmol) in N,N-dimethylformamide (15 mL) was added and the reaction mixture heated for 4 minutes at 70° C. The reaction mixture was concentrated under reduced pressure and the crude material purified by silica gel column chromatography (12-70% ethyl acetate-hexane). The purified material was dissolved in dichloromethane (5 mL) and trifluoroacetic acid (5 mL) and the reaction stirred at room temperature for one hour. The reaction was concentrated under reduced pressure. The remaining residue was dissolved in dichloromethane and washed with saturated sodium bicarbonate solution. The organic layer was concentrated to provide 2-((6-(8-azabicyclo[3.2.1]octan-3-yl(methyl)amino)-3,5-dicyano-4-ethylpyridin-2-yl)thio)-2-phenylacetamide (63 mg, 28%). LCMS m/z=461 [M+H]⁺.
¹H NMR (400 MHz, DMSO-d₆) δ ppm 1.22 (t, J=7.58 Hz, 3H) 1.57 (t, J=11.75 Hz, 2H) 1.78-2.00 (m, 4H) 2.18-2.37 (m, 2H) 2.78 (q, J=7.58 Hz, 2H) 3.16 (s, 4H) 3.86 (br. s., 2H) 5.00 (t, J=7.83 Hz, 1H) 5.49 (s, 1H) 7.34-7.48 (m, 3H) 7.54 (d, J=7.07 Hz, 2H) 7.66 (br. s., 1H) 8.12 (s, 1H).

Example 63

2-((3,5-Dicyano-4-cyclopropyl-6-(2-(hydroxymethyl)morpholino)pyridin-2-yl)thio)-2-phenylacetamide

Step 1: 2-Chloro-4-cyclopropyl-6-(2-(hydroxymethyl)morpholino)pyridine-3,5-dicarbonitrile

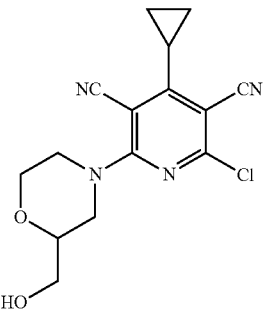 [SMILES: N#Cc1c(Cl)nc(N2CCOC(CO)C2)c(C#N)c1C1CC1]

To a solution of 2,6-dichloro-4-cyclopropylpyridine-3,5-dicarbonitrile (synthesis described in example 3 step 2, 237 mg, 1 mmol) in N,N-dimethylformamide (10 mL) was added morpholin-2-ylmethanol (117 mg, 1 mmol), followed by Et₃N (0.14 mL, 1 mmol). The reaction was stirred at room temperature for 30 minutes, and then diluted with water (20 mL). The precipitated solid was collected by filtration and dried in an oven to afford 2-chloro-4-cyclopropyl-6-(2-(hydroxymethyl)morpholino)pyridine-3,5-dicarbonitrile (280 mg, 88%). LCMS m/z=319 [M+H]⁺.

Step 2: 2-((3,5-Dicyano-4-cyclopropyl-6-(2-(hydroxymethyl)morpholino)pyridin-2-yl)thio)-2-phenylacetamide

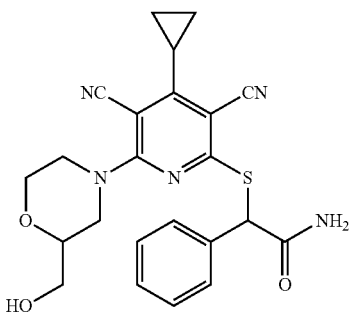 [SMILES: N#Cc1c(SC(C(N)=O)c2ccccc2)nc(N2CCOC(CO)C2)c(C#N)c1C1CC1]

A solution of 2-chloro-4-cyclopropyl-6-(2-(hydroxymethyl)morpholino)pyridine-3,5-dicarbonitrile (280 mg, 0.88 mmol) and potassium thioacetate (121 mg, 1.06 mmol) in N,N-dimethylformamide (9 mL) was stirred at room temperature for 30 minutes, then 2-amino-2-oxo-1-phenylethyl methanesulfonate (synthesis described in example 3 step 5, 242 mg, 1.06 mmol) and Et$_3$N (0.25 mL, 1.76 mmol) were added. The reaction mixture was stirred at room temperature overnight then diluted with water (20 mL). The precipitated solid was collected by filtration and purified by silica gel column chromatography (MeOH:DCM 1:20) to afford 2-((3, 5-dicyano-4-cyclopropyl-6-(2-(hydroxymethyl)morpholino)pyridin-2-yl)thio)-2-phenylacetamide (102 mg, 26%). LCMS m/z=450 [M+H]$^+$. $^1$H NMR (400 MHz, CDCl$_3$) δ ppm 7.50-7.33 (m, 5H), 6.75 (d, J=22.0 Hz, 1H), 5.91 (d, J=38.7 Hz, 1H), 5.31 (d, J=7.3 Hz, 1H), 4.73 (dd, J=35.2, 13.5 Hz, 1H), 4.45 (t, J=14.5 Hz, 1H), 4.02 (d, J=11.5 Hz, 1H), 3.77-3.56 (m, 4H), 3.52-3.42 (m, 1H), 3.07-2.95 (m, 1H), 2.19 (br s, 1H), 2.13-2.05 (m, 1H), 1.35-1.26 (m, 2H), 1.22-1.11 (m, 2H).

Example 64

(R)-2-((3,5-dicyano-6-(dimethylamino)-4-ethylpyridin-2-yl)thio)-2-phenylacetamide

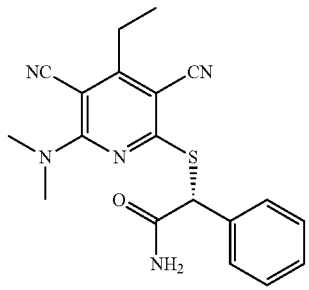 [SMILES: CCc1c(C#N)c(S[C@@H](C(N)=O)c2ccccc2)nc(N(C)C)c1C#N]

2-[[3,5-Dicyano-6-(dimethylamino)-4-ethyl-2-pyridyl]sulfanyl]-2-phenyl-acetamide (synthesis described in example 3 step 6, 496 mg), was dissolved in 30 mg portions in 300 volumes of boiling methanol (9 mL) and resolved by chiral HPLC on a Lux-2 cellulose, 5 microns column (30 mm×250 mm) and eluted with 100% methanol (50 mL/min). Collected a total of about 900 mL of product solution which was concentrated to dryness. The solid was dried at 40° C. under high vacuum to a final, constant weight to afford (R)-2-((3,5-dicyano-6-(dimethylamino)-4-ethylpyridin-2-yl)thio)-2-phenylacetamide (232 mg) as a white solid. LCMS m/z=366 [M+H]$^+$. Chiral HPLC: >99.8% ee chiral purity. Optical Rotation: −316 degrees (C=0.2, chloroform-d, 21° C.). $^1$H NMR (DMSO-d$_6$) δ ppm 7.91 (s, 1H), 7.52 (d, J=7.1 Hz, 2H), 7.29-7.42 (m, 4H), 5.59 (s, 1H), 3.34 (s, J=7.8 Hz, 6H), 2.76 (q, J=7.4 Hz, 2H), 1.20 (t, J=7.6 Hz, 3H).

Example 64(a) Alternative Route (R)-2-((3,5-dicyano-6-(dimethylamino)-4-ethylpyridin-2-yl)thio)-2-phenylacetamide

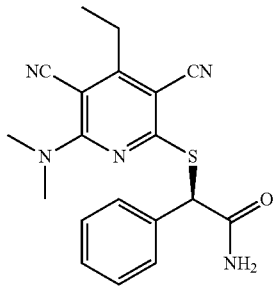 [SMILES: CCc1c(C#N)c(S[C@@H](C(N)=O)c2ccccc2)nc(N(C)C)c1C#N]

To a solution of (S)-2-amino-2-oxo-1-phenylethyl 4-methylbenzenesulfonate (synthesis described in example 418 step 3, 65.7 mg, 0.215 mmol), 2-(dimethylamino)-4-ethyl-6-mercaptopyridine-3,5-dicarbonitrile (synthesis described in example 92, step 3, 50 mg, 0.215 mmol) in N,N-dimethylformamide (1 mL) was added triethylamine (0.060 mL, 0.430 mmol). The reaction was stirred at room temperature for six hours. The mixture was poured into H$_2$O (5 mL), and stirred for 10 minutes, then filtered and washed with additional H$_2$O (5 mL), dried at the pump overnight to afford 67 mg of crude. The sample was purified by flash chromatography (0-100% EtOAc in CHCl$_3$). The product fractions were concentrated, and the residue was triturated with DCM and filtered to afford (R)-2-((3,5-dicyano-6-(dimethylamino)-4-ethylpyridin-2-yl)thio)-2-phenylacetamide (40 mg, 0.109 mmol, 51% yield) as a white solid. LCMS(ES) m/z=388.0 [M+Na]$^+$. $^1$H NMR (DMSO-d$_6$) δ ppm 7.93 (s, 1H), 7.46-7.56 (m, 2H), 7.27-7.44 (m, 4H), 5.59 (s, 1H), 3.32-3.36 (m, 6H), 2.76 (q, J=7.4 Hz, 2H), 1.21 (t, J=7.5 Hz, 3H). Chiral HPLC indicated 99.5% ee.

Example 65

(R)-2-[(3,5-Dicyano-4-ethyl-6-morpholino-2-pyridyl)sulfanyl]-2-phenyl-acetamide

Step 1: 2-Chloro-4-ethyl-6-morpholinopyridine-3,5-dicarbonitrile

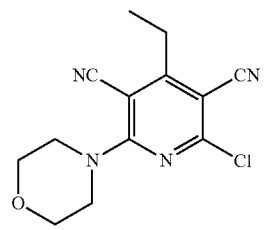 [SMILES: CCc1c(C#N)c(Cl)nc(N2CCOCC2)c1C#N]

To a solution of 2,6-dichloro-4-ethyl-pyridine-3,5-dicarbonitrile (synthesis described in example 3 step 2, 1.0 g, 4.42 mmol) in tetrahydrofuran (25 mL) was added morpholine (0.386 mL, 4.42 mmol) at room temperature. The mixture was stirred for 15 minutes then an additional one equivalent of morpholine (0.386 mL, 4.42 mmol) was added. The mixture was then stirred for 75 minutes before the addition of 0.5 equivalents more of morpholine (0.19 mL, 2.21 mmol). After 30 minutes, the reaction mixture was filtered, the collected solid washed with tetrahydrofuran (2×25 mL), and the filtrate concentrated under reduced pressure. The resulting solid was dissolved in ethyl acetate (25 mL), filtered through a hydrophobic frit, dry loaded onto $SiO_2$, and purified by silica gel column chromatography (0-30% ethyl acetate/hexane) to give 2-chloro-4-ethyl-6-morpholino-pyridine-3,5-dicarbonitrile (926 mg, 76%) as a white powder. LCMS m/z=275 [M–H]$^-$.

Step 2: 2-((3,5-Dicyano-4-ethyl-6-morpholinopyridin-2-yl)thio)-2-phenylacetamide

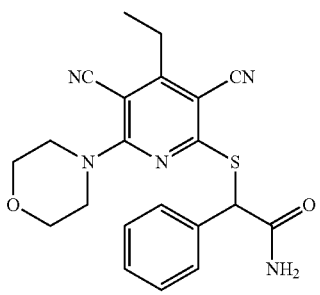 [SMILES: CCc1c(C#N)c(SC(C(N)=O)c2ccccc2)nc(N2CCOCC2)c1C#N]

Sodium borohydride (114 mg, 3.01 mmol) was added portionwise over 5 minutes to a solution of S-(2-amino-2-oxo-1-phenyl-ethyl)ethanethioate, (synthesis described in example 3 step 5, 0.46 g, 2.2 mmol) in ethanol (20 mL) at 70° C. The reaction mixture was stirred at 70-80° C. for 15 minutes. The reaction was removed from the heat source and 2-chloro-4-ethyl-6-morpholino-pyridine-3,5-dicarbonitrile (590 mg, 2.13 mmol) was added. The resultant mixture was heated at 80° C. for 15 minutes, allowed to cool to room temperature, then further cooled with an ice/water bath. The solid that was present was collected by filtration and washed with ice-cold ethanol (5 mL), cold aqueous ethanol (50% aqueous, 10 mL), water (2×15 mL), and dried in vacuo. The solid was then washed with diethyl ether/hexane (1:1, 10 mL), hexane (10 mL), and dried in vacuo at 50° C. to afford racemic 2-[(3,5-dicyano-4-ethyl-6-morpholino-2-pyridyl)sulfanyl]-2-phenyl-acetamide (542 mg, 62%) as a white solid. LCMS m/z=408 [M+H]$^+$.

Step 3: (R)-2-[(3,5-Dicyano-4-ethyl-6-morpholino-2-pyridyl)sulfanyl]-2-phenyl-acetamide

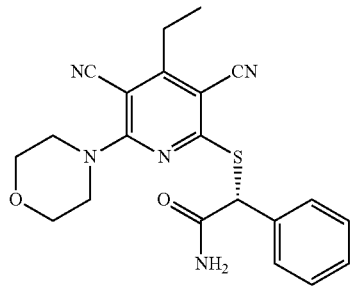 [SMILES: CCc1c(C#N)c(S[C@@H](C(N)=O)c2ccccc2)nc(N2CCOCC2)c1C#N]

Racemic 2-[(3,5-dicyano-4-ethyl-6-morpholino-2-pyridyl)sulfanyl]-2-phenyl-acetamide (232 mg), was dissolved in 20 mg portions in 400 volumes (8 mL) of boiling methanol and filtered. The sample was resolved by chiral HPLC using a Chromega Chiral, CC4, 5 microns column (30 mm×250 mm) eluting with 100% methanol (42 mL/min). Collected a total of about 400 mL of product solution which was concentrated to near dryness to afford a white slurry. The slurry was filtered, rinsed with a minimum amount of methanol and dried at 40° C. under high vacuum to a final, constant weight to afford (R)-2-[(3,5-dicyano-4-ethyl-6-morpholino-2-pyridyl)sulfanyl]-2-phenyl-acetamide (102 mg) as a white solid. LCMS m/z=408 [M+H]$^+$. 99.2% ee chiral purity. Optical Rotation: –285 degrees (C.=0.20, DMSO-$d_6$, 23° C.). $^1$H NMR (DMSO-$d_6$) δ ppm 7.89 (s, 1H), 7.47-7.56 (m, 2H), 7.28-7.44 (m, 4H), 5.52 (s, 1H), 3.90 (t, J=4.7 Hz, 4H), 3.60-3.75 (m, 4H), 2.77 (q, J=7.6 Hz, 2H), 1.21 (t, J=7.6 Hz, 3H)

Example 66

N-(4-((3,5-Dicyano-4-ethyl-6-(4-(pyrrolidin-1-yl)piperidin-1-yl)pyridin-2-ylthio)methyl)benzyl)acetamide trifluoroacetate

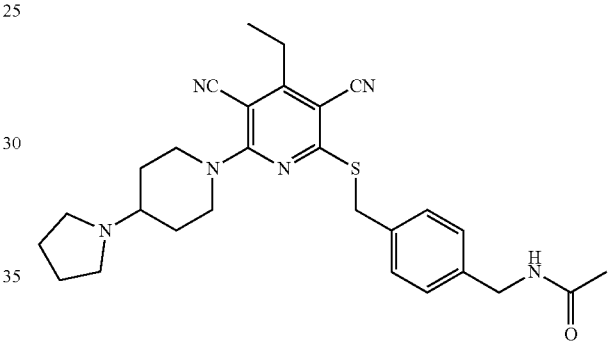

Step 1: 2-Chloro-4-ethyl-6-(4-(pyrrolidin-1-yl)piperidin-1-yl)pyridine-3,5-dicarbonitrile

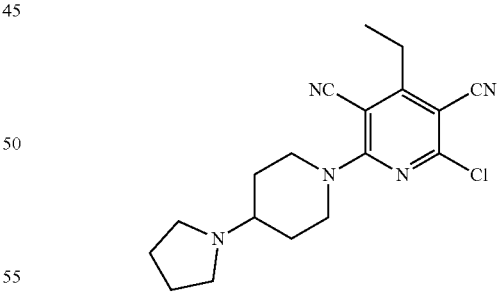

A solution of 4-(pyrrolidin-1-yl)piperidinyl (1.5 g, 9.72 mmol) in dichloromethane (30 mL) was added to a mixture of 2,6-dichloro-4-ethylpyridine-3,5-dicarbonitrile (synthesis described in example 3 step 2, 2.198 g, 9.72 mmol) and triethylamine (1.355 mL, 9.72 mmol) in dichloromethane (30 mL) at 0° C. The resultant mixture was warmed to 25° C. and stirred for 12 hours. The reaction mixture was partitioned with water (30 mL) and the layers separated. The organic layer was concentrated and the remaining residue purified by silica gel column chromatography (petroleum ether:ethyl acetate 2:1) to give 2-chloro-4-ethyl-6-(4-(pyrrolidin-1-yl)piperidin-1-yl)pyridine-3,5-dicarbonitrile (3.6 g). LCMS m/z=344 [M+H]$^+$.

Step 2: 4-(Aminomethyl)phenyl)methanol

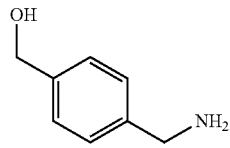

To a cooled suspension of lithium aluminum hydride (5.79 g, 153 mmol) in tetrahydrofuran (50 mL) at 0° C. was added a solution of 4-formylbenzonitrile (5 g, 38.1 mmol) in tetrahydrofuran (50 mL). The resultant mixture was stirred at room temperature overnight then recooled to 0° C. and treated with a solution of aqueous sodium hydroxide solution (5N, 32.1 mL). The resultant mixture was then filtrated and the filtrate concentrated in vacuo to provide (4-(aminomethyl)phenyl)methanol (4.5 g, 73%) as a white solid. LCMS m/z=138.1 [M+H]$^+$.

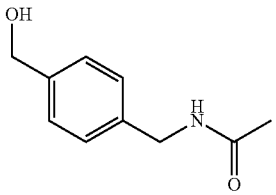

Step 3: N-(4-(Hydroxymethyl)benzyl)acetamide

A solution of (4-(aminomethyl)phenyl)methanol (0.96 g, 7.00 mmol) and acetic anhydride (7.14 g, 70.0 mmol) in acetic acid (20 mL) was stirred in a sealed tube at 110° C. for 6 hours. After cooling to room temperature, the reaction was concentrated in vacuo. The residue was diluted with methanol (15 mL), treated with lithium hydroxide (0.838 g, 35.0 mmol), and stirred at room temperature overnight. The reaction was concentrated and the remaining material partitioned between ethyl acetate (50 mL) and water (25 mL). The layers were separated and the organic layer washed with saturated sodium chloride solution (25 mL), dried over sodium sulfate, and concentrated in vacuo to give the crude product. The crude product was purified by silica gel column chromatography (dichloromethane:methanol 15:1) to give N-(4-(hydroxymethyl)benzyl)acetamide (0.23 g, 17%). $^1$H NMR (400 MHz, DMSO-d$_6$) δ ppm 8.32 (br. s, 1H), 7.23 (dd, J=24.5, 8.0 Hz, 4H), 5.14 (t, J=5.7 Hz, 1H), 4.47 (d, J=5.6 Hz, 2H), 4.22 (d, J=5.9 Hz, 2H), 1.86 (s, 3H).

Step 4: N-(4-((3,5-Dicyano-4-ethyl-6-(4-(pyrrolidin-1-yl)piperidin-1-yl)pyridin-2-ylthio)methyl)benzyl) acetamide trifluoroacetate

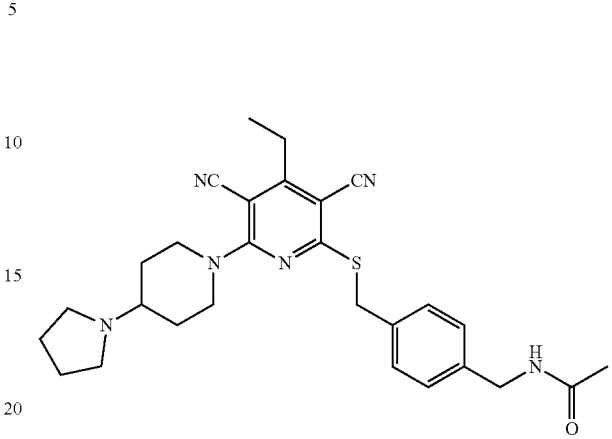

To a solution of N-(4-(hydroxymethyl)benzyl)acetamide (180 mg, 1.004 mmol) and triethylamine (305 mg, 3.01 mmol) in tetrahydrofuran (8 mL) was added methanesulfonyl chloride (173 mg, 1.507 mmol) at 0° C. The resultant mixture was stirred at 0° C. for 0.5 hour and at room temperature for an additional 1 hour. The reaction was partitioned between ethyl acetate (50 mL) and water (25 mL). The layers were separated and the organic layer washed with saturated sodium chloride solution (25 mL), dried over sodium sulfate, and concentrated in vacuo to give crude 4-(acetamidomethyl)benzyl methanesulfonate (0.27 g) as a brown solid. To a solution of 2-chloro-4-ethyl-6-(4-(pyrrolidin-1-yl)piperidin-1-yl)pyridine-3,5-dicarbonitrile (0.361 g, 1.049 mmol) in N,N-dimethylformamide (10 mL) was added potassium thioacetate (0.180 g, 1.574 mmol). The reaction mixture was stirred at room temperature for two hours and then was treated with potassium carbonate (0.145 g, 1.049 mmol). After stirring at room temperature for 1 hour, crude 4-(acetamidomethyl)benzyl methanesulfonate (0.27 g, 1.049 mmol) was added and the mixture was stirred at room temperature overnight. The reaction was concentrated in vacuo and the residue partitioned between ethyl acetate (50 mL) and water (25 mL). The layers were separated. The organic layer was washed with saturated sodium chloride solution (25 mL), dried over sodium sulfate, and concentrated in vacuo to give the crude product as a brown solid. The crude product was purified by prep-HPLC to provide N-(4-(((3,5-dicyano-4-ethyl-6-(4-(pyrrolidin-1-yl)piperidin-1-yl)pyridin-2-yl)thio)methyl)benzyl)acetamide trifluoroacetate (120 mg). LCMS m/z=503 [M+H]$^+$. $^1$H NMR (400 MHz, DMSO-d$_6$) δ ppm 1.22 (t, J=7.6 Hz, 3H), 1.66 (dd, J=21.2, 12.2 Hz, 2H), 1.87 (s, 5H), 2.02 (s, 2H), 2.21 (d, J=10.7 Hz, 2H), 2.79 (q, J=7.5 Hz, 2H), 3.25-3.04 (m, 4H), 3.60-3.40 (m, 3H), 4.22 (d, J=5.9 Hz, 2H), 4.50 (s, 2H), 4.61 (d, J=13.6 Hz, 2H), 7.22 (d, J=8.0 Hz, 2H), 7.37 (d, J=8.0 Hz, 2H), 8.37 (t, J=5.7 Hz, 1H), 9.92 (s, 1H).

Example 67

2-{[3,5-dicyano-4-ethyl-6-(5-methyl-1,4-diazepan-1-yl)pyridin-2-yl]sulfanyl}-2-phenylacetamide

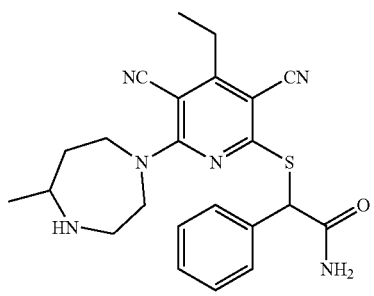 [SMILES: CCc1c(C#N)c(SC(C(N)=O)c2ccccc2)nc(N2CCNC(C)CC2)c1C#N]

To a solution of 2-[(6-bromo-3,5-dicyano-4-ethyl-2-pyridyl)sulfanyl]-2-phenyl-acetamide (synthesis described in example 6 step 1, 30 mg, 0.07 mmol) and triethylamine (0.02 mL, 0.16 mmol) in tetrahydrofuran (2 mL) was added 5-methyl-[1,4]diazepene (9 mg, 0.08 mmol). The mixture was allowed to stir at ambient temperature for 17 hours. The product mixture was diluted water (7.5 mL), filtered, washed with water (2×10 mL) and dried in vacuo at 50° C. to afford 2-[[3,5-dicyano-4-ethyl-6-(5-methyl-1,4-diazepan-1-yl)-2-pyridyl]sulfanyl]-2-phenyl-acetamide as a complex mix of diastereomers (24 mg, 74% yield) as an off-white solid. $^1$H NMR (300 MHz, DMSO-$d_6$) δ ppm 7.91 (br s, 1H), 7.54-7.44 (m, 2H), 7.44-7.28 (m, 4H), 5.52 (d, J=2.3 Hz, 1H), 4.19-4.03 (m, 1H), 4.01-3.85 (m, 1H), 3.84-3.58 (m, 2H), 3.22-3.03 (m, 1H), 2.89 (br d, J=10.5 Hz, 1H), 2.84-2.69 (m, 3H), 1.89 (br s, 1H), 1.45 (br d, J=13.7 Hz, 1H), 1.36 (s, 1H), 1.28-1.09 (m, 3H), 1.09-0.87 (m, 3H). LCMS m/z=433 [M−H]$^−$.

Example 68

2-(4-(Aminomethyl)benzylthio)-4-ethyl-6-(4-(pyrrolidin-1-yl)piperidin-1-yl)pyridine-3,5-dicarbonitrile 2,2,2-trifluoroacetate Step 1: 2-chloro-4-ethyl-6-(4-(pyrrolidin-1-yl)piperidin-1-yl)pyridine-3,5-dicarbonitrile

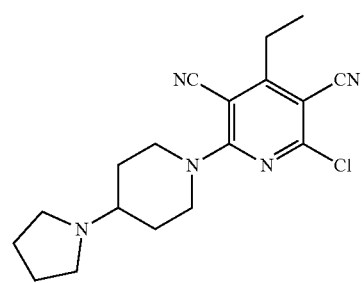 [SMILES: CCc1c(C#N)c(Cl)nc(N2CCC(N3CCCC3)CC2)c1C#N]

A solution of 4-(pyrrolidin-1-yl)piperidine (1.5 g, 9.72 mmol) in dichloromethane (30 mL) was added to a mixture of 2,6-dichloro-4-ethylpyridine-3,5-dicarbonitrile (synthesis described in example 3, step 2, 2.19 g, 9.72 mmol) and triethylamine (1.355 mL, 9.72 mmol) in dichloromethane (30 mL) at 0° C. The mixture was warmed to 25° C. and stirred for 12 hours. The mixture was washed with water (30 mL), the organic phase was concentrated and purified by column chromatography (PE:EA=2:1) to give 2-chloro-4-ethyl-6-(4-(pyrrolidin-1-yl)piperidin-1-yl)pyridine-3,5-dicarbonitrile (3.6 g). LCMS m/z=344.1 [M+H]$^+$.

Step 2: (4-(Aminomethyl)phenyl)methanol

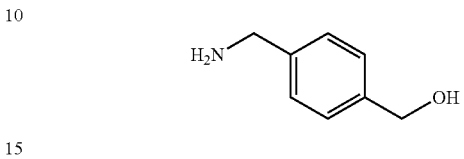

To a cooled suspension of LiAlH$_4$ (5.79 g, 153 mmol) in tetrahydrofuran (50 mL) was added a solution of 4-formylbenzonitrile (5 g, 38.1 mmol) in tetrahydrofuran (50 mL) at 0° C. The resultant mixture was stirred at room temperature overnight then cooled and treated with a solution of aqueous sodium hydroxide solution (5N, 32.1 mL) at 0° C. The resultant mixture was filtrated and concentrated under reduced pressure to give (4-(aminomethyl)phenyl)methanol (4.5 g, 27.9 mmol, 73% yield) as a gray solid. LCMS m/z=138.1 [M+H]$^+$.

Step 3: tert-Butyl 4-(hydroxymethyl)benzylcarbamate

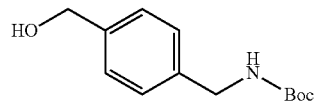 [SMILES: CC(C)(C)OC(=O)NCc1ccc(CO)cc1]

The mixture of (4-(aminomethyl)phenyl)methanol (1 g, 7.29 mmol) and di-tert-butyl dicarbonate (1.59 g, 7.29 mmol) in dichloromethane (30 mL) was stirred at room temperature overnight then concentrated under reduced pressure and the crude product was added to a silica gel column and was eluted with dichloromethane:ethyl acetate (1:1) to give tert-butyl 4-(hydroxymethyl)benzylcarbamate (0.8 g, 2.28 mmol, 31% yield) as a white solid. $^1$H NMR (400 MHz, DMSO-$d_6$) δ ppm 7.37 (s, 1H), 7.22 (dd, J=27.8, 8.0 Hz, 4H), 5.13 (t, J=5.7 Hz, 1H), 4.46 (d, J=5.7 Hz, 2H), 4.10 (d, J=6.1 Hz, 2H), 1.36 (s, 9H).

Step 4: tert-Butyl 4-((3,5-dicyano-4-ethyl-6-(4-(pyrrolidin-1-yl)piperidin-1-yl)pyridin-2-ylthio)methyl)benzylcarbamate

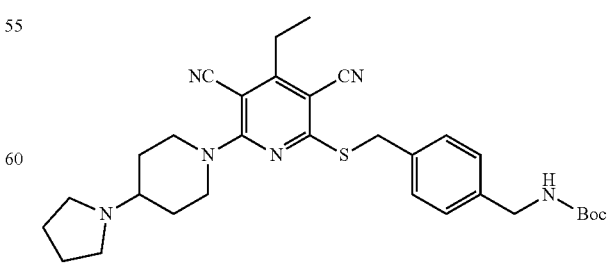

To a solution of tert-butyl 4-(hydroxymethyl)benzylcarbamate (350 mg, 1.47 mmol) and triethylamine (448 mg, 4.42 mmol) in tetrahydrofuran (10 mL) was added methanesulfonyl chloride (253 mg, 2.212 mmol) at 0° C. The resultant mixture was stirred at 0° C. for 0.5 hour and at room temperature for 1 hour then diluted with ethyl acetate (50 mL). The organic phase was washed with water (25 mL) and saturated brine (25 mL), dried over sodium sulfate and evaporated in vacuo to afford crude 4-(((tert-butoxycarbonyl)amino)methyl)benzyl methanesulfonate (500 mg) as a brown solid. To a solution of 2-chloro-4-ethyl-6-(4-(pyrrolidin-1-yl)piperidin-1-yl)pyridine-3,5-dicarbonitrile (545 mg) in N,N-dimethylformamide (15 mL) was added potassium ethanethioate (272 mg, 2.37 mmol). The mixture was stirred at room temperature for 2 hours then treated with potassium carbonate (438 mg, 3.17 mmol). The resultant mixture was stirred at room temperature for 1 hour then treated with the brown solid of crude 4-(((tert-butoxycarbonyl)amino)methyl)benzyl methanesulfonate (500 mg). The mixture was stirred at room temperature overnight then concentrated under reduced pressure. The residue was diluted with ethyl acetate (100 mL). The organic phase was washed with water (50 mL) and saturated brine (50 mL), dried over sodium sulfate and evaporated in vacuo to give crude tert-butyl 4-((3,5-dicyano-4-ethyl-6-(4-(pyrrolidin-1-yl)piperidin-1-yl)pyridin-2-ylthio)methyl)benzylcarbamate (0.8 g) as a brown solid, which was used in next step without further purification. LCMS m/z=561.2 [M+H]⁺.

Step 6: 2-((4-(Aminomethyl)benzyl)thio)-4-ethyl-6-(4-(pyrrolidin-1-yl)piperidin-1-yl)pyridine-3,5-dicarbonitrile, Trifluoroacetic Acid Salt

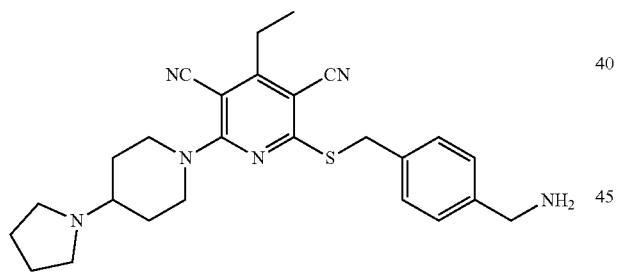

To a solution of crude tert-butyl 4-(((3,5-dicyano-4-ethyl-6-(4-(pyrrolidin-1-yl)piperidin-1-yl)pyridin-2-yl)thio) methyl)benzylcarbamate (0.78 g) in dichloromethane (20 mL) was added 2,2,2-trifluoroacetic acid (1.58 g, 13.9 mmol) at room temperature. The resultant mixture was stirred at room temperature overnight, then concentrated under reduced pressure and the crude product was purified by prep-HPLC to give 2-((4-(aminomethyl)benzyl)thio)-4-ethyl-6-(4-(pyrrolidin-1-yl)piperidin-1-yl)pyridine-3,5-dicarbonitrile, trifluoroacetic acid salt (150 mg, 0.261 mmol) as a white solid. LCMS m/z=460.7 [M+H]⁺. ¹H NMR (400 MHz, DMSO) δ ppm 10.30 (s, 1H), 8.28 (s, 2H), 7.45 (q, J=8.2 Hz, 4H), 4.62 (d, J=13.5 Hz, 2H), 4.53 (s, 2H), 4.03 (q, J=5.6 Hz, 2H), 3.63-3.41 (m, 3H), 3.25-3.05 (m, 4H), 2.79 (q, J=7.5 Hz, 2H), 2.22 (d, J=10.4 Hz, 2H), 2.02 (s, 2H), 1.93-1.81 (m, 2H), 1.70 (td, J=12.0, 8.9 Hz, 2H), 1.22 (t, J=7.6 Hz, 3H).

Example 69 tert-Butyl 4-(((3,5-dicyano-4-ethyl-6-(4-methyl-1,4-diazepan-1-yl)pyridin-2-yl)thio)methyl)benzylcarbamate Step 1: 4-Ethyl-2-mercapto-6-(4-methyl-1,4-diazepan-1-yl)pyridine-3,5-dicarbonitrile

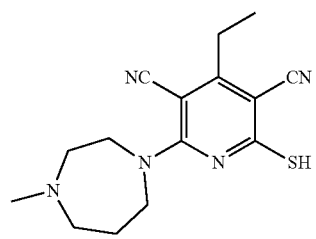 [SMILES: CCc1c(C#N)c(S)nc(N2CCCN(C)CC2)c1C#N]

To a solution of 2,6-dichloro-4-ethylpyridine-3,5-dicarbonitrile (synthesis described in example 3, step 2, 3.0 g, 13.27 mmol) in ethanol (20 mL) at –20° C. was added a solution of 1-methyl-1,4-diazepane (1.82 mL, 14.66 mmol) in ethanol (20 mL). The reaction mixture was then stirred at –20° C. for 2 hours. To the reaction mixture was then added potassium thioacetate (2.3 g, 20.14 mmol) and triethylamine (4.62 mL, 33.2 mmol). The reaction mixture was then warmed to 20° C. and stirred at the same temperature while progress was monitored by LCMS. After stirring overnight at 20° C., the heterogeneous reaction mixture was filtered and the solid washed with ethanol and diethyl ether. The solid was dried in the vacuum oven to yield 4-ethyl-2-mercapto-6-(4-methyl-1,4-diazepan-1-yl)pyridine-3,5-dicarbonitrile (5.2 g, 130%). LCMS m/z=302 [M+H]⁺.

Step 2: tert-Butyl 4-(((3,5-dicyano-4-ethyl-6-(4-methyl-1,4-diazepan-1-yl)pyridin-2-yl)thio)methyl) benzylcarbamate

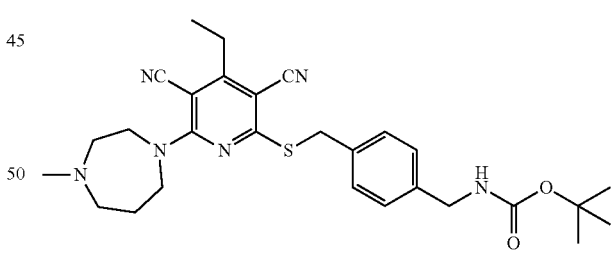

To a suspension of 4-ethyl-2-mercapto-6-(4-methyl-1,4-diazepan-1-yl)pyridine-3,5-dicarbonitrile (500 mg, 1.659 mmol) and triethylamine (0.185 mL, 1.327 mmol) in N,N-dimethylformamide (4.0 mL) at 0° C. was added a solution of tert-butyl 4-(bromomethyl)benzylcarbamate (398 mg, 1.327 mmol) in N,N-dimethylformamide (4.0 mL). The reaction mixture was then stirred at 0° C. over the weekend. The reaction mixture was diluted with ethyl acetate and this mixture washed with water (3×). The combined aqueous layers were then back extracted with ethyl acetate (1×). The combined organic layers were washed with saturated brine, dried (magnesium sulfate) and concentrated to obtain the crude desired product. The crude desired product was purified by normal phase chromatography (Biotage Isolera, 25 g SNAP ULTRA column, dichloromethane/methanol 0-5%) to obtain tert-butyl 4-(((3,5-dicyano-4-ethyl-6-(4-methyl-1,4-diazepan-1-yl)pyridin-2-yl)thio)methyl)benzylcarbamate (404 mg, 47%) as an orange gum. LCMS m/z=521 [M+H]$^+$. $^1$H NMR (400 MHz, DMSO-d$_6$) δ ppm 7.39 (t, J=6.08 Hz, 1H), 7.34 (d, J=8.11 Hz, 2H), 7.19 (d, J=8.11 Hz, 2H), 4.47 (s, 2H), 4.09 (d, J=5.83 Hz, 2H), 3.81-3.94 (m, 4H), 2.78 (q, J=7.60 Hz, 2H), 2.62-2.69 (m, 2H), 2.24 (s, 3H), 1.87-1.97 (m, 2H), 1.39 (s, 9H), 1.22 (t, J=7.60 Hz, 3H), (2H obscured by DMSO).

Example 70

4-(((3,5-Dicyano-4-ethyl-6-(4-methyl-1,4-diazepan-1-yl)pyridin-2-yl)thio)methyl)benzamide

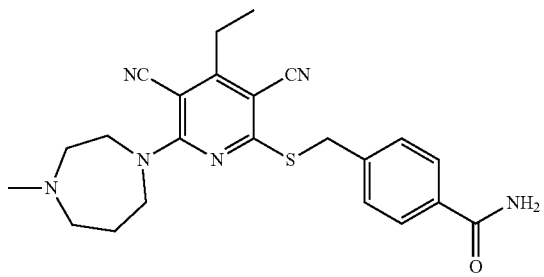 [SMILES: CCc1c(C#N)c(SCc2ccc(C(N)=O)cc2)nc(N2CCCN(C)CC2)c1C#N]

To a suspension of 4-ethyl-2-mercapto-6-(4-methyl-1,4-diazepan-1-yl)pyridine-3,5-dicarbonitrile (synthesis described in example 69, step 1, 60 mg, 0.199 mmol) and 4-(bromomethyl)benzamide (42 mg, 0.196 mmol) in N,N-dimethylformamide (1.0 mL) at room temperature was added triethylamine (0.055 mL, 0.398 mmol). The reaction mixture was then stirred at room temperature overnight. The reaction mixture was filtered and the filtrate was purified by reverse phase HPLC (Gilson, 30 mm×50 mm Gemini Column, NH$_4$OH modifier) to obtain the purified desired product. The isolated material was repurified by reverse phase HPLC (Gilson, 30 mm×50 mm Gemini Column, NH$_4$OH modifier) to obtain 4-(((3,5-dicyano-4-ethyl-6-(4-methyl-1,4-diazepan-1-yl)pyridin-2-yl)thio)methyl)benzamide (8 mg, 9%) as a white solid. LCMS m/z=435 [M+H]$^+$. $^1$H NMR (400 MHz, DMSO-d$_6$) δ ppm 7.96 (br. s., 1H), 7.65-7.90 (m, J=8.36 Hz, 2H), 7.42-7.65 (m, J=8.36 Hz, 2H), 7.37 (s, 1H), 4.55 (s, 2H), 3.81-3.90 (m, 4H), 2.78 (q, J=7.60 Hz, 2H), 2.55-2.62 (m, 2H), 2.43-2.48 (m, 2H), 2.21 (s, 3H), 1.84-1.98 (m, 2H), 1.22 (t, J=7.60 Hz, 3H).

Example 71

2-((4-(Aminomethyl)benzyl)thio)-4-ethyl-6-(4-methyl-1,4-diazepan-1-yl)pyridine-3,5-dicarbonitrile, 2Hydrochloride

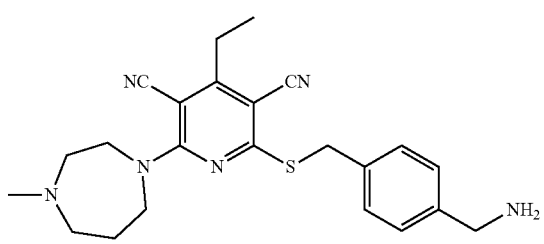 [SMILES: CCc1c(C#N)c(SCc2ccc(CN)cc2)nc(N2CCCN(C)CC2)c1C#N]

A suspension of tert-butyl 4-(((3,5-dicyano-4-ethyl-6-(4-methyl-1,4-diazepan-1-yl)pyridin-2-yl)thio)methyl)benzylcarbamate (synthesis described in example 69, step 2, 393 mg, 0.755 mmol) in a solution of HCl (4 M, 4 mL, 16.0 mmol) in dioxane was stirred at room temperature for 2 hours. The reaction mixture was then concentrated. The resulting material was suspended in ethyl acetate and sonicated. The solid was filtered and sequentially washed with ethyl acetate and diethyl ether. The solid was dried in the vacuum oven to yield 2-((4-(aminomethyl)benzyl)thio)-4-ethyl-6-(4-methyl-1,4-diazepan-1-yl)pyridine-3,5-dicarbonitrile, 2Hydrochloride (288 mg, 77% yield) as a pale pink solid. LCMS m/z=421 [M+H]$^+$. $^1$H NMR (400 MHz, DMSO-d$_6$) δ ppm 11.09 (br. s., 1H), 8.42 (br. s., 3H), 7.42-7.50 (m, 4H), 4.52 (d, J=1.77 Hz, 2H), 4.31 (d, J=12.42 Hz, 1H), 3.83-4.04 (m, 4H), 3.43-3.53 (m, 2H), 3.14-3.32 (m, 2H), 2.82 (q, J=7.44 Hz, 2H), 2.73 (br. s., 3H), 2.22 (br. s., 1H), 1.24 (t, J=7.60 Hz, 3H) (2H obscured by DMSO).

Example 72

2-(4-(((3,5-Dicyano-4-ethyl-6-(4-methyl-1,4-diazepan-1-yl)pyridin-2-yl)thio)methyl)phenyl)acetic acid

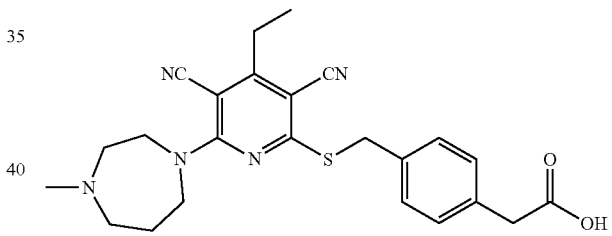

To a suspension of 4-ethyl-2-mercapto-6-(4-methyl-1,4-diazepan-1-yl)pyridine-3,5-dicarbonitrile (synthesis described in example 69, step 1, 75 mg, 0.249 mmol) and triethylamine (0.062 mL, 0.448 mmol) in N,N-dimethylformamide (0.5 mL) at 0° C. was added a solution of 2-(4-(bromomethyl)phenyl)acetic acid (46 mg, 0.201 mmol) in N,N-dimethylformamide (0.5 mL). After stirring overnight at 0° C., the reaction mixture was warmed to room temperature, filtered, and purified by reverse phase HPLC (Gilson, 30 mm×50 mm Gemini Column, NH$_4$OH modifier) to provide 2-(4-(((3,5-dicyano-4-ethyl-6-(4-methyl-1,4-diazepan-1-yl)pyridin-2-yl)thio)methyl)phenyl)acetic acid (48 mg, 43% yield) as an orange gum. LCMS m/z=450 [M+H]$^+$. $^1$H NMR (400 MHz, DMSO-d$_6$) δ ppm 7.26 (d, J=8.11 Hz, 2H), 7.16 (d, J=8.11 Hz, 2H), 4.45 (s, 2H), 3.82-3.96 (m, 4H), 3.30 (s, 2H), 2.78 (q, J=7.60 Hz, 2H), 2.60-2.70 (m, 2H), 2.24 (s, 3H), 1.84-1.99 (m, 2H), 1.22 (t, J=7.60 Hz, 3H), (2H obscured by DMSO and acid H not observed).

Example 73

4-(((3,5-Dicyano-4-ethyl-6-(4-methyl-1,4-diazepan-1-yl)pyridin-2-yl)thio)methyl)benzoic acid

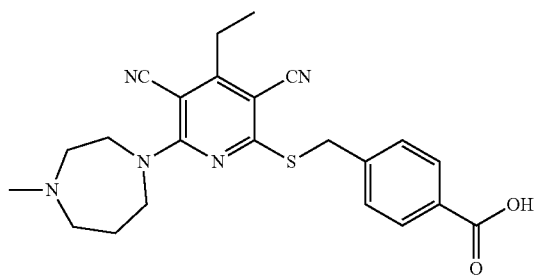 [SMILES: CCc1c(C#N)c(SCc2ccc(C(=O)O)cc2)nc(N2CCCN(C)CC2)c1C#N]

To a suspension of 4-ethyl-2-mercapto-6-(4-methyl-1,4-diazepan-1-yl)pyridine-3,5-dicarbonitrile (synthesis described in example 69, step 1, 75 mg, 0.249 mmol) and triethylamine (0.062 mL, 0.448 mmol) in N,N-dimethylformamide (0.5 mL) at 0° C. was added a solution of 4-(bromomethyl)benzoic acid (43 mg, 0.200 mmol) in N,N-dimethylformamide (0.5 mL). After stirring overnight at 0° C., the reaction mixture was warmed to room temperature, filtered, and purified by reverse phase HPLC (Gilson, 30 mm×50 mm Gemini Column, NH$_4$OH modifier) to give 4-(((3,5-dicyano-4-ethyl-6-(4-methyl-1,4-diazepan-1-yl)pyridin-2-yl)thio)methyl)benzoic acid (47 mg, 43% yield) as a light yellow solid. LCMS m/z=436 [M+H]$^+$. $^1$H NMR (400 MHz, DMSO-d$_6$) δ ppm 7.86 (d, J=8.36 Hz, 2H), 7.43 (d, J=8.11 Hz, 2H), 4.55 (s, 2H), 3.74-3.92 (m, 4H), 2.78 (q, J=7.44 Hz, 2H), 2.56-2.63 (m, 2H), 2.44-2.49 (m, 2H), 2.21 (s, 3H), 1.86-1.96 (m, 2H), 1.22 (t, J=7.60 Hz, 3H), (carboxylic acid proton not observed).

Example 74

2-(Dimethylamino)-4-ethyl-6-(((6-oxo-1,6-dihydropyridin-3-yl)methyl)thio)pyridine-3,5-dicarbonitrile

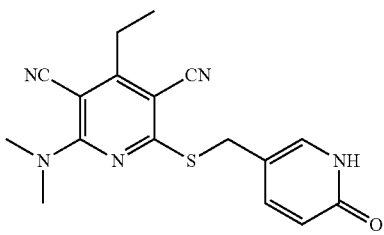 [SMILES: CCc1c(C#N)c(SCc2ccc(=O)[nH]c2)nc(N(C)C)c1C#N]

48% Hydrobromic acid (3 mL, 26.5 mmol) was added to 5-(hydroxymethyl)pyridin-2(1H)-one (400 mg, 3.20 mmol) at 0° C. and then heated at 110° C. for 16 hours. The mixture was concentrated to afford a crude black liquid (400 mg). To a solution of 2-chloro-6-(dimethylamino)-4-ethylpyridine-3,5-dicarbonitrile (synthesis described in example 3, step 3, 200 mg, 0.823 mmol) in N,N-dimethylformamide (10 mL) was added potassium thioacetate (188 mg, 1.646 mmol) and the reaction mixture was stirred at room temperature for 2 hours. After 2 hours the reaction mixture was cooled to 0° C., then potassium carbonate (228 mg, 1.646 mmol) and the crude black liquid (400 mg) were added and the mixture was stirred at room temperature for 1 hour. The reaction mass was diluted with ethyl acetate (100 mL) and washed with aqueous HCl solution (1N, 2×100 mL). The organic layer was dried over anhydrous Na$_2$SO$_4$, filtered and the filtrate evaporated under vacuum to give crude compound. The crude compound was purified by silica gel column chromatography (100-200 mesh, eluted with 3-4% methanol in DCM) to afford 2-(dimethylamino)-4-ethyl-6-(((6-oxo-1,6-dihydropyridin-3-yl)methyl)thio)pyridine-3,5-dicarbonitrile (115 mg, 41%) as a brown solid. LCMS m/z=340.1 [M+H]$^+$. $^1$H NMR (400 MHz, DMSO-d$_6$) δ ppm 11.5 (s, 1H), 7.4 (dd, J=2.4 Hz, J=2.8 Hz, 1H), 7.4 (s, 1H), 6.2 (d, J=9.2 Hz, 1H), 4.2 (s, 2H), 3.2-3.4 (2s, 6H), 2.7 (q, J=7.6 Hz, 2H), 1.2 (t, J=7.6 Hz, 3H).

Example 75

N-(4-(((3,5-Dicyano-4-ethyl-6-(4-methyl-1,4-diazepan-1-yl)pyridin-2-yl)thio)methyl)thiazol-2-yl)acetamide Step 1: N-(4-(Chloromethyl)thiazol-2-yl)acetamide

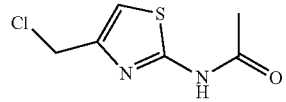

A solution of 4-(chloromethyl)thiazol-2-amine, hydrochloride (249 mg, 1.345 mmol) in tetrahydrofuran (3 mL) was cooled in an ice bath then acetyl chloride (0.115 mL, 1.614 mmol) was added. Then a solution of triethylamine (0.375 mL, 2.69 mmol) in tetrahydrofuran (3 mL) was slowly added. The reaction was stirred for 30 minutes in the ice bath, then the reaction was then diluted with EtOAc (10 mL) then washed with water. The organic layer was separated and the aqueous layer was extracted with EtOAc (2×10 mL). The organics were combined and washed with saturated aqueous sodium chloride solution, dried over MgSO$_4$, filtered and concentrated to give a white solid. The solid was then triturated with DCM and hexane then isolated by filtration to give N-(4-(chloromethyl)thiazol-2-yl)acetamide (175 mg, 0.918 mmol, 68% yield) as a white solid. LCMS m/z=190.9 [M+H]$^+$.

Step 2: N-(4-(((3,5-Dicyano-4-ethyl-6-(4-methyl-1,4-diazepan-1-yl)pyridin-2-yl)thio)methyl)thiazol-2-yl)acetamide

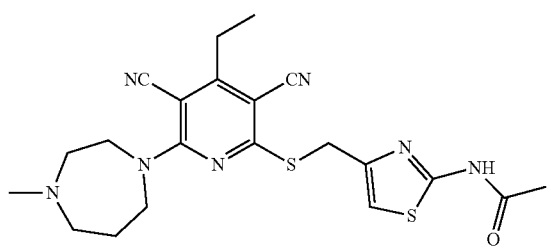 [SMILES: CCc1c(C#N)c(SCc2csc(NC(C)=O)n2)nc(N2CCCN(C)CC2)c1C#N]

To 4-ethyl-2-mercapto-6-(4-methyl-1,4-diazepan-1-yl)pyridine-3,5-dicarbonitrile (synthesis described in example 69, step 1, 52 mg, 0.138 mmol) in N,N-dimethylformamide (2 mL) was added N-(4-(chloromethyl)thiazol-2-yl)acetamide (26.3 mg, 0.138 mmol) and triethylamine (0.038 mL, 0.276 mmol). The reaction was then heated at 50° C. for 0.5 hour. The reaction was allowed to cool to room temperature then water (10 mL) was added. Mixture was then extracted with EtOAc (3×10 mL). The organics were combined, washed with saturated aqueous sodium chloride solution, dried over MgSO$_4$, then filtered and concentrated by reduced pressure then loaded on to double stacked 2×10 g Biotage Ultra column conditioned with hexane then ran 2 minutes at 100% Hexane then 2 minutes at 100% DCM then a gradient of 0 to 10% MeOH in DCM over 28 minutes to give the desired product fractions. The fractions with the desired product were combined then concentrated by reduced pressure to give N-(4-(((3,5-dicyano-4-ethyl-6-(4-methyl-1,4-diazepan-1-yl)pyridin-2-yl)thio)methyl)thiazol-2-yl)acetamide (19 mg, 0.042 mmol, 30% yield) as a white solid. LCMS m/z=456.4 [M+H]$^+$. $^1$H NMR (400 MHz, DMSO-d$_6$) δ ppm 12.16 (s, 1H), 7.03 (s, 1H), 4.47 (s, 2H), 3.83-3.92 (m, 4H), 2.78 (q, J=7.52 Hz, 2H), 2.60 (br. s., 2H), 2.46 (br. s., 2H), 2.22 (s, 3H), 2.12 (s, 3H), 1.93 (br. s., 2H), 1.22 (t, J=7.60 Hz, 3H).

Example 76

4-(((3,5-Dicyano-4-ethyl-6-(4-methyl-1,4-diazepan-1-yl)pyridin-2-yl)thio)methyl)benzenesulfonamide

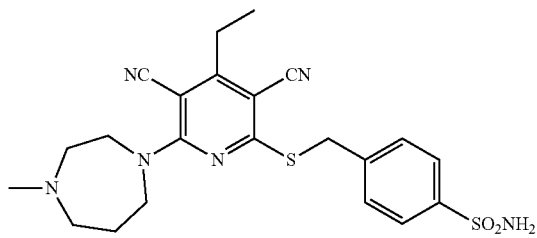 [SMILES: CCc1c(C#N)c(SCc2ccc(S(N)(=O)=O)cc2)nc(N2CCCN(C)CC2)c1C#N]

A solution of 4-(bromomethyl)benzenesulfonamide was prepared by the following procedure. 4-Methylbenzenesulfonamide (0.5 g, 2.92 mmol) was dissolved in chloroform (10 mL) and N-bromosuccinimide (0.546 g, 3.07 mmol) and benzoyl peroxide (0.035 g, 0.146 mmol) were added and the reaction was heated overnight at 63° C. The succinimide crystallized out at room temperature to afford a crude solution of 4-(bromomethyl)benzenesulfonamide. 4-Ethyl-2-mercapto-6-(4-methyl-1,4-diazepan-1-yl)pyridine-3,5-dicarbonitrile (synthesis described in example 69, step 1, 180 mg, 0.597 mmol) was dissolved in chloroform and diisopropylethylamine (209 µl, 1.194 mmol) was added followed by the solution of 4-(bromomethyl)benzenesulfonamide in chloroform portionwise (in total ca. 1 equivalent) until all the starting thiol disappeared in the LCMS. After stirring at room temperature for one hour, the solvent was evaporated and the crude residue was taken up in ethyl acetate, washed with water and dried. The ethyl acetate was removed under vacuum and the crude product was loaded onto a 12 g silica column and purified by silica gel chromatography (eluting with 25-100% ethyl acetate in hexane, then 10-70% (ethyl acetate containing 26% ethanol and 0.1% ammonium hydroxide in ethyl acetate) to provide 60 mg of 87% pure material. This 87% pure material was dissolved in 1 mL of DMSO and purified by reverse phase chromatography (10-90% acetonitrile in water with 0.1% TFA) to provide 4-(((3,5-dicyano-4-ethyl-6-(4-methyl-1,4-diazepan-1-yl)pyridin-2-yl)thio)methyl)benzenesulfonamide (25 mg, 0.053 mmol, 8.9% yield). LCMS m/z=472.4 [M+H]$^+$. $^1$H NMR (400 MHz, DMSO-d$_6$) δ ppm 7.78 (d, J=8.36 Hz, 2H), 7.60 (s, 2H), 7.36 (s, 2H), 4.58 (s, 2H), 3.77-3.89 (m, 4H), 2.72-2.83 (m, 2H), 2.57-2.65 (m, 2H), 2.41-2.48 (m, 2H), 2.22 (s, 3H), 1.84-1.95 (m, 2H), 1.22 (s, 3H).

Example 77

N-(4-(((3,5-Dicyano-4-ethyl-6-(4-methyl-1,4-diazepan-1-yl)pyridin-2-yl)thio)methyl)benzyl)acetamide

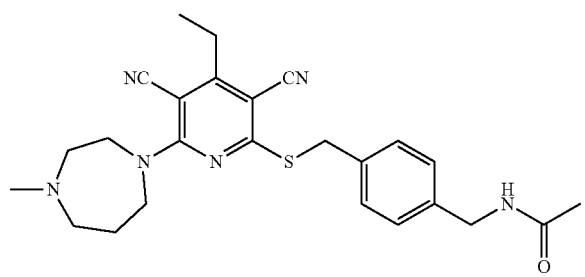 [SMILES: CCc1c(C#N)c(SCc2ccc(CNC(C)=O)cc2)nc(N2CCCN(C)CC2)c1C#N]

To a solution of 2-((4-(aminomethyl)benzyl)thio)-4-ethyl-6-(4-methyl-1,4-diazepan-1-yl)pyridine-3,5-dicarbonitrile, 2Hydrochloride (synthesis described in example 71, 131 mg, 0.265 mmol) and triethylamine (0.111 mL, 0.796 mmol) in dichloromethane (1 mL) at room temperature was added a solution of acetic anhydride (0.025 mL, 0.265 mmol) in dichloromethane (0.5 mL). After stirring at room temperature for 2 hours, the reaction mixture was concentrated to obtain the crude product. The crude product was purified by reverse phase HPLC (Gilson, 30 mm×50 mm Gemini Column, NH$_4$OH modifier) to obtain N-(4-(((3,5-dicyano-4-ethyl-6-(4-methyl-1,4-diazepan-1-yl)pyridin-2-yl)thio)methyl)benzyl) acetamide (47 mg, 38% yield) as a white solid LCMS m/z=463 [M+H]$^+$. $^1$H NMR (400 MHz, DMSO-d$_6$) δ ppm 8.34 (t, J=5.70 Hz, 1H), 7.34 (d, J=8.11 Hz, 2H), 7.21 (d, J=8.36 Hz, 2H), 4.47 (s, 2H), 4.21 (d, J=5.83 Hz, 2H), 3.82-3.94 (m, 4H), 2.78 (q, J=7.60 Hz, 2H), 2.61-2.68 (m, 2H), 2.45-2.49 (m, J=5.60 Hz, 2H), 2.24 (s, 3H), 1.89-1.97 (m, 2H), 1.86 (s, 3H), 1.22 (t, J=7.48 Hz, 3H).

Example 78 tert-Butyl (2-((4-(((3,5-dicyano-4-ethyl-6-(4-methyl-1,4-diazepan-1-yl)pyridin-2-yl)thio)methyl)benzyl)amino)-2-oxoethyl)carbamate

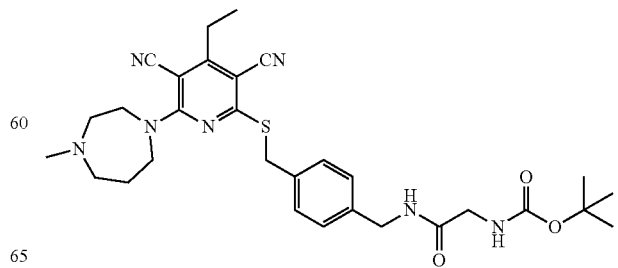

To a solution of Boc-glycine (47.2 mg, 0.270 mmol) in N,N-dimethylformamide (1.3 mL) at room temperature was added HATU (102 mg, 0.270 mmol). The reaction mixture was then stirred at room temperature for 15 minutes at which time 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 133 mg, 0.270 mmol) and triethylamine (0.038 mL, 0.270 mmol) were added. After stirring at room temperature overnight, the reaction was filtered and purified by reverse phase HPLC (Gilson, 30 mm×50 mm Gemini Column, NH$_4$OH modifier) to provide the purified desired product. The isolated material was then taken up in ethyl acetate and washed with water. The organic layer was then dried over magnesium sulfate and concentrated to obtain tert-butyl (2-((4-(((3,5-dicyano-4-ethyl-6-(4-methyl-1,4-diazepan-1-yl)pyridin-2-yl)thio)methyl)benzyl)amino)-2-oxoethyl)carbamate (129 mg, 83%) as a light brown gum. LCMS m/z=578 [M+H]$^+$. $^1$H NMR (400 MHz, DMSO-d$_6$) δ ppm 8.28 (t, J=5.83 Hz, 1H), 7.33 (d, J=8.36 Hz, 2H), 7.21 (d, J=7.86 Hz, 2H), 7.01 (t, J=6.08 Hz, 1H), 4.47 (s, 2H), 4.25 (d, J=5.83 Hz, 2H), 3.83-3.95 (m, 4H), 3.55 (d, J=6.08 Hz, 2H), 2.78 (q, J=7.60 Hz, 2H), 2.62-2.70 (m, 2H), 2.24 (s, 3H), 1.88-1.98 (m, 2H), 1.39 (s, 9H), 1.22 (t, J=7.60 Hz, 3H). 2H obscured by DMSO.

Example 79

N-(4-(((3,5-Dicyano-4-ethyl-6-(4-methyl-1,4-diazepan-1-yl)pyridin-2-yl)thio)methyl)benzyl)methanesulfonamide

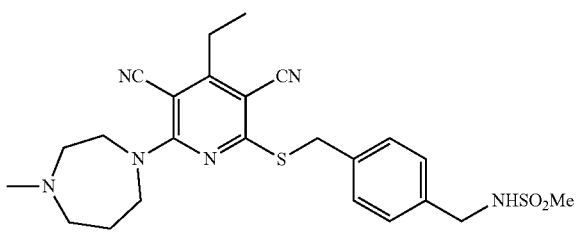

tert-Butyl 4-(((3,5-dicyano-4-ethyl-6-(4-methyl-1,4-diazepan-1-yl)pyridin-2-yl)thio)methyl)benzylcarbamate (synthesis described in example 69, step 2, 100 mg, 0.192 mmol) was dissolved in dichloromethane (2 mL) at 25° C. Trifluoroacetic acid (1.480 mL, 19.21 mmol) was added and the reaction was stirred for 1 hour. The mixture was concentrated and the residue taken up in dichloromethane, washed with saturated aqueous sodium bicarbonate solution, dried then concentrated. The residue was dissolved in DCM and DIEA (0.067 mL, 0.384 mmol) was added followed by dropwise addition of methanesulfonyl chloride (0.015 mL, 0.192 mmol) in 1 mL of DCM at room temperature. After 15 minutes, the solvent and DIEA were evaporated. The residue was dissolved in DCM, washed with sodium bicarbonate solution followed by water and the organics were dried and concentrated. Purification of the residue by silica gel chromatography (eluting with 10-100% (26% ethanol in ethyl acetate containing ammonium hydroxide 1%) in ethyl acetate) provided N-(4-(((3,5-dicyano-4-ethyl-6-(4-methyl-1,4-diazepan-1-yl)pyridin-2-yl)thio)methyl)benzyl)methanesulfonamide (40 mg). LCMS m/z=499.2 [M+H]$^+$. $^1$H NMR (400 MHz, DMSO-d$_6$) δ ppm 7.55 (t, J=6.46 Hz, 1H), 7.36-7.41 (m, 2H), 7.30-7.34 (m, 2H), 4.49 (s, 2H), 4.13-4.15 (d, J=6.34 Hz, 2H), 3.8-3.98 (m, 4H), 2.85 (s, 3H), 2.75-2.8 (m, 2H), 2.64 (d, J=4.56 Hz, 2H), 2.45-2.5 (m, 2H), 2.24 (s, 3H), 1.84-1.99 (m, 2H), 1.22 (t, J=7.60 Hz, 3H).

Example 80

2-Amino-N-(4-(((3,5-dicyano-4-ethyl-6-(4-methyl-1,4-diazepan-1-yl)pyridin-2-yl)thio)methyl)benzyl)acetamide

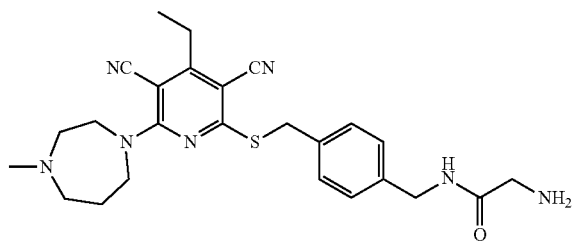 [SMILES: CCc1c(C#N)c(SCc2ccc(CNC(=O)CN)cc2)nc(N2CCCN(C)CC2)c1C#N]

A suspension of tert-butyl (2-((4-(((3,5-dicyano-4-ethyl-6-(4-methyl-1,4-diazepan-1-yl)pyridin-2-yl)thio)methyl)benzyl)amino)-2-oxoethyl)carbamate (synthesis described in example 69, step 2, 105 mg, 0.182 mmol) in a solution of HCl in dioxane (4 M, 2 mL, 8.0 mmol) was stirred at room temperature for 2 hours. The reaction mixture was concentrated. The resulting material was suspended in methanol, and treated with isopropylamine. This mixture was purified by reverse phase HPLC (Gilson, 30 mm×50 mm Gemini Column, NH$_4$OH modifier) to yield 2-amino-N-(4-(((3,5-dicyano-4-ethyl-6-(4-methyl-1,4-diazepan-1-yl)pyridin-2-yl)thio)methyl)benzyl)acetamide (39 mg, 45%) as a sticky pale orange oil. LCMS m/z=478 [M+H]$^+$. $^1$H NMR (400 MHz, DMSO-d$_6$) δ ppm 8.29 (s, 1H), 7.34 (d, J=8.11 Hz, 2H), 7.23 (d, J=8.36 Hz, 2H), 4.47 (s, 2H), 4.27 (d, J=6.08 Hz, 2H), 3.82-3.95 (m, 4H), 3.12 (s, 2H), 2.78 (q, J=7.52 Hz, 2H), 2.60-2.69 (m, 2H), 2.24 (s, 3H), 1.88-1.97 (m, 2H), 1.80 (br. s., 2H), 1.22 (t, J=7.60 Hz, 3H), (2H obscured by DMSO).

Example 81

2-(4-Aminopiperidin-1-yl)-6-(benzylthio-4-ethylpyridine-3,5-dicarbonitrile

Step 1: tert-Butyl (1-(6-chloro-3,5-dicyano-4-ethylpyridin-2-yl)piperidin-4-yl)carbamate

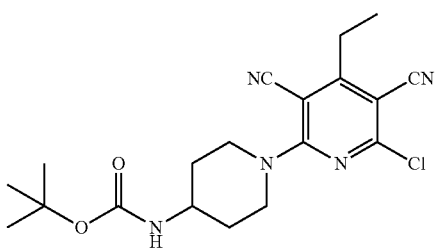 [SMILES: CCc1c(C#N)c(Cl)nc(N2CCC(NC(=O)OC(C)(C)C)CC2)c1C#N]

To a stirred solution of 2,6-dichloro-4-ethylpyridine-3,5-dicarbonitrile (synthesis described in example 3, step 2, 1 g, 4.19 mmol) in tetrahydrofuran (15 mL) was added tert-butyl piperidin-4-ylcarbamate (0.839 g, 4.19 mmol) followed by triethylamine (1.168 mL, 8.38 mmol) at 0° C. The mixture was stirred at room temperature for 16 hours. The reaction mixture was concentrated under vacuum, obtained crude residue was diluted with water (40 mL) and extracted with ethyl acetate (2×100 mL). Combined organic layer was dried over anhydrous $Na_2SO_4$, filtered and the filtrate was concentrated under reduced pressure to give tert-butyl (1-(6-chloro-3,5-dicyano-4-ethylpyridin-2-yl)piperidin-4-yl)carbamate (1 g, 60.1%) as an off-white solid. LCMS m/z=390.3 $[M+H]^+$.

Step 2: tert-Butyl (1-(6-(benzylthio)-3,5-dicyano-4-ethylpyridin-2-yl)piperidin-4-yl)carbamate

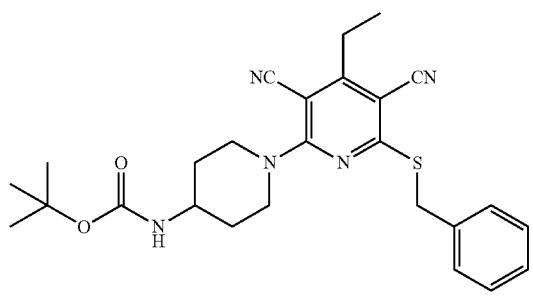 [SMILES: CCc1c(C#N)c(SCc2ccccc2)nc(N2CCC(NC(=O)OC(C)(C)C)CC2)c1C#N]

To a stirred solution of tert-butyl (1-(6-chloro-3,5-dicyano-4-ethylpyridin-2-yl)piperidin-4-yl) carbamate (700 mg, 1.763 mmol) in N,N-dimethylformamide (7 mL) was added phenylmethanethiol (219 mg, 1.763 mmol) followed by potassium carbonate (268 mg, 1.939 mmol) at 0° C. The reaction mixture was stirred at room temperature for 16 hours. The reaction mixture was quenched with cold water (30 mL) and extracted with EtOAc (2×100 mL). The combined organic layers were dried over $Na_2SO_4$, filtered and the filtrate concentrated under vacuum to give crude tert-butyl (1-(6-(benzylthio)-3,5-dicyano-4-ethylpyridin-2-yl)piperidin-4-yl)carbamate (500 mg). LCMS m/z=478.2 $[M+H]^+$ (81% purity by LCMS).

Step 3: 2-(4-Aminopiperidin-1-yl)-6-(benzylthio)-4-ethylpyridine-3,5-dicarbonitrile

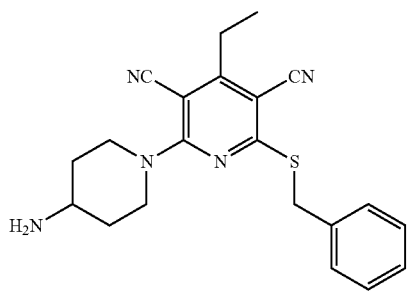 [SMILES: CCc1c(C#N)c(SCc2ccccc2)nc(N2CCC(N)CC2)c1C#N]

To a stirred solution of crude tert-butyl (1-(6-(benzylthio)-3,5-dicyano-4-ethylpyridin-2-yl)piperidin-4-yl)carbamate (430 mg) in 1,4-dioxane (10 mL) was added HCl (4 M in dioxane, 3 mL, 12 mmol) at 0° C. and stirred at room temperature for 4 hours. The reaction mixture was concentrated under vacuum, the crude residue was diluted with water (30 mL) and adjusted to pH 8 with saturated sodium bicarbonate solution (50 mL), then extracted with ethyl acetate (2×50 mL). The combined organic layers were dried over $Na_2SO_4$, filtered and filtrate concentrated under vacuum to give crude compound. The crude compound was purified by silica gel column chromatography (100-200 mesh, eluted by 4-5% methanol in DCM) to give 2-(4-aminopiperidin-1-yl)-6-(benzylthio)-4-ethylpyridine-3,5-dicarbonitrile (170 mg) as a brown gum. LCMS m/z=378.4 $[M+H]^+$. $^1H$ NMR (400 MHz, DMSO-$d_6$) δ ppm 7.38 (d, J=6.8 Hz, 2H), 7.3 (t, J=7.2 Hz, 2H), 7.26 (d, J=6.8 Hz, 1H), 4.5 (s, 2H), 4.4 (d, J=12.8 Hz, 2H), 3.2-3.4 (m, 2H), 2.9-3.0 (m, 1H), 2.7 (q, J=8 Hz, 2H), 1.8-1.9 (m, 2H), 1.2-1.4 (m, 2H), 1.2 (t, J=8 Hz, 3H).

Example 82

4-(((3,5-Dicyano-4-ethyl-6-(4-methyl-1,4-diazepan-1-yl)pyridin-2-yl)thio)methyl)benzyl acetate

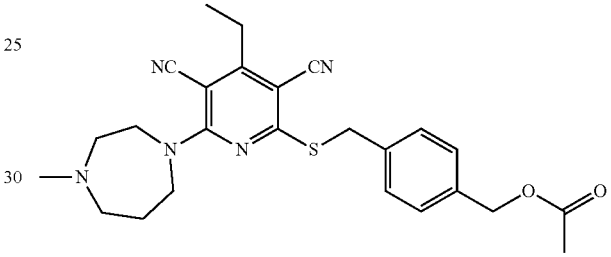

1,4-Phenylenedimethanol (1.0 g, 7.24 mmol) was dissolved in tetrahydrofuran (20 mL) and triethylamine (2.018 mL, 14.48 mmol) was added followed by a solution of acetic anhydride (0.683 mL, 7.24 mmol) in 2 mL of tetrahydrofuran. The reaction was stirred overnight and then heated to 60° C. for 1 hour. The reaction was cooled to 10° C. and methanesulfonyl chloride (0.564 mL, 7.24 mmol) was added along with triethylamine (2.018 mL, 14.48 mmol). The reaction was warmed to 25° C. and stirred for 1 hour and warmed to 60° C. for 30 minutes to afford a crude solution of 4-(((methylsulfonyl)oxy)methyl)benzyl acetate. 4-Ethyl-2-mercapto-6-(4-methyl-1,4-diazepan-1-yl)pyridine-3,5-dicarbonitrile (synthesis described in example 69, step 1, 250 mg, 0.829 mmol) was dissolved in tetrahydrofuran (20 mL) and DIEA (0.435 mL, 2.488 mmol) was added followed by the solution of 4-(((methylsulfonyl)oxy)methyl)benzyl acetate portionwise (in total ca. 1 equivalent) until all the starting thiol disappeared in the LCMS. The reaction was stirred for 1 hour and heated to 60° C. for 30 minutes. The tetrahydrofuran was evaporated and the crude product was dissolved in dichloromethane and loaded on to a 12 g silica column and purified (eluting with ethyl acetate for 7 minutes then a gradient of 0-45% (26% ethanol in ethyl acetate containing 0.1% ammonium hydroxide) in ethyl acetate). Pure product fractions were combined to provide 4-(((3,5-dicyano-4-ethyl-6-(4-methyl-1,4-diazepan-1-yl)pyridin-2-yl)thio)methyl)benzyl acetate (180 mg, 0.378 mmol, 46% yield). LCMS m/z=464.4 $[M+H]^+$. $^1H$ NMR (CHLOROFORM-d) δ ppm 7.33-7.42 (m, 4H), 5.12 (s, 2H), 4.43 (s, 2H), 4.18 (br. s., 2H), 3.97 (t, J=6.2 Hz, 2H), 2.77-3.16 (m, 6H), 2.64 (br. s., 3H), 2.26-2.55 (m, 2H), 2.15 (s, 3H), 1.37 (t, J=7.6 Hz, 3H).

Example 83

2-(4-(((3,5-Dicyano-4-ethyl-6-(4-methyl-1,4-diazepan-1-yl)pyridin-2-yl)thio)methyl)phenyl acetamide

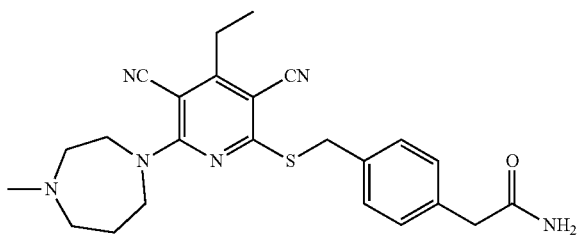 [SMILES: CCc1c(C#N)c(SCc2ccc(CC(N)=O)cc2)nc(N2CCCN(C)CC2)c1C#N]

To a solution of 2-(4-(((3,5-dicyano-4-ethyl-1,4-diazepan-1-yl)pyridin-2-yl)thio)methyl)phenyl)acetic acid (synthesis described in example 72, 51 mg, 0.113 mmol) in N,N-dimethylformamide (0.7 mL) at room temperature was added HATU (43 mg, 0.113 mmol). The reaction mixture was then stirred at room temperature for 30 minutes at which time 0.05 mL of a solution of ammonia (7 M, 0.05 mL, 0.350 mmol) in methanol was added. The reaction mixture was then warmed to 40° C. and stirred at the same temperature for 6 hours. The reaction mixture was allowed to cool and stir at room temperature overnight. The mixture was filtered and purified by reverse phase HPLC (Gilson, 30 mm×50 mm Gemini Column, NH$_4$OH modifier) to obtain 2-(4-(((3,5-dicyano-4-ethyl-6-(4-methyl-1,4-diazepan-1-yl)pyridin-2-yl)thio)methyl)phenyl)acetamide (35 mg, 69% yield) as a white solid. LCMS m/z=449 [M+H]$^+$. $^1$H NMR (400 MHz, CHLOROFORM-d) δ ppm 7.39 (d, J=8.11 Hz, 2H), 7.29 (d, J=8.1 Hz, 2H), 5.43 (br. s., 2H), 4.44 (s, 2H), 3.99-4.06 (m, 2H), 3.96 (t, J=5.96 Hz, 2H), 3.62 (s, 2H), 2.96 (q, J=7.60 Hz, 2H), 2.80 (br. s., 2H), 2.66 (br. s., 2H), 2.44 (s, 3H), 2.11 (br. s., 2H), 1.36 (t, J=7.60 Hz, 3H).

Example 84

2-(4-(((3,5-Dicyano-4-ethyl-6-(4-methyl-1,4-diazepan-1-yl)pyridin-2-yl)thio)methyl)phenyl)-N-methylacetamide

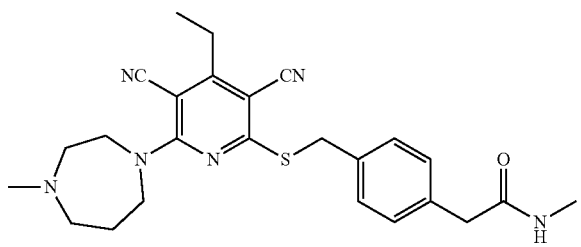

To a solution of 2-(4-(((3,5-dicyano-4-ethyl-6-(4-methyl-1,4-diazepan-1-yl)pyridin-2-yl)thio)methyl)phenyl)acetic acid (synthesis described in example 72, 51 mg, 0.113 mmol) in N,N-dimethylformamide (0.7 mL) at room temperature was added HATU (43 mg, 0.113 mmol). The reaction mixture was then stirred at room temperature for 30 minutes at which time a solution of methylamine (2 M, 0.170 mL, 0.340 mmol) in ethanol was added. The reaction mixture was then warmed to 40° C. and stirred at the same temperature for 6 hours. The reaction mixture was allowed to cool to room temperature and stir overnight. The mixture was filtered and purified by reverse phase HPLC (Gilson, 30 mm×50 mm Gemini Column, NH$_4$OH modifier) to obtain 2-(4-(((3,5-dicyano-4-ethyl-6-(4-methyl-1,4-diazepan-1-yl)pyridin-2-yl)thio)methyl)phenyl)-N-methylacetamide (37 mg, 71% yield) as a white solid. LCMS m/z=463 [M+H]$^+$. $^1$H NMR (400 MHz, DMSO-d$_6$) δ ppm 7.91-7.99 (m, 1H), 7.32 (d, J=8.11 Hz, 2H), 7.21 (d, J=8.11 Hz, 2H), 4.47 (s, 2H), 3.83-3.95 (m, 4H), 3.36 (s, 2H), 2.78 (q, J=7.60 Hz, 2H), 2.62-2.69 (m, 2H), 2.56 (d, J=4.82 Hz, 3H), 2.45-2.49 (m, 2H), 2.23 (s, 3H), 1.87-1.97 (m, 2H), 1.22 (t, J=7.60 Hz, 3H).

Example 85

4-Ethyl-2-((4-(hydroxymethyl)benzyl)thio)-6-(4-methyl-1,4-diazepan-1-yl)pyridine-3,5-dicarbonitrile

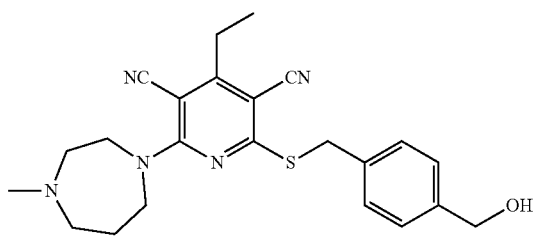 [SMILES: CCc1c(C#N)c(SCc2ccc(CO)cc2)nc(N2CCCN(C)CC2)c1C#N]

4-(((3,5-Dicyano-4-ethyl-6-(4-methyl-1,4-diazepan-1-yl)pyridin-2-yl)thio)methyl)benzyl acetate (synthesis described in example 82, 120 mg, 0.259 mmol) was dissolved in a 1:2 mixture of tetrahydrofuran:ethanol and 1 mL of 1N NaOH was added and the reaction was stirred for 3 hours. The pH of the solution was adjusted to 7 with 1N HCl and the solvent was evaporated. The residue was partitioned between water and DCM. The DCM layer was dried with sodium sulfate, filtered and the solvent evaporated to give 4-ethyl-2-((4-(hydroxymethyl)benzyl)thio)-6-(4-methyl-1,4-diazepan-1-yl)pyridine-3,5-dicarbonitrile (63 mg, 0.149 mmol, 17.9% yield. LCMS m/z=422.4 [M+H]$^+$. $^1$H NMR (400 MHz, DMSO-d$_6$) δ ppm 7.21-7.41 (m, 4H), 5.19 (t, J=5.58 Hz, 1H), 4.45-4.52 (m, 4H), 3.85-3.96 (m, 4H), 3.3-3.35 (m, 2H), 2.75-2.8 (q, J=7.60 Hz, 2H), 2.66-2.65 (br. s., 2H), 2.20-2.30 (m, 3H), 1.86-2.01 (m, 2H), 1.22 (t, J=7.60 Hz, 3H).

Example 86

N-(4-(((3,5-Dicyano-4-ethyl-6-(4-methyl-1,4-diazepan-1-yl)pyridin-2-yl)thio)methyl)benzyl)-2-hydroxyacetamide

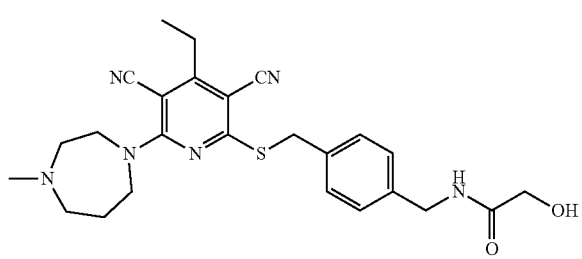 [SMILES: CCc1c(C#N)c(SCc2ccc(CNC(=O)CO)cc2)nc(N2CCCN(C)CC2)c1C#N]

To a solution of 2-hydroxyacetic acid (8 mg, 0.105 mmol) in N,N-dimethylformamide (0.7 mL) at room temperature was added HATU (39 mg, 0.103 mmol). The reaction mixture was then stirred at room temperature for 30 minutes at which time 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (0.042 mL, 0.304 mmol) were added. After 2.5 hours, the mixture was filtered and purified by reverse phase HPLC (Gilson, 30 mm×50 mm Gemini Column, NH$_4$OH modifier) to obtain N-(4-(((3,5-dicyano-4-ethyl-6-(4-methyl-1,4-diazepan-1-yl)pyridin-2-yl)thio)methyl)benzyl)-2-hydroxyacetamide (24 mg, 50% yield) as an off white solid. LCMS m/z=479 [M+H]$^+$. $^1$H NMR (400 MHz, DMSO-d$_6$) δ ppm 8.28 (t, J=6.21 Hz, 1H), 7.33 (d, J=8.11 Hz, 2H), 7.23 (d, J=8.11 Hz, 2H), 5.52 (t, J=5.83 Hz, 1H), 4.47 (s, 2H), 4.27 (d, J=6.34 Hz, 2H), 3.78-3.95 (m, 6H), 2.78 (q, J=7.44 Hz, 2H), 2.61-2.68 (m, 2H), 2.44-2.49 (m, 2H), 2.24 (s, 3H), 1.83-1.97 (m, 2H), 1.22 (t, J=7.60 Hz, 3H).

Example 87

N-(4-(((3,5-Dicyano-4-ethyl-6-(4-methyl-1,4-diazepan-1-yl)pyridin-2-yl)thio) methyl)benzyl)propionamide

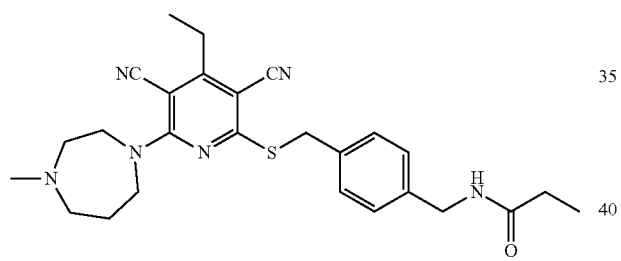

To a solution of 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (42.4 µl, 0.304 mmol) in N,N-dimethylformamide (1.0 mL) at 0° C. was added propionyl chloride (8.80 µl, 0.101 mmol). The reaction mixture was then stirred at 0° C. for 2 hours. After warming to room temperature, the reaction mixture was filtered and purified by reverse phase HPLC (Gilson, 30 mm×50 mm Gemini Column, NH$_4$OH modifier) to give N-(4-(((3,5-dicyano-4-ethyl-6-(4-methyl-1,4-diazepan-1-yl)pyridin-2-yl)thio) methyl)benzyl)propionamide (31 mg, 64% yield) as an off white solid. LCMS m/z=477 [M+H]$^+$. $^1$H NMR (400 MHz, DMSO-d$_6$) δ ppm 8.26 (t, J=5.96 Hz, 1H), 7.34 (d, J=8.11 Hz, 2H), 7.20 (d, J=8.11 Hz, 2H), 4.47 (s, 2H), 4.22 (d, J=5.83 Hz, 2H), 3.80-3.96 (m, 4H), 2.78 (q, J=7.35 Hz, 2H), 2.60-2.68 (m, 2H), 2.43-2.49 (m, 2H), 2.24 (s, 3H), 2.13 (q, J=7.60 Hz, 2H), 1.86-2.00 (m, 2H), 1.18-1.26 (m, 3H), 1.01 (t, J=7.60 Hz, 3H).

Example 88

N-(4-(((3,5-Dicyano-4-ethyl-6-(4-methyl-1,4-diazepan-1-yl)pyridin-2-yl)thio)methyl)benzyl)isobutyramide

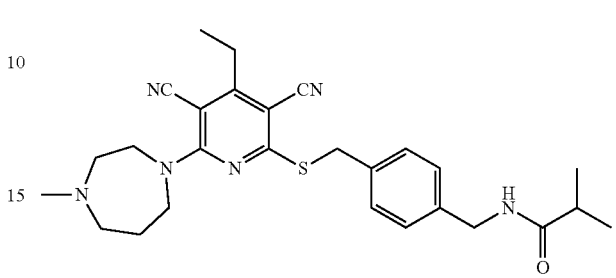

To a solution of 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (42.4 µl, 0.304 mmol) in N,N-dimethylformamide (1.0 mL) at 0° C. was added isobutyryl chloride (10.7 µl, 0.102 mmol). The reaction mixture was then stirred at 0° C. for 2 hours. After allowing to warm to room temperature, the reaction mixture was filtered and purified by reverse phase HPLC (Gilson, 30 mm×50 mm Gemini Column, NH$_4$OH modifier) to provide N-(4-(((3,5-dicyano-4-ethyl-6-(4-methyl-1,4-diazepan-1-yl)pyridin-2-yl)thio) methyl)benzyl)isobutyramide (30 mg, 60% yield) as an off white solid. LCMS m/z=491 [M+H]$^+$. $^1$H NMR (400 MHz, DMSO-d$_6$) δ ppm 8.25 (t, J=5.96 Hz, 1H), 7.30-7.38 (m, J=8.36 Hz, 2H), 7.15-7.23 (m, J=8.36 Hz, 2H), 4.47 (s, 2H), 4.22 (d, J=5.83 Hz, 2H), 3.81-3.98 (m, 4H), 2.78 (q, J=7.60 Hz, 2H), 2.67 (br. s., 2H), 2.34-2.46 (m, 1H), 2.25 (s, 3H), 1.83-2.01 (m, 2H), 1.22 (t, J=7.60 Hz, 3H), 1.02 (d, J=6.84 Hz, 6H). 2H obscured by DMSO.

Example 89

N-(4-(((3,5-Dicyano-4-ethyl-6-(4-methyl-1,4-diazepan-1-yl)pyridin-2-yl)thio)methyl)benzyl)-3-methylbutanamide

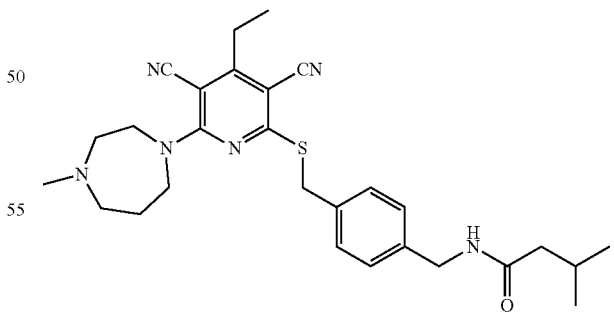

To a solution of 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (42.4 µl, 0.304 mmol) in N,N-dimethylformamide (1.0 mL) at 0° C. was added 3-methylbutanoyl chloride (12.4 µl, 0.102 mmol). The reaction mixture was then stirred at 0° C. for 2 hours. After allowing to warm to room temperature, the reaction mixture was filtered and purified by reverse phase HPLC (Gilson, 30 mm×50 mm Gemini Column, NH$_4$OH modifier) to obtain N-(4-(((3,5-dicyano-4-ethyl-6-(4-methyl-1,4-diazepan-1-yl)pyridin-2-yl)thio)methyl)benzyl)-3-methylbutanamide (32 mg, 63%) as an off white solid. LCMS m/z=505 [M+H]$^+$. $^1$H NMR (400 MHz, DMSO-d$_6$) δ ppm 8.29 (t, J=5.96 Hz, 1H), 7.31-7.36 (m, J=8.11 Hz, 2H), 7.17-7.24 (m, J=8.11 Hz, 2H), 4.47 (s, 2H), 4.23 (d, J=6.08 Hz, 2H), 3.82-3.95 (m, 4H), 2.78 (q, J=7.60 Hz, 2H), 2.61-2.69 (m, 2H), 2.45-2.49 (m, 2H), 2.24 (s, 3H), 1.98-2.03 (m, 3H), 1.89-1.96 (m, 2H), 1.22 (t, J=7.60 Hz, 3H), 0.87 (d, J=6.34 Hz, 6H).

Example 90

4-Ethyl-2-((4-(((2-hydroxyethyl)amino)methyl)benzyl)thio)-6-(4-methyl-1,4-diazepan-1-yl)pyridine-3,5-dicarbonitrile

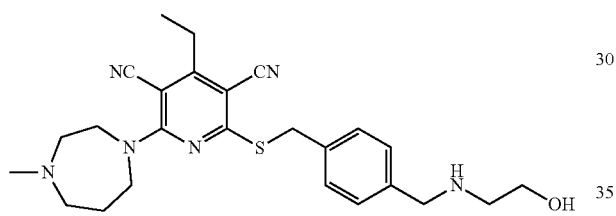

To a solution of 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol), and triethylamine (16.57 µl, 0.119 mmol) in N,N-dimethylformamide (0.4 mL) at 0° C. was added a solution of 2-bromoethanol (8.5 µl, 0.120 mmol) in N,N-dimethylformamide (0.6 mL). After stirring at 0° C. overnight, the reaction was then heated at 40° C. for another 24 hours. An additional 8.5 uL of 2-bromoethanol and 16.6 uL of triethylamine were added to the reaction mixture and it was allowed to stir at 40° C. over the weekend. The reaction mixture was cooled to room temperature, filtered, and purified by reverse phase HPLC (Gilson, 30 mm×50 mm Gemini Column, NH$_4$OH modifier) to provide 4-ethyl-2-((4-(((2-hydroxyethyl)amino)methyl)benzyl)thio)-6-(4-methyl-1,4-diazepan-1-yl)pyridine-3,5-dicarbonitrile (6 mg, 11% yield) as a light brown gum. LCMS m/z=465 [M+H]$^+$. $^1$H NMR (400 MHz, DMSO-d$_6$) δ ppm 7.33 (d, J=8.11 Hz, 2H), 7.28 (d, J=8.11 Hz, 2H), 4.43-4.51 (m, 3H), 3.81-3.95 (m, 4H), 3.67 (s, 2H), 3.45 (q, J=5.66 Hz, 2H), 2.78 (q, J=7.60 Hz, 2H), 2.63-2.68 (m, 2H), 2.53-2.56 (m, 2H), 2.47 (d, J=5.58 Hz, 2H), 2.23 (s, 3H), 2.03 (br. s., 1H), 1.85-1.98 (m, 2H), 1.22 (t, J=7.60 Hz, 3H).

Example 91

N-(4-(((3,5-Dicyano-6-(4-methyl-1,4-diazepan-1-yl)-4-(methylamino)pyridin-2-yl)thio)methyl)benzyl)acetamide Step 1: 2-Amino-6-mercapto-4-(methylthio)pyridine-3,5-dicarbonitrile

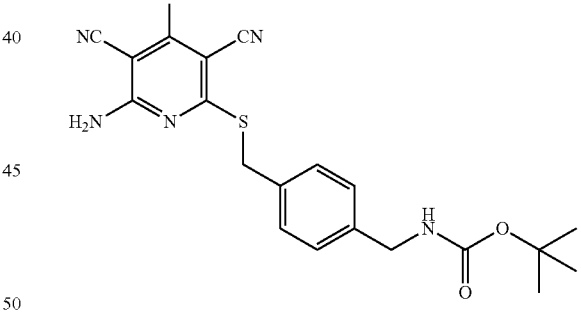

2-(Bis(methylthio)methylene)malononitrile (10 g, 58.7 mmol) and cyanothioacetamide (7.06 g, 70.5 mmol) were added to a round-bottom flask and dissolved in N,N-dimethylformamide (21 mL). Triethylamine (16.37 mL, 117 mmol) was added dropwise at room temperature and the mixture was stirred for 18 hours. The reaction mixture was added to 300 mL of 3N hydrochloric acid. The resulting precipitate was filtered off, washed with water and dried with suction to afford 2-amino-6-mercapto-4-(methylthio)pyridine-3,5-dicarbonitrile (13.5 g, 54.7 mmol, 93% yield). LCMS m/z=222.9 [M+H]$^+$.

Step 2: tert-Butyl 4-(((6-amino-3,5-dicyano-4-(methylthio)pyridin-2-yl)thio)methyl)benzylcarbamate 2-Amino-6-mercapto-4-(methylthio)pyridine-3,5-dicarbonitrile (1 g, 4.50 mmol) and sodium bicarbonate (1 g, 11.90 mmol) were added to a round-bottom flask and suspended in N,N-dimethylformamide (30 mL). The mixture was stirred and tert-butyl 4-(bromomethyl)benzylcarbamate (1.5 g, 5.00 mmol) was added to the mixture slowly. The solution was stirred at room temperature for 1 hour. Aqueous saturated NaHCO$_3$ was added to the mixture and the aqueous phase was extracted with EtOAc (3×). The combined organics were washed with brine, dried over magnesium sulfate, filtered and concentrated to a yellow oil. This residue was triturated with DCM/heptane and filtered off the precipitate to afford, tert-butyl 4-(((6-amino-3,5-dicyano-4-(methylthio)pyridin-2-yl)thio)methyl)benzylcarbamate (1.65 g, 3.74 mmol, 83% yield). LCMS m/z=442.2 [M+H]$^+$.

Step 3: N-(4-(((6-Amino-3,5-dicyano-4-(methylthio) pyridin-2-yl)thio)methyl)benzyl)acetamide

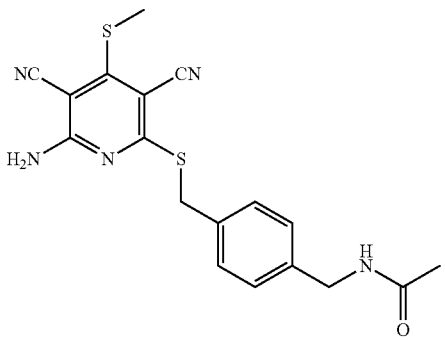 [SMILES: CSc1c(C#N)c(N)nc(SCc2ccc(CNC(C)=O)cc2)c1C#N]

Tert-butyl 4-(((6-amino-3,5-dicyano-4-(methylthio)pyridin-2-yl)thio)methyl)benzylcarbamate (414 mg, 0.938 mmol) and HCl (12 mL, 48.0 mmol; 4 M in 1,4-dioxane) were added to a round-bottom flask and stirred at room temperature for 15 minutes. This mixture was concentrated in-vacuo, suspended in EtOAc/ether, and the solid was filtered off and washed with ether/heptane. This precipitate was suspended in DCM (10 mL) and triethylamine (0.392 mL, 2.81 mmol) and acetic anhydride (0.088 mL, 0.938 mmol) were added. This mixture was stirred at room temperature for 15 minutes and LCMS analysis indicated desired product. The suspension was cooled to 0° C. and the precipitate was collected by filtration. The precipitate was washed with ether/heptane to afford, N-(4-(((6-amino-3,5-dicyano-4-(methylthio)pyridin-2-yl)thio)methyl)benzyl)acetamide (402 mg) of crude material that was carried forward without purification. LCMS m/z=384.2 [M+H]$^+$.

Step 4: N-(4-(((3,5-Dicyano-6-(4-methyl-1,4-diazepan-1-yl)-4-(methylamino)pyridin-2-yl)thio)methyl)benzyl)acetamide

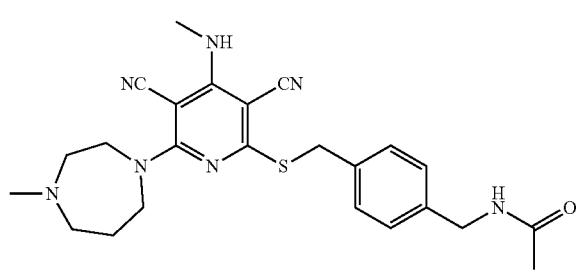 [SMILES: CNc1c(C#N)c(SCc2ccc(CNC(C)=O)cc2)nc(N2CCCN(C)CC2)c1C#N]

N-(4-(((6-Amino-3,5-dicyano-4-(methylthio)pyridin-2-yl)thio)methyl)benzyl)acetamide (290 mg; crude material from the previous step) and copper(II) chloride (200 mg, 1.488 mmol) were added to a round-bottom flask and suspended in acetonitrile (10 mL). The mixture was heated to 40° C. for 5 minutes. Tert-butyl nitrite (0.15 mL, 1.266 mmol) was added to the mixture slowly and the mixture was stirred at 45° C. for 60 minutes. Reaction seemed to stall by LCMS analysis so 0.05 mL of tert-butyl nitrite and 50 mg of CuCl$_2$ were added to the heated mixture and continued to be monitored by LCMS every 20 minutes. Tert-butyl nitrite (0.05 mL) and CuCl$_2$ (50 mg) were added until LCMS analysis indicated near complete consumption of starting material. The mixture was filtered through a small pad of silica gel/Celite® and washed with EtOAc:EtOH 4:1. The filtrate was treated with 1-methyl-1,4-diazepane (0.235 mL, 1.891 mmol) and DIPEA (1 mL). The solution turned blue and was monitored reaction by LCMS until consumption of chloro intermediate. The solution was concentrated and the residue was purified using reverse phase column chromatography (0-50-100% 0.1% aqueous NH$_4$OH in acetonitrile). The desired fractions were pooled and concentrated to afford a residue. Methanamine (4 mL, 51.5 mmol; 40% in H$_2$O) was added to the residue and stirred at 50° C. for 2 hours. Concentrated to a residue, which was then purified on C18 Aq. Column using reverse phase Isco Chromatography (0-40-50-100% 0.1% aq. NH$_4$OH/Acetonitrile) and the desired fractions were pooled and concentrated by stream of nitrogen to afford, N-(4-(((3,5-dicyano-6-(4-methyl-1,4-diazepan-1-yl)-4-(methylamino)pyridin-2-yl)thio)methyl)benzyl)acetamide (24 mg, 0.05 mmol, 6% yield). LCMS m/z=464.3 [M+H]$^+$. $^1$H NMR (400 MHz, CDCl$_3$) δ ppm 8.32 (s, 1H) 7.32 (d, J=8.11 Hz, 2H) 7.16-7.26 (m, 3H) 4.40 (s, 2H) 4.21 (d, J=5.83 Hz, 2H) 3.69-3.85 (m, 4H) 3.13 (s, 3H) 2.58-2.66 (m, 2H) 2.42-2.47 (m, 2H) 2.22 (s, 3H) 1.92 (d, J=4.82 Hz, 2H) 1.85 (s, 3H).

Example 92

2-(((2-Acetyl-1,2,3,4-tetrahydroisoquinolin-6-yl)methyl)thio)-6-(dimethylamino)-4-ethylpyridine-3,5-dicarbonitrile

Step 1: tert-Butyl 6-(hydroxymethyl)-3,4-dihydroisoquinoline-2(1H)-carboxylate

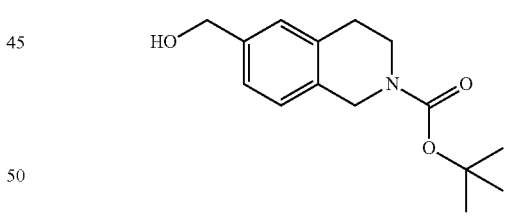

Borane-tetrahydrofuran complex in tetrahydrofuran (1.0 M, 15.87 mL, 15.87 mmol) was added dropwise to a stirred solution of 2-(tert-butoxycarbonyl)-1,2,3,4-tetrahydroisoquinoline-6-carboxylic acid (2.0 g, 7.21 mmol) in tetrahydrofuran (50 mL) at ambient temperature under argon in a sealed flask. After stirring for 3 hours, the mixture was carefully quenched with water and sodium hydrogen carbonate solution was added. The mixture was extracted with ethyl acetate (×2) and the combined extracts were washed with brine, dried (anhydrous Na$_2$SO$_4$) and evaporated to give tert-butyl 6-(hydroxymethyl)-3,4-dihydroisoquinoline-2(1H)-carboxylate (2.0 g). LCMS m/z=207.9 [M+H-isobutylene]$^+$.

Step 2: tert-Butyl 6-(bromomethyl)-3,4-dihydroisoquinoline-2(1H)-carboxylate

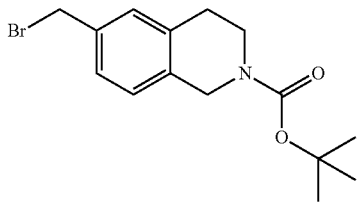 [SMILES: CC(C)(C)OC(=O)N1CCc2cc(CBr)ccc2C1]

A solution of tert-butyl 6-(hydroxymethyl)-3,4-dihydroisoquinoline-2(1H)-carboxylate (2.0 g, 7.59 mmol) in chloroform (25 mL) with N-ethyl-N-isopropylpropan-2-amine (2.045 mL, 11.39 mmol) at 0° C. was treated with dibromotriphenylphosphorane (4.81 g, 11.39 mmol), stirred for 1 hour and then evaporated. Flash chromatography (silica gel 40 g, 0-30% dichloromethane in heptane) gave tert-butyl 6-(bromomethyl)-3,4-dihydroisoquinoline-2(1H)-carboxylate (1.33 g, 4.08 mmol, 54% yield). LCMS m/z=270.0, 272.0 [M+H-isobutylene]$^+$.

Step 3: 2-(Dimethylamino)-4-ethyl-6-mercaptopyridine-3,5-dicarbonitrile

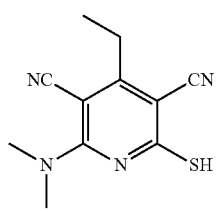 [SMILES: CCc1c(C#N)c(S)nc(N(C)C)c1C#N]

To a suspension of dimethylamine, hydrochloride (9.02 g, 111 mmol) and 2,6-dichloro-4-ethylpyridine-3,5-dicarbonitrile (synthesis described in example 3 step 2, 25 g, 111 mmol) in ethanol (100 mL) at 20° C. was added slowly dropwise a solution of triethylamine (30.8 mL, 221 mmol) in ethanol (20 mL). The reaction mixture was then stirred at 20° C. for 15 minutes before warming to 0° C. The reaction mixture was then stirred at 0° C., gradually warming to room temperature for 1 hour. To the reaction mixture was then added triethylamine (15.41 mL, 111 mmol) and potassium thioacetate (20.21 g, 177 mmol). The heterogeneous reaction mixture was then warmed to 40° C. and stirred at the same temperature while progress was monitored by LCMS. After 4 hours, LCMS indicates little intermediate remained and desired product was present. Therefore the crude reaction was concentrated, then partitioned between 1N aqueous HCl solution and chloroform. The organic layer was washed sequentially with brine, water, dried over sodium sulfate, then filtered to remove the drying agent. The solution was concentrated in vacuo, and the residue was triturated with diethyl ether and dried in the vacuum oven to afford 2-(dimethylamino)-4-ethyl-6-mercaptopyridine-3,5-dicarbonitrile (22.2 g, 96 mmol, 86% yield) as a brown solid. LCMS m/z=233.1 [M+H]$^+$.

Step 4: tert-Butyl 6-(((3,5-dicyano-6-(dimethylamino)-4-ethylpyridin-2-yl)thio)methyl)-3,4-dihydroisoquinoline-2(1H)-carboxylate

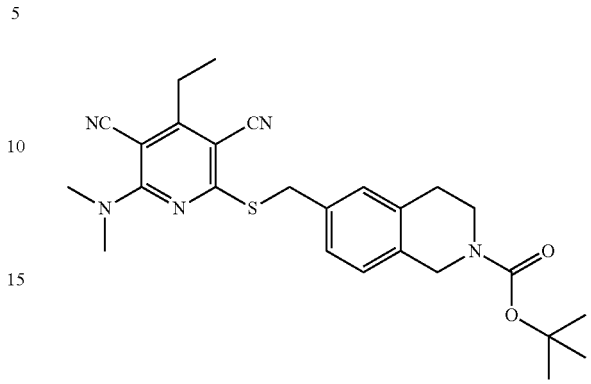

A solution of tert-butyl 6-(bromomethyl)-3,4-dihydroisoquinoline-2(1H)-carboxylate (256 mg, 0.785 mmol) in chloroform (20 mL) and N-ethyl-N-isopropylpropan-2-amine (0.211 mL, 1.177 mmol) was treated with 2-(dimethylamino)-4-ethyl-6-mercaptopyridine-3,5-dicarbonitrile (182 mg, 0.785 mmol), then stirred for 1 hour. As the mercaptopyridine was impure, further aliquots were added to push the reaction to completion. The mixture was applied to silica gel and flash chromatography (silica gel 40 g, 0-30% ethyl acetate in heptane) gave tert-butyl 6-(((3,5-dicyano-6-(dimethylamino)-4-ethylpyridin-2-yl)thio)methyl)-3,4-dihydroisoquinoline-2(1H)-carboxylate (290 mg, 0.607 mmol, 77% yield). LCMS m/z=378.2 [M+H-Boc]$^+$.

Step 5: 2-(Dimethylamino)-4-ethyl-6-(((1,2,3,4-tetrahydroisoquinolin-6-yl)methyl)thio)pyridine-3,5-dicarbonitrile

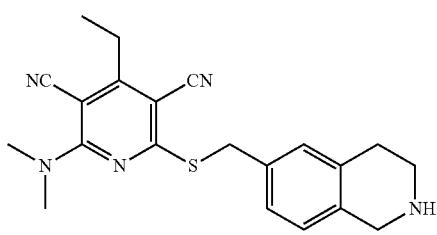 [SMILES: CCc1c(C#N)c(SCc2ccc3c(c2)CCNC3)nc(N(C)C)c1C#N]

A solution of tert-butyl 6-(((3,5-dicyano-6-(dimethylamino)-4-ethylpyridin-2-yl)thio)methyl)-3,4-dihydroisoquinoline-2(1H)-carboxylate (290 mg, 0.607 mmol) in chloroform (10 mL) was treated with trifluoroacetic acid (1.00 mL, 12.98 mmol) and stirred for 1 hour. The mixture was evaporated and azeotroped twice more with chloroform. The residue was taken up in ethanol and potassium carbonate was added with heat to ensure removal of the trifluoroacetic acid. The mixture was cooled, filtered through Celite® and evaporated. The residue was taken up in chloroform and refiltered to remove any residual potassium carbonate. The residue was crystallized from ether, the solid collected, washed with diethyl ether and heptane then dried (50° C., high vac) to give 2-(dimethylamino)-4-ethyl-6-(((1,2,3,4-tetrahydroisoquinolin-6-yl)methyl)thio)pyridine-3,5-dicarbonitrile (60 mg, 0.159 mmol, 26.2% yield). The mother liquors were evaporated to afford a residue (~100 mg), which was taken through to the next step. LCMS m/z=378.2 [M+H]⁺.

Step 6: 2-(((2-Acetyl-1,2,3,4-tetrahydroisoquinolin-6-yl)methyl)thio)-6-(dimethylamino)-4-ethylpyridine-3,5-dicarbonitrile

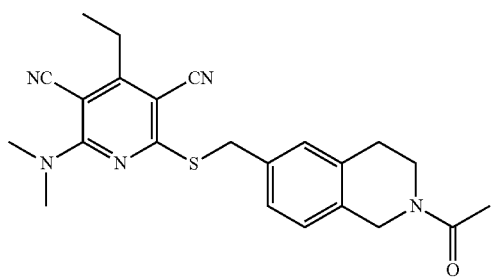 [SMILES: CCc1c(C#N)c(SCc2ccc3c(c2)CCN(C(C)=O)C3)nc(N(C)C)c1C#N]

A solution of 2-(dimethylamino)-4-ethyl-6-(((1,2,3,4-tetrahydroisoquinolin-6-yl)methyl)thio)pyridine-3,5-dicarbonitrile (100 mg, 0.265 mmol) in acetone (10 mL) with potassium carbonate (183 mg, 1.324 mmol) was treated with acetyl chloride (0.023 mL, 0.318 mmol) and stirred for 1 hour. The mixture was evaporated, the residue slurried in chloroform and filtered through Celite® and washed through with chloroform. The solution was evaporated to a gum that was stirred in diethyl ether, the resulting solid was collected, washed with diethyl ether and heptane then dried (50° C., high vac) to give 2-(((2-acetyl-1,2,3,4-tetrahydroisoquinolin-6-yl)methyl)thio)-6-(dimethylamino)-4-ethylpyridine-3,5-dicarbonitrile (60 mg, 0.143 mmol, 54% yield). LCMS m/z=420.3 [M+H]⁺. ¹H NMR (400 MHz, DMSO-d₆) δ ppm 7.20-7.27 (m, 2H), 7.11-7.17 (m, 1H), 4.61 (s, 1H), 4.56 (s, 1H), 4.47 (s, 2H), 3.63 (t, J=6.0 Hz, 2H), 3.35 (s, 6H), 2.84 (t, J=5.8 Hz, 1H), 2.69-2.80 (m, 3H), 2.07 (s, 3H), 1.21 (t, J=7.6 Hz, 3H).

Example 93

2-((4-Cyanobenzyl)thio)-4-ethyl-6-(4-methyl-1,4-diazepan-1-yl)pyridine-3,5-dicarbonitrile

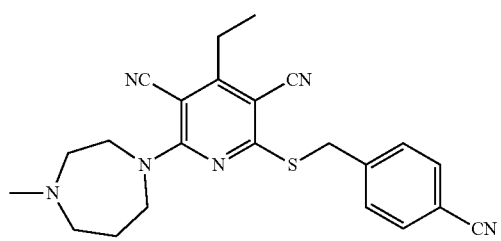 [SMILES: CCc1c(C#N)c(SCc2ccc(C#N)cc2)nc(N2CCCN(C)CC2)c1C#N]

4-Ethyl-2-mercapto-6-(4-methyl-1,4-diazepan-1-yl)pyridine-3,5-dicarbonitrile (synthesis described in example 69, step 1, 200 mg, 0.664 mmol) was dissolved in N,N-dimethylformamide (3 mL) and the solution was cooled to 0° C. Et₃N (0.185 mL, 1.327 mmol) was added followed by dropwise addition of 4-(bromomethyl)benzonitrile (104 mg, 0.531 mmol) dissolved in N,N-dimethylformamide. The reaction was fast and was followed by LCMS until the starting thiol disappeared. The N,N-dimethylformamide was evaporated and the crude residue was taken up in ethyl acetate, washed with water and dried with sodium sulfate. The crude material was purified using a 12 g silica column (eluting with a gradient of 0 to 47% (26% ethanol in ethyl acetate containing 0.1 ammonium hydroxide) in ethyl acetate) to provide 2-((4-cyanobenzyl)thio)-4-ethyl-6-(4-methyl-1,4-diazepan-1-yl)pyridine-3,5-dicarbonitrile (250 mg, 0.600 mmol, 90% yield). LCMS m/z=417.2 [M+H]⁺. ¹H NMR (METHANOL-d₄) δ ppm 7.72-7.77 (m, 2H), 7.61-7.67 (m, 2H), 4.62 (s, 2H), 4.03-4.13 (m, 2H), 3.99 (t, J=6.2 Hz, 2H), 3.28 (m, 4H), 2.96 (q, J=7.6 Hz, 2H), 2.81 (s, 3H), 2.22-2.33 (m, 2H), 1.34 (t, J=7.6 Hz, 3H).

Example 94

2-Amino-N-(1-(6-(benzylthio)-3,5-dicyano-4-ethylpyridin-2-yl)piperidin-4-yl)acetamide, Trifluoroacetic Acid Salt Step 1: Benzyl 4-(2-((tert-butoxycarbonyl)amino)acetamido)piperidine-1-carboxylate

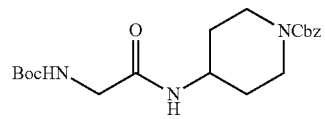 [SMILES: CC(C)(C)OC(=O)NCC(=O)NC1CCN(C(=O)OCc2ccccc2)CC1]

To a solution of 2-((tert-butoxycarbonyl)amino)acetic acid (300 mg, 1.71 mmol) in tetrahydrofuran (10 mL) was added CDI (417 mg, 2.57 mmol). The mixture was stirred for 2 hours at 60° C. and then cooled to room temperature, then benzyl 4-aminopiperidine-1-carboxylate (401 mg, 1.71 mmol) was added and the mixture stirred overnight. The reaction mixture was concentrated under reduced pressure and the residue was diluted with ethyl acetate (20 mL), washed with water (3×20 mL) and then the organic layer was concentrated under reduced pressure to give crude benzyl 4-(2-((tert-butoxycarbonyl)amino) acetamido)piperidine-1-carboxylate (500 mg) as a white solid. LCMS m/z=414.1 [M+Na]⁺.

Step 2: tert-Butyl (2-oxo-2-(piperidin-4-ylamino)ethyl)carbamate

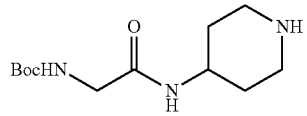

To a solution of benzyl 4-(2-((tert-butoxycarbonyl)amino)acetamido)piperidine-1-carboxylate (500 mg) in methanol (20 mL) was added palladium on carbon (15 wt %, 40.8 mg, 0.383 mmol). The mixture was stirred overnight at room temperature under a hydrogen atmosphere, then filtered and concentrated under reduced pressure to give crude tert-butyl (2-oxo-2-(piperidin-4-ylamino)ethyl)carbamate (300 mg) as a white solid. LCMS m/z=258.1 [M+H]⁺.

Step 3: tert-Butyl (2-((1-(6-chloro-3,5-dicyano-4-ethylpyridin-2-yl)piperidin-4-yl)amino)-2-oxoethyl)carbamate

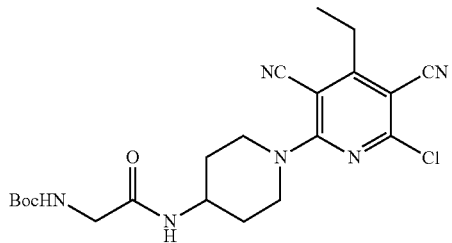 [SMILES: CCc1c(C#N)c(Cl)nc(N2CCC(NC(=O)CNC(=O)OC(C)(C)C)CC2)c1C#N]

To a solution of 2,6-dichloro-4-ethylpyridine-3,5-dicarbonitrile (synthesis described in example 3, step 2, 264 mg, 1.16 mmol) in dichloromethane (5 mL) was added tert-butyl (2-oxo-2-(piperidin-4-ylamino)ethyl)carbamate (300 mg, 1.16 mmol) and triethylamine (0.162 mL, 1.16 mmol). The mixture was stirred for 30 minutes at room temperature and then washed with brine (2×50 mL). The organic layer was concentrated under reduced pressure to give crude tert-butyl (2-((1-(6-chloro-3,5-dicyano-4-ethylpyridin-2-yl)piperidin-4-yl)amino)-2-oxoethyl)carbamate (500 mg) as a yellow solid. LCMS m/z=469.0 [M+Na]+.

Step 4: tert-Butyl (2-((1-(6-(benzylthio)-3,5-dicyano-4-ethylpyridin-2-yl)piperidin-4-yl)amino)-2-oxoethyl)carbamate

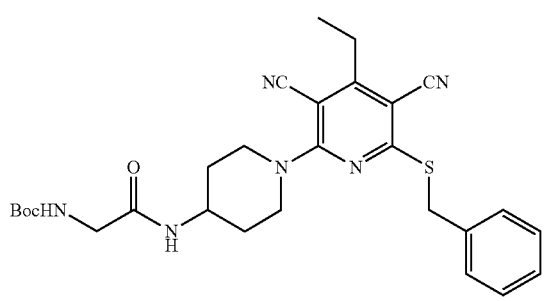 [SMILES: CCc1c(C#N)c(SCc2ccccc2)nc(N2CCC(NC(=O)CNC(=O)OC(C)(C)C)CC2)c1C#N]

To a solution of tert-butyl (2-((1-(6-chloro-3,5-dicyano-4-ethylpyridin-2-yl)piperidin-4-yl)amino)-2-oxoethyl)carbamate (500 mg, 1.1 mmol) in N,N-dimethylformamide (20 mL) was added phenylmethanethiol (139 mg, 1.1 mmol) and cesium carbonate (729 mg, 2.2 mmol). The mixture was stirred overnight at room temperature and then concentrated under reduced pressure. The residue was diluted in ethyl acetate (50 mL) and washed with brine (3×50 mL). The organic layer was concentrated under reduced pressure to give crude tert-butyl (2-((1-(6-(benzylthio)-3,5-dicyano-4-ethylpyridin-2-yl)piperidin-4-yl)amino)-2-oxoethyl)carbamate (500 mg) as a red solid. LCMS m/z=557.1 [M+Na]+.

Step 5: 2-Amino-N-(1-(6-(benzylthio)-3,5-dicyano-4-ethylpyridin-2-yl)piperidin-4-yl) acetamide, Trifluoroacetic Acid Salt

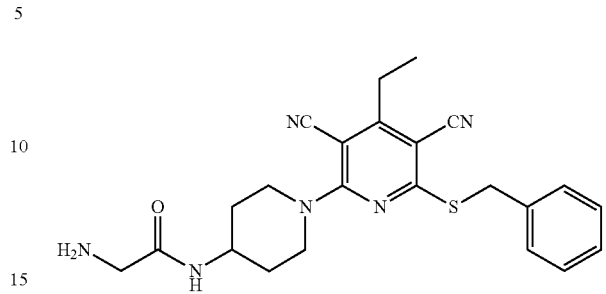

To a solution of crude tert-butyl (2-((1-(6-(benzylthio)-3,5-dicyano-4-ethylpyridin-2-yl)piperidin-4-yl)amino)-2-oxoethyl)carbamate (500 mg) in dichloromethane (20 mL) was added trifluoroacetic acid (4 mL, 51.9 mmol). The mixture was stirred overnight and concentrated under reduced pressure to give the crude product which was further purified by prep-HPLC to give 2-amino-N-(1-(6-(benzylthio)-3,5-dicyano-4-ethylpyridin-2-yl)piperidin-4-yl)acetamide, trifluoroacetic acid salt (120 mg, 0.219 mmol) as a white solid. LCMS m/z=435.1 [M+H]+. $^1$H NMR (400 MHz, DMSO-$d_6$) δ ppm 8.42 (d, J=7.4 Hz, 1H), 8.02 (s, 3H), 7.42 (d, J=7.1 Hz, 2H), 7.32 (dt, J=25.0, 7.1 Hz, 3H), 4.51 (s, 2H), 4.39 (d, J=13.5 Hz, 2H), 3.99 (m, 1H), 3.55 (s, 2H), 3.41 (t, J=11.3 Hz, 2H), 2.78 (q, J=7.5 Hz, 2H), 1.93 (d, J=10.4 Hz, 2H), 1.49 (dd, J=20.6, 10.2 Hz, 2H), 1.22 (t, J=7.6 Hz, 3H).

Example 95

2-Amino-N-(1-(6-(benzylthio)-3,5-dicyano-4-ethylpyridin-2-yl)piperidin-4-yl)-2-methylpropanamide, Formic Acid Salt

Step 1: 3-((tert-Butoxycarbonyl)amino)-3-methylbutanoic acid

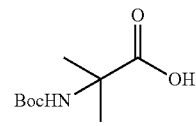

3-Amino-3-methylbutanoic acid (2.06 g, 17.5 mmol) was dissolved in water (40 mL) and (Boc)$_2$O (4.08 mL, 17.5 mmol) and sodium hydroxide (0.703 g, 17.5 mmol) in water (20 mL) was added at 0° C. The mixture was stirred at room temperature for 12 hours. The solution was diluted with sat. NH$_4$Cl solution (200 mL) and ethyl acetate (60 mL), the organic phase was separated, washed with water (30 mL) and brine (30 mL), dried and concentrated under reduced pressure to give the product 3-((tert-butoxycarbonyl)amino)-3-methylbutanoic acid (2.1 g, 9.67 mmol, 55% yield) as a white solid. $^1$H NMR (400 MHz, DMSO-$d_6$) δ ppm 12.17 (s, 1H), 7.03 (s, 1H), 1.37 (s, 9H), 1.30 (s, 6H).

Step 2: Benzyl 4-(2-((tert-butoxycarbonyl)amino)-2-methylpropan amido)piperidine-1-carboxylate

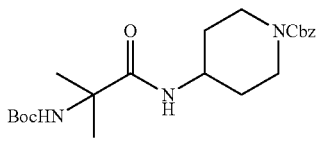 [SMILES: CC(C)(C)OC(=O)NC(C)(C)C(=O)NC1CCN(C(=O)OCc2ccccc2)CC1]

To a solution of 2-((tert-butoxycarbonyl)amino)-2-methylpropanoic acid (300 mg, 1.47 mmol) in N,N-dimethylformamide (5 mL) was added benzyl 4-aminopiperidine-1-carboxylate (346 mg, 1.47 mmol), HATU (842 mg, 2.21 mmol) and DIPEA (0.773 mL, 4.43 mmol). The resulting mixture was stirred overnight at 80° C. then concentrated under reduced pressure to give the crude product. The crude product was added to a silica gel column and was eluted with dichloromethane/methanol to give benzyl 4-(2-((tert-butoxycarbonyl)amino)-2-methylpropanamido)piperidine-1-carboxylate (500 mg, 1.192 mmol, 81% yield) as a white solid. LCMS m/z=442.1 [M+Na]$^+$.

Step 3: tert-Butyl (2-methyl-1-oxo-1-(piperidin-4-ylamino)propan-2-yl)carbamate

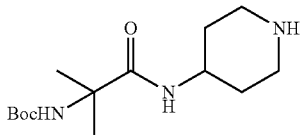 [SMILES: CC(C)(C)OC(=O)NC(C)(C)C(=O)NC1CCNCC1]

To a solution of benzyl 4-(2-((tert-butoxycarbonyl)amino)-2-methylpropanamido)piperidine-1-carboxylate (500 mg, 1.192 mmol) in methanol (20 mL) was added palladium on carbon (15 wt %, 38.1 mg, 0.358 mmol). The mixture was stirred overnight at room temperature under a hydrogen atmosphere, then filtered and concentrated under reduced pressure to give tert-butyl (2-methyl-1-oxo-1-(piperidin-4-ylamino)propan-2-yl)carbamate (340 mg, 1.19 mmol, 100% yield) as gray solid. LCMS m/z=286.1 [M+H]$^+$.

Step 4: tert-Butyl (1-((1-(6-chloro-3,5-dicyano-4-ethylpyridin-2-yl)piperidin-4-yl)amino)-2-methyl-1-oxopropan-2-yl)carbamate

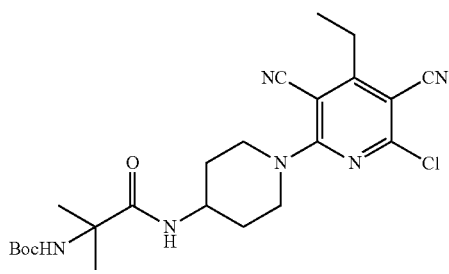 [SMILES: CCc1c(C#N)c(Cl)nc(N2CCC(NC(=O)C(C)(C)NC(=O)OC(C)(C)C)CC2)c1C#N]

To a solution of 2,6-dichloro-4-ethylpyridine-3,5-dicarbonitrile (synthesis described in example 3, step 2, 238 mg, 1.05 mmol) in dichloromethane (20 mL) was added tert-butyl (2-methyl-1-oxo-1-(piperidin-4-ylamino)propan-2-yl)carbamate (300 mg, 1.05 mmol) and triethylamine (0.207 mL, 1.48 mmol) The mixture was stirred for 30 minutes at room temperature and then washed with brine (2×50 mL). Then the organic layer was concentrated under reduced pressure to give crude tert-butyl (1-((1-(6-chloro-3,5-dicyano-4-ethylpyridin-2-yl)piperidin-4-yl)amino)-2-methyl-1-oxopropan-2-yl)carbamate (500 mg) as a yellow solid. LCMS m/z=497.1 [M+Na]$^+$.

Step 5: 2-Amino-N-(1-(6-(benzylthio)-3,5-dicyano-4-ethylpyridin-2-yl)piperidin-4-yl)-2-methylpropanamide, Formic Acid Salt

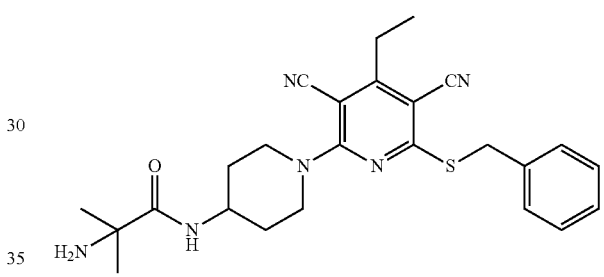

To a solution of tert-butyl (1-((1-(6-chloro-3,5-dicyano-4-ethylpyridin-2-yl)piperidin-4-yl)amino)-2-methyl-1-oxopropan-2-yl)carbamate (500 mg) in N,N-dimethylformamide (20 mL) was added phenylmethanethiol (131 mg, 1.1 mmol) and cesium carbonate (686 mg, 2.1 mmol). The mixture was stirred at room temperature overnight and then concentrated under reduced pressure. The mixture was diluted with ethyl acetate (50 mL) and washed with brine (3×50 mL). The organic layer was concentrated under reduced pressure to give 500 mg of a red oil. This oil was dissolved in dichloromethane (20 mL) was added trifluoroacetic acid (4 mL, 51.9 mmol). The mixture was stirred overnight and then concentrated under reduced pressure to give the crude product which was purified by prep-HPLC to give 2-amino-N-(1-(6-(benzylthio)-3,5-dicyano-4-ethylpyridin-2-yl)piperidin-4-yl)-2-methylpropanamide, formic acid salt (120 mg, 0.23 mmol). LCMS m/z=463.1 [M+H]$^+$. $^1$H NMR (400 MHz, DMSO) δ ppm 8.16 (s, 3H), 8.08 (d, J=7.6 Hz, 1H), 7.42 (d, J=7.3 Hz, 2H), 7.38-7.24 (m, 3H), 4.51 (s, 3H), 4.47 (s, 1H), 4.00 (d, J=6.8 Hz, 1H), 3.32 (t, J=12.0 Hz, 2H), 2.78 (q, J=7.5 Hz, 2H), 1.88 (d, J=10.3 Hz, 2H), 1.54 (dd, J=21.1, 11.4 Hz, 2H), 1.45 (s, 6H), 1.22 (t, J=7.6 Hz, 3H). 2H not observed.

Example 96

3-Amino-N-(4-(((3,5-dicyano-4-ethyl-6-(4-methyl-1,4-diazepan-1-yl)pyridin-2-yl)thio)methyl)benzyl)propanamide Step 1: tert-Butyl (3-((4-(((3,5-dicyano-4-ethyl-6-(4-methyl-1,4-diazepan-1-yl)pyridin-2-yl)thio)methyl)benzyl)amino)-3-oxopropyl)carbamate

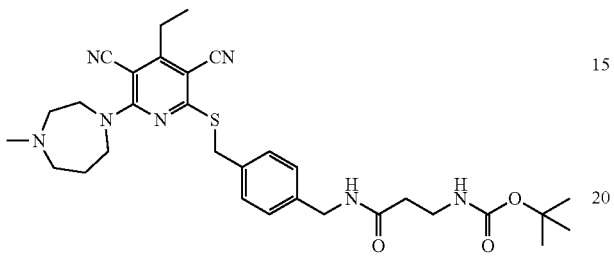

To a solution of 3-((tert-butoxycarbonyl)amino)propanoic acid (32 mg, 0.169 mmol) in N,N-dimethylformamide (1.3 mL) at room temperature was added HATU (102 mg, 0.270 mmol). The reaction mixture was then stirred at room temperature for 30 minutes at which time 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 133 mg, 0.270 mmol) and triethylamine (0.038 mL, 0.270 mmol) were added. The reaction mixture was then allowed to stir at room temperature overnight. The mixture was filtered and purified by reverse phase HPLC (Gilson, 30 mm×50 mm Gemini Column, NH4OH modifier) to obtain tert-butyl (3-((4-(((3,5-dicyano-4-ethyl-6-(4-methyl-1,4-diazepan-1-yl)pyridin-2-yl)thio)methyl)benzyl)amino)-3-oxopropyl)carbamate (60 mg, 67%) as a pale orange gum. LCMS m/z=592 [M+H]$^+$.

Step 2: 3-Amino-N-(4-(((3,5-dicyano-4-ethyl-6-(4-methyl-1,4-diazepan-1-yl)pyridin-2-yl)thio)methyl)benzyl)propanamide

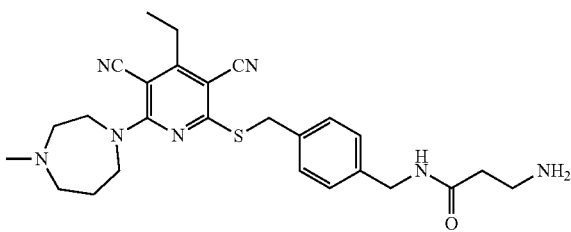 [SMILES: CCc1c(C#N)c(SCc2ccc(CNC(=O)CCN)cc2)nc(N2CCCN(C)CC2)c1C#N]

A suspension of tert-butyl (3-((4-(((3,5-dicyano-4-ethyl-6-(4-methyl-1,4-diazepan-1-yl)pyridin-2-yl)thio)methyl)benzyl)amino)-3-oxopropyl)carbamate (34 mg, 0.057 mmol) in a solution of HCl (4 M, 1.5 mL, 6.0 mmol) in dioxane was stirred at room temperature for 2 hours. The reaction mixture was then concentrated. The resulting material was suspended in MeOH, and free based with isopropylamine. This mixture was purified by reverse phase HPLC (Gilson, 30 mm×50 mm Gemini Column, NH$_4$OH modifier) to yield 3-amino-N-(4-(((3,5-dicyano-4-ethyl-6-(4-methyl-1,4-diazepan-1-yl)pyridin-2-yl)thio)methyl)benzyl)propanamide (20 mg, 70.8%) as a pale orange gum. LCMS m/z=492 [M+H]$^+$. $^1$H NMR (400 MHz, DMSO-d$_6$) δ ppm 8.40 (t, J=5.83 Hz, 1H), 7.30-7.38 (m, J=8.11 Hz, 2H), 7.17-7.25 (m, J=8.11 Hz, 2H), 4.47 (s, 2H), 4.24 (d, J=6.08 Hz, 2H), 3.83-3.94 (m, 4H), 2.71-2.83 (m, 4H), 2.61-2.69 (m, 2H), 2.48 (d, J=5.83 Hz, 2H), 2.24 (s, 3H), 2.21 (t, J=6.59 Hz, 2H), 1.86-1.99 (m, 2H), 1.50 (br. s., 2H), 1.22 (t, J=7.60 Hz, 3H).

Example 97

(S)-2-Amino-N-(4-(((3,5-dicyano-4-ethyl-6-(4-methyl-1,4-diazepan-1-yl)pyridin-2-yl)thio)methyl)benzyl)propanamide Step 1: (S)-tert-Butyl (1-((4-(((3,5-dicyano-4-ethyl-6-(4-methyl-1,4-diazepan-1-yl)pyridin-2-yl)thio)methyl)benzyl)amino)-1-oxopropan-2-yl)carbamate

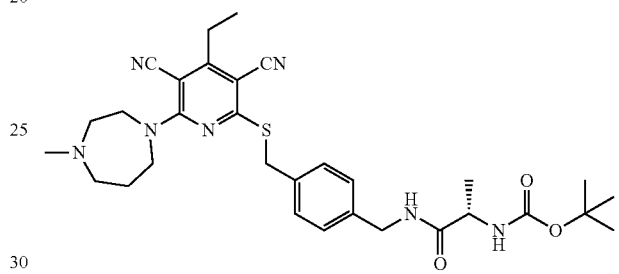

To a solution of (S)-2-((tert-butoxycarbonyl)amino)propanoic acid (20 mg, 0.106 mmol)) in N,N-dimethylformamide (1.3 mL) at 20° C. was added HATU (39 mg, 0.103 mmol). The reaction mixture was allowed to stir at the same temperature for 30 minutes, at which time 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (0.042 mL, 0.304 mmol) were added. After stirring at 20° C. overnight, the reaction mixture was filtered and purified by reverse phase HPLC (Gilson, 30 mm×50 mm Gemini Column, NH$_4$OH modifier) to obtain (S)-tert-butyl (1-((4-(((3,5-dicyano-4-ethyl-6-(4-methyl-1,4-diazepan-1-yl)pyridin-2-1)thio)methyl)benzyl)amino)-1-oxopropan-2-yl)carbamate (52 mg, 87%) as an off white solid. LCMS m/z=592 [M+H]$^+$.

Step 2: (S)-2-Amino-N-(4-(((3,5-dicyano-4-ethyl-6-(4-methyl-1,4-diazepan-1-yl)pyridin-2-yl)thio)methyl)benzyl)propanamide

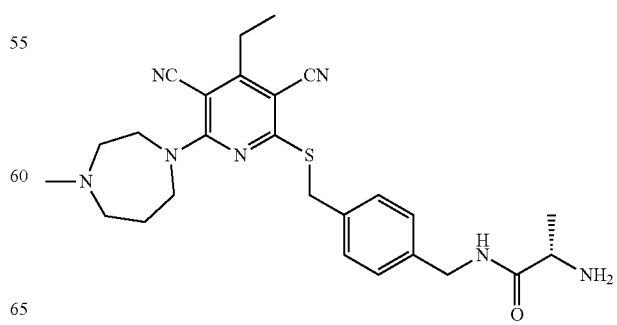

A suspension of (S)-tert-butyl (1-((4-(((3,5-dicyano-4-ethyl-6-(4-methyl-1,4-diazepan-1-yl)pyridin-2-yl)thio)methyl)benzyl)amino)-1-oxopropan-2-yl)carbamate (30 mg, 0.051 mmol) in a solution of HCl (4 M, 1.5 mL, 6.0 mmol) in dioxane was stirred at room temperature for 2 hours. The reaction mixture was then concentrated. The resulting material was suspended in methanol and free based with isopropylamine. This mixture was purified by reverse phase HPLC (Gilson, 30 mm×50 mm Gemini Column, NH$_4$OH modifier) to yield (S)-2-amino-N-(4-(((3,5-dicyano-4-ethyl-6-(4-methyl-1,4-diazepan-1-yl)pyridin-2-1)thio)methyl)benzyl)propanamide (23 mg, 92%) as a white solid. LCMS m/z=492 [M+H]$^+$. $^1$H NMR (400 MHz, DMSO-d$_6$) δ ppm 8.29 (t, J=6.08 Hz, 1H), 7.30-7.38 (m, J=8.11 Hz, 2H), 7.17-7.25 (m, J=8.11 Hz, 2H), 4.47 (s, 2H), 4.25 (d, J=5.83 Hz, 2H), 3.81-3.94 (m, 4H), 3.28 (q, J=6.84 Hz, 1H), 2.78 (q, J=7.44 Hz, 2H), 2.60-2.70 (m, 2H), 2.45-2.49 (m, 2H), 2.24 (s, 3H), 1.89-1.97 (m, 2H), 1.83 (br. s., 2H), 1.22 (t, J=7.60 Hz, 3H), 1.14 (d, J=7.10 Hz, 3H).

Example 98

(R)-2-Amino-N-(4-(((3,5-dicyano-4-ethyl-6-(4-methyl-1,4-diazepan-1-yl)pyridin-2-yl)thio)methyl)benzyl)propanamide Step 1: (R)-tert-Butyl (1-((4-(((3,5-dicyano-4-ethyl-6-(4-methyl-1,4-diazepan-1-yl)pyridin-2-yl)thio)methyl)benzyl)amino)-1-oxopropan-2-yl)carbamate

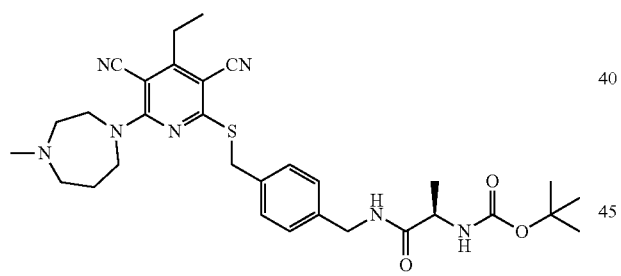

To a solution of (R)-2-((tert-butoxycarbonyl)amino)propanoic acid (20 mg, 0.106 mmol)) in N,N-dimethylformamide (1.3 mL) at 20° C. was added HATU (39 mg, 0.103 mmol). The reaction mixture was allowed to stir at the same temperature for 30 minutes, at which time 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (0.042 mL, 0.304 mmol) were added. The reaction mixture was then stirred at 20° C. overnight. The reaction mixture was filtered and purified by reverse phase HPLC (Gilson, 30 mm×50 mm Gemini Column, NH$_4$OH modifier) to give (R)-tert-butyl (1-((4-(((3,5-dicyano-4-ethyl-6-(4-methyl-1,4-diazepan-1-yl)pyridin-2-1)thio)methyl)benzyl)amino)-1-oxopropan-2-yl)carbamate (54 mg, 90%) as an off white solid. LCMS m/z=592 [M+H]$^+$.

Step 2: (R)-2-Amino-N-(4-(((3,5-dicyano-4-ethyl-6-(4-methyl-1,4-diazepan-1-yl)pyridin-2-yl)thio)methyl)benzyl)propanamide

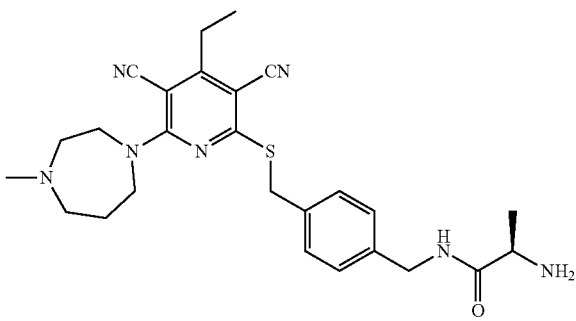 [SMILES: CCc1c(C#N)c(SCc2ccc(CNC(=O)[C@@H](C)N)cc2)nc(N2CCCN(C)CC2)c1C#N]

A suspension of (R)-tert-butyl (1-((4-(((3,5-dicyano-4-ethyl-6-(4-methyl-1,4-diazepan-1-yl)pyridin-2-yl)thio)methyl)benzyl)amino)-1-oxopropan-2-yl)carbamate (34 mg, 0.054 mmol) in a solution of HCl (4 M, 1.5 mL, 6.0 mmol) in dioxane was stirred at room temperature for 2 hours. The reaction mixture was then concentrated. The resulting material was suspended in methanol, and free based with isopropylamine. This mixture was purified by reverse phase HPLC (Gilson, 30 mm×50 mm Gemini Column, NH$_4$OH modifier) to yield (R)-2-amino-N-(4-(((3,5-dicyano-4-ethyl-6-(4-methyl-1,4-diazepan-1-yl)pyridin-2-1)thio)methyl)benzyl)propanamide (19 mg, 72%) as a white solid. LCMS m/z=492 [M+H]$^+$. $^1$H NMR (400 MHz, DMSO-d$_6$) δ ppm 8.29 (t, J=5.96 Hz, 1H), 7.30-7.38 (m, J=8.11 Hz, 2H), 7.17-7.25 (m, J=8.11 Hz, 2H), 4.47 (s, 2H), 4.25 (d, J=5.83 Hz, 2H), 3.82-3.94 (m, 4H), 3.28 (q, J=6.84 Hz, 1H), 2.78 (q, J=7.60 Hz, 2H), 2.60-2.69 (m, 2H), 2.45-2.48 (m, 2H), 2.24 (s, 3H), 1.89-1.99 (m, 2H), 1.83 (br. s., 2H), 1.22 (t, J=7.60 Hz, 3H), 1.14 (d, J=6.84 Hz, 3H).

Example 99

1-(4-(((3,5-Dicyano-4-ethyl-6-(4-methyl-1,4-diazepan-1-yl)pyridin-2-yl)thio)methyl)benzyl)-3-ethylurea

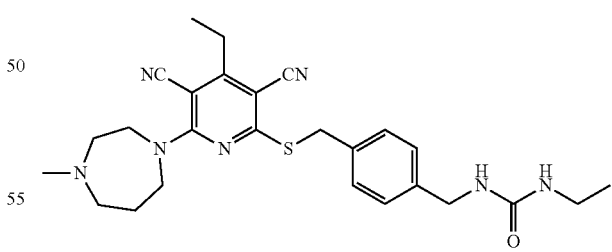

To a solution of 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (0.028 mL, 0.203 mmol) in N,N-dimethylformamide (1.0 mL) at room temperature was added ethyl isocyanate (8.02 μl, 0.101 mmol). The reaction mixture was then stirred at room temperature for 2 hours. The reaction mixture was diluted with methanol, filtered, and purified by reverse phase HPLC (Gilson, 30 mm×50 mm Gemini Column, NH₄OH modifier) to provide 1-(4-(((3,5-dicyano-4-ethyl-6-(4-methyl-1,4-diazepan-1-yl)pyridin-2-yl)thio)methyl)benzyl)-3-ethylurea (27 mg, 54%) as an off white solid. LCMS m/z=492 [M+H]⁺. ¹H NMR (400 MHz, DMSO-d₆) δ ppm 7.30-7.37 (m, J=8.11 Hz, 2H), 7.16-7.23 (m, J=8.11 Hz, 2H), 6.28 (t, J=5.96 Hz, 1H), 5.88 (t, J=5.70 Hz, 1H), 4.47 (s, 2H), 4.16 (d, J=6.08 Hz, 2H), 3.82-3.94 (m, 4H), 3.02 (dq, J=5.70, 7.14 Hz, 2H), 2.78 (q, J=7.60 Hz, 2H), 2.60-2.69 (m, 2H), 2.44-2.49 (m, 2H), 2.24 (s, 3H), 1.89-1.97 (m, 2H), 1.22 (t, J=7.60 Hz, 3H), 0.99 (t, J=7.10 Hz, 3H).

Example 100

1-(4-(((3,5-Dicyano-4-ethyl-6-(4-methyl-1,4-diazepan-1-yl)pyridin-2-yl)thio)methyl)benzyl)-3-phenylurea 1-(4-(((3,5-Dicyano-4-ethyl-6-(4-methyl-1,4-diazepan-1-yl)pyridin-2-yl)thio)methyl)benzyl)-3-phenylurea

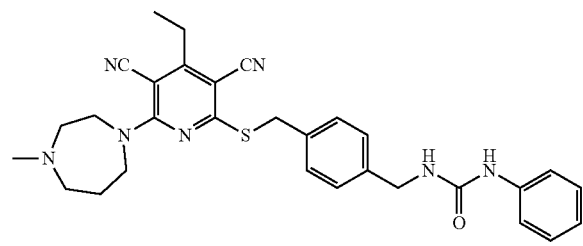 [SMILES: CCc1c(C#N)c(SCc2ccc(CNC(=O)Nc3ccccc3)cc2)nc(N2CCCN(C)CC2)c1C#N]

To a solution of 2-((4-(aminomethyl)benzyl)thio)-4-ethyl-6-(4-methyl-1,4-diazepan-1-yl)pyridine-3,5-dicarbonitrile, 2 hydrochloride (synthesis described in example 71, 50 mg, 0.101 mmol) and triethylamine (0.028 mL, 0.203 mmol) in N,N-dimethylformamide (1.0 mL) at room temperature was added phenyl isocyanate (0.011 mL, 0.101 mmol). The reaction mixture was then stirred at room temperature for 2 hours. The reaction mixture was diluted with methanol, filtered, and purified by reverse phase HPLC (Gilson, 30 mm×50 mm Gemini Column, NH₄OH modifier) to give 1-(4-(((3,5-dicyano-4-ethyl-6-(4-methyl-1,4-diazepan-1-yl)pyridin-2-yl)thio)methyl)benzyl)-3-phenylurea (32 mg, 59%) as an off white solid. LCMS m/z=540 [M+H]⁺. ¹H NMR (400 MHz, DMSO-d₆) δ ppm 8.56 (s, 1H), 7.33-7.43 (m, 4H), 7.15-7.30 (m, 4H), 6.85-6.93 (m, 1H), 6.61 (t, J=5.96 Hz, 1H), 4.48 (s, 2H), 4.27 (d, J=6.08 Hz, 2H), 3.80-3.94 (m, 4H), 2.77 (q, J=7.60 Hz, 2H), 2.59-2.68 (m, 2H), 2.44-2.49 (m, 2H), 2.22 (s, 3H), 1.85-1.96 (m, 2H), 1.22 (t, J=7.60 Hz, 3H).

Example 101

N-(4-(((3,5-Dicyano-6-(4-methyl-1,4-diazepan-1-yl)-4-(methylthio)pyridin-2-yl)thio)methyl)benzyl)acetamide

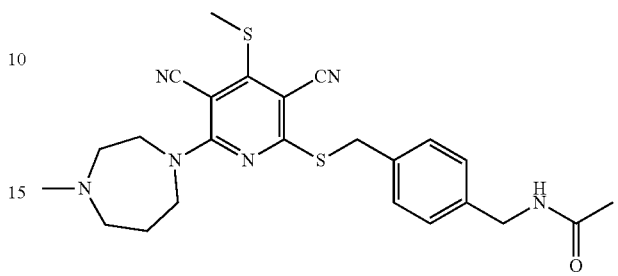

N-(4-(((6-Amino-3,5-dicyano-4-(methylthio)pyridin-2-yl)thio)methyl)benzyl)acetamide (synthesis described in example 91, step 3, 940 mg, 2.451 mmol) and copper(II) chloride (515 mg, 3.83 mmol) were added to a round-bottom flask and suspended in acetonitrile (100 mL). The mixture was heated to 40° C. for 5 minutes. Tert-butyl nitrite (0.5 mL, 4.22 mmol) in acetonitrile (20 mL) was added to the mixture slowly and the mixture was stirred at 50° C. for 60 minutes. LCMS analysis indicated that the reaction seemed to stall; tert-butyl nitrite (0.05 mL) and CuCl₂ (50 mg) were added to the heated mixture and continued to be monitored by LCMS every 20 min. Tert-butyl nitrite (0.05 mL) and CuCl₂ (50 mg) were added until LCMS analysis indicated near complete consumption of starting material (~10 iterations). The mixture was filtered through a small pad of silica gel/Celite® and washed with EtOAc:EtOH 4:1. The filtrate was treated with 1-methyl-1,4-diazepane (0.761 mL, 6.13 mmol) and DIPEA (1 mL). The solution turned blue and was monitored reaction by LCMS until consumption of chloro intermediate. The solution was concentrated and the residue was purified by reverse phase column chromatography (0-50-100% of 0.1% aqueous NH₄OH in acetonitrile). The desired fractions were pooled, concentrated and then lyophilized to afford, N-(4-(((3,5-dicyano-6-(4-methyl-1,4-diazepan-1-yl)-4-(methylthio)pyridin-2-yl)thio)methyl)benzyl)acetamide (365 mg, 0.759 mmol, 31.0% yield). LCMS m/z=481.3 [M+H]⁺. ¹H NMR (400 MHz, DMSO-d₆) δ ppm 8.33 (t, J=5.83 Hz, 1H) 7.34 (d, J=8.11 Hz, 2H) 7.21 (d, J=8.11 Hz, 2H) 4.47 (s, 2H) 4.21 (d, J=5.83 Hz, 2H) 3.76-3.90 (m, 4H) 2.76 (s, 3H) 2.64 (br. s., 2H) 2.42-2.49 (m, 2H) 2.23 (s, 3H) 1.94 (d, J=4.82 Hz, 2H) 1.85 (s, 3H).

Example 102

(E)-3-(4-(((3,5-Dicyano-6-(dimethylamino)-4-ethylpyridin-2-yl)thio)methyl)phenyl)acrylic acid, Trifluoroacetic Acid Salt Step 1: (E)-tert-Butyl 3-(4-(hydroxymethyl)phenyl)acrylate

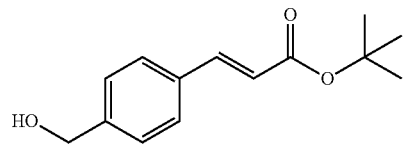 [SMILES: CC(C)(C)OC(=O)/C=C/c1ccc(CO)cc1]

Into a 100 mL RBF were added (4-bromophenyl)methanol (2.12 g, 11.33 mmol), triphenylphosphine (0.268 g, 1.020 mmol), palladium(II) acetate (0.102 g, 0.453 mmol), triethylamine (20 mL, 143 mmol) and tert-butyl acrylate (4.98 mL, 34.0 mmol) in that order. The reaction was then heated at 90° C. After 4 hours the reaction was checked with LCMS and observed no starting material and product. The reaction was let cooled to room temperature then filtered over a bed of Celite® then concentrated by reduced pressure and then loaded onto a double stacked 25 g then 10 g Biotage Ultra column conditioned with hexane then ran 2 minutes at 100% hexane then a gradient of 0 to 50% EtOAc in hexane over 30 minutes to isolated (E)-tert-butyl 3-(4-(hydroxymethyl)phenyl)acrylate (2.29 g, 9.77 mmol, 86% yield) as a dark amber color oil. LCMS m/z=179.0 [M+H-isobutylene]$^+$.

Step 2: (E)-tert-Butyl 3-(4-(chloromethyl)phenyl)acrylate

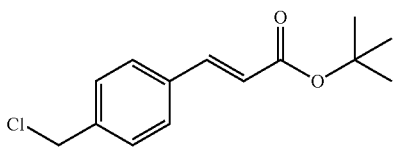 [SMILES: CC(C)(C)OC(=O)/C=C/c1ccc(CCl)cc1]

To (E)-tert-butyl 3-(4-(hydroxymethyl)phenyl)acrylate (502 mg, 2.143 mmol) in dichloromethane (20 mL) was cooled in ice bath then added thionyl chloride (0.172 mL, 2.357 mmol) then a diluted solution of DIEA (0.412 mL, 2.357 mmol) in DCM (5 mL) was slowly added. The reaction was let stir at room temp for 1 hour. The reaction was concentrated by reduced pressure then loaded directly onto a 10 g Biotage Ultra column conditioned with hexane then ran 2 minutes at 100% hexane then a gradient of 0 to 25% EtOAc in hexane over 28 minutes to isolated (E)-tert-butyl 3-(4-(chloromethyl)phenyl)acrylate (416 mg, 1.646 mmol, 77% yield) as an oil which solidified upon standing. LCMS m/z=197.0 [M+H-isobutylene]$^+$.

Step 3: (E)-tert-Butyl 3-(4-(((3,5-dicyano-6-(dimethylamino)-4-ethylpyridin-2-yl)thio)methyl)phenyl)acrylate

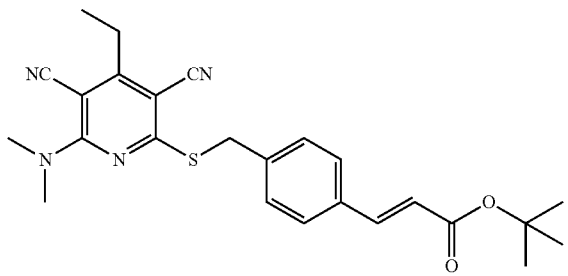 [SMILES: CCc1c(C#N)c(SCc2ccc(/C=C/C(=O)OC(C)(C)C)cc2)nc(N(C)C)c1C#N]

To 2-chloro-6-(dimethylamino)-4-ethylpyridine-3,5-dicarbonitrile (synthesis described in example 3, step 3, 105 mg, 0.447 mmol) in N,N-dimethylformamide (2.5 mL) was added potassium thioacetate (66.4 mg, 0.582 mmol) and triethylamine (0.187 mL, 1.342 mmol). The reaction was then heated at 50° C. for 0.5 hour. (E)-tert-butyl 3-(4-(chloromethyl)phenyl)acrylate (113 mg, 0.447 mmol) was then added and continue heating at 50° C. for 1 hour. The reaction was cool to room temperature then water (10 mL) was added and a solid formed. The solid was isolated by filtration then dissolved in 1.5 mL of N,N-dimethylformamide then loaded on to a 25 g Biotage Ultra column conditioned with hexane then ran 2 minutes at 100% hexane then a gradient of 0 to 35% EtOAc in hexane 28 minutes to give the desired product fractions. The fractions with the desired product were combined then concentrated by reduced pressure to give (E)-tert-butyl 3-(4-(((3,5-dicyano-6-(dimethylamino)-4-ethylpyridin-2-yl)thio)methyl)phenyl)acrylate (168 mg, 0.375 mmol, 84% yield) as an oil. LCMS m/z=449.3 [M+H]$^+$.

Step 4: (E)-3-(4-(((3,5-Dicyano-6-(dimethylamino)-4-ethylpyridin-2-yl)thio)methyl)phenyl)acrylic acid, Trifluoroacetic Acid Salt

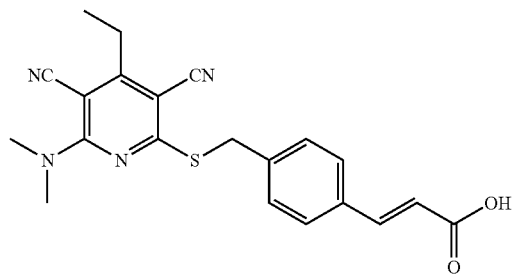 [SMILES: CCc1c(C#N)c(SCc2ccc(/C=C/C(=O)O)cc2)nc(N(C)C)c1C#N]

To (E)-tert-butyl 3-(4-(((3,5-dicyano-6-(dimethylamino)-4-ethylpyridin-2-yl)thio)methyl)phenyl)acrylate (46 mg, 0.103 mmol) was added a premixed solution of trifluoroacetic acid (200 µl, 2.60 mmol) in dichloromethane (1.8 mL). The solution was then allowed to stir at room temperature. After 4 hours no starting material was observed. The reaction was then concentrated by reduced pressure to give a solid, then acetonitrile (3 mL) was added to suspend the solid. The solid was then isolated by filtration to give (E)-3-(4-(((3,5-dicyano-6-(dimethylamino)-4-ethylpyridin-2-yl)thio)methyl)phenyl)acrylic acid, trifluoroacetic acid salt (28 mg, 0.055 mmol, 53.9% yield) as a white solid. LCMS m/z=393.2 [M+H]$^+$. $^1$H NMR (400 MHz, DMSO-d$_6$) δ ppm 12.43 (b, 1H), 7.65 (d, J=8.11 Hz, 2H), 7.56 (d, J=15.97 Hz, 1H), 7.45 (d, J=8.11 Hz, 2H), 6.51 (d, J=15.97 Hz, 1H), 4.55 (s, 2H), 3.32 (s, 6H), 2.77 (q, J=7.60 Hz, 2H), 1.21 (t, J=7.60 Hz, 3H)

Example 103

N-(4-(((3,5-Dicyano-4-ethyl-6-((2-hydroxyethyl)(methyl)amino)pyridin-2-yl)thio)methyl)benzyl)acetamide

Step 1: 2-Chloro-4-ethyl-6-((2-hydroxyethyl)(methyl)amino)pyridine-3,5-dicarbonitrile

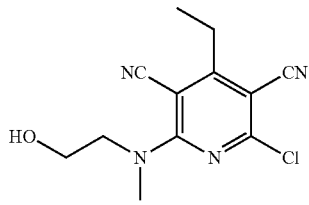 [SMILES: CCc1c(C#N)c(Cl)nc(N(C)CCO)c1C#N]

To a solution of 2,6-dichloro-4-ethylpyridine-3,5-dicarbonitrile (synthesis described in example 3, step 2, 2.25 g, 9.99 mmol) in dichloromethane (30 mL) was added triethylamine (4.18 mL, 30 mmol) and then 2-(methylamino)ethanol (750 mg, 9.99 mmol) at 0° C. The mixture was warmed to 25° C. and stirred for 16 hours. The mixture was poured to water and extracted with dichloromethane (2×25 mL). The organic phase was concentrated under reduced pressure and the residue was purified by column chromatography (eluted by dichloromethane:methanol 100:1) to give 2-chloro-4-ethyl-6-((2-hydroxyethyl)(methyl)amino)pyridine-3,5-dicarbonitrile (2.3 g, 8.69 mmol, 87% yield). LCMS m/z=265.0 [M+H]$^+$.

Step 2: 4-(Acetamidomethyl)benzyl acetate

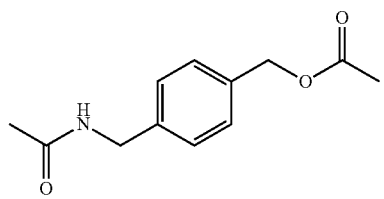 [SMILES: CC(=O)NCc1ccc(COC(C)=O)cc1]

To a solution of (4-(aminomethyl)phenyl)methanol (19 g, 139 mmol) in tetrahydrofuran (150 mL) was added triethylamine (57.9 mL, 416 mmol) and then acetyl chloride (21.6 mL, 305 mmol) dropwise at 0° C. The mixture was then warmed to 25° C. and stirred for 16 hours. The mixture was concentrated under reduced pressure and the residue was partitioned between water (40 mL) and ethyl acetate (60 mL). The organic phase was separated and concentrated to give crude 4-(acetamidomethyl)benzyl acetate (26 g). LCMS m/z=443.1 [2M+H]$^+$, 222.1 [M+H]$^+$ (minor).

Step 3: N-(4-(Hydroxymethyl)benzyl)acetamide

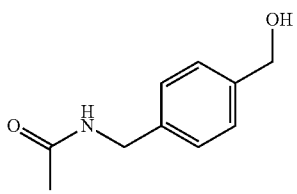

To a solution of 4-(acetamidomethyl)benzyl acetate (26 g, 118 mmol) in tetrahydrofuran (80 mL) was added water (40 mL) and lithium hydroxide (8.44 g, 353 mmol) at 0° C. The mixture was stirred at 25° C. for 16 hours. The mixture was evaporated to remove tetrahydrofuran and the residue was extracted with ethyl acetate (2×50 mL). The organic phase was concentrated and washed with ethyl acetate to give N-(4-(hydroxymethyl)benzyl)acetamide (8.7 g, 48.5 mmol, 41% yield) as a light yellow solid. $^1$H NMR (400 MHz, DMSO-d$_6$) δ ppm 8.33 (brs, 1H), 7.26 (d, J=8 Hz, 2H), 7.20 (d, J=8 Hz, 2H), 5.16 (t, J=6 Hz, 1H), 4.47 (d, J=8 Hz, 2H), 4.22 (d, J=4 Hz, 2H), 1.87 (s, 3H).

Step 4: N-(4-((3,5-Dicyano-4-ethyl-6-((2-hydroxyethyl)(methyl)amino)pyridin-2-ylthio)methyl)benzyl)acetamide

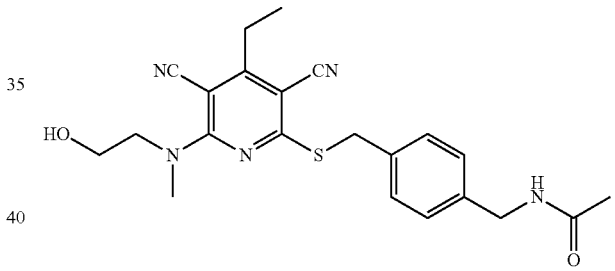

To a suspension of N-(4-(hydroxymethyl)benzyl)acetamide (930 mg, 5.19 mmol) in dichloromethane (30 mL) was added carbon tetrabromide (1893 mg, 5.71 mmol) and then triphenylphosphine (1497 mg, 5.71 mmol) at 0° C. The mixture was warmed to 25° C. and stirred for 16 hours. The mixture was poured to water (20 mL). The organic phase was separated and concentrated under reduced pressure to give the crude product which was purified by column chromatography then washed with petroleum ether:ethyl acetate (3:1, 50 mL) to give crude N-(4-(bromomethyl)benzyl)acetamide (1.4 g). To a solution of 2-chloro-4-ethyl-6-((2-hydroxyethyl)(methyl)amino)pyridine-3,5-dicarbonitrile (264 mg, 0.997 mmol) in N,N-dimethylformamide (15 mL) was added potassium ethanethioate (171 mg, 1.496 mmol) and then potassium carbonate (414 mg, 2.99 mmol). The mixture was stirred at 25° C. for 16 hours, then potassium carbonate (474 mg, 1.144 mmol) and crude N-(4-(bromomethyl)benzyl)acetamide (435 mg) were added. The mixture was stirred at 25° C. for 16 hours. The mixture was poured into water (15 mL) and extracted with ethyl acetate (2×25 mL). The organic phase was concentrated under reduced pressure to give the crude product which was purified by column chromatography (dichloromethane:methanol 30:1) and then recrystallized from methanol to give N-(4-(((3,5-dicyano-4-ethyl-6-((2-hydroxyethyl)(methyl)amino)pyridin-2-yl)thio)methyl)benzyl)acetamide (300 mg, 0.708 mmol). LCMS m/z=424.3 [M+H]$^+$. $^1$H NMR (400 MHz, DMSO-d$_6$) δ ppm 8.33 (brs, 1H), 7.35 (d, J=8 Hz, 2H), 7.21 (d, J=8 Hz, 2H), 4.88 (t, J=6 Hz, 1H), 4.47 (s, 2H), 4.22 (d, J=4 Hz, 2H), 3.86 (t, J=4 Hz, 2H), 3.64 (d, J=4 Hz, 2H), 3.41 (s, 3H), 2.77 (m, 2H), 1.86 (s, 3H), 1.21 (t, J=8 Hz, 3H).

Example 104

4-(((3,5-Dicyano-4-ethyl-6-(4-methyl-1,4-diazepan-1-yl)pyridin-2-yl)thio)methyl)-N-methylbenzenesulfonamide

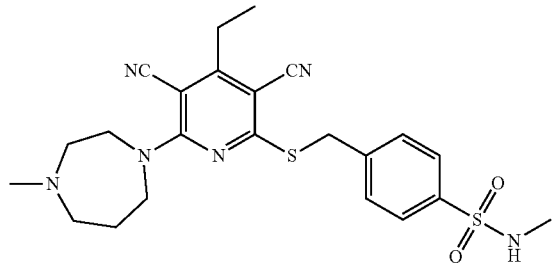

To a solution of N,4-dimethylbenzenesulfonamide (1 g, 5.40 mmol) in carbon tetrachloride (10 mL) was added N-bromosuccinimide (0.961 g, 5.40 mmol) and benzoyl peroxide (0.065 g, 0.270 mmol). The vial was capped and heated at 110° C. for 5 hours. The reaction was cooled to room temperature to afford a crude solution of 4-(bromomethyl)-N-methylbenzenesulfonamide. The crude solution of 4-(bromomethyl)-N-methylbenzenesulfonamide was then added portionwise to a separately prepared solution of 4-ethyl-2-mercapto-6-(4-methyl-1,4-diazepan-1-yl)pyridine-3,5-dicarbonitrile (synthesis described in example 69, step 1, 180 mg, 0.597 mmol) and DIEA (209 µl, 1.194 mmol) in chloroform until all of the starting thiol had been consumed as determined by LCMS analysis. The reaction was stirred for 1 hour, concentrated, and the remaining crude mixture partitioned between ethyl acetate and water. The layers were separated, and the organic layer dried and concentrated under reduced pressure. The crude product was purified by silica gel chromatography (12 g silica gel column, eluting with 100% ethyl acetate then a 10-70% gradient of (26% ethanol/ethyl acetate containing 0.1% ammonium hydroxide) in ethyl acetate to provide 4-(((3,5-dicyano-4-ethyl-6-(4-methyl-1,4-diazepan-1-yl)pyridin-2-yl)thio)methyl)-N-methylbenzenesulfonamide (60 mg, 20% yield) LCMS m/z=485.6 [M+H]$^+$. $^1$H NMR (400 MHz, METHANOL-d$_4$) δ ppm 7.82 (d, J=8.4 Hz, 2H), 7.55 (d, J=8.4 Hz, 2H), 4.61 (s, 2H), 3.84-4.02 (m, 4H), 2.93 (q, J=7.6 Hz, 2H), 2.68-2.75 (m, 2H), 2.58-2.65 (m, 2H), 2.53 (s, 3H), 2.36 (s, 3H), 1.97-2.11 (m, 2H), 1.33 (t, J=7.60 Hz, 3H).

Example 105

N-(4-(((3,5-Dicyano-4-ethoxy-6-(4-methyl-1,4-diazepan-1-yl)pyridin-2-yl)thio)methyl)benzyl)acetamide Step 1: 2-(Diethoxymethylene)malononitrile

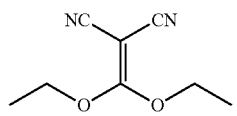

Ethene-1,1,2,2-tetracarbonitrile (6.1 g, 47.6 mmol) and urea (0.858 g, 14.29 mmol) were added to a round-bottom flask and suspended in ethanol (40 mL, 773 mmol). The mixture was heated at 40° C. for 50 minutes. The solution was cooled to room temperature, then cooled to −78° C. and stirred for 30 minutes as an off-white precipitate formed. The cooled suspension was filtered and the precipitate was collected by filtration and washed with cold ether to afford 2-(diethoxymethylene)malononitrile (2.5 g, 15.04 mmol, 31% yield). LCMS m/z=166.9 [M+H]$^+$.

Step 2: 2-Amino-6-chloro-4-ethoxypyridine-3,5-dicarbonitrile

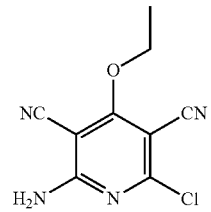

Malononitrile (1.10 g, 16.65 mmol) and potassium tert-butoxide (2.0 g, 17.82 mmol) were added to a round-bottom flask and suspended in ethanol (100 mL). The mixture was heated at 45° C. for 5 minutes. 2-(Diethoxymethylene)malononitrile (2.5 g, 15.04 mmol) in EtOH (10 mL) was added to the mixture slowly and the reaction was heated at reflux for 1.5 hours. The reaction mixture was then filtered and the filtrate concentrated in vacuo. To the remaining material was sequentially added acetone (100 mL) and concentrated hydrochloric acid (15 mL). The mixture was stirred at 50° C. for 2 hours, cooled to room temperature, and then further cooled to 0° C. The precipitate that formed was collected by filtration to afford 2-amino-6-chloro-4-ethoxypyridine-3,5-dicarbonitrile (2.3 g, 10.33 mmol, 69% yield). LCMS m/z=223.0, 225.0 [M+H]$^+$.

Step 3: 2-Amino-4-ethoxy-6-mercaptopyridine-3,5-dicarbonitrile

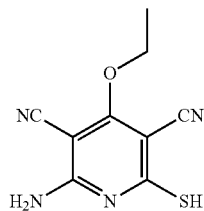

2-Amino-6-chloro-4-ethoxypyridine-3,5-dicarbonitrile (767 mg, 3.45 mmol) and potassium thioacetate (600 mg, 5.25 mmol) were added to a round-bottom flask and suspended in ethanol (50 mL). Triethylamine (1.5 mL, 10.76 mmol) was added and the mixture stirred at room temperature for 4 hours. Additional potassium thioacetate (201 mg) was added and the reaction stirred for 1 hour. A final portion of potassium thioacetate (311 mg) was then added and the reaction stirred overnight. A precipitate had formed and the mixture was cooled to 0° C. The solid was collected by filtration and washed with diethyl ether/heptane to afford 2-amino-4-ethoxy-6-mercaptopyridine-3,5-dicarbonitrile (1.26 g) as a crude solid. This material was used as is without further purification. LCMS m/z=221.0 [M+H]$^+$.

Step 4: tert-Butyl 4-(((6-amino-3,5-dicyano-4-ethoxypyridin-2-yl)thio)methyl)benzylcarbamate

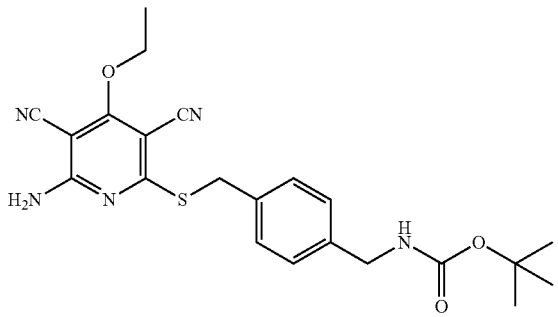 [SMILES: CCOc1c(C#N)c(N)nc(SCc2ccc(CNC(=O)OC(C)(C)C)cc2)c1C#N]

2-Amino-4-ethoxy-6-mercaptopyridine-3,5-dicarbonitrile (1.275 g; crude material from previous step) and sodium bicarbonate (1.05 g, 12.50 mmol) were added to a round-bottom flask and suspended in N,N-dimethylformamide (30 mL). To this mixture was slowly added tert-butyl 4-(bromomethyl)benzylcarbamate (2 g, 6.66 mmol) and the reaction allowed to stir at room temperature for 1 hour. The mixture was partitioned between ethyl acetate and saturated sodium chloride solution. The layers were separated and the aqueous layer was back-extracted with ethyl acetate (3×). The combined organic layers were washed with saturated sodium chloride solution, dried over magnesium sulfate, filtered and concentrated. The resultant yellow oil was triturated with DCM/heptane and the precipitate collected by filtration to afford tert-butyl 4-(((6-amino-3,5-dicyano-4-ethoxypyridin-2-yl)thio)methyl)benzylcarbamate (2.54 g, 3.47 mmol, 60%). LCMS m/z=440.3 [M+H]$^+$.

Step 5: 2-Amino-6-((4-(aminomethyl)benzyl)thio)-4-ethoxypyridine-3,5-dicarbonitrile hydrochloride

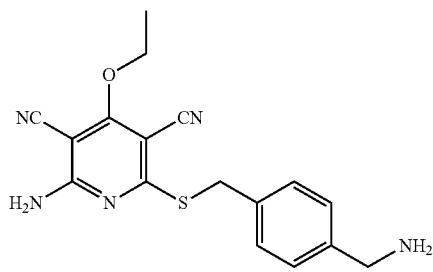 [SMILES: CCOc1c(C#N)c(N)nc(SCc2ccc(CN)cc2)c1C#N]

tert-Butyl 4-(((6-amino-3,5-dicyano-4-ethoxypyridin-2-yl)thio)methyl)benzylcarbamate (2.54 g, 3.47 mmol) and hydrogen chloride solution (18 mL, 72.0 mmol; 4N in 1,4-dioxane) were added to a round-bottom flask and stirred at 50° C. for 15 minutes. This mixture was concentrated in vacuo, suspended in ethyl acetate/ether, and the solid collected by filtration. The solid was then washed with ether/heptane to afford crude 2-amino-6-((4-(aminomethyl)benzyl)thio)-4-ethoxypyridine-3,5-dicarbonitrile hydrochloride (2.4 g). This material was used as is without further purification. LCMS m/z=340.2 [M+H]$^+$.

Step 6: N-(4-(((6-Amino-3,5-dicyano-4-ethoxypyridin-2-yl)thio)methyl)benzyl)acetamide

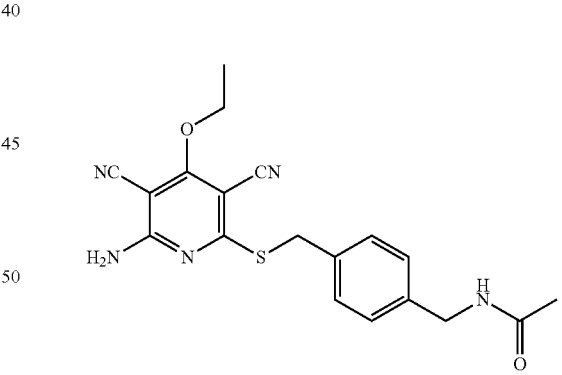

2-Amino-6-((4-(aminomethyl)benzyl)thio)-4-ethoxypyridine-3,5-dicarbonitrile hydrochloride (900 mg, crude material from previous step) was suspended in dichloromethane (20 mL) and triethylamine (0.831 mL, 5.96 mmol) and acetic anhydride (0.197 mL, 2.087 mmol) were added. The mixture was stirred at room temperature for 15 minutes. The suspension was cooled to 0° C., filtered, and the collected solid washed with ether/heptane to afford crude N-(4-(((6-amino-3,5-dicyano-4-ethoxypyridin-2-yl)thio)methyl)benzyl)acetamide (999 mg). This material was used as is without further purification. LCMS m/z=382.2 [M+H]$^+$.

417

Step 7: N-(4-(((6-Chloro-3,5-dicyano-4-ethoxypyridin-2-yl)thio)methyl)benzyl)acetamide

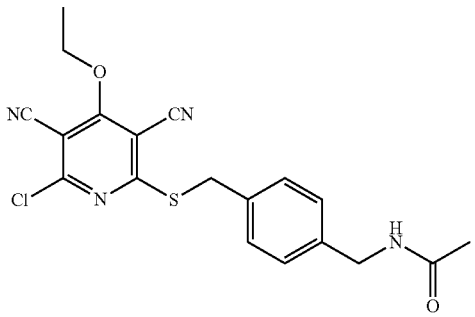 [SMILES: CCOc1c(C#N)c(Cl)nc(SCc2ccc(CNC(C)=O)cc2)c1C#N]

N-(4-(((6-Amino-3,5-dicyano-4-ethoxypyridin-2-yl)thio)methyl)benzyl)acetamide (999 mg, crude material from the previous step) and copper(II) chloride (600 mg, 4.46 mmol) were added to a round-bottom flask and suspended in acetonitrile (100 mL). This mixture was heated to 40° C. for 5 min. Tert-butyl nitrite (0.575 mL, 4.85 mmol) was slowly added to the mixture and the mixture was stirred at 50° C. for 4 hours. An additional amount of tert-butyl nitrite (0.1 mL) and CuCl$_2$ (150 mg) were added to the heated mixture and stirred for 1 hour. A final portion of tert-butyl nitrite (0.15 mL) and CuCl$_2$ (220 mg) were added. After 1 hour, the reaction was judged complete by LCMS analysis. The mixture was filtered through a small pad of silica gel/Celite® and washed with ethyl acetate:ethanol 4:1. The filtrate was concentrated to afford N-(4-(((6-chloro-3,5-dicyano-4-ethoxypyridin-2-yl)thio)methyl)benzyl)acetamide (660 mg, 1.399 mmol, 53% yield) as a burnt-orange/brown solid. LCMS m/z=401.1, 403.1 [M+H]$^+$.

Step 8: N-(4-(((3,5-Dicyano-4-ethoxy-6-(4-methyl-1,4-diazepan-1-yl)pyridin-2-yl)thio)methyl)benzyl)acetamide

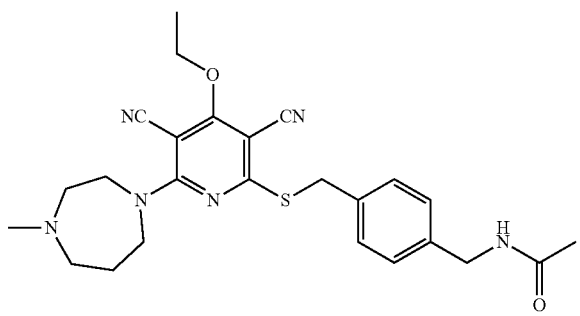 [SMILES: CCOc1c(C#N)c(SCc2ccc(CNC(C)=O)cc2)nc(N2CCCN(C)CC2)c1C#N]

N-(4-(((6-Chloro-3,5-dicyano-4-ethoxypyridin-2-yl)thio)methyl)benzyl)acetamide (60 mg, 0.127 mmol) and 1-methyl-1,4-diazepane (0.1 mL, 0.806 mmol) were added to a vial. Tetrahydrofuran (12 mL) and DIPEA (0.1 mL, 0.573 mmol) were added and the mixture was stirred at room temperature for 15 minutes. The reaction mixture was concentrated. The remaining residue was purified by reverse phase column chromatography (0-40-50-100% of 0.1% aqueous NH$_4$OH in acetonitrile) and lyophilized to afford N-(4-(((3,5-dicyano-4-ethoxy-6-(4-methyl-1,4-diazepan-1-yl)pyridin-2-yl)thio)methyl)benzyl)acetamide (19 mg, 0.039 mmol, 30%) as a white solid. LCMS m/z=479.3 [M+H]$^+$. $^1$H NMR (400 MHz, DMSO-d$_6$) δ ppm 8.33 (t, J=6.0 Hz, 1H), 7.34 (d, J=8.1 Hz, 2H), 7.21 (d, J=8.1 Hz, 2H), 4.55 (q, J=6.8 Hz, 2H), 4.46 (s, 2H), 4.21 (d, J=6.1 Hz, 2H), 3.92-3.78 (m, 4H), 2.70-2.58 (m, 2H), 2.46-2.38 (m, 2H), 2.23 (s, 3H), 1.98-1.87 (m, 2H), 1.86 (s, 3H), 1.37 (t, J=7.1 Hz, 3H).

Example 106

2-({3,5-Dicyano-4-ethyl-6-[4-(2-methoxyethyl)-1,4-diazepan-1-yl]pyridin-2-yl}sulfanyl)-2-phenylacetamide Step 1: 2-((3,5-Dicyano-6-(1,4-diazepan-1-yl)-4-ethylpyridin-2-yl)thio)-2-phenylacetamide

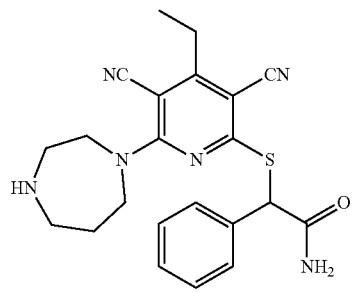 [SMILES: CCc1c(C#N)c(SC(C(N)=O)c2ccccc2)nc(N2CCCNCC2)c1C#N]

To a solution of 2-[(6-bromo-3,5-dicyano-4-ethyl-2-pyridyl)sulfanyl]-2-phenyl-acetamide (synthesis describe in example 6, step 1, 500 mg, 1.25 mmol) in tetrahydrofuran (25 mL) was added 1,4-diazepane (1.57 g, 15.64 mmol). The reaction mixture was allowed to stir for 15 minutes at room temperature. The solvent was concentrated to give a slurry which was partitioned between EtOAc (100 mL) and water (100 mL). The phases were separated and the aqueous phase was washed with EtOAc (100 mL). The combined organics were washed with water (150 mL), brine (150 mL), filtered through a hydrophobic frit and the solvent was removed under reduced pressure. The resulting residue was triturated with diethyl ether, filtered, washed with diethyl ether (25 mL) and dried. The crude product was dissolved in 10% MeOH/CH$_2$Cl$_2$, absorbed onto SiO$_2$ (3 g) and purified by silica gel chromatography (12 g RediSep cartridge, using 20% (MeOH containing 5% NH$_3$) in CH$_2$Cl$_2$ as the eluent to afford 2-[[3,5-dicyano-6-(1,4-diazepan-1-yl)-4-ethyl-2-pyridyl]sulfanyl]-2-phenyl-acetamide (339 mg, 65% yield) as a light yellow solid. LCMS m/z=419.2 [M−H]$^-$.

Step 2: 2-({3,5-Dicyano-4-ethyl-6-[4-(2-methoxy-ethyl)-1,4-diazepan-1-yl]pyridin-2-yl}sulfanyl)-2-phenylacetamide

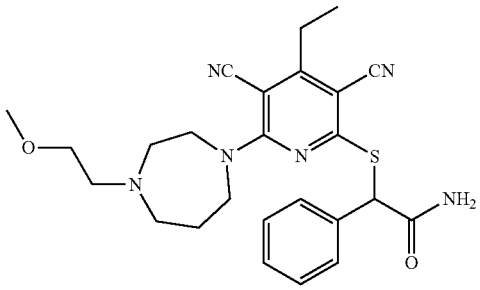 [SMILES: CCc1c(C#N)c(SC(C(N)=O)c2ccccc2)nc(N2CCCN(CCOC)CC2)c1C#N]

To a solution of 2-[[3,5-dicyano-6-(1,4-diazepan-1-yl)-4-ethyl-2-pyridyl]sulfanyl]-2-phenyl-acetamide (30 mg, 0.07 mmol) in acetonitrile (3 mL) was added 2-bromoethyl methylether (0.013 mL, 0.14 mmol) followed by N,N-diisopropylethylamine (0.035 mL, 0.21 mmol). The reaction mixture was allowed to stir at 65° C. for 5 hours before the further addition of 2-bromoethyl methylether (0.033 mL, 0.36 mmol) and heating at 65° C. for an additional 17 hours. The product mixture was cooled then water (7.5 mL) was added, and the mixture was stirred for 30 minutes, filtered, washed with water (2×10 mL) and dried in vacuo at 50° C. The crude product was absorbed onto $SiO_2$ (0.7 g) and purified by silica gel chromatography (4 g RediSep cartridge, using 20% (MeOH containing 5% $NH_3$) in DCM) to afford 2-[[3,5-dicyano-4-ethyl-6-[4-(2-methoxyethyl)-1,4-diazepan-1-yl]-2-pyridyl]sulfanyl]-2-phenyl-acetamide (25 mg, 73% yield) as a white solid. LCMS m/z=477.3 [M−H]⁻. ¹H NMR (300 MHz, DMSO-$d_6$) δ ppm 7.91 (s, 1H), 7.52-7.31 (m, 6H), 5.51 (s, 1H), 3.97-3.81 (m, 4H), 3.43-3.38 (m, 2H), 3.23 (s, 3H), 2.87-2.68 (m, 4H), 2.67-2.56 (m, 4H), 1.89 (m, 2H), 1.21 (t, J=7.6 Hz, 3H).

Example 107

2-((3,5-dicyano-4-ethyl-6-(4-(2-hydroxypropyl)-1,4-diazepan-1-yl)pyridin-2-yl)thio)-2-phenylacetamide

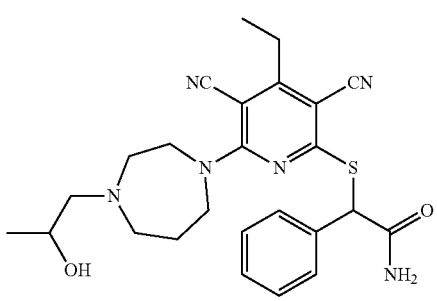 [SMILES: CCc1c(C#N)c(SC(C(N)=O)c2ccccc2)nc(N2CCCN(CC(C)O)CC2)c1C#N]

To a solution of 2-[[3,5-dicyano-6-(1,4-diazepan-1-yl)-4-ethyl-2-pyridyl]sulfanyl]-2-phenyl-acetamide (synthesis described in example 106, step 1, 30 mg, 0.07 mmol) in acetonitrile (3 mL) was added 1-bromopropan-2-ol (0.013 mL, 0.14 mmol) followed by N,N-diisopropylethylamine (0.035 mL, 0.21 mmol). The reaction mixture was stirred at 65° C. for 5 hours before the further addition of 1-bromopropan-2-ol (0.064 mL, 0.70 mmol) and heating at 65° C. for an additional 17 hours. The product mixture was cooled to ambient temperature, water (7.5 mL) was added, stirred for 30 minutes, filtered, washed with water (2×10 mL) and dried in vacuo at 50° C. The crude product was absorbed onto $SiO_2$ (0.7 g) and purified by silica gel chromatography (4 g RediSep cartridge) using 10% (MeOH containing 5% $NH_3$) in $CH_2Cl_2$ as the eluent to afford 2-[[3,5-dicyano-4-ethyl-6-[4-(2-hydroxypropyl)-1,4-diazepan-1-yl]-2-pyridyl]sulfa-nyl]-2-phenyl-acetamide (21 mg, 62% yield) as a white solid. LCMS m/z=477.3 [M−H]⁻. ¹H NMR (300 MHz, DMSO-$d_6$) δ ppm 7.91 (s, 1H), 7.54-7.45 (m, 2H), 7.43-7.30 (m, 4H), 5.51 (s, 1H), 4.27 (d, J=3.9 Hz, 1H), 4.01-3.80 (m, 4H), 3.79-3.58 (m, 1H), 2.90-2.69 (m, 4H), 2.68-2.53 (m, 2H), 2.47-2.22 (m, 2H), 1.89 (br s, 2H), 1.21 (t, J=7.6 Hz, 3H), 1.01 (d, J=6.0 Hz, 3H).

Example 108

Methyl 2-[4-(6-{[carbamoyl(phenyl)methyl]sulfa-nyl}-3,5-dicyano-4-ethylpyridin-2-yl)-1,4-diazepan-1-yl]acetate

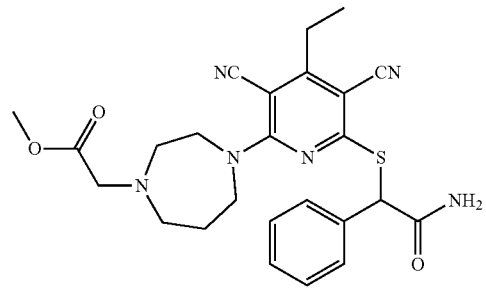 [SMILES: CCc1c(C#N)c(SC(C(N)=O)c2ccccc2)nc(N2CCCN(CC(=O)OC)CC2)c1C#N]

To a solution of 2-[[3,5-dicyano-6-(1,4-diazepan-1-yl)-4-ethyl-2-pyridyl]sulfanyl]-2-phenyl-acetamide (synthesis described in example 106, step 1, 30 mg, 0.07 mmol) in acetonitrile (3 mL) was added methyl chloroacetate (0.013 mL, 0.14 mmol) followed by N,N-diisopropylethylamine (0.035 mL, 0.21 mmol). The reaction mixture was stirred at 65° C. for 1 hour and additional methyl chloroacetate (0.013 mL, 0.14 mmol) followed by N,N-diisopropylethylamine (0.035 mL, 0.21 mmol) were added. The mixture was heated for a further 2 hours then further methyl chloroacetate (0.013 mL, 0.14 mmol) followed by N,N-diisopropylethylamine (0.035 mL, 0.21 mmol) were added. After a total of 10 hours of heating the reaction mixture was allowed to cool to ambient temperature, water (7.5 mL) was added, and the mixture was stirred for 30 minutes, filtered, washed with water (2×10 mL) and dried in vacuo at 50° C. The crude product was loaded onto $SiO_2$ using dichloromethane and a small amount of methanol, and purified by silica gel chromatography (4 g RediSep cartridge), using 5% (MeOH containing 5% $NH_3$) in $CH_2Cl_2$ as eluent to afford methyl 2-[4-[6-(2-amino-2-oxo-1-phenyl-ethyl)sulfanyl-3,5-di-cyano-4-ethyl-2-pyridyl]-1,4-diazepan-1-yl]acetate (23 mg, 65% yield), as a white solid. LCMS m/z=491.3 [M−H]⁻. ¹H NMR (300 MHz, DMSO-$d_6$) δ ppm 7.91 (s, 1H), 7.52-7.30 (m, 6H), 5.51 (s, 1H), 3.97-3.84 (m, 4H), 3.62 (s, 3H), 3.49-3.35 (m, 2H), 2.96-2.84 (m, 2H), 2.81-2.71 (m, 4H), 1.88 (br s, 2H), 1.21 (t, J=7.6 Hz, 3H).

Example 109

2-{[3,5-Dicyano-4-cyclopropyl-6-(4-methyl-5-oxo-1,4-diazepan-1-yl)pyridin-2-yl]sulfanyl}-2-phenylacetamide

Step 1: 2-Chloro-4-cyclopropyl-6-(4-methyl-5-oxo-1,4-diazepan-1-yl)pyridine-3,5-dicarbonitrile

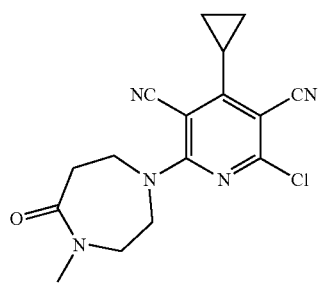 [SMILES: CN1CCN(c2nc(Cl)c(C#N)c(C3CC3)c2C#N)CCC1=O]

To a solution of 2,6-dichloro-4-cyclopropylpyridine-3,5-dicarbonitrile (synthesis described in example 4, step 2, 300 mg, 1.260 mmol) in N,N-dimethylformamide (10 mL) was added 4-methyl-1,4-diazepan-5-one (162 mg, 1.260 mmol) and triethylamine (0.176 mL, 1.260 mmol). The reaction mixture was stirred at room temperature for 1 hour. Water was added to the reaction, the solid was filtered and dried to give 2-chloro-4-cyclopropyl-6-(4-methyl-5-oxo-1,4-diazepan-1-yl)pyridine-3,5-dicarbonitrile (350 mg) as a solid. LCMS m/z=329.8 [M+H]$^+$.

Step 2: 2-{[3,5-Dicyano-4-cyclopropyl-6-(4-methyl-5-oxo-1,4-diazepan-1-yl)pyridin-2-yl]sulfanyl}-2-phenylacetamide

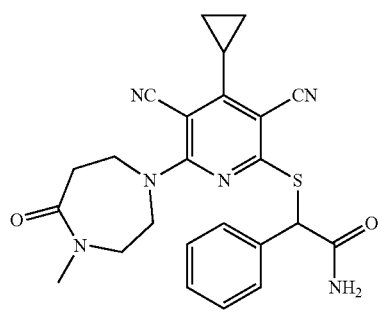 [SMILES: CN1CCN(c2nc(SC(C(N)=O)c3ccccc3)c(C#N)c(C3CC3)c2C#N)CCC1=O]

A solution of 2-chloro-4-cyclopropyl-6-(4-methyl-5-oxo-1,4-diazepan-1-yl)pyridine-3,5-dicarbonitrile (350 mg, 1.061 mmol) and potassium thioacetate (145 mg, 1.274 mmol) in N,N-dimethylformamide (10 mL) was stirred at room temperature for 30 minutes. Then 2-amino-2-oxo-1-phenylethyl methanesulfonate (292 mg, 1.274 mmol) and Et$_3$N (0.296 mL, 2.123 mmol) was added. The reaction mixture was stirred at room temperature overnight. Water was added to the reaction and the resulting solid was filtered and purified by Flash column chromatography (eluted by DCM:MeOH 20:1) to give 2-{[3,5-dicyano-4-cyclopropyl-6-(4-methyl-5-oxo-1,4-diazepan-1-yl)pyridin-2-yl]sulfanyl}-2-phenylacetamide (192.5 mg) as a solid. LCMS m/z=460.6 [M+H]$^+$. $^1$H NMR (400 MHz, CDCl$_3$) δ ppm 7.52-7.45 (m, 2H), 7.44-7.36 (m, 3H), 6.75 (br s, 1H), 5.79 (br s, 1H), 5.44 (s, 1H), 4.10-3.90 (m, 4H), 3.75-3.62 (m, 2H), 3.08-2.91 (m, 5H), 2.18-2.06 (m, 1H), 1.37-1.28 (m, 2H), 1.23-1.13 (m, 2H).

Example 110

2-{[3,5-Dicyano-4-cyclopropyl-6-(5-oxo-1,4-diazepan-1-yl)pyridin-2-yl]sulfanyl}-2-phenylacetamide

Step 1: 2-Chloro-4-cyclopropyl-6-(5-oxo-1,4-diazepan-1-yl)pyridine-3,5-dicarbonitrile

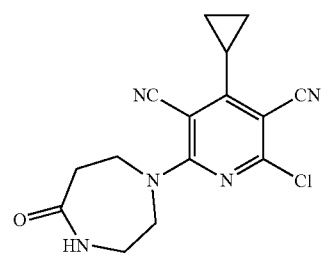 [SMILES: N#Cc1c(Cl)nc(N2CCNC(=O)CC2)c(C#N)c1C1CC1]

To a solution of 2,6-dichloro-4-cyclopropylpyridine-3,5-dicarbonitrile (synthesis described in example 4, step 2, 237 mg, 1 mmol) in N,N-dimethylformamide (10 mL) at room temperature was added 1,4-diazepan-5-one (114 mg, 1 mmol), followed by Et$_3$N (0.14 mL, 1 mmol). The mixture was stirred at room temperature for 50 minutes, then diluted with water. The precipitated solid was collected by filtration and purified by silica gel column chromatography (DCM:MeOH 20:1) to give 2-chloro-4-cyclopropyl-6-(5-oxo-1,4-diazepan-1-yl)pyridine-3,5-dicarbonitrile (200 mg, 55%). LCMS m/z=316.0 [M+H]$^+$.

Step 2: 2-{[3,5-Dicyano-4-cyclopropyl-6-(5-oxo-1,4-diazepan-1-yl)pyridin-2-yl]sulfanyl}-2-phenylacetamide

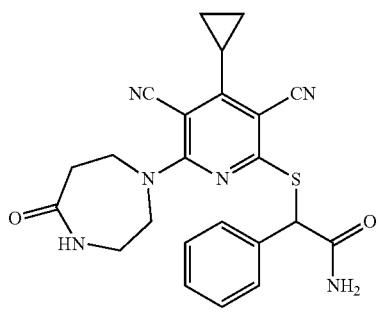 [SMILES: N#Cc1c(SC(C(N)=O)c2ccccc2)nc(N2CCNC(=O)CC2)c(C#N)c1C1CC1]

A solution of 2-chloro-4-cyclopropyl-6-(5-oxo-1,4-diazepan-1-yl)pyridine-3,5-dicarbonitrile (200 mg, 0.55 mmol) and KSAc (75 mg, 0.66 mmol) in N,N-dimethylformamide (6 mL) was stirred at room temperature for 30 minutes then 2-amino-2-oxo-1-phenylethyl methanesulfonate (151 mg, 0.66 mmol) and Et$_3$N (0.15 mL, 1.1 mmol) were added to the solution. The mixture was stirred at room temperature overnight then diluted with water. The precipitated solid was collected by filtration and purified by silica gel column chromatography (DCM:MeOH 10:1) to give 2-{[3,5-dicyano-4-cyclopropyl-6-(5-oxo-1,4-diazepan-1-yl)pyridin-2-yl]sulfanyl}-2-phenylacetamide (76 mg, 31%). LCMS m/z=446.8 [M+H]$^+$. $^1$H NMR (400 MHz, DMSO-d$_6$) δ ppm 7.91 (s, 1H), 7.74-7.69 (m, 1H), 7.55-7.46 (m, 2H), 7.44-7.30 (m, 4H), 5.50 (s, 1H), 4.03-3.83 (m, 4H), 3.36-3.32 (m, 2H), 2.74-2.61 (m, 2H), 2.17-2.08 (m, 1H), 1.19-1.08 (m, 2H), 1.02-0.91 (m, 2H).

Example 111

2-{[3,5-Dicyano-4-ethyl-6-(4-methyl-5-oxo-1,4-diazepan-1-yl)pyridin-2-yl]sulfanyl}-2-phenylacetamide

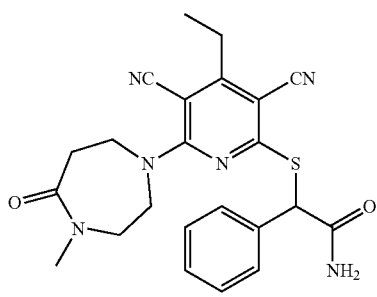 [SMILES: CCc1c(C#N)c(SC(C(N)=O)c2ccccc2)nc(N2CCC(=O)N(C)CC2)c1C#N]

To a solution of 2-[(6-bromo-3,5-dicyano-4-ethyl-2-pyridyl)sulfanyl]-2-phenyl-acetamide (synthesis described in example 6, step 1, 35 mg, 0.09 mmol) and triethylamine (0.03 mL, 0.19 mmol) in tetrahydrofuran (2 mL) was added 4-methyl-1,4-diazepan-5-one hydrochloride (16 mg, 0.10 mmol). The reaction mixture was stirred at room temperature for 1.5 hours. The mixture was diluted with EtOAc (20 mL), washed with water (20 mL), the aqueous phase was washed with EtOAc (20 mL) and the combined extracts were washed with brine (2×25 mL), filtered through a hydrophobic frit and the solvent removed under reduced pressure. The residue was triturated with diethyl ether and dried in vacuo at 50° C. to afford 2-[[3,5-dicyano-4-ethyl-6-(4-methyl-5-oxo-1,4-diazepan-1-yl)-2-pyridyl]sulfanyl]-2-phenyl-acetamide (17 mg, 43% yield) as a yellow solid. LCMS m/z=447.2 [M−H]$^-$. $^1$H NMR (300 MHz, DMSO-d$_6$) δ ppm 7.93 (s, 1H), 7.54-7.31 (m, 6H), 5.54 (s, 1H), 4.13-3.90 (m, 4H), 3.64 (br s, 2H), 2.89-2.74 (m, 7H), 1.22 (t, J=7.6 Hz, 3H).

Example 112

2-{[3,5-Dicyano-6-(1,4-diazepan-1-yl)-4-ethylpyridin-2-yl]sulfanyl}-2-phenylacetamide Step 1: tert-Butyl 4-[6-(2-amino-2-oxo-1-phenylethyl)sulfanyl-3,5-dicyano-4-ethyl-2-pyridyl]-1,4-diazepane-1-carboxylate

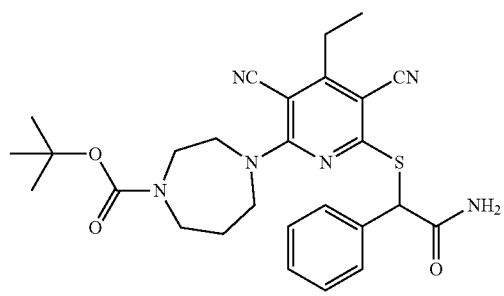 [SMILES: CCc1c(C#N)c(SC(C(N)=O)c2ccccc2)nc(N2CCCN(C(=O)OC(C)(C)C)CC2)c1C#N]

A solution of 2-[(6-bromo-3,5-dicyano-4-ethyl-2-pyridyl)sulfanyl]-2-phenyl-acetamide (synthesis described in example 6, step 1, 117 mg, 0.29 mmol) in tetrahydrofuran (3 mL) was treated with N1-Boc-1,4-diazepane (0.12 mL, 0.64 mmol) and stirred at room temperature for 3 hours. The product mixture was loaded onto SiO$_2$ (0.9 g) and purified by silica gel chromatography (12 g RediSep cartridge, eluting with 0-10% MeOH in CH$_2$Cl$_2$) to afford tert-butyl 4-[6-(2-amino-2-oxo-1-phenyl-ethyl)sulfanyl-3,5-dicyano-4-ethyl-2-pyridyl]-1,4-diazepane-1-carboxylate (118 mg, 77% yield) as a colorless glass. LCMS m/z=519 [M−H]$^-$.

Step 2: 2-{[3,5-Dicyano-6-(1,4-diazepan-1-yl)-4-ethylpyridin-2-yl]sulfanyl}-2-phenylacetamide, hydrochloride

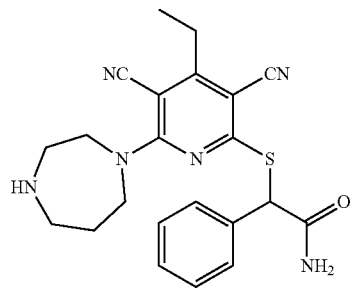 [SMILES: CCc1c(C#N)c(SC(C(N)=O)c2ccccc2)nc(N2CCCNCC2)c1C#N]

A solution of tert-butyl 4-[6-(2-amino-2-oxo-1-phenyl-ethyl)sulfanyl-3,5-dicyano-4-ethyl-2-pyridyl]-1,4-diazepane-1-carboxylate (111 mg, 0.21 mmol) in CH$_2$Cl$_2$ (0.5 mL) was treated with 2 M HCl in diethyl ether (0.3 mL, 0.6 mmol) and MeOH (2 mL), followed by an additional portion of 2 M HCl in diethyl ether (0.7 mL, 1.4 mmol) and stirred at room temperature for 18 hours. The solution was concentrated to 1 mL volume by evaporation at 45° C., then treated with 3 M HCl in methanol (1 mL) for 30 minutes, then concentrated. The residue was triturated with diethyl ether and evaporated to dryness to furnish 2-[[3,5-dicyano-6-(1,4-diazepan-1-yl)-4-ethyl-2-pyridyl]sulfanyl]-2-phenyl-acetamide hydrochloride (87 mg, 89% yield) as a pale yellow solid. LCMS m/z=419.2 [M–H]⁻. ¹H NMR (300 MHz, DMSO-d₆) δ ppm 9.11 (br s, 2H), 8.01 (s, 1H), 7.55-7.31 (m, 6H), 5.51 (s, 1H), 4.23-4.10 (m, 2H), 4.10-3.87 (m, 2H), 3.30-3.12 (m, 3H), 2.93-2.68 (m, 2H), 2.18 (br s, 2H), 1.22 (t, J=7.5 Hz, 3H).

Example 113

2-({3,5-Dicyano-6-[4-(2-hydroxyethyl)-1,4-diazepan-1-yl]-4-(2,2,2-trifluoroethyl)pyridin-2-yl}sulfanyl)-2-phenylacetamide Step 1: 2-((6-Amino-3,5-dicyano-4-(2,2,2-trifluoroethyl)pyridin-2-yl)thio)-2-phenylacetamide

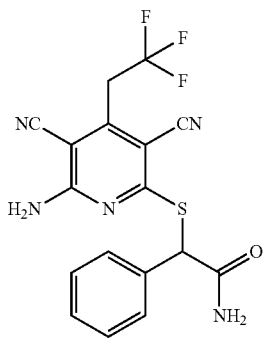 [SMILES: N#Cc1c(N)nc(SC(C(N)=O)c2ccccc2)c(C#N)c1CC(F)(F)F]

3,3,3-Trifluoropropanal hydrate (0.31 mL, 3.08 mmol), N-methylmorpholine (0.68 mL, 6.15 mmol) and 2-cyanothioacetamide (0.62 g, 6.15 mmol) were mixed and dissolved in ethanol (10 mL). The resultant orange solution was stirred at ambient temperature for 72 hours. The product mixture was concentrated under reduced pressure and attempts to crystallize with ethanol/isohexane/diethyl ether mixtures failed to furnish the desired product as a solid, resulting in an orange oil (282 mg) which was used without further purification. A solution of this oil (250 mg) and 2-chloro-2-phenyl-acetamide (121 mg, 0.72 mmol) in N,N-dimethylformamide (10 mL) was stirred at ambient temperature for 72 hours. The mixture was quenched with water and extracted into EtOAc before washing further with saturated aqueous sodium chloride followed by water. The organic layer was dried over anhydrous sodium sulfate and concentrated under reduced pressure to afford a red oil which was split into two portions. Approximately 60 mg was purified by preparative HPLC to furnish 2-[[6-amino-3,5-dicyano-4-(2,2,2-trifluoroethyl)-2-pyridyl]sulfanyl]-2-phenyl-acetamide (4.5 mg) as a cream solid. LCMS m/z=390 [M–H]⁻. ¹H NMR (300 MHz, DMSO-d₆) δ ppm 8.16 (br s, 1H), 7.85-7.66 (m, 1H), 7.65-7.59 (m, 2H), 7.41-7.27 (m, 5H), 5.57 (s, 1H), 3.78 (q, J=10.5 Hz, 2H).

The remainder of the crude oil was triturated with isohexane, filtered under reduced pressure, and washed with isohexane to afford 2-[[6-amino-3,5-dicyano-4-(2,2,2-trifluoroethyl)-2-pyridyl]sulfanyl]-2-phenyl-acetamide (180 mg) as a brown crystalline solid.

Step 2: 2-((3,5-Dicyano-6-(4-(2-hydroxyethyl)-1,4-diazepan-1-yl)-4-(2,2,2-trifluoroethyl)pyridin-2-yl)thio)-2-phenylacetamide

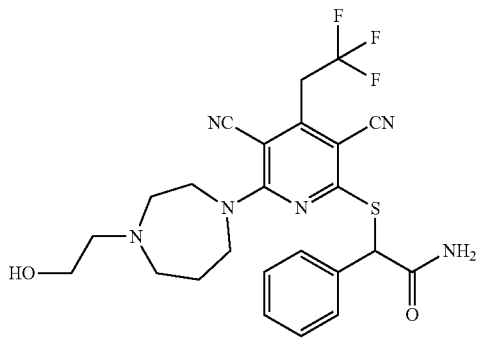 [SMILES: N#Cc1c(SC(C(N)=O)c2ccccc2)nc(N2CCCN(CCO)CC2)c(C#N)c1CC(F)(F)F]

A stirred suspension of 2-[[6-amino-3,5-dicyano-4-(2,2,2-trifluoroethyl)-2-pyridyl]sulfanyl]-2-phenyl-acetamide, (180 mg, 0.46 mmol) in dry acetonitrile (10 mL) was treated with copper (II) bromide (175 mg, 0.78 mmol) and tert-butylnitrite (0.1 mL, 0.8 mmol) and then heated at 70° C. for 20 minutes under an atmosphere of nitrogen gas. The mixture was cooled to ambient temperature, diluted with EtOAc (20 mL) and washed with brine (10 mL) followed by water (10 mL). The organic layer was dried over anhydrous sodium sulfate and concentrated under reduced pressure to afford a dark green oil. Stirring with isohexane:diethyl ether (1:1, approximately 50 mL) resulted in precipitation of a solid. The mixture was filtered and the solution was concentrated in vacuo to furnish a green oil (54 mg). To a mixture of 48 mg of this oil and triethylamine (0.03 mL, 0.23 mmol) in tetrahydrofuran (2 mL) was added 2-(1,4-diazepan-1-yl)ethanol (17 mg, 0.12 mmol). The mixture was stirred at ambient temperature for 1 h. The mixture was diluted with EtOAc (20 mL), washed with water (3×20 mL), saturated aqueous sodium chloride solution (25 mL), dried over anhydrous sodium sulfate and concentrated under reduced pressure. The residue was purified by preparative HPLC to furnish 2-[[3,5-dicyano-6-[4-(2-hydroxyethyl)-1,4-diazepan-1-yl]-4-(2,2,2-trifluoroethyl)-2-pyridyl]sulfanyl]-2-phenyl-acetamide (5.7 mg) as a yellow film. LCMS m/z=517.3 [M–H]⁻. ¹H NMR (300 MHz, METHANOL-d4) δ ppm 7.62-7.33 (m, 5H), 5.50 (s, 1H), 4.21-3.99 (m, 4H), 3.95-3.80 (m, 4H), 3.45-3.35 (m, 2H), 3.30-3.14 (m, 2H), 3.07 (t, J=5.5 Hz, 2H), 2.43-2.22 (m, 2H).

Example 114

(2R)-2-({3,5-Dicyano-4-ethyl-6-[4-(2-hydroxyethyl)-1,4-diazepan-1-yl]pyridin-2-yl}amino)-2-phenylacetamide Step 1: (R)-2-((6-chloro-3,5-dicyano-4-ethylpyridin-2-yl)amino)-2-phenylacetamide

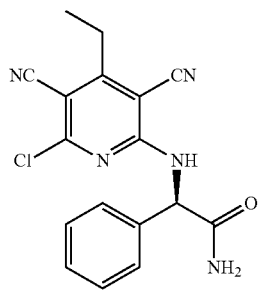 [SMILES: CCc1c(C#N)c(Cl)nc(N[C@@H](C(N)=O)c2ccccc2)c1C#N]

A stirred solution of 2,6-dichloro-4-ethyl-pyridine-3,5-dicarbonitrile (synthesis described in example 3, step 2, 333 mg, 1.47 mmol) in tetrahydrofuran (50 mL) was treated with (R)-2-amino-2-phenylacetamide (446 mg, 2.97 mmol) in one portion at 20° C. After 2 hours the mixture was diluted with EtOAc (100 mL), washed with water (3×100 mL), saturated aqueous sodium chloride, dried through a hydrophobic frit and concentrated under reduced pressure to furnish crude (R)-2-((6-chloro-3,5-dicyano-4-ethylpyridin-2-yl)amino)-2-phenylacetamide (511 mg) as a white solid. LCMS m/z=338 [M−H]$^-$.

Step 2: (R)-2-((3,5-dicyano-4-ethyl-6-(4-(2-hydroxyethyl)-1,4-diazepan-1-yl)pyridin-2-yl)amino)-2-phenylacetamide

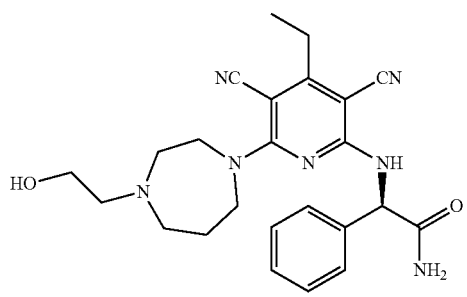 [SMILES: CCc1c(C#N)c(N[C@@H](C(N)=O)c2ccccc2)nc(N2CCCN(CCO)CC2)c1C#N]

A solution of 2-(1,4-diazepan-1-yl)ethanol (44 mg, 0.31 mmol) in tetrahydrofuran (3 mL) was treated with (R)-2-((6-chloro-3,5-dicyano-4-ethylpyridin-2-yl)amino)-2-phenylacetamide, (48 mg, 0.14 mmol) and stirred at room temperature for 1 hour. The mixture was loaded onto SiO$_2$ (1 g) and purified by silica gel chromatography (4 g RediSep cartridge, eluting with 0-25% (methanol containing 5% NH$_3$) in CH$_2$Cl$_2$) followed by trituration with diethyl ether to give (R)-2-((3,5-dicyano-4-ethyl-6-(4-(2-hydroxyethyl)-1,4-diazepan-1-yl)pyridin-2-yl)amino)-2-phenylacetamide (56 mg, 89% yield), as a white solid. LCMS m/z=446 [M−H]$^-$. $^1$H NMR (300 MHz, DMSO-d$_6$) δ ppm 7.84 (s, 1H), 7.51-7.25 (m, 6H), 7.11 (br d, J=5.7 Hz, 1H), 5.44 (d, J=6.0 Hz, 1H), 4.52 (br s, 1H), 3.74 (br s, 4H), 3.50 (br s, 2H), 3.21-2.52 (m, 8H), 2.05-1.75 (m, 2H), 1.20 (t, J=7.6 Hz, 3H).

Example 115

2-({6-[(3S)-3-Aminopyrrolidin-1-yl]-3,5-dicyano-4-cyclopropylpyridin-2-yl}sulfanyl)-2-phenylacetamide Step 1: tert-Butyl (S)-(1-(6-chloro-3,5-dicyano-4-cyclopropylpyridin-2-yl)pyrrolidin-3-yl)carbamate

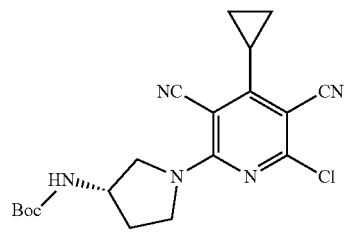 [SMILES: CC(C)(C)OC(=O)N[C@H]1CCN(c2nc(Cl)c(C#N)c(C3CC3)c2C#N)C1]

To a solution of 2,6-dichloro-4-cyclopropylpyridine-3,5-dicarbonitrile (synthesis described in example 4, step 2, 238 mg, 1 mmol) in N,N-dimethylformamide (10 mL) at room temperature was added tert-butyl (S)-pyrrolidin-3-ylcarbamate (186 mg, 1 mmol), followed by triethylamine (101 mg, 1 mmol). The mixture was stirred at room temperature for 1 hour, then diluted with water (50 mL) and extracted with EtOAc (50 mL×2). The combined organic layers were dried and concentrated under vacuum to give tert-butyl (S)-(1-(6-chloro-3,5-dicyano-4-cyclopropylpyridin-2-yl)pyrrolidin-3-yl)carbamate (300 mg, 77%) as a brown oil. LCMS m/z=409.9 [M+Na]$^+$.

Step 2: tert-Butyl ((3S)-1-(6-((2-amino-2-oxo-1-phenylethyl)thio)-3,5-dicyano-4-cyclopropylpyridin-2-yl)pyrrolidin-3-yl)carbamate

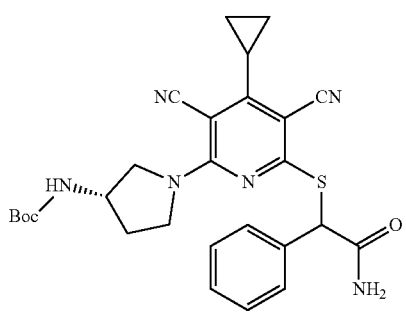 [SMILES: CC(C)(C)OC(=O)N[C@H]1CCN(c2nc(SC(C(N)=O)c3ccccc3)c(C#N)c(C3CC3)c2C#N)C1]

A solution of tert-butyl (S)-(1-(6-chloro-3,5-dicyano-4-cyclopropylpyridin-2-yl)pyrrolidin-3-yl)carbamate (300 mg, 0.77 mmol) and KSAc (106 mg, 0.92 mmol) in N,N-dimethylformamide (10 mL) was stirred at room temperature for 30 minutes then 2-amino-2-oxo-1-phenylethyl methanesulfonate (212 mg, 0.92 mmol) and Et$_3$N (155 mg, 1.54 mmol) were added to the solution. The mixture was stirred at room temperature for 12 hours then diluted with water (50 mL) and extracted with EtOAc (50 mL×2). The combined organic layers were dried over anhydrous Na$_2$SO$_4$, concentrated under vacuum, and purified by silica gel column chromatography (0-2% MeOH in DCM) to give tert-butyl ((3S)-1-(6-((2-amino-2-oxo-1-phenylethyl)thio)-3,5-dicyano-4-cyclopropylpyridin-2-yl)pyrrolidin-3-yl)carbamate (280 mg, 70%) as a white solid. LCMS m/z=518.8 [M+H]$^+$.

Step 3: 2-({6-[(3S)-3-Aminopyrrolidin-1-yl]-3,5-dicyano-4-cyclopropylpyridin-2-yl}sulfanyl)-2-phenylacetamide

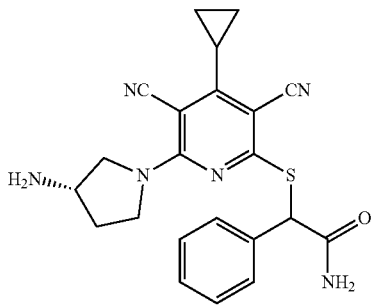 [SMILES: N#Cc1c(SC(C(N)=O)c2ccccc2)nc(N2CC[C@H](N)C2)c(C#N)c1C1CC1]

To a solution of tert-butyl ((3S)-1-(6-((2-amino-2-oxo-1-phenylethyl)thio)-3,5-dicyano-4-cyclopropylpyridin-2-yl)pyrrolidin-3-yl)carbamate (280 mg, 0.54 mmol) in DCM (6 mL) at room temperature was added trifluoroacetic acid (3 mL). The mixture was stirred at room temperature for 12 hours then concentrated, poured into water (50 mL), basified with sat. NaHCO$_3$ solution (to pH=9), and extracted with DCM (50 mL×2). The combined organic layers were dried, concentrated, and the residue was purified by silica gel column chromatography (CH$_2$Cl$_2$:MeOH 20:1) to give 2-({6-[(3S)-3-aminopyrrolidin-1-yl]-3,5-dicyano-4-cyclopropylpyridin-2-yl}sulfanyl)-2-phenylacetamide (80 mg, 36%) as a white solid. LCMS m/z=418.9 [M+H]$^+$. $^1$H NMR (400 MHz, DMSO) δ ppm 7.90 (br s, 1H), 7.55-7.47 (m, 2H), 7.43-7.25 (m, 4H), 5.58 (s, 1H), 4.01-3.70 (m, 3H), 3.65-3.44 (m, 3H), 2.16-1.92 (m, 3H), 1.80-1.65 (m, 1H), 1.17-1.08 (m, 2H), 0.96-0.90 (m, 2H).

Example 116

2-((3,5-Dicyano-4-ethyl-6-(2,9-diazaspiro[5.5]undecan-9-yl)pyridin-2-yl)thio)-2-phenylacetamide

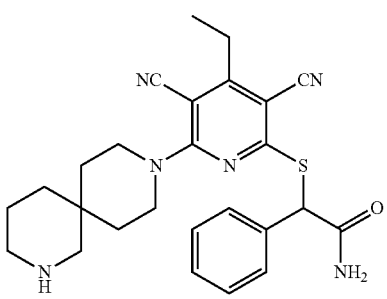 [SMILES: CCc1c(C#N)c(SC(C(N)=O)c2ccccc2)nc(N2CCC3(CCCNC3)CC2)c1C#N]

To a mixture of 2-[(6-bromo-3,5-dicyano-4-ethyl-2-pyridyl)sulfanyl]-2-phenyl-acetamide (synthesis described in example 6, step 1, 30 mg, 0.07 mmol) and tert-butyl 2,9-diazaspiro[5.5]undecane-2-carboxylate hydrochloride (24 mg, 0.08 mmol) in tetrahydrofuran (2 mL) was added triethylamine (0.03 mL, 0.22 mmol). The resulting mixture was stirred for 2 hours and was then diluted with EtOAc (20 mL), washed with water (3×20 mL) followed by saturated aqueous sodium chloride (25 mL), filtered through a hydrophobic frit, and the solvent removed under reduced pressure. The material was loaded onto SiO$_2$ (0.5 g) and purified by silica gel chromatography (4 g RediSep cartridge using 0-10% MeOH in CH$_2$Cl$_2$ as the eluent) to afford a colorless oil. The oil was dissolved in CH$_2$Cl$_2$ (2 mL), and trifluoroacetic acid (0.5 mL, 6.73 mmol) was added. The reaction mixture was stirred at room temperature for 0.5 hours, the solvent was removed under reduced pressure and the residue was triturated with diethyl ether and dried in vacuo at 50° C. Further purification by preparative HPLC afforded 2-[[3,5-dicyano-6-(2,9-diazaspiro[5.5]undecan-9-yl)-4-ethyl-2-pyridyl]sulfanyl]-2-phenyl-acetamide (13 mg, 37% yield) as a white solid. LCMS m/z=473 [M−H]$^−$. $^1$H NMR (300 MHz, DMSO-d$_6$) δ ppm 8.30 (s, 1H), 7.94 (s, 1H), 7.54-7.48 (m, 2H), 7.42-7.29 (m, 4H), 5.53 (s, 1H), 4.05-3.67 (m, 4H), 3.38 (br s, 2H), 2.78-2.71 (m, 4H), 1.61 (br s, 2H), 1.56-1.45 (m, 6H), 1.20 (t, J=7.6 Hz, 3H).

Example 117

2-((3,5-Dicyano-4-ethyl-6-(hexahydro-1H-pyrrolo[1,2-a][1,4]diazepin-2(3H)-yl)pyridin-2-yl)thio)-2-phenylacetamide

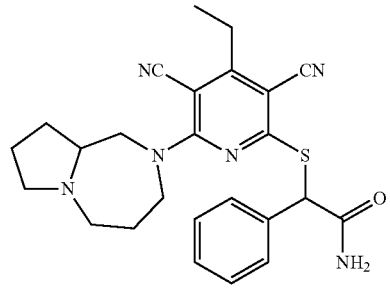 [SMILES: CCc1c(C#N)c(SC(C(N)=O)c2ccccc2)nc(N2CCCN3CCCC3C2)c1C#N]

To a mixture of 2-[(6-bromo-3,5-dicyano-4-ethyl-2-pyridyl)sulfanyl]-2-phenyl-acetamide (synthesis described in example 6, step 1, 30 mg, 0.07 mmol) and 2,3,4,5,7,8,9,9a-octahydro-1H-pyrrolo[1,2-a][1,4]diazepine (12 mg, 0.08 mmol) in tetrahydrofuran (2 mL) was added triethylamine (0.02 mL, 0.16 mmol) and the resulting mixture was stirred for 1 hour. Water (5 mL) was added and stirring was continued for 30 minutes before the precipitate was filtered, washed with water (3×10 mL) and dried in vacuo at 50° C. to afford a mixture of diastereomers of 2-((3,5-Dicyano-4-ethyl-6-(hexahydro-1H-pyrrolo[1,2-a][1,4]diazepin-2(3H)-yl)pyridin-2-yl)thio)-2-phenylacetamide (29 mg, 84% yield) as an off white powder. LCMS m/z=459 [M−H]$^−$. $^1$H NMR (300 MHz, DMSO-d$_6$) δ ppm 7.99-7.86 (m, 1H), 7.48-7.25 (m, 6H), 5.50-5.40 (m, 1H), 4.72-4.47 (m, 1H), 4.37-3.99 (m, 2H), 3.96-3.67 (m, 2H), 3.69-3.40 (m, 3H), 3.14-2.90 (m, 2H), 2.85-2.65 (m, 2H), 2.30-2.15 (m, 1H), 2.10 (br s, 2H), 2.02-1.60 (m, 2H), 1.20-1.13 (m, 3H).

Example 118

2-((3,5-Dicyano-4-ethyl-6-(2-methyl-2,9-diazaspiro[5.5]undecan-9-yl)pyridin-2-yl)thio)-2-phenylacetamide

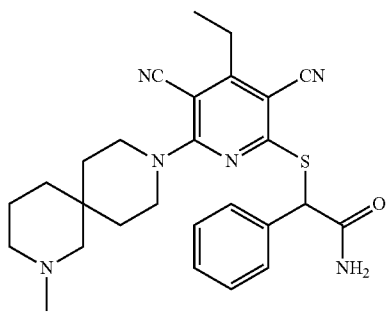 [SMILES: CCc1c(C#N)c(SC(C(N)=O)c2ccccc2)nc(N2CCC3(CCCN(C)C3)CC2)c1C#N]

To a mixture of 2-[(6-bromo-3,5-dicyano-4-ethyl-2-pyridyl)sulfanyl]-2-phenyl-acetamide (synthesis described in example 6, step 1, 30 mg, 0.07 mmol) and 2-methyl-2,9-diazaspiro[5.5]undecane hydrochloride (17 mg, 0.08 mmol) in tetrahydrofuran (2 mL) was added triethylamine (0.03 mL, 0.22 mmol) and the resultant mixture was stirred for 18 hours. The mixture was diluted with EtOAc (20 mL), washed with water (3×20 mL), saturated sodium chloride (25 mL), filtered through a hydrophobic frit and the solvent removed under reduced pressure. The crude product was purified by preparative HPLC to afford a mixture of diastereoisomers of 2-[[3,5-dicyano-4-ethyl-6-(2-methyl-2,9-diazaspiro[5.5]undecan-9-yl)-2-pyridyl]sulfanyl]-2-phenyl-acetamide (15 mg, 41% yield) as a white powder. LCMS m/z=487.3 [M−H]−. 1H NMR (300 MHz, DMSO-d$_6$) δ ppm 7.91 (s, 1H), 7.54-7.48 (m, 2H), 7.42-7.29 (m, 4H), 5.53 (s, 1H), 3.95-3.84 (m, 2H), 3.84-3.70 (m, 2H), 2.80-2.70 (m, 2H), 2.32-2.19 (m, 4H), 2.15 (s, 3H), 1.73-1.43 (m, 6H), 1.33 (br s, 2H), 1.20 (t, J=7.6 Hz, 3H).

Example 119

2-((3,5-Dicyano-6-(2-(cyclopropylmethyl)-2,9-diazaspiro[5.5]undecan-9-yl)-4-ethylpyridin-2-yl)thio)-2-phenylacetamide hydrochloride

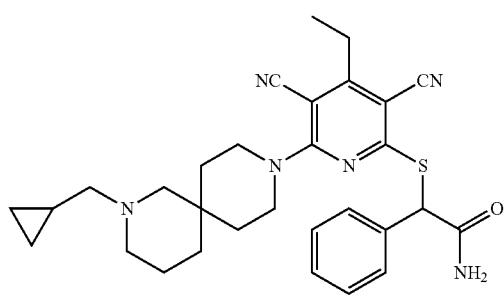 [SMILES: CCc1c(C#N)c(SC(C(N)=O)c2ccccc2)nc(N2CCC3(CCCN(CC4CC4)C3)CC2)c1C#N]

To a mixture of 2-[(6-bromo-3,5-dicyano-4-ethyl-2-pyridyl)sulfanyl]-2-phenyl-acetamide (synthesis described in example 6, step 1, 27 mg, 0.07 mmol) and 2-(cyclopropylmethyl)-2,9-diazaspiro[5.5]undecane dihydrochloride (21 mg, 0.07 mmol) in tetrahydrofuran (2 mL) was added triethylamine (0.04 mL, 0.27 mmol). The reaction mixture was stirred for 18 hours before diluting with EtOAc (20 mL), washing with water (3×20 mL), saturated sodium chloride solution (25 mL), filtering through a hydrophobic frit and removing the solvent under reduced pressure. The crude product was purified by preparative HPLC, and the resulting residue was dissolved in DCM, filtered through a hydrophobic frit, and the solvent removed under reduced pressure. The subsequent residue was dissolved in MeOH (2 mL) and methanolic HCl (3 M, 0.4 mL) was added. The solvent was removed and the desired product was triturated with diethyl ether and dried in vacuo at 50° C. to afford 2-[[3,5-dicyano-6-[2-(cyclopropylmethyl)-2,9-diazaspiro[5.5]undecan-9-yl]-4-ethyl-2-pyridyl]sulfanyl]-2-phenylacetamide hydrochloride (18 mg, 47% yield) as a white powder. LCMS m/z=527.4 [M−H]−. 1H NMR (300 MHz, DMSO-d$_6$) δ ppm 9.35 (br s, 1H), 7.96 (s, 1H), 7.55-7.49 (m, 2H), 7.47-7.27 (m, 4H), 5.54 (s, 1H), 4.06-3.88 (m, 2H), 3.88-3.71 (m, 2H), 3.60-3.43 (m, 2H), 3.17-3.01 (m, 1H), 2.93-2.71 (m, 5H), 2.06-1.74 (m, 6H), 1.48 (br s, 2H), 1.36-1.27 (m, 1H), 1.21 (t, J=7.6 Hz, 3H), 0.66 (br d, J=7.8 Hz, 2H), 0.54-0.30 (m, 2H).

Example 120

2-((3,5-Dicyano-6-(4-(3-(dimethylamino)propyl)piperazin-1-yl)-4-ethylpyridin-2-yl)thio-2-phenylacetamide

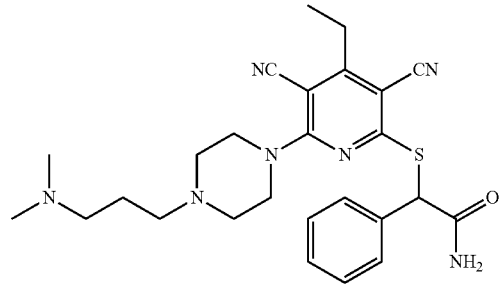 [SMILES: CCc1c(C#N)c(SC(C(N)=O)c2ccccc2)nc(N2CCN(CCCN(C)C)CC2)c1C#N]

To a mixture of 2-[(6-bromo-3,5-dicyano-4-ethyl-2-pyridyl)sulfanyl]-2-phenyl-acetamide (synthesis described in example 6, step 1, 30 mg, 0.07 mmol) and N,N-dimethyl-3-piperazin-1-yl-propan-1-amine (15 mg, 0.09 mmol) in tetrahydrofuran (2 mL) was added triethylamine (0.02 mL, 0.16 mmol) and the reaction mixture was allowed to stir at room temperature for 72 hours. The product mixture was diluted with ethyl acetate (20 mL), washed with water (3×20 mL), saturated sodium chloride (25 mL), filtered through a hydrophobic frit and the solvent was removed under reduced pressure. The crude product was purified by silica gel chromatography (4 g RediSep cartridge using 0-10% (methanol containing 5% ammonia) in dichloromethane as the eluent) followed by trituration of the isolated product with diethyl ether and subsequent drying in vacuo to afford 2-((3,5-dicyano-6-(4-(3-(dimethylamino)propyl)piperazin-1-yl)-4-ethylpyridin-2-yl)thio)-2-phenylacetamide (20 mg, 54% yield) as a white solid. LCMS m/z=490.3 [M−H]−. 1H NMR (300 MHz, DMSO-d$_6$) δ ppm 7.91 (s, 1H), 7.54-7.49 (m, 2H), 7.42-7.31 (m, 4H), 5.53 (s, 1H), 3.92-3.81 (m, 4H), 2.80-2.71 (m, 2H), 2.47-2.45 (m, 2H), 2.40-2.24 (m, 6H), 2.22 (s, 6H), 1.67-1.57 (m, 2H), 1.20 (t, J=7.5 Hz, 3H).

Example 121

2-((3,5-Dicyano-4-ethyl-6-(4-(pyrrolidin-3-yl)piperidin-1-yl)pyridin-2-yl)thio)-2-phenylacetamide; 2,2,2-trifluoroacetic acid

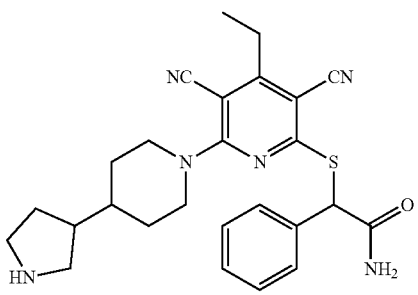 [SMILES: CCc1c(C#N)c(SC(C(N)=O)c2ccccc2)nc(N2CCC(C3CCNC3)CC2)c1C#N]

To a mixture of 2-[(6-bromo-3,5-dicyano-4-ethyl-2-pyridyl)sulfanyl]-2-phenyl-acetamide (synthesis described in example 6, step 1, 27 mg, 0.07 mmol) and tert-butyl 3-(4-piperidyl)pyrrolidine-1-carboxylate (19 mg, 0.07 mmol) in tetrahydrofuran (2 mL) was added triethylamine (0.02 mL, 0.15 mmol). The reaction mixture was stirred for 1 hour. The mixture was diluted with ethyl acetate (20 mL), washed with water (3×20 mL), saturated sodium chloride (25 mL), filtered through a hydrophobic frit and the solvent removed under reduced pressure. The crude product was purified by silica gel chromatography (4 g RediSep cartridge, using 0-10% methanol in dichloromethane as eluent). The resulting residue was dissolved in dichloromethane (2 mL), trifluoroacetic acid (0.5 mL, 6.73 mmol) was added, and the subsequent mixture was stirred at ambient temperature for 0.5 hour. The solvent was removed under reduced pressure and the product was triturated with diethyl ether, dried in vacuo at 50° C. to furnish 2-[[3,5-dicyano-4-ethyl-6-(4-pyrrolidin-3-yl)-1-piperidyl)-2-pyridyl]sulfanyl]-2-phenyl-acetamide; 2,2,2-trifluoroacetic acid (34 mg, 86% yield) as a yellow solid. LCMS m/z=473.3 [M−H]−. 1H NMR (300 MHz, DMSO-d6) δ ppm 8.67 (br s, 2H), 7.92 (s, 1H), 7.55-7.49 (m, 2H), 7.43-7.30 (m, 4H), 5.53 (s, 1H), 4.69-4.47 (m, 2H), 3.42-3.17 (m, 3H), 3.24-2.95 (m, 4H), 2.85-2.71 (m, 3H), 2.15-1.88 (m, 2H), 1.87-1.71 (m, 2H), 1.63-1.47 (m, 2H), 1.21 (t, J=7.6 Hz, 3H).

Example 122

2-((6-([4,4'-Bipiperidin]-1-yl)-3,5-dicyano-4-ethylpyridin-2-yl)thio)-2-phenylacetamide; 2,2,2-trifluoroacetic acid

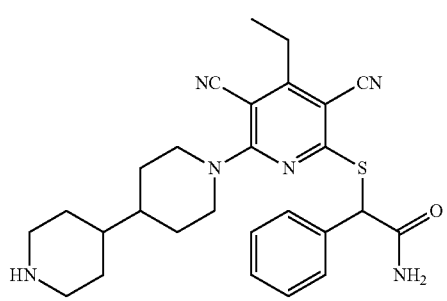 [SMILES: CCc1c(C#N)c(SC(C(N)=O)c2ccccc2)nc(N2CCC(C3CCNCC3)CC2)c1C#N]

To a mixture of 2-[(6-bromo-3,5-dicyano-4-ethyl-2-pyridyl)sulfanyl]-2-phenyl-acetamide (synthesis described in example 6, step 1, 25 mg, 0.06 mmol) and tert-butyl 4-(4-piperidyl)piperidine-1-carboxylate (18 mg, 0.07 mmol) in tetrahydrofuran (2 mL) was added triethylamine (0.02 mL, 0.12 mmol). The resulting mixture was stirred for 3 hours. The product mixture was diluted with ethyl acetate (20 mL), washed with water (3×20 mL), saturated sodium chloride solution (25 mL), filtered through a hydrophobic frit, and the solvent removed under reduced pressure. The crude product was dissolved in dichloromethane, absorbed onto silica gel (0.5 g) and purified by silica gel chromatography (4 g RediSep cartridge, using 0-10% methanol in dichloromethane as the eluent). The recovered residue was dissolved in dichloromethane (2 mL) and trifluoroacetic acid (0.5 mL, 6.73 mmol) was added. The reaction was stirred for 30 minutes at room temperature, and concentrated. The resulting residue was triturated with diethyl ether and dried in vacuo at 50° C. to afford 2-[[3,5-dicyano-4-ethyl-6-[4-(4-piperidyl)-1-piperidyl]-2-pyridyl]sulfanyl]-2-phenyl-acetamide; 2,2,2-trifluoroacetic acid (30 mg, 80% yield) as a white solid. LCMS: 487.3 [M−H]−. 1H NMR (300 MHz, DMSO-d6) δ ppm 8.44 (br s, 1H), 8.25-8.04 (m, 1H), 7.92 (s, 1H), 7.57-7.47 (m, 2H), 7.45-7.27 (m, 4H), 5.54 (s, 1H), 4.73-4.53 (m, 2H), 3.30-3.22 (m, 2H), 3.21-2.97 (m, 2H), 2.88-2.68 (m, 4H), 1.90-1.75 (m, 4H), 1.62-1.40 (m, 2H), 1.42-1.25 (m, 4H), 1.20 (t, J=7.6 Hz, 3H).

Example 123

2-((6-(4-(2-Aminoethyl)piperazin-1-yl)-3,5-dicyano-4-ethylpyridin-2-yl)thio)-2-phenylacetamide

Step 1: tert-Butyl (2-(4-benzylpiperazin-1-yl)ethyl)carbamate

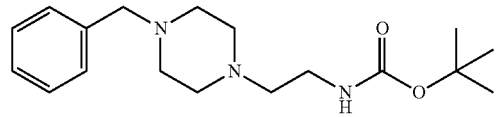 [SMILES: CC(C)(C)OC(=O)NCCN1CCN(Cc2ccccc2)CC1]

To a solution of 1-benzylpiperazine (500 mg, 2.84 mmol) in acetonitrile (30 mL) was added tert-butyl (2-bromoethyl)carbamate (950 mg, 4.26 mmol) and K2CO3 (784 mg, 5.68 mmol). The mixture was stirred at 70° C. for 12 hours then concentrated under vacuum and purified by silica gel column chromatography (DCM:MeOH 20:1) to give tert-butyl (2-(4-benzylpiperazin-1-yl)ethyl) (730 mg, 81%) as an oil. LCMS m/z=320.0 [M+H]+.

Step 2: tert-Butyl (2-(4-(6-chloro-3,5-dicyano-4-ethylpyridin-2-yl)piperazin-1-yl)ethyl)carbamate

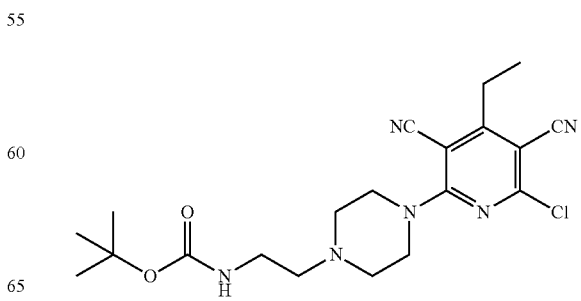

To a solution of tert-butyl (2-(4-benzylpiperazin-1-yl)ethyl)carbamate (730 mg, 2.3 mmol) in MeOH (20 mL) was added Pd/C (73 mg). The mixture was stirred at room temperature under a hydrogen atmosphere overnight. The mixture was filtered and the filtrate was concentrated under vacuum to give 400 mg of a residue. To a solution of 2,6-dichloro-4-ethylpyridine-3,5-dicarbonitrile (synthesis described in example 3, step 2, 393 mg, 1.75 mmol) in N,N-dimethylformamide (15 mL) at room temperature was added the residue above and Et$_3$N (0.24 mL 1.75 mmol). The mixture was stirred at room temperature for 5 minutes, then diluted with water, and extracted with EtOAc. The combined organic layers were washed with water and brine, concentrated under vacuum, and purified by silica gel column chromatography (petroleum ether:ethyl acetate 40:60) to give tert-butyl (2-(4-(6-chloro-3,5-dicyano-4-ethylpyridin-2-yl)piperazin-1-yl)ethyl)carbamate (560 mg, 77%). LCMS m/z=419.0 [M+H]$^+$.

Step 3: tert-Butyl (2-(4-(6-((2-amino-2-oxo-1-phenylethyl)thio)-3,5-dicyano-4-ethylpyridin-2-yl)piperazin-1-yl)ethyl)carbamate

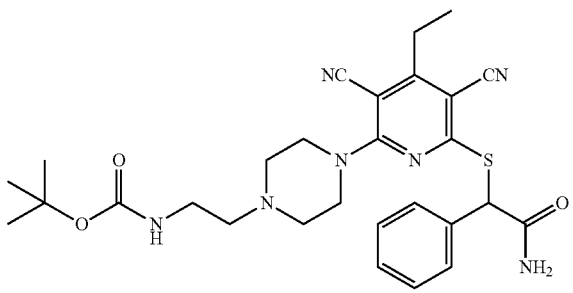 [SMILES: CCc1c(C#N)c(SC(C(N)=O)c2ccccc2)nc(N2CCN(CCNC(=O)OC(C)(C)C)CC2)c1C#N]

A solution of tert-butyl (2-(4-(6-chloro-3,5-dicyano-4-ethylpyridin-2-yl)piperazin-1-yl)ethyl)carbamate (300 mg, 0.72 mmol) and KSAc (98 mg, 0.86 mmol) in N,N-dimethylformamide (8 mL) was stirred at room temperature for 30 minutes then 2-amino-2-oxo-1-phenylethyl methanesulfonate (synthesis described in example 3, step 5, 197 mg, 0.86 mmol) and Et$_3$N (0.2 mL, 1.44 mmol) were added to the solution. The mixture was stirred at room temperature overnight then diluted with water. The precipitated solid was collected by filtration and purified by silica gel column chromatography (DCM:MeOH 20:1) to give tert-butyl (2-(4-(6-((2-amino-2-oxo-1-phenylethyl)thio)-3,5-dicyano-4-ethylpyridin-2-yl)piperazin-1-yl)ethyl)carbamate (210 mg, 53%). LCMS m/z=549.8 [M+H]$^+$.

Step 4: 2-((6-(4-(2-Aminoethyl)piperazin-1-yl)-3,5-dicyano-4-ethylpyridin-2-yl)thio)-2-phenylacetamide

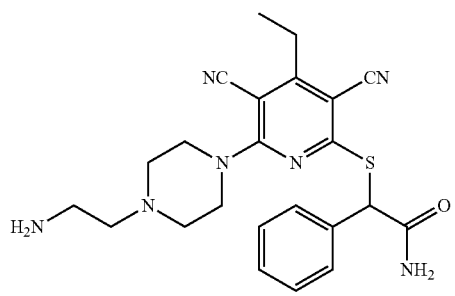 [SMILES: CCc1c(C#N)c(SC(C(N)=O)c2ccccc2)nc(N2CCN(CCN)CC2)c1C#N]

To a solution of tert-butyl (2-(4-(6-((2-amino-2-oxo-1-phenylethyl)thio)-3,5-dicyano-4-ethylpyridin-2-yl)piperazin-1-yl)ethyl)carbamate (210 mg, 0.38 mmol) in DCM (4 mL) at room temperature was added trifluoroacetic acid (3 mL). The mixture was stirred at room temperature overnight then concentrated under vacuum, neutralized with saturated aqueous sodium bicarbonate solution, and extracted with DCM. The organic layer was washed with brine, concentrated under vacuum, and purified by silica gel column chromatography (DCM:MeOH 5:1) to give 2-((6-(4-(2-aminoethyl)piperazin-1-yl)-3,5-dicyano-4-ethylpyridin-2-yl)thio)-2-phenylacetamide (135 mg, 79%). LCMS m/z=449.8 [M+H]$^+$. $^1$H NMR (400 MHz, CD$_3$OD) δ ppm 7.57-7.53 (m, 2H), 7.45-7.37 (m, 3H), 5.50 (s, 1H), 4.06-3.96 (m, 4H), 3.12-3.06 (m, 2H), 2.92 (q, J=7.6 Hz, 2H), 2.70-2.62 (m, 6H), 1.32 (t, J=7.6 Hz, 3H). 4H not observed.

Example 124

2-((6-(4-(3-Aminopropyl)piperazin-1-yl)-3,5-dicyano-4-cyclopropylpyridin-2-yl)thio)-2-phenylacetamide Step 1: tert-Butyl 4-(6-((2-amino-2-oxo-1-phenylethyl)thio)-3,5-dicyano-4-cyclopropylpyridin-2-yl)piperazine-1-carboxylate

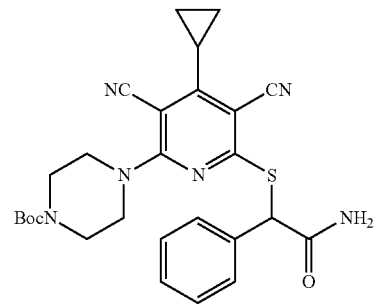 [SMILES: CC(C)(C)OC(=O)N1CCN(c2nc(SC(C(N)=O)c3ccccc3)c(C#N)c(C3CC3)c2C#N)CC1]

A mixture of tert-butyl 4-(6-chloro-3,5-dicyano-4-cyclopropylpyridin-2-yl)piperazine-1-carboxylate (synthesis described in example 30, step 1, 1.2 g, 3.1 mmol) and potassium thioacetate (423 mg, 3.71 mmol) in N,N-dimethylformamide (25 mL) was stirred at room temperature for 30 minutes, then 2-amino-2-oxo-1-phenylethyl methanesulfonate (synthesis described in example 3, step 5, 850 mg, 3.71 mmol) and Et$_3$N (939 mg, 9.3 mmol) were added to the reaction. The mixture was stirred at room temperature for 12 hours, then poured into water (100 mL), and extracted with EtOAc (100 mL×2). The combined organic layers were dried and concentrated. The remaining residue was purified by silica gel column chromatography (MeOH:CH$_2$Cl$_2$ 1:80) to give tert-butyl 4-(6-((2-amino-2-oxo-1-phenylethyl)thio)-3,5-dicyano-4-cyclopropylpyridin-2-yl)piperazine-1-carboxylate (1.45 g, 90%) as a brown oil. LCMS m/z=518.9 [M+H]$^+$.

Step 2: 2-((3,5-Dicyano-4-cyclopropyl-6-(piperazin-1-yl)pyridin-2-yl)thio)-2-phenylacetamide

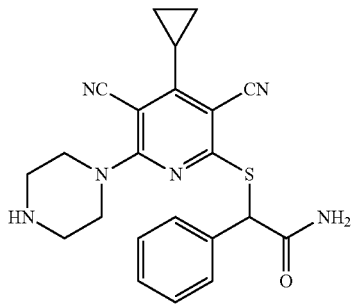 [SMILES: N#Cc1c(SC(C(N)=O)c2ccccc2)nc(N2CCNCC2)c(C#N)c1C1CC1]

A mixture of tert-butyl 4-(6-((2-amino-2-oxo-1-phenylethyl)thio)-3,5-dicyano-4-cyclopropylpyridin-2-yl)piperazine-1-carboxylate (1.45 g, 2.79 mmol) and trifluoroacetic acid (2 mL) in dichloromethane (6 mL) was stirred at room temperature for 12 hours. After the reaction mixture was concentrated, the remaining residue was poured into water (100 mL), basified with saturated NaHCO$_3$ solution to pH 9, and extracted with DCM (100 mL×2). The combined organic layers were dried, and concentrated to give 2-((3,5-dicyano-4-cyclopropyl-6-(piperazin-1-yl)pyridin-2-yl)thio)-2-phenylacetamide (1.0 g, 85%) as a white solid. LCMS m/z=419.0 [M+H]$^+$.

Step 3: tert-Butyl (3-(4-(6-((2-amino-2-oxo-1-phenylethyl)thio)-3,5-dicyano-4-cyclopropylpyridin-2-yl)piperazin-1-yl)propyl)carbamate

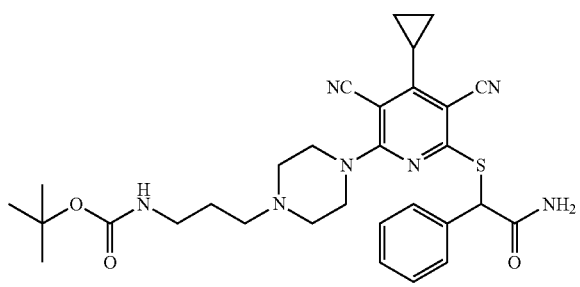 [SMILES: CC(C)(C)OC(=O)NCCCN1CCN(c2nc(SC(C(N)=O)c3ccccc3)c(C#N)c(C3CC3)c2C#N)CC1]

A mixture of 2-((3,5-dicyano-4-cyclopropyl-6-(piperazin-1-yl)pyridin-2-yl)thio)-2-phenylacetamide (500 mg, 1.19 mmol), tert-butyl (3-bromopropyl)carbamate (341 mg, 1.43 mmol), K$_2$CO$_3$ (328 mg, 2.38 mmol) in acetonitrile (10 mL) was stirred at 70° C. for 12 hours. The reaction mixture was concentrated and the remaining residue purified by silica gel column chromatography (CH$_2$Cl$_2$:methanol 30:1) to give tert-butyl (3-(4-(6-((2-amino-2-oxo-1-phenylethyl)thio)-3,5-dicyano-4-cyclopropylpyridin-2-yl)piperazin-1-yl)propyl)carbamate (200 mg, 29% yield) as a brown oil. LCMS m/z=576.0 [M+H]$^+$.

Step 4: 2-((6-(4-(3-Aminopropyl)piperazin-1-yl)-3,5-dicyano-4-cyclopropylpyridin-2-yl)thio)-2-phenylacetamide

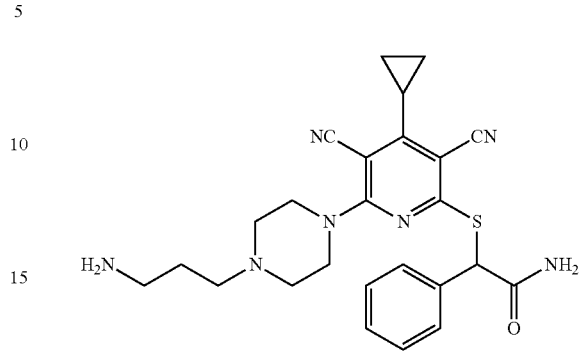

A mixture of tert-butyl (3-(4-(6-((2-amino-2-oxo-1-phenylethyl)thio)-3,5-dicyano-4-cyclopropylpyridin-2-yl)piperazin-1-yl)propyl)carbamate (200 mg, 0.34 mmol) and trifluoroacetic acid (1 mL) in dichloromethane (5 mL) was stirred at room temperature for 12 hours. The reaction mixture was concentrated. The residue was poured into water (50 mL), made basic by the addition of saturated aqueous sodium bicarbonate solution, and extracted with CH$_2$Cl$_2$ (50 mL×2). The combined organic layers were dried and concentrated. The remaining residue was purified by silica gel column chromatography (CH$_2$Cl$_2$:methanol 30:1) to give 2-((6-(4-(3-aminopropyl)piperazin-1-yl)-3,5-dicyano-4-cyclopropylpyridin-2-yl)thio)-2-phenylacetamide (80 mg, 48% yield) as a white solid. LCMS m/z=475.9 [M+H]$^+$. $^1$H NMR (400 MHz, CD3OD) δ ppm 7.63-7.55 (m, 2H), 7.46-7.36 (m, 3H), 5.57 (s, 1H), 4.55-3.55 (m, 4H), 3.33-2.99 (m, 8H), 2.25-2.10 (m, 3H), 1.30-1.23 (m, 2H), 1.16-1.07 (m, 2H). 4H not observed.

Example 125

2-((3,5-Dicyano-4-cyclopropyl-6-(4-((4-methylpiperazin-1-yl)methyl)piperidin-1-yl)pyridin-2-yl)thio-2-phenylacetamide trifluoroacetate

Step 1: 2-Chloro-4-cyclopropyl-6-(4-((4-methylpiperazin-1-yl)methyl)piperidin-1-yl)pyridine-3,5-dicarbonitrile

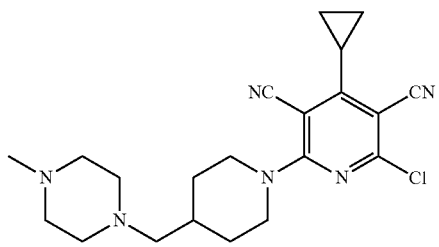 [SMILES: CN1CCN(CC2CCN(c3nc(Cl)c(C#N)c(C4CC4)c3C#N)CC2)CC1]

2,6-Dichloro-4-cyclopropylpyridine-3,5-dicarbonitrile (synthesis described in example 4, step 2, 500 mg, 2.1 mmol) and 1-methyl-4-(piperidin-4-ylmethyl)piperazine (500 mg, 2.5 mmol) were dissolved in dichloromethane (100 mL) and triethylamine (250 mg, 2.5 mmol) was added. The reaction mixture was stirred at ambient temperature for one hour. The mixture was washed with brine (2×100 mL) dried over anhydrous sodium sulfate and concentrated under reduced pressure to afford the title compound (700 mg, 1.8 mmol). LCMS m/z=398.8 [M+H]+.

Step 2: 4-Cyclopropyl-2-mercapto-6-(4-((4-methylpiperazin-1-yl)methyl)piperidin-1-yl)pyridine-3,5-dicarbonitrile

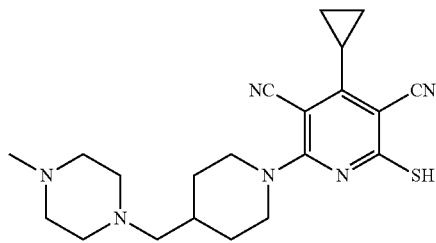 [SMILES: CN1CCN(CC2CCN(c3nc(S)c(C#N)c(C4CC4)c3C#N)CC2)CC1]

To a solution of 2-chloro-4-cyclopropyl-6-(4-((4-methylpiperazin-1-yl)methyl)piperidin-1-yl)pyridine-3,5-dicarbonitrile (700 mg, 1.8 mmol) in N,N-dimethylformamide (20 mL) was added potassium thioacetate (208 mg, 1.8 mmol). The mixture was stirred for 3 hours, then the mixture was diluted with ethyl acetate (200 mL) and washed with brine (2×100 mL), dried over anhydrous sodium sulfate and concentrated under reduced pressure to afford the title compound (700 mg, 1.8 mmol). LCMS m/z=396.9 [M+H]+.

Step 3: 2-((3,5-Dicyano-4-cyclopropyl-6-(4-((4-methylpiperazin-1-yl)methyl)piperidin-1-yl)pyridin-2-yl)thio)-2-phenylacetamide trifluoroacetate

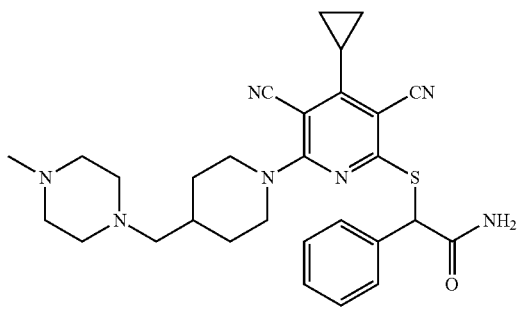 [SMILES: CN1CCN(CC2CCN(c3nc(SC(C(N)=O)c4ccccc4)c(C#N)c(C4CC4)c3C#N)CC2)CC1]

4-Cyclopropyl-2-mercapto-6-(4-((4-methylpiperazin-1-yl)methyl)piperidin-1-yl)pyridine-3,5-dicarbonitrile (700 mg, 1.7 mmol) was dissolved in N,N-dimethylformamide (50 mL) and then 2-amino-2-oxo-1-phenylethyl methanesulfonate (synthesis described in example 3, step 5, 500 mg, 1.9 mmol) and potassium carbonate (300 mg, 1.9 mmol) were added. The reaction mixture was stirred overnight at room temperature. Then the mixture was diluted with ethyl acetate (200 mL), washed with brine (2×100 mL), dried over sodium sulfate and concentrated under reduced pressure. The residue was purified by prep-HPLC to give the title compound (200 mg, 17.3%). LCMS m/z=529.8 [M+H]+. 1H-NMR (400 MHz, methanol-$d_4$) δ ppm 7.54 (dd, J=7.9, 1.4 Hz, 2H), 7.45-7.35 (m, 3H), 5.51 (s, 1H), 4.66 (t, J=14.1 Hz, 2H), 3.41 (s, 4H), 3.18 (td, J=12.4, 6.2 Hz, 2H), 3.05 (s, 3H), 2.92 (s, 3H), 2.64 (d, J=7.1 Hz, 2H), 2.16-1.92 (m, 4H), 1.43-1.29 (m, 3H), 1.28-1.21 (m, 2H), 1.14-1.03 (m, 2H). 2H not observed.

Example 126

2-((6-(4-Acetylpiperazin-1-yl)-3,5-dicyano-4-ethylpyridin-2-yl)thio)-2-phenylacetamide

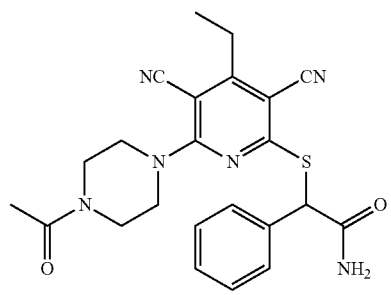 [SMILES: CCc1c(C#N)c(SC(C(N)=O)c2ccccc2)nc(N2CCN(C(C)=O)CC2)c1C#N]

A solution of 2-[(6-bromo-3,5-dicyano-4-ethyl-2-pyridyl)sulfanyl]-2-phenyl-acetamide, (synthesis described in example 6, step 1, 21 mg, 0.05 mmol) in tetrahydrofuran (2 mL) was treated with 1-acetylpiperazine (20 mg, 0.16 mmol) and stirred at ambient temperature for 18 hours. The reaction mixture was dry loaded onto silica gel (0.9 g) and purified by silica gel chromatography (4 g RediSep cartridge, eluting with 0-5% MeOH in $CH_2Cl_2$) to afford 2-[[6-(4-acetylpiperazin-1-yl)-3,5-dicyano-4-ethyl-2-pyridyl]sulfanyl]-2-phenyl-acetamide (22 mg, 0.049 mmol, 94% yield), as a white solid. LCMS m/z=449 [M+H]+. 1H NMR (300 MHz, DMSO-$d_6$) δ ppm 7.91 (s, 1H), 7.55-7.30 (m, 6H), 5.54 (s, 1H), 4.05-3.79 (m, 4H), 3.67-3.53 (m, 4H), 2.78 (q, J=7.6 Hz, 2H), 2.06 (s, 3H), 1.17 (t, J=7.3 Hz, 3H).

Example 127

2-((3,5-Dicyano-4-cyclopropyl-6-(dimethylamino)pyridin-2-yl)thio)-2-phenylacetamide

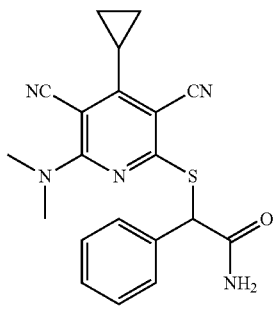 [SMILES: CN(C)c1nc(SC(C(N)=O)c2ccccc2)c(C#N)c(C2CC2)c1C#N]

A stirred suspension of 2-[(6-amino-3,5-dicyano-4-cyclopropyl-2-pyridyl)sulfanyl]-2-phenyl-acetamide (synthesis described in example 51, step 2, 200 mg, 0.57 mmol) in dry acetonitrile (10 mL) was treated with copper(II) bromide (217 mg, 0.97 mmol) and tert-butylnitrite (0.12 mL, 1 mmol) then heated to 70° C. for 20 minutes under an atmosphere of nitrogen gas. The reaction mixture was then cooled, loaded directly onto silica gel (1.2 g) and purified by silica gel chromatography (4 g RediSep cartridge, eluting with 20-100% EtOAc in isohexane) to give 92 mg of a crude pale green solid which appeared to be degrading and unstable. A solution of the crude solid (35 mg) in tetrahydrofuran (4 mL) and ethanol (1 mL) was treated with dimethylamine solution (2 M in methanol, 0.01 mL, 0.21 mmol) and stirred at ambient temperature for 30 minutes. The product mixture was concentrated under reduced pressure and the remaining residue purified by preparative HPLC to furnish 2-[[3,5-dicyano-4-cyclopropyl-6-(dimethylamino)-2-pyridyl]sulfanyl]-2-phenyl-acetamide (7.2 mg), as a cream solid. LCMS m/z=376.1 [M–H]⁻. ¹H NMR (300 MHz, DMSO-d₆) δ ppm 7.90 (s, 1H), 7.55-7.47 (m, 2H), 7.47-7.22 (m, 4H), 5.58 (s, 1H), 3.31 (s, 6H), 2.28-1.95 (m, 1H), 1.24-0.87 (m, 4H).

Example 128

2-(4-Chlorophenyl)-2-((3,5-dicyano-6-(dimethylamino)-4-ethylpyridin-2-yl)thio)acetamide

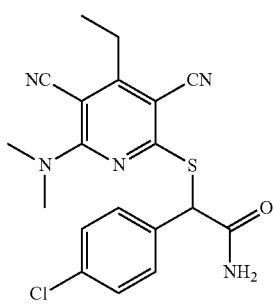 [SMILES: CCc1c(C#N)c(SC(C(N)=O)c2ccc(Cl)cc2)nc(N(C)C)c1C#N]

To a suspension of 2-(4-chlorophenyl)-2-hydroxy-acetic acid (250 mg, 1.34 mmol) in DCE (10 mL) was added thionyl chloride (0.29 mL, 4.02 mmol) at ambient temperature and the reaction mixture was heated at reflux for 1 hour. The product mixture was concentrated under reduced pressure to furnish crude 2-chloro-2-(4-chlorophenyl)acetyl chloride (244 mg) as a cream solid which was not purified. The cream solid (240 mg) was dissolved in ammonium hydroxide solution (10 mL, 157.66 mmol) at ambient temperature and the reaction mixture was heated at reflux until evolution of HCl gas ceased. The product mixture was concentrated under reduced pressure and triturated with diethyl ether to afford 2-chloro-2-(4-chlorophenyl)acetamide (78 mg) as a cream solid which was not well characterized due to instability. 2-(Dimethylamino)-4-ethyl-6-sulfanyl-pyridine-3,5-dicarbonitrile (synthesis described in example 92, step 3, 25 mg, 0.11 mmol) was dissolved in N,N-dimethylformamide (10 mL) followed by the addition of 2-chloro-2-(4-chlorophenyl)acetamide, (24 mg, 0.12 mmol) and then sodium hydrogen carbonate (20 mg, 0.24 mmol). The reaction mixture was allowed to stir at ambient temperature for 16 hours. The product mixture was diluted with water and the resultant precipitate was washed with water followed by diethyl ether under reduced pressure to furnish 2-(4-chlorophenyl)-2-[[3,5-dicyano-6-(dimethylamino)-4-ethyl-2-pyridyl]sulfanyl]acetamide (13 mg, 0.0325 mmol), as a cream solid. LCMS m/z=398.1 [M–H]⁻. ¹H NMR (300 MHz, CDCl₃) δ ppm 7.44-7.36 (m, 4H), 6.58 (br s, 1H), 5.48 (br s, 1H), 5.43 (s, 1H), 3.42 (s, 6H), 2.94 (q, J=7.7 Hz, 2H), 1.34 (t, J=7.6 Hz, 3H).

Example 129

2-((3,5-Dicyano-4-ethyl-6-(4-(2-hydroxyethyl)piperazin-1-yl)pyridin-2-yl)thio)-2-phenylacetamide

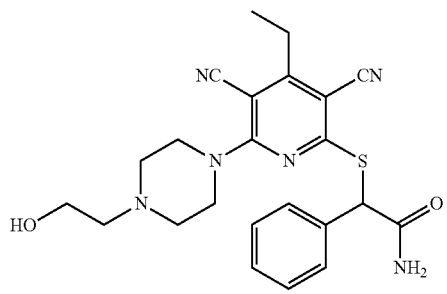 [SMILES: CCc1c(C#N)c(SC(C(N)=O)c2ccccc2)nc(N2CCN(CCO)CC2)c1C#N]

A solution of 2-[(6-bromo-3,5-dicyano-4-ethyl-2-pyridyl)sulfanyl]-2-phenyl-acetamide, (synthesis described in example 6, step 1, 15 mg, 0.04 mmol) in tetrahydrofuran (1 mL) was treated with 1-(2-hydroxyethyl)piperazine (0.012 mL, 0.09 mmol) and stirred at ambient temperature for 18 hours. The product mixture was dry loaded onto SiO₂ (0.9 g) and purified by silica gel chromatography (4 g RediSep cartridge eluting with 0-10% MeOH, 0-1% NH₃/CH₂Cl₂) to give 2-[[3,5-dicyano-4-ethyl-6-[4-(2-hydroxyethyl)piperazin-1-yl]-2-pyridyl]sulfanyl]-2-phenyl-acetamide (12 mg, 0.0266 mmol, 71% yield), as a white solid. LCMS m/z=451 [M+H]⁺. ¹H NMR (300 MHz, DMSO-d₆) δ ppm 7.92 (s, 1H), 7.52 (d, J=6.7 Hz, 2H), 7.45-7.28 (m, 4H), 5.53 (s, 1H), 4.59-4.40 (m, 1H), 3.98-3.76 (m, 4H), 3.66-3.44 (m, 2H), 2.75 (q, J=7.5 Hz, 2H), 2.48-2.40 (m, 6H), 1.20 (t, J=7.5 Hz, 3H).

Example 130

2-[(3,5-Dicyano-4-cyclopropyl-6-morpholino-2-pyridyl)sulfanyl]-2-phenyl-acetamide

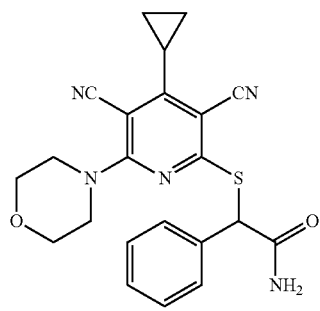 [SMILES: N#Cc1c(SC(C(N)=O)c2ccccc2)nc(N2CCOCC2)c(C#N)c1C1CC1]

A stirred suspension of 2-[(6-amino-3,5-dicyano-4-cyclopropyl-2-pyridyl)sulfanyl]-2-phenyl-acetamide (synthesis described in example 51, step 2, 200 mg, 0.57 mmol) in dry acetonitrile (10 mL) was treated with copper(II) bromide (217 mg, 0.97 mmol) and tert-butylnitrite (0.12 mL, 1 mmol) then heated to 70° C. for 20 minutes under an atmosphere of nitrogen gas. The reaction mixture was then cooled, loaded directly onto silica gel (1.2 g) and purified by silica gel chromatography (4 g RediSep cartridge, eluting with 20-100% EtOAc in isohexane) to give 92 mg of a crude pale green solid which appeared to be degrading and unstable. A solution of the crude solid (50 mg) in tetrahydrofuran (1 mL) and ethanol (0.5 mL) was treated with morpholine (0.03 mL, 0.29 mmol) and stirred at ambient temperature for 30 minutes. The product mixture was concentrated under reduced pressure and purified by preparative HPLC (high pH) to afford 2-[(3,5-dicyano-4-cyclopropyl-6-morpholino-2-pyridyl)sulfanyl]-2-phenyl-acetamide (8.8 mg, 0.0210 mmol), as an off-white solid. LCMS m/z=418.1 [M−H]−. 1H NMR (300 MHz, DMSO-d6) δ ppm 7.88 (s, 1H), 7.64-7.47 (m, 2H), 7.44-7.20 (m, 4H), 5.51 (s, 1H), 3.93-3.81 (m, 4H), 3.74-3.66 (m, 4H), 2.15-2.07 (m, 1H), 1.17-1.10 (m, 2H), 1.01-0.94 (m, 2H).

Example 131

2-((6-(4-Benzoylpiperazin-1-yl)-3,5-dicyano-4-ethylpyridin-2-yl)thio)-2-phenylacetamide

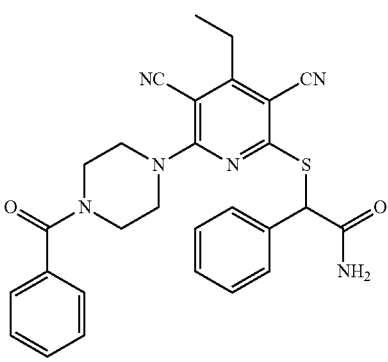 [SMILES: CCc1c(C#N)c(SC(C(N)=O)c2ccccc2)nc(N2CCN(C(=O)c3ccccc3)CC2)c1C#N]

A solution of 2-[(6-bromo-3,5-dicyano-4-ethyl-2-pyridyl)sulfanyl]-2-phenyl-acetamide, (synthesis described in example 6, step 1, 15 mg, 0.04 mmol) in tetrahydrofuran (1 mL) was treated with N-benzoylpiperazine (17.78 mg, 0.09 mmol) and stirred at ambient temperature for 18 hours. The product mixture was dry loaded onto SiO2 (0.9 g) and purified by silica gel chromatography (4 g RediSep cartridge eluting with 0-10% MeOH, 0-1% NH3/CH2Cl2) followed by trituration with diethyl ether to furnish 2-[[6-(4-benzoylpiperazin-1-yl)-3,5-dicyano-4-ethylpyrindin-2-yl)thio)-2-phenylacetamide (13 mg, 0.0255 mmol, 68% yield) as an off-white solid. LCMS m/z=509.1 [M−H]−. 1H NMR (300 MHz, DMSO-d6) δ ppm 7.87 (br s, 1H), 7.56-7.43 (m, 7H), 7.43-7.30 (m, 4H), 5.52 (s, 1H), 3.98 (br s, 4H), 3.77 (br s, 2H), 3.52 (br s, 2H), 2.78 (q, J=7.3 Hz, 2H), 1.22 (t, J=7.3 Hz, 3H).

Example 132

2-((3,5-Dicyano-4-ethyl-6-((5S,6S)-6-hydroxy-1-(methylsulfonyl)-1,8-diazaspiro[4.5]decan-8-yl)pyridin-2-yl)thio)-2-phenylacetamide

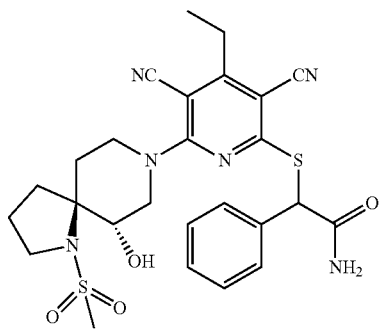 [SMILES: CCc1c(C#N)c(SC(C(N)=O)c2ccccc2)nc(N2CC[C@@]3(CCCN3S(C)(=O)=O)[C@@H](O)C2)c1C#N]

To a mixture of 2-[(6-bromo-3,5-dicyano-4-ethyl-2-pyridyl)sulfanyl]-2-phenyl-acetamide (synthesis described in example 6, step 1, 27 mg, 0.07 mmol) and (5S,6S)-1-methylsulfonyl-1,8-diazaspiro[4.5]decan-6-ol (17.34 mg, 0.07 mmol) in tetrahydrofuran (2 mL) was added triethylamine (0.02 mL, 0.15 mmol). The reaction mixture was stirred for 72 hours. The mixture was diluted with EtOAc (20 mL), washed with water (3×20 mL), brine (25 mL), filtered through a hydrophobic frit and the solvent was removed under reduced pressure. The residue was dissolved in DMSO and purified by preparative HPLC to afford 2-((3,5-dicyano-4-ethyl-6-((5S,6S)-6-hydroxy-1-(methylsulfonyl)-1,8-diazaspiro[4.5]decan-8-yl)pyridin-2-yl)thio)-2-phenylacetamide (4 mg, 11% yield) as a white powder. LCMS m/z=533.3 [M−H]−. 1H NMR (300 MHz, CDCl3) δ ppm 7.55-7.30 (m, 6H), 7.07 (br s, 1H), 5.80 (br s, 1H), 5.30 (s, 1H), 4.81 (dd, J=4.5, 10.8 Hz, 1H), 4.45-4.32 (m, 1H), 4.23-4.08 (m, 1H), 4.08-3.83 (m, 1H), 3.70-3.52 (m, 1H), 3.45-3.26 (m, 2H), 3.05 (s, 3H), 3.01-2.91 (m, 2H), 2.91-2.78 (m, 1H), 2.56-2.21 (m, 2H), 2.07-1.70 (m, 3H), 1.37 (t, J=7.6 Hz, 3H).

Example 133

2-((3,5-Dicyano-6-(4,4-difluoropiperidin-1-yl)-4-ethylpyridin-2-yl)thio)-2-phenylacetamide

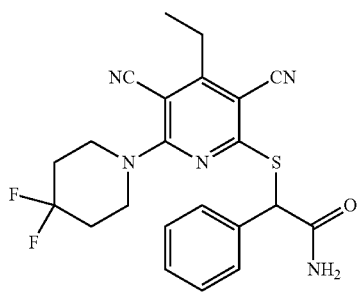

To a mixture of 2-[(6-bromo-3,5-dicyano-4-ethyl-2-pyridyl)sulfanyl]-2-phenyl-acetamide (synthesis described in example 6, step 1, 30 mg, 0.070 mmol) in tetrahydrofuran (2 mL) was added 4,4-difluoropiperidine hydrochloride (13 mg, 0.08 mmol) followed by triethylamine (0.023 mL, 0.16 mmol). The reaction mixture was stirred for 17 hours. The reaction mixture was diluted with ethyl acetate (20 mL), washed with water (3×20 mL), saturated aqueous sodium chloride solution (25 mL), filtered through a hydrophobic frit, and the solvent removed under reduced pressure. The resulting solid was triturated with diethyl ether and dried in vacuo at 50° C. to afford 2-[[3,5-dicyano-6-(4,4-difluoro-1-piperidyl)-4-ethyl-2-pyridyl]sulfanyl]-2-phenyl-acetamide (22 mg, 67%), as a yellow solid. LCMS m/z=440.2 [M−H]⁻. ¹H NMR (300 MHz, DMSO-d₆) δ ppm 7.91 (s, 1H), 7.59-7.47 (m, 2H), 7.46-7.30 (m, 4H), 5.53 (s, 1H), 3.96 (br t, J=5.5 Hz, 4H), 2.86-2.70 (m, 2H), 2.29-2.03 (m, 4H), 1.22 (t, J=7.6 Hz, 3H).

Example 134

(R)-2-((3,5-Dicyano-4-ethyl-6-((R)-3-hydroxypyrrolidin-1-yl)pyridin-2-yl)thio)-2-phenylacetamide Step1: (R)-2-Chloro-4-ethyl-6-(3-hydroxypyrrolidin-1-yl)pyridine-3,5-dicarbonitrile

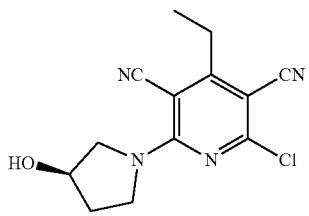 [SMILES: CCc1c(C#N)c(Cl)nc(N2CC[C@@H](O)C2)c1C#N]

To a solution of 2,6-dichloro-4-ethylpyridine-3,5-dicarbonitrile (synthesis described in example 3, step 2, 600 mg, 2.65 mmol) and (R)-pyrrolidin-3-ol (231 mg, 2.65 mmol) in N,N-dimethylformamide (15 mL) was added triethylamine (0.370 mL, 2.65 mmol). The reaction mixture was stirred at room temperature for 30 minutes. The mixture was poured into water (100 mL), and extracted with ethyl acetate (100 mL×2). The combined organic layers were dried and concentrated to give (R)-2-chloro-4-ethyl-6-(3-hydroxypyrrolidin-1-yl)pyridine-3,5-dicarbonitrile (560 mg, 76% yield) as a pale solid. LCMS m/z=277.0 [M+H]⁺.

Step 2: 2-((3,5-Dicyano-4-ethyl-6-((R)-3-hydroxypyrrolidin-1-yl)pyridin-2-yl)thio)-2-phenylacetamide

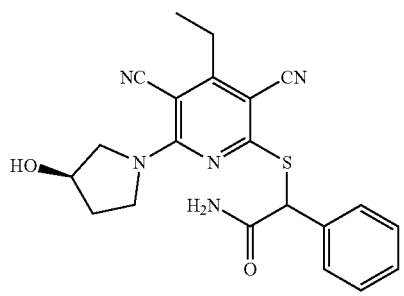 [SMILES: CCc1c(C#N)c(SC(C(N)=O)c2ccccc2)nc(N2CC[C@@H](O)C2)c1C#N]

A solution of (R)-2-chloro-4-ethyl-6-(3-hydroxypyrrolidin-1-yl)pyridine-3,5-dicarbonitrile (500 mg, 1.81 mmol) and potassium thioacetate (248 mg, 2.17 mmol) in N,N-dimethylformamide (15 mL) was stirred at room temperature for 30 minutes, then 2-amino-2-oxo-1-phenylethyl methanesulfonate (synthesis described in example 3, step 5, 497 mg, 2.17 mmol) and triethylamine (0.504 mL, 3.61 mmol) were added to the solution. The mixture was stirred at room temperature for 12 hours, then poured into water (50 mL), and extracted with ethyl acetate (50 mL×2). The combined organic layers were dried, concentrated, and the remaining residue purified by silica gel column chromatography (MeOH:DCM 1:50) to afford 2-((3,5-dicyano-4-ethyl-6-((R)-3-hydroxypyrrolidin-1-yl)pyridin-2-yl)thio)-2-phenylacetamide (400 mg, 54%) as a white solid. LCMS m/z=408.0 [M+H]⁺.

Step 3: (R)-2-((3,5-Dicyano-4-ethyl-6-((R)-3-hydroxypyrrolidin-1-yl)pyridin-2-yl)thio)-2-phenylacetamide

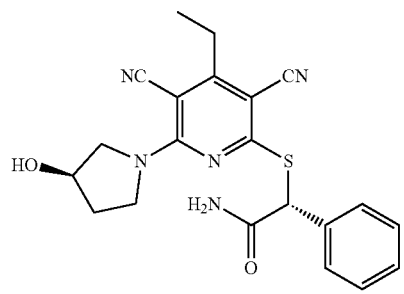 [SMILES: CCc1c(C#N)c(S[C@@H](C(N)=O)c2ccccc2)nc(N2CC[C@@H](O)C2)c1C#N]

2-((3,5-Dicyano-4-ethyl-6-((R)-3-hydroxypyrrolidin-1-yl)pyridin-2-yl)thio)-2-phenylacetamide (300 mg, 0.736 mmol) was separated by chiral prep-HPLC (column chiralpak-IB, eluent hexane-EtOH (with diethylamine)) to give (R)-2-((3,5-dicyano-4-ethyl-6-((R)-3-hydroxypyrrolidin-1-yl)pyridin-2-yl)thio)-2-phenylacetamide (80 mg). LCMS m/z=408.1 [M+H]⁺. ¹H NMR (400 MHz, DMSO-d₆) δ ppm 7.92 (br s, 1H), 7.53 (br s, 1H), 7.52-7.49 (m, 1H), 7.44-7.23 (m, 4H), 5.61 (s, 1H), 5.15 (s, 1H), 4.41 (s, 1H), 4.01-3.66 (m, 4H), 2.74 (q, J=7.5 Hz, 2H), 2.05-1.86 (m, 2H), 1.21 (q, J=7.4 Hz, 3H).

Example 135

2-((3,5-dicyano-4-(furan-2-yl)-6-(4-methyl-1,4-diazepan-1-yl)pyridin-2-yl)thio)-2-phenylacetamide Step 1: Ammonium 3,5-dicyano-4-(furan-2-yl)-6-hydroxypyridin-2-olate

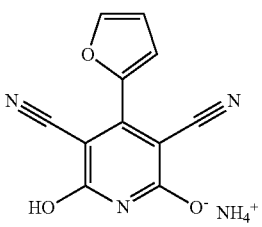 [SMILES: N#Cc1c([O-])nc(O)c(C#N)c1-c1ccco1 ; [NH4+]]

To a solution of furan-2-carbaldehyde (13.9 g, 145 mmol) and 2-cyanoacetamide (12.16 g, 145 mmol) in water (150 mL) was added ammonium hydroxide (7.99 mL, 25%, aqueous). The reaction was stirred at room temperature for 18 hours. The mixture was filtered and the filter cake was washed with cold methanol. The solid was triturated with methanol and dried in an oven to give ammonium 3,5-dicyano-4-(furan-2-yl)-6-hydroxypyridin-2-olate (13 g, crude) as a pale yellow solid. LCMS m/z=226.1 [M]⁻.

Step 2: 2,6-dichloro-4-(furan-2-yl)pyridine-3,5-dicarbonitrile

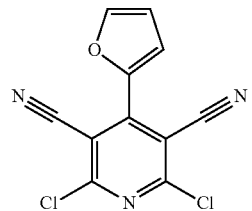 [SMILES: N#Cc1c(Cl)nc(Cl)c(C#N)c1-c1ccco1]

Ammonium 3,5-dicyano-4-(furan-2-yl)-6-hydroxypyridin-2-olate (9 g, 36.8 mmol) was added slowly to POCl₃ (90 mL) in a sealed tube. The mixture was stirred at 150° C. overnight. The solvent was removed under reduced pressure. The residue was poured into ice-water. The solid was collected by filtration, dried and purified by silica gel column chromatography (eluted by DCM-hexanes 0-10%) to give 2,6-dichloro-4-(furan-2-yl)pyridine-3,5-dicarbonitrile (500 mg, 5%) as a light yellow solid. $^1$H NMR (400 MHz, CDCl₃) δ ppm 7.90-7.88 (m, 2H), 6.79 (dd, J=3.7, 1.7 Hz, 1H).

Step 3: 2-((3,5-dicyano-4-(furan-2-yl)-6-(4-methyl-1,4-diazepan-1-yl)pyridin-2-yl)thio)-2-phenylacetamide

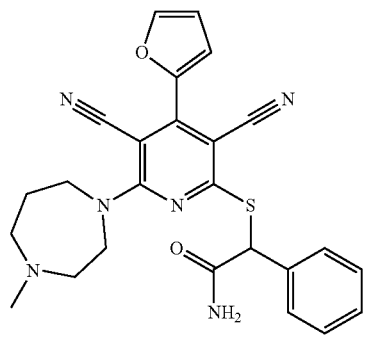 [SMILES: CN1CCCN(c2nc(SC(C(N)=O)c3ccccc3)c(C#N)c(-c3ccco3)c2C#N)CC1]

To a solution of 2,6-dichloro-4-(furan-2-yl)pyridine-3,5-dicarbonitrile (200 mg, 0.76 mmol) in N,N-dimethylformamide (10 mL) was added 1-methyl-1,4-diazepane (82 mg, 0.72 mmol), followed by triethylamine (0.105 mL, 0.76 mmol) dropwise. The reaction was stirred at room temperature for 1 hour. KSAc (104 mg, 0.91 mmol) was added to the mixture. The reaction was stirred at room temperature for 30 minutes then 2-amino-2-oxo-1-phenylethyl methanesulfonate (synthesis described in example 3, step 5, 208 mg, 0.91 mmol) and triethylamine (0.21 mL, 1.52 mmol) were added to the solution. The mixture was stirred at room temperature overnight then concentrated under vacuum and purified by silica gel column chromatography (eluted by MeOH-DCM 0-10%) and triturated with diethyl ether to give 2-{[3,5-dicyano-6-(dimethylamino)-4-ethylpyridin-2-yl]sulfanyl}-2-phenylacetamide (26 mg, 7.12%) as a pale yellow solid. LCMS m/z=473.3 [M+H]⁺. $^1$H NMR (400 MHz, CDCl₃) δ ppm 7.72 (s, 1H), 7.48-7.35 (m, 6H), 6.65 (s, 2H), 5.63 (br s, 1H), 5.39 (s, 1H), 4.15-3.82 (m, 4H), 3.01-2.83 (m, 2H), 2.79-2.58 (m, 2H), 2.46 (s, 3H), 2.25-2.07 (m, 2H).

Example 136

2-((6-(4-Amino-4-methylpiperidin-1-yl)-3,5-dicyano-4-ethylpyridin-2-yl)thio)-2-phenylacetamide Step 1: tert-Butyl (1-(6-chloro-3,5-dicyano-4-ethylpyridin-2-yl)-4-methylpiperidin-4-yl)carbamate

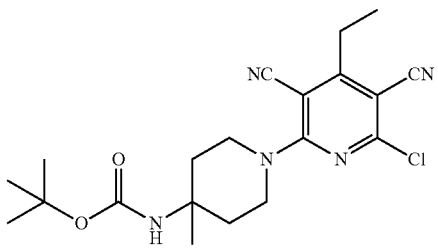 [SMILES: CCc1c(C#N)c(Cl)nc(N2CCC(C)(NC(=O)OC(C)(C)C)CC2)c1C#N]

To a solution of 2,6-dichloro-4-ethylpyridine-3,5-dicarbonitrile (synthesis described in example 3, step 2, 316 mg, 1.400 mmol) in dichloromethane (30 mL) was added tert-butyl (4-methylpiperidin-4-yl)carbamate (300 mg, 1.400 mmol) and triethylamine (142 mg 1.400 mmol). The mixture was stirred at room temperature for 12 hours. The mixture was diluted with DCM (50 mL), washed with water and brine, dried, concentrated to give tert-butyl (1-(6-chloro-3,5-dicyano-4-ethylpyridin-2-yl)-4-methylpiperidin-4-yl)carbamate (320 mg, 57% yield) as a brown oil. LCMS m/z=426.0 [M+Na]⁺.

Step 2: tert-Butyl (1-(6-((2-amino-2-oxo-1-phenylethyl)thio)-3,5-dicyano-4-ethylpyridin-2-yl)-4-methylpiperidin-4-yl)carbamate

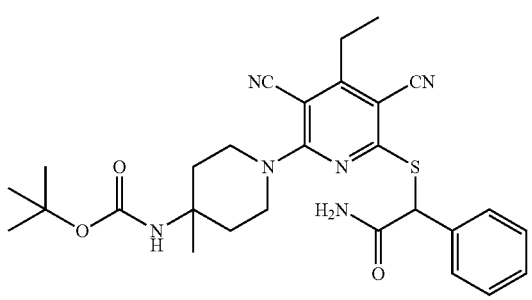 [SMILES: CCc1c(C#N)c(SC(C(N)=O)c2ccccc2)nc(N2CCC(C)(NC(=O)OC(C)(C)C)CC2)c1C#N]

To a solution of tert-butyl (1-(6-chloro-3,5-dicyano-4-ethylpyridin-2-yl)-4-methylpiperidin-4-yl)carbamate (320 mg, 0.792 mmol) in DMF (4 mL) was added potassium thioacetate (136 mg, 1.188 mmol). The mixture was stirred at room temperature for 1 hour, and was combined with a similar reaction conducted using 123 mg (0.305 mmol) of tert-butyl (1-(6-chloro-3,5-dicyano-4-ethylpyridin-2-yl)-4-methylpiperidin-4-yl)carbamate as starting material. To the

449 combined reaction was added potassium carbonate (303 mg, 2.192 mmol). The mixture was stirred at room temperature for one hour, and 2-amino-2-oxo-1-phenylethyl methanesulfonate (synthesis described in example 3, step 5, 377 mg, 1.644 mmol) was added. The mixture was stirred at room temperature for 12 hours. The mixture was diluted with water (60 mL) and extracted with ethyl acetate (30 mL×3). The organic phase was washed with water and brine, dried, concentrated and purified on a silica gel column (petroleum ether/ethyl acetate=1/1) to give tert-butyl (1-(6-((2-amino-2-oxo-1-phenylethyl)thio)-3,5-dicyano-4-ethylpyridin-2-yl)-4-methylpiperidin-4-yl)carbamate (540 mg, 1.010 mmol). LCMS m/z=535.2 [M+H]$^+$.

Step 3: 2-((6-(4-Amino-4-methylpiperidin-1-yl)-3,5-dicyano-4-ethylpyridin-2-yl)thio)-2-phenylacetamide

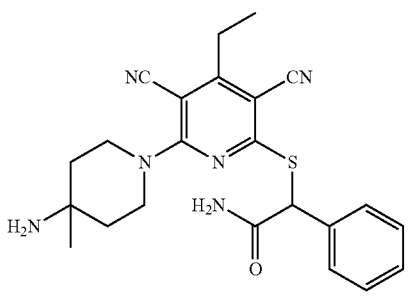 [SMILES: CCc1c(C#N)c(SC(C(N)=O)c2ccccc2)nc(N2CCC(C)(N)CC2)c1C#N]

tert-Butyl (1-(6-((2-amino-2-oxo-1-phenylethyl)thio)-3,5-dicyano-4-ethylpyridin-2-yl)-4-methylpiperidin-4-yl)carbamate (230 mg, 0.430 mmol) was added to a solution of trifluoroacetic acid (1 mL) in dichloromethane (10 mL). The solution was stirred at room temperature for 6 hours. The pH was adjusted to 7-8. The mixture was concentrated and the residue was purified by prep-HPLC to give the product 2-((6-(4-amino-4-methylpiperidin-1-yl)-3,5-dicyano-4-ethylpyridin-2-yl)thio)-2-phenylacetamide (130 mg, 70% yield) as a white solid. LCMS m/z=435.1 [M+H]$^+$. $^1$H NMR (400 MHz, DMSO-d$_6$) δ ppm 7.93 (s, 3H), 7.52 (d, J=7.0 Hz, 2H), 7.44-7.31 (m, 4H), 5.53 (s, 1H), 4.36-4.09 (m, 2H), 3.79-3.61 (m, 2H), 2.78 (q, J=7.4 Hz, 2H), 1.86-1.71 (m, 4H), 1.39 (s, 3H), 1.22 (t, J=7.6 Hz, 3H).

450

Example 137

2-Amino-N-(1-(6-((2-amino-2-oxo-1-phenylethyl)thio)-3,5-dicyano-4-ethylpyridin-2-yl)piperidin-4-yl)acetamide, Trifluoroacetic Acid Salt Step 1: tert-Butyl(2-((1-(6-((2-amino-2-oxo-1-phenylethyl)thio)-3,5-dicyano-4-ethylpyridin-2-yl)piperidin-4-yl)amino)-2-oxoethyl)carbamate

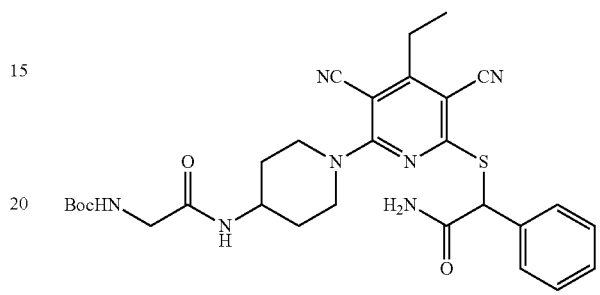

A mixture of 2,6-dichloro-4-ethylpyridine-3,5-dicarbonitrile (synthesis described in example 3 step 2, 1.212 g, 5.36 mmol), tert-butyl (2-oxo-2-(piperidin-4-ylamino)ethyl)carbamate (1.38 g, 5.36 mmol) and triethylamine (1.085 g, 10.73 mmol) in dichloromethane (30 mL) was stirred at room temperature overnight then concentrated in vacuo. The residue was purified on a silica gel column eluting with hexanes/EtOAc (1/1) to afford 1.5 g of residue. To a solution of this residue (0.9 g) in N,N-dimethylformamide (15 mL) was added potassium ethanethioate (0.276 g, 2.416 mmol) and the mixture was stirred at room temperature overnight, then treated with K$_2$CO$_3$ (0.557 g, 4.03 mmol) at room temperature. The resultant mixture was stirred at room temperature for 1 hour then treated with 2-amino-2-oxo-1-phenylethyl methanesulfonate (synthesis described in example 3 step 5, 0.699 g, 3.02 mmol). The resultant mixture was stirred at room temperature overnight then diluted with EtOAc and washed with water and brine. The organic phase was dried over Na$_2$SO$_4$ and concentrated in vacuo, and the residue was triturated with EtOAc/hexane (1/1) to give tert-butyl (2-((1-(6-((2-amino-2-oxo-1-phenylethyl)thio)-3,5-dicyano-4-ethylpyridin-2-yl)piperidin-4-yl)amino)-2-oxoethyl)carbamate (0.6 g). LCMS m/z=578.3 [M+H]$^+$.

Step 3: 2-Amino-N-(1-(6-((2-amino-2-oxo-1-phenylethyl)thio)-3,5-dicyano-4-ethylpyridin-2-yl)piperidin-4-yl)acetamide 2,2,2-trifluoroacetate

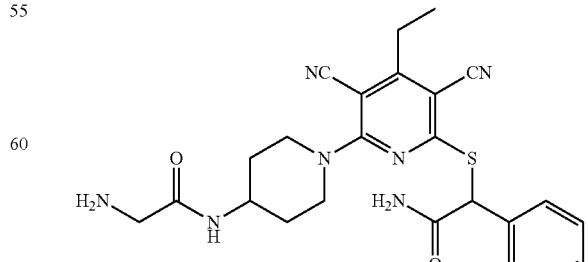

To a solution of tert-butyl (2-((1-(6-((2-amino-2-oxo-1-phenylethyl)thio)-3,5-dicyano-4-ethylpyridin-2-yl)piperidin-4-yl)amino)-2-oxoethyl)carbamate (0.55 g) in dichloromethane (10 mL) was added 2,2,2-trifluoroacetic acid (868 mg, 7.62 mmol) at 0° C. The resultant mixture was stirred at room temperature for 2 hours then concentrated in vacuo, and the residue was purified by prep-HPLC (eluted with Me-CN/TFA 0.1%) to give 2-amino-N-(1-(6-((2-amino-2-oxo-1-phenylethyl)thio)-3,5-dicyano-4-ethylpyridin-2-yl)piperidin-4-yl)acetamide 2,2,2-trifluoroacetate (120 mg). LCMS m/z=478.1 [M+H]+. 1H NMR (400 MHz, DMSO-d6) δ ppm 8.43 (d, J=7.4 Hz, 1H), 8.03 (s, 2H), 7.95 (s, 1H), 7.52 (d, J=7.0 Hz, 2H), 7.43-7.31 (m, 4H), 5.54 (s, 1H), 4.42 (m, 2H), 4.00 (m, 1H), 3.56 (q, J=5.6 Hz, 2H), 3.41 (t, J=12.4 Hz, 2H), 2.77 (m, 2H), 1.94 (d, J=10.4 Hz, 2H), 1.57-1.41 (m, 2H), 1.21 (t, J=7.6 Hz, 3H).

Example 138

(2S)-2-Amino-N-(1-(6-((2-amino-2-oxo-1-phenylethyl)thio)-3,5-dicyano-4-ethylpyridin-2-yl)piperidin-4-yl)propanamide, Trifluoroacetic Acid Salt Step 1: Benzyl4-(2-(tert-butoxycarbonylamino)acetamido)piperidine-1-carboxylate

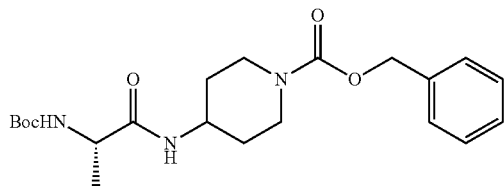 [SMILES: C[C@H](NC(=O)OC(C)(C)C)C(=O)NC1CCN(C(=O)OCc2ccccc2)CC1]

A mixture of benzyl 4-aminopiperidine-1-carboxylate (6.4 g, 27.3 mmol), (S)-2-((tert-butoxycarbonyl)amino)propanoic acid (5.17 g, 27.3 mmol), 1H-benzo[d][1,2,3]triazol-4-ol (4.43 g, 32.8 mmol), N1-((ethylimino)methylene)-N3,N3-dimethylpropane-1,3-diamine (5.09 g, 32.8 mmol) and 4-methylmorpholine (5.53 g, 54.6 mmol) in N,N-dimethylformamide (30 mL) was stirred at room temperature overnight then concentrated in vacuo. The residue was diluted with EtOAc and washed with aqueous 1N HCl solution, saturated NaHCO3 solution and brine. The organic phase was dried over sodium sulfate and concentrated in vacuum. The residue was purified by silica gel chromatography eluting with hexanes/EtOAc to give (S)-benzyl 4-(2-((tert-butoxycarbonyl)amino)propanamido)piperidine-1-carboxylate (8.6 g, 58% yield). LCMS m/z=428.1 [M+Na]+.

Step 2: (S)-tert-Butyl 1-oxo-1-(piperidin-4-ylamino)propan-2-ylcarbamate

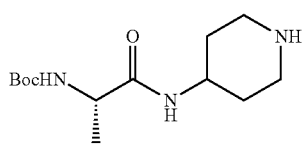 [SMILES: C[C@H](NC(=O)OC(C)(C)C)C(=O)NC1CCNCC1]

To a solution of (S)-benzyl 4-(2-((tert-butoxycarbonyl)amino)propanamido)piperidine-1-carboxylate (2.34 g, 5.77 mmol) in methanol (50 mL) was added 10% Pd/C (0.7 g) at room temperature. The mixture was stirred at room temperature under H2 overnight then filtered and concentrated in vacuo to give crude (S)-tert-butyl (1-oxo-1-(piperidin-4-ylamino)propan-2-yl)carbamate (1.56 g). LCMS m/z=272.2 [M+H]+.

Step 3: tert-Butyl(S)-1-(1-(6-(2-amino-2-oxo-1-phenylethylthio)-3,5-dicyano-4-ethylpyridin-2-yl)piperidin-4-ylamino)-1-oxopropan-2-ylcarbamate

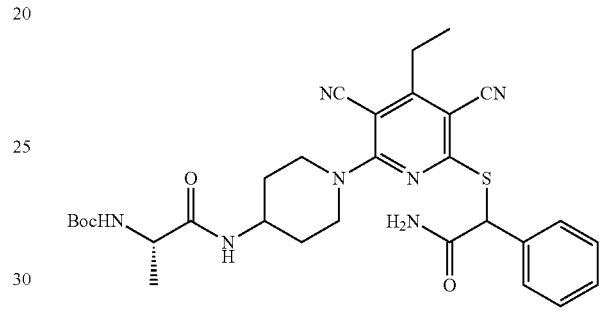

A mixture of 2,6-dichloro-4-ethylpyridine-3,5-dicarbonitrile (synthesis described in example 3 step 2, 1.300 g, 5.75 mmol), (S)-tert-butyl (1-oxo-1-(piperidin-4-ylamino)propan-2-yl)carbamate (1.56 g, 5.75 mmol) and triethylamine (1.163 g, 11.50 mmol) in dichloromethane (30 mL) was stirred at room temperature overnight then concentrated in vacuo and the residue was purified by silica gel chromatography eluting with hexanes/EtOAc (1/1) to give (S)-tert-butyl (1-((1-(6-chloro-3,5-dicyano-4-ethylpyridin-2-yl)piperidin-4-yl)amino)-1-oxopropan-2-yl)carbamate (1.8 g, 3.90 mmol, 68% yield). To a solution of (S)-tert-butyl (1-((1-(6-chloro-3,5-dicyano-4-ethylpyridin-2-yl)piperidin-4-yl)amino)-1-oxopropan-2-yl)carbamate (920 mg, 1.996 mmol) in N,N-dimethylformamide (15 mL) was added potassium ethanethioate (274 mg, 2.395 mmol) and the mixture was stirred at room temperature overnight then treated with K2CO3 (552 mg, 3.99 mmol) at room temperature. The resultant mixture was stirred at room temperature for 1 hour then treated with 2-amino-2-oxo-1-phenylethyl methanesulfonate (synthesis described in example 3 step 5, 692 mg, 2.99 mmol). The resultant mixture was stirred at room temperature overnight then diluted with EtOAc and washed with water and brine. The organic phase was dried over Na2SO4 and concentrated in vacuo. The residue was triturated with EtOAc/hexane (1/1) to give tert-butyl ((2S)-1-(((1-(6-((2-amino-2-oxo-1-phenylethyl)thio)-3,5-dicyano-4-ethylpyridin-2-yl)piperidin-4-yl)amino)-1-oxopropan-2-yl)carbamate (0.7 g). LCMS m/z=592.3 [M+H]+.

Step 4: (2S)-2-Amino-N-(1-(6-((2-amino-2-oxo-1-phenylethyl)thio)-3,5-dicyano-4-ethylpyridin-2-yl)piperidin-4-yl)propanamide, Trifluoroacetic Acid Salt

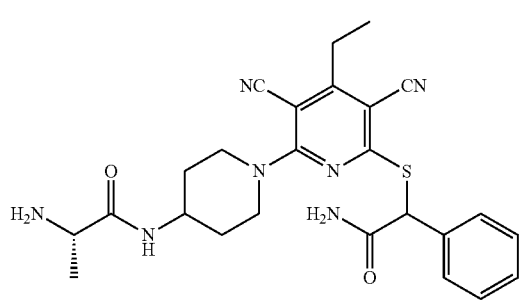 [SMILES: CCc1c(C#N)c(SC(C(N)=O)c2ccccc2)nc(N2CCC(NC(=O)[C@H](C)N)CC2)c1C#N]

To a solution of tert-butyl ((2S)-1-((1-(6-((2-amino-2-oxo-1-phenylethyl)thio)-3,5-dicyano-4-ethylpyridin-2-yl)piperidin-4-yl)amino)-1-oxopropan-2-yl)carbamate (0.65 g, 1.098 mmol) in dichloromethane (10 mL) was added 2,2,2-trifluoroacetic acid (1.253 g, 10.98 mmol) at 0° C. The mixture was stirred at room temperature for 2 hours then concentrated in vacuo. The residue was purified by prep-HPLC column (eluted with Me-CN/TFA 0.1%) to give (2S)-2-amino-N-(1-(6-((2-amino-2-oxo-1-phenylethyl)thio)-3,5-dicyano-4-ethylpyridin-2-yl)piperidin-4-yl)propanamide, trifluoroacetic acid salt (110 mg, 17% yield). LCMS m/z=492.1 [M+H]$^+$. $^1$H NMR (400 MHz, DMSO-$d_6$) δ ppm 8.44 (d, J=7.2 Hz, 1H), 8.13 (s, 2H), 7.96 (s, 1H), 7.53 (d, J=7.1 Hz, 2H), 7.45-7.28 (m, 4H), 5.55 (s, 1H), 4.44 (t, J=11.2 Hz, 2H), 3.98 (m, 1H), 3.89-3.76 (m, 1H), 3.40 (m, 2H), 2.77 (q, J=7.5 Hz, 2H), 1.93 (m, 2H), 1.50 (m, 2H), 1.36 (d, J=6.9 Hz, 3H), 1.21 (t, J=7.6 Hz, 3H).

Example 139

2-((6-(4-(3-Aminooxetane-3-carbonyl)piperazin-1-yl)-3,5-dicyano-4-ethylpyridin-2-yl)thio)-2-phenylacetamide, Formic Acid Salt Step 1: 3-((tert-Butoxycarbonyl)amino)oxetane-3-carboxylic acid

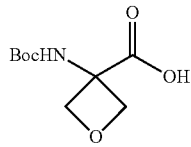

A mixture of 3-aminooxetane-3-carboxylic acid (800 mg, 6.83 mmol), tetramethylammonium hydroxide (507 mg, 5.56 mmol), di-tert-butyl dicarbonate (1640 mg, 7.51 mmol) in acetonitrile (30 mL) was stirred for 12 hours at 50° C. The mixture was concentrated and the residue was purified by flash column chromatography to afford 3-((tert-butoxycarbonyl)amino)oxetane-3-carboxylic acid (1.3 g, 88% yield). LCMS m/z=218.1 [M+H]$^+$.

Step 2: tert-Butyl (3-(4-(6-((2-amino-2-oxo-1-phenylethyl)thio)-3,5-dicyano-4-ethylpyridin-2-yl)piperazine-1-carbonyl)oxetan-3-yl)carbamate

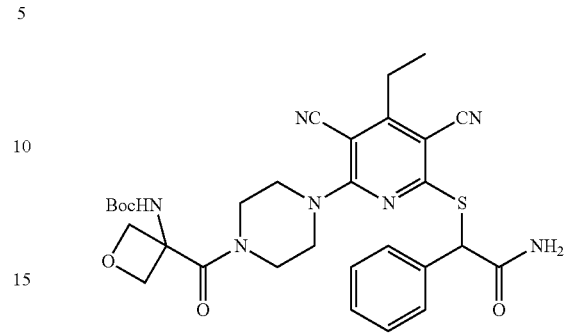

3-((tert-Butoxycarbonyl)amino)oxetane-3-carboxylic acid (120 mg, 0.552 mmol), 2-((3,5-dicyano-4-ethyl-6-(piperazin-1-yl)pyridin-2-yl)thio)-2-phenylacetamide (synthesis described in example 55, 247 mg, 0.608 mmol), N-((ethylimino)methylene)-N,N-dimethylpropane-1,3-diamine (103 mg, 0.663 mmol) were added into N,N-dimethylformamide (10 mL) and stirred for 4 hours at 30° C. Water (30 mL) was then added and the mixture was extracted with ethyl acetate (30 mL×3). The organic phase was dried over sodium sulfate, concentrated and purified by flash column chromatography to afford tert-butyl (3-(4-(6-((2-amino-2-oxo-1-phenylethyl)thio)-3,5-dicyano-4-ethylpyridin-2-yl)piperazine-1-carbonyl)oxetan-3-yl)carbamate (230 mg, 69% yield). LCMS m/z=628.2 [M+Na]$^+$.

Step 3: 2-((6-(4-(3-Aminooxetane-3-carbonyl)piperazin-1-yl)-3,5-dicyano-4-ethylpyridin-2-yl)thio)-2-phenylacetamide, Formic Acid Salt

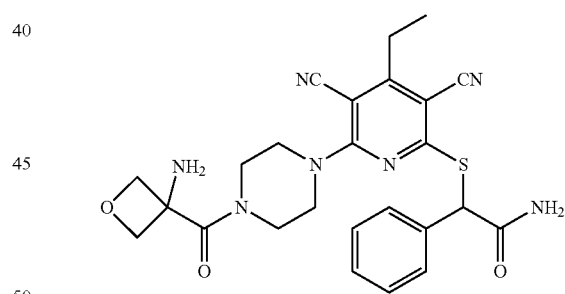

tert-Butyl (3-(4-(6-((2-amino-2-oxo-1-phenylethyl)thio)-3,5-dicyano-4-ethylpyridin-2-yl)piperazine-1-carbonyl)oxetan-3-yl)carbamate (230 mg, 0.380 mmol) was added into dichloromethane (20 mL) followed by 2,2,2-trifluoroacetic acid (3 mL, 39.5 mmol). The mixture was stirred for 3 hours at 25° C., and then washed with water (30 mL×2). The organic phase was dried over sodium sulfate, concentrated and purified by prep-HPLC to afford 2-((6-(4-(3-aminooxetane-3-carbonyl)piperazin-1-yl)-3,5-dicyano-4-ethylpyridin-2-yl)thio)-2-phenylacetamide, formic acid salt (100 mg, 48% yield). LCMS m/z=506.1 [M+H]$^+$. $^1$H NMR (400 MHz, DMSO-$d_6$) δ ppm 8.44 (s, 1H), 7.95 (s, 1H), 7.52 (d, J=7.1 Hz, 2H), 7.43-7.32 (m, 3H), 5.55 (s, 1H), 4.90 (d, J=6.1 Hz, 2H), 4.41 (d, J=6.1 Hz, 2H), 4.00-3.85 (m, 4H), 3.64-3.58 (m, 2H), 3.49-3.44 (m, 2H), 2.78 (q, J=7.5 Hz, 2H), 1.22 (t, J=7.6 Hz, 3H).

Example 140

4-Amino-N-(1-(6-((2-amino-2-oxo-1-phenylethyl) thio)-3,5-dicyano-4-ethylpyridin-2-yl)piperidin-4-yl) tetrahydro-2H-pyran-4-carboxamide, Trifluoroacetic Acid Salt

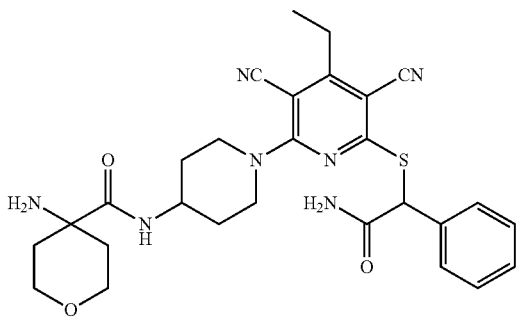 [SMILES: CCc1c(C#N)c(SC(C(N)=O)c2ccccc2)nc(N2CCC(NC(=O)C3(N)CCOCC3)CC2)c1C#N]

To a solution of 2-((6-(4-aminopiperidin-1-yl)-3,5-dicyano-4-ethylpyridin-2-yl)thio)-2-phenylacetamide (synthesis described in example 143, step 2, 1 g, 2.378 mmol) in dichloromethane (50 mL) were added HATU (0.904 g, 2.378 mmol), triethylamine (0.241 g, 2.378 mmol) and 4-((tert-butoxycarbonyl)amino)tetrahydro-2H-pyran-4-carboxylic acid (0.583 g, 2.378 mmol). The mixture was stirred at 25° C. overnight. Then it was concentrated under reduced pressure and the residue was purified on a silica gel column which was eluted with Hexane/EtOAc. The resulting Boc derivative was dissolved in DCM (20 mL) and TFA (2 g) was added. The mixture was stirred at room temperature for overnight. The reaction mixture was concentrated and the residue was purified by prep-HPLC to give 4-amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide, trifluoroacetic acid salt (120 mg, 0.181 mmol, 8% yield). LCMS m/z=548 [M+H]$^+$. $^1$H NMR (400 MHz, DMSO-d$_6$) δ ppm 8.42 (s, 3H), 8.28 (d, J=7.6 Hz, 1H), 7.94 (s, 1H), 7.53 (d, J=7.0 Hz, 2H), 7.43-7.32 (m, 4H), 5.54 (s, 1H), 4.53 (t, J=14.9 Hz, 2H), 4.05 (s, 1H), 3.73 (s, 4H), 3.33 (dd, J=11.5, 6.3 Hz, 2H), 2.77 (q, J=7.4 Hz, 2H), 2.33-2.20 (m, 2H), 1.89 (d, J=13.5 Hz, 2H), 1.68 (d, J=13.0 Hz, 2H), 1.62-1.47 (m, 2H), 1.22 (t, J=7.6 Hz, 3H).

Example 141

2-((6-(4-(4-Aminotetrahydro-2H-pyran-4-carbonyl) piperazin-1-yl)-3,5-dicyano-4-ethylpyridin-2-yl) thio)-2-phenylacetamide, Trifluoroacetic Acid Salt

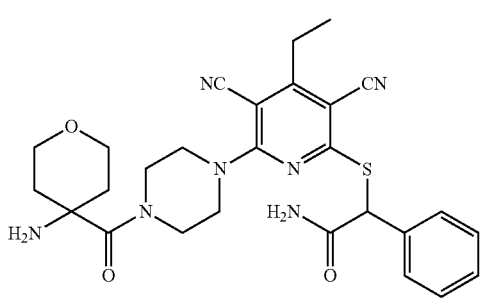 [SMILES: CCc1c(C#N)c(SC(C(N)=O)c2ccccc2)nc(N2CCN(C(=O)C3(N)CCOCC3)CC2)c1C#N]

To a solution of 2-((3,5-dicyano-4-ethyl-6-(piperazin-1-yl)pyridin-2-yl)thio)-2-phenylacetamide (synthesis described in Example 55, 800 mg, 1.968 mmol) in dichloromethane (50 mL) was added HATU (748 mg, 1.968 mmol), triethylamine (199 mg, 1.968 mmol) and 4-((tert-butoxycarbonyl)amino)tetrahydro-2H-pyran-4-carboxylic acid (483 mg, 1.968 mmol). The mixture was stirred at 25° C. overnight, concentrated under reduced pressure and the residue was loaded on a silica gel column which was eluted with hexane/EtOAc to give the Boc derivative. The Boc derivative was dissolved in DCM (5 mL) and TFA (2 g) and the mixture was stirred at room temperature overnight. The reaction mixture was concentrated and purified by prep-HPLC to give 2-((6-(4-(4-aminotetrahydro-2H-pyran-4-carbonyl)piperazin-1-yl)-3,5-dicyano-4-ethylpyridin-2-yl) thio)-2-phenylacetamide, trifluoroacetic acid salt (120 mg, 9% yield). LCMS m/z=534 [M+H]$^+$. $^1$H NMR (400 MHz, DMSO-d$_6$) δ ppm 8.53 (s, 3H), 7.97 (s, 1H), 7.53 (d, J=7.0 Hz, 2H), 7.46-7.31 (m, 4H), 5.57 (s, 1H), 4.01 (s, 4H), 3.94-3.65 (m, 8H), 2.79 (q, J=7.5 Hz, 2H), 2.35 (m, 2H), 1.77 (d, J=14.6 Hz, 2H), 1.23 (t, J=7.6 Hz, 3H).

Example 142

2-((3,5-Dicyano-6-(4-(2-hydroxyethyl)-1,4-diazepan-1-yl)-4-methoxypyridin-2-yl)thio)-2-phenylacetamide Step 1: (2-(Dimethoxymethylene)malononitrile)

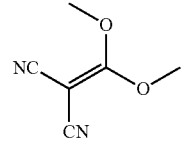

The reaction mixture of ethene-1,1,2,2-tetracarbonitrile (10.23 g, 80 mmol), urea (1.439 g, 23.96 mmol) and methanol (30.7 ml, 759 mmol) was stirred for 50 minutes. Ether (150 mL) was added to the reaction mixture, then cooled to −78° C. with stirring for 60 minutes. The solid was filtered and washed with cold ether/hexane to afford 2-(dimethoxymethylene)malononitrile (8.35 g, 60.5 mmol, 76% yield) as a pale yellow solid. LCMS m/z=138.9 [M+H]$^+$.

Step 2: 2-Amino-6-chloro-4-methoxypyridine-3,5-dicarbonitrile

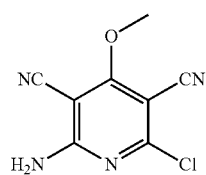

The reaction mixture of malononitrile (0.488 g, 7.38 mmol) and potassium tert-butoxide (0.870 g, 7.60 mmol) in methanol (15 mL) was stirred for 30 minutes at 50° C., then 2-(dimethoxymethylene)malononitrile (1 g, 7.24 mmol) in methanol (15 mL) was added to the mixture slowly. The reaction mixture was heated at 50° C. for additional 100 minutes. The solvent was removed under reduced pressure, then acetone (20 mL) was added followed by concentrated HCl (5 mL, 165 mmol), precipitate formed instantly. The reaction mixture was stirred at 45° C. overnight. The reaction mixture was cooled to room temperature, the solid was filtered and then was triturated with water to afford 2-amino-6-chloro-4-methoxypyridine-3,5-dicarbonitrile (322 mg, 1.544 mmol, 21% yield) as an off-white solid. LCMS m/z=209.1 [M+H]⁺.

Step 3: 2-((6-Amino-3,5-dicyano-4-methoxypyridin-2-yl)thio)-2-phenylacetamide

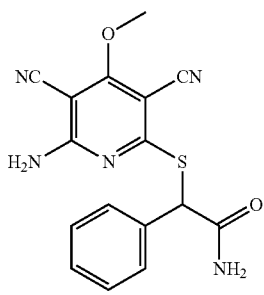 [SMILES: COc1c(C#N)c(N)nc(SC(C(N)=O)c2ccccc2)c1C#N]

The reaction mixture of S-(2-amino-2-oxo-1-phenylethyl) ethanethioate (synthesis described in Example 62 step 5, 385 mg, 1.841 mmol) and NaBH₄ (87 mg, 2.301 mmol) in ethanol (10 mL) was heated at 50° C. for 25 minutes (bubbles stopped). The reaction mixture was cooled down to room temperature and added into a slurry solution of 2-amino-6-chloro-4-methoxypyridine-3,5-dicarbonitrile (320 mg, 1.534 mmol) in ethanol (15 mL). The reaction mixture was stirred at room temperature for 3 hours. The solid was filtered to afford 2-((6-amino-3,5-dicyano-4-methoxypyridin-2-yl)thio)-2-phenylacetamide (517 mg, 1.417 mmol, 92% yield) as an off-white solid. LCMS m/z=340.2 [M+H]⁺.

Step 4: 2-((6-Chloro-3,5-dicyano-4-methoxypyridin-2-yl)thio)-2-phenylacetamide

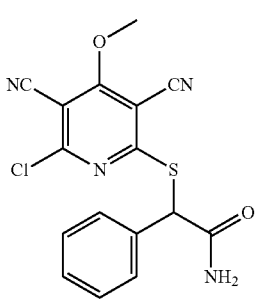 [SMILES: COc1c(C#N)c(Cl)nc(SC(C(N)=O)c2ccccc2)c1C#N]

To a slurry solution of 2-((6-amino-3,5-dicyano-4-methoxypyridin-2-yl)thio)-2-phenylacetamide (515 mg, 1.518 mmol) in acetonitrile (60 mL) was added copper(II) chloride (377 mg, 2.81 mmol). The mixture was heated at 50° C. for 5 minutes and tert-butyl nitrite (0.334 mL, 2.81 mmol) was added dropwise. The reaction mixture was heated at 50° C. for 4 hours, then was brought to room temperature. The solid was filtered. The filtrate was concentrated down, and the residue was mixed with EtOAc and water, and the layers were separated. The aqueous layer was extracted with EtOA two times. The combined organics were washed with water and brine, dried over Na₂SO₄, concentrated down. The residue was purified by silica (40 g column, using 0-100% EtOAc/Hexane). The resulting fractions were concentrated down and triturated with EtOAc to afford 2-((6-chloro-3,5-dicyano-4-methoxypyridin-2-yl)thio)-2-phenylacetamide (192 mg, 0.503 mmol, 33% yield) as an off-white solid. LCMS m/z=359.1 [M+H]⁺.

Step 5: 2-((3,5-Dicyano-6-(4-(2-hydroxyethyl)-1,4-diazepan-1-yl)-4-methoxypyridin-2-yl)thio)-2-phenylacetamide

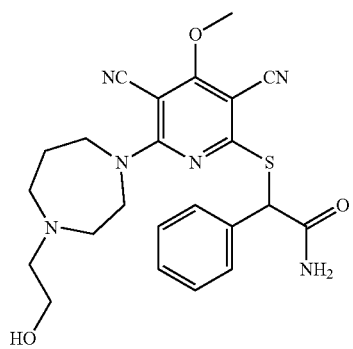 [SMILES: COc1c(C#N)c(SC(C(N)=O)c2ccccc2)nc(N2CCCN(CCO)CC2)c1C#N]

To a solution of 2-((6-chloro-3,5-dicyano-4-methoxpyridin-2-yl)thio)-2-phenylacetamide (195 mg, 0.511 mmol) in N,N-dimethylformamide (5 mL) was added 2-(1,4-diazepan-1-yl) ethan-1-ol (88 mg, 0.613 mmol). The mixture was stirred at room temperature for 4 hours. The reaction mixture was concentrated down and purified by RP-HPLC (30-50% acetonitrile/water, 0.1% NH₄OH in water) to afford 2-((3,5-dicyano-6-(4-(2-hydroxyethyl)-1,4-diazepan-1-yl)-4-methoxypyridin-2-yl)thio)-2-phenylacetamide (148 mg, 0.317 mmol, 62% yield) as a white solid. LCMS m/z=467.3 [M+H]⁺. ¹H NMR (400 MHz, DMSO-d) δ ppm 1.84-1.92 (m, 2H), 2.52-2.56 (m, 2H), 2.58-2.70 (m, 2H), 2.70-2.89 (m, 2H), 3.47 (q, J=6.2 Hz, 2H), 3.78-3.94 (m, 4H), 4.24 (s, 3H), 6 4.39 (t, J=5.3 Hz, 1H), 5.51 (s, 1H), 7.29-7.43 (m, 4H), 7.45-7.53 (m, 2H), 7.91 (s, 1H).

Example 143

2-((6-(4-Aminopiperidin-1-yl)-3,5-dicyano-4-ethylpyridin-2-yl)thio)-2-phenylacetamide

Step 1: tert-Butyl (1-(6-((2-amino-2-oxo-1-phenylethyl)thio)-3,5-dicyano-4-ethylpyridin-2-yl)piperidin-4-yl)carbamate

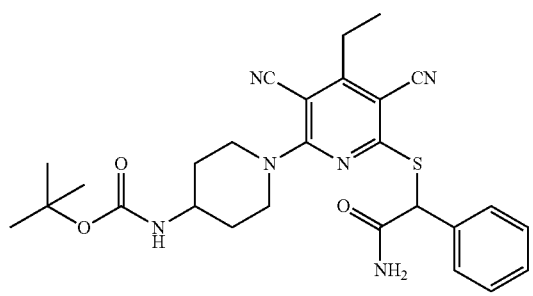 [SMILES: CCc1c(C#N)c(SC(C(N)=O)c2ccccc2)nc(N2CCC(NC(=O)OC(C)(C)C)CC2)c1C#N]

To a suspension of 2,6-dichloro-4-ethylpyridine-3,5-dicarbonitrile (synthesis described in example 3, step 2, 300 mg, 1.327 mmol) in ethanol (2 mL) at −20° C. was added a solution of tert-butyl piperidin-4-ylcarbamate (292 mg, 1.460 mmol) in ethanol (2.5 mL). The reaction mixture was then stirred at 20° C. for 30 minutes. To the reaction mixture was then warmed to 0° C. and then the potassium thioacetate (227 mg, 1.991 mmol) and Et$_3$N (0.462 mL, 3.32 mmol) were added to the reaction mixture along with additional ethanol (5 mL). The heterogeneous reaction mixture was then warmed to 20° C. and stirred at the same temperature overnight. To the reaction mixture was added 2-amino-2-oxo-1-phenylethyl methanesulfonate (synthesis described in example 3, step 5, 608 mg, 2.65 mmol). After stirring at 20° C. for 2.5 hours, the reaction temperature was increased to 40° C. After stirring 2.5 hours at 40° C., the heterogeneous mixture was cooled to room temperature and filtered. The solids were washed with EtOH, water, EtOH, and then Et$_2$O. The isolated material was then dried in the vacuum oven to afford tert-butyl (1-(6-((2-amino-2-oxo-1-phenylethyl)thio)-3,5-dicyano-4-ethylpyridin-2-yl)piperidin-4-yl)carbamate 520 mg as an off-white solid. LCMS m/z=521.4 [M+H]$^+$.

Step 2: 2-((6-(4-Aminopiperidin-1-yl)-3,5-dicyano-4-ethylpyridin-2-yl)thio)-2-phenylacetamide

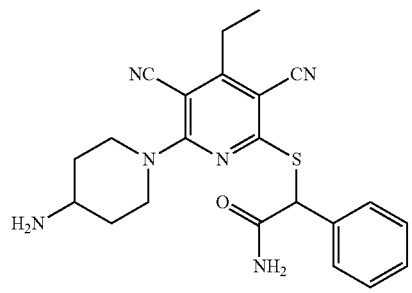 [SMILES: CCc1c(C#N)c(SC(C(N)=O)c2ccccc2)nc(N2CCC(N)CC2)c1C#N]

tert-butyl (1-(6-((2-amino-2-oxo-1-phenylethyl)thio)-3,5-dicyano-4-ethylpyridin-2-yl) piperidin-4-yl) carbamate (505 mg, 0.970 mmol) was suspended in 20 mL of a 4 M solution of HCl (80 mmol) in dioxane. The reaction mixture was then stirred at room temperature for 2 hours. The reaction mixture was then concentrated and the crude was suspended in dioxane and the mixture filtered. The solids were washed with dioxane and dried to afford a white solid which was suspended in MeOH and free based with isopropylamine. This mixture was purified by reverse phase HPLC (Gilson, 30 mm×50 mm Gemini Column, NH$_4$OH modifier) to afford 2-((6-(4-aminopiperidin-1-yl)-3,5-dicyano-4-ethylpyridin-2-yl)thio)-2-phenylacetamide (149 mg) as a white solid. LCMS m/z=421.1 [M+H]$^+$. $^1$H NMR (400 MHz, DMSO-d$_6$) δ ppm 7.94 (s, 1H), 7.50-7.54 (m, 2H), 7.31-7.41 (m, 4H), 5.53 (s, 1H), 4.41 (d, J=13.43 Hz, 2H), 3.25-3.31 (m, 2H), 2.87-2.96 (m, 1H), 2.75 (q, J=7.60 Hz, 2H), 1.84 (d, J=12.42 Hz, 2H), 1.24-1.38 (m, 2H), 1.20 (t, J=7.60 Hz, 3H). (2H obscured by water).

Example 144

2-((6-((2-Aminoethyl)(methyl)amino)-3,5-dicyano-4-ethylpyridin-2-yl)thio)-2-phenylacetamide, Trifluoroacetic Acid Salt

Step 1: tert-Butyl (2-((6-chloro-3,5-dicyano-4-ethylpyridin-2-yl)(methyl)amino)ethyl)carbamate

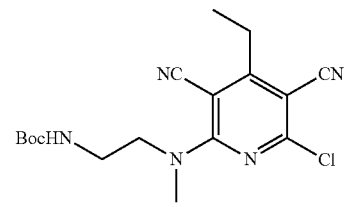

To solution of 2,6-dichloro-4-ethylpyridine-3,5-dicarbonitrile (synthesis described in Example 3 step 2, 1 g, 4.42 mmol) in DCM (50 mL) was added tert-butyl (2-(methylamino)ethyl)carbamate (0.771 g, 4.42 mmol) and triethylamine (0.448 g, 4.42 mmol). The reaction mixture was stirred at 25° C. overnight and then concentrated to give tert-butyl (2-((6-chloro-3,5-dicyano-4-ethylpyridin-2-yl)(methyl)amino)ethyl)carbamate (1.4 g, 87% yield). LCMS m/z=386.1 [M+Na]$^+$.

Step 2: tert-Butyl (2-((3,5-dicyano-4-ethyl-6-mercaptopyridin-2-yl)(methyl)amino)ethyl)carbamate

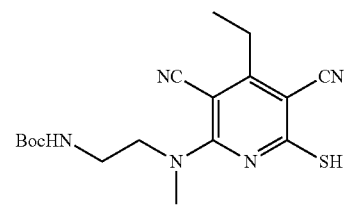 [SMILES: CCc1c(C#N)c(S)nc(N(C)CCNC(=O)OC(C)(C)C)c1C#N]

To a solution of tert-butyl (2-((6-chloro-3,5-dicyano-4-ethylpyridin-2-yl)(methyl)amino)ethyl)carbamate (1.4 g, 3.85 mmol) in N,N-dimethylformamide (150 mL) was added potassium thioacetate (0.714 g, 6.25 mmol). The reaction mixture was stirred at 25° C. overnight. The reaction mixture was concentrated and the residue was loaded to a silica gel column which was eluted with DCM/MeOH to give tert-butyl (2-((3,5-dicyano-4-ethyl-6-mercaptopyridin-2-yl)(methyl)amino)ethyl)carbamate (700 mg, 50% yield). LCMS m/z=384.1 [M+Na]⁺.

Step 3: tert-Butyl (2-((6-((2-amino-2-oxo-1-phenyl-ethyl)thio)-3,5-dicyano-4-ethylpyridin-2-yl)(methyl)amino)ethyl)carbamate

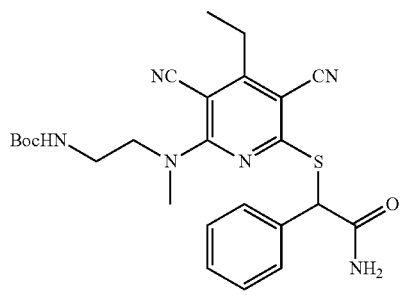 [SMILES: CCc1c(C#N)c(SC(C(N)=O)c2ccccc2)nc(N(C)CCNC(=O)OC(C)(C)C)c1C#N]

To a solution of tert-butyl (2-((3,5-dicyano-4-ethyl-6-mercaptopyridin-2-yl)(methyl)amino)ethyl)carbamate (700 mg, 1.937 mmol) in DMF (150 mL) was added 2-amino-2-oxo-1-phenylethyl methanesulfonate (synthesis described in Example 3 step 5, 1 g, 4.36 mmol) and potassium acetate (190 mg, 1.937 mmol). The reaction mixture was stirred at 25° C. overnight., and water (100 mL) was added followed by extraction with EA (100 mL×3). The organic phase was dried over sodium sulfate and evaporated. The residue was purified by prep-HPLC to give tert-butyl (2-((6-((2-amino-2-oxo-1-phenylethyl)thio)-3,5-dicyano-4-ethylpyridin-2-yl)(methyl)amino)ethyl)carbamate (500 mg, 1.011 mmol, 52% yield). LCMS m/z=517.1 [M+Na]⁺. ¹H NMR (400 MHz, DMSO-d₆) δ ppm 7.82 (s, 1H), 7.45 (m, 6H), 6.93 (s, 1H), 5.58 (s, 1H), 3.81 (s, 2H), 3.40 (s, 3H), 3.21 (s, 2H), 2.76 (s, 2H), 1.34 (s, 9H), 1.20 (s, 3H).

Step 4: 2-((6-((2-Aminoethyl)(methyl)amino)-3,5-dicyano-4-ethylpyridin-2-yl)thio)-2-phenylacetamide, Trifluoroacetic Acid Salt

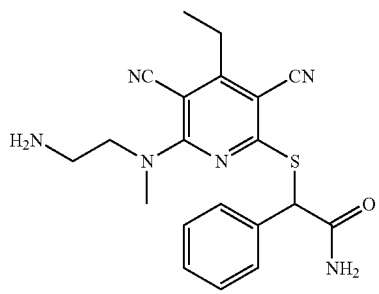 [SMILES: CCc1c(C#N)c(SC(C(N)=O)c2ccccc2)nc(N(C)CCN)c1C#N]

To a solution of tert-butyl (2-((6-((2-amino-2-oxo-1-phenylethyl)thio)-3,5-dicyano-4-ethylpyridin-2-yl)(methyl)amino)ethyl)carbamate (200 mg, 0.404 mmol) in DCM (30 mL) was added 2,2,2-trifluoroacetic acid (46.1 mg, 0.404 mmol). The reaction mixture was stirred at 25° C. overnight. The mixture was concentrated and the residue was further purified by prep-HPLC to give 2-((6-((2-aminoethyl)(methyl)amino)-3,5-dicyano-4-ethylpyridin-2-yl)thio)-2-phenylacetamide, trifluoroacetic acid salt (100 mg, 48% yield). LCMS m/z=395.1 [M+H]⁺. ¹H NMR (400 MHz, DMSO-d₆) δ ppm 8.01 (s, 1H), 7.93 (s, 3H), 7.56-7.46 (m, 3H), 7.45-7.33 (m, 3H), 5.49 (s, 1H), 4.00 (t, J=6.1 Hz, 2H), 3.46 (s, 3H), 3.12 (dt, J=11.4, 5.8 Hz, 2H), 2.80 (q, J=7.5 Hz, 2H), 1.23 (t, J=7.6 Hz, 3H).

Example 145

2-((6-((2-Amino-2-oxoethyl)(methyl)amino)-3,5-dicyano-4-ethylpyridin-2-yl)thio)-2-phenylacetamide

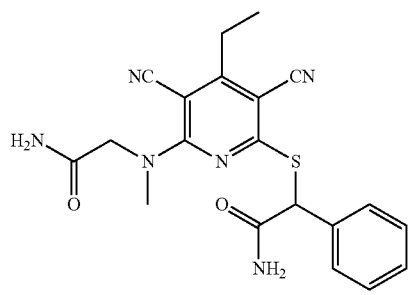 [SMILES: CCc1c(C#N)c(SC(C(N)=O)c2ccccc2)nc(N(C)CC(N)=O)c1C#N]

To a suspension of 2,6-dichloro-4-ethylpyridine-3,5-dicarbonitrile (synthesis described in example 3, step 2, 1.7 g, 7.52 mmol) in ethanol (30 mL) mechanically stirring at −20° C. was added a solution of 2-(methylamino)acetamide, Hydrochloride (1.0 g, 8.03 mmol) and Et₃N (2.17 mL, 15.57 mmol) in ethanol (30 mL). The reaction mixture was then stirred at −20° C. for 45 minutes. To the reaction mixture was then added potassium ethanethioate (1.3 g, 11.38 mmol) and Et₃N (2.62 mL, 18.80 mmol). The heterogeneous reaction mixture was then warmed to 40° C. and stirred at the same temperature. After stirring overnight at 40° C., the reaction mixture was cooled to room temperature. To the room temperature reaction mixture was added 2-amino-2-oxo-1-phenylethyl methanesulfonate (synthesis described in example 3, step 5, 2.6 g, 11.34 mmol). The reaction was warmed to 40° C. and stirred at the same temperature for 3.5 hours. The reaction mixture cooled to 20° C. and then was filtered. The solid was then washed with 300 mL of EtOH, followed by 300 mL of water. The resulting white solid was then again washed with EtOH (200 mL) followed by 100 mL of Et₂O. The solid was then dried in the vacuum oven overnight to obtain 2-((6-((2-amino-2-oxoethyl)(methyl)amino)-3,5-dicyano-4-ethylpyridin-2-yl)thio)-2-phenylacetamide (1.53 g, 3.75 mmol, 50% yield) as a white solid. LCMS m/z=409.3 [M+H]⁺. ¹H NMR (400 MHz, DMSO-d₆) δ ppm 7.83 (s, 1H), 7.62 (s, 1H), 7.47-7.53 (m, 2H), 7.32-7.42 (m, 5H), 5.59 (s, 1H), 4.52 (d, J=17.49 Hz, 1H), 4.29 (d, J=17.24 Hz, 1H), 3.39 (s, 3H), 2.77 (q, J=7.60 Hz, 2H), 1.21 (t, J=7.48 Hz, 3H)

Example 146

2-((3,5-Dicyano-4-ethyl-6-(3-hydroxyazetidin-1-yl)pyridin-2-yl)thio)-2-phenylacetamide Step 1: 2-Chloro-4-ethyl-6-(3-hydroxyazetidin-1-yl)pyridine-3,5-dicarbonitrile

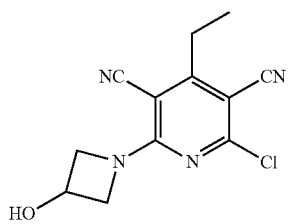 [SMILES: CCc1c(C#N)c(Cl)nc(N2CC(O)C2)c1C#N]

To a solution of 2,6-dichloro-4-ethylpyridine-3,5-dicarbonitrile (synthesis described in example 3 step 2, 300 mg, 1.31 mmol) in dichloromethane (10 mL) was added triethylamine (0.366 mL, 2.63 mmol) followed by azetidin-3-ol hydrochloride (144 mg, 1.31 mmol). The reaction mixture was stirred for 30 minutes at room temperature. The reaction mixture was diluted with DCM (30 mL). The organic layer was washed with water (20 mL) and saturated brine solution (20 mL). The organic layer was dried over anhydrous sodium sulfate, filtered and evaporated to afford 2-chloro-4-ethyl-6-(3-hydroxyazetidin-1-yl)pyridine-3,5-dicarbonitrile (300 mg) as an off-white solid. LCMS m/z=263.0 [M+H]$^+$.

Step 2: 2-((3,5-Dicyano-4-ethyl-6-(3-hydroxyazetidin-1-yl)pyridin-2-yl)thio)-2-phenylacetamide

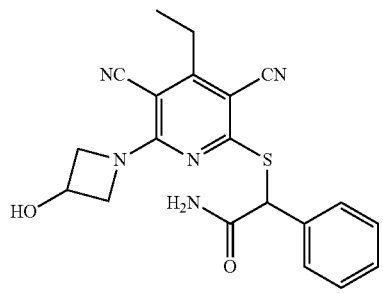 [SMILES: CCc1c(C#N)c(SC(C(N)=O)c2ccccc2)nc(N2CC(O)C2)c1C#N]

2-Chloro-4-ethyl-6-(3-hydroxyazetidin-1-yl)pyridine-3,5-dicarbonitrile (300 mg, 0.994 mmol) and potassium thioacetate (227 mg, 1.987 mmol) were dissolved in N,N-dimethylformamide (20 mL) was added and stirred for 2 hours at room temperature. Then potassium carbonate (275 mg, 1.987 mmol) and 2-amino-2-oxo-1-phenylethyl methanesulfonate (synthesis described in example 3 step 5, 485 mg, 1.987 mmol) were added to the reaction mixture at 0° C. The reaction mixture was stirred overnight at room temperature. The reaction mixture was diluted with HCl solution (1N, 100 mL) and ethyl acetate (80 mL). The organic layer was separated, dried over anhydrous sodium sulfate, filtered and evaporated. The crude product was purified using silica-gel (100-200 mesh, eluting with 3-4% methanol in DCM) to afford 2-((3,5-dicyano-4-ethyl-6-(3-hydroxyazetidin-1-yl)pyridin-2-yl)thio)-2-phenylacetamide (120 mg) as a brown solid. LCMS m/z=394.2 [M+H]$^+$. $^1$H NMR (400 MHz, DMSO-d$_6$) δ ppm 7.84 (br s, 1H), 7.51 (d, J=6.80 Hz, 2H), 7.41-7.16 (m, 4H), 5.87 (br d, J=5.70 Hz, 1H), 5.55 (s, 1H), 4.74-4.37 (m, 3H), 4.16 (m, 2H), 2.69 (q, J=7.45 Hz, 2H), 1.18 (t, J=7.56 Hz, 3H).

Example 147

2-(3,5-Dicyano-4-ethyl-6-((2-hydroxyethyl)(methyl)amino)pyridin-2-ylthio)-2-phenylacetamide Step 1: 2-Chloro-4-ethyl-6-((2-hydroxyethyl)(methyl)amino)pyridine-3,5-dicarbonitrile

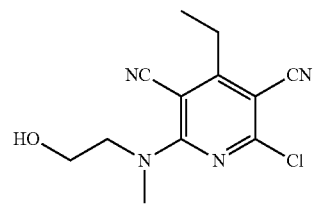 [SMILES: CCc1c(C#N)c(Cl)nc(N(C)CCO)c1C#N]

To a solution of 2,6-dichloro-4-ethylpyridine-3,5-dicarbonitrile (synthesis described in Example 3 step 2, 4.3 g, 19.02 mmol) in dichloromethane (50 mL) was added triethylamine (7.95 mL, 57.1 mmol) and then 2-(methylamino)ethanol (1.43 g, 19.02 mmol) at 0° C. The mixture was warmed to 25° C. and stirred for 16 hours. The mixture was poured into water (30 mL) and extracted with DCM (25 mL×2). The organic phase was concentrated and the residue was purified by column chromatography using DCM/MeOH (100/1) to give 2-chloro-4-ethyl-6-((2-hydroxyethyl)(methyl)amino)pyridine-3,5-dicarbonitrile as a brown solid (5.1 g, 86% yield). LCMS m/z=265.0 [M+H]$^+$.

Step 2: 2-(3,5-Dicyano-4-ethyl-6-((2-hydroxyethyl)(methyl)amino)pyridin-2-ylthio)-2-phenylacetamide

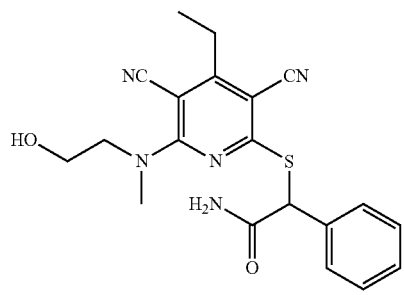 [SMILES: CCc1c(C#N)c(SC(C(N)=O)c2ccccc2)nc(N(C)CCO)c1C#N]

To a solution of 2-chloro-4-ethyl-6-((2-hydroxyethyl)(methyl)amino)pyridine-3,5-dicarbonitrile (2.1 g, 7.93 mmol) in N,N-dimethylformamide (15 mL) were added potassium ethanethioate (1.359 g, 11.90 mmol) and then K$_2$CO$_3$ (3.29 g, 23.80 mmol). The mixture was stirred at 25° C. for 16 hours, and then a solution of 2-amino-2-oxo-1-phenylethyl methanesulfonate (synthesis described in example 3 step 5, 1.923 g, 8.39 mmol) in N,N-dimethylformamide (20 mL) was added. The mixture was stirred at 25° C. for 16 hours. The mixture was poured to water (40 mL) and extracted with ethyl acetate (40 mL×2). The organic phase was concentrated to dryness and the residue was purified by column chromatography using DCM/MeOH (50/1) to give 2-((3,5-dicyano-4-ethyl-6-((2-hydroxyethyl)(methyl)amino)pyridin-2-yl)thio)-2-phenylacetamide (600 mg, 1.517 mmol, 18% yield) as a light yellow solid. LCMS m/z=396.1 [M+H]$^+$. $^1$H NMR (400 MHz, DMSO-d$_6$) δ ppm 7.94 (s, 1H), 7.51 (d, J=8 Hz, 2H), 7.31-7.40 (m, 4H), 5.55 (s, 1H), 4.86 (m, 1H), 3.86 (m, 2H), 3.62 (m, 2H), 3.40 (s, 3H), 2.75 (m, 2H), 1.21 (m, 3H).

Example 148

2-Amino-N-(1-(6-((2-amino-2-oxo-1-phenylethyl)thio)-3,5-dicyano-4-ethylpyridin-2-yl)piperidin-4-yl-2-methylpropanamide Step 1: tert-Butyl (1-((1-(6-((2-amino-2-oxo-1-phenylethyl)thio)-3,5-dicyano-4-ethylpyridin-2-yl)piperidin-4-yl)amino)-2-methyl-1-oxopropan-2-yl)carbamate

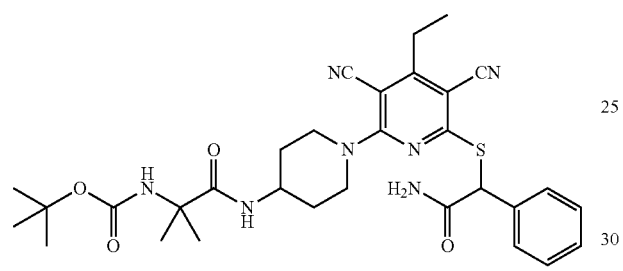

2-((tert-Butoxycarbonyl)amino)-2-methylpropanoic acid (410 mg, 2.017 mmol) and HATU (1151 mg, 3.03 mmol) were dissolved in N,N-dimethylformamide (4 mL) and triethylamine (408 mg, 4.03 mmol) was added. Then 2-((6-(4-aminopiperidin-1-yl)-3,5-dicyano-4-ethylpyridin-2-yl)thio)-2-phenylacetamide (synthesis described in example 143, step 2, 848 mg, 2.017 mmol) was added. The solution was stirred at room temperature for 12 hours. The solution was diluted with water (60 mL) and ethyl acetate (60 mL). The organic phase was washed with water (30 mL) and brine (30 mL), dried, concentrated and the residue was purified on a silica gel column using ethyl acetate to afford tert-butyl (1-((1-(6-((2-amino-2-oxo-1-phenylethyl)thio)-3,5-dicyano-4-ethylpyridin-2-yl)piperidin-4-yl)amino)-2-methyl-1-oxopropan-2-yl)carbamate (900 mg, 74% yield) as a white solid. LCMS m/z=628.2 [M+Na]$^+$.

Step 2: 2-Amino-N-(1-(6-((2-amino-2-oxo-1-phenylethyl)thio)-3,5-dicyano-4-ethylpyridin-2-yl)piperidin-4-yl)-2-methylpropanamide

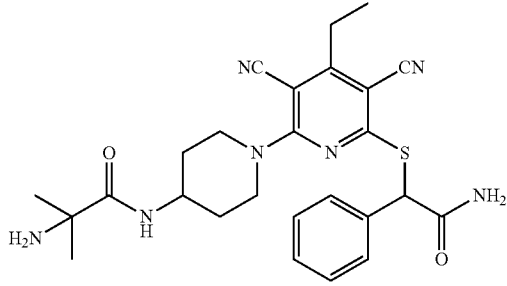 [SMILES: CCc1c(C#N)c(SC(C(N)=O)c2ccccc2)nc(N2CCC(NC(=O)C(C)(C)N)CC2)c1C#N]

tert-Butyl (1-((1-(6-((2-amino-2-oxo-1-phenylethyl)thio)-3,5-dicyano-4-ethylpyridin-2-yl)piperidin-4-yl)amino)-2-methyl-1-oxopropan-2-yl)carbamate (850 mg, 1.403 mmol) was dissolved in a solution of trifluoroacetic acid (1 mL) in dichloromethane (10 mL). The solution was stirred at room temperature for 3 hours. The solution was quenched with saturated NaHCO$_3$ solution (30 mL) and extracted with ethyl acetate (30 mL). The organic phase was washed with water (30 mL) and brine (30 mL), dried, concentrated and the residue was purified on a silica gel column using DCM/MeOH (10/1) to afford 2-amino-N-(1-(6-((2-amino-2-oxo-1-phenylethyl)thio)-3,5-dicyano-4-ethylpyridin-2-yl)piperidin-4-yl)-2-methylpropanamide (129 mg, 18% yield) as a white solid. LCMS m/z=506.1 [M+H]$^+$. $^1$H NMR (400 MHz, DMSO-d$_6$) δ ppm 7.93 (s, 1H), 7.77 (d, J=8.0 Hz, 1H), 7.52 (d, J=7.2 Hz, 2H), 7.45-7.28 (m, 4H), 5.54 (s, 1H), 4.49 (t, J=13.4 Hz, 2H), 3.97-3.78 (m, 1H), 3.37-3.24 (m, 3H), 2.77 (q, J=7.5 Hz, 2H), 2.02 (s, 2H), 1.87 (d, J=12.1 Hz, 2H), 1.64-1.42 (m, 2H), 1.28-1.14 (m, 9H).

Example 149

2-((6-(4-(2-Aminoethoxy)piperidin-1-yl)-3,5-dicyano-4-ethylpyridin-2-yl)thio)-2-phenylacetamide, Trifluoroacetic Acid Salt Step 1: tert-Butyl (2-(piperidin-4-yloxy)ethyl)carbamate

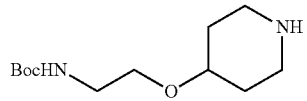

tert-Butyl (2-(pyridin-4-yloxy)ethyl)carbamate (1.9 g, 7.97 mmol) was dissolved in acetic acid (20 mL) and platinum(IV) oxide (0.030 g, 0.132 mmol) was added. The mixture was stirred under H$_2$ (0.4 MPa) for 12 hours. The mixture was filtered and the filtrate was concentrated to give tert-butyl (2-(piperidin-4-yloxy)ethyl)carbamate (2 g, 98% yield). $^1$H NMR (400 MHz, DMSO-d$_6$) δ ppm 6.84 (s, 1H), 3.49-3.45 (m, 1H), 3.39-3.36 (m, 2H), 3.36-3.33 (m, 4H), 2.79-2.73 (m, 2H), 1.86-1.80 (m, 2H), 1.56 (m, 2H), 1.37 (s, 9H).

Step 2: tert-Butyl (2-((1-(6-chloro-3,5-dicyano-4-ethylpyridin-2-yl)piperidin-4-yl)oxy) ethyl)carbamate

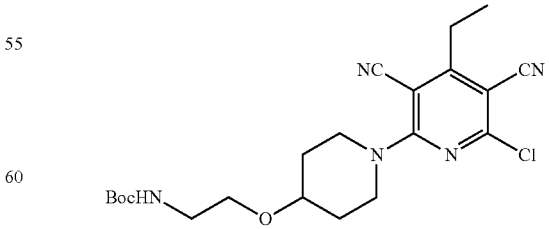

2,6-Dichloro-4-ethylpyridine-3,5-dicarbonitrile (synthesis described in Example 3 step 2, 925 mg, 4.09 mmol) and tert-butyl (2-(piperidin-4-yloxy)ethyl)carbamate (1000 mg, 0.409 mmol) were dissolved in DCM (20 mL) and triethylamine (0.507 mL, 4.09 mmol) was added. The solution was stirred at room temperature for 12 hours. Water (20 mL) was added and the separated organic phase was washed with brine (30 mL), dried and concentrated to give tert-butyl (2-((1-(6-chloro-3,5-dicyano-4-ethylpyridin-2-yl)piperidin-4-yl)oxy)ethyl)carbamate (1360 mg, 77% yield). LCMS: m/z=456.1 [M+Na]$^+$.

Step 3: tert-Butyl (2-((1-(5-((2-amino-2-oxo-1-phenylethyl)thio)-2,4-dicyano-3-ethylphenyl) piperidin-4-yl)oxy)ethyl)carbamate

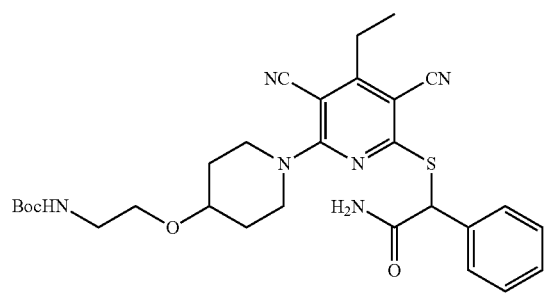 [SMILES: CCc1c(C#N)c(SC(C(N)=O)c2ccccc2)nc(N2CCC(OCCNC(=O)OC(C)(C)C)CC2)c1C#N]

tert-Butyl (2-((1-(5-chloro-2,4-dicyano-3-ethylphenyl)piperidin-4-yl)oxy)ethyl)carbamate (300 mg, 0.691 mmol) was dissolved in N,N-dimethylformamide (6 mL) and potassium thioacetate (118 mg, 1.037 mmol) was added. The solution was stirred at room temperature for 1 hour and K$_2$CO$_3$ (191 mg, 1.383 mmol) was then added. The mixture was stirred at room temperature for 1 hour and then 2-amino-2-oxo-1-phenylethyl methanesulfonate (synthesis described in Example 3 step 5, 238 mg, 1.037 mmol) was added. The mixture was stirred at room temperature for 12 hours. The mixture was diluted with water and extracted with ethyl acetate (40 mL). The organic phase was washed with brine (30 mL), dried and concentrated and the residue was purified on a silica gel column using petroleum ether/ethyl acetate (1/1) to give tert-butyl (2-((1-(5-((2-amino-1-phenylethyl)thio)-2,4-dicyano-3-ethylphenyl)piperidin-4-yl)oxy)ethyl)carbamate (300 mg, 77% yield). LCMS: m/z=586.8 [M+Na]$^+$.

Step 4: 2-((6-(4-(2-Aminoethoxy)piperidin-1-yl)-3,5-dicyano-4-ethylpyridin-2-yl)thio)-2-phenylacetamide, Trifluoroacetic Acid Salt

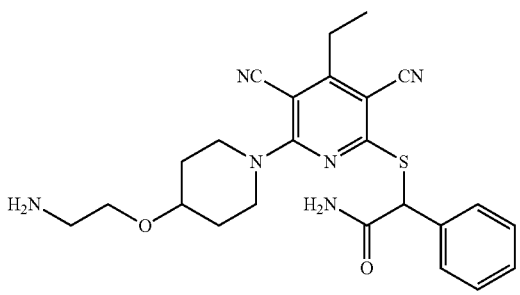 [SMILES: CCc1c(C#N)c(SC(C(N)=O)c2ccccc2)nc(N2CCC(OCCN)CC2)c1C#N]

tert-Butyl(2-((1-(6-((2-amino-2-oxo-1-phenylethyl)thio)-3,5-dicyano-4-ethylpyridin-2-yl)piperidin-4-yl)oxy)ethyl)carbamate (300 mg, 0.531 mmol) was added to dichloromethane (20 mL) and a solution of 2,2,2-trifluoroacetic acid (100 mg, 0.877 mmol) in 5 mL of dichloromethane was added at 0° C. The mixture was stirred overnight and then concentrated. The residue was purified by prep-HPLC to give 2-((6-(4-(2-aminoethoxy)piperidin-1-yl)-3,5-dicyano-4-ethylpyridin-2-yl)thio)-2-phenylacetamide, trifluoroacetic acid salt (100 mg, 33% yield). LCMS m/z=465.1 [M+H]$^+$. $^1$H NMR (400 MHz, DMSO-d$_6$): δ ppm 7.93 (s, 1H), 7.82 (s, 2H), 7.53 (d, J=7.2 Hz, 2H), 7.41-7.34 (m, 4H), 5.53 (s, 1H), 4.12 (m, 2H), 3.70-3.62 (m, 5H), 3.03 (m, 2H), 2.75 (m, 2H), 1.95 (m, 2H), 1.61 (m, 2H), 1.23 (t, J=7.6 Hz, 3H).

Example 150

1-(6-((2-Amino-2-oxo-1-phenylethyl)thio)-3,5-dicyano-4-ethylpyridin-2-yl)pyrrolidin-3-yl dihydrogen phosphate

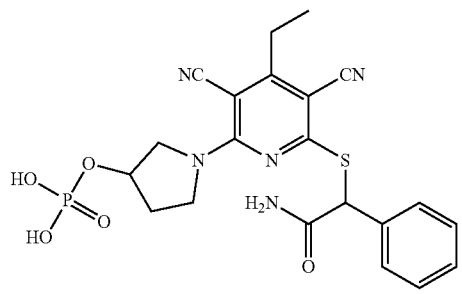 [SMILES: CCc1c(C#N)c(SC(C(N)=O)c2ccccc2)nc(N2CCC(OP(=O)(O)O)C2)c1C#N]

To a stirred suspension of 2-((3,5-dicyano-4-ethyl-6-(3-hydroxypyrrolidin-1-yl)pyridin-2-yl)thio)-2-phenylacetamide (synthesis described in example 370, step 2, 400 mg, 0.911 mmol) in triethylamine (0.190 mL, 1.367 mmol) was added triethyl phosphate (4 mL, 0.911 mmol), and the reaction mixture was cooled to 0° C. After 5 minutes, POCl$_3$ (0.127 mL, 1.367 mmol) was added and the reaction mixture was vigorously stirred at 0° C. for 1.5 hours. The reaction mixture was quenched with water (1.5 mL) and stirred for 10 minutes. The reaction mixture was purified by Grace machine and the pure fractions were concentrated to afford 110 mg (with two LC peaks corresponding to two diastereomers with abundances of 65% and 14%). The above 110 mg of product was combined with 300 mg of material from a separate batch that was prepared in an analogous manner (with two LC peaks corresponding to two diastereomers with abundances of 14% and 19%) and subjected to prep-HPLC purification. The pure fractions were lyophilized to afford 70 mg of an off-white solid which showed triethyl phosphate residual peaks. The solid was triturated with 5% EtOAc in hexane (6 mL), followed by 10% EtOAc in hexane (2×5 mL) and finally 20% EtOAc in hexane (6 mL). The solid was dried under vacuum to afford 1-(6-((2-amino-2-oxo-1-phenylethyl)thio)-3,5-dicyano-4-ethylpyridin-2-yl)pyrrolidin-3-yl dihydrogen phosphate (62 mg) as a grey solid. LCMS m/z=486.3 [M–H]$^-$. $^1$H NMR (D$_2$O-Exchange) (400 MHz, DMSO-d$_6$) δ ppm 7.58-7.51 (m, 2H), 7.44-7.32 (m, 3H), 5.68-5.58 (m, 1H), 4.80-4.76 (m, 1H), 4.09-3.86 (m, 4H), 2.76-2.72 (m, 2H), 2.20-2.16 (m, 1H), 2.07-1.99 (m, 1H), 1.29-1.11 (m, 3H).

Example 151

2-((6-((2-Amino-2-oxo-1-phenylethyl)thio)-3,5-di-cyano-4-ethylpyridin-2-yl)(methyl)amino)ethyl dihydrocien phosphate

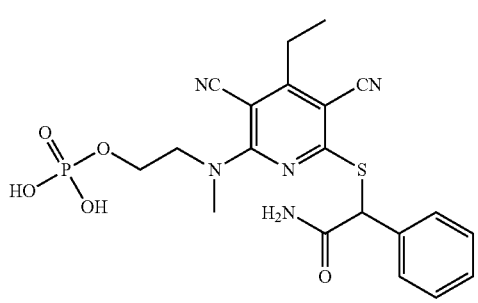 [SMILES: CCc1c(C#N)c(SC(C(N)=O)c2ccccc2)nc(N(C)CCOP(=O)(O)O)c1C#N]

To a suspension of 2-((3,5-dicyano-4-ethyl-6-((2-hydroxyethyl)(methyl)amino)pyridin-2-yl)thio)-2-phenylacetamide (synthesis described in example 147 step 2, 300 mg, 0.759 mmol) in triethylamine (159 µL, 1.138 mmol) was added triethyl phosphate (2583 µL, 15.17 mmol), and the mixture was cooled to 0° C. Phosphoryl trichloride (174 mg, 1.138 mmol) was then added and the mixture vigorously stirred at 0° C. for 1.5 hours. The reaction mixture was quenched with water (1.5 mL) and stirred for 10 minutes. It was then basified with NaOH (1 M, 20 mL), diluted with ethyl acetate (40 mL), and stirred for 10 minutes. The layers were separated and the aqueous layer was acidified with HCl (1N, 50 mL) and extracted with ethyl acetate (3×50 mL). The organic layer was dried over $Na_2SO_4$ and concentrated under vacuum to afford 90 mg of crude compound which was purified by prep-HPLC purification. The pure fractions were lyophilized to afford 15 mg as an off white solid. This material was combined with 7 mg of product from a separate batch. The combined material was dissolved in acetonitrile (2 mL) and water (5 mL). This solution was frozen and lyophilized to afford 2-((6-((2-amino-2-oxo-1-phenylethyl)thio)-3,5-dicyano-4-ethylpyridin-2-yl)(methyl)amino)ethyl dihydrogenphosphate (15 mg) as an off-white solid. LCMS m/z=474.3 [M–H]⁻. $^1$H NMR (400 MHz, DMSO-$d_6$) δ ppm 9.87 (br s, 1H), 7.96-7.60 (m, 2H), 7.31-7.27 (m, 3H), 6.94 (br s, 1H), 6.52 (br s, 1H), 6.24 (br s, 1H), 6.10 (s, 1H), 4.00-3.88 (m, 2H), 3.86-3.72 (m, 2H), 3.40 (s, 3H), 2.74 (q, J=7.5 Hz, 2H), 1.19 (t, J=7.6 Hz, 3H).

Example 152

1-(6-((2-Amino-2-oxo-1-phenylethyl)thio)-3,5-di-cyano-4-ethylpyridin-2-yl)azetidin-3-yl dihydrogen phosphate

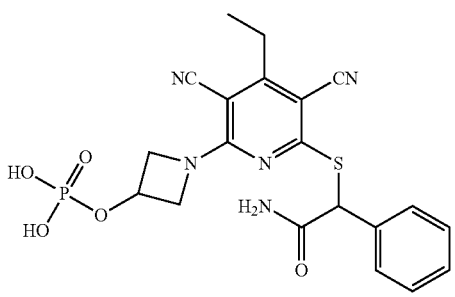 [SMILES: CCc1c(C#N)c(SC(C(N)=O)c2ccccc2)nc(N2CC(OP(=O)(O)O)C2)c1C#N]

POCl₃ (0.067 mL, 0.716 mmol) was added dropwise to a mixture of 2-((3,5-dicyano-4-ethyl-6-(3-hydroxyazetidin-1-yl)pyridin-2-yl)thio)-2-phenylacetamide (synthesis described in example 146 step 2, 200 mg, 0.477 mmol), triethylamine (0.100 mL, 0.716 mmol), and triethyl phosphate (0.5 mL, 0.477 mmol) at 0° C. The reaction mixture was stirred for 1 hour at the same temperature. The reaction mixture was quenched with ice cold water (50 mL), and the pH of the reaction mixture was adjusted to pH ~11 by the slow addition of NaOH (1N, 40 mL). Then the reaction mixture was washed with ethyl acetate (2×30 mL). Then the aqueous layer was slowly acidified with HCl (1N, 30 mL) to pH 1 and extracted with ethyl acetate (2×50 mL). The combined organic layers were dried over anhydrous $Na_2SO_4$, filtered, and concentrated. The resultant crude purified by prep-HPLC. Then the pure fractions were lyophilized and dried to afford 1-(6-((2-amino-2-oxo-1-phenylethyl)thio)-3,5-dicyano-4-ethylpyridin-2-yl)azetidin-3-yl dihydrogen phosphate (54 mg, 24% yield) as a white solid. LCMS m/z=472.3 [M–H]⁻. $^1$H NMR (400 MHz, DMSO-$d_6$): δ ppm 8.25 (s, 1H), 7.72-7.52 (m, 2H), 7.44-7.26 (m, 3H), 7.20 (s, 1H), 6.75 (bs, 2H), 5.63 (s, 1H), 4.89-4.77 (m, 1H), 4.77-4.56 (m, 2H), 4.41-4.24 (m, 2H), 2.66 (q, J=7.7 Hz, 2H), 1.16 (t, J=7.6 Hz, 3H).

Example 153

(2S)-2-((1-(6-((2-Amino-2-oxo-1-phenylethyl)thio)-3,5-dicyano-4-ethylpyridin-2-yl)piperidin-4-yl)oxy)ethyl 2-amino-3-methylbutanoate Step 1: (2S)-2-((1-(6-((2-Amino-2-oxo-1-phenylethyl)thio)-3,5-dicyano-4-ethylpyridin-2-yl)piperidin-4-yl)oxy)ethyl2-((tert-butoxycarbonyl)amino)-3-methylbutanoate

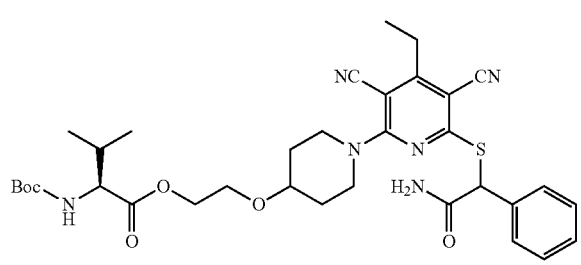 [SMILES: CCc1c(C#N)c(SC(C(N)=O)c2ccccc2)nc(N2CCC(OCCOC(=O)[C@@H](NC(=O)OC(C)(C)C)C(C)C)CC2)c1C#N]

To a solution of 1H-benzo[d][1,2,3]triazol-4-ol (0.058 g, 0.430 mmol), (S)-2-((tert-butoxycarbonyl)amino)-3-methylbutanoic acid (0.560 g, 2.58 mmol) and EDC (0.494 g, 2.58 mmol) in dichloromethane (10 mL) was added triethylamine (0.261 g, 2.58 mmol) at room temperature. The resultant mixture was stirred at room temperature for 1 hour then treated with 2-((3,5-dicyano-4-ethyl-6-(4-(2-hydroxyethoxy)piperidin-1-yl)pyridin-2-yl)thio)-2-phenylacetamide (synthesis described in example 224, step 4, 0.2 g, 0.430 mmol). The resultant mixture was stirred at room temperature overnight then concentrated in vacuo. The residue was purified by a silica gel column using DCM/MeOH (50/1) to give (2S)-2-((1-(6-((2-amino-2-oxo-1-phenylethyl)thio)-3,5-dicyano-4-ethylpyridin-2-yl)piperidin-4-yl)oxy)ethyl 2-((tert-butoxycarbonyl)amino)-3-methylbutanoate (250 mg). LCMS m/z=687.2 [M+Na]+.

Step 2: (2S)-2-((1-(6-((2-Amino-2-oxo-1-phenylethyl)thio)-3,5-dicyano-4-ethylpyridin-2-yl)piperidin-4-yl)oxy)ethyl 2-amino-3-methylbutanoate

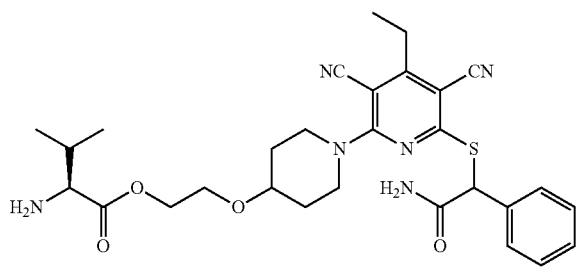 [SMILES: CCc1c(C#N)c(SC(C(N)=O)c2ccccc2)nc(N2CCC(OCCOC(=O)[C@@H](N)C(C)C)CC2)c1C#N]

To a solution of (2S)-2-((1-(6-((2-amino-2-oxo-1-phenylethyl)thio)-3,5-dicyano-4-ethylpyridin-2-yl)piperidin-4-yl)oxy)ethyl 2-((tert-butoxycarbonyl)amino)-3-methylbutanoate (230 mg, 0.346 mmol) in dichloromethane (5 mL) was added 2,2,2-trifluoroacetic acid (394 mg, 3.46 mmol) at room temperature. The resultant mixture was stirred at room temperature overnight then concentrated in vacuo and the residue was diluted with EtOAc (50 mL) and washed with saturated sodium bicarbonate solution (25 mL), water (10 mL) and saturated brine (10 mL), dried over sodium sulfate and evaporated in vacuo. The crude product was added to a silica gel column and was eluted with DCM/MeOH (30/1) to give (2S)-2-((1-(6-((2-amino-2-oxo-1-phenylethyl)thio)-3,5-dicyano-4-ethylpyridin-2-yl)piperidin-4-yl)oxy)ethyl 2-amino-3-methylbutanoate (120 mg, 59% yield). LCMS m/z=565.1 [M+H]+. $^1$H NMR (400 MHz, DMSO-$d_6$) δ ppm 7.93 (s, 1H), 7.52 (d, J=7.2 Hz, 2H), 7.44-7.30 (m, 4H), 5.53 (s, 1H), 4.26 (m, 1H), 4.19-4.05 (m, 3H), 3.74-3.55 (m, 5H), 3.16 (s, 1H), 2.76 (q, J=7.5 Hz, 2H), 2.03-1.77 (m, 5H), 1.62-1.48 (m, 2H), 1.22 (t, J=7.6 Hz, 3H), 0.88 (dd, J=15.8, 6.8 Hz, 6H).

Example 154

2-((1-(6-((2-Amino-2-oxo-1-phenylethyl)thio)-3,5-dicyano-4-ethylpyridin-2-yl)piperidin-4-epoxy)ethyl dihydrogen phosphate

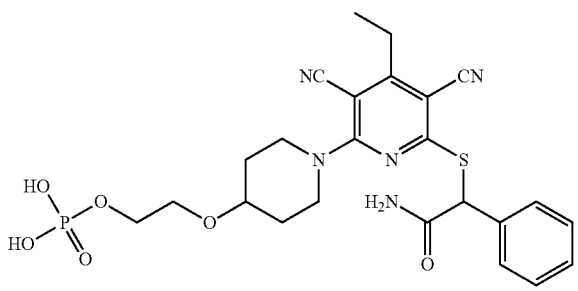 [SMILES: CCc1c(C#N)c(SC(C(N)=O)c2ccccc2)nc(N2CCC(OCCOP(=O)(O)O)CC2)c1C#N]

A mixture of triethyl phosphate (58.7 mg, 0.322 mmol) and phosphoryl trichloride (148 mg, 0.967 mmol) was stirred at 0° C. and 10 minutes later the resultant mixture was treated with 2-((3,5-dicyano-4-ethyl-6-(4-(2-hydroxyethoxy)piperidin-1-yl)pyridin-2-yl)thio)-2-phenylacetamide (synthesis described in example 224, step 4, 150 mg, 0.322 mmol) at 0° C. The resultant mixture was stirred at 0° C. for 1 hour then at room temperature for 2 hours then quenched with crushed ice. The resultant mixture was dissolved in Me-CN (10 mL) and purified by prep HPLC (eluted with Me-CN/formic acid 0.1%) to give 2-((1-(6-((2-amino-2-oxo-1-phenylethyl)thio)-3,5-dicyano-4-ethylpyridin-2-yl)piperidin-4-yl)oxy)ethyl dihydrogen phosphate (90 mg, 0.163 mmol, 51% yield). LCMS m/z=546.0 [M+H]+. $^1$H NMR (400 MHz, DMSO-$d_6$) δ ppm 11.55-10.42 (br, 2H), 7.94 (s, 1H), 7.52 (d, J=7.3 Hz, 2H), 7.43-7.31 (m, 4H), 5.53 (s, 1H), 4.17-4.07 (m, 2H), 3.94 (m, 2H), 3.72-3.56 (m, 5H), 2.76 (m, 2H), 1.99-1.89 (m, 2H), 1.63-1.51 (m, 2H), 1.21 (t, J=7.6 Hz, 3H).

Example 155

1-(6-((2-Amino-2-oxo-1-phenylethyl)thio)-3,5-dicyano-4-ethylpyridin-2-yl)piperidin-4-yl dihydrogen phosphate

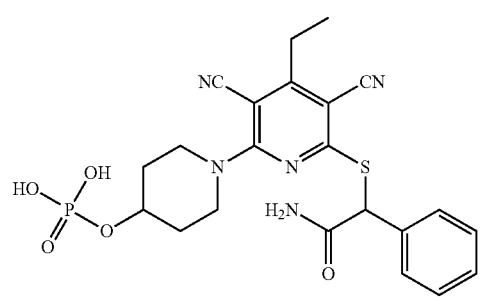 [SMILES: CCc1c(C#N)c(SC(C(N)=O)c2ccccc2)nc(N2CCC(OP(=O)(O)O)CC2)c1C#N]

POCl$_3$ (0.130 mL, 1.392 mmol) was added dropwise to a mixture of 2-((3,5-dicyano-4-ethyl-6-(4-hydroxypiperidin-1-yl)pyridin-2-yl)thio)-2-phenylacetamide (synthesis described in example 48, 400 mg, 0.928 mmol), triethylamine (0.194 mL, 1.392 mmol) and triethyl phosphate (4 mL, 23.50 mmol) at 0° C., and the reaction mixture was stirred for 1 hour at the same temperature. After 1 hour additional triethylamine (0.194 mL, 1.392 mmol) and POCl₃ (0.130 mL, 1.392 mmol) were added dropwise at 0° C. and stirred for 1 hour at the same temperature. The reaction mixture was quenched with ice cold water (70 mL), and the pH of the reaction mixture was adjusted to pH 11 with slow addition of NaOH (1N, 50 mL).The solution was washed with EtOAc (2×30 mL). Then the aqueous layer was slowly acidified with HCl (1N, 30 mL) to pH 1 and extracted with EtOAc (2×50 mL). The combined organic layers were dried over anhydrous Na₂SO₄, filtered, concentrated and dried to obtain the crude product. The crude material was subjected to prep HPLC and the pure fractions were lyophilized and dried to obtain 1-(6-((2-amino-2-oxo-1-phenylethyl)thio)-3,5-dicyano-4-ethylpyridin-2-yl)piperidin-4-yl dihydrogen phosphate (90 mg, 19% yield) as a white solid. LCMS m/z=500.1 [M−H]⁻. ¹H NMR (400 MHz, DMSO-d₆) δ ppm 8.03 (br s, 1H), 7.58-7.44 (m, 2H), 7.40-7.25 (m, 4H), 5.56 (s, 1H), 4.36-4.27 (m, 1H), 4.04-3.93 (m, 2H), 3.81-3.71 (m, 2H), 2.74 (q, J=7.67 Hz, 2H), 1.99-1.83 (m, 2H), 1.70 (m, 2H), 1.19 (t, J=7.56 Hz, 3H).

Example 156

N-(4-(((6-(4-Aminopiperidin-1-yl)-3,5-dicyano-4-ethylpyridin-2-yl)thio)methyl)benzyl)acetamide, Trifluoroacetic Acid Salt Step 1: tert-Butyl (1-(6-((4-(acetamidomethyl)benzyl)thio)-3,5-dicyano-4-ethylpyridin-2-yl)piperidin-4-yl)carbamate

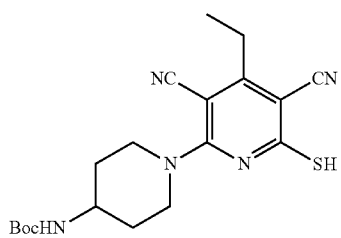 [SMILES: CCc1c(C#N)c(S)nc(N2CCC(NC(=O)OC(C)(C)C)CC2)c1C#N]

To a solution of tert-butyl (1-(6-chloro-3,5-dicyano-4-ethylpyridin-2-yl)piperidin-4-yl)carbamate (synthesis described in Example 81 step 1, 3 g, 7.69 mmol) in N,N-dimethylformamide (50 mL) was added K₂CO₃ (1.063 g, 7.69 mmol) and then potassium ethanethioate (0.879 g, 7.69 mmol). The mixture was stirred at 25° C. for 2 hours and was used in the next step without further purification. LCMS m/z=410.1 [M+Na]⁺.

Step 2: tert-Butyl (1-(6-((4-(acetamidomethyl)benzyl)thio)-3,5-dicyano-4-ethylpyridin-2-yl)piperidin-4-yl)carbamate

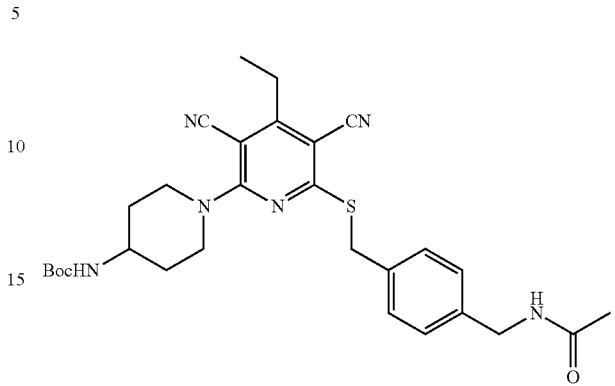

To the above mixture (Example 156, Step 1) was added N-(4-(bromomethyl)benzyl)acetamide (6 g, 12.39 mmol). The mixture was stirred at 25° C. for 16 hours. The mixture was filtered and concentrated. The residue was diluted with ethyl acetate (40 mL) and washed with water (20 mL). The organic phase was concentrated and the residue was purified by column chromatography using DCM-MeOH (50/1), and the product was then recrystallized with ethyl acetate-petroleum ether (1/1) to give tert-butyl(1-(6-((4-(acetamidomethyl)benzyl)thio)-3,5-dicyano-4-ethylpyridin-2-yl)piperidin-4-yl)carbamate (3.3 g, 6.01 mmol) as a yellow solid. LCMS m/z=549.2 [M+H]⁺.

Step 3: N-(4-(((6-(4-Aminopiperidin-1-yl)-3,5-dicyano-4-ethylpyridin-2-yl)thio)methyl) benzyl)acetamide, Trifluoroacetic Acid Salt

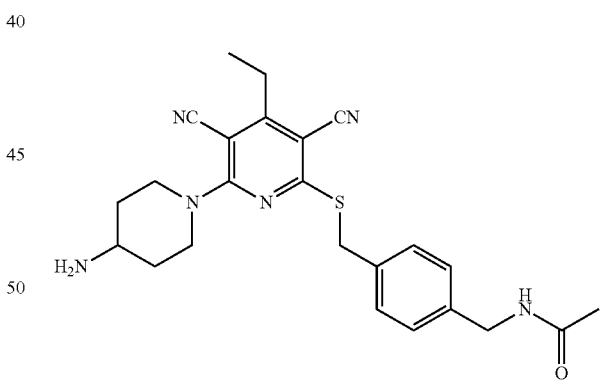

To a solution of tert-butyl (1-(6-((4-(acetamidomethyl)benzyl)thio)-3,5-dicyano-4-ethylpyridin-2-yl)piperidin-4-yl)carbamate (2.9 g, 5.29 mmol) in dichloromethane (30 mL) was added TFA (3.26 mL, 42.3 mmol) at 0° C. The mixture was warmed to 25° C. and stirred for 4 hours. The mixture was concentrated and the residue was diluted with methyl t-butyl ether (30 mL). The mixture was stirred for 1 hour and filtered to give N-(4-(((6-(4-aminopiperidin-1-yl)-3,5-dicyano-4-ethylpyridin-2-yl)thio)methyl)benzyl)acetamide, trifluoroacetic acid salt (2 g) as an off-white solid. LCMS m/z=449.1 [M+H]⁺. ¹H NMR (400 MHz, DMSO-d₆) δ ppm 8.37 (br, 1H), 8.10 (s, 3H), 7.36 (d, J=8 Hz, 2H), 7.21

(d, J=8 Hz, 2H), 4.49-4.56 (m, 4H), 4.22 (m, 2H), 3.27 (m, 2H), 2.77 (m, 2H), 2.04 (m, 2H), 1.87 (s, 3H), 1.54 (m, 2H), 1.22 (m, 3H).

Example 157

2-((3,5-Dicyano-6-(dimethylamino)-4-ethylpyridin-2-yl)thio)-2-(piperidin-4-yl)acetamide Step 1: Tert-butyl 4-(2-methoxy-2-oxoethyl)piperidine-1-carboxylate

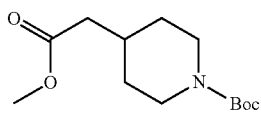 [SMILES: COC(=O)CC1CCN(C(=O)OC(C)(C)C)CC1]

Triethylamine (6.44 g, 63.6 mmol) was added to a solution of methyl 2-(piperidin-4-yl)acetate (4.0 g, 25.4 mmol) in dichloromethane (35 mL). Then di-tert-butyl dicarbonate (8.33 g, 38.2 mmol) was added dropwise at 0° C. The reaction mixture was stirred 3 hours at 0° C. then overnight at room temperature. After washing with water (3×50 mL), concentration under vacuum afforded tert-butyl 4-(2-methoxy-2-oxoethyl)piperidine-1-carboxylate (5.7 g, 22 mmol, 87% yield) as a white solid. LCMS m/z=158.1 [M+H-100]$^+$.

Step 2: Tert-butyl 4-(1-bromo-2-methoxy-2-oxo-ethyl)piperidine-1-carboxylate

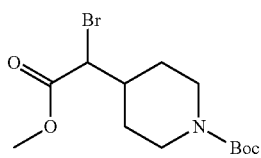 [SMILES: COC(=O)C(Br)C1CCN(C(=O)OC(C)(C)C)CC1]

A solution of tert-butyl 4-(2-methoxy-2-oxoethyl)piperidine-1-carboxylate (5.0 g, 19.43 mmol) in THF (5 mL) was added to LHMDS (1.0 M in THF) (35.0 mL, 35.0 mmol) at −78° C. and the reaction mixture was stirred at −78° C. for 3 hours. Lithium bis(trimethylsilyl) amide (5.86 g, 35 mmol) was added dropwise and the mixture was stirred for 1 hour at −78° C. then bromine (3.76 g, 23.5 mmol) was added dropwise. The mixture was stirred at −78° C. for 2 hours, then allowed to warm to 0° C. and stirred for an additional 30 minutes. The mixture was diluted with ethyl acetate and washed with saturated NaHCO$_3$ solution, then washed with H$_2$O. The organics were dried over Na$_2$SO$_4$, then the drying agent was filtered and solvent removed in vacuo to afford tert-butyl 4-(1-bromo-2-methoxy-2-oxoethyl)piperidine-1-carboxylate (5.7 g, 10 mmol, 52% yield) as a yellow oil. LCMS m/z=358.1 [M+Na]$^+$.

Step 3: tert-Butyl 4-(2-amino-1-bromo-2-oxoethyl) piperidine-1-carboxylate

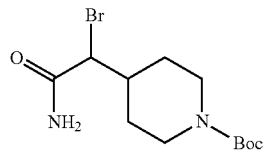 [SMILES: CC(C)(C)OC(=O)N1CCC(C(Br)C(N)=O)CC1]

A solution of lithium hydroxide (0.236 g, 9.81 mmol) in water (7.0 mL) was added to a solution of tert-butyl 4-(1-bromo-2-methoxy-2-oxoethyl)piperidine-1-carboxylate (2.2 g, 6.5 mmol) in MeOH (21 mL) and THF (7 mL). The reaction mixture was stirred 3 hours at room temperature. The solvent was removed in vacuo to provide a white solid, which was acidified with 1N HCl. The crude product was extracted with ethyl acetate and the organics were washed with brine and dried over Na$_2$SO$_4$. The drying agent was filtered and the solvent removed in vacuo to afford 2-bromo-2-(1-(tert-butoxycarbonyl)piperidin-4-yl)acetic acid (1.0 g) as a yellow oil. This material was used in the next step without further purification. Triethylamine (0.471 g, 4.66 mmol) and isobutyl carbonochloridate (0.636 g, 4.66 mmol) were added to a cooled (0° C.) solution of 2-bromo-2-(1-(tert-butoxycarbonyl)piperidin-4-yl)acetic acid (1.0 g, 3.10 mmol) in 25 mL of dichloromethane. The reaction mixture was allowed to warm to room temperature and stirred for 15 minutes under a nitrogen atmosphere. Ammonium hydroxide (7.01 g, 200 mmol) was added. The reaction mixture was stirred for 5 minutes. The reaction mixture was washed with sodium bicarbonate solution (1×10 mL), 1N HCl solution (15 mL), and brine (10 mL). The organic layers were combined, dried over magnesium sulfate, filtered, and concentrated under reduced pressure to afford tert-butyl 4-(2-amino-1-bromo-2-oxoethyl)piperidine-1-carboxylate (1 g, 1.87 mmol) as a yellow oil. LCMS m/z=343.0 [M+Na]$^+$.

Step 4: tert-Butyl 4-(2-amino-1-((3,5-dicyano-6-(dimethylamino)-4-ethylpyridin-2-yl)thio)-2-oxo-ethyl)piperidine-1-carboxylate

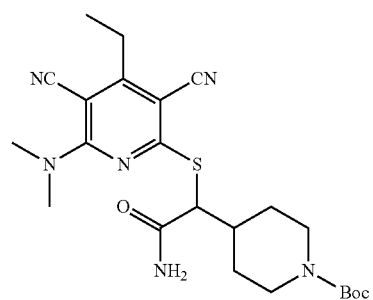 [SMILES: CCc1c(C#N)c(SC(C(N)=O)C2CCN(C(=O)OC(C)(C)C)CC2)nc(N(C)C)c1C#N]

To a solution of 2-chloro-6-(dimethylamino)-4-ethylpyridine-3,5-dicarbonitrile (synthesis described in example 3, step 3, 0.482 g, 2.06 mmol) in N,N-dimethylformamide (25 mL) was added potassium ethanethioate (0.256 g, 2.24 mmol). The reaction mixture was stirred 30 minutes at room temperature, then tert-butyl 4-(2-amino-1-bromo-2-oxoethyl)piperidine-1-carboxylate (1.0 g, 1.9 mmol) and triethylamine (0.473 g, 4.67 mmol) was added to the reaction. The reaction mixture was stirred overnight at room temperature. The mixture was poured onto 30 mL of water. The resulting solution was extracted with 3×20 mL of ethyl acetate. The organic layers were combined, washed with aqueous sodium carbonate and brine, dried and concentrated under vacuum to afford a crude product as a yellow oil. The residue was loaded onto a silica gel column and eluted with ethyl acetate/hexane (1:2) to give tert-butyl 4-(2-amino-1-((3,5-dicyano-6-(dimethylamino)-4-ethylpyridin-2-yl)thio)-2-oxoethyl)piperidine-1-carboxylate (350 mg, 0.74 mmol) as a yellow solid. LCMS m/z=495.1 [M+Na]⁺.

Step 5: 2-((3,5-dicyano-6-(dimethylamino)-4-ethylpyridin-2-yl)thio)-2-(piperidin-4-yl)acetamide

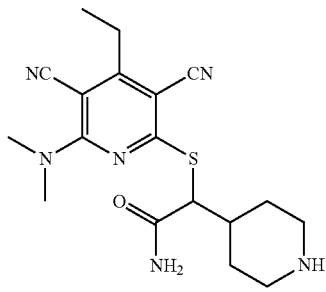 [SMILES: CCc1c(C#N)c(SC(C(N)=O)C2CCNCC2)nc(N(C)C)c1C#N]

To a solution of tert-butyl 4-(2-amino-1-((3,5-dicyano-6-(dimethylamino)-4-ethylpyridin-2-yl)thio)-2-oxoethyl)piperidine-1-carboxylate (350 mg, 0.74 mmol) in DCM (3 mL) was added trifluoroacetic acid (3.0 mL), then the reaction mixture was stirred overnight at room temperature. The solvent and TFA were removed under reduced pressure to give a yellow solid. The solid was purified by prep-TLC to afford 2-((3,5-dicyano-6-(dimethylamino)-4-ethylpyridin-2-yl)thio)-2-(piperidin-4-yl)acetamide (220 mg, 0.57 mmol, 76% yield) as a yellow solid. LCMS m/z=373.1 [M+H]⁺. $^1$H NMR (400 MHz, MeOD) δ ppm 4.49 (d, J=6.7 Hz, 1H), 3.42 (s, 6H), 3.18-3.11 (m, 2H), 2.91 (q, J=7.6 Hz, 2H), 2.72-2.60 (m, 2H), 2.23-2.12 (m, 1H), 1.96-1.90 (m, 1H), 1.88-1.80 (m, 1H), 1.65-1.53 (m, 1H), 1.51-1.40 (m, 1H), 1.31 (t, J=7.6 Hz, 4H).

Example 158

2-((3,5-Dicyano-4-ethyl-6-(4-(propylsulfonyl)piperazin-1-yl)pyridin-2-yl)thio)-2-phenylacetamide

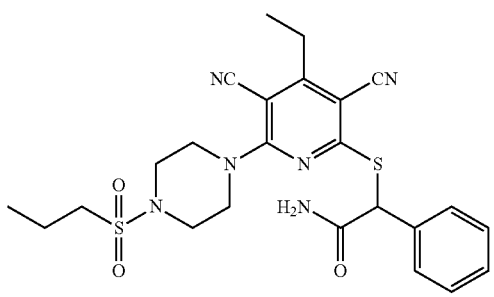 [SMILES: CCCS(=O)(=O)N1CCN(c2nc(SC(C(N)=O)c3ccccc3)c(C#N)c(CC)c2C#N)CC1]

A solution of 2-[(3,5-dicyano-4-ethyl-6-piperazin-1-yl)-2-pyridyl)sulfanyl]-2-phenyl-acetamide (synthesis described in example 55, 36 mg, 0.09 mmol) in DCM (5 mL) was treated with N,N-diisopropylethylamine (0.02 mL, 0.11 mmol) followed by 1-propanesulfonyl chloride (0.01 mL, 0.11 mmol) at room temperature. Additional N,N-diisopropylethylamine (0.004 mL, 0.02 mmol) and 1-propanesulfonyl chloride (0.003 mL, 0.02 mmol) were added after 20 hours. After a further 2 hours the mixture was diluted with EtOAc (15 mL), washed with aqueous NaOH (1 M, 5 mL), water (5 mL), aqueous HCl (2 M, 5 mL), water (5 mL) and brine then dried through a hydrophobic frit and concentrated. The resulting solid was triturated with diethyl ether to afford 2-[[3,5-dicyano-4-ethyl-6-(4-propylsulfonylpiperazin-1-yl)-2-pyridyl]sulfanyl]-2-phenyl-acetamide (33 mg, 73% yield) as an off-white solid. LCMS m/z=513.2 [M+H]⁺. $^1$H NMR (300 MHz, DMSO-d₆, D₂O exchange) δ ppm 7.55-7.46 (m, 2H), 7.44-7.32 (m, 3H), 5.50 (s, 1H), 4.01-3.86 (m, 4H), 3.35-3.22 (m, 4H), 3.03 (br t, J=8.8 Hz, 2H), 2.76 (q, J=7.4 Hz, 2H), 1.77-1.61 (m, 2H), 1.19 (br t, J=7.5 Hz, 3H), 0.98 (t, J=7.4 Hz, 3H).

Example 159

2-((3,5-Dicyano-4-ethyl-6-(4-(phenylsulfonyl)piperazin-1-yl)pyridin-2-yl)thio)-2-phenylacetamide

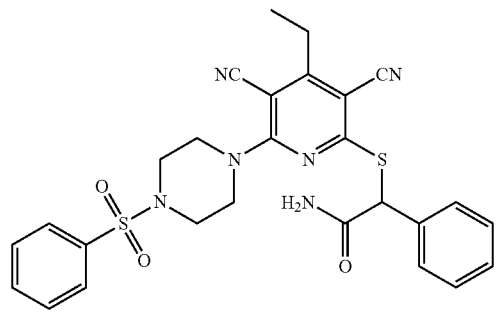 [SMILES: CCc1c(C#N)c(SC(C(N)=O)c2ccccc2)nc(N2CCN(S(=O)(=O)c3ccccc3)CC2)c1C#N]

A suspension of 2-[(3,5-dicyano-4-ethyl-6-piperazin-1-yl)-2-pyridyl)sulfanyl]-2-phenyl-acetamide (synthesis described in example 55, 25 mg, 0.06 mmol) in DCM (2 mL) was treated with N,N-diisopropylethylamine (0.013 mL, 0.080 mmol) then benzenesulphonyl chloride (0.009 mL, 0.07 mmol) at room temperature. After 20 hours the mixture was diluted with EtOAc (10 mL), washed with aqueous NaOH (0.5 M, 5 mL), water (5 mL), aqueous HCl (2 M, 5 mL), water (5 mL) and brine then dried through a hydrophobic frit and concentrated. The residue was triturated with diethyl ether to afford 2-[[6-[4-(benzenesulfonyl)piperazin-1-yl]-3,5-dicyano-4-ethyl-2-pyridyl]sulfanyl]-2-phenyl-acetamide (31 mg, 92% yield) as an off-white solid. LCMS m/z=547.2 [M+H]⁺. $^1$H NMR (300 MHz, DMSO-d₆) δ ppm 7.90 (s, 1H), 7.79-7.64 (m, 5H), 7.51-7.31 (m, 6H), 5.48 (s, 1H), 4.05-3.89 (m, 4H), 3.09-2.94 (m, 4H), 2.72 (q, J=7.3 Hz, 2H), 1.16 (t, J=7.6 Hz, 3H).

Example 160

2-((3,5-Dicyano-4-ethyl-6-((R)-3-hydroxypyrrolidin-1-yl)pyridin-2-yl)thio)-2-phenylacetamide

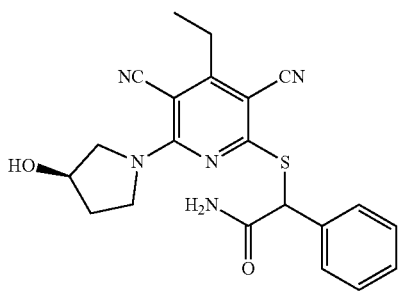 [SMILES: CCc1c(C#N)c(SC(C(N)=O)c2ccccc2)nc(N2CC[C@@H](O)C2)c1C#N]

A solution of 2-[(6-bromo-3,5-dicyano-4-ethyl-2-pyridyl)sulfanyl]-2-phenyl-acetamide (synthesis described in example 6, step 1, 17 mg, 0.04 mmol) in THF (1 mL) was treated with (R)-3-pyrrolidinol (0.009 mL, 0.11 mmol) and stirred at room temperature for 3 hours then loaded onto SiO$_2$ (0.9 g) and chromatographed on SiO$_2$ (4 g RediSep cartridge) eluting with 0-15% MeOH/DCM to give 2-[[3,5-dicyano-4-ethyl-6-[(3R)-3-hydroxypyrrolidin-1-yl]-2-pyridyl]sulfanyl]-2-phenyl-acetamide (12 mg, 70% yield) as a white solid. LCMS m/z=408.1 [M+H]+. $^1$H NMR (300 MHz, DMSO-d$_6$) δ ppm 7.91 (br s, 1H), 7.57-7.48 (m, 2H), 7.43-7.27 (m, 4H), 5.61 (s, 1H), 5.21-5.10 (m, 1H), 4.42 (br s, 1H), 4.01-3.72 (m, 4H), 2.74 (q, J=7.3 Hz, 2H), 2.03-1.84 (m, 2H), 1.20 (t, J=7.6 Hz, 3H).

Example 161

2-((3,5-Dicyano-4-ethyl-6-(2-oxa-6-azaspiro[3.4]octan-6-yl)pyridin-2-yl)thio)-2-phenylacetamide

Step 1: 2-Chloro-4-ethyl-6-(2-oxa-6-azaspiro[3.4]octan-6-yl)pyridine-3,5-dicarbonitrile

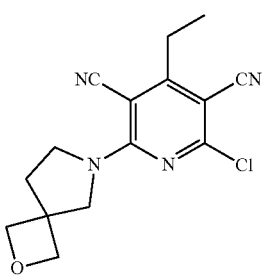 [SMILES: CCc1c(C#N)c(Cl)nc(N2CCC3(COC3)C2)c1C#N]

To a solution of 2,6-dichloro-4-ethylpyridine-3,5-dicarbonitrile (synthesis described in example 3 step 2, 680 mg, 3 mmol) and 2-oxa-6-azaspiro[3.4]octane, oxalic acid salt (480 mg, 1.5 mmol) in dichloromethane (20 mL) was added Et$_3$N (610 mg, 6 mmol) at 0° C. The mixture was stirred at room temperature overnight was and then diluted with EtOAc then washed with water and brine. The organic phase was worked up to give crude 2-chloro-4-ethyl-6-(2-oxa-6-azaspiro[3.4]octan-6-yl)pyridine-3,5-dicarbonitrile (860 mg) that was used in next step without further purification. LCMS m/z=303.0 [M+H]+.

Step 2: 2-((3,5-Dicyano-4-ethyl-6-(2-oxa-6-azaspiro[3.4]octan-6-yl)pyridin-2-yl)thio)-2-phenylacetamide

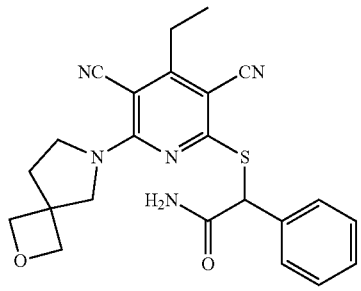 [SMILES: CCc1c(C#N)c(SC(C(N)=O)c2ccccc2)nc(N2CCC3(COC3)C2)c1C#N]

To a solution of crude 2-chloro-4-ethyl-6-(2-oxa-6-azaspiro[3.4]octan-6-yl)pyridine-3,5-dicarbonitrile (860 mg) in N,N-dimethylformamide (20 mL) was added KSAc (460 mg, 4 mmol). The mixture was stirred at room temperature for 2 hours and then K$_2$CO$_3$ (1.24 g, 9 mmol) was added at room temperature. The mixture was stirred at room temperature for 2 hours then treated with 2-amino-2-oxo-1-phenylethyl methanesulfonate (synthesis described in example 3, step 5, 2.06 g, 9 mmol). The mixture was stirred at room temperature overnight. The resultant mixture was diluted with EtOAc (60 mL) and washed with water (60 mL) and brine (60 mL). The organic phase was worked up and then purified by gradient chromatography using petroleum ether/EA (1/1 to 1/2) to give 2-((3,5-dicyano-4-ethyl-6-(2-oxa-6-azaspiro[3.4]octan-6-yl)pyridin-2-yl)thio)-2-phenylacetamide (200 mg) as a white solid. LCMS m/z=434.0 [M+H]+. $^1$H NMR (400 MHz, DMSO-d$_6$) δ ppm 7.93 (s, 1H), 7.55-7.51 (m, 2H), 7.43-7.31 (m, 4H), 5.60 (s, 1H), 4.65-4.60 (m, 2H), 4.55-4.52 (m, 2H), 4.08-3.80 (m, 4H), 2.75 (q, J=6.0 Hz, 2H), 2.27 (t, J=6.0 Hz, 2H), 1.20 (t, J=6 Hz, 3H).

Example 162

(R)-2-((3,5-Dicyano-4-ethyl-6-(4-ethyl-1,4-diazepan-1-yl)pyridin-2-yl)amino)-2-phenylacetamide

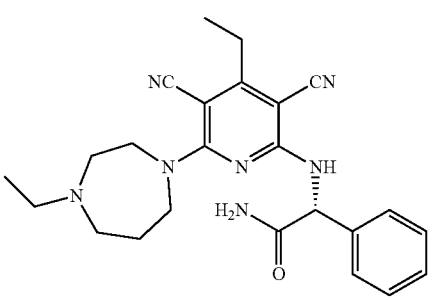 [SMILES: CCc1c(C#N)c(N[C@@H](C(N)=O)c2ccccc2)nc(N2CCCN(CC)CC2)c1C#N]

A solution of (2R)-2-[(6-chloro-3,5-dicyano-4-ethyl-2-pyridyl)amino]-2-phenyl-acetamide (synthesis described in example 41, step 1, 33 mg, 0.10 mmol) in THF (1 mL) was treated with N-ethylhomopiperazine (0.04 mL, 0.24 mmol) and stirred at room temperature for 19 hours then loaded onto SiO$_2$ (0.9 g) and chromatographed on SiO$_2$ (4 g RediSep cartridge) eluting with 0-15% gradient of (5% NH$_3$ in MeOH/DCM. The purified product was triturated with diethyl ether to give (2R)-2-[[3,5-dicyano-4-ethyl-6-(4-ethyl-1,4-diazepan-1-yl)-2-pyridyl]amino]-2-phenyl-acetamide (38 mg, 91% yield) as a white solid. LCMS m/z=432.4 [M+H]+. $^1$H NMR (300 MHz, DMSO-$d_6$) δ ppm 7.80 (s, 1H), 7.49-7.25 (m, 6H), 7.07 (d, J=5.9 Hz, 1H), 5.43 (d, J=6.0 Hz, 1H), 3.85-3.61 (m, 4H), 2.78-2.60 (m, 3H), 2.49-2.33 (m, 5H), 1.89-1.68 (m, 2H), 1.20 (t, J=7.5 Hz, 3H), 0.93 (t, J=7.1 Hz, 3H).

Example 163

(R)-2-((3,5-Dicyano-4-ethyl-6-(4-(3-(pyrrolidin-1-yl)propyl)-1,4-diazepan-1-yl)pyridin-2-yl)amino)-2-phenylacetamide

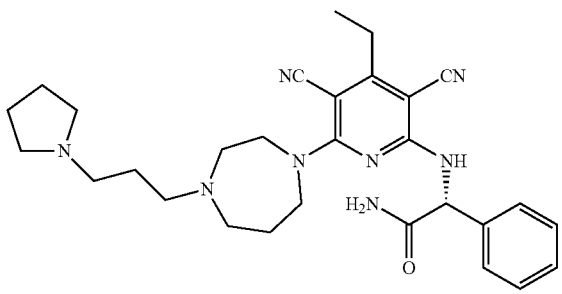 [SMILES: CCc1c(C#N)c(N[C@@H](C(N)=O)c2ccccc2)nc(N2CCCN(CCCN3CCCC3)CC2)c1C#N]

A mixture of (2R)-2-[(6-chloro-3,5-dicyano-4-ethyl-2-pyridyl)amino]-2-phenyl-acetamide (synthesis described in example 41, step 1, 23 mg, 0.07 mmol) and 1-(3-pyrrolidin-1-ylpropyl)-1,4-diazepane (16 mg, 0.08 mmol) in THF (1 mL) was treated with triethylamine (0.02 mL, 0.15 mmol) and stirred for 18 hours. The mixture was diluted with DCM, loaded onto $SiO_2$ (1 g), chromatographed on $SiO_2$ (4 g RediSep cartridge) eluting with 0-40% MeOH, 0-2% $NH_3$/DCM, followed by trituration with $Et_2O$ to give (2R)-2-[[3,5-dicyano-4-ethyl-6-[4-(3-pyrrolidin-1-ylpropyl)-1,4-diazepan-1-yl]-2-pyridyl]amino]-2-phenyl-acetamide (26 mg, 75% yield) as a white solid. LCMS m/z=515.4 [M+H]+. $^1$H NMR (300 MHz, DMSO-$d_6$) δ ppm 7.86 (s, 1H), 7.53-7.25 (m, 6H), 7.08 (d, J=6.0 Hz, 1H), 5.44 (d, J=6.0 Hz, 1H), 3.89-3.61 (m, 6H), 2.93-2.55 (m, 10H), 2.42-2.34 (m, 2H), 1.87-1.69 (m, 6H), 1.66-1.53 (m, 2H), 1.20 (t, J=7.5 Hz, 3H).

Example 164

2-(3,5-Dicyano-4-cyclopropyl-6-(3-hydroxypiperidin-1-yl)pyridin-2-ylthio)-2-phenylacetamide Step 1: tert-Butyl 3-hydroxypiperidine-1-carboxylate

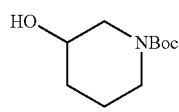

To a solution of tert-butyl 3-oxopiperidine-1-carboxylate (1 g, 5 mmol) in methanol (25 mL) was added $NaBH_4$ (360 mg, 10 mmol). The reaction mixture was stirred at 0° C. for 2 hours. The solvent was removed under reduced pressure, and the residue was dissolved in dichloromethane and filtered. The filtrate was concentrated to give tert-butyl 3-hydroxypiperidine-1-carboxylate (1 g, 99%) which was used in the next step without further purification. $^1$H NMR (400 MHz, $CDCl_3$) δ ppm 3.81-3.70 (m, 2H), 3.60-3.51 (m, 1H), 3.18-3.02 (m, 2H), 1.95 (s, 1H), 1.91-1.86 (m, 1H), 1.82-1.72 (m, 1H), 1.59-1.42 (m, 11H).

Step 2: 2-Chloro-4-cyclopropyl-6-(3-hydroxypiperidin-1-yl)pyridine-3,5-dicarbonitrile

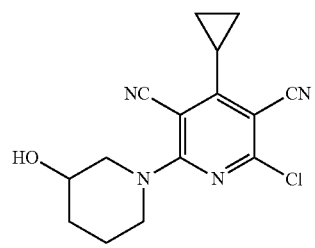 [SMILES: N#Cc1c(Cl)nc(N2CCCC(O)C2)c(C#N)c1C1CC1]

tert-Butyl 3-hydroxypiperidine-1-carboxylate (1 g, 5 mmol) and HCl (2.0 M in EtOAc, 5 mL) were stirred at room temperature overnight. The solvent was removed under reduced pressure. The residue was neutralized by Sat. $NaHCO_3$ (aq), and extracted with DCM. The organic layer was washed with brine, dried and purified by column chromatography, eluting with MeOH/DCM, 0-10%, to give piperidin-3-ol (450 mg).

To a solution of 2,6-dichloro-4-cyclopropylpyridine-3,5-dicarbonitrile (synthesis described in example 4, step 2, 236 mg, 1 mmol) in DMF (10 mL) were added piperidin-3-ol (101 mg, 1 mmol) and triethyl amine (0.14 mL, 1 mmol). The reaction mixture was stirred at room temperature for 5 minutes. Water was added to the reaction mixture. The solid was filtered, and purified by column chromatography, eluting with petroleum ether/ethyl acetate (0-33%), to give 2-chloro-4-cyclopropyl-6-(3-hydroxypiperidin-1-yl)pyridine-3,5-dicarbonitrile (210 mg, 70%). LCMS m/z=303.0 [M+H]+.

Step 3: 2-(3,5-Dicyano-4-cyclopropyl-6-(3-hydroxypiperidin-1-yl)pyridin-2-ylthio)-2-phenylacetamide

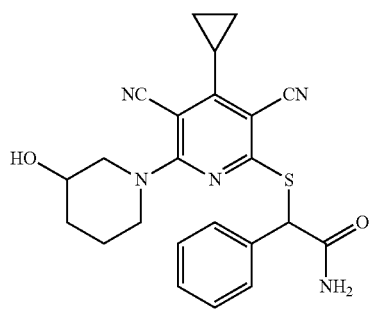 [SMILES: N#Cc1c(SC(C(N)=O)c2ccccc2)nc(N2CCCC(O)C2)c(C#N)c1C1CC1]

A solution of potassium thioacetate (95 mg, 0.83 mmol) and 2-chloro-4-cyclopropyl-6-(3-hydroxypiperidin-1-yl)pyridine-3,5-dicarbonitrile (210 mg, 0.7 mmol) in N,N-dimethylformamide (DMF) (7 mL) was stirred at room temperature for 30 minutes. Then 2-amino-2-oxo-1-phenylethyl methanesulfonate (synthesis described in example 3, step 5, 191 mg, 0.83 mmol) and triethylamine (0.19 mL, 1.4 mmol) were added. The reaction mixture was stirred at room temperature overnight. Water was added to the reaction mixture. The solid was filtered and purified by column chromatography, eluting with DCM/MeOH (0-5%), to give 2-(3,5-dicyano-4-cyclopropyl-6-(3-hydroxpiperidin-1-yl) pyridin-2-ylthio)-2-phenylacetamide (110 mg, 36%). LCMS m/z=433.9 [M+H]$^+$. $^1$H NMR (400 MHz, CDCl$_3$) δ ppm 7.48-7.43 (m, 2H), 7.42-7.33 (m, 3H), 6.91-6.80 (m, 1H), 5.80-5.65 (m, 1H), 5.29-5.20 (m, 1H), 4.64-4.45 (m, 1H), 4.04-3.98 (m, 0.5H), 3.94-3.87 (m, 1.5H), 3.81-3.75 (m, 0.5H), 3.65-3.56 (m, 0.5H), 3.48-3.39 (m, 0.5H), 3.07-2.98 (m, 0.5H), 2.32 (br s, 1H), 2.12-1.88 (m, 3H), 1.79-1.69 (m, 0.5H), 1.64-1.49 (m, 1.5H), 1.33-1.24 (m, 2H), 1.21-1.06 (m, 2H).

Example 165

2-((3,5-Dichloro-4-ethyl-6-(4-methyl-1,4-diazepan-1-yl) pyridin-2-ylthio-2-phenylacetamide Step 1: 3,5-Dichloro-4-ethyl-2,6-difluoropyridine

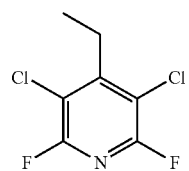

3,5-dichloro-2,4,6-trifluoropyridine (2.32 g, 11.49 mmol) was dissolved in tetrahydrofuran (18 mL) and cooled to −78° C. Ethylmagnesium chloride (6.32 mL, 12.64 mmol) was added dropwise to the cooled solution and after 20 minutes the reaction was quenched with saturated aqueous sodium bicarbonate solution. The reaction was diluted with EtOAc which formed an emulsion-like mixture. HCl was added until pH ~6 which also broke up the emulsion and formed a solution. Extracted with EtOAc (3×) and the combined organics were dried over MgSO$_4$, filtered and concentrated to afford 3,5-dichloro-4-ethyl-2,6-difluoropyridine (1.76 g, 8.3 mmol). LCMS m/z=211.9 [M+H]$^+$.

Step 2: 2-((3,5-Dichloro-4-ethyl-6-fluoropyridin-2-yl)thio)-2-phenylacetamide

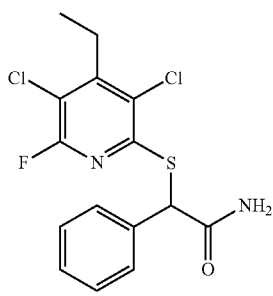 [SMILES: CCc1c(Cl)c(F)nc(SC(C(N)=O)c2ccccc2)c1Cl]

S-(2-amino-2-oxo-1-phenylethyl) ethanethioate (synthesis described in example 62 step 5, 401 mg, 1.916 mmol) and NaBH$_4$ (75 mg, 1.982 mmol) were added to a vial and suspended in ethanol (30 mL). The mixture was heated to 60° C. for 5 minutes (bubbles/evolution of gas stopped). 3,5-dichloro-4-ethyl-2,6-difluoropyridine (346 mg, 1.632 mmol) in EtOH (15 mL) was added to the mixture and the material was stirred at room temperature for 15 minutes. The mixture was concentrated, triturated with Et$_2$O/heptane and filtered off a gum and the filtrate was concentrated to afford 2-((3,5-dichloro-4-ethyl-6-fluoropyridin-2-yl)thio)-2-phenylacetamide (445 mg, 1.078 mmol, 66% yield). LCMS m/z=359.0 [M+H]$^+$.

Step 3: 2-((3,5-Dichloro-4-ethyl-6-(4-methyl-1,4-diazepan-1-yl) pyridin-2-yl)thio)-2-phenylacetamide

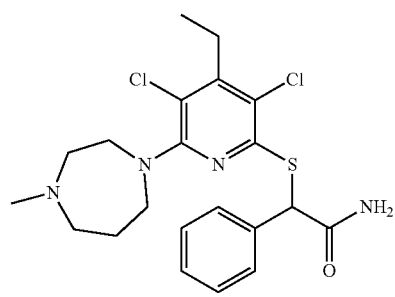 [SMILES: CCc1c(Cl)c(SC(C(N)=O)c2ccccc2)nc(N2CCCN(C)CC2)c1Cl]

2-((3,5-Dichloro-4-ethyl-6-fluoropyridin-2-yl)thio)-2-phenylacetamide (440 mg, 1.225 mmol) and 1-methyl-1,4-diazepane (0.228 mL, 1.837 mmol) were added to a vial and suspended in tetrahydrofuran (12 mL). The mixture was refluxed at 80° C. for 16 hours then heated at 100° C. for another 8 hours. A tan solid precipitated out which was filtered off. This material was purified on silica gel (40 g column; EtOAc to 3:1 EtOAc:EtOH w/1.5% NH$_4$OH). The desired fractions were pooled and concentrated to afford 2-((3,5-dichloro-4-ethyl-6-(4-methyl-1,4-diazepan-1-yl) pyridin-2-yl)thio)-2-phenylacetamide (160 mg, 0.353 mmol, 29% yield) as an off-white solid. LCMS m/z=453.1 [M+H]$^+$. $^1$H NMR (400 MHz, CHLOROFORM-d) δ ppm 7.44-7.51 (m, 2H) 7.31-7.43 (m, 3H) 6.80 (br. s., 1H) 5.66 (br. s., 1H) 5.45 (s, 1H) 3.54-3.78 (m, 4H) 2.92 (q, J=7.58 Hz, 2H) 2.81-2.87 (m, 2H) 2.60-2.77 (m, 2H) 2.43 (s, 3H) 1.96-2.15 (m, 2H) 1.18 (t, J=7.58 Hz, 3H).

Example 166

2-((3,5-Dicyano-6-(1,1-dioxidothiomorpholino)-4-ethylpyridin-2-yl)thio)-2-phenylacetamide

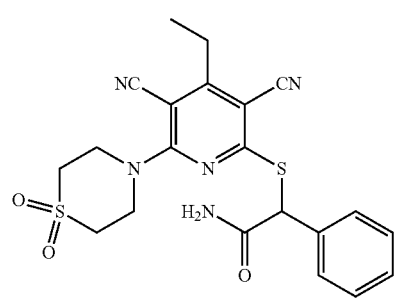 [SMILES: CCc1c(C#N)c(SC(C(N)=O)c2ccccc2)nc(N2CCS(=O)(=O)CC2)c1C#N]

To a mixture of 2-[(6-bromo-3,5-dicyano-4-ethyl-2-pyridyl)sulfanyl]-2-phenyl-acetamide (synthesis described in example 6, step 1, 30 mg, 0.07 mmol) and triethylamine (0.02 mL, 0.16 mmol) in THF (2 mL) was added thiomorpholine dioxide (11 mg, 0.08 mmol). The reaction mixture was stirred at room temperature for 17 hours. Water (5 mL) was added, and the mixture was stirred for 30 minutes, filtered and washed with water (3×10 mL). An attempt to dissolve the gummy solid in EtOAc resulted in a white fluffy solid which was dried in vacuo at 50° C. to afford 2-[[3,5-dicyano-6-(1,1-dioxo-1,4-thiazinan-4-yl)-4-ethyl-2-pyridyl]sulfanyl]-2-phenyl-acetamide (8 mg, 23% yield) as a white powder. LCMS m/z=454.2 [M−H]⁻. ¹H NMR (300 MHz, DMSO-d₆, D₂O exchange) δ ppm 7.50-7.28 (m, 5H), 5.47 (s, 1H), 4.32-4.27 (m, 2H), 4.20-4.11 (m, 2H), 3.35-3.18 (m, 4H), 2.76 (q, J=7.4 Hz, 2H), 1.17 (t, J=7.6 Hz, 3H).

Example 167

2-((3,5-Dicyano-4-ethyl-6-(methyl(2-(piperazin-1-yl)ethyl)amino)pyridin-2-yl)thio)-2-phenylacetamide Step 1: tert-Butyl 4-(2-(((benzyloxy)carbonyl)(methyl)amino)ethyl)piperazine-1-carboxylate

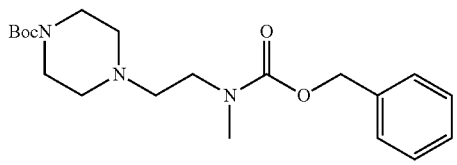 [SMILES: CN(CCN1CCN(C(=O)OC(C)(C)C)CC1)C(=O)OCc1ccccc1]

To a solution of tert-butyl piperazine-1-carboxylate (558 mg, 3.00 mmol) and benzyl methyl(2-oxoethyl)carbamate (621 mg, 3.00 mmol) in dichloromethane (DCM) (30 mL) was added sodium triacetoxyborohydride (1270 mg, 5.99 mmol). The reaction mixture was stirred at room temperature overnight. The reaction was diluted with DCM and washed with sat. NaHCO₃ solution. The organic layer was dried, concentrated and purified by column chromatography, eluting with EtOAc-hexanes (0-33%). to give tert-butyl 4-(2-(((benzyloxy)carbonyl)(methyl)amino)ethyl)piperazine-1-carboxylate (950 mg, 84%). LCMS m/z=378.0 [M+H]⁺.

Step 2: tert-Butyl 4-(2-(methylamino)ethyl)piperazine-1-carboxylate

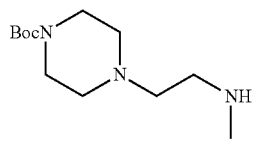

To a solution of tert-butyl 4-(2-(((benzyloxy)carbonyl)(methyl)amino)ethyl)piperazine-1-carboxylate (950 mg, 2.52 mmol) in methanol (25 mL) was added palladium on carbon (10%, 27 mg, 10 mol %). The reaction mixture was stirred under a hydrogen atmosphere at room temperature overnight. The mixture was filtered and the filtrate was concentrated to give tert-butyl 4-(2-(methylamino)ethyl)piperazine-1-carboxylate (490 mg, 80%) as a yellow oil. 1H NMR (400 MHz, CDCl₃) δ ppm 3.48-3.42 (m, 4H), 2.72 (t, J=6.0 Hz, 2H), 2.53 (t, J=6.1 Hz, 2H), 2.48 (d, J=5.9 Hz, 3H), 2.44-2.38 (m, 4H), 1.48 (s, 9H).

Step 3: tert-Butyl 4-(2-((6-((2-amino-2-oxo-1-phenylethyl)thio)-3,5-dicyano-4-ethylpyridin-2-yl)(methyl)amino)ethyl)piperazine-1-carboxylate

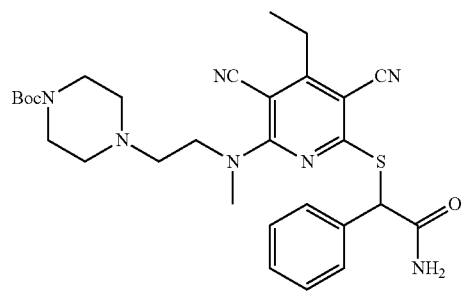 [SMILES: CCc1c(C#N)c(SC(C(N)=O)c2ccccc2)nc(N(C)CCN2CCN(C(=O)OC(C)(C)C)CC2)c1C#N]

To a solution of 2,6-dichloro-4-ethylpyridine-3,5-dicarbonitrile (synthesis described in example 3, step 2, 455 mg, 2.01 mmol) in DMF (20 mL) were added tert-butyl 4-(2-(methylamino)ethyl)piperazine-1-carboxylate (490 mg, 2.01 mmol) and triethylamine (0.281 mL, 2.01 mmol). The reaction mixture was stirred at room temperature for 30 minutes. Water was added to the reaction. The solid was filtered and dried to give tert-butyl 4-(2-((6-chloro-3,5-dicyano-4-ethylpyridin-2-yl)(methyl)amino)ethyl) piperazine-1-carboxylate (640 mg).

A solution of potassium thioacetate (203 mg, 1.77 mmol) and tert-butyl 4-(2-((6-chloro-3,5-dicyano-4-ethylpyridin-2-yl)(methyl)amino)ethyl)piperazine-1-carboxylate (640 mg, 1.48 mmol) in N,N-dimethylformamide (15 mL) was stirred at room temperature for 30 minutes. Then 2-amino-2-oxo-1-phenylethyl methanesulfonate (synthesis described in example 3, step 5, 407 mg, 1.77 mmol) and triethylamine (0.41 mL, 2.96 mmol) were added. The reaction mixture was stirred at room temperature overnight. Water was added to the reaction. The solid was filtered and purified by column chromatography, eluting with MeOH/DCM (0-5%), to give tert-butyl 4-(2-((6-((2-amino-2-oxo-1-phenylethyl)thio)-3,5-dicyano-4-ethylpyridin-2-yl)(methyl)amino)ethyl) piperazine-1-carboxylate (450 mg, 54%). LCMS m/z=564.3 [M+H]⁺.

Step 4: 2-((3,5-Dicyano-4-ethyl-6-(methyl(2-(piperazin-1-yl)ethyl)amino)pyridin-2-yl)thio)-2-phenylacetamide

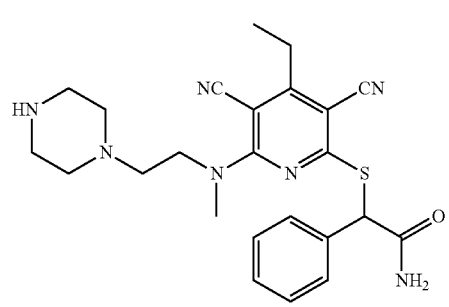 [SMILES: CCc1c(C#N)c(SC(C(N)=O)c2ccccc2)nc(N(C)CCN2CCNCC2)c1C#N]

To a solution of tert-butyl 4-(2-((6-((2-amino-2-oxo-1-phenylethyl)thio)-3,5-dicyano-4-ethylpyridin-2-yl)(methyl)amino)ethyl)piperazine-1-carboxylate (450 mg, 0.80 mmol) in dichloromethane (5 mL) was added trifluoroacetic acid (0.12 mL, 1.60 mmol). The reaction mixture was stirred at room temperature overnight. The solvent was removed and the residue was re-dissolved with water, neutralized with Sat. NaHCO₃ solution, extracted with DCM. The organic layer was concentrated and purified by column chromatography, eluting with MeOH/DCM (0-20%), to give 2-((3,5-dicyano-4-ethyl-6-(methyl(2-(piperazin-1-yl)ethyl)amino)pyridin-2-yl)thio)-2-phenylacetamide (236 mg, 64%). LCMS m/z=464.2 [M+H]⁺. ¹H NMR (400 MHz, CDCl₃) δ ppm 7.48-7.42 (m, 2H), 7.41-7.32 (m, 3H), 7.23 (br s, 1H), 5.80 (br s, 1H), 5.40 (s, 1H), 4.17-4.08 (m, 1H), 3.76-3.66 (m, 1H), 3.45 (s, 3H), 2.98-2.83 (m, 6H), 2.80-2.72 (m, 1H), 2.71-2.63 (m, 1H), 2.61-2.50 (s, 4H), 2.40 (br s, 1H),1.32 (t, J=7.6 Hz, 3H).

Example 168

(R)-2-((3,5-Dicyano-4-ethyl-6-((S)-3-hydroxypyrrolidin-1-yl)pyridin-2-yl)thio)-2-phenylacetamide Step 1: (S)-2-Chloro-4-ethyl-6-(3-hydroxypyrrolidin-1-yl)pyridine-3,5-dicarbonitrile

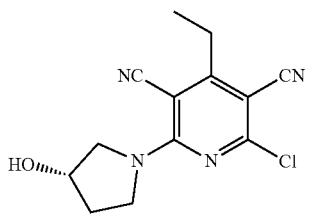

To a solution of 2,6-dichloro-4-ethylpyridine-3,5-dicarbonitrile (described in example 3, step 2, 678 mg, 3.00 mmol) and (S)-pyrrolidin-3-ol (261 mg, 3.00 mmol) in N,N-dimethylformamide (20 mL) was added triethylamine (0.418 mL, 3.00 mmol) at room temperature, and the resulting mixture was stirred at room temperature for 1 hour. The reaction mixture was poured onto water (100 mL), and extracted with EtOAc (100 mL×2). The combined organic layers were dried and concentrated to give (S)-2-chloro-4-ethyl-6-(3-hydroxypyrrolidin-1-yl)pyridine-3,5-dicarbonitrile (620 mg, 75% yield) as a pale solid. LCMS m/z=276.9 [M+H]⁺.

Step 2: 2-((3,5-Dicyano-4-ethyl-6-((S)-3-hydroxypyrrolidin-1-yl)pyridin-2-yl)thio)-2-phenylacetamide

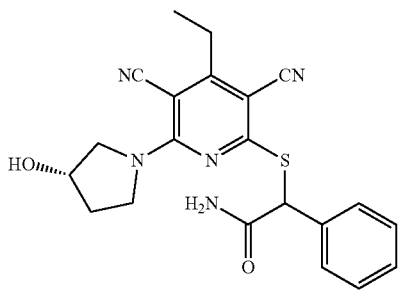 [SMILES: CCc1c(C#N)c(SC(C(N)=O)c2ccccc2)nc(N2CC[C@H](O)C2)c1C#N]

A solution of (S)-2-chloro-4-ethyl-6-(3-hydroxypyrrolidin-1-yl)pyridine-3,5-dicarbonitrile (500 mg, 1.81 mmol), potassium thioacetate (248 mg, 2.17 mmol) in N,N-dimethylformamide (DMF) (15 mL) was stirred at room temperature for 30 minutes then 2-amino-2-oxo-1-phenylethyl methanesulfonate (synthesis described in example 3, step 5, 497 mg, 2.17 mmol) and triethylamine (0.50 mL, 3.6 mmol) were added to the solution. The reaction mixture was stirred at room temperature for 12 hours. The reaction mixture was poured into water (100 mL), and extracted with EtOAc (100 mL×2). The combined organic layers were dried, concentrated, and purified by silica gel column (eluted by MeOH/DCM 0-2%) to give 2-((3,5-dicyano-4-ethyl-6-((S)-3-hydroxypyrrolidin-1-yl)pyridin-2-yl)thio)-2-phenylacetamide (380 mg, 51% yield) as a white solid. LCMS m/z=407.9 [M+H]⁺.

Step 3: (R)-2-((3,5-Dicyano-4-ethyl-6-((S)-3-hydroxypyrrolidin-1-yl)pyridin-2-yl)thio)-2-phenylacetamide

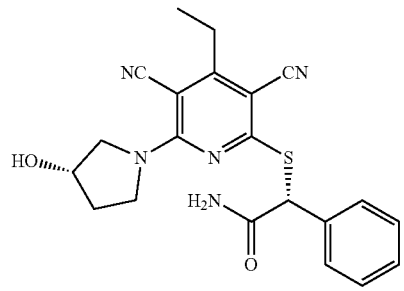

2-((3,5-Dicyano-4-ethyl-6-((S)-3-hydroxypyrrolidin-1-yl)pyridin-2-yl)thio)-2-phenylacetamide (250 mg, 0.62 mmol) was separated with chiral HPLC (chiralpak-IC column, HEX-EtOH (FA) to give (R)-2-((3,5-dicyano-4-ethyl-6-((S)-3-hydroxypyrrolidin-1-yl)pyridin-2-yl)thio)-2-phenyl acetamide. Absolute configuration of the chiral center adjacent to sulfur was was confirmed by VCD analysis. (30 mg). LCMS m/z=408.1 [M+H]⁺. ¹H NMR (400 MHz, DMSO-d₆) δ ppm 7.91 (br s, 1H), 7.52 (vbr s, 1H), 7.52-7.49 (m, 1H), 7.44-7.22 (m, 4H), 5.61 (s, 1H), 5.14 (d, J=3.4 Hz, 1H), 4.41 (s, 1H), 4.05-3.65 (m, 4H), 2.74 (q, J=7.4 Hz, 2H), 2.07-1.85 (m, 2H), 1.21 (q, J=7.6 Hz, 3H).

Example 170

2-((6-((2-(4-(Aminomethyl)-4-hydroxypiperidin-1-yl)ethyl)(methyl)amino)-3,5-dicyano-4-ethylpyridin-2-yl)thio)-2-phenylacetamide Step 1: tert-Butyl ((4-hydroxy-1-(2-(methylamino)ethyl)piperidin-4-yl)methyl) carbamate

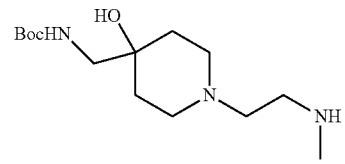 [SMILES: CNCCN1CCC(O)(CNC(=O)OC(C)(C)C)CC1]

489

To a solution of tert-butyl ((4-hydroxypiperidin-4-yl)methyl)carbamate (320 mg, 1.39 mmol) and benzyl methyl (2-oxoethyl)carbamate (288 mg, 1.39 mmol) in dichloromethane (14 mL) was added sodium triacetoxyborohydride (589 mg, 2.78 mmol). The reaction mixture was stirred at room temperature overnight then diluted with DCM and washed with sat. NaHCO₃ solution. The organic layer was dried, concentrated and purified by Flash column chromatography (eluted by petroleum ether/EtOAc, 3:1) to give 400 mg of a residue. The residue was dissolved in methanol (10 mL), and palladium on carbon (10%, 10 mg, 0.1 mmol) was added. The reaction mixture was stirred at room temperature under H₂ atmosphere overnight. The mixture was filtered and the filtrate was concentrated to give tert-butyl ((4-hydroxy-1-(2-(methylamino)ethyl)piperidin-4-yl)methyl)carbamate (270 mg, 0.939 mmol, 68% yield). ¹H NMR (400 MHz, CDCl₃) δ ppm 5.07 (br. s, 1H), 3.19-3.10 (m, 2H), 2.71 (t, J=6.1 Hz, 2H), 2.66-2.58 (m, 2H), 2.56-2.50 (m, 2H), 2.46 (s, 3H), 2.44-2.36 (m, 2H), 1.69-1.57 (m, 4H), 1.45 (s, 9H). One proton not observed.

Step 2: tert-Butyl ((1-(2-((6-chloro-3,5-dicyano-4-ethylpyridin-2-yl)(methyl) amino)ethyl)-4-hydroxypiperidin-4-yl)methyl)carbamate

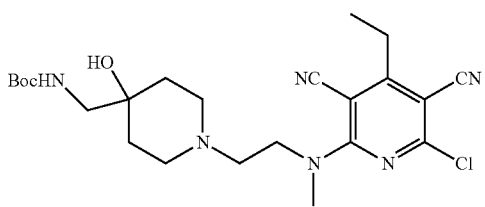 [SMILES: CCc1c(C#N)c(Cl)nc(N(C)CCN2CCC(O)(CNC(=O)OC(C)(C)C)CC2)c1C#N]

To a solution of 2,6-dichloro-4-ethylpyridine-3,5-dicarbonitrile (synthesis described in example 3, step 2, 212 mg, 0.94 mmol) in N,N-dimethylformamide (10 mL) were added tert-butyl ((4-hydroxy-1-(2-(methylamino)ethyl) piperidin-4-yl)methyl)carbamate (270 mg, 0.94 mmol) and triethylamine (0.13 mL, 0.94 mmol). The reaction mixture was stirred at room temperature for 30 minutes. Water was added to the reaction mixture and the solid was filtered and purified by Flash column chromatography (eluted with DCM/MeOH, 20:1) to give tert-butyl ((1-(2-((6-chloro-3,5-dicyano-4-ethylpyridin-2-yl)(methyl)amino)ethyl)-4-hydroxypiperidin-4-yl)methyl) carbamate (300 mg, 67% yield). LCMS m/z=477.2 [M+H]⁺. ¹H NMR (400 MHz, CDCl₃) δ ppm 4.95 (s, 1H), 3.92 (t, J=6.3 Hz, 2H), 3.47 (s, 3H), 3.19-3.11 (m, 2H), 2.98 (q, J=7.6 Hz, 2H), 2.83-2.48 (m, 6H), 1.71-1.56 (m, 4H), 1.46 (s, 9H), 1.36 (t, J=7.6 Hz, 3H). Two protons not observed.

490

Step 3: tert-Butyl ((1-(2-((6-((2-amino-2-oxo-1-phenylethyl)thio)-3,5-dicyano-4-ethylpyridin-2-yl)(methyl)amino)ethyl)-4-hydroxypiperidin-4-yl)methyl) carbamate

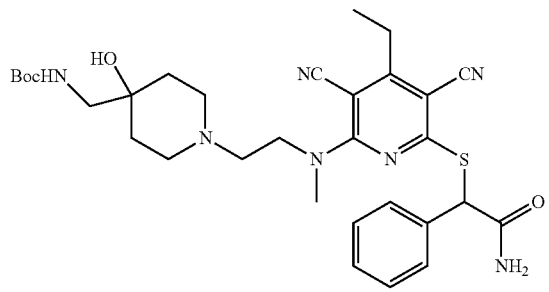 [SMILES: CCc1c(C#N)c(SC(C(N)=O)c2ccccc2)nc(N(C)CCN2CCC(O)(CNC(=O)OC(C)(C)C)CC2)c1C#N]

A solution of tert-butyl ((1-(2-((6-chloro-3,5-dicyano-4-ethylpyridin-2-yl)(methyl)amino)ethyl)-4-hydroxypiperidin-4-yl)methyl)carbamate (0.413 mL, 0.63 mmol) and potassium thioacetate (86 mg, 0.76 mmol) in N,N-dimethylformamide (6 mL) was stirred at room temperature for 30 minutes. Triethylamine (0.175 mL, 1.26 mmol) and 2-amino-2-oxo-1-phenylethyl methanesulfonate (synthesis described in example 3, step 5, 173 mg, 0.76 mmol) were added to the reaction. The reaction mixture was stirred at 25° C. overnight. Water was added and the solid was filtered and purified by Flash column chromatography (eluted by eluted by DCM/MeOH, 20:1) to give tert-butyl ((1-(2-((6-((2-amino-2-oxo-1-phenylethyl)thio)-3,5-dicyano-4-ethylpyridin-2-yl)(methyl)amino)ethyl)-4-hydroxypiperidin-4-yl)methyl) carbamate (250 mg, 65% yield). ¹H NMR (400 MHz, CDCl₃) δ ppm 7.48 (d, J=6.0 Hz, 2H), 7.45-7.35 (m, 3H), 5.82 (s, 1H), 5.46 (s, 1H), 4.93 (s, 1H), 4.31-4.20 (m, 1H), 3.81-3.67 (m, 1H), 3.47 (s, 3H), 3.18-3.09 (m, 2H), 2.93 (q, J=7.6 Hz, 2H), 2.90-2.51 (m, 6H), 1.70-1.53 (m, 5H), 1.46 (s, 9H), 1.33 (t, J=7.6 Hz, 3H). One proton not observed.

Step 4: 2-((6-((2-(4-(Aminomethyl)-4-hydroxypiperidin-1-yl)ethyl)(methyl)amino)-3,5-dicyano-4-ethylpyridin-2-yl)thio)-2-phenylacetamide

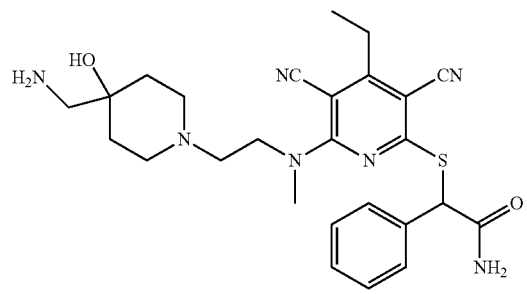 [SMILES: CCc1c(C#N)c(SC(C(N)=O)c2ccccc2)nc(N(C)CCN2CCC(O)(CN)CC2)c1C#N]

To a solution of tert-butyl ((1-(2-((6-((2-amino-2-oxo-1-phenylethyl)thio)-3,5-dicyano-4-ethylpyridin-2-yl)(methyl)amino)ethyl)-4-hydroxypiperidin-4-yl)methyl)carbamate (250 mg, 0.41 mmol) in dichloromethane (5 mL) was added trifluoroacetic acid (0.06 mL, 0.8 mmol). The reaction mixture was stirred at room temperature overnight. The solvent was removed and the residue was re-dissolved with water, neutralized with saturated NaHCO₃ solution, and extracted with DCM. The organic layer was dried, concentrated and purified by Flash column chromatography (eluted with DCM/MeOH, 5:1) to give 2-((6-((2-(4-(aminomethyl)-4-hydroxypiperidin-1-yl)ethyl)(methyl)amino)-3,5-dicyano-4-ethylpyridin-2-yl)thio)-2-phenylacetamide (122 mg, 59%). LCMS m/z=508.3 [M+H]⁺. ¹H NMR (400 MHz, CDCl₃) δ ppm 7.62 (br s, 1H), 7.49-7.42 (m, 2H), 7.42-7.31 (m, 3H), 5.62 (br s, 1H), 5.40 (s, 1H), 4.28-4.19 (m, 1H), 3.67-3.57 (m, 1H), 3.46 (s, 3H), 2.91 (q, J=7.6 Hz, 2H), 2.86-2.80 (m, 1H), 2.78-2.65 (m, 3H), 2.62-2.45 (m, 4H), 1.65 (br s, 3H), 1.56-1.50 (m, 2H), 1.45-1.36 (m, 2H), 1.31 (t, J=7.6 Hz, 3H).

Example 171

2-((4-Cyano-3-(1,4-diazepan-1-yl)-6,7-dihydro-5H-cyclopenta[c]pyridin-1-yl)thio)-2-phenylacetamide Step 1: 1,3-Dichloro-6,7-dihydro-5H-cyclopenta[c]pyridine-4-carbonitrile

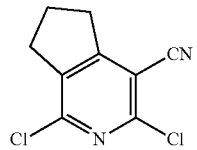

Ethyl 2-oxocyclopentanecarboxylate (3.90 g, 25.00 mmol) was dissolved in methanol (20 mL) and 2-cyanoacetamide (2.102 g, 25 mmol) and KOH (1.473 g, 26.3 mmol) were added the reaction was refluxed for 18 hours. After 18 hours the reaction was cooled and a white solid filtered off and washed with methanol. The methanol was pumped off to obtain 2.78 g of a residue. 1 g of the residue was placed in a large microwave vial and benzyltrimethylammonium chloride (3.16 g, 17.03 mmol) was added. Then POCl₃ (10.58 ml, 114 mmol) was added dropwise with stirring (bubbling and exothermimg was observed). The vial was sealed and heated in the microwave to 165° C. for 5.5 hours. Cooled to room temp, the reaction was added slowly to ice/water/DCM. The layers were separated and the water layer washed twice with DCM. The combined organics over sodium sulfate, filtered and evaporated the DCM. Normal phase chromatography on silica gel (24 g column, eluted with 0-25% ethyl acetate in hexane gave 1,3-dichloro-6,7-dihydro-5H-cyclopenta[c]pyridine-4-carbonitrile (0.650 g, 3.05 mmol, 54% yield). LCMS m/z=212.8 [M+H]⁺.

Step 2: 2-((3-chloro-4-cyano-6,7-dihydro-5H-cyclopenta[c]pyridin-1-yl)thio)-2-phenylacetamide

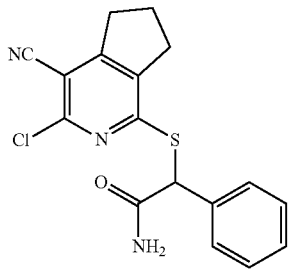 [SMILES: N#Cc1c(Cl)nc(SC(C(N)=O)c2ccccc2)c2c1CCC2]

S-(2-amino-2-oxo-1-phenylethyl) ethanethioate (synthesis described in example 62 step 5, 216 mg, 1.033 mmol) was dissolved in 15 ml ethanol and sodium borohydride (46.2 mg, 1.22 mmol) was added portionwise at 65° C. and stirred for 15 minutes at this temp. The mixture was removed from the heat, cooled and 1,3-dichloro-6,7-dihydro-5H-cyclopenta[c]pyridine-4-carbonitrile (200 mg, 0.939 mmol) was added and the reaction again heated for 3 minutes at 75° C. The reaction was concentrated to a solid which was purified on a 12 g silica gel column (eluting with 15-70% ethyl acetate in hexane) to afford 2-((3-chloro-4-cyano-6,7-dihydro-5H-cyclopenta[c]pyridin-1-yl)thio)-2-phenylacetamide (182 mg, 0.529 mmol, 56% yield). LCMS m/z=343.9 [M+H]⁺.

Step 3: 2-((4-Cyano-3-(1,4-diazepan-1-yl)-6,7-dihydro-5H-cyclopenta[c]pyridin-1-yl)thio)-2-phenylacetamide

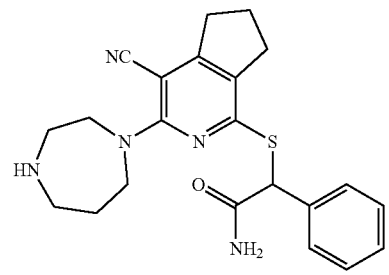 [SMILES: N#Cc1c(N2CCCNCC2)nc(SC(C(N)=O)c2ccccc2)c2c1CCC2]

2-((3-Chloro-4-cyano-6,7-dihydro-5H-cyclopenta[c]pyridin-1-yl)thio)-2-phenylacetamide (180 mg, 0.524 mmol) was dissolved in 1,4-dioxane (20 mL) and tert-butyl 1,4-diazepane-1-carboxylate (189 mg, 0.942 mmol) was added as was DIEA (0.091 mL, 0.524 mmol) The microwave vial was capped and heated on a hot plate at 120° C. for 48 hours with stirring. The dioxane was evaporated and the crude was dissolved in DCM and purified on a 12 g silica column, eluting with 12-70% ethyl acetate in hexane to give tert-butyl 4-(1-((2-amino-2-oxo-1-phenylethyl)thio)-4-cyano-6,7-dihydro-5H-cyclopenta[c]pyridin-3-yl)-1,4-diazepane-1-carboxylate (120 mg) LCMS m/z=508.4 [M+H]⁺. The product was treated with DCM/TFA 1;1 for an hour at room temperature. The solvents were evaporated and the residue pumped on a high vacuum to give a solid which was dissolved into water, neutralized with excess saturated sodium bicarbonate and extracted into DCM to afford 2-((4-cyano-3-(1,4-diazepan-1-yl)-6,7-dihydro-5H-cyclopenta[c]pyridin-1-yl)thio)-2-phenylacetamide (80 mg, 0.196 mmol, 38% yield). LCMS m/z=408.1 [M+H]⁺. ¹H NMR (400 MHz, DMSO-d₆) δ ppm 1.74-1.92 (m, 2H) 1.99-2.17 (m, 2H) 2.57-2.71 (m, 2H) 2.77 (t, J=5.45 Hz, 2H) 2.83-3.00 (m, 4H) 3.74-3.93 (m, 4H) 6-5.52 (s, 1H) 7.19-7.43 (m, 4H) 7.44-7.54 (m, 2H) 7.85 (s, 1H) 8.3 (s, 1H).

Example 172

2-((6-(4-(1H-Imidazol-1-yl)piperidin-1-yl)-3,5-dicyano-4-ethylpyridin-2-yl)thio)-2-phenylacetamide Step 1: 2-(4-(1H-Imidazol-1-yl)piperidin-1-yl)-4-ethyl-6-mercaptopyridine-3,5-dicarbonitrile

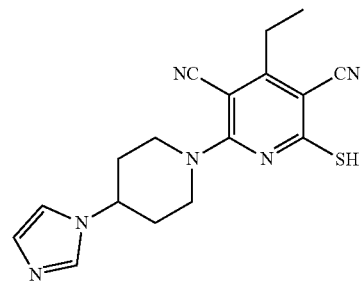 [SMILES: CCc1c(C#N)c(S)nc(N2CCC(n3ccnc3)CC2)c1C#N]

4-(1H-Imidazol-1-yl)piperidine (343 mg, 2.27 mmol) was dissolved in DCM (5 mL) and to this mixture was added 2,6-dichloro-4-ethylpyridine-3,5-dicarbonitrile (synthesis described in Example 3 step 2, 0.513 g, 2.270 mmol) and triethylamine (0.230 g, 2.270 mmol). The mixture was stirred at room temperature for 12 hours. The mixture was diluted with DCM, washed with brine, dried and concentrated to give 2-(4-(1H-imidazol-1-yl)piperidin-1-yl)-6-chloro-4-ethylpyridine-3,5-dicarbonitrile (380 mg). The crude product and potassium ethanethioate (259 mg, 2.27 mmol) were added to N,N-dimethylformamide (10 mL) and the mixture was stirred for 4 hours at 25° C. The mixture was adjusted to pH 5 with 1N HCl, diluted with water (30 mL) and extracted with DCM (30 mL×3). The organic layer was dried over sodium sulfate and concentrated to give 2-(4-(1H-imidazol-1-yl)piperidin-1-yl)-4-ethyl-6-mercaptopyridine-3,5-dicarbonitrile (220 mg, 29% yield). LCMS m/z=339.1 [M+H]$^+$.

Step 2: 2-((6-(4-(1H-Imidazol-1-yl)piperidin-1-yl)-3,5-dicyano-4-ethylpyridin-2-yl)thio)-2-phenylacetamide

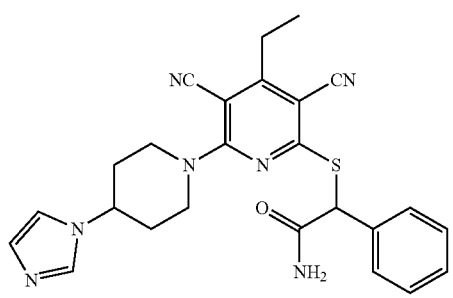 [SMILES: CCc1c(C#N)c(SC(C(N)=O)c2ccccc2)nc(N2CCC(n3ccnc3)CC2)c1C#N]

2-(4-(1H-Imidazol-1-yl)piperidin-1-yl)-4-ethyl-6-mercaptopyridine-3,5-dicarbonitrile (180 mg, 0.532 mmol), 2-amino-2-oxo-1-phenylethyl methanesulfonate (244 mg, 1.064 mmol) and potassium carbonate (73.5 mg, 0.532 mmol) were added to N,N-dimethylformamide (10 mL). The mixture was stirred for 4 hours at 40° C. Then water (20 mL) was added to the mixture and the resulting mixture was extracted with DCM (30 mL×3). The combined organic layer was dried over sodium sulfate, concentrated and the residue was purified by prep-HPLC to afford 2-((6-(4-(1H-imidazol-1-yl)piperidin-1-yl)-3,5-dicyano-4-ethylpyridin-2-yl)thio)-2-phenylacetamide (20 mg, 8% yield). LCMS m/z=471.7 [M+H]$^+$. $^1$H NMR (400 MHz, MeOD) δ ppm 8.26 (s, 1H), 8.11 (s, 1H), 7.65-7.50 (m, 2H), 7.46-7.32 (m, 3H), 7.16 (s, 1H), 5.54 (s, 1H), 4.87 (m, 2H), 4.63-4.48 (m, 1H), 3.47-3.29 (m, 2H), 2.94 (q, J=7.6 Hz, 2H), 2.27 (d, J=12.4 Hz, 2H), 2.08 (tt, J=12.7, 6.3 Hz, 2H), 1.33 (t, J=7.6 Hz, 3H).

Example 173

2-((3,5-Dicyano-4-ethyl-6-(4-(pyridin-4-ylmethyl)piperazin-1-yl)pyridin-2-yl)thio)-2-phenylacetamide Step 1: tert-Butyl 4-(pyridin-4-ylmethyl)piperazine-1-carboxylate

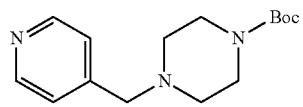 [SMILES: CC(C)(C)OC(=O)N1CCN(Cc2ccncc2)CC1]

To a solution of 4-(bromomethyl)pyridine (300 mg, 1.74 mmol) in Acetonitrile (10 mL) was added Potassium carbonate (362 mg, 2.62 mmol), followed by the addition of tert-butyl piperazine-1-carboxylate (325 mg, 1.74 mmol). The mixture was stirred overnight at room temperature. Then EtOAc and H$_2$O were added. The layers were separated, and the aqueous layer was extracted with EtOAc. The combined organic phase was washed brine, dried over Na$_2$SO$_4$, and concentrated to give tert-butyl 4-(pyridin-4-ylmethyl)piperazine-1-carboxylate (378 mg). LCMS m/z=278.1 [M+H]$^+$.

Step 2: 1-(Pyridin-4-ylmethyl)piperazine

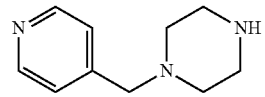 [SMILES: c1cc(CN2CCNCC2)ccn1]

A solution of tert-butyl tert-butyl 4-(pyridin-4-ylmethyl)piperazine-1-carboxylate (332 mg, 1.20 mmol) in 3.0 mL dichloromethane and 3.0 mL trifluoroacetic acid was stirred overnight at ambient temperature. All volatiles were removed in vacuo to give 1-(pyridin-4-ylmethyl)piperazine (212 mg), which was used in the next step without purification. LCMS m/z=177.9 [M+H]$^+$.

Step 3: 2-Chloro-4-ethyl-6-(4-(pyridin-4-ylmethyl)piperazin-1-yl)pyridine-3,5-dicarbonitrile

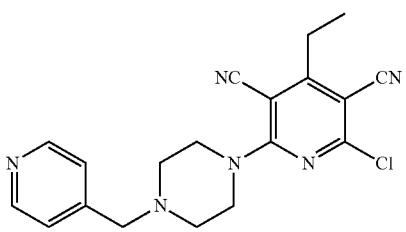 [SMILES: CCc1c(C#N)c(Cl)nc(N2CCN(Cc3ccncc3)CC2)c1C#N]

To a solution of 1-(pyridin-4-ylmethyl)piperazine (180 mg) in Acetonitrile (10.0 mL) was added triethylamine (0.637 mL, 4.57 mmol), followed by the addition of 2,6-dichloro-4-ethylpyridine-3,5-dicarbonitrile (synthesis described in example 3, step 2, 230 mg, 1.02 mmol). The reaction was stirred for 3 hours at room temperature. The mixture was poured into 20 mL of water. The resulting solution was extracted with 3×20 mL of ethyl acetate. The organic layers were combined, washed with aqueous sodium carbonate and brine, dried and concentrated under vacuum to afford a crude product as a yellow oil. The residue was applied on a silica gel column and eluted with ethyl acetate/hexane (1:2 to 1:0) to give 2-chloro-4-ethyl-6-(4-(pyridin-4-ylmethyl)piperazin-1-yl)pyridine-3,5-dicarbonitrile (166 mg, 0.45 mmol). LCMS m/z=366.7 [M+H]$^+$.

Step 4: 2-((3,5-Dicyano-4-ethyl-6-(4-(pyridin-4-ylmethyl)piperazin-1-yl)pyridin-2-yl)thio)-2-phenylacetamide

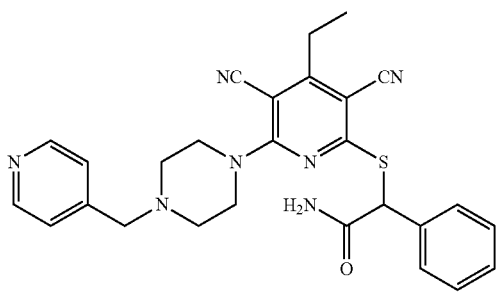 [SMILES: CCc1c(C#N)c(SC(C(N)=O)c2ccccc2)nc(N2CCN(Cc3ccncc3)CC2)c1C#N]

Potassium thioacetate (60 mg, 0.52 mmol) was added to a solution of 2-chloro-4-ethyl-6-(4-(pyridin-4-ylmethyl)piperazin-1-yl)pyridine-3,5-dicarbonitrile (160 mg, 0.44 mmol) in N,N-dimethylformamide (5.0 mL). After 30 minutes, 2-amino-2-oxo-1-phenylethyl methanesulfonate (synthesis described in example 3, step 5, 100 mg, 0.44 mmol) was added to the reaction mixture, followed by triethylamine (0.122 mL, 0.872 mmol). The reaction mixture was stirred overnight at room temperature. Water was added to the reaction and the solid that formed was filtered. The solid was then purified by Prep-HPLC to afford 2-((3,5-dicyano-4-ethyl-6-(4-(pyridin-4-ylmethyl)piperazin-1-yl)pyridin-2-yl)thio)-2-phenylacetamide (30 mg, 0.059 mmol, 14% yield) as a yellow solid. LCMS m/z=497.7 [M+H]$^+$. $^1$H NMR (400 MHz, DMSO-d$_6$) δ ppm 8.54 (d, J=5.7 Hz, 2H), 7.90 (s, 1H), 7.48 (d, J=6.7 Hz, 2H), 7.41-7.30 (m, 5H), 5.50 (s, 1H), 3.90 (s, 4H), 3.60 (s, 2H), 2.79-2.71 (m, 2H), 1.21-1.16 (m, 6.7 Hz, 3H). 5H not observed.

Example 174

2-((3,5-Dicyano-6-(2-(dimethylamino)ethoxy)-4-ethylpyridin-2-yl)thio)-2-phenylacetamide Step 1: 2-Chloro-6-(2-(dimethylamino)ethoxy)-4-ethylpyridine-3,5-dicarbonitrile

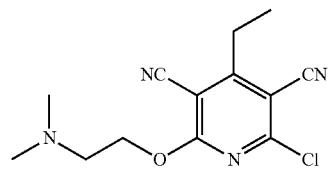 [SMILES: CCc1c(C#N)c(Cl)nc(OCCN(C)C)c1C#N]

To a solution of 2,6-dichloro-4-ethylpyridine-3,5-dicarbonitrile (synthesis described in example 3, step 2, 300 mg, 1.33 mmol) and 2-(dimethylamino)ethanol (118 mg, 1.33 mmol) in acetonitrile (10 mL) was added triethylamine (0.185 mL, 1.32 mmol), The reaction mixture stirred under nitrogen at 20° C. for 3 hours. The reaction mixture was evaporated and the residue partitioned between ethyl acetate (100 mL) and water (50 mL). The organic phase was washed with water (50 mL), dried over sodium sulphate, filtered, and evaporated in vacuo to give the crude product 2-chloro-6-(2-(dimethylamino)ethoxy)-4-ethylpyridine-3,5-dicarbonitrile (300 mg) as a brown oil. LCMS m/z=279.1 [M+H]$^+$.

Step 2: 2-((3,5-Dicyano-6-(2-(dimethylamino)ethoxy)-4-ethylpyridin-2-yl)thio)-2-phenylacetamide

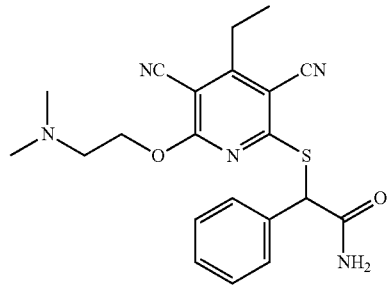 [SMILES: CCc1c(C#N)c(OCCN(C)C)nc(SC(C(N)=O)c2ccccc2)c1C#N]

A solution of 2-chloro-6-(2-(dimethylamino)ethoxy)-4-ethylpyridine-3,5-dicarbonitrile (300 mg, 1.08 mmol), potassium thioacetate (148 mg, 1.29 mmol) and triethylamine (0.450 mL, 3.2 mmol) in N,N-dimethylformamide (20 mL) was stirred under nitrogen at 20° C. for 2 hours. Then 2-amino-2-oxo-1-phenylethyl methanesulfonate (synthesis described in example 3, step 5, 247 mg, 1.08 mmol) was added. The reaction mixture was stirred at room temperature for 3 hours. The reaction mixture was cooled to room temperature and partitioned between dichloromethane (50 mL) and water (50 mL). The organic phase was washed with water (50 mL), dried over sodium sulphate and evaporated in vacuo to give the crude product. The crude product was purified with silica gel column (eluted with CH$_2$Cl$_2$/MeOH, 20:1) to give 2-((3,5-dicyano-6-(2-(dimethylamino)ethoxy)-4-ethylpyridin-2-yl)thio)-2-phenylacetamide (50 mg) as a white solid. LCMS m/z=410.1 [M+H]$^+$. $^1$H NMR (400 MHz, DMSO-d$_6$+D$_2$O) δ ppm 7.54-7.52 (m, 2H), 7.44-7.38

(m, 3H), 5.62 (s, 1H), 4.92-4.79 (m, 2H), 3.60-3.55 (m, 2H), 2.90-2.84 (m, 8H), 1.23 (t, J=7.6 Hz, 3H).

Example 175

2-((1-(6-((2-Amino-2-oxo-1-phenylethyl)thio)-3,5-dicyano-4-cyclopropylpyridin-2-yl)piperidin-3-yl)amino)acetic acid

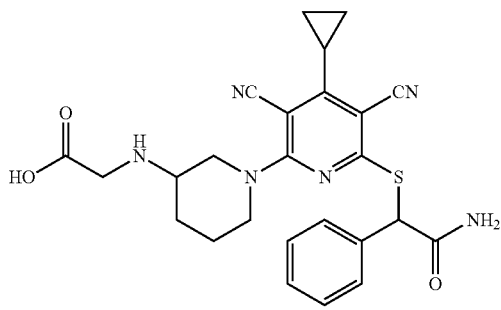 [SMILES: N#Cc1c(SC(C(N)=O)c2ccccc2)nc(N2CCCC(NCC(=O)O)C2)c(C#N)c1C1CC1]

To a solution of 2-((6-(3-aminopiperidin-1-yl)-3,5-dicyano-4-cyclopropylpyridin-2-yl)thio)-2-phenylacetamide (synthesis described in Example 25, step 2, 500 mg, 1.156 mmol) in DMF (5 mL) was added tert-butyl 2-bromoacetate (225 mg, 1.156 mmol) and potassium carbonate (320 mg, 2.312 mmol). The mixture was stirred at 70° C. overnight. The reaction mixture was concentrated. The residue was added to a silica gel column and was eluted with hexanes/EtOAc (1:1) to give tert-butyl 2-((1-(6-((2-amino-2-oxo-1-phenylethyl)thio)-3,5-dicyano-4-cyclopropylpyridin-2-yl)piperidin-3-yl)amino)acetate (500 mg, 79% yield). To a solution of tert-butyl 2-((1-(6-((2-amino-2-oxo-1-phenylethyl)thio)-3,5-dicyano-4-cyclopropylpyridin-2-yl)piperidin-3-yl)amino)acetate (500 mg, 0.915 mmol) in dichloromethane (100 mL) was added 2,2,2-trifluoroacetic acid (521 mg, 4.57 mmol). The reaction mixture was stirred at 25° C. overnight. The reaction mixture was concentrated and the residue was purified by prep-HPLC to give two unknown diastereomers of 2-((1-(6-((2-Amino-2-oxo-1-phenylethyl)thio)-3,5-dicyano-4-cyclopropylpyridin-2-yl)piperidin-3-yl)amino)acetic acid (diastereoisomer 2, 45 mg). $^1$H NMR (400 MHz, DMSO-$d_6$) δ ppm 9.22 (s, 2H), 7.96 (s, 1H), 7.55-7.36 (m, 6H), 5.50 (s, 1H), 4.59 (d, J=9.7 Hz, 1H), 4.33 (d, J=13.3 Hz, 1H), 4.02 (s, 2H), 3.39-3.19 (m, 2H), 3.17 (t, J=11.2 Hz, 1H), 2.25-2.10 (m, 2H), 1.90 (d, J=12.9 Hz, 1H), 1.72-1.55 (m, 2H), 1.17 (d, J=8.8 Hz, 2H), 1.04-0.94 (m, 2H). LCMS m/z=491.1 [M+H]$^+$.

Example 176

2-((3,5-Dicyano-4-ethyl-6-(4-(oxazol-2-ylmethyl)piperazin-1-yl)pyridin-2-yl)thio)-2-phenylacetamide

Step 1: 4-(6-chloro-3,5-dicyano-4-ethylpyridin-2-yl)piperazine-1-carboxylate

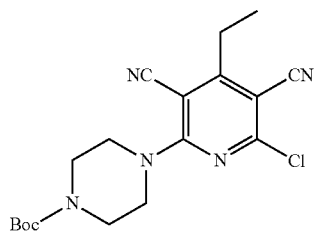 [SMILES: CCc1c(C#N)c(Cl)nc(N2CCN(C(=O)OC(C)(C)C)CC2)c1C#N]

2,6-Dichloro-4-ethylpyridine-3,5-dicarbonitrile (synthesis described in example 3, step 2, 4.0 g, 17.69 mmol) was dissolved in tetrahydrofuran (50 mL) and tert-butyl piperazine-1-carboxylate (3.30 g, 17.69 mmol) was added. The reaction was stired at 50° C. for 0.5 hours. The THF was filtered then cooled and crystals formed which were filtered off after several hours. Drying overnight the solid crystals weighed 5.6 g. The filtrate THF was evaporated off and the solid left was partioned between ethyl acetate and water. More product was insoluble in either and was filtered off. The ethyl acetate was dried, concentrated and hexane added to give crystals to give tert-butyl 4-(6-chloro-3,5-dicyano-4-ethylpyridin-2-yl)piperazine-1-carboxylate (6.4 g, 17.03 mmol, 96% yield). LCMS m/z=276.0 [M+H]$^+$.

Step 2: 2-((3,5-Dicyano-4-ethyl-6-(piperazin-1-yl)pyridin-2-yl)thio)-2-phenylacetamide, Trifluoroacetic Acid Salt

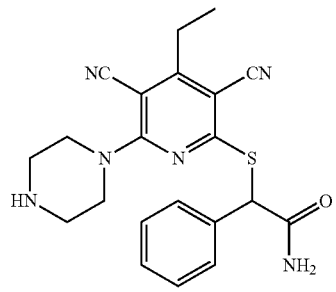 [SMILES: CCc1c(C#N)c(SC(C(N)=O)c2ccccc2)nc(N2CCNCC2)c1C#N]

S-(2-amino-2-oxo-1-phenylethyl) ethanethioate (synthesis described in example 62 step 5, 2.171 g, 10.38 mmol) was dissolved in ethanol (50 mL), heated to 70° C. and NaBH$_4$ (0.423 g, 11.17 mmol) was added portionwise. After 30 minutes the bubbling stopped and then tert-butyl 4-(6-chloro-3,5-dicyano-4-ethylpyridin-2-yl)piperazine-1-carboxylate (3 g, 7.98 mmol) dissolved in a mixture of warm ethanol (120 mL) and 50 mL of tetrahydrofuran was slowly added and the reaction was heated at 70° C. for 30 minutes. The solvents were evaporated and the crude was taken up in DCM and washed with water. The DCM was dried with sodium sulfate and evaporated to give 3.5 g of crude product which was dissolved in DCM and loaded on to a 80 g silica col. Elution with ethyl acetate/hexane 12-75% ended when the pressure shut down the instrument. The column was sawed open and the crystallized band isolated by stirring with DCM/1% methanol and filtering off the silica gel to afford tert-butyl 4-(6-((2-amino-2-oxo-1-phenylethyl)thio)-3,5-dicyano-4-ethylpyridin-2-yl)piperazine-1-carboxylate (1.85 g, 3.65 mmol, 46% yield). LCMS m/z=507.2 [M+H]+. The pure product was dissolved in 30 mL of DCM and 20 mL of TFA was added. It was stirred 1 hour at room temperature and the TFA evaporated and chased with DCM and pumped down. Trituration with DCM caused crystals to form. Obtained 2-((3,5-dicyano-4-ethyl-6-(piperazin-1-yl)pyridin-2-yl)thio)-2-phenylacetamide, Trifluoroacetic acid salt (1.9 g, 3.65 mmol). This intermediate was not characterized as the Trifluoroacetic acid salt.

Step 3: 2-((3,5-Dicyano-4-ethyl-6-(4-(oxazol-2-ylmethyl)piperazin-1-yl)pyridin-2-yl)thio)-2-phenylacetamide

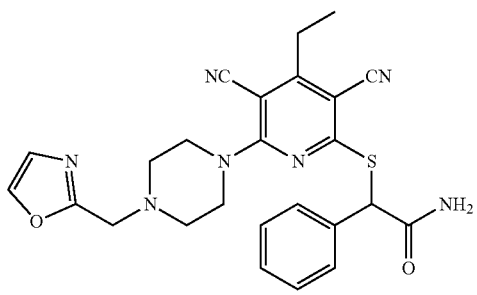 [SMILES: CCc1c(C#N)c(SC(C(N)=O)c2ccccc2)nc(N2CCN(Cc3ncco3)CC2)c1C#N]

2-((3,5-Dicyano-4-ethyl-6-(piperazin-1-yl)pyridin-2-yl)thio)-2-phenylacetamide, Trifluoroacetic acid salt (synthesis described in example 176 step 2, 215 mg, 0.413 mmol) was dissolved in dichloromethane (15 mL) and DIEA (0.144 mL, 0.826 mmol) was added followed by acetic acid (0.047 mL, 0.826 mmol) was added followed by oxazole-2-carbaldehyde (80 mg, 0.826 mmol). The reaction was stirred for 30 minutes and sodium triacetoxyborohydride (448 mg, 2.116 mmol) was added. The reaction was stirred at 25° C. for 18 hours. The DCM solution was washed with water, dried, and loaded on a 12 gram silica column and eluted with ethyl acetate/ethanol 4-25% then 25% ethanol in ethyl acetate, 1% overall in ammonium hydroxide to afford 2-((3,5-dicyano-4-ethyl-6-(4-(oxazol-2-ylmethyl)piperazin-1-yl)pyridin-2-yl)thio)-2-phenylacetamide (150 mg, 0.308 mmol). 1H NMR (400 MHz, DMSO-d6) δ ppm 1.06-1.28 (m, 3H) 2.59 (t, J=4.69 Hz, 4H) 2.68-2.85 (m, 2H) 3.76 (s, 2H) 3.89 (d, J=4.82 Hz, 4H) 5.53 (s, 1H) 7.21 (s, 1H) 7.38 (s, 4H) 7.50 6 (s, 2H) 7.84-7.95 (m, 1H) 8.11 (d, J=0.76 Hz, 1H). LCMS m/z=488.2 [M+H]+.

Example 177

2-((6-(4-((1H-Pyrrol-2-yl) methyl) piperazin-1-yl)-3,5-dicyano-4-ethylpyridin-2-yl)thio)-2-phenylacetamide

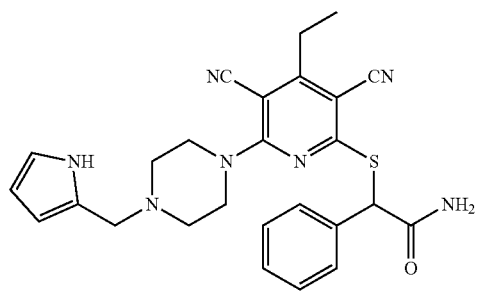 [SMILES: CCc1c(C#N)c(SC(C(N)=O)c2ccccc2)nc(N2CCN(Cc3ccc[nH]3)CC2)c1C#N]

2-((3,5-Dicyano-4-ethyl-6-(piperazin-1-yl)pyridin-2-yl)thio)-2-phenylacetamide 2,2,2-trifluoroacetate (synthesis described in example 176 step 2, 215 mg, 0.413 mmol) was dissolved in dichloromethane (15 mL) and DIEA (0.144 mL, 0.826 mmol). Then acetic acid (0.047 mL, 0.826 mmol) was added followed by 1H-pyrrole-2-carbaldehyde (79 mg, 0.826 mmol). The reaction was stirred for 30 minutes and sodium triacetoxyborohydride (350 mg, 1.652 mmol) was added. The reaction was stirred at 25° C. for 18 hours. The DCM solution was washed with water, dried with sodium sulfate and evaporated. It was loaded on a 12 g silica column and eluted with ethyl acetate/ethanol 4-25% then 25% ethanol in ethyl acetate, which contained 1% ammonium hydroxide. Obtained 2-((6-(4-((1H-pyrrol-2-yl)methyl)piperazin-1-yl)-3,5-dicyano-4-ethylpyridin-2-yl)thio)-2-phenylacetamide (75 mg, 0.154 mmol, 37% yield). LCMS m/z=486.2 [M+H]+. 1H NMR (400 MHz, DMSO-d6) δ ppm 1.13-1.33 (t, 3H) 2.4-2.46 (t, 2H) 2.75 (q, J=7.52 Hz, 2H) 2.9-3.3 (t, 2H) 3.41-3.56 (m, 2H) 3.87 (br. s., 4H) 5.52 (s, 1H) 5.84-6.04 (m, 2H) 6 6.67 (d, J=1.52 Hz, 1H) 7.21-7.44 (m, 4H) 7.45-7.57 (m, 2H) 7.88 (s, 1H) 10.71 (br. s., 1H).

Example 178

2-((3,5-Dicyano-6-(3,4-dihydro-2,7-naphthyridin-2(1H)-yl)-4-ethylpyridin-2-yl)thio)-2-phenylacetamide

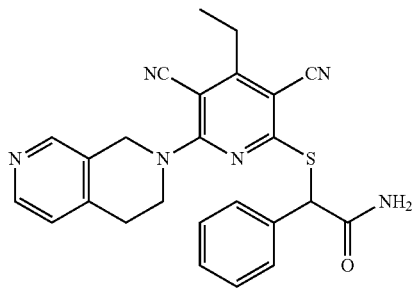 [SMILES: CCc1c(C#N)c(SC(C(N)=O)c2ccccc2)nc(N2CCc3ccncc3C2)c1C#N]

2-((6-chloro-3,5-dicyano-4-ethylpyridin-2-yl)thio)-2-phenylacetamide (synthesis described in example 52, step 1, 60.5 mg, 0.170 mmol) and 1,2,3,4-tetrahydro-2,7-naphthyridine hydrochloride (40 mg, 0.234 mmol) were added to a vial and suspended in tetrahydrofuran (6 mL). DIPEA (0.044 mL, 0.254 mmol) was added and the mixture was heated to 65° C. for 2 hours and then 55° C. for 3 hours. The mixture was concentrated, and the material was passed through a silica gel plug (EtOAc; 1:1 EtOAc:IPA, and then 3:1 EtOAc: EtOH w/1% NH$_4$OH), then purified on Basic HPLC RP (30×50 column; 20-80% water w/0.1% NH$_4$OH/acetonitrile) then freeze dried to afford 2-((3,5-dicyano-6-(3,4-dihydro-2,7-naphthyridin-2 (1H)-yl)-4-ethylpyridin-2-yl) thio)-2-phenylacetamide (15 mg, 0.032 mmol, 19% yield). LCMS m/z=455.1 [M+H]$^+$. $^1$H NMR (400 MHz, DMSO-d$_6$) δ ppm 8.50 (s, 1H) 8.40 (d, J=5.07 Hz, 1H) 8.00 (s, 1H) 7.56 (d, J=7.10 Hz, 2H) 7.31-7.50 (m, 4H) 7.29 (d, J=4.82 Hz, 1H) 5.63 (s, 1H) 5.00 (q, J=16.73 Hz, 2H) 3.99-4.12 (m, 2H) 3.03 (t, J=5.70 Hz, 2H) 2.80 (q, J=7.60 Hz, 2H) 1.23 (t, J=7.48 Hz, 3H).

Example 181

2-((3,5-Dicyano-4-ethyl-6-((S)-3-hydroxypyrrolidin-1-yl)pyridin-2-yl)thio)-2-(pyridin-3-yl)acetamide Step 1: 2-Amino-2-oxo-1-(pyridin-3-yl)ethyl methanesulfonate

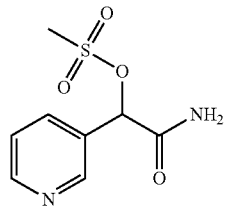

To a stirring solution of 2-hydroxy-2-(pyridin-3-yl)acetamide (400 mg, 2.63 mmol) and Et$_3$N (0.733 mL, 5.26 mmol) in tetrahydrofuran (20 mL) was added methanesulfonyl chloride (361 mg, 3.15 mmol) at room temperature, and the resulting mixture was stirred at room temperature for 5 hours. The reaction mixture was concentrated and the residue purified by silica gel chromatography (eluted by DCM/MeOH, 50:1) to give 2-amino-2-oxo-1-(pyridin-3-yl)ethyl methanesulfonate (300 mg, 50% yield) as a brown solid. LCMS m/z=230.9 [M+H]$^+$.

Step 2: 2-((3,5-Dicyano-4-ethyl-6-((S)-3-hydroxypyrrolidin-1-yl)pyridin-2-yl)thio)-2-(pyridin-3-yl) acetamide

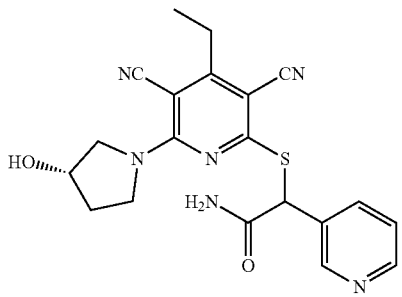 [SMILES: CCc1c(C#N)c(SC(C(N)=O)c2cccnc2)nc(N2CC[C@H](O)C2)c1C#N]

A solution of (S)-2-chloro-4-ethyl-6-(3-hydroxypyrrolidin-1-yl)pyridine-3,5-dicarbonitrile (synthesis described in example 168, step 1, 300 mg, 1.08 mmol), potassium thioacetate (149 mg, 1.30 mmol) in N,N-dimethylformamide (15 mL) was stirred at room temperature for 30 minutes then 2-amino-2-oxo-1-(pyridin-3-yl)ethyl methanesulfonate (300 mg, 1.30 mmol) and Et$_3$N (0.302 mL, 2.17 mmol) were added at room temperature. The resulting mixture was stirred at room temperature for 12 hours. The reaction mixture was poured into water (50 mL) and extracted with EtOAc (50 mL×2). The combined organic layers were dried and concentrated, and the residue was purified by silica gel column (eluting with DCM/MeOH, 100:1) to give 2-((3,5-dicyano-4-ethyl-6-((S)-3-hydroxypyrrolidin-1-yl)pyridin-2-yl)thio)-2-(pyridin-3-yl)acetamide (120 mg, 27% yield) as a white solid. LCMS m/z=409.0 [M+H]$^+$. $^1$H NMR (400 MHz, DMSO) δ ppm 8.85-8.65 (m, 1H), 8.62-8.42 (m, 1H), 8.15-7.98 (m, 1H), 7.95-7.80 (m, 1H), 7.60-7.25 (m, 2H), 5.70 (s, 1H), 5.30-5.05 (m, 1H), 4.50-4.30 (m, 1H), 4.10-3.60 (m, 4H), 2.85-2.65 (m, 2H), 2.10-1.82 (m, 2H), 1.30-1.10 (m, 3H).

Example 182

2-((6-(4-((1H-Pyrrol-3-yl)methyl)piperazin-1-yl)-3,5-dicyano-4-ethylpyridin-2-yl)thio)-2-phenylacetamide

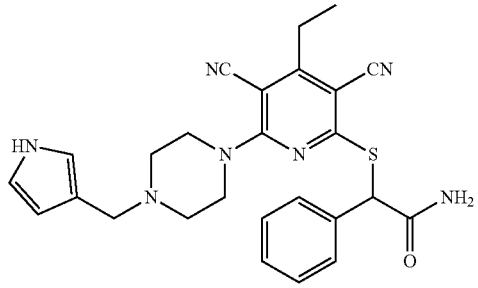 [SMILES: CCc1c(C#N)c(SC(C(N)=O)c2ccccc2)nc(N2CCN(Cc3cc[nH]c3)CC2)c1C#N]

2-((3,5-Dicyano-4-ethyl-6-(piperazin-1-yl)pyridin-2-yl) thio)-2-phenylacetamide 2,2,2-trifluoroacetate (synthesis described in example 176 step 2, 215 mg, 0.413 mmol) was dissolved in dichloromethane (15 mL) and DIEA (0.144 mL, 0.826 mmol). Acetic acid (0.047 mL, 0.826 mmol) was added followed by 1H-pyrrole-3-carbaldehyde (79 mg, 0.826 mmol). The reaction was stirred for 30 minutes and sodium triacetoxyborohydride (350 mg, 1.652 mmol) was added. The reaction was stirred at 25° C. for 18 hours. The DCM solution was washed with water, dried, and evaporated. It was loaded on a 12 g silica column with 5 mL of DCM and eluted with ethyl acetate/ethanol 4-25%, then 25% ethanol in ethyl acetate, containing 1% ammonium hydroxide. Obtained 2-((6-(4-((1H-pyrrol-3-yl)methyl)piperazin-1-yl)-3,5-dicyano-4-ethylpyridin-2-yl)thio)-2-phenylacetamide (70 mg, 0.142 mmol, 35% yield) LCMS m/z=486.2 [M+H]$^+$. $^1$H NMR (400 MHz, DMSO-d$_6$) δ ppm 1.10-1.29 (m, 3H) 2.45 (br. s., 4H) 2.76 (br. s., 2H) 3.4-3.5 (m, 2H) 3.86 (br. s., 4H) 5.52 (s, 1H) 5.95-6.05 (m, 1H) 6.65 (m, 2H) 7.37 (d, J=7.86 Hz, 4H) 7.45-7.60 (m, 2H) 7.91 (s, 1H) 10.59-10.73 (m, 1H).

Example 183

2-((3,5-Dicyano-4-ethyl-6-(4-(isoxazol-3-ylmethyl)piperazin-1-yl)pyridin-2-yl)thio)-2-phenylacetamide

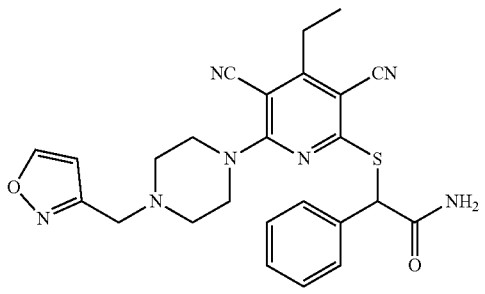 [SMILES: CCc1c(C#N)c(SC(C(N)=O)c2ccccc2)nc(N2CCN(Cc3ccon3)CC2)c1C#N]

2-((3,5-Dicyano-4-ethyl-6-(piperazin-1-yl)pyridin-2-yl)thio)-2-phenylacetamide 2,2,2-trifluoroacetate (synthesis described in example 176 step 2, 215 mg, 0.413 mmol) was dissolved in dichloromethane (15 mL) and DIEA (0.144 mL, 0.826 mmol). Acetic acid (0.047 mL, 0.826 mmol) was added followed by isoxazole-3-carbaldehyde (80 mg, 0.826 mmol). The reaction was stirred for 30 minutes and sodium triacetoxyborohydride (350 mg, 1.652 mmol) was added. The reaction was stirred at 25° C. for 18 hours. The DCM solution was washed with water. The DCM solution was dried with sodium sulfate and evaporated. The crude was loaded on a 12 g silica column with 25 mL of DCM and eluted with ethyl acetate/ethanol 4-25% then 25% ethanol in ethyl acetate, containing 1% ammonium hydroxide. Obtained 2-((3,5-dicyano-4-ethyl-6-(4-(isoxazol-3-ylmethyl)piperazin-1-yl)pyridin-2-yl)thio)-2-phenylacetamide (130 mg, 0.267 mmol, 65% yield). LCMS m/z=488.2 [M+H]$^+$. $^1$H NMR (400 MHz, DMSO-d$_6$) δ ppm 2.53-2.56 (m, 4H) 2.61-2.88 (m, 2H) 3.61-3.77 (m, 2H) 3.8-3.9 (m, 4,H) 5.51 (s, 1H) 6.60 (d, J=1.77 Hz, 1H) 7.19-7.42 (m, 5H) 7.49-7.51 (m, 1H) 7.90 (s, 1H) 8.91 (d, J=1.52 Hz, 1H).

Example 184

2-((3,5-Dicyano-4-ethyl-6-(4-(oxazol-5-ylmethyl)piperazin-1-yl)pyridin-2-yl)thio)-2-phenylacetamide

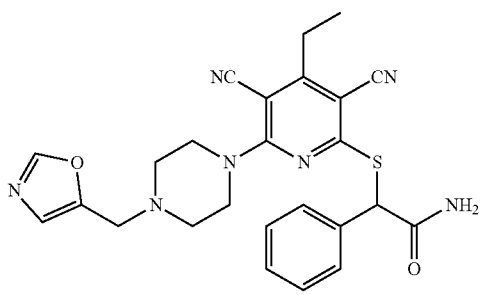 [SMILES: CCc1c(C#N)c(SC(C(N)=O)c2ccccc2)nc(N2CCN(Cc3cnco3)CC2)c1C#N]

2-((3,5-Dicyano-4-ethyl-6-(piperazin-1-yl)pyridin-2-yl)thio)-2-phenylacetamide 2,2,2-trifluoroacetate (synthesis described in example 176 step 2, 215 mg, 0.413 mmol) was dissolved in dichloromethane (15 mL) and DIEA (0.144 mL, 0.826 mmol). Acetic acid (0.047 mL, 0.826 mmol) was added followed by oxazole-5-carbaldehyde (80 mg, 0.826 mmol). The reaction was stirred for 30 minutes and sodium triacetoxyborohydride (350 mg, 1.652 mmol) was added. The reaction was stirred at 25° C. for 18 hours. The DCM solution was washed with water, dried with sodium sulfate and evaporated. It was loaded on a 12 g silica column with 15 mL of DCM and eluted with ethyl acetate/ethanol (4-25% ethanol) then 25% ethanol in ethyl acetate containing 1% ammonium hydroxide. The purified product was purified further on a Gilson reverse phase HPLC eluting with 0.1% ammonium hydroxide in water and acetonitrile (10-90%) gradient to afford 2-((3,5-dicyano-4-ethyl-6-(4-(oxazol-5-ylmethyl)piperazin-1-yl)pyridin-2-yl)thio)-2-phenylacetamide (45 mg, 0.092 mmol). LCMS m/z=488.2 [M+H]$^+$. $^1$H NMR (400 MHz, DMSO-d$_6$) δ ppm 1.20 (t, J=7.60 Hz, 4H) 2.75 (d, J=7.60 Hz, 2H) 3.32 (s, 1H) 3.68 (s, 2H) 3.88 (br. s., 5H) 5.52 (s, 1H) 7.12 (s, 1H) 7.30-7.43 (m, 5H) 7.44-7.57 (m, 2H) 7.91 (s, 1H) 8.35 (s, 1H)

Example 185

2-((3,5-Dicyano-4-ethyl-6-(4-(isoxazol-4-ylmethyl)piperazin-1-vhpyridin-2-yl)thio)-2-phenylacetamide

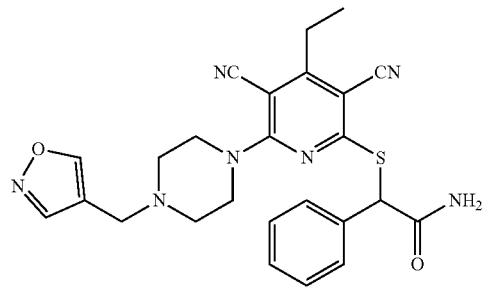 [SMILES: CCc1c(C#N)c(SC(C(N)=O)c2ccccc2)nc(N2CCN(Cc3cnoc3)CC2)c1C#N]

2-((3,5-Dicyano-4-ethyl-6-(piperazin-1-yl)pyridin-2-yl)thio)-2-phenylacetamide 2,2,2-trifluoroacetate (synthesis described in example 176 step 2, 215 mg, 0.413 mmol) was dissolved in dichloromethane (15 mL) and DIEA (0.161 mL, 0.826 mmol). Acetic acid (0.047 mL, 0.826 mmol) was added followed by isoxazole-4-carbaldehyde (80 mg, 0.826 mmol). The reaction was stirred for 30 minutes and sodium triacetoxyborohydride (350 mg, 1.652 mmol) was added. The reaction was stirred at 25° C. for 18 hours. Washed the DCM solution with water. The DCM solution was dried with sodium sulfate, evaporated and purified on a 12 g silica column eluting with ethyl acetate/ethanol (4-25%) then 25% ethanol in ethyl acetate containing 1% ammonium hydroxide. The partially purified product obtained was purified further on a Gilson HPLC eluting with 0.1 ammonium hydroxide in water and acetonitrile (10-90%) gradient. Obtained 2-((3,5-dicyano-4-ethyl-6-(4-(isoxazol-4-ylmethyl)piperazin-1-yl)pyridin-2-yl)thio)-2-phenylacetamide (150 mg, 0.308 mmol, 75% yield) LCMS m/z=488.2 [M+H]$^+$. $^1$H NMR (400 MHz, DMSO-d$_6$) δ ppm 1.01-1.39 (m, 3H) 1.46-1.48 (m, 4H) 2.70-2.76 (m, 2H) 3.46-3.48 (s, 2H) 3.86-3.88 (t, J=4.82 Hz, 4H) 5.51 (s, 1H) 7.17-7.46 (m, 4H) 7.61 (m, 2H) 7.90 (s, 1H) 8.60 (m, 1H) 8.90 (s, 1H).

Example 186

3-Amino-N-(1-(6-((2-amino-2-oxo-1-phenylethyl)thio)-3,5-dicyano-4-ethylpyridin-2-yl)piperidin-4-yl)oxetane-3-carboxamide Step 1: Benzyl 4-(3-((tert-butoxycarbonyl)amino)oxetane-3-carboxamido)piperidine-1-carboxylate

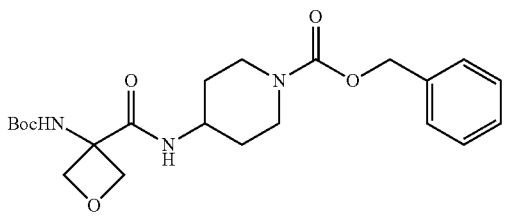 [SMILES: CC(C)(C)OC(=O)NC1(C(=O)NC2CCN(C(=O)OCc3ccccc3)CC2)COC1]

3-((tert-Butoxycarbonyl)amino)oxetane-3-carboxylic acid (500 mg, 2.302 mmol), benzyl 4-aminopiperidine-1-carboxylate (593 mg, 2.53 mmol), 1H-benzo[d][1,2,3]triazol-1-ol (373 mg, 2.76 mmol) were added into N,N-dimethylformamide (25 mL). The mixture was stirred for 12 hours at 25° C. and then water (30 mL) was added. The mixture was extracted with ethyl acetate (30 mL×3), dried over sodium sulfate, concentrated and purified by flash column chromatography to afford benzyl 4-(3-((tert-butoxycarbonyl)amino)oxetane-3-carboxamido)piperidine-1-carboxylate (630 mg, 63% yield). LCMS m/z=456.1 [M+Na]$^+$.

Step 2: tert-Butyl (3-(piperidin-4-ylcarbamoyl)oxetan-3-yl)carbamate

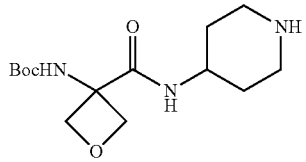 [SMILES: CC(C)(C)OC(=O)NC1(C(=O)NC2CCNCC2)COC1]

Benzyl 4-(3-((tert-butoxycarbonyl)amino)oxetane-3-carboxamido)piperidine-1-carboxylate (750 mg, 1.730 mmol) and Pd/C (10%, 75 mg) were added into methanol (25 mL). The mixture was stirred for 2 hours at 25° C. under a hydrogen filled balloon. The mixture was filtered, concentrated and purified by flash column chromatography to afford tert-butyl (3-(piperidin-4-ylcarbamoyl)oxetan-3-yl)carbamate (460 mg, 89% yield). LCMS m/z=299.8 [M+H]$^+$.

Step 3: tert-Butyl (3-((1-(6-chloro-3,5-dicyano-4-ethylpyridin-2-yl)piperidin-4-yl)carbamoyl)oxetan-3-yl)carbamate

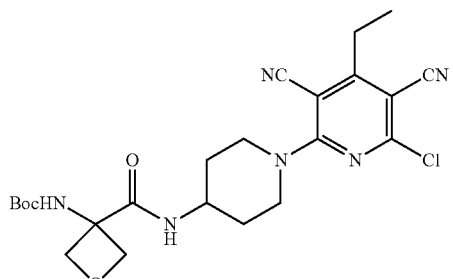

tert-Butyl (3-(piperidin-4-ylcarbamoyl)oxetan-3-yl)carbamate (460 mg, 1.537 mmol), 2,6-dichloro-4-ethylpyridine-3,5-dicarbonitrile (synthesis described in example 3 step 2, 347 mg, 1.537 mmol) and triethylamine (311 mg, 3.07 mmol) were added into dichloromethane (30 mL). The mixture was stirred for 6 hours at 25° C., and was then washed with water (30 mL). The organic layer was dried over sodium sulfate and concentrated. The residue was purified by flash column chromatography to afford tert-butyl (3-((1-(6-chloro-3,5-dicyano-4-ethylpyridin-2-yl)piperidin-4-yl)carbamoyl)oxetan-3-yl)carbamate (540 mg, 72% yield). LCMS m/z=511.1 [M+Na]$^+$.

Step 4: tert-Butyl (3-((1-(3,5-dicyano-4-ethyl-6-mercaptopyridin-2-yl)piperidin-4-yl)carbamoyl)oxetan-3-yl)carbamate

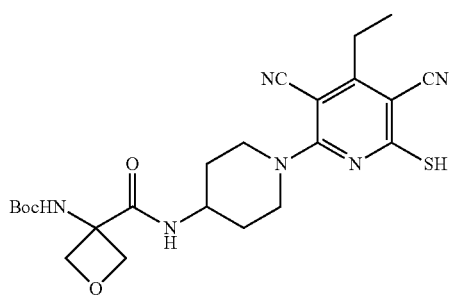 [SMILES: CCc1c(C#N)c(Cl)nc(N2CCC(NC(=O)C3(NC(=O)OC(C)(C)C)COC3)CC2)c1C#N]

tert-Butyl (3-((1-(6-chloro-3,5-dicyano-4-ethylpyridin-2-yl)piperidin-4-yl)carbamoyl)oxetan-3-yl)carbamate (220 mg, 0.450 mmol) and potassium ethanethioate (61.7 mg, 0.540 mmol) were added to N,N-dimethylformamide (12 mL). The mixture was stirred for 4 hours at 20° C., washed with water (20 mL) and extracted with ethyl acetate (20 mL×3). The organic layer was concentrated to afford tert-butyl (3-((1-(3,5-dicyano-4-ethyl-6-mercaptopyridin-2-yl)piperidin-4-yl)carbamoyl)oxetan-3-yl)carbamate (150 mg, 69% yield). LCMS m/z=509.1 [M+Na]$^+$.

Step 5: tert-Butyl (3-((1-(6-((2-amino-2-oxo-1-phenylethyl)thio)-3,5-dicyano-4-ethylpyridin-2-yl)piperidin-4-yl)carbamoyl)oxetan-3-yl)carbamate

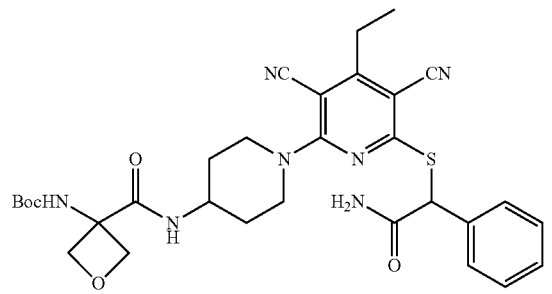 [SMILES: CCc1c(C#N)c(SC(C(N)=O)c2ccccc2)nc(N2CCC(NC(=O)C3(NC(=O)OC(C)(C)C)COC3)CC2)c1C#N]

tert-Butyl (3-((1-(3,5-dicyano-4-ethyl-6-mercaptopyridin-2-yl)piperidin-4-yl)carbamoyl)oxetan-3-yl)carbamate (150 mg, 0.308 mmol), 2-amino-2-oxo-1-phenylethyl methanesulfonate (synthesis described in example 3 step 5, 106 mg, 0.462 mmol) and potassium carbonate (85 mg, 0.617 mmol) were added into N,N-dimethylformamide (15 mL). The mixture was stirred for 12 hours at 40° C. and then water (30 mL) was added. The mixture was extracted with ethyl acetate (20 mL×3). The organic layer was dried over sodium sulfate, concentrated and purified by flash column chromatography to afford tert-butyl (3-((1-(6-((2-amino-2-oxo-1-phenylethyl)thio)-3,5-dicyano-4-ethylpyridin-2-yl)piperidin-4-yl)carbamoyl)oxetan-3-yl)carbamate (180 mg, 94% yield). LCMS m/z=620 [M+H]$^+$.

Step 6: 3-Amino-N-(1-(6-((2-amino-2-oxo-1-phenylethyl)thio)-3,5-dicyano-4-ethylpyridin-2-yl)piperidin-4-yl)oxetane-3-carboxamide

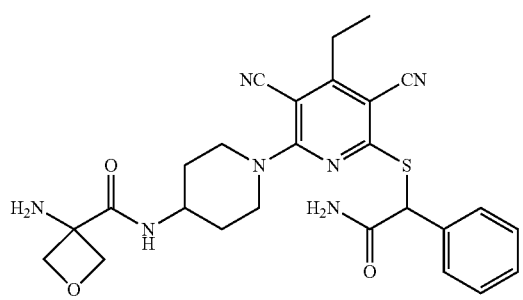 [SMILES: CCc1c(C#N)c(SC(C(N)=O)c2ccccc2)nc(N2CCC(NC(=O)C3(N)COC3)CC2)c1C#N]

To a solution of 2,2,2-trifluoroacetic acid (2 mL, 0.387 mmol) in dichloromethane (12 mL) was added tert-butyl (3-((1-(6-((2-amino-2-oxo-1-phenylethyl)thio)-3,5-dicyano-4-ethylpyridin-2-yl)piperidin-4-yl)carbamoyl)oxetan-3-yl)carbamate (240 mg, 0.387 mmol). The mixture was stirred for 3 hours at 25° C. and then water (20 mL) was added. The mixture was extracted with DCM (20 mL×3). The organic phase was dried over sodium sulfate, concentrated and purified by prep-HPLC to afford 3-amino-N-(1-(6-((2-amino-2-oxo-1-phenylethyl)thio)-3,5-dicyano-4-ethylpyridin-2-yl)piperidin-4-yl)oxetane-3-carboxamide (78 mg, 39% yield). LCMS m/z=520.1 [M+H]$^+$. $^1$H NMR (400 MHz, DMSO-d$_6$) δ ppm 8.01 (dd, J=45.0, 37.2 Hz, 2H), 7.52 (d, J=7.1 Hz, 2H), 7.45-7.22 (m, 3H), 5.53 (s, 1H), 5.17 (br. s, 1H), 4.77 (d, J=6.2 Hz, 2H), 4.51 (t, J=14.1 Hz, 2H), 4.38 (d, J=6.3 Hz, 2H), 4.09-3.85 (m, 1H), 3.46-3.19 (m, 2H), 2.89-2.65 (m, 2H), 1.89 (d, J=12.6 Hz, 2H), 1.65-1.42 (m, 2H), 1.21 (t, J=7.6 Hz, 3H).

Example 187

2-((6-(4-((1H-Pyrazol-4-yl)methyl)piperazin-1-yl)-3,5-dicyano-4-ethylpyridin-2-yl)thio)-2-phenylacetamide

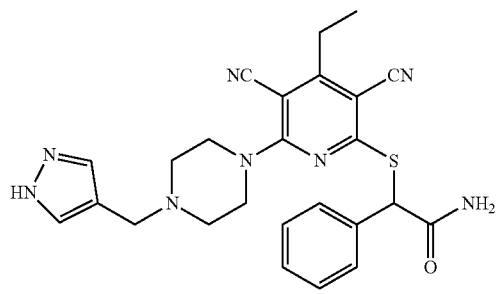 [SMILES: CCc1c(C#N)c(SC(C(N)=O)c2ccccc2)nc(N2CCN(Cc3cn[nH]c3)CC2)c1C#N]

2-((3,5-Dicyano-4-ethyl-6-(piperazin-1-yl)pyridin-2-yl)thio)-2-phenylacetamide 2,2,2-trifluoroacetate (synthesis described in example 176 step 2, 215 mg, 0.413 mmol) was dissolved in dichloromethane (15 mL) and DIEA (0.144 mL, 0.826 mmol). Acetic acid (0.047 mL, 0.826 mmol) was added followed by 1H-pyrazole-4-carbaldehyde (79 mg, 0.826 mmol) The reaction was stirred for 30 minutes and sodium triacetoxyborohydride (350 mg, 1.652 mmol) was added. The reaction was stirred at 25° C. for 18 Hous. The DCM solution was washed with water, a solution of saturated sodium bicarbonate, and then water. The DCM solution was dried then evaporated and the resulting solid was triturated with ethyl acetate to give after filtration pure product. The solid was dried in vacuum oven overnight to afford 2-((6-(4-((1H-pyrazol-4-yl)methyl)piperazin-1-yl)-3,5-dicyano-4-ethylpyridin-2-yl)thio)-2-phenylacetamide (75 mg, 0.149 mmol, 36% yield) LCMS m/z=487.2 [M+H]$^+$. $^1$H NMR (400 MHz, DMSO-d$_6$) δ ppm 1.20 (t, J=7.60 Hz, 3H) 2.44 (br. s., 4H) 2.75 (d, J=7.60 Hz, 2H) 3.44 (s, 2H) 3.86 (d, J=4.82 Hz, 4H) 5.52 (s, 1H) 7.28-7.44 (m, 4H) 7.46-7.61 (m, 5H) 7.91 (s, 1H).

Example 188

2-((6-(4-((1H-Imidazol-5-yl)methyl)piperazin-1-yl)-3,5-dicyano-4-ethylpyridin-2-yl)thio)-2-phenylacetamide

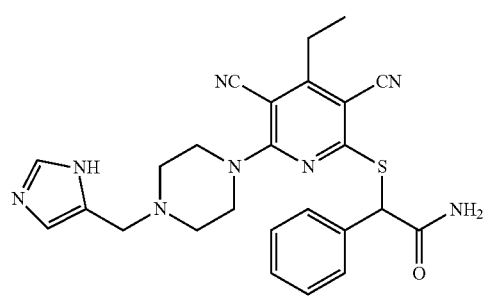 [SMILES: CCc1c(C#N)c(SC(C(N)=O)c2ccccc2)nc(N2CCN(Cc3cnc[nH]3)CC2)c1C#N]

2-((3,5-Dicyano-4-ethyl-6-(piperazin-1-yl)pyridin-2-yl)thio)-2-phenylacetamide 2,2,2-trifluoroacetate (synthesis described in example 176 step 2, 215 mg, 0.413 mmol) was dissolved in dichloromethane (15 mL) and DIEA (0.144 mL, 0.826 mmol). Acetic acid (0.047 mL, 0.826 mmol) was added followed by 1H-imidazole-5-carbaldehyde (79 mg, 0.826 mmol). The reaction was stirred for 30 minutes and sodium triacetoxyborohydride (438 mg, 2.065 mmol) was added. The reaction was stirred at 25° C. for 18 hours. DCM (15 mL) was added to the reaction and the solution was washed with saturated sodium bicarbonate solution and water. The separated DCM and was dried with sodium sulfate and evaporated to give crude product which was purified on a Gilson reverse phase HPLC eluting with 0.1% ammonium hydroxide in water and acetonitrile (10-90% gradient). Obtained 2-((6-(4-((1H-imidazol-5-yl)methyl)piperazin-1-yl)-3,5-dicyano-4-ethylpyridin-2-yl)thio)-2-phenylacetamide (45 mg, 0.092 mmol, 22% yield) LCMS m/z=487.1 [M+H]$^+$. $^1$H NMR (400 MHz, DMSO-d$_6$) δ ppm 1.03-1.37 (m, 3H) 2.5-2.6 (m, 2H) 2.73-2.74 (m, 2H) 3.31-3.33 (m, 2H) 3.50-3.56 (m, 2H) 3.86 (4H, m) 3.8 (2H, m) 5.52 (s, 1H) 6.99-7.19 (m, 1H) 7.25-7.41 (m, 3H) 7.48-7.49 (m, 1H) 7.56-7.57 (m, 1H) 7.91 (s, 1H) 11.91 (s, 1H).

Example 189

2-((3,5-Dicyano-4-ethyl-6-(4-(1-hydroxy-2-methylpropan-2-yl)piperazin-1-yl)pyridin-2-ylthio-2-phenylacetamide Step 1: 2-(4-(6-((2-Amino-2-oxo-1-phenylethyl)thio)-3,5-dicyano-4-ethylpyridin-2-yl) piperazin-1-yl)-2-methylpropanoic acid

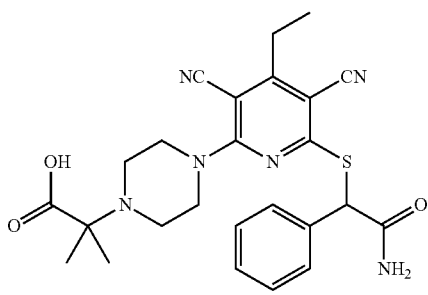 [SMILES: CCc1c(C#N)c(SC(C(N)=O)c2ccccc2)nc(N2CCN(C(C)(C)C(=O)O)CC2)c1C#N]

To a solution of 2-((3,5-dicyano-4-ethyl-6-(piperazin-1-yl)pyridin-2-yl)thio)-2-phenylacetamide, trifluoroacetic acid salt (synthesis described in example 176 step 2, 1040 mg, 2.00 mmol) and K$_2$CO$_3$ (552 mg, 4.00 mmol) in acetonitrile (20 mL) under nitrogen at room temperature was added a solution of 2-bromo-2-methylpropanoic acid (667 mg, 4.00 mmol) in acetonitrile (20 mL) in one charge during 1 minute. The reaction mixture was stirred at 25° C. for 15 hours and was then diluted with ethyl acetate (50 mL) and washed with water (50 mL). The aqueous layer was acidified with 3N HCl solution and extracted with ethyl acetate (50 mL). The organic layer was washed with saturated brine (25 mL) and water (50 mL), dried over sodium sulfate and evaporated in vacuo to give the crude product (600 mg, 61% yield) as a yellow solid. LCMS m/z=493 [M+H]$^+$.

Step 2: 2-((3,5-Dicyano-4-ethyl-6-(4-(1-hydroxy-2-methylpropan-2-yl)piperazin-1-yl)pyridin-2-yl)thio)-2-phenylacetamide

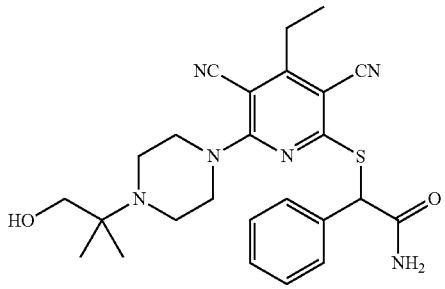 [SMILES: CCc1c(C#N)c(SC(C(N)=O)c2ccccc2)nc(N2CCN(C(C)(C)CO)CC2)c1C#N]

To a solution of 2-(4-(6-((2-amino-2-oxo-1-phenylethyl)thio)-3,5-dicyano-4-ethylpyridin-2-yl)piperazin-1-yl)-2-methylpropanoic acid (400 mg, 0.812 mmol) in tetrahydrofuran (10 mL) stirred under nitrogen at room temperature was added a solution of 1,1'-carbonyldiimidazole (263 mg, 1.62 mmol) in tetrahydrofuran (10 mL) in one charge during 1 minute. The reaction mixture was stirred at 25° C. for 5 hours. Then the reaction mixture was added dropwise to a solution of NaBH$_4$ (61.4 mg) in water (5 mL) at 0° C. The reaction was then stirred under nitrogen for 5 hours. The reaction was extracted with ethyl acetate (50 mL), washed with 2 M hydrochloric acid (10 mL), water (50 mL) and saturated brine (50 mL), dried over sodium sulfate and concentrated. The crude was purified by prep-HPLC to give 2-((3,5-dicyano-4-ethyl-6-(4-(1-hydroxy-2-methylpropan-2-yl)piperazin-1-yl)pyridin-2-yl)thio)-2-phenylacetamide (11 mg, 3% yield) as a white solid. LCMS m/z=479.1 [M+H]$^+$. $^1$H NMR (400 MHz, MeOD) δ ppm 7.56 (d, J=6.4 Hz, 2H), 7.47-7.35 (m, 3H), 5.51 (s, 1H), 4.11 (s, 4H), 3.58 (s, 2H), 3.06 (s, 4H), 2.93 (q, J=7.6 Hz, 2H), 1.32 (t, J=7.6 Hz, 3H), 1.22 (s, 6H).

Example 190

2-((6-(4-((1H-Imidazol-2-yl)methyl)piperazin-1-yl)-3,5-dicyano-4-ethylpyridin-2-yl)thio-2-phenylacetamide

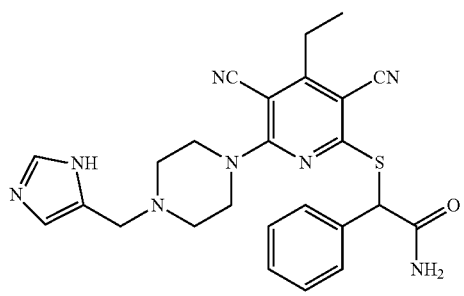 [SMILES: CCc1c(C#N)c(SC(C(N)=O)c2ccccc2)nc(N2CCN(Cc3cnc[nH]3)CC2)c1C#N]

2-((3,5-Dicyano-4-ethyl-6-(piperazin-1-yl)pyridin-2-yl)thio)-2-phenylacetamide, 2,2,2-trifluoroacetate (synthesis described in example 176 step 2, 215 mg, 0.413 mmol) was dissolved in dichloromethane (25 mL) and N,N-diisopropylethylamine (0.144 mL, 0.826 mmol) was added. To the solution was added acetic acid (0.061 mL, 1.058 mmol)

followed by 1H-imidazole-2-carbaldehyde (79 mg, 0.826 mmol). The mixture was stirred for 3 hours, and sodium triacetoxyborohydride (438 mg, 2.065 mmol) was then added. The reaction was stirred at 25° C. for 18 hours. The solution was washed with saturated sodium bicarbonate solution and then stirred for 2 hours with 1N sodium hydroxide. The layers were separated and the organic phase dried over sodium sulfate. The solvent was evaporated and the white solid obtained was triturated with ethyl acetate. The solid was collected, washed with ethyl acetate, then hexane and dried in the vacuum oven at 40° C. to afford 2-((6-(4-((1H-imidazol-2-yl)methyl)piperazin-1-yl)-3,5-dicyano-4-ethylpyridin-2-yl)thio)-2-phenylacetamide (105 mg, 51% yield). LCMS m/z=487.1 [M+H]+. 1H NMR (400 MHz, DMSO-d6) δ ppm 1.20 (t, J=7.60 Hz, 3H), 2.52-2.55 (m, 4H), 2.75 (d, J=7.60 Hz, 2H), 3.58 (d, J=1.01 Hz, 2H), 3.88 (d, J=3.04 Hz, 4H), 5.52 (s, 1H), 6.83 (s, 1H), 7.07 (s, 1H), 7.30-7.42 (m, 4H), 7.46-7.54 (m, 2H), 7.91 (s, 1H), 11.90-11.99 (m, 1H).

Example 191

2-((3,5-Dicyano-6-(dimethylamino)-4-methoxypyridin-2-yl)thio)-2-phenylacetamide

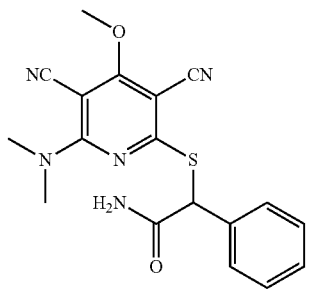 [SMILES: COc1c(C#N)c(SC(C(N)=O)c2ccccc2)nc(N(C)C)c1C#N]

2-((6-Amino-3,5-dicyano-4-methoxypyridin-2-yl)thio)-2-phenylacetamide (synthesis described in example 142, step 3, 100 mg, 0.206 mmol) and copper(II) chloride (70 mg, 0.521 mmol) were added to a vial and suspended in acetonitrile (10 mL). The mixture was heated to 50° C. for 5 minutes. tert-butyl nitrite (0.06 mL, 0.506 mmol) was added to the mixture slowly and the material was stirred at 50° C. for 60 minutes. After 1 hour, 0.03 mL of tert-butyl nitrite and 40 mg of CuCl2 were added to the heated mixture. Filtered through a small pad of silica gel/Celite® and washed with EtOAc/EtOH (4:1) The filtrate was treated with dimethylamine hydrochloride (80 mg, 0.981 mmol) and. 3 mL of DIPEA was added to the mixture. Solution turned blue. Concentrated solution; purified residue on C18 reverse phase isco (0-50-100% 0.1% aq. NH4OH/Acetonitrile) and the desired fractions were pooled and worked up with EtOAc (3×) and brine. Combined organics were dried over MgSO4, filtered and concentrated to afford 2-((3,5-dicyano-6-(dimethylamino)-4-methoxpyridin-2-yl)thio)-2-phenylacetamide (28 mg, 0.076 mmol, 37% yield). LCMS m/z=368.3 [M+H]+. 1H NMR (400 MHz, DMSO-d6) δ ppm 7.85-7.99 (m, 1H) 7.46-7.59 (m, 2H) 7.24-7.46 (m, 4H) 5.58 (s, 1H) 4.23 (s, 3H) 3.31 (s, 6H).

Example 192

2-((3,5-Dicyano-6-(dimethylamino)-4-ethoxypyridin-2-yl)thio)-2-phenylacetamide

Step 1: 2-Amino-6-chloro-4-ethoxypyridine-3,5-dicarbonitrile

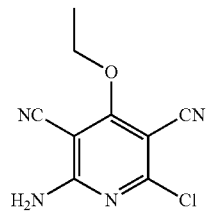

To a mixture of tetracyanoethylene (3 g, 23 mmol) and urea (478 mg, 7.96 mmol) was added ethanol (10 mL) under nitrogen. The deep purple mixture was heated to 35° C. for 15 minutes, cooled to room temperature and diluted with Et2O (40 mL). The mixture was cooled to −78° C. for 3 hours, and the solid was washed with cold Et2O and air dried to afford 2.59 g of a white powder. This powder (2.59 g) was added as a solution in ethanol (5 mL) to a 60° C. mixture of malononitrile (0.99 mL, 15.59 mmol) and potassium tert-butoxide (1.75 g, 15.59 mmol) in ethanol (5 mL) under nitrogen. The mixture was heated at reflux for 2 hours, cooled, and the solvent was removed under reduced pressure. The resulting solid was triturated with Et2O and dried in vacuo at 50° C. to afford 3.5 g of a light brown powder. To a mixture of this powder (1.5 g) in acetone (25 mL) was added concentrated hydrochloric acid (6 mL, 194 mmol) dropwise. The resulting mixture was heated at 50° C. for 17 hours, and was then cooled, poured onto water (50 mL) and stirred for 15 minutes. The solid was washed with water (2×25 mL) and dried in vacuo at 50° C. to afford 2-amino-6-chloro-4-ethoxypyridine-3,5-dicarbonitrile (672 mg, 45% yield) as a brown powder. LCMS m/z=221.0 [M−H]−.

Step 2: 2-((6-Amino-3,5-dicyano-4-ethoxypyridin-2-yl)thio)-2-phenylacetamide

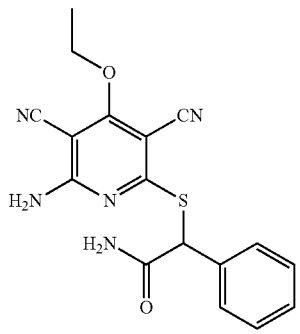 [SMILES: CCOc1c(C#N)c(N)nc(SC(C(N)=O)c2ccccc2)c1C#N]

To a solution of S-(2-amino-2-oxo-1-phenyl-ethyl) ethanethioate (synthesis described in example 62 step 5, 493 mg, 2.36 mmol) in ethanol (15 mL) was added sodium borohydride (127 mg, 3.37 mmol) at 75° C. The mixture was stirred for 15 minutes, and the resulting solution was added to a hot suspension of 2-amino-6-chloro-4-ethoxy-pyridine- 3,5-dicarbonitrile (500 mg, 2.25 mmol) in ethanol (10 mL) and heated at 75° C. for 15 minutes. The mixture was cooled to room temperature, and then in an ice cold water bath. The resulting mixture was filtered, washed with water (2×10 mL), Et$_2$O (2×10 mL) and dried in vacuo at 50° C. to afford 2-[(6-amino-3,5-dicyano-4-ethoxy-2-pyridyl)sulfanyl]-2-phenyl-acetamide (491 mg, 62% yield) as a white powder that was used in the subsequent step without further purification. LCMS m/z=352.2 [M−H]$^−$.

Step 3: 2-((6-Bromo-3,5-dicyano-4-ethoxypyridin-2-yl)thio)-2-phenylacetamide

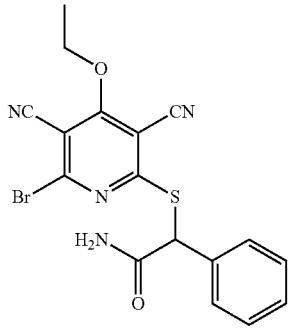

To a suspension of 2-[(6-amino-3,5-dicyano-4-ethoxy-2-pyridyl)sulfanyl]-2-phenyl-acetamide (460 mg, 1.30 mmol) in acetonitrile (40 mL) under nitrogen was added tert-butylnitrite (0.27 mL, 2.28 mmol) followed by copper(II) bromide (494 mg, 2.21 mmol) and the mixture was heated to 75° C. for 30 minutes. The mixture was cooled, absorbed onto SiO$_2$ (2.5 g) and chromatographed on SiO$_2$ (12 g RediSep cartridge) using 0-25% EtOAc:DCM to afford 2-[(6-bromo-3,5-dicyano-4-ethoxy-2-pyridyl)sulfanyl]-2-phenyl-acetamide (254 mg 47% yield) as a yellow powder. LCMS m/z=417.1 [M−H]$^−$.

Step 4: 2-((3,5-Dicyano-6-(dimethylamino)-4-ethoxypyridin-2-yl)thio)-2-phenylacetamide

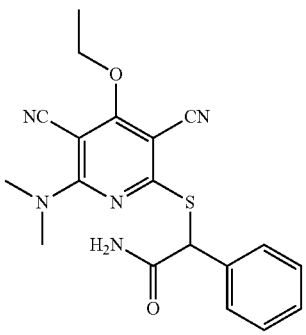 [SMILES: CCOc1c(C#N)c(SC(C(N)=O)c2ccccc2)nc(N(C)C)c1C#N]

To a solution of 2-[(6-bromo-3,5-dicyano-4-ethoxy-2-pyridyl)sulfanyl]-2-phenyl-acetamide (40 mg, 0.10 mmol) in THF (2 mL) was added dimethylamine (0.24 mL, 0.48 mmol) and the mixture was stirred at room temperature for 1 hour. The mixture was diluted with water (10 mL), stirred for 15 minutes, filtered, washed with water (2×10 mL), Et$_2$O (10 mL) and dried in vacuo at 50° C. to afford 2-[[3,5-dicyano-6-(dimethylamino)-4-ethoxy-2-pyridyl]sulfanyl]-2-phenyl-acetamide (30 mg, 82% yield) as an off white powder. LCMS m/z=380.2 [M−H]$^−$. $^1$H NMR (300 MHz, DMSO-d$_6$) δ ppm 7.91 (s, 1H), 7.54-7.48 (m, 2H), 7.42-7.30 (m, 4H), 5.58 (s, 1H), 4.53 (q, J=7.0 Hz, 2H), 3.31 (s, 6H), 1.36 (t, J=7.0 Hz, 3H).

Example 193

2-((3,5-Dicyano-4-ethoxy-6-(4-(2-hydroxyethyl)-1,4-diazepan-1-yl) pyridin-2-ylthio-2-phenylacetamide Step 1: 2-((6-Chloro-3,5-dicyano-4-ethoxypyridin-2-yl)thio)-2-phenylacetamide

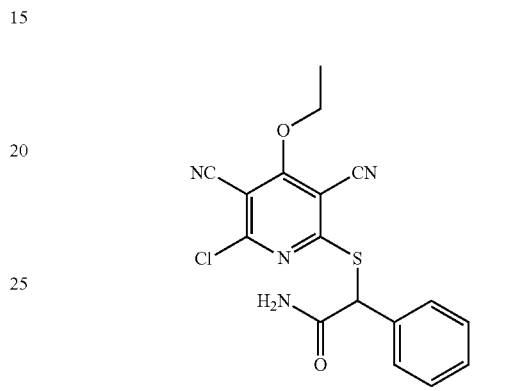

2-((6-Amino-3,5-dicyano-4-ethoxypyridin-2-yl)thio)-2-phenylacetamide (synthesis described in example 192, step 2, 355 mg, 1.005 mmol) was dissolved in acetonitrile (45 mL) and copper(II) chloride (250 mg, 1.859 mmol) was added. The mixture was stirred and heated to 50° C. for 5 minutes and tert-butyl nitrite (0.22 mL, 1.856 mmol) was added dropwise. The mixture was heated to 50° C. for 1.5 hours. Cooled to room temperature and filtered off a small amount of residue. The filtrate was worked up with EtOAc (3×) and brine. The combined organics were dried over MgSO$_4$, filtered and concentrated. Purified on silica gel (80 g column, 100% DCM→5% IPA in DCM w/1% NH$_4$OH). The desired fractions were pooled and concentrated to afford 2-((6-chloro-3,5-dicyano-4-ethoxypyridin-2-yl)thio)-2-phenylacetamide (206 mg, 0.553 mmol, 55% yield). LCMS m/z=373.1 [M+H]$^+$.

Step 2: 2-((3,5-Dicyano-4-ethoxy-6-(4-(2-hydroxyethyl)-1,4-diazepan-1-yl) pyridin-2-yl)thio)-2-phenylacetamide

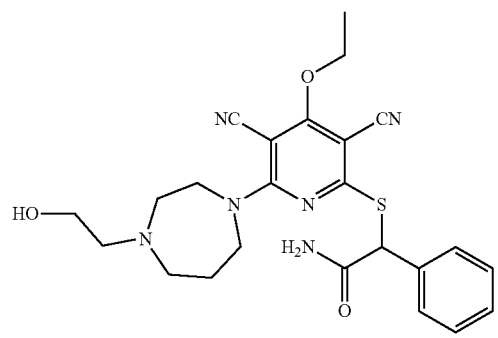 [SMILES: CCOc1c(C#N)c(SC(C(N)=O)c2ccccc2)nc(N2CCCN(CCO)CC2)c1C#N]

2-((6-Chloro-3,5-dicyano-4-ethoxypyridin-2-yl)thio)-2-phenylacetamide (102 mg, 0.274 mmol) was dissolved in tetrahydrofuran (10 mL) and 2-(1,4-diazepan-1-yl) ethanol (59 mg, 0.409 mmol) was added. The mixture was stirred at room temperature for 3 hours. The material was concentrated and purified on silica gel (40 g column, 100% DCM→7% IPA in DCM w/1% NH$_4$OH). The desired fractions were pooled and concentrated to afford 2-((3,5-dicyano-4-ethoxy-6-(4-(2-hydroxyethyl)-1,4-diazepan-1-yl)pyridin-2-yl)thio)-2-phenylacetamide (76 mg, 0.158 mmol, 58% yield). LCMS m/z=481.4 [M+H]$^+$. $^1$H NMR (400 MHz, DMSO-d$_6$) δ ppm 7.92 (s, 1H) 7.45-7.53 (m, 2H) 7.29-7.44 (m, 4H) 5.50 (s, 1H) 4.54 (q, J=6.93 Hz, 2H) 4.40 (t, J=5.20 Hz, 1H) 3.78-3.95 (m, 4H) 3.47 (q, J=6.08 Hz, 2H) 2.70-2.91 (m, 2H) 2.52-2.69 (m, 4H) 1.88 (br. s., 2H) 1.36 (t, J=6.97 Hz, 3H).

Example 194

2-((3,5-Dicyano-4-ethyl-6-(4-(2-hydroxy-2-methylpropyl)-1,4-diazepan-1-yl)pyridin-2-yl)thio)-2-phenylacetamide Step 1: 2-Chloro-4-ethyl-6-(4-(2-hydroxy-2-methylpropyl)-1,4-diazepan-1-yl)pyridine-3,5-dicarbonitrile

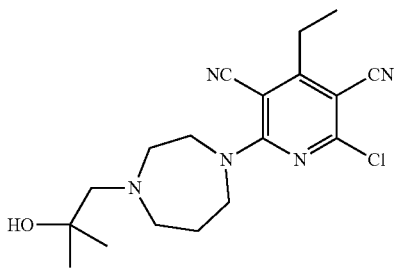 [SMILES: CCc1c(C#N)c(Cl)nc(N2CCCN(CC(C)(C)O)CC2)c1C#N]

To a stirred solution of 2,6-dichloro-4-ethylpyridine-3,5-dicarbonitrile (synthesis described in example 3 step 2, 1 g, 4.42 mmol) in dichloromethane (10 mL) was added triethylamine (1.233 mL, 8.85 mmol) at 0° C., and after 2 minutes, 1-(1,4-diazepan-1-yl)-2-methylpropan-2-ol (0.838 g, 4.87 mmol) was added at 0° C. The reaction was stirred for 10 minutes at the same temperature then diluted with water (20 mL) and extracted with DCM (2×10 mL). The combined organic layers were dried over anhydrous sodium sulphate, filtered and concentrated to dryness under vacuum to obtain the crude product. The crude material was combined with crude material from a separate batch (150 mg, LCMS purity ca. 90%) and purified by column chromatography using silica-gel (100-200 mesh, eluting with 30-40% petroleum ether/ethyl acetate). Collected fractions were concentrated under reduced pressure to afford 2-chloro-4-ethyl-6-(4-(2-hydroxy-2-methylpropyl)-1,4-diazepan-1-yl)pyridine-3,5-dicarbonitrile (1.5 g) as an off-white solid. LCMS m/z=362.1 [M+H]$^+$.

Step 2: 2-((3,5-Dicyano-4-ethyl-6-(4-(2-hydroxy-2-methylpropyl)-1,4-diazepan-1-yl)pyridin-2-yl)thio)-2-phenylacetamide

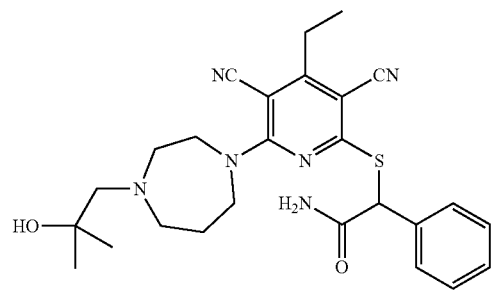 [SMILES: CCc1c(C#N)c(SC(C(N)=O)c2ccccc2)nc(N2CCCN(CC(C)(C)O)CC2)c1C#N]

To a stirred solution of 2-chloro-4-ethyl-6-(4-(2-hydroxy-2-methylpropyl)-1,4-diazepan-1-yl)pyridine-3,5-dicarbonitrile (500 mg, 1.382 mmol) in N,N-dimethylformamide (10 mL) was added potassium thioacetate (316 mg, 2.76 mmol) at room temperature, and the solution was stirred for 2 hours at the same temperature. To the reaction mixture, potassium carbonate (382 mg, 2.76 mmol) and 2-amino-2-oxo-1-phenylethyl methanesulfonate (synthesis described in example 3 step 5, 317 mg, 1.382 mmol) were added at room temperature, and the resulting mixture was stirred for 12 hours at room temperature. The reaction mixture was diluted with ice water (50 mL) and extracted with ethyl acetate (2×50 mL). The combined organic layers were dried over anhydrous sodium sulphate, filtered and concentrated to dryness under vacuum to obtain the crude product. The crude material was purified by column chromatography using silica-gel (100-200 mesh, eluting with 70-80% ethyl acetate in petroleum ether). The pure fractions were concentrated under reduced pressure to afford 2-((3,5-dicyano-4-ethyl-6-(4-(2-hydroxy-2-methylpropyl)-1,4-diazepan-1-yl)pyridin-2-yl)thio)-2-phenylacetamide (300 mg, 44% yield) as brown solid. LCMS m/z=493.3 [M+H]$^+$. $^1$H NMR (400 MHz, DMSO-d$_6$) δ ppm 7.88 (s, 1H), 7.57-7.46 (m, 2H), 7.41-7.19 (m, 4H), 5.51 (s, 1H), 4.03-3.98 (m, 1H), 3.95-3.57 (m, 4H), 3.00-2.84 (m, 2H), 2.82-2.59 (m, 4H), 2.41-2.27 (m, 2H), 1.87 (br s, 2H), 1.29-1.13 (m, 3H), 1.08-0.62 (m, 6H).

Example 195

2-((3,5-Dicyano-4-ethyl-6-(4-(thiazol-5-ylmethyl)piperazin-1-yl)pyridin-2-yl)thio)-2-phenylacetamide

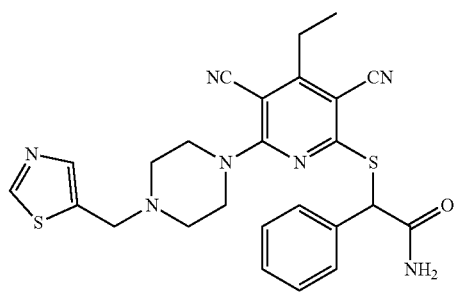 [SMILES: CCc1c(C#N)c(SC(C(N)=O)c2ccccc2)nc(N2CCN(Cc3cncs3)CC2)c1C#N]

2-((3,5-Dicyano-4-ethyl-6-(piperazin-1-yl)pyridin-2-yl)thio)-2-phenylacetamide, 2,2,2-trifluoroacetate (synthesis described in example 176 step 2, 215 mg, 0.413 mmol) was dissolved in dichloromethane (15 mL), and N,N-diisopropylethylamine (0.144 mL, 0.826 mmol) was added. To the solution was added acetic acid (0.047 mL, 0.826 mmol) followed by thiazole-5-carbaldehyde (93 mg, 0.826 mmol). The reaction was stirred for 30 minutes and sodium triacetoxyborohydride (350 mg, 1.652 mmol) was added. The reaction was stirred at 25° C. for 18 hours, and then dichloromethane (30 mL) was added. The solution was then washed with saturated sodium bicarbonate solution and water. The organic phase was then dried over sodium sulfate and concentrated. The residue was triturated with ethyl acetate and the resulting solid was collected by filtration and dried in a vacuum oven overnight to afford 2-((3,5-dicyano-4-ethyl-6-(4-(thiazol-5-ylmethyl)piperazin-1-yl)pyridin-2-yl)thio)-2-phenylacetamide (100 mg, 46% yield). LCMS m/z=504.4 [M+H]$^+$. $^1$H NMR (400 MHz, DMSO-d$_6$) δ ppm 1.10-1.25 (m, 3H), 2.55-2.56 (4 protons likely obscured by DMSO), 2.74-2.77 (m, 2H), 3.84-3.90 (m, 6H), 5.52 (s, 1H), 7.31-7.38 (m, 4H), 7.49-7.51 (m, 2H), 7.81-7.83 (m, 1H), 7.89 (d, J=1.77 Hz, 1H), 9.08 (d, J=1.77 Hz, 1H).

Example 196

2-((3,5-Dicyano-4-ethyl-6-(piperazin-1-yl)pyridin-2-yl)thio)-2-(4-fluorophenyl)acetamide, Trifluoroacetic Acid Salt Step 1: 4-(3,5-Dicyano-4-ethyl-6-mercaptopyridin-2-yl)piperazine-1-carboxylate

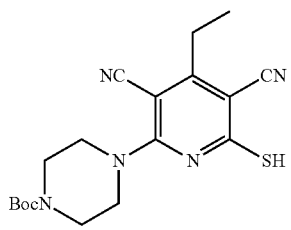 [SMILES: CCc1c(C#N)c(S)nc(N2CCN(C(=O)OC(C)(C)C)CC2)c1C#N]

To a solution of tert-butyl 4-(6-chloro-3,5-dicyano-4-ethylpyridin-2-yl)piperazine-1-carboxylate (synthesis described in example 176 step 1, 500 mg, 1.330 mmol) in N,N-dimethylformamide (50 mL) was added potassium thioacetate (304 mg, 2.66 mmol). The mixture was stirred at 25° C. overnight. The residue was loaded to a silica gel column which was eluted with hexanes/EtOAc to give tert-butyl 4-(3,5-dicyano-4-ethyl-6-mercaptopyridin-2-yl)piperazine-1-carboxylate (400 mg, 81% yield). LCMS m/z=396 [M+Na]$^+$.

Step 2: tert-Butyl 4-(3,5-dicyano-4-ethyl-6-(1-(4-fluorophenyl)-2-methoxy-2-oxoethyl)pyridin-2-yl)piperazine-1-carboxylate

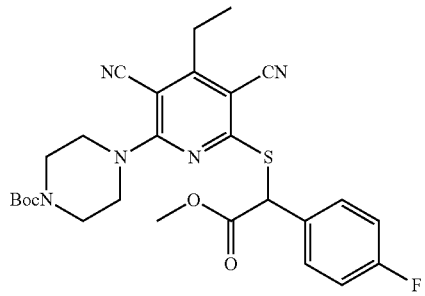 [SMILES: CCc1c(C#N)c(SC(C(=O)OC)c2ccc(F)cc2)nc(N2CCN(C(=O)OC(C)(C)C)CC2)c1C#N]

To a solution of tert-butyl 4-(3,5-dicyano-4-ethyl-6-mercaptopyridin-2-yl)piperazine-1-carboxylate (400 mg, 1.071 mmol) in dichloromethane (150 mL) was added methyl 2-bromo-2-(4-fluorophenyl)acetate (265 mg, 1.071 mmol) and triethylamine (108 mg, 1.071 mmol). The reaction mixture was stirred at 25° C. overnight. The reaction was concentrated and the residue was loaded on a silica gel column which was eluted with hexane/EtOAc to give tert-butyl 4-(3,5-dicyano-4-ethyl-6-(1-(4-fluorophenyl)-2-methoxy-2-oxoethyl)pyridin-2-yl)piperazine-1-carboxylate (400 mg, 74% yield). LCMS m/z=407 [M-Boc+H]$^+$.

Step 3: 2-((3,5-Dicyano-4-ethyl-6-(piperazin-1-yl)pyridin-2-yl)thio)-2-(4-fluorophenyl)acetamide, Trifluoroacetic Acid Salt

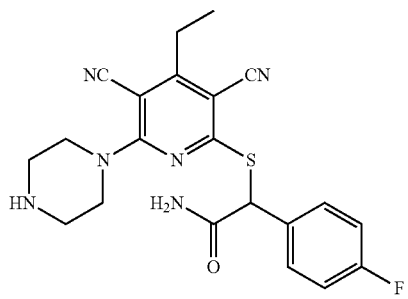 [SMILES: CCc1c(C#N)c(SC(C(N)=O)c2ccc(F)cc2)nc(N2CCNCC2)c1C#N]

Into a solution of tert-butyl 4-(3,5-dicyano-4-ethyl-6-((1-(4-fluorophenyl)-2-methoxy-2-oxoethyl)thio)pyridin-2-yl)piperazine-1-carboxylate (400 mg, 0.741 mmol) in methanol (50 mL) was bubbled ammonia (505 mg, 29.7 mmol). The mixture was stirred at 25° C. overnight and then it was evaporated. The residual material was dissolved in a mixture of DCM (50 mL) and 2,2,2-trifluoroacetic acid (845 mg, 7.41 mmol). The mixture was stirred overnight at 25° C. and was then evaporated. The residue was purified by prep-HPLC to give 2-((3,5-dicyano-4-ethyl-6-(piperazin-1-yl)pyridin-2-yl)thio)-2-(4-fluorophenyl)acetamide, trifluoroacetic acid salt (90 mg, 23% yield). LCMS m/z=425 [M+H]$^+$. $^1$H NMR (400 MHz, DMSO-d$_6$) δ ppm 9.12 (s, 2H), 7.95 (s, 1H), 7.63-7.39 (m, 3H), 7.36-7.20 (m, 2H), 5.78 (s, 1H), 4.17-4.01 (m, 4H), 3.25 (s, 4H), 2.81 (q, J=7.5 Hz, 2H), 1.23 (t, J=7.6 Hz, 3H).

Example 197

2-((3,5-Dicyano-4-ethyl-6-(4-(isothiazol-4-ylmethyl)piperazin-1-yl)pyridin-2-yl)thio)-2-phenylacetamide

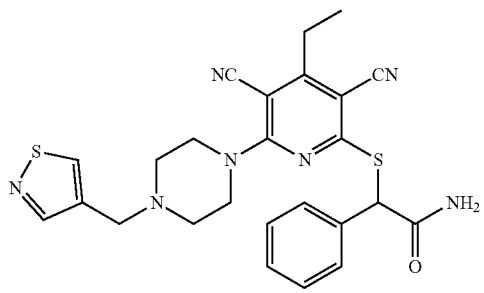 [SMILES: CCc1c(C#N)c(SC(C(N)=O)c2ccccc2)nc(N2CCN(Cc3cnsc3)CC2)c1C#N]

2-((3,5-Dicyano-4-ethyl-6-(piperazin-1-yl)pyridin-2-yl)thio)-2-phenylacetamide, 2,2,2-trifluoroacetate (synthesis described in example 176 step 2, 215 mg, 0.413 mmol) was dissolved in dichloromethane (15 mL), and N,N-diisopropylethylamine (0.144 mL, 0.826 mmol) was added. To the solution was added acetic acid (0.047 mL, 0.826 mmol) followed by isothiazole-4-carbaldehyde (93 mg, 0.826 mmol). The reaction was stirred for 30 minutes, and sodium triacetoxyborohydride (350 mg, 1.652 mmol) was added. The reaction was stirred at 25° C. for 18 hours, and then dichloromethane (30 mL) was added. The solution was washed with water and saturated aqueous sodium bicarbonate. During this process, a white solid was observed to form, and this solid was collected by filtration. The solution was dried over sodium sulfate, filtered, and concentrated to give impure product. The previously isolated white solid was determined to be pure 2-((3,5-dicyano-4-ethyl-6-(4-(isothiazol-4-ylmethyl)piperazin-1-yl)pyridin-2-yl)thio)-2-phenylacetamide (130 mg, 62% yield). LCMS m/z=504.2 [M+H]$^+$. $^1$H NMR (400 MHz, DMSO-d$_6$) δ ppm 8.91 (s, 1H), 8.51-8.56 (m, 1H), 7.89 (s, 1H), 7.47-7.55 (m, 2H), 7.26-7.42 (m, 4H), 5.51 (s, 1H), 3.89 (t, J=4.82 Hz, 4H), 3.69 (s, 2H), 2.75 (q, J=7.60 Hz, 2H), 1.20 (t, J=7.60 Hz, 3H).

Example 198

2-((3,5-Dicyano-6-(dimethylamino)-4-ethylpyridin-2-yl)thio)-2-(4-fluorophenyl)acetamide

Step 1: 2-(Dimethylamino)-4-ethyl-6-mercaptopyridine-3,5-dicarbonitrile

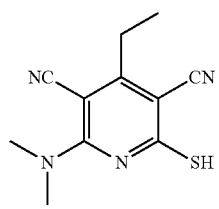 [SMILES: CCc1c(C#N)c(S)nc(N(C)C)c1C#N]

To a solution of 2-chloro-6-(dimethylamino)-4-ethylpyridine-3,5-dicarbonitrile (synthesis described in Example 3 step 3, 700 mg, 2.98 mmol) in DMF (50 mL) was added potassium thioacetate (700 mg, 6.13 mmol). The mixture was stirred overnight at 25° C. and was used without purification. LCMS m/z=233 [M+H]$^+$.

Step 2: Methyl 2-((3,5-dicyano-6-(dimethylamino)-4-ethylpyridin-2-yl)thio)-2-(4-fluorophenyl)acetate

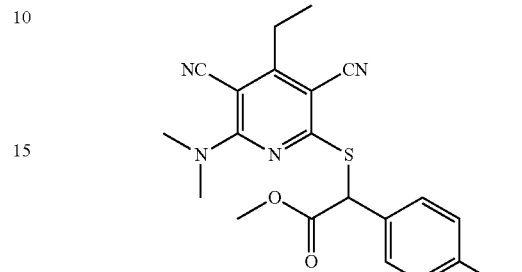

To a solution of 2-(dimethylamino)-4-ethyl-6-mercaptopyridine-3,5-dicarbonitrile (692 mg, 2.98 mmol) in N,N-dimethylformamide (50 mL) was added methyl 2-bromo-2-(4-fluorophenyl)acetate (736 mg, 2.98 mmol) and triethylamine (302 mg, 2.98 mmol). The reaction was stirred at 25° C. overnight. The mixture was partially evaporated and the residue was added to ice water. The resulting solid was collected by filtration to give methyl 2-((3,5-dicyano-6-(dimethylamino)-4-ethylpyridin-2-yl)thio)-2-(4-fluorophenyl)acetate (400 mg, 34% yield) as a white solid. LCMS m/z=399 [M+H]$^+$.

Step 3: 2-((3,5-Dicyano-6-(dimethylamino)-4-ethylpyridin-2-yl)thio)-2-(4-fluorophenyl)acetamide

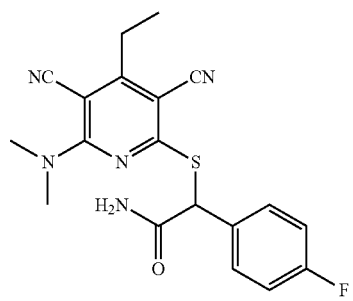 [SMILES: CCc1c(C#N)c(SC(C(N)=O)c2ccc(F)cc2)nc(N(C)C)c1C#N]

Into a solution of methyl 2-((3,5-dicyano-6-(dimethylamino)-4-ethylpyridin-2-yl)thio)-2-(4-fluorophenyl)acetate (400 mg, 1.004 mmol) in methanol (50 mL) was bubbled ammonia (17.1 mg, 1.004 mmol). The reaction mixture was stirred at 25° C. overnight. The mixture was evaporated and the residue was purified by prep-HPLC to give 2-((3,5-dicyano-6-(dimethylamino)-4-ethylpyridin-2-yl)thio)-2-(4-fluorophenyl)acetamide (300 mg, 78% yield). LCMS m/z=384 [M+H]$^+$. $^1$H NMR (400 MHz, DMSO-d$_6$) δ ppm 7.91 (s, 1H), 7.53 (td, J=7.7, 1.5 Hz, 1H), 7.45 (d, J=4.2 Hz, 1H), 7.41 (dd, J=10.4, 4.8 Hz, 1H), 7.25 (dd, J=17.2, 9.7 Hz, 2H), 5.84 (s, 1H), 3.33 (s, 6H), 2.77 (q, J=7.5 Hz, 2H), 1.21 (t, J=7.6 Hz, 3H).

Example 199

2-((3,5-Dicyano-6-(dimethylamino-4-ethylpyridin-2-ylthio-2-(5-fluoropyridin-2-yl)acetamide Step 1: 2-(5-Fluoropyridin-2-yl)-2-hydroxyacetamide

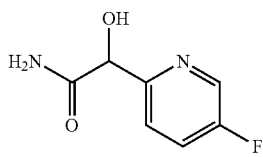 [SMILES: NC(=O)C(O)c1ccc(F)cn1]

To a solution of ethyl 2-(5-fluoropyridin-2-yl)-2-oxoacetate (2.7 g, 13.69 mmol) in ethanol (30 mL) at −20° C. was added NaBH$_4$ (0.570 g, 15.06 mmol). The reaction mixture was stirred at −20° C. for 1 hour. The reaction was quenched by addition of saturated NH$_4$Cl and extracted with DCM. The organic phase was concentrated and purified by flash column chromatography eluting with petroleum ether/EtOAc in a gradient from 0% to 100% to give ethyl 2-(5-fluoropyridin-2-yl)-2-hydroxyacetate (1.7 g, 62% yield) as a yellow oil. To a solution of ethyl 2-(5-fluoropyridin-2-yl)-2-hydroxyacetate (1.7 g, 8.54 mmol) in methanol (5 mL) was added NH$_3$ (7N in methanol, 8 mL) at room temperature. The reaction mixture was stirred at room temperature overnight, concentrated and the residue was purified by flash column chromatography eluting with DCM/methanol from 0% to 10% to give 2-(5-fluoropyridin-2-yl)-2-hydroxyacetamide (1 g, 69% yield) as a white solid. LCMS m/z=171.0 [M+H]$^+$.

Step 2: 2-((3,5-Dicyano-6-(dimethylamino)-4-ethylpyridin-2-yl)thio)-2-(5-fluoropyridin-2-yl)acetamide

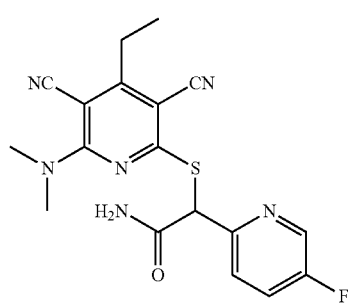 [SMILES: CCc1c(C#N)c(SC(C(N)=O)c2ccc(F)cn2)nc(N(C)C)c1C#N]

To a solution of 2-(5-fluoropyridin-2-yl)-2-hydroxyacetamide (1 g, 5.88 mmol) and triethylamine (1.065 mL, 7.64 mmol) in dichloromethane (15 mL) at 0° C. was added methanesulfonyl chloride (0.741 g, 6.47 mmol) dropwise. The reaction mixture was stirred at room temperature for 1 hour. The reaction was then washed with water and concentrated. The residue was purified by flash column eluting with DCM/methanol (0 to 10%) to give 2-amino-1-(5-fluoropyridin-2-yl)-2-oxoethylmethanesulfonate (600 mg, 41% yield) as a white solid. To a solution of 2-chloro-6-(dimethylamino)-4-ethylpyridine-3,5-dicarbonitrile (156 mg, 0.665 mmol) in N,N-dimethylformamide (10 mL) was added potassium ethanethioate (83 mg, 0.725 mmol). The reaction mixture was stirred at room temperature for 1 hour, and K$_2$CO$_3$ (100 mg, 0.725 mmol) and 2-amino-1-(5-fluoropyridin-2-yl)-2-oxoethyl methanesulfonate (150 mg, 0.604 mmol) were then added. The reaction mixture was stirred at room temperature overnight. Water (50 mL) was added and the resulting mixture was filtered to give the crude product, which was purified by flash column chromatography eluting with DCM/methanol (0 to 10%) to give 2-((3,5-dicyano-6-(dimethylamino)-4-ethylpyridin-2-yl)thio)-2-(5-fluoropyridin-2-yl)acetamide (60.5 mg, 26% yield) as a brown solid. LCMS m/z=385 [M+H]$^+$. $^1$H NMR (400 MHz, DMSO-d$_6$) δ ppm 8.56 (d, J=2.8 Hz, 1H), 7.91 (s, 1H), 7.81-7.70 (m, 2H), 7.42 (s, 1H), 5.76 (s, 1H), 3.30 (s, 6H), 2.76 (q, J=7.7 Hz, 2H), 1.21 (t, J=7.6 Hz, 3H).

Example 200

2-((3,5-Dicyano-4-ethyl-6-(4-(furan-3-ylmethyl)piperazin-1-yl)pyridin-2-yl)thio)-2-phenylacetamide

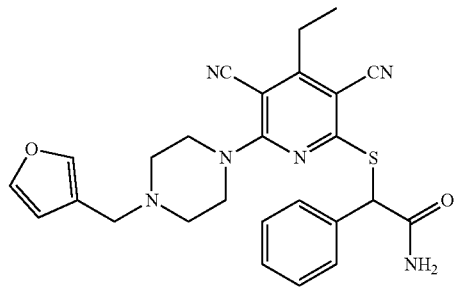 [SMILES: CCc1c(C#N)c(SC(C(N)=O)c2ccccc2)nc(N2CCN(Cc3ccoc3)CC2)c1C#N]

2-((3,5-Dicyano-4-ethyl-6-(piperazin-1-yl)pyridin-2-yl)thio)-2-phenylacetamide, 2,2,2-trifluoroacetate (synthesis described in Example 176 step 2, 215 mg, 0.413 mmol) was dissolved in dichloromethane (15 mL) and N,N-diisopropylethylamine (0.144 mL, 826 mmol) was added. To the solution was added acetic acid (0.047 mL, 0.826 mmol) followed by furan-3-carbaldehyde (79 mg, 0.826 mmol). The reaction was stirred for 30 minutes and sodium triacetoxyborohydride (350 mg, 1.652 mmol) was added. The reaction was stirred at 25° C. for 18 hours, and dichloromethane (30 mL) was added. The solution was washed with saturated sodium bicarbonate and water. The organic phase was dried over sodium sulfate and concentrated. The residue was triturated with dichloromethane, collected by filtration and dried in a vacuum oven to afford 2-((3,5-dicyano-4-ethyl-6-(4-(furan-3-ylmethyl)piperazin-1-yl)pyridin-2-yl)thio)-2-phenylacetamide (100 mg, 48% yield). LCMS m/z=487.3 [M+H]$^+$. $^1$H NMR (400 MHz, DMSO-d$_6$) δ ppm 1.20 (t, J=7.60 Hz, 3H), 2.47 (br. s., 4H), 2.75 (q, J=7.43 Hz, 2H), 3.40 (s, 2H), 3.88 (t, J=4.82 Hz, 4H), 5.52 (s, 1H), 6.44-6.50 (m, 1H), 7.29-7.43 (m, 4H), 7.47-7.54 (m, 2H), 7.62 (s, 1H), 7.63-7.68 (m, 1H), 7.91 (s, 1H).

Example 201

2-((3,5-Dicyano-4-ethyl-6-((2-morpholinoethyl)thio)pyridin-2-yl)thio)-2-phenylacetamide

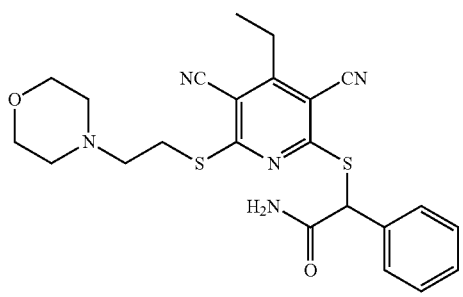 [SMILES: CCc1c(C#N)c(SCCN2CCOCC2)nc(SC(C(N)=O)c2ccccc2)c1C#N]

A mixture of 2-((6-chloro-3,5-dicyano-4-ethylpyridin-2-yl)thio)-2-phenylacetamide (synthesis described in example 52, step 1, 240 mg, 0.67 mmol) and potassium thioacetate (77 mg, 0.67 mmol) in N,N-dimethylformamide (20 mL) was stirred at 20° C. for 0.5 hour. Then 4-(2-chloroethyl)morpholine (201 mg, 1.35 mmol) and triethylamine (0.375 mL, 2.69 mmol) were added. The mixture was stirred for 15 hours. The mixture was then concentrated in vacuo to obtain the crude product and purified further by column chromatography to obtain 2-((3,5-dicyano-4-ethyl-6-((2-morpholinoethyl)thio)pyridin-2-yl)thio)-2-phenylacetamide (25 mg, 8% yield). LCMS m/z=468.1 [M+H]$^+$. $^1$H NMR (400 MHz, CD$_3$OD) δ ppm 7.60-7.52 (m, 2H), 7.49-7.37 (m, 3H), 5.71 (s, 1H), 3.68 (dd, J=10.0, 5.4 Hz, 4H), 3.64 (dd, J=13.7, 6.8 Hz, 1H), 3.54 (dd, J=13.7, 6.7 Hz, 1H), 2.95 (q, J=7.6 Hz, 2H), 2.81 (dd, J=13.1, 6.3 Hz, 1H), 2.73 (dd, J=13.4, 6.3 Hz, 1H), 2.56 (s, 4H), 1.34 (d, J=7.6 Hz, 3H).

Example 202

2-((3,5-Dicyano-6-(4-methyl-1,4-diazepan-1-yl)-4-(methylthio)pyridin-2-yl)thio)-2-phenylacetamide

Step 1: 2-Amino-6-mercapto-4-(methylthio)pyridine-3,5-dicarbonitrile

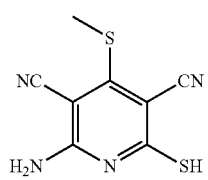

2-(bis(methylthio)methylene)malononitrile (10 g, 58.7 mmol) and cyanothioacetamide (7.06 g, 70.5 mmol) was initially charged in N,N-dimethylformamide (21 mL), and triethylamine (16.37 mL, 117 mmol) was added dropwise at room temperature. The mixture was stirred at room temperature for 18 hours. The reaction mixture was added to 300 mL of 3N hydrochloric acid. The resulting precipitate was filtered off with suction, washed with water and dried. This afforded 2-amino-6-mercapto-4-(methylthio) pyridine-3,5-dicarbonitrile (13.5 g, 54.7 mmol, 93% yield). LCMS m/z=222.9 [M+H]$^+$.

Step 2: 2-((6-Amino-3,5-dicyano-4-(methylthio)pyridin-2-yl)thio)-2-phenylacetamide

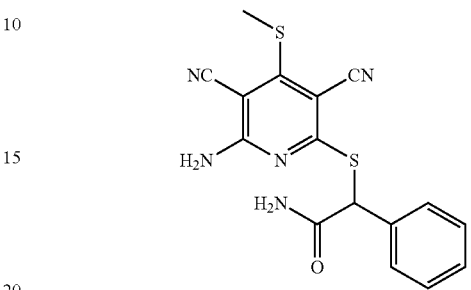

2-Amino-6-mercapto-4-(methylthio) pyridine-3,5-dicarbonitrile (3 g, 12.15 mmol), sodium hydrogencarbonate (4 g, 47.6 mmol) and 2-chloro-2-phenylacetamide (2.5 g, 14.74 mmol) were combined in N,N-dimethylformamide (100 mL) and stirred at room temperature for 24 hours under nitrogen. Water was added and the precipitate was filtered off and to afford 2-((6-amino-3,5-dicyano-4-(methylthio)pyridin-2-yl)thio)-2-phenylacetamide (4.02 g, 10.63 mmol, 88% yield) LCMS m/z=356.1 [M+H]$^+$.

Step 3: 2-((6-Chloro-3,5-dicyano-4-(methylthio)pyridin-2-yl)thio)-2-phenylacetamide

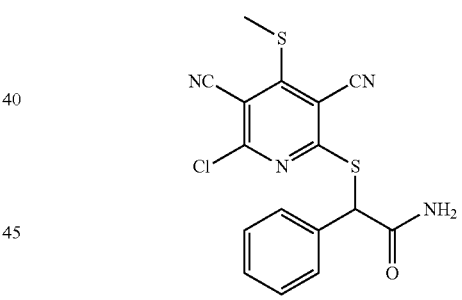

2-((6-amino-3,5-dicyano-4-(methylthio)pyridin-2-yl)thio)-2-phenylacetamide (2.25 g, 6.33 mmol) and copper(II) chloride (1.42 g, 10.56 mmol) were suspended in dichloromethane (100 mL). The mixture was heated to 40° C. for 5 minutes. 2-methyl-2-nitropropane (1.351 mL, 11.39 mmol) in acetonitrile (30 mL) was added to the mixture slowly and the material was stirred at 45° C. for 60 minutes. Then 50° C. for 1 hour, then 55° C. for 1 hour and then 60° C. and stirred with LCMS monitoring until disappearance of starring material. Cooled to room temperature and filtered off solid. Filtrate was concentrated. Worked up with EtOAc (3×) and aq sat. NaHCO$_3$. The combined organics were washed with brine, dried over magnesium sulfate, filtered and concentrated to afford 2-((6-chloro-3,5-dicyano-4-(methylthio)pyridin-2-yl)thio)-2-phenylacetamide (2.6 g, 3.12 mmol) as a yellow oil without further purification. LCMS m/z=375.0 [M+H]$^+$.

Step 4: 2-((3,5-Dicyano-6-(4-methyl-1,4-diazepan-1-yl)-4-(methylthio) pyridin-2-yl) thio)-2-phenylacetamide

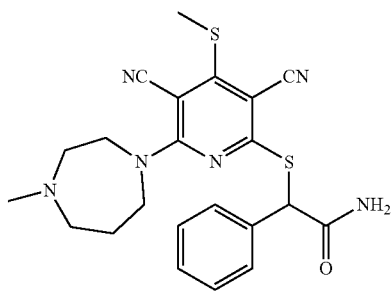 [SMILES: CSc1c(C#N)c(SC(C(N)=O)c2ccccc2)nc(N2CCCN(C)CC2)c1C#N]

2-((6-Chloro-3,5-dicyano-4-(methylthio) pyridin-2-yl) thio)-2-phenylacetamide (2.6 g, 3.12 mmol) was dissolved in tetrahydrofuran (100 mL) and cooled to −40° C. 1-methyl-1,4-diazepane (400 µl, 3.19 mmol) was added and the mixture was stirred at room temperature for 150 minutes. Worked up with EtOAc (3×) and aq saturated NaHCO$_3$. The combined organics were washed with brine, dried over magnesium sulfate, filtered and concentrated to a yellow oil. Purified on silica gel (80 g column, 100% DCM to 10% IPA in DCM w/1% NH$_4$OH). The desired fractions were pooled and concentrated to afford 833 mg of residue. 150 mg of this residue was purified on silica gel (80 g column: 100% DCM→10% IPA in DCM w/1% NH$_4$OH; very later runner). The desired fractions were pooled and concentrated to afford 2-((3,5-dicyano-6-(4-methyl-1,4-diazepan-1-yl)-4-(methylthio)pyridin-2-yl)thio)-2-phenylacetamide (99 mg, 0.219 mmol). LCMS m/z=453.2 [M+H]$^+$. $^1$H NMR (400 MHz, DMSO-d$_6$) δ ppm 7.92 (s, 1H) 7.45-7.57 (m, 2H) 7.27-7.45 (m, 4H) 5.50 (s, 1H) 3.77-3.99 (m, 4H) 2.57-2.78 (m, 5H) 2.46 (br. s., 1H) 2.25 (s, 3H) 1.87-2.02 (m, 2H). One proton was not observed.

Example 203

2-((3,5-Dichloro-4-ethyl-6-(4-(2-hydroxyethyl)-1,4-diazepan-1-yl)pyridin-2-yl)thio)-2-phenylacetamide

Step 1: 2-((3,5-Dichloro-4-ethyl-6-fluoropyridin-2-yl)thio)-2-phenylacetamide

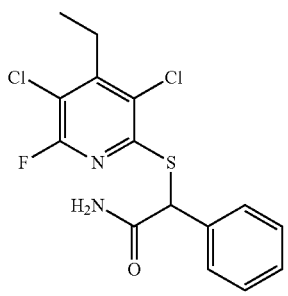 [SMILES: CCc1c(Cl)c(F)nc(SC(C(N)=O)c2ccccc2)c1Cl]

3,5-Dichloro-2,4,6-trifluoropyridine (2.01 g, 9.95 mmol) was dissolved in tetrahydrofuran (40 mL) and cooled to −78° C. ethylmagnesium chloride (6.2 mL, 12.40 mmol) was added slowly to the cooled solution and stirred for 30 minutes. Gradually allowed to warm to 0° C. and monitored by LCMS until disappearance of starting material. Worked up with EtOAc (3×) and aq. saturated NaHCO$_3$. The combined organics were washed with brine, dried over magnesium sulfate, filtered and gently concentrated to afford a volatile yellow oil. S-(2-Amino-2-oxo-1-phenylethyl) ethanethioate (synthesis described in example 62, step 5, 2.291 g, 10.95 mmol) was dissolved in ethanol (40 mL) and NaBH$_4$ (0.527 g, 13.93 mmol) was added. The mixture was stirred and heated to 40° C. for 30 minutes and gas evolution had ceased. The mixture was allowed to cool to room temperature and added to a solution of the yellow oil above in ethanol (10 mL). The mixture was stirred for 30 minutes at room temperature. Cooled to 0° C. and filtered off a solid byproduct. Filtrate was concentrated to a yellow oil. Purified on silica gel (80 g column, 100% DCM to 5% IPA in DCM w/1% NH$_4$OH). The desired fractions were pooled and concentrated to afford 2-((3,5-dichloro-4-ethyl-6-fluoropyridin-2-yl)thio)-2-phenylacetamide (1.79 g, 4.98 mmol, 50% yield). LCMS m/z=359.0 [M+H]$^+$.

Step 2: 2-((3,5-Dichloro-4-ethyl-6-(4-(2-hydroxyethyl)-1,4-diazepan-1-yl)pyridin-2-yl)thio)-2-phenylacetamide

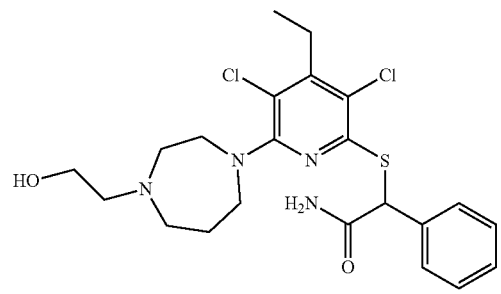 [SMILES: CCc1c(Cl)c(SC(C(N)=O)c2ccccc2)nc(N2CCCN(CCO)CC2)c1Cl]

2-((3,5-Dichloro-4-ethyl-6-fluoropyridin-2-yl)thio)-2-phenylacetamide (320 mg, 0.891 mmol) was added to a vial and dissolved in tetrahydrofuran (6 mL). 2-(1,4-diazepan-1-yl) ethanol (167 mg, 1.158 mmol) was added and the mixture was heated to 70° C. for 20 hours. Cooled to room temperature and the material was concentrated. The material was purified on Basic Gilson HPLC (C18 column, 20-70% water w/0.1% NH$_4$OH/acetonitrile) and the desired fractions were pooled and concentrated to afford 2-((3,5-dichloro-4-ethyl-6-(4-(2-hydroxyethyl)-1,4-diazepan-1-yl)pyridin-2-yl)thio)-2-phenylacetamide (120 mg, 0.248 mmol, 28% yield). LCMS m/z=483.2 [M+H]$^+$. $^1$H NMR (400 MHz, DMSO-d$_6$) δ ppm 7.83 (s, 1H) 7.45-7.57 (m, 2H) 7.17-7.43 (m, 4H) 5.46 (s, 1H) 4.37 (t, J=5.32 Hz, 1H) 3.40-3.61 (m, 6H) 2.62-2.89 (m, 6H) 2.55 (t, J=6.46 6 Hz, 2H) 1.78-1.95 (m, 2H) 1.09 (t, J=7.48 Hz, 3H).

Example 204

2-((3,5-Dicyano-4-ethyl-6-(hexahydropyrrolo[3,4-b][1,4]oxazin-6(2H)-yl)pyridin-2-yl)thio)-2-phenylacetamide Step 1: tert-Butyl 6-(6-chloro-3,5-dicyano-4-ethylpyridin-2-yl)hexahydropyrrolo[3,4-b][1,4]oxazine-4(4aH)-carboxylate

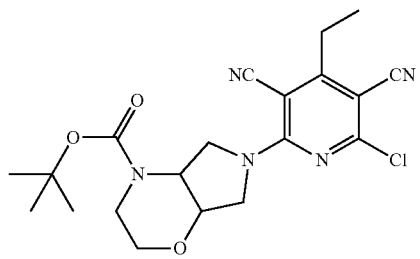 [SMILES: CCc1c(C#N)c(Cl)nc(N2CC3OCCN(C(=O)OC(C)(C)C)C3C2)c1C#N]

2,6-Dichloro-4-ethylpyridine-3,5-dicarbonitrile (250 mg, 1.106 mmol) was dissolved in tetrahydrofuran (4 mL) and tert-butyl hexahydropyrrolo[3,4-b][1,4]oxazine-4(4aH)-carboxylate (252 mg, 1.106 mmol) was added followed by N,N-diisopropylethylamine (0.386 mL, 2.212 mmol). The reaction was stirred at 50° C. for 4 hours. The solvent was evaporated, and the resulting solid was dissolved in ethyl acetate and washed with water, dried with sodium sulfate, and concentrated. The residue was dissolved in dichloromethane (5 mL) and purified by gradient silica gel chromatography using 10-80% ethyl acetate in hexanes as eluent to give tert-butyl 6-(6-chloro-3,5-dicyano-4-ethylpyridin-2-yl)hexahydropyrrolo[3,4-b][1,4]oxazine-4(4aH)-carboxylate (412 mg, 89% yield). LCMS m/z=418.0 [M+H]$^+$.

Step 2: 2-((3,5-Dicyano-4-ethyl-6-(hexahydropyrrolo[3,4-b][1,4]oxazin-6(2H)-yl)pyridin-2-yl)thio)-2-phenylacetamide

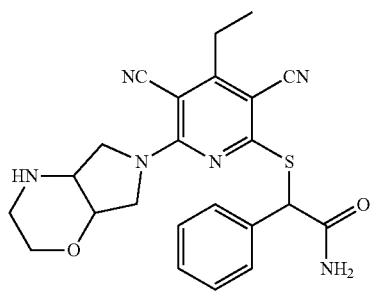 [SMILES: CCc1c(C#N)c(SC(C(N)=O)c2ccccc2)nc(N2CC3NCCOC3C2)c1C#N]

S-(2-Amino-2-oxo-1-phenylethyl) ethanethioate (synthesis described in example 62 step 5, 268 mg, 1.282 mmol) was dissolved in ethanol (3 mL), heated to 70° C., and NaBH$_4$ (52.2 mg, 1.380 mmol) was added portionwise. After 3 minutes the solution was added to tert-butyl 6-(6-chloro-3,5-dicyano-4-ethylpyridin-2-yl)hexahydropyrrolo[3,4-b][1,4]oxazine-4(4aH)-carboxylate (412 mg, 0.986 mmol) in tetrahydrofuran (4 mL). The reaction was heated at 70° C. for 10 minutes, and the solvent was evaporated. The residue was then dissolved in ethyl acetate and washed with water. The organic phase was dried with sodium sulfate, concentrated, and purified by gradient silica gel chromatography using 10 to 70% ethyl acetate in hexanes as eluent to give tert-butyl 6-(6-((2-amino-2-oxo-1-phenylethyl)thio)-3,5-dicyano-4-ethylpyridin-2-yl)hexahydropyrrolo[3,4-b][1,4]oxazine-4(4aH)-carboxylate (250 mg, 46% yield). LCMS m/z=549.3 [M+H]$^+$. This material was then stirred in a mixture of dichloromethane (5 mL) and TFA (5 mL) for 1 hour at room temperature. The solution was concentrated a solution of the residue in dichloromethane was then washed with saturated sodium bicarbonate solution and water. The organic phase was dried with sodium sulfate, concentrated, and dried at 40° C. overnight to afford 2-((3,5-dicyano-4-ethyl-6-(hexahydropyrrolo[3,4-b][1,4]oxazin-6(2H)-yl)pyridin-2-yl)thio)-2-phenylacetamide (200 mg, 45% yield). LCMS m/z=449.2 [M+H]$^+$. $^1$H NMR (400 MHz, DMSO-d$_6$) δ ppm 1.05-1.35 (m, 3H), 2.50-2.61 (m, 2H), 2.70-2.80 (m, 2H), 2.85-2.96 (m, 1H), 3.40-4.05 (m, 8H), 5.67-5.65 (m, 1H), 7.21-7.45 (m, 4H), 7.50-7.57 (m, 2H), 7.94 (d, J=9.38 Hz, 1H).

Example 205

2-((3,5-Dicyano-4-ethyl-6-(4-methyl-1,4-diazepan-1-yl)pyridin-2-yl)thio)-2-(5-methylpyridin-2-yl)acetamide Step 1: 2-Hydroxy-2-(5-methylpyridin-2-yl)acetamide

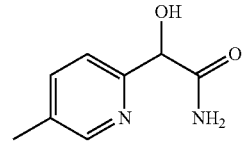

To a solution of 5-methylpicolinaldehyde (1.00 g, 8.26 mmol) in DCM (40 mL) was added trimethylsilanecarbonitrile (1.446 mL, 11.56 mmol). The mixture was stirred at room temperature overnight. The mixture was concentrated down to afford a brown oil, which was treated with conc. sulfuric acid (5 mL, 94 mmol) for 4 hours, then poured the reaction mixture into ice, and adjusted the pH to 9 using NH$_4$OH. The mixture was concentrated down with silica, purified by silica column (CombiFlash®, 40 g column) using 0-10% MeOH/DCM to afford 2-hydroxy-2-(5-methylpyridin-2-yl)acetamide (1.04 g, 6.26 mmol, 76% yield) as a yellow wax solid. LCMS m/z=167.0 [M+H]$^+$.

Step 2: 2-Amino-1-(5-methylpyridin-2-yl)-2-oxoethyl methanesulfonate

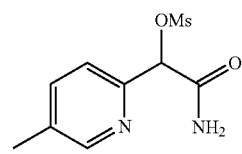 [SMILES: Cc1ccc(C(OS(C)(=O)=O)C(N)=O)nc1]

To a slurry solution of 2-hydroxy-2-(5-methylpyridin-2-yl)acetamide (1.04 g, 6.26 mmol) and TEA (1.745 mL, 12.52 mmol) in THF (25 mL) was added methanesulfonyl chloride

529

(0.585 mL, 7.51 mmol) dropwise. The reaction mixture was stirred at room temperature for 3 hours, then diluted with DCM, washed with water and brine, dried over Na₂SO₄, concentrated down to afford 2-amino-1-(5-methylpyridin-2-yl)-2-oxoethyl methanesulfonate (1.49 g, 6.10 mmol, 97% yield) as an orange waxy solid. LCMS m/z=245.0 [M+H]⁺.

Step 3: 2-((3,5-Dicyano-4-ethyl-6-(4-methyl-1,4-diazepan-1-yl)pyridin-2-yl)thio)-2-(5-methylpyridin-2-yl)acetamide

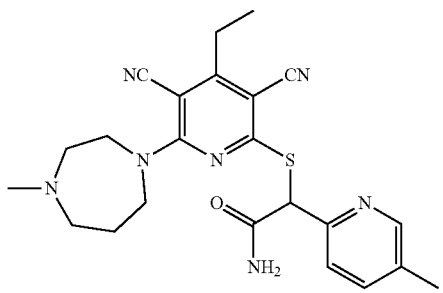

To a solution of 2,6-dichloro-4-ethylpyridine-3,5-dicarbonitrile (synthesis described in example 3, step 2, 150 mg, 0.664 mmol) in DMF (5 mL) at ice water bath temperature was added the solution of 1-methyl-1,4-diazepane (0.094 mL, 0.730 mmol) in DMF (2 mL) dropwise. After stirring for 10 minutes, the mixture was brought to room temperature and stirred for additional 30 minutes. Then potassium thioacetate (99 mg, 0.863 mmol) and TEA (0.277 mL, 1.991 mmol) were added to the reaction mixture, which was stirred at 50° C. for additional 2 hours. Then 2-amino-1-(5-methylpyridin-2-yl)-2-oxoethyl methanesulfonate (194 mg, 0.796 mmol) was added to the reaction solution. The reaction mixture was stirred at room temperature over the weekend. The reaction mixture was diluted with water (40 mL), extracted with EtOAc (4×). The combined organics were washed with brine and dried over Na₂SO₄, and concentrated down. The residue was purified by silica (CombiFlash®, 40 g column, 0-100% (1% NH₄OH+9% MeOH+90% DCM)/DCM) to afford 2-((3,5-dicyano-4-ethyl-6-(4-methyl-1,4-diazepan-1-yl)pyridin-2-yl)thio)-2-(5-methylpyridin-2-yl)acetamide as a yellow solid. LCMS m/z=450.3 [M+H]⁺. ¹H NMR (400 MHz, DMSO-d₆) δ ppm 1.22 (t, J=7.6 Hz, 3H), 1.91 (br. s., 2H), 2.24 (s, 3H), 2.29 (s, 3H), 2.40-2.49 (m, 2H), 2.52-2.57 (m, 1H), 2.58-2.70 (m, 1H), 2.77 (q, J=7.6 Hz, 2H), 3.78-3.99 (m, 4H), 5.59 (s, 1H), 7.38 (s, 1H), 7.50 (d, J=8.1 Hz, 1H), 7.64 (dd, J=8.0, 1.6 Hz, 1H), 7.84 (s, 1H), 8.33-8.41 (m, 1H).

Example 206

2-((3,5-Dicyano-4-ethyl-6-(4-methyl-1,4-diazepan-1-yl)pyridin-2-yl)thio)-2-(6-fluoropyridin-2-yl)acetamide Step 1: 2-Bromo-2-(6-fluoropyridin-2-yl)acetamide

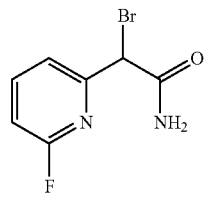 [SMILES: NC(=O)C(Br)c1cccc(F)n1]

To a slight slurry solution of 2-(6-fluoropyridin-2-yl)acetic acid (580 mg, 3.74 mmol) in DCM (20 mL) was added tribromophosphine (1 M in DCM, 4.11 mL, 4.11 mmol), after stirring for 30 minutes, bromine (0.288 mL, 5.61 mmol) in DCM (5 mL) was added dropwise, and the mixture was stirred at room temperature overnight. The reaction mixture was concentrated down, and the residue was diluted with DCM (10 mL) and added NH₄OH (2.5 mL) dropwise, and stirred for 1 hour. The mixture was concentrated down and purified by silica to afford 2-bromo-2-(6-fluoropyridin-2-yl)acetamide (255 mg, 1.094 mmol, 29% yield) as a brown solid. LCMS m/z=232.9 [M+H]⁺.

Step 2: 2-((3,5-Dicyano-4-ethyl-6-(4-methyl-1,4-diazepan-1-yl)pyridin-2-yl)thio)-2-(6-fluoropyridin-2-yl)acetamide

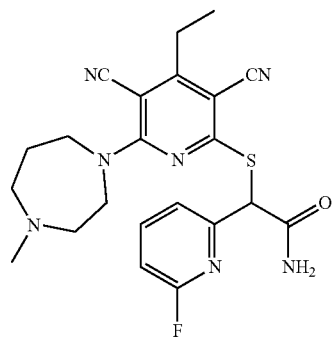 [SMILES: CCc1c(C#N)c(SC(C(N)=O)c2cccc(F)n2)nc(N2CCCN(C)CC2)c1C#N]

To a solution of 2,6-dichloro-4-ethylpyridine-3,5-dicarbonitrile (synthesis described in example 3, step 2, 150 mg, 0.664 mmol) in DMF (5 mL) at ice water bath temperature was added the solution of 1-methyl-1,4-diazepane (0.094 mL, 0.730 mmol) in DMF (2 mL) dropwise. After stirring for 10 minutes, the mixture was brought to room temperature and stirred for 30 minutes. Then potassium thioacetate (99 mg, 0.863 mmol) and TEA (0.277 mL, 1.991 mmol) were added to the reaction mixture, which was stirred at 50° C. for additional 1 hour. Then 2-bromo-2-(6-fluoropyridin-2-yl)acetamide (155 mg, 0.664 mmol) was added to the reaction solution. The reaction mixture was stirred at room temperature overnight. The reaction mixture was diluted with DCM, and washed with water and brine, dried over Na₂SO₄, and concentrated down. The residue was purified by RP-HPLC (20-50% A-CN/water, 0.1% NH₄OH in water), and the resulting fractions were concentrated down and the residue was further purified by silica (CombiFlash®, 40 g column, 0-100% (1% NH₄OH+9% MeOH+90% DCM)/DCM) to afford 2-((3,5-dicyano-4-ethyl-6-(4-methyl-1,4-diazepan-1-yl)pyridin-2-yl)thio)-2-(6-fluoro-pyridin-2-yl)acetamide (108 mg, 0.238 mmol, 36% yield) as an off white solid. LCMS m/z=454.3 [M+H]⁺. ¹H NMR (400 MHz, DMSO-d₆) δ ppm 1.17-1.28 (m, 3H), 1.78-1.99 (m, 2H), 2.23 (s, 3H), 2.35-2.50 (m, 3H), 2.59-2.69 (m, 1H), 2.78 (q, J=7.6 Hz, 2H), 3.75-3.96 (m, 4H), 5.62 (s, 1H), 7.17 (dd, J=8.1, 2.5 Hz, 1H), 7.51 (s, 1H), 7.58 (dd, J=7.5, 2.2 Hz, 1H), 7.95-8.09 (m, 2H).

Example 207

2-((3,5-Dicyano-6-(4-(dimethylamino)piperidin-1-yl)-4-ethylpyridin-2-yl)thio)-2-(4-fluorophenyl)acetamide Step 1: 2-Chloro-6-(4-(dimethylamino)piperidin-1-yl)-4-ethylpyridine-3,5-dicarbonitrile

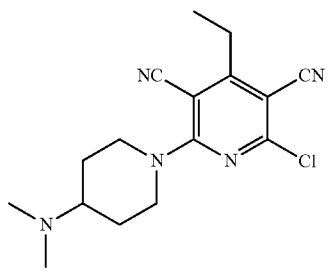 [SMILES: CCc1c(C#N)c(Cl)nc(N2CCC(N(C)C)CC2)c1C#N]

To a stirred solution of 2,6-dichloro-4-ethylpyridine-3,5-dicarbonitrile (synthesis described in example 3 step 2, 300 mg, 1.327 mmol) in dichloromethane (5 mL) was added triethylamine (0.185 mL, 1.327 mmol) and N,N-dimethylpiperidin-4-amine (170 mg, 1.327 mmol) at 0° C. The reaction mixture was stirred for 5 minutes at the same temperature. The reaction mixture was quenched with ice cold water (50 mL) and extracted with dichloromethane (2×50 mL). The combined organic layers were washed with water (2×100 mL) and concentrated under vacuum to afford (350 mg, 76% yield) as a semi solid. LCMS m/z=318.2 [M+H]⁺.

Step 2: 2-(4-Fluorophenyl)-2-hydroxyacetamide

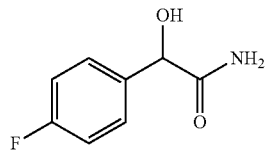 [SMILES: NC(=O)C(O)c1ccc(F)cc1]

To a stirred solution of 2-(4-fluorophenyl)-2-hydroxy-acetic acid (1 g, 5.88 mmol) in methanol (10 mL) was added acetyl chloride (1.254 mL, 17.63 mmol) at 0° C., and the reaction mixture was stirred at room temperature for 5 hours. The reaction mixture was concentrated under reduced pressure to remove all volatiles. Then methanol (10 mL) and ammonium hydroxide (7.0 mL, 44.9 mmol) were added to the reaction mixture, and the mixture was stirred at room temperature for 16 hours under a nitrogen atmosphere. The reaction mixture was concentrated under reduced pressure to remove the all volatiles, then cold ethanol (5 mL) was added to the crude material. The resulting mixture was stirred for 5 minutes then filtered to afford 2-(4-fluorophenyl)-2-hydroxyacetamide (620 mg, 62% yield) as an off-white solid. ¹H NMR (400 MHz, DMSO-d₆) δ ppm 7.49-7.39 (m, 2H), 7.37 (bs, 1H), 7.19-7.09 (m, 3H), 6.03 (d, J=4.7 Hz, 1H), 4.85 (d, J=4.7 Hz, 1H).

Step 3: 2-Amino-1-(4-fluorophenyl)-2-oxoethyl methanesulfonate

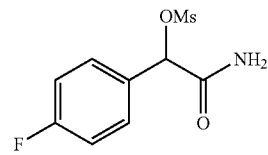 [SMILES: CS(=O)(=O)OC(C(N)=O)c1ccc(F)cc1]

To a stirred suspension of 2-(4-fluorophenyl)-2-hydroxy-acetamide (600 mg, 3.55 mmol) in acetonitrile (10 mL) was added triethylamine (0.494 mL, 3.55 mmol) at 0° C., and the reaction mixture was stirred for 10 minutes at 0° C. Methanesulfonyl chloride (0.276 mL, 3.55 mmol) was added at 0° C., and the reaction mixture was allowed to slowly warm to room temperature and was stirred for 6 hours at room temperature. The reaction mixture concentrated under reduced pressure. The residue was diluted with water (10 mL) and extracted with EtOAc (2×25 mL). The combined organic layers were dried over Na₂SO₄, filtered and concentrated under reduced pressure. The crude material was triturated with diethyl ether (15 mL) and filtered to obtain 2-amino-1-(4-fluorophenyl)-2-oxoethyl methanesulfonate (450 mg, 51% yield) as a pale yellow solid. ¹H NMR (400 MHz, DMSO-d₆) δ ppm 7.81 (s, 1H), 7.65-7.41 (m, 3H), 7.32-7.15 (m, 2H), 5.86 (s, 1H), 3.22 (s, 3H).

Step 4: 2-((3,5-Dicyano-6-(4-(dimethylamino)piperidin-1-yl)-4-ethylpyridin-2-yl)thio)-2-(4-fluorophenyl)acetamide

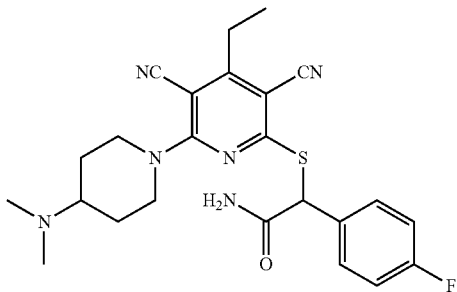 [SMILES: CCc1c(C#N)c(SC(C(N)=O)c2ccc(F)cc2)nc(N2CCC(N(C)C)CC2)c1C#N]

To a stirred solution of 2-chloro-6-(4-(dimethylamino)piperidin-1-yl)-4-ethylpyridine-3,5-dicarbonitrile (350 mg, 1.005 mmol) in N,N-dimethylformamide (10 mL), was added potassium thioacetate (230 mg, 2.010 mmol) at room temperature, and the mixture was stirred for 2 hours at the same temperature. Then potassium carbonate (278 mg, 2.010 mmol) and 2-amino-1-(4-fluorophenyl)-2-oxoethyl methanesulfonate (373 mg, 1.508 mmol) were added and the reaction mixture was stirred for 16 hours at room temperature. The reaction mixture was diluted with cold water (50 mL) and extracted with EtOAc (2×35 mL). The combined organic layers were dried over $Na_2SO_4$, filtered and concentrated under reduced the pressure. The crude material was purified by column chromatography using silica-gel (100-200 mesh, eluting with DCM/MeOH) to afford 2-((3,5-dicyano-6-(4-(dimethylamino)piperidin-1-yl)-4-ethylpyridin-2-yl)thio)-2-(4-fluorophenyl)acetamide (134 mg, 27% yield) as a light brown solid. LCMS m/z=467.2 [M+H]$^+$. $^1$H NMR (400 MHz, DMSO-d$_6$) δ ppm 7.94 (br s, 1H), 7.56 (dd, J=8.55, 5.26 Hz, 2H), 7.35 (br s, 1H), 7.22 (t, J=8.77 Hz, 2H), 5.57 (s, 1H), 4.60 (d, J=11.84 Hz, 2H), 3.17 (t, J=11.95 Hz, 2H), 2.84-2.66 (m, 3H), 2.37 (br s, 6H), 1.95 (d, J=12.28 Hz, 2H), 1.47 (br d, J=15.13 Hz, 2H), 1.17-1.23 (m, 3H).

Example 208

2-((3,5-Dicyano-4-ethyl-6-(4-methyl-1,4-diazepan-1-yl) pyridin-2-yl) thio-2-(4-methylpyridin-2-yl) acetamide Step 1:
2-Hydroxy-2-(4-methylpyridin-2-yl)acetamide

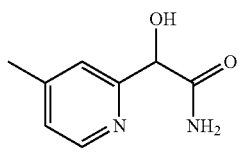

To a solution of 4-methylpicolinaldehyde (1.03 g, 8.50 mmol) in DCM (40 mL) was added trimethylsilanecarbonitrile (1.383 mL, 11.05 mmol). The mixture was stirred at room temperature overnight. The reaction mixture was concentrated down to afford a brown oil, which was treated with conc. sulfuric acid (5 mL, 94 mmol) for 4 hours, then poured the reaction mixture into ice, and adjusted the pH to 9 using $NH_4OH$. The mixture was concentrated down with silica, purified by silica column (CombiFlash®, 40 g column, 0-8% MeOH/DCM) to afford 2-hydroxy-2-(4-methylpyridin-2-yl) acetamide (435 mg, 2.62 mmol, 31% yield) as a yellow wax solid. LCMS m/z=167.0 [M+H]$^+$.

Step 2:
2-Amino-1-(4-methylpyridin-2-yl)-2-oxoethyl methanesulfonate

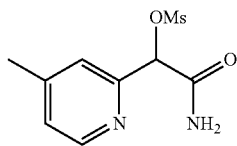

To a slurry of 2-hydroxy-2-(4-methylpyridin-2-yl)acetamide (435 mg, 2.62 mmol) and TEA (0.730 mL, 5.24 mmol) in THF (15 mL) was added methanesulfonyl chloride (0.245 mL, 3.14 mmol) dropwise. The reaction mixture was stirred at room temperature overnight. The reaction mixture was diluted with DCM and water, separated the layers. The aqueous layer was extracted with DCM (2×). The combined organics were washed with brine, dried over $Na_2SO_4$, concentrated down to afford 2-amino-1-(4-methylpyridin-2-yl)-2-oxoethyl methanesulfonate (568 mg, 2.325 mmol, 89% yield) as a brown wax solid. LCMS m/z=245.1 [M+H]$^+$.

Step 3: 2-((3,5-Dicyano-4-ethyl-6-(4-methyl-1,4-diazepan-1-yl) pyridin-2-yl) thio)-2-(4-methylpyridin-2-yl)acetamide

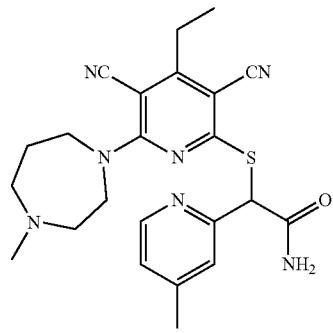 [SMILES: CCc1c(C#N)c(SC(C(N)=O)c2cc(C)ccn2)nc(N2CCCN(C)CC2)c1C#N]

To a solution of 2,6-dichloro-4-ethylpyridine-3,5-dicarbonitrile (synthesis described in example 3, step 2, 130 mg, 0.575 mmol) in DMF (3.5 mL) was added a solution of 1-methyl-1,4-diazepane (0.081 mL, 0.633 mmol) in DMF (1.5 mL) dropwise. After stirring for 60 minutes. Then potassium thioacetate (85 mg, 0.748 mmol) and TEA (0.240 mL, 0 1.725 mmol) were added to the reaction mixture, which was stirred at 50° C. for additional 2 hours. Then 2-amino-1-(4-methylpyridin-2-yl)-2-oxoethyl methanesulfonate (169 mg, 0.690 mmol) was added to the reaction solution. The reaction mixture was stirred at room temperature overnight. The reaction mixture was loaded on Celite® and purified by silica (CombiFlash®, 24 g column, 100% hexane for 3 minutes, then 0-20% MeOH/DCM). The resulting fractions were concentrated down and triturated with ethanol to afford 2-((3,5-dicyano-4-ethyl-6-(4-methyl-1,4-diazepan-1-yl) pyridin-2-yl)thio)-2-(4-methylpyridin-2-yl) acetamide (77 mg, 0.171 mmol, 30% yield) as an off-white solid. LCMS m/z=450.2 [M+H]$^+$. $^1$H NMR (400 MHz, DMSO-d$_6$) δ ppm 1.22 (t, J=7.6 Hz, 3H), 1.92 (br. s., 2H), 2.25 (s, 3H), 2.33 (s, 3H), 2.46 (br. s., 2H), 2.56 (br. s 1H), 2.66 (d, J=13.4 Hz, 1H), 2.78 (q, J=7.6 Hz, 2 6H), 3.81-3.99 (m, 4H), 5.58 (s, 1H), 7.20 (d, J=4.3 Hz, 1H), 7.38 (s, 1H), 7.45 (s, 1H), 7.84 (s, 1H), 8.40 (d, J=5.1 Hz, 1H).

Example 209

2-((3,5-Dicyano-4-ethyl-6-(4-methyl-1,4-diazepan-1-yl)pyridin-2-yl)thio)-2-(3-methoxypyridin-2-yl)acetamide

Step 1: 2-Hydroxy-2-(3-methoxypyridin-2-yl)acetamide

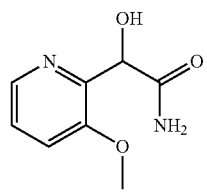

To a solution of 3-methoxypicolinaldehyde (1.07 g, 7.57 mmol) in DCM (40 mL) was added trimethylsilanecarbonitrile (1.231 mL, 9.84 mmol). The mixture was stirred at room temperature overnight. The mixture was concentrated down to afford a brown oil, which was treated with conc. sulfuric acid (5 mL, 94 mmol) for 4 hours, then poured the reaction mixture into ice, and adjusted the pH to 9 using NH₄OH. The mixture was concentrated down with Celite®, purified by silica column (CombiFlash®, 40 g column, 0-6% MeOH/DCM) to afford 2-hydroxy-2-(3-methoxypyridin-2-yl)acetamide (983 mg, 5.40 mmol, 71% yield) as a beige solid. LCMS m/z=183.0 [M+H]⁺.

Step 2: 2-Amino-1-(3-methoxypyridin-2-yl)-2-oxoethyl methanesulfonate

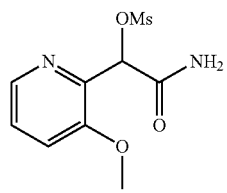 [SMILES: COc1cccnc1C(OS(C)(=O)=O)C(N)=O]

To a slurry of 2-hydroxy-2-(3-methoxypyridin-2-yl)acetamide (980 mg, 5.38 mmol) and TEA (1.500 mL, 10.76 mmol) in THF (25 mL) was added methanesulfonyl chloride (0.503 mL, 6.46 mmol) dropwise. The reaction mixture was stirred at room temperature for 3 hours. dichloromethane (10 mL) and N,N-dimethylformamide (5.00 mL) were added to the reaction mixture, which was stirred for another 1 hour. The reaction mixture was diluted with more DCM and washed with water and brine, dried over Na₂SO₄, concentrated down to afford 2-amino-1-(3-methoxpyridin-2-yl)-2-oxoethyl methanesulfonate (499 mg, 1.917 mmol, 36% yield) as a light yellow solid. LCMS m/z=261.0 [M+H]⁺.

Step 3: 2-((3,5-Dicyano-4-ethyl-6-(4-methyl-1,4-diazepan-1-yl)pyridin-2-yl)thio)-2-(3-methoxypyridin-2-yl)acetamide

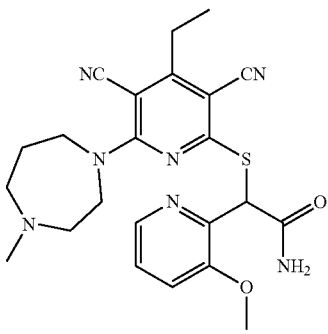 [SMILES: CCc1c(C#N)c(SC(C(N)=O)c2ncccc2OC)nc(N2CCCN(C)CC2)c1C#N]

To a solution of 2,6-dichloro-4-ethylpyridine-3,5-dicarbonitrile (synthesis described in example 3, step 2, 130 mg, 0.575 mmol) in DMF (3 mL) was added the solution of 1-methyl-1,4-diazepane (0.081 mL, 0.633 mmol) in DMF (1 mL) dropwise. After stirring for 60 minutes, potassium thioacetate (92 mg, 0.805 mmol) and TEA (0.240 mL, 1.725 mmol) were added to the reaction mixture, which was stirred at 50° C. for additional 2 hours. Then 2-amino-1-(3-methoxypyridin-2-yl)-2-oxoethyl methanesulfonate (150 mg, 0.575 mmol) was added to the reaction solution. The reaction mixture was stirred at room temperature overnight. The mixture was loaded on Celite® and purified by silica (CombiFlashe, 24 g column) using 100% hexane for 5 minutes, then 0-20% MeOH/DCM. The resulting fractions were concentrated down and the residue was triturated with ethanol to afford 2-((3,5-dicyano-4-ethyl-6-(4-methyl-1,4-diazepan-1-yl)pyridin-2-yl)thio)-2-(3-methoxypyridin-2-yl)acetamide (84 mg, 0.180 mmol, 31% yield) as an off-white solid. LCMS m/z=466.3 [M+H]⁺. ¹H NMR (400 MHz, CHLOROFORM-d) δ ppm 1.34 (t, J=7.6 Hz, 3H), 2.14-2.31 (m., 2H), 2.59 (br. s., 3H), 2.68-3.35 (m, 6H), 3.91 (s, 3H), 4.06 (t, J=5.7 Hz, 2H), 4.22 (br. s., 2H), 5.55 (br. s., 1H), 6.15 (br. s., 1H), 7.10 (br. s., 1H), 7.25-7.32 (m, 2H), 8.21 (dd, J=4.4, 1.4 Hz, 1H).

Example 210

2-((3,5-Dicyano-6-(4-(dimethylamino)piperidin-1-yl)-4-ethylpyridin-2-yl)thio)-2-(2,4-difluorophenyl)acetamide

Step 1: 2-(2,4-Difluorophenyl)-2-hydroxyacetamide

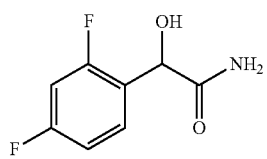 [SMILES: NC(=O)C(O)c1ccc(F)cc1F]

To a solution of 2-(2,4-difluorophenyl)-2-hydroxyacetic acid (2 g, 10.63 mmol) in methanol (20 mL) was added acetyl chloride (2.268 mL, 31.9 mmol) at 0° C., and the mixture was stirred for 5 hours at room temperature. The reaction mixture was concentrated under reduced pressure to obtain the crude product. To this, methanol (20 mL) and ammonium hydroxide (14 mL, 360 mmol) were added at room temperature, and the mixture was stirred for 15 hours. The reaction mixture was concentrated under reduced pressure, and the residue was washed with chilled ethanol (10 mL) to afford 2-(2,4-difluorophenyl)-2-hydroxyacetamide (1.8 g, 70% yield) as an off-white solid. LCMS m/z=187.9 [M+H]+.

Step 2: 2-Amino-1-(2,4-difluorophenyl)-2-oxoethyl methanesulfonate

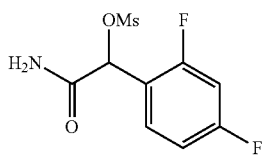 [SMILES: CS(=O)(=O)OC(C(N)=O)c1ccc(F)cc1F]

To a stirred solution of 2-(2,4-difluorophenyl)-2-hydroxyacetamide (1.8 g, 9.62 mmol) in dichloromethane (18 mL) was added triethylamine (4.02 mL, 28.9 mmol) at room temperature. After 5 minutes mesyl chloride (0.899 mL, 11.54 mmol) was added at 0° C., and the resulting mixture was stirred for 1 hour at room temperature. Water (20 mL) was added, and the mixture was extracted with DCM (2×20 mL). The combined organic layers were dried over anhydrous sodium sulphate, filtered and concentrated under reduced pressure to afford 2-amino-1-(2,4-difluorophenyl)-2-oxoethyl methanesulfonate (1.6 g, 57% yield) as an off-white solid. $^1$H NMR (400 MHz, CDCl$_3$) δ ppm 7.45 (td, J=8.39, 6.25 Hz, 1H), 7.00-6.87 (m, 2H), 6.50 (bs, 1H), 6.08 (s, 1H), 5.78 (bs, 1H), 2.97 (s, 3H).

Step 3: 2-((3,5-Dicyano-6-(4-(dimethylamino)piperidin-1-yl)-4-ethylpyridin-2-yl)thio)-2-(2,4-difluorophenyl)acetamide

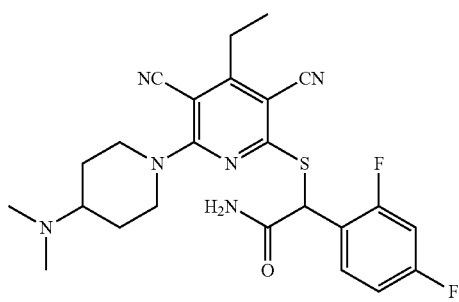 [SMILES: CCc1c(C#N)c(SC(C(N)=O)c2ccc(F)cc2F)nc(N2CCC(N(C)C)CC2)c1C#N]

To a solution of 2-chloro-6-(4-(dimethylamino)piperidin-1-yl)-4-ethylpyridine-3,5-dicarbonitrile (synthesis described in example 207 step 1, 600 mg, 1.888 mmol) in N,N-dimethylformamide (10 mL) was added potassium thioacetate (431 mg, 3.78 mmol) at room temperature and the resulting mixture was stirred for 2 hours at the same temperature. Potassium carbonate (522 mg, 3.78 mmol) and 2-amino-1-(2,4-difluorophenyl)-2-oxoethyl methanesulfonate (501 mg, 1.888 mmol) were added, and the mixture was stirred for 12 hours at room temperature. The reaction mixture was diluted with ice water (50 mL) and extracted with ethyl acetate (2×50 mL). The combined organic layers were dried over anhydrous sodium sulphate, filtered and concentrated under vacuum to get crude product. This crude product was purified by column chromatography using silica gel (100-200 mesh, eluting with 60-70% petroleum ether/ethyl acetate). The pure fractions were concentrated under reduced pressure to afford 2-((3,5-dicyano-6-(4-(dimethylamino)piperidin-1-yl)-4-ethylpyridin-2-yl)thio)-2-(2,4-difluorophenyl)acetamide (120 mg, 13% yield) as a pale brown solid. LCMS m/z=485.1 [M+H]+. $^1$H NMR (400 MHz, DMSO-d$_6$) δ ppm 7.91 (s, 1H), 7.57 (td, J=8.77, 6.58 Hz, 1H), 7.47 (s, 1H), 7.39-7.30 (m, 1H), 7.13 (td, J=8.50, 2.30 Hz, 1H), 5.76 (s, 1H), 4.51 (d, J=14.69 Hz, 2H), 3.17 (t, J=12.61 Hz, 2H), 2.77 (q, J=7.53 Hz, 2H), 2.47-2.39 (m, 1H), 2.21 (s, 6H), 1.85 (d, J=12.28 Hz, 2H), 1.52-1.32 (m, 2H), 1.21 (t, J=7.78 Hz, 3H).

Example 211

2-((3,5-Dicyano-4-ethyl-6-(4-(pyrrolidin-1-yl)piperidin-1-yl)pyridin-2-yl)thio)-2-(5-fluoropyridin-2-yl)acetamide, Formic Acid Salt Step 1: 2-Chloro-4-ethyl-6-(4-(pyrrolidin-1-yl)piperidin-1-yl)pyridine-3,5-dicarbonitrile

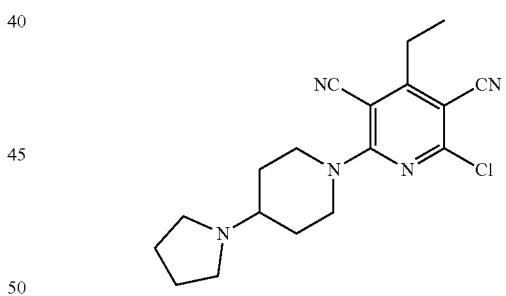

A solution of 4-(pyrrolidin-1-yl)piperidine (1.5 g, 9.72 mmol) in dichloromethane (30 mL) was added to a mixture of 2,6-dichloro-4-ethylpyridine-3,5-dicarbonitrile (synthesis described in Example 3 step 2, 2.198 g, 9.72 mmol) and triethylamine (4.07 mL, 29.2 mmol) in dichloromethane (30 mL) at 0° C. The mixture was warmed to 25° C. and stirred for 12 hours. The mixture was washed with water (30 mL). The organic phase was concentrated and the residue was purified by column chromatography using petroleum ether/EtOAc (2/1) to give 2-chloro-4-ethyl-6-(4-(pyrrolidin-1-yl)piperidin-1-yl)pyridine-3,5-dicarbonitrile (3.6 g, 92% yield). LCMS m/z=344.1 [M+H]+.

Step 2: 2-((3,5-Dicyano-4-ethyl-6-(4-(pyrrolidin-1-yl)piperidin-1-yl)pyridin-2-yl)thio)-2-(5-fluoropyridin-2-yl)acetamide, Formic Acid Salt

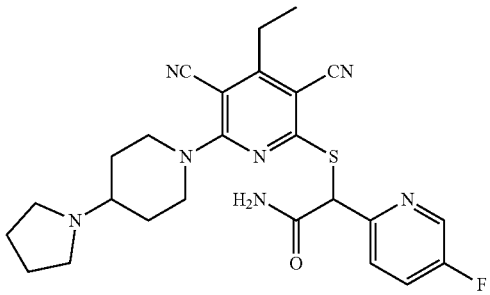 [SMILES: CCc1c(C#N)c(SC(C(N)=O)c2ccc(F)cn2)nc(N2CCC(N3CCCC3)CC2)c1C#N]

To a solution of 2-chloro-4-ethyl-6-(4-(pyrrolidin-1-yl)piperidin-1-yl)pyridine-3,5-dicarbonitrile (344 mg, 1.000 mmol) in N,N-dimethylformamide (10 mL) was added potassium thioacetate (126 mg, 1.100 mmol) at 0° C. The mixture was warmed to 25° C. and stirred for 2 hours. The mixture was concentrated and the residue was purified by column chromatography using DCM/MeOH (100/1) to give 4-ethyl-2-mercapto-6-(4-(pyrrolidin-1-yl)piperidin-1-yl)pyridine-3,5-dicarbonitrile (290 mg, 85% yield). To a solution of 2-amino-1-(5-fluoropyridin-2-yl)-2-oxoethyl methanesulfonate (211 mg, 0.849 mmol) in N,N-dimethylformamide (3 mL) was added a solution of 4-ethyl-2-mercapto-6-(4-(pyrrolidin-1-yl)piperidin-1-yl)pyridine-3,5-dicarbonitrile (290 mg, 0.849 mmol) in N,N-dimethylformamide (3 mL). The mixture was stirred at 25° C. for 16 hours. The mixture was concentrated and the residue was purified by prep-HPLC to give 2-((3,5-dicyano-4-ethyl-6-(4-(pyrrolidin-1-yl)piperidin-1-yl)pyridin-2-yl)thio)-2-(5-fluoropyridin-2-yl)acetamide, formic acid salt (110 mg, 24% yield) as an off-white solid. LCMS m/z=494.1 [M+H]$^+$. $^1$H NMR (400 MHz, DMSO-d$_6$) δ ppm 8.57 (s, 1H), 8.19 (s, 1H), 7.94 (s, 1H), 7.71 (m, 2H), 7.45 (s, 1H), 5.70 (s, 1H), 4.40 (d, J=12 Hz, 2H), 3.26 (t, J=12 Hz, 2H), 2.76 (m, 2H), 2.62 (m, 4H), 2.51 (m, 1H), 1.93 (m, 2H), 1.72 (s, 4H), 1.49 (m, 1H), 1.37 (m, 1H), 1.21 (m, 3H).

Example 212

2-((3,5-Dicyano-4-ethoxy-6-(4-(2-hydroxyethyl)-1,4-diazepan-1-yl)pyridin-2-yl)thio)propanamide

Step 1: 2-((6-Amino-3,5-dicyano-4-ethoxypyridin-2-yl)thio)propanamide

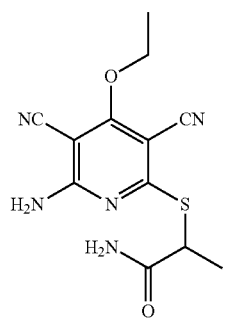 [SMILES: CCOc1c(C#N)c(N)nc(SC(C)C(N)=O)c1C#N]

S-(1-amino-1-oxopropan-2-yl) ethanethioate (356 mg, 2.419 mmol) was dissolved in ethanol (40 mL) and NaBH$_4$ (111 mg, 2.93 mmol) was added. The mixture was stirred and heated to 40° C. for 30 minutes and gas evolution had ceased. The mixture was allowed to cool to room temperature and added to 2-amino-6-chloro-4-ethoxypyridine-3,5-dicarbonitrile (522 mg, 2.345 mmol) in ethanol (20 mL). The mixture was stirred for 5 hours at room temperature. Cooled to 0° C. and filtered to afford 2-((6-amino-3,5-dicyano-4-ethoxypyridin-2-yl)thio)propanamide (749 mg, 2.262 mmol, 96% yield). LCMS m/z=292.1 [M+H]$^+$.

Step 2: 2-((6-Chloro-3,5-dicyano-4-ethoxypyridin-2-yl)thio)propanamide

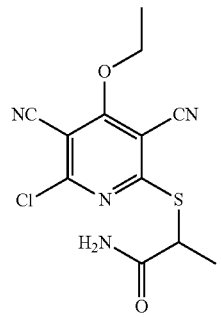 [SMILES: CCOc1c(C#N)c(Cl)nc(SC(C)C(N)=O)c1C#N]

2-((6-Amino-3,5-dicyano-4-ethoxypyridin-2-yl)thio)propanamide (370 mg, 1.118 mmol) was dissolved in acetonitrile (20 mL) and copper(II) chloride (270 mg, 2.012 mmol) was added. The mixture was stirred and heated to 45° C. for 5 minutes and tert-butyl nitrite (0.24 mL, 2.025 mmol) was added dropwise. The mixture was heated to 45° C. for 1 hour. Cooled to room temperature and worked up with EtOAc (3×) and aqueous saturated NaHCO$_3$. Combined organics were washed with brine, dried over MgSO$_4$, filtered and concentrated. Purified on silica gel (80 g column: 100% DCM to 5% IPA in DCM w/1% NH$_4$OH). The desired fractions were pooled and concentrated to afford 2-((6-chloro-3,5-dicyano-4-ethoxypyridin-2-yl)thio)propanamide (180 mg, 0.527 mmol, 47% yield). LCMS m/z=311.1 [M+H]$^+$.

Step 3: 2-((3,5-Dicyano-4-ethoxy-6-(4-(2-hydroxyethyl)-1,4-diazepan-1-yl)pyridin-2-yl)thio)propanamide

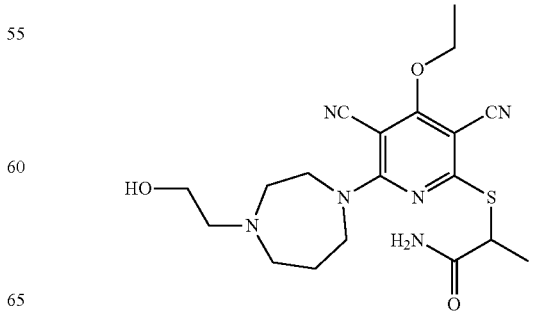

2-((6-Chloro-3,5-dicyano-4-ethoxypyridin-2-yl)thio)propanamide (100 mg, 0.283 mmol) was dissolved in tetrahydrofuran (6 mL) and 2-(1,4-diazepan-1-yl)ethanol (49.0 mg, 0.340 mmol) was added. The mixture was stirred and for 30 minutes. Concentrated. Purified on silica gel (80 g column: 100% DCM→10% IPA in DCM w/1% NH₄OH). The desired fractions were pooled and concentrated to afford 2-((3,5-dicyano-4-ethoxy-6-(4-(2-hydroxyethyl)-1,4-diazepan-1-yl)pyridin-2-yl)thio)propanamide (90 mg, 0.215 mmol, 76% yield). LCMS m/z=419.3 [M+H]⁺. ¹H NMR (400 MHz, DMSO-d₆) δ ppm 7.69 (s, 1H) 7.24 (s, 1H) 4.49-4.59 (m, 2H) 4.35-4.45 (m, 2H) 3.76-4.00 (m, 4H) 3.47 (q, J=6.17 Hz, 2H) 2.74-2.95 (m, 2H) 2.64-2.74 (m, 1H) 2.57-2.64 (m, 1H) 2.54 (t, J=6.34 Hz, 2H) 1.84-1.97 (m, 2H) 1.50 (d, J=7.10 Hz, 3H) 1.37 (t, J=7.10 Hz, 3H).

Example 213

2-((3,5-Dicyano-6-(4-(2-hydroxyethyl)-1,4-diazepan-1-yl)-4-propoxypyridin-2-yl)thio)-2-phenylacetamide Step 1: 2-Amino-6-chloro-4-propoxypyridine-3,5-dicarbonitrile

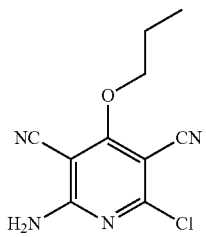 [SMILES: CCCOc1c(C#N)c(N)nc(Cl)c1C#N]

Ethene-1,1,2,2-tetracarbonitrile (4 g, 31.2 mmol) and urea (0.563 g, 9.37 mmol) were suspended in propan-1-ol (40 mL, 535 mmol). The mixture was heated to 40° C. for 120 minutes. Cooled to room temperature and then cooled to −78° C. and stirred for 30 minutes and an off-white precipitate formed. The cooled solution was filtered and the residue washed with cold ether. The filtrate was passed through a silica gel plug and eluted with 1:1 Et₂O:EtOAc. The product was combined with the residue to afford 2-(dipropoxymethylene)malononitrile (3.3 g). Malononitrile (2210 mg, 33.5 mmol) and potassium tert-butoxide (4.07 g, 36.3 mmol) were suspended in 1-propanol (175 mL). The mixture was heated to 45° C. for 5 minutes. 2-(dipropoxymethylene)malononitrile (2.2 g, 11.33 mmol) in PrOH (10 mL) was added to the mixture slowly and the material was refluxed for 3 hours. A solid had formed which was filtered off and the filtrate was concentrated in vacuo and acetone (100 mL) was added followed by 20 mL of concentrated HCl. Stirred at 50° C. for 130 minutes and then cooled to room temperature and eventually 0° C. The mixture was filtered to afford 2-amino-6-chloro-4-propoxypyridine-3,5-dicarbonitrile (1.53 g, 6.47 mmol). LCMS m/z=237.0 [M+H]⁺.

Step 2: 2-((6-Amino-3,5-dicyano-4-propoxypyridin-2-yl)thio)-2-phenylacetamide

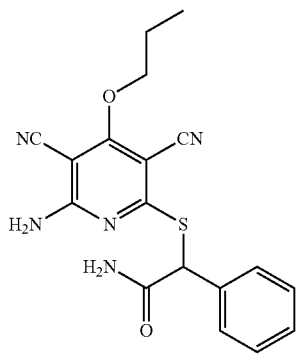 [SMILES: CCCOc1c(C#N)c(N)nc(SC(C(N)=O)c2ccccc2)c1C#N]

S-(2-amino-2-oxo-1-phenylethyl) ethanethioate (synthesis described in example 62, step 5, 760 mg, 3.63 mmol) was dissolved in ethanol (60 mL) and NaBH₄ (164 mg, 4.33 mmol) was added. The mixture was stirred and heated to 40° C. for 30 minutes and gas evolution had ceased. The mixture was allowed to cool to room temperature and added to 2-amino-6-chloro-4-propoxypyridine-3,5-dicarbonitrile (820 mg, 3.46 mmol) in ethanol (10 mL). The mixture was stirred for 3 hours at room temperature. Cooled to 0° C. and filtered off product to afford 2-((6-amino-3,5-dicyano-4-propoxypyridin-2-yl)thio)-2-phenylacetamide (934 mg, 2.110 mmol, 61% yield). LCMS m/z=368.1 [M+H]⁺.

Step 3: 2-((6-Chloro-3,5-dicyano-4-propoxypyridin-2-yl)thio)-2-phenylacetamide

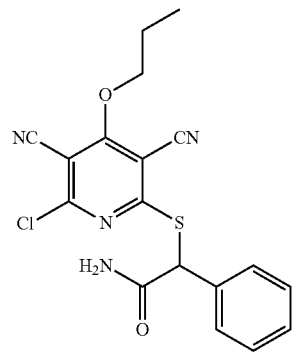 [SMILES: CCCOc1c(C#N)c(Cl)nc(SC(C(N)=O)c2ccccc2)c1C#N]

2-((6-Amino-3,5-dicyano-4-propoxypyridin-2-yl)thio)-2-phenylacetamide (588 mg, 1.328 mmol) was dissolved in acetonitrile (25 mL) and copper(II) chloride (351 mg, 2.61 mmol) was added. The mixture was stirred and heated to 45° C. for 5 minutes and tert-butyl nitrite (0.29 mL, 2.447 mmol) was added dropwise. The mixture was heated to 50° C. for 5 hours. Cooled to room temperature and filtered off an orange solid. The filtrate was concentrated and purified on silica gel (80 g column: 100% DCM to 5% IPA in DCM w/1% NH₄OH). The desired fractions were pooled and concentrated to afford 2-((6-chloro-3,5-dicyano-4-propoxypyridin-2-yl)thio)-2-phenylacetamide (129 mg, 0.293 mmol, 22% yield). LCMS m/z=387.1 [M+H]⁺.

Step 4: 2-((3,5-Dicyano-6-(4-(2-hydroxyethyl)-1,4-diazepan-1-yl)-4-propoxypyridin-2-yl)thio)-2-phenylacetamide

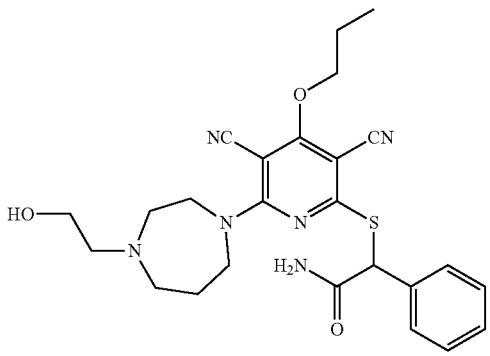 [SMILES: CCCOc1c(C#N)c(SC(C(N)=O)c2ccccc2)nc(N2CCCN(CCO)CC2)c1C#N]

2-((6-Chloro-3,5-dicyano-4-propoxpyridin-2-yl)thio)-2-phenylacetamide (65 mg, 0.151 mmol) was dissolved in tetrahydrofuran (5 mL) and 2-(1,4-diazepan-1-yl) ethanol (26.2 mg, 0.181 mmol) was added. The mixture was stirred at room temperature for 3 hours. The material was concentrated and purified on silica gel (40 g column: 100% DCM to 7% IPA in DCM w/1% NH$_4$OH). The desired fractions were pooled and concentrated to afford 2-((3,5-dicyano-6-(4-(2-hydroxyethyl)-1,4-diazepan-1-yl)-4-propoxpyridin-2-yl)thio)-2-phenylacetamide (61 mg, 0.120 mmol, 79% yield). LCMS m/z=495.3 [M+H]$^+$. $^1$H NMR (400 MHz, DMSO-d$_6$) δ ppm 7.92 (s, 1H) 7.45-7.54 (m, 2H) 7.30-7.43 (m, 4H) 5.50 (s, 1H) 4.46 (td, J=6.27, 1.39 Hz, 2H) 4.40 (t, J=5.32 Hz, 1H) 3.78-3.95 (m, 4H) 3.47 6 (q, J=6.08 Hz, 2H) 2.70-2.89 (m, 2H) 2.57-2.70 (m, 2H) 2.52-2.56 (m, 2H) 1.89 (d, J=5.07 Hz, 2H) 1.68-1.81 (m, 2H) 0.94-1.04 (m, 3H).

Example 214

2-((3,5-Dicyano-4-ethyl-6-(4-methyl-1,4-diazepan-1-yl)pyridin-2-yl)thio)-2-(4-methoxypyridin-2-yl)acetamide Step 1:
2-Hydroxy-2-(4-methoxypyridin-2-yl)acetamide

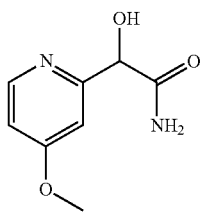

To a solution of 4-methoxypicolinaldehyde (1.01 g, 7.36 mmol) in DCM (40 mL) was added trimethylsilanecarbonitrile (1.106 mL, 8.84 mmol). The mixture was stirred at room temperature overnight. The mixture was concentrated down to afford a light brown oil, which was treated with conc. sulfuric acid (5 mL, 94 mmol) for 4 hours, then poured the reaction mixture into ice, and adjusted the PH to 9 using NH$_4$OH. The mixture was concentrated down with Celite®, purified by silica column(CombiFlash®, 40 g column) using 0-10% MeOH/DCM to afford 2-hydroxy-2-(4-methoxypyridin-2-yl)acetamide (748 mg, 4.11 mmol, 55.7% yield) as a yellow solid. LCMS m/z=183.0 [M+H]$^+$.

Step 2:
2-Amino-1-(4-methoxypyridin-2-yl)-2-oxoethyl methanesulfonate

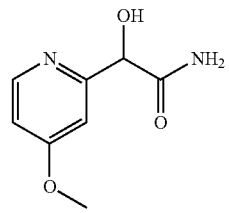

To a slurry of 2-hydroxy-2-(4-methoxypyridin-2-yl)acetamide (745 mg, 4.09 mmol) and TEA (1.140 mL, 8.18 mmol) in THF (25 mL) was added methanesulfonyl chloride (0.382 mL, 4.91 mmol) dropwise. The reaction mixture was stirred at room temperature overnight. The reaction mixture was diluted with DCM and water, separated the layers. The aqueous layer was extracted with DCM (4×). The combined organics were washed with brine, dried over Na$_2$SO$_4$, concentrated down. The residue was triturated with DCM to afford 2-amino-1-(4-methoxypyridin-2-yl)-2-oxoethyl methanesulfonate (237 mg, 0.911 mmol, 22% yield) as an off white solid. LCMS m/z=261.0 [M+H]$^+$.

Step 3: 2-((3,5-Dicyano-4-ethyl-6-(4-methyl-1,4-diazepan-1-yl)pyridin-2-yl)thio)-2-(4-methoxypyridin-2-yl)acetamide

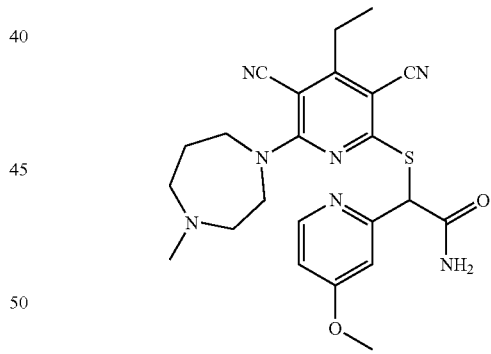

To a solution of 2,6-dichloro-4-ethylpyridine-3,5-dicarbonitrile (synthesis described in example 3, step 2, 110 mg, 0.487 mmol) in DMF (3 mL) was added a solution of 1-methyl-1,4-diazepane (0.069 mL, 0.535 mmol) in DMF (1.5 mL) dropwise. After stirring for 60 minutes, potassium thioacetate (72.2 mg, 0.633 mmol) and TEA (0.203 mL, 1.460 mmol) were added to the reaction mixture, which was stirred at 50° C. for additional 1 hour. Then 2-amino-1-(4-methoxypyridin-2-yl)-2-oxoethyl methanesulfonate (139 mg, 0.535 mmol) was added to the reaction solution. The reaction mixture was stirred at room temperature overnight. The reaction mixture was purified by reverse phase HPLC (20-50% A-CN/water, 0.1% NH$_4$ON in water). The resulting fractions were concentrated down, and the residue was triturated with methanol to afford 2-((3,5-dicyano-4-ethyl-6-(4-methyl-1,4-diazepan-1-yl)pyridin-2-yl)thio)-2-(4-methoxypyridin-2-yl)acetamide (83 mg, 0.178 mmol, 37% yield) as a light yellow solid. LCMS m/z=466.3 [M+H]+. 1H NMR (400 MHz, DMSO-d6) δ ppm 1.22 (t, J=7.6 Hz, 3H), 1.81-2.01 (m, 2H), 2.24 (s, 3H), 2.37-2.49 (m, 2H), 2.54-2.70 (m, 2H), 2.78 (q, J=7.6 Hz, 2H), 3.79-3.98 (m, 7H), 5.56 (s, 1H), 6.96 (dd, J=5.7, 2.4 Hz, 1H), 7.18 (d, J=2.5 Hz, 1H), 7.40 (s, 1H), 7.82 (s, 1H), 8.36 (d, J=5.8 Hz, 1H).

Example 215

2-((3,5-Dicyano-4-ethyl6-(2-methyl-2,8-diazaspiro[4.5]decan-8-yl)pyridin-2-yl)thio)-2-phenylacetamide Step 1: 2-Chloro-4-ethyl-6-(2-methyl-2,8-diazaspiro[4.5]decan-8-yl)pyridine-3,5-dicarbonitrile

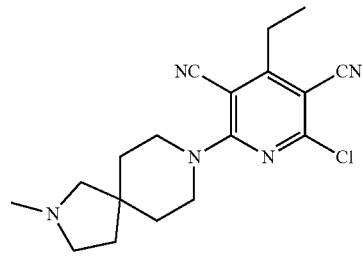 [SMILES: CCc1c(C#N)c(Cl)nc(N2CCC3(CCN(C)C3)CC2)c1C#N]

To a solution of 2,6-dichloro-4-ethylpyridine-3,5-dicarbonitrile (synthesis described in Example 3, step 2, 350 mg, 1.548 mmol) in tetrahydrofuran (2 mL) was added 2-methyl-2,8-diazaspiro[4.5]decane (239 mg, 1.548 mmol) followed by N,N-diisopropylethylamine (0.541 mL, 3.10 mmol). The reaction was stirred at 50° C. for 18 hours. The solvent was evaporated and the resulting solid was triturated with water and collected by filtration. The wet solid was dissolved in dichloromethane (100 mL), washed with water, and the organic phase was dried with sodium sulfate, filtered, and concentrated to afford 2-chloro-4-ethyl-6-(2-methyl-2,8-diazaspiro[4.5]decan-8-yl)pyridine-3,5-dicarbonitrile (350 mg, 66% yield). LCMS m/z=344.2 [M+H]+.

Step 2: 2-((3,5-Dicyano-4-ethyl-6-(2-methyl-2,8-diazaspiro[4.5]decan-8-yl)pyridin-2-yl)thio)-2-phenylacetamide

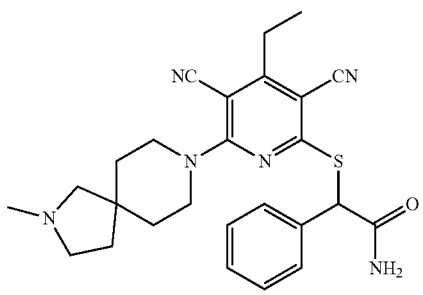 [SMILES: CCc1c(C#N)c(SC(C(N)=O)c2ccccc2)nc(N2CCC3(CCN(C)C3)CC2)c1C#N]

To a 70° C. solution of S-(2-amino-2-oxo-1-phenylethyl) ethanethioate (synthesis described in Example 62, step 5, 276 mg, 1.32 mmol) in ethanol (10 mL) was added NaBH4 (53.9 mg, 1.425 mmol) portionwise. After 3 minutes the solution was added to 2-chloro-4-ethyl-6-(2-methyl-2,8-diazaspiro[4.5]decan-8-yl)pyridine-3,5-dicarbonitrile (350 mg, 1.018 mmol) in ethanol (10 mL) and tetrahydrofuran (3.0 mL), and the reaction was heated at 70° C. for 60 minutes. The material was purified by automated gradient reverse phase chromatography eluting with acetonitrile-water containing 0.1% TFA (10-90% acetonitrile). Fractions containing the desired product were combined, and the solution was partially concentrated to remove acetonitrile. To the solution was added dropwise a saturated solution of sodium bicarbonate, and the resulting solid was collected by filtration and dried over sodium sulfate to afford 2-((3,5-dicyano-4-ethyl-6-(2-methyl-2,8-diazaspiro[4.5]decan-8-yl)pyridin-2-yl)thio)-2-phenylacetamide (100 mg, 19% yield). LCMS m/z=475.3 [M+H]+. 1H NMR (400 MHz, DMSO-d6) δ ppm 7.92 (br. s., 1H), 7.47-7.54 (m, 2H), 7.27-7.43 (m, 5H), 5.52 (s, 1H), 3.66-3.98 (m, 4H), 2.75 (q, J=7.44 Hz, 2H), 2.23-2.34 (m, 3H), 1.53-1.75 (m, 6H), 1.20 (t, J=7.60 Hz, 3H).

Example 216

2-((3,5-Dicyano-6-(4-(dimethylamino)piperidin-1-yl)-4-ethylpyridin-2-yl)thio)-2-(3,4-difluorophenyl)acetamide Step 1: 2-(3,4-Difluorophenyl)-2-hydroxyacetamide

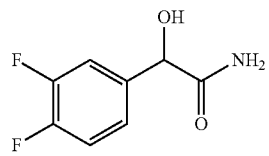 [SMILES: NC(=O)C(O)c1ccc(F)c(F)c1]

To a stirred solution of 2-(3,4-difluorophenyl)-2-hydroxyacetic acid (2 g, 10.63 mmol) in methanol (20 mL) was added acetyl chloride (2.268 mL, 31.9 mmol) at 0° C., and the mixture was stirred at room temperature for 5 hours. The reaction mixture was concentrated under reduced pressure to remove all volatiles. Methanol (20 mL) and ammonium hydroxide (14 mL, 360 mmol) were added, and the reaction mixture was stirred for 16 hours at room temperature under a nitrogen atmosphere. The reaction mixture was concentrated under reduced pressure, then cold ethanol (5 mL) was added, and the mixture was stirred for 5 minutes. The mixture was filtered to afford 2-(3,4-difluorophenyl)-2-hydroxyacetamide (1.6 g) as an off-white solid. LCMS m/z=186.0 [M−H]−.

Step 2: 2-Amino-1-(3,4-difluorophenyl)-2-oxoethyl methanesulfonate

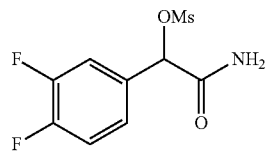 [SMILES: CS(=O)(=O)OC(C(N)=O)c1ccc(F)c(F)c1]

To a stirred suspension of 2-(3,4-difluorophenyl)-2-hydroxyacetamide (1.6 g, 6.97 mmol) in dichloromethane (20 mL) was added triethylamine (1.944 mL, 13.95 mmol) at 0° C. The reaction mixture was stirred for 10 minutes at 0° C. Then methanesulfonyl chloride (0.598 mL, 7.67 mmol) was added. The reaction mixture was slowly allowed to warm to room temperature and was stirred for 6 hours. The reaction mixture was concentrated under reduced pressure, diluted with water (50 mL) and extracted with EtOAc (2×60 mL). The combined organic layers were dried over anhydrous Na₂SO₄, filtered and concentrated under reduced pressure. The crude compound was triturated with diethyl ether (25 mL), filtered and dried to afford 2-amino-1-(3,4-difluorophenyl)-2-oxoethyl methanesulfonate (1 g, 54% yield) as a pale yellow solid. ¹H NMR (400 MHz, DMSO-d₆): δ ppm 7.83 (s, 1H), 7.71-7.43 (m, 3H), 7.35 (dt, J=8.6, 2.9 Hz, 1H), 5.88 (s, 1H), 3.26 (s, 3H).

Step 3: 2-((3,5-Dicyano-6-(4-(dimethylamino)piperidin-1-yl)-4-ethylpyridin-2-yl)thio)-2-(3,4-difluorophenyl)acetamide

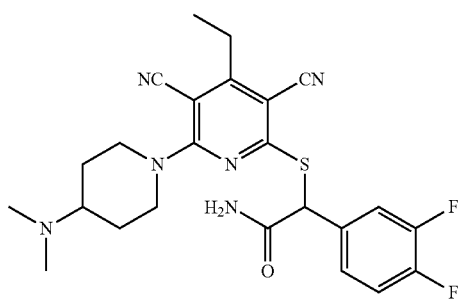 [SMILES: CCc1c(C#N)c(SC(C(N)=O)c2ccc(F)c(F)c2)nc(N2CCC(N(C)C)CC2)c1C#N]

To a stirred solution of 2-chloro-6-(4-(dimethylamino)piperidin-1-yl)-4-ethylpyridine-3,5-dicarbonitrile (synthesis described in example 207 step 1, 500 mg, 1.417 mmol) in N,N-dimethylformamide (20 mL) was added potassium thioacetate (324 mg, 2.83 mmol) at room temperature, and the reaction mixture was stirred for 2 hours at room temperature. Then potassium carbonate (392 mg, 2.83 mmol) followed by 2-amino-1-(3,4-difluorophenyl)-2-oxoethyl methanesulfonate (413 mg, 1.558 mmol) were added, and the reaction mixture was stirred for 16 hours at room temperature. The reaction mixture was quenched with cold water (50 mL) and extracted with EtOAc (2×100 mL). The combined organic layers were dried over Na₂SO₄, filtered and concentrated under reduced the pressure. The residue was purified by column chromatography using silica gel (mesh 100-200, eluting with 10% MeOH/DCM). The obtained solid was washed with 50% ethyl acetate in diethyl ether, filtered, and dried under vacuum to afford 2-((3,5-dicyano-6-(4-(dimethylamino)piperidin-1-yl)-4-ethylpyridin-2-yl)thio)-2-(3,4-difluorophenyl)acetamide (130 mg, 19% yield). LCMS m/z=485.2 [M+H]⁺. ¹H NMR (400 MHz, DMSO-d₆) δ ppm 7.98 (s, 1H), 7.62-7.53 (m, 1H), 7.51-7.36 (m, 3H), 5.59 (s, 1H), 4.55 (br d, J=10.74 Hz, 2H), 3.24-3.14 (m, 2H), 2.76 (q, J=7.60 Hz, 2H), 2.53-2.51 (m, 1H), 2.37-2.19 (m, 6H), 1.89 (br s, 2H), 1.49-1.30 (m, 2H), 1.20 (t, J=7.67 Hz, 3H).

Example 217

1-(6-((2-Amino-2-oxo-1-phenylethyl)thio)-3,5-dicyano-4-ethylpyridin-2-yl)piperidine-4-carboxamide Step 1: 1-(6-Chloro-3,5-dicyano-4-ethylpyridin-2-yl)piperidine-4-carboxamide

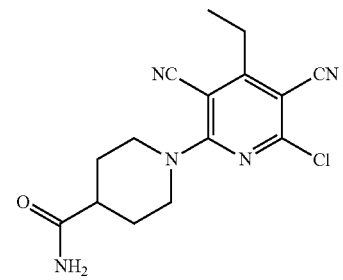 [SMILES: CCc1c(C#N)c(Cl)nc(N2CCC(C(N)=O)CC2)c1C#N]

To a stirred solution of 2,6-dichloro-4-ethylpyridine-3,5-dicarbonitrile (synthesis described in example 3 step 2, 1 g, 4.42 mmol) in dichloromethane (15 mL) was added piperidine-4-carboxamide (0.566 g, 4.42 mmol) followed by triethylamine (1.847 mL, 13.25 mmol) at 0° C. The reaction mixture was stirred for 8 hours at room temperature. The reaction mixture was concentrated under reduced pressure, diluted with water (50 mL) and extracted with DCM (2×80 mL). The combined organic layers were dried over anhydrous Na₂SO₄, filtered and concentrated under reduced pressure. The obtained crude material was triturated with diethyl ether (25 mL), filtered and dried to afford 1-(6-chloro-3,5-dicyano-4-ethylpyridin-2-yl)piperidine-4-carboxamide (800 mg, 55% yield) as a light brown solid. LCMS m/z=318.0 [M+H]⁺.

Step 2: 1-(6-((2-Amino-2-oxo-1-phenylethyl)thio)-3,5-dicyano-4-ethylpyridin-2-yl)piperidine-4-carboxamide

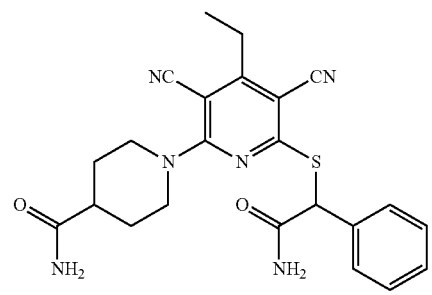 [SMILES: CCc1c(C#N)c(SC(C(N)=O)c2ccccc2)nc(N2CCC(C(N)=O)CC2)c1C#N]

To a stirred solution of 1-(6-chloro-3,5-dicyano-4-ethylpyridin-2-yl)piperidine-4-carboxamide (500 mg, 1.496 mmol) in N,N-dimethylformamide (20 mL) was added potassium thioacetate (342 mg, 2.99 mmol) at room temperature, and the reaction mixture was stirred for 2 hours at room temperature. Potassium carbonate (413 mg, 2.99 mmol) was added followed by 2-amino-2-oxo-1-phenylethyl methanesulfonate (synthesis described in example 3 step 5, 527 mg, 2.244 mmol), and the reaction mixture was stirred for 16 hours at room temperature. The reaction mixture was quenched with cold water (50 mL) and extracted with EtOAc (2×100 mL). The combined organic layers were dried over Na₂SO₄, filtered and concentrated under reduced the pressure. The crude material was purified by column chromatography using silica gel (mesh 100-200, eluting with DCM/MeOH) to afford 1-(6-((2-amino-2-oxo-1-phenylethyl)thio)-3,5-dicyano-4-ethylpyridin-2-yl)piperidine-4-carboxamide (109 mg, 15% yield) as a light brown solid. LCMS m/z=449.2 [M+H]⁺. ¹H NMR (400 MHz, DMSO-d₆) δ ppm 7.90 (s, 1H), 7.55-7.49 (m, 2H), 7.42-7.27 (m, 5H), 6.82 (br s, 1H), 5.53 (s, 1H), 4.57-4.46 (m, 2H), 3.26-3.14 (m, 2H), 2.81-2.69 (m, 2H), 2.47-2.41 (m, 1H), 1.85 (br d, J=14.03 Hz, 2H), 1.68-1.56 (m, 2H), 1.24-1.17 (m, 3H).

Example 218

2-((3,5-Dicyano-6-((2-(dimethylamino)ethyl)thio)-4-ethylpyridin-2-yl)thio)-2-phenylacetamide

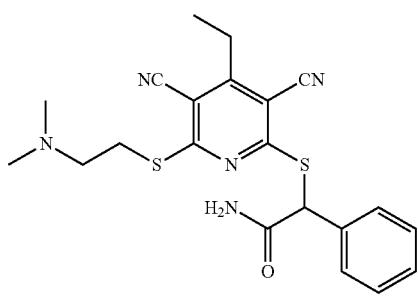 [SMILES: CCc1c(C#N)c(SCCN(C)C)nc(SC(C(N)=O)c2ccccc2)c1C#N]

A mixture of 2-((6-chloro-3,5-dicyano-4-ethylpyridin-2-yl)thio)-2-phenylacetamide (synthesis described in example 52, step 1, 220 mg, 0.62 mmol) and potassium thioacetate (74 mg, 0.65 mmol) in DMF (20 mL) was stirred at 20° C. for 0.5 hour. Then 2-chloro-N,N-dimethylethanamine (332 mg, 3.08 mmol) and triethylamine (0.344 mL, 2.47 mmol) were added. The mixture was stirred for another 13.5 hours. The reaction mixture was partitioned between ethyl acetate and water. The organic phase was dried with anhydrous sodium sulfate, filtered and concentrated in vacuo to obtain the crude product and purified by column chromatography to obtain 2-((3,5-dicyano-6-((2-(dimethylamino)ethyl)thio)-4-ethylpyridin-2-yl)thio)-2-phenylacetamide (110 mg, 42% yield). LCMS m/z=426.2 [M+H]⁺. ¹H NMR (400 MHz, CDCl₃) δ ppm 8.09 (s, 1H), 7.55-7.47 (m, 2H), 7.42-7.33 (m, 3H), 5.80 (s, 1H), 5.56 (s, 1H), 3.82-3.71 (m, 1H), 3.16 (dd, J=12.1, 5.5 Hz, 1H), 2.93 (m, 3H), 2.60 (d, J=5.8 Hz, 1H), 2.37 (s, 6H), 1.32 (t, J=7.6 Hz, 3H).

Example 219

2-((3,5-Dicyano-6-((3S,4R)-3,4-dihydroxypyrrolidin-1-yl)-4-ethylpyridin-2-yl)thio)-2-phenylacetamide Step 1: tert-Butyl 2,5-dihydro-1H-pyrrole-1-carboxylate

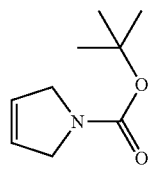

To a suspension of 2,5-dihydro-1H-pyrrole (5 g, 72.4 mmol) in dichloromethane (50 mL) stirred under nitrogen at 0° C., were added triethylamine (11.09 mL, 80 mmol) followed by di-tert-butyl dicarbonate (19.95 mL, 87 mmol). The reaction mixture was stirred at 25° C. for 2 hours. The reaction mixture was poured into water (100 mL) and extracted with DCM (3×100 mL). The combined organic layers were washed with water (2×50 mL), dried over sodium sulphate, filtered and evaporated in vacuo to give the crude product tert-butyl 2,5-dihydro-1H-pyrrole-1-carboxylate (10 g) as a pale yellow liquid. ¹H NMR (400 MHz, CDCl₃) δ ppm 5.83-5.70 (m, 2H), 4.18-4.04 (m, 4H), 1.48 (s, 9H).

Step 2: (3R,4S)-tert-Butyl 3,4-dihydroxypyrrolidine-1-carboxylate

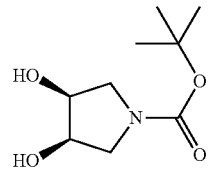

A solution of tert-butyl 2,5-dihydro-1H-pyrrole-1-carboxylate (9 g, 38.7 mmol), in acetone (80 mL) was added dropwise to a mixture of NMO (4.98 g, 42.5 mmol), osmium tetroxide (0.607 mL, 1.933 mmol) and water (80 mL) while keeping the temperature at 0° C. The reaction mixture was stirred at room temperature for 16 hours. The reaction mixture was concentrated to remove the acetone and then extracted with ethyl acetate (3×250 mL). The combined organic layers were washed with water (2×100 mL) and brine solution, dried over Na₂SO₄, filtered and concentrated. The crude material was purified by silica gel chromatography (100-200 mesh), eluting with 100% EtOAc, to afford (3R,4S)-tert-butyl 3,4-dihydroxypyrrolidine-1-carboxylate (8 g) as a light brown liquid. LCMS m/z=202.0 [M−H]⁻.

Step 3: (3R,4S)-Pyrrolidine-3,4-diol, Hydrochloride

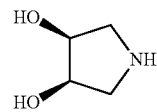

To a solution of (3R,4S)-tert-butyl 3,4-dihydroxypyrrolidine-1-carboxylate (1 g, 4.36 mmol), in 1,4-dioxane (10 mL) was added HCl (4 M in 1,4-dioxane, 1.1 mL) at 0° C. The reaction mixture was stirred at 27° C. for 2 hours. The solvents were evaporated and the resulting solids were triturated with diethyl ether (2×20 mL), filtered and dried in vacuo to afford (3R,4S)-pyrrolidine-3,4-diol, Hydrochloride (450 mg, 74.0% yield) as a light brown solid. ¹H NMR (400 MHz, DMSO-d₆) δ 9.27 (bs, 2H), 5.32 (s, 2H), 4.07 (s, 2H), 3.20 (dd, J=11.6, 5.2 Hz, 2H), 2.95 (dd, J=11.7, 4.7 Hz, 2H).

Step 4: 2-Chloro-6-((3S,4R)-3,4-dihydroxypyrrolidin-1-yl)-4-ethylpyridine-3,5-dicarbonitrile

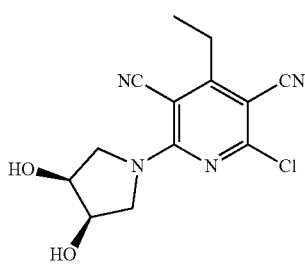 [SMILES: CCc1c(C#N)c(Cl)nc(N2C[C@@H](O)[C@@H](O)C2)c1C#N]

To a solution of (3R,4S)-pyrrolidine-3,4-diol, hydrochloride (339 mg, 2.431 mmol) in dichloromethane (10 mL) stirred under nitrogen at 0° C. was added triethylamine (0.616 mL, 4.42 mmol). The reaction mixture was stirred at 0° C. for 10 minutes. Then 2,6-dichloro-4-ethylpyridine-3,5-dicarbonitrile (synthesis described in example 3 step 2, 500 mg, 2.210 mmol) was added at the same temperature. The reaction was stirred at 27° C. for 2 hours. The reaction mixture was poured into ice cold water (50 mL) and extracted with DCM (3×50 mL)., The combined organic layers were washed with water (2×50 mL), dried over Na₂SO₄, filtered and evaporated to yield 2-chloro-6-((3S,4R)-3,4-dihydroxypyrrolidin-1-yl)-4-ethylpyridine-3,5-dicarbonitrile (600 mg, 91% yield) as a light brown solid. LCMS m/z=293.0 [M+H]⁺.

Step 5: 2-((3,5-Dicyano-6-((3S,4R)-3,4-dihydroxypyrrolidin-1-yl)-4-ethylpyridin-2-yl)thio)-2-phenylacetamide

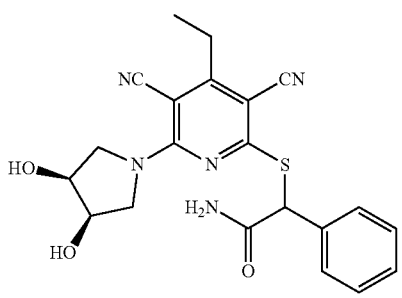 [SMILES: CCc1c(C#N)c(SC(C(N)=O)c2ccccc2)nc(N2C[C@@H](O)[C@@H](O)C2)c1C#N]

To a solution of 2-chloro-6-((3S,4R)-3,4-dihydroxypyrrolidin-1-yl)-4-ethylpyridine-3,5-dicarbonitrile (500 mg, 1.684 mmol) in N,N-dimethylformamide (5 mL) was added potassium thioacetate (385 mg, 3.37 mmol) at room temperature under nitrogen. The suspension was stirred for 2 hours at room temperature. Then potassium carbonate (465 mg, 3.37 mmol), followed by 2-amino-2-oxo-1-phenylethyl methanesulfonate (synthesis described in example 3 step 5, 593 mg, 2.53 mmol) were added at 0° C. The reaction mixture was stirred at 27° C. for 16 hours. The reaction mixture was poured into ice cold water (25 mL) and extracted with ethyl acetate (3×50 mL). The combined organic layers were dried over sodium sulphate, filtered and evaporated under vacuum. The crude product was purified by silica gel chromatography (100-200 mesh, eluting with 100% ethyl acetate) to afford 2-((3,5-dicyano-6-((3S,4R)-3,4-dihydroxypyrrolidin-1-yl)-4-ethylpyridin-2-yl)thio)-2-phenylacetamide (180 mg, 25% yield) as a light brown solid. LCMS m/z=424.1 [M+H]⁺. ¹H NMR (400 MHz, DMSO-d₆) δ ppm 7.91 (s, 1H), 7.55-7.47 (m, 2H), 7.42-7.28 (m, 3H), 7.26 (s, 1H), 5.60 (s, 1H), 5.12 (br s, 2H), 4.13 (br s, 2H), 4.05-3.86 (m, 2H), 3.78-3.59 (m, 2H), 2.74 (q, J=7.67 Hz, 2H), 1.20 (t, J=7.6 Hz, 3H).

Example 220

2-((3,5-Dicyano-4-ethyl-6-(4-methyl-1,4-diazepan-1-yl)pyridin-2-yl)thio)-2-(3-fluoropyridin-2-yl) acetamide Step 1: 2-(3-Fluoropyridin-2-yl)-2-hydroxyacetamide

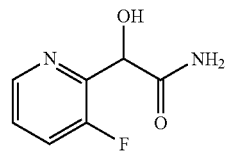 [SMILES: NC(=O)C(O)c1ncccc1F]

To a solution of 3-fluoropicolinaldehyde (1.0 g, 7.99 mmol) in dichloromethane (40 mL) was added trimethylsilanecarbonitrile (1.300 mL, 10.39 mmol). The mixture was stirred at room temperature overnight. The mixture was concentrated down to afford a brown oil, which was treated with conc. H₂SO₄ (5 mL, 94 mmol) for 4 hours, then poured the reaction mixture into ice, and adjusted the pH to 9 using NH₄OH. The reaction mixture was concentrated down with Celite®, purified by silica column (CombiFlash®, 40 g column) using 0-10% MeOH/DCM to afford 2-(3-fluoropyridin-2-yl)-2-hydroxyacetamide (1.21 g, 7.11 mmol, 89% yield) as an off-white solid. LCMS m/z=171.0 [M+H]⁺.

Step 2: 2-Amino-1-(3-fluoropyridin-2-yl)-2-oxoethyl methanesulfonate

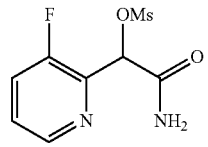 [SMILES: CS(=O)(=O)OC(C(N)=O)c1ncccc1F]

To a slurry of 2-(3-fluoropyridin-2-yl)-2-hydroxyacetamide (1.21 g, 7.11 mmol) and TEA (1.982 mL, 14.22 mmol) in THF (35 mL) and dichloromethane (15.0 mL) was added methanesulfonyl chloride (0.665 mL, 8.53 mmol) dropwise. The reaction mixture was stirred at room tem-

Step 3: 2-((3,5-Dicyano-4-ethyl-6-(4-methyl-1,4-diazepan-1-yl)pyridin-2-yl)thio)-2-(3-fluoropyridin-2-yl)acetamide

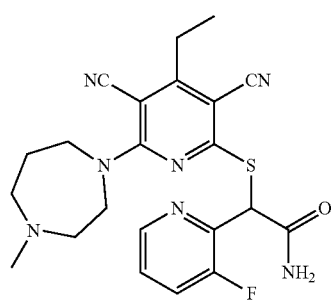 [SMILES: CCc1c(C#N)c(SC(C(N)=O)c2ncccc2F)nc(N2CCCN(C)CC2)c1C#N]

To a solution of 2,6-dichloro-4-ethylpyridine-3,5-dicarbonitrile (synthesis described in example 3, step 2, 110 mg, 0.487 mmol) in DMF (3 mL) was added the solution of 1-methyl-1,4-diazepane (0.069 mL, 0.535 mmol) in DMF (1.5 mL) dropwise. After stirring for 60 minutes, potassium thioacetate (72.2 mg, 0.633 mmol) and TEA (0.203 mL, 1.460 mmol) were added to the reaction mixture, which was stirred at 50° C. for additional 1 hour. Then 2-amino-1-(3-fluoropyridin-2-yl)-2-oxoethyl methanesulfonate (133 mg, 0.535 mmol) was added to the reaction solution. The reaction mixture was stirred at room temperature overnight. The reaction mixture was purified by silica (CombiFlash®, 24 g column using 0-20% MeOH/DCM as eluent). The resulting fractions were concentrated down and the residue was triturated with methanol to afford 2-((3,5-dicyano-4-ethyl-6-(4-methyl-1,4-diazepan-1-yl)pyridin-2-yl)thio)-2-(3-fluoropyridin-2-yl)acetamide (67 mg, 0.148 mmol, 30% yield) as an off-white solid. LCMS m/z=454.2 [M+H]$^+$. $^1$H NMR (400 MHz, DMSO-d$_6$) δ ppm 1.23 (t, J=7.6 Hz, 3H), 2.03 (br. s, 2H), 2.30 (s, 3H), 2.40 (br. s, 2H), 2.77-2.82 (m, 2H), 3.09 (d, J=6.6 Hz, 2H), 3.79-4.10 (m, 4H), 5.96 (s, 1H), 7.51 (quin, J=4.2 Hz, 2H), 7.74 (s, 1H), 7.78-7.86 (m, 1H), 8.43 (d, J=4.8 Hz, 1H).

Example 221

2-((3,5-Dicyano-4-ethyl-6-(4-methyl-1,4-diazepan-1-yl)pyridin-2-yl)thio)-2-(5-methoxypyridin-2-yl)acetamide

Step 1: 2-Hydroxy-2-(5-methoxypyridin-2-yl)acetamide

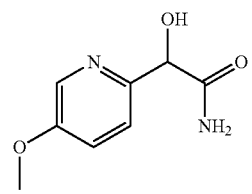

To a solution of 5-methoxypicolinaldehyde (1.0 g, 7.29 mmol) in dichloromethane (40 mL) was added trimethylsilanecarbonitrile (1.095 mL, 8.75 mmol). The mixture was stirred at room temperature overnight. The mixture was concentrated down to afford a brown oil. The above crude was treated with conc. H$_2$SO$_4$ (5 mL, 94 mmol) for 4 hours, then poured the reaction mixture into ice, and adjusted the pH to 9 using NH$_4$OH. The reaction mixture was concentrated down with Celite®, purified by silica column (CombiFlash®, 40 g column) using 0-10% MeOH/DCM to afford 2-hydroxy-2-(5-methoxypyridin-2-yl) acetamide (1.09 g, 5.98 mmol, 82% yield) as a beige solid. LCMS m/z=183.0 [M+H]$^+$.

Step 2: 2-Amino-1-(5-methoxypyridin-2-yl)-2-oxoethyl methanesulfonate

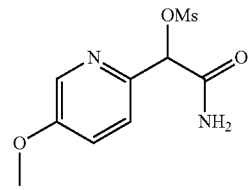 [SMILES: COc1ccc(C(OS(C)(=O)=O)C(N)=O)nc1]

To a slurry solution of 2-hydroxy-2-(5-methoxypyridin-2-yl)acetamide (1.09 g, 5.98 mmol) and TEA (1.668 mL, 11.97 mmol) in THF (35 mL) was added methanesulfonyl chloride (0.559 mL, 7.18 mmol), The reaction mixture was stirred at room temperature overnight. The reaction mixture was diluted with DCM and water, separated the layers. The aqueous layer was extracted with DCM (4×). The combined organics were washed with brine, dried over Na$_2$SO$_4$, concentrated down. The residue was triturated with DCM to afford 2-amino-1-(5-methoxypyridin-2-yl)-2-oxoethyl methanesulfonate (533 mg, 2.048 mmol, 34% yield) as a yellow solid. LCMS m/z=261.0 [M+H]$^+$.

Step 3: 2-((3,5-Dicyano-4-ethyl-6-(4-methyl-1,4-diazepan-1-yl)pyridin-2-yl)thio)-2-(5-methoxypyridin-2-yl)acetamide

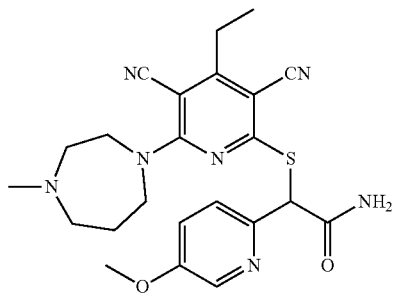 [SMILES: CCc1c(C#N)c(SC(C(N)=O)c2ccc(OC)cn2)nc(N2CCCN(C)CC2)c1C#N]

To a solution of 2,6-dichloro-4-ethylpyridine-3,5-dicarbonitrile (synthesis described in example 3, step 2, 110 mg, 0.487 mmol) in DMF (3 mL) was added the solution of 1-methyl-1,4-diazepane (0.069 mL, 0.535 mmol) in DMF (1.5 mL) dropwise. After stirring for 60 minutes, potassium thioacetate (72.2 mg, 0.633 mmol) and TEA (0.203 mL, 1.460 mmol) were added to the reaction mixture, which was stirred for additional 3 hours. Then 2-amino-1-(5-methoxypyridin-2-yl)-2-oxoethyl methanesulfonate (139 mg, 0.535 mmol) was added to the reaction solution. The reaction mixture was stirred at room temperature overnight. The slurry reaction mixture was diluted with water (40 mL), and stirred for 20 minutes. The solid was filtered and triturated with methanol to afford 2-((3,5-dicyano-4-ethyl-6-(4-methyl-1,4-diazepan-1-yl)pyridin-2-yl)thio)-2-(5-methoxypyridin-2-yl)acetamide (85 mg, 0.183 mmol, 38% yield) as an off-white solid. LCMS m/z=466.3 [M+H]$^+$. $^1$H NMR (400 MHz, DMSO-d$_6$) δ ppm 1.22 (t, J=7.6 Hz, 3H), 1.87-1.98 (m, 2H), 2.24 (s, 3H), 2.41-2.49 (m, 2H), 2.54-2.59 (m, 1H), 2.60-2.69 (m, 1H), 2.77 (q, J=7.4 Hz, 2H), 3.83 (s, 3H), 3.84-3.98 (m, 4H), 5.58 (s, 1H), 7.34-7.46 (m, 2H), 7.55 (d, J=8.6 Hz, 1H), 7.83 (s, 1H), 8.25 (d, J=2.5 Hz, 1H).

Example 222

2-((3,5-Dicyano-4-ethyl-6-(4-(1-hydroxy-2-methylpropan-2-yl)piperazin-1-yl)pyridin-2-yl)thio)-2-(4-fluorophenyl)acetamide

Step 1: 2-Chloro-4-ethyl-6-(4-(1-hydroxy-2-methylpropan-2-yl)piperazin-1-yl)pyridine-3,5-dicarbonitrile

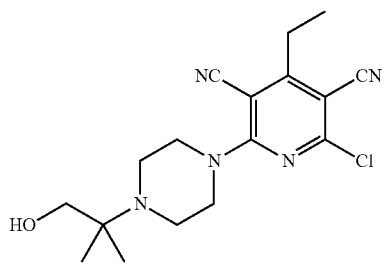 [SMILES: CCc1c(C#N)c(Cl)nc(N2CCN(C(C)(C)CO)CC2)c1C#N]

To a solution of 2-methyl-2-(piperazin-1-yl)propan-1-ol hydrochloride (691 mg, 2.99 mmol) in dichloromethane (5 mL) were added triethylamine (1.136 mL, 8.15 mmol) and 2,6-dichloro-4-ethylpyridine-3,5-dicarbonitrile (synthesis described in example 3 step 2, 615 mg, 2.72 mmol) at 0° C. The reaction mixture was stirred for 2 hours at 27° C. The reaction mixture was quenched with ice cold water (50 mL) and extracted with DCM (3×50 mL). The combined organic layers were washed with water (2×50 mL), dried over Na$_2$SO$_4$, filtered and concentrated under vacuum to afford 2-chloro-4-ethyl-6-(4-(1-hydroxy-2-methylpropan-2-yl)piperazin-1-yl)pyridine-3,5-dicarbonitrile (800 mg) as an off white solid. LCMS m/z=348.1 [M+H]$^+$.

Step 2: 2-((3,5-Dicyano-4-ethyl-6-(4-(1-hydroxy-2-methylpropan-2-yl)piperazin-1-yl)pyridin-2-yl)thio)-2-(4-fluorophenyl)acetamide

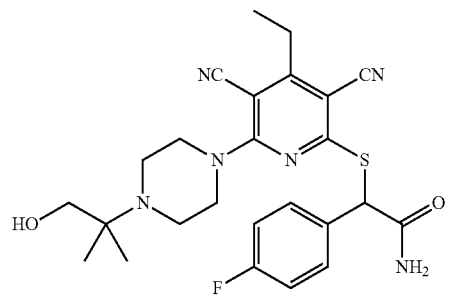 [SMILES: CCc1c(C#N)c(SC(C(N)=O)c2ccc(F)cc2)nc(N2CCN(C(C)(C)CO)CC2)c1C#N]

To a solution of 2-amino-1-(4-fluorophenyl)-2-oxoethyl methanesulfonate (synthesis described in example 207 step 3, 604 mg, 2.150 mmol) in N,N-dimethylformamide (10 mL) was added potassium thioacetate (327 mg, 2.87 mmol) at room temperature. The reaction mixture was stirred at room temperature for 2 hours. Then potassium carbonate (396 mg, 2.87 mmol) was added at the same temperature and the reaction was stirred for 2 hours. After this, 2-chloro-4-ethyl-6-(4-(1-hydroxy-2-methylpropan-2-yl)piperazin-1-yl)pyridine-3,5-dicarbonitrile (500 mg, 1.433 mmol) was added at room temperature and the reaction mixture was stirred for 16 hours at room temperature. The reaction mixture was quenched with ice water (12 mL) and extracted with ethyl acetate (30 mL). The combined organics were dried over sodium sulphate, filtered and concentrated. The crude product was purified by silica-gel column chromatography (100-200 mesh, eluting with 2-3% methanol in DCM) to afford a pale brown solid which was washed with a mixture of 70% ethyl acetate in diethyl ether (30 mL), filtered and dried to afford 2-((3,5-dicyano-4-ethyl-6-(4-(1-hydroxy-2-methylpropan-2-yl)piperazin-1-yl)pyridin-2-yl)thio)-2-(4-fluorophenyl)acetamide (250 mg, 34% yield). LCMS m/z=497.2 [M+H]$^+$. $^1$H NMR (400 MHz, DMSO-d$_6$) δ ppm 7.90 (s, 1H), 7.60-7.49 (m, 2H), 7.34 (s, 1H), 7.22 (t, J=8.77 Hz, 2H), 5.56 (s, 1H), 4.34 (br s, 1H), 3.85 (br s, 4H), 3.31 (br d, J=5.26 Hz, 2H), 2.75 (q, J=7.53 Hz, 2H), 2.69-2.52 (m, 4H), 1.20 (t, J=7.6 Hz, 3H), 1.09-0.78 (m, 6H).

Example 223

2-((3,5-Dicyano-4-ethyl-6-(4-methyl-1,4-diazepan-1-yl)pyridin-2-yl)thio)-2-(3-(trifluoromethyl)phenyl)acetamide

Step 1: 2-Hydroxy-2-(3-(trifluoromethyl)phenyl)acetamide

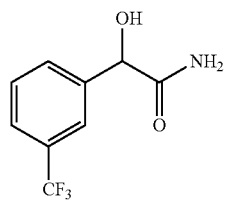 [SMILES: NC(=O)C(O)c1cccc(C(F)(F)F)c1]

To a solution of CDI (324 mg, 1.999 mmol) in N,N-dimethylformamide (0.5 mL) at 20° C. was added a solution of 2-hydroxy-2-(3-(trifluoromethyl) phenyl)acetic acid (220 mg, 0.999 mmol) in N,N-dimethylformamide (0.5 mL) dropwise. The reaction mixture was then stirred at 20° C. for 1 hour at which time the mixture was added the ammonium hydroxide (2.6 mL, 20.03 mmol) while stirring at 20° C. The reaction mixture was then stirred at the same temperature overnight. After stirring overnight at room temperature, the reaction mixture was concentrated and the resulting material was purified by reverse phase HPLC (Gilson, 30 mm Gemini Column, NH$_4$OH modifier) to afford 2-hydroxy-2-(3-(trifluoromethyl)phenyl)acetamide (95 mg, 0.433 mmol) as a pale yellow solid. LCMS m/z=220 [M+H]$^+$.

Step 2: 2-Amino-2-oxo-1-(3-(trifluoromethyl)phenyl)ethyl methanesulfonate

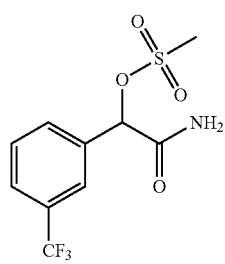 [SMILES: CS(=O)(=O)OC(C(N)=O)c1cccc(C(F)(F)F)c1]

To a solution of 2-hydroxy-2-(3-(trifluoromethyl) phenyl)acetamide (95 mg, 0.433 mmol), DIEA (0.091 mL, 0.520 mmol), and DMAP (5 mg, 0.041 mmol) in dichloromethane (2.0 mL) at 0° C. was added methanesulfonyl chloride (0.034 mL, 0.433 mmol). The reaction mixture was then warmed to 20° C. and stirred at the same temperature overnight. The reaction mixture was diluted with DCM and washed with 1N HCl (2×), sat. brine (1×), and then water. The organic layer was then dried (MgSO$_4$) and concentrated to obtain 2-amino-2-oxo-1-(3-(trifluoromethyl)phenyl)ethyl methanesulfonate (128 mg, 0.431 mmol) as an orange gum. LCMS m/z=298 [M+H]$^+$.

Step 3: 2-((3,5-Dicyano-4-ethyl-6-(4-methyl-1,4-diazepan-1-yl)pyridin-2-yl)thio)-2-(3-(trifluoromethyl)phenyl)acetamide

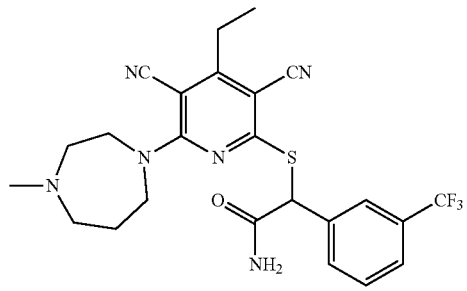 [SMILES: CCc1c(C#N)c(SC(C(N)=O)c2cccc(C(F)(F)F)c2)nc(N2CCCN(C)CC2)c1C#N]

To a suspension of 4-ethyl-2-mercapto-6-(4-methyl-1,4-diazepan-1-yl) pyridine-3,5-dicarbonitrile (synthesis described in example 69, step 1, 24 mg, 0.080 mmol) and 2-amino-2-oxo-1-(3-(trifluoromethyl)phenyl)ethyl methanesulfonate (49 mg, 0.165 mmol) in N,N-dimethylformamide (0.5 mL) at room temperature was added Et$_3$N (0.022 mL, 0.159 mmol). The reaction mixture was then stirred at room temperature overnight. The reaction mixture was filtered. The filtrate was purified by reverse phase HPLC (Gilson, 30 mm Gemini Column, NH$_4$OH modifier) to obtain 2-((3,5-dicyano-4-ethyl-6-(4-methyl-1,4-diazepan-1-yl)pyridin-2-yl)thio)-2-(3-(trifluoromethyl)phenyl)acetamide (13 mg, 0.026 mmol) as a light tan solid. LCMS m/z=503 [M+H]$^+$. $^1$H NMR (400 MHz, DMSO-d$_6$) δ ppm 8.07 (s, 1H), 7.88 (s, 1H), 7.84 (d, J=7.86 Hz, 1H), 7.73 (d, J=7.86 Hz, 1H), 7.65 (t, J=7.73 Hz, 1H), 7.48 (s, 1H), 5.67 (s, 1H), 3.76-3.96 (m, 4H), 2.77 (q, J=7.35 Hz, 2H), 2.56-2.68 (m, 2H), 2.42-2.49 (m, 2H), 2.24 (s, 3H), 1.92 (br. s., 2H), 1.21 (t, J=7.60 Hz, 3H).

Example 224

2-((3,5-Dicyano-4-ethyl-6-(4-(2-hydroxyethoxy)piperidin-1-yl)pyridin-2-yl)thio)-2-phenylacetamide

Step 1: 2-(Pyridin-4-yloxy)ethanol

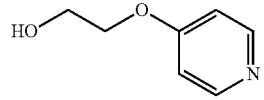

A mixture of pyridin-4(1H)-one (10 g, 105 mmol), 2-bromoethanol (15.77 g, 126 mmol) and K$_2$CO$_3$ (29.1 g, 210 mmol) in N,N-dimethylformamide (100 mL) was stirred at 130° C. overnight. The resultant mixture was cooled and concentrated in vacuo. The residue was diluted with MeOH (200 mL), and the suspension was filtered and concentrated in vacuo. The residue was purified by silica gel chromatography eluting with CH$_2$Cl$_2$/MeOH to give 2-(pyridin-4-yloxy)ethanol (2 g, 12% yield). LCMS m/z=140.1 [M+H]$^+$.

Step 2: 2-(Piperidin-4-yloxy)ethanol

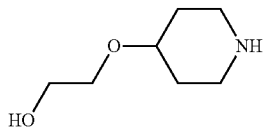

To a solution of 2-(pyridin-4-yloxy)ethanol (1.5 g, 10.78 mmol) in acetic acid (30 mL) was added PtO$_2$ (500 mg). The resultant mixture was stirred at 60° C. under 0.4 MPa of H$_2$ overnight. The resultant mixture was filtered and concentrated in vacuo to give 2-(piperidin-4-yloxy)ethanol (3 g) as a colorless oil. LCMS m/z=146.2 [M+H]$^+$.

Step 3: 2-Chloro-4-ethyl-6-(4-(2-hydroxyethoxy) piperidin-1-yl)pyridine-3,5-dicarbonitrile

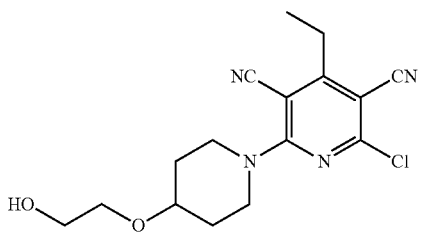 [SMILES: CCc1c(C#N)c(Cl)nc(N2CCC(OCCO)CC2)c1C#N]

To a solution of 2-(piperidin-4-yloxy)ethanol (437 mg, 3.01 mmol) and triethylamine (913 mg, 9.02 mmol) in dichloromethane (10 mL) was added 2,6-dichloro-4-ethylpyridine-3,5-dicarbonitrile (synthesis described in example 3, step 2, 680 mg, 3.01 mmol). The resultant mixture was stirred room temperature overnight and then combined with a previous similar reaction run on approximately half scale. The combined material was concentrated in vacuo and purified by silica gel column chromatography eluting with DCM/EtOAc (1/1) to give 2-chloro-4-ethyl-6-(4-(2-hydroxyethoxy)piperidin-1-yl)pyridine-3,5-dicarbonitrile (600 mg). $^1$H NMR (400 MHz, DMSO-d$_6$) δ ppm 4.61 (t, J=5.3 Hz, 1H), 4.08 (m, 2H), 3.72-3.61 (m, 3H), 3.49 (m, 4H), 2.84 (q, J=7.6 Hz, 2H), 2.02-1.89 (m, 2H), 1.68-1.52 (m, 2H), 1.25 (t, J=7.6 Hz, 3H).

Step 4: 2-(3,5-Dicyano-4-ethyl-6-(4-(2-hydroxyethoxy)piperidin-1-yl)pyridin-2-ylthio)-2-phenylacetamide

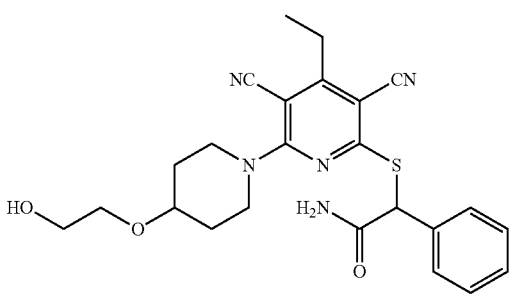 [SMILES: CCc1c(C#N)c(SC(C(N)=O)c2ccccc2)nc(N2CCC(OCCO)CC2)c1C#N]

To a solution of 2-chloro-4-ethyl-6-(4-(2-hydroxyethoxy) piperidin-1-yl)pyridine-3,5-dicarbonitrile (334 mg, 0.998 mmol) in N,N-dimethylformamide (5 mL) was added potassium ethanethioate (171 mg, 1.496 mmol) at room temperature. The mixture was stirred at room temperature for 3 hours then treated with K$_2$CO$_3$ (276 mg, 1.995 mmol). The resultant mixture was stirred at room temperature for another 1 hour then treated with 2-amino-2-oxo-1-phenylethyl methanesulfonate (synthesis described in example 3, step 5, 229 mg, 0.998 mmol). The resultant mixture was stirred at room temperature overnight then concentrated in vacuo and the residue was diluted with EtOAc (50 mL). The organic phase was washed with water (10 mL) and saturated brine (10 mL), dried over sodium sulfate and evaporated in vacuo to give the crude product as a brown solid. The crude product was added to a prep-HPLC column and was eluted with Me-CN/TFA 0.1% to give 2-((3,5-dicyano-4-ethyl-6-(4-(2-hydroxyethoxy)piperidin-1-yl)pyridin-2-yl)thio)-2-phenylacetamide (110 mg, 23% yield). LCMS m/z=466.1 [M+H]$^+$. $^1$H NMR (400 MHz, DMSO-d$_6$) δ ppm 7.92 (s, 1H), 7.52 (d, J=7.2 Hz, 2H), 7.42-7.31 (m, 4H), 5.53 (s, 1H), 4.60 (s, 1H), 4.12 (m, 2H), 3.69-3.57 (m, 3H), 3.50 (dt, J=8.0, 3.9 Hz, 4H), 2.76 (q, J=7.6 Hz, 2H), 1.93 (s, 2H), 1.64-1.50 (m, 2H), 1.21 (t, J=7.6 Hz, 3H).

Example 225

2-((3,5-Dicyano-4-ethyl-6-(4-methyl-1,4-diazepan-1-yl) pyridin-2-yl)thio-2-(2-fluoropyridin-3-yl)acetamide

Step 1: 2-(2-Fluoropyridin-3-yl)-2-hydroxyacetamide

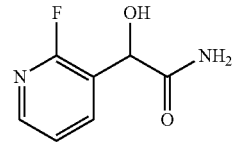 [SMILES: NC(=O)C(O)c1cccnc1F]

To a solution of 2-fluoronicotinaldehyde (1.1 g, 8.79 mmol) in dichloromethane (30 mL) was added trimethylsilanecarbonitrile (1.210 mL, 9.67 mmol). The mixture was stirred at room temperature overnight. The mixture was concentrated down to afford a brown oil, which was treated with conc. H$_2$SO$_4$ (5 mL, 94 mmol) for 4 hours, then poured the reaction mixture into ice, and adjusted the pH to 9 using NH$_4$OH. The reaction mixture was concentrated down with Celite®, purified by silica column (CombiFlash®, 40 g column) using 0-15% MeOH/DCM to afford 2-(2-fluoropyridin-3-yl)-2-hydroxyacetamide (911 mg, 5.35 mmol, 61% yield) as a yellow wax solid. LCMS m/z=171.0 [M+H]$^+$.

Step 2: 2-Amino-1-(2-fluoropyridin-3-yl)-2-oxoethyl methanesulfonate

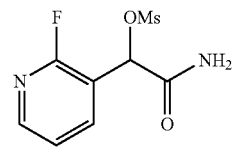

To a slurry solution of 2-(2-fluoropyridin-3-yl)-2-hydroxyacetamide (899 mg, 5.28 mmol) and TEA (1.473 mL, 10.57 mmol) in THF (30 mL) was added methanesulfonyl chloride (0.494 mL, 6.34 mmol) dropwise, The reaction mixture was stirred at room temperature overnight. The reaction mixture was diluted with DCM and water, separated the layers. The aqueous layer was extracted with DCM (2×). The combined organics were washed with brine, dried over $Na_2SO_4$, concentrated down. The residue was triturated with DCM to afford 2-amino-1-(2-fluoropyridin-3-yl)-2-oxoethyl methanesulfonate (525 mg, 2.115 mmol, 40% yield) as a beige solid. LCMS m/z=249.0 $[M+H]^+$.

Step 3: 2-((3,5-Dicyano-4-ethyl-6-(4-methyl-1,4-diazepan-1-yl) pyridin-2-yl)thio)-2-(2-fluoropyridin-3-yl)acetamide

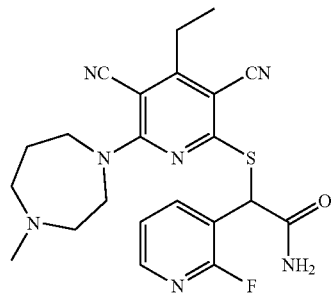 [SMILES: CCc1c(C#N)c(SC(C(N)=O)c2cccnc2F)nc(N2CCCN(C)CC2)c1C#N]

To a solution of 2,6-dichloro-4-ethylpyridine-3,5-dicarbonitrile (synthesis described in example 3, step 2, 110 mg, 0.487 mmol) in DMF (3 mL) was added the solution of 1-methyl-1,4-diazepane (0.069 mL, 0.535 mmol) in DMF (1.5 mL) dropwise. After stirring for 60 minutes, potassium thioacetate (72.2 mg, 0.633 mmol) and TEA (0.203 mL, 1.460 mmol) were added to the reaction mixture, which was stirred for additional 3 hours. Then 2-amino-1-(2-fluoropyridin-3-yl)-2-oxoethyl methanesulfonate (133 mg, 0.535 mmol) was added to the reaction solution. The reaction mixture was stirred at room temperature overnight. The reaction mixture was diluted with water and extracted with EtOAc (3×). The combined organics were washed with brine and dried over $Na_2SO_4$, concentrated down and purified by silica (CombiFlash®, 24 g column) using 10-20% MeOH/DCM as eluent. The resulting fractions were concentrated down to afford 2-((3,5-dicyano-4-ethyl-6-(4-methyl-1,4-diazepan-1-yl) pyridin-2-yl)thio)-2-(2-fluoropyridin-3-yl)acetamide (101 mg, 0.223 mmol, 46% yield) as a light yellow solid. LCMS m/z=454.2 $[M+H]^+$. 1H NMR (400 MHz, DMSO-$d_6$) [ ppm 1.22 (t, J=7.5 Hz, 3H), 1.77-1.96 (m, 2H), 2.22 (s, 3H), 2.36-2.49 (m, 3H), 2.58-2.69 (m, 1H), 2.78 (q, J=7.6 Hz, 2H), 3.75-3.94 (m, 4H), 5.77 (s, 1H), 7.36-7.45 (m, 1H), 7.60 (s, 1H), 8.00-8.08 (m, 2H), 8.22 (d, J=4.8 Hz, 1H)

Example 228

2-((3,5-Dicyano-4-ethyl-6-(4-methyl-1,4-diazepan-1-yl) pyridin-2-yl)thio-2-(6-fluoropyridin-3-yl)acetamide Step 1: 2-(6-Fluoropyridin-3-yl)-2-hydroxyacetamide

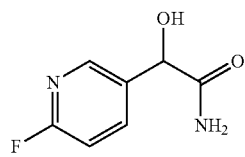

To a slurry solution of 6-fluoronicotinaldehyde (1.0 g, 7.99 mmol) in dichloromethane (40 mL) was added trimethylsilanecarbonitrile (1.200 mL, 9.59 mmol). The mixture was stirred at room temperature overnight. The slurry mixture was concentrated down to afford a brown wax oil, which was treated with conc. $H_2SO_4$ (5 mL, 94 mmol) for 4 hours, then poured the slurry reaction mixture into ice, and adjusted the pH to 9 using $NH_4OH$. The mixture was filtered to get rid of solid and the mother liquor was concentrated down with Celite®, purified by silica column (CombiFlash®, 40 g column) using 0-15% MeOH/DCM to afford 2-(6-fluoropyridin-3-yl)-2-hydroxyacetamide (235 mg, 1.381 mmol, 17% yield) as a yellow wax. LCMS m/z=170.9 $[M+H]^+$.

Step 2: 2-Amino-1-(6-fluoropyridin-3-yl)-2-oxoethyl methanesulfonate

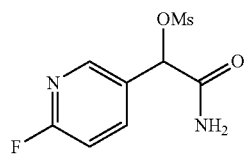

To a slurry solution of 2-(6-fluoropyridin-3-yl)-2-hydroxyacetamide (235 mg, 1.381 mmol) and TEA (0.385 mL, 2.76 mmol) in THF (12 mL) was added methanesulfonyl chloride (0.129 mL, 1.657 mmol) dropwise. The reaction mixture was stirred at room temperature overnight. The reaction mixture was concentrated down and purified by silica column(CombiFlash®, 24 g column, 0-10% MeOH/DCM) to afford 2-amino-1-(6-fluoropyridin-3-yl)-2-oxoethyl methanesulfonate (288 mg, 1.160 mmol, 84% yield) as an off-white solid. LCMS m/z=249.0 $[M+H]^+$.

Step 3: 2-((3,5-Dicyano-4-ethyl-6-(4-methyl-1,4-diazepan-1-yl) pyridin-2-yl)thio)-2-(6-fluoropyridin-3-yl)acetamide

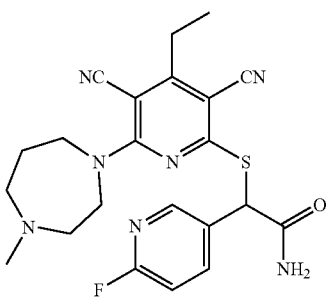 [SMILES: CCc1c(C#N)c(SC(C(N)=O)c2ccc(F)nc2)nc(N2CCCN(C)CC2)c1C#N]

To a solution of 2,6-dichloro-4-ethylpyridine-3,5-dicarbonitrile (synthesis described in example 3, step 2, 110 mg, 0.487 mmol) in DMF (3 mL) was added the solution of 1-methyl-1,4-diazepane (0.069 mL, 0.535 mmol) in DMF (1.5 mL) dropwise. After stirring for 60 minutes, potassium thioacetate (72.2 mg, 0.633 mmol) and TEA (0.203 mL, 1.460 mmol) were added to the reaction mixture, which was stirred for additional 3 hours. Then 2-amino-1-(6-fluoropyridin-3-yl)-2-oxoethyl methanesulfonate (121 mg, 0.487 mmol) was added to the reaction solution. The reaction mixture was stirred at room temperature overnight. The reaction mixture was purified by silica (CombiFlash®, 24 g column) using 10-20% MeOH/DCM as eluent. The resulting fractions were concentrated down and triturated with methanol to afford 2-((3,5-dicyano-4-ethyl-6-(4-methyl-1,4-diazepan-1-yl)pyridin-2-yl)thio)-2-(6-fluoropyridin-3-yl)acetamide (56 mg, 0.123 mmol, 25% yield) as a white solid. LCMS m/z=454.2 [M+H]$^+$. $^1$H NMR (400 MHz, DMSO-d) δ ppm 1.21 (t, J=7.6 Hz, 3H), 1.84-2.00 (m, 2H), 2.25 (s, 3H), 2.42-2.49 (m, 2H), 2.53-2.62 (m, 1H), 2.62-2.73 (m, 1H), 2.77 (q, J=7.4 Hz, 2H), 6 3.79-3.99 (m, 4H), 5.64 (s, 1H), 7.24 (dd, J=8.5, 2.7 Hz, 1H), 7.52 (s, 1H), 8.00-8.13 (m, 2H), 8.36 (d, J=2.5 Hz, 1H)

Example 230

3-((6-(2-Amino-2-oxo-1-phenylethylthio)-3,5-dicyano-4-ethylpyridin-2-yl)(methyl)amino)propanamide Step 1: Methyl 3-((6-chloro-3,5-dicyano-4-ethylpyridin-2-yl)(methyl)amino)propanoate

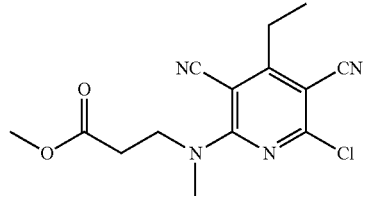 [SMILES: CCc1c(C#N)c(Cl)nc(N(C)CCC(=O)OC)c1C#N]

To a solution of methyl 3-(methylamino)propanoate (1 g) and triethylamine (3.46 g, 34.1 mmol) in dichloromethane (30 mL) was added 2,6-dichloro-4-ethylpyridine-3,5-dicarbonitrile (synthesis described in example 3, step 2, 1.930 g, 8.54 mmol) at room temperature. The resultant mixture was stirred at room temperature for 3 hours then concentrated in vacuo. The residue was added to a silica gel column and was eluted with Hexane/EtOAc (1:1) to give methyl 3-((6-chloro-3,5-dicyano-4-ethylpyridin-2-yl)(methyl)amino)propanoate (350 mg, 0.685 mmol). LCMS m/z=307.0 [M+H]$^+$.

Step 2: Methyl 3-((6-((2-amino-2-oxo-1-phenylethyl)thio)-3,5-dicyano-4-ethylpyridin-2-yl)(methyl)amino)propanoate

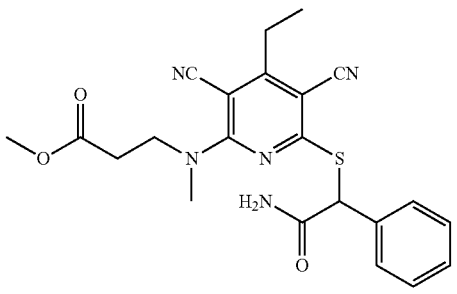 [SMILES: CCc1c(C#N)c(SC(C(N)=O)c2ccccc2)nc(N(C)CCC(=O)OC)c1C#N]

To a solution of methyl 3-((6-chloro-3,5-dicyano-4-ethylpyridin-2-yl)(methyl)amino)propanoate (350 mg, 1.141 mmol) in N,N-dimethylformamide (15 mL) was added potassium ethanethioate (195 mg, 1.712 mmol). The mixture was stirred at room temperature for 2 hours then treated with K$_2$CO$_3$ (315 mg, 2.282 mmol). The resultant mixture was stirred at room temperature for 1 hour then treated with 2-amino-2-oxo-1-phenylethyl methanesulfonate (synthesis described in example 3, step 5, 262 mg, 1.141 mmol). The resultant mixture was stirred at room temperature overnight then concentrated in vacuo. The residue was diluted with EtOAc (50 mL). The organic phase was washed with water (25 mL) and saturated brine (25 mL), dried over sodium sulphate and evaporated in vacuo to give the crude product as a brown solid. The crude product was added to a silica gel column and was eluted with hexane/EtOAc (1:3) to give methyl 3-((6-((2-amino-2-oxo-1-phenylethyl)thio)-3,5-dicyano-4-ethylpyridin-2-yl)(methyl)amino)propanoate (300 mg, 0.549 mmol, 48% yield). LCMS m/z=438.1 [M+H]$^+$.

Step 3: 3-((6-(2-Amino-2-oxo-1-phenylethylthio)-3,5-dicyano-4-ethylpyridin-2-yl)(methyl)amino)propanamide

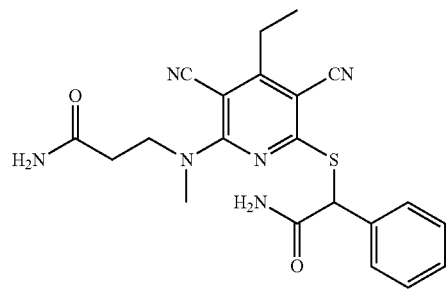 [SMILES: CCc1c(C#N)c(SC(C(N)=O)c2ccccc2)nc(N(C)CCC(N)=O)c1C#N]

A mixture of methyl 3-((6-((2-amino-2-oxo-1-phenylethyl)thio)-3,5-dicyano-4-ethylpyridin-2-yl)(methyl)amino)propanoate (240 mg, 0.549 mmol) and NH$_3$ in MeOH (7 M, 20 mL) was stirred at room temperature overnight. In a second batch, a mixture of methyl 3-((6-((2-amino-2-oxo-1-phenylethyl)thio)-3,5-dicyano-4-ethylpyridin-2-yl)(methyl)amino)propanoate (30 mg, 0.069 mmol) and NH₃ in MeOH (7 M, 2 mL) was stirred overnight at room temperature. The two reaction mixtures were combined and concentrated in vacuo, and the residue was purified by silica gel chromatography (eluting with DCM/MeOH, 20:1) to give 3-((6-((2-amino-2-oxo-1-phenylethyl)thio)-3,5-dicyano-4-ethylpyridin-2-yl)(methyl)amino)propanamide (120 mg). LCMS m/z=423.1 [M+H]⁺. ¹H NMR (400 MHz, DMSO) δ ppm 7.94 (s, 1H), 7.58 (s, 1H), 7.51 (d, J=7.0 Hz, 2H), 7.41-7.33 (m, 4H), 7.12 (s, 1H), 5.69 (s, 1H), 4.16-4.05 (m, 1H), 3.95-3.85 (m, 1H), 3.37 (s, 3H), 2.77 (d, J=7.6 Hz, 2H), 1.21 (t, J=7.6 Hz, 3H).

Example 231

2-((3,5-Dicyano-4-ethyl-6-(4-(oxetan-3-yloxy)piperidin-1-yl)pyridin-2-yl)thio)-2-phenylacetamide Step 1: 2-Chloro-4-ethyl-6-(4-(oxetan-3-yloxy)piperidin-1-yl)pyridine-3,5-dicarbonitrile

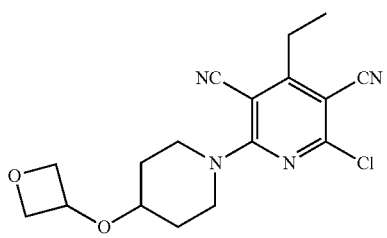 [SMILES: CCc1c(C#N)c(Cl)nc(N2CCC(OC3COC3)CC2)c1C#N]

To a mixture of oxetan-3-yl 4-methylbenzenesulfonate (800 mg, 3.50 mmol) and pyridin-4-ol (367 mg, 3.86 mmol) in N,N-dimethylformamide (10 mL) was added K₂CO₃ (1453 mg, 10.51 mmol). The mixture was heated to 80° C. and stirred for 12 hours. The mixture was poured onto water (20 mL) and extracted with ethyl acetate (20 mL×2). The combined organic layers were concentrated to give crude 4-(oxetan-3-yloxy) pyridine which was combined with a batch of material that was prepared in a similar manner and purified by column chromatography (PE/EA=2/1) to give 4-(oxetan-3-yloxy)-pyridine. To a solution of 4-(oxetan-3-yloxy)pyridine (600 mg, 3.97 mmol) in acetic acid (10 mL) was added platinum(IV) oxide (270 mg, 1.191 mmol). The mixture was heated to 60° C. under hydrogen (4 atm) and stirred for 12 hours. The mixture was filtered and concentrated to give crude 4-(oxetan-3-yloxy)piperidine (600 mg) as a black gum, which was used without further purification. To a solution of 2,6-dichloro-4-ethylpyridine-3,5-dicarbonitrile (synthesis described in example 3 step 2, 863 mg, 3.82 mmol) in dichloromethane (20 mL) was added TEA (2.66 mL, 19.08 mmol) followed by a solution of the crude 4-(oxetan-3-yloxy)piperidine (600 mg) in dichloromethane (20 mL) at 0° C. The mixture was warmed to 25° C. and stirred for 16 hours. The mixture was poured onto water (30 mL), and the organic phase was separated and concentrated to give a residue, which was purified by column chromatography (dichloromethane) to give 2-chloro-4-ethyl-6-(4-(oxetan-3-yloxy)piperidin-1-yl)pyridine-3,5-dicarbonitrile (700 mg, 2.018 mmol) as a brown solid. ¹H NMR (400 MHz, CDCl₃): δ ppm 4.79-4.82 (m, 2H), 4.67-4.71 (m, 3H), 4.11-4.17 (m, 2H), 3.78-3.84 (m, 2H), 3.64-3.69 (m, 1H), 2.96-3.02 (m, 2H), 1.91-1.98 (m, 2H),1.72-1.80 (m, 2H), 1.35-1.39 (m, 3H).

Step 2: 2-((3,5-Dicyano-4-ethyl-6-(4-(oxetan-3-yloxy)piperidin-1-yl)pyridin-2-yl)thio)-2-phenylacetamide

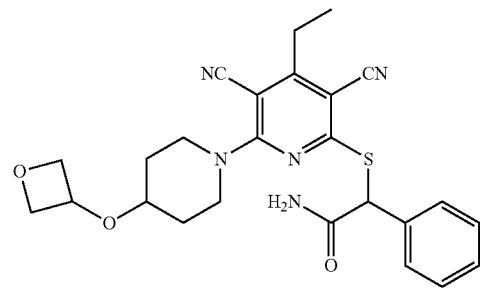 [SMILES: CCc1c(C#N)c(SC(C(N)=O)c2ccccc2)nc(N2CCC(OC3COC3)CC2)c1C#N]

To a solution of 2-chloro-4-ethyl-6-(4-(oxetan-3-yloxy)piperidin-1-yl)pyridine-3,5-dicarbonitrile (346 mg, 0.998 mmol) in N,N-dimethylformamide (15 mL) was added potassium ethanethioate (137 mg, 1.197 mmol). The mixture was stirred at 25° C. for 2 hours. Triethylamine (0.486 mL, 3.48 mmol) and 2-amino-2-oxo-1-phenylethyl methanesulfonate (synthesis described in example 3 step 5, 266 mg, 1.161 mmol) were then added. The mixture was stirred at 25° C. for 12 hours. The mixture was concentrated to give a residue, which was purified by column chromatography (dichloromethane/methanol, 100:1). The desired fractions were concentrated, and the resulting solid was then recrystallized from acetonitrile (15 mL) to give 2-((3,5-dicyano-4-ethyl-6-(4-(oxetan-3-yloxy)piperidin-1-yl)pyridin-2-yl)thio)-2-phenylacetamide (100 mg, 0.209 mmol) as an off-white solid. LCMS m/z=478.1 [M+H]⁺. ¹H NMR (400 MHz, DMSO-d₆): δ ppm 7.92 (s, 1H), 7.51-7.53 (m, 2H), 7.34-7.41 (m, 4H), 5.53 (s, 1H), 4.69-4.73 (m, 3H), 4.46 (s, 2H), 4.17-4.20 (m, 2H), 3.64-3.66 (m, 1H), 3.51-3.54 (m, 2H), 2.73-2.79 (m, 2H), 1.87-1.89 (m, 2H), 1.47-1.54 (m, 2H), 1.19-1.23 (m, 3H).

Example 232

2-((3,5-Dicyano-6-(4-((2,2-difluoroethyl) amino-4-methylpiperidin-1-yl)-4-ethylpyridin-2-yl) thio-2-phenylacetamide Step 1:
N-(2,2-Difluoroethyl)-4-methylpiperidin-4-amine

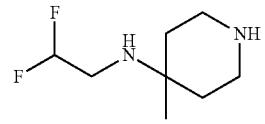

To a solution of benzyl 4-amino-4-methylpiperidine-1-carboxylate (400 mg, 1.611 mmol) in acetonitrile (10 mL) was added N,N-diisopropylethylamine (0.844 mL, 4.83 mmol). The mixture was cooled to 0° C. and 2,2-difluoroethyl trifluoromethanesulfonate (414 mg, 1.933 mmol) was added dropwise with stirring for 20 minutes, followed by warming to room temperature and stirring for 1 hour. The reaction was then heated at 50° C. for 18 hours. The reaction was concentrated, and to the residue was added ethyl acetate followed by washing with water. The organic phase was dried with sodium sulfate, concentrated, and the residue was purified by gradient silica gel chromatography eluting with ethyl acetate-hexane (10-100%) to afford benzyl 4-((2,2-difluoroethyl)amino)-4-methylpiperidine-1-carboxylate (184 mg, 36% yield). LCMS m/z=313.3 [M+H]$^+$. To a solution of the benzyl 4-((2,2-difluoroethyl)amino)-4-methylpiperidine-1-carboxylate (184 mg, 0.589 mmol) in ethanol (20 mL) was added Pd/C (17 mg), and the mixture was shaken under 30 psi hydrogen for 2 hours. The mixture was filtered and concentrated to give N-(2,2-difluoroethyl)-4-methylpiperidin-4-amine (80 mg, 28% yield). LCMS m/z=179.1 [M+H]$^+$.

Step 2: 2-Chloro-6-(4-((2,2-difluoroethyl)amino)-4-methylpiperidin-1-yl)-4-ethylpyridine-3,5-dicarbonitrile

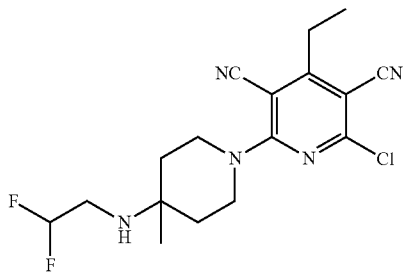 [SMILES: CCc1c(C#N)c(Cl)nc(N2CCC(C)(NCC(F)F)CC2)c1C#N]

2,6-Dichloro-4-ethylpyridine-3,5-dicarbonitrile (synthesis described in example 3, step 2, 95 mg, 0.421 mmol), N-(2,2-difluoroethyl)-4-methylpiperidin-4-amine (75 mg, 0.421 mmol) and N,N-diisopropylethylamine (0.147 mL, 0.842 mmol) were added to tetrahydrofuran (10 mL) and heated to 55° C. with stirring for 2 hours. The solvent was evaporated and the residue was triturated with water. The residue was dissolved in ethyl acetate, washed with water, and dried with sodium sulfate to give 2-chloro-6-(4-((2,2-difluoroethyl)amino)-4-methylpiperidin-1-yl)-4-ethylpyridine-3,5-dicarbonitrile (150 mg, 97% yield) which was used in the next step without further purification. LCMS m/z=368.3 [M+H]$^+$.

Step 3: 2-((3,5-Dicyano-6-(4-((2,2-difluoroethyl) amino)-4-methylpiperidin-1-yl)-4-ethylpyridin-2-yl) thio)-2-phenylacetamide

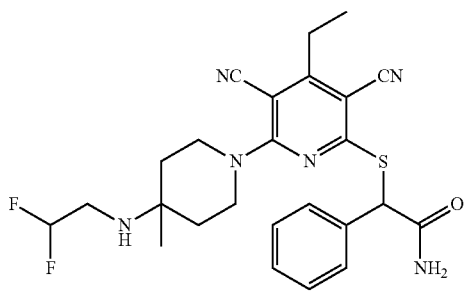 [SMILES: CCc1c(C#N)c(SC(C(N)=O)c2ccccc2)nc(N2CCC(C)(NCC(F)F)CC2)c1C#N]

A solution of S-(2-amino-2-oxo-1-phenylethyl) ethanethioate (synthesis described in Example 62, step 5, 0.111 g, 0.530 mmol) in ethanol (8 mL) was heated to 70° C., and NaBH$_4$ (0.022 g, 0.571 mmol) was added portionwise. After 10 minutes the solution was added portionwise to a 70° C. solution of 2-chloro-6-(4-((2,2-difluoroethyl) amino)-4-methylpiperidin-1-yl)-4-ethylpyridine-3,5-dicarbonitrile (0.150 g, 0.408 mmol) in ethanol (8 mL). After a further 10 minutes the solvent was evaporated and the solid was partitioned between ethyl acetate and water. The mixture was filtered, and the organic phase was dried with sodium sulfate and concentrated. The residue was dissolved in a small amount of dichloromethane and purified by gradient silica gel chromatography using 10-80% ethyl acetate in hexanes as the eluent to afford 2-((3,5-dicyano-6-(4-((2,2-difluoroethyl) amino)-4-methylpiperidin-1-yl)-4-ethylpyridin-2-yl)thio)-2-phenylacetamide (25 mg, 12% yield). LCMS m/z=499.4 [M+H]$^+$. $^1$H NMR (400 MHz, DMSO-d$_6$) δ ppm 1.07 (s, 3H), 1.21 (t, J=8.00 Hz, 3H), 1.39-1.54 (m, 2H), 1.66 (d, J=12.93 Hz, 2H), 1.91-1.98 (m, 1H), 2.75 (q, J=7.35 Hz, 2H), 2.80-2.94 (m, 2H), 3.62-3.76 (m, 2H), 4.01-4.10 (m, 2H), 5.53 (s, 1H), 5.96 (tt, J=60.00, 4.00 Hz, 1H), 7.30-7.42 (m, 4H), 7.48-7.56 (m, 2H), 7.93 (s, 1H).

Example 233

2-((3,5-Dicyano-4-ethyl-6-(4-methyl-1,4-diazepan-1-yl)pyridin-2-yl)thio)-2-(4-(trifluoromethyl)phenyl) acetamide Step 1:
2-Hydroxy-2-(4-(trifluoromethyl)phenyl)acetamide

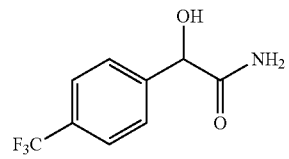 [SMILES: NC(=O)C(O)c1ccc(C(F)(F)F)cc1]

To a solution of CDI (324 mg, 1.999 mmol) in N,N-dimethylformamide (0.5 mL) at 20° C. was added a solution of 2-hydroxy-2-(4-(trifluoromethyl)phenyl)acetic acid (220 mg, 0.999 mmol) in N,N-dimethylformamide (0.5 mL) dropwise. The reaction mixture was then stirred at 20° C. for 1 hour at which time the mixture was added to the ammonium hydroxide (2.6 mL, 20.03 mmol) while stirring at 20° C. The reaction mixture was then stirred at the same temperature overnight. After stirring overnight at 20° C. The reaction mixture was concentrated and the resulting material was purified by reverse phase HPLC (Gilson, 30 mm Gemini Column, NH$_4$OH modifier) to obtain 2-hydroxy-2-(4-(trifluoromethyl)phenyl)acetamide (87 mg) as an off white solid. LCMS m/z=220 [M+H]$^+$.

Step 2:
2-Amino-2-oxo-1-(4-(trifluoromethyl)phenyl)ethyl methanesulfonate

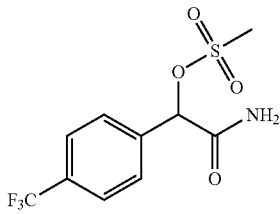 [SMILES: CS(=O)(=O)OC(C(N)=O)c1ccc(C(F)(F)F)cc1]

To a solution of 2-hydroxy-2-(4-(trifluoromethyl)phenyl)acetamide (82 mg, 0.374 mmol), DIEA (0.078 mL, 0.449 mmol), and DMAP (5 mg, 0.041 mmol) in dichloromethane (2.0 mL) at room temperature was added methanesulfonyl chloride (0.035 mL, 0.449 mmol). The reaction mixture was then stirred at the same temperature over the weekend. An additional 0.5 eq of methanesulfonyl chloride was added to the reaction mixture and it was allowed to stir for an additional 24 hours at room temperature. The reaction mixture was diluted with DCM and washed with 1N HCl (2×), saturated brine (1×), and then water. The organic layer was then dried (MgSO$_4$) and concentrated to obtain the crude product. The crude product was purified by normal phase chromatography (Biotage Isolera, 10 g SNAP ULTRA column, DCM/MeOH 0-10%) to obtain 2-amino-2-oxo-1-(4-(trifluoromethyl)phenyl)ethyl methanesulfonate (68 mg) as an off-white solid. LCMS m/z=298 [M+H]$^+$.

Step 3: 2-((3,5-Dicyano-4-ethyl-6-(4-methyl-1,4-diazepan-1-yl)pyridin-2-yl)thio)-2-(4-(trifluoromethyl)phenyl)acetamide

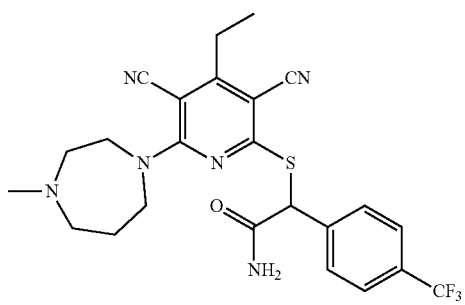 [SMILES: CCc1c(C#N)c(SC(C(N)=O)c2ccc(C(F)(F)F)cc2)nc(N2CCCN(C)CC2)c1C#N]

To a suspension of 4-ethyl-2-mercapto-6-(4-methyl-1,4-diazepan-1-yl) pyridine-3,5-dicarbonitrile (synthesis described in Example 69, Step 1, 68 mg, 0.226 mmol) and 2-amino-2-oxo-1-(4-(trifluoromethyl) phenyl)ethyl methanesulfonate (49 mg, 0.165 mmol) in N,N-dimethylformamide (1.0 mL) at room temperature was added Et$_3$N (0.063 mL, 0.451 mmol). The reaction mixture was then stirred at room temperature overnight (20 hours). The reaction mixture was filtered and the filtrate was purified by reverse phase HPLC (Gilson, 30 mm×50 mm Gemini Column, NH$_4$OH modifier) to afford 2-((3,5-dicyano-4-ethyl-6-(4-methyl-1,4-diazepan-1-yl)pyridin-2-yl)thio)-2-(4-(trifluoromethyl)phenyl)acetamide (44 mg, 0.088 mmol) as a light yellow solid. LCMS m/z=503.5 [M+H]$^+$. $^1$H NMR (400 MHz, DMSO-d$_6$) δ ppm 8.08 (s, 1H), 7.76 (q, J=8.36 Hz, 4H), 7.50 (s, 1H), 5.66 (s, 1H), 3.76-3.96 (m, 4H), 2.77 (q, J=7.60 Hz, 2H), 2.61 (d, J=4.31 Hz, 2H), 2.38-2.48 (m, 2H), 2.22 (s, 3H), 1.82-2.00 (m, 2H), 1.21 (t, J=7.60 Hz, 3H).

Example 234

2-((6-(4-Aminopiperazin-1-yl)-3,5-dicyano-4-ethylpyridin-2-yl)thio)-2-phenylacetamide, Trifluoroacetic Acid Salt Step 1: tert-Butyl (4-(6-chloro-3,5-dicyano-4-ethylpyridin-2-yl)piperazin-1-yl)carbamate

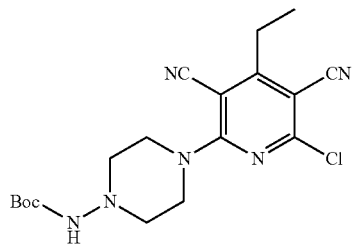 [SMILES: CCc1c(C#N)c(Cl)nc(N2CCN(NC(=O)OC(C)(C)C)CC2)c1C#N]

To a solution of 2,6-dichloro-4-ethylpyridine-3,5-dicarbonitrile (synthesis described in example 3 step 2, 2.246 g, 9.94 mmol) in dichloromethane (30 mL) was added TEA (4.16 mL, 29.8 mmol) followed by a solution of tert-butyl piperazin-1-ylcarbamate (2 g, 9.94 mmol) in dichloromethane (30 mL) at 0° C. The mixture was warmed to 25° C. and stirred for 16 hours. The mixture was poured onto water (30 mL). The layers were separated and the organic phase was concentrated. The residue was purified by column chromatography (eluting with dichloromethane) to give tert-butyl (4-(6-chloro-3,5-dicyano-4-ethylpyridin-2-yl)piperazin-1-yl)carbamate (2.5 g, 6.40 mmol, 64% yield) as a brown solid. LCMS m/z=413.1 [M+Na]$^+$.

Step 2: tert-Butyl (4-(6-((2-amino-2-oxo-1-phenylethyl)thio)-3,5-dicyano-4-ethylpyridin-2-yl)piperazin-1-yl)carbamate

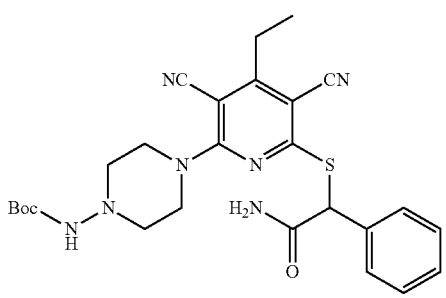 [SMILES: CCc1c(C#N)c(SC(C(N)=O)c2ccccc2)nc(N2CCN(NC(=O)OC(C)(C)C)CC2)c1C#N]

To a solution of tert-butyl (4-(6-chloro-3,5-dicyano-4-ethylpyridin-2-yl)piperazin-1-yl)carbamate (500 mg, 1.279 mmol) in N,N-dimethylformamide (15 mL) was added potassium ethanethioate (219 mg, 1.919 mmol). The mixture was stirred at 25° C. for 2 hours. 2-Amino-2-oxo-1-phenylethyl methanesulfonate (synthesis described in example 3, step 5, 275 mg, 1.200 mmol) was then added, and the mixture was stirred at 25° C. for 16 hours. The mixture was poured onto water (20 mL) and extracted with ethyl acetate (20 mL×2). The organic phase was concentrated and the residue was purified by column chromatography (dichloromethane/methanol, 100:1) to give tert-butyl (4-(6-((2-amino-2-oxo-1-phenylethyl)-thio)-3,5-dicyano-4-ethylpyridin-2-yl)piperazin-1-yl)carbamate (300 mg) as a light yellow solid. LCMS m/z=544.1 [M+Na]+.

Step 3: 2-((6-(4-Aminopiperazin-1-yl)-3,5-dicyano-4-ethylpyridin-2-yl)thio)-2-phenylacet-amide, Trifluoroacetic Acid Salt

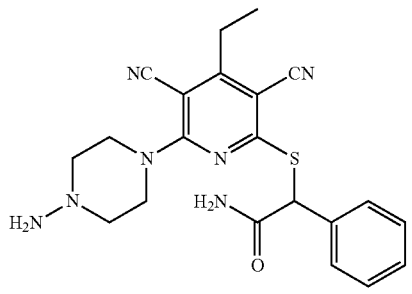 [SMILES: CCc1c(C#N)c(SC(C(N)=O)c2ccccc2)nc(N2CCN(N)CC2)c1C#N]

To a mixture of TFA (3 mL, 38.9 mmol) and dichloromethane (15 mL) was added tert-butyl (4-(6-((2-amino-2-oxo-1-phenylethyl)thio)-3,5-dicyano-4-ethylpyridin-2-yl)piperazin-1-yl)carbamate (300 mg, 0.575 mmol). The mixture was stirred at 25° C. for 12 hours. The mixture was concentrated and the residue was washed with ethyl acetate (5 mL) to give 2-((6-(4-aminopiperazin-1-yl)-3,5-dicyano-4-ethylpyridin-2-yl)thio)-2-phenylacetamide, trifluoroacetic acid salt (110 mg, 0.205 mmol, 36% yield) as an off-white solid. LCMS m/z=422.1 [M+H]+. 1H NMR (400 MHz, DMSO-d6) δ ppm 9.45 (br s, 2H), 7.94 (s, 1H), 7.51-7.53 (m, 2H), 7.36-7.42 (m, 4H), 5.54 (s, 1H), 3.98 (br s, 4H), 3.01 (br s, 4H), 2.76-2.81 (m, 2H), 1.20-1.24 (m, 3H).

Example 235

2-((6-((2-Amino-2-oxoethyl)thio)-3,5-dicyano-4-ethylpyridin-2-yl)thio)-2-phenylacetamide

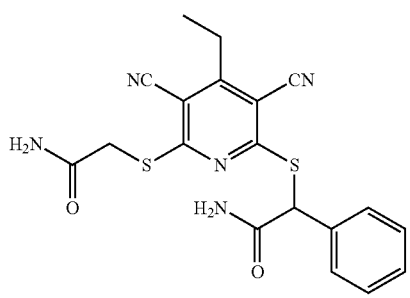 [SMILES: CCc1c(C#N)c(SCC(N)=O)nc(SC(C(N)=O)c2ccccc2)c1C#N]

A mixture of 2-((6-chloro-3,5-dicyano-4-ethylpyridin-2-yl)thio)-2-phenylacetamide (synthesis described in example 52, step 1, 260 mg, 0.73 mmol) and potassium thioacetate (100 mg, 0.87 mmol) in DMF (30 mL) was stirred at 20° C. for 0.5 hour. Then 2-chloroacetamide (273 mg, 2.91 mmol) and triethylamine (0.406 mL, 2.91 mmol) were added, the mixture was stirred at room temperature for 13.5 hour. After the reaction, the reaction mixture was partitioned between ethyl acetate and water. The organic phase was dried with anhydrous sodium sulfate, filtered and concentrated in vacuo to obtain the crude product, which was purified by column chromatography to obtain 2-((6-((2-Amino-2-oxoethyl)thio)-3,5-dicyano-4-ethylpyridin-2-yl)thio)-2-phenylacetamide (133 mg, 44% yield). LCMS m/z=412.0 [M+H]+. 1H NMR (400 MHz, DMSO-d6) δ ppm 7.80 (m, 2H), 7.70-7.35 (m, 7H), 5.84 (s, 1H), 4.22 (d, J=15.5 Hz, 1H), 4.09 (d, J=15.4 Hz, 1H), 2.83 (q, J=6.9 Hz, 2H), 1.24 (t, J=6.9 Hz, 3H).

Example 236

2-((3,5-Dicyano-4-ethyl-6-(pyrrolo[3,4-c]pyrazol-5(1H,4H,6H)-yl)pyridin-2-yl)thio)-2-phenylacetamide Step 1: 2-Chloro-4-ethyl-6-(pyrrolo[3,4-c]pyrazol-5(1H,4H,6H)-yl)pyridine-3,5-dicarbonitrile

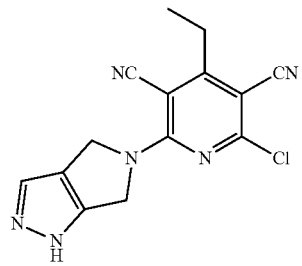 [SMILES: CCc1c(C#N)c(Cl)nc(N2Cc3cn[nH]c3C2)c1C#N]

To a stirred solution of 2,6-dichloro-4-ethylpyridine-3,5-dicarbonitrile (synthesis described in example 3 step 2, 600 mg, 2.65 mmol) in dichloromethane (20 mL) was added 1,4,5,6-tetrahydropyrrolo[3,4-c]pyrazole, 2 hydrochloride (531 mg, 2.92 mmol) followed by triethylamine (1.108 mL, 7.95 mmol) at 0° C. The reaction mixture was stirred for 5 hours at room temperature. The reaction mixture was concentrated under reduced pressure, diluted with water (60 mL) and extracted with DCM (2×80 mL),The combined organic layers were dried over anhydrous Na2SO4, filtered and concentrated under reduced pressure. The residue was triturated with diethyl ether (30 mL), filtered and dried to afford 2-chloro-4-ethyl-6-(pyrrolo[3,4-c]pyrazol-5(1H,4H, 6H)-yl)pyridine-3,5-dicarbonitrile (500 mg, 62% yield) as an off-white solid. LCMS m/z=299.1 [M+H]+.

Step 2: 2-((3,5-Dicyano-4-ethyl-6-(pyrrolo[3,4-c]pyrazol-5(1H,4H,6H)-yl)pyridin-2-yl)thio)-2-phenylacetamide

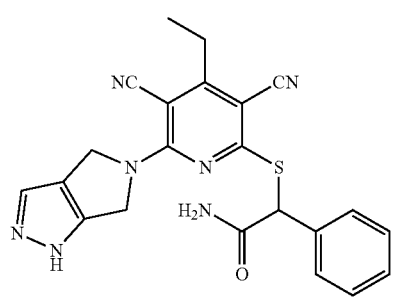 [SMILES: CCc1c(C#N)c(SC(C(N)=O)c2ccccc2)nc(N2Cc3cn[nH]c3C2)c1C#N]

573

To a stirred solution of 2-chloro-4-ethyl-6-(pyrrolo[3,4-c]pyrazol-5(1H,4H,6H)-yl)pyridine-3,5-dicarbonitrile (500 mg, 1.653 mmol) in N,N-dimethylformamide (20 mL) was added potassium thioacetate (377 mg, 3.31 mmol) at room temperature, and the reaction mixture was stirred for 2 hours. Then potassium carbonate (457 mg, 3.31 mmol) was added followed by 2-amino-2-oxo-1-phenylethyl methanesulfonate (synthesis described in example 3 step 5, 582 mg, 2.479 mmol). The reaction mixture was stirred for 16 hours at room temperature. The reaction mixture was quenched with cold water (50 mL) and extracted with EtOAc (2×100 mL). The combined organic layers were dried over $Na_2SO_4$, filtered and concentrated under reduced the pressure. The crude material was purified by column chromatography using silica gel (100-200 mesh, eluting with DCM/MeOH) to afford 240 mg of a brown solid. The solid was further purified by Prep-HPLC. Pure fractions was lyophilized to afford 2-((3,5-dicyano-4-ethyl-6-(pyrrolo[3,4-c]pyrazol-5(1H,4H,6H)-yl)pyridin-2-yl)thio)-2-phenylacetamide (30 mg) as an off-white solid. LCMS m/z=430.1 [M+H]$^+$. $^1$H NMR (400 MHz, DMSO-d$_6$) δ ppm 12.83 (br s, 1H), 7.99 (br s, 1H), 7.65 (br s, 1H), 7.60-7.49 (m, 2H), 7.47-7.14 (m, 4H), 5.71 (s, 1H), 5.14-4.72 (m, 4H), 2.87-2.72 (m, 2H), 1.30-1.16 (m, 3H).

Example 237

2-((3,5-Dicyano-6-(dimethylamino)-4-ethylpyridin-2-yl)thio)-2-(5-methoxypyridin-2-yl)acetamide Step 1:
2-Hydroxy-2-(5-methoxypyridin-2-yl)acetamide

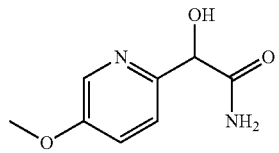

To a solution of 5-methoxypicolinaldehyde (1.0 g, 7.29 mmol) in dichloromethane (40 mL) was added trimethylsilanecarbonitrile (1.095 mL, 8.75 mmol). The mixture was stirred at room temperature overnight. The mixture was concentrated down to afford a brown oil, which was treated with conc. $H_2SO_4$ (5 mL, 94 mmol) for 4 hours, then poured the reaction mixture into ice, and adjusted the pH to 9 using $NH_4OH$. The reaction mixture was concentrated down with Celite®, purified by silica column (CombiFlash®, 40 g column, 0-10% MeOH/DCM) to afford 2-hydroxy-2-(5-methoxypyridin-2-yl)acetamide (1.09 g, 5.98 mmol, 82% yield) as a beige solid. LCMS m/z=183.0 [M+H]$^+$.

Step 2:
2-Amino-1-(5-methoxypyridin-2-yl)-2-oxoethyl methanesulfonate

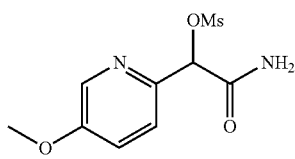 [SMILES: COc1ccc(C(OS(C)(=O)=O)C(N)=O)nc1]

574

To a slurry solution of 2-hydroxy-2-(5-methoxypyridin-2-yl)acetamide (1.09 g, 5.98 mmol) and TEA (1.668 mL, 11.97 mmol) in THF (35 mL) was added methanesulfonyl chloride (0.559 mL, 7.18 mmol), The reaction mixture was stirred at room temperature overnight. The reaction mixture was diluted with DCM and water, separated the layers. The aqueous layer was extracted with DCM (4×). The combined organics were washed with brine, dried over $Na_2SO_4$, concentrated down. The residue was triturated with DCM to afford 2-amino-1-(5-methoxypyridin-2-yl)-2-oxoethyl methanesulfonate (533 mg, 2.048 mmol, 34% yield) as a yellow solid. LCMS m/z=261.0 [M+H]$^+$.

Step 3: 2-((3,5-Dicyano-6-(dimethylamino)-4-ethylpyridin-2-yl)thio)-2-(5-methoxypyridin-2-yl)acetamide

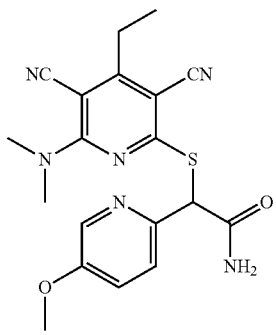 [SMILES: CCc1c(C#N)c(SC(C(N)=O)c2ccc(OC)cn2)nc(N(C)C)c1C#N]

To a solution of 2,6-dichloro-4-ethylpyridine-3,5-dicarbonitrile (synthesis described in example 3, step 2, 100 mg, 0.442 mmol) in DMF (3 mL) was added the solution of dimethylamine (2 M in THF, 0.243 mL, 0.487 mmol) in DMF (1.5 mL) dropwise and then TEA (0.154 mL, 1.106 mmol). After stirring for 2 hours, potassium thioacetate (65.7 mg, 0.575 mmol) was added to the reaction mixture, which was stirred for additional 3 hours. Then 2-amino-1-(5-methoxypyridin-2-yl)-2-oxoethyl methanesulfonate (127 mg, 0.487 mmol) was added to the reaction solution. The reaction mixture was stirred at room temperature overnight. The reaction mixture was purified by reverse phase HPLC (20-50% acetonitrile/water, 0.1% $NH_4OH$ in water) to afford 2-((3,5-dicyano-6-(dimethylamino)-4-ethylpyridin-2-yl)thio)-2-(5-methoxypyridin-2-yl)acetamide (86 mg, 0.217 mmol, 49% yield) as an off-white solid. LCMS m/z=397.2 [M+H]$^+$. $^1$H NMR (400 MHz, DMSO-d$_6$) δ ppm 1.21 (t, J=7.5 Hz, 3H), 2.76 (q, J=7.4 Hz, 2H), 3.32 (s, 6H), 3.83 (s, 3H), 5.66 (s, 1H), 7.34 (s, 1H), 7.43 (dd, J=8.6, 3.0 Hz, 1H), 7.57 (d, J=8.6 Hz, 1H), 7.82 (s, 1H), 8.24 (d, J=2.8 Hz, 1H).

Example 238

2-((3,5-Dicyano-6-(dimethylamino)-4-ethylpyridin-2-yl)thio)-2-(5-methylpyridin-2-yl)acetamide

Step 1: 2-Hydroxy-2-(5-methylpyridin-2-yl)acetamide

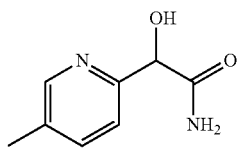

To a solution of 5-methylpicolinaldehyde (1.00 g, 8.26 mmol) in DCM (40 mL) was added trimethylsilanecarbonitrile (1.446 mL, 11.56 mmol). The mixture was stirred at room temperature overnight. The mixture was concentrated down to afford a brown oil, which was treated with concentrated sulfuric acid (5 mL, 94 mmol) for 4 hours, then the reaction mixture was poured into ice, and adjusted the pH to 9 using NH$_4$OH. The reaction mixture was concentrated down with silica, purified by silica column (CombiFlash®, 40 g column) using 0-10% MeOH/DCM to afford 2-hydroxy-2-(5-methylpyridin-2-yl)acetamide (1.04 g, 6.26 mmol, 76% yield) as a yellow wax solid. LCMS m/z=167.0 [M+H]$^+$.

Step 2: 2-Amino-1-(5-methylpyridin-2-yl)-2-oxoethyl methanesulfonate

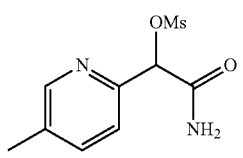

To a slurry solution of 2-hydroxy-2-(5-methylpyridin-2-yl)acetamide (1.04 g, 6.26 mmol) and TEA (1.745 mL, 12.52 mmol) in THF (25 mL) was added methanesulfonyl chloride (0.585 mL, 7.51 mmol). The reaction mixture was stirred at room temperature for 3 hours. The reaction mixture was diluted with DCM and washed with water and brine, dried over Na$_2$SO$_4$, concentrated down to afford 2-amino-1-(5-methylpyridin-2-yl)-2-oxoethyl methanesulfonate (1.49 g, 6.10 mmol, 97% yield) as an orange waxy solid. LCMS m/z=245.0 [M+H]$^+$.

Step 3: 2-((3,5-Dicyano-6-(dimethylamino)-4-ethylpyridin-2-yl)thio)-2-(5-methylpyridin-2-yl)acetamide

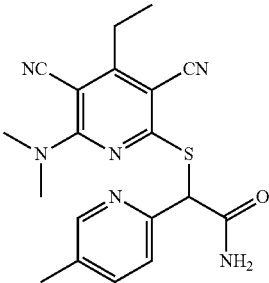 [SMILES: CCc1c(C#N)c(SC(C(N)=O)c2ccc(C)cn2)nc(N(C)C)c1C#N]

To a solution of 2,6-dichloro-4-ethylpyridine-3,5-dicarbonitrile (synthesis described in example 3, step 2, 100 mg, 0.442 mmol) in DMF (3 mL) was added the solution of dimethylamine (2 M in THF, 0.243 mL, 0.487 mmol) in DMF (1.5 mL) dropwise and TEA (0.154 mL, 1.106 mmol). After stirring for 2 hours, then potassium thioacetate (65.7 mg, 0.575 mmol) was added to the reaction mixture, which was stirred for additional 3 hours. Then 2-amino-1-(5-methylpyridin-2-yl)-2-oxoethyl methanesulfonate (119 mg, 0.487 mmol) was added to the reaction solution. The reaction mixture was stirred at room temperature overnight. The reaction mixture was purified by RP-HPLC (20-50% acetonitrile/water, 0.1% NH$_4$OH in water) to afford an off white solid, which was triturated with methanol to afford 2-((3,5-dicyano-6-(dimethylamino)-4-ethylpyridin-2-yl)thio)-2-(5-methylpyridin-2-yl)acetamide (68 mg, 0.179 mmol, 40% yield) as an off-white solid. LCMS m/z=381.2 [M+H]$^+$. $^1$H NMR (400 MHz, DMSO-d$_6$) δ ppm 1.21 (t, J=7.5 Hz, 3H), 2.29 (s, 3H), 2.76 (q, J=7.6 Hz, 2H), 3.31 (s, 6H), 5.67 (s, 1H), 7.35 (s, 1H), 7.53 (d, J=7.9 Hz, 1H), 7.64 (dd, J=8.0, 1.6 Hz, 1H), 7.84 (s, 1H), 8.35-8.40 (m, 1H).

Example 239

2-((3,5-Dicyano-4-ethyl-6-(4-methyl-1,4-diazepan-1-yl)pyridin-2-yl)thio)-2-(2-fluoropyridin-4-yl)acetamide

Step 1: 2-(2-Fluoropyridin-4-yl)-2-hydroxyacetamide

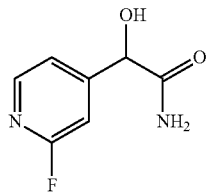 [SMILES: NC(=O)C(O)c1ccnc(F)c1]

To a solution of 2-fluoroisonicotinaldehyde (1.0 g, 7.99 mmol) in dichloromethane (30 mL) was added trimethylsilanecarbonitrile (1.200 mL, 9.59 mmol). The mixture was stirred at room temperature overnight. The mixture was concentrated down to afford a light brown oil, which was treated with conc. H$_2$SO$_4$ (5 mL, 94 mmol) for 4 hours, then poured the reaction mixture into ice, and adjusted the pH to 9 using NH₄OH. The reaction mixture was concentrated down with silica, purified by silica column (CombiFlash®, 40 g column) using 0-10% MeOH/DCM to afford 2-(2-fluoropyridin-4-yl)-2-hydroxyacetamide (829 mg, 4.87 mmol, 61% yield) as a yellow solid. LCMS m/z=171.0 [M+H]⁺.

Step 2:
2-Amino-1-(2-fluoropyridin-4-yl)-2-oxoethyl methanesulfonate

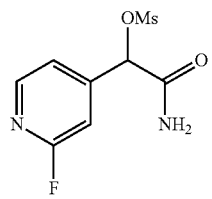 [SMILES: CS(=O)(=O)OC(C(N)=O)c1ccnc(F)c1]

To a slurry solution of 2-(2-fluoropyridin-4-yl)-2-hydroxyacetamide (829 mg, 4.87 mmol) and TEA (1.358 mL, 9.74 mmol) in THF (25 mL) was added methanesulfonyl chloride (0.456 mL, 5.85 mmol), The reaction mixture was stirred at room temperature overnight. The reaction mixture was concentrated down with silica and purified by silica column (CombiFlash®, 40 g column) using 0-10% MeOH/DCM to afford 2-amino-1-(2-fluoropyridin-4-yl)-2-oxoethyl methanesulfonate (925 mg, 3.73 mmol, 76% yield) as an off white solid. LCMS m/z=249.0 [M+H]⁺.

Step 3: 2-((3,5-Dicyano-4-ethyl-6-(4-methyl-1,4-diazepan-1-yl)pyridin-2-yl)thio)-2-(2-fluoropyridin-4-yl)acetamide

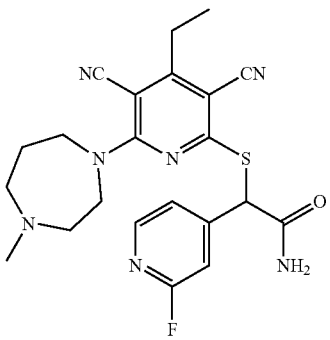 [SMILES: CCc1c(C#N)c(SC(C(N)=O)c2ccnc(F)c2)nc(N2CCCN(C)CC2)c1C#N]

To a solution of 2,6-dichloro-4-ethylpyridine-3,5-dicarbonitrile (synthesis described in example 3, step 2, 100 mg, 0.442 mmol) in DMF (2.5 mL) was added the solution of 1-methyl-1,4-diazepane (0.062 mL, 0.487 mmol) in DMF (1.5 mL) dropwise. After stirring for 60 minutes, potassium thioacetate (65.7 mg, 0.575 mmol) and TEA (0.185 mL, 1.327 mmol) were added to the reaction mixture, which was stirred for additional 3 hours. Then 2-amino-1-(2-fluoropyridin-4-yl)-2-oxoethyl methanesulfonate (121 mg, 0.487 mmol) was added to the reaction solution. The reaction mixture was stirred at room temperature overnight. The reaction mixture was purified by silica (CombiFlash®, 12 g column) using 10-20% MeOH/DCM as eluent. The resulting fractions were concentrated down and purified by second silica column (12 g, 20% MeOH/DCM) to afford 2-((3,5-dicyano-4-ethyl-6-(4-methyl-1,4-diazepan-1-yl)pyridin-2-yl)thio)-2-(2-fluoropyridin-4-yl)acetamide (50 mg, 0.110 mmol, 25% yield) as a white solid. LCMS m/z=454.3 [M+H]⁺. ¹H NMR (400 MHz, DMSO-d₆) δ ppm 1.21 (t, J=7.6 Hz, 3H), 1.88 (br. s., 2H), 2.22 (s, 3H), 2.31-2.49 (m, 3H), 2.57-2.69 (m, 1H), 2.77 (q, J=7.6 Hz, 2H), 3.71-3.96 (m, 4H), 5.66 (s, 1H), 7.30 (s, 1H), 7.50 (d, J=5.3 Hz, 1H), 7.61 (s, 1H), 8.12 (s, 1H), 8.27 (d, J=5.1 Hz, 1H).

Example 240

2-((3,5-Dicyano-4-ethyl-6-(4-hydroxy-4-(hydroxymethyl)piperidin-1-yl)pyridin-2-yl)thio)-2-phenylacetamide Step 1: 2-Chloro-4-ethyl-6-(4-hydroxy-4-(hydroxymethyl)piperidin-1-yl)pyridine-3,5-dicarbonitrile

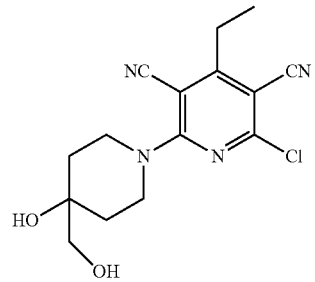

2,6-Dichloro-4-ethylpyridine-3,5-dicarbonitrile (synthesis described in example 3 step 2, 1.13 g, 5.00 mmol), 4-(hydroxymethyl)piperidin-4-ol (0.656 g, 5.00 mmol) and triethylamine (2.090 mL, 15.00 mmol) were dissolved in dichloromethane (5 mL). The mixture was stirred for 12 hours. The mixture was diluted with DCM and washed with brine. The organic layer was dried and concentrated, and the residue was purified by column to give 2-chloro-4-ethyl-6-(4-hydroxy-4-(hydroxymethyl)piperidin-1-yl)pyridine-3,5-dicarbonitrile (1.2 g, 3.74 mmol, 75% yield). LCMS m/z=321 [M+H]⁺.

Step 2: 2-((3,5-Dicyano-4-ethyl-6-(4-hydroxy-4-(hydroxymethyl)piperidin-1-yl)pyridin-2-yl)thio)-2-phenylacetamide

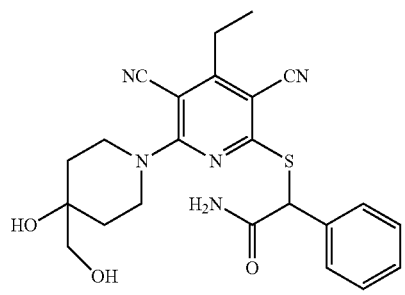 [SMILES: CCc1c(C#N)c(SC(C(N)=O)c2ccccc2)nc(N2CCC(O)(CO)CC2)c1C#N]

2-Chloro-4-ethyl-6-(4-hydroxy-4-(hydroxymethyl)piperidin-1-yl)pyridine-3,5-dicarbonitrile (640 mg, 1.995 mmol) and potassium thioacetate (456 mg, 3.99 mmol) were dissolved in N,N-dimethylformamide (3 mL). The mixture was stirred at room temperature for 1 hour. Then potassium carbonate (551 mg, 3.99 mmol) and 2-amino-2-oxo-1-phenylethyl methanesulfonate (synthesis described in example 3 step 5, 915 mg, 3.99 mmol) were added. The mixture was stirred at room temperature for 12 hours. Solids were removed by filtration, and the filtrate was concentrated and purified by prep-HPLC to give 2-((3,5-dicyano-4-ethyl-6-(4-hydroxy-4-(hydroxymethyl)piperidin-1-yl)pyridin-2-yl)thio)-2-phenylacetamide (110 mg, 0.244 mmol, 12% yield). LCMS m/z=452 [M+H]$^+$. $^1$H NMR (400 MHz, DMSO-d$_6$) δ ppm 7.93 (s, 1H), 7.52 (d, J=7.3 Hz, 2H), 7.38-7.33 (m, 4H), 5.54 (s, 1H), 4.69 (t, J=5.7 Hz, 1H), 4.46 (s, 1H), 4.41-4.37 (m, 2H), 3.44 (t, J=13.2 Hz, 2H), 3.24 (d, J=5.7 Hz, 2H), 2.75 (q, J=7.6 Hz, 2H), 1.67 (tt, J=12.9, 6.5 Hz, 2H), 1.53-1.49 (m, 2H), 1.21 (t, J=7.6 Hz, 3H).

Example 241

2-((3,5-Dicyano-4-ethyl-6-(2-oxo-3-oxa-1,8-diazaspiro[4.5]decan-8-yl)pyridin-2-yl)thio)-2-phenylacetamide Step 1: 2-Chloro-4-ethyl-6-(2-oxo-3-oxa-1,8-diazaspiro[4.5]decan-8-yl)pyridine-3,5-dicarbonitrile

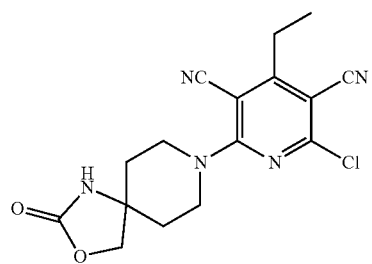 [SMILES: CCc1c(C#N)c(Cl)nc(N2CCC3(CC2)COC(=O)N3)c1C#N]

2,6-Dichloro-4-ethylpyridine-3,5-dicarbonitrile (synthesis described in example 3 step 2, 250 mg, 1.106 mmol), 3-oxa-1,8-diazaspiro[4.5]decan-2-one (173 mg, 1.106 mmol) and triethylamine (112 mg, 1.106 mmol) were added to dichloromethane (10 mL). The mixture was stirred at 25° C. for 3 hours, and then the volatiles were evaporated under vacuum. DCM (50 mL) and water (20 mL) were added to the residue. The organic layer was separated and washed with brine, dried and concentrated. The residue was purified by silica gel chromatography to give 2-chloro-4-ethyl-6-(2-oxo-3-oxa-1,8-diazaspiro[4.5]decan-8-yl)pyridine-3,5-dicarbonitrile (100 mg, 0.289 mmol, 26% yield). LCMS m/z=345.9 [M+H]$^+$.

Step 2: 2-((3,5-Dicyano-4-ethyl-6-(2-oxo-3-oxa-1,8-diazaspiro[4.5]decan-8-yl)pyridin-2-yl)thio)-2-phenylacetamide

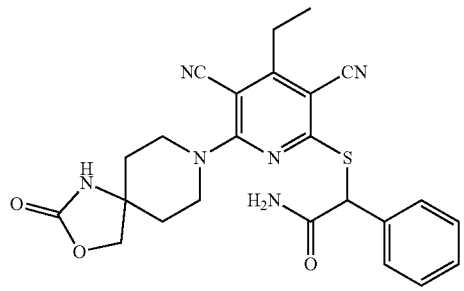 [SMILES: CCc1c(C#N)c(SC(C(N)=O)c2ccccc2)nc(N2CCC3(CC2)COC(=O)N3)c1C#N]

2-Chloro-4-ethyl-6-(2-oxo-3-oxa-1,8-diazaspiro[4.5]decan-8-yl)pyridine-3,5-dicarbonitrile (120 mg, 0.347 mmol) and potassium ethanethioate (79 mg, 0.694 mmol) were added to N,N-dimethylformamide (20 mL). The mixture was stirred for 2 hours. 2-Amino-2-oxo-1-phenylethyl methanesulfonate (synthesis described in example 3 step 5, 159 mg, 0.694 mmol) was then added, and the mixture was stirred for 15 hours. The solvent was evaporated under vacuum. Then DCM (20 mL) and water (10 mL) were added to the residue and the organic layer was separated and washed with brine, dried and concentrated. The residue was purified by prep-HPLC to give 2-((3,5-dicyano-4-ethyl-6-(2-oxo-3-oxa-1,8-diazaspiro[4.5]decan-8-yl)pyridin-2-yl)thio)-2-phenylacetamide (70 mg, 0.147 mmol, 42% yield). LCMS m/z=477.1 [M+H]$^+$. $^1$H NMR (400 MHz, DMSO-d$_6$) δ ppm 8.29 (s, 1H), 7.92 (s, 1H), 7.52 (d, J=7.3 Hz, 2H), 7.41-7.33 (m, 4H), 5.53 (s, 1H), 4.14 (s, 2H), 4.04-4.00 (m, 2H), 3.91-3.79 (m, 2H), 2.77 (q, J=7.5 Hz, 2H), 1.88-1.67 (m, 4H), 1.21 (t, J=7.6 Hz, 3H).

Example 242

2-((6-(4-Amino-4-(hydroxymethyl)piperidin-1-yl)-3,5-dicyano-4-ethylpyridin-2-yl)thio)-2-phenylacetamide, Trifluoroacetic Acid Salt Step 1: tert-Butyl (1-(6-chloro-3,5-dicyano-4-ethylpyridin-2-yl)-4-(hydroxymethyl) piperidin-4-yl) carbamate

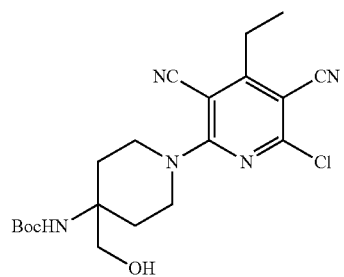 [SMILES: CCc1c(C#N)c(Cl)nc(N2CCC(CO)(NC(=O)OC(C)(C)C)CC2)c1C#N]

2,6-Dichloro-4-ethylpyridine-3,5-dicarbonitrile (synthesis described in example 3 step 2, 400 mg, 1.769 mmol), tert-Butyl (4-(hydroxymethyl)piperidin-4-yl)carbamate (408 mg, 1.769 mmol) and triethylamine (179 mg, 1.769 mmol) were added to dichloromethane (30 mL). The mixture was stirred at 25° C. for 5 hours. Then DCM (50 mL) and water (30 mL) were added. The organic layer was separated and washed with brine, dried and concentrated. The residue was purified by silica gel chromatography to give tert-butyl (1-(6-chloro-3,5-dicyano-4-ethylpyridin-2-yl)-4-(hydroxymethyl)piperidin-4-yl)carbamate (350 mg, 0.834 mmol, 47% yield). LCMS m/z=442.1 [M+Na]⁺.

Step 2: tert-Butyl (1-(6-((2-amino-2-oxo-1-phenylethyl)thio)-3,5-dicyano-4-ethylpyridin-2-yl)-4-(hydroxymethyl)piperidin-4-yl)carbamate

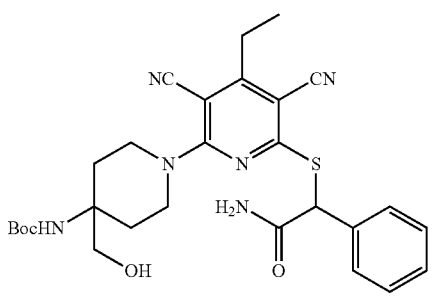 [SMILES: CCc1c(C#N)c(SC(C(N)=O)c2ccccc2)nc(N2CCC(CO)(NC(=O)OC(C)(C)C)CC2)c1C#N]

tert-Butyl (1-(6-chloro-3,5-dicyano-4-ethylpyridin-2-yl)-4-(hydroxymethyl)piperidin-4-yl) carbamate (300 mg, 0.714 mmol) and potassium ethanethioate (163 mg, 1.429 mmol) were added to N,N-dimethylformamide (20 mL). The mixture was stirred at 25° C. for 2 hours then 2-amino-2-oxo-1-phenylethyl methanesulfonate (synthesis described in example 3 step 5, 328 mg, 1.429 mmol) was added. The mixture was stirred for 15 hours. The solvent was evaporated under vacuum. Then DCM (50 mL) and water (20 mL) were added to the residue. The organic layer was separated and washed with brine, dried and concentrated. The residue was purified by silica gel chromatography to give tert-butyl (1-(6-((2-amino-2-oxo-1-phenylethyl)thio)-3,5-dicyano-4-ethylpyridin-2-yl)-4-(hydroxymethyl)piperidin-4-yl)carbamate (150 mg, 0.272 mmol, 38% yield). LCMS m/z=550.9 [M+H]⁺.

Step 3: 2-((6-(4-Amino-4-(hydroxymethyl)piperidin-1-yl)-3,5-dicyano-4-ethylpyridin-2-yl)thio)-2-phenylacetamide, Trifluoroacetic Acid Salt

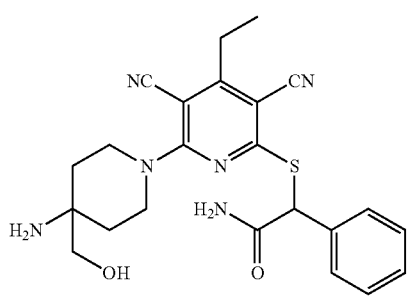 [SMILES: CCc1c(C#N)c(SC(C(N)=O)c2ccccc2)nc(N2CCC(N)(CO)CC2)c1C#N]

tert-Butyl (1-(6-((2-amino-2-oxo-1-phenylethyl)thio)-3,5-dicyano-4-ethylpyridin-2-yl)-4-(hydroxymethyl)piperidin-4-yl)carbamate (150 mg, 0.272 mmol) was added to dichloromethane (20 mL), and a solution of 2,2,2-trifluoroacetic acid (31.1 mg, 0.272 mmol) in 5 mL of dichloromethane was added at 0° C. The mixture was stirred overnight, and then the solvent was removed. The residue was purified by prep-HPLC to give 2-((6-(4-amino-4-(hydroxymethyl)piperidin-1-yl)-3,5-dicyano-4-ethylpyridin-2-yl)thio)-2-phenylacetamide, trifluoroacetic acid salt (38 mg, 0.067 mmol, 25% yield). LCMS m/z=451.1 [M+H]⁺. ¹H NMR (400 MHz, DMSO-d₆) δ ppm 8.06 (bs, 3H), 7.98 (s, 1H), 7.52 (d, J=7.2 Hz, 2H), 7.41-7.34 (m, 4H), 5.60 (bs, 1H), 5.54 (s, 1H), 4.21-3.99 (m, 2H), 3.92-3.68 (m, 2H), 3.62 (s, 2H), 2.78 (q, J=7.5 Hz, 2H), 1.92-1.89 (m, 2H), 1.86-1.59 (m, 2H), 1.22 (t, J=7.6 Hz, 3H).

Example 243

2-((6-(4-(Aminomethyl)-4-hydroxypiperidin-1-yl)-3,5-dicyano-4-ethylpyridin-2-yl)thio)-2-phenylacetamide, Trifluoroacetic Acid Salt Step 1: tert-Butyl ((1-(6-chloro-3,5-dicyano-4-ethylpyridin-2-yl)-4-hydroxypiperidin-4-yl) methyl) carbamate

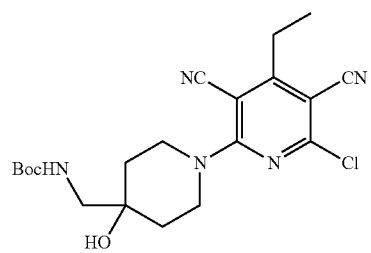 [SMILES: CCc1c(C#N)c(Cl)nc(N2CCC(O)(CNC(=O)OC(C)(C)C)CC2)c1C#N]

To a solution of 2,6-dichloro-4-ethylpyridine-3,5-dicarbonitrile (synthesis described in example 3 step 2, 1 g, 4.42 mmol) in dichloromethane (50 mL) were added tert-butyl ((4-hydroxypiperidin-4-yl)methyl)carbamate (1.019 g, 4.42 mmol) and triethylamine (0.448 g, 4.42 mmol). The reaction mixture was stirred at 25° C. for 15 hours. The solvent was removed and water (50 mL) and DCM (50 mL) were added to the residue. The organic phase was dried over Na₂SO₄ and concentrated. The residue was purified by column chromatography on silica gel (PE/EA=1:2) to give the product tert-butyl ((1-(6-chloro-3,5-dicyano-4-ethylpyridin-2-yl)-4-hydroxypiperidin-4-yl)methyl)carbamate (1.1 g, 2.62 mmol, 59% yield). LCMS m/z=441.8 [M+Na]⁺.

Step 2: tert-Butyl ((1-(6-((2-amino-2-oxo-1-phenylethyl)thio)-3,5-dicyano-4-ethylpyridin-2-yl)-4-hydroxypiperidin-4-yl)methyl)carbamate

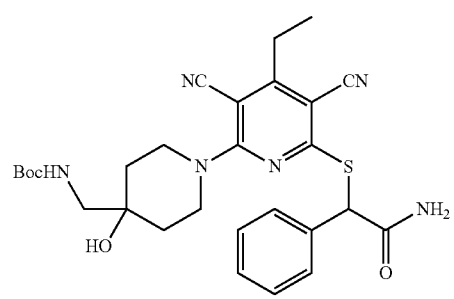 [SMILES: CCc1c(C#N)c(SC(C(N)=O)c2ccccc2)nc(N2CCC(O)(CNC(=O)OC(C)(C)C)CC2)c1C#N]

To a solution of tert-butyl ((1-(6-chloro-3,5-dicyano-4-ethylpyridin-2-yl)-4-hydroxypiperidin-4-yl)methyl)carbamate (2 g, 4.76 mmol) in N,N-dimethylformamide (80 mL) was added potassium ethanethioate (1.088 g, 9.53 mmol). The mixture was stirred at 25° C. for 2 h then 2-amino-2-oxo-1-phenylethyl methanesulfonate (synthesis described in example 3 step 5, 2.184 g, 9.53 mmol) was added. The mixture was stirred at 25° C. for 15 hours. The solvent was removed and water (50 mL) and DCM (50 mL) were added to the residue. The organic phase was dried over $Na_2SO_4$ and concentrated. The residue was purified by column chromatography on silica gel (PE/EA=5:1) to give tert-butyl ((1-(6-((2-amino-2-oxo-1-phenylethyl)thio)-3,5-dicyano-4-ethylpyridin-2-yl)-4-hydroxpiperidin-4-yl)methyl) carbamate (2 g, 3.63 mmol, 76% yield) as a pale yellow solid. LCMS m/z=550.8 $[M+H]^+$.

Step 6: 2-((6-(4-(Aminomethyl)-4-hydroxypiperidin-1-yl)-3,5-dicyano-4-ethylpyridin-2-yl)thio)-2-phenylacetamide, Trifluoroacetic Acid Salt

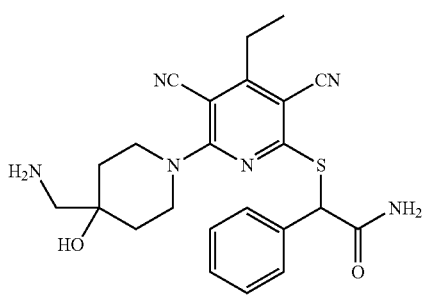 [SMILES: CCc1c(C#N)c(SC(C(N)=O)c2ccccc2)nc(N2CCC(O)(CN)CC2)c1C#N]

To a solution of tert-butyl ((1-(6-((2-amino-2-oxo-1-phenylethyl)thio)-3,5-dicyano-4-ethylpyridin-2-yl)-4-hydroxypiperidin-4-yl)methyl)carbamate (1 g, 1.816 mmol) in dichloromethane (30 mL) was added 2,2,2-trifluoroacetic acid (0.621 g, 5.45 mmol). The mixture was stirred at 25° C. for 15 hours. The solvent was removed under reduced pressure to give 2-((6-(4-(aminomethyl)-4-hydroxypiperidin-1-yl)-3,5-dicyano-4-ethylpyridin-2-yl)thio)-2-phenylacetamide trifluoroacetic acid salt (200 mg, 0.444 mmol, 24% yield) as a solid. LCMS m/z=450.9 $[M+H]^+$. $^1$H NMR (400 MHz, DMSO-$d_6$) δ ppm 7.94 (s, 1H), 7.86 (br s, 3H), 7.52 (d, J=7.2 Hz, 2H), 7.39-7.33 (m, 4H), 5.55 (s, 1H), 4.41-4.29 (m, 2H), 3.52 (t, 2H), 2.93-2.71 (m, 4H), 1.69-1.63 (m, 4H), 1.21 (t, 3H).

Example 244

2-(3-Benzoylphenyl)-2-((3,5-dicyano-4-ethyl-6-(4-(2-hydroxyethyl)-1,4-diazepan-1-yl)pyridin-2-yl)thio)acetamide Step 1: (3-(Bromomethyl)phenyl)(phenyl)methanone

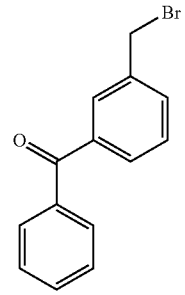

A solution of phenyl(m-tolyl)methanone (2.0 g, 10 mmol), 1-bromopyrrolidine-2,5-dione (2.0 g, 11 mmol), and (E)-2,2'-(diazene-1,2-diyl)bis(2-methylpropanenitrile) (0.167 g, 1.02 mmol) in CCl4 (60 mL) was refluxed overnight. After cooling to room temperature, the reaction mixture was washed with water (3×20 mL), dried, and concentrated under vacuum. The residue was applied to a silica gel column and eluted with ethyl acetate/hexane, 1:20 to give (3-(bromomethyl)phenyl)(phenyl)methanone (1.85 g, 6.73 mmol, 66% yield) as a white solid. LCMS m/z=274.8 $[M+H]^+$.

Step 2: 2-(3-Benzoylphenyl)acetonitrile

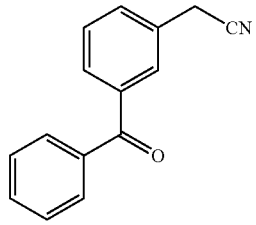 [SMILES: N#CCc1cccc(C(=O)c2ccccc2)c1]

To a solution of (3-(bromomethyl)phenyl)(phenyl)methanone (2.74 g, 9.96 mmol) in acetonitrile (40.0 mL) was added potassium carbonate (3.44 g, 24.9 mmol). Trimethylsilanecarbonitrile (3.95 g, 39.8 mmol) was added dropwise to the reaction mixture at 0° C. Then the mixture was stirred overnight at 80° C. The reaction mixture was cooled to room temperature. The resulting solution was diluted with 50 mL of water, then extracted with 3×40 mL of ethyl acetate. The organic layers were combined, washed with sodium carbonate (aq.) and brine, dried and concentrated under vacuum. The residue was applied to a silica gel column and eluted with ethyl acetate/hexanes, 1:5 to give 2-(3-benzoylphenyl)acetonitrile (800 mg, 3.62 mmol, 36% yield). LCMS m/z=222.1 $[M+H]^+$.

Step 3: 2-(3-Benzoylphenyl)-2-bromoacetonitrile

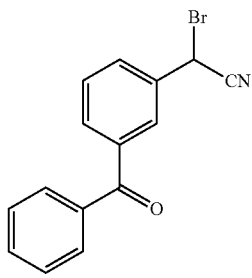 [SMILES: N#CC(Br)c1cccc(C(=O)c2ccccc2)c1]

To a solution of 2-(3-benzoylphenyl)acetonitrile (800 mg, 3.62 mmol) in carbon tetrachloride (30 mL) was added 1-bromopyrrolidine-2,5-dione (772 mg, 4.34 mmol), followed by the addition of (E)-2,2'-(diazene-1,2-diyl)bis(2-methylpropanenitrile) (297 mg, 1.81 mmol). Then the mixture was refluxed for 2 days. After cooling to room temperature, the mixture was washed with water. The organic layer was washed with water, dried over MgSO$_4$ and evaporated to dryness. The crude material was applied to a silica gel column to afford 2-(3-benzoylphenyl)-2-bromoacetonitrile (440 mg, 1.47 mmol, 41% yield) as a yellow solid. LCMS m/z=300.0 [M+H]$^+$.

Step 4: 2-(3-Benzoylphenyl)-2-bromoacetamide

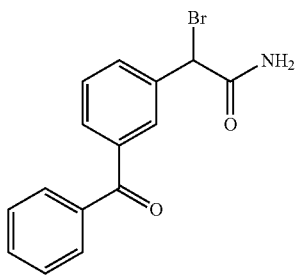 [SMILES: NC(=O)C(Br)c1cccc(C(=O)c2ccccc2)c1]

To a solution of 2-(3-benzoylphenyl)-2-bromoacetonitrile (440 mg, 1.47 mmol) in tetrahydrofuran (18 mL) and water (6 mL) was added palladium(II) chloride (26 mg, 0.15 mmol), followed by the addition of acetamide (260 mg, 4.40 mmol). Then the mixture was stirred 2 hours at room temperature. The resulting solution was extracted with 3×20 mL of ethyl acetate. The organic layers were combined, washed with aqueous sodium carbonate and brine, dried, and concentrated under vacuum. The residue was applied to a silica gel column and eluted with ethyl acetate/hexane, 1:2 to give 2-(3-benzoylphenyl)-2-bromoacetamide (352 mg, 1.11 mmol, 75% yield) as a yellow oil. LCMS m/z=318.0 [M+H]$^+$

Step 5: tert-Butyl 4-(2-hydroxyethyl)-1,4-diazepane-1-carboxylate

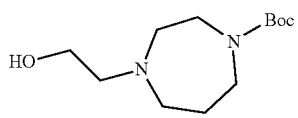

To a solution of tert-butyl 1,4-diazepane-1-carboxylate (1.0 g, 4.99 mmol) in toluene (30 mL) was added 2-bromoethanol (0.936 g, 7.49 mmol). The mixture was stirred overnight at 80° C. The solvent and was removed under reduced pressure. Ethyl acetate (30 mL) was added and the mixture was stirred 2 hours at room temperature. The solids were collected by filtration. The resulting mixture was washed with 2×30 mL of ethyl acetate to afford tert-butyl 4-(2-hydroxyethyl)-1,4-diazepane-1-carboxylate (900 mg, 3.68 mmol) as a white solid. LCMS m/z=245.0 [M+H]$^+$.

Step 6: 2-Chloro-4-ethyl-6-(4-(2-hydroxyethyl)-1,4-diazepan-1-yl)pyridine-3,5-dicarbonitrile

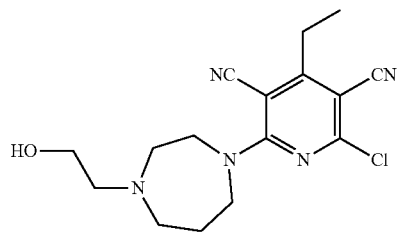 [SMILES: CCc1c(C#N)c(Cl)nc(N2CCCN(CCO)CC2)c1C#N]

To a solution of tert-butyl 4-(2-hydroxyethyl)-1,4-diazepane-1-carboxylate (400 mg, 1.64 mmol) in DCM (6.0 mL) was added trifluoroacetic acid (6.0 mL). The reaction mixture was stirred overnight at room temperature. The solvent and trifluoroacetic acid were removed under reduced pressure to afford a yellow oil. To a solution of 2,6-dichloro-4-ethylpyridine-3,5-dicarbonitrile (synthesis described in example 3, step 2, 376 mg, 1.66 mmol) and triethylamine (337 mg, 3.33 mmol) in acetonitrile (20 mL) was added the yellow oil above. Then the mixture was stirred overnight at room temperature. The reaction was quenched by the addition of 60 mL of water. The resulting solution was extracted with 3×40 mL of ethyl acetate. The organic layers were combined, washed with aqueous sodium carbonate and brine, dried and concentrated under vacuum to afford 2-chloro-4-ethyl-6-(4-(2-hydroxyethyl)-1,4-diazepan-1-yl)pyridine-3,5-dicarbonitrile (400 mg, 1.20 mmol) as a yellow solid. LCMS m/z=334.1 [M+H]$^+$.

Step 7: 2-(3-Benzoylphenyl)-2-((3,5-dicyano-4-ethyl-6-(4-(2-hydroxyethyl)-1,4-diazepan-1-yl)pyridin-2-yl)thio)acetamide

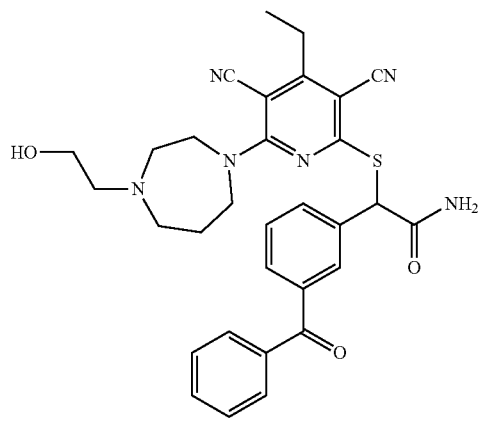 [SMILES: CCc1c(C#N)c(SC(C(N)=O)c2cccc(C(=O)c3ccccc3)c2)nc(N2CCCN(CCO)CC2)c1C#N]

To a solution of 2-chloro-4-ethyl-6-(4-(2-hydroxyethyl)-1,4-diazepan-1-yl)pyridine-3,5-dicarbonitrile (200 mg, 0.60 mmol) in N,N-dimethylformamide (20 mL) was added potassium ethanethioate (75 mg, 0.66 mmol). The reaction mixture was stirred 30 minutes at room temperature, then 2-(3-benzoylphenyl)-2-bromoacetamide (191 mg, 0.599 mmol) and triethylamine (152 mg, 1.50 mmol) was added to the reaction. The reaction mixture was stirred overnight at room temperature. The mixture was poured onto 20 mL of water. The resulting mixture was extracted with 3×20 mL of ethyl acetate. The organic layers were combined, washed with sodium carbonate (aq.) and brine, dried and concentrated under vacuum to afford the crude product as a yellow oil. The residue was purified by prep-HPLC to give 2-(3-benzoylphenyl)-2-((3,5-dicyano-4-ethyl-6-(4-(2-hydroxyethyl)-1,4-diazepan-1-yl)pyridin-2-yl)thio)acetamide (40 mg, 0.07 mmol) as a yellow solid. LCMS m/z=568.9 [M+H]$^+$. $^1$H NMR (400 MHz, MeOD) δ ppm 7.98 (s, 1H), 7.84 (s, 1H), 7.78 (t, J=8.1 Hz, 3H), 7.68 (s, 1H), 7.58 (dt, J=15.4, 7.7 Hz, 3H), 5.66 (s, 1H), 4.01 (dd, J=15.9, 10.1 Hz, 4H), 3.71 (t, J=5.7 Hz, 2H), 3.06 (s, 2H), 2.97-2.85 (m, 4H), 2.80 (s, 2H), 2.11 (s, 2H), 1.32 (t, J=7.6 Hz, 3H).

Example 245

2-(4-Benzoylphenyl)-2-((3,5-dicyano-4-ethyl-6-(4-(2-hydroxyethyl)-1,4-diazepan-1-yl)pyridin-2-yl)thio)acetamide Step 1: (4-(Bromomethyl)phenyl)(phenyl)methanone

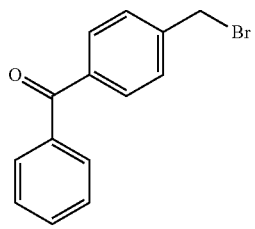 [SMILES: O=C(c1ccccc1)c1ccc(CBr)cc1]

A solution of phenyl(p-tolyl)methanone (5.0 g, 25.5 mmol), 1-bromopyrrolidine-2,5-dione (4.99 g, 28.0 mmol), and (E)-2,2'-(diazene-1,2-diyl)bis(2-methylpropanenitrile) (0.209 g, 1.27 mmol) in CCl$_4$ (80.0 mL) was refluxed overnight. After cooling to room temperature, the reaction mixture was washed with water (3×50) mL, dried and concentrated under vacuum. The residue was applied to a silica gel column and eluted with ethyl acetate/hexane, 1:20 to give (4-(bromomethyl)phenyl)(phenyl)methanone (4.5 g, 16 mmol, 64% yield) as a white solid. LCMS m/z=275.0 [M+H]$^+$.

Step 2: 2-(4-Benzoylphenyl)acetonitrile

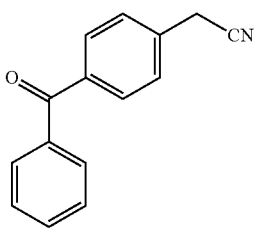 [SMILES: N#CCc1ccc(C(=O)c2ccccc2)cc1]

To a solution of (4-(bromomethyl)phenyl)(phenyl)methanone (2.74 g, 9.96 mmol) in acetonitrile (40.0 ml) was added potassium carbonate (3.44 g, 24.9 mmol). Trimethylsilanecarbonitrile (3.95 g, 39.8 mmol) was added dropwise to the reaction mixture at 0° C. The mixture was stirred overnight at 80° C. The reaction mixture was cooled to room temperature. The resulting solution was diluted with 50 mL of water and extracted with ethyl acetate (3×40 mL). The organic layers were combined, washed with aqueous sodium carbonate and brine, dried and concentrated under vacuum. The residue was applied to a silica gel column and eluted with ethyl acetate/hexane (1:5) to give 2-(4-benzoylphenyl)acetonitrile (820 mg, 3.71 mmol, 37% yield). LCMS m/z=222.1 [M+H]$^+$.

Step 3: 2-(4-Benzoylphenyl)-2-bromoacetonitrile

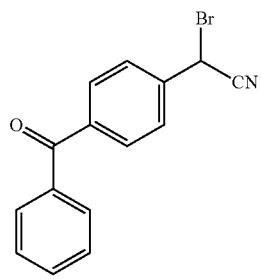 [SMILES: N#CC(Br)c1ccc(C(=O)c2ccccc2)cc1]

To a solution of 2-(4-benzoylphenyl)acetonitrile (820 mg, 3.71 mmol) in carbon tetrachloride (30 mL) was added N-bromosuccinimide (792 mg, 4.45 mmol) and AIBN (304 mg, 1.85 mmol). The mixture was refluxed for 2 days. After cooling to room temperature, the mixture was washed with water. The organic layer was washed with water, dried (MgSO$_4$) and evaporated to dryness. The residue was purified by silica gel column to afford 2-(4-benzoylphenyl)-2-bromoacetonitrile (380 mg, 1.27 mmol, 34% yield) as a yellow solid. LCMS m/z=300.0 [M+H]$^+$.

Step 4: 2-(4-Benzoylphenyl)-2-bromoacetamide

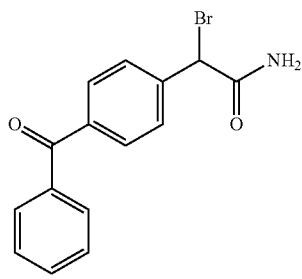 [SMILES: NC(=O)C(Br)c1ccc(C(=O)c2ccccc2)cc1]

A solution of 2-(4-benzoylphenyl)-2-bromoacetonitrile (380 mg, 1.27 mmol) in tetrahydrofuran (18 mL) and water (6 mL) was added palladium(II) chloride (22 mg, 0.13 mmol), followed by the addition of acetamide (224 mg, 3.80 mmol). The mixture was stirred 2 hours at room temperature. The resulting solution was extracted with ethyl acetate (3×20 mL). The organic layers were combined, washed with aqueous sodium carbonate and brine, dried and concentrated under vacuum. The residue was applied to a silica gel column and eluted with ethyl acetate/hexane (1:2) to give 2-(4-benzoylphenyl)-2-bromoacetamide (300 mg, 0.94 mmol, 74% yield) as a yellow oil. LCMS m/z=318.0 [M+H]⁺.

Step 5: 2-(4-Benzoylphenyl)-2-((3,5-dicyano-4-ethyl-6-(4-(2-hydroxyethyl)-1,4-diazepan-1-yl)pyridin-2-yl)thio)acetamide

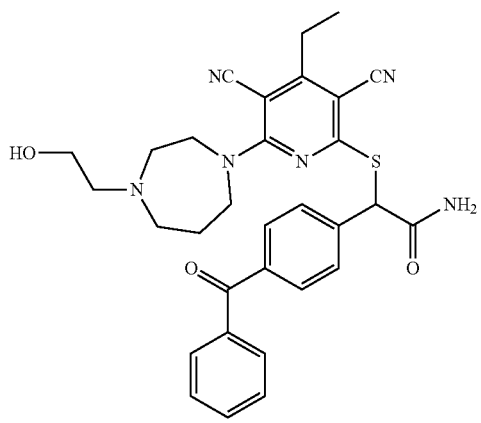 [SMILES: CCc1c(C#N)c(SC(C(N)=O)c2ccc(C(=O)c3ccccc3)cc2)nc(N2CCCN(CCO)CC2)c1C#N]

To a solution of 2-chloro-4-ethyl-6-(4-(2-hydroxyethyl)-1,4-diazepan-1-yl)pyridine-3,5-dicarbonitrile (synthesis described in example 244, step 6, 200 mg, 0.60 mmol) in N,N-dimethylformamide (20 mL) was added potassium ethanethioate (75 mg, 0.66 mmol). The reaction mixture was stirred 30 minutes at room temperature. 2-(4-Benzoylphenyl)-2-bromoacetamide (191 mg, 0.60 mmol) and triethylamine (152 mg, 1.50 mmol) were then added to the reaction mixture, and the mixture was stirred overnight at room temperature. The mixture was poured onto 20 mL of water. The resulting mixture was extracted with ethyl acetate (3×20 mL). The organic layers were combined, washed with aqueous sodium carbonate and brine, dried and concentrated under vacuum to afford the crude product as a yellow oil. The residue was purified by prep-HPLC to give 2-(4-benzoylphenyl)-2-((3,5-dicyano-4-ethyl-6-(4-(2-hydroxyethyl)-1,4-diazepan-1-yl)pyridin-2-yl)thio)acetamide (70 mg, 0.12 mmol, 20% yield) as a yellow solid. LCMS m/z=568.9 [M+H]⁺. ¹H NMR (400 MHz, MeOD) δ ppm 7.83 (m, J=15.5, 7.8 Hz, 4H), 7.76-7.66 (m, 3H), 7.57 (t, J=7.7 Hz, 2H), 5.60 (s, 1H), 4.09 (bs, 4H), 3.94-3.90 (m, 2H), 3.60 (bs, 6H), 2.97 (q, J=7.5 Hz, 2H), 2.41 (bs, 2H), 1.34 (t, J=7.6 Hz, 3H).

Example 246

2-((3,5-Dicyano-4-ethyl-6-(4-methyl-1,4-diazepan-1-yl)pyridin-2-yl)thio)-2-(2-methylpyridin-4-yl)acetamide Step 1: 2-Hydroxy-2-(2-methylpyridin-4-yl)acetamide

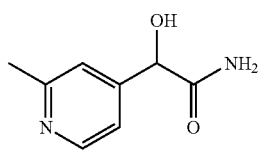

To a solution of 2-methylisonicotinaldehyde (1.0 g, 8.26 mmol) in dichloromethane (25 mL) was added trimethylsilanecarbonitrile (1.239 mL, 9.91 mmol). The mixture was stirred at room temperature overnight. The mixture was concentrated down to afford a light brown oil, which was treated with conc. H₂SO₄ (5 mL, 94 mmol) for 4 hours, then poured the reaction mixture into ice, and adjusted the pH to 9 using NH₄OH. The mixture was concentrated down with silica, purified by silica column (CombiFlash®, 40 g column) using 0-10% MeOH/DCM to afford 2-hydroxy-2-(2-methylpyridin-4-yl)acetamide (487 mg, 2.93 mmol, 36% yield) as a yellow solid. LCMS m/z=167.0 [M+H]⁺.

Step 2: 2-Amino-1-(2-methylpyridin-4-yl)-2-oxoethyl methanesulfonate

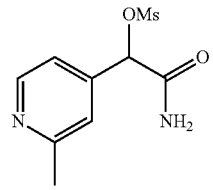 [SMILES: Cc1cc(C(OS(C)(=O)=O)C(N)=O)ccn1]

To a slurry solution of 2-hydroxy-2-(2-methylpyridin-4-yl)acetamide (487 mg, 2.93 mmol) and TEA (0.817 mL, 5.86 mmol) in THF (20 mL) was added methanesulfonyl chloride (0.274 mL, 3.52 mmol). The reaction mixture was stirred at room temperature overnight. The reaction mixture was concentrated down with silica and purified by silica column (CombiFlash®, 40 g column, using 0-10% MeOH/DCM) to afford 2-amino-1-(2-methylpyridin-4-yl)-2-oxoethyl methanesulfonate (520 mg, 2.129 mmol, 73% yield) as an off white solid. LCMS m/z=245.0 [M+H]⁺.

Step 3: 2-((3,5-Dicyano-4-ethyl-6-(4-methyl-1,4-diazepan-1-yl)pyridin-2-yl)thio)-2-(2-methylpyridin-4-yl)acetamide

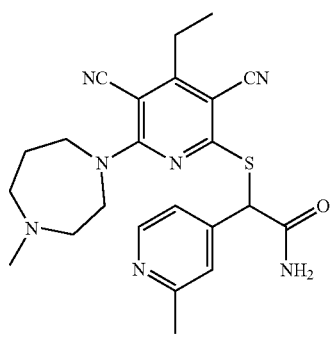 [SMILES: CCc1c(C#N)c(SC(C(N)=O)c2ccnc(C)c2)nc(N2CCCN(C)CC2)c1C#N]

The reaction mixture of 4-ethyl-2-mercapto-6-(4-methyl-1,4-diazepan-1-yl)pyridine-3,5-dicarbonitrile (synthesis described in example 69, step 1, 99 mg, 0.328 mmol), 2-amino-1-(2-methylpyridin-4-yl)-2-oxoethyl methanesulfonate (80 mg, 0.328 mmol) and TEA (0.091 mL, 0.655 mmol) in DMF (4 mL) was stirred at room temperature overnight. The reaction mixture was purified by silica (CombiFlash®, 24 g column) using 15-20% MeOH/DCM as eluent. The resulting fractions were concentrated down and was purified by second silica column (12 g column) using 20% MeOH/DCM to afford 2-((3,5-dicyano-4-ethyl-6-(4-methyl-1,4-diazepan-1-yl)pyridin-2-yl)thio)-2-(2-methylpyridin-4-yl)acetamide (60 mg, 0.133 mmol, 41% yield) as an off-white solid. LCMS m/z=450.2 [M+H]⁺. ¹H NMR (400 MHz, DMSO-d₆) δ ppm 1.21 (t, J=7.6 Hz, 3H), 1.92 (br. s., 2H), 2.21-2.33 (m, 3H), 2.47 (s, 3H), 2.71-2.61 (m, 4H), 2.77 (q, J=7.5 Hz, 2H), 3.75-4.01 (m, 4H), 5.52 (s, 1H), 7.28-7.33 (m, 1H), 7.37 (s, 1H), 7.50 (s, 1H), 8.05 (s, 1H), 8.44 (d, J=5.1 Hz, 1H).

Example 247

2-((3,5-Dicyano-4-ethyl-6-(4-methyl-1,4-diazepan-1-yl)pyridin-2-yl)thio)-2-(3-(pyrrolidin-1-yl)phenyl)acetamide Step 1:
2-Hydroxy-2-(3-(pyrrolidin-1-yl)phenyl)acetamide

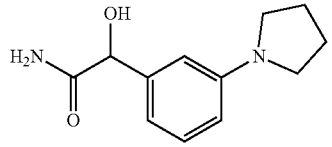 [SMILES: NC(=O)C(O)c1cccc(N2CCCC2)c1]

To a solution of 3-(pyrrolidin-1-yl)benzaldehyde (351 mg, 2.003 mmol) in dichloromethane (10 mL) at 20° C. was added the trimethylsilyl cyanide (0.349 mL, 2.60 mmol). The reaction mixture was then allowed to stir overnight at the same temp. After stirring overnight at 20° C., LCMS indicates little desired product being generated. A catalytic amount of zinc iodide (32.0 mg, 0.100 mmol) was added to the reaction mixture. The reaction mixture was then warmed to 40° C. and stirred at the same temp for an additional 24 hours. The mixture was then concentrated down by rotovap. The resulting brown oil was then treated with concentrated sulfuric acid (1.1 mL, 20.64 mmol) and this mixture stirred at room temperature for 4 hours at which time LCMS indicates no intermediate remains and desired product is present. The reaction mixture was then poured over ice and the pH was adjusted to 9 with NH₄OH. The mixture was then concentrated to obtain the crude product. The crude product was purified by reverse phase HPLC (Gilson, 30 mm Gemini Column, NH₄OH modifier) to obtain 2-hydroxy-2-(3-(pyrrolidin-1-yl)phenyl)acetamide (81 mg) LCMS m/z=221.1 [M+H]⁺.

Step 2: 2-Amino-2-oxo-1-(3-(pyrrolidin-1-yl)phenyl)ethyl methanesulfonate

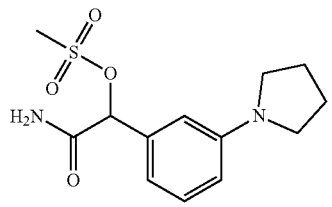 [SMILES: CS(=O)(=O)OC(C(N)=O)c1cccc(N2CCCC2)c1]

To a solution of 2-hydroxy-2-(3-(pyrrolidin-1-yl) phenyl) acetamide (79 mg, 0.359 mmol), DIEA (0.078 mL, 0.448 mmol), and DMAP (4 mg, 0.033 mmol) in dichloromethane (2.0 mL) at 0° C. was added methanesulfonyl chloride (0.035 mL, 0.448 mmol). The reaction mixture was then warmed to 20° C. and stirred at the same temperature overnight. The reaction mixture was diluted with DCM and washed with 1N HCl (2×), saturated brine (1×), and then water. The organic layer was then dried (MgSO₄) and concentrated to obtain 2-amino-2-oxo-1-(3-(pyrrolidin-1-yl)phenyl)ethyl methanesulfonate (39 mg) as a brown oil. LCMS m/z=299.1 [M+H]⁺.

Step 3: 2-((3,5-Dicyano-4-ethyl-6-(4-methyl-1,4-diazepan-1-yl)pyridin-2-yl)thio)-2-(3-(pyrrolidin-1-yl)phenyl)acetamide

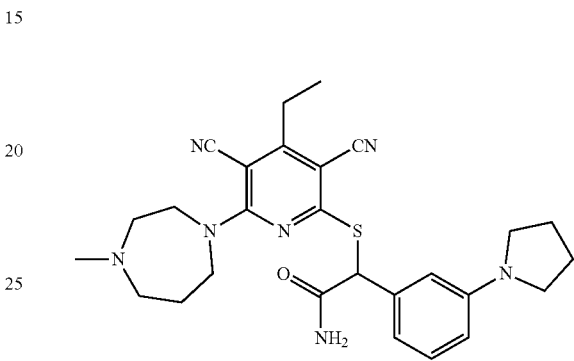

To a suspension of 4-ethyl-2-mercapto-6-(4-methyl-1,4-diazepan-1-yl)pyridine-3,5-dicarbonitrile (synthesis described in example 69, step 1, 68 mg, 0.226 mmol) and 2-amino-2-oxo-1-(4-(trifluoromethyl)phenyl)ethyl methanesulfonate (49 mg, 0.165 mmol) in N,N-dimethylformamide (1.0 mL) at room temperature was added Et₃N (0.063 mL, 0.451 mmol). The reaction mixture was then stirred at room temperature. After stirring overnight at room temperature, the crude was purified by reverse phase HPLC (Gilson, 30 mm×50 mm Gemini Column, NH₄OH modifier) to obtain 2-((3,5-dicyano-4-ethyl-6-(4-methyl-1,4-diazepan-1-yl)pyridin-2-yl)thio)-2-(3-(pyrrolidin-1-yl)phenyl)acetamide (7 mg). LCMS m/z=504.3 [M+H]⁺. ¹H NMR (400 MHz, DMSO-d₆) δ ppm 7.81 (s, 1H), 7.28 (s, 1H), 7.14 (t, J=7.86 Hz, 1H), 6.69 (d, J=8.11 Hz, 1H), 6.63-6.66 (m, 1H), 6.48 (dd, J=1.77, 8.36 Hz, 1H), 5.38 (s, 1H), 3.95 (t, J=4.31 Hz, 2H), 3.90 (t, J=6.08 Hz, 2H), 3.15-3.24 (m, 4H), 2.77 (q, J=7.60 Hz, 2H), 2.64-2.70 (m, 2H), 2.26 (s, 3H), 1.91-1.98 (m, 6H), 1.21 (t, J=7.60 Hz, 3H). Two protons not observed.

Example 248

2-((3,5-Dicyano-4-ethyl-6-(4-methyl-1,4-diazepan-1-yl)pyridin-2-yl)thio)-2-(3-fluoropyridin-4-yl)acetamide Step 1:
2-(3-Fluoropyridin-4-yl)-2-hydroxyacetamide

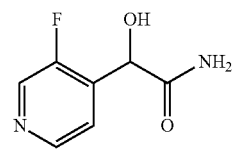 [SMILES: NC(=O)C(O)c1ccncc1F]

To a solution of 3-fluoroisonicotinaldehyde (1.0 g, 7.99 mmol) in dichloromethane (25 mL) was added trimethylsilanecarbonitrile (1.200 mL, 9.59 mmol). The mixture was stirred at room temperature overnight. The mixture was concentrated down to afford a light brown oil, which was treated with concentrated $H_2SO_4$ (5 mL, 94 mmol) for 4 hours, then poured the reaction mixture into ice, and adjusted the pH to 9 using $NH_4OH$. The solid was filtered to afford 2-(3-fluoropyridin-4-yl)-2-hydroxyacetamide (748 mg, 4.40 mmol, 55% yield) as an off white solid. LCMS m/z=171.0 $[M+H]^+$.

Step 2:
2-Amino-1-(3-fluoropyridin-4-yl)-2-oxoethyl methanesulfonate

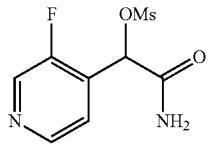 [SMILES: CS(=O)(=O)OC(C(N)=O)c1ccncc1F]

To a slurry solution of 2-(3-fluoropyridin-4-yl)-2-hydroxyacetamide (745 mg, 4.38 mmol) and TEA (1.221 mL, 8.76 mmol) in THF (20 mL) was added methanesulfonyl chloride (0.409 mL, 5.25 mmol). The reaction mixture was stirred at room temperature overnight. The reaction mixture was concentrated down with silica and purified by silica column (CombiFlash®, 40 g column, 0-10% MeOH/DCM) to afford 2-amino-1-(3-fluoropyridin-4-yl)-2-oxoethyl methanesulfonate (970 mg, 3.91 mmol, 89% yield) as a beige solid. LCMS m/z=249.1 $[M+H]^+$.

Step 3: 2-((3,5-Dicyano-4-ethyl-6-(4-methyl-1,4-diazepan-1-yl)pyridin-2-yl)thio)-2-(3-fluoropyridin-4-yl)acetamide

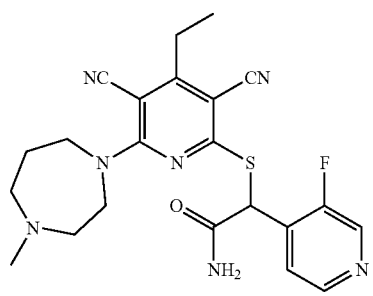 [SMILES: CCc1c(C#N)c(SC(C(N)=O)c2ccncc2F)nc(N2CCCN(C)CC2)c1C#N]

The reaction mixture of 4-ethyl-2-mercapto-6-(4-methyl-1,4-diazepan-1-yl)pyridine-3,5-dicarbonitrile (synthesis described in example 69, step 1, 109 mg, 0.363 mmol), 2-amino-1-(3-fluoropyridin-4-yl)-2-oxoethyl methanesulfonate (75 mg, 0.302 mmol) and TEA (0.084 mL, 0.604 mmol) in DMF (3 mL) was stirred at room temperature overnight. The reaction mixture was purified by silica (CombiFlash®, 12 g column using 10-20% MeOH/DCM as eluent). The resulting fractions were concentrated down and purified by second silica column (12 g column, 20% MeOH/DCM) to afford 2-((3,5-dicyano-4-ethyl-6-(4-methyl-1,4-diazepan-1-yl)pyridin-2-yl)thio)-2-(3-fluoropyridin-4-yl)acetamide (79 mg, 0.174 mmol, 58% yield) as an off white solid.

LCMS m/z=454.3 $[M+H]^+$. $^1H$ NMR (400 MHz, DMSO-$d_6$) δ ppm 1.22 (t, J=7.6 Hz, 3H), 1.91 (br. s., 2H), 2.23-2.31 (m, 3H), 2.34-2.49 (m, 2H), 2.55-2.73 (m, 2H), 2.79 (q, J=7.6 Hz, 2H), 3.68-3.98 (m, 4H), 5.84 (s, 1H), 7.57 (dd, J=6.3, 5.1 Hz, 1H), 7.65 (s, 1H), 8.07 (s, 1H), 8.46 (d, J=4.8 Hz, 1H), 8.63 (d, J=1.5 Hz, 1H).

Example 249

2-((3,5-Dicyano-4-ethyl-6-(4-methyl-1,4-diazepan-1-yl)pyridin-2-yl)thio)-2-(2,5-difluoropyridin-4-yl)acetamide Step 1:
2-(2,5-Difluoropyridin-4-yl)-2-hydroxyacetamide

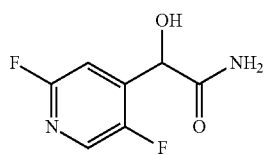 [SMILES: NC(=O)C(O)c1cc(F)ncc1F]

To a solution of 2,5-difluoroisonicotinaldehyde (1.9 g, 13.28 mmol) in dichloromethane (50 mL) was added trimethylsilanecarbonitrile (1.993 mL, 15.93 mmol). The mixture was stirred at room temperature overnight. The mixture was concentrated down to afford a brown oil, which was treated with concentrated $H_2SO_4$ (7 mL, 131 mmol) for 4 hours, then poured the reaction mixture into ice, and adjusted the pH to 9 using $NH_4OH$. The reaction mixture was concentrated down with Celite®, purified by silica column (CombiFlash®, 40 g column using 0-15% MeOH/DCM) to afford 2-(2,5-difluoropyridin-4-yl)-2-hydroxyacetamide (1.41 g, 7.49 mmol, 56% yield) as a yellow solid. LCMS m/z=189.0 $[M+H]^+$.

Step 2:
2-Amino-1-(2,5-difluoropyridin-4-yl)-2-oxoethyl methanesulfonate

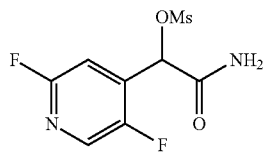 [SMILES: CS(=O)(=O)OC(C(N)=O)c1cc(F)ncc1F]

To a slurry solution of 2-(2,5-difluoropyridin-4-yl)-2-hydroxyacetamide (1.41 g, 7.49 mmol) and TEA (2.089 mL, 14.99 mmol) in THF (40 mL) was added methanesulfonyl chloride (0.701 mL, 8.99 mmol). The reaction mixture was stirred at room temperature overnight. The reaction mixture was diluted with DCM and water, separated the layers. The aqueous layer was extracted with DCM (2×). The combined organics were washed with brine, dried over $Na_2SO_4$, concentrated down to afford 2-amino-1-(2,5-difluoropyridin-4-yl)-2-oxoethyl methanesulfonate (1.88 g, 7.06 mmol, 94% yield) as a yellow solid. LCMS m/z=267.0 $[M+H]^+$.

Step 3: 2-((3,5-Dicyano-4-ethyl-6-(4-methyl-1,4-diazepan-1-yl)pyridin-2-yl)thio)-2-(2,5-difluoropyridin-4-yl)acetamide

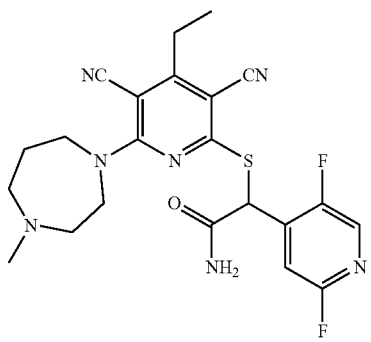 [SMILES: CCc1c(C#N)c(SC(C(N)=O)c2cc(F)ncc2F)nc(N2CCCN(C)CC2)c1C#N]

The reaction mixture of 4-ethyl-2-mercapto-6-(4-methyl-1,4-diazepan-1-yl) pyridine-3,5-dicarbonitrile (synthesis described in example 69, step 1, 109 mg, 0.361 mmol), 2-amino-1-(2,5-difluoropyridin-4-yl)-2-oxoethyl methanesulfonate (80 mg, 0.301 mmol) and TEA (0.084 mL, 0.601 mmol) in DMF (3 mL) was stirred at room temperature overnight. The reaction mixture was purified by silica (CombiFlash®, 12 g column using 10-20% MeOH/DCM as eluent). The resulting fractions were concentrated down and purified by second silica column (12 g using 20% MeOH/DCM) to afford 2-((3,5-dicyano-4-ethyl-6-(4-methyl-1,4-diazepan-1-yl) pyridin-2-yl)thio)-2-(2,5-difluoropyridin-4-yl) acetamide (44 mg, 0.093 mmol, 31% yield) as an off white solid. LCMS m/z=472.3 [M+H]$^+$. $^1$H NMR (400 MHz, Pyridine-d$_5$) δ ppm 9.33 (s, 1H), 9.21 (s, 1H), 8.29 (s, 1H), 7.75 (dd, J=4.6, 2.8 Hz, 1H), 6.28 (s, 1H), 4.15 (t, J=4.4 Hz, 2H), 3.82-3.93 (m, 2H), 3.00-3.18 (m, 2H), 2.72-2.86 (m, 4H), 2.43 (s, 3H), 2.17 (br. s., 2H), 1.15 (t, J=7.6 Hz, 3H).

Example 250

2-((3,5-Dicyano-6-(4-(2,5-dioxoimidazolidin-1-yl)piperidin-1-yl)-4-ethylpyridin-2-yl)thio)-2-phenylacetamide

Step 1: 3-(1-Benzylpiperidin-4-yl) imidazolidine-2,4-dione

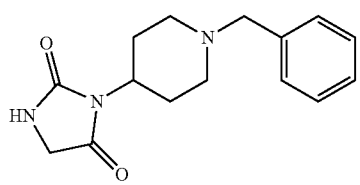 [SMILES: O=C1CNC(=O)N1C1CCN(Cc2ccccc2)CC1]

A solution of 1-benzylpiperidin-4-amine (5 g, 26.3 mmol) in CHCl$_3$ (30 mL) was added dropwise to a stirred solution of ethyl 2-isocyanatoacetate (2.5 g, 19.36 mmol) in CHCl$_3$ (70 mL), and the reaction mixture was stirred for 15 minutes. Then reaction mixture was then evaporated and dried to obtain a yellow solid. The yellow solid was taken up in a solution of EtOH (15 mL) and HCl (10 M, aqueous, 15 mL) and heated to reflux for 3 hours. After 3 hours, the EtOH was evaporated, and the solution was neutralized with NaOH solution (5N, 30 mL) and then saturated solution of NaHCO$_3$ (30 mL). The mixture was extracted with DCM (2×50 mL), and the combined organic layers were dried over anhydrous Na$_2$SO$_4$, filtered, and concentrated. The crude compound was purified by silica-gel chromatography (100-200 mesh, using 0-70% EtOAc in petroleum ether as eluent). Pure fractions were collected, concentrated and dried to get 3-(1-benzylpiperidin-4-yl)imidazolidine-2,4-dione (3 g, 55% yield) as a yellow solid. LCMS m/z=274.2 [M+H]$^+$.

Step 2: 3-(Piperidin-4-yl) imidazolidine-2,4-dione

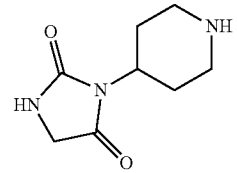 [SMILES: O=C1CNC(=O)N1C1CCNCC1]

10% Pd/C (600 mg, 0.564 mmol) was added to a solution of 3-(1-benzylpiperidin-4-yl)imidazolidine-2,4-dione (2.7 g, 9.60 mmol) in MeOH (200 mL) at room temperature and the reaction mixture was allowed to stir under an atmosphere of hydrogen (balloon) for 16 hours. The reaction mixture was filtered through a Celite® bed, washing with MeOH (300 mL). The filtrate was concentrated and dried to obtain 3-(piperidin-4-yl)imidazolidine-2,4-dione (1 g) as a grey solid. LCMS m/z=184.2 [M+H]$^+$.

Step 3: 2-Chloro-6-(4-(2,5-dioxoimidazolidin-1-yl)piperidin-1-yl)-4-ethylpyridine-3,5-dicarbonitrile

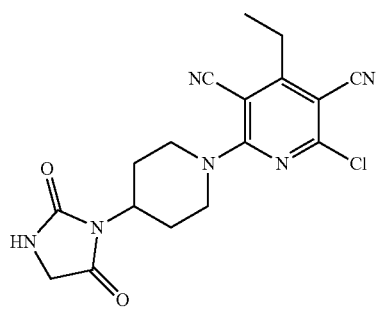 [SMILES: CCc1c(C#N)c(Cl)nc(N2CCC(N3C(=O)CNC3=O)CC2)c1C#N]

3-(Piperidin-4-yl)imidazolidine-2,4-dione (399 mg, 2.095 mmol) was added to a solution of triethylamine (0.549 mL, 3.14 mmol) and 2,6-dichloro-4-ethylpyridine-3,5-dicarbonitrile (synthesis described in example 3 step 2, 500 mg, 2.095 mmol) in dichloromethane (10 mL) at 0° C., and the reaction mixture was stirred for 1 hour at room temperature. The reaction mixture was quenched with ice cold water (50 mL) and extracted with ethyl acetate (2×50 mL). The combined organic layers were dried over anhydrous Na$_2$SO$_4$, filtered, and concentrated to afford 2-chloro-6-(4-(2,5-dioxoimidazolidin-1-yl)piperidin-1-yl)-4-ethylpyridine-3,5-dicarbonitrile (400 mg, 39% yield) as a grey color solid. LCMS m/z=371.0 [M−H]$^-$.

Step 4: 2-((3,5-Dicyano-6-(4-(2,5-dioxoimidazolidin-1-yl)piperidin-1-yl)-4-ethylpyridin-2-yl)thio)-2-phenylacetamide

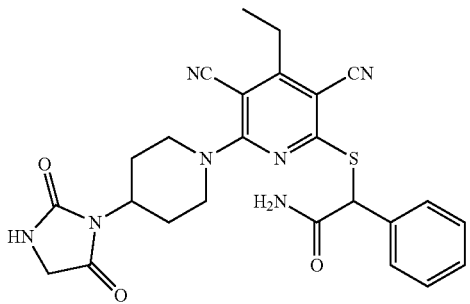 [SMILES: CCc1c(C#N)c(SC(C(N)=O)c2ccccc2)nc(N2CCC(N3C(=O)CNC3=O)CC2)c1C#N]

A solution of 2-chloro-6-(4-(2,5-dioxoimidazolidin-1-yl)piperidin-1-yl)-4-ethylpyridine-3,5-dicarbonitrile (400 mg, 0.805 mmol) and potassium thioacetate (184 mg, 1.609 mmol) in N,N-dimethylformamide (10 mL) was stirred for two hours at room temperature. Potassium carbonate (222 mg, 1.609 mmol) and 2-amino-2-oxo-1-phenylethyl methanesulfonate (synthesis described in example 3 step 5, 388 mg, 1.609 mmol) were then added, and the reaction mixture was stirred at room temperature for 16 hours. The reaction mixture was diluted with ethyl acetate (100 mL), and the organic layer was washed with HCl (1N, 2×100 mL). The organic layer was dried over anhydrous $Na_2SO_4$, filtered and evaporated to yield a black gummy solid which was purified by prep-HPLC to afford 2-((3,5-dicyano-6-(4-(2,5-dioxoimidazolidin-1-yl)piperidin-1-yl)-4-ethylpyridin-2-yl)thio)-2-phenylacetamide (160 mg, 40% yield) as a yellow solid. LCMS m/z=504.4 $[M+H]^+$. $^1$H NMR (400 MHz, DMSO-$d_6$) δ ppm 8.04 (s, 1H), 7.90 (s, 1H), 7.56-7.47 (m, 2H), 7.41-7.24 (m, 4H), 5.54 (s, 1H), 4.69 (d, J=13.37 Hz, 2H), 4.24-4.09 (m, 1H), 3.88 (s, 2H), 3.20 (t, J=12.50 Hz, 2H), 2.76 (q, J=7.67 Hz, 2H), 2.37-2.22 (m, 2H), 1.75 (d, J=9.21 Hz, 2H), 1.21 (t, J=7.56 Hz, 3H).

Example 251

4-Amino-1-(6-((2-amino-2-oxo-1-phenylethyl)thio-3,5-dicyano-4-ethylpyridin-2-yl) piperidine-4-carboxamide Step 1: 4-Aminopiperidine-4-carboxamide

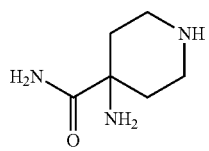

To a stirred solution of 4-amino-1-benzylpiperidine-4-carboxamide (2 g, 8.40 mmol) in methanol (20 mL) under nitrogen at 0° C. was added palladium on carbon (10%, 2 g, 1.879 mmol). The reaction mixture was stirred at room temperature for 5 hours under a hydrogen atmosphere. The reaction mixture was filtered through Celite® bed, washing with methanol (50 mL). The filtrate was concentrated under reduced pressure to give 4-aminopiperidine-4-carboxamide (1.2 g) as an off-white solid. LCMS m/z=144.2 $[M+H]^+$.

Step 2: 4-Amino-1-(6-chloro-3,5-dicyano-4-ethylpyridin-2-yl)piperidine-4-carboxamide

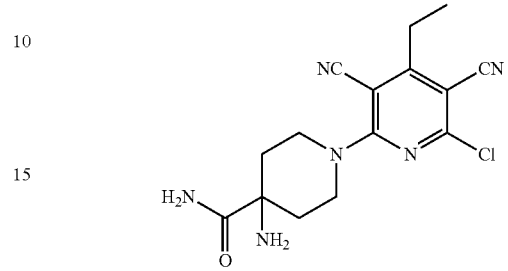

To a solution of 2,6-dichloro-4-ethylpyridine-3,5-dicarbonitrile (synthesis described in example 3 step 2, 1.4 g, 6.2 mmol) in dichloromethane (15 mL) was added triethylamine (1.726 mL, 12.39 mmol) at 0° C. After 2 minutes a solution of 4-aminopiperidine-4-carboxamide (0.887 g, 6.19 mmol) in N,N-dimethylformamide (15 mL) was added and the mixture was stirred for 10 minutes at 0° C. The reaction mixture was quenched with water (50 mL) and extracted with DCM (2×30 mL). The combined organic layers were dried over anhydrous sodium sulphate, filtered and concentrated to dryness. The crude compound was purified by silica-gel column chromatography (100-200 mesh, eluting with 3-4% methanol in DCM) to afford 4-amino-1-(6-chloro-3,5-dicyano-4-ethylpyridin-2-yl)piperidine-4-carboxamide (2.2 g, 4.49 mmol, 73% yield) as a pink solid. LCMS m/z=333.1 $[M+H]^+$.

Step 3: 4-Amino-1-(6-((2-amino-2-oxo-1-phenylethyl)thio)-3,5-dicyano-4-ethylpyridin-2-yl)piperidine-4-carboxamide

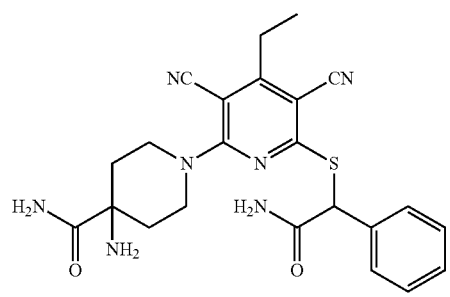 [SMILES: CCc1c(C#N)c(SC(C(N)=O)c2ccccc2)nc(N2CCC(N)(C(N)=O)CC2)c1C#N]

To a stirred solution of S-(2-amino-2-oxo-1-phenylethyl) ethanethioate (synthesis described in example 62 step 5, 1.15 g, 4.89 mmol) in N,N-dimethylformamide (5 mL) were added potassium carbonate (1.014 g, 7.34 mmol) and 4-amino-1-(6-chloro-3,5-dicyano-4-ethylpyridin-2-yl)piperidine-4-carboxamide (2.186 g, 4.40 mmol), and the mixture was stirred for 14 hours at room temperature. The reaction mixture was quenched with cold water (30 mL) and extracted with EtOAc (2×20 mL). The combined organic layers were dried over anhydrous $Na_2SO_4$, filtered and concentrated under vacuum. The crude product was purified by silica gel column chromatography (100-200 mesh, eluting with 3-4% methanol in DCM) to afford 4-amino-1-(6-((2-amino-2-oxo-1-phenylethyl)thio)-3,5-dicyano-4-ethylpyridin-2-yl)piperidine-4-carboxamide (95 mg, 4% yield) as an off-white solid. LCMS m/z=464.4 [M+H]⁺. ¹H NMR (400 MHz, DMSO-d₆) δ ppm 7.89 (s, 1H), 7.51 (d, J=7.02 Hz, 2H), 7.43 (br s, 1H), 7.39-7.28 (m, 4H), 6.99 (br s, 1H), 5.53 (s, 1H), 4.31 (d, J=13.37 Hz, 2H), 3.68-3.55 (m, 2H), 2.75 (q, J=7.38 Hz, 2H), 2.12-1.90 (m, 4H), 1.49 (d, J=13.59 Hz, 2H), 1.21 (t, J=7.67 Hz, 3H).

Example 252

2-((3,5-Dicyano-6-(4-(2,5-dioxopyrrolidin-1-yl)piperidin-1-yl)-4-ethylpyridin-2-yl)thio)-2-phenylacetamide Step 1:
1-(1-Benzylpiperidin-4-yl)pyrrolidine-2,5-dione

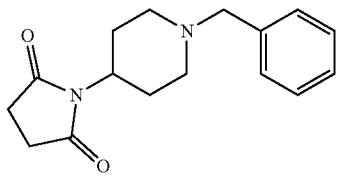 [SMILES: O=C1CCC(=O)N1C1CCN(Cc2ccccc2)CC1]

To a solution of dihydrofuran-2,5-dione (2.5 g, 24.98 mmol) in acetic acid (75 mL) was added 1-benzylpiperidin-4-amine (4.75 g, 24.98 mmol) at room temperature. The reaction mixture was stirred for 72 hours at 100° C. The acetic acid was removed by distillation. Then the mixture was quenched with saturated sodium bicarbonate solution (100 mL) and extracted with DCM (100 mL). The organic phase was dried over sodium sulphate, filtered and concentrated. The crude product was purified by column chromatography using silica-gel (mesh 100-200, eluting with 100% dichloromethane). The pure fractions were concentrated under reduced pressure to afford (3.2 g, 41% yield) as an off-white solid. LCMS m/z=273.16 [M+H]⁺.

Step 2: 1-(Piperidin-4-yl) pyrrolidine-2,5-dione

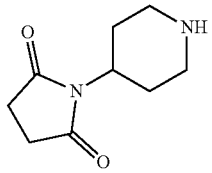 [SMILES: O=C1CCC(=O)N1C1CCNCC1]

To a solution of 1-(1-benzylpiperidin-4-yl)pyrrolidine-2,5-dione (3.2 g, 10.35 mmol) in methanol (100 mL) was added Pd—C (10%, 1.102 g, 10.35 mmol), and the mixture was placed under an atmosphere of hydrogen (balloon). The reaction mixture was stirred for 24 hours at room temperature under a hydrogen atmosphere. The reaction mixture was filtered through Celite®, washing with MeOH (20 mL). The filtrate was concentrated, and the resulting residue was purified by column chromatography using neutral alumina (eluting with 5% MeOH in DCM). The pure fractions were concentrated under reduced pressure to afford (2.0 g) as an off-white solid. LCMS m/z=183.2 [M+H]⁺.

Step 3: 2-Chloro-6-(4-(2,5-dioxopyrrolidin-1-yl)piperidin-1-yl)-4-ethylpyridine-3,5-dicarbonitrile

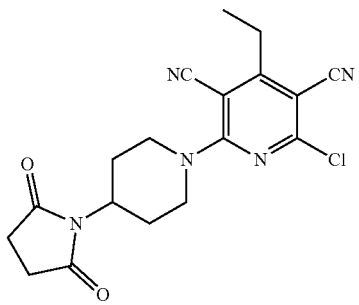 [SMILES: CCc1c(C#N)c(Cl)nc(N2CCC(N3C(=O)CCC3=O)CC2)c1C#N]

To a solution of 2,6-dichloro-4-ethylpyridine-3,5-dicarbonitrile (synthesis described in example 3 step 2, 500 mg, 2.095 mmol) in dichloromethane (10 mL) was added triethylamine (0.549 mL, 3.94 mmol) at 0° C. After 2 minutes, 1-(piperidin-4-yl)pyrrolidine-2,5-dione (441 mg, 2.095 mmol) was added, and the reaction was stirred for 5 minutes at 0° C. The reaction mixture was quenched with ice cold water (20 mL) and extracted with ethyl acetate (2×50 mL). The combined organic layers were dried over Na₂SO₄, filtered and concentrated to afford the crude product which was purified by column chromatography using silica gel (mesh 100-200, eluting with 35% EtOAc in hexane). The pure fractions were concentrated under reduced pressure to afford (700 mg, 88% yield) as an off-white solid. LCMS m/z=372.2 [M+H]⁺.

Step 4: 2-((3,5-Dicyano-6-(4-(2,5-dioxopyrrolidin-1-yl)piperidin-1-yl)-4-ethylpyridin-2-yl)thio)-2-phenylacetamide

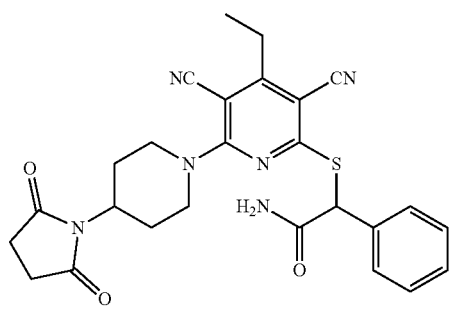 [SMILES: CCc1c(C#N)c(SC(C(N)=O)c2ccccc2)nc(N2CCC(N3C(=O)CCC3=O)CC2)c1C#N]

To a solution of 2-chloro-6-(4-(2,5-dioxopyrrolidin-1-yl)piperidin-1-yl)-4-ethylpyridine-3,5-dicarbonitrile (500 mg, 1.324 mmol) in N,N-dimethylformamide (10 mL) was added potassium thioacetate (303 mg, 2.65 mmol). The reaction mixture was stirred at room temperature for 2 hours. Potassium carbonate (366 mg, 2.65 mmol), followed by 2-amino-2-oxo-1-phenylethyl methanesulfonate (synthesis described in example 3 step 5, 320 mg, 1.324 mmol) were added, and the reaction mixture was stirred at room temperature for 16 hours. The reaction mixture was diluted with ice cold water (100 mL) and extracted with EtOAc (2×100 mL). The combined organic layers were washed with HCl (1N, 2×500 mL), dried over anhydrous Na₂SO₄, filtered and concentrated. The crude product was purified by column chromatography using silica gel (100-200 mesh, 0-5% MeOH in DCM as eluent). The pure fractions were collected, concentrated and dried to afford 2-((3,5-dicyano-6-(4-(2,5-dioxopyrrolidin-1-yl)piperidin-1-yl)-4-ethylpyridin-2-yl)thio)-2-phenylacetamide (250 mg, 37% yield) as a pale brown solid. LCMS m/z=503.4 [M+H]$^+$. $^1$H NMR (400 MHz, DMSO-d$_6$) δ ppm 7.89 (s, 1H), 7.54-7.49 (m, 2H), 7.41-7.26 (m, 4H), 5.54 (s, 1H), 4.68 (d, J=13.37 Hz, 2H), 4.30-4.20 (m, 1H), 3.25-3.14 (m, 2H), 2.76 (q, J=7.60 Hz, 2H), 2.61 (s, 4H), 2.35-2.22 (m, 2H), 1.70 (d, J=9.65 Hz, 2H), 1.21 (t, J=7.56 Hz, 3H).

Example 254

2-((3,5-dicyano-4-ethyl-6-(4-methyl-1,4-diazepan-1-yl)pyridin-2-yl)thio)-2-phenylacetamide (Isomer 1)

ISOMER 1

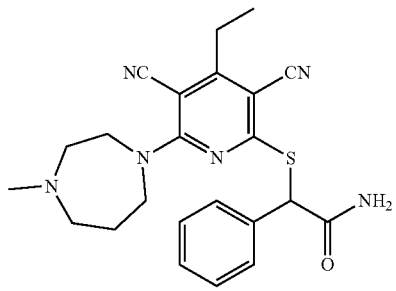

Racemic 2-((3,5-dicyano-4-ethyl-6-(4-methyl-1,4-diazepan-1-yl)pyridin-2-yl)thio)-2-phenylacetamide (synthesis described in example 56, 302 mg) was resolved by chiral HPLC (IC 21×250 mm, 5 micron, MeOH as eluent) to afford the first eluting enantiomer (isomer 1) of 2-((3,5-dicyano-4-ethyl-6-(4-methyl-1,4-diazepan-1-yl)pyridin-2-yl)thio)-2-phenylacetamide (96.3 mg, 95.8% ee). LCMS m/z=435.2 [M+H]$^+$. $^1$H NMR (400 MHz, METHANOL-d$_4$) δ ppm 7.52 (d, J=1.27 Hz, 2H) 7.41 (d, J=7.60 Hz, 3H) 5.51 (s, 1H) 4.05 (s, 4H) 2.93 (d, J=7.60 Hz, 2H) 2.77-2.88 (m, 2H) 2.59-2.72 (m, 2H) 2.43 (s, 3H) 2.04-2.17 (m, 2H) 1.32 (t, J=7.60 Hz, 3H).

Example 255

2-((3,5-dicyano-4-ethyl-6-(4-methyl-1,4-diazepan-1-yl)pyridin-2-yl)thio)-2-phenylacetamide (Isomer 2)

ISOMER 2

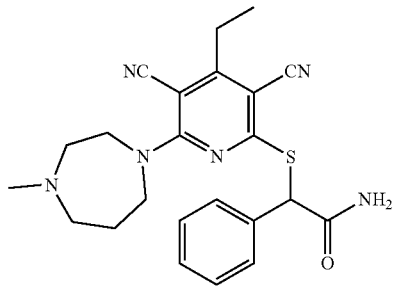

Also isolated from the above resolution (example 254) was the second eluting enantiomer (isomer 2) of 2-((3,5-dicyano-4-ethyl-6-(4-methyl-1,4-diazepan-1-yl)pyridin-2-yl)thio)-2-phenylacetamide (104.0 mg, 95.8% ee). LCMS m/z=435.2 [M+H]$^+$. $^1$H NMR (400 MHz, METHANOL-d$_4$) δ ppm 7.50-7.57 (2H, m) 7.33-7.47 (3H, m) 5.51 (1H, s) 3.94-4.10 (4H, m) 2.93 (2H, d, J=7.60 Hz) 2.86 (2H, br. s.) 2.59-2.76 (2H, m) 2.42 (3H, s) 2.05-2.17 (2H, m) 1.32 (3H, t, J=7.60 Hz).

Example 256

2-((3,5-Dicyano-4-ethyl6-(2-oxo-1-oxa-3,8-diazaspiro[4.5]decan-8-yl)pyridin-2-yl)thio)-2-phenylacetamide Step 1: 2-Chloro-4-ethyl-6-(2-oxo-1-oxa-3,8-diazaspiro[4.5]decan-8-yl)pyridine-3,5-dicarbonitrile

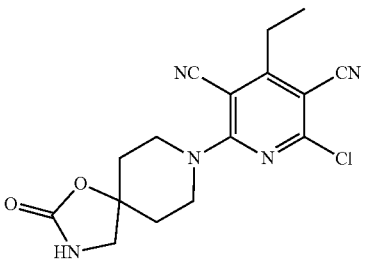 [SMILES: CCc1c(C#N)c(Cl)nc(N2CCC3(CC2)CNC(=O)O3)c1C#N]

A mixture of 2,6-dichloro-4-ethylpyridine-3,5-dicarbonitrile (synthesis described in example 3 step 2, 1.5 g, 6.64 mmol), 1-oxa-3,8-diazaspiro[4.5]decan-2-one (1.036 g, 6.64 mmol) and triethylamine (0.671 g, 6.64 mmol) was stirred at 25° C. for 15 hours. Solvent was evaporated under vacuum. Then DCM (50 mL) and water (30 mL) were added to the residue, and the organic layer was separated and washed with brine, dried and concentrated. The residue was purified by silica gel chromatography (PE/EA=2:1) to give 2-chloro-4-ethyl-6-(2-oxo-1-oxa-3,8-diazaspiro[4.5]decan-8-yl)pyridine-3,5-dicarbonitrile (800 mg, 2.314 mmol, 35% yield). LCMS m/z=368.0 [M+Na]$^+$.

Step 2: 2-((3,5-Dicyano-4-ethyl-6-(2-oxo-1-oxa-3,8-diazaspiro[4.5]decan-8-yl)pyridin-2-yl)thio)-2-phenylacetamide

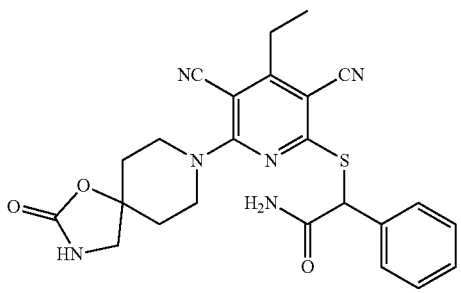 [SMILES: CCc1c(C#N)c(SC(C(N)=O)c2ccccc2)nc(N2CCC3(CC2)CNC(=O)O3)c1C#N]

2-Chloro-4-ethyl-6-(2-oxo-1-oxa-3,8-diazaspiro[4.5]decan-8-yl)pyridine-3,5-dicarbonitrile (300 mg, 0.868 mmol) and potassium ethanethioate (198 mg, 1.735 mmol) were added to N,N-dimethylformamide (30 mL). The mixture was stirred for 2 hours. Then 2-amino-2-oxo-1-phenylethyl methanesulfonate (synthesis described in example 3 step 5, 398 mg, 1.735 mmol) was added, and the mixture was stirred for 15 hours. The solvent was evaporated under vacuum. Then DCM (30 mL) and water (20 mL) were added. The organic layer was separated, washed with brine, dried and concentrated. The residue was purified by prep-HPLC to give 2-((3,5-dicyano-4-ethyl-6-(2-oxo-1-oxa-3,8-diazaspiro[4.5]decan-8-yl)pyridin-2-yl)thio)-2-phenylacetamide (100 mg, 0.210 mmol, 24% yield). LCMS m/z=477.1 [M+H]$^+$. $^1$H NMR (400 MHz, DMSO-d$_6$): δ ppm 7.92 (s, 1H), 7.62 (s, 1H), 7.53-7.51 (m, 2H), 7.41-7.34 (m, 4H), 5.54 (s, 1H), 4.24-4.17 (m, 2H), 3.64 (t, 2H), 3.31 (s, 2H), 2.78-2.74 (m, 2H), 1.87-1.94 (m, 4H), 1.23 (t, 3H).

Example 258

1-(6-((2-Amino-2-oxo-1-phenylethyl)thio)-3,5-dicyano-4-ethylpyridin-2-yl)-4-hydroxy piperidine-4-carboxamide Step 1:
1-Benzyl-4-hydroxypiperidine-4-carboxamide

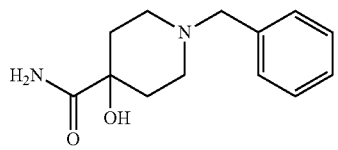 [SMILES: NC(=O)C1(O)CCN(Cc2ccccc2)CC1]

To a stirred solution of 1-benzyl-4-hydroxypiperidine-4-carbonitrile (1 g, 3.56 mmol) in dichloromethane (10 mL) under nitrogen at 0° C. was added H$_2$SO$_4$ (3 mL, 56.3 mmol). The reaction mixture was stirred at room temperature for 2 hours. Then ammonium hydroxide (28%, 7 mL, 50.3 mmol) was added at 0° C., and the mixture was stirred for 14 hours at room temperature. The reaction mixture was extracted with DCM (2×20 mL). The combined organic layers were dried over anhydrous sodium sulphate, filtered and concentrated under reduced pressure to afford 1-benzyl-4-hydroxypiperidine-4-carboxamide (750 mg) as an off-white solid. LCMS m/z=235.1 [M+H]$^+$.

Step 2: 4-Hydroxypiperidine-4-carboxamide

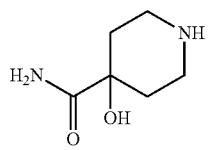

To a stirred solution of 1-benzyl-4-hydroxypiperidine-4-carboxamide (740 mg, 3.14 mmol) in methanol (15 mL) under nitrogen at 0° C. was added palladium on carbon (10%, 740 mg, 0.695 mmol). The reaction mixture was stirred at room temperature for 5 hours under a hydrogen atmosphere. The reaction mixture was filtered through Celite®, rinsing with methanol. The filtrate was concentrated under reduced pressure to afford 4-hydroxypiperidine-4-carboxamide (350 mg) as an off-white solid. $^1$H NMR (400 MHz, DMSO-d$_6$): δ ppm 7.11 (s, 1H), 6.97 (s, 1H), 5.05 (s, 1H), 2.78-2.63 (m, 4H), 1.76 (td, J=12.39, 5.26 Hz, 2H), 1.31 (d, J=11.62 Hz, 2H).

Step 3: 1-(6-Chloro-3,5-dicyano-4-ethylpyridin-2-yl)-4-hydroxypiperidine-4-carboxamide

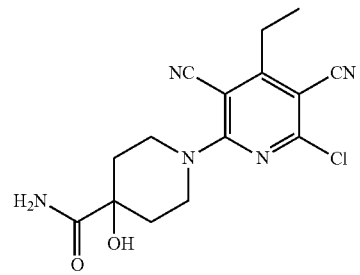 [SMILES: CCc1c(C#N)c(Cl)nc(N2CCC(O)(C(N)=O)CC2)c1C#N]

To a stirred solution of 2,6-dichloro-4-ethylpyridine-3,5-dicarbonitrile (synthesis described in example 3 step 2, 550 mg, 2.433 mmol) in dichloromethane (5 mL) at 0° C. was added triethylamine (0.678 mL, 4.87 mmol). After 2 minutes 4-hydroxypiperidine-4-carboxamide (351 mg, 2.433 mmol) in N,N-dimethylformamide (5 mL) was added, and the reaction mixture was stirred for 10 minutes at 0° C. The reaction mixture was diluted with water (20 mL) and extracted with DCM (2×10 mL). The combined organic layers were dried over anhydrous sodium sulphate, filtered and concentrated under vacuum. The obtained crude product was purified by column chromatography using silica-gel (100-200 mesh, eluting with 3-4% methanol in DCM) to afford 1-(6-chloro-3,5-dicyano-4-ethylpyridin-2-yl)-4-hydroxypiperidine-4-carboxamide (800 mg, 97% yield) as a pink-colored solid. LCMS m/z=334.1 [M+H]$^+$.

Step 4: 1-(6-((2-Amino-2-oxo-1-phenylethyl)thio)-3,5-dicyano-4-ethylpyridin-2-yl)-4-hydroxypiperidine-4-carboxamide

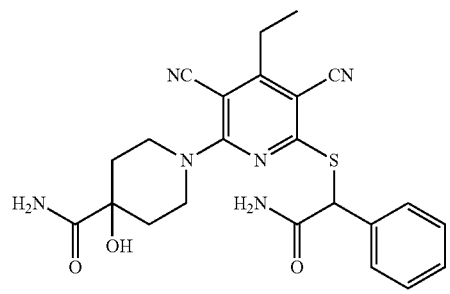 [SMILES: CCc1c(C#N)c(SC(C(N)=O)c2ccccc2)nc(N2CCC(O)(C(N)=O)CC2)c1C#N]

To a stirred solution of 1-(6-chloro-3,5-dicyano-4-ethylpyridin-2-yl)-4-hydroxypiperidine-4-carboxamide (400 mg, 1.174 mmol) in N,N-dimethylformamide (5 mL) was added potassium thioacetate (268 mg, 2.349 mmol) at room temperature and stirred for 2 hours at the same temperature. To the reaction mixture, potassium carbonate (325 mg, 2.349 mmol) and 2-amino-2-oxo-1-phenylethyl methanesulfonate (synthesis described in example 3 step 5, 272 mg, 1.174 mmol) were added at room temperature and stirred for 14 hours at room temperature. The reaction mixture was diluted with water (50 mL) and extracted with ethyl acetate (2×30 mL). The combined organic layers were dried over anhydrous sodium sulphate, filtered and concentrated under vacuum to afford the crude. The obtained crude was purified by column chromatography using silica gel (mesh 100-200, eluted with 3-4% methanol in DCM) to afford 1-(6-((2-amino-2-oxo-1-phenylethyl)thio)-3,5-dicyano-4-ethylpyridin-2-yl)-4-hydroxypiperidine-4-carboxamide (260 mg, 47% yield) as an off-white solid. LCMS m/z=465.5 [M+H]⁺. ¹H NMR (400 MHz, DMSO-d₆) δ ppm 7.89 (s, 1H), 7.55-7.47 (m, 2H), 7.42-7.26 (m, 5H), 7.15 (br s, 1H), 5.53 (s, 2H), 4.44 (d, J=9.87 Hz, 2H), 3.50-3.36 (m, 2H), 2.76 (q, J=7.45 Hz, 2H), 2.05-1.91 (m, 2H), 1.62 (d, J=13.81 Hz, 2H), 1.21 (t, J=7.56 Hz, 3H).

Example 259

1-(6-((2-Amino-2-oxo-1-phenylethylthio-3,5-dicyano-4-ethylpyridin-2-yl)azetidin-3-yl carbamate Step 1: 1-Benzhydrylazetidin-3-yl carbamate

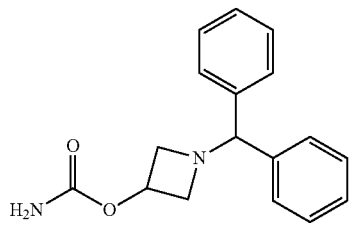 [SMILES: NC(=O)OC1CN(C(c2ccccc2)c2ccccc2)C1]

To a stirred solution of 1-benzhydrylazetidin-3-ol (2 g, 8.36 mmol) in ethyl acetate (50 mL) was added 2,2,2-trichloroacetyl isocyanate (1.25 mL, 8.36 mmol) at 0° C. and the mixture was stirred for 1 hour. Then the reaction mixture was concentrated under reduced pressure. The resulting residue was dissolved in methanol (50 mL), and water (4 mL) and sodium formate (0.568 g, 8.36 mmol) were added. The reaction mixture was stirred for 24 hours at room temperature. The reaction mixture was concentrated under reduced pressure and the residue was diluted with EtOAc (70 mL). The organic layer was washed with saturated sodium bicarbonate solution (20 mL), saturated brine (10 mL), dried over anhydrous sodium sulphate, filtered and concentrated under reduced pressure. The resulting residue was triturated with diethyl ether (20 mL) to afford 1-benzhydrylazetidin-3-yl carbamate (900 mg, 34% yield) as an off-white solid. LCMS m/z=283.1 [M+H]⁺.

Step 2: 1-(6-Chloro-3,5-dicyano-4-ethylpyridin-2-yl)azetidin-3-yl carbamate

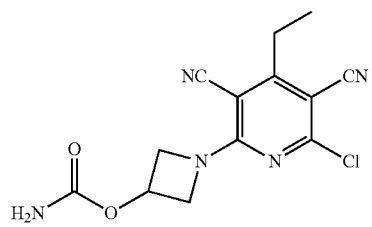 [SMILES: CCc1c(C#N)c(Cl)nc(N2CC(OC(N)=O)C2)c1C#N]

To a stirred solution of 1-benzhydrylazetidin-3-yl carbamate (900 mg, 2.82 mmol) in methanol (10 mL) under a nitrogen atmosphere at 0° C. was added Pd/C (10%, 600 mg, 0.564 mmol). The reaction mixture was stirred at room temperature for 16 hours under a hydrogen atmosphere. The reaction mixture was filtered through Celite®, washing with methanol (20 mL). The filtrate was concentrated under reduced pressure, diluted with HCl (2N, 20 mL) and stirred for 30 minutes. The solution was concentrated under reduced the pressure to afford azetidin-3-yl carbamate hydrochloride (400 mg) as an off-white solid, which was used crude in the next step. To a stirred solution of 2,6-dichloro-4-ethylpyridine-3,5-dicarbonitrile (synthesis described in example 3 step 2, 500 mg, 2.095 mmol) in tetrahydrofuran (10 mL) was added azetidin-3-yl carbamate hydrochloride (320 mg, 2.095 mmol), water (10 mL) and sodium bicarbonate (176 mg, 2.095 mmol) at 0° C. The reaction mixture was stirred for 1 hour at room temperature. The reaction mixture was concentrated under reduced pressure and the resulting residue was diluted with water (30 mL) and extracted with ethyl acetate (2×120 mL). The combined organic layers were dried over anhydrous Na₂SO₄, filtered, concentrated under reduced pressure and dried to afford 1-(6-chloro-3,5-dicyano-4-ethylpyridin-2-yl)azetidin-3-yl carbamate (430 mg). LCMS m/z=303.9 [M−H]⁻.

Step 3: 1-(6-((2-Amino-2-oxo-1-phenylethyl)thio)-3,5-dicyano-4-ethylpyridin-2-yl)azetidin-3-yl carbamate

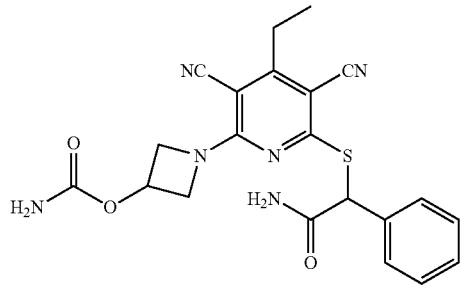

To a stirred solution of 1-(6-chloro-3,5-dicyano-4-ethylpyridin-2-yl)azetidin-3-yl carbamate (420 mg, 1.038 mmol) in N,N-dimethylformamide (10 mL), was added potassium thioacetate (237 mg, 2.076 mmol) at room temperature and stirred for 2 hours at the same temperature. Potassium carbonate (215 mg, 1.557 mmol) and 2-amino-2-oxo-1-phenylethyl methanesulfonate (synthesis described in example 3 step 5, 308 mg, 1.246 mmol) were added at room temperature and the reaction mixture was stirred for 16 hours at room temperature. The reaction mixture was diluted with cold water (50 mL) and extracted with EtOAc (2×100 mL). The combined organic layers were dried over Na₂SO₄, filtered and concentrated under reduced pressure to afford the crude compound. The crude was purified though column chromatography using silica gel (100-200 mesh, eluted with 100% EtOAc) to afford a brown solid which was dissolved in 10% MeOH in DCM (50 mL). Charcoal (500 mg) was added and the mixture was heated at 50° C. for 5 minutes, then filtered through a Celite® bed, washing with 10% MeOH in DCM (25 mL). The filtrate was concentrated under reduced pressure to afford 1-(6-((2-amino-2-oxo-1-phenylethyl)thio)-3,5-dicyano-4-ethylpyridin-2-yl)azetidin- 3-yl carbamate (217 mg, 48% yield) as an off-white solid. LCMS m/z=437.5 [M+H]+. 1H NMR (400 MHz, DMSO-d6) δ ppm 7.86 (s, 1H), 7.56-7.48 (m, 2H), 7.40-7.32 (m, 3H), 7.26 (s, 1H), 6.92-6.71 (m, 2H), 5.57 (s, 1H), 5.18-5.10 (m, 1H), 4.80-4.66 (m, 2H), 4.29 (d, J=8.99 Hz, 2H), 2.70 (q, J=7.53 Hz, 2H), 1.18 (t, J=7.67 Hz, 3H).

Example 260

2-((3,5-Dicyano-6-(4-(2,4-dioxooxazolidin-3-yl)piperidin-1-yl)-4-ethylpyridin-2-yl)thio)-2-phenylacetamide Step 1: 3-(1-Benzylpiperidin-4-yl)oxazolidine-2,4-dione

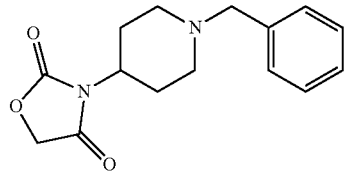 [SMILES: O=C1COC(=O)N1C1CCN(Cc2ccccc2)CC1]

To a solution of methyl 2-hydroxyacetate (1.298 mL, 16.82 mmol) in DMF (40 mL) was added 1,1'-Carbonyldiimidazole (CDI, 2.73 g, 16.82 mmol) at room temperature and the reaction mixture was stirred for 2 hours at room temperature. To this 1-benzylpiperidin-4-amine (3.44 mL, 16.82 mmol) was added and the reaction mixture was stirred for 16 hours at 60° C. The reaction mixture was cooled to room temperature, water was added, and the mixture was stirred for 10 minutes. A solid precipitated which was collected by filtration and dried to afford 3-(1-benzylpiperidin-4-yl) oxazolidine-2,4-dione (1.8 g, 37% yield). LCMS m/z=275.2 [M+H]+.

Step 2: 3-(Piperidin-4-yl)oxazolidine-2,4-dione

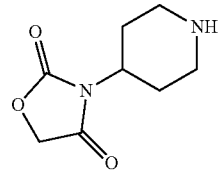 [SMILES: O=C1COC(=O)N1C1CCNCC1]

To a solution of 3-(1-benzylpiperidin-4-yl)oxazolidine-2,4-dione (1.8 g, 6.22 mmol) in methanol (60 mL) was added palladium hydroxide on carbon (20%, 600 mg, 0.854 mmol) at 0° C. The reaction mixture was stirred for 12 hours at room temperature under a hydrogen atmosphere in a Paar shaker. The reaction mixture was filtered through Celite®, washing with MeOH (20 mL). The filtrate was concentrated under reduced pressure to afford the crude product. This crude product was purified by column chromatography (neutral alumina, eluted with 5% MeOH in DCM). The pure fractions were concentrated under reduced pressure to afford desired 3-(piperidin-4-yl)oxazolidine-2,4-dione (340 mg, 26% yield) as an off-white sticky solid. LCMS m/z=185.1 [M+H]+.

Step 3: 2-Chloro-6-(4-(2,4-dioxooxazolidin-3-yl)piperidin-1-yl)-4-ethylpyridine-3,5-dicarbonitrile

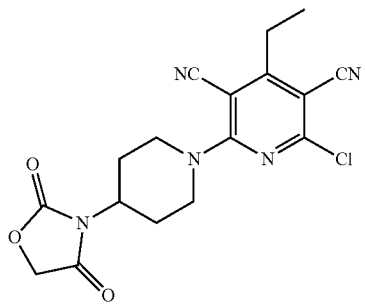 [SMILES: CCc1c(C#N)c(Cl)nc(N2CCC(N3C(=O)COC3=O)CC2)c1C#N]

To a solution of 2,6-dichloro-4-ethylpyridine-3,5-dicarbonitrile (synthesis described in example 3 step 2, 400 mg, 1.752 mmol) in dichloromethane (15 mL) was added triethylamine (0.488 mL, 3.50 mmol) at 0° C. After 2 minutes 3-(piperidin-4-yl)oxazolidine-2,4-dione (323 mg, 1.752 mmol) was slowly added over a period of 20 minutes at 0° C. and stirred for 6 hours at same temperature. The reaction mixture was quenched with ice water (20 mL) and extracted with DCM (2×50 mL). The combined organic layers were dried over sodium sulphate, filtered and concentrated to afford the crude which was purified by flash column chromatography using silica-gel (60-120 mesh, eluting with 50% ethyl acetate in petroleum ether) to afford 2-chloro-6-(4-(2, 4-dioxooxazolidin-3-yl)piperidin-1-yl)-4-ethylpyridine-3,5-dicarbonitrile (200 mg, 30% yield) as an off-white solid. LCMS m/z=374.3 [M+H]+.

Step 4: 2-((3,5-Dicyano-6-(4-(2,4-dioxooxazolidin-3-yl)piperidin-1-yl)-4-ethylpyridin-2-yl)thio)-2-phenylacetamide

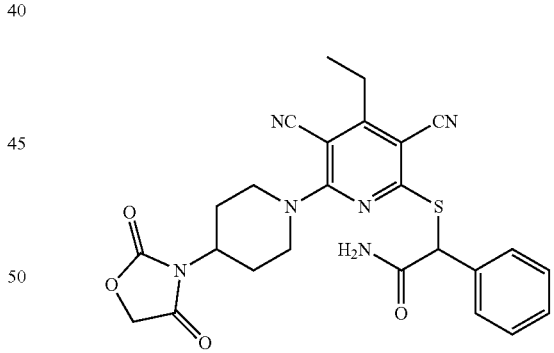

A solution of 2-chloro-6-(4-(2,4-dioxooxazolidin-3-yl)piperidin-1-yl)-4-ethylpyridine-3,5-dicarbonitrile (180 mg, 0.470 mmol) and potassium thioacetate (107 mg, 0.941 mmol) in N,N-dimethylformamide (5 mL) was stirred for 2 hours at room temperature. Then, potassium carbonate (130 mg, 0.941 mmol) and 2-amino-2-oxo-1-phenylethyl methanesulfonate (synthesis described in example 3 step 5, 218 mg, 0.941 mmol) were added and the reaction mixture was stirred for 16 hours at room temperature. The reaction mixture was diluted with ethyl acetate (100 mL) and washed with HCl (1N, 2×100 mL). The organic layer was dried over anhydrous Na2SO4, filtered and evaporated to get crude (300 mg) as a black gummy solid. The crude was purified through silica gel (100-200 mesh, eluted with 50% ethyl acetate in hexane). Pure fractions were concentrated under vacuum and dried to afford 2-((3,5-dicyano-6-(4-(2,4-dioxooxazolidin-3-yl)piperidin-1-yl)-4-ethylpyridin-2-yl)thio)-2-phenylacetamide (30 mg, 12% yield) as an off-white solid. LCMS m/z=505.5 [M+H]⁺. ¹H NMR (400 MHz, DMSO-d₆) δ ppm 7.90 (br s, 1H), 7.52 (d, J=7.02 Hz, 2H), 7.44-7.24 (m, 4H), 5.55 (s, 1H), 4.79 (s, 2H), 4.68 (d, J=12.06 Hz, 2H), 4.26-4.17 (m, 1H), 3.26-3.19 (m, 2H), 2.83-2.71 (m, 2H), 2.21 (d, J=11.18 Hz, 2H), 1.87 (d, J=12.72 Hz, 2H), 1.21 (t, J=7.78 Hz, 3H).

Example 261

3-((6-((2-Amino-2-oxo-1-phenylethyl)thio)-3,5-dicyano-4-ethylpyridin-2-yl)(methyl)amino)-2-hydroxy-2-methylpropanamide Step 1: 3-((6-Chloro-3,5-dicyano-4-ethylpyridin-2-yl)(methyl)amino)-2-hydroxy-2-methylpropanamide

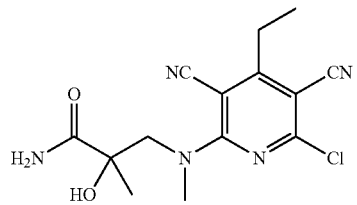 [SMILES: CCc1c(C#N)c(Cl)nc(N(C)CC(C)(O)C(N)=O)c1C#N]

2,6-Dichloro-4-ethylpyridine-3,5-dicarbonitrile (synthesis described in example 3 step 2, 0.513 g, 2.270 mmol), 2-hydroxy-2-methyl-3-(methylamino)propanamide (0.3 g, 2.270 mmol) and triethylamine (0.230 g, 2.270 mmol) were dissolved in DCM (5 mL). The mixture was stirred at room temperature for 12 hours. The mixture was diluted with DCM and washed with brine. The organic layer was dried and concentrated. The residue was purified by column to give 3-((6-chloro-3,5-dicyano-4-ethylpyridin-2-yl)(methyl)amino)-2-hydroxy-2-methylpropanamide (280 mg, 0.870 mmol, 38% yield). LCMS m/z=322 [M+H]⁺.

Step 2: 3-((6-((2-Amino-2-oxo-1-phenylethyl)thio)-3,5-dicyano-4-ethylpyridin-2-yl)(methyl)amino)-2-hydroxy-2-methylpropanamide

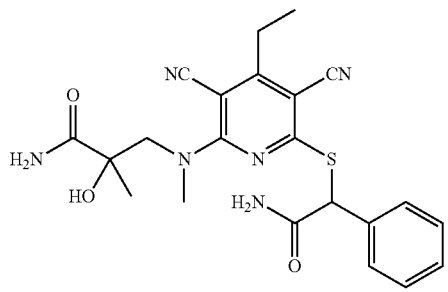 [SMILES: CCc1c(C#N)c(SC(C(N)=O)c2ccccc2)nc(N(C)CC(C)(O)C(N)=O)c1C#N]

3-((6-Chloro-3,5-dicyano-4-ethylpyridin-2-yl)(methyl)amino)-2-hydroxy-2-methylpropanamide (280 mg, 0.870 mmol) and potassium thioacetate (199 mg, 1.740 mmol) were dissolved in N,N-dimethylformamide (3 mL). The mixture was stirred at room temperature for 1 hour, then potassium carbonate (241 mg, 1.740 mmol) and 2-amino-2-oxo-1-phenylethyl methanesulfonate (synthesis described in example 3 step 5, 399 mg, 1.74 mmol) were added. The mixture was stirred at room temperature for 12 hours then filtered. The filtrate was concentrated and purified by prep-HPLC to give 3-((6-((2-amino-2-oxo-1-phenylethyl)thio)-3,5-dicyano-4-ethylpyridin-2-yl)(methyl)amino)-2-hydroxy-2-methylpropanamide (40 mg, 0.088 mmol, 10% yield). LCMS m/z=453.1 [M+H]⁺. ¹H NMR (400 MHz, DMSO-d₆) δ ppm 7.80 (s, 1H), 7.52-7.49 (m, 4H), 7.43-7.29 (m, 4H), 5.90 (s, 0.5H), 5.76 (s, 0.5H), 5.73-5.71 (m, 1H), 4.59 (d, J=14.3 Hz, 0.5H), 4.44 (d, J=14.3 Hz, 0.5H), 3.98 (d, J=14.1 Hz, 0.5H), 3.80 (d, J=14.2 Hz, 0.5H), 3.46 (s, 3H), 2.77-2.75 (m, 2H), 1.31-1.18 (m, 3H), 1.23-1.18 (m, 3H).

Example 262

2-((3,5-Dicyano-4-ethyl-6-(3-(hydroxymethyl)azetidin-1-yl)pyridin-2-yl)thio)-2-phenylacetamide Step 1: 2-Chloro-4-ethyl-6-(3-(hydroxymethyl)azetidin-1-yl)pyridine-3,5-dicarbonitrile

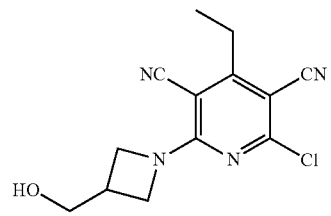 [SMILES: CCc1c(C#N)c(Cl)nc(N2CC(CO)C2)c1C#N]

To a solution of 2,6-dichloro-4-ethylpyridine-3,5-dicarbonitrile (synthesis described in example 3 step 2, 1 g, 4.42 mmol) in dichloromethane (50 mL) were added azetidin-3-ylmethanol (0.385 g, 4.42 mmol) and TEA (1.233 mL, 8.85 mmol). Then the reaction mixture was stirred for 30 min. The mixture was washed with water (2×50 mL). The combined organic layers were concentrated to give the crude product (1 g) as a yellow solid, which was used directly in the next step. LCMS m/z=277.0 [M+H]⁺.

Step 2: 2-((3,5-Dicyano-4-ethyl-6-(3-(hydroxymethyl)azetidin-1-yl)pyridin-2-yl)thio)-2-phenylacetamide

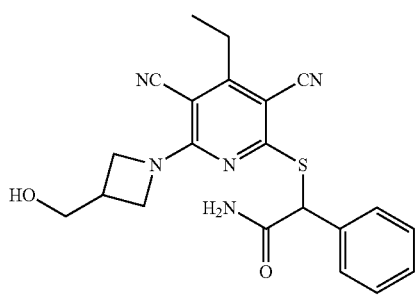 [SMILES: CCc1c(C#N)c(SC(C(N)=O)c2ccccc2)nc(N2CC(CO)C2)c1C#N]

To a solution of 2-chloro-4-ethyl-6-(3-(hydroxymethyl)azetidin-1-yl)pyridine-3,5-dicarbonitrile (1 g, 3.61 mmol) in N,N-dimethylformamide (2 mL) was added potassium thioacetate (0.413 g, 3.61 mmol). The reaction mixture was stirred for 2 hours then to this mixture were added potassium carbonate (0.499 g, 3.61 mmol) and 2-amino-2-oxo-1-phenylethyl methanesulfonate (synthesis described in example 3 step 5, 0.828 g, 3.61 mmol). The reaction mixture was stirred overnight. The reaction mixture was diluted with ethyl acetate (50 mL) and washed with brine (5×50 mL). The organic layer was concentrated, and the residue was purified on a silica gel column eluting with DCM/MeOH to give 300 mg of a white solid. A portion of this material (100 mg) was further purified by prep-HPLC to give 2-((3,5-Dicyano-4-ethyl-6-(3-(hydroxymethyl)azetidin-1-yl)pyridin-2-yl)thio)-2-phenylacetamide (20 mg). LCMS m/z=408 [M+H]$^+$. $^1$H NMR (400 MHz, DMSO-d$_6$) δ ppm 7.88 (s, 1H), 7.52 (d, J=7.2 Hz, 2H), 7.43-7.19 (m, 4H), 5.57 (s, 1H), 4.93 (t, J=4.9 Hz, 1H), 4.50-4.15 (m, 4H), 3.62 (t, J=5.1 Hz, 2H), 2.84 (s, 1H), 2.75-2.62 (m, 2H), 1.20 (dd, J=19.9, 12.5 Hz, 3H).

Example 263

2-(3,5-Dicyano-4-ethyl-6-(piperazin-1-yl)pyridin-2-ylthio)-2-(thiophen-3-yl)acetamide Step 1: 2-(Thiophen-3-yl)-2-(trimethylsilyloxy)acetonitrile

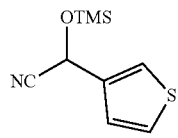

Thiophene-2-carbaldehyde (2.8 g, 25 mmol) and trimethylsilanecarbonitrile (2.97 g, 30 mmol) were dissolved in chloroform (5 mL). The solution was cooled in a cold water bath (10° C.), and zinc(II) iodide (0.8 g, 2.5 mmol) was added. After 8 hours of stirring, the solution was diluted with Et$_2$O (100 mL) and washed with aqueous sodium thiosulfate (50 mL) and saturated sodium bicarbonate (50 mL). The organic solution was dried with magnesium sulfate, filtered, and evaporated to afford 2-(thiophen-2-yl)-2-((trimethylsilyl)oxy)acetonitrile (5 g, 23.66 mmol, 95% yield). $^1$H NMR (400 MHz, CDCl$_3$) δ ppm 7.44 (s, 1H), 7.40 (dd, J=5.0, 3.0 Hz, 1H), 7.17 (d, J=5.0 Hz, 1H), 5.59 (s, 1H), 0.25 (s, 9H).

Step 2: 2-Hydroxy-2-(thiophen-3-yl)acetamide

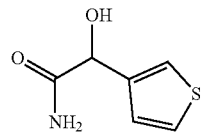

To a solution of 2-(thiophen-3-yl)-2-((trimethylsilyl)oxy) acetonitrile (1 g, 4.73 mmol), acetamide (1.174 g, 19.87 mmol) in tetrahydrofuran (12 mL) and water (4 mL) stirred under nitrogen at room temperature was added palladium(II) chloride (0.084 g, 0.47 mmol). The reaction mixture was stirred at room temperature overnight. The reaction mixture was filtered and the filtrate was concentrated. The residue was added to a silica gel column (eluted with CH$_2$Cl$_2$/MeOH, collected fractions: DCM/MeOH (15:1-10:1)) to afford 2-hydroxy-2-(thiophen-3-yl)acetamide (600 mg) as a light yellow solid. 1H NMR (400 MHz, DMSO-d$_6$) δ ppm 7.45 (dd, J=4.9, 3.0 Hz, 1H), 7.37 (d, J=2.9 Hz, 1H), 7.11 (d, J=4.9 Hz, 1H), 6.68 (s, 2H), 4.91 (s, 1H).

Step 3: 2-Amino-2-oxo-1-(thiophen-3-yl)ethyl methanesulfonate

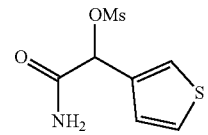

To a solution of 2-hydroxy-2-(thiophen-3-yl)acetamide (520 mg, 3.31 mmol) and triethylamine (502 mg, 4.96 mmol) in dichloromethane (10 mL) stirred at 0° C. was added methanesulfonyl chloride (417 mg, 3.64 mmol) dropwise. The reaction mixture was stirred at room temperature for 2 hours. The solvent was removed and the crude product was purified by silica gel column (eluted with CH$_2$Cl$_2$/MeOH) to afford 2-amino-2-oxo-1-(thiophen-3-yl)ethyl methanesulfonate (118 mg, 0.50 mmol). 1H NMR (400 MHz, DMSO-d$_6$) δ ppm 7.79 (s, 1H), 7.61 (d, J=2.0 Hz, 1H), 7.55 (dd, J=5.0, 3.0 Hz, 1H), 7.47 (s, 1H), 7.21 (dd, J=5.0, 1.0 Hz, 1H), 5.58 (s, 1H), 3.34 (s, 3H).

Step 4: tert-Butyl 4-(6-(2-amino-2-oxo-1-(thiophen-3-yl)ethylthio)-3,5-dicyano-4-ethylpyridin-2-yl)piperazine-1-carboxylate

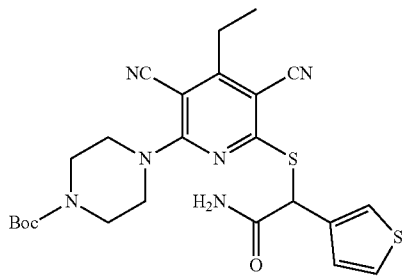 [SMILES: CCc1c(C#N)c(SC(C(N)=O)c2ccsc2)nc(N2CCN(C(=O)OC(C)(C)C)CC2)c1C#N]

To a solution of tert-butyl 4-(6-chloro-3,5-dicyano-4-ethylpyridin-2-yl)piperazine-1-carboxylate (synthesis described in example 176, step 1, 189 mg, 0.503 mmol) and potassium ethanethioate (57.4 mg, 0.503 mmol) in N,N-dimethylformamide (10 mL) stirred in air at room temp was added triethylamine (0.210 mL, 1.509 mmol) dropwise over 1 minute. The reaction mixture was stirred at room temp for 2 hours. To this reaction mixture was added 2-amino-2-oxo-1-(thiophen-3-yl)ethyl methanesulfonate (118 mg, 0.50 mmol), and the resulting mixture was stirred at room temperature for 1 day. The solvent was removed and the residue

Step 5: 2-(3,5-Dicyano-4-ethyl-6-(piperazin-1-yl)pyridin-2-ylthio)-2-(thiophen-3-yl)acetamide was washed with water. The crude product was added to a silica gel column and was eluted with CH$_2$Cl$_2$/MeOH to afford tert-butyl 4-(6-((2-amino-2-oxo-1-(thiophen-3-yl)ethyl)thio)-3,5-dicyano-4-ethylpyridin-2-yl)piperazine-1-carboxylate (150 mg, 0.29 mmol, 58% yield). $^1$H NMR (300 MHz, CDCl$_3$) δ 7.36 (m, 3H), 7.15 (m, 2H), 5.45 (s, 1H), 3.89 (m, 4H), 3.58 (m, 4H), 2.91 (q, J=7.6 Hz, 2H), 1.46 (s, 9H), 1.32 (t, J=7.6 Hz, 3H).

Step 5: 2-(3,5-Dicyano-4-ethyl-6-(piperazin-1-yl)pyridin-2-ylthio)-2-(thiophen-3-yl)acetamide

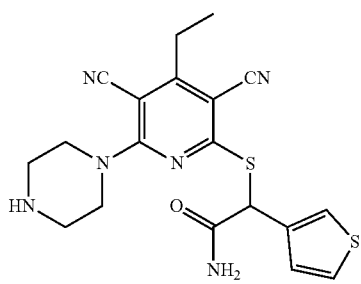 [SMILES: CCc1c(C#N)c(SC(C(N)=O)c2ccsc2)nc(N2CCNCC2)c1C#N]

To a solution of tert-butyl 4-(6-((2-amino-2-oxo-1-(thiophen-3-yl)ethyl)thio)-3,5-dicyano-4-ethylpyridin-2-yl)piperazine-1-carboxylate (150 mg, 0.29 mmol) in dichloromethane (10 mL) stirred at 0° C. was added trifluoroacetic acid (2 mL, 26.0 mmol) dropwise. The reaction mixture was stirred at room temperature for 2 hours. The solvent was removed and the residue was dissolved in 2 mL MeOH. A saturated solution of sodium carbonate was added to adjust the pH to 13, then the MeOH was removed by reduced pressure, and the mixture was extracted with dichloromethane and concentrated. The crude was purified with prep-TLC to get 2-((3,5-dicyano-4-ethyl-6-(piperazin-1-yl)pyridin-2-yl)thio)-2-(thiophen-3-yl)acetamide (61 mg, 0.15 mmol, 52%) as a white solid. LCMS m/z=413.2 [M+H]$^+$. $^1$H NMR (400 MHz, DMSO-d$_6$) δ ppm 7.88 (s, 1H), 7.59-7.50 (m, 2H), 7.34 (s, 1H), 7.18 (d, J=4.9 Hz, 1H), 5.62 (s, 1H), 3.95-3.72 (m, 4H), 2.92-2.76 (m, 4H), 2.76 (d, J=7.6 Hz, 2H), 1.23 (d, J=3.2 Hz, 1H), 1.21 (t, J=7.6 Hz, 3H).

Example 264

(S)-2-((1-(6-((4-(Acetamidomethyl)benzyl)thio)-3,5-dicyano-4-ethylpyridin-2-yl)piperidin-4-yl)oxy)ethyl 2-amino-3-methylbutanoate

Step 1: N-(4-(((3,5-Dicyano-4-ethyl-6-(4-(2-hydroxyethoxy)piperidin-1-yl)pyridin-2-yl)thio)methyl)benzyl)acetamide To a solution of 2-chloro-4-ethyl-6-(4-(2-hydroxyethoxy)piperidin-1-yl)pyridine-3,5-dicarbonitrile (synthesis described in example 224, step 3, 1 g, 2.99 mmol) in N,N-dimethylformamide (10 mL) was added potassium ethanethioate (0.512 g, 4.48 mmol). The mixture was stirred at room temperature for 2 hours then treated with K$_2$CO$_3$ (0.826 g, 5.97 mmol). The resultant mixture was stirred at room temperature for 1 hour then treated with N-(4-(bromomethyl)benzyl)acetamide (0.868 g, 3.58 mmol) and the mixture was stirred at room temperature overnight. The resultant mixture was concentrated in vacuo, and the residue was diluted with EtOAc (100 mL). The organic phase was washed with water (25 mL×2) and saturated brine (25 mL), dried over sodium sulphate and evaporated in vacuo to give the crude product as a brown solid. The crude product was added to a silica gel column and was eluted with CH$_2$Cl$_2$/MeOH (20:1) to give N-(4-(((3,5-dicyano-4-ethyl-6-(4-(2-hydroxyethoxy)piperidin-1-yl)pyridin-2-yl)thio)methyl)benzyl)acetamide (0.8 g). LCMS m/z=494.1 [M+H]$^+$.

Step 2: (S)-2-((1-(6-((4-(Acetamidomethyl)benzyl)thio)-3,5-dicyano-4-ethylpyridin-2-yl)piperidin-4-yl)oxy)ethyl 2-((tert-butoxycarbonyl)amino)-3-methylbutanoate

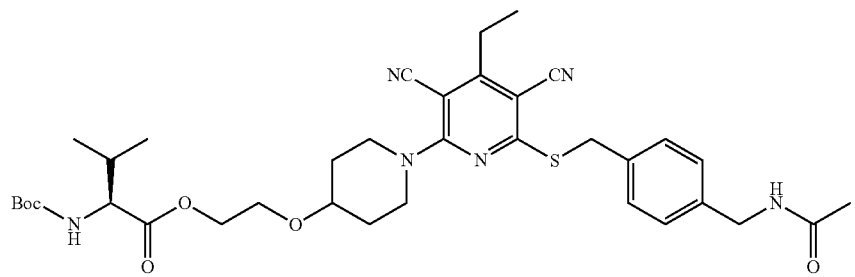 [SMILES: CCc1c(C#N)c(SCc2ccc(CNC(C)=O)cc2)nc(N2CCC(OCCOC(=O)[C@@H](NC(=O)OC(C)(C)C)C(C)C)CC2)c1C#N]

To a solution of 1H-benzo[d][1,2,3]triazol-4-ol (109 mg, 0.810 mmol), (S)-2-((tert-butoxycarbonyl)amino)-3-methylbutanoic acid (352 mg, 1.621 mmol) and N1-((ethylimino)methylene)-N3,N3-dimethylpropane-1,3-diamine (377 mg, 2.431 mmol) in dichloromethane (20 mL) was added triethylamine (246 mg, 2.431 mmol) at room temperature. The mixture was stirred at room temperature for 30 minutes then treated with N-(4-(((3,5-dicyano-4-ethyl-6-(4-(2-hydroxyethoxy)piperidin-1-yl)pyridin-2-yl)thio)methyl)benzyl)acetamide (200 mg). The resultant mixture was stirred at room temperature overnight then concentrated in vacuo. The residue was added to a silica gel column and was eluted with CH$_2$Cl$_2$/MeOH (50:1) to give (S)-2-((1-(6-((4-(acetamidomethyl)benzyl)thio)-3,5-dicyano-4-ethylpyridin-2-yl)piperidin-4-yl)oxy)ethyl 2-((tert-butoxycarbonyl)amino)-3-methylbutanoate (300 mg). LCMS m/z=715.2 [M+Na]$^+$.

Step 3: (S)-2-((1-(6-((4-(Acetamidomethyl)benzyl)thio)-3,5-dicyano-4-ethylpyridin-2-yl)piperidin-4-yl)oxy)ethyl 2-amino-3-methylbutanoate

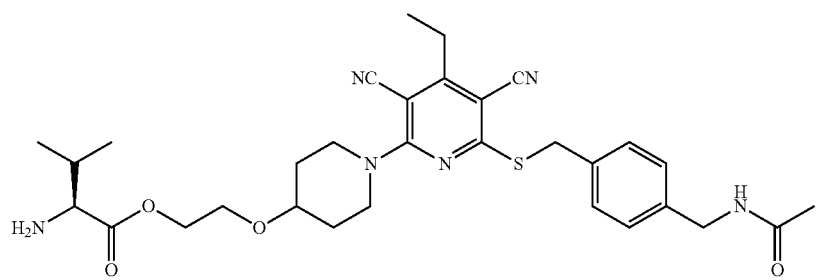 [SMILES: CCc1c(C#N)c(SCc2ccc(CNC(C)=O)cc2)nc(N2CCC(OCCOC(=O)[C@@H](N)C(C)C)CC2)c1C#N]

To a solution of (S)-2-((1-(6-((4-(acetamidomethyl)benzyl)thio)-3,5-dicyano-4-ethylpyridin-2-yl)piperidin-4-yl)oxy)ethyl 2-((tert-butoxycarbonyl)amino)-3-methylbutanoate (280 mg) in dichloromethane (5 mL) was added 2,2,2-trifluoroacetic acid (922 mg, 8.08 mmol). The resultant mixture was stirred at room temperature for 2 hours then concentrated in vacuo. The residue was diluted with EtOAc (50 mL) and washed with saturated sodium bicarbonate solution (50 mL), water (25 mL) and saturated brine (25 mL). The organic layer was dried over sodium sulphate and evaporated in vacuo to give the crude product as a yellow solid. The crude product was added to a silica gel column and was eluted with DCM/MeOH (30:1) to give (S)-2-((1-(6-((4-(acetamidomethyl)benzyl)thio)-3,5-dicyano-4-ethylpyridin-2-yl)piperidin-4-yl)oxy)ethyl 2-amino-3-methylbutanoate (120 mg, 0.198 mmol). LCMS m/z=593.2 [M+H]$^+$. $^1$H NMR (400 MHz, DMSO-d$_6$) δ ppm 8.36-8.30 (m, 1H), 7.35 (d, J=8.0 Hz, 2H), 7.21 (d, J=8.0 Hz, 2H), 4.47 (s, 2H), 4.32-4.19 (m, 3H), 4.17-4.04 (m, 3H), 3.71-3.58 (m, 5H), 3.16 (d, J=5.3 Hz, 1H), 2.77 (q, J=7.6 Hz, 2H), 2.24-1.76 (m, 8H), 1.63-1.50 (m, 2H), 1.22 (dd, J=13.0, 5.4 Hz, 3H), 0.86 (dd, J=15.4, 6.8 Hz, 6H).

Example 266

2-((3,5-Dicyano-4-ethyl-6-(4-methyl-1,4-diazepan-1-yl) pyridin-2-yl) thio-2-(5-methylpyridin-3-yl) acetamide Step 1:
2-Hydroxy-2-(5-methylpyridin-3-yl)acetamide

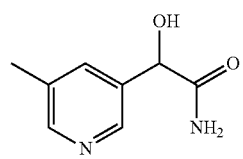

To a solution of 5-methylnicotinaldehyde (1.0 g, 8.26 mmol) in dichloromethane (20 mL) was added trimethylsilanecarbonitrile (1.239 mL, 9.91 mmol). The mixture was stirred at room temperature overnight. The mixture was concentrated down to afford a light brown oil. The above crude was treated with concentrated H$_2$SO$_4$ (6 mL, 113 mmol) for 4 hours, then poured the reaction mixture into ice, and adjusted the pH to 9 using NH$_4$OH. The reaction mixture was concentrated down with silica, purified by silica column (CombiFlash®, 40 g column using 0-10% MeOH/DCM) to afford 2-hydroxy-2-(5-methylpyridin-3-yl)acetamide (636 mg, 3.83 mmol, 46% yield) as a yellow oil. LCMS m/z=166.9 [M+H]$^+$.

Step 2:
2-Amino-1-(5-methylpyridin-3-yl)-2-oxoethyl methanesulfonate

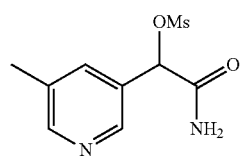 [SMILES: Cc1cncc(C(OS(C)(=O)=O)C(N)=O)c1]

To a solution of 2-hydroxy-2-(5-methylpyridin-3-yl)acetamide (636 mg, 3.83 mmol) and TEA (1.067 mL, 7.65 mmol) in tetrahydrofuran (20 mL) was added methanesulfonyl chloride (0.358 mL, 4.59 mmol). The mixture was stirred at room temperature overnight. The reaction mixture was concentrated down with silica and purified by silica column (CombiFlash®, 24 g column using 0-10% MeOH/DCM) to afford 2-amino-1-(5-methylpyridin-3-yl)-2-oxoethyl methanesulfonate (798 mg, 3.27 mmol, 85% yield) as a yellow solid. LCMS m/z=245.1 [M+H]⁺.

Step 3: 2-((3,5-Dicyano-4-ethyl-6-(4-methyl-1,4-diazepan-1-yl) pyridin-2-yl)thio)-2-(5-methylpyridin-3-yl)acetamide

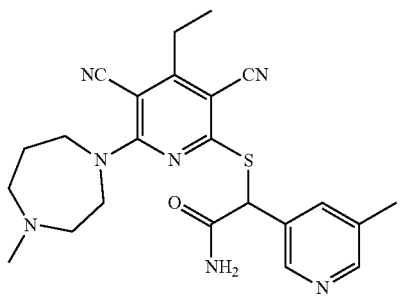 [SMILES: CCc1c(C#N)c(SC(C(N)=O)c2cncc(C)c2)nc(N2CCCN(C)CC2)c1C#N]

The reaction mixture of 4-ethyl-2-mercapto-6-(4-methyl-1,4-diazepan-1-yl)pyridine-3,5-dicarbonitrile (synthesis described in example 69, step 1, 107 mg, 0.354 mmol), 2-amino-1-(5-methylpyridin-3-yl)-2-oxoethyl methanesulfonate (72 mg, 0.295 mmol) and TEA (0.082 mL, 0.590 mmol) in DMF (3 mL) was stirred at room temperature overnight. The reaction mixture was purified by silica (CombiFlash®, 12 g column) using 10-20% MeOH/DCM as eluent. The resulting fractions were concentrated down and purified by second silica column (12 g column using 20% MeOH/DCM) to afford 2-((3,5-dicyano-4-ethyl-6-(4-methyl-1,4-diazepan-1-yl) pyridin-2-yl)thio)-2-(5-methylpyridin-3-yl)acetamide (51 mg, 0.113 mmol, 39% yield) as an off-white solid. LCMS m/z=450.2 [M+H]⁺. ¹H NMR (400 MHz, DMSO-d₆) δ ppm 1.21 (t, J=7.6 Hz, 3H), 1.86-2.00 (m, 2H), 2.26 (s, 3H), 2.31 (s, 3H), 2.41-2.48 (m, 1H), 2.52-2.63 (m, 2H), 2.63-2.72 (m, 1H), 2.77 (q, J=7.6 6 Hz, 2H), 3.80-4.01 (m, 4H), 5.56 (s, 1H), 7.45 (s, 1H), 7.70 (s, 1H), 8.00 (s, 1H), 8.38 (d, J=1.3 Hz, 1H), 8.50 (d, J=2.0 Hz, 1H).

Example 267

(S)-2-((6-((4-(Acetamidomethyl)benzyl)thio)-3,5-dicyano-4-ethylpyridin-2-yl(methyl)amino)ethyl 2-amino-3-methylbutanoate, Trifluoroacetic Acid Salt Step 1: N-(4-(((3,5-Dicyano-4-ethyl-6-((2-hydroxyethyl)(methyl)amino)pyridin-2-yl)thio) methyl)benzyl)acetamide

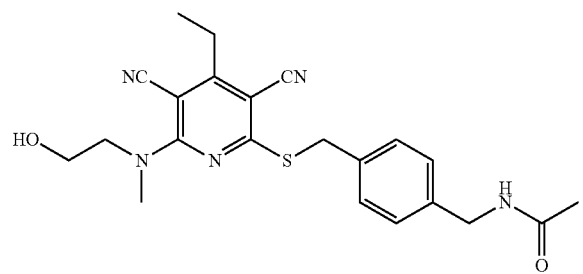 [SMILES: CCc1c(C#N)c(SCc2ccc(CNC(C)=O)cc2)nc(N(C)CCO)c1C#N]

To a solution of 2-chloro-4-ethyl-6-((2-hydroxyethyl)(methyl)amino)pyridine-3,5-dicarbonitrile (synthesis described in Example 147, step 1, 264 mg, 0.997 mmol) in N,N-dimethylformamide (15 mL) were added potassium ethanethioate (171 mg, 1.496 mmol) and then K₂CO₃ (414 mg, 2.99 mmol). The mixture was stirred at 25° C. for 16 hours. K₂CO₃ (474 mg, 3.43 mmol) and N-(4-(bromomethyl)benzyl)acetamide (435 mg, 1.258 mmol) were then added. The mixture was stirred at 25° C. for 16 hours. The mixture was poured onto water (15 mL) and extracted with ethyl acetate (25 mL×2). The combined organic layers were concentrated, and the residue was purified by column chromatography (DCM/MeOH=30:1). The desired fractions were concentrated and the resulting solid was then recrystallized from methanol to give N-(4-(((3,5-dicyano-4-ethyl-6-((2-hydroxyethyl)(methyl)amino)pyridin-2-yl)thio) methyl)benzyl)acetamide (300 mg, 0.708 mmol, 62% yield). LCMS m/z=424.3 [M+H]⁺.

Step 2: (S)-2-((6-((4-(Acetamidomethyl)benzyl)thio)-3,5-dicyano-4-ethylpyridin-2-yl) (methyl)amino)ethyl 2-((tert-butoxycarbonyl)amino)-3-methylbutanoate

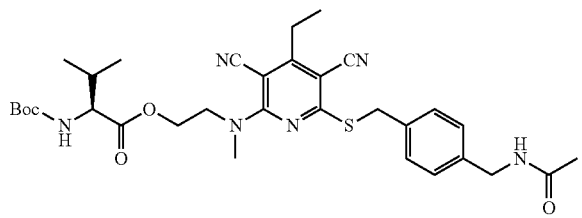 [SMILES: CCc1c(C#N)c(SCc2ccc(CNC(C)=O)cc2)nc(N(C)CCOC(=O)[C@@H](NC(=O)OC(C)(C)C)C(C)C)c1C#N]

To a solution of (S)-2-((tert-butoxycarbonyl)amino)-3-methylbutanoic acid (128 mg, 0.590 mmol) in tetrahydrofuran (15 mL) were added HOBt (136 mg, 0.885 mmol), TEA (0.25 mL,1.77 mmol) and then N-(3-dimethylaminopropyl)-N-ethylcarbodiimide hydrochloride (170 mg, 0.885 mmol). The mixture was stirred at 25° C. for 0.5 hours. Then N-(4-(((3,5-dicyano-4-ethyl-6-((2-hydroxyethyl)(methyl) amino)pyridin-2-yl)thio)methyl)benzyl)acetamide (250 mg, 0.590 mmol) was added. The mixture was stirred for 16 hours. The mixture was concentrated under reduced pressure. The residue was diluted with ethyl acetate (20 mL) and washed with water (10 mL). The organic phase was concentrated and the residue was purified by column chromatography (DCM/MeOH=50:1) to give (S)-2-((6-((4-(acetamidomethyl)benzyl)thio)-3,5-dicyano-4-ethylpyridin-2-yl) (methyl)amino)ethyl 2-((tert-butoxycarbonyl)amino)-3-methylbutanoate (150 mg, 0.241 mmol, 41% yield). LCMS m/z=645.2 [M+Na]⁺.

Step 3: (S)-2-((6-((4-(Acetamidomethyl)benzyl)thio)-3,5-dicyano-4-ethylpyridin-2-yl)(methyl)amino)ethyl 2-amino-3-methylbutanoate, Trifluoroacetic Acid Salt

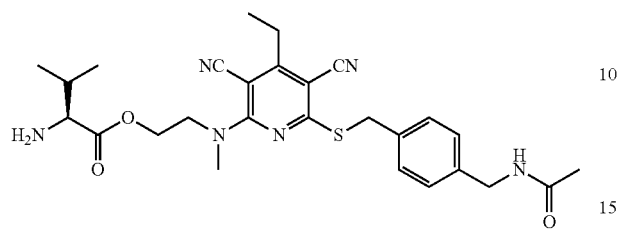

To a mixture of TFA (1 mL, 12.98 mmol) in dichloromethane (8 mL) was added (S)-2-((6-((4-(acetamidomethyl)benzyl)thio)-3,5-dicyano-4-ethylpyridin-2-yl)(methyl)amino) ethyl 2-((tert-butoxycarbonyl)amino)-3-methylbutanoate (100 mg, 0.161 mmol) at 0° C. The mixture was stirred at 25° C. for 16 hours. The mixture was concentrated, and the residue was washed with ethyl acetate to give (S)-2-((6-((4-(acetamidomethyl)benzyl)thio)-3,5-dicyano-4-ethylpyridin-2-yl) (methyl)amino)ethyl 2-amino-3-methylbutanoate, trifluoroacetic acid salt (50 mg, 0.079 mmol, 49% yield). LCMS m/z=523.4 [M+H]$^+$. $^1$H NMR (400 MHz, DMSO-d$_6$) δ ppm 8.36-8.44 (m, 4H), 7.36 (d, J=8 Hz, 2H), 7.22 (d, J=8 Hz, 2H), 4.52-4.46 (m, 3H), 4.39-4.34 (m, 1H), 4.23-4.18 (m, 3H), 4.06-4.00 (m, 1H), 3.89 (br s, 1H), 3.44 (s, 3H), 2.82-2.76 (m, 2H), 2.08-2.03 (m, 1H), 1.87 (s, 3H), 1.24-1.20 (m, 3H), 0.89-0.86 (m, 6H).

Example 268

2-Amino-N-(4-(((3,5-dicyano-6-(dimethylamino)-4-ethylpyridin-2-yl)thio)methyl)benzyl)acetamide

Step 1: tert-Butyl 4-(((3,5-dicyano-6-(dimethylamino)-4-ethylpyridin-2-yl)thio)methyl)benzylcarbamate

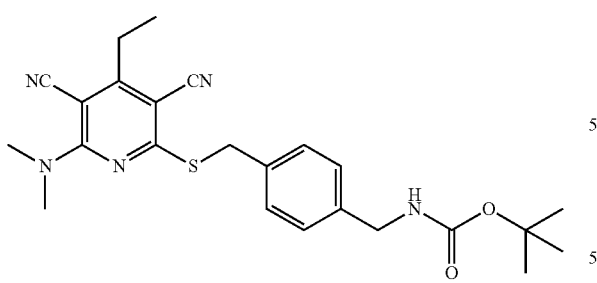

To a suspension of 2-(dimethylamino)-4-ethyl-6-mercaptopyridine-3,5-dicarbonitrile (synthesis described in example 92, step 3, 700 mg, 3.01 mmol) and Et$_3$N (0.420 mL, 3.01 mmol) in chloroform (5 mL) at −20° C. was added a solution of tert-butyl 4-(bromomethyl)benzylcarbamate (905 mg, 3.01 mmol) in chloroform (10 mL). The reaction mixture was then stirred at −20° C. for 2 hours. The reaction mixture was then diluted with EtOAc, and this mixture washed with water (3×). The combined aqueous layers were then back extracted with EtOAc (1×). The combined organic layers were washed with brine, dried (MgSO$_4$) and concentrated. The crude was then purified by normal phase chromatography (Biotage Isolera, 50 g SNAP ULTRA column, hexane/EtOAc) to obtain tert-butyl 4-(((3,5-dicyano-6-(dimethylamino)-4-ethylpyridin-2-yl)thio)methyl)benzylcarbamate (1.12 g) as a white solid. LCMS m/z=474.3 [M+Na]$^+$.

Step 2: 2-((4-(Aminomethyl)benzyl)thio)-6-(dimethylamino)-4-ethylpyridine-3,5-dicarbonitrile, 2Hydrochloride

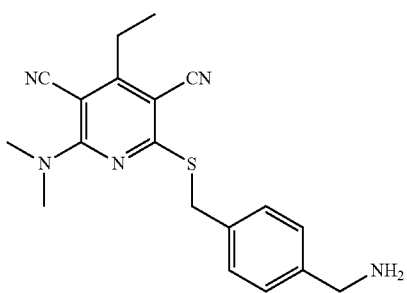 [SMILES: CCc1c(C#N)c(SCc2ccc(CN)cc2)nc(N(C)C)c1C#N]

A suspension of tert-butyl 4-(((3,5-dicyano-6-(dimethylamino)-4-ethylpyridin-2-yl)thio) methyl) benzylcarbamate (1.1 g, 2.436 mmol) in a solution of HCl (4 M, dioxane, 10 mL, 40 mmol) at room temperature was stirred at room temperature. After stirring 2.5 hours at room temperature, the reaction mixture was then concentrated. The resulting material was then suspended in EtOAc and sonicated. The solid was filtered and washed with EtOAc and then Et$_2$O. The solid was dried in the vac oven to yield 2-((4-(aminomethyl)benzyl)thio)-6-(dimethylamino)-4-ethylpyridine-3,5-dicarbonitrile, 2Hydrochloride (936 mg) as a white solid LCMS m/z=352.3 [M+H]$^+$.

Step 3: tert-Butyl (2-((4-(((3,5-dicyano-6-(dimethylamino)-4-ethylpyridin-2-yl)thio)methyl)benzyl)amino)-2-oxoethyl)carbamate

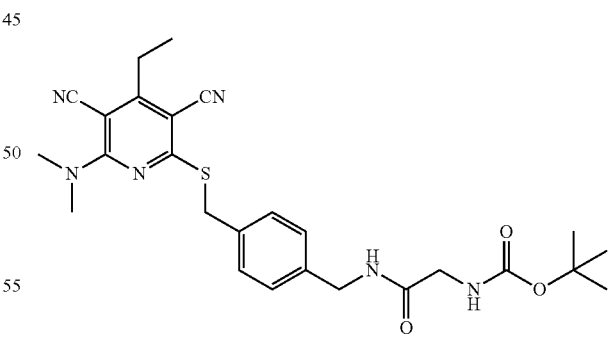

To a solution of Boc-glycine (35 mg, 0.200 mmol) in N,N-dimethylformamide (1.0 mL) at room temperature was added HATU (75 mg, 0.198 mmol). The reaction mixture was then stirred at room temperature for 15 minutes at which time the 2-((4-(aminomethyl)benzyl)thio)-6-(dimethylamino)-4-ethylpyridine-3,5-dicarbonitrile, Hydrochloride (84 mg, 0.217 mmol) and Et$_3$N (0.038 mL, 0.270 mmol) were added. The reaction mixture was allowed to stir at room temperature overnight. The mixture was filtered, and purified by reverse phase HPLC (Gilson, 30 mm×50 mm Gemini Column, NH$_4$OH modifier) to obtain tert-butyl (2-((4-(((3,5-dicyano-6-(dimethylamino)-4-ethylpyridin-2-yl)thio)methyl)benzyl)amino)-2-oxoethyl)carbamate (83 mg) as a white solid. LCMS m/z=531.3 [M+Na]$^+$.

Step 4: 2-Amino-N-(4-(((3,5-dicyano-6-(dimethylamino)-4-ethylpyridin-2-yl)thio)methyl)benzyl)acetamide

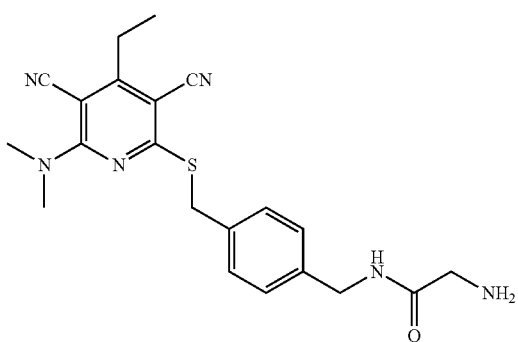 [SMILES: CCc1c(C#N)c(SCc2ccc(CNC(=O)CN)cc2)nc(N(C)C)c1C#N]

tert-Butyl (2-((4-(((3,5-dicyano-6-(dimethylamino)-4-ethylpyridin-2-yl)thio)methyl)benzyl)amino)-2-oxoethyl)carbamate (58 mg, 0.114 mmol) was suspended in a solution of HCl (4 M, dioxane, 1000 µl, 4.0 mmol) at room temperature. After stirring for 2 hours at room temperature, the reaction mixture was then concentrated. The resulting material was suspended in MeOH, and free based with isopropylamine. This mixture was purified by reverse phase HPLC (Gilson, 30 mm×50 mm Gemini Column, NH$_4$OH modifier) to yield 2-amino-N-(4-(((3,5-dicyano-6-(dimethylamino)-4-ethylpyridin-2-yl)thio)methyl)benzyl)acetamide (33 mg) as a light beige solid. LCMS m/z=409.3 [M+H]$^+$. $^1$H NMR (400 MHz, DMSO-d$_6$) δ ppm 8.30 (t, J=5.83 Hz, 1H), 7.36 (d, J=8.11 Hz, 2H), 7.22 (d, J=8.36 Hz, 2H), 4.50 (s, 2H), 4.27 (d, J=6.08 Hz, 2H), 3.12 (s, 2H), 2.76 (q, J=7.44 Hz, 2H), 1.84 (br. s., 2H), 1.21 (t, J=7.60 Hz, 3H). Six protons not observed.

Example 269

4-Ethyl-2-(4-methyl-1,4-diazepan-1-yl)-6-((4-((2-oxopyrrolidin-1-yl)methyl)benzyl)thio)pyridine-3,5-dicarbonitrile Step 1:
1-(4-(Hydroxymethyl)benzyl)pyrrolidin-2-one

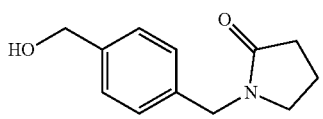 [SMILES: O=C1CCCN1Cc1ccc(CO)cc1]

To a solution of pyrrolidin-2-one (0.152 mL, 2.0 mmol) in tetrahydrofuran (5 mL) at 0° C. was added sodium hydride (60 wt %, 80 mg, 2.000 mmol). The reaction mixture was then stirred at the same temperature for 30 minutes at which time the (4-(bromomethyl)phenyl)methanol (402 mg, 2.000 mmol) was added. The reaction mixture was then warmed to 20° C. and stirred at the same temperature over the weekend. The reaction mixture was diluted with EtOAc and washed with water. The aqueous layer was back extracted with EtOAc (2×). The combined organic layers were then washed with saturated brine (1×), dried (Na$_2$SO$_4$) and concentrated. The crude was purified by reverse phase HPLC (Gilson, 30 mm×50 mm Gemini Column, NH$_4$OH modifier) to obtain 1-(4-(hydroxymethyl)benzyl)pyrrolidin-2-one (83 mg) as a yellow-tan solid. LCMS m/z=206.2 [M+H]$^+$.

Step 2: 1-(4-(Chloromethyl)benzyl)pyrrolidin-2-one

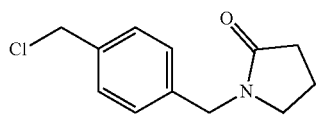 [SMILES: O=C1CCCN1Cc1ccc(CCl)cc1]

To a solution of 1-(4-(hydroxymethyl)benzyl)pyrrolidin-2-one (80 mg, 0.390 mmol), DMAP (5 mg, 0.041 mmol), and DIEA (0.136 mL, 0.780 mmol) in dichloromethane (2.0 mL) at room temperature was added methanesulfonyl chloride (0.030 mL, 0.390 mmol). The reaction mixture was then continued stirring at room temperature for 6 hours. An additional equivalent of both the methanesulfonyl chloride (0.030 mL, 0.390 mmol) and DIEA (0.136 mL, 0.780 mmol) were added and the reaction mixture stirred overnight at room temperature. After stirring overnight, the reaction mixture was diluted with DCM and washed with 1N HCl (2×), saturated brine (1×), and then water. The organic layer was then dried (MgSO$_4$) and concentrated to obtain 1-(4-(chloromethyl) benzyl) pyrrolidin-2-one (87 mg) as a tan solid. LCMS m/z=224.0 [M+H]$^+$.

Step 3: 4-Ethyl-2-(4-methyl-1,4-diazepan-1-yl)-6-(4-((2-oxopyrrolidin-1-yl)methyl)benzyl)thio)pyridine-3,5-dicarbonitrile

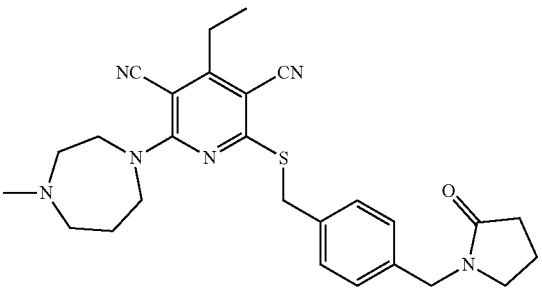 [SMILES: CCc1c(C#N)c(SCc2ccc(CN3CCCC3=O)cc2)nc(N2CCCN(C)CC2)c1C#N]

To solutions of 4-ethyl-2-mercapto-6-(4-methyl-1,4-diazepan-1-yl) pyridine-3,5-dicarbonitrile (synthesis described in example 69, step 1, 53 mg, 0.176 mmol) and 2-(dimethylamino)-4-ethyl-6-mercaptopyridine-3,5-dicarbonitrile (44 mg, 0.189 mmol) in N,N-dimethylformamide (1.0 mL) at 20° C., each in its respective reaction vessel, was added Et$_3$N (0.027 mL, 0.192 mmol). To these solutions was then added 1-(4-(chloromethyl) benzyl) pyrrolidin-2-one (43 mg, 0.192 mmol). The reaction mixtures were then stirred at the same temp for 6 hours at which time, the reaction mixture was warmed to room temperature, filtered and then purified by reverse phase HPLC (Gilson, 30 mm Gemini Column, NH$_4$OH modifier) to obtain 4-ethyl-2-(4-methyl-1,4-diazepan-1-yl)-6-((4-((2-oxopyrrolidin-1-yl)methyl)benzyl)thio)pyridine-3,5-dicarbonitrile (57 mg) as a light brown oil. LCMS m/z=489.4 [M+H]⁺. ¹H NMR (400 MHz, DMSO-d₆) δ ppm 7.34-7.40 (m, J=8.11 Hz, 2H), 7.16-7.20 (m, J=8.11 Hz, 2H), 4.49 (s, 2H), 4.34 (s, 2H), 3.82-3.94 (m, 4H), 3.18-3.23 (m, 2H), 2.78 (q, J=7.60 Hz, 2H), 2.60-2.65 (m, 2H), 2.45-2.49 (m, 2H), 2.25-2.31 (m, 2H), 2.23 (s, 3H), 1.87-1.95 (m, 4H), 1.22 (t, J=7.60 Hz, 3H)

Example 270

2-((6-(4-(3-Amino-2-oxopyrrolidin-1-yl)piperidin-1-yl)-3,5-dicyano-4-ethylpyridin-2-yl)thio-2-phenylacetamide, Formic Acid Salt Step 1: Benzyl 4-(2-((tert-butoxycarbonyl)amino)-4-(methylthio)butanamido)piperidine-1-carboxylate

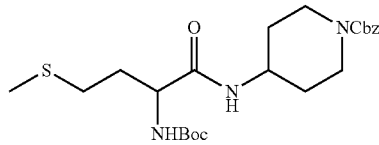 [SMILES: CSCCC(NC(=O)OC(C)(C)C)C(=O)NC1CCN(C(=O)OCc2ccccc2)CC1]

To a solution of 2-((tert-butoxycarbonyl)amino)-4-(methylthio)butanoic acid (12.5 g, 50.1 mmol), HATU (22.88 g, 60.2 mmol) and DIEA (17.51 mL, 100 mmol) in N,N-dimethylformamide (100 mL) at room temperature was added neat benzyl 4-aminopiperidine-1-carboxylate (12.92 g, 55.1 mmol) over 1 minute. The reaction mixture was stirred at 25° C. for 15 hours. The mixture was poured into NaOH (1N, 100 mL) and extracted with ethyl acetate (200 mL). The combined organic layers were washed with HCl (1N, 50 mL) and brine (100 mL). The combined organic layers were dried over sodium sulphate, filtered and concentrated. The residue was purified by silica gel chromatography (eluted with DCM/MeOH) to give benzyl 4-(2-((tert-butoxycarbonyl)amino)-4-(methylthio)butanamido)piperidine-1-carboxylate (20 g, 86% yield). LCMS m/z=466 [M+H]⁺.

Step 2: 4-((1-((Benzyloxy)carbonyl)piperidin-4-yl)amino)-3-((tert-butoxycarbonyl)amino)-4-oxobutyl)dimethylsulfonium iodide

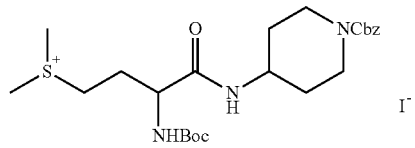

A mixture of benzyl 4-(2-((tert-butoxycarbonyl)amino)-4-(methylthio)butanamido)piperidine-1-carboxylate (20 g, 43 mmol) in MeI (54 mL) was stirred at 25° C. for 15 hours. The reaction mixture was evaporated to dryness to give (4-((1-((benzyloxy)carbonyl)piperidin-4-yl)amino)-3-((tert-butoxycarbonyl)amino)-4-oxobutyl)dimethylsulfonium iodide (20 g). LCMS m/z=480 [M]⁺.

Step 3: Benzyl 4-(3-((tert-butoxycarbonyl)amino)-2-oxopyrrolidin-1-yl) piperidine-1-carboxylate

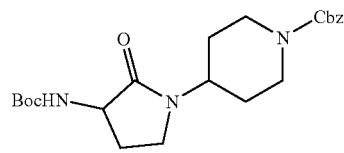 [SMILES: CC(C)(C)OC(=O)NC1CCN(C2CCN(C(=O)OCc3ccccc3)CC2)C1=O]

To a solution of 4-((1-((benzyloxy)carbonyl)piperidin-4-yl)amino)-3-((tert-butoxycarbonyl)amino)-4-oxobutyl)dimethylsulfonium iodide (20 g, 32.9 mmol) and NaH (1.198 g, 49.9 mmol) in dichloromethane (100 mL) under nitrogen at 0° C. was added neat DMF (19.3 mL, 250 mmol) dropwise over 1 minute. The reaction mixture was stirred at 25° C. for 4 hours. The mixture was poured into saturated ammonium chloride (70 mL) and the solution was extracted with dichloromethane (3×200 mL). The combined organic layers were washed with brine, dried over MgSO₄, filtered and concentrated in vacuo. The crude was purified by silica gel chromatography (eluted with DCM/MeOH) to afford benzyl 4-(3-((tert-butoxycarbonyl)amino)-2-oxopyrrolidin-1-yl) piperidine-1-carboxylate (12 g). LCMS m/z=440 [M+Na]⁺.

Step 4: tert-Butyl (2-oxo-1-(piperidin-4-yl)pyrrolidin-3-yl)carbamate

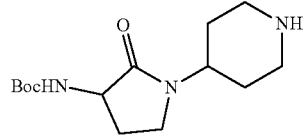 [SMILES: CC(C)(C)OC(=O)NC1CCN(C2CCNCC2)C1=O]

A suspension of benzyl 4-(3-((tert-butoxycarbonyl)amino)-2-oxopyrrolidin-1-yl) piperidine-1-carboxylate (1.5 g, 3.59 mmol) and Pd/C (5%, 191 mg, 1.796 mmol) in acetic acid (10 mL) under hydrogen was stirred at 50° C. for 15 hours. The mixture was filtered and concentrated to give a yellow solid (1.0 g), which was used as is in the next step. LCMS m/z=284 [M+H]⁺.

Step 5: tert-Butyl (1-(1-(6-chloro-3,5-dicyano-4-ethylpyridin-2-yl)piperidin-4-yl)-2-oxopyrrolidin-3-yl)carbamate

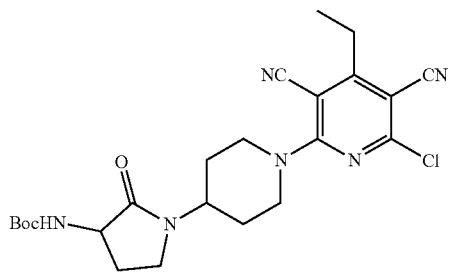 [SMILES: CCc1c(C#N)c(Cl)nc(N2CCC(N3CCC(NC(=O)OC(C)(C)C)C3=O)CC2)c1C#N]

To a solution of 2,6-dichloro-4-ethylpyridine-3,5-dicarbonitrile (synthesis described in example 3, step 2, 1.35 g, 5.97 mmol) and tert-butyl (2-oxo-1-(piperidin-4-yl)pyrrolidin-3-yl)carbamate (1.692 g, 5.97 mmol) in dichloromethane (15 mL) stirred under nitrogen at 0° C. was added neat TEA (1.67 mL, 11.94 mmol) dropwise over 15 minutes. The reaction mixture was stirred at 25° C. for 15 hours. The mixture was diluted with DCM (100 mL), and the organic layer was washed with 2 M hydrochloric acid (50 mL), water (50 mL) and saturated brine (50 mL), dried over sodium sulphate and concentrated in vacuo to give 1.6 g of a yellow solid. LCMS m/z=495 [M+Na]$^+$.

Step 6: tert-Butyl (1-(1-(6-((2-amino-2-oxo-1-phenylethyl)thio)-3,5-dicyano-4-ethylpyridin-2-yl)piperidin-4-yl)-2-oxopyrrolidin-3-yl)carbamate

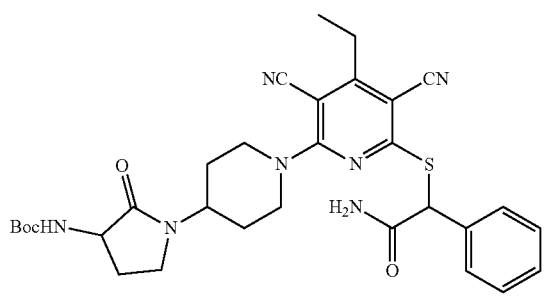 [SMILES: CCc1c(C#N)c(SC(C(N)=O)c2ccccc2)nc(N2CCC(N3CCC(NC(=O)OC(C)(C)C)C3=O)CC2)c1C#N]

To a solution of tert-butyl (1-(1-(6-chloro-3,5-dicyano-4-ethylpyridin-2-yl)piperidin-4-yl)-2-oxopyrrolidin-3-yl)carbamate (700 mg, 1.480 mmol) in N,N-dimethylformamide (5 mL) was added potassium ethanethioate (341 mg, 2.96 mmol). The reaction mixture was stirred at 25° C. for 1 hour. Solid $K_2CO_3$ (205 mg, 1.48 mmol) and 2-amino-2-oxo-1-phenylethyl methanesulfonate (synthesis described in example 3, step 5, 509 mg, 2.22 mmol) were added. The reaction mixture was stirred at 25° C. for 15 hours. The reaction mixture was quenched with water then partitioned between ethyl acetate (100 mL) and 2 M hydrochloric acid (100 mL). The organic layer was separated and evaporated in vacuo, and the residue was purified by silica gel chromatography (eluted with DCM/MeOH) to give the product (200 mg, 22% yield). LCMS m/z=626 [M+Na]$^+$.

Step 7: 2-((6-(4-(3-Amino-2-oxopyrrolidin-1-yl)piperidin-1-yl)-3,5-dicyano-4-ethylpyridin-2-yl)thio)-2-phenylacetamide, Formic Acid Salt

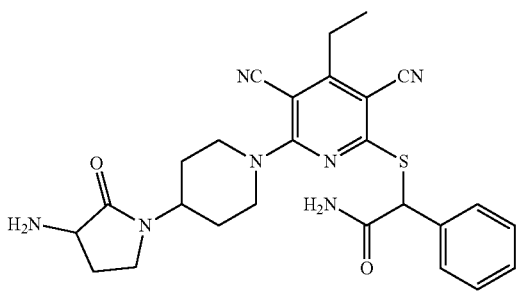 [SMILES: CCc1c(C#N)c(SC(C(N)=O)c2ccccc2)nc(N2CCC(N3CCC(N)C3=O)CC2)c1C#N]

To a solution of tert-butyl (1-(1-(6-((2-amino-2-oxo-1-phenylethyl)thio)-3,5-dicyano-4-ethylpyridin-2-yl)piperidin-4-yl)-2-oxopyrrolidin-3-yl)carbamate (200 mg, 0.331 mmol) in dichloromethane (20 mL) under nitrogen at room temperature was added 2,2,2-trifluoroacetic acid (0.510 mL, 6.63 mmol) in one charge over 1 minute. The reaction mixture was stirred at 25° C. for 15 hours. The mixture was concentrated and the residue was washed with diethyl ether and acetonitrile then purified by prep-HPLC using Me-CN/0.5% formic acid as eluent to give 2-((6-(4-(3-Amino-2-oxopyrrolidin-1-yl)piperidin-1-yl)-3,5-dicyano-4-ethylpyridin-2-yl)thio)-2-phenylacetamide, Formic acid salt (6 mg, 3% yield). LCMS m/z=504.1 [M+H]$^+$. $^1$H NMR (400 MHz, MeOD) δ ppm 8.41 (bs, 1H), 7.55 (d, J=7.2 Hz, 2H), 7.46-7.30 (m, 3H), 6.62 (bs, 1H), 5.53 (s, 1H), 4.82-4.77 (m, 2H), 4.24-4.20 (m, 1H), 4.02-3.97 (m, 1H), 3.59-3.49 (m, 1H), 3.47-3.40 (m, 1H), 3.30-3.13 (m, 2H), 2.92 (q, J=7.5 Hz, 2H), 2.56-2.51 (m, 1H), 1.92-1.85 (m, 5H), 1.32 (t, J=7.6 Hz, 3H).

Example 272

2-((4-(Aminomethyl) benzyl)thio)-6-(dimethylamino)-4-ethylpyridine-3,5-dicarbonitrile, Hydrochloride Step 1: tert-Butyl 4-(((3,5-dicyano-6-(dimethylamino)-4-ethylpyridin-2-yl)thio)methyl) benzylcarbamate

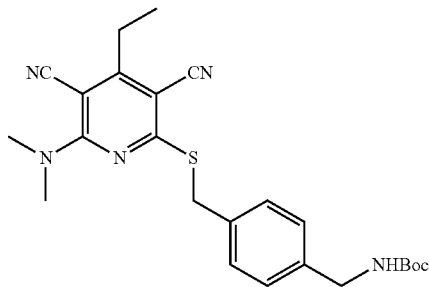 [SMILES: CCc1c(C#N)c(SCc2ccc(CNC(=O)OC(C)(C)C)cc2)nc(N(C)C)c1C#N]

2-(dimethylamino)-4-ethyl-6-mercaptopyridine-3,5-dicarbonitrile (synthesis described in example 92, step 3, 109 mg, 0.469 mmol) was dissolved in N,N-dimethylformamide (3 mL) and the solution was cooled to 0° C. Triethylamine (0.098 mL, 0.704 mmol) was added followed by dropwise addition of tert-butyl 4-(bromomethyl) benzylcarbamate (141 mg, 0.469 mmol) dissolved in additional DMF (1 mL). The reaction was followed by LCMS until the starting material was consumed. The DMF was evaporated and the crude taken up in ethyl acetate and washed with water, then dried with sodium sulfate. The material was purified by chromatography on silica gel eluted with a gradient of 0-15% of (a solution of 2 M ammonia in methanol)/chloroform. The fractions corresponding to product by LCMS were combined, then concentrated in vacuo to provide tert-butyl 4-(((3,5-dicyano-6-(dimethylamino)-4-ethylpyridin-2-yl)thio)methyl)benzylcarbamate (159 mg, 0.352 mmol, 75% yield) as a tan solid. LCMS m/z=452.4 [M+H]$^+$.

Step 2: 2-((4-(Aminomethyl)benzyl)thio)-6-(dimethylamino)-4-ethylpyridine-3,5-dicarbonitrile, Hydrochloride

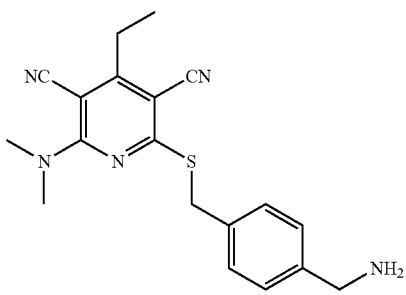 [SMILES: CCc1c(C#N)c(SCc2ccc(CN)cc2)nc(N(C)C)c1C#N]

To a solution of tert-butyl 4-(((3,5-dicyano-6-(dimethylamino)-4-ethylpyridin-2-yl)thio)methyl)benzylcarbamate (143 mg, 0.317 mmol) dissolved in 1,4-dioxane (4 mL) and cooled in an ice water bath was added HCl (4 M in dioxane, 0.962 mL, 31.7 mmol). The reaction was warmed to room temperature and the yellow solution gradually became a suspension after stirring overnight at room temperature. The solid was collected by filtration and washed with diethyl ether. The resulting off-white solid was dried in vacuo at 55° C. to provide 2-((4-(aminomethyl)benzyl)thio)-6-(dimethylamino)-4-ethylpyridine-3,5-dicarbonitrile, Hydrochloride (119 mg, 0.307 mmol, 97% yield) as an off-white solid. LCMS m/z=352.2 [M+H]$^+$. $^1$H NMR (400 MHz, DMSO-d$_6$) δ ppm 8.25 (br. s., 3H), 7.49-7.45 (m, 2H), 7.44-7.40 (m, 2H), 4.54 (s, 2H), 4.05-3.97 (m, 2H), 3.34 (s, 6H), 2.77 (q, J=7.6 Hz, 2H), 1.21 (t, J=7.6 Hz, 3H).

Example 273

N-(4-(((3,5-Dicyano-6-(dimethylamino-4-ethylpyridin-2-yl)thio) methyl) phenyl) acetamide

Step 1: 2-((4-Aminobenzyl)thio)-6-(dimethylamino)-4-ethylpyridine-3,5-dicarbonitrile

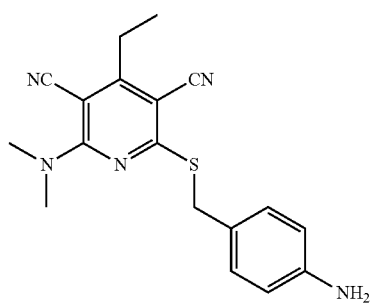 [SMILES: CCc1c(C#N)c(SCc2ccc(N)cc2)nc(N(C)C)c1C#N]

At 0° C., to the solution of 2-(dimethylamino)-4-ethyl-6-mercaptopyridine-3,5-dicarbonitrile (synthesis described in example 92, step 3, 400 mg, 1.722 mmol) and TEA (0.480 mL, 3.44 mmol) in DCM (8 mL) was added a solution of tert-butyl (4-(bromomethyl)phenyl)carbamate (493 mg, 1.722 mmol) in DCM (4 mL) dropwise. The reaction mixture was stirred at room temperature overnight. The reaction mixture was concentrated down and the residue was treated with 20% TFA/DCM (10 mL) for 2 hours. The reaction mixture was concentrated down and basified with NH$_4$OH in methanol, then concentrated down with silica and purified by column (CombiFlash®, 24 g column) using 0-50% EtOAc/hexane to afford 2-((4-aminobenzyl)thio)-6-(dimethylamino)-4-ethylpyridine-3,5-dicarbonitrile (454 mg, 1.345 mmol, 78% yield) as an off white solid. LCMS m/z=338.2 [M+H]$^+$. 1H NMR (400 MHz, DMSO-d$_6$) L ppm 1.21 (t, J=7.6 Hz, 3H), 2.76 (q, J=7.6 Hz, 2H), 3.36 (s, 6H), 4.35 (s, 2H), 5.12 (s, 2H), 6.50 (d, J=8.6 Hz, 2H), 7.05 (d, J=8.4 Hz, 2H).

Step 2: N-(4-(((3,5-Dicyano-6-(dimethylamino)-4-ethylpyridin-2-yl) thio) methyl) phenyl) acetamide

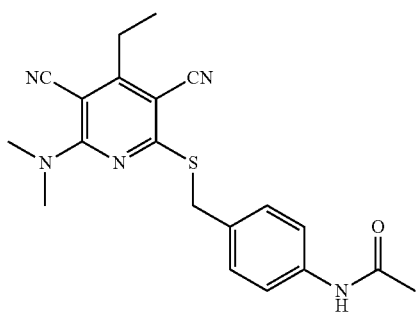 [SMILES: CCc1c(C#N)c(SCc2ccc(NC(C)=O)cc2)nc(N(C)C)c1C#N]

At 0° C., to a solution of 2-((4-aminobenzyl)thio)-6-(dimethylamino)-4-ethylpyridine-3,5-dicarbonitrile (80 mg, 0.237 mmol) and TEA (0.083 mL, 0.593 mmol) in THF (3 mL) was added acetyl chloride (0.025 mL, 0.356 mmol). The reaction mixture was stirred at room temperature overnight. The reaction mixture was concentrated down and purified by RP-HPLC (30-60% acetonitrile/water, 0.1% NH$_4$OH in water) to afford N-(4-(((3,5-dicyano-6-(dimethylamino)-4-ethylpyridin-2-yl)thio) methyl) phenyl)acetamide (55 mg, 0.145 mmol, 61% yield) as an off-white solid. LCMS m/z=380.2 [M+H]$^+$. 1H NMR (400 MHz, DMSO-d$_6$) δ ppm 1.21 (t, J=7.6 Hz, 3H), 2.03 (s, 3H), 2.76 (q, J=7.4 Hz, 2H), 4.46 (s, 2H), 7.33 (m, J=8.6 Hz, 2H), 7.53 (m, J=8.6 Hz, 2H), 9.97 (s, 1H). Six protons not observed.

Example 274

1-(6-((2-Amino-2-oxo-1-phenylethyl)thio)-3,5-dicyano-4-ethylpyridin-2-yl)piperidin-4-yl (2S)-2-amino-3-methylbutanoate

Step 1: 1-(6-((2-Amino-2-oxo-1-phenylethyl)thio)-3,5-dicyano-4-ethylpyridin-2-yl)piperidin-4-yl (2S)-2-((tert-butoxycarbonyl)amino)-3-methylbutanoate

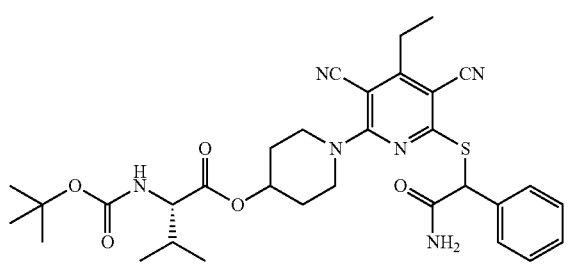 [SMILES: CCc1c(C#N)c(SC(C(N)=O)c2ccccc2)nc(N2CCC(OC(=O)[C@@H](NC(=O)OC(C)(C)C)C(C)C)CC2)c1C#N]

629

To a solution of (S)-2-((tert-butoxycarbonyl)amino)-3-methylbutanoic acid (153 mg, 0.705 mmol) and triethylamine (0.098 mL, 0.705 mmol) in tetrahydrofuran (2.000 mL) and N,N-dimethylformamide (2 mL) was added 2,4,6-trichlorobenzoyl chloride (172 mg, 0.705 mmol) at 0° C., and the reaction mixture was stirred for 3 hours at the same temperature. Then DMAP (86 mg, 0.705 mmol) was added followed by 2-((3,5-dicyano-4-ethyl-6-(4-hydroxypiperidin-1-yl)pyridin-2-yl)thio)-2-phenylacetamide (synthesis described in example 48, 300 mg, 0.705 mmol) at 0° C. The reaction mixture was stirred at 27° C. for 3 hours. The reaction mixture was poured into ice cold water (50 mL) and extracted with ethyl acetate (3×50 mL). The combined organic phases were washed with saturated sodium chloride solution (50 mL), dried over sodium sulphate and concentrated in vacuo to give the crude product. The crude product was purified by silica gel chromatography (100-200 mesh eluted with 50% hexane/EtOAc) to afford 1-(6-((2-amino-2-oxo-1-phenylethyl)thio)-3,5-dicyano-4-ethylpyridin-2-yl)piperidin-4-yl (2S)-2-((tert-butoxycarbonyl)amino)-3-methylbutanoate (300 mg, 69% yield) as a light brown solid. LCMS m/z=621.6 [M+H]$^+$.

Step 2: 1-(6-((2-Amino-2-oxo-1-phenylethyl)thio)-3,5-dicyano-4-ethylpyridin-2-yl)piperidin-4-yl (2S)-2-amino-3-methylbutanoate

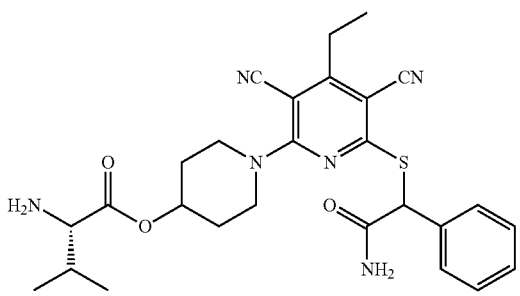 [SMILES: CCc1c(C#N)c(SC(C(N)=O)c2ccccc2)nc(N2CCC(OC(=O)[C@@H](N)C(C)C)CC2)c1C#N]

Hydrochloric acid (4 M in 1,4-dioxane, 2.5 mL, 10.00 mmol) was added to a stirred solution of 1-(6-((2-amino-2-oxo-1-phenylethyl)thio)-3,5-dicyano-4-ethylpyridin-2-yl)piperidin-4-yl (2S)-2-((tert-butoxycarbonyl)amino)-3-methylbutanoate (250 mg, 0.392 mmol) in 1,4-dioxane (2 mL) at 0° C., and then the reaction mixture was stirred at room temperature for 2 hours. The reaction mixture was concentrated under reduced pressure to afford crude product (200 mg) as a light brown solid. The crude compound was purified by prep-HPLC under basic conditions to afford 1-(6-((2-amino-2-oxo-1-phenylethyl)thio)-3,5-dicyano-4-ethylpyridin-2-yl)piperidin-4-yl (2S)-2-amino-3-methylbutanoate (83 mg, 40% yield) as a white solid. LCMS m/z=521.3 [M+H]$^+$. $^1$H NMR (400 MHz, DMSO-d$_6$) δ ppm 7.90 (s, 1H), 7.67-7.47 (m, 2H), 7.43-7.16 (m, 4H), 5.53 (s, 1H), 5.08-5.01 (m, 1H), 4.09-4.01 (m, 2H), 3.88-3.76 (m, 2H), 3.13 (d, J=5.4 Hz, 1H), 2.76 (q, J=7.5 Hz, 2H), 2.01-1.93 (m, 3H), 1.72-1.62 (m, 4H), 1.21 (t, J=7.6 Hz, 3H), 0.90 (d, J=6.8 Hz, 3H), 0.85 (d, J=6.8 Hz, 3H).

Example 275

2-((6-((2-Amino-2-oxo-1-phenylethyl)thio)-3,5-dicyano-4-ethylpyridin-2-yl) (methyl) aminoethyl (2S-2-amino-3-methylbutanoate Step 1: 2-((6-((2-Amino-2-oxo-1-phenylethyl)thio)-3,5-dicyano-4-ethylpyridin-2-yl) (methyl)amino) ethyl (2S)-2-((tert-butoxycarbonyl)amino)-3-methylbutanoate

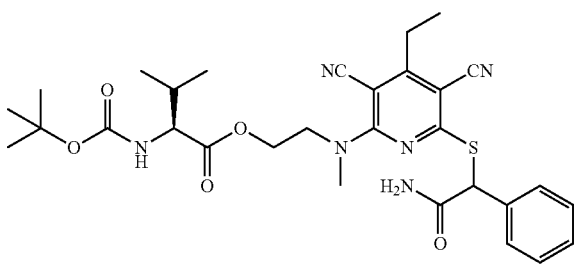 [SMILES: CCc1c(C#N)c(SC(C(N)=O)c2ccccc2)nc(N(C)CCOC(=O)[C@@H](NC(=O)OC(C)(C)C)C(C)C)c1C#N]

To a solution of (S)-2-((tert-butoxycarbonyl)amino)-3-methylbutanoic acid (149 mg, 0.688 mmol) and triethylamine (0.096 mL, 0.688 mmol) in tetrahydrofuran (2.000 mL) and N,N-dimethylformamide (2 mL) was added 2,4,6-trichlorobenzoyl chloride (168 mg, 0.688 mmol) at 0° C., and the reaction mixture was stirred for 1 hour at the same temperature. Then DMAP (84 mg, 0.688 mmol) followed by 2-((3,5-dicyano-4-ethyl-6-((2-hydroxyethyl)(methyl)amino)pyridin-2-yl)thio)-2-phenylacetamide (synthesis described in Example 147, Step 2, 300 mg, 0.688 mmol) were added at 0° C. The reaction mixture was stirred at 27° C. for 2 hours. The reaction mixture was poured into ice cold water (50 mL) and extracted with ethyl acetate (3×50 mL). The combined organic layers were washed with saturated sodium chloride solution (50 mL), dried over sodium sulphate and evaporated in vacuo to give the crude product. The crude product was purified by silica gel column (100-200 mesh, eluting with 50% hexane/EtOAc) to afford 2-((6-((2-amino-2-oxo-1-phenylethyl)thio)-3,5-dicyano-4-ethylpyridin-2-yl)(methyl)amino)ethyl (2S)-2-((tert-butoxycarbonyl)amino)-3-methylbutanoate (260 mg, 59% yield) as a light brown solid. LCMS m/z=595.3 [M+H]$^+$.

Step 2: 2-((6-((2-Amino-2-oxo-1-phenylethyl)thio)-3,5-dicyano-4-ethylpyridin-2-yl) (methyl) amino) ethyl (2S)-2-amino-3-methylbutanoate

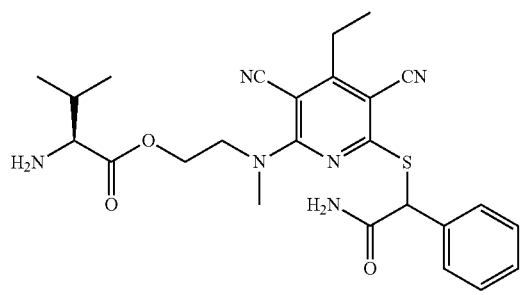 [SMILES: CCc1c(C#N)c(SC(C(N)=O)c2ccccc2)nc(N(C)CCOC(=O)[C@@H](N)C(C)C)c1C#N]

Hydrochloric acid (4 M in 1,4-dioxane, 2.5 mL, 10.00 mmol) was added to a stirred solution of 2-((6-((2-amino-2-oxo-1-phenylethyl)thio)-3,5-dicyano-4-ethylpyridin-2-yl)(methyl)amino)ethyl (2S)-2-((tert-butoxycarbonyl)amino)-3-methylbutanoate (260 mg, 0.437 mmol) in 1,4-dioxane (5 mL) at 0° C. and the reaction mixture was stirred at room temperature for 2 hours. The reaction mixture was concentrated under reduced pressure to afford a light brown solid. The crude compound was purified by prep-HPLC under basic conditions to afford 2-((6-((2-amino-2-oxo-1-phenylethyl)thio)-3,5-dicyano-4-ethylpyridin-2-yl)(methyl)amino)ethyl (2S)-2-amino-3-ethylbutanoate (85 mg, 38% yield) as a white solid. LCMS m/z=495.3 [M+H]+. 1H NMR (400 MHz, DMSO-d6) δ ppm 7.90 (br s, 1H), 7.50 (d, J=8.33 Hz, 2H), 7.41-7.29 (m, 4H), 5.53 (d, J=3.07 Hz, 1H), 4.33-3.99 (m, 4H), 3.39 (d, J=1.97 Hz, 3H), 3.05 (dd, J=11.40, 5.26 Hz, 1H), 2.77 (q, J=7.60 Hz, 2H), 1.74-1.55 (m, 3H), 1.20 (t, J=7.45 Hz, 3H), 0.66-0.85 (m, 6H).

Example 276

2,2'-((3,5-Dicyano-4-ethylpyridine-2,6-diyl)bis(sulfanediyl))bis(2-phenylacetamide)

Step 1: 2-Mercapto-2-phenylacetamide

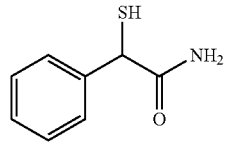 [SMILES: NC(=O)C(S)c1ccccc1]

To a suspension of S-(2-amino-2-oxo-1-phenylethyl) ethanethioate (synthesis described in example 62, step 5, 502 mg, 2.4 mmol) in methanol (20 mL) stirred at 0° C. was added sodium ethoxide (164 mg, 2.4 mmol) in one charge. The reaction mixture was stirred at 0° C. for 2 hours. The reaction mixture was concentrated to afford crude 2-mercapto-2-phenylacetamide (400 mg) which was used without purification. LCMS m/z=168.1 [M+H]+.

Step 2: 2,2'-((3,5-Dicyano-4-ethylpyridine-2,6-diyl)bis(sulfanediyl))bis(2-phenylacetamide)

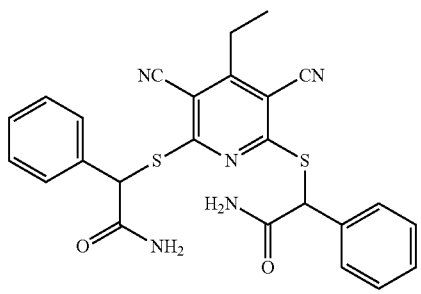 [SMILES: CCc1c(C#N)c(SC(C(N)=O)c2ccccc2)nc(SC(C(N)=O)c2ccccc2)c1C#N]

To a solution of 2,6-dichloro-4-ethylpyridine-3,5-dicarbonitrile (synthesis described in example 3 step 2, 226 mg, 1.00 mmol) and triethylamine (0.56 mL, 4.00 mmol) in N,N-dimethylformamide (15 mL) stirred in air at room temperature was added 2-mercapto-2-phenylacetamide (401 mg, 2.40 mmol). The reaction mixture was stirred at 25° C. for 12 hours. The reaction mixture was concentrated and the residue was purified by flash column chromatography to afford 2,2'-((3,5-dicyano-4-ethylpyridine-2,6-diyl)bis(sulfanediyl))bis(2-phenylacetamide) (135 mg, 27%) as a light yellow solid. LCMS m/z=487.9 [M+H]+. 1H NMR (400 MHz, DMSO-d6) δ ppm 8.06 (br s, 2H), 7.78 (br s, 2H), 7.53-7.49 (m, 4H), 7.48-7.39 (m, 6H), 5.81 (s, 2H), 2.83 (q, J=7.6 Hz, 2H), 1.23 (t, J=7.6 Hz, 3H).

Example 277

(2S)-(1-(6-((2-Amino-2-oxo-1-phenylethylthio-3,5-dicyano-4 ethylpyridin-2-yl)azetidin-3-ylmethyl 2-amino-3-methylbutanoate TFA Salt Step 1: (2S)-(1-(6-((2-Amino-2-oxo-1-phenylethyl)thio)-3,5-dicyano-4-ethylpyridin-2-yl)azetidin-3-yl)methyl2-((tert-butoxycarbonyl)amino)-3-methylbutanoate

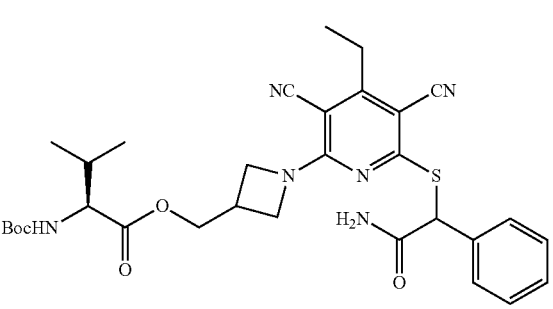 [SMILES: CCc1c(C#N)c(SC(C(N)=O)c2ccccc2)nc(N2CC(COC(=O)[C@@H](NC(=O)OC(C)(C)C)C(C)C)C2)c1C#N]

To a solution of 2-((3,5-dicyano-4-ethyl-6-(3-(hydroxymethyl) azetidin-1-yl)pyridin-2-yl)thio)-2phenylacetamide (150 mg, 0.368 mmol) in dichloromethane (20 mL) were added (S)-2-((tert-butoxycarbonyl)amino)-3-methylbutanoic acid (160 mg, 0.736 mmol), HOBT (113 mg, 0.736 mmol), EDC (353 mg, 1.841 mmol) and TEA (0.257 mL, 1.841 mmol). The reaction mixture was stirred for 5 hours. The reaction mixture was washed with brine (2×20 mL) and the organic layer concentrated under reduced pressure. The crude residue was purified by silica gel chromatography (eluting with DCM/MeOH) to give (2S)-(1-(6-((2-amino-2-oxo-1-phenylethyl)thio)-3,5-dicyano-4-ethylpyridin-2-yl) azetidin-3-yl)methyl 2-((tert-butoxycarbonyl)amino)-3-methylbutanoate (200 mg). LCMS m/z=607.1 [M+H]+.

Step 2: (2S)-(1-(6-((2-Amino-2-oxo-1-phenylethyl)thio)-3,5-dicyano-4 ethylpyridin-2-yl)azetidin-3-yl)methyl 2-amino-3-methylbutanoate TFA Salt

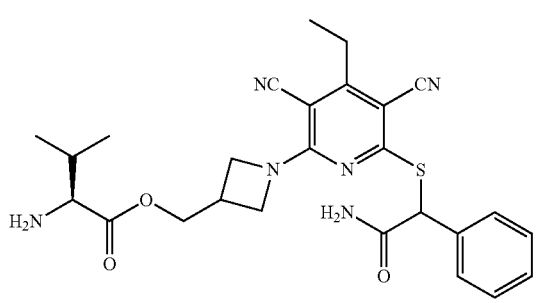 [SMILES: CCc1c(C#N)c(SC(C(N)=O)c2ccccc2)nc(N2CC(COC(=O)[C@@H](N)C(C)C)C2)c1C#N]

(2S)-(1-(6-((2-Amino-2-oxo-1-phenylethyl)thio)-3,5-di-cyano-4-ethylpyridin-2-yl) azetidin-3-yl)methyl-2-((tert-butoxycarbonyl)amino)-3-methylbutanoate (200 mg, 0.330 mmol) was added to TFA (2 mL, 26 mmol) in dichloromethane (10 mL). The reaction mixture was stirred for 5 hours. The mixture was diluted with dichloromethane (30 mL) and washed with brine (2×20 mL). The organic layer was concentrated under reduced pressure. The crude residue was purified by silica gel chromatography (eluting with DCM/MeOH) to give (2S)-(1-(6-((2-amino-2-oxo-1-phenylethyl)thio)-3,5-dicyano-4 ethylpyridin-2-yl)azetidin-3-yl)methyl 2-amino-3-methylbutanoate TFA salt (150 mg). LCMS m/z=507.1 [M+H]⁺. ¹H NMR (400 MHz, DMSO-d₆) δ ppm 8.47 (s, 3H), 7.94 (s, 1H), 7.53 (d, J=7.2 Hz, 2H), 7.43-7.23 (m, 4H), 5.60 (s, 0.5H), 5.58 (s, 0.5H), 4.68-4.06 (m, 6H), 3.97 (s, 1H), 3.19-3.06 (m, 1H), 2.70 (q, J=7.4 Hz, 2H), 2.21-2.07 (m, 1H), 1.18 (t, J=7.5 Hz, 3H), 1.03-0.84 (m, 6H).

Example 278

N-(4-(((3,5-Dicyano-6-(dimethylamino)-4-ethylpyridin-2-yl)thio)methyl)benzyl)-2-hydroxyacetamide

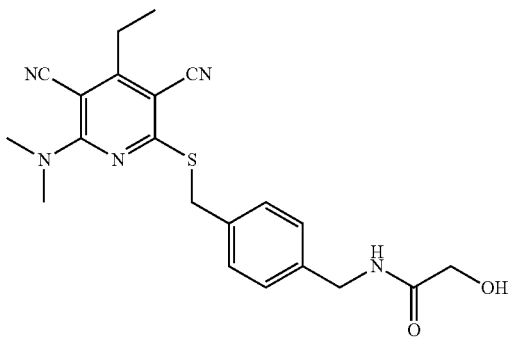 [SMILES: CCc1c(C#N)c(SCc2ccc(CNC(=O)CO)cc2)nc(N(C)C)c1C#N]

To a solution of 2-hydroxyacetic acid (10 mg, 0.131 mmol) in N,N-dimethylformamide (1.0 mL) at room temperature was added HATU (49.0 mg, 0.129 mmol). The reaction mixture was then stirred at 20° C. for 30 minutes at which time the 2-((4-(aminomethyl)benzyl)thio)-6-(dimethylamino)-4-ethylpyridine-3,5-dicarbonitrile, Hydrochloride (synthesis described in example 272, step 2, 50 mg, 0.129 mmol) and Et₃N (0.042 mL, 0.304 mmol) were added. The reaction mixture was then stirred at room over the weekend at 20° C. before warming to room temperature. The mixture was filtered, and purified by reverse phase HPLC (Gilson, 30 mm×50 mm Gemini Column, NH₄OH modifier) to obtain N-(4-(((3,5-dicyano-6-(dimethylamino)-4-ethylpyridin-2-yl)thio)methyl)benzyl)-2-hydroxyacetamide (36 mg) as an off-white solid. LCMS m/z=410.4 [M+H]⁺. ¹H NMR (400 MHz, DMSO-d₆) δ ppm 8.29 (d, J=6.08 Hz, 1H), 7.36 (t, J=7.10 Hz, 2H), 7.23 (d, J=7.60 Hz, 2H), 5.51 (br. s., 1H), 4.50 (d, J=6.59 Hz, 2H), 4.23-4.32 (m, 2H), 3.85 (br. s., 2H), 3.36 (br. s., 6H), 2.72-2.80 (m, 2H), 1.18-1.25 (m, 3H).

Example 279

3-Amino-N-(4-(((3,5-dicyano-6-(dimethylamino)-4-ethylpyridin-2-yl)thio)methyl)benzyl)propanamide Step 1: tert-Butyl (3-((4-(((3,5-dicyano-6-(dimethylamino)-4-ethylpyridin-2-yl)thio)methyl)benzyl)amino)-3-oxopropyl)carbamate

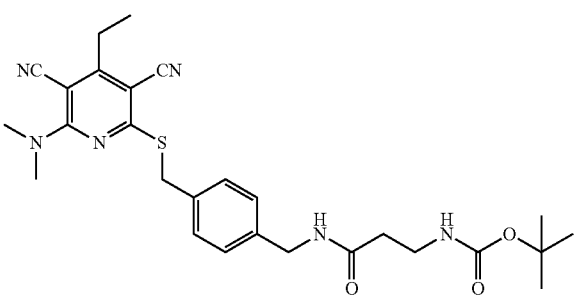 [SMILES: CCc1c(C#N)c(SCc2ccc(CNC(=O)CCNC(=O)OC(C)(C)C)cc2)nc(N(C)C)c1C#N]

To a solution of 3-((tert-butoxycarbonyl)amino)propanoic acid (27 mg, 0.143 mmol)) in N,N-dimethylformamide (1.0 mL) at 20° C. was added HATU (54 mg, 0.142 mmol). The reaction mixtures were then stirred at 20° C. for 30 minutes at which time the 2-((4-(aminomethyl)benzyl)thio)-6-(dimethylamino)-4-ethylpyridine-3,5-dicarbonitrile, Hydrochloride (synthesis described in example 272, step 2, 50 mg, 0.129 mmol) followed by Et₃N (0.036 mL, 0.258 mmol) were added. The reaction mixtures were then stirred at 20° C. for 3.5 hours. The reactions were warmed to room temperature. The reaction mixtures were then filtered and purified by reverse phase HPLC (Gilson, 30 mm×50 mm Gemini Column, NH₄OH modifier) to obtain tert-butyl (3-((4-(((3,5-dicyano-6-(dimethylamino)-4-ethylpyridin-2-yl)thio)methyl)benzyl)amino)-3-oxopropyl)carbamate (52 mg) as a white solid. LCMS m/z=545.4 [M+Na]⁺.

Step 2: 3-Amino-N-(4-(((3,5-dicyano-6-(dimethylamino)-4-ethylpyridin-2-yl)thio)methyl)benzyl)propanamide

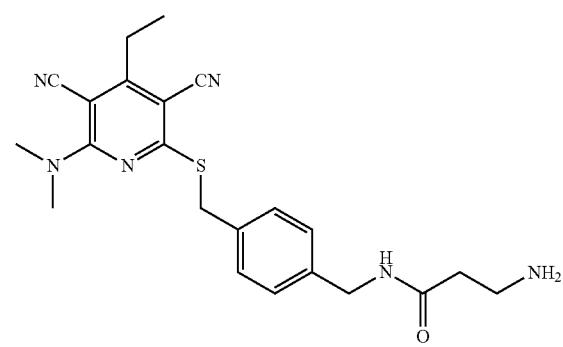 [SMILES: CCc1c(C#N)c(SCc2ccc(CNC(=O)CCN)cc2)nc(N(C)C)c1C#N]

tert-Butyl (3-((4-(((3,5-dicyano-6-(dimethylamino)-4-ethylpyridin-2-yl)thio)methyl)benzyl)amino)-3-oxo propyl) carbamate (34 mg, 0.065 mmol)) was suspended in a solution of 4 M HCl (1500 µl, 6.0 mmol) in dioxane at room temperature. The reaction mixture was stirred at room temperature for 2 hours then the reaction mixture was concentrated. The residue was suspended in MeOH, and free based with isopropylamine. The mixture was purified by reverse phase HPLC (Gilson, 30 mm×50 mm Gemini Column, NH$_4$OH modifier) to yield 3-amino-N-(4-(((3,5-dicyano-6-(dimethylamino)-4-ethylpyridin-2-yl)thio)methyl)benzyl)propanamide (23 mg) as a white solid. LCMS m/z=423.4 [M+H]$^+$. $^1$H NMR (400 MHz, DMSO-d$_6$) δ ppm 8.40 (t, J=5.83 Hz, 1H), 7.36 (d, J=8.11 Hz, 2H), 7.21 (d, J=8.36 Hz, 2H), 4.50 (s, 2H), 4.24 (d, J=5.83 Hz, 2H), 2.72-2.81 (m, 4H), 2.21 (t, J=6.59 Hz, 2H), 1.43 (br. s., 2H), 1.21 (t, J=7.60 Hz, 3H). Six protons not observed.

Example 281

2-((6-(3-Aminoazetidin-1-yl)-3,5-dicyano-4-ethylpyridin-2-yl)thio)-2-phenylacetamide Step 1: tert-Butyl (1-(6-chloro-3,5-dicyano-4-ethylpyridin-2-yl)azetidin-3-yl)carbamate

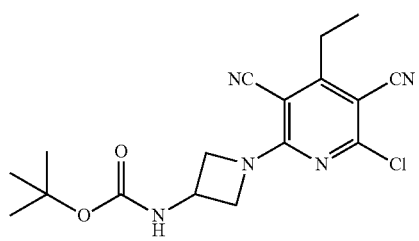 [SMILES: CCc1c(C#N)c(Cl)nc(N2CC(NC(=O)OC(C)(C)C)C2)c1C#N]

To a solution of tert-butyl azetidin-3-ylcarbamate (1.587 g, 9.22 mmol) in dichloromethane (25 mL) were added triethylamine (3.50 mL, 25.1 mmol) and 2,6-dichloro-4-ethylpyridine-3,5-dicarbonitrile (synthesis described in example 3 step 2, 2 g, 8.38 mmol) at 0° C. The reaction mixture was stirred for 2 hours at 27° C. The reaction mixture was quenched with ice cold water (250 mL) and extracted with DCM (3×250 mL). The combined organic layers were washed with water (250 mL), dried over Na$_2$SO$_4$, filtered and concentrated under vacuum to afford tert-butyl (1-(6-chloro-3,5-dicyano-4-ethylpyridin-2-yl)azetidin-3-yl)carbamate (2.4 g) as an off-white solid. LCMS m/z=362.5 [M+H]$^+$.

Step 2: tert-Butyl (1-(6-((2-amino-2-oxo-1-phenylethyl)thio)-3,5-dicyano-4-ethylpyridin-2-yl)azetidin-3-yl)carbamate

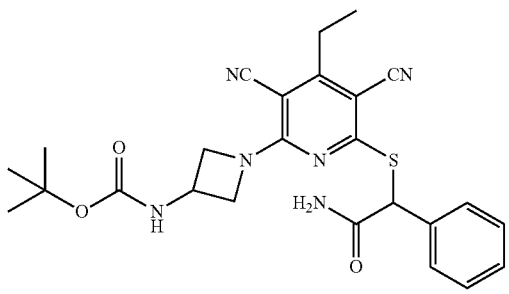 [SMILES: CCc1c(C#N)c(SC(C(N)=O)c2ccccc2)nc(N2CC(NC(=O)OC(C)(C)C)C2)c1C#N]

To a solution of tert-butyl (1-(6-chloro-3,5-dicyano-4-ethylpyridin-2-yl)azetidin-3-yl)carbamate (2.4 g, 5.89 mmol) in N,N-dimethylformamide (20 mL), was added potassium thioacetate (1.344 g, 11.77 mmol) at room temperature, and the reaction mixture was stirred for 2 hours at the same temperature. Potassium carbonate (1.627 g, 11.77 mmol) followed by 2-amino-2-oxo-1-phenylethyl methanesulfonate (synthesis described in example 3 step 5, 2.072 g, 8.83 mmol) were added at 0° C. The reaction mixture was stirred for 16 hours at room temperature. The reaction mixture was poured into ice cold water (250 mL) and extracted with ethyl acetate (3×250 mL). The combined organic layers were washed with water (200 mL) and saturated brine solution (200 mL), dried over sodium sulphate, filtered and concentrated in vacuo. The residue was triturated with DCM (1 mL) and 10% EtOAc in n-pentane (2×30 mL). The resulting solid was further purified by silica gel chromatography (100-200 mesh, eluted with 3% methanol in DCM) to afford tert-butyl (1-(6-((2-amino-2-oxo-1-phenylethyl)thio)-3,5-dicyano-4-ethylpyridin-2-yl)azetidin-3-yl)carbamate (1 g, 72% yield) as an off-white solid. LCMS m/z=493.2 [M+H]$^+$.

Step 3: 2-((6-(3-Aminoazetidin-1-yl)-3,5-dicyano-4-ethylpyridin-2-yl)thio)-2-phenyl acetamide

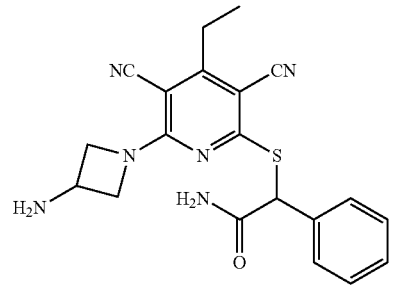 [SMILES: CCc1c(C#N)c(SC(C(N)=O)c2ccccc2)nc(N2CC(N)C2)c1C#N]

TFA (0.513 mL, 3.33 mmol) in dichloromethane (5 mL) was added to a stirred solution of tert-butyl (1-(6-((2-amino-2-oxo-1-phenylethyl)thio)-3,5-dicyano-4-ethylpyridin-2-yl)azetidin-3-yl)carbamate (700 mg, 1.331 mmol) in dichloromethane (5 mL) at 0° C. The reaction mixture was stirred at room temperature for 2 hours. The reaction mixture was concentrated under reduced pressure to afford 700 mg of a light brown solid. 400 mg of this material was purified by prep-HPLC to afford 2-((6-(3-aminoazetidin-1-yl)-3,5-dicyano-4-ethylpyridin-2-yl)thio)-2-phenylacetamide (140 mg) of an off-white solid. LCMS m/z=393.1 [M+H]$^+$. $^1$H NMR (400 MHz, DMSO-d$_6$) δ ppm 7.87 (s, 1H), 7.62-7.46 (m, 2H), 7.46-7.17 (m, 4H), 5.55 (s, 1H), 4.63-4.48 (m, 2H), 4.08-3.81 (m, 3H), 2.68 (q, J=7.4 Hz, 2H), 2.22 (bs, 2H), 1.17 (t, J=7.6 Hz, 3H).

Example 282

(S)-1-(6-((4-(Acetamidomethyl)benzyl)thio)-3,5-dicyano-4-ethylpyridin-2-yl)azetidin-3-yl 2-amino-3-methylbutanoate, Trifluoroacetic Acid Salt

Step 1: 2-Chloro-4-ethyl-6-(3-hydroxyazetidin-1-yl)pyridine-3,5-dicarbonitrile

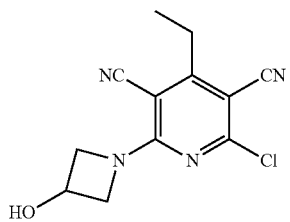 [SMILES: CCc1c(C#N)c(Cl)nc(N2CC(O)C2)c1C#N]

2,6-Dichloro-4-ethylpyridine-3,5-dicarbonitrile (1 g, 4.42 mmol), azetidin-3-ol (0.323 g, 4.42 mmol) and triethylamine (0.448 g, 4.42 mmol) were added to dichloromethane (100 mL). The mixture was stirred at 25° C. for 2 hours. The solvent was evaporated under vacuum. The remaining residue was partitioned between DCM (100 mL) and water (50 mL). The layers were separated and the organic layer washed with brine, dried and concentrated. The crude residue was purified by silica gel chromatography to provide 2-chloro-4-ethyl-6-(3-hydroxyazetidin-1-yl)pyridine-3,5-dicarbonitrile (900 mg) as a white solid. LCMS m/z=263 [M+H]$^+$.

Step 2: N-(4-(((3,5-Dicyano-4-ethyl-6-(3-hydroxyazetidin-1-yl)pyridin-2-yl)thio) methyl)benzyl)acetamide

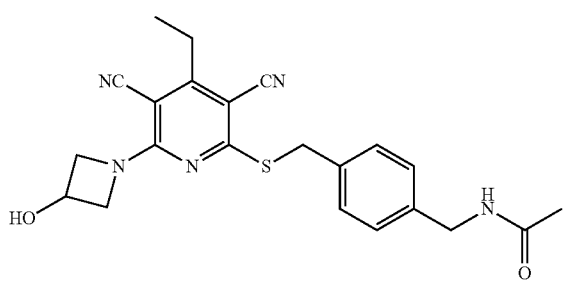 [SMILES: CCc1c(C#N)c(SCc2ccc(CNC(C)=O)cc2)nc(N2CC(O)C2)c1C#N]

2-Chloro-4-ethyl-6-(3-hydroxyazetidin-1-yl)pyridine-3,5-dicarbonitrile (850 mg, 3.24 mmol) and potassium ethanethioate (739 mg, 6.47 mmol)) were added to N,N-dimethylformamide (50 mL). After the mixture was stirred for 2 hours, N-(4-(bromomethyl)benzyl)acetamide (1175 mg, 4.85 mmol) was added. The mixture was stirred for 15 hours. The solvent was evaporated under vacuum and the remaining residue partitioned between DCM (40 mL) and water (20 mL). The organic layer was separated, washed with brine, dried and concentrated. The crude residue was purified by silica gel chromatography (ethyl acetate:petroleum ether=1:2) to give N-(4-(((3,5-dicyano-4-ethyl-6-(3-hydroxyazetidin-1-yl)pyridin-2-yl)thio)methyl) benzyl)acetamide (500 mg) as a white solid. LCMS m/z=422.1 [M+H]$^+$.

Step 3: (S)-1-(6-((4-(Acetamidomethyl)benzyl)thio)-3,5-dicyano-4-ethylpyridin-2-yl) azetidin-3-yl 2-((tert-butoxycarbonyl)amino)-3-methylbutanoate

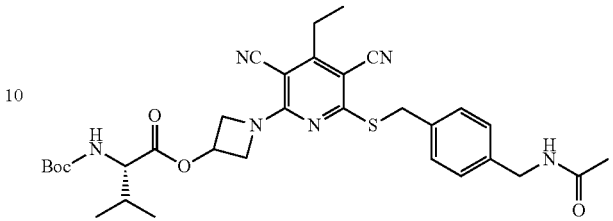

N-(4-(((3,5-Dicyano-4-ethyl-6-(3-hydroxyazetidin-1-yl)pyridin-2-yl)thio)methyl)benzyl)acetamide (180 mg, 0.427 mmol), (S)-2-((tert-butoxycarbonyl)amino)-3-methylbutanoic acid (93 mg, 0.427 mmol), N$^1$-((ethylimino)methylene)-N$^3$,N$^3$-dimethylpropane-1,3-diamine (265 mg, 1.708 mmol), HOBt (229 mg, 1.495 mmol) and triethylamine (173 mg, 1.708 mmol) were added to dichloromethane (50 mL). The mixture was stirred at 25° C. for 15 hours. Water (50 mL) was added to the mixture. The organic layer was separated, washed with brine, dried and concentrated. The crude residue was purified by silica gel chromatography (ethyl acetate:petroleum ether=1:5) to give (S)-1-(6-((4-(acetamidomethyl)benzyl)thio)-3,5-dicyano-4-ethylpyridin-2-yl)azetidin-3-yl 2-((tert-butoxycarbonyl)amino)-3-methylbutanoate (350 mg) as a pale yellow solid. LCMS m/z=643.2 [M+Na]$^+$.

Step 4: (S)-1-(6-((4-(Acetamidomethyl)benzyl)thio)-3,5-dicyano-4-ethylpyridin-2-yl) azetidin-3-yl 2-amino-3-methylbutanoate, Trifluoroacetic Acid Salt

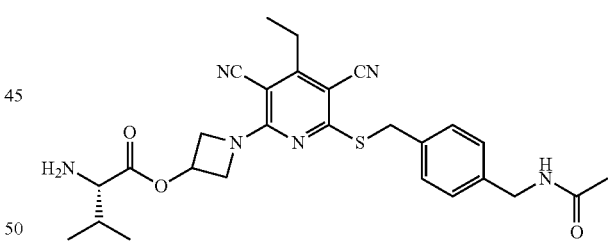

(S)-1-(6-((4-(Acetamidomethyl)benzyl)thio)-3,5-dicyano-4-ethylpyridin-2-yl)azetidin-3-yl)-2-((tert-butoxycarbonyl)amino)-3-methylbutanoate (350 mg, 0.564 mmol) was added to dichloromethane (20 mL) and then 2,2,2-trifluoroacetic acid (129 mg, 1.128 mmol) was added at 0° C. The mixture was stirred at 25° C. for 15 hours. The solvent was removed and the remaining residue purified by prep-HPLC to give (S)-1-(6-((4-(acetamidomethyl)benzyl)thio)-3,5-dicyano-4-ethylpyridin-2-yl)azetidin-3-yl 2-amino-3-methylbutanoate, trifluoroacetic acid salt (100 mg) as a white solid. LCMS m/z=521.1 [M+H]$^+$. $^1$H NMR (400 MHz, DMSO-d$_6$) δ ppm 8.52 (s, 3H), 8.36 (t, J=5.8 Hz, 1H), 7.36 (d, J=8.0 Hz, 2H), 7.20 (d, J=8.0 Hz, 2H), 5.42 (ddd, J=10.4, 6.9, 3.8 Hz, 1H), 4.84 (s, 2H), 4.48 (s, 2H), 4.42 (s, 2H), 4.22 (d, J=5.9 Hz, 2H), 4.01 (s, 1H), 2.72 (q, J=7.7 Hz, 2H), 2.24 (dd, J=11.9, 6.8 Hz, 1H), 1.87 (s, 3H), 1.20 (t, J=7.6 Hz, 3H), 1.04 (d, J=6.9 Hz, 3H), 1.00 (d, J=6.9 Hz, 3H).

Example 283

2-((3,5-Dicyano-4-ethyl-6-methylpyridin-2-yl)thio)-2-phenylacetamide

Step 1: 2-Chloro-4-ethyl-6-methylpyridine-3,5-dicarbonitrile

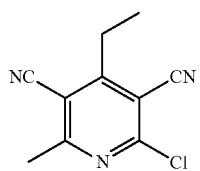

NBS (3.51 g, 19.73 mmol) was added to a stirred solution of 4-ethyl-6-methyl-2-oxo-1,2-dihydropyridine-3-carbonitrile (1.6 g, 9.87 mmol) in $H_2SO_4$ (5 mL, 94 mmol) and trifluoroacetic acid (5 mL, 64.9 mmol) at 0° C. The mixture was stirred at 0° C. for 15 hours. Then it was poured into ice water and the solid was filtered to obtain crude material. A mixture of this crude (1.2 g) and cyanocopper (535 mg, 5.97 mmol) in N-methyl-2-pyrrolidone (40 mL) was stirred at 200° C. for 48 hours under nitrogen atmosphere. Then it was cooled to room temperature and extracted with ethyl acetate and water, the organic layer was concentrated in vacuo to dryness and purified by column chromatograph to obtain crude. A mixture of this crude (320 mg) and $POCl_3$ (20 ml, 215 mmol) was stirred at 150° C. for 18 hours in the sealed tube. After cooling the reaction, the reaction mixture was concentrated in vacuo to obtain the crude product and purified further by column chromatograph to obtain 2-chloro-4-ethyl-6-methylpyridine-3,5-dicarbonitrile (289 mg, 1.41 mmol). $^1$H NMR (400 MHz, $CDCl_3$) δ 3.08 (q, J=7.7 Hz, 2H), 2.82 (s, 3H), 1.38 (t, J=7.7 Hz, 3H).

Step 2: 2-((3,5-Dicyano-4-ethyl-6-methylpyridin-2-yl)thio)-2-phenylacetamide

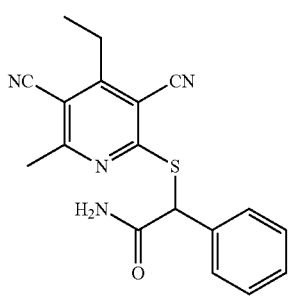 [SMILES: CCc1c(C#N)c(C)nc(SC(C(N)=O)c2ccccc2)c1C#N]

A mixture of 2-chloro-4-ethyl-6-methylpyridine-3,5-dicarbonitrile (110 mg, 0.54 mmol) and potassium ethanethioate (64.1 mg, 0.56 mmol) in DMF (10 mL) was stirred at 20° C. for 1 hour. Then 2-bromo-2-phenylacetamide (229 mg, 1.07 mmol) and triethylamine (0.224 mL, 1.61 mmol) were added, and the mixture was stirred for another 13 hours. Then it was washed with water and extracted with ethyl acetate, the organic layer was dried, filtered and concentrated in vacuo to dryness. The residue was purified by column chromatography to afford 2-((3,5-dicyano-4-ethyl-6-methylpyridin-2-yl)thio)-2-phenylacetamide (90 mg, 50.0%) as a white solid. LCMS m/z=337.2 $[M+H]^+$. $^1$H NMR (400 MHz, $CDCl_3$) δ ppm 7.50 (m, 2H), 7.38 (m, 3H), 6.08 (s, 1H), 5.72 (s, 1H), 5.65 (s, 1H), 2.98 (s, 2H), 2.78 (s, 3H), 1.34 (s, 3H).

Example 284

N-(4-(((3,5-Dicyano-4-ethyl-6-methylpyridin-2-yl)thio)methyl)benzyl)acetamide

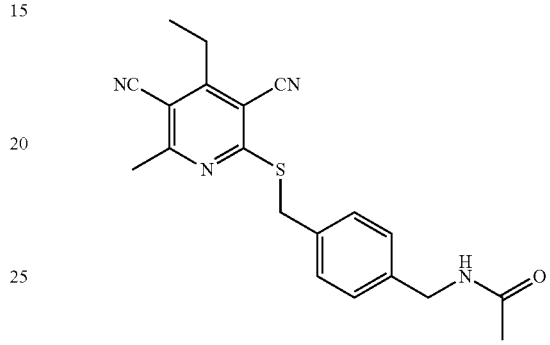

A mixture of 2-chloro-4-ethyl-6-methylpyridine-3,5-dicarbonitrile (synthesis described in example 283 step 1, 110 mg, 0.54 mmol) and potassium ethanethioate (64.1 mg, 0.56 mmol) in DMF (10 mL) was stirred at 20° C. for 1 hour. Then N-(4-(bromomethyl)benzyl)acetamide (259 mg, 1.07 mmol) and triethylamine (0.224 mL, 1.61 mmol) were added, and the mixture was stirred for another 13 hours. Then it was washed with water and extracted with ethyl acetate and the organic layer was dried, filtered and concentrated. The residue was purified by column chromatograph to afford N-(4-(((3,5-dicyano-4-ethyl-6-methylpyridin-2-yl)thio)methyl)benzyl)acetamide (110 mg, 56%) as a white solid. LCMS m/z=365.1 $[M+H]^+$. $^1$H NMR (400 MHz, $CDCl_3$) δ ppm 7.37 (d, J=7.7 Hz, 2H), 7.24 (d, J=7.8 Hz, 2H), 5.76 (s, 1H), 4.49 (s, 2H), 4.41 (d, J=5.1 Hz, 2H), 3.01-2.91 (m, 2H), 2.79 (s, 3H), 2.03 (s, 3H), 1.33 (t, J=7.6 Hz, 3H).

Example 285

2-(4-(((3,5-Dicyano-6-(dimethylamino)-4-ethylpyridin-2-yl)thio)methyl)-1H-pyrazol-1-yl)acetamide Step 1: Methyl 2-(4-(((3,5-dicyano-6-(dimethylamino)-4-ethylpyridin-2-yl)thio)methyl)-1H-pyrazol-1-yl)acetate

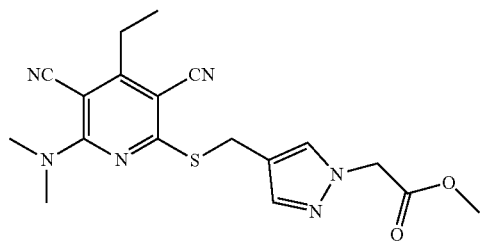

To a solution of methyl 2-(4-(hydroxymethyl)-1H-pyrazol-1-yl)acetate (1.7 g, 9.99 mmol) in dichloromethane (35 mL) was added triethylamine (2.78 mL, 19.98 mmol) and methane sulfonyl chloride (1.168 mL, 14.99 mmol) at room temperature. The reaction mixture was stirred at the same temperature for 20 minutes. The volatiles were distilled off at room temperature to afford the crude product which was used without purification in the next step. To a solution of 2-chloro-6-(dimethylamino)-4-ethylpyridine-3,5-dicarbonitrile (synthesis described in example 3 step 3, 1.7 g, 7.24 mmol) in N,N-dimethylformamide (34 mL) was added potassium thioacetate (1.655 g, 14.49 mmol), and the reaction mixture was stirred at room temperature for 2 hours. After 2 hours the reaction mixture was cooled to 0° C. then potassium carbonate (2.002 g, 14.49 mmol) was added followed by methyl 2-(4-(((methylsulfonyl)oxy)methyl)-1H-pyrazol-1-yl)acetate (2.338 g, 9.42 mmol) in DMF at room temperature, and the reaction mixture was stirred at room temperature for 1 hour. The reaction mixture was diluted with water (100 mL) and extracted with ethyl acetate (200 mL). The organic layer was dried over anhydrous Na$_2$SO$_4$, filtered and the filtrate evaporated under redcued pressure to afford methyl 2-(4-(((3,5-dicyano-6-(dimethylamino)-4-ethylpyridin-2-yl)thio)methyl)-1H-pyrazol-1-yl)acetate (1.9 g). LCMS (m/z)=385.3 [M+H]$^+$.

Step 2: 2-(4-(((3,5-Dicyano-6-(dimethylamino)-4-ethylpyridin-2-yl)thio)methyl)-1H-pyrazol-1-yl)acetic acid

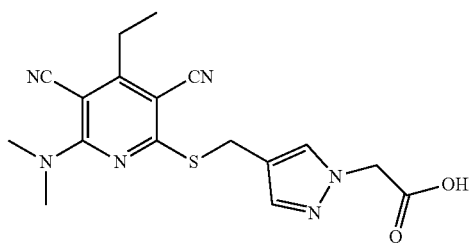 [SMILES: CCc1c(C#N)c(SCc2cnn(CC(=O)O)c2)nc(N(C)C)c1C#N]

To methyl 2-(4-(((3,5-dicyano-6-(dimethylamino)-4-ethylpyridin-2-yl)thio)methyl)-1H-pyrazol-1-yl)acetate (800 mg, 2.081 mmol) in methanol (8 mL), water (4 mL), and tetrahydrofuran (8 mL) was added LiOH (249 mg, 10.40 mmol) at room temperature, and the reaction mixture was stirred at room temperature for 1 hour. The mixture was diluted with water (10 mL) and acidified with dilute HCl. The resulting solid was filtered and dried to obtain 2-(4-(((3,5-dicyano-6-(dimethylamino)-4-ethylpyridin-2-yl)thio)methyl)-1H-pyrazol-1-yl)acetic acid (670 mg). LCMS m/z=371.2 [M+H]$^+$.

Step 3: 2-(4-(((3,5-Dicyano-6-(dimethylamino)-4-ethylpyridin-2-yl)thio)methyl)-1H-pyrazol-1-yl)acetamide

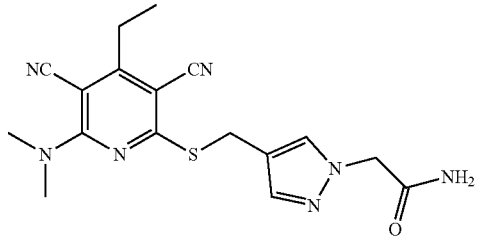 [SMILES: CCc1c(C#N)c(SCc2cnn(CC(N)=O)c2)nc(N(C)C)c1C#N]

Ammonium chloride (234 mg, 4.38 mmol) was added to a stirred solution of 2-(4-(((3,5-dicyano-6-(dimethylamino)-4-ethylpyridin-2-yl)thio)methyl)-1H-pyrazol-1-yl)acetic acid (330 mg, 0.877 mmol), HATU (500 mg, 1.315 mmol) and diisopropylethylamine (0.766 mL, 4.38 mmol) in N,N-dimethylformamide (6 mL) at room temperature, and then the reaction mixture was stirred at room temperature for 2 hours. The reaction mixture was diluted with ice cold water (60 mL), and the resulting solid was collected by filtration. This solid was dissolved in acetonitrile (30 mL) and heated with charcoal (1 g) at 50° C. for 15 minutes. The mixture was then filtered through Celite® and the filtrate was concentrated and dried to obtain 2-(4-(((3,5-dicyano-6-(dimethylamino)-4-ethylpyridin-2-yl)thio)methyl)-1H-pyrazol-1-yl)acetamide (260 mg, 79% yield) as an off-white solid. LCMS (m/z)=370.0 [M+H]$^+$. $^1$H NMR (400 MHz, DMSO-d$_6$) δ ppm 7.69 (s, 1H), 7.47-7.37 (m, 2H), 7.22 (br s, 1H), 4.70 (s, 2H), 4.36 (s, 2H), 3.36 (s, 6H), 2.77 (q, J=7.60 Hz, 2H), 1.21 (t, J=7.56 Hz, 3H).

Example 286

N-(1-(6-((2-Amino-2-oxo-1-phenylethyl)thio)-3,5-dicyano-4-ethylpyridin-2-yl)piperidin-4-yl)-2-hydroxyacetamide Step 1: tert-Butyl (1-(6-((2-amino-2-oxo-1-phenylethyl)thio)-3,5-dicyano-4-ethylpyridin-2-yl)piperidin-4-yl)carbamate

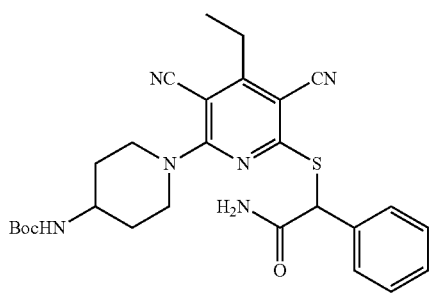 [SMILES: CCc1c(C#N)c(SC(C(N)=O)c2ccccc2)nc(N2CCC(NC(=O)OC(C)(C)C)CC2)c1C#N]

To a stirred solution of tert-butyl (1-(6-chloro-3,5-dicyano-4-ethylpyridin-2-yl)piperidin-4-yl)carbamate (synthesis described in example 81 step 1, 900 mg, 1.800 mmol) in N,N-dimethylformamide (10 mL), was added potassium thioacetate (411 mg, 3.60 mmol) at room temperature, and the reaction mixture was stirred for 2 hours at the same temperature. Then potassium carbonate (373 mg, 2.70 mmol) was added followed by 2-amino-2-oxo-1-phenylethyl methanesulfonate (synthesis described in example 3 step 5, 534 mg, 2.160 mmol) at room temperature. The reaction mixture was stirred at room temperature for 16 hours and then quenched in cold water (50 mL) and extracted with ethyl acetate (2×100 mL). The combined the organic layers were dried over Na$_2$SO$_4$, filtered, concentrated and purified by column chromatography using silica gel (100-200 mesh, eluting with ethyl acetate in hexane) to afford tert-butyl (1-(6-((2-amino-2-oxo-1-phenylethyl)thio)-3,5-dicyano-4-ethylpyridin-2-yl)piperidin-4-yl)carbamate (700 mg). LCMS m/z=519.0 [M–H]$^-$.

Step 2: 2-((6-(4-Aminopiperidin-1-yl)-3,5-dicyano-4-ethylpyridin-2-yl)thio)-2-phenyl acetamide hydrochloride

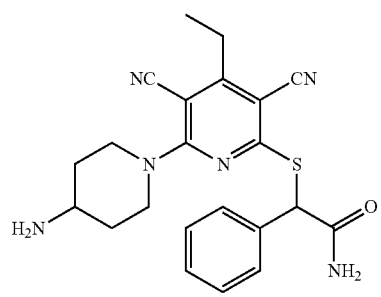 [SMILES: CCc1c(C#N)c(SC(C(N)=O)c2ccccc2)nc(N2CCC(N)CC2)c1C#N]

To a stirred solution of tert-butyl (1-(6-((2-amino-2-oxo-1-phenylethyl)thio)-3,5-dicyano-4-ethylpyridin-2-yl)piperidin-4-yl)carbamate (700 mg, 0.936 mmol) in 1,4-dioxane (10 mL) was added HCl (4 M in 1,4 dioxane, 3 mL, 12.00 mmol) at 0° C., the reaction mixture was stirred for 4 hours at room temperature. The reaction mixture was concentrated and triturated with diethyl ether (30 mL) to afford 2-((6-(4-aminopiperidin-1-yl)-3,5-dicyano-4-ethylpyridin-2-yl)thio)-2-phenylacetamide hydrochloride (450 mg, 90% yield) as a brown solid. LCMS m/z=421.1 [M+H]$^+$.

Step 3: 2-((1-(6-((2-Amino-2-oxo-1-phenylethyl)thio)-3,5-dicyano-4-ethylpyridin-2-yl)piperidin-4-yl)amino)-2-oxoethyl acetate

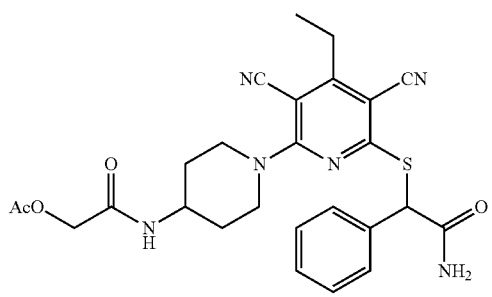 [SMILES: CCc1c(C#N)c(SC(C(N)=O)c2ccccc2)nc(N2CCC(NC(=O)COC(C)=O)CC2)c1C#N]

To a stirred solution of 2-acetoxyacetic acid (100 mg, 0.845 mmol) in N,N-dimethylformamide (10 mL) was added DIPEA (0.295 mL, 1.690 mmol) and HATU (643 mg, 1.690 mmol) at 0° C., and the solution was stirred for 10 minutes. After 10 minutes 2-((6-(4-aminopiperidin-1-yl)-3,5-dicyano-4-ethylpyridin-2-yl)thio)-2-phenylacetamide hydrochloride (450 mg, 0.845 mmol) was added at room temperature, and the reaction mixture was stirred for 3 hours at room temperature. The reaction mixture was concentrated under reduced pressure, diluted with water (30 mL), and extracted with ethyl acetate (2×80 mL). The combined organic layers were dried over anhydrous Na$_2$SO$_4$, filtered, and concentrated under reduced pressure. The residue was purified by column chromatography using silica gel (100-200 mesh, eluting with 50% ethyl acetate in hexane) to afford 2-((1-(6-((2-amino-2-oxo-1-phenylethyl)thio)-3,5-dicyano-4-ethylpyridin-2-yl)piperidin-4-yl)amino)-2-oxoethyl acetate (350 mg) as a brown solid. LCMS m/z=521.2 [M+H]$^+$.

Step 4: N-(1-(6-((2-Amino-2-oxo-1-phenylethyl)thio)-3,5-dicyano-4-ethylpyridin-2-yl)piperidin-4-yl)-2-hydroxyacetamide

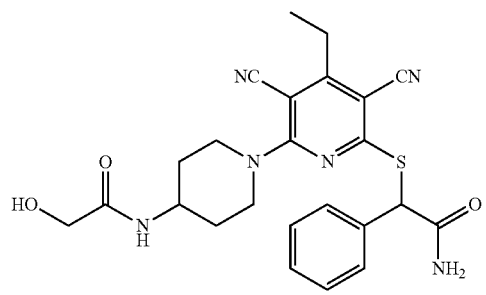 [SMILES: CCc1c(C#N)c(SC(C(N)=O)c2ccccc2)nc(N2CCC(NC(=O)CO)CC2)c1C#N]

To a stirred solution of 2-((1-(6-((2-amino-2-oxo-1-phenylethyl)thio)-3,5-dicyano-4-ethylpyridin-2-yl)piperidin-4-yl)amino)-2-oxoethyl acetate (350 mg, 0.555 mmol)) in tetrahydrofuran (5 mL) was added water (2.5 mL) followed by lithium hydroxide hydrate (23.28 mg, 0.555 mmol) at room temperature. The reaction mixture was stirred for 30 minutes at room temperature. The reaction mixture was quenched with cold water (20 mL) and extracted with ethyl acetate (2×80 mL). The combined organic layers were dried over Na$_2$SO$_4$, filtered and concentrated under reduced the pressure. The crude material was washed with DCM (15 mL), stirred for 10 minutes, then filtered and dried under reduced the pressure to afford N-(1-(6-((2-amino-2-oxo-1-phenylethyl)thio)-3,5-dicyano-4-ethylpyridin-2-yl)piperidin-4-yl)-2-hydroxyacetamide (145 mg, 52% yield) as an off-white solid. LCMS m/z=479.1 [M+H]$^+$. $^1$H NMR (400 MHz, DMSO-d$_6$) δ ppm 7.91 (s, 1H), 7.68 (d, J=8.11 Hz, 1H), 7.55-7.46 (m, 2H), 7.41-7.27 (m, 4H), 5.53 (s, 1H), 5.45-5.36 (m, 1H), 4.51 (t, J=11.62 Hz, 2H), 4.05-3.94 (m, 1H), 3.81 (d, J=5.70 Hz, 2H), 3.30-3.23 (m, 2H), 2.76 (q, J=7.53 Hz, 2H), 1.91-1.80 (m, 2H), 1.69-1.50 (m, 2H), 1.27-1.17 (m, 3H).

Example 287

N-(4-(((3,5-Dicyano-6-(dimethylamino)-4-ethylpyridin-2-yl)thio)methyl)phenyl) methanesulfonamide

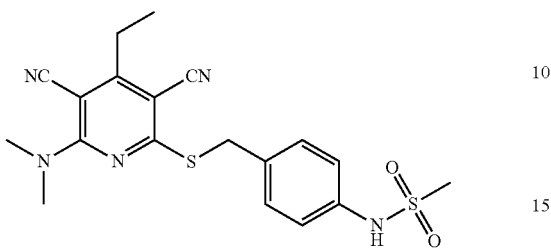

At 0° C., to the solution of 2-((4-aminobenzyl)thio)-6-(dimethylamino)-4-ethylpyridine-3,5-dicarbonitrile (synthesis described in example 273, step 1, 73 mg, 0.216 mmol) and TEA (0.075 mL, 0.541 mmol) in THF (3 mL) was added a solution of methanesulfonyl chloride (0.025 mL, 0.325 mmol) in THF (0.5 mL) dropwise. The reaction mixture was stirred at room temperature for 30 minutes. The reaction mixture was concentrated down and purified by RP-HPLC (30-60% acetonitrile/water, 0.1% NH$_4$OH in water) to afford N-(4-(((3,5-dicyano-6-(dimethylamino)-4-ethylpyridin-2-yl)thio)methyl)phenyl) methanesulfonamide (49 mg, 0.118 mmol, 55% yield) as an off-white solid. LCMS m/z=416.3 [M+H]$^+$. 1 H NMR (400 MHz, DMSO-d$_6$) δ ppm 1.21 (t, J=7.6 Hz, 3H), 2.76 (q, J=7.4 Hz, 2H), 2.96 (s, 3H), 3.34 (s, 6H), 4.47 (s, 2H), 7.12-7.17 (m, 2H), 7.36 (d, J=8.6 Hz, 2H). One proton not observed.

Example 288

N-(1-(6-((2-Amino-2-oxo-1-phenylethyl)thio)-3,5-dicyano-4-ethylpyridin-2-yl)azetidin-3-yl)-2-hydroxyacetamide Step 1: 2-((1-(6-((2-Amino-2-oxo-1-phenylethyl)thio)-3,5-dicyano-4-ethylpyridin-2-yl)azetidin-3-yl)amino)-2-oxoethyl acetate

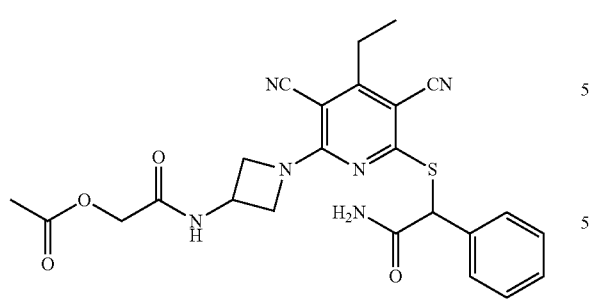

To a stirred solution of 2-acetoxyacetic acid (210 mg, 1.782 mmol) in N,N-dimethylformamide (5 mL) was added HATU (678 mg, 1.782 mmol) at 0° C. After 10 minutes 2-((6-(3-aminoazetidin-1-yl)-3,5-dicyano-4-ethylpyridin-2-yl)thio)-2-phenylacetamide (synthesis described in example 281 step 3, 350 mg, 0.891 mmol) was added followed by DIPEA (0.623 mL, 3.56 mmol) at 0° C. Then the reaction mixture was stirred at room temperature for 2 hours. The reaction mixture was poured into ice cold water (30 mL) and extracted with ethyl acetate (3×30 mL). The combined organic layers were washed with saturated brine solution, dried over Na$_2$SO$_4$, filtered and concentrated. The residue was triturated with diethyl ether (2×15 mL) and dried to afford 2-((1-(6-((2-amino-2-oxo-1-phenylethyl)thio)-3,5-dicyano-4-ethylpyridin-2-yl)azetidin-3-yl)amino)-2-oxoethyl acetate (400 mg) as a light brown solid. LCMS m/z=493.3 [M+H]$^+$.

Step 2: N-(1-(6-((2-Amino-2-oxo-1-phenylethyl)thio)-3,5-dicyano-4-ethylpyridin-2-yl)azetidin-3-yl)-2-hydroxyacetamide

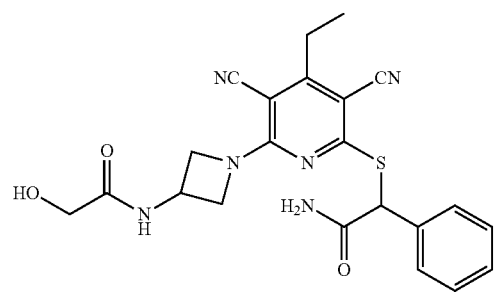 [SMILES: CCc1c(C#N)c(SC(C(N)=O)c2ccccc2)nc(N2CC(NC(=O)CO)C2)c1C#N]

To a solution of 2-((1-(6-((2-amino-2-oxo-1-phenylethyl)thio)-3,5-dicyano-4-ethylpyridin-2-yl)azetidin-3-yl)amino)-2-oxoethyl acetate (350 mg, 0.580 mmol) in tetrahydrofuran (2 mL) stirred under nitrogen at 0° C. was added a solution of LiOH (27.8 mg, 1.161 mmol) in water (2 mL) dropwise over 5 minutes. Then the reaction mixture was stirred at 0° C. for 30 minutes. The reaction mixture was poured into ice cold water (10 mL) and extracted with ethyl acetate (3×25 mL). The combined organic layers were washed with saturated brine (25 mL), dried over sodium sulphate, filtered and concentrated. The residue was purified by prep-HPLC to afford N-(1-(6-((2-amino-2-oxo-1-phenylethyl)thio)-3,5-dicyano-4-ethylpyridin-2-yl)azetidin-3-yl)-2-hydroxyacetamide (90 mg, 34% yield) as a white solid. LCMS m/z=451.0 [M+H]$^+$. $^1$H NMR (400 MHz, DMSO-d$_6$) δ ppm 8.56 (d, J=7.23 Hz, 1H), 7.84 (s, 1H), 7.57-7.47 (m, 2H), 7.39-7.29 (m, 3H), 7.23 (s, 1H), 5.57-5.50 (m, 2H), 4.80-4.59 (m, 3H), 4.38 (br s, 2H), 3.86 (d, J=5.70 Hz, 2H), 2.70 (q, J=7.45 Hz, 2H), 1.18 (t, J=7.6 Hz, 3H).

Example 289

(S)-1-(6-((4-(Acetamidomethyl)benzyl)thio)-3,5-dicyano-4-ethylpyridin-2-yl)piperidin-4-yl 2-amino-3-methylbutanoate Step 1: 2-chloro-4-ethyl-6-(4-hydroxypiperidin-1-yl)pyridine-3,5-dicarbonitrile

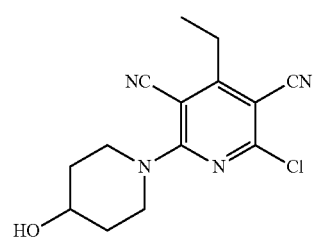 [SMILES: CCc1c(C#N)c(Cl)nc(N2CCC(O)CC2)c1C#N]

To a cooled solution of 2,6-dichloro-4-ethylpyridine-3,5-dicarbonitrile (synthesis described in example 3, step 2, 2 g, 8.67 mmol) and TEA (2.417 mL, 17.34 mmol) in dichloromethane (40 mL) was added piperidin-4-ol (0.877 g, 8.67 mmol). The reaction mixture was stirred at room temperature for 30 minutes. The reaction mixture was diluted with DCM (60 mL). Organic layer was washed with water (50 mL) and sat. brine solution (50 mL). Finally dried over anhydrous sodium sulfate, filtered and evaporated to afford 2-chloro-4-ethyl-6-(4-hydroxypiperidin-1-yl)pyridine-3,5-dicarbonitrile (2.2 g, 7.17 mmol, 83% yield) as off white solid. LCMS m/z=291.2 [M+H]$^+$.

Step 2: N-(4-(((3,5-Dicyano-4-ethyl-6-(4-hydroxypiperidin-1-yl)pyridin-2-yl)thio) methyl) benzyl)acetamide

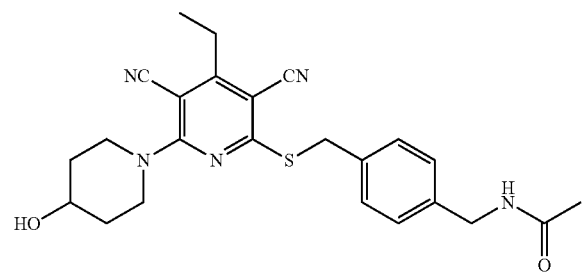 [SMILES: CCc1c(C#N)c(SCc2ccc(CNC(C)=O)cc2)nc(N2CCC(O)CC2)c1C#N]

To a stirred solution of 2-chloro-4-ethyl-6-(4-hydroxpiperidin-1-yl)pyridine-3,5-dicarbonitrile (1 g, 3.27 mmol) in N,N-dimethylformamide (10 mL) was added potassium thioacetate (0.746 g, 6.53 mmol) and the resulting mixture was stirred at room temperature for 2 hours. Then, potassium carbonate (0.903 g, 6.53 mmol) and N-(4-(bromomethyl)benzyl)acetamide (3.16 g, 3.27 mmol) were added and the reaction mixture was stirred at room temperature for 1 hour. The organic phase was diluted with ethyl acetate (200 mL) and washed with HCl (1N, 2×100 mL). The organic layer was dried over anhydrous Na$_2$SO$_4$, filtered and evaporated. The crude product was purified by silica gel column chromatography (100-200 mesh, eluted with 50% ethyl acetate in hexane) to afford N-(4-(((3,5-dicyano-4-ethyl-6-(4-hydroxypiperidin-1-yl)pyridin-2-yl)thio)methyl)benzyl)acetamide (1 g, 67% yield) as an off-white solid. LCMS m/z=450.2 [M+H]$^+$.

Step 3: (S)-1-(6-((4-(Acetamidomethyl)enzyl)thio)-3,5-dicyano-4-ethylpyridin-2-yl) piperidin-4-yl 2-((tert-butoxycarbonyl)amino)-3-methylbutanoate

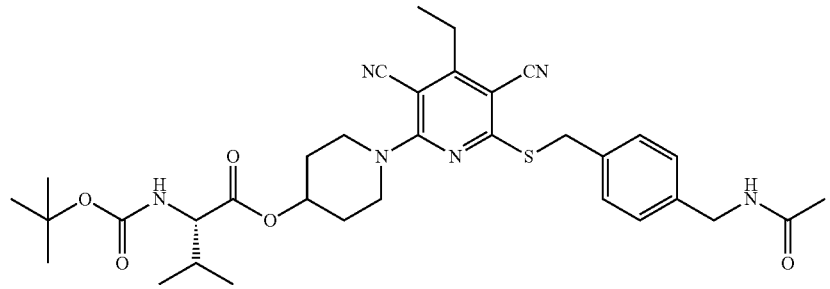 [SMILES: CCc1c(C#N)c(SCc2ccc(CNC(C)=O)cc2)nc(N2CCC(OC(=O)[C@@H](NC(=O)OC(C)(C)C)C(C)C)CC2)c1C#N]

To a solution of 2,4,6-trichlorobenzoyl chloride (269 mg, 1.101 mmol), (S)-2-((tert-butoxycarbonyl)amino)-3-methylbutanoic acid (478 mg, 2.202 mmol) in N,N-dimethylformamide (2 mL) and tetrahydrofuran (20 mL) was added triethylamine (0.153 mL, 1.101 mmol) and the reaction then stirred for 5 hours at 0° C. Then, N-(4-(((3,5-dicyano-4-ethyl-6-(4-hydroxypiperidin-1-yl)pyridin-2-yl)thio)methyl) benzyl)acetamide (500 mg, 1.101 mmol) and DMAP (135 mg, 1.101 mmol) were added at 0° C. and the reaction mixture was stirred at room temperature for 1 hour. The reaction mixture was quenched with ice-cold water (100 mL) and extracted with ethyl acetate (2×100 mL). The combined organic layers were dried over anhydrous Na$_2$SO$_4$, filtered and evaporated. The crude product was purified by silica gel column chromatography (100-200 mesh, eluted with 20% ethyl acetate in hexane) to afford (S)-1-(6-((4-(acetamidomethyl)benzyl)thio)-3,5-dicyano-4-ethylpyridin-2-yl)piperidin-4-yl 2-((tert-butoxycarbonyl)amino)-3-methylbutanoate (450 mg, 61% yield) as a light yellow solid. LCMS m/z=649.4 [M+H]$^+$.

Step 4: (S)-1-(6-((4-(Acetamidomethyl)benzyl)thio)-3,5-dicyano-4-ethylpyridin-2-yl) piperidin-4-yl 2-amino-3-methylbutanoate

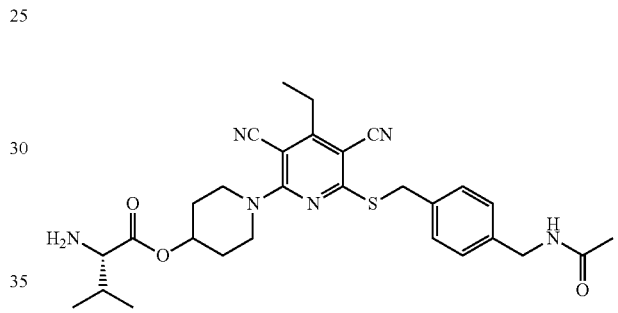

To a stirred solution of (S)-1-(6-((4-(acetamidomethyl)benzyl)thio)-3,5-dicyano-4-ethylpyridin-2-yl)piperidin-4-yl 2-((tert-butoxycarbonyl)amino)-3-methylbutanoate (450 mg, 0.666 mmol) in 1,4-dioxane (5 mL) was added HCl (4 M in 1,4-dioxane, 5 mL, 20 mmol) at 0° C. and then the reaction mixture was stirred at room temperature for 45 minutes. The reaction mixture was concentrated under reduced pressure and the crude was purified by prep-HPLC to afford (S)-1-(6-((4-(acetamidomethyl)benzyl)thio)-3,5-dicyano-4-ethylpyridin-2-yl)piperidin-4-yl 2-amino-3-methylbutanoate (135 mg, 36% yield) as a white solid. LCMS m/z=549.2 [M+H]$^+$. $^1$H NMR (400 MHz, DMSO-d$_6$) δ ppm 8.32-8.23 (m, 1H), 7.35 (d, J=8.11 Hz, 2H), 7.20 (d, J=8.11 Hz, 2H), 5.11-4.97 (m, 1H), 4.47 (s, 2H), 4.21 (d, J=5.92 Hz, 2H), 4.11-3.98 (m, 2H), 3.85-3.71 (m, 2H), 3.13

(d, J=5.48 Hz, 1H), 2.77 (q, J=7.23 Hz, 2H), 1.99 (br dd, J=12.93, 3.51 Hz, 2H), 1.93-1.81 (m, 4H), 1.69 (br d, J=3.07 Hz, 4H), 1.22 (t, J=7.56 Hz, 3H), 0.87 (dd, J=19.07, 6.80 Hz, 6H).

Example 290

N-(1-(6-((4-(Acetamidomethyl)benzyl)thio)-3,5-dicyano-4-ethylpyridin-2-yl)piperidin-4-yl)acetamide Step 1: tert-Butyl (1-(6-((4-(acetamidomethyl)benzyl)thio)-3,5-dicyano-4-ethylpyridin-2-yl)piperidin-4-yl) carbamate

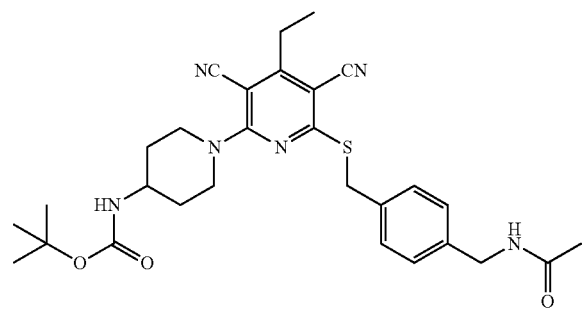 [SMILES: CCc1c(C#N)c(SCc2ccc(CNC(C)=O)cc2)nc(N2CCC(NC(=O)OC(C)(C)C)CC2)c1C#N]

To a suspension of 2,6-dichloro-4-ethylpyridine-3,5-dicarbonitrile (synthesis described in example 3, step 2, 100 mg, 0.442 mmol) in ethanol (1 mL) at −20° C. was added a solution of tert-butyl piperidin-4-ylcarbamate (97 mg, 0.487 mmol) in ethanol (1 mL). The reaction mixture was then stirred at −20° C. for 1 hour. To the reaction mixture was then added potassium ethanethioate (76 mg, 0.664 mmol) and Et₃N (0.154 mL, 1.106 mmol). The heterogeneous reaction mixture was then warmed to 20° C. and stirred at the same temperature overnight. To the reaction mixture was added N-(4-(bromomethyl)benzyl)acetamide (107 mg, 0.442 mmol). The reaction was continued stirring at 20° C. After stirring for 2.5 hours, the reaction mixture was filtered, the solid was washed and discarded. The filtrate was concentrated and the resulting material was purified by reverse phase HPLC (Gilson, 30 mm×50 mm Gemini Column, NH₄OH modifier) to obtain tert-butyl (1-(6-((4-(acetamidomethyl)benzyl)thio)-3,5-dicyano-4-ethylpyridin-2-yl)piperidin-4-yl)carbamate (95 mg, 0.173 mmol, 39% yield). LCMS m/z=545.4 [M+Na]⁺.

Step 2: N-(4-(((6-(4-aminopiperidin-1-yl)-3,5-dicyano-4-ethylpyridin-2-yl) thio)methyl)benzyl)acetamide

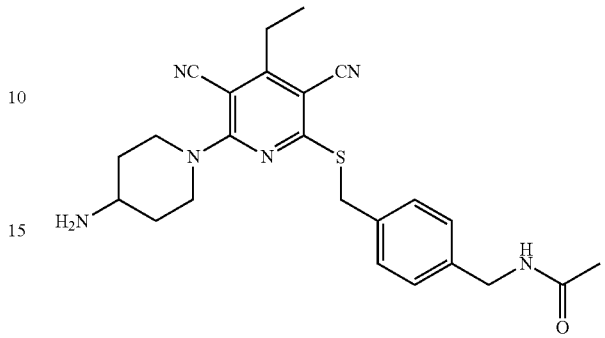

A suspension of tert-butyl (1-(6-((4-(acetamidomethyl)benzyl)thio)-3,5-dicyano-4-ethylpyridin-2-yl)piperidin-4-yl)carbamate (78 mg, 0.142 mmol) in a solution of 4 M HCl (2000 μl, 8.0 mmol) in dioxane at room temperature was stirred at room temperature for 1.5 hours, then the reaction mixture was then concentrated. The resulting material was suspended in MeOH, and free based with isopropylamine, A-CN was required to resolubilize the material for purification. This mixture was purified by reverse phase HPLC (Gilson, 30 mm×50 mm Gemini Column, NH₄OH modifier) to yield N-(4-(((6-(4-aminopiperidin-1-yl)-3,5-dicyano-4-ethylpyridin-2-yl)thio)methyl)benzyl)acetamide (59 mg) as a white solid. LCMS m/z=449.5 [M+H]⁺.

Step 3: N-(1-(6-((4-(Acetamidomethyl)benzyl)thio)-3,5-dicyano-4-ethylpyridin-2-yl)piperidin-4-yl)acetamide

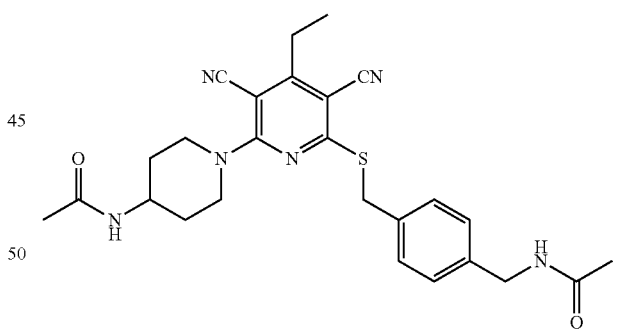

To a solution of N-(4-(((6-(4-aminopiperidin-1-yl)-3,5-dicyano-4-ethylpyridin-2-yl)thio)methyl)benzyl)acetamide (20 mg, 0.045 mmol) and DIEA (8.57 μl, 0.049 mmol) in chloroform (1 mL) at room temperature was added acetic anhydride (4.63 μl, 0.049 mmol). The reaction mixture was then stirred at room temperature for 2 hours. The reaction mixture was then concentrated by rotovap. The resulting pale yellow oil was purified by reverse phase HPLC to obtain N-(1-(6-((4-(acetamidomethyl)benzyl)thio)-3,5-dicyano-4-ethylpyridin-2-yl)piperidin-4-yl)acetamide (19 mg) as a white solid. LCMS m/z=491.5 [M+H]⁺. ¹H NMR (400 MHz, DMSO-d₆) δ ppm 8.34 (t, J=5.83 Hz, 1H), 7.90 (d, J=7.60 Hz, 1H), 7.34-7.38 (m, J=8.11 Hz, 2H), 7.19-7.23 (m, J=8.11 Hz, 2H), 4.47 (s, 2H), 4.40 (d, J=13.18 Hz, 2H), 4.21 (d, J=5.83 Hz, 2H), 3.90 (dd, J=3.55, 7.35 Hz, 1H), 2.77 (q, J=7.60 Hz, 2H), 1.87-1.93 (m, 2H), 1.86 (s, 3H), 1.81 (s, 3H), 1.37-1.50 (m, 2H), 1.21 (t, J=7.60 Hz, 3H). Two protons not observed.

Example 291

2-(4-(((3,5-Dicyano-6-(dimethylamino)-4-ethylpyridin-2-yl)thio)methyl)phenyl)-N-(2-hydroxyethyl)acetamide Step 1: (2-(4-(((3,5-Dicyano-6-(dimethylamino)-4-ethylpyridin-2-yl)thio)methyl)phenyl)acetic acid

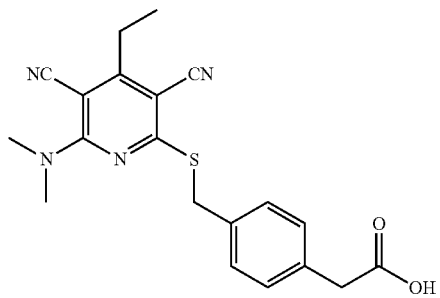 [SMILES: CCc1c(C#N)c(SCc2ccc(CC(=O)O)cc2)nc(N(C)C)c1C#N]

To a suspension of 2-(dimethylamino)-4-ethyl-6-mercaptopyridine-3,5-dicarbonitrile (synthesis described in example 92, step 3, 232 mg, 0.999 mmol) and Et$_3$N (0.139 mL, 0.999 mmol) in chloroform (1 mL) at 0° C. was added a solution of 2-(4-(bromomethyl)phenyl)acetic acid (229 mg, 0.999 mmol) in chloroform (4.0 mL). The reaction mixture was then stirred at 0° C. overnight. The reaction mixture was warmed to room temperature, and concentrated. The crude was purified by reverse phase HPLC (Gilson, 30 mm Gemini Column, NH$_4$OH modifier) to obtain (2-(4-(((3, 5-dicyano-6-(dimethylamino)-4-ethylpyridin-2-yl)thio)methyl)phenyl)acetic acid (246 mg) as a white solid LCMS m/z=381.2 [M+H]$^+$.

Step 2: 2-(4-(((3,5-Dicyano-6-(dimethylamino)-4-ethylpyridin-2-yl)thio)methyl)phenyl)-N-(2-hydroxyethyl)acetamide

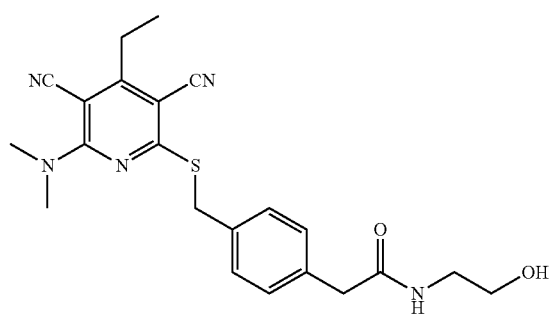 [SMILES: CCc1c(C#N)c(SCc2ccc(CC(=O)NCCO)cc2)nc(N(C)C)c1C#N]

To a solution of (2-(4-(((3,5-dicyano-6-(dimethylamino)-4-ethylpyridin-2-yl)thio)methyl)phenyl)acetic acid (67 mg, 0.176 mmol) in N,N-dimethylformamide (1.5 mL) at room temperature was added HATU (67 mg, 0.176 mmol). The reaction mixture was then stirred at room temperature for 30 minutes at which time the ethanolamine (0.021 mL, 0.352 mmol) and Et$_3$N (0.025 mL, 0.176 mmol) were added. The reaction mixture was then stirred at 40° C. overnight then reaction mixtures were cooled to room temperature, filtered, and purified by reverse phase HPLC (Gilson, 30 mm×50 mm Gemini Column, NH$_4$OH modifier) to obtain 2-(4-(((3,5-dicyano-6-(dimethylamino)-4-ethylpyridin-2-yl)thio)methyl)phenyl)-N-(2-hydroxyethyl)acetamide (54 mg) as a white solid. LCMS m/z=424.4 [M+H]$^+$. $^1$H NMR (400 MHz, DMSO-d$_6$) δ ppm 8.07 (t, J=5.45 Hz, 1H), 7.31-7.35 (m, J=8.11 Hz, 2H), 7.19-7.23 (m, J=8.11 Hz, 2H), 4.69 (t, J=5.20 Hz, 1H), 4.49 (s, 2H), 3.36-3.42 (m, 4H), 3.10 (q, J=5.91 Hz, 2H), 2.76 (q, J=7.60 Hz, 2H), 1.21 (t, J=7.60 Hz, 3H). Six protons not observed.

Example 292

4-(((3,5-Dicyano-6-(dimethylamino)-4-ethylpyridin-2-yl)thio)methyl)-N-(2-hydroxyethyl)benzamide Step 1: 4-(((3,5-Dicyano-6-(dimethylamino)-4-ethylpyridin-2-yl)thio)methyl)benzoic acid

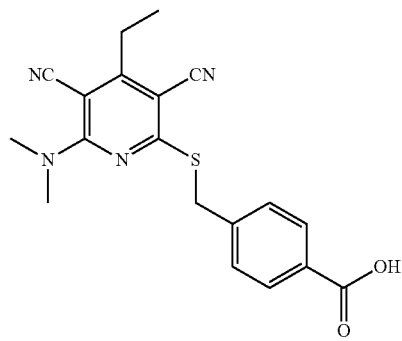 [SMILES: CCc1c(C#N)c(SCc2ccc(C(=O)O)cc2)nc(N(C)C)c1C#N]

To a suspension of 2-(dimethylamino)-4-ethyl-6-mercaptopyridine-3,5-dicarbonitrile (synthesis described in example 92, step 3, 232 mg, 0.999 mmol) and Et$_3$N (0.139 mL, 0.999 mmol) in chloroform (1 mL) at 0° C. was added a solution of 4-(bromomethyl)benzoic acid (215 mg, 0.999 mmol) in chloroform (4.0 mL). The reaction mixture was then stirred at 0° C. overnight. After stirring overnight at 0° C., the reaction mixture was warmed to room temperature, and concentrated. The crude was purified by reverse phase HPLC (Gilson, 30 mm Gemini Column, NH$_4$OH modifier) to obtain 4-(((3,5-dicyano-6-(dimethylamino)-4-ethylpyridin-2-yl)thio)methyl)benzoic acid (331 mg) as a sticky white solid. LCMS m/z=367.2 [M+H]$^+$.

Step 2: 4-(((3,5-Dicyano-6-(dimethylamino)-4-ethylpyridin-2-yl)thio)methyl)-N-(2-hydroxyethyl)benzamide

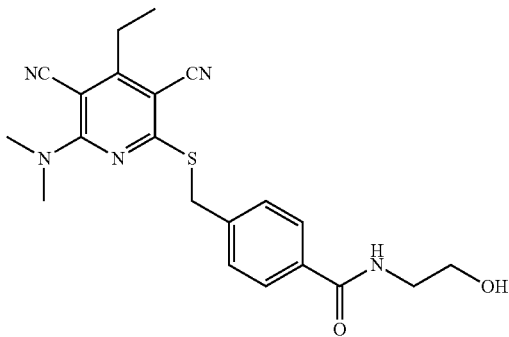 [SMILES: CCc1c(C#N)c(SCc2ccc(C(=O)NCCO)cc2)nc(N(C)C)c1C#N]

To a solution of 4-(((3,5-dicyano-6-(dimethylamino)-4-ethylpyridin-2-yl)thio)methyl)benzoic acid (65 mg, 0.177 mmol)) in N,N-dimethylformamide (1.5 mL) at room temperature was added HATU (67 mg, 0.176 mmol). The reaction mixture was then stirred at room temperature for 30 minutes at which time the ethanolamine (0.021 mL, 0.352 mmol) and Et$_3$N (0.025 mL, 0.176 mmol) were added. The reaction mixture was then stirred at 40° C. overnight then reaction mixtures were cooled to room temperature, filtered, and purified by reverse phase HPLC (Gilson, 30 mm×50 mm Gemini Column, NH$_4$OH modifier) to obtain 4-(((3,5-dicyano-6-(dimethylamino)-4-ethylpyridin-2-yl)thio)methyl)-N-(2-hydroxyethyl)benzamide (47 mg) as a white solid. LCMS m/z=410.3 [M+H]$^+$. $^1$H NMR (400 MHz, DMSO-d$_6$) δ ppm 8.43 (t, J=5.58 Hz, 1H), 7.79-7.83 (m, 2H), 7.47-7.51 (m, J=8.36 Hz, 2H), 4.70-4.78 (m, 1H), 4.57 (s, 2H), 3.50 (q, J=5.49 Hz, 2H), 3.31 (s, 6H), 3.29-3.33 (m, 2H), 2.77 (q, J=7.60 Hz, 2H), 1.21 (t, J=7.60 Hz, 3H)

Example 293

2-((3-Cyano-4-ethyl-5-methyl-6-(piperazin-1-yl)pyridin-2-yl)thio)-2-phenylacetamide

Step 1: 4-Ethyl-2,6-dihydroxy-5-methylnicotinonitrile

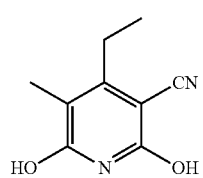

To a solution of ethyl 2-methyl-3-oxopentanoate (5 g, 31.6 mmol) and 2-cyanoacetamide (2.66 g, 31.6 mmol) in methanol (50 mL) was added a solution of KOH (1.951 g, 34.8 mmol) in 50 mL MeOH. The mixture was stirred at reflux overnight. The mixture was filtered. The solid was dissolved in 50 mL hot water, then adjusted pH with concentrated HCl to pH 2, then filtered and dried in vacuum to give the desired product 4-ethyl-2,6-dihydroxy-5-methylnicotinonitrile (1.25 g, 7.02 mmol, 22.19% yield) as a white solid. $^1$H NMR (400 MHz, DMSO) δ 11.20 (s, 2H), 2.62 (q, J=8 Hz, 2H), 1.95 (s, 3H), 1.12 (t, J=8 Hz, 3H).

Step 2: 2,6-Dichloro-4-ethyl-5-methylnicotinonitrile

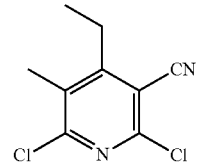

A solution of 4-ethyl-2,6-dihydroxy-5-methylnicotinonitrile (2.5 g, 14.03 mmol) in phosphoryl trichloride (15 mL) was stirred at 150° C. overnight, then concentrated in vacuo. The residue was diluted with DCM (50 mL), washed with saturated aqueous NH$_4$Cl, brine (50 mL), dried over Na$_2$SO$_4$, filtered and dried in vacuum to afford 2,6-dichloro-4-ethyl-5-methylnicotinonitrile (650 mg, 3.02 mmol) as a yellow solid. $^1$H NMR (400 MHz, CDCl$_3$) δ ppm 2.97 (q, J=7.6 Hz, 2H), 2.43 (s, 3H), 1.29 (t, J=7.6 Hz, 3H).

Step 3: tert-Butyl 4-(6-chloro-5-cyano-4-ethyl-3-methylpyridin-2-yl)piperazine-1-carboxylate

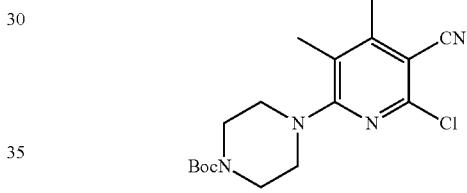

To a solution of 2,6-dichloro-4-ethyl-5-methylnicotinonitrile (440 mg, 2.05 mmol) in acetonitrile (20 mL) was added tert-butyl piperazine-1-carboxylate (381 mg, 2.05 mmol) and triethylamine (0.570 mL, 4.09 mmol).The mixture was stirred at 120° C. for overnight in a sealed tube. The mixture was concentrated in vacuo and the residue was purified by Flash column chromatography (petroleum ether:EtOAc=4:1) to afford tert-butyl 4-(6-chloro-5-cyano-4-ethyl-3-methylpyridin-2-yl)piperazine-1-carboxylate (560 mg, 1.54 mmol, 75% yield) as a yellow solid. LCMS m/z=387.0 [M+Na]$^+$.

Step 4: tert-Butyl-4-(6-((2-amino-2-oxo-1-phenylethyl)thio)-5-cyano-4-ethyl-3-methylpyridin-2-yl)piperazine-1-carboxylate

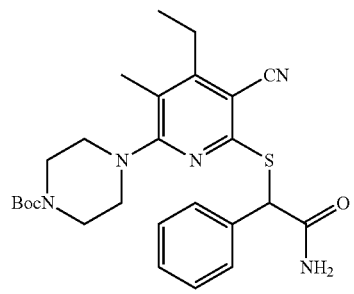 [SMILES: CCc1c(C)c(N2CCN(C(=O)OC(C)(C)C)CC2)nc(SC(C(N)=O)c2ccccc2)c1C#N]

To a solution of tert-butyl 4-(6-chloro-5-cyano-4-ethyl-3-methylpyridin-2-yl)piperazine-1-carboxylate (500 mg, 1.37 mmol) in N,N-dimethylformamide (15 mL) was added 2-mercapto-2-phenylacetamide (synthesis described in example 276 step 1, 687 mg, 4.11 mmol), KI (455 mg, 2.74 mmol) and triethylamine (0.573 mL, 4.11 mmol). The mixture was stirred at 60° C. for 1.5 hour under nitrogen in a microwave reactor, then concentrated in vacuo. The residue was dissolved with ethyl acetate (100 mL), washed with brine (100 mL×2), dried over Na$_2$SO$_4$, filtered and evaporated in vacuum. The residue was purified by Flash column chromatography (petroleum ether:EtOAc=1:1) to afford tert-butyl-4-(6-((2-amino-2-oxo-1-phenylethyl)thio)-5-cyano-4-ethyl-3-methylpyridin-2-yl)piperazine-1-carboxylate (160 mg, 0.32 mmol, 24% yield). LCMS: m/z=496.2 [M+H]$^+$.

Step 5: 2-((3-Cyano-4-ethyl-5-methyl-6-(piperazin-1-yl)pyridin-2-yl)thio)-2-phenylacetamide

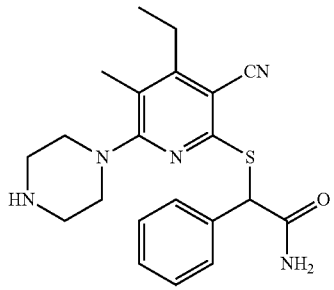 [SMILES: CCc1c(C)c(N2CCNCC2)nc(SC(C(N)=O)c2ccccc2)c1C#N]

To a solution of tert-butyl 4-(6-((2-amino-2-oxo-1-phenylethyl)thio)-5-cyano-4-ethyl-3-methylpyridin-2-yl)piperazine-1-carboxylate (120 mg, 0.24 mmol) in dichloromethane (20 mL) was added trifluoroacetic acid (1 mL, 12.98 mmol). The mixture was stirred at room temperature for 2 hours. The mixture was concentrated in vacuo and the residue was dissolved with ethyl acetate (100 mL), washed with saturated aqueous NaHCO$_3$ (50 mL), brine (50 mL×2), dried over Na$_2$SO$_4$, filtered and concentrated in vacuo. The residue was purified by silica gel column (DCM:MeOH=20:1-10:1) to afford 2-((3-cyano-4-ethyl-5-methyl-6-(piperazin-1-yl)pyridin-2-yl)thio)-2-phenylacetamide (20 mg, 0.051 mmol, 21% yield) as a yellow solid. LCMS m/z=396.3 [M+H]$^+$. $^1$H NMR (400 MHz, DMSO-d$_6$) δ ppm δ 7.88 (b, 1H), 7.53 (m, 2H), 7.40-7.28 (m, 3H), 7.25 (b, 1H), 5.59 (s, 1H), 3.51 (s, 1H), 3.25-3.08 (m, 4H), 2.81 (m, 4H), 2.69-2.63 (m, 2H), 2.12 (s, 3H), 1.11 (t, J=7.6 Hz, 3H).

Example 294

2-((4-(1H-Imidazol-1-yl)benzyl)thio)-4-ethyl-6-(4-methyl-1,4-diazepan-1-yl)pyridine-3,5-dicarbonitrile Step 1: 1-(4-(Chloromethyl) phenyl)-1H-imidazole

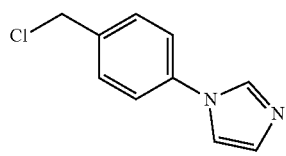 [SMILES: ClCc1ccc(-n2ccnc2)cc1]

To a solution of (4-(1H-imidazol-1-yl)phenyl)methanol (100 mg, 0.574 mmol), DIEA (0.110 mL, 0.631 mmol), and DMAP (7.01 mg, 0.057 mmol) in dichloromethane (2.5 mL) at 20° C. was added methanesulfonic anhydride (110 mg, 0.631 mmol). The reaction mixture was then warmed to 20° C. and stirred at the same temp for 3 hours at which time the reaction mixture was diluted with DCM and washed with 1N HCl (2×), sat. brine (1×), and then water. The aqueous layer was concentrated to obtain crude1-(4-(chloromethyl)phenyl)-1H-imidazole (328 mg) as an oil-solid mixture. LCMS m/z=193.1 [M+H]$^+$.

Step 2: 2-((4-(1H-Imidazol-1-yl)benzyl)thio)-4-ethyl-6-(4-methyl-1,4-diazepan-1-yl)pyridine-3,5-dicarbonitrile

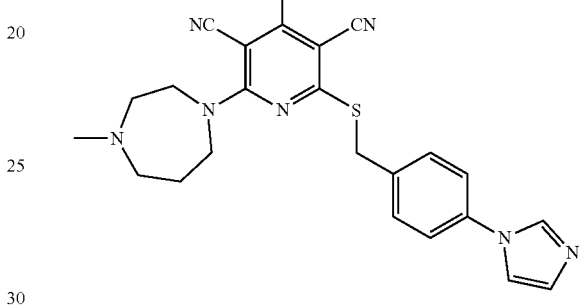

To a solution of 4-ethyl-2-mercapto-6-(4-methyl-1,4-diazepan-1-yl)pyridine-3,5-dicarbonitrile (synthesis described in example 69, step 1, 104 mg, 0.344 mmol) and Et$_3$N (0.060 mL, 0.430 mmol) in N,N-dimethylformamide (3 mL) at room temperature was added crude 1-(4-(chloromethyl)phenyl)-1H-imidazole (83 mg). The reaction mixture was then stirred at room temperature for 2 hours. The reaction mixture was filtered and purified by reverse phase HPLC (Gilson, 30 mm Gemini Column, NH$_4$OH modifier) to obtain 2-((4-(1H-imidazol-1-yl)benzyl)thio)-4-ethyl-6-(4-methyl-1,4-diazepan-1-yl)pyridine-3,5-dicarbonitrile (38 mg) as a light beige solid. LCMS m/z=458.3 [M+H]$^+$. $^1$H NMR (400 MHz, DMSO-d$_6$) δ ppm 8.25 (t, J=1.14 Hz, 1H), 7.74 (t, J=1.39 Hz, 1H), 7.61-7.66 (m, 2H), 7.52-7.56 (m, 2H), 7.09-7.12 (m, 1H), 4.56 (s, 2H), 3.84-3.93 (m, 4H), 2.79 (q, J=7.60 Hz, 2H), 2.59-2.64 (m, 2H), 2.45-2.49 (m, 2H), 2.21 (s, 3H), 1.89-1.97 (m, 2H), 1.23 (t, J=7.60 Hz, 3H)

Example 295

2-((4-Cyano-3-methylbenzyl)thio)-4-ethyl-6-(4-methyl-1,4-diazepan-1-yl)pyridine-3,5-dicarbonitrile

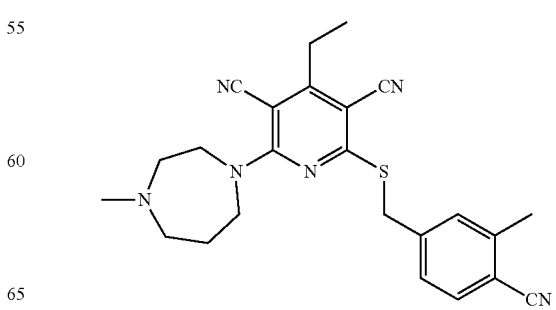

To a suspension of 2,6-dichloro-4-ethylpyridine-3,5-dicarbonitrile (synthesis described in example 3, step 2, 300 mg, 1.327 mmol) in ethanol (3 mL) at −20° C. was added a solution of 1-methyl-1,4-diazepane (0.173 mL, 1.393 mmol) in ethanol (5 mL). The reaction mixture was then stirred at −20° C. for 15 minutes. To the reaction mixture was then added potassium thioacetate (227 mg, 1.991 mmol) and Et$_3$N (0.647 mL, 4.64 mmol). The heterogeneous reaction mixture was then warmed to 40° C. and stirred at the same temperature overnight. To the reaction mixture was added 4-(bromomethyl)-2-methylbenzonitrile (558 mg, 2.65 mmol). The reaction was continued stirring at 40° C. After stirring for 1.5 hours at 40° C. The reaction mixture was cooled to room temperature and concentrated. The crude was initially purified by normal phase chromatography (Biotage Isolera, 100 g SNAP ULTRA column, hexanes/EtOAc, flushed with DCM/MeOH) then repurified by reverse phase HPLC (Gilson, 30 mm×50 mm Gemini Column, NH$_4$OH modifier) to yield 2-((4-cyano-3-methylbenzyl)thio)-4-ethyl-6-(4-methyl-1,4-diazepan-1-yl)pyridine-3,5-dicarbonitrile (179 mg) as a yellow oil. LCMS m/z=431.4 [M+H]$^+$. $^1$H NMR (400 MHz, DMSO-d$_6$) δ ppm 7.74 (d, J=8.11 Hz, 1H), 7.50 (s, 1H), 7.38-7.43 (m, 1H), 4.55 (s, 2H), 3.77-3.88 (m, 4H), 2.78 (q, J=7.60 Hz, 2H), 2.47 (s, 3H), 2.42-2.46 (m, 2H), 2.21 (s, 3H), 1.86-1.93 (m, 2H), 1.22 (t, J=7.60 Hz, 3H). Two protons not observed.

Example 296 tert-Butyl (4-(((3,5-dicyano-4-ethyl-6-(4-methyl-1,4-diazepan-1-yl)pyridin-2-yl)thio)methyl)phenyl)carbamate

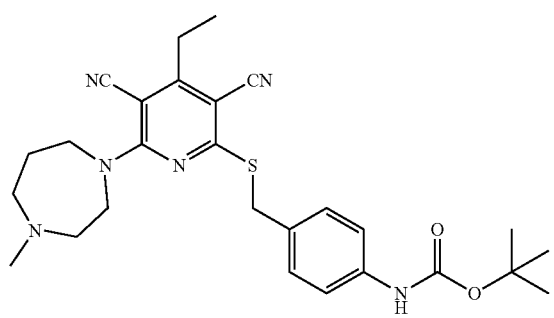 [SMILES: CCc1c(C#N)c(SCc2ccc(NC(=O)OC(C)(C)C)cc2)nc(N2CCCN(C)CC2)c1C#N]

To the solution of 4-ethyl-2-mercapto-6-(4-methyl-1,4-diazepan-1-yl)pyridine-3,5-dicarbonitrile (600 mg, 1.493 mmol) and TEA (0.416 mL, 2.99 mmol) in DMF (5 mL) was added a solution of tert-butyl (4-(bromomethyl)phenyl)carbamate (427 mg, 1.493 mmol) in DMF (2 mL) dropwise. The reaction mixture was stirred at room temperature for 30 minutes. The reaction mixture was diluted with water (30 mL) and the solid was filtered. The solid was purified by Silica(ComiFlash, 24 g column using 0-10% MeOH/DCM) to afford an off-white solid. A portion of this material was purified by RP-HPLC (40-70% acetonitrile/water, 0.1% NH$_4$OH in water) to afford tert-butyl (4-(((3,5-dicyano-4-ethyl-6-(4-methyl-1,4-diazepan-1-yl)pyridin-2-yl)thio)methyl)phenyl)carbamate (10 mg) as an off-white solid. LCMS m/z=507.3 [M+H]$^+$. $^1$H NMR (400 MHz, DMSO-d$_6$) δ ppm 1.19-1.24 (m, 3H), 1.47 (s, 9H), 1.89-1.99 (m, 2H), 2.24 (s, 3H), 2.47 (br. s., 2H), 2.61-2.68 (m, 2H), 2.78 (q, J=7.6 Hz, 2H), 3.85-3.94 (m, 4H), 4.42 (s, 2H), 7.27 (m, J=8.6 Hz, 2H), 7.41 (m, J=8.6 Hz, 2H), 9.38 (s, 1H).

Example 297

2-((4-Aminobenzyl)thio)-4-ethyl-6-(4-methyl-1,4-diazepan-1-yl)pyridine-3,5-dicarbonitrile

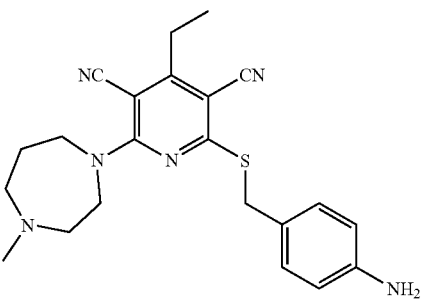

tert-Butyl (4-(((3,5-dicyano-4-ethyl-6-(4-methyl-1,4-diazepan-1-yl)pyridin-2-yl)thio)methyl)phenyl)carbamate (synthesis described in example 296) was treated with DCM (3 mL) and TFA (1.5 mL) for 1 hour, The reaction mixture was concentrated down and basified with NH$_4$OH, then concentrated down and purified by silica column (CombiFlash®, 24 g column using 0-10% MeOH/DCM) to afford 2-((4-aminobenzyl)thio)-4-ethyl-6-(4-methyl-1,4-diazepan-1-yl)pyridine-3,5-dicarbonitrile (278 mg, 0.684 mmol, 46% yield) as an off white solid. LCMS m/z=407.2 [M+H]$^+$. 1H NMR (400 MHz, DMSO-d$_6$) δ ppm 1.22 (t, J=7.6 Hz, 3H), 1.89-2.00 (m, 2H), 2.26 (s, 3H), 2.49 (br. s., 2H), 2.66-2.73 (m, 2H), 2.77 (q, J=7.6 Hz, 2H), 3.88-3.97 (m, 4H), 4.33 (s, 2H), 5.12 (s, 2H), 6.48-6.54 (m, 2H), 7.04 (d, J=8.4 Hz, 2H).

Example 298

N-(4-(((3,5-Dicyano-4-ethyl-6-(4-methyl-1,4-diazepan-1-yl)pyridin-2-yl)thio)methyl)phenyl)acetamide

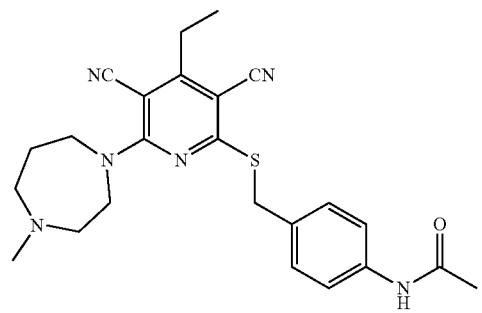 [SMILES: CCc1c(C#N)c(SCc2ccc(NC(C)=O)cc2)nc(N2CCCN(C)CC2)c1C#N]

At 0° C. to the solution of 2-((4-aminobenzyl)thio)-4-ethyl-6-(4-methyl-1,4-diazepan-1-yl)pyridine-3,5-dicarbonitrile (synthesis described in example 297, 60 mg, 0.148 mmol) in THF (2 mL) was added a solution of acetyl chloride (0.014 mL, 0.192 mmol) in THF (0.5 mL) dropwise. The reaction mixture was stirred for 30 minutes. The reaction mixture was concentrated down and purified by RP-HPLC (30-60% acetonitrile/water, 0.1% NH$_4$OH in water) to afford N-(4-(((3,5-dicyano-4-ethyl-6-(4-methyl-1,4-diazepan-1-yl)pyridin-2-yl)thio)methyl)phenyl)acetamide (43 mg, 0.096 mmol, 65% yield) as an off-white solid. LCMS m/z=449.3 [M+H]+. 1H NMR (400 MHz, DMSO-d6) δ ppm 1.22 (t, J=7.6 Hz, 3H), 1.88-1.98 (m, 2H), 2.03 (s, 3H), 2.24 (s, 3H), 2.49-2.46 (m, 2H), 2.59-2.70 (m, 2H), 2.78 (q, J=7.6 Hz, 2H), 3.84-3.95 (m, 4H), 4.44 (s, 2H), 7.31 (m, J=8.6 Hz, 2H), 7.53 (m, J=8.6 Hz, 2H), 9.97 (s, 1H).

Example 299

N-(4-(((3,5-Dicyano-4-ethyl-6-(4-methyl-1,4-diazepan-1-yl)pyridin-2-yl)thio)methyl)phenyl) methanesulfonamide

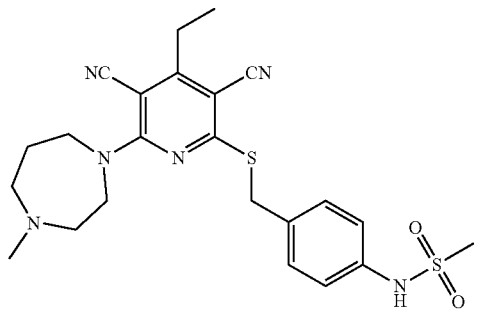

At 0° C., to the solution of 2-((4-aminobenzyl)thio)-4-ethyl-6-(4-methyl-1,4-diazepan-1-yl) pyridine-3,5-dicarbonitrile (synthesis described in example 297, 60 mg, 0.148 mmol) and TEA (0.062 mL, 0.443 mmol) in THF (3 mL) was added a solution of mesyl-Cl (0.017 mL, 0.221 mmol) in THF (0.5 mL) dropwise. The reaction mixture was stirred for 30 minutes. The reaction mixture was concentrated down and purified by RP-HPLC (20-60% acetonitrile/water, 0.1% NH4OH in water) to afford N-(4-(((3,5-dicyano-4-ethyl-6-(4-methyl-1,4-diazepan-1-yl)pyridin-2-yl)thio)methyl)phenyl) methanesulfonamide (38 mg, 0.078 mmol, 53% yield) as a white solid. LCMS m/z=485.3 [M+H]+. 1H NMR (400 MHz, DMSO-d6) δ ppm 1.22 (t, J=7.6 Hz, 3H), 1.85-1.99 (m, 2H), 2.24 (s, 3H), 2.49-2.46 (m, 2H), 2.63-2.68 (m, 2H), 2.78 (q, J=7.6 Hz, 2H), 2.96 (s, 3H), 3.83-3.95 6 (m, 4H), 4.45 (s, 2H), 7.12-7.17 (m, 2H), 7.35 (d, J=8.6 Hz, 2H). One proton not observed.

Example 300

2-(((6-Aminopyridin-3-yl)methyl)thio)-4-ethyl-6-(4-methyl-1,4-diazepan-1-yl)pyridine-3,5-dicarbonitrile

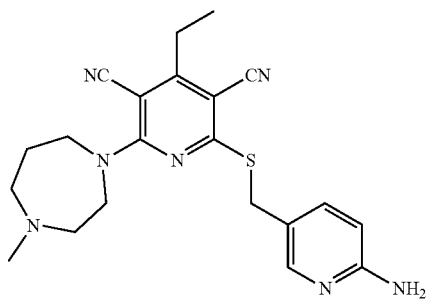 [SMILES: CCc1c(C#N)c(SCc2ccc(N)nc2)nc(N2CCCN(C)CC2)c1C#N]

At 0° C., to the solution of 4-ethyl-2-mercapto-6-(4-methyl-1,4-diazepan-1-yl)pyridine-3,5-dicarbonitrile (761 mg, 2.020 mmol) and TEA (0.563 mL, 4.04 mmol) in DMF (6 mL) was added a slurry solution of tert-butyl (5-(bromomethyl)pyridin-2-yl)carbamate (580 mg, 2.020 mmol) in DMF (5 mL) slowly. The reaction mixture was gradually brought to room temperature and stirred overnight. The reaction mixture was diluted with water, and extracted with DCM (2×). The combined organics were washed with water and brine, dried over Na2SO4, concentrated down and purified with silica (CombiFlash®, 40 g column eluting with 100% hexane, then 0-10% MeOH/DCM) to afford a light yellow solid. To the solid in DCM (3 mL) was added TFA (0.156 mL, 2.020 mmol). The reaction mixture was stirred for 4 hours, then concentrated down and basified with aq. NH4OH (5 mL), then extracted with EtOAc (3×). The combined organics was washed with water and brine, dried over Na2SO4, concentrated down to afford 2-(((6-aminopyridin-3-yl)methyl)thio)-4-ethyl-6-(4-methyl-1,4-diazepan-1-yl)pyridine-3,5-dicarbonitrile (355 mg, 0.871 mmol, 43% yield) as a light brown solid. LCMS m/z=408.2 [M+H]+. 1H NMR (400 MHz, DMSO-d6) δ ppm 1.22 (t, J=7.6 Hz, 3H), 1.92-2.00 (m, 2H), 2.27 (s, 3H), 2.51-2.57 (m, 2H), 2.70 (br. s., 2H), 2.78 (q, J=7.6 Hz, 2H), 3.87-3.97 (m, 4H), 4.33 (s, 2H), 5.98 (s, 2H), 6.37-6.45 (m, 1H), 7.38 (dd, J=8.4, 2.5 Hz, 1H), 7.92 (d, J=2.0 Hz, 1H).

Example 301

N-(4-(((3,5-Dicyano-4-ethyl-6-(4-methyl-1,4-diazepan-1-yl)pyridin-2-yl)thio)methyl)phenyl)-2-hydroxyacetamide

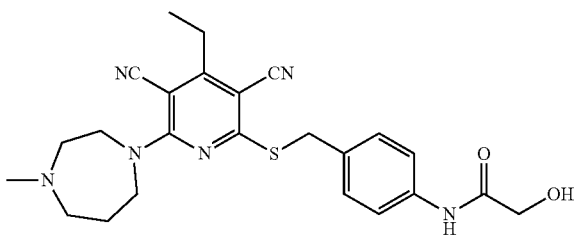 [SMILES: CCc1c(C#N)c(SCc2ccc(NC(=O)CO)cc2)nc(N2CCCN(C)CC2)c1C#N]

A solution of 2-((4-aminobenzyl)thio)-4-ethyl-6-(4-methyl-1,4-diazepan-1-yl)pyridine-3,5-dicarbonitrile (synthesis described in example 297, 55 mg, 0.135 mmol), 2-hydroxyacetic acid (30.9 mg, 0.406 mmol), EDC (38.9 mg, 0.203 mmol), 1-hydroxy-7-azabenzotriazole (27.6 mg, 0.203 mmol) and N-methylmorpholine (0.045 mL, 0.406 mmol) in DMF (3 mL) was stirred at room temperature overnight. The reaction mixture was purified by RP-HPLC (20-50% acetonitrile/water, 0.1% NH4OH in water) to afford N-(4-(((3,5-dicyano-4-ethyl-6-(4-methyl-1,4-diazepan-1-yl) pyridin-2-yl)thio)methyl)phenyl)-2-hydroxyacetamide (20 mg, 0.043 mmol, 32% yield) as a white solid. LCMS m/z=465.3 [M+H]+. 1H NMR (400 MHz, DMSO-d6) δ ppm 1.22 (t, J=7.6 Hz, 3H), 1.84-2.02 (m, 2H), 2.24 (s, 3H), 2.49-2.46 (m, 2H), 2.60-2.70 (m, 2H), 2.78 (q, J=7.6 Hz, 2H), 3.84-3.94 (m, 4H), 3.98 (d, J=3.8 Hz, 2H), 4.45 (s, 2H), 5.68 (br. s., 1H), 7.33 (m, J=8.6 Hz, 2H), 7.66 (m, J=8.6 Hz, 2H), 9.70 (s, 1H).

Example 302

2-Amino-N-(4-(((3,5-dicyano-4-ethyl-6-(4-methyl-1,4-diazepan-1-yl)pyridin-2-yl)thio)methyl)phenyl)acetamide

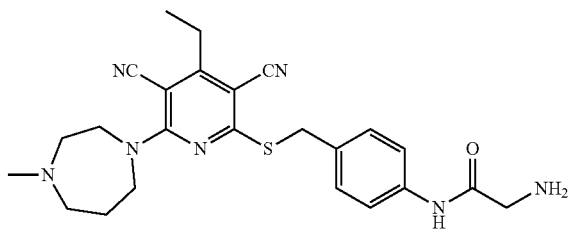 [SMILES: CCc1c(C#N)c(SCc2ccc(NC(=O)CN)cc2)nc(N2CCCN(C)CC2)c1C#N]

A solution of 2-((4-aminobenzyl)thio)-4-ethyl-6-(4-methyl-1,4-diazepan-1-yl) pyridine-3,5-dicarbonitrile (synthesis described in example 297, 55 mg, 0.135 mmol), 2-((tert-butoxycarbonyl) amino) acetic acid (71.1 mg, 0.406 mmol), EDC (38.9 mg, 0.203 mmol), 1-hydroxy-7-azabenzotriazole (27.6 mg, 0.203 mmol) and N-methylmorpholine (0.045 mL, 0.406 mmol) in DMF (2 mL) was stirred at room temperature overnight. The reaction mixture was purified by RP-HPLC (30-70% acetonitrile/water, 0.1% NH$_4$OH in water) to afford a light yellow solid. To the solidin DCM (2 mL) was added TFA (1 mL), stirred for 1 hour. The reaction mixture was concentrated down and basified with TEA and concentrated down again. The residue was purified by RP-HPLC (5-40% acetonitrile/water, 0.1% NH$_4$OH in water) to afford 2-amino-N-(4-(((3,5-dicyano-4-ethyl-6-(4-methyl-1,4-diazepan-1-yl)pyridin-2-yl)thio)methyl)phenyl)acetamide (22 mg, 0.047 mmol, 35% yield) as an off-white solid. LCMS m/z=464.3 [M+H]$^+$. $^1$H NMR (400 MHz, DMSO-d$_6$) δ ppm 1.22 (t, J=7.6 Hz, 3H), 1.88-1.99 (m, 2H), 2.24 (s, 3H), 2.47-2.49 (m, 2H), 2.60-2.69 (m, 2H), 2.78 (q, J=7.6 Hz, 2H), 3.25 (s, 2H), 3.82-6 3.96 (m, 4H), 4.45 (s, 2H), 7.33 (m, J=8.6 Hz, 2H), 7.60 (m, J=8.6 Hz, 2H). Three protons not observed.

Example 303

2-((3,5-Dicyano-4-ethyl-6-(5-methyl-2,5-diazabicyclo[2.2.1]heptan-2-yl)pyridin-2-yl)thio)-2-phenylacetamide Step 1: 2-Chloro-4-ethyl-6-(5-methyl-2,5-diazabicyclo[2.2.1]heptan-2-yl)pyridine-3,5-dicarbonitrile

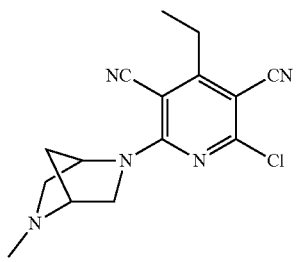 [SMILES: CCc1c(C#N)c(Cl)nc(N2CC3CC2CN3C)c1C#N]

To a stirred solution of 2-methyl-2,5-diazabicyclo[2.2.1]heptane, 2-hydrobromide (974 mg, 3.55 mmol) in dichloromethane (30 mL) was added triethylamine (2.477 mL, 17.77 mmol) and stirred for 10 minutes at room temperature. 2,6-dichloro-4-ethylpyridine-3,5-dicarbonitrile (synthesis described in example 3 step 2, 800 mg, 3.54 mmol) was added to the reaction mixture and stirred at room temperature for 16 hours. The reaction mixture was quenched with water (40 mL) and extracted with DCM (2×50 mL). The combined organic layers were washed with water (40 mL), brine solution (40 mL), dried over anhydrous Na$_2$SO$_4$, filtered and concentrated under reduced pressure to obtain the crude compound. The crude material was purified by silica gel chromatography (100-200 mesh, eluent 3% MeOH in DCM) to afford 2-chloro-4-ethyl-6-(5-methyl-2,5-diazabicyclo[2.2.1]heptan-2-yl)pyridine-3,5-dicarbonitrile (600 mg) as a pale yellow solid. LCMS m/z=302.2 [M+H]$^+$.

Step 2: 2-((3,5-Dicyano-4-ethyl-6-(5-methyl-2,5-diazabicyclo[2.2.1]heptan-2-yl)pyridin-2-yl)thio)-2-phenylacetamide

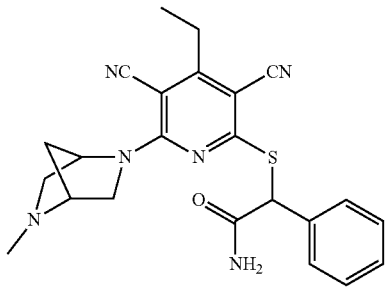 [SMILES: CCc1c(C#N)c(SC(C(N)=O)c2ccccc2)nc(N2CC3CC2CN3C)c1C#N]

To a stirred solution of 2-chloro-4-ethyl-6-(5-methyl-2,5-diazabicyclo[2.2.1]heptan-2-yl)pyridine-3,5-dicarbonitrile (550 mg) in N,N-dimethylformamide (15 mL) was added potassium thioacetate (312 mg, 2.73 mmol) under a nitrogen atmosphere. The resulting reaction mixture was stirred at room temperature for 30 minutes. To the reaction was added potassium carbonate (378 mg, 2.73 mmol) and 2-amino-2-oxo-1-phenylethyl methanesulfonate (synthesis described in example 3 step 5, 418 mg, 1.823 mmol). The resulting reaction mixture was stirred at room temperature for 16 hours. The reaction mixture was diluted with ice cold water (30 mL) and extracted with EtOAc (3×30 mL). The combined organic layers were washed with ice cold water (2×30 mL), brine solution (30 mL), dried over anhydrous Na$_2$SO$_4$, filtered and concentrated under reduced pressure to obtain the crude compound. The crude material was purified by silica gel chromatography (100-200 mesh, eluent: 5% MeOH in DCM) to obtain a brown solid. The solid was washed with diethyl ether, filtered and dried to afford 2-((3,5-dicyano-4-ethyl-6-(5-methyl-2,5-diazabicyclo[2.2.1]heptan-2-yl)pyridin-2-yl)thio)-2-phenylacetamide (335 mg) as a pale brown solid. LCMS m/z=433.2 [M+H]$^+$. $^1$H NMR (400 MHz, CHLOROFORM-d) δ ppm 7.29-7.49 (m, 5H), 6.49-6.65 (m, 1H), 5.41-5.52 (m, 1H), 5.32 (d, J=7.2 Hz, 1H), 5.17 (br s, 1H), 3.86-3.98 (m, 2H), 3.54 (s, 1H), 2.73-3.03 (m, 4H), 2.45 (s, 3H), 2.04 (d, J=10.3 Hz, 1H), 1.83 (d, J=10.3 Hz, 1H), 1.32 (t, J=7.6 Hz, 3H).

Example 304

2-((3,5-Dicyano-4-ethyl-6-(4-(2-(pyrrolidin-1-yl)ethyl)piperazin-1-yl)pyridin-2-yl)thio)-2-phenylacetamide

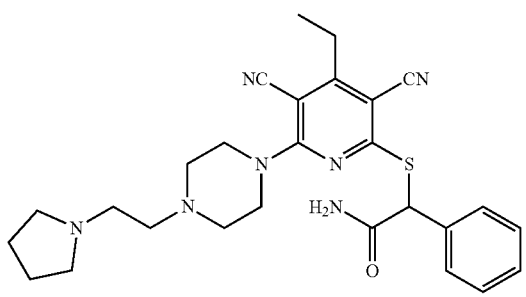 [SMILES: CCc1c(C#N)c(SC(C(N)=O)c2ccccc2)nc(N2CCN(CCN3CCCC3)CC2)c1C#N]

A solution of 2-[(6-bromo-3,5-dicyano-4-ethyl-2-pyridyl)sulfanyl]-2-phenyl-acetamide (synthesis described in example 6, step 1, 15 mg, 0.04 mmol) in THF (1 mL) was treated with 1-[2-(pyrrolidinyl)ethyl]piperazine (0.02 mL, 0.09 mmol), stirred at room temperature for 18 hours, then was loaded onto $SiO_2$ (0.9 g) and chromatographed on $SiO_2$ (4 g RediSep cartridge) eluting with 0-10% MeOH, 0-1% $NH_3$/DCM followed by trituration with $Et_2O$ to give 2-[[3,5-dicyano-4-ethyl-6-[4-(2-pyrrolidin-1-ylethyl)piperazin-1-yl]-2-pyridyl]sulfanyl]-2-phenyl-acetamide (16 mg, 85% yield) as a pale yellow solid. LCMS m/z=504.3 [M+H]$^+$. $^1$H NMR (300 MHz, DMSO-$d_6$) δ ppm 7.91 (s, 1H), 7.55-7.48 (m, 2H), 7.42-7.31 (m, 4H), 5.53 (s, 1H), 3.93-3.78 (m, 4H), 3.34-3.32 (m, 4H), 2.75 (q, J=7.5 Hz, 2H), 2.60-2.54 (m, 2H), 2.48-2.42 (m, 6H), 1.71-1.63 (m, 4H), 1.20 (t, J=7.6 Hz, 3H).

Example 305

2-((3,5-Dicyano-6-(dimethylamino)-4-ethylpyridin-2-yl)thio)-2-phenylacetamide-2-d Step 1: 2-Phenylacetamide-2,2-d2

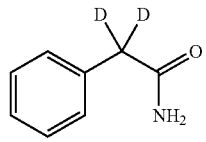 [SMILES: [2H]C([2H])(C(N)=O)c1ccccc1]

A 20-mL microwave vial was charged with 2-phenylacetamide (2 g, 14.80 mmol), $K_2CO_3$ (2.045 g, 14.80 mmol), $D_2O$ (10 mL, 553 mmol). The vial was sealed and heated at 100° C. for 30 minutes in a microwave reactor. LCMS analysis indicated that the reaction was incomplete, so the reaction was heated at 120° C. for 15 minutes in a microwave reactor. LCMS analysis indicated good conversion, with ca. 25% hydrolysis to the acid. The reaction was poured into chloroform (50 mL), separated and the aqueous layer washed with additional chloroform (20 mL). The combined organics were dried over sodium sulfate, filtered, concentrated to afford 2-phenylacetamide-2,2-$d_2$ (1 g) as a white solid. $^1$H NMR analysis indicated 94.5% D incorporation. A 20-mL microwave vial was charged with the white solid above, $K_2CO_3$ (0.256 g, 1.850 mmol), $D_2O$ (10 mL, 553 mmol). The vial was sealed and heated at 120° C. for 15 minutes in a microwave reactor. The reaction was poured into chloroform (50 mL), separated and the organic layer was dried over sodium sulfate, filtered, concentrated to afford 2-phenylacetamide-2,2-$d_2$ (650 mg, 4.74 mmol, 32.0% yield) as a white solid. $^1$H NMR analysis indicated 99.3% D incorporation. LCMS m/z=137.9 [M+H]$^+$.

Step 2: 2-Bromo-2-phenylacetamide-2-d

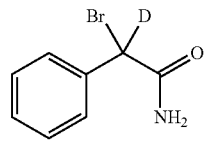

A solution of 2-phenylacetamide-2,2-$d_2$ (400 mg, 2.92 mmol), N-bromosuccinimide (778 mg, 4.37 mmol) in dichloromethane (32 mL) was split between 16×4 mL screw-cap vials, and irradiated with Blue LED light using an Aldrich (ALKIT001) micro photochemical reactor. The reactions were stirred for 75 minutes. LCMS analysis indicated good conversion, so the reactions were combined, washed with water (2×20 mL), then the organic layer was dried over sodium sulfate, filtered, concentrated to afford a residue which was purified by flash chromatography (0-50% EtOAc in hexanes, 25-g column) to afford 2-bromo-2-phenylacetamide-2-d (160 mg, 0.744 mmol, 26% yield) as an orange solid. LCMS m/z=214.8, 216.9 [M+H]$^+$.

Step 3: 2-((3,5-Dicyano-6-(dimethylamino)-4-ethylpyridin-2-yl)thio)-2-phenylacetamide-2-d

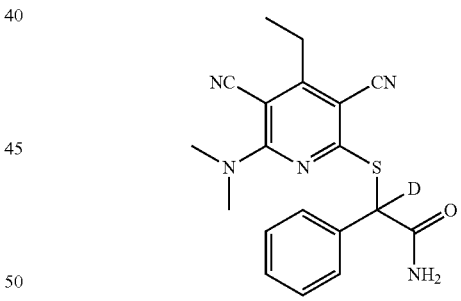

To a solution of 2-bromo-2-phenylacetamide-2-d (46.3 mg, 0.215 mmol), 2-(dimethylamino)-4-ethyl-6-mercaptopyridine-3,5-dicarbonitrile (synthesis described in example 92, step 3, 50 mg, 0.215 mmol) in N,N-dimethylformamide (1 mL) was added triethylamine (0.060 mL, 0.430 mmol). The reaction was stirred at room temperature for seven minutes, then the mixture was poured into $D_2O$ (5 mL), and stirred for 10 minutes, then filtered and washed with additional $D_2O$ (5 mL), dried at the pump for an hour, then in a vacuum oven overnight to afford 70 mg of a grey solid. The grey solid was suspended in $H_2O$ (5 mL) and sonicated and filtered to afford 2-((3,5-dicyano-6-(dimethylamino)-4-ethylpyridin-2-yl)thio)-2-phenylacetamide-2-d (61 mg, 0.166 mmol, 77% yield) as a grey solid. LCMS m/z=367.1 [M+H]$^+$. $^1$H NMR (DMSO-$d_6$) δ ppm 7.90-7.95 (m, 1H), 7.49-7.56 (m, 2H), 7.27-7.43 (m, 4H), 3.34 (s, 6H), 2.76 (d, J=7.6 Hz, 2H), 1.20 (t, J=7.6 Hz, 3H). Six protons not observed.

Example 308

(R)-2-((3,5-Dicyano-6-(dimethylamino)-4-ethylpyridin-2-yl)thio)-2-phenylacetamide-2-d

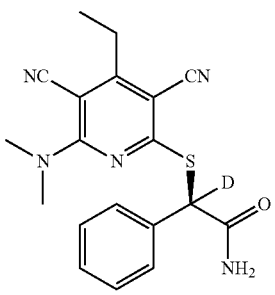 [SMILES: [2H][C@](Sc1nc(N(C)C)c(C#N)c(CC)c1C#N)(C(N)=O)c1ccccc1]

2-((3,5-Dicyano-6-(dimethylamino)-4-ethylpyridin-2-yl)thio)-2-phenylacetamide-2-d (synthesis described in example 305 step 3, ca. 50 mg) was dissolved in EtOH and purified by chiral HPLC (AD-H column, 40:60 Heptane: EtOH) to afford (R)-2-((3,5-dicyano-6-(dimethylamino)-4-ethylpyridin-2-yl)thio)-2-phenylacetamide-2-d (20 mg, 0.055 mmol) as a white solid. Optical rotation=−308 deg (conc=0.117, MeOH). LCMS m/z=367.1 [M+H]$^+$. $^1$H NMR (DMSO-d$_6$) δ ppm 7.93 (s, 1H), 7.49-7.56 (m, 2H), 7.31-7.42 (m, 4H), 3.34 (s, 6H), 2.76 (q, J=7.6 Hz, 2H), 1.16-1.24 (m, 3H). Six protons not observed.

Example 310

2-((6-(4-(4-Bromobenzoyl)piperazin-1-yl)-3,5-dicyano-4-ethylpyridin-2-yl)thio)-2-phenylacetamide

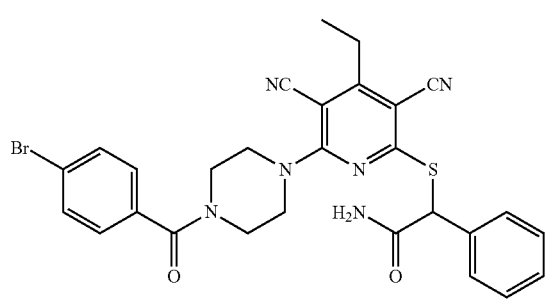 [SMILES: CCc1c(C#N)c(SC(C(N)=O)c2ccccc2)nc(N2CCN(C(=O)c3ccc(Br)cc3)CC2)c1C#N]

A suspension of 2-[(3,5-dicyano-4-ethyl-6-piperazin-1-yl)-2-pyridyl)sulfanyl]-2-phenyl-acetamide (synthesis described in example 55, 18 mg, 0.04 mmol) in DCM (2 mL) was treated with 4-bromobenzoyl chloride (11 mg, 0.05 mmol) in DCM (0.5 mL) to give a solution. Pyridine (0.007 mL, 0.09 mmol) was added at room temperature. After 90 minutes additional 4-bromobenzoyl chloride (3 mg, 0.01 mmol) in DCM (0.13 mL) was added. After another 90 minutes the mixture was diluted with EtOAc (15 mL), washed with 2 M HCl (10 mL), water (10 mL), 2 M NaOH (10 mL), water (10 mL) and brine before drying through a hydrophobic frit. After concentration in vacuo, trituration of the solid with Et$_2$O gave 2-[[6-[4-(4-bromobenzoyl)piperazin-1-yl]-3,5-dicyano-4-ethyl-2-pyridyl]sulfanyl]-2-phenyl-acetamide (24 mg, 92% yield) as a white solid. LCMS m/z=587.1 [M−H]$^-$. $^1$H NMR (300 MHz, DMSO-d$_6$) δ ppm 7.86 (br s, 1H), 7.75-7.65 (m, 2H), 7.54-7.31 (m, 8H), 5.51 (s, 1H), 4.23-3.85 (m, 4H), 3.80-3.64 (m, 2H), 3.62-3.45 (m, 2H), 2.85-2.72 (m, 2H), 1.21 (br t, J=7.5 Hz, 3H).

Example 318

2-((3,5-Dicyano-4-ethyl-6-(4-(2-hydroxyethyl)-1,4-diazepan-1-yl)pyridin-2-yl)thio)-2-phenylacetamide Step 1: tert-Butyl 4-(6-chloro-3,5-dicyano-4-ethylpyridin-2-yl)-1,4-diazepane-1-carboxylate

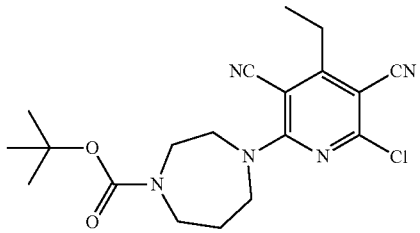 [SMILES: CCc1c(C#N)c(Cl)nc(N2CCCN(C(=O)OC(C)(C)C)CC2)c1C#N]

To a stirred solution of 2,6-dichloro-4-ethylpyridine-3,5-dicarbonitrile (synthesis described in example 3 step 2, 1 g, 4.17 mmol) in dichloromethane (20 mL) was added tert-butyl 1,4-diazepane-1-carboxylate (0.834 g, 4.17 mmol) followed by triethylamine (0.581 mL, 4.17 mmol) at 0° C. The reaction was stirred for 1 hour at room temperature. The reaction mixture was concentrated under reduced pressure, diluted with water (40 mL) and extracted with dichloromethane (2×100 mL). The combined organic layers were dried over anhydrous Na$_2$SO$_4$, filtered and concentrated under reduced pressure to afford tert-butyl 4-(6-chloro-3,5-dicyano-4-ethylpyridin-2-yl)-1,4-diazepane-1-carboxylate (1.2 g) as a brown solid. LCMS m/z=390.3 [M+H]$^+$.

Step 2: tert-Butyl 4-(6-((2-amino-2-oxo-1-phenylethyl)thio)-3,5-dicyano-4-ethylpyridin-2-yl)-1,4-diazepane-1-carboxylate

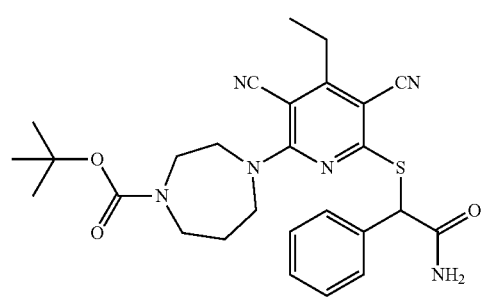 [SMILES: CCc1c(C#N)c(SC(C(N)=O)c2ccccc2)nc(N2CCCN(C(=O)OC(C)(C)C)CC2)c1C#N]

To a solution of tert-butyl 4-(6-chloro-3,5-dicyano-4-ethylpyridin-2-yl)-1,4-diazepane-1-carboxylate (1 g) in N,N-dimethylformamide (20 mL) was added potassium thioacetate (415 mg, 3.63 mmol) and the mixture was stirred for 2 hours at room temperature. Then, potassium carbonate (502 mg, 3.63 mmol) and 2-amino-2-oxo-1-phenylethyl methanesulfonate (synthesis described in example 3 step 5, 604 mg, 2.423 mmol) were added and the reaction mixture was stirred for two hours at room temperature. The reaction mixture was quenched in cold water (10 mL) and extracted with ethyl acetate (2×20 mL). The combined organic layers were dried over anhydrous Na$_2$SO$_4$, filtered and concentrated under reduced pressure to afford tert-butyl 4-(6-((2-amino-2-oxo-1-phenylethyl)thio)-3,5-dicyano-4-ethylpyridin-2-yl)-1,4-diazepane-1-carboxylate (1 g) as a brown solid. LCMS m/z=521.4 [M+H]$^+$.

Step 3: 2-((3,5-Dicyano-6-(1,4-diazepan-1-yl)-4-ethylpyridin-2-yl)thio)-2-phenylacetamide

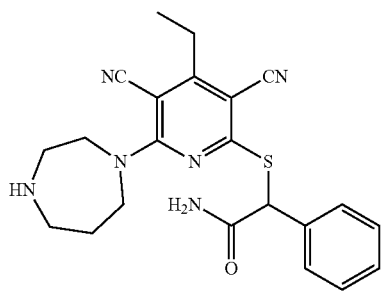 [SMILES: CCc1c(C#N)c(SC(C(N)=O)c2ccccc2)nc(N2CCCNCC2)c1C#N]

To a stirred solution of (tert-butyl 4-(6-((2-amino-2-oxo-1-phenylethyl)thio)-3,5-dicyano-4-ethylpyridin-2-yl)-1,4-diazepane-1-carboxylate (900 mg) in 1,4-dioxane (15 mL) was added HCl (4 M in 1,4-dioxane, 3.45 mL, 13.81 mmol) at 0° C. and the reaction mixture was stirred for 4 hours at 25° C. The reaction mixture was concentrated under reduced pressure and the crude product was triturated with diethyl ether (2×40 mL), filtered and dried under vacuum to afford 2-((3,5-dicyano-6-(1,4-diazepan-1-yl)-4-ethylpyridin-2-yl)thio)-2-phenylacetamide, Hydrochloride (600 mg) as an off-white solid. LCMS m/z=421.4 [M+H]$^+$.

Step 4: 2-((3,5-Dicyano-4-ethyl-6-(4-(2-hydroxyethyl)-1,4-diazepan-1-yl)pyridin-2-yl)thio)-2-phenylacetamide

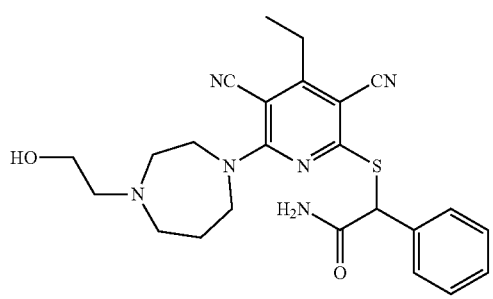 [SMILES: CCc1c(C#N)c(SC(C(N)=O)c2ccccc2)nc(N2CCCN(CCO)CC2)c1C#N]

To a stirred solution of 2-((3,5-dicyano-6-(1,4-diazepan-1-yl)-4-ethylpyridin-2-yl)thio)-2-phenylacetamide, Hydrochloride (300 mg) in dichloromethane (10 mL) was added triethylamine (0.294 mL, 2.107 mmol) followed by 2-bromoethanol (65.8 mg, 0.527 mmol) at 0° C. The reaction mixture was stirred for 2 hours at 25° C. The reaction mixture was concentrated under reduced pressure, then diluted with water (15 mL) and extracted with dichloromethane (2×30 mL). The combined organic layers were dried over anhydrous Na$_2$SO$_4$, filtered and concentrated under reduced pressure. The crude material was purified by prep-HPLC to afford 2-((3,5-dicyano-4-ethyl-6-(4-(2-hydroxyethyl)-1,4-diazepan-1-yl)pyridin-2-yl)thio)-2-phenylacetamide (80 mg, 31% yield) as an off-white solid. LCMS m/z=465.3 [M+H]$^+$. $^1$H NMR (400 MHz, DMSO-d$_6$) δ ppm 7.91 (s, 1H), 7.49 (br d, J=7.02 Hz, 2H), 7.40-7.23 (m, 4H), 5.51 (s, 1H), 4.38 (t, J=5.48 Hz, 1H), 3.95-3.80 (m, 4H), 3.47 (q, J=5.92 Hz, 2H), 2.88-2.72 (m, 4H), 2.56-2.52 (m, 2H), 2.52-2.42 (m, 2H), 1.89 (br s, 2H), 1.21 (t, J=7.56 Hz, 3H).

Example 319

2-((3,5-Dicyano-6-(4-cyanopiperidin-1-yl)-4-ethylpyridin-2-yl)thio)-2-phenylacetamide

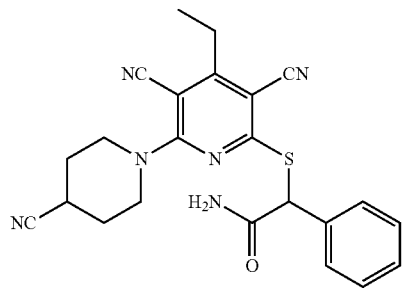 [SMILES: CCc1c(C#N)c(SC(C(N)=O)c2ccccc2)nc(N2CCC(C#N)CC2)c1C#N]

To a mixture of 2-[(6-bromo-3,5-dicyano-4-ethyl-2-pyridyl)sulfanyl]-2-phenyl-acetamide (synthesis described in example 6, step 1, 40 mg, 0.10 mmol) and triethylamine (0.03 mL, 0.22 mmol) in THF (2 mL) was added 4-cyanopiperidine (0.01 mL, 0.11 mmol). The resultant mixture was stirred for 17 hours at room temperature. The mixture was diluted with EtOAc (20 mL), washed with water (20 mL), the aqueous phase was extracted with EtOAc (20 mL) and the organic extracts were combined. The extracts were washed with brine (2×25 mL), and filtration through a hydrophobic frit and removal of solvent under reduced pressure gave a residue which was triturated with Et$_2$O and dried in vacuo at 50° C. to afford 2-[[3,5-dicyano-6-(4-cyano-1-piperidyl)-4-ethyl-2-pyridyl]sulfanyl]-2-phenyl-acetamide (38 mg, 89% yield) as an orange powder. LCMS m/z=429.3 [M−H]$^−$. $^1$H NMR (300 MHz, DMSO-d$_6$) δ ppm 7.92 (br s, 1H), 7.55-7.49 (m, 2H), 7.43-7.32 (m, 4H), 5.52 (s, 1H), 4.19-4.07 (m, 2H), 3.71-3.57 (m, 2H), 3.28-3.17 (m, 1H), 2.77 (q, J=7.7 Hz, 2H), 2.12-1.98 (m, 2H), 1.88-1.70 (m, 2H), 1.21 (t, J=7.6 Hz, 3H).

Example 320

(S)-2-((3,5-Dicyano-4-ethyl-6-((S)-3-hydroxypyrrolidin-1-yl)pyridin-2-yl)thio)-2-phenylacetamide

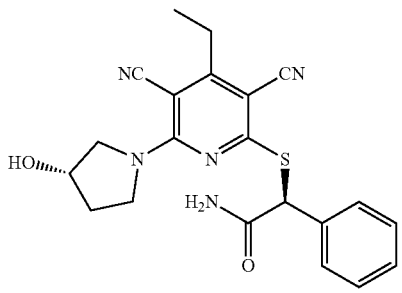 [SMILES: CCc1c(C#N)c(S[C@H](C(N)=O)c2ccccc2)nc(N2CC[C@H](O)C2)c1C#N]

2-((3,5-Dicyano-4-ethyl-6-((S)-3-hydroxypyrrolidin-1-yl)pyridin-2-yl)thio)-2-phenylacetamide (synthesis described in example 168, step 3, 250 mg, 0.62 mmol) was separated with chiral HPLC (chiralpak-IC column, HEX-EtOH (FA)) to give (S)-2-((3,5-dicyano-4-ethyl-6-((S)-3-hydroxypyrrolidin-1-yl)pyridin-2-yl)thio)-2-phenylacetamide (29 mg). LCMS m/z=408.1 [M+H]$^+$. $^1$H NMR (400 MHz, DMSO-d$_6$) δ ppm 7.91 (br s, 1H), 7.52 (br s, 1H), 7.52-7.49 (m, 1H), 7.45-7.25 (m, 4H), 5.61 (s, 1H), 5.14 (d, J=3.5 Hz, 1H), 4.41 (s, 1H), 4.05-3.69 (m, 4H), 2.74 (q, J=7.4 Hz, 2H), 2.03-1.85 (m, 2H), 1.21 (q, J=7.4 Hz, 3H).

Example 321

2-((6-(4-Amino-4-methylpiperidin-1-yl)-3,5-dicyano-4-cyclopropylpyridin-2-yl)thio)-2-phenylacetamide

Step 1: tert-Butyl (1-(6-chloro-3,5-dicyano-4-cyclopropylpyridin-2-yl)-4-methylpiperidin-4-yl)carbamate

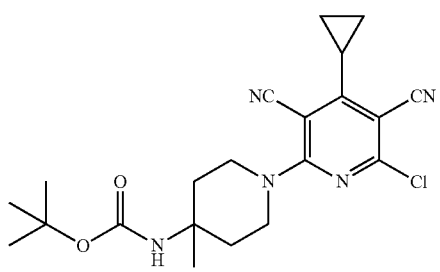 [SMILES: CC1(NC(=O)OC(C)(C)C)CCN(c2nc(Cl)c(C#N)c(C3CC3)c2C#N)CC1]

To a solution of 2,6-dichloro-4-cyclopropylpyridine-3,5-dicarbonitrile (333 mg, 1.400 mmol) in dichloromethane (30 mL) was added tert-butyl (4-methylpiperidin-4-yl)carbamate (300 mg, 1.400 mmol) and triethylamine (142 mg, 1.400 mmol). The mixture was stirred at room temperature for 12 hours. The mixture was diluted with DCM (50 mL), washed with water and brine, dried and concentrated to give crude tert-butyl (1-(6-chloro-3,5-dicyano-4-cyclopropylpyridin-2-yl)-4-methylpiperidin-4-yl)carbamate (620 mg) as a brown oil. LCMS m/z=438.1 [M+Na]$^+$.

Step 2: tert-Butyl (1-(3,5-dicyano-4-cyclopropyl-6-mercaptopyridin-2-yl)-4-methylpiperidin-4-yl)carbamate

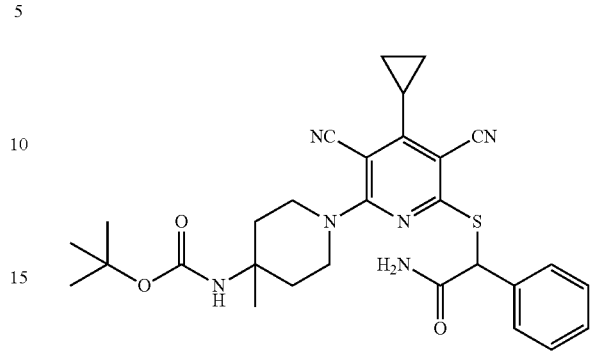

To a solution of tert-butyl (1-(6-chloro-3,5-dicyano-4-cyclopropylpyridin-2-yl)-4-methylpiperidin-4-yl)carbamate (620 mg) in DMF (4 mL) was added potassium thioacetate (204 mg, 1.789 mmol). The mixture was stirred at room temperature for 1 hour. The reaction mixture was diluted with N,N-dimethylformamide (4 mL) and potassium carbonate (414 mg, 3.00 mmol) was added. The mixture was stirred at room temperature for 1 hour. Then, 2-Amino-2-oxo-1-phenylethyl methanesulfonate (516 mg, 2.249 mmol) was added and the mixture stirred at room temperature for 12 hours. The mixture was diluted with water (80 mL) and extracted with ethyl acetate (30 mL×3). The combined organic layers were washed with water, brine, dried, and concentrated to give the crude product. Purification of the crude material by silica gel chromatography (eluted with 1:2 ethyl acetate: petroleum ether) provided tert-butyl (1-(6-((2-amino-2-oxo-1-phenylethyl)thio)-3,5-dicyano-4-cyclopropylpyridin-2-yl)-4-methylpiperidin-4-yl)carbamate (600 mg). LCMS m/z=547.1 [M+H]$^+$.

Step 3: 2-((6-(4-Amino-4-methylpiperidin-1-yl)-3,5-dicyano-4-cyclopropylpyridin-2-yl)thio)-2-phenylacetamide, Formic Acid Salt

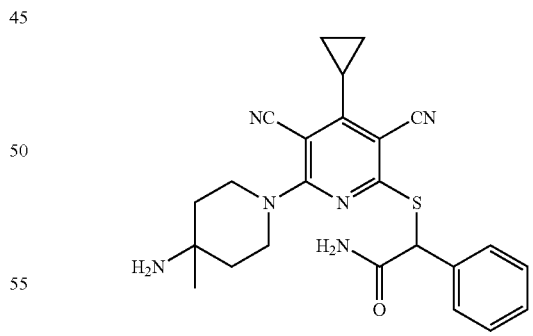

tert-Butyl (1-(6-((2-amino-2-oxo-1-phenylethyl)thio)-3,5-dicyano-4-cyclopropylpyridin-2-yl)-4-methylpiperidin-4-yl)carbamate (300 mg) was dissolved in dichloromethane (DCM) (10 mL) and trifluoroacetic acid (1 mL). The solution was stirred at room temperature for 6 hours. The solution was concentrated and the remaining residue purified by prep-HPLC to afford 2-((6-(4-amino-4-methylpiperidin-1-yl)-3,5-dicyano-4-cyclopropylpyridin-2-yl)thio)-2-phenylacetamide, Formic acid salt (30 mg) as a light pale solid.

LCMS m/z=447.1 [M+H]+. 1H NMR (400 MHz, DMSO-d6) δ ppm 8.35 (s, 1H), 7.97 (s, 1H), 7.55-7.49 (m, 2H), 7.45-7.30 (m, 4H), 5.53 (s, 1H), 3.99-3.89 (m, 2H), 3.88-3.76 (m, 2H), 2.16-2.07 (m, 1H), 1.73-1.57 (m, 4H), 1.26 (s, 3H), 1.18-1.07 (m, 2H), 1.02-0.93 (m, 2H).

Example 322

2-((3,5-Dicyano-4-ethyl-6-((S)-3-hydroxypyrrolidin-1-yl)pyridin-2-yl)thio)-2-(pyridin-2-yl)acetamide Step 1: 2-Amino-2-oxo-1-(pyridin-2-yl)ethyl methanesulfonate

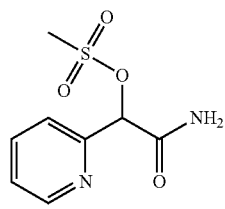

To a stirred solution of 2-hydroxy-2-(pyridin-2-yl)acetamide (300 mg, 1.97 mmol) and Et3N (0.55 mL, 3.94 mmol) in dichloromethane (10 mL) was added methanesulfonyl chloride (271 mg, 2.37 mmol) at room temperature, and the resulting mixture was stirred at room temperature for 5 hours. The reaction mixture was poured into water (50 mL), and extracted with DCM (50 mL×2), and the combined organic layers were dried, concentrated to afford 2-amino-2-oxo-1-(pyridin-2-yl)ethyl methanesulfonate (380 mg, 84% yield) as a pale solid. LCMS m/z=230.9 [M+H]+.

Step 2: 2-((3,5-Dicyano-4-ethyl-6-((S)-3-hydroxypyrrolidin-1-yl)pyridin-2-yl)thio)-2-(pyridin-2-yl)acetamide

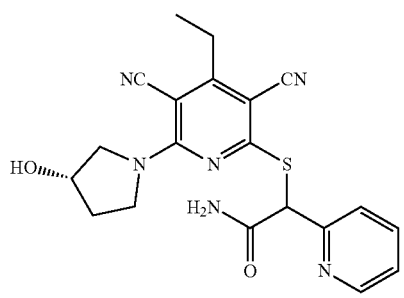 [SMILES: CCc1c(C#N)c(SC(C(N)=O)c2ccccn2)nc(N2CC[C@H](O)C2)c1C#N]

A solution of potassium thioacetate (149 mg, 1.30 mmol), (S)-2-chloro-4-ethyl-6-(3-hydroxypyrrolidin-1-yl)pyridine-3,5-dicarbonitrile (synthesis described in example 168, step 1, 300 mg, 1.08 mmol) in N,N-dimethylformamide (15 mL) was stirred at room temperature for 30 minutes then 2-amino-2-oxo-1-(pyridin-2-yl)ethyl methanesulfonate (300 mg, 1.30 mmol) and Et3N (0.30 mL, 2.17 mmol) were added to the solution. The reaction mixture was stirred at room temperature for 12 hours. The reaction mixture was poured into water (50 mL), and extracted with EtOAc (50 mL×2). The combined organic layers were dried, filtered, concentrated and purified by silica gel column (eluted by DCM/MeOH 30/1) to afford 2-((3,5-dicyano-4-ethyl-6-((S)-3-hydroxypyrrolidin-1-yl)pyridin-2-yl)thio)-2-(pyridin-2-yl)acetamide (120 mg, 27% yield) as a white solid. LCMS m/z=408.9 [M+H]+. 1H NMR (400 MHz, DMSO) δ 8.54 (d, J=4.2 Hz, 1H), 7.88 (br s, 1H), 7.83 (td, J=7.7, 1.6 Hz, 1H), 7.64 (d, J=7.8 Hz, 1H), 7.40-7.31 (m, 2H), 5.73 (s, 1H), 5.18-5.04 (m, 1H), 4.39 (br s, 1H), 4.04-3.55 (m, 4H), 2.75 (q, J=7.5 Hz, 2H), 2.10-1.85 (m, 2H), 1.21 (t, J=7.6 Hz, 3H).

Example 324

2-((3,5-Dichloro-4-ethyl-6-(piperazin-1-yl)pyridin-2-yl)thio)-2-phenylacetamide

Step 1: tert-Butyl 4-(6-((2-amino-2-oxo-1-phenylethyl)thio)-3,5-dichloro-4-ethylpyridin-2-yl) piperazine-1-carboxylate

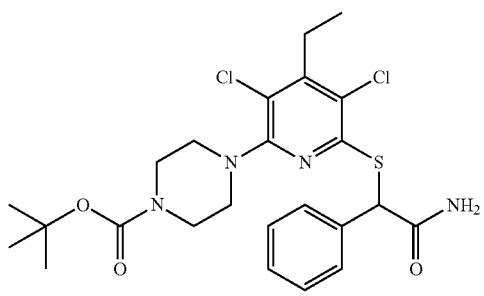 [SMILES: CCc1c(Cl)c(SC(C(N)=O)c2ccccc2)nc(N2CCN(C(=O)OC(C)(C)C)CC2)c1Cl]

2-((3,5-Dichloro-4-ethyl-6-fluoropyridin-2-yl)thio)-2-phenylacetamide (synthesis described in example 165, step 2, 100 mg, 0.184 mmol) and tert-butyl piperazine-1-carboxylate (49 mg, 0.263 mmol) were added to a vial and suspended in dimethyl sulfoxide (3 mL). The mixture was heated to 90° C. for 20 hours and 140° C. for 4 hours. The precipitate was filtered to afford tert-butyl 4-(6-((2-amino-2-oxo-1-phenylethyl)thio)-3,5-dichloro-4-ethylpyridin-2-yl)piperazine-1-carboxylate (44 mg). LCMS m/z=525.1 [M+H]+.

Step 2: 2-((3,5-Dichloro-4-ethyl-6-(piperazin-1-yl)pyridin-2-yl)thio)-2-phenylacetamide

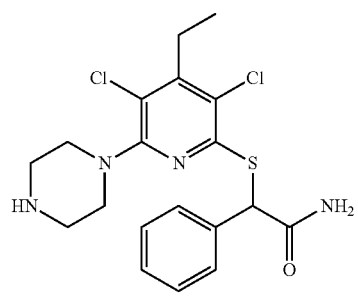 [SMILES: CCc1c(Cl)c(SC(C(N)=O)c2ccccc2)nc(N2CCNCC2)c1Cl]

tert-butyl 4-(6-((2-amino-2-oxo-1-phenylethyl)thio)-3,5-dichloro-4-ethylpyridin-2-yl)piperazine-1-carboxylate (43 mg, 0.082 mmol) was dissolved in dichloromethane (3 mL) and TFA (0.4 mL, 5.19 mmol) was added. The mixture was stirred at room temperature for 60 minutes, then was concentrated by blowing air over the mixture and purified by basic gilson HPLC (20-80% water with 0.1% NH4OH/

Acetonitrile). Desired fractions were concentrated and freeze dried to afford 2-((3,5-dichloro-4-ethyl-6-(piperazin-1-yl)pyridin-2-yl)thio)-2-phenylacetamide (22 mg, 0.051 mmol, 63% yield). LCMS m/z=425.1 [M+H]$^+$. $^1$H NMR (400 MHz, DMSO-d$_6$) δ ppm 7.85 (s, 1H) 7.47-7.59 (m, 2H) 7.22-7.40 (m, 4H) 5.50 (s, 1H) 3.08-3.22 (m, 4H) 2.74-2.88 (m, 6H) 1.09 (t, J=7.48 Hz, 3H). One proton was not observed.

Example 328 tert-Butyl (1-(6-((2-amino-2-oxo-1-phenylethyl)thio)-3,5-dicyano-4-ethylpyridin-2-yl)piperidin-4-yl)carbamate

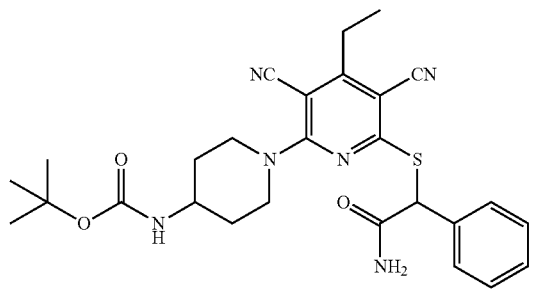 [SMILES: CCc1c(C#N)c(SC(C(N)=O)c2ccccc2)nc(N2CCC(NC(=O)OC(C)(C)C)CC2)c1C#N]

To a suspension of 2,6-dichloro-4-ethylpyridine-3,5-dicarbonitrile (synthesis described in example 3, step 2, 300 mg, 1.327 mmol) in ethanol (2 mL) at −20° C. was added a solution of tert-butyl piperidin-4-ylcarbamate (292 mg, 1.460 mmol) in ethanol (2.5 mL). The reaction mixture was then stirred at −20° C. for 30 minutes then warmed to 0° C. and then the potassium thioacetate (227 mg, 1.991 mmol) and Et$_3$N (0.462 mL, 3.32 mmol) were added to the reaction mixture along with additional ethanol (5 mL). The heterogeneous reaction mixture was then warmed to 20° C. and stirred at the same temperature overnight. To the reaction mixture was added 2-amino-2-oxo-1-phenylethyl methanesulfonate (synthesis described in example 3, step 5, 608 mg, 2.65 mmol). The reaction was continued stirring at 20° C. for 2.5 hours, then the reaction temperature was increased to 40° C. and the reaction was stirred for 2.5 hours at 40° C. The heterogeneous mixture was cooled to room temperature and filtered. The solids were washed with EtOH, water, EtOH, and then Et$_2$O. The isolated material was then dried in the vac oven to yield tert-butyl (1-(6-((2-amino-2-oxo-1-phenylethyl)thio)-3,5-dicyano-4-ethylpyridin-2-yl)piperidin-4-yl)carbamate (520 mg). LCMS m/z=521.4 [M+H]$^+$. $^1$H NMR (400 MHz, DMSO-d$_6$) δ ppm 7.96 (s, 1H), 7.47-7.57 (m, 2H), 7.29-7.43 (m, 4H), 6.96 (d, J=7.86 Hz, 1H), 5.54 (s, 1H), 4.45 (d, J=10.65 Hz, 2H), 3.61 (br. s., 1H), 3.21-3.32 (m, 2H), 2.75 (q, J=7.60 Hz, 2H), 1.88 (d, J=10.39 Hz, 2H), 1.43-1.49 (m, 2H), 1.41 (s, 9H), 1.20 (t, J=7.60 Hz, 3H).

Example 329

N-(4-(1(3,5-Dicyano-4-ethyl-6-(3-oxopiperazin-1-yl)pyridin-2-yl)thio) methyl) benzyl) acetamide Step 1: 2-Chloro-4-ethyl-6-(3-oxopiperazin-1-yl)pyridine-3,5-dicarbonitrile

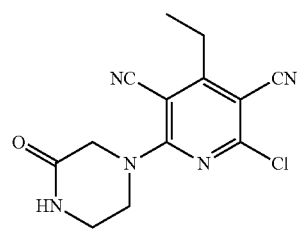 [SMILES: CCc1c(C#N)c(Cl)nc(N2CCNC(=O)C2)c1C#N]

To a solution of 2,6-dichloro-4-ethylpyridine-3,5-dicarbonitrile (synthesis described in example 3 step 2, 700 mg, 3.10 mmol) in dichloromethane (30 mL) was added triethylamine (0.432 mL, 3.10 mmol) followed by piperazin-2-one (310 mg, 3.10 mmol) at 0° C. The reaction mixture was stirred for 3 hours at 25° C. The reaction mixture was quenched with ice cold water (100 mL) and extracted with DCM (2×100 mL). The combined organic layers were washed with water (2×100 mL) and dried over anhydrous sodium sulfate, filtered and concentrated in vacuo to afford 2-chloro-6-(dimethylamino)-4-ethylpyridine-3,5-dicarbonitrile (800 mg) as a semi solid. LCMS m/z=287.9 [M−H]$^−$.

Step 2: N-(4-(((3,5-Dicyano-4-ethyl-6-(3-oxopiperazin-1-yl)pyridin-2-yl)thio)methyl)benzyl)acetamide

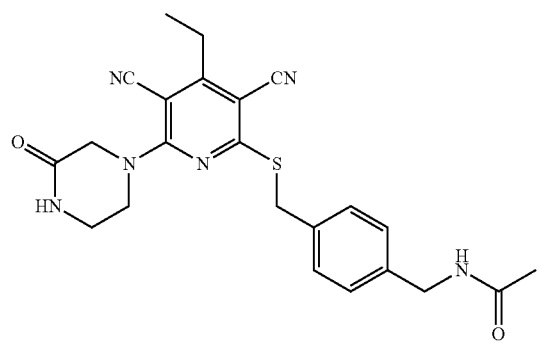 [SMILES: CCc1c(C#N)c(SCc2ccc(CNC(C)=O)cc2)nc(N2CCNC(=O)C2)c1C#N]

To solution of 2-chloro-4-ethyl-6-(3-oxopiperazin-1-yl)pyridine-3,5-dicarbonitrile (250 mg) in N,N-dimethylformamide (5 mL) was added potassium thioacetate (181 mg, 1.584 mmol) and the mixture was stirred for 2 hours at room temperature. Potassium carbonate (219 mg, 1.584 mmol) and N-(4-(bromomethyl)benzyl)acetamide (652 mg) were added and the reaction was stirred for 1 hour at room temperature. Water (50 mL) was added to the reaction mixture and extracted with ethyl acetate (2×30 mL). The combined organic layers were dried over anhydrous sodium sulphate, filtered and concentrated to dryness under vacuum. The crude material was purified by silica gel column chromatography (mesh 100-200, eluted with 3-4% methanol in DCM) to afford N-(4-(((3,5-dicyano-4-ethyl-6-(3-oxopiperazin-1-yl)pyridin-2-yl)thio)methyl)benzyl)acetamide (230 mg, 63% yield) as an off-white solid. LCMS m/z=449.1 [M+H]⁺. ¹H NMR (400 MHz, DMSO-d₆): δ ppm 8.28 (t, J=6.0 Hz, 1H), 8.23 (s, 1H), 7.36 (d, J=8.11 Hz, 2H), 7.21 (d, J=8.33 Hz, 2H), 4.50 (s, 2H), 4.36 (s, 2H), 4.21 (d, J=5.70 Hz, 2H), 4.06-3.96 (m, 2H), 3.33-3.30 (m, 2H), 2.79 (q, J=7.53 Hz, 2H), 1.86 (s, 3H), 1.31-1.16 (m, 3H).

Example 330

2-((6-(3-(2-Amino-2-oxoethyl)azetidin-1-yl)-3,5-dicyano-4-ethylpyridin-2-yl)thio)-2-phenylacetamide Step 1: 2-(Azetidin-3-yl)acetamide hydrochloride

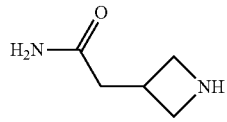

To a solution of tert-butyl 3-(2-amino-2-oxoethyl)azetidine-1-carboxylate (2.6 g) in 1,4-dioxane (12 mL) was added HCl (4 M in 1,4-dioxane, 5 mL, 20.00 mmol) at 0° C., and the reaction mixture was stirred for 4 hours at room temperature. The mixture was concentrated under reduced pressure, the remaining material triturated with diethyl ether (20 mL), filtered and dried to afford 2-(azetidin-3-yl)acetamide hydrochloride (600 mg) as an off-white solid. ¹H NMR (400 MHz, DMSO-d₆): δ ppm 8.15 (s, 4H), 4.41-4.32 (m, 1H), 4.15-4.06 (m, 1H), 4.02-3.90 (m, 1H), 3.86-3.74 (m, 1H), 2.71-2.62 (m, 1H), 2.51-2.41 (m, 2H).

Step 2: 2-(1-(6-Chloro-3,5-dicyano-4-ethylpyridin-2-yl)azetidin-3-yl)acetamide

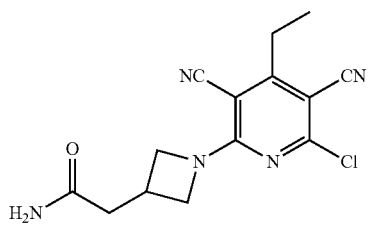

To a solution of 2,6-dichloro-4-ethylpyridine-3,5-dicarbonitrile (synthesis described in example 3 step 2, 800 mg) in tetrahydrofuran (10 mL) was added 2-(azetidin-3-yl)acetamide hydrochloride (505 mg) and water (10 mL), followed by sodium bicarbonate (282 mg, 3.35 mmol) at 0° C. The reaction mixture was stirred for 16 hours at room temperature. The reaction mixture was concentrated under reduced pressure, diluted with water (50 mL), and extracted with EtOAc (2×120 mL). The combined organic layers were dried over anhydrous Na₂SO₄, filtered and concentrated under reduced pressure. The crude material was purified by silica gel column chromatography (60-120 mesh, eluted with 100% EtOAc) to afford 2-(1-(6-chloro-3,5-dicyano-4-ethylpyridin-2-yl)azetidin-3-yl)acetamide (280 mg), as an off-white solid. LCMS m/z=304.1 [M+H]⁺.

Step 3: 2-((6-(3-(2-Amino-2-oxoethyl)azetidin-1-yl)-3,5-dicyano-4-ethylpyridin-2-yl)thio)-2-phenylacetamide

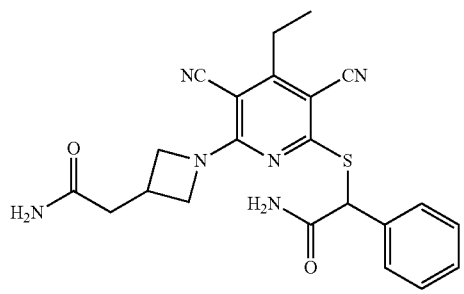 [SMILES: CCc1c(C#N)c(SC(C(N)=O)c2ccccc2)nc(N2CC(CC(N)=O)C2)c1C#N]

To a solution of 2-(1-(6-chloro-3,5-dicyano-4-ethylpyridin-2-yl)azetidin-3-yl)acetamide (250 mg) in N,N-dimethylformamide (6 mL), was added potassium thioacetate (146 mg, 1.281 mmol) at room temperature, and the reaction mixture was stirred for 2 hours at the same temperature. Then potassium carbonate (133 mg, 0.960 mmol) was added followed by 2-amino-2-oxo-1-phenylethylmethanesulfonate (synthesis described in example 3 step 5, 177 mg) and the reaction mixture was stirred for 14 hours at room temperature. The reaction mixture was quenched in cold water (50 mL) and extracted with EtOAc (2×50 mL). The combined organic layers were dried over anhydrous Na₂SO₄, filtered and concentrated under reduced pressure to give the crude compound. The crude was purified by silica gel column chromatography (100-200 mesh, eluted with 5% MeOH in DCM) to obtain 2-((6-(3-(2-amino-2-oxoethyl)azetidin-1-yl)-3,5-dicyano-4-ethylpyridin-2-yl)thio)-2-phenylacetamide (170 mg) as a dark brown solid. The brown solid was dissolved in 10% MeOH in DCM (50 mL), and charcoal (500 mg) was added. The resultant mixture was heated at 50° C. for 5 minutes, filtered through a Celite® bed and washed with 10% MeOH in DCM (30 mL). The filtrate was concentrated under reduced pressure to afford 2-((6-(3-(2-amino-2-oxoethyl)azetidin-1-yl)-3,5-dicyano-4-ethylpyridin-2-yl)thio)-2-phenylacetamide (140 mg) as an off-white solid. LCMS m/z=435.1 [M+H]⁺. ¹H NMR (400 MHz, DMSO-d₆) δ ppm 7.87 (s, 1H), 7.53-7.48 (m, 2H), 7.40-7.27 (m, 4H), 7.24 (s, 1H), 6.86 (br s, 1H), 5.56 (s, 1H), 4.54 (br s, 2H), 4.12 (br s, 2H), 3.06-2.96 (m, 1H), 2.68 (q, J=7.67 Hz, 2H), 2.56-2.51 (m, 2H), 1.17 (t, J=7.56 Hz, 3H).

Example 331

N-(4-(((3,5-Dicyano-4-ethyl-6-(3-hydroxypyrrolidin-1-yl)pyridin-2-yl)thio)methyl)benzyl)acetamide

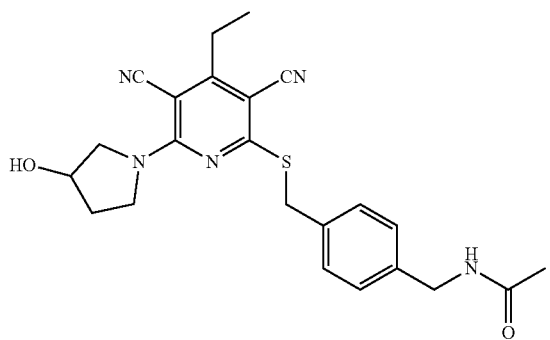 [SMILES: CCc1c(C#N)c(SCc2ccc(CNC(C)=O)cc2)nc(N2CCC(O)C2)c1C#N]

To a solution of 2-chloro-4-ethyl-6-(3-hydroxypyrrolidin-1-yl)pyridine-3,5-dicarbonitrile (synthesis described in Example 370, Step 1, 250 mg) in N,N-dimethylformamide (10 mL), was added potassium thioacetate (100 mg, 0.880 mmol) at 25° C. The reaction mixture was stirred for 2 hours at the same temperature, then potassium carbonate (122 mg, 0.880 mmol) was added followed by N-(4-(bromomethyl)benzyl)acetamide (577 mg). The reaction mixture was stirred for 4 hours at 25° C. The reaction mixture was quenched with cold water (50 mL) and extracted with EtOAc (2×150 mL). The combined organic layers were dried over $Na_2SO_4$, filtered and concentrated under reduced pressure. The crude material was purified by silica gel column chromatography (100-200 mesh eluted with 5% MeOH in DCM) to afford a brown solid. The brown solid was dissolved in 10% MeOH in DCM (50 mL), charcoal (500 mg) was added, and the resultant mixture heated at 50° C. for 5 minutes. The mixture was filtered through a Celite® bed, washed with 10% MeOH in DCM (40 mL), and the filtrate concentrated under reduced pressure to afford N-(4-(((3,5-dicyano-4-ethyl-6-(3-hydroxpyrrolidin-1-yl)pyridin-2-yl)thio)methyl)benzyl)acetamide (162 mg) as an off-white solid. LCMS m/z=436.1 [M+H]$^+$. $^1$H NMR (400 MHz, DMSO-$d_6$) δ ppm 8.30 (t, J=6.0 Hz, 1H), 7.35 (d, J=8.1 Hz, 2H), 7.20 (d, J=8.1 Hz, 2H), 5.11 (d, J=3.6 Hz, 1H), 4.49 (s, 2H), 4.42-4.37 (m, 1H), 4.21 (d, J=5.9 Hz, 2H), 3.93-3.83 (m, 3H), 3.77-3.69 (m, 1H), 2.76 (q, J=7.6 Hz, 2H), 1.99-1.91 (m, 2H), 1.85 (s, 3H), 1.21 (t, J=7.6 Hz, 3H).

Example 332

N-(4-(1-(3,5-Dicyano-6-(4-(dimethylamino)piperidin-1-yl)-4-ethylpyridin-2-ylthio)propyl)benzyl)acetamide, Trifluoroacetic Acid Salt Step 1: 1-(4-(Aminomethyl)phenyl)propan-1-ol

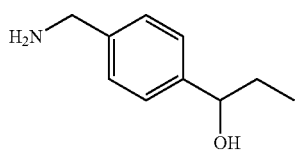

To a solution of 4-propionylbenzonitrile (3.6 g, 22.62 mmol) in THF (150 mL) was added LAH (1.717 g, 45.2 mmol) at 0° C. The resultant mixture was stirred at room temperature overnight then poured into water. The mixture was exacted with ethyl acetate (500 mL) and the organic phase washed with water (250 mL), brine (250 mL), dried over sodium sulfate and evaporated under reduced pressure to give the title compound 1-(4-(aminomethyl)phenyl)propan-1-ol (3.6 g). LCMS m/z=166.2 [M+H]$^+$.

Step 2: N-(4-(1-(3,5-dicyano-6-(4-(dimethylamino)piperidin-1-yl)-4-ethylpyridin-2-ylthio)propyl)benzyl)acetamide, Trifluoroacetic Acid Salt

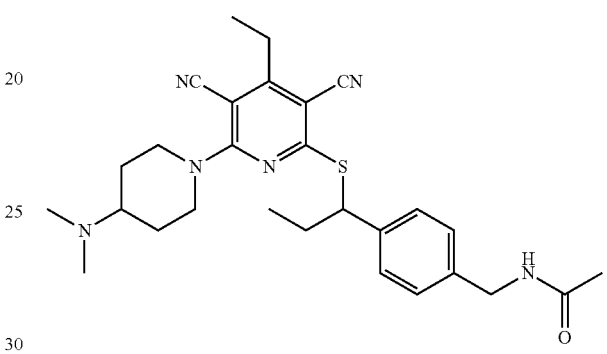

To a solution of 1-(4-(aminomethyl)phenyl)propan-1-ol (3.6 g, 21.79 mmol) in N,N-dimethylformamide (50 mL) was added acetic anhydride (8.90 g, 87 mmol) at room temperature. The mixture was stirred at room temperature overnight. The resultant mixture was diluted with ethyl acetate (50 mL), washed with water (25 mL) and brine (25 mL), dried over sodium sulfate, and evaporated under reduced pressure. To this residue was added toluene (50 mL) and Lawesson's reagent (1.951 g, 4.82 mmol). The mixture was stirred at 110° C. overnight. The resultant mixture was cooled and evaporated under reduced pressure to give the crude product, which was purified by silica gel chromatography (eluting with petroleum ether/ethyl acetate=2:1) to provide a residue. To a solution of 2-chloro-6-(4-(dimethylamino)piperidin-1-yl)-4-ethylpyridine-3,5-dicarbonitrile (1.423 g, 4.48 mmol) and potassium carbonate (1.238 g, 8.96 mmol) in N,N-dimethylformamide (50 mL) was added at room temperature the residue from above. The mixture was stirred at room temperature overnight. The mixture was diluted with ethyl acetate (60 mL), washed with water (30 mL), and saturated brine (30 mL). The organic phase was dried over anhydrous sodium sulfate and concentrated under reduced pressure. The crude residue was purified by prep-HPLC to give N-(4-(1-((3,5-dicyano-6-(4-(dimethylamino)piperidin-1-yl)-4-ethylpyridin-2-yl)thio)propyl)benzyl)acetamide, trifluoroacetic acid salt (6 mg). LCMS m/z=505.2 [M+H]$^+$. $^1$H NMR (400 MHz, CDCl3) δ ppm 12.28 (s, 1H), 7.36 (d, J=7.9 Hz, 2H), 7.25 (t, J=6.1 Hz, 2H), 6.87 (s, 1H), 6.01-5.55 (m, 2H), 4.80-4.63 (m, 2H), 4.55 (d, J=12.3 Hz, 1H), 4.43 (dt, J=15.4, 7.2 Hz, 2H), 3.47 (s, 1H), 3.07 (t, J=12.6 Hz, 1H), 2.97-2.92 (m, 1H), 2.86 (d, J=11.3 Hz, 3H), 2.77 (s, 3H), 2.15-2.02 (m, 6H), 1.76 (tdd, J=20.6, 13.0, 7.6 Hz, 1H), 1.49 (dd, J=21.3, 12.8 Hz, 1H), 1.32 (t, J=7.6 Hz, 3H), 0.99 (t, J=7.3 Hz, 3H), 0.90 (t, J=7.4 Hz, 1H).

Example 333

(2R)-1-(6-((2-Amino-2-oxo-1-phenylethyl)thio)-3,5-dicyano-4-ethylpyridin-2-yl)azetidin-3-yl 2-amino-3-methylbutanoate Step 1: (2S)-1-(6-((2-Amino-2-oxo-1-phenylethyl)thio)-3,5-dicyano-4-ethylpyridin-2-yl)azetidin-3-yl 2-((tert-butoxycarbonyl)amino)-3-methylbutanoate

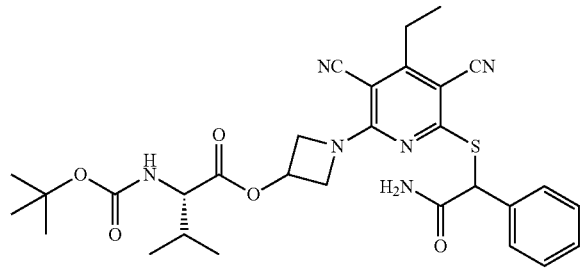 [SMILES: CCc1c(C#N)c(SC(C(N)=O)c2ccccc2)nc(N2CC(OC(=O)[C@@H](NC(=O)OC(C)(C)C)C(C)C)C2)c1C#N]

To a solution of 2,4,6-trichlorobenzoyl chloride (231 mg, 0.945 mmol) and (S)-2-((tert-butoxycarbonyl)amino)-3-methylbutanoic acid (437 mg, 1.891 mmol) in N,N-dimethylformamide (2 mL) and tetrahydrofuran (20 mL) was added triethylamine (0.132 mL, 0.945 mmol) and the mixture was stirred for 5 hours at 0° C. Then, 2-((3,5-dicyano-4-ethyl-6-(3-hydroxyazetidin-1-yl)pyridin-2-yl)thio)-2-phenylacetamide (synthesis described in example 146, step 2, 400 mg, 0.945 mmol) and DMAP (116 mg, 0.945 mmol) were added at 0° C. The reaction mixture was stirred at room temperature for 1 hour. The reaction mixture was quenched with ice cold water (50 mL) and extracted with ethyl acetate (2×100 mL). The combined organic layers were dried over anhydrous $Na_2SO_4$, filtered and concentrated. The crude material was purified by silica gel column chromatography (100-200 mesh, eluted with 20% ethyl acetate in hexane) to afford (2S)-1-(6-((2-amino-2-oxo-1-phenylethyl)thio)-3,5-dicyano-4-ethylpyridin-2-yl)azetidin-3-yl 2-((tert-butoxycarbonyl)amino)-3-methylbutanoate (250 mg) as a brown solid. LCMS m/z=593.4 [M+H]$^+$.

Step 2: (2R)-1-(6-((2-Amino-2-oxo-1-phenylethyl)thio)-3,5-dicyano-4-ethylpyridin-2-yl)azetidin-3-yl 2-amino-3-methylbutanoate

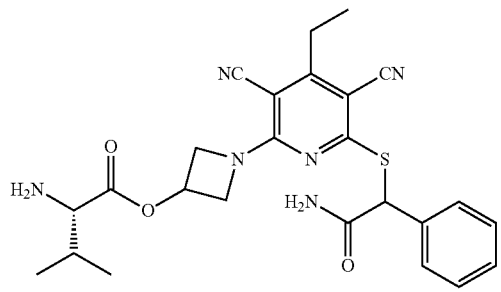 [SMILES: CCc1c(C#N)c(SC(C(N)=O)c2ccccc2)nc(N2CC(OC(=O)[C@@H](N)C(C)C)C2)c1C#N]

To a solution of (2S)-1-(6-((2-amino-2-oxo-1-phenylethyl)thio)-3,5-dicyano-4-ethylpyridin-2-yl)azetidin-3-yl 2-((tert-butoxycarbonyl)amino)-3-methylbutanoate (250 mg) in 1,4-dioxane (2 mL) was added HCl (4 M in 1,4-dioxane, 2 mL, 8.00 mmol) at 0° C. The reaction mixture was stirred at room temperature for 45 minutes. The reaction mixture was concentrated under reduced pressure to afford the crude product which was purified by prep-SFC to afford (2R)-1-(6-((2-Amino-2-oxo-1-phenylethyl)thio)-3,5-dicyano-4-ethylpyridin-2-yl)azetidin-3-yl 2-amino-3-methylbutanoate (20 mg). LCMS m/z=493.1 [M+H]$^+$. $^1$H NMR (400 MHz, DMSO-$d_6$) δ ppm 7.86 (br s, 1H), 7.51 (br d, J=7.23 Hz, 2H), 7.41-7.23 (m, 4H), 5.57 (s, 1H), 5.29 (br s, 1H), 4.80 (br s, 2H), 4.36 (br s, 2H), 3.23-3.19 (m, 1H), 2.70 (q, J=7.53 Hz, 2H), 1.92 (br d, J=6.58 Hz, 3H), 1.24 (br s, 1H), 1.18 (br t, J=7.56 Hz, 3H), 0.82-0.97 (m, 6H).

Example 335

N-(5-(((3,5-dicyano-4-ethyl-6-(4-methyl-1,4-diazepan-1-yl)pyridin-2-yl)thio)methyl)pyridin-2-yl)methanesulfonamide

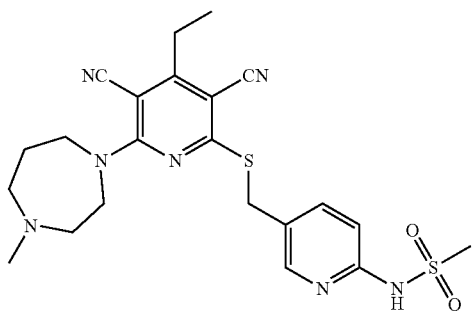 [SMILES: CCc1c(C#N)c(SCc2ccc(NS(C)(=O)=O)nc2)nc(N2CCCN(C)CC2)c1C#N]

At 0° C., to the solution of 2-(((6-aminopyridin-3-yl)methyl)thio)-4-ethyl-6-(4-methyl-1,4-diazepan-1-yl)pyridine-3,5-dicarbonitrile (synthesis described in example 300, 60 mg, 0.147 mmol) in THF (2 mL) was added a solution of mesyl-Cl (0.025 mL, 0.321 mmol) in THF (0.5 mL) dropwise, then added TEA (0.062 mL, 0.442 mmol) dropwise. The reaction mixture was stirred for 30 minutes, then added more mesyl-Cl (0.008 mL, 0.102 mmol) to the solution. The reaction mixture was concentrated down and purified by RP-HPLC (20-60% acetonitrile/water, 0.1% $NH_4OH$ in water) to afford N-(5-(((3,5-dicyano-4-ethyl-6-(4-methyl-1,4-diazepan-1-yl)pyridin-2-yl)thio)methyl)pyridin-2-yl)methanesulfonamide (16 mg, 0.033 mmol, 22% yield) as a white solid. LCMS m/z=486.3 [M+H]$^+$. 1H NMR (400 MHz, DMSO-$d_6$) δ ppm 1.22 (t, J=7.6 Hz, 3H), 1.87-1.97 (m, 2H), 2.24 (s, 3H), 2.47 (br. s., 2H), 2.59-2.70 (m, 2H), 2.78 (q, J=7.6 Hz, 2H), 3.26 (s, 3H), 3.82-3.97 (m, 4H), 4.46 (s, 2H), 6.94 (d, J=8.6 Hz, 1H), 7.75 (dd, J=8.6, 2.5 Hz, 1H), 8.26 (d, J=2.0 Hz, 1H), 10.79 (br. s., 1H).

Example 336

2-(6-(4-(Acetamidomethyl)benzylthio)-3,5-dicyano-4-ethylpyridin-2-ylthio)-2-phenylacetamide Step 1: (4-(Aminomethyl)phenyl)methanol

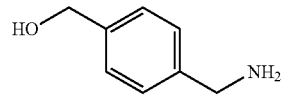

To a suspension of lithium aluminium hydride (7.07 g, 186 mmol) in tetrahydrofuran (400 mL) stirred in air at 0° C. was added a solution of methyl 4-cyanobenzoate (10 g, 62.1 mmol) in tetrahydrofuran (400 mL) dropwise over 15 minutes. The reaction mixture was stirred at 50° C. for 15 hours and then cooled to 0° C. and quenched by the slow addition of water (7 mL), 15% NaOH (7 mL), and water (21 mL). The resulting precipitate was stirred for an additional 30 minutes and filtered. The filtrated was concentrated in vacuo to give (4-(aminomethyl)phenyl)methanol (6.8 g, 80% yield) as a light yellow oil. LCMS m/z=138.0 [M+H]$^+$.

Step 2: N-(4-(Hydroxymethyl)benzyl)acetamide

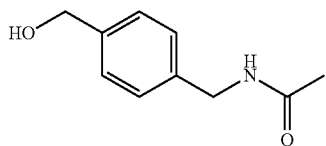

To a solution of (4-(aminomethyl)phenyl)methanol (6.8 g, 49.6 mmol) and triethylamine (20.73 mL, 149 mmol) in dichloromethane (150 mL) stirred in air at 0° C. was added a solution of acetic anhydride (5.57 g, 54.5 mmol) in dichloromethane (150 mL) dropwise over 5 minutes. The reaction mixture was stirred at 25° C. for 12 hours. The reaction mixture was concentrated and the residue was purified by flash chromatography to afford N-(4-(hydroxymethyl)benzyl)acetamide (6.5 g, 73% yield) as a white solid. LCMS m/z=180.0 [M+H]$^+$.

Step 3: N-(4-(Chloromethyl)benzyl)acetamide

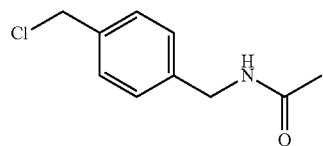

To a solution of N-(4-(hydroxymethyl)benzyl)acetamide (6.5 g, 36.3 mmol) and triethylamine (7.58 mL, 54.4 mmol) in dichloromethane (15 mL) stirred in air at 0° C. was added a solution of methanesulfonyl chloride (4.15 g, 36.3 mmol) in dichloromethane (15 mL) dropwise over 5 minutes. The reaction mixture was stirred at 25° C. for 12 hours. The reaction mixture was concentrated and the crude was purified by column chromatography (eluted by MeOH-DCM=0-2.5%) to afford N-(4-(chloromethyl)benzyl)acetamide (5.3 g) as a white solid. LCMS m/z=198.1 [M+H]$^+$.

Step 4: S-4-(Acetamidomethyl)benzyl ethanethioate

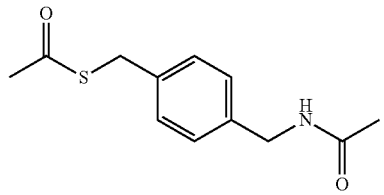 [SMILES: CC(=O)NCc1ccc(CSC(C)=O)cc1]

To a solution of N-(4-(chloromethyl)benzyl)acetamide (2.96 g, 14.98 mmol) in N,N-dimethylformamide (40 mL) stirred in air at room temperature was added potassium ethanethioate (1.88 g, 16.47 mmol). The reaction mixture was stirred at 25° C. for 0.5 hour. The reaction mixture was concentrated and the residue was purified by flash column chromatography to afford S-4-(acetamidomethyl)benzyl ethanethioate (3.4 g, 96%) as a white solid. LCMS m/z=238.0 [M+H]$^+$.

Step 5: Pyridin-1-ium (E)-1,1-dicyano-2-(cyano (isocyano)methylene)butan-1-ide

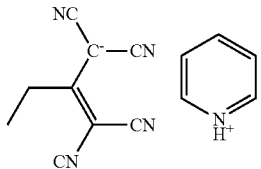

To a solution of malononitrile (25 g, 378 mmol) and 1,1,1-triethoxybutane (40 g, 210 mmol) in pyridine (16 mL) stirred in air at 20° C. The reaction mixture was stirred at 120° C. for 1 hour. The mixture was concentrated, EtOAc was added, and the solid was filtered to obtain pyridin-1-ium (E)-1,1-dicyano-2-(cyano(isocyano)methylene)butan-1-ide (10 g, 19%) which was used in the next step without further purification. $^1$H NMR (400 MHz, DMSO) δ ppm 8.93 (d, J=5.1 Hz, 2H), 8.62-8.54 (m, 1H), 8.06 (dd, J=7.7, 6.6 Hz, 1H), 2.33 (q, J=7.5 Hz, 2H), 1.09 (t, J=7.6 Hz, 3H).

Step 6: 2-Amino-6-chloro-4-ethylpyridine-3,5-dicarbonitrile

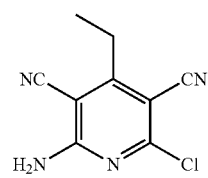

A solution of concentrated hydrochloric acid (67.0 mL) and Pyridin-1-ium (E)-1,1-dicyano-2-(cyano(isocyano) methylene)butan-1-ide (10 g, 40.1 mmol) in acetone (100 mL) was stirred at 50° C. for 16 hours. The dark brown mixture was cooled, and the precipitated solid was filtered to obtain 2-amino-6-chloro-4-ethylpyridine-3,5-dicarbonitrile (7 g, 84%). LCMS m/z=205.2 [M−H]$^−$.

Step 7: N-(4-((6-Amino-3,5-dicyano-4-ethylpyridin-2-ylthio)methyl)benzyl)acetamide

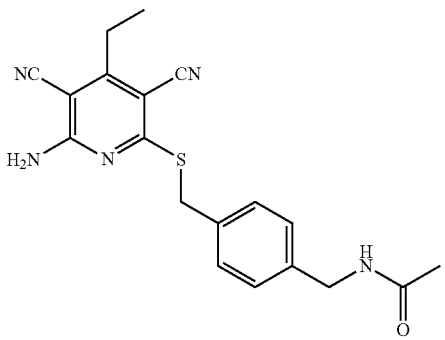 [SMILES: CCc1c(C#N)c(N)nc(SCc2ccc(CNC(C)=O)cc2)c1C#N]

To a solution of S-4-(acetamidomethyl)benzyl ethanethioate (3.4 g, 14.33 mmol) in methanol (30 mL) stirred in air at 0° C. was added a solution of sodium methoxide (0.77 g, 14.33 mmol) in methanol (30 mL). The reaction mixture was stirred at 0° C. for 2 hours. The reaction mixture was concentrated to give a residue which was dissolved in N,N-dimethylformamide (15 mL). To the solution was added 2-amino-6-chloro-4-ethylpyridine-3,5-dicarbonitrile (2.96 g, 14.33 mmol) and triethylamine (3.99 mL, 28.7 mmol). The reaction mixture was stirred at 25° C. for 12 hours. The reaction mixture was evaporated and the residue partitioned between dichloromethane (100 mL) and water (50 mL). The organic phase was washed with brine (25 mL), dried over sodium sulfate, filtered, and evaporated in vacuo to give the crude product as a yellow solid which was purified by flash chromatography to afford N-(4-((6-amino-3,5-dicyano-4-ethylpyridin-2-ylthio)methyl)benzyl)acetamide (3.4 g, 96%) as a white solid. LCMS m/z=365.8 [M+H]$^+$.

Step 8: N-(4-((6-Chloro-3,5-dicyano-4-ethylpyridin-2-ylthio)methyl)benzyl)acetamide

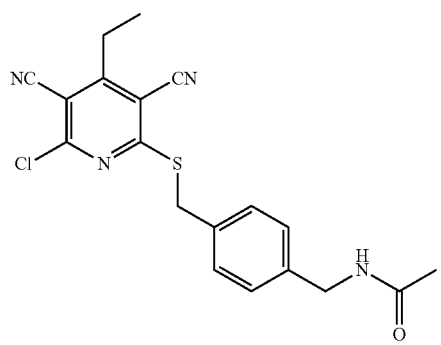 [SMILES: CCc1c(C#N)c(Cl)nc(SCc2ccc(CNC(C)=O)cc2)c1C#N]

To a solution of copper(II) chloride (806 mg, 6 mmol) in CH$_3$—CN (10 mL) stirred at 0° C. was added a solution of tert-butyl nitrite (618 mg, 6 mmol) in CH$_3$—CN (10 mL). The resulting mixture was stirred at 0° C. for 0.5 hour. To the mixture was added a solution of N-(4-((6-amino-3,5-dicyano-4-ethylpyridin-2-ylthio)methyl)benzyl)acetamide (730 mg, 2 mmol). The reaction mixture was stirred at 60° C. for 2 hours. After concentration, the crude product was purified by column chromatography to afford N-(4-((6-chloro-3,5-dicyano-4-ethylpyridin-2-ylthio)methyl)benzyl)acetamide (345 mg, 45% yield) as a light yellow solid. LCMS m/z=384.8 [M+H]$^+$.

Step 9: 2-(6-(4-(Acetamidomethyl)benzylthio)-3,5-dicyano-4-ethylpyridin-2-ylthio)-2-phenyl acetamide

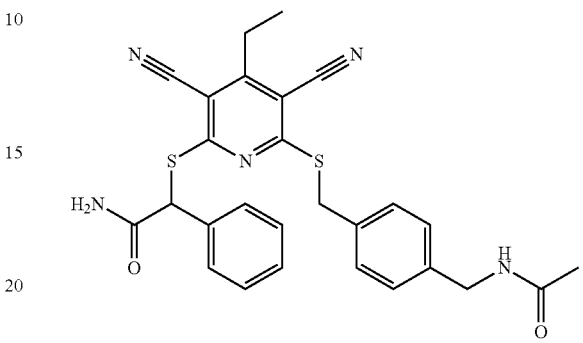

To a solution of S-(2-amino-2-oxo-1-phenylethyl) ethanethioate (synthesis described in example 62, step 5, 188 mg, 0.90 mmol) in methanol (10 mL) stirred in air at 0° C. was added a solution of sodium methoxide (33 wt % in methanol, 0.15 mL, 0.90 mmol). The reaction mixture was stirred at 0° C. for 2 hours. After concentration, the residue was dissolved in DMF, and to the mixture were added N-(4-(((6-chloro-3,5-dicyano-4-ethylpyridin-2-yl)thio)methyl)benzyl)acetamide (345 mg, 0.90 mmol) and triethylamine (0.25 mL, 1.79 mmol). The reaction mixture was stirred at 25° C. for 12 hours. The reaction mixture was partitioned between EtOAc (50 mL) and water (15 mL), and the organic phase was washed with water (15 mL×2), brine (15 mL), dried over Na$_2$SO$_4$, filtered and concentrated. The crude was purified by flash column chromatography to afford 2-(6-(4-(acetamidomethyl)benzylthio)-3,5-dicyano-4-ethylpyridin-2-ylthio)-2-phenylacetamide (105 mg, 22%) as a white solid. LCMS m/z=515.8 [M+H]$^+$. $^1$H NMR (400 MHz, DMSO-d$_6$) δ ppm 8.37 (t, J=5.9 Hz, 1H), 8.04 (s, 1H), 7.54 (d, J=6.7 Hz, 2H), 7.47 (s, 1H), 7.42-7.35 (m, 5H), 7.26 (d, J=8.0 Hz, 2H), 5.80 (s, 1H), 4.67-4.55 (m, 2H), 4.25 (d, J=5.9 Hz, 2H), 2.81 (q, J=7.5 Hz, 2H), 1.87 (s, 3H), 1.23 (t, J=7.6 Hz, 3H).

Example 337

4-Ethyl-2-((4-(pyridin-3-yl)benzyl)thio)-6-(4-(pyrrolidin-1-yl)piperidin-1-yl)pyridine-3,5-dicarbonitrile Step 1: tert-Butyl 4-(pyrrolidin-1-yl)piperidine-1-carboxylate

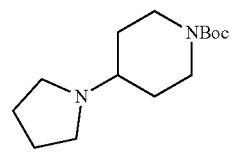 [SMILES: CC(C)(C)OC(=O)N1CCC(N2CCCC2)CC1]

A solution of tert-butyl 4-oxopiperidine-1-carboxylate (5.49 g, 27.5 mmol) and pyrrolidine (1.78 g, 25.03 mmol) and sodium triacetoxyborohydride (10.61 g, 50.1 mmol) in dichloromethane (30 mL) was stirred in air at 20° C. for 18 hours. The mixture was concentrated and the residue was purified by Flash column chromatography (eluted by MeOH-DCM 0-5%) to afford tert-butyl 4-(pyrrolidin-1-yl)piperidine-1-carboxylate (3.1 g, 49%) pale-yellow oil. LCMS m/z=255.0 [M+H]$^+$.

Step 2: 4-(Pyrrolidin-1-yl)piperidine

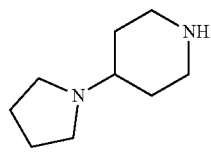 [SMILES: C1CCN(C2CCNCC2)C1]

To a solution of tert-butyl 4-(pyrrolidin-1-yl)piperidine-1-carboxylate (3.1 g, 12.19 mmol) in methanol (20 mL) was added a solution of hydrogen chloride in MeOH (5 mL, 33%). The reaction mixture was stirred at 20° C. for 3 hours then concentrated to give 4-(pyrrolidin-1-yl)piperidine, 2 Hydrochloride (3 g). LCMS m/z=155.2 [M+H]$^+$.

Step 3: 2-Chloro-4-ethyl-6-(4-(pyrrolidin-1-yl)piperidin-1-yl)pyridine-3,5-dicarbonitrile

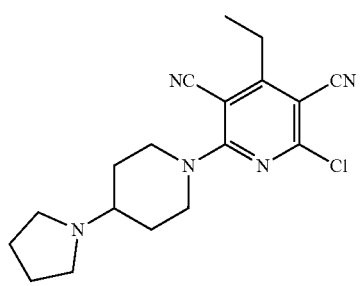 [SMILES: CCc1c(C#N)c(Cl)nc(N2CCC(N3CCCC3)CC2)c1C#N]

To a solution of 4-(pyrrolidin-1-yl)piperidine di-HCl salt (3 g, 13.21 mmol) and 2,6-dichloro-4-ethylpyridine-3,5-dicarbonitrile (synthesis described in example 3 step 2, 2.99 g, 13.21 mmol) in N,N-dimethylformamide (20 mL) was added triethylamine (4.01 g, 39.6 mmol) dropwise. The reaction mixture was stirred at 20° C. for 18 hours. The mixture was concentrated and purified by Flash column chromatography (eluted by MeOH-DCM 0-1%) to give 2-chloro-4-ethyl-6-(4-(pyrrolidin-1-yl)piperidin-1-yl)pyridine-3,5-dicarbonitrile (3 g, 66%) as a yellow solid. LCMS m/z=343.6 [M+H]$^+$.

Step 4: 2-((4-Bromobenzyl)thio)-4-ethyl-6-(4-(pyrrolidin-1-yl)piperidin-1-yl)pyridine-3,5-dicarbonitrile

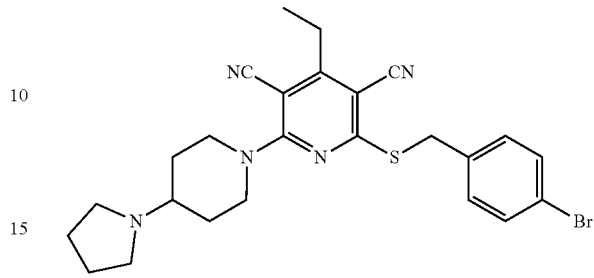

A solution of 2-chloro-4-ethyl-6-(4-(pyrrolidin-1-yl)piperidin-1-yl)pyridine-3,5-dicarbonitrile (3 g, 8.72 mmol), triethylamine (1.324 g, 13.09 mmol) and (4-bromophenyl)methanethiol (1.95 g, 9.60 mmol) in N,N-dimethylformamide (20 mL) was stirred at 20° C. for 18 hours then concentrated. The residue was purified by Flash column chromatography (eluted by MeOH-DCM 0-1%) to give 2-((4-bromobenzyl)thio)-4-ethyl-6-(4-(pyrrolidin-1-yl)piperidin-1-yl)pyridine-3,5-dicarbonitrile as a yellow solid (2.5 g, 56%). LCMS m/z=509.8 [M+H]$^+$.

Step 5: 4-Ethyl-2-((4-(pyridin-3-yl)benzyl)thio)-6-(4-(pyrrolidin-1-yl)piperidin-1-yl)pyridine-3,5-dicarbonitrile

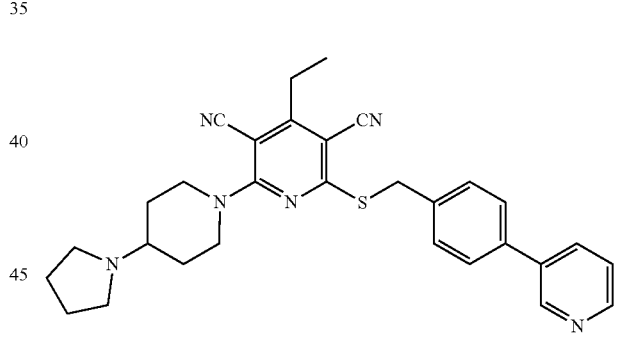

To a solution of 1,1'-bis(diphenylphosphino)ferrocenedichloro palladium(II) dichloromethane complex (71 mg, 0.01 mmol), pyridin-3-ylboronic acid (58 mg, 0.47 mmol) and 2-((4-bromobenzyl)thio)-4-ethyl-6-(4-(pyrrolidin-1-yl)piperidin-1-yl)pyridine-3,5-dicarbonitrile (500 mg, 0.98 mmol) in 1,4-dioxane (10 mL) was added a solution of sodium carbonate (156 mg, 1.47 mmol) in water (2 mL) at 20° C. The mixture was stirred at 100° C. for 18 hours. The mixture was concentrated under vacuum and purified by silica gel column to afford 4-ethyl-2-((4-(pyridin-3-yl)benzyl)thio)-6-(4-(pyrrolidin-1-yl)piperidin-1-yl)pyridine-3,5-dicarbonitrile (117 mg, 23%) as a light yellow solid. LCMS m/z=508.9 [M+H]$^+$. $^1$H NMR (400 MHz, CDCl$_3$) δ ppm 8.83 (s, 1H), 8.60 (d, J=4.6 Hz, 1H), 7.87 (d, J=7.9 Hz, 1H), 7.56 (d, J=8.2 Hz, 2H), 7.48 (d, J=8.2 Hz, 2H), 7.37 (dd, J=7.9, 4.8 Hz, 1H), 4.61 (d, J=13.2 Hz, 2H), 4.46 (s, 2H), 3.20 (t, J=12.4 Hz, 2H), 2.92 (q, J=7.6 Hz, 2H), 2.85-2.45 (m, 4H), 2.20-1.67 (m, 9H), 1.33 (t, J=7.6 Hz, 3H).

Example 338

4-Ethyl-2-((4-(pyridin-4-yl)benzyl)thio)-6-(4-(pyrrolidin-1-yl)piperidin-1-yl)pyridine-3,5-dicarbonitrile

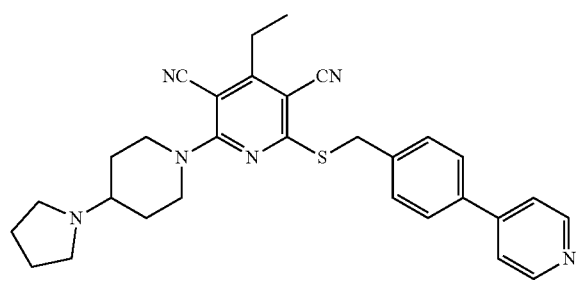 [SMILES: CCc1c(C#N)c(SCc2ccc(-c3ccncc3)cc2)nc(N2CCC(N3CCCC3)CC2)c1C#N]

To a solution of 1,1'-bis(diphenylphosphino)ferrocenedichloro palladium(II) dichloromethane complex (50 mg, 0.07 mmol), pyridin-4-ylboronic acid (101 mg, 0.82 mmol) and 2-((4-bromobenzyl)thio)-4-ethyl-6-(4-(pyrrolidin-1-yl)piperidin-1-yl)pyridine-3,5-dicarbonitrile (synthesis described in example 337 step 4, 350 mg, 0.69 mmol) in 1,4-dioxane (10 mL) was added a solution of sodium carbonate (109 mg, 1.03 mmol) in water (2 mL) at 20° C. The mixture was stirred at 100° C. for 18 hours. The mixture was concentrated under vacuum and purified by silica gel column to afford 4-ethyl-2-((4-(pyridin-4-yl)benzyl)thio)-6-(4-(pyrrolidin-1-yl)piperidin-1-yl)pyridine-3,5-dicarbonitrile (118 mg, 33%) as a light yellow solid. LCMS m/z=508.9 [M+H]$^+$. $^1$H NMR (400 MHz, CDCl$_3$) δ ppm 8.66 (dd, J=4.6, 1.5 Hz, 2H), 7.62 (d, J=8.2 Hz, 2H), 7.54-7.45 (m, 4H), 4.62 (d, J=12.0 Hz, 2H), 4.46 (s, 2H), 3.18 (t, J=12.6 Hz, 2H), 2.99-2.50 (m, 6H), 2.18-1.70 (m, 9H), 1.33 (t, J=7.6 Hz, 2H).

Example 339

2-Amino-N-(1-(3,5-dicyano-4-ethyl-6-((4-sulfamoylbenzyl)thio)pyridin-2-yl)piperidin-4-yl)acetamide hydrochloride

Step 1: 2-(4-Aminopiperidin-1-yl)-6-chloro-4-ethylpyridine-3,5-dicarbonitrile, Hydrochloride

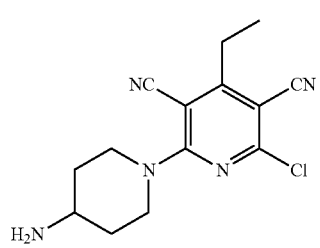 [SMILES: CCc1c(C#N)c(Cl)nc(N2CCC(N)CC2)c1C#N]

To a solution of tert-butyl (1-(6-chloro-3,5-dicyano-4-ethylpyridin-2-yl)piperidin-4-yl)carbamate (synthesis described in example 81, step 1, 1.5 g, 3.57 mmol) in 1,4-dioxane (5 mL), 4 M HCl in 1,4 dioxane (12 mL, 48.0 mmol) was added at room temperature and stirred for 4 hours. The reaction mixture was concentrated completely, and the residue was washed with diethyl ether (2×30 mL) to afford 2-(4-aminopiperidin-1-yl)-6-chloro-4-ethylpyridine-3,5-dicarbonitrile, Hydrochloride (1.03 g, 3.12 mmol, 87% yield) as off white solid. LCMS m/z=290.1 [M+H]$^+$.

Step 2: tert-Butyl (2-((1-(6-chloro-3,5-dicyano-4-ethylpyridin-2-yl)piperidin-4-yl)amino)-2-oxoethyl)carbamate

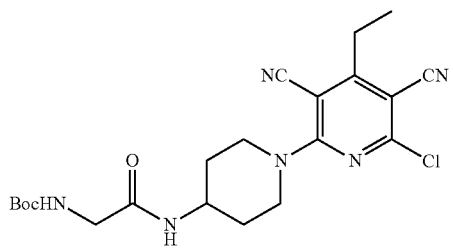 [SMILES: CCc1c(C#N)c(Cl)nc(N2CCC(NC(=O)CNC(=O)OC(C)(C)C)CC2)c1C#N]

To a solution of 2-(4-aminopiperidin-1-yl)-6-chloro-4-ethylpyridine-3,5-dicarbonitrile, Hydrochloride (1 g, 3.07 mmol) in N,N-dimethylformamide (15 mL) were added HATU (1.748 g, 4.60 mmol), diisopropylethylamine (1.071 mL, 6.13 mmol) and 2-((tert-butoxycarbonyl)amino)acetic acid (0.537 g, 3.07 mmol) at room temperature and the reaction mixture was stirred at room temperature for 16 hours. The reaction mixture was diluted with water (20 mL) and extracted with ethyl acetate (2×20 mL). The organic layers were concentrated to afford tert-butyl (2-((1-(6-chloro-3,5-dicyano-4-ethylpyridin-2-yl)piperidin-4-yl)amino)-2-oxoethyl)carbamate (1.7 g) as an off-white solid. LCMS m/z=447.1 [M+H]$^+$.

Step 3: tert-Butyl (2-((1-(3,5-dicyano-4-ethyl-6-((4-sulfamoylbenzyl)thio)pyridin-2-yl) piperidin-4-yl) amino)-2-oxoethyl)carbamate

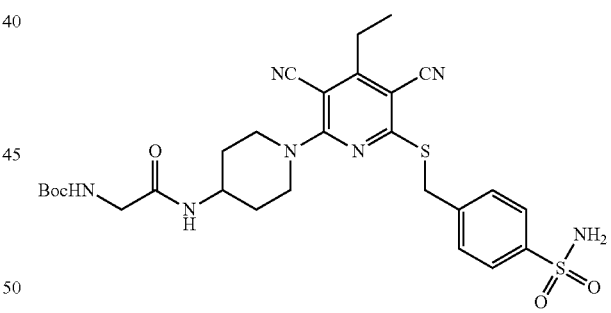

To a solution of tert-butyl (2-((1-(6-chloro-3,5-dicyano-4-ethylpyridin-2-yl)piperidin-4-yl)amino)-2-oxoethyl)carbamate (0.7 g) in N,N-dimethylformamide (5 mL) was added potassium thioacetate (0.308 g, 2.70 mmol) at room temperature. After stirring at room temperature for 2 hours, potassium carbonate (0.372 g, 2.70 mmol) and 4-(bromomethyl)benzenesulfonamide (0.337 g, 1.348 mmol) were added and the reaction mixture was stirred at room temperature for 16 hours. Water (20 mL) was added and the reaction mixture extracted with EtOAc (2×20 mL). The organic layers were dried over anhydrous Na$_2$SO$_4$, filtered and concentrated to dryness under vacuum. The crude material was purified by silica gel column chromatography (100-200 mesh, eluted with 30-40% ethyl acetate in petroleum ether) to afford tert-butyl (2-((1-(3,5-dicyano-4-ethyl- 6-((4-sulfamoylbenzyl)thio)pyridin-2-yl)piperidin-4-yl)amino)-2-oxoethyl)carbamate (420 mg) as an off-white solid. LCMS m/z=614.5 [M+H]⁺.

Step 4: 2-Amino-N-(1-(3,5-dicyano-4-ethyl-6-((4-sulfamoylbenzyl)thio)pyridin-2-yl)piperidin-4-yl)acetamide hydrochloride

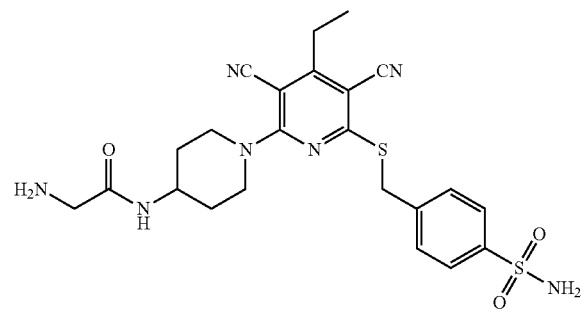 [SMILES: CCc1c(C#N)c(SCc2ccc(S(N)(=O)=O)cc2)nc(N2CCC(NC(=O)CN)CC2)c1C#N]

To a stirred solution of tert-butyl (2-((1-(3,5-dicyano-4-ethyl-6-((4-sulfamoylbenzyl)thio)pyridin-2-yl)piperidin-4-yl)amino)-2-oxoethyl)carbamate (0.4 g) in 1,4-dioxane (5 mL) was added hydrochloric acid (4 M, 1,4-dioxane, 0.332 mL, 1.328 mmol) under nitrogen at 20° C. The reaction mixture was stirred at 25° C. for 2 hours. Diethyl ether (20 mL) was added to the reaction and the mixture filtered to afford 2-amino-N-(1-(3,5-dicyano-4-ethyl-6-((4-sulfamoylbenzyl)thio)pyridin-2-yl)piperidin-4-yl)acetamide hydrochloride (0.230 g) as an off-white solid. LCMS m/z=514.2 [M+H]⁺. ¹H NMR (400 MHz, DMSO-d₆) δ ppm 8.50 (br s, 1H), 8.05 (br s, 3H), 7.78 (d, J=8.55 Hz, 2H), 7.59 (d, J=8.55 Hz, 2H), 7.34 (s, 2H), 4.57 (s, 2H), 4.34 (br d, J=13.59 Hz, 2H), 3.99 (br s, 1H), 3.54 (br s, 2H), 3.41 (br t, J=11.62 Hz, 2H), 2.77 (q, J=7.31 Hz, 2H), 1.91 (br d, J=10.74 Hz, 2H), 1.48 (q, J=9.72 Hz, 2H), 1.22 (t, J=7.56 Hz, 3H).

Example 340

2-((3,5-Dicyano-4-ethyl-6-(methyl((5-oxo-4,5-dihydro-1H-1,2,4-triazol-3-yl)methyl)amino)pyridin-2-yl)thio)-2-phenylacetamide

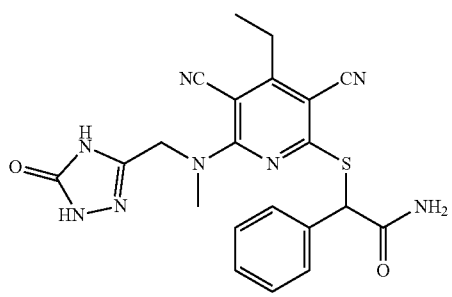 [SMILES: CCc1c(C#N)c(SC(C(N)=O)c2ccccc2)nc(N(C)Cc2n[nH]c(=O)[nH]2)c1C#N]

The first reaction mixture of S-(2-amino-2-oxo-1-phenylethyl) ethanethioate (synthesis described in example 62 step 5, 112 mg, 0.535 mmol) and NaBH₄ (36.8 mg, 0.973 mmol) in ethanol (3 mL) was heated at 60° C. for 25 minutes (bubbles stopped), then cooled down. To a solution of 2,6-dichloro-4-ethylpyridine-3,5-dicarbonitrile (synthesis described in example 3, step 2, 110 mg, 0.487 mmol) in DMF (2.0 mL) was added the slurry solution of 3-((methylamino)methyl)-1H-1,2,4-triazol-5(4H)-one, Hydrochloride (91 mg, 0.535 mmol) and TEA (0.136 mL, 0.973 mmol) in DMF (2.5 mL) slowly. This second reaction mixture was stirred at room temperature for 20 minutes. The first and second reaction mixtures were combined, then stirred overnight. The reaction mixture was diluted with water (30 mL), and stirred for 30 minutes. The solid was filtered and purified by RP-HPLC (5-30% acetonitrile/water, 0.1% NH₄OH in water) to afford 2-((3,5-dicyano-4-ethyl-6-(methyl((5-oxo-4,5-dihydro-1H-1,2,4-triazol-3-yl)methyl)amino)pyridin-2-yl)thio)-2-phenylacetamide (44 mg, 0.098 mmol, 20% yield) as a white solid. LCMS m/z=449.2 [M+H]⁺. ¹H NMR (400 MHz, DMSO-d₆) δ ppm 1.22 (t, J=7.6 Hz, 3H), 2.79 (q, J=7.4 Hz, 2H), 3.33 (s, 3H), 4.68 (d, J=16.5 Hz, 1H), 5.07 (d, J=16.5 Hz, 1H), 5.58 (s, 1H), 7.30-7.40 (m, 4H), 7.44-7.50 (m, 2H), 7.89 (s, 1H), 11.42 (s, 2H).

Example 341

2-((6-(((4H-1,2,4-Triazol-3-yl)methyl)(methyl)amino)-3,5-dicyano-4-ethylpyridin-2-yl)thio)-2-phenylacetamide

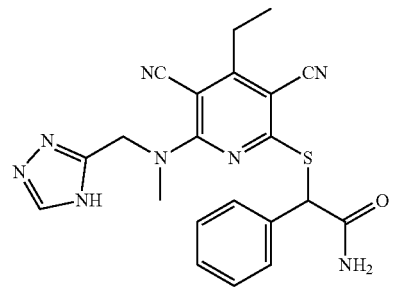 [SMILES: CCc1c(C#N)c(SC(C(N)=O)c2ccccc2)nc(N(C)Cc2nnc[nH]2)c1C#N]

The first reaction mixture of S-(2-amino-2-oxo-1-phenylethyl) ethanethioate (synthesis described in example 62 step 5, 112 mg, 0.535 mmol) and NaBH₄ (36.8 mg, 0.973 mmol) in ethanol (3 mL) was heated at 60° C. for 25 minutes (bubbles stopped), then cooled down. To a solution of 2,6-dichloro-4-ethylpyridine-3,5-dicarbonitrile (synthesis described in example 3, step 2, 110 mg, 0.487 mmol) in DMF (2.0 mL) was added the slurry of N-methyl-1-(4H-1,2,4-triazol-3-yl)methanamine, Hydrochloride (84 mg, 0.535 mmol) and TEA (0.136 mL, 0.973 mmol) in DMF (2.5 mL) slowly. This second reaction mixture was stirred at room temperature for 20 minutes. The first and second reaction mixtures were combined, then stirred for one hour. The reaction mixture was concentrated down and purified by RP-HPLC (10-40% acetonitrile/water, 0.1% NH₄OH in water) to afford 2-((6-(((4H-1,2,4-triazol-3-yl)methyl)(methyl)amino)-3,5-dicyano-4-ethylpyridin-2-yl)thio)-2-phenylacetamide (75 mg, 0.173 mmol, 36% yield) as a white solid. LCMS m/z=433.2 [M+H]⁺. ¹H NMR (400 MHz, DMSO-d₆) δ ppm 1.21 (t, J=7.6 Hz, 3H), 2.77 (q, J=7.6 Hz, 2H), 3.41 (s, 3H), 4.91 (d, J=16.2 Hz, 1H), 5.35 (d, J=16.2 Hz, 1H), 5.60 (s, 1H), 7.27-7.40 (m, 5H), 7.42-7.47 (m, 2H), 7.95 (s, 1H), 8.44 (br. s., 1H).

Example 342

2-((3,5-Dicyano-4-ethoxy-6-methylpyridin-2-yl)thio)-2-phenylacetamide

Step 1: 2-Amino-4-ethoxy-6-methylpyridine-3,5-dicarbonitrile

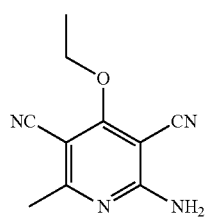

2-Amino-6-chloro-4-ethoxypyridine-3,5-dicarbonitrile (synthesis described in example 192, step 1, 370 mg, 1.662 mmol), 2,4,6-trimethyl-1,3,5,2,4,6-trioxatriborinane (0.35 mL, 2.504 mmol), cesium carbonate (1820 mg, 5.59 mmol), and $PdCl_2(dppf)$-$CH_2Cl_2$ adduct (127 mg, 0.156 mmol) were added to a mirowave vial and suspended in 1,4-dioxane (18 mL): Water (1.00 mL). The mixture was heated in a microwave reactor for 1 hour at 90° C. Filtered through a pad of Celite® and worked up the filtrate with brine and EtOAc (3×). The combined organics were washed with brine, dried over $MgSO_4$, filtered and concentrated to a residue. This residue was purified on C18 Aq. Column using reverse phase Isco Chromatography (0-60-70-100% 0.1% aq. $NH_4OH$/Acetonitrile). The desired fractions were pooled and concentrated to afford 2-amino-4-ethoxy-6-methylpyridine-3,5-dicarbonitrile (95 mg, 0.470 mmol, 28% yield). LCMS m/z=203.0 $[M+H]^+$.

Step 2: 4-Ethoxy-2-mercapto-6-methylpyridine-3,5-dicarbonitrile

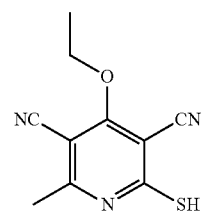

2-Amino-4-ethoxy-6-methylpyridine-3,5-dicarbonitrile (87 mg, 0.430 mmol) and copper(II) chloride (124 mg, 0.922 mmol) were suspended in acetonitrile (20 mL) and the mixture was heated to 50° C. tert-Butyl nitrite (0.13 mL, 0.987 mmol) was added dropwise to the heated mixture and the suspension was allowed to stir at 60° C. for 30 minutes. Cooled to 0° C. and diluted with EtOAc and brine. Extracted with EtOAc (4×) and the combined organics were washed with brine, dried over $MgSO_4$, filtered and concentrated to produce a residue. Potassium thioacetate (102 mg, 0.893 mmol) was added and suspended in EtOH (15 mL) along with TEA (0.070 mL, 0.502 mmol). The mixture was heated to 60° C. for 25 minutes. Filtered off undesired salts and the filtrate was concentrated to a residue that was purified on C18 Aq. Column using reverse phase Isco Chromatography (0-65-100% 0.1% aq. $NH_4OH$/Acetonitrile). The desired fractions were pooled and concentrated to afford crude 4-ethoxy-2-mercapto-6-methylpyridine-3,5-dicarbonitrile (65 mg, 78% purity). LCMS m/z=242.4 $[M+Na]^+$.

Step 3: 2-((3,5-Dicyano-4-ethoxy-6-methylpyridin-2-yl)thio)-2-phenylacetamide

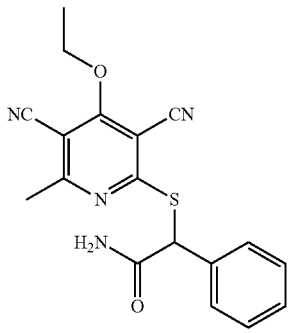

4-Ethoxy-2-mercapto-6-methylpyridine-3,5-dicarbonitrile (65 mg, 78% purity) 2-chloro-2-phenylacetamide (46 mg, 0.271 mmol), and sodium bicarbonate (95 mg, 1.131 mmol) were suspended in N,N-dimethylformamide (6 mL) and the mixture was stirred for 5 hours at room temperature. Added the material directly to a RP Isco C18 column for purification. (0-55-100% 0.1% aq. $NH_4OH$/Acetonitrile). The desired fractions were pooled and concentrated to afford 2-((3,5-dicyano-4-ethoxy-6-methylpyridin-2-yl)thio)-2-phenylacetamide (34 mg). LCMS m/z=353.1 $[M+H]^+$. $^1H$ NMR (400 MHz, DMSO-$d_6$) δ ppm 7.94 (s, 1H) 7.52-7.60 (m, 2H) 7.27-7.42 (m, 4H) 5.72 (s, 1H) 4.72 (q, J=6.84 Hz, 2H) 2.65 (s, 3H) 1.39 (t, J=6.97 Hz, 3H).

Example 343

2-(4-(((3,5-Dicyano-4-ethyl-6-(4-methyl-1,4-diazepan-1-yl)pyridin-2-yl)thio)methyl)phenyl)-N-(2-hydroxyethyl)acetamide Step 1: 2-(4-(((3,5-Dicyano-4-ethyl-6-(4-methyl-1,4-diazepan-1-yl)pyridin-2-yl)thio)methyl)phenyl)acetic acid

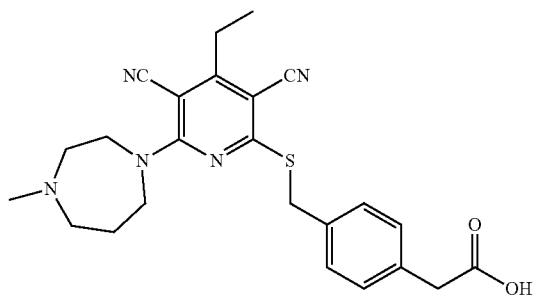 [SMILES: CCc1c(C#N)c(SCc2ccc(CC(=O)O)cc2)nc(N2CCCN(C)CC2)c1C#N]

To a suspension of 4-ethyl-2-mercapto-6-(4-methyl-1,4-diazepan-1-yl)pyridine-3,5-dicarbonitrile (synthesis described in example 69, step 1, 232 mg, 0.770 mmol) and $Et_3N$ (0.107 mL, 0.770 mmol) in chloroform (1 mL) at 0° C. was added a solution of 2-(4-(bromomethyl)phenyl)acetic acid (141 mg, 0.616 mmol) in chloroform (2.5 mL). The reaction mixture was then stirred at 0° C. overnight. After stirring overnight at 0° C., the reaction mixture was warmed to room temperature. The reaction mixture was filtered. The filtrate was concentrated. The crude was purified by reverse phase HPLC (Gilson, 30 mm×50 mm Gemini Column, NH₄OH modifier) to obtain 2-(4-(((3,5-dicyano-4-ethyl-6-(4-methyl-1,4-diazepan-1-yl)pyridin-2-yl)thio)methyl)phenyl)acetic acid (126 mg) as a white solid. LCMS m/z=450.3 [M+H]⁺.

Step 2: 2-(4-(((3,5-Dicyano-4-ethyl-6-(4-methyl-1,4-diazepan-1-yl)pyridin-2-yl)thio)methyl)phenyl)-N-(2-hydroxyethyl)acetamide

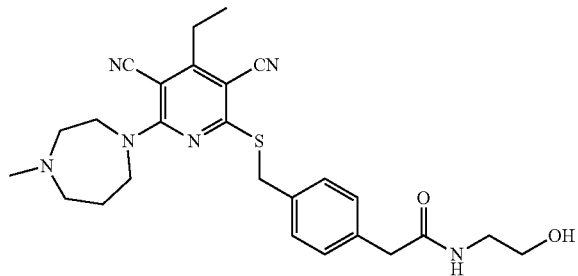 [SMILES: CCc1c(C#N)c(SCc2ccc(CC(=O)NCCO)cc2)nc(N2CCCN(C)CC2)c1C#N]

To a solution of 2-(4-(((3,5-dicyano-4-ethyl-1,4-diazepan-1-yl)pyridin-2-yl)thio)methyl)phenyl)acetic acid (50 mg, 0.111 mmol) in N,N-dimethylformamide (0.7 mL) at room temperature was added HATU (44 mg, 0.116 mmol). The reaction mixture was then stirred at room temperature for 20 minutes at which time ethanolamine (7.2 µL, 0.119 mmol) was added. The reaction mixture was then stirred at room temperature while progress was monitored by LCMS. After 4 hours, the mixture was filtered, and the filtrate was purified by reverse phase HPLC (Gilson, 30 mm×50 mm Gemini Column, NH₄OH modifier) to afford 2-(4-(((3,5-dicyano-4-ethyl-6-(4-methyl-1,4-diazepan-1-yl)pyridin-2-yl)thio)methyl)phenyl)-N-(2-hydroxyethyl)acetamide (41 mg) as a white solid. LCMS m/z=493.3 [M+H]⁺. ¹H NMR (400 MHz, DMSO-d₆) δ ppm 8.06 (t, J=5.45 Hz, 1H), 7.28-7.34 (m, J=8.11 Hz, 2H), 7.15-7.25 (m, J=8.11 Hz, 2H), 4.69 (t, J=5.45 Hz, 1H), 4.47 (s, 2H), 3.82-3.95 (m, 4H), 3.36-3.42 6 (m, 4H), 3.10 (q, J=6.08 Hz, 2H), 2.78 (q, J=7.60 Hz, 2H), 2.62-2.68 (m, 2H), 2.48 (d, J=5.58 Hz, 2H), 2.24 (s, 3H), 1.88-1.97 (m, 2H), 1.22 (t, J=7.60 Hz, 3H).

Example 344

2-(((1H-Indol-5-yl)methyl)thio)-4-ethyl-6-(4-(pyrrolidin-1-yl)piperidin-1-yl)pyridine-3,5-dicarbonitrile Step 1: tert-Butyl 5-formyl-1H-indole-1-carboxylate

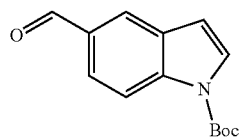 [SMILES: CC(C)(C)OC(=O)n1ccc2cc(C=O)ccc21]

To a solution of 1H-indole-5-carbaldehyde (2.5 g, 17.22 mmol), triethylamine (4.36 g, 43.1 mmol) and N,N-dimethylpyridin-4-amine (0.021 g, 0.172 mmol) in dichloromethane (30 mL) was added N,N-dimethylpyridin-4-amine (0.021 g, 0.172 mmol). The reaction mixture was stirred overnight at room temperature. The resulting solution was diluted with water (30 mL), extracted with ethyl acetate (3×20 mL). The organic layers were combined, washed with aqueous sodium carbonate and brine, dried, filtered, and concentrated under vacuum to afford tert-butyl 5-formyl-1H-indole-1-carboxylate (2.96 g, 12.06 mmol, 70% yield) as a yellow oil. LCMS m/z=246.1 [M+H]⁺.

Step 2: tert-Butyl 5-(hydroxymethyl)-1H-indole-1-carboxylate

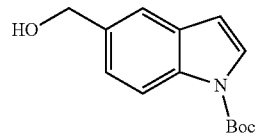 [SMILES: CC(C)(C)OC(=O)n1ccc2cc(CO)ccc21]

To a solution of tert-butyl 5-formyl-1H-indole-1-carboxylate (3.0 g, 12.23 mmol) in methanol (30 mL) was added sodium tetrahydroborate (0.463 g, 12.23 mmol) at 0° C. The reaction mixture was stirred at 0° C. for 3 hours then overnight at room temperature. The resulting solution was diluted with water (40 mL), then extracted with ethyl acetate (3×30 mL). The organic layers were combined, washed with aqueous sodium carbonate and brine, dried and concentrated under vacuum to afford tert-butyl 5-(hydroxymethyl)-1H-indole-1-carboxylate (2.5 g, 10.11 mmol, 83% yield) as a yellow oil. LCMS m/z=270.3 [M+Na]⁺.

Step 3: 2-Chloro-4-ethyl-6-(4-(pyrrolidin-1-yl)piperidin-1-yl)pyridine-3,5-dicarbonitrile

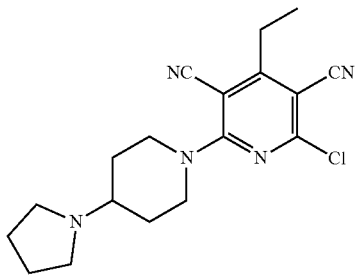 [SMILES: CCc1c(C#N)c(Cl)nc(N2CCC(N3CCCC3)CC2)c1C#N]

To a solution of 2,6-dichloro-4-ethylpyridine-3,5-dicarbonitrile (synthesis described in example 3 step 2, 500 mg, 2.21 mmol) and triethylamine (336 mg, 3.32 mmol) in acetonitrile (20 mL) was added 4-(pyrrolidin-1yl)piperidine (341 mg, 2.21 mmol). The reaction mixture was stirred overnight at room temperature. The resulting solution was diluted with water (50 mL), then extracted with ethyl acetate (3×20 mL). The organic layers were combined, washed with aqueous sodium carbonate and brine, dried, filtered, and concentrated under vacuum. The residue was applied on a silica gel column (eluted with ethyl acetate/hexane 1/20) to afford 2-chloro-4-ethyl-6-(4-(pyrrolidin-1-yl)piperidin-1-yl)pyridine-3,5-dicarbonitrile (620 mg, 1.80 mmol, 82% yield) as a yellow solid. LCMS m/z=344.2 [M+H]⁺.

Step 4: tert-Butyl 5-(((3,5-dicyano-4-ethyl-6-(4-(pyrrolidin-1-yl)piperidin-1-yl)pyridin-2-yl)thio)methyl)-1H-indole-1-carboxylate

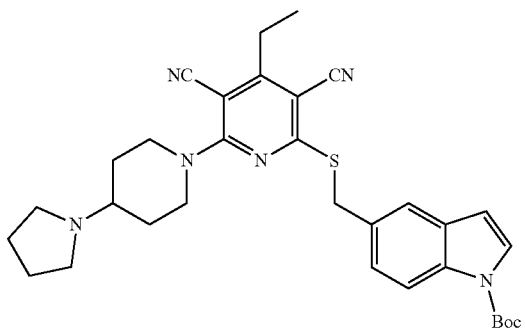 [SMILES: CCc1c(C#N)c(SCc2ccc3c(ccn3C(=O)OC(C)(C)C)c2)nc(N2CCC(N3CCCC3)CC2)c1C#N]

To a solution of tert-butyl 5-(hydroxymethyl)-1H-indole-1-carboxylate (2.8 g, 11.32 mmol), triethylamine (1.719 g, 16.98 mmol) in dichloromethane (30 mL) was added dropwise methanesulfonyl chloride (1.297 g, 11.32 mmol) at 0° C. The reaction mixture was stirred for 3 hours at room temperature. The resulting solution was diluted with water (20 mL), extracted with ethyl acetate (3×15 mL). The organic layers were combined, washed with aqueous sodium carbonate and brine, dried and concentrated under vacuum to afford a yellow oil (3.1 g). To a solution of 2-chloro-4-ethyl-6-(4-(pyrrolidin-1-yl)piperidin-1-yl)pyridine-3,5-dicarbonitrile (620 mg, 1.80 mmol) in N,N-dimethylformamide (15 mL) was added potassium ethanethioate (247 mg, 2.16 mmol). After the reaction mixture stirring 30 minutes at room temperature the yellow oil above (645 mg) and triethylamine (456 mg, 4.51 mmol) were added to the reaction, and the reaction mixture was stirred overnight at room temperature. Water (20 mL) was added and the resulting solution was extracted with ethyl acetate (3×20 mL). The organic layers were combined, washed with aqueous sodium carbonate and brine, dried, filtered, and concentrated under vacuum. The residue was purified on a silica gel column (eluted with ethyl MeOH/DCM 1/20) to afford tert-butyl 5-(((3,5-dicyano-4-ethyl-6-(4-(pyrrolidin-1-yl)piperidin-1-yl)pyridin-2-yl)thio)methyl)-1H-indole-1-carboxylate (340 mg, 0.60 mmol) as a yellow solid. LCMS m/z=571.4 [M+H]$^+$.

Step 5: 2-(((1H-Indol-5-yl)methyl)thio)-4-ethyl-6-(4-(pyrrolidin-1-yl)piperidin-1-yl)pyridine-3,5-dicarbonitrile

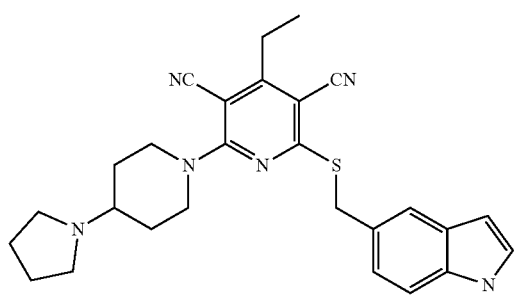 [SMILES: CCc1c(C#N)c(SCc2ccc3[nH]ccc3c2)nc(N2CCC(N3CCCC3)CC2)c1C#N]

A solution of tert-butyl 5-(((3,5-dicyano-4-ethyl-6-(4-(pyrrolidin-1-yl)piperidin-1-yl)pyridin-2-yl)thio)methyl)-1H-indole-1-carboxylate (120 mg, 0.21 mmol) in DCM (3 mL) was refluxed. Then trifluoroacetic acid (0.016 mL, 0.21 mmol) was added to the reaction and the mixture was refluxed for 10 minutes. The reaction mixture was cooled to room temperature and the pH of the solution was adjusted to 10~11 with Na$_2$CO$_3$. The resulting solution was extracted with DCM (3×10 mL). The organic layers were combined, washed with aqueous sodium carbonate and brine, dried and concentrated under vacuum. The residue was purified by prep-HPLC to afford 2-(((1H-indol-5-yl)methyl)thio)-4-ethyl-6-(4-(pyrrolidin-1-yl)piperidin-1-yl)pyridine-3,5-dicarbonitrile (30 mg, 0.06 mmol, 30% yield) as a yellow solid. LCMS m/z=471.1 [M+H]$^+$. $^1$H NMR (400 MHz, CDCl$_3$) δ ppm 8.36 (s, 1H), 7.65 (s, 1H), 7.38 (d, J=8.3 Hz, 1H), 7.27-7.15 (m, 2H), 6.53 (s, 1H), 4.62 (d, J=13.5 Hz, 2H), 4.55 (s, 2H), 3.26 (t, J=11.7 Hz, 2H), 2.91 (q, J=7.6 Hz, 2H), 2.65 (s, 4H), 2.42 (s, 1H), 2.04 (d, J=11.0 Hz, 2H), 1.85 (s, 4H), 1.70-1.59 (m, 2H), 1.33 (t, J=7.6 Hz, 3H).

Example 345

4-(((6-(4-Aminopiperidin-1-yl)-3,5-dicyano-4-ethylpyridin-2-yl)thio)methyl) benzenesulfonamide

Step 1: tert-Butyl (1-(3,5-dicyano-4-ethyl-6-((4-sulfamoylbenzyl)thio)pyridin-2-yl)piperidin-4-yl) carbamate

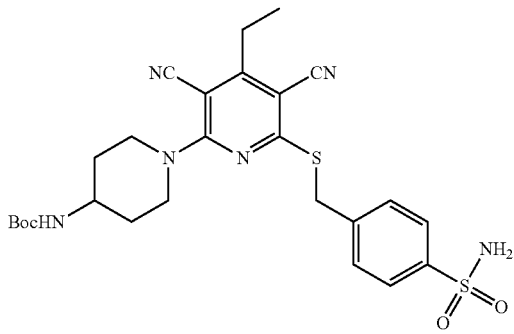 [SMILES: CCc1c(C#N)c(SCc2ccc(S(N)(=O)=O)cc2)nc(N2CCC(NC(=O)OC(C)(C)C)CC2)c1C#N]

To a solution of tert-butyl (1-(6-chloro-3,5-dicyano-4-ethylpyridin-2-yl)piperidin-4-yl)carbamate (synthesis described in Example 81 step 1, 1.5 g) in N,N-dimethylformamide (10 mL) was added potassium thioacetate (0.659 g, 5.77 mmol) at room temperature and stirred at room temperature for 2 hours. To the reaction mixture was added potassium carbonate (1.063 g, 7.69 mmol) and 4-(bromomethyl)benzenesulfonamide (0.962 g, 3.85 mmol) and the resulting mixture was stirred at room temperature for 16 hours. Water (20 mL) was added and the mixture was extracted with ethyl acetate (2×20 mL). The organic layers were dried over anhydrous Na$_2$SO$_4$, filtered and concentrated. The crude compound was purified by silica gel column chromatography (100-200, eluted with 30-40% ethyl acetate/petroleum ether) to afford tert-butyl (1-(3,5-dicyano-4-ethyl-6-((4-sulfamoylbenzyl)thio)pyridin-2-yl)piperidin-4-yl)carbamate (750 mg) as an off-white solid. LCMS m/z=557.0 [M+H]$^+$.

Step 2: 4-(((6-(4-Aminopiperidin-1-yl)-3,5-dicyano-4-ethylpyridin-2-yl)thio)methyl) benzenesulfonamide

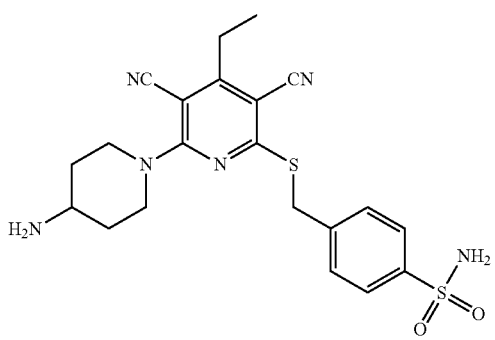 [SMILES: CCc1c(C#N)c(SCc2ccc(S(N)(=O)=O)cc2)nc(N2CCC(N)CC2)c1C#N]

To a stirred solution of tert-butyl (1-(3,5-dicyano-4-ethyl-6-((4-sulfamoylbenzyl)thio)pyridin-2-l)piperidin-4-yl)carbamate (500 mg) in 1,4-dioxane (5 mL) was added HCl (4 M in 1,4-dioxane, 5 mL, 20 mmol) at 0° C. and stirred at room temperature for 4 hours. The reaction mixture was concentrated under reduced pressure, then washed with diethyl ether (2×10 mL) to obtain the crude product. The crude material was purified by prep-HPLC to afford 4-(((6-(4-aminopiperidin-1-yl)-3,5-dicyano-4-ethylpyridin-2-yl)thio)methyl)benzenesulfonamide (150 mg, 38% yield) as an off-white solid. LCMS m/z=457.0 [M+H]$^+$. $^1$H NMR (400 MHz, DMSO-d$_6$, D$_2$O exchange) δ ppm 7.77 (d, J=8.4 Hz, 2H), 7.59 (d, J=8.4 Hz, 2H) 4.56 (s, 2H), 4.38-4.31 (m, 2H), 3.30-3.24 (m, 2H), 2.93-2.83 (m, 1H), 2.76 (q, J=7.60 Hz, 2H), 1.80 (br dd, J=13.26, 3.62 Hz, 2H), 1.30-1.17 (m, 5H). Four protons not observed.

Example 346

2-((Benzo[1,3]dioxol-5-ylmethyl)thio)-4-ethyl-6-(4-methyl-1,4-diazepan-1-yl)pyridine-3,5-dicarbonitrile

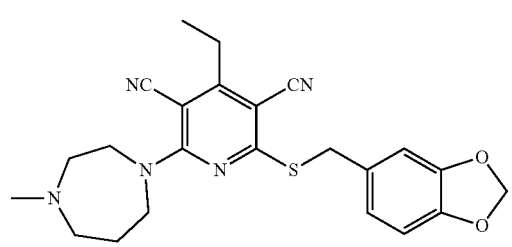 [SMILES: CCc1c(C#N)c(SCc2ccc3c(c2)OCO3)nc(N2CCCN(C)CC2)c1C#N]

A solution of benzo[d][1,3]dioxol-5-ylmethanol (60 mg, 0.394 mmol) in diethyl ether (5 mL) was treated with thionyl chloride (0.029 mL, 0.394 mmol), followed by N,N-diisopropylethylamine (0.069 mL, 0.394 mmol) and stirred for 2 hours then concentrated. The residue was azeotroped two times with chloroform. To a solution of the residue in chloroform (5 mL) was added N,N-diisopropylethylamine (0.069 mL, 0.394 mmol) followed by 4-ethyl-2-mercapto-6-(4-methyl-1,4-diazepan-1-yl)pyridine-3,5-dicarbonitrile (synthesis described in example 69, step 1, 149 mg, 0.394 mmol), and the reaction was stirred overnight. Gradient silica gel chromatography using 0% methanol/0% NH$_4$OH in dichloromethane to 5% methanol/1% NH$_4$OH in dichloromethane as eluent followed by crystallization from diethyl ether gave 2-((benzo[d][1,3]dioxol-5-ylmethyl)thio)-4-ethyl-6-(4-methyl-1,4-diazepan-1-yl)pyridine-3,5-dicarbonitrile (34 mg, 20% yield). LCMS m/z 436.2 [M+H]$^+$. $^1$H NMR (400 MHz, MeOH-d$_4$) δ ppm 1.32 (t, 3H), 2.01-2.14 (m, 2H), 2.38 (s, 3H), 2.59-2.69 (m, 2H), 2.73-2.82 (m, 2H), 2.87-2.97 (m, 2H), 3.94-4.06 (m, 4H), 4.44 (s, 2H), 5.95 (s, 2H), 6.74-6.82 (m, 1H), 6.90 (m, 2H).

Example 347

2-(((3,3-Dimethoxy-2-oxoindolin-5-yl)methyl)thio)-4-ethyl-6-(4-methyl-1,4-diazepan-1-yl)pyridine-3,5-dicarbonitrile

Step 1: tert-Butyl 5-methyl-2,3-dioxoindoline-1-carboxylate

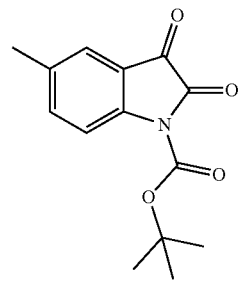 [SMILES: Cc1ccc2c(c1)C(=O)C(=O)N2C(=O)OC(C)(C)C]

To a mixture of 5-methylindoline-2,3-dione (5.15 g, 32.0 mmol) and Boc-anhydride (7.67 g, 35.2 mmol) in THF (50 mL) at 20° C. was added DMAP (0.10 g, 0.819 mmol). The mixture was stirred for 1 hour, and then evaporated to a yellow solid that was slurried in diethyl ether. The solid was collected and washed with heptane to give tert-butyl 5-methyl-2,3-dioxoindoline-1-carboxylate (4.5 g, 54% yield). LCMS m/z=284.0 [M+Na]$^+$.

Step 2: tert-Butyl 5-(bromomethyl)-2,3-dioxoindoline-1-carboxylate

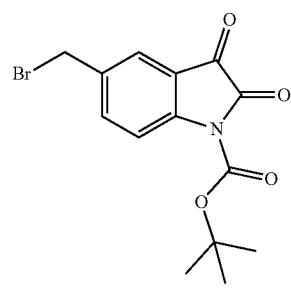 [SMILES: CC(C)(C)OC(=O)N1C(=O)C(=O)c2cc(CBr)ccc21]

A mixture of tert-butyl 5-methyl-2,3-dioxoindoline-1-carboxylate (4.25 g, 16.27 mmol), NBS (3.2 g, 17.98 mmol), and benzoyl peroxide (30 mg, 0.124 mmol) in carbon tetrachloride (20 ml, 207 mmol) was stirred at 80° C. for 3 hours. The mixture was concentrated directly onto silica gel and purified by gradient flash chromatography using 100% heptane to 100% dichloromethane as eluent to give tert-butyl 5-(bromomethyl)-2,3-dioxoindoline-1-carboxylate (3.1 g, 9.11 mmol, 56% yield) as a yellow solid. LCMS m/z 362.0 [M+Na]⁺.

Step 3: 2-(((3,3-Dimethoxy-2-oxoindolin-5-yl) methyl)thio)-4-ethyl-6-(4-methyl-1,4-diazepan-1-yl) pyridine-3,5-dicarbonitrile

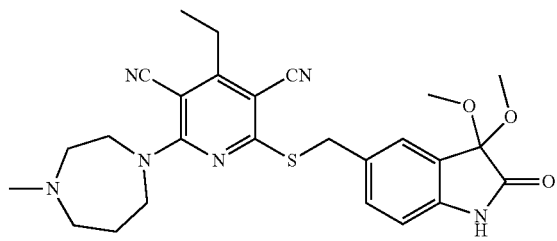 [SMILES: CCc1c(C#N)c(SCc2ccc3c(c2)C(OC)(OC)C(=O)N3)nc(N2CCCN(C)CC2)c1C#N]

A solution of 4-ethyl-2-mercapto-6-(4-methyl-1,4-diazepan-1-yl)pyridine-3,5-dicarbonitrile (synthesis described in Example 69, step 1, 177 mg, 0.470 mmol) and triethylamine (0.197 mL, 1.411 mmol) in chloroform (25 mL) was stirred over an ice salt bath, treated dropwise with tert-butyl 5-(bromomethyl)-2,3-dioxoindoline-1-carboxylate (160 mg, 0.470 mmol) in chloroform (25 mL), and stirred overnight allowing the mixture to reach ambient temperature. The solution was evaporated to a low volume and purified by gradient silica gel chromatography using dichloromethane to 25% ethanol, 1% methanol, 1% ammonia in ethyl acetate. The eluted product was concentrated, and to a solution of the residue in chloroform (5 mL) was added 4 M HCl in dioxane (3 mL, 99 mmol). The solution was stirred overnight, and purified by gradient reverse phase chromatography using 30-80% acetonitrile-1% ammonia in water to give 2-(((3,3-dimethoxy-2-oxoindolin-5-yl)methyl)thio)-4-ethyl-6-(4-methyl-1,4-diazepan-1-yl)pyridine-3,5-dicarbonitrile (55 mg, 23% yield). LCMS m/z=507.2 [M+H]⁺. ¹H NMR (400 MHz, METHANOL-d₄) δ ppm 1.32 (t, J=7.60 Hz, 3H), 2.00-2.12 (m, 2H), 2.35 (s, 3H), 2.57-2.66 (m, 2H), 2.68-2.77 (m, 2H), 2.88-2.98 (m, 2H), 3.50 (s, 6H), 3.98 (d, J=5.83 Hz, 4H), 4.52 (s, 2H), 6.83-6.91 (m, 1H), 7.36-7.43 (m, 1H), 7.44-7.52 (m, 1H).

Example 348

2-(((2,3-Dioxoindolin-5-yl)methyl)thio)-4-ethyl-6-(4-methyl-1,4-diazepan-1-yl)pyridine-3,5-dicarbonitrile

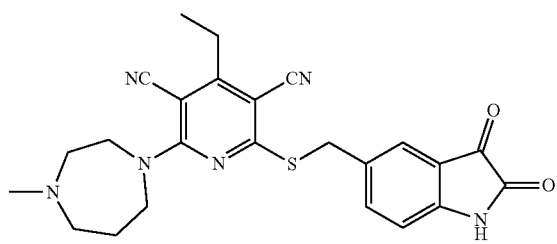 [SMILES: CCc1c(C#N)c(SCc2ccc3c(c2)C(=O)C(=O)N3)nc(N2CCCN(C)CC2)c1C#N]

Also isolated from the above reaction (example 347, step 3) was 2-(((2,3-dioxoindolin-5-yl)methyl)thio)-4-ethyl-6-(4-methyl-1,4-diazepan-1-yl)pyridine-3,5-dicarbonitrile (12 mg, 0.026 mmol, 6% yield). LCMS m/z=461.1 [M+H]⁺. 1H NMR (400 MHz, METHANOL-d₄) ⌊ ppm 1.32 (t, 3H), 2.04-2.13 (m, 2H), 2.41 (s, 3H), 2.65-2.73 (m, 2H), 2.75-2.86 (m, 2H), 2.89-2.97 (m, 2H), 3.95-4.03 (m, 4H), 4.51 (s, 2H), 6.83-6.97 (m, 1H), 7.35-7.69 (m, 2H).

Example 349

N-(4-(((6-(((4H-1,2,4-Triazol-3-yl)methyl)(methyl) amino)-3,5-dicyano-4-ethylpyridin-2-yl)thio)methyl) benzyl)acetamide

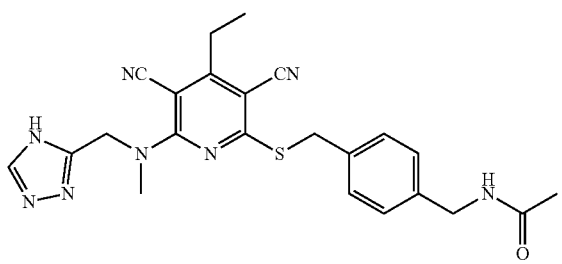 [SMILES: CCc1c(C#N)c(SCc2ccc(CNC(C)=O)cc2)nc(N(C)Cc2nnc[nH]2)c1C#N]

The first reaction mixture of N-(4-(bromomethyl)benzyl) acetamide (130 mg, 0.535 mmol) and potassium thioacetate (72.2 mg, 0.633 mmol) in ethanol (3 mL) was stirred at 60° C. for 20 minutes. Then added NaBH₄ (36.8 mg, 0.973 mmol), and stirred at 60° C. for 20 more minutes. To a solution of 2,6-dichloro-4-ethylpyridine-3,5-dicarbonitrile (synthesis described in example 3, step 2,110 mg, 0.487 mmol) in DMF (1.0 mL) was added a slurry solution of N-methyl-1-(4H-1,2,4-triazol-3-yl)methanamine, Hydrochloride (84 mg, 0.535 mmol) and TEA (0.136 mL, 0.973 mmol) in DMF (2.0 mL) slowly. The second reaction mixture was stirred at room temperature for 20 minutes. The first and second reaction mixtures were combined and stirred at room temperature overnight. Added more TEA (0.136 mL, 0.973 mmol), and stirred for additional 2 hours. The reaction mixture was filtered and purified by RP-HPLC (10-40% acetonitrile/water, 0.1% NH₄OH in water) to afford N-(4-(((6-(((4H-1,2,4-triazol-3-yl)methyl)(methyl)amino)-3,5-dicyano-4-ethylpyridin-2-yl)thio)methyl)benzyl)acetamide (55 mg, 0.119 mmol, 25% yield) as an off-white solid. LCMS m/z=461.1 [M+H]⁺. ¹H NMR (400 MHz, DMSO-d₆) δ ppm 1.22 (t, J=7.6 Hz, 3H), 1.86 (s, 3H), 2.78 (q, J=7.6 Hz, 2H), 3.51 (s, 3H), 4.21 (d, J=5.8 Hz, 2H), 4.36 (s, 2H), 5.06 (s, 2H), 7.17 (m, J=8.1 Hz, 2H), 7.25 (m, J=8.1 Hz, 2H), 8.33 (d, J=5.8 Hz, 2H). One proton not observed.

Example 350

4-Ethyl-2-((4-(pyridin-2-yl)benzyl)thio)-6-(4-(pyrrolidin-1-yl)piperidin-1-yl)pyridine-3,5-dicarbonitrile

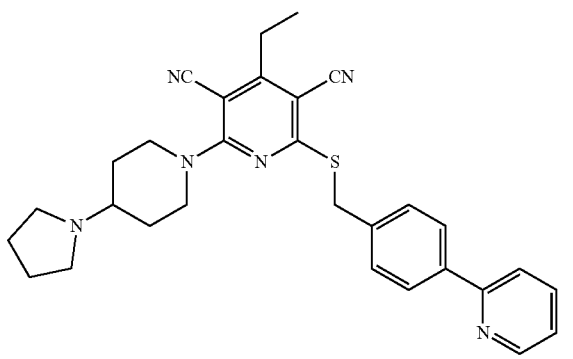 [SMILES: CCc1c(C#N)c(SCc2ccc(-c3ccccn3)cc2)nc(N2CCC(N3CCCC3)CC2)c1C#N]

To a solution of 4,4,4',4',5,5,5',5'-octamethyl-2,2'-bi(1,3,2-dioxaborolane) (418 mg, 1.65 mmol), potassium acetate (202 mg, 2.06 mmol), 2-((4-bromobenzyl)thio)-4-ethyl-6-(4-(pyrrolidin-1-yl)piperidin-1-yl)pyridine-3,5-dicarbonitrile (synthesis described in example 337 step 4, 700 mg, 1.37 mmol) in 1,4-dioxane (8 mL) was added 1,1'-bis(diphenylphosphino)ferrocenedichloro palladium(II) dichloromethane complex (100 mg, 0.14 mmol). The mixture was stirred at 90° C. for 15 hours under argon atmosphere. Potassium carbonate (284 mg, 2.06 mmol), 1,1'-bis(diphenylphosphino)ferrocenedichloro palladium(II) dichloromethane complex (100 mg, 0.14 mmol), Water (2 mL) and 2-chloropyridine (234 mg, 2.06 mmol) were added to the solution. The reaction was stirred for 18 hours at 100° C. under argon atmosphere then concentrated under vacuum and purified by prep-HPLC to give 4-ethyl-2-((4-(pyridin-2-yl)benzyl)thio)-6-(4-(pyrrolidin-1-yl)piperidin-1-yl)pyridine-3,5-dicarbonitrile (41 mg, 6% yield) as a light yellow solid. LCMS m/z=508.9 [M+H]$^+$. $^1$H NMR (400 MHz, CDCl$_3$) δ ppm 8.68 (d, J=4.6 Hz, 1H), 7.96 (d, J=8.2 Hz, 2H), 7.79-7.70 (m, 2H), 7.48 (d, J=8.2 Hz, 2H), 7.26-7.22 (m, 1H), 4.55 (d, J=13.5 Hz, 2H), 4.46 (s, 2H), 3.21 (t, J=11.8 Hz, 2H), 2.90 (q, J=7.6 Hz, 2H), 2.72-2.52 (m, 4H), 2.45-2.33 (m, 1H), 2.04-1.96 (m, 2H), 1.85-1.76 (m, 4H), 1.68-1.57 (m, 2H), 1.32 (t, J=7.6 Hz, 3H).

Example 351

2-((3,5-Dicyano-4,6-diethylpyridin-2-ylthio-2-phenylacetamide

Step 1: 4,6-Diethyl-2-oxo-1,2-dihydropyridine-3-carbonitrile

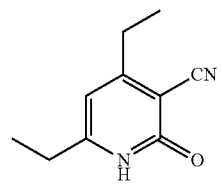

KOH (2.408 g, 42.9 mmol) was added to a stirred mixture of heptane-3,5-dione (5 g, 39.0 mmol) and 2-cyanoacetamide (3.44 g, 41.0 mmol) in methanol (200 mL) at room temperature and the mixture was stirred at 80° C. for 14 hours. Then it was concentrated in vacuo to remove the solvent, the residue was dissolved in water, and diluted HCl solution was added making the solution pH-3, the resulting solid was filtered to afford 4,6-diethyl-2-oxo-1,2-dihydropyridine-3-carbonitrile (5.8 g). LCMS m/z=177.2 [M+H]$^+$.

Step 2: 5-Bromo-4,6-diethyl-2-oxo-1,2-dihydropyridine-3-carbonitrile

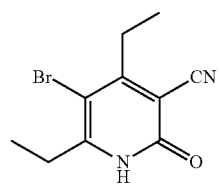

NBS (7.68 g, 43.1 mmol) was added to a stirred solution of 4,6-diethyl-2-oxo-1,2-dihydropyridine-3-carbonitrile (3.8 g, 21.56 mmol) in 2,2,2-trifluoroacetic acid (15 mL, 21.56 mmol) and sulfuric acid (15 mL, 21.56 mmol) at 0° C., the mixture was stirred for 14 hours. Then the mixture was poured into the crushed ice-water and the resulting solid was filtered to afford 5-bromo-4,6-diethyl-2-oxo-1,2-dihydropyridine-3-carbonitrile (4.2 g, 16.46 mmol, 76%). LCMS m/z=255.0, 257.0 [M+H]$^+$.

Step 3: 4,6-Diethyl-2-oxo-1,2-dihydropyridine-3,5-dicarbonitrile

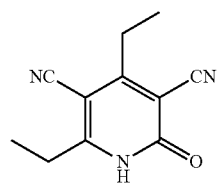

A mixture of 5-bromo-4,6-diethyl-2-oxo-1,2-dihydropyridine-3-carbonitrile (2.2 g, 8.62 mmol) and cyanocopper (0.927 g, 10.35 mmol) in N-methyl-2-pyrrolidone (30 mL) was stirred at 170° C. for 24 hours under nitrogen atmosphere. Then the solvent was removed under high vacuum. the residue was purified by column chromatography (petroleum ether:ethyl acetate=2:1) to afford 4,6-diethyl-2-oxo-1,2-dihydropyridine-3,5-dicarbonitrile (490 mg, 2.44 mmol, 28% yield). LCMS m/z=202.2 [M+H]$^+$.

Step 4: 2-Chloro-4,6-diethylpyridine-3,5-dicarbonitrile

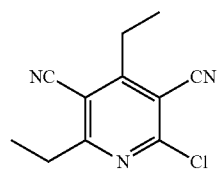

A mixture of 4,6-diethyl-2-oxo-1,2-dihydropyridine-3,5-dicarbonitrile (490 mg, 2.44 mmol) and phosphoryl trichloride (15 mL, 2.44 mmol) was stirred at 155° C. for 20 hours in a sealed tube. The mixture was concentrated in vacuo to remove the solvent. The residue was purified by column chromatography (petroleum ether/ethyl acetate=4/1) to afford 2-chloro-4,6-diethylpyridine-3,5-dicarbonitrile (354 mg, 1.61 mmol, 66% yield). $^1$H NMR (400 MHz, CDCl$_3$) δ 3.11 (m, 4H), 1.41 (m, 6H).

Step 5: 2-((3,5-Dicyano-4,6-diethylpyridin-2-yl)thio)-2-phenylacetamide

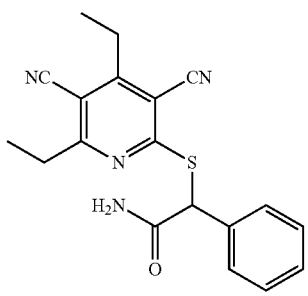 [SMILES: CCc1nc(SC(C(N)=O)c2ccccc2)c(C#N)c(CC)c1C#N]

A mixture of 2-chloro-4,6-diethylpyridine-3,5-dicarbonitrile (330 mg, 1.50 mmol), 2-mercapto-2-phenylacetamide (synthesis described in example 276 step 1, 377 mg, 2.25 mmol) and triethylamine (0.628 mL, 4.51 mmol) in DMF (20 mL) was stirred at 20° C. for 14 hours. Then water was added and extracted with ethyl acetate, the organic layer was concentrated and the residue was purified by column chromatography to afford 2-((3,5-dicyano-4,6-diethylpyridin-2-yl)thio)-2-phenylacetamide (93 mg, 18%). LCMS m/z=373.2 [M+Na]$^+$. $^1$H NMR (400 MHz, DMSO-d$_6$) δ ppm 7.97 (s, 1H), 7.57 (m, 2H), 7.42-7.26 (m, 4H), 5.76 (s, 1H), 2.99 (q, J=7.5 Hz, 2H), 2.85 (q, J=7.6 Hz, 2H), 1.30 (t, J=7.5 Hz, 3H), 1.22 (t, J=7.6 Hz, 3H).

Example 352

2-((6-((2-(4H-1,2,4-Triazol-4-yl)ethyl)(methyl)amino)-3,5-dicyano-4-ethylpyridin-2-yl)thio)-2-phenylacetamide Step 1: 2-((2-(4H-1,2,4-Triazol-4-yl)ethyl)(methyl)amino)-6-chloro-4-ethylpyridine-3,5-dicarbonitrile

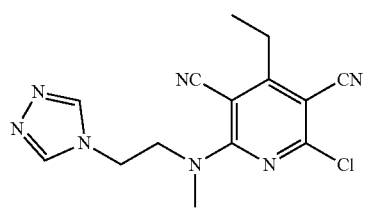 [SMILES: CCc1c(C#N)c(Cl)nc(N(C)CCn2cnnc2)c1C#N]

To a stirred solution of N-methyl-2-(4H-1,2,4-triazol-4-yl)ethanamine (335 mg, 2.65 mmol) in dichloromethane (20 mL) was added triethylamine (1.151 mL, 7.96 mmol) followed by 2,6-dichloro-4-ethylpyridine-3,5-dicarbonitrile (synthesis described in example 3 step 2, 600 mg, 2.65 mmol). The reaction mixture was stirred at room temperature for 1 hour. Water (40 mL) was added and the mixture extracted with DCM (2×23 mL). The combined organic layers were dried over Na$_2$SO$_4$, and concentrated under reduced pressure to obtain the crude material. The crude material was purified by silica gel chromatography (60-120 mesh; 10% MeOH in EtOAc as eluent) to afford 2-((2-(4H-1,2,4-triazol-4-yl)ethyl)(methyl)amino)-6-chloro-4-ethylpyridine-3,5-dicarbonitrile (500 mg). LCMS m/z=316.0 [M+H]$^+$.

Step 2: 2-((6-((2-(4H-1,2,4-Triazol-4-yl)ethyl)(methyl)amino)-3,5-dicyano-4-ethylpyridin-2-yl)thio)-2-phenylacetamide

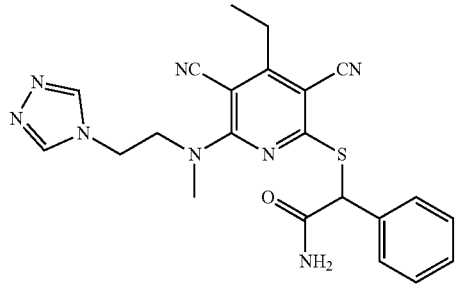 [SMILES: CCc1c(C#N)c(SC(C(N)=O)c2ccccc2)nc(N(C)CCn2cnnc2)c1C#N]

To a stirred solution of 2-((2-(4H-1,2,4-triazol-4-yl)ethyl)(methyl)amino)-6-chloro-4-ethylpyridine-3,5-dicarbonitrile (500 mg, 1.583 mmol) in N,N-dimethylformamide (20 mL) was added potassium thioacetate (271 mg, 2.375 mmol). The reaction mixture was stirred at room temperature for 30 minutes. K$_2$CO$_3$ (328 mg, 2.375 mmol) was added followed by 2-amino-2-oxo-1-phenylethyl methanesulfonate (synthesis described in example 3 step 5, 363 mg, 1.583 mmol). The reaction mixture was stirred at room temperature for 16 hours. Water (100 mL) was added and the mixture was extracted with ethyl acetate (2×50 mL). The combined organic layers were dried over Na$_2$SO$_4$ and concentrated under reduced pressure to obtain crude the product. The crude material was purified by silica gel chromatography (60-120 mesh; 3% MeOH/CH$_2$Cl$_2$ as eluent) to provide a residue which was washed with n-pentane (20 mL) to afford 2-((6-((2-(4H-1,2,4-triazol-4-yl)ethyl)(methyl)amino)-3,5-dicyano-4-ethylpyridin-2-yl)thio)-2-phenylacetamide (260 mg). LCMS m/z=447.2 [M+H]$^+$. $^1$H NMR (400 MHz, Chloroform-d) δ ppm 8.32 (s, 2H), 7.48-7.36 (m, 5H), 6.63 (br s, 1H), 5.76 (br s, 1H), 5.21 (s, 1H), 4.38-4.30 (m, 3H), 4.08-3.98 (m, 1H), 3.43 (s, 3H), 2.98-2.90 (q, J=7.6 Hz, 2H), 1.34 (t, J=7.2 Hz, 3H).

Example 354

N-(4-(((3,5-Dicyano-4-ethyl-6-(4-methyl-1,4-diazepan-1-yl)pyridin-2-yl)thio)methyl)phenyl)-N-methylacetamide Step 1: 4-Ethyl-2-(4-methyl-1,4-diazepan-1-yl)-6-((4-(methylamino)benzyl)thio)pyridine-3,5-dicarbonitrile

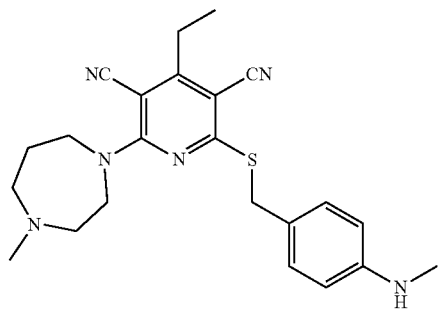

To the solution of 4-ethyl-2-mercapto-6-(4-methyl-1,4-diazepan-1-yl)pyridine-3,5-dicarbonitrile (synthesis described in example 69, step 1, 400 mg, 1.062 mmol) and TEA (0.296 mL, 2.123 mmol) in DMF (4 mL) was added a solution of tert-butyl (4-(bromomethyl)phenyl)(methyl)carbamate (335 mg, 1.062 mmol) in DMF (2 mL). The reaction mixture was stirred at room temperature for 2 hours. The reaction mixture was purified by RP-HPLC (50-80% acetonitrile/water, 0.1% NH₄OH in water) to afford a light yellow wax solid. To the above solid in dichloromethane (4.00 mL) was added TFA (1 mL, 12.98 mmol), stirred for 1 hour. The reaction mixture was concentrated down and the residue was partitioned between DCM and water, and then basified with NH₄OH. The layers were separated and the aqueous layer was washed with DCM two more times. The combined slurry organics were washed with water, and then mixed with some methanol to get a clear solution, dried over Na₂SO₄, concentrated down to afford 4-ethyl-2-(4-methyl-1,4-diazepan-1-yl)-6-((4-(methylamino)benzyl)thio)pyridine-3,5-dicarbonitrile (190 mg, 0.452 mmol, 43% yield) as an off-white solid. LCMS m/z=421.4 [M+H]$^+$.

Step 2: N-(4-(((3,5-Dicyano-4-ethyl-6-(4-methyl-1,4-diazepan-1-yl)pyridin-2-yl)thio)methyl)phenyl)-N-methylacetamide

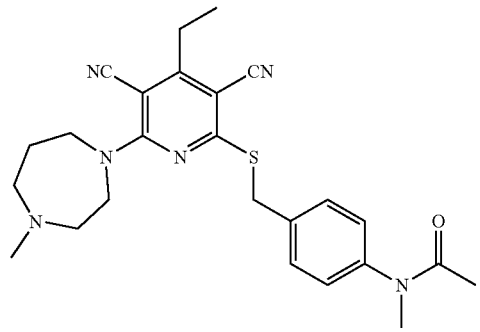 [SMILES: CCc1c(C#N)c(SCc2ccc(N(C)C(C)=O)cc2)nc(N2CCCN(C)CC2)c1C#N]

At 0° C., to the solution of 4-ethyl-2-(4-methyl-1,4-diazepan-1-yl)-6-((4-(methylamino)benzyl)thio)pyridine-3,5-dicarbonitrile (50 mg, 0.119 mmol) with TEA (0.033 mL, 0.238 mmol) in THF (2 mL) was added a solution of acetyl chloride (0.013 mL, 0.178 mmol) in THF (0.5 mL) dropwise. The reaction mixture was stirred for 20 minutes. The reaction mixture was concentrated down and purified by RP-HPLC (30-40% acetonitrile/water, 0.1% NH₄OH in water) to afford N-(4-(((3,5-dicyano-4-ethyl-6-(4-methyl-1,4-diazepan-1-yl)pyridin-2-yl)thio)methyl)phenyl)-N-methylacetamide (38 mg, 0.082 mmol, 69% yield) as an off-white glass solid. LCMS m/z=463.2 [M+H]$^+$. $^1$H NMR (400 MHz, DMSO-d₆) δ ppm 1.23 (t, J=7.6 Hz, 3H), 1.76 (br. s., 3H), 1.86-1.95 (m, 2H), 2.23 (s, 3H), 2.44-2.49 (m, 2H), 2.60-2.69 (m, 2H), 2.79 (q, J=7.6 Hz, 2H), 3.12 (br. s., 3H), 3.79-3.95 (m, 4H), 4.53 (s, 2H), 7.30 (m, J=7.9 Hz, 2H), 7.46 (m, J=7.9 Hz, 2H).

Example 355

N-(4-(((3,5-Dicyano-4-ethyl-6-(4-methyl-1,4-diazepan-1-yl)pyridin-2-yl) thio)methyl)phenyl)-N-methylmethanesulfonamide

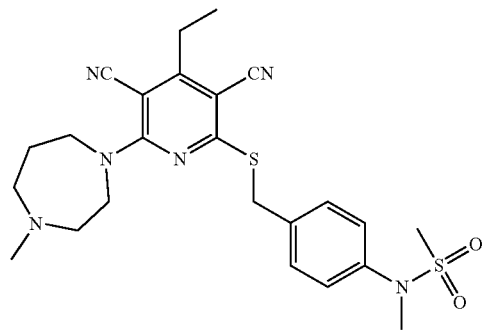 [SMILES: CCc1c(C#N)c(SCc2ccc(N(C)S(C)(=O)=O)cc2)nc(N2CCCN(C)CC2)c1C#N]

At 0° C., to a solution of 4-ethyl-2-(4-methyl-1,4-diazepan-1-yl)-6-((4-(methylamino) benzyl)thio) pyridine-3,5-dicarbonitrile (synthesis described in example 354, step 1, 50 mg, 0.119 mmol) with TEA (0.033 mL, 0.238 mmol) in THF (2 mL) was added a solution of methanesulfonyl chloride (0.028 mL, 0.357 mmol) in THF (0.5 mL) dropwise. The reaction mixture was stirred overnight. The reaction mixture was concentrated down and purified by RP-HPLC (30-50% acetonitrile/water, 0.1% NH₄OH in water) to afford N-(4-(((3,5-dicyano-4-ethyl-6-(4-methyl-1,4-diazepan-1-yl)pyridin-2-yl)thio)methyl)phenyl)-N-methylmethanesulfonamide (37 mg, 0.074 mmol, 62% yield) as an off-white solid. LCMS m/z=499.2 [M+H]$^+$. $^1$H NMR (400 MHz, DMSO-d₆) δ ppm 1.22 (t, J=7.6 Hz, 3H), 1.83-1.98 (m, 2H), 2.24 (s, 3H), 2.48-2.45 (m, 2H), 2.61-2.70 (m, 2H), 2.78 (q, J=7.6 Hz, 2H), 2.93 (s, 3H), 3.22 (s, 3H), 3.80-3.94 (m, 4H), 4.51 (s, 2H), 7.33-7.40 (m, 2H), 7.40-7.47 (m, 2H).

Example 356

2-((6-(((1H-Pyrazol-3-yl)methyl)(methyl)amino)-3,5-dicyano-4-ethylpyridin-2-yl)thio)-2-phenylacetamide Step 1: (1H-Pyrazol-3-yl)methanol

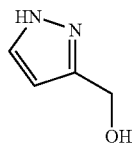

To a solution of aluminum(III) lithium hydride (2.71 g, 71.4 mmol) in tetrahydrofuran (20 mL) stirred under nitrogen at 0° C. was added 1H-pyrazole-3-carboxylic acid (4 g, 35.7 mmol). The reaction mixture was stirred at room temperature for 1 hour then refluxed overnight. The mixture was cooled to 0° C. The reaction was then quenched by the addition of water (2.7 mL), then a solution of NaOH (10%, 5.4 mL), then water (8.1 mL). The mixture was stirred for 30 minutes at 0° C., then filtered through a Celite® pad. The solvent was removed under reduced pressure and the residue was purified by silica gel column (eluted with ethyl acetate/hexane 1/2) to afford (1H-pyrazol-3-yl)methanol (1.9 g, 19.37 mmol, 54% yield) as a yellow oil. LCMS m/z=81.1 [M+H—H$_2$O]$^+$.

Step 2: 3-(Chloromethyl)-1H-pyrazole

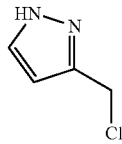

To a solution of (1H-pyrazol-3-yl)methanol (1.9 g, 19.37 mmol) in dichloromethane (20 mL) stirred under nitrogen at 0° C. was added a solution of sulfurous dichloride (5.76 g, 48.4 mmol) in DCM (5.0 mL). The reaction mixture was stirred at 0° C. for 2 hours. The reaction mixture was warmed to room temperature. The resulting solution was diluted with water and ice. then adjusted to pH 6-7 with sodium bicarbonate. The resulting solution was extracted with ethyl acetate (3×30 mL). The organic layers were combined, washed with aqueous sodium carbonate and brine, dried and concentrated in vacuo to afford 3-(chloromethyl)-1H-pyrazole (0.9 g, 7.72 mmol, 40% yield) as a yellow oil. LCMS m/z=117.0 [M+H]$^+$.

Step 3: N-Methyl-1-(1H-pyrazol-3-yl)methanamine

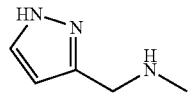

A solution of methanamine (311 mg, 10 mmol) in tetrahydrofuran (5 mL) was added dropwise to a solution of 3-(chloromethyl)-1H-pyrazole (300 mg, 2.57 mmol) in tetrahydrofuran (5 mL). The mixture was stirred for 10 minutes at room temperature. The solvent was removed by distillation under vacuum to afford N-methyl-1-(1H-pyrazol-3-yl)methanamine (300 mg, 1.62 mmol, 63% yield) as a yellow oil. LCMS m/z=112.1 [M+H]$^+$.

Step 4: 2-(((1H-Pyrazol-3-yl)methyl)(methyl)amino)-6-chloro-4-ethylpyridine-3,5-dicarbonitrile

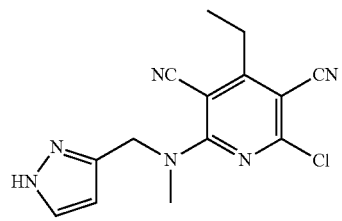 [SMILES: CCc1c(C#N)c(Cl)nc(N(C)Cc2cc[nH]n2)c1C#N]

To a solution of 2,6-dichloro-4-ethylpyridine-3,5-dicarbonitrile (synthesis described in example 3 step 2, 366 mg, 1.62 mmol) and triethylamine (246 mg, 2.43 mmol) in acetonitrile (15 mL) stirred at room temperature was added N-methyl-1-(1H-pyrazol-3-yl)methanamine (300 mg, 1.62 mmol) in acetonitrile (5 mL) and the reaction mixture was stirred at room temperature for 2 hours. The resulting solution was diluted with water (50 mL), then extracted with ethyl acetate (3×20 mL). The organic layers were combined, washed with aqueous sodium carbonate and brine, dried, filtered, and concentrated under vacuum. The residue was purified by silica gel column (eluted with ethyl acetate/hexane 1/2) to afford 2-(((1H-pyrazol-4-yl)methyl)(methyl)amino)-6-chloro-4-ethylpyridine-3,5-dicarbonitrile (200 mg, 0.67 mmol, 41% yield) as a yellow oil. LCMS m/z=301.0 [M+H]$^+$.

Step 5: 2-((6-(((1H-Pyrazol-3-yl)methyl)(methyl)amino)-3,5-dicyano-4-ethylpyridin-2-yl)thio)-2-phenylacetamide

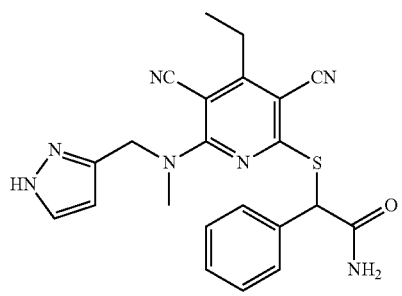 [SMILES: CCc1c(C#N)c(SC(C(N)=O)c2ccccc2)nc(N(C)Cc2cc[nH]n2)c1C#N]

Two individual reactions were conducted which were combined on work up. A solution of 2-(((1H-pyrazol-3-yl)methyl)(methyl)amino)-6-chloro-4-ethylpyridine-3,5-dicarbonitrile (170 mg, 0.57 mmol) and potassium thioacetate (194 mg, 1.70 mmol) in N,N-dimethylformamide (10 mL) was stirred 20 minutes at room temperature. Then 2-bromo-2-phenylacetamide (423 mg, 1.98 mmol) and triethylamine (0.315 mL, 2.26 mmol) were added. The mixture was stirred overnight at room temperature. Separately, a solution of 2-(((1H-pyrazol-3-yl)methyl)(methyl)amino)-6-chloro-4-ethylpyridine-3,5-dicarbonitrile (30 mg, 0.100 mmol) and potassium thioacetate (22.78 mg, 0.200 mmol) in N,N-dimethylformamide (5.0 mL) was stirred 20 minutes at room temperature. Then 2-bromo-2-phenylacetamide (53.4 mg, 0.249 mmol) and TEA (0.056 mL, 0.399 mmol) were added. The mixture was stirred overnight at room temperature. The two reaction mixtures were combined. Water (30 mL) was added and the resulting solution was extracted with ethyl acetate (3×20 mL). The organic layers were combined, washed with aqueous sodium carbonate and brine, dried and concentrated under vacuum. The residue was purified by prep-TLC (eluted with ethyl acetate) to afford 2-((6-(((1H-pyrazol-3-yl)methyl)(methyl)amino)-3,5-dicyano-4-ethylpyridin-2-yl)thio)-2-phenylacetamide (84 mg, 0.19 mmol, 34% yield) as a white solid. LCMS m/z=432.1 [M+H]$^+$. $^1$H NMR (400 MHz, DMSO-d$_6$) δ ppm 12.82 (s, 1H), 7.93 (s, 1H), 7.73 (s, 1H), 7.46 (d, J=6.4 Hz, 2H), 7.34 (d, J=7.2 Hz, 4H), 6.22 (d, J=2.0 Hz, 1H), 5.60 (s, 1H), 5.20 (d, J=15.6 Hz, 1H), 4.87 (d, J=16.0 Hz, 1H), 3.32 (s, 3H), 2.77 (q, J=7.3 Hz, 2H), 1.21 (t, J=7.6 Hz, 3H).

Example 357

4-((3,5-Dicyano-4-ethyl-6-(4-methyl-1,4-diazepan-1-yl)pyridin-2-ylthio)methyl)phenylboronic acid

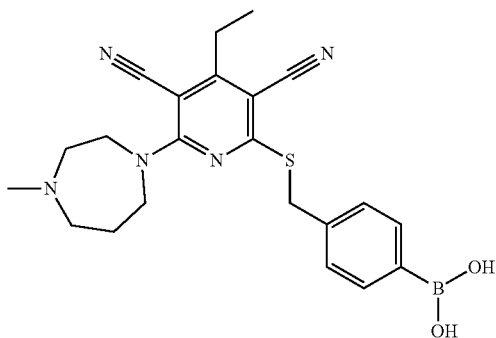 [SMILES: CCc1c(C#N)c(SCc2ccc(B(O)O)cc2)nc(N2CCCN(C)CC2)c1C#N]

To a solution of 4-ethyl-2-mercapto-6-(4-methyl-1,4-diazepan-1-yl)pyridine-3,5-dicarbonitrile (synthesis described in example 69 step 1, 400 mg, 1.33 mmol) in N,N-dimethylformamide (15 mL) stirred in air at 20° C. were added (4-(bromomethyl)phenyl)boronic acid (285 mg, 1.33 mmol) and triethylamine (0.37 mL, 2.65 mmol). The reaction mixture was stirred at 25° C. for 5 hours. The reaction mixture was quenched with water, and the precipitate formed was collected by filtration, dried in vacuo, and the residue was purified by flash column chromatography to give 4-((3,5-dicyano-4-ethyl-6-(4-methyl-1,4-diazepan-1-yl)pyridin-2-ylthio)methyl)phenylboronic acid (260 mg, 45%) as an orange solid. LCMS m/z=436.1 [M+H]$^+$. $^1$H NMR (400 MHz, DMSO) δ 9.63 (br s, 1H), 8.07 (br s, 2H), 7.76 (d, J=7.8 Hz, 2H), 7.37 (d, J=7.9 Hz, 2H), 4.50 (s, 2H), 4.30-4.18 (m, 1H), 4.03-3.93 (m, 1H), 3.87-3.74 (m, 2H), 3.53-3.41 (m, 2H), 3.28-3.18 (m, 2H), 2.88-2.74 (m, 5H), 2.27-2.17 (m, 2H), 1.24 (t, J=7.6 Hz, 3H).

Example 358

N-(4-(((3,5-Dicyano-4-ethyl-6-(4-methyl-1,4-diazepan-1-yl)pyridin-2-yl)thio)methyl)benzyl)-2-(methylamino)acetamide Step 1: tert-Butyl (2-((4-(((3,5-dicyano-4-ethyl-6-(4-methyl-1,4-diazepan-1-yl)pyridin-2-yl)thio)methyl)benzyl)amino)-2-oxoethyl)(methyl)carbamate

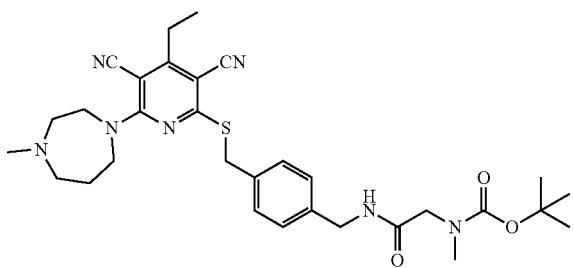 [SMILES: CCc1c(C#N)c(SCc2ccc(CNC(=O)CN(C)C(=O)OC(C)(C)C)cc2)nc(N2CCCN(C)CC2)c1C#N]

To a solution of N-(tert-butoxycarbonyl)-N-methylglycine (22 mg, 0.116 mmol) in N,N-dimethylformamide (0.75 mL) at room temperature was added HATU (43 mg, 0.113 mmol). The reaction mixture was then stirred at room temperature for 30 minutes at which time the 2-((4-(aminomethyl)benzyl)thio)-4-ethyl-6-(4-methyl-1,4-diazepan-1-yl)pyridine-3,5-dicarbonitrile, 2Hydrochloride (synthesis described in example 71, 50 mg, 0.101 mmol) and Et$_3$N (0.044 mL, 0.314 mmol) were added. The reaction mixture was then continued stirring at room temperature while progress was monitored by LCMS. After 2 hours, the mixture was filtered, and the filtrate purified by reverse phase HPLC (Gilson, 30 mm×50 mm Gemini Column, NH$_4$OH modifier) to obtain the pure tert-butyl (2-((4-(((3,5-dicyano-4-ethyl-6-(4-methyl-1,4-diazepan-1-yl)pyridin-2-yl)thio)methyl)benzyl)amino)-2-oxoethyl)(methyl)carbamate (35 mg) as an off white solid. LCMS m/z=592.4 [M+H]$^+$.

Step 2: N-(4-(((3,5-Dicyano-4-ethyl-6-(4-methyl-1,4-diazepan-1-yl)pyridin-2-yl)thio)methyl)benzyl)-2-(methylamino)acetamide

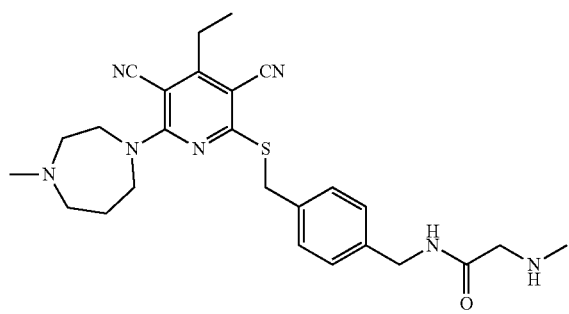

tert-Butyl (2-((4-(((3,5-dicyano-4-ethyl-6-(4-methyl-1,4-diazepan-1-yl)pyridin-2-yl)thio)methyl)benzyl)amino)-2-oxoethyl)(methyl)carbamate (25 mg, 0.042 mmol) was suspended in a solution of 4 M HCl (1.000 mL, 4.0 mmol) in dioxane at room temperature. The reaction mixture was stirred at room temperature for 1 hour. The reaction mixture was concentrated. The resulting material was suspended in MeOH, and free based with isopropylamine. This mixture was purified by reverse phase HPLC (Gilson, 30 mm×50 mm Gemini Column, NH$_4$OH modifier) to yield N-(4-(((3,5-dicyano-4-ethyl-6-(4-methyl-1,4-diazepan-1-yl)pyridin-2-yl)thio)methyl)benzyl)-2-(methylamino)acetamide (17 mg) as a white solid. LCMS m/z=492.4 [M+H]$^+$. $^1$H NMR (400 MHz, DMSO-d$_6$) δ ppm 8.29 (t, J=6.08 Hz, 1H), 7.30-7.37 (m, J=8.11 Hz, 2H), 7.18-7.25 (m, J=8.11 Hz, 2H), 4.47 (s, 2H), 4.27 (d, J=6.34 Hz, 2H), 3.83-3.95 (m, 4H), 3.07 (s, 2H), 2.78 (q, J=7.60 Hz, 2H), 2.62-2.66 (m, 2H), 2.45-2.49 (m, 2H), 2.25 (s, 3H), 2.24 (s, 3H), 1.88-1.96 (m, 2H), 1.22 (t, J=7.60 Hz, 3H). One proton not observed.

Example 359

2-((3,5-Dicyano-6-(6,7-dihydro-1H-[1,2,3]triazolo[4,5-c]pyridin-5(4H)-yl)-4-ethylpyridin-2-yl)thio)-2-phenylacetamide Step 1: 2-Chloro-6-(6,7-dihydro-1H-[1,2,3]triazolo[4,5-c]pyridin-5(4H)-yl)-4-ethylpyridine-3,5-dicarbonitrile

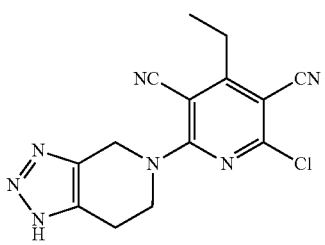 [SMILES: CCc1c(C#N)c(Cl)nc(N2CCc3[nH]nnc3C2)c1C#N]

To a stirred solution of 4,5,6,7-tetrahydro-1H-[1,2,3]triazolo[4,5-c]pyridine (0.659 g, 5.31 mmol) in DCM (50 mL) was added at room temperature TEA (2.220 mL, 15.92 mmol) followed by 2,6-dichloro-4-ethylpyridine-3,5-dicarbonitrile (synthesis described in example 3 step 2, 1.2 g, 5.31 mmol). The reaction mixture was stirred at 28° C. for 16 hours. Water (10 mL) was added and the reaction mixture extracted with DCM (10 mL). The organic layer was dried over Na$_2$SO$_4$, and concentrated under reduced pressure to obtain the crude product. The crude material was purified by silica gel chromatography using 5% MeOH in DCM as eluent to afford 2-chloro-6-(6,7-dihydro-1H-[1,2,3]triazolo[4,5-c]pyridin-5(4H)-yl)-4-ethylpyridine-3,5-dicarbonitrile (1 g). LCMS m/z=314.0 [M+H]$^+$.

Step 2: 2-((3,5-Dicyano-6-(6,7-dihydro-1H-[1,2,3]triazolo[4,5-c]pyridin-5(4H)-yl)-4-ethylpyridin-2-yl)thio)-2-phenylacetamide

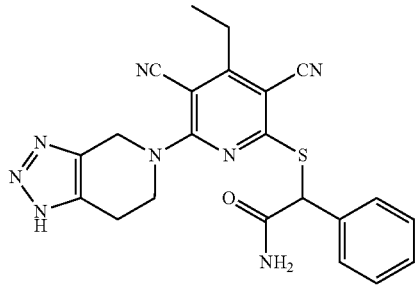 [SMILES: CCc1c(C#N)c(SC(C(N)=O)c2ccccc2)nc(N2CCc3[nH]nnc3C2)c1C#N]

To a stirred solution of 2-chloro-6-(6,7-dihydro-1H-[1,2,3]triazolo[4,5-c]pyridin-5(4H)-yl)-4-ethylpyridine-3,5-dicarbonitrile (1 g, 3.19 mmol) in N,N-dimethylformamide (10 mL) was added potassium thioacetate (0.546 g, 4.78 mmol). The reaction mixture was stirred at room temperature for 30 minutes, then 2-amino-2-oxo-1-phenylethyl methanesulfonate (synthesis described in example 3 step 5, 0.731 g, 3.19 mmol) and K$_2$CO$_3$ (0.661 g, 4.78 mmol) were added. The reaction mixture was stirred at 28° C. for 16 hours. Water (100 mL) was added and the mixture was extracted with ethyl acetate (2×50 mL). The combined organic layers were dried over Na$_2$SO$_4$ and concentrated under reduced pressure to obtain the crude product. The crude material was purified by silica gel chromatography 2-3% MeOH in DCM as eluent to afford 2-((3,5-dicyano-6-(6,7-dihydro-1H-[1,2,3]triazolo[4,5-c]pyridin-5(4H)-yl)-4-ethylpyridin-2-yl)thio)-2-phenylacetamide (93 mg). LCMS m/z=445.1 [M+H]$^+$. $^1$H NMR (400 MHz, DMSO-d$_6$) δ ppm 14.71 (br s, 1H), 8.00 (br s, 1H), 7.58-7.54 (d, J=7.1 Hz, 2H), 7.42-7.30 (m, 4H), 5.64 (s, 1H) 5.03-4.96 (m, 2H) 4.14-4.07 (m, 2H) 2.86-3.02 (m, 2H), 2.85-2.75 (q, J=7.45 Hz, 2H), 1.25 (t, J=7.56 Hz, 3H).

Example 360

2-((4-Amino-3-fluorobenzyl)thio)-4-ethyl-6-(4-methyl-1,4-diazepan-1-yl)pyridine-3,5-dicarbonitrile

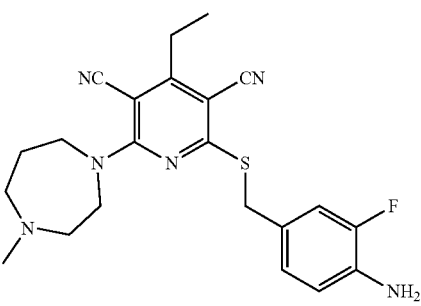 [SMILES: CCc1c(C#N)c(SCc2ccc(N)c(F)c2)nc(N2CCCN(C)CC2)c1C#N]

To the solution of 4-ethyl-2-mercapto-6-(4-methyl-1,4-diazepan-1-yl)pyridine-3,5-dicarbonitrile (synthesis described in example 69, step 1, 400 mg, 1.062 mmol) and TEA (0.296 mL, 2.123 mmol) in DMF (4 mL) was added a solution of tert-butyl (4-(bromomethyl)-2-fluorophenyl)carbamate (323 mg, 1.062 mmol) in DMF (2 mL). The reaction mixture was stirred at room temperature overnight. The reaction mixture was purified by RP-HPLC (50-80% acetonitrile/water, 0.1% NH₄OH in water) to afford an off-white solid. To the above solid in dichloromethane (4.00 mL) was added TFA (1 mL, 12.98 mmol), stirred for 1 hour. The reaction mixture was concentrated down and the residue was partitioned between DCM and water, and then basified with NH₄OH. The layers were separated and the aqueous layer was extracted with DCM two more times. The combined organics were washed with brine, dried over $Na_2SO_4$, concentrated down to afford 2-((4-amino-3-fluorobenzyl)thio)-4-ethyl-6-(4-methyl-1,4-diazepan-1-yl)pyridine-3,5-dicarbonitrile (208 mg, 0.490 mmol, 46% yield) as an off-white solid. LCMS m/z=425.2 [M+H]⁺. ¹H NMR (400 MHz, DMSO-d₆) δ ppm 1.22 (t, J=7.6 Hz, 3H), 1.88-2.01 (m, 2H), 2.25 (s, 3H), 2.48 (br. s., 2H), 2.64-2.71 (m, 2H), 2.78 (q, J=7.6 Hz, 2H), 3.85-3.99 (m, 4H), 4.36 (s, 2H), 5.18 (s, 2H), 6.70 (dd, J=9.5, 8.2 Hz, 1H), 6.91 (dd, J=8.2, 1.9 Hz, 1H), 7.03 (dd, J=12.4, 1.8 Hz, 1H).

Example 361

N-(4-(((3,5-Dicyano-4-ethyl-6-(4-methyl-1,4-diazepan-1-yl)pyridin-2-yl)thio)methyl)-2-fluorophenyl)methanesulfonamide

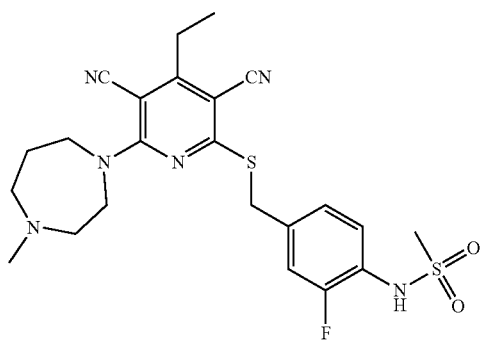 [SMILES: CCc1c(C#N)c(SCc2ccc(NS(C)(=O)=O)c(F)c2)nc(N2CCCN(C)CC2)c1C#N]

At 0° C., to the solution of 2-((4-amino-3-fluorobenzyl)thio)-4-ethyl-6-(4-methyl-1,4-diazepan-1-yl)pyridine-3,5-dicarbonitrile (synthesis described in example 360, 50 mg, 0.118 mmol) with TEA (0.033 mL, 0.236 mmol) in THF (2 mL) was added a solution of mesyl chloride (0.028 mL, 0.353 mmol) in THF (1 mL) dropwise. The reaction mixture was stirred for 40 minutes. The reaction mixture was concentrated down and purified by RP-HPLC (5-50% acetonitrile/water, 0.1% NH₄OH in water) to afford N-(4-(((3,5-dicyano-4-ethyl-6-(4-methyl-1,4-diazepan-1-yl)pyridin-2-yl)thio)methyl)-2-fluorophenyl)methanesulfonamide (12 mg, 0.024 mmol, 20% yield) as an off-white foam solid. LCMS m/z=503.1 [M+H]⁺. ¹H NMR (400 MHz, DMSO-d₆) δ ppm 1.21-1.25 (m, 3H), 1.99 (br. s., 2H), 2.28-2.44 (m, 3H), 2.50 (br. s., 2H), 2.79 (q, J=7.5 Hz, 4H), 3.02 (s, 3H), 3.77-4.04 (m, 4H), 4.50 (s, 2H), 7.24 (dd, J=8.4, 1.8 Hz, 1H), 7.30-7.39 (m, 2H), 9.70 (br. s., 1H).

Example 362

N-(4-(((3,5-Dicyano-4-ethyl-6-(4-methyl-1,4-diazepan-1-yl)pyridin-2-yl) thio)methyl-2-fluorophenyl) acetamide

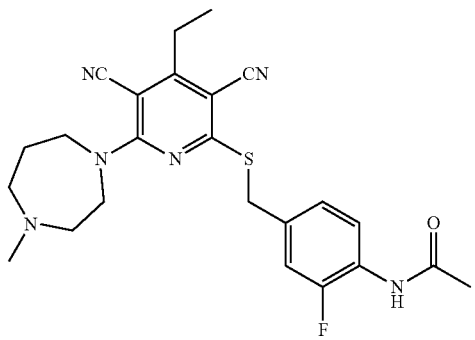 [SMILES: CCc1c(C#N)c(SCc2ccc(NC(C)=O)c(F)c2)nc(N2CCCN(C)CC2)c1C#N]

At 0° C., to the solution of 2-((4-amino-3-fluorobenzyl)thio)-4-ethyl-6-(4-methyl-1,4-diazepan-1-yl) pyridine-3,5-dicarbonitrile (synthesis described in example 360, 60 mg, 0.141 mmol) with TEA (0.039 mL, 0.283 mmol) in THF (2 mL) was added a solution of acetyl chloride (0.030 mL, 0.424 mmol) in THF (1 mL) dropwise (very slow addition, monitored by LCMS). The reaction mixture was stirred for 2 hours. The reaction mixture was concentrated down and purified by RP-HPLC (30-50% acetonitrile/water, 0.1% NH₄OH in water) to afford N-(4-(((3,5-dicyano-4-ethyl-6-(4-methyl-1,4-diazepan-1-yl)pyridin-2-yl)thio)methyl)-2-fluorophenyl)acetamide (42 mg, 0.090 mmol, 64% yield) as an off-white glass solid. LCMS m/z=467.2 [M+H]⁺. ¹H NMR (400 MHz, DMSO-d₆) δ ppm 1.22 (t, J=7.6 Hz, 3H), 1.86-1.98 (m, 2H), 2.07 (s, 3H), 2.23 (s, 3H), 2.49-2.45 (m, 2H), 2.59-2.65 (m, 2H), 2.78 (q, J=7.6 Hz, 2H), 3.82-3.94 (m, 4H), 4.48 (s, 2H), 7.18 (dd, J=8.4, 1.5 Hz, 1H), 7.28 (dd, J=11.7, 1.8 Hz, 1H), 7.83 (t, J=8.2 Hz, 1H), 9.74 (s, 1H).

Example 363

2-(4-Aminopiperidin-1-yl)-4-ethyl-6-(((1-(2-hydroxyethyl)-1H-pyrazol-4-yl)methyl)thio)pyridine-3,5-dicarbonitrile Step 1: Methyl 2-(4-(((6-(4-((tert-butoxycarbonyl)amino)piperidin-1-yl)-3,5-dicyano-4-ethylpyridin-2-yl)thio)methyl)-1H-pyrazol-1-yl)acetate

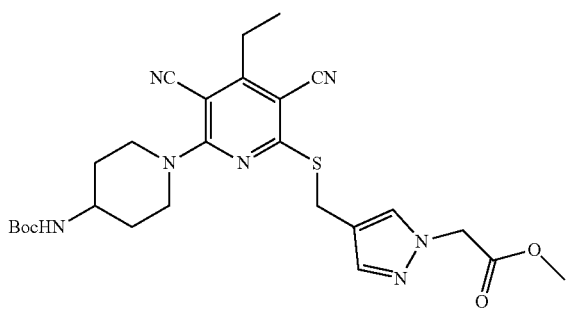 [SMILES: CCc1c(C#N)c(SCc2cnn(CC(=O)OC)c2)nc(N2CCC(NC(=O)OC(C)(C)C)CC2)c1C#N]

715

To a solution of methyl 2-(4-(hydroxymethyl)-1H-pyrazol-1-yl)acetate (600 mg, 3.53 mmol) in dichloromethane (12 mL) TEA (0.983 mL, 7.05 mmol) was added followed by addition of MsCl (0.412 mL, 5.29 mmol) at room temperature and stirred at the same temperature for 20 minutes. The DCM, TEA were distilled off at room temperature to afford crude methyl 2-(4-(((methylsulfonyl)oxy)methyl)-1H-pyrazol-1-yl)acetate (550 mg). To a solution of tert-butyl (1-(6-chloro-3,5-dicyano-4-ethylpyridin-2-yl)piperidin-4-yl)carbamate (synthesis described in example 81, step 1, 500 mg) in N,N-dimethylformamide (10 mL) was added potassium thioacetate (293 mg, 2.56 mmol) at room temperature and stirred for 1 hour at room temperature. Potassium carbonate (0.354 g, 2.56 mmol) was then added followed by a solution of the crude methyl 2-(4-(((methylsulfonyl)oxy)methyl)-1H-pyrazol-1-yl)acetate (478 mg) in DMF. The reaction was stirred at room temperature for 2 hours. The reaction was quenched with water (200 mL) and extracted with ethyl acetate (300 mL). The organic layer was dried over anhydrous Na$_2$SO$_4$, filtered and concentrated under reduced pressure. The crude material was purified by silica gel column chromatography (100-200 mesh, eluted with 5% MeOH in DCM) to afford methyl 2-(4-(((3,5-dicyano-6-(dimethylamino)-4-ethylpyridin-2-yl)thio)methyl)-1H-pyrazol-1-yl)acetate (500 mg). LCMS m/z=540.4 [M+H]$^+$.

Step 2: tert-Butyl (1-(3,5-dicyano-4-ethyl-6-(((1-(2-hydroxyethyl)-1H-pyrazol-4-yl)methyl)thio)pyridin-2-yl)piperidin-4-yl)carbamate

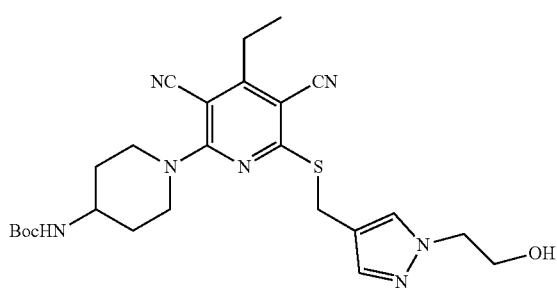 [SMILES: CCc1c(C#N)c(SCc2cnn(CCO)c2)nc(N2CCC(NC(=O)OC(C)(C)C)CC2)c1C#N]

To a solution of methyl 2-(4-(((6-(4-((tert-butoxycarbonyl)amino)piperidin-1-yl)-3,5-dicyano-4-ethylpyridin-2-yl)thio)methyl)-1H-pyrazol-1-yl)acetate (500 mg) in methanol (10 mL) was added NaBH$_4$ (175 mg, 4.63 mmol) portionwise at room temperature and the reaction mixture was stirred at room temperature for 16 hours. The reaction mixture was diluted with water, neutralized with dilute HCl, and extracted with dichloromethane. The organic layer was dried over anhydrous Na$_2$SO$_4$, filtered and the filtrate concentrated to afford tert-butyl (1-(3,5-dicyano-4-ethyl-6-(((1-(2-hydroxyethyl)-1H-pyrazol-4-yl)methyl)thio)pyridin-2-yl)piperidin-4-yl)carbamate (500 mg). LCMS m/z=512.1 [M+H]$^+$.

Step 3: 2-(4-Aminopiperidin-1-yl)-4-ethyl-6-(((1-(2-hydroxyethyl)-1H-pyrazol-4-yl)methyl)thio)pyridine-3,5-dicarbonitrile

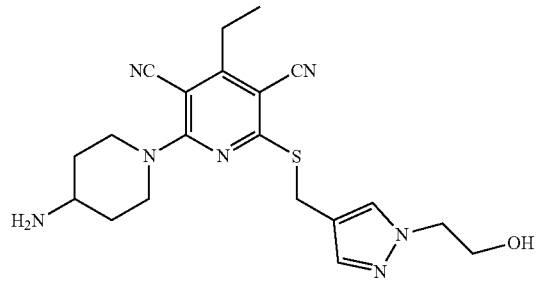 [SMILES: CCc1c(C#N)c(SCc2cnn(CCO)c2)nc(N2CCC(N)CC2)c1C#N]

To a stirred solution of tert-butyl (1-(3,5-dicyano-4-ethyl-6-(((1-(2-hydroxyethyl)-1H-pyrazol-4-yl)methyl)thio)pyridin-2-yl)piperidin-4-yl)carbamate (500 mg) in 1,4-dioxane (4 mL) was added HCl (4 M in 1,4-dioxane, 1.222 mL, 4.89 mmol) at room temperature and stirred at room temperature for 1 hour. The reaction mixture was concentrated under reduced pressure and the crude material diluted with water (20 mL), neutralized with saturated sodium bicarbonate solution, and extracted with ethyl acetate (3×50 mL). The combined organic layers were washed with brine (30 mL), dried over anhydrous Na$_2$SO$_4$, filtered and concentrated under reduced pressure. The crude product was purified by prep-HPLC to afford 2-(4-aminopiperidin-1-yl)-4-ethyl-6-(((1-(2-hydroxyethyl)-1H-pyrazol-4-yl)methyl)thio)pyridine-3,5-dicarbonitrile (90 mg) as an off-white solid. LCMS m/z=412.2 [M+H]$^+$. $^1$H NMR (400 MHz, DMSO-d$_6$) δ ppm 7.68 (s, 1H), 7.40 (s, 1H), 4.42 (br d, J=13.59 Hz, 2H), 4.33 (s, 2H), 4.08 (t, J=5.70 Hz, 2H), 3.69 (t, J=5.59 Hz, 2H), 3.36 (br s, 2H), 2.98-2.87 (m, 1H), 2.77 (q, J=7.60 Hz, 2H), 1.85 (br dd, J=12.72, 3.29 Hz, 2H), 1.38-1.27 (m, 2H), 1.22 (t, J=7.67 Hz, 3H). Three protons not observed.

Example 364

2-((6-(((1H-Imidazol-2-yl)methyl)(methyl)amino)-3,5-dicyano-4-ethylpyridin-2-yl)thio)-2-phenylacetamide Step 1: 2-(((1H-Imidazol-2-yl)methyl)(methyl)amino)-6-chloro-4-ethylpyridine-3,5-dicarbonitrile

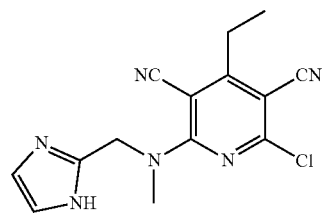 [SMILES: CCc1c(C#N)c(Cl)nc(N(C)Cc2ncc[nH]2)c1C#N]

To a stirred solution of 1-(1H-imidazol-2-yl)-N-methylmethanamine (123 mg, 1.106 mmol) in dichloromethane (15 mL) was added triethylamine (0.308 mL, 2.212 mmol) at 0° C. followed by the addition of 2,6-dichloro-4-ethylpyridine-3,5-dicarbonitrile (synthesis described in example 3 step 2, 250 mg, 1.106 mmol). The reaction mixture was stirred for 30 minutes at 0° C. The reaction mixture was quenched with water (5.0 mL) and extracted with dichloromethane (50 mL). The organic layer was washed with saturated brine solution (10 mL), dried over Na₂SO₄, filtered, and concentrated under reduced pressure to give 2-(((1H-imidazol-2-yl)methyl)(methyl)amino)-6-chloro-4-ethylpyridine-3,5-dicarbonitrile (250 mg). LCMS m/z=301.0 [M+H]⁺.

Step 2: 2-((6-(((1H-Imidazol-2-yl)methyl)(methyl)amino)-3,5-dicyano-4-ethylpyridin-2-yl)thio)-2-phenylacetamide

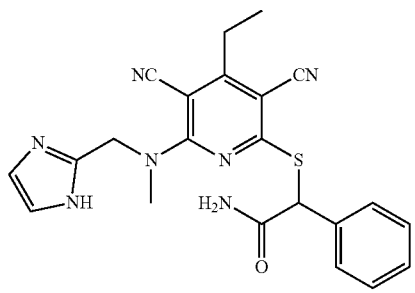 [SMILES: CCc1c(C#N)c(SC(C(N)=O)c2ccccc2)nc(N(C)Cc2ncc[nH]2)c1C#N]

To a solution of 2-(((1H-imidazol-2-yl)methyl)(methyl)amino)-6-chloro-4-ethylpyridine-3,5-dicarbonitrile (250 mg) in N,N-dimethylformamide (5.0 mL) was added potassium thioacetate (190 mg, 1.663 mmol) at room temperature. The reaction mixture was stirred for 2 hours at 28° C. Then potassium carbonate (230 mg, 1.663 mmol) and 2-amino-2-oxo-1-phenylethyl methanesulfonate (synthesis described in example 3 step 5, 191 mg, 0.831 mmol) were added at 0° C. The reaction mixture was stirred for 16 hours at 28° C. The reaction mixture was diluted with ice cold water (50 mL) and extracted with ethyl acetate (2×100 mL). The combined organic layers were washed with water (100 mL), dried over anhydrous Na₂SO₄, filtered, and concentrated. The crude material was purified by column chromatography (neutral alumina, eluted with 2% MeOH in DCM) to afford 2-((6-(((1H-imidazol-2-yl)methyl)(methyl)amino)-3,5-dicyano-4-ethylpyridin-2-yl)thio)-2-phenylacetamide (102 mg,) as a pale brown solid. LCMS m/z=432.2 [M+H]⁺. ¹H NMR (400 MHz, DMSO-d₆) δ ppm 12.05 (br s, 1H), 8.17 (s, 1H), 7.50-7.23 (m, 6H), 7.04 (br s, 2H), 5.51 (s, 1H), 5.23 (d, J=16.00 Hz, 1H), 4.84 (d, J=15.9 Hz, 1H), 3.41 (s, 3H), 2.78 (q, J=7.5 Hz, 2H), 1.21 (t, J=7.67 Hz, 3H).

Example 365

2-((6-(((1H-Imidazol-5-yl)methyl)(methyl)amino)-3,5-dicyano-4-ethylpyridin-2-yl)thio-2-phenylacetamide Step 1: 2-(((1H-Imidazol-5-yl)methyl)(methyl)amino)-6-chloro-4-ethylpyridine-3,5-dicarbonitrile

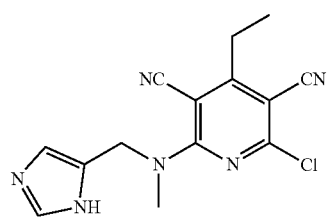 [SMILES: CCc1c(C#N)c(Cl)nc(N(C)Cc2cnc[nH]2)c1C#N]

To a stirred solution of 1-(1H-imidazol-5-yl)-N-methyl-methanamine (0.492 g, 4.42 mmol) in dichloromethane (50 mL) was added triethylamine (1.233 mL, 8.85 mmol) at 0° C. followed by the addition of 2,6-dichloro-4-ethylpyridine-3,5-dicarbonitrile (synthesis described in example 3 step 2, 1 g, 4.42 mmol). The reaction mixture was stirred for 30 minutes at 0° C. The reaction mixture was quenched with water (5.0 mL) and extracted with dichloromethane (50 mL). The organic layer was washed with saturated brine solution (10 mL), dried over Na₂SO₄, filtered, and concentrated under reduced pressure to afford 2-(((1H-imidazol-5-yl)methyl)(methyl)amino)-6-chloro-4-ethylpyridine-3,5-dicarbonitrile (600 mg,). LCMS m/z=301.0 [M+H]⁺.

Step 2: 2-((6-(((1H-Imidazol-5-yl)methyl)(methyl)amino)-3,5-dicyano-4-ethylpyridin-2-yl)thio)-2-phenylacetamide

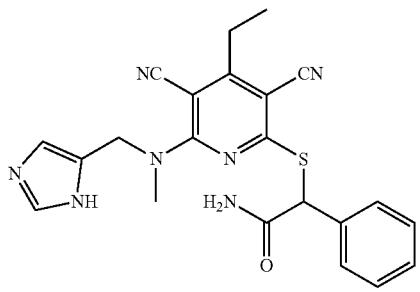 [SMILES: CCc1c(C#N)c(SC(C(N)=O)c2ccccc2)nc(N(C)Cc2cnc[nH]2)c1C#N]

To a stirred solution of 2-(((1H-imidazol-5-yl)methyl)(methyl)amino)-6-chloro-4-ethylpyridine-3,5-dicarbonitrile (600 mg) in N,N-dimethylformamide (15 mL) was added potassium thioacetate (456 mg, 3.99 mmol) at room temperature. The reaction mixture was stirred at room temperature for 2 hours. Then potassium carbonate (551 mg, 3.99 mmol) and 2-amino-2-oxo-1-phenylethyl methanesulfonate (synthesis described in example 3 step 5, 457 mg, 1.995 mmol) was added at 28° C. The reaction mixture was stirred for 16 hours at 28° C. The reaction mixture was diluted with cold water and extracted with ethyl acetate (2×60 mL). The combined organic layers were dried over sodium sulfate, filtered, and concentrated under reduced pressure to afford a brown gum. The crude compound was purified by reversed-phase C-18 column chromatography using the Grace Reveleris purification instrument (20-25% acetonitrile in water). The product was further purified by Prep HPLC and the product fractions concentrated. The remaining material was diluted with water, stirred for 10 minutes which gave a precipitate, and was filtered to afford 2-((6-(((1H-imidazol-5-yl)methyl)(methyl)amino)-3,5-dicyano-4-ethylpyridin-2-yl)thio)-2-phenylacetamide (160 mg) as an off-white solid. LCMS m/z=432.1 [M+H]⁺. ¹H NMR (400 MHz, DMSO-d₆) δ ppm 12.04 (br s, 1H) 8.02 (br s, 1H) 7.68-7.60 (m, 1H) 7.46 (dd, J=7.78, 1.43 Hz, 2H) 7.40-7.14 (m, 4H), 7.12 (s, 1H), 5.64 (s, 1H), 5.05 (d, J=15.35 Hz, 1H), 4.79 (d, J=15.35 Hz, 1H), 3.34 (s, 3H), 2.76 (q, J=7.53 Hz, 2H), 1.20 (t, J=7.56 Hz, 3H).

Example 366

(2R)-2-Amino-N-(1-(6-((2-amino-2-oxo-1-phenylethyl)thio)-3,5-dicyano-4-ethylpyridin-2-yl)piperidin-4-yl)propanamide, Hydrochloride Step 1: tert-Butyl ((2R)-1-((1-(6-((2-amino-2-oxo-1-phenylethyl)thio)-3,5-dicyano-4-ethylpyridin-2-yl)piperidin-4-yl)amino)-1-oxopropan-2-yl)carbamate

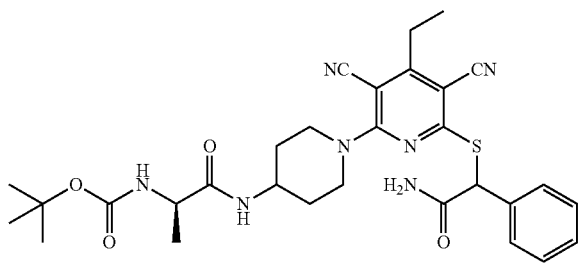 [SMILES: CCc1c(C#N)c(SC(C(N)=O)c2ccccc2)nc(N2CCC(NC(=O)[C@@H](C)NC(=O)OC(C)(C)C)CC2)c1C#N]

To a stirred solution of (R)-2-((tert-butoxycarbonyl)amino)propanoic acid (198 mg, 1.049 mmol) in dichloromethane (5 mL) was added diisopropylethylamine (0.561 mL, 3.15 mmol) at room temperature. The reaction mixture was stirred at the same temperature for 5 minutes then propylphosphonic anhydride (0.936 mL, 1.573 mmol) and 2-((6-(4-aminopiperidin-1-yl)-3,5-dicyano-4-ethylpyridin-2-yl)thio)-2-phenylacetamide, Hydrochloride (synthesis described in example 286 step 2, 500 mg, 1.049 mmol) were added and the reaction mixture was stirred for 16 hours. The reaction mixture was diluted with dichloromethane (100 mL) then washed with cold water (100 mL). The organic layer was dried over $Na_2SO_4$, filtered, and concentrated under reduced pressure to give a residue which was triturated with petroleum ether (100 mL) to afford tert-butyl ((2R)-1-((1-(6-((2-amino-2-oxo-1-phenylethyl)thio)-3,5-dicyano-4-ethylpyridin-2-yl)piperidin-4-yl)amino)-1-oxopropan-2-yl)carbamate (500 mg) as an off-white solid. LCMS m/z=592.1 $[M+H]^+$.

Step 2: (2R)-2-Amino-N-(1-(6-((2-amino-2-oxo-1-phenylethyl)thio)-3,5-dicyano-4-ethylpyridin-2-yl)piperidin-4-yl)propanamide, Hydrochloride

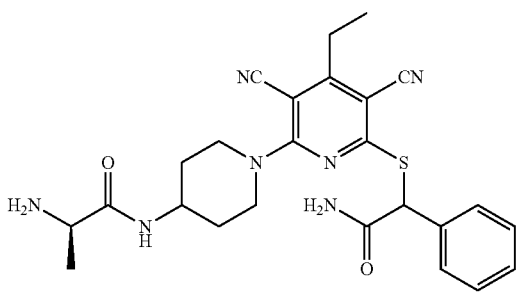 [SMILES: CCc1c(C#N)c(SC(C(N)=O)c2ccccc2)nc(N2CCC(NC(=O)[C@@H](C)N)CC2)c1C#N]

To a stirred solution of tert-butyl ((2R)-1-((1-(6-((2-amino-2-oxo-1-phenylethyl)thio)-3,5-dicyano-4-ethylpyridin-2-yl)piperidin-4-yl)amino)-1-oxopropan-2-yl)carbamate (500 mg) in 1,4-dioxane (15 mL) was added HCl (4 M in 1,4-dioxane, 1.955 mL, 7.82 mmol) at 5° C. The resultant reaction mixture was stirred at room temperature for 8 hours. The reaction mixture was diluted with diethyl ether (50 mL) to afford a precipitate and stirred for 10 minutes at room temperature. The precipitated solid was filtered through a Buchner funnel and the solid cake was washed with excess diethyl ether. The solid was triturated with diethyl ether (200 mL), dried, then lyophilized to afford (2R)-2-amino-N-(1-(6-((2-amino-2-oxo-1-phenylethyl)thio)-3,5-dicyano-4-ethylpyridin-2-yl)piperidin-4-yl)propanamide, Hydrochloride (360 mg). LCMS m/z=492.1 $[M+H]^+$. $^1$H NMR (400 MHz, DMSO-$d_6$) δ ppm 8.51 (br s, 1H), 8.15 (br s, 3H), 7.95 (br s, 1H), 7.53 (d, J=7.23 Hz, 2H), 7.42-6.99 (m, 4H), 5.61-5.50 (m, 1H), 4.42 (br dd, J=13.37, 4.17 Hz, 2H), 4.04-3.72 (m, 2H), 3.50-3.35 (m, 2H), 2.76 (q, J=7.6 Hz, 2H) 1.98-1.82 (m, 2H), 1.60-1.40 (m, 2H), 1.38 (d, J=6.8 Hz, 3H), 1.21 (t, J=7.6 Hz, 3H).

Example 367

N-(4-(((3,5-Dicyano-4-ethyl-6-(3-hydroxypyrrolidin-1-yl)pyridin-2-yl)thio)methyl)benzyl-2-hydroxyacetamide Step 1: tert-Butyl (4-(((3,5-dicyano-4-ethyl-6-(3-hydroxypyrrolidin-1-yl)pyridin-2-yl)thio)methyl)benzyl)carbamate

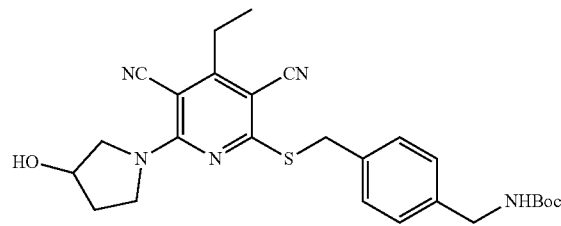 [SMILES: CCc1c(C#N)c(SCc2ccc(CNC(=O)OC(C)(C)C)cc2)nc(N2CCC(O)C2)c1C#N]

To a solution of 2-chloro-4-ethyl-6-(3-hydroxypyrrolidin-1-yl)pyridine-3,5-dicarbonitrile (synthesis described in Example 370, step 1, 1 g) in N,N-dimethylformamide (20 mL) was added potassium thioacetate (0.392 g, 3.43 mmol) at room temperature and the reaction mixture was stirred at room temperature for 2 hours. Then potassium carbonate (0.949 g, 6.87 mmol) and tert-butyl 4-(chloromethyl)benzylcarbamate (900 mg, 3.52 mmol) were added and the mixture was stirred at room temperature for 1 hour. The reaction mixture was diluted with water (100 mL) and extracted with ethyl acetate (2×100 mL). The combined organic layers were washed with cold water (2×100 mL), brine solution (100 mL), dried over anhydrous $Na_2SO_4$, filtered and concentrated. The crude material was purified by silica gel column (100-200 mesh, eluted with 3% MeOH in DCM) to afford tert-butyl 4-(((3,5-dicyano-4-ethyl-6-(3-hydroxypyrrolidin-1-yl)pyridin-2-yl)thio)methyl)benzylcarbamate (500 mg) as an off-white solid. LCMS m/z=494.1 $[M+H]^+$.

Step 2: 2-((4-(Aminomethyl)benzyl)thio)-4-ethyl-6-(3-hydroxypyrrolidin-1-yl)pyridine-3,5-dicarbonitrile, Hydrochloride

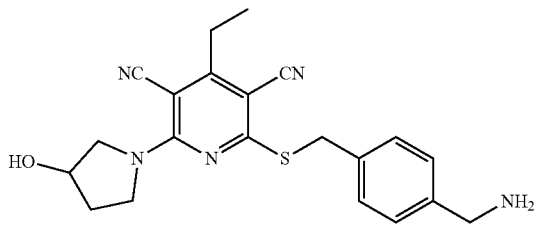 [SMILES: CCc1c(C#N)c(SCc2ccc(CN)cc2)nc(N2CCC(O)C2)c1C#N]

To a stirred solution of tert-butyl 4-(((3,5-dicyano-4-ethyl-6-(3-hydroxypyrrolidin-1-yl)pyridin-2-yl)thio)methyl)benzylcarbamate (500 mg) in 1,4-dioxane (5 mL) under nitrogen at 0° C. was added HCl (4 M in 1,4-dioxane, 5 mL, 20.00 mmol). The reaction mixture was stirred at room temperature for 3 hours. The reaction mixture was concentrated under vacuum, then washed with diethyl ether and dried to afford 2-((4-(aminomethyl)benzyl)thio)-4-ethyl-6-(3-hydroxypyrrolidin-1-yl)pyridine-3,5-dicarbonitrile, Hydrochloride (440 mg) as an off white solid. LCMS m/z=394.1 [M+H]$^+$.

Step 3: N-(4-(((3,5-Dicyano-4-ethyl-6-(3-hydroxypyrrolidin-1-yl)pyridin-2-yl)thio)methyl) benzyl)-2-hydroxyacetamide

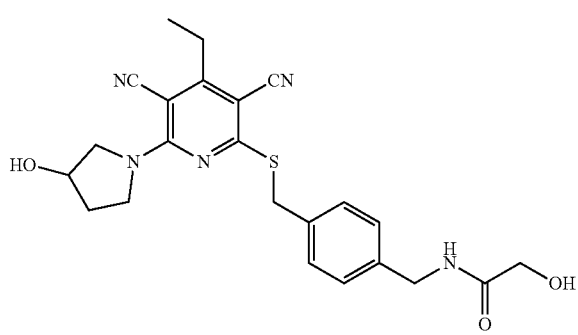 [SMILES: CCc1c(C#N)c(SCc2ccc(CNC(=O)CO)cc2)nc(N2CCC(O)C2)c1C#N]

To a stirred solution of 2-((4-(aminomethyl)benzyl)thio)-4-ethyl-6-(3-hydroxypyrrolidin-1-yl)pyridine-3,5-dicarbonitrile, Hydrochloride (440 mg), 2-hydroxyacetic acid (146 mg, 1.924 mmol) and HATU (366 mg, 0.962 mmol) in N,N-dimethylformamide (10 mL) under nitrogen at 0° C. was added diisopropylethylamine (0.504 mL, 2.89 mmol). The reaction mixture was stirred at room temperature for 5 hours. The reaction mixture was poured into ice cold water (50 mL) and extracted with ethyl acetate (2×50 mL). The combined organic layers were washed with saturated NH$_4$Cl (2×50 mL), water (2×50 mL) and saturated brine solution (50 mL), then dried over anhydrous Na$_2$SO$_4$, filtered and concentrated to afford a black gummy solid. The crude material was purified by silica gel column (100-200 mesh, eluted with 3% MeOH in DCM) to afford N-(4-(((3,5-dicyano-4-ethyl-6-(3-hydroxypyrrolidin-1-yl)pyridin-2-yl)thio)methyl)benzyl)-2-hydroxyacetamide (230 mg) as an off-white solid. LCMS m/z=452.2 [M+H]$^+$. $^1$H NMR (400 MHz, DMSO-d$_6$) δ ppm 8.29-8.17 (m, 1H), 7.34 (d, J=8.11 Hz, 2H), 7.22 (d, J=8.11 Hz, 2H), 5.54-5.37 (m, 1H), 5.11 (d, J=3.29 Hz, 1H), 4.49 (s, 2H), 4.40 (br s, 1H), 4.27 (d, J=6.14 Hz, 2H), 4.24-3.84 (m, 5H), 3.81-3.66 (m, 1H) 2.75 (q, J=7.50 Hz, 2H) 2.14-1.83 (m, 2H), 1.21 (t, J=7.67 Hz, 3H).

Example 368

4-(2-Amino-1-((3,5-dicyano-4-ethyl-6-(4-methyl-1,4-diazepan-1-yl)pyridin-2-yl)thio)-2-oxoethyl)benzamide

Step 1: 4-(Cyano((trimethylsilyl)oxy)methyl)benzonitrile

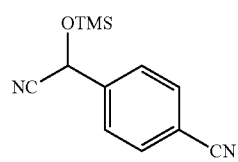

To a mixture of 4-formylbenzonitrile (6.55 g, 49.9 mmol) and potassium 1,3-dioxoisoindolin-2-ide (1.156 g, 6.24 mmol) was added trimethylsilanecarbonitrile (5.95 g, 59.9 mmol). The mixture was stirred at room temperature for 2 hours. The reaction was quenched by adding water (40 mL), then extracted with ethyl acetate (2×100 mL). The combined organic layers were washed with water (25 mL), dried over Na$_2$SO$_4$ and concentrated to afford 4-(cyano((trimethylsilyl)oxy)methyl)benzonitrile (8.2 g, 35.6 mmol, 71% yield) as a yellow solid. $^1$H NMR (400 MHz, CDCl$_3$) δ 7.75 (d, J=8.3 Hz, 2H), 7.63 (d, J=8.3 Hz, 2H), 5.57 (s, 1H), 0.30 (s, 9H).

Step 2: 4-(Cyano(hydroxy)methyl)benzonitrile

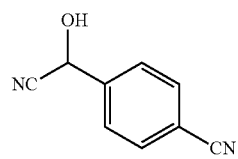 [SMILES: N#Cc1ccc(C(O)C#N)cc1]

To a solution of 4-(cyano((trimethylsilyl)oxy)methyl)benzonitrile (8.2 g, 35.6 mmol) in 1,4-dioxane (50 mL) stirred in air at room temperature was bubbled HCl (gas) for 30 minutes. The reaction mixture was stirred at room temperature for overnight. The mixture was concentrated in vacuo to afford 4-(cyano(hydroxy)methyl)benzonitrile (1.9 g, 12.01 mmol, 34% yield) as a grey solid. $^1$H NMR (400 MHz, DMSO) δ 7.81 (d, J=8.3 Hz, 2H), 7.63 (d, J=8.2 Hz, 2H), 6.33 (d, J=4.9 Hz, 1H), 4.97 (d, J=4.9 Hz, 1H).

Step 3: 4-(2-Amino-1-hydroxy-2-oxoethyl)benzamide

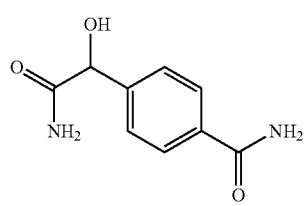 [SMILES: NC(=O)c1ccc(C(O)C(N)=O)cc1]

To a solution of 4-(cyano(hydroxy)methyl)benzonitrile (680 mg, 4.30 mmol) in tetrahydrofuran (15 mL) and water (5 mL) stirred under nitrogen at room temperature was added acetamide (1524 mg, 25.8 mmol) and palladium(II) chloride (152 mg, 0.86 mmol). The reaction mixture was stirred at room temperature for overnight. The mixture was concentrated in vacuo, and the residue was dissolved with DCM (100 mL). The solid was filtered off and washed with DCM (2×20 mL). The filtrate was concentrated then dried in vacuo to afford 4-(2-amino-1-hydroxy-2-oxoethyl)benzamide (1.5 g, 1.55 mmol, 36% yield) as a brown solid. LCMS m/z=195.2 [M+H]$^+$.

Step 4: 2-Amino-1-(4-carbamoylphenyl)-2-oxoethyl methanesulfonate

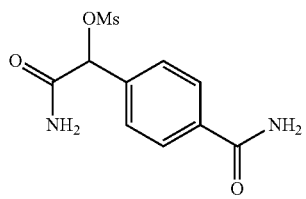 [SMILES: CS(=O)(=O)OC(C(N)=O)c1ccc(C(N)=O)cc1]

To a suspension of 4-(2-amino-1-hydroxy-2-oxoethyl)benzamide (1.2 g, 1.24 mmol) in dichloromethane (150 mL) stirred in air at room temperature was added triethylamine (0.875 g, 8.65 mmol) and methanesulfonyl chloride (0.708 g, 6.18 mmol). The reaction mixture was stirred at room temperature for overnight. The mixture was concentrated and the residue was washed with ethyl acetate (3×30 mL) then purified by silica gel column (eluted with DCM/MeOH=1:0-5:1) to afford 2-amino-1-(4-carbamoylphenyl)-2-oxoethyl methanesulfonate (0.8 g, 0.91 mmol, 74% yield) as a yellowish solid. LCMS m/z=273.0 [M+H]$^+$.

Step 5: 4-(2-Amino-1-((3,5-dicyano-4-ethyl-6-(4-methyl-1,4-diazepan-1-yl)pyridin-2-yl)thio)-2-oxoethyl)benzamide

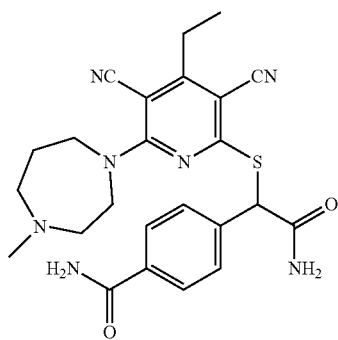 [SMILES: CCc1c(C#N)c(SC(C(N)=O)c2ccc(C(N)=O)cc2)nc(N2CCCN(C)CC2)c1C#N]

To a suspension of 4-ethyl-2-mercapto-6-(4-methyl-1,4-diazepan-1-yl)pyridine-3,5-dicarbonitrile (synthesis described in example 69 step 1, 75 mg, 0.25 mmol) in N,N-dimethylformamide (9 mL) stirred in air at room temperature was added 2-amino-1-(4-carbamoylphenyl)-2-oxoethyl methanesulfonate (339 mg, 0.37 mmol) and triethylamine (50.4 mg, 0.50 mmol). The reaction mixture was stirred at room temperature for overnight. The mixture was concentrated and the residue was washed with DCM (20 mL) and filtered. The filtrate was concentrated in vacuum to give a crude which was purified by prep HPLC column and eluted with Me-CN/trifluoroacetic acid 0.1%. The product solution was concentrated in vacuo, and adjusted pH to 13 with Na$_2$CO$_3$ solution. Dried in vacuum and the residue was washed with water (3×2 mL) to afford 4-(2-amino-1-((3,5-dicyano-4-ethyl-6-(4-methyl-1,4-diazepan-1-yl)pyridin-2-yl)thio)-2-oxoethyl)benzamide (65 mg, 0.14 mmol, 55% yield) was obtained as a white solid. LCMS m/z=478.1 [M+H]$^+$. $^1$H NMR (400 MHz, methanol-d$_4$) δ 7.92 (d, J=8.2 Hz, 2H), 7.65 (d, J=8.3 Hz, 2H), 5.61 (s, 1H), 4.02 (m, 4H), 2.93 (m, 2H), 2.89-2.68 (m, 4H), 2.43 (s, 3H), 2.16-2.06 (m, 2H), 1.32 (t, J=7.6 Hz, 3H). Four protons not observed.

Example 369

2-((3,5-Dicyano-4-cyclopropyl-6-(3-hydroxypyrrolidin-1-yl)pyridin-2-yl)thio)-2-phenylacetamide Step 1: 2-Chloro-4-cyclopropyl-6-(3-hydroxypyrrolidin-1-yl)pyridine-3,5-dicarbonitrile

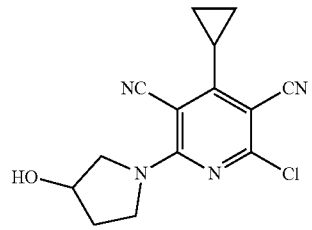 [SMILES: N#Cc1c(Cl)nc(N2CCC(O)C2)c(C#N)c1C1CC1]

To a solution of 2,6-dichloro-4-cyclopropylpyridine-3,5-dicarbonitrile (synthesis described in example 4, step 2, 1 g, 4.20 mmol) and pyrrolidin-3-ol (0.366 g, 4.20 mmol) in dichloromethane (20 mL) was added triethylamine (1.171 mL, 8.40 mmol) at 0° C. The resultant mixture was stirred at room temperature for 0.5 hour. The mixture was concentrated in vacuo. The residue was purified by silica gel chromatography (200 g silica; eluted with 50% EtOAc/hexane) to afford 2-chloro-4-cyclopropyl-6-(3-hydroxypyrrolidin-1-yl)pyridine-3,5-dicarbonitrile (0.9 g) as an off-white solid. LCMS m/z=289.0 [M+H]$^+$.

Step 2: 2-((3,5-Dicyano-4-cyclopropyl-6-(3-hydroxypyrrolidin-1-yl)pyridin-2-yl)thio)-2-phenylacetamide

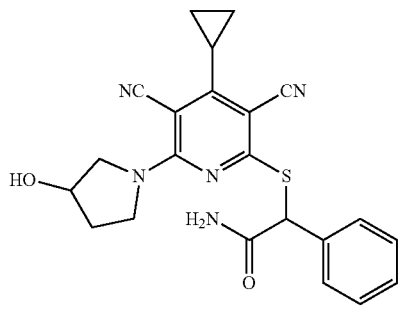 [SMILES: N#Cc1c(SC(C(N)=O)c2ccccc2)nc(N2CCC(O)C2)c(C#N)c1C1CC1]

To a solution of 2-chloro-4-cyclopropyl-6-(3-hydroxypyrrolidin-1-yl)pyridine-3,5-dicarbonitrile (500 mg) in N,N-dimethylformamide (20 mL) was added potassium ethanethioate (297 mg, 2.60 mmol) at room temperature. The mixture was stirred at room temperature for 2 hours then treated with $K_2CO_3$ (479 mg, 3.46 mmol). After stirring at room temperature for 0.5 hour, 2-amino-2-oxo-1-phenylethyl methanesulfonate (synthesis described in example 3, step 5, 595 mg, 2.60 mmol) was added and the resultant mixture stirred at room temperature overnight. The mixture was concentrated in vacuo and the residue diluted with EtOAc (100 mL). The mixture was filtered and the filtrate concentrated in vacuo. The remaining residue was purified by prep-HPLC to afford 2-((3,5-dicyano-4-cyclopropyl-6-(3-hydroxypyrrolidin-1-yl)pyridin-2-yl)thio)-2-phenylacetamide (200 mg) as a yellow solid. LCMS m/z=419.8 [M+H]$^+$. $^1$H NMR (400 MHz, DMSO-$d_6$) δ ppm 7.90 (s, 1H), 7.55-7.49 (m, 2H), 7.42-7.26 (m, 4H), 5.60 (s, 1H), 5.13 (d, J=7.5, 1H), 4.41 (s, 1H), 3.99-3.66 (m, 4H), 2.14-2.06 (m, 1H), 2.03-1.87 (m, 2H), 1.17-1.08 (m, 2H), 1.02-0.88 (m, 2H).

Example 370

2-((3,5-Dicyano-4-ethyl-6-(3-hydroxypyrrolidin-1-yl)pyridin-2-yl)thio)-2-phenylacetamide Step 1: 2-Chloro-4-ethyl-6-(3-hydroxypyrrolidin-1-yl)pyridine-3,5-dicarbonitrile

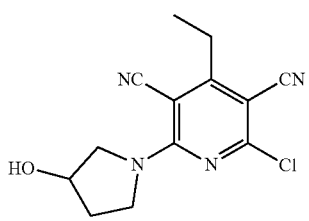 [SMILES: CCc1c(C#N)c(Cl)nc(N2CCC(O)C2)c1C#N]

To a stirred solution of 2,6-dichloro-4-ethylpyridine-3,5-dicarbonitrile (synthesis described in example 3, step 2, 16.6 g, 73.4 mmol) and triethylamine (14.86 g, 147 mmol) in dichloromethane (200 mL) at 0° C. was added a solution of 3-((tert-butyldimethylsilyl)oxy)pyrrolidine (14.79 g, 73.4 mmol) in dichloromethane (200 mL) dropwise over 5 minutes. The reaction mixture was stirred at 20° C. for 15 hours. To the mixture was added water (100 mL) and DCM (100 mL). The layers were separated and the organic layer dried over anhydrous sodium sulfate and concentrated to dryness. The residue was purified by silica gel chromatography (eluted with 16% EtOAc/petroleum ether solvent gradient) to afford 2-chloro-4-ethyl-6-(3-hydroxypyrrolidin-1-yl)pyridine-3,5-dicarbonitrile (15.0 g) as a white solid. LCMS m/z=277.0 [M+H]$^+$.

Step 2: 2-((3,5-Dicyano-4-ethyl-6-(3-hydroxypyrrolidin-1-yl)pyridin-2-yl)thio)-2-phenylacetamide

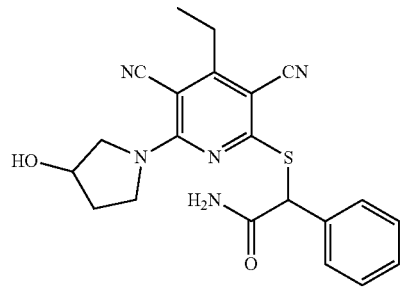 [SMILES: CCc1c(C#N)c(SC(C(N)=O)c2ccccc2)nc(N2CCC(O)C2)c1C#N]

To a stirred solution of 2-chloro-4-ethyl-6-(3-hydroxypyrrolidin-1-yl)pyridine-3,5-dicarbonitrile (1600 mg, 5.78 mmol) in N,N-dimethylformamide (20 mL) at room temperature was added a solution of potassium thioacetate (1321 mg, 11.5 mmol) in N,N-dimethylformamide (20 mL) over 1 minute. The reaction mixture was stirred at 25° C. for 1 hour. $K_2CO_3$ (1598 mg, 11.56 mmol) and a solution of 2-amino-2-oxo-1-phenylethyl methanesulfonate (synthesis described in example 3, step 5, 1988 mg, 8.67 mmol) in N,N-dimethylformamide (20 mL) were subsequently added. The reaction mixture was stirred at 25° C. for 15 hours. The reaction mixture was quenched with water (100 mL) and partitioned between ethyl acetate (100 mL) and hydrochloric acid (2 M, 100 mL). The layers were separated and the organic layer was dried over anhydrous sodium sulfate (10 g) and concentrated in vacuo to give the crude product. Purification of the crude material by prep-HPLC provided 2-((3,5-Dicyano-4-ethyl-6-(3-hydroxypyrrolidin-1-yl)pyridin-2-yl)thio)-2-phenylacetamide (400 mg) as a pale yellow solid. LCMS m/z=407.8 [M+H]$^+$. $^1$H NMR (400 MHz, DMSO-$d_6$) δ ppm 7.91 (s, 1H), 7.52 (d, J=7.6 Hz, 2H), 7.45-7.25 (m, 4H), 5.61 (s, 1H), 5.13 (br. s, 1H), 4.42 (s, 1H), 4.02-3.70 (m, 4H), 2.75 (q, J=7.5 Hz, 2H), 2.07-1.86 (m, 2H), 1.20 (t, J=7.6 Hz, 3H).

Example 371

N-(4-(((6-((2-Amino-2-oxoethyl)(methyl) amino-3,5-dicyano-4-ethylpyridin-2-yl) thio) methyl) benzyl-2-hydroxyacetamide Step 1: 2-((6-chloro-3,5-dicyano-4-ethylpyridin-2-yl)(methyl)amino)acetamide

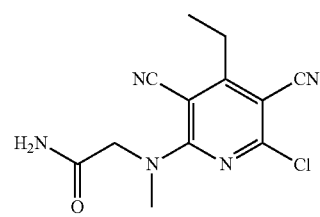 [SMILES: CCc1c(C#N)c(Cl)nc(N(C)CC(N)=O)c1C#N]

To a solution of 2,6-dichloro-4-ethylpyridine-3,5-dicarbonitrile (6 g, 26.5 mmol) in dichloromethane (100 mL) stirred under nitrogen at 0° C. was added TEA (11.10 mL, 80 mmol) and followed by 2-(methylamino)acetamide (2.339 g, 26.5 mmol). The reaction mixture was stirred at room temperature for 1 hour. The reaction mixture was diluted with ice cold water (200 mL), extracted with DCM (2×200 mL), Combined organic layer was washed with brine solution (200 mL) and dried over anhydrous Na$_2$SO$_4$, filtered and evaporated to afford 2-((6-chloro-3,5-dicyano-4-ethylpyridin-2-yl)(methyl)amino)acetamide (5 g) as off white solid. LCMS m/z=278.0 [M+H]$^+$.

Step 2: tert-Butyl 4-(((6-((2-amino-2-oxoethyl)(methyl)amino)-3,5-dicyano-4-ethylpyridin-2-yl)thio)methyl)benzylcarbamate

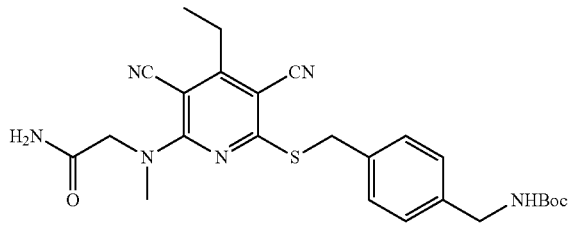 [SMILES: CCc1c(C#N)c(SCc2ccc(CNC(=O)OC(C)(C)C)cc2)nc(N(C)CC(N)=O)c1C#N]

To a solution of 2-((6-chloro-3,5-dicyano-4-ethylpyridin-2-yl)(methyl)amino)acetamide (1 g) in N,N-dimethylformamide (20 mL) was added potassium thioacetate (0.745 g, 6.52 mmol) at room temperature and the reaction mixture was stirred at room temperature for 2 hours. Then, potassium carbonate (0.902 g, 6.52 mmol) and tert-butyl 4-(chloromethyl)benzylcarbamate (1 g, 3.91 mmol) were added and the reaction stirred at room temperature for 1 hour. The reaction mixture was diluted with dichloromethane (100 mL) and washed with water (2×100 mL) and brine solution (100 mL). The organic layer was dried over anhydrous Na$_2$SO$_4$, filtered and concentrated. The crude material was purified by silica gel column (100-200 mesh, eluted with 4% MeOH in DCM). The collected fractions were dried to afford tert-butyl 4-(((6-((2-amino-2-oxoethyl)(methyl)amino)-3,5-dicyano-4-ethylpyridin-2-yl)thio)methyl)benzylcarbamate (600 mg) as an off-white solid. LCMS m/z=495.2 [M+H]$^+$.

Step 3: 2-((6-((4-(Aminomethyl)benzyl)thio)-3,5-dicyano-4-ethylpyridin-2-yl)(methyl)amino)acetamide, Hydrochloride

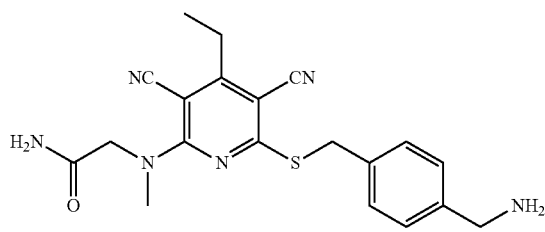 [SMILES: CCc1c(C#N)c(SCc2ccc(CN)cc2)nc(N(C)CC(N)=O)c1C#N]

To a stirred solution of tert-butyl 4-(((6-((2-amino-2-oxoethyl)(methyl)amino)-3,5-dicyano-4-ethylpyridin-2-yl)thio)methyl)benzylcarbamate (600 mg) in 1,4-dioxane (10 mL) under nitrogen at 0° C. was added HCl (4 M in 1,4-dioxane). The reaction mixture was stirred at room temperature for 5 hours. The reaction mixture was concentrated, washed with diethyl ether and dried to afford 2-((6-((4-(aminomethyl)benzyl)thio)-3,5-dicyano-4-ethylpyridin-2-yl)(methyl)amino)acetamide, Hydrochloride (500 mg) as an off-white solid. LCMS m/z=395.1 [M+H]$^+$.

Step 4: N-(4-(((6-((2-Amino-2-oxoethyl)(methyl)amino)-3,5-dicyano-4-ethylpyridin-2-yl)thio)methyl)benzyl)-2-hydroxyacetamide

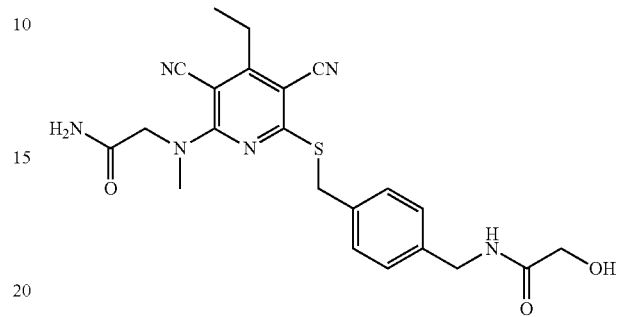

To a solution of 2-((6-((4-(aminomethyl)benzyl)thio)-3,5-dicyano-4-ethylpyridin-2-yl)(methyl)amino)acetamide, Hydrochloride (500 mg), 2-hydroxyacetic acid (100 mg, 1.309 mmol) and HATU (415 mg, 1.091 mmol) in N,N-dimethylformamide (20 mL) was added diisopropylethylamine (0.571 mL, 3.27 mmol) at 0° C. and the reaction mixture was stirred at room temperature for 5 hours. The reaction mixture was diluted with dichloromethane (100 mL) and washed with saturated solution of NH$_4$Cl (2×50 mL). The organic layer was washed with cold water (2×100 mL), brine (100 mL) and dried over anhydrous Na$_2$SO$_4$, filtered and concentrated. The crude product was purified by silica gel column (100-200 mesh and was eluted with 3% MeOH in DCM) to afford N-(4-(((6-((2-amino-2-oxoethyl)(methyl)amino)-3,5-dicyano-4-ethylpyridin-2-yl)thio)methyl)benzyl)-2-hydroxyacetamide (180 mg) as an off-white solid. LCMS m/z=453.3 [M+H]$^+$. $^1$H NMR (400 MHz, DMSO-d$_6$) δ ppm 8.26-8.21 (m, 1H), 7.53 (br s, 1H), 7.33 (d, J=8.11 Hz, 2H), 7.22 (d, J=8.2 Hz, 2H), 7.16 (br s, 1H), 5.48-5.44 (m, 1H), 4.43 (s, 2H), 4.33 (s, 2H), 4.28 (d, J=6.14 Hz, 2H), 3.85 (d, J=5.92 Hz, 2H), 3.43 (s, 3H), 2.78 (q, J=7.67 Hz, 2H), 1.22 (t, J=7.56 Hz, 3H).

Example 372

(2R)-2-Amino-N-(1-(6-((2-amino-2-oxo-1-phenylethyl)thio)-3,5-dicyano-4-cyclopropyl pyridin-2-yl)piperidin-4-yl)propanamide Step 1: tert-Butyl (1-(6-chloro-3,5-dicyano-4-cyclopropylpyridin-2-yl)piperidin-4-yl)carbamate

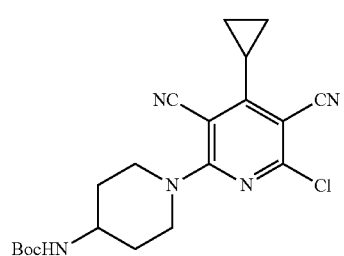 [SMILES: CC(C)(C)OC(=O)NC1CCN(c2nc(Cl)c(C#N)c(C3CC3)c2C#N)CC1]

To a solution of 2,6-dichloro-4-cyclopropylpyridine-3,5-dicarbonitrile (synthesis described in example 4 step 2, 6 g) in dichloromethane (100 mL) was added tert-butyl piperidin-4-ylcarbamate (4.59 g, 22.93 mmol) followed by triethylamine (3.20 mL, 22.93 mmol) at 0° C. The reaction mixture was stirred for 1 hour at 0° C. The reaction mixture was concentrated under reduced pressure, diluted with water (100 mL), and extracted with ethyl acetate (2×200 mL). The organic layers were combined, dried over anhydrous Na$_2$SO$_4$, filtered and concentrated under reduced pressure to afford tert-butyl (1-(6-chloro-3,5-dicyano-4-cyclopropylpyridin-2-yl)piperidin-4-yl)carbamate (9 g). LCMS m/z=402.2 [M+H]$^+$.

Step 2: tert-Butyl (1-(6-((2-amino-2-oxo-1-phenylethyl)thio)-3,5-dicyano-4-cyclopropylpyridin-2-yl)piperidin-4-yl)carbamate

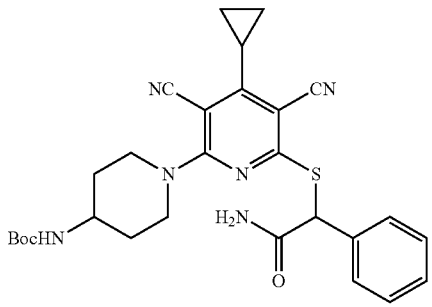 [SMILES: CC(C)(C)OC(=O)NC1CCN(c2nc(SC(C(N)=O)c3ccccc3)c(C#N)c(C3CC3)c2C#N)CC1]

To a solution of tert-butyl (1-(6-chloro-3,5-dicyano-4-cyclopropylpyridin-2-yl)piperidin-4-yl)carbamate (8 g, 17.87 mmol) in N,N-dimethylformamide (80 mL) was added potassium thioacetate (3.06 g, 26.8 mmol) at room temperature, and the reaction mixture was stirred for 2 hours at the same temperature. Then potassium carbonate (3.70 g, 26.8 mmol) was added followed by 2-amino-2-oxo-1-phenylethyl methanesulfonate (synthesis described in example 3 step 5, 4.66 g, 17.87 mmol) at room temperature. The reaction mixture was stirred for 2 hours at room temperature. The reaction mixture was quenched in cold water (200 mL), and a solid precipitated. The solid was collected by filtration, washed with diethyl ether (50 mL), then dried to afford tert-butyl (1-(6-((2-amino-2-oxo-1-phenylethyl)thio)-3,5-dicyano-4-cyclopropylpyridin-2-yl)piperidin-4-yl)carbamate (7 g). LCMS m/z=533.2 [M+H]$^+$ Step 3: 2-((6-(4-Aminopiperidin-1-yl)-3,5-dicyano-4-cyclopropylpyridin-2-yl)thio)-2-phenylacetamide, Hydrochloride

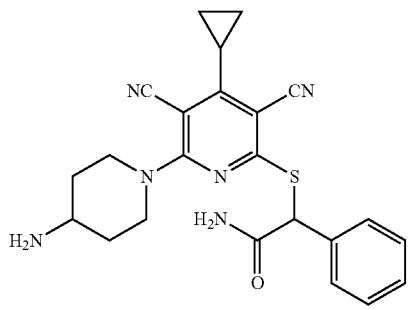 [SMILES: N#Cc1c(SC(C(N)=O)c2ccccc2)nc(N2CCC(N)CC2)c(C#N)c1C1CC1]

To a solution of tert-butyl (1-(6-((2-amino-2-oxo-1-phenylethyl)thio)-3,5-dicyano-4-cyclopropylpyridin-2-yl)piperidin-4-yl)carbamate (6 g) in 1,4-dioxane (60 mL) was added HCl (4 M in 1,4-dioxane, 21.43 mL, 86 mmol) at 0° C. and the reaction mixture was stirred for 4 hours at 25° C. The reaction mixture was concentrated under reduced pressure and the crude material was triturated with diethyl ether (2×200 mL), filtered and dried under vacuum to afford 2-((6-(4-aminopiperidin-1-yl)-3,5-dicyano-4-cyclopropylpyridin-2-yl)thio)-2-phenylacetamide, Hydrochloride (4.5 g) as an off-white solid. LCMS m/z=433.2 [M+H]$^+$.

Step 4: tert-Butyl ((2R)-1-((1-(6-((2-amino-2-oxo-1-phenylethyl)thio)-3,5-dicyano-4-cyclopropylpyridin-2-yl)piperidin-4-yl)amino)-1-oxopropan-2-yl)carbamate

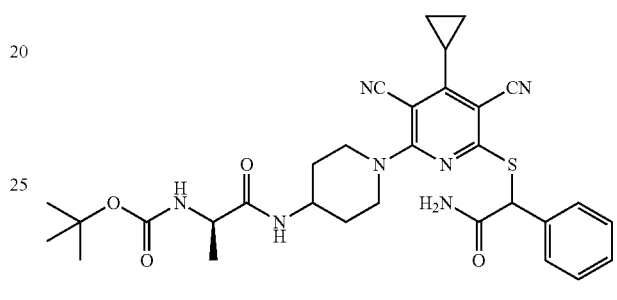

To a solution of (R)-2-((tert-butoxycarbonyl)amino)propanoic acid (179 mg, 0.948 mmol) in N,N-dimethylformamide (10 mL) was added diisopropylethylamine (0.414 mL, 2.371 mmol) and HATU (451 mg, 1.185 mmol) at 0° C. The reaction mixture was stirred for 10 minutes at the same temperature then 2-((6-(4-aminopiperidin-1-yl)-3,5-dicyano-4-cyclopropylpyridin-2-yl)thio)-2-phenylacetamide, Hydrochloride (450 mg, 0.790 mmol) was added at room temperature and the reaction mixture was stirred for 3 hours at room temperature. The reaction mixture was concentrated under reduced pressure, diluted with water (30 mL), and extracted with ethyl acetate (2×80 mL). The combined organic layers were dried over anhydrous Na$_2$SO$_4$, filtered, and concentrated under reduced pressure to afford tert-butyl ((2R)-1-((1-(6-((2-amino-2-oxo-1-phenylethyl)thio)-3,5-dicyano-4-cyclopropylpyridin-2-yl)piperidin-4-yl)amino)-1-oxopropan-2-yl)carbamate (400 mg) as a brown solid. LCMS m/z=604.2 [M+H]$^+$.

Step 5: (2R)-2-Amino-N-(1-(6-((2-amino-2-oxo-1-phenylethyl)thio)-3,5-dicyano-4-cyclo propylpyridin-2-yl)piperidin-4-yl)propanamide

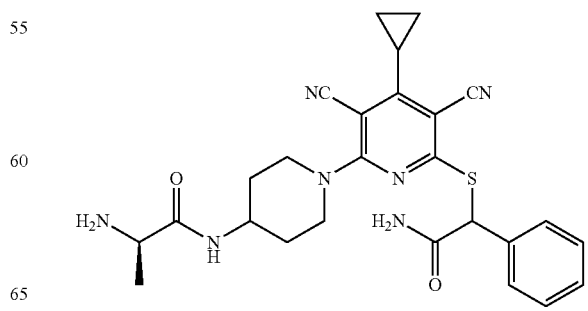

731

To a solution of tert-butyl ((2R)-1-((1-(6-((2-amino-2-oxo-1-phenylethyl)thio)-3,5-dicyano-4-cyclopropylpyridin-2-yl)piperidin-4-yl)amino)-1-oxopropan-2-yl)carbamate (400 mg) in 1,4-dioxane (10 mL), was added HCl (4 M in dioxane, 1.320 mL, 5.28 mmol) at 0° C. and the reaction mixture was stirred for 4 hours at 25° C. The reaction mixture was concentrated under reduced pressure and the crude product was triturated with diethyl ether (2×20 mL), filtered and concentrated. The crude material was purified by prep-HPLC to afford (2R)-2-amino-N-(1-(6-((2-amino-2-oxo-1-phenylethyl)thio)-3,5-dicyano-4-cyclopropylpyridin-2-yl)piperidin-4-yl)propanamide (185 mg, 69% yield) as an off-white solid. LCMS m/z=504.1 [M+H]$^+$. $^1$H NMR (400 MHz, DMSO-$d_6$) δ ppm 7.88 (s, 1H), 7.74 (br d, J=7.89 Hz, 1H), 7.56-7.49 (m, 2H), 7.42-7.28 (m, 4H), 5.52 (s, 1H), 4.39 (br t, J=12.17 Hz, 2H), 3.95-3.84 (m, 1H), 3.33 (br s, 2H), 3.22 (s, 1H), 2.14-2.10 (m, 1H), 1.87 (br d, J=9.87 Hz, 4H), 1.56-1.44 (m, 2H), 1.19-1.10 (m, 5H), 1.01-0.95 (m, 2H).

Example 373

2-((6-((2-Aminoethyl)(methyl)amino)-3,5-dicyano-4-cyclopropylpyridin-2-yl)thio)-2-phenylacetamide, Hydrochloride Step 1: tert-Butyl(2-((6-chloro-3,5-dicyano-4-cyclopropylpyridin-2yl)(methyl)amino) ethyl)carbamate

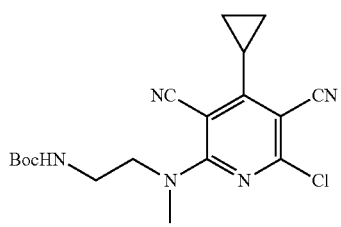 [SMILES: CN(CCNC(=O)OC(C)(C)C)c1nc(Cl)c(C#N)c(C2CC2)c1C#N]

To a stirred solution of 2,6-dichloro-4-cyclopropylpyridine-3,5-dicarbonitrile (synthesis described in example 4 step 2, 1.5 g) in dichloromethane (20 mL) was added triethylamine (1.652 mL, 11.85 mmol) followed by tert-butyl (2-(methylarnino)ethyl)carbamate (1.032 g, 5.92 mmol) at 0° C. The reaction mixture was stirred for 2 hours at room temperature. The reaction mixture was concentrated under reduced pressure, diluted with water (50 mL) and extracted with dichloromethane (2×100 mL). The combined organic layers were dried over anhydrous Na$_2$SO$_4$, filtered and concentrated under reduced pressure to afford tert-butyl (2-((6-chloro-3,5-dicyano-4-cyclopropylpyridin-2-yl)(methyl)amino)ethyl)carbamate (1.6 g) as an off-white solid. LCMS m/z=376.1 [M+H]$^+$.

Step 2: tert-Butyl(2-((6-((2-amino-2-oxo-1-phenylethyl)thio)-3,5-dicyano-4-cyclopropyl pyridin-2-yl)(methyl)amino)ethyl)carbamate

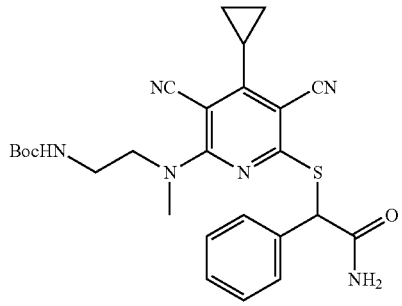 [SMILES: CN(CCNC(=O)OC(C)(C)C)c1nc(SC(C(N)=O)c2ccccc2)c(C#N)c(C2CC2)c1C#N]

To a solution of tert-butyl (2-((6-chloro-3,5-dicyano-4-cyclopropylpyridin-2-yl)(methyl)amino)ethyl)carbamate (1.3 g) in N,N-dimethylformamide (20 mL) was added potassium thioacetate (0.552 g, 4.83 mmol) at room temperature and the reaction mixture was stirred for 2 hours at the same temperature. Then potassium carbonate (0.668 g, 4.83 mmol) was added followed by 2-amino-2-oxo-1-phenylethyl methanesulfonate (synthesis described in example 3 step 5, 1.231 g) at room temperature. The reaction mixture was stirred for 2 hours at room temperature. The reaction mixture was quenched in cold water (80 mL), filtered and dried under reduced pressure. Diethyl ether (40 mL) was added and the mixture stirred for 15 minutes, then filtered and dried under reduced pressure to afford tert-butyl (2-((6-((2-amino-2-oxo-1-phenylethyl)thio)-3,5-dicyano-4-cyclopropylpyridin-2-yl)(methyl)amino)ethyl)carbamate (850 mg) as an off-white solid. LCMS m/z=507.2 [M+H]$^+$.

Step 3: 2-((6-((2-Aminoethyl)(methyl)amino)-3,5-dicyano-4-cyclopropylpyridin-2-yl)thio)-2-phenylacetamide, Hydrochloride

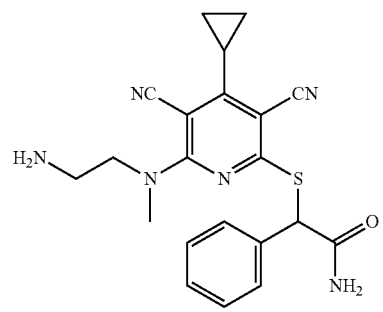 [SMILES: CN(CCN)c1nc(SC(C(N)=O)c2ccccc2)c(C#N)c(C2CC2)c1C#N]

To a stirred solution of tert-butyl (2-((6-((2-amino-2-oxo-1-phenylethyl)thio)-3,5-dicyano-4-cyclopropylpyridin-2-yl)(methyl)amino)ethyl)carbamate (700 mg) in 1,4-dioxane (10 mL) was added HCl (4 M in 1,4-dioxane, 3.20 mL, 12.80 mmol) at 0° C., then the reaction mixture was stirred for 4 hours at 25° C. The reaction mixture was concentrated under reduced pressure and the crude residue was triturated with diethyl ether (2×20 mL), filtered and dried under vacuum to afford 2-((6-((2-aminoethyl)(methyl)amino)-3,5-dicyano-4-cyclopropylpyridin-2-yl)thio)-2-phenylacetamide, Hydrochloride (550 mg) as an off-white solid. LCMS m/z=407.2

733

[M+H]+. 1H NMR (400 MHz, DMSO-d6) δ ppm 8.21 (br s, 1H), 8.10 (br s, 3H), 7.63-7.55 (m, 2H), 7.46-7.26 (m, 4H), 5.69 (s, 1H), 4.14-3.97 (m, 2H), 3.40 (s, 3H), 3.17-3.06 (m, 2H), 2.12 (tt, J=8.74, 5.73 Hz, 1H), 1.22-1.12 (m, 2H), 1.00-0.91 (m, 2H).

Example 374

2-Amino-N-(1-(6-((2-amino-2-oxo-1-phenylethyl)thio)-3,5-dicyano-4-cyclopropylpyridin-2-yl)piperidin-4-yl)-2-methylpropanamide Step 1: tert-Butyl (1-((1-(6-((2-amino-2-oxo-1-phenylethyl)thio)-3,5-dicyano-4-cyclopropyl pyridin-2-yl)piperidin-4-yl)amino)-2-methyl-1-oxopropan-2-yl)carbamate

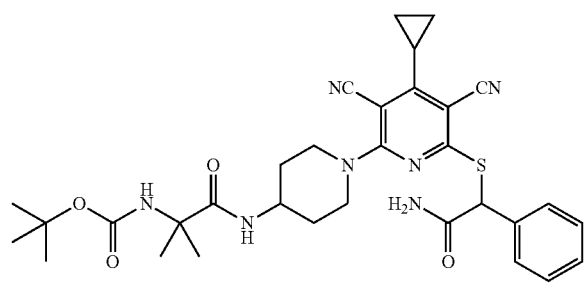 [SMILES: CC(C)(C)OC(=O)NC(C)(C)C(=O)NC1CCN(c2nc(SC(C(N)=O)c3ccccc3)c(C#N)c(C3CC3)c2C#N)CC1]

To a stirred solution of 2-((6-(4-aminopiperidin-1-yl)-3,5-dicyano-4-cyclopropylpyridin-2-yl)thio)-2-phenylacetamide, Hydrochloride (synthesis described in example 372 step 3, 400 mg) in N,N-dimethylformamide (30 mL) was added diisopropylethylamine (0.261 mL, 1.495 mmol) and HATU (379 mg, 0.997 mmol) at 0° C. The reaction mixture for 10 minutes at the same temperature, then 2-((tert-butoxycarbonypamino)-2-methylpropanoic acid (152 mg, 0.747 mmol) was added at room temperature. The reaction mixture was stirred for 3 hours at room temperature, then was diluted with water (20 mL) and extracted with ethyl acetate (2×50 mL). The combined organic layers were dried over anhydrous Na2SO4,filtered and concentrated to afford tert-butyl (1-((1-(6-((2-amino-2-oxo-1-phenylethyl)thio)-3,5-dicyano-4-cyclopropylpyridin-2-yl)piperidin-4-yl)amino)-2-methyl-1-oxopropan-2-yl)carbamate (500 mg). 1H NMR (400 MHz, DMSO-d6) δ ppm 8.16 (d, J=7.7 Hz, 2H), 7.98 (s, 1H), 7.52 (d, J=7.3 Hz, 2H), 7.40-7.29 (m, 4H), 5.54 (s, 1H), 4.54-4.93 (m, 2H), 4.25-4.18 (m, 1H), 4.04-3.97 (m, 2H), 3.57 (s, 6H), 3.43-3.37 (m, 2H), 2.16-2.08 (m, 1H), 1.87 (d, J=12.4 Hz, 2H), 1.46 (s, 9H), 1.31-1.23 (m, 2H), 1.00-0.94 (m, 2H).

734

Step 2: 2-Amino-N-(1-(6-((2-amino-2-oxo-1-phenylethyl)thio)-3,5-dicyano-4-cyclopropyl pyridin-2-yl)piperidin-4-yl)-2-methylpropanamide, Hydrochloride

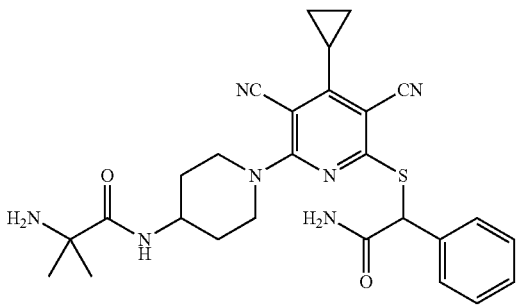 [SMILES: CC(C)(N)C(=O)NC1CCN(c2nc(SC(C(N)=O)c3ccccc3)c(C#N)c(C3CC3)c2C#N)CC1]

To a stirred solution of tert-butyl (1-((1-(6-((2-amino-2-oxo-1-phenylethyl)thio)-3,5-dicyano-4-cyclopropylpyridin-2-yl)piperidin-4-yl)amino)-2-methyl-1-oxopropan-2-yl)carbamate (700 mg, which is from two batches that were combined) in 1,4-dioxane (20 mL) was added HCl (4 M in dioxane, 2.83 mL, 11.33 mmol) at 0° C., and the reaction mixture was stirred for 4 hours at 25° C. The reaction mixture was concentrated under reduced pressure and the residue was triturated with diethyl ether (2×20 mL), filtered and dried under vacuum. The residue was washed with diethyl ether (30 mL) and n-pentane (30 mL) then dried under vacuum to obtain 250 mg of material with 87.6% purity. This material was further subjected to prep-HPLC purification (using 10 mM Ammonium bicarbonate solution with acetonitrile) to afford 2-amino-N-(1-(6-((2-amino-2-oxo-1-phenylethyl)thio)-3,5-dicyano-4-cyclopropylpyridin-2-yl)piperidin-4-yl)-2-methylpropanamide (120 mg) as an off-white solid. LCMS m/z=518.4 [M+H]+. 1H NMR (400 MHz, DMSO-d6) δ ppm 7.88 (s, 1H), 7.74 (br d, J=7.89 Hz, 1H), 7.58-7.49 (m, 2H), 7.43-7.28 (m, 4H), 5.52 (s, 1H), 4.41 (br t, J=13.92 Hz, 2H), 3.93-3.80 (m, 1H), 3.28-3.17 (m, 2H), 2.18-2.08 (m, 1H), 1.97-1.80 (m, 4H), 1.57-1.42 (m, 2H), 1.20-1.06 (m, 8H), 1.00-0.91 (m, 2H).

Example 375

4-(2-Amino-1-((3,5-dicyano-6-(dimethylamino)-4-ethylpyridin-2-yl)thio)-2-oxoethyl)benzamide

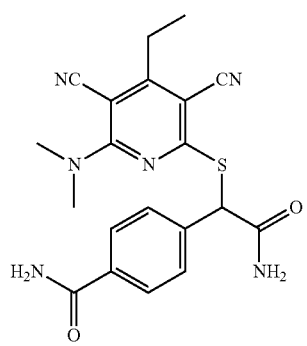 [SMILES: CCc1c(C#N)c(SC(C(N)=O)c2ccc(C(N)=O)cc2)nc(N(C)C)c1C#N]

To a solution of 2-chloro-6-(dimethylamino)-4-ethylpyridine-3,5-dicarbonitrile (synthesis described in example 3 step 3, 59 mg, 0.25 mmol) in N,N-dimethylformamide (9 mL) stirred in air at room temperature was added potassium ethanethioate (28.7 mg, 0.25 mmol) and triethylamine (0.070 mL, 0.50 mmol). The reaction mixture was stirred at room temperature for 1.5 hour. Then 2-amino-1-(4-carbamoylphenyl)-2-oxoethyl methanesulfonate (339 mg, 0.37 mmol) was added. The reaction mixture was stirred at room temperature overnight. The mixture was concentrated in vacuo and the residue was washed with DCM (3×10 mL). The solid was purified by Prep-HPLC (eluted with Me-CN/trifluoroacetic acid 0.1%). Collected fractions were adjusted pH to 13 with $Na_2CO_3$ solution then concentrated in vacuum and the resulting solid was washed with water (3×2 mL), then dried in vacuum to afford 4-(2-amino-1-((3,5-dicyano-6-(dimethylamino)-4-ethylpyridin-2-yl)thio)-2-oxoethyl)benzamide (66 mg, 0.16 mmol, 64% yield) as a white solid. LCMS m/z=409.1 $[M+H]^+$. $^1$H NMR (400 MHz, methanol-$d_4$) δ ppm 7.91 (d, J=8.1 Hz, 2H), 7.66 (d, J=7.4 Hz, 2H), 5.69 (s, 1H), 3.41 (s, 6H), 2.91 (m, 2H), 1.31 (m, 3H).

Example 376

2-(6-(4-Aminopiperidin-1-yl)-3-cyano-4-ethyl-5-methylpyridin-2-ylthio)-2-phenylacetamide Step 1: tert-Butyl 1-(6-chloro-5-cyano-4-ethyl-3-methylpyridin-2-yl)piperidin-4-ylcarbamate

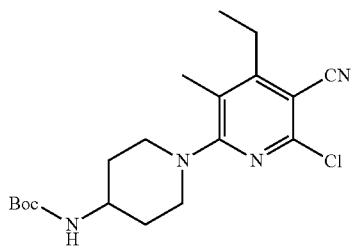 [SMILES: CCc1c(C)c(N2CCC(NC(=O)OC(C)(C)C)CC2)nc(Cl)c1C#N]

To a solution of 2,6-dichloro-4-ethyl-5-methylnicotinonitrile (synthesis described in example 293 step 2, 1 g, 4.65 mmol), and triethylamine (1.411 g, 13.95 mmol) in acetonitrile (50 mL) stirred at room temperature, was added tert-butyl piperidin-4-ylcarbamate (1.117 g, 5.58 mmol). The reaction mixture was stirred at 90° C. overnight. The organic phase was concentrated in vacuo, washed with water (50 mL) and saturated brine (25 mL), extracted with dichloromethane (100 mL), dried over sodium sulphate, filtered, and concentrated in vacuo. The residue was purified by prep-HPLC to afford tert-butyl 1-(6-chloro-5-cyano-4-ethyl-3-methylpyridin-2-yl)piperidin-4-ylcarbamate (1 g, 57%) as a yellow solid. LCMS m/z=378.9 $[M+H]^+$.

Step 2: tert-Butyl 1-(6-(2-amino-2-oxo-1-phenylethylthio)-5-cyano-4-ethyl-3-methylpyridin-2-yl)piperidin-4-ylcarbamate

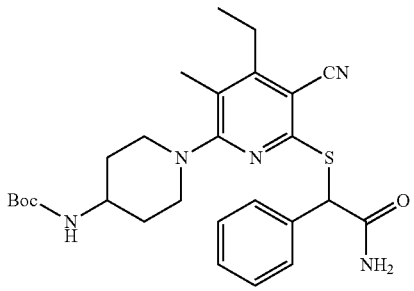 [SMILES: CCc1c(C)c(N2CCC(NC(=O)OC(C)(C)C)CC2)nc(SC(C(N)=O)c2ccccc2)c1C#N]

A solution of tert-butyl (1-(6-chloro-5-cyano-4-ethyl-3-methylpyridin-2-yl)piperidin-4-yl)carbamate (1 g, 2.64 mmol), 2-mercapto-2-phenylacetamide (synthesis described in example 276 step 1, 1.324 g, 7.92 mmol) and triethylamine (0.801 g, 7.92 mmol) in N,N-dimethylformamide (35 mL) was stirred at 60° C. in a microwave reactor for 12 hours. The mixture was concentrated in vacuo to afford a yellow solid which was purified by silica gel (eluted with $CH_2Cl_2$/MeOH=20:1-10:1) to afford tert-butyl 1-(6-(2-amino-2-oxo-1-phenylethylthio)-5-cyano-4-ethyl-3-methylpyridin-2-yl)piperidin-4-ylcarbamate (300 mg, 22%) as off-white solid. LCMS m/z=509.9 $[M+H]^+$.

Step 3: 2-(6-(4-Aminopiperidin-1-yl)-3-cyano-4-ethyl-5-methylpyridin-2-ylthio)-2-phenylacetamide

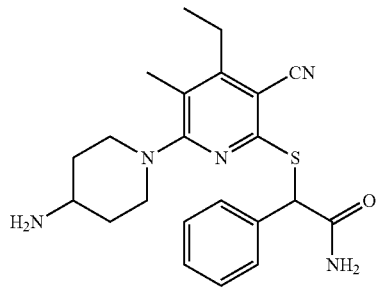 [SMILES: CCc1c(C)c(N2CCC(N)CC2)nc(SC(C(N)=O)c2ccccc2)c1C#N]

A solution of tert-butyl (1-(6-((2-amino-2-oxo-1-phenylethyl)thio)-5-cyano-4-ethyl-3-methylpyridin-2-yl)piperidin-4-yl)carbamate (300 mg, 0.59 mmol) and 2,2,2-trifluoroacetic acid (67.1 mg, 0.59 mmol) in dichloromethane (20 mL) was stirred at 27° C. for 2 hours. The organic phase was washed with saturated sodium bicarbonate solution (25 mL), water (25 mL) and saturated brine (25 mL), dried over sodium sulphate, filtered, and concentrated in vacuo. The residue was purified by silica gel column (eluted with DCM:MeOH=10:1) to afford 2-(6-(4-aminopiperidin-1-yl)-3-cyano-4-ethyl-5-methylpyridin-2-ylthio)-2-phenylacetamide (57 mg, 24%). LCMS m/z=409.9 $[M+H]^+$. $^1$H NMR (400 MHz, MeOD) δ ppm 7.55 (d, J=6.9 Hz, 2H), 7.47-7.26 (m, 3H), 5.58 (s, 1H), 3.72 (s, 2H), 3.08-2.87 (m, 3H), 2.80 (q, J=7.5 Hz, 2H), 2.23 (s, 3H), 2.00 (d, J=12.0 Hz, 2H), 1.57 (dd, J=19.7, 7.5 Hz, 2H), 1.21 (t, J=7.6 Hz, 3H).

Example 377

2-(4-(2-(Dimethylamino)ethoxy)benzylthio)-4-ethyl-6-(4-methyl-1,4-diazepan-1-yl)pyridine-3,5-dicarbonitrile

Step 1: Methyl 4-(2-(tert-butyldimethylsilyloxy)ethoxy)benzoate

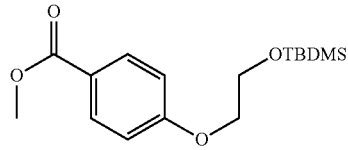 [SMILES: COC(=O)c1ccc(OCCO[Si](C)(C)C(C)(C)C)cc1]

A mixture of methyl 4-hydroxybenzoate (3.0 g, 19.72 mmol) (2-bromoethoxy)(tert-butyl)dimethylsilane (5.66 g, 23.66 mmol) and cesium carbonate (7.71 g, 23.66 mmol) in N,N-dimethylformamide (20 mL) was stirred at 40-50° C. for 2 hours then stirred at 70-80° C. for 18 hours. Water (80 mL) was added into the mixture. The resulting mixture was extracted with ethyl acetate (2×30 mL). The organic layer was washed with brine (20 mL), then concentrated. The crude was purified by silica gel column chromatography (0-10% ethyl acetate in petroleum ether) to afford methyl 4-(2-(tert-butyldimethylsilyloxy)ethoxy)benzoate (1.4 g, 23% yield). $^1$H NMR (400 MHz, CDCl$_3$) δ 8.00 (d, J=8.8 Hz, 2H), 6.95 (d, J=8.8 Hz, 2H), 4.12 (t, J=4.0 Hz, 2H), 4.01 (t, J=4.0 Hz, 2H), 3.91 (s, 3H), 0.93 (s, 9H), 0.12 (s, 6H).

Step 2: (4-(2-(tert-Butyldimethylsilyloxy)ethoxy)phenyl)methanol

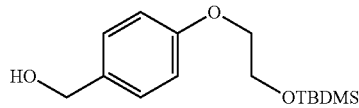 [SMILES: CC(C)(C)[Si](C)(C)OCCOc1ccc(CO)cc1]

To a solution of methyl 4-(2-(tert-butyldimethylsilyloxy)ethoxy)benzoate (850 mg, 2.74 mmol) in tetrahydrofuran (10 mL) was added LiAlH$_4$ (208 mg, 5.48 mmol) in portions at 0-5° C. The mixture was stirred at 0-5° C. for 1 hour then stirred at 20-30° C. for 1 hour. Ethyl acetate (20 mL) was added into the mixture followed by 5 drops of water. Then the mixture was filtered and the filtrate was concentrated and purified by flash chromatography (1-10% ethyl acetate in petroleum ether) to afford (4-(2-(tert-butyldimethylsilyloxy)ethoxy)phenyl)methanol (435 mg, 56% yield). $^1$H NMR (400 MHz, DMSO) δ 7.22 (d, J=8.5 Hz, 2H), 6.88 (d, J=8.5 Hz, 2H), 5.05 (t, J=5.7 Hz, 1H), 4.41 (d, J=5.7 Hz, 2H), 4.00 (t, J=4.0 Hz, 2H), 3.91 (t, J=4.0 Hz, 2H), 0.88 (s, 9H), 0.07 (s, 6H).

Step 3: 2-(4-(2-(tert-Butyldimethylsilyloxy)ethoxy)benzylthio)-4-ethyl-6-(4-methyl-1,4-diazepan-1-yl)pyridine-3,5-dicarbonitrile

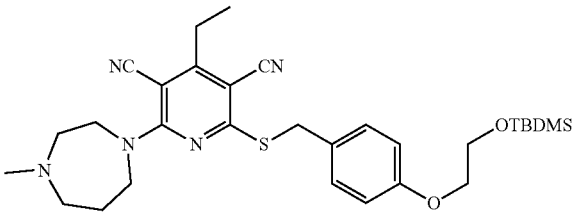 [SMILES: CCc1c(C#N)c(SCc2ccc(OCCO[Si](C)(C)C(C)(C)C)cc2)nc(N2CCCN(C)CC2)c1C#N]

To a mixture of 4-(2-((tert-butyldimethylsilyl)oxy)ethoxy)phenol (195 mg, 0.73 mmol) N-ethyl-N-isopropyl-propan-2-amine (141 mg, 1.09 mmol) in dichloromethane (5 mL), was added methanesulfonyl chloride (92 mg, 0.80 mmol). The mixture was stirred at 20-30° C. for 2 hours to afford a crude solution of 4-(2-((tert-butyldimethylsilyl)oxy)ethoxy)phenyl methanesulfonate. To a mixture of 4-ethyl-2-mercapto-6-(4-methyl-1,4-diazepan-1-yl)pyridine-3,5-dicarbonitrile (synthesis described in example 69 step 1, 230 mg, 0.76 mmol) and triethylamine (116 mg, 1.15 mmol) in N,N-dimethylformamide (10 mL) was added the above solution of 4-(2-((tert-butyldimethylsilyl)oxy)ethoxy)phenyl methanesulfonate. The mixture was stirred at 20-30° C. for 16 hours. Water (40 mL) was added to the mixture. The resulting mixture was extracted with DCM (2×20 mL) and the combined organic layer was washed with water (20 mL) brine (20 mL), then concentrated. The crude was purified by flash chromatography (eluted by petroleum ether:ethyl acetate=100:1-1:1) to afford 2-(4-(2-(tert-butyldimethylsilyloxy)ethoxy)benzylthio)-4-ethyl-6-(4-methyl-1,4-diazepan-1-yl)pyridine-3,5-dicarbonitrile (160 mg, 37% yield). LCMS m/z=566.2 [M+H]$^+$.

Step 4: 4-Ethyl-2-(4-(2-hydroxyethoxy)benzylthio)-6-(4-methyl-1,4-diazepan-1-yl)pyridine-3,5-dicarbonitrile

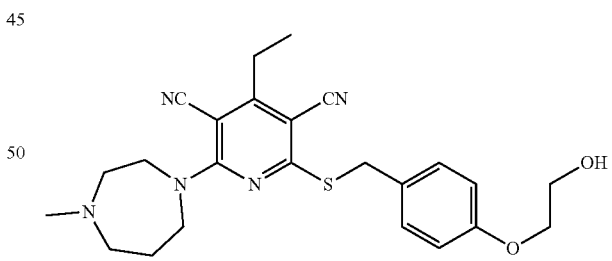

2-((4-(2-((tert-butyldimethylsilyl)oxy)ethoxy)benzyl)thio)-4-ethyl-6-(4-methyl-1,4-diazepan-1-yl)pyridine-3,5-dicarbonitrile (150 mg, 0.27 mmol) was added to a solution of HCl (2 M in MeOH, 5 mL) and the mixture was stirred for 1 hour at 20-30° C. The mixture was adjusted pH to 7 with ammonia water, then concentrated. The solid was stirred for 30 minutes with DCM (30 mL), then filtered. The organic phase was purified by flash chromatography (100% DCM to 5:1 DCM:MeOH) to afford 4-ethyl-2-(4-(2-hydroxyethoxy)benzylthio)-6-(4-methyl-1,4-diazepan-1-yl)pyridine-3,5-dicarbonitrile (60 mg, 50%). LCMS m/z=452.3 [M+H]$^+$.

Step 5: 2-(4-(2-(Dimethylamino)ethoxy)benzylthio)-4-ethyl-6-(4-methyl-1,4-diazepan-1-yl)pyridine-3,5-dicarbonitrile

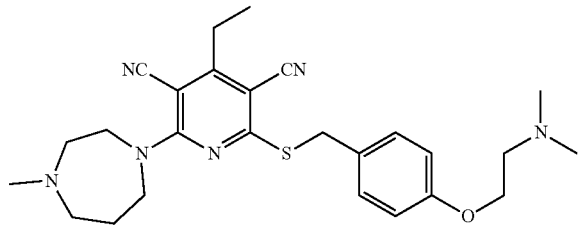

To a mixture of 4-ethyl-2-((4-(2-hydroxyethoxy)benzyl)thio)-6-(4-methyl-1,4-diazepan-1-yl)pyridine-3,5-dicarbonitrile (55 mg, 0.12 mmol) and triethylamine (18.49 mg, 0.18 mmol) in dichloromethane (5 mL), 4-methylbenzene-1-sulfonyl chloride (25.5 mg, 0.13 mmol) was added. The mixture was stirred at 20-30° C. for 5 hours, then dimethylamine (0.6 mL, 1.22 mmol, 2 M THF solution) was added. The mixture was stirred at reflux for 5 hours. Water (20 mL) was added into the mixture. The resulting mixture was extracted with DCM (2×15 mL). The combined organic layer was washed with water (20 mL) and brine (20 mL), then concentrated. The solid was purified by flash chromatography (100% DCM to 10:1 DCM:MeOH with 5% NH$_4$OH) to afford 2-(4-(2-(dimethylamino)ethoxy)benzylthio)-4-ethyl-6-(4-methyl-1,4-diazepan-1-yl)pyridine-3,5-dicarbonitrile (35 mg, 60% yield). LCMS m/z=479.2 [M+H]$^+$. $^1$H NMR (400 MHz, CDCl$_3$) δ ppm 7.31-7.25 (m, 2H), 6.89 (d, J=8.6 Hz, 2H), 4.38 (s, 2H), 4.14 (t, J=5.5 Hz, 2H), 4.04-3.99 (m, 2H), 3.96 (t, J=6.1 Hz, 2H), 2.94 (q, J=7.6 Hz, 2H), 2.85 (t, J=5.4 Hz, 2H), 2.81-2.76 (m, 2H), 2.67-2.60 (m, 2H), 2.44 (s, 6H), 2.42 (s, 3H), 2.15-2.06 (m, 2H), 1.34 (t, J=7.6 Hz, 3H).

Example 378

2-((3,5-Dicyano-4-ethyl-6-(4-methyl-1,4-diazepan-1-yl)pyridin-2-yl)thio)-2-(4-1N-methylsulfamoyl)phenyl)acetamide Step 1: 4-Formyl-N-methylbenzenesulfonamide

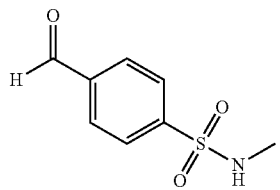

Triethylamine (12.44 mL, 89 mmol) was added dropwise to a stirred solution of 4-iodobenzene-1-sulfonyl chloride (9 g, 29.8 mmol) and methanamine hydrochloride (6.03 g, 89 mmol) in DCM (200 mL) and the mixture was stirred at 20° C. for 10 hours. Then water was added, and the organic layer was separated and dried with anhydrous Na$_2$SO$_4$, filtered and concentrated to afford a residue. This residue, dicya-nozinc (8.02 g, 68.3 mmol) and tetrakis(triphenylphosphine)palladium (1.579 g, 1.37 mmol) in DMF (100 mL) was stirred at 95° C. for 16 hours. After cooling the reaction, the reaction mixture was concentrated and the residue partitioned between ethyl acetate and water. The organic phase was dried with anhydrous sodium sulfate, filtered and concentrated and the residue was purified by column chromatograph to afford a crude product (4.7 g). A mixture of the product from the previous step, nickel (0.281 g, 4.79 mmol) and formic acid (60 mL, 23.95 mmol) was stirred at 125° C. for 14 hours under nitrogen atmosphere. After cooling the reaction, the reaction mixture was filtered and the filtrate was concentrated in vacuo. The residue was purified by column chromatography. LCMS m/z=200.1 [M+H]$^+$.

Step 2: 4-(Cyano((trimethylsilyl)oxy)methyl)-N-methylbenzenesulfonamide

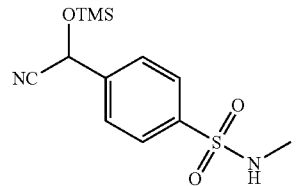

A mixture of 4-formyl-N-methylbenzenesulfonamide (2 g, 10.0 mmol), trimethylsilanecarbonitrile (50 mL, 10.04 mmol) and potassium 1,3-dioxoisoindolin-2-ide (0.232 g, 1.26 mmol) was stirred at 20° C. for 24 hours. The mixture was concentrated, and the residue was purified by column chromatography to afford 4-(cyano((trimethylsilyl)oxy)methyl)-N-methylbenzenesulfonamide (0.83 g, 28% yield). LCMS m/z=321.0 [M+Na]$^+$.

Step 3: 2-Hydroxy-2-(4-(N-methylsulfamoyl)phenyl)acetamide

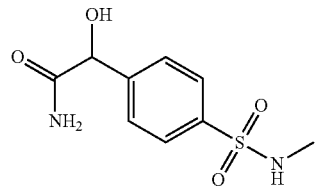 [SMILES: CNS(=O)(=O)c1ccc(C(O)C(N)=O)cc1]

A mixture of 4-(cyano((trimethylsilyl)oxy)methyl)-N-methylbenzenesulfonamide (914 mg, 3.06 mmol), palladium(II) chloride (109 mg, 0.61 mmol) and acetamide (1809 mg, 30.6 mmol) in tetrahydrofuran (18 mL) and water (6.00 mL) was stirred at 20° C. for 16 hours. The reaction mixture was concentrated. The residue was purified by column chromatography to afford 2-hydroxy-2-(4-(N-methylsulfamoyl)phenyl)acetamide (860 mg, 89% yield). 1H NMR (400 MHz, DMSO-d$_6$) δ ppm 7.73 (d, J=8.3 Hz, 2H), 7.64 (d, J=8.3 Hz, 2H), 7.49 (s, 1H), 7.41 (q, J=4.8 Hz, 1H), 7.31 (s, 1H), 6.29 (d, J=4.8 Hz, 1H), 4.96 (d, J=4.7 Hz, 1H), 2.40 (d, J=4.8 Hz, 3H).

741

Step 4: 2-Amino-1-(4-(N-methylsulfamoyl)phenyl)-2-oxoethyl methanesulfonate

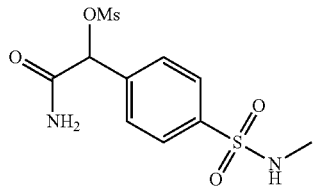 [SMILES: CNS(=O)(=O)c1ccc(C(OS(C)(=O)=O)C(N)=O)cc1]

MsCl (0.172 mL, 2.21 mmol) was added to a stirred mixture of 2-hydroxy-2-(4-(N-methylsulfamoyl)phenyl)acetamide (450 mg, 1.84 mmol) and triethylamine (0.770 mL, 5.53 mmol) in dichloromethane (20 mL). The mixture was stirred at 0° C. for 5 hours. The mixture was concentrated, and the residue was purified by column chromatography 2-amino-1-(4-N-methylsulfamoyl)phenyl)-2-oxoethyl methanesulfonate (345 mg, 58% yield). LCMS m/z=345 [M+Na]$^+$.

Step 5: 2-((3,5-Dicyano-4-ethyl-6-(4-methyl-1,4-diazepan-1-yl)pyridin-2-yl)thio)-2-(4-(N-methylsulfamoyl)phenyl)acetamide

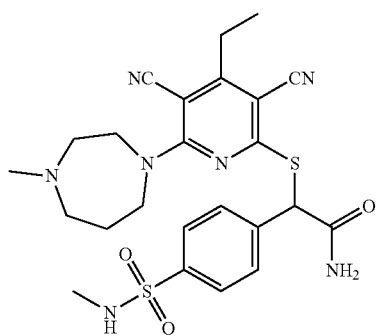 [SMILES: CCc1c(C#N)c(SC(C(N)=O)c2ccc(S(=O)(=O)NC)cc2)nc(N2CCCN(C)CC2)c1C#N]

A mixture of 4-ethyl-2-mercapto-6-(4-methyl-1,4-diazepan-1-yl)pyridine-3,5-dicarbonitrile (synthesis described in example 69 step 1, 150 mg, 0.50 mmol), 2-amino-1-(4-(N-methylsulfamoyl)phenyl)-2-oxoethyl methanesulfonate (168 mg, 0.52 mmol) and triethylamine (0.208 mL, 1.49 mmol) in DMF (10 mL) was stirred at 20° C. for 15 hours. The reaction mixture was concentrated and the residue partitioned between dichloromethane and water. The organic phase was dried over anhydrous sodium sulfate, filtered and concentrated and the residue was purified by column chromatography to afford 2-((3,5-dicyano-4-ethyl-6-(4-methyl-1,4-diazepan-1-yl)pyridin-2-yl)thio)-2-(4-(N-methylsulfamoyl)phenyl)acetamide (61 mg, 23%). LCMS m/z=528.0 [M+H]$^+$. $^1$H NMR (400 MHz, CD$_3$OD) δ ppm 7.88 (d, J=8.4 Hz, 2H), 7.76 (d, J=8.4 Hz, 2H), 4.04 (t, J=4.9 Hz, 2H), 3.99 (t, J=6.0 Hz, 2H), 2.93 (q, J=7.6 Hz, 2H), 2.87 (dt, J=9.6, 4.8 Hz, 2H), 2.74 (d, J=6.7 Hz, 2H), 2.56 (s, 3H), 2.46 (s, 3H), 2.15-2.07 (m, 2H), 1.32 (t, J=7.6 Hz, 3H).

742

Example 379

4-Ethyl-2-(4-methyl-1,4-diazepan-1-yl)-6-((4-(methylsulfonyl)benzyl)thio)pyridine-3,5-dicarbonitrile Step 1: 4-(Methylsulfonyl)benzyl methanesulfonate

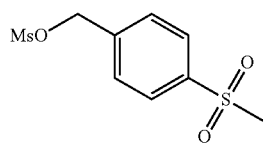 [SMILES: CS(=O)(=O)OCc1ccc(S(C)(=O)=O)cc1]

MsCl (0.460 mL, 5.91 mmol) was added to a stirred mixture of (4-(methylsulfonyl)phenyl)methanol (1 g, 5.37 mmol) and triethylamine (2.245 mL, 16.11 mmol) in DCM (25 mL) at 0° C. and the mixture was stirred at 0° C. for 5 hours. The reaction mixture was concentrated and the residue partitioned between dichloromethane and water. The organic phase was dried with anhydrous sodium sulfate, filtered and concentrated, and the residue was purified by column chromatography to afford 4-(methylsulfonyl)benzyl methanesulfonate (1.1 g, 78% yield). LCMS m/z=287.0 [M+Na]$^+$.

Step 2: 4-Ethyl-2-(4-methyl-1,4-diazepan-1-yl)-6-((4-(methylsulfonyl)benzyl)thio)pyridine-3,5-dicarbonitrile

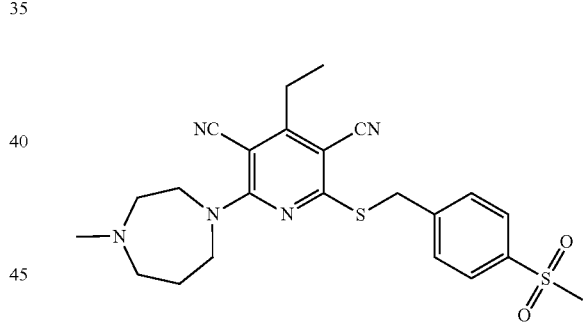

A mixture of 4-ethyl-2-mercapto-6-(4-methyl-1,4-diazepan-1-yl)pyridine-3,5-dicarbonitrile (synthesis described in example 69 step 1, 140 mg, 0.46 mmol), 4-(methylsulfonyl)benzyl methanesulfonate (141 mg, 0.53 mmol) and triethylamine (0.194 mL, 1.39 mmol) in DMF (20 mL) was stirred at 20° C. for 14 hours. The reaction mixture was concentrated and the residue partitioned between dichloromethane and water. The organic phase was dried over anhydrous sodium sulfate, filtered and concentrated in vacuo and the residue was purified by column chromatography to afford 4-ethyl-2-(4-methyl-1,4-diazepan-1-yl)-6-((4-(methylsulfonyl)benzyl)thio)pyridine-3,5-dicarbonitrile (70 mg, 32% yield). LCMS m/z=470.2 [M+H]$^+$. $^1$H NMR (400 MHz, CDCl$_3$) δ ppm 7.90 (d, J=8.3 Hz, 2H), 7.57 (d, J=8.2 Hz, 2H), 4.48 (s, 2H), 3.98-3.90 (m, 2H), 3.87 (t, J=6.0 Hz, 2H), 3.05 (s, 3H), 2.93 (q, J=7.6 Hz, 2H), 2.75-2.66 (m, 2H), 2.62-2.53 (m, 2H), 2.38 (s, 3H), 2.05-1.98 (m, 2H), 1.33 (t, J=7.6 Hz, 3H).

Example 380

2-(4-Aminopiperidin-1-yl)-6-(((1-(2,3-dihydroxypropyl)-1H-pyrazol-4-yl)methyl)thio)-4-ethylpyridine-3,5-dicarbonitrile, Hydrochloride Step 1: Ethyl 1-((2,2-dimethyl-1,3-dioxolan-4-yl)methyl)-1H-pyrazole-4-carboxylate

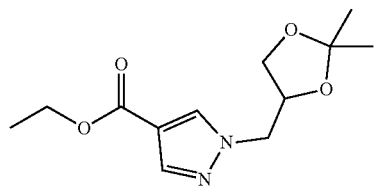 [SMILES: CCOC(=O)c1cnn(CC2COC(C)(C)O2)c1]

To a solution of (2,2-dimethyl-1,3-dioxolan-4-yl)methanol (2.358 g, 17.84 mmol), triphenylphosphine (9.36 g, 35.7 mmol), and DEAD (5.65 mL, 35.7 mmol) in tetrahydrofuran (50 mL) was added ethyl 1H-pyrazole-4-carboxylate (2.5 g, 17.84 mmol) slowly at room temperature and the reaction mixture was stirred at room temperature for 16 hours. The crude compound was purified by silica gel chromatography (eluted with 20% EtOAc in petroleum ether) to afford ethyl 1-((2,2-dimethyl-1,3-dioxolan-4-yl) methyl)-1H-pyrazole-4-carboxylate (3 g). LCMS m/z=255.3 [M+H]⁺.

Step 2: (1-((2,2-Dimethyl-1,3-dioxolan-4-yl)methyl)-1H-pyrazol-4-yl)methanol

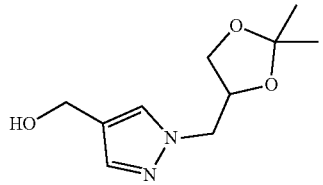

To a suspension of LAH (0.896 g, 23.60 mmol) in tetrahydrofuran (30 mL) was added a solution of ethyl 1-((2,2-dimethyl-1,3-dioxolan-4-yl)methyl)-1H-pyrazole-4-carboxylate (3 g) in tetrahydrofuran (30 mL) slowly at 0° C. and the reaction mixture was stirred for 16 hours at room temperature. The reaction was quenched with a saturated solution of sodium sulfate and stirred with ethyl acetate (50 mL). The organic layer was separated and concentrated under reduced pressure to provide (1-((2,2-dimethyl-1,3-dioxolan-4-yl)methyl)-1H-pyrazol-4-yl)methanol (1.8 g). LCMS m/z=213.1 [M+H]⁺.

Step 3: 4-(Bromomethyl)-1-((2,2-dimethyl-1,3-dioxolan-4-yl)methyl)-1H-pyrazole

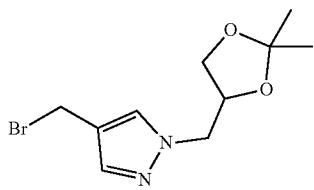

To a solution of (1-((2,2-dimethyl-1,3-dioxolan-4-yl)methyl)-1H-pyrazol-4-yl)methanol (1.5 g) in dichloromethane (10 mL) was added triphenylphosphine (1.204 g, 4.45 mmol) at room temperature. The resultant reaction mixture was stir for 5 minutes, then CBr4 (1.507 g, 4.45 mmol) was added in two to three portions at room temperature under an argon atmosphere. The reaction mixture was stirred for 2 hours at room temperature. The reaction mixture was concentrated under reduced pressure to afford 4-(bromomethyl)-1-((2,2-dimethyl-1,3-dioxolan-4-yl)methyl)-1H-pyrazole (1.0 g) as a pale yellow semi-solid. LCMS m/z=275.1 [M+H]⁺.

Step 4: tert-Butyl (1-(3,5-dicyano-6-(((1-((2,2-dimethyl-1,3-dioxolan-4-yl)methyl)-1H-pyrazol-4-yl)methyl)thio)-4-ethylpyridin-2-yl)piperidin-4-yl)carbamate

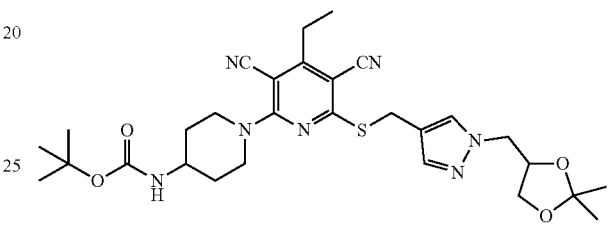

To the solution of tert-butyl (1-(6-chloro-3,5-dicyano-4-ethylpyridin-2-yl)piperidin-4-yl)carbamate (synthesis described in example 81 step 1, 500 mg) in N,N-dimethylformamide (3.0 mL) was added potassium thioacetate (148 mg, 1.270 mmol) at room temperature and the resulting mixture was stirred for 2 hours at the same temperature. To the reaction mixture were added potassium carbonate (181 mg, 1.270 mmol) and 4-(bromomethyl)-1-((2,2-dimethyl-1,3-dioxolan-4-yl)methyl)-1H-pyrazole (688 mg, 1.270 mmol) at room temperature and the mixture was stirred for 5 hours at room temperature. The reaction mixture was poured into ice cold water (20 mL) and extracted with ethyl acetate (20 mL). The organic layer was washed with water (50 mL), dried over sodium sulfate, and concentrated under reduced pressure to afford a brown solid. The crude material was purified by silica gel chromatography (100-200 mesh, eluted with 20% MeOH in DCM) to get a light brown solid. The solid was triturated with diethyl ether (5 mL) to afford tert-butyl(1-(3,5-dicyano-6-(((14(2,2-dimethyl-1,3-d ioxolan-4-yl)methyl)-1H-pyrazol-4-yl)methyl)thio)-4-ethylpyridin-2-yl)piperidin-4-yl)carbamate (400 mg) as a light brown solid. LCMS m/z=582.5 [M+H]⁺.

Step 5: 2-(4-Aminopiperidin-1-yl)-6-(((1-(2,3-dihydroxypropyl)-1H-pyrazol-4-yl)methyl)thio)-4-ethylpyridine-3,5-dicarbonitrile, Hydrochloride

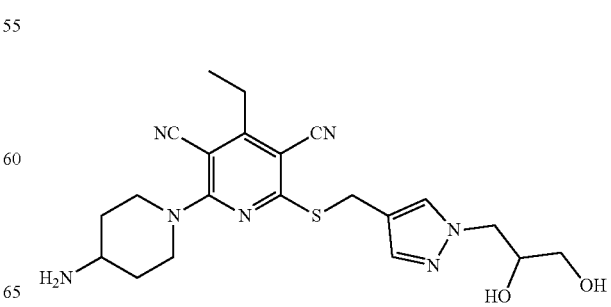

To a solution of tert-butyl (1-(3,5-dicyano-6-(((1-((2,2-dimethyl-1,3-dioxolan-4-yl)methyl)-1H-pyrazol-4-yl)methyl)thio)-4-ethylpyridin-2-yl)piperidin-4-yl)carbamate (350 mg) in 1,4-dioxane (10 mL) was added HCl (4 M in 1,4-dioxane, 2.388 mL, 9.55 mmol) and stirred at 25° C. for 16 hours. The reaction mixture was concentrated under reduced pressure and the crude product was triturated with diethyl ether (2×20 mL), filtered and dried under vacuum. The crude solid was washed with diethyl ether (50 mL) and n-pentane (30 mL) then dried under vacuum to afford 2-(4-aminopiperidin-1-yl)-6-(((1-(2,3-dihydroxypropyl)-1H-pyrazol-4-yl)methyl)thio)-4-ethylpyridine-3,5-dicarbonitrile, Hydrochloride (220 mg). LCMS m/z=442.4 [M+H]+. 1H NMR (400 MHz, DMSO-$d_6$) δ ppm 8.20 (br s, 3H), 7.68 (s, 1H), 7.41 (s, 1H), 4.56 (br d, J=13.37 Hz, 2H), 4.35-4.15 (m, 5H), 3.94 (br dd, J=13.70, 7.56 Hz, 1H), 3.8-3.70 (m, 1H), 3.46-3.25 (m, 5H), 2.78 (q, J=7.38 Hz, 2H), 2.14-2.04 (m, 2H), 1.72-1.59 (m, 2H), 1.22 (t, J=7.67 Hz, 3H).

Example 381

2-((3,5-Dicyano-4-ethyl-6-(16-fluoro-1,4-diazepan-1-yl)pyridin-2-yl)thio)-2-phenylacetamide Step 1: tert-Butyl 4-(6-((2-amino-2-oxo-1-phenylethyl)thio)-3,5-dicyano-4-ethylpyridin-2-yl)-6-fluoro-1,4-diazepane-1-carboxylate

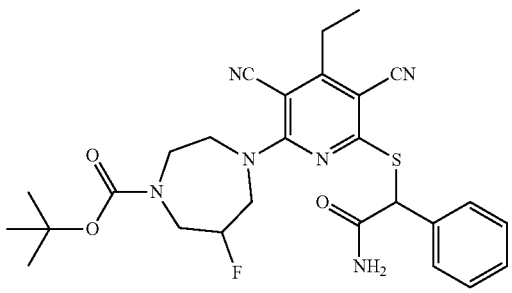 [SMILES: CCc1c(C#N)c(SC(C(N)=O)c2ccccc2)nc(N2CCN(C(=O)OC(C)(C)C)CC(F)C2)c1C#N]

To a suspension of 2,6-dichloro-4-ethylpyridine-3,5-dicarbonitrile (synthesis described in example 3, step 2, 100 mg, 0.442 mmol) in ethanol (1 mL) at −20° C. was added a solution of tert-butyl 6-fluoro-1,4-diazepane-1-carboxylate (101 mg, 0.464 mmol) in ethanol (1 mL). The reaction mixture was then stirred at −20° C. for 1 hour at which time an equivalent of triethylamine (0.062 mL, 0.442 mmol) was added to the reaction mixture at −20° C. The reaction mixture was warmed to 0° C. and stirred at the same temperature overnight. To the reaction mixture was then added potassium ethanethioate (76 mg, 0.664 mmol) and Et3N (0.154 mL, 1.106 mmol). The heterogeneous reaction mixture was then warmed to 20° C. and stirred at the same temperature for 7 hours. To the reaction mixture was added 2-amino-2-oxo-1-phenylethyl methanesulfonate (101 mg, 0.442 mmol). The reaction was stirred for 3.5 hours at 20° C. After stirring for 3.5 hours additional ethanol (2 mL) was added and the temperature was increased to 40° C. The heterogeneous reaction mixture was stirred at 40° C. over the weekend. The reaction mixture was cooled to room temperature. The solid was filtered and washed with ethanol and water. The solid was then dried in the vacuum oven to obtain tert-butyl 4-(6-((2-amino-2-oxo-1-phenylethyl)thio)-3,5-dicyano-4-ethylpyridin-2-yl)-6-fluoro-1,4-diazepane-1-carboxylate (109 mg) of an off-white solid. A 25 mg aliquot was taken and purified by reverse phase HPLC (Gilson, 30 mm×50 mm Gemini Column, NH4OH modifier) to yield tert-butyl 4-(6-((2-amino-2-oxo-1-phenylethyl)thio)-3,5-dicyano-4-ethylpyridin-2-yl)-6-fluoro-1,4-diazepane-1-carboxylate (15 mg) of a white solid LCMS m/z=539.3 [M+H]+.

Step 2: 2-((3,5-Dicyano-4-ethyl-6-(6-fluoro-1,4-diazepan-1-yl)pyridin-2-yl)thio)-2-phenylacetamide

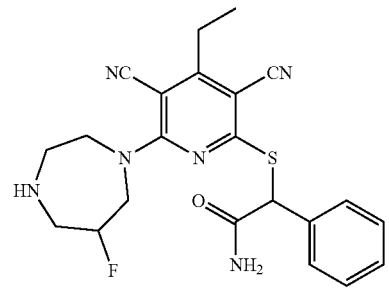 [SMILES: CCc1c(C#N)c(SC(C(N)=O)c2ccccc2)nc(N2CCNCC(F)C2)c1C#N]

tert-Butyl 4-(6-((2-amino-2-oxo-1-phenylethyl)thio)-3,5-dicyano-4-ethylpyridin-2-yl)-6-fluoro-1,4-diazepane-1-carboxylate (84 mg, 0.156 mmol) was suspended in a solution of 4 M HCl (1.500 mL, 6.0 mmol) in dioxane at room temperature. The reaction mixture was stirred at room temperature overnight at which time the reaction mixture was concentrated. The resulting material was suspended in MeOH, and free based with isopropylamine. This mixture was purified by reverse phase HPLC (Gilson, 30 mm×50 mm Gemini Column, NH4OH modifier) to yield the 2-((3,5-dicyano-4-ethyl-6-(6-fluoro-1,4-diazepan-1-yl)pyridin-2-yl)thio)-2-phenylacetamide (40 mg) as a white solid. LCMS m/z=439.2 [M+H]+. 1H NMR (400 MHz, DMSO-$d_6$) δ 7.95 (d, J=12.93 Hz, 1H), 7.47-7.54 (m, 2H), 7.29-7.42 (m, 4H), 5.53 (d, J=2.53 Hz, 1H), 4.87 (dd, J=5.20, 18.12 Hz, 1H), 4.48 (dt, J=4.94, 15.52 Hz, 1H), 4.01-4.27 (m, 2H), 3.65-3.78 (m, 1H), 2.81-3.08 (m, 4H), 2.78 (q, J=7.52 Hz, 2H), 1.21 (t, J=7.60 Hz, 3H). One proton not observed.

Example 382

2-((6-(4-Amino-3,3-difluoropiperidin-1-yl)-3,5-dicyano-4-ethylpyridin-2-yl)thio)-2-phenylacetamide

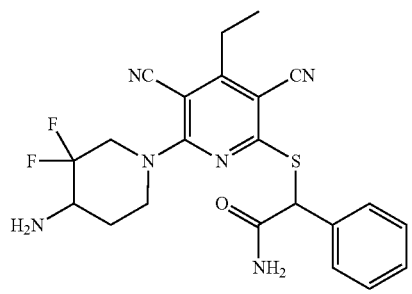 [SMILES: CCc1c(C#N)c(SC(C(N)=O)c2ccccc2)nc(N2CCC(N)C(F)(F)C2)c1C#N]

tert-Butyl (1-(6-((2-amino-2-oxo-1-phenylethyl)thio)-3,5-dicyano-4-ethylpyridin-2-yl)-3,3-difluoropiperidin-4-yl)carbamate (synthesis described in example 383, 113 mg, 0.203 mmol) was suspended in a solution of 4 M HCl (2.000 mL, 8.0 mmol) in dioxane at room temperature. The reaction mixture was stirred at room temperature overnight. The reaction mixture was concentrated. The resulting material was suspended in MeOH, and free based with isopropylamine. This mixture was purified by reverse phase HPLC (Gilson, 30 mm×50 mm Gemini Column, NH$_4$OH modifier) to yield 2-((6-(4-amino-3,3-difluoropiperidin-1-yl)-3,5-dicyano-4-ethylpyridin-2-yl)thio)-2-phenylacetamide (75 mg) as a white solid. LCMS m/z=457.2 [M+H]$^+$. $^1$H NMR (400 MHz, DMSO-d$_6$) δ ppm 7.98 (s, 1H), 7.51-7.56 (m, 2H), 7.31-7.42 (m, 4H), 5.56 (s, 1H), 4.44-4.58 (m, 1H), 4.10-4.26 (m, 1H), 3.76-3.91 (m, 1H), 3.52-3.64 (m, 1H), 3.15-3.29 (m, 1H), 2.78 (q, J=7.60 Hz, 2H), 1.90-2.01 (m, 1H), 1.83 (br. s., 2H), 1.63 (d, J=9.12 Hz, 1H), 1.21 (t, J=7.73 Hz, 3H).

Example 383 tert-Butyl (1-(6-((2-amino-2-oxo-1-phenylethyl)thio)-3,5-dicyano-4-ethylpyridin-2-yl)-3,3-difluoropiperidin-4-yl) carbamate

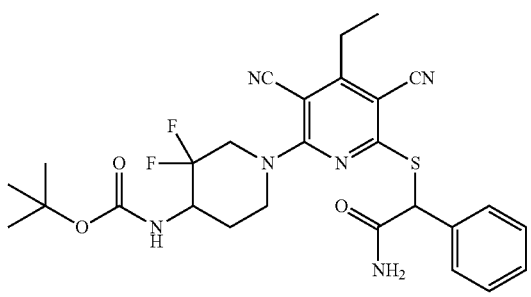 [SMILES: CCc1c(C#N)c(SC(C(N)=O)c2ccccc2)nc(N2CCC(NC(=O)OC(C)(C)C)C(F)(F)C2)c1C#N]

To a suspension of 2,6-dichloro-4-ethylpyridine-3,5-dicarbonitrile (synthesis described in example 3, step 2, 100 mg, 0.442 mmol) in ethanol (1 mL) at −20° C. was added a solution of tert-butyl (3,3-difluoropiperidin-4-yl)carbamate (110 mg, 0.464 mmol) in ethanol (1 mL). The reaction mixture was then stirred at −20° C. for 1 hour at which time LCMS indicates the reaction is progressing slowly. Triethylamine (0.062 mL, 0.442 mmol) was added to the reaction mixture at −20° C. The reaction mixture was warmed to 0° C. and stirred at the same temperature for 3 hours. To the reaction mixture was then added potassium ethanethioate (76 mg, 0.664 mmol) and Et$_3$N (0.154 mL, 1.106 mmol). The heterogeneous reaction mixture was then warmed to 20° C. and stirred at the same temperature while progress was monitored by LCMS. After stirring for overnight at 20° C. To the reaction mixture was added 2-amino-2-oxo-1-phenylethyl methanesulfonate (101 mg, 0.442 mmol). The reaction was continued stirring at 20° C. After stirring for 3.5 hours, additional ethanol (2 mL) was added and the temperature was increased to 40° C. The heterogeneous reaction mixture was continued to stir at 40° C. over the weekend. The reaction mixture was cooled to room temperature. The solid was filtered and washed with ethanol and water. The solid was then dried in the vacuum oven to obtain tert-butyl (1-(6-((2-amino-2-oxo-1-phenylethyl)thio)-3,5-dicyano-4-ethylpyridin-2-yl)-3,3-difluoropiperidin-4-yl) carbamate (140 mg) as a white solid which was used in subsequent reactions without further purification. A 26 mg aliquot was taken and purified by reverse phase HPLC (Gilson, 30 mm×50 mm Gemini Column, NH$_4$OH modifier) to afford tert-butyl (1-(6-((2-amino-2-oxo-1-phenylethyl)thio)-3,5-dicyano-4-ethylpyridin-2-yl)-3,3-difluoropiperidin-4-yl) carbamate (13 mg) as a white solid. LCMS m/z=579.3 [M+Na]$^+$. $^1$H NMR (400 MHz, DMSO-d$_6$) δ ppm 7.97 (s, 1H), 7.50-7.56 (m, 2H), 7.27-7.43 (m, 5H), 5.55 (d, J=6.34 Hz, 1H), 4.65-4.77 (m, 1H), 4.36-4.48 (m, 1H), 4.19 (br. s., 1H), 3.67-3.83 (m, 1H), 3.41-3.54 (m, 1H), 2.78 (q, J=7.60 Hz, 2H), 1.89-2.00 (m, 1H), 1.71-1.85 (m, 1H), 1.42 (s, 9H), 1.21 (t, J=7.60 Hz, 3H).

Example 384

4-Ethyl-2-(4-methyl-1,4-diazepan-1-yl)-6-((4-(4-methylpiperazin-1-yl)benzyl)thio)pyridine-3,5-dicarbonitrile

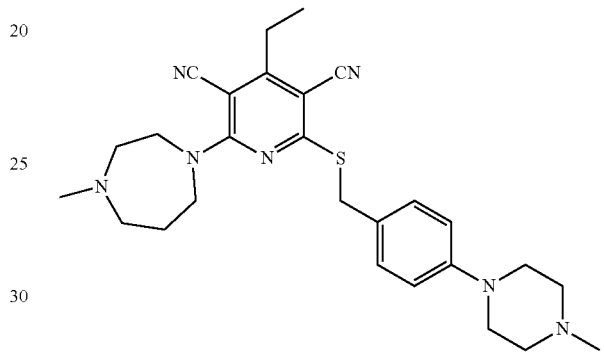

To a solution of (4-(4-methylpiperazin-1-yl)phenyl)methanol (103 mg, 0.499 mmol), DIEA (0.131 mL, 0.749 mmol), and DMAP (6.10 mg, 0.050 mmol) in dichloromethane (2.5 mL) at 20° C. was added methanesulfonyl chloride (0.058 mL, 0.749 mmol). The reaction mixture was stirred at the same temp while progress was monitored by LCMS. After stirring 24 hours at 20° C., the reaction mixture was concentrated and the resulting material purified by normal phase chromatography (Biotage Isolera, 10 g SNAP ULTRA column, DCM/MeOH) to obtain 123 mg of a brown solid. A portion of this material (27 mg) in N,N-dimethylformamide (0.5 mL) was added to a suspension of 4-ethyl-2-mercapto-6-(4-methyl-1,4-diazepan-1-yl)pyridine-3,5-dicarbonitrile (synthesis described in Example 69, step 1, 46 mg, 0.122 mmol) and Et$_3$N (0.017 mL, 0.122 mmol) in N,N-dimethylformamide (0.5 mL) at 0° C. The reaction mixture was then stirred at 0° C. overnight. After stirring overnight at 0° C., the reaction mixture was warmed to room temperature. The reaction mixture was filtered. The filtrate was purified by reverse phase HPLC (Gilson, 30 mm×50 mm Gemini Column, NH$_4$OH modifier) then re-purified by reverse phase HPLC (Gilson, 30 mm×50 mm Gemini Column, NH$_4$OH modifier) to obtain 4-ethyl-2-(4-methyl-1,4-diazepan-1-yl)-6-((4-(4-methylpiperazin-1-yl)benzyl)thio)pyridine-3,5-dicarbonitrile (6 mg) as a yellow oil LCMS m/z=490.4 [M+H]$^+$. $^1$H NMR (400 MHz, METHANOL-d$_4$) δ ppm 7.26-7.30 (m, J=8.62 Hz, 2H), 6.92-6.97 (m, 2H), 4.44 (s, 2H), 3.95-4.03 (m, 4H), 3.18-3.24 (m, 4H), 2.91 (q, J=7.60 Hz, 2H), 2.76-2.80 (m, 2H), 2.62-2.67 (m, 6H), 2.38 (s, 3H), 2.37 (s, 3H), 2.04-2.11 (m, 2H), 1.31 (t, J=7.60 Hz, 3H).

Example 385

4-Ethyl-2-(4-methyl-1,4-diazepan-1-yl)-6-((4-(((2-oxopyrrolidin-3-yl)amino)methyl)benzyl)thio)pyridine-3,5-dicarbonitrile

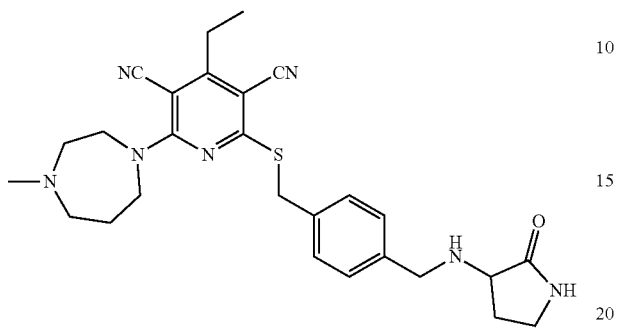

To a suspension of 2-((4-(aminomethyl)benzyl)thio)-4-ethyl-6-(4-methyl-1,4-diazepan-1-yl)pyridine-3,5-dicarbonitrile, 2Hydrochloride (synthesis described in example 71, 53 mg, 0.107 mmol) and Et₃N (0.045 mL, 0.322 mmol) in N,N-dimethylformamide (0.5 mL) at 0° C. was added a solution of 3-bromopyrrolidin-2-one (17 mg, 0.104 mmol) in N,N-dimethylformamide (0.3 mL). The reaction mixture was then stirred at 0° C. overnight. The temperature was increased to 20° C. and the reaction mixture was stirred at the same temperature for an additional 24 hours. The reaction mixture was filtered and purified by reverse phase HPLC (Gilson, 30 mm Gemini Column, NH₄OH modifier) to obtain 4-ethyl-2-(4-methyl-1,4-diazepan-1-yl)-6-((4-(((2-oxopyrrolidin-3-yl)amino)methyl)benzyl)thio)pyridine-3,5-dicarbonitrile (6 mg) as a pale yellow oil LCMS m/z=504.3 [M+H]⁺. ¹H NMR (400 MHz, METHANOL-d₄) δ ppm 7.34-7.42 (m, 4H), 4.51 (s, 2H), 3.93-4.01 (m, 4H), 3.80-3.90 (m, 2H), 3.38-3.43 (m, 1H), 3.37 (s, 2H), 3.25-3.31 (m, 1H), 2.92 (q, J=7.60 Hz, 2H), 2.73-2.80 (m, 2H), 2.59-2.65 (m, 2H), 2.36 (s, 3H), 2.05 (td, J=5.92, 11.22 Hz, 2H), 1.92 (qd, J=9.17, 12.55 Hz, 1H), 1.32 (t, J=7.60 Hz, 3H).

Example 386

2-((3,5-Dicyano-4-cyclopropyl-6-((2-hydroxyethyl)(methyl)amino)pyridin-2-yl)thio)-2-phenylacetamide Step 1: 2-Chloro-4-cyclopropyl-6-((2-hydroxyethyl)(methyl)amino)pyridine-3,5-dicarbonitrile

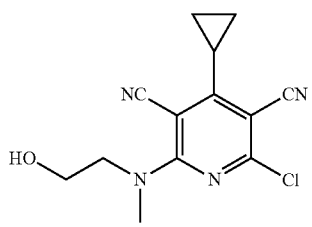 [SMILES: CN(CCO)c1nc(Cl)c(C#N)c(C2CC2)c1C#N]

To a solution of 2,6-dichloro-4-cyclopropylpyridine-3,5-dicarbonitrile (synthesis described in example 4, step 2, 0.5 g, 2.100 mmol) and 2-(methylamino)ethanol (0.166 g, 2.205 mmol) in dichloromethane (10 mL) was added triethylamine (0.585 mL, 4.20 mmol) at 0° C. The mixture was stirred at room temperature for 0.5 hours. The resultant mixture was concentrated in vacuo. The residue was purified by silica gel chromatography (100 g silica; eluted with 3% MeOH/DCM) to afford 2-chloro-4-cyclopropyl-6-((2-hydroxyethyl)(methyl)amino)pyridine-3,5-dicarbonitrile (0.5 g) as a yellow solid. LCMS m/z=276.9 [M+H]⁺.

Step 2: 2-((3,5-Dicyano-4-cyclopropyl-6-((2-hydroxyethyl)(methyl)amino)pyridin-2-yl)thio)-2-phenylacetamide

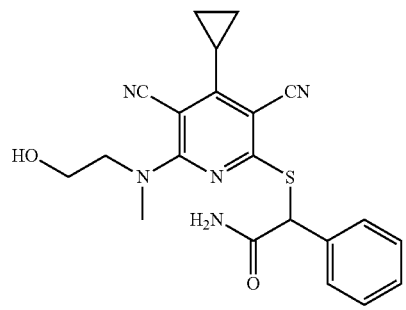 [SMILES: CN(CCO)c1nc(SC(C(N)=O)c2ccccc2)c(C#N)c(C2CC2)c1C#N]

To a solution of 2-chloro-4-cyclopropyl-6-((2-hydroxyethyl)(methyl)amino)pyridine-3,5-dicarbonitrile (0.5 g) in N,N-dimethylformamide (15 mL) was added potassium ethanethioate (0.310 g, 2.71 mmol). The mixture was stirred at room temperature for 2 hours then treated with K₂CO₃ (0.499 g, 3.61 mmol). After stirring at room temperature for 0.5 hour, 2-amino-2-oxo-1-phenylethyl methanesulfonate (synthesis described in example 3, step 5, 0.621 g, 2.71 mmol) was added and the mixture was stirred at room temperature overnight. The resultant mixture was concentrated in vacuo. The remaining residue was purified by prep-HPLC to afford 2-((3,5-dicyano-4-cyclopropyl-6-((2-hydroxyethyl)(methyl)amino)pyridin-2-yl)thio)-2-phenylacetamide (210 mg) as an off-white solid. LCMS m/z=407.8 [M+H]⁺. ¹H NMR (400 MHz, DMSO-d₆) δ ppm 7.87 (s, 1H), 7.50 (d, J=7.3 Hz, 2H), 7.42-7.30 (m, 4H), 5.52 (s, 1H), 4.80 (s, 1H), 3.93-3.79 (m, 2H), 3.65 (s, 2H), 3.37 (s, 3H), 2.14-2.07 (m, 1H), 1.16-1.10 (m, 2H), 0.97-0.90 (m, 2H).

Example 387

2-((3,5-Dicyano-4-cyclopropyl-6-(13-hydroxyazetidin-1-yl)pyridin-2-yl)thio)-2-phenylacetamide Step 1: 2-Chloro-4-cyclopropyl-6-(3-hydroxyazetidin-1-yl)pyridine-3,5-dicarbonitrile

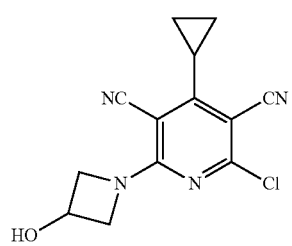 [SMILES: N#Cc1c(Cl)nc(N2CC(O)C2)c(C#N)c1C1CC1]

2,6-Dichloro-4-cyclopropylpyridine-3,5-dicarbonitrile (1 g, 4.20 mmol), azetidin-3-ol (0.307 g, 4.20 mmol) and triethylamine (0.425 g, 4.20 mmol) were added to dichloromethane (50 mL). The mixture was stirred at 25° C. for 3 hours. The solvent was removed and the remaining residue partitioned between water (100 mL) and DCM (100 mL). The organic phase was dried and concentrated. The crude residue was purified by silica gel chromatography to give 2-chloro-4-cyclopropyl-6-(3-hydroxyazetidin-1-yl)pyridine-3,5-dicarbonitrile (700 mg) as a white solid. LCMS: m/z=275.0 [M+H]$^+$.

Step 2: 2-((3,5-Dicyano-4-cyclopropyl-6-(3-hydroxyazetidin-1-yl)pyridin-2-yl)thio)-2-phenylacetamide

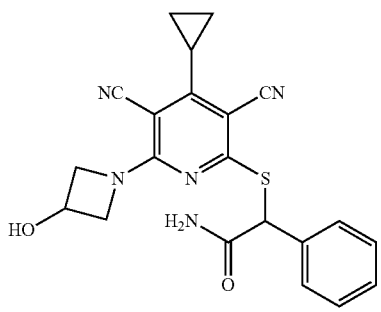 [SMILES: N#Cc1c(SC(C(N)=O)c2ccccc2)nc(N2CC(O)C2)c(C#N)c1C1CC1]

To a solution of 2-chloro-4-cyclopropyl-6-(3-hydroxyazetidin-1-yl)pyridine-3,5-dicarbonitrile (700 mg, 2.55 mmol) in N,N-dimethylformamide (50 mL) was added potassium ethanethioate (582 mg, 5.10 mmol). The mixture was stirred at 25° C. for 2 hours and then 2-amino-2-oxo-1-phenylethyl methanesulfonate (synthesis described in example 3, step 5, 1168 mg, 5.10 mmol) was added. The mixture was stirred at 25° C. for 15 hours. The solvent was removed and the remaining residue partitioned between water (100 mL) and DCM (100 mL). The insoluble solid was collected by filtration to provide the crude product. The crude material was purified by prep-HPLC to provide 2-((3,5-dicyano-4-cyclopropyl-6-(3-hydroxyazetidin-1-yl)pyridin-2-yl)thio)-2-phenylacetamide (210 mg). LCMS m/z=405.8 [M+H]$^+$.
$^1$H NMR (400 MHz, DMSO-d$_6$) δ 7.87 (s, 1H), 7.51 (d, J=7.2 Hz, 2H), 7.38-7.29 (m, 4H), 5.90 (d, J=5.8 Hz, 1H), 5.54 (s, 1H), 4.62-4.48 (m, 3H), 4.25-4.05 (m, 2H), 2.12-1.99 (m, 1H), 1.21-1.03 (m, 2H), 0.99-0.87 (m, 2H).

Example 388

1-(6-((2-Amino-2-oxo-1-phenylethyl)thio)-3,5-dicyano-4-ethylpyridin-2-yl)pyrrolidine-3-carboxamide

Step 1: 1-(6-Chloro-3,5-dicyano-4-ethylpyridin-2-yl)pyrrolidine-3-carboxamide

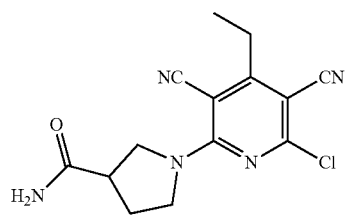 [SMILES: CCc1c(C#N)c(Cl)nc(N2CCC(C(N)=O)C2)c1C#N]

To a solution of 2,6-dichloro-4-ethylpyridine-3,5-dicarbonitrile (synthesis described in example 3, step 2, 1.6 g, 7.08 mmol) in dichloromethane (100 mL) was added triethylamine (0.716 g, 7.08 mmol) and pyrrolidine-3-carboxamide (0.808 g, 7.08 mmol). The reaction mixture was stirred at 25° C. for 15 hours. The solvent was removed and the remaining residue partitioned between water (50 mL) and DCM (50 mL). The organic phase was dried over Na$_2$SO$_4$ and concentrated. The residue was purified by silica gel chromatography (eluting with 2:1 ethyl acetate: petroleum ether) to provide 1-(6-chloro-3,5-dicyano-4-ethylpyridin-2-yl)pyrrolidine-3-carboxamide (500 mg) as a pale brown solid. LCMS m/z=304.0 [M+H]$^+$.

Step 2: 1-(6-((2-Amino-2-oxo-1-phenylethyl)thio)-3,5-dicyano-4-ethylpyridin-2-yl) pyrrolidine-3-carboxamide

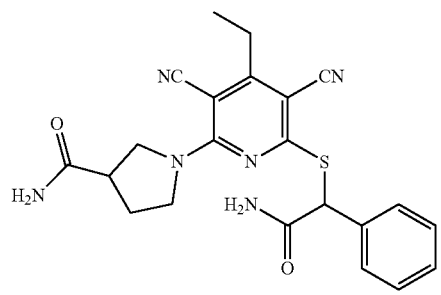 [SMILES: CCc1c(C#N)c(SC(C(N)=O)c2ccccc2)nc(N2CCC(C(N)=O)C2)c1C#N]

To a solution of 1-(6-chloro-3,5-dicyano-4-ethylpyridin-2-yl)pyrrolidine-3-carboxamide (500 mg, 1.646 mmol) in N,N-dimethylformamide (40 mL) was added potassium ethanethioate (188 mg, 1.646 mmol). The mixture was stirred at 25° C. for 2 hours and then 2-amino-2-oxo-1-phenylethyl methanesulfonate (synthesis described in example 3, step 5, 377 mg, 1.646 mmol) was added. The mixture was stirred at 25° C. for 15 hours. The solvent was removed and the remaining residue partitioned between water (50 mL) and DCM (50 mL). The insoluble solid was collected by filtration to provide the crude. The crude material was purified by prep-HPLC to afford 1-(6-((2-amino-2-oxo-1-phenylethyl)thio)-3,5-dicyano-4-ethylpyridin-2-yl)pyrrolidine-3-carboxamide (400 mg) as a white solid. LCMS m/z=434.8 [M+H]+. 1H NMR (400 MHz, DMSO-d6) δ ppm 7.91 (d, J=6.5 Hz, 1H), 7.61-7.48 (m, 3H), 7.41-7.26 (m, 4H), 7.07 (s, 1H), 5.61 (s, 0.5H), 5.59 (s, 0.5H), 3.95 (m, 4H), 3.05 (m, 1H), 2.75 (q, J=7.3 Hz, 2H), 2.18 (m, 1H), 2.00 (m, 1H), 1.20 (t, 3H).

Example 390

2-(((1H-Benzo[d]imidazol-5-yl)methyl)thio)-4-ethyl-6-(4-methyl-1,4-diazepan-1-yl)pyridine-3,5-dicarbonitrile Step 1: tert-Butyl 5-methyl-1H-benzo[d]imidazole-1-carboxylate and tert-butyl 6-methyl-1H-benzo[d]imidazole-1-carboxylate

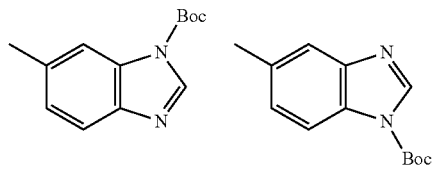 [SMILES: Cc1ccc2ncn(C(=O)OC(C)(C)C)c2c1 ; Cc1ccc2c(c1)ncn2C(=O)OC(C)(C)C]

To a solution of 5-methyl-1H-benzo[d]imidazole (2.0 g, 15.13 mmol), triethylamine (5.27 mL, 37.8 mmol) in dichloromethane (30 mL) was added di-tert-butyl dicarbonate (5.27 mL, 22.70 mmol). The reaction mixture was stirred overnight at room temperature, and the resulting solution was diluted with water (30 mL), extracted with ethyl acetate (3×20 mL). The organic layers were combined, washed with aqueous sodium carbonate and brine, dried, filtered, and concentrated under vacuum to afford a mixture of tert-butyl 5-methyl-1H-benzo[d]imidazole-1-carboxylate and tert-butyl 6-methyl-1H-benzo[d]imidazole-1-carboxylate (3.12 g) as a yellow oil. LCMS m/z=177.1 [M+H-isobutylene]+.

Step 2: tert-Butyl 5-(bromomethyl)-1H-benzo[d]imidazole-1-carboxylate and tert-butyl 6-(bromomethyl)-1H-benzo[d]imidazole-1-carboxylate

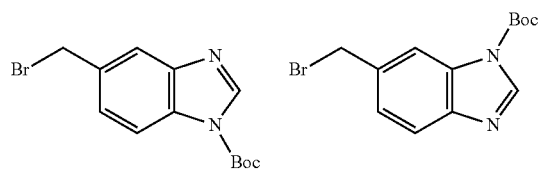 [SMILES: CC(C)(C)OC(=O)n1cnc2cc(CBr)ccc21 ; CC(C)(C)OC(=O)n1cnc2ccc(CBr)cc21]

To a solution of a mixture of 5-methyl-1H-benzo[d]imidazole-1-carboxylate and tert-butyl 6-methyl-1H-benzo[d]imidazole-1-carboxylate (1.0 g, 4.31 mmol) and NBS (0.766 g, 4.31 mmol) in CCl4 (30 mL) stirred under nitrogen at room temperature was added AIBN (0.071 g, 0.431 mmol). The reaction mixture was refluxed overnight. The reaction mixture was cooled to room temperature, washed with water (3×50 mL), and concentrated to afford a mixture of tert-butyl 5-(bromomethyl)-1H-benzo[d]imidazole-1-carboxylate and tert-butyl 6-(bromomethyl)-1H-benzo[d]imidazole-1-carboxylate (0.7 g) as a yellow oil. LCMS m/z=211.0 [M+H-boc]+.

Step 3: tert-Butyl 5-(((3,5-dicyano-4-ethyl-6-(4-methyl-1,4-diazepan-1-yl)pyridin-2-yl)thio)methyl)-1H-benzo[d]imidazole-1-carboxylate and tert-butyl 6-(((3,5-dicyano-4-ethyl-6-(4-methyl-1,4-diazepan-1-yl)pyridin-2-yl)thio)methyl)-1H-benzo[d]imidazole-1-carboxylate

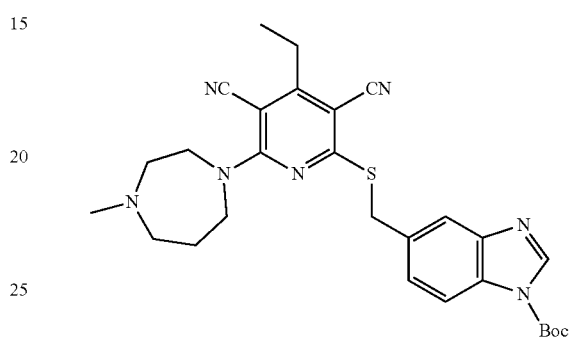

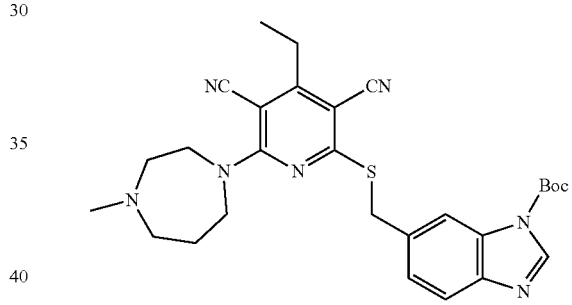

To a solution of 4-ethyl-2-mercapto-6-(4-methyl-1,4-diazepan-1-yl)pyridine-3,5-dicarbonitrile (synthesis described in example 69 step 1, 581 mg, 1.93 mmol) and triethylamine (488 mg, 4.82 mmol) in DMF (20 mL) was added a mixture of tert-butyl 5-(bromomethyl)-1H-benzo[d]imidazole-1-carboxylate and tert-butyl 6-(bromomethyl)-1H-benzo[d]imidazole-1-carboxylate (600 mg, 1.93 mmol). The reaction mixture was stirred at room temperature for 2 hours. The mixture was poured into 20 mL of water. The resulting solution was extracted with ethyl acetate (3×20 mL). The organic layers were combined, washed with brine and water, then dried and concentrated. The residue was purified by silica gel column (0-50% ethyl acetate in hexane) to afford a mixture of tert-butyl 5-(((3,5-dicyano-4-ethyl-6-(4-methyl-1,4-diazepan-1-yl)pyridin-2-yl)thio)methyl)-1H-benzo[d]imidazole-1-carboxylate and tert-butyl 6-(((3,5-dicyano-4-ethyl-6-(4-methyl-1,4-diazepan-1-yl)pyridin-2-yl)thio)methyl)-1H-benzo[d]imidazole-1-carboxylate (410 mg, 0.77 mmol) as a yellow solid. LCMS m/z=532.1 [M+H]+.

Step 4: 2-(((1H-Benzo[d]imidazol-5-yl)methyl)thio)-4-ethyl-6-(4-methyl-1,4-diazepan-1-yl)pyridine-3,5-dicarbonitrile

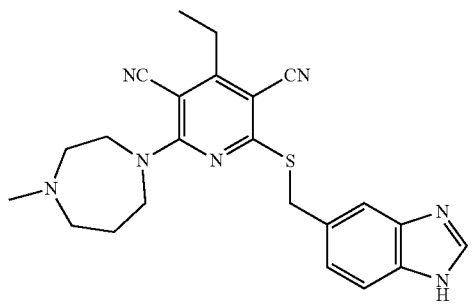 [SMILES: CCc1c(C#N)c(SCc2ccc3[nH]cnc3c2)nc(N2CCCN(C)CC2)c1C#N]

To a mixture of tert-butyl 5-(((3,5-dicyano-4-ethyl-6-(4-methyl-1,4-diazepan-1-yl)pyridin-2-yl)thio)methyl)-1H-benzo[d]imidazole-1-carboxylate and tert-butyl 6-(((3,5-dicyano-4-ethyl-6-(4-methyl-1,4-diazepan-1-yl)pyridin-2-yl)thio)methyl)-1H-benzo[d]imidazole-1-carboxylate (430 mg, 0.81 mmol) in DCM (5.0 mL) was added trifluoroacetic acid (5.0 mL), then the reaction mixture was stirred overnight at room temperature. The residue was diluted with water, then adjusted to pH 13 with Na$_2$CO$_3$. The resulting solution was extracted with ethyl acetate (3×15 mL). The organic layers were combined, washed with aqueous sodium carbonate and brine, dried and concentrated under vacuum. The residue was purified by silica gel column (50% ethyl acetate n hexane) to afford 2-(((1H-benzo[d]imidazol-5-yl)methyl)thio)-4-ethyl-6-(4-methyl-1,4-diazepan-1-yl)pyridine-3,5-dicarbonitrile (310 mg, 0.71 mmol) as a yellow oil. LCMS m/z=432.1 [M+H]$^+$. $^1$H NMR (400 MHz, MeOD) δ ppm 8.18 (s, 1H), 7.67 (s, 1H), 7.59 (d, J=8.3 Hz, 1H), 7.34 (d, J=8.3 Hz, 1H), 4.65 (s, 2H), 3.97 (d, J=4.8 Hz, 4H), 2.95-2.86 (m, 2H), 2.71-2.63 (m, 2H), 2.62-2.56 (m, 2H), 2.28 (s, 3H), 2.09-1.99 (m, 2H), 1.32 (t, J=6.1 Hz, 3H).

Example 391

2-((6-((3-Aminopropyl) (methyl) amino-3,5-dicyano-4-cyclopropylpyridin-2-yl)thio-2-phenylacetamide, Hydrochloride Step 1: tert-Butyl (3-((6-chloro-3,5-dicyano-4-cyclopropylpyridin-2-yl)(methyl)amino)propyl)carbamate

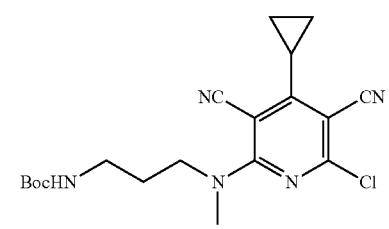 [SMILES: CN(CCCNC(=O)OC(C)(C)C)c1nc(Cl)c(C#N)c(C2CC2)c1C#N]

To a solution of 2,6-dichloro-4-cyclopropylpyridine-3,5-dicarbonitrile (synthesis described in example 4 step 2, 1 g) in dichloromethane (15 mL) was added at 0° C. triethylamine (0.984 mL, 7.06 mmol) followed by tert-butyl (3-(methyl amino)propyl)carbamate (0.996 g, 5.29 mmol). The reaction mixture was stirred for 2 hours at the same temperature. The reaction mixture was diluted with dichloromethane (25 mL) and washed with water (100 mL). The organic layer was dried over Na$_2$SO$_4$, filtered and concentrated under reduced pressure to afford tert-butyl (3-((6-chloro-3,5-dicyano-4-cyclopropylpyridin-2-yl)(methyl)amino)propyl)carbamate (800 mg) as an off-white solid. LCMS m/z=390.5 [M+H]$^+$.

Step 2: tert-Butyl (3-((6-((2-amino-2-oxo-1-phenylethyl)thio)-3,5-dicyano-4-cyclopropyl pyridin-2-yl)(methyl)amino)propyl)carbamate

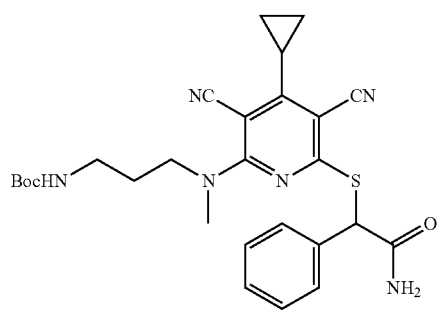 [SMILES: CN(CCCNC(=O)OC(C)(C)C)c1nc(SC(C(N)=O)c2ccccc2)c(C#N)c(C2CC2)c1C#N]

To a solution of tert-butyl (3-((6-chloro-3,5-dicyano-4-cyclopropylpyridin-2-yl)(methyl)amino) propyl)carbamate (800 mg) in N,N-dimethylformamide (10 mL), was added potassium thioacetate (447 mg, 3.91 mmol) at room temperature and the mixture was stirred for 2 hours. To the reaction mixture were added potassium carbonate (541 mg, 3.91 mmol) and 2-amino-2-oxo-1-phenylethyl methanesulfonate (synthesis described in example 3 step 5, 992 mg, 2.94 mmol) and the mixture was stirred for 4 hours. Water (80 mL) was added to the reaction and the mixture extracted with ethyl acetate (2×100 mL). The combined organic layers were dried over anhydrous sodium sulfate, filtered and concentrated. The crude material was purified by silica gel chromatography (100-200 mesh, 70% ethyl acetate in petroleum ether) to afford tert-butyl (3-((6-((2-amino-2-oxo-1-phenylethyl)thio)-3,5-dicyano-4-cyclopropyl-pyridin-2-yl) (methyl) amino)propyl)carbamate (550 mg) as a brown solid. LCMS m/z=521.4 [M+H]$^+$.

Step 3: 2-((6-((3-Aminopropyl) (methyl) amino)-3,5-dicyano-4-cyclopropylpyridin-2-yl)thio)-2-phenylacetamide, Hydrochloride

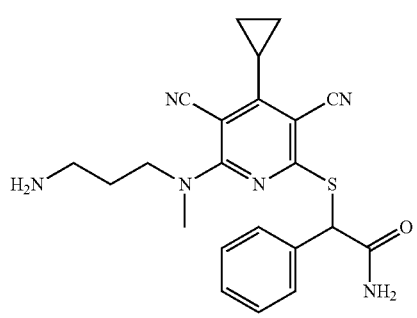 [SMILES: CN(CCCN)c1nc(SC(C(N)=O)c2ccccc2)c(C#N)c(C2CC2)c1C#N]

To a solution of tert-butyl (3-((6-((2-amino-2-oxo-1-phenylethyl)thio)-3,5-dicyano-4-cyclopropylpyridin-2-yl)(methyl)amino)propyl)carbamate (350 mg) in 1,4-dioxane (3 mL) was added HCl (4 M in 1,4-dioxane, 3.5 mL, 14.00 mmol) at 20° C. The reaction mixture was stirred at room temperature for 4 hours. Diethyl ether (20 mL) was added to the reaction mixture and a solid was obtained. The solid was collected by filtration to afford 2-((6-((3-aminopropyl)(methyl)amino)-3,5-dicyano-4-cyclopropylpyridin-2-yl)thio)-2-phenylacetamide, Hydrochloride (250 mg) as an off-white solid. LCMS m/z=421.2 [M+H]$^+$. $^1$H NMR (400 MHz, DMSO-d$_6$) δ ppm 8.04 (s, 1H), 7.95 (br s, 3H), 7.56-7.51 (m, 2H), 7.43-7.32 (m, 4H), 5.52 (s, 1H), 3.88-3.71 (m, 2H), 3.32 (s, 3H), 2.88-2.76 (m, 2H), 2.11 (tt, J=8.77, 5.70 Hz, 1H), 1.94 (quin, J=7.45 Hz, 2H), 1.18-1.11 (m, 2H) 0.99-0.93 (m, 2H).

Example 392

2-((3,5-Dicyano-4-cyclopropyl-6-((2-(3-hydroxyazetidin-1-yl)-2-oxoethyl)(methyl)amino)pyridin-2-yl)thio)-2-phenyl)acetamide Step 1: tert-Butyl 2-((6-chloro-3,5-dicyano-4-cyclopropylpyridin-2-yl)(methyl)amino) acetate

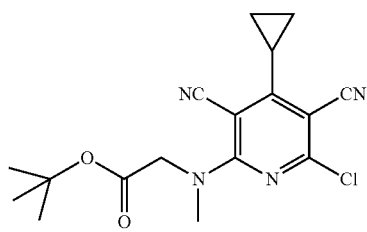 [SMILES: CN(CC(=O)OC(C)(C)C)c1nc(Cl)c(C#N)c(C2CC2)c1C#N]

To a stirred solution of 2,6-dichloro-4-cyclopropylpyridine-3,5-dicarbonitrile (synthesis described in example 4 step 2, 4.5 g) in dichloromethane (45 mL) was added at 0° C. triethylamine (2.53 mL, 17.77 mmol) followed by tert-butyl 2-(methylamino)acetate (2.58 g, 17.77 mmol). The reaction mixture was stirred for 2 hours at the same temperature. The reaction mixture was diluted with dichloromethane (200 mL). The organic layer was washed with saturated sodium chloride solution (100 mL), water (100 mL), dried over Na$_2$SO$_4$, filtered and concentrated under reduced pressure to give 5.8 g crude product. The crude compound was triturated with petroleum ether and a small amount of diethyl ether to get a precipitate. The solid was collected by filtration, washed with excess petroleum ether, and dried under vacuum to afford tert-butyl 2-((6-chloro-3,5-dicyano-4-cyclopropylpyridin-2-yl)(methyl)amino)acetate (5 g) as an off-white solid. LCMS m/z=345.0 [M–H]$^-$.

Step 2: tert-Butyl 2-((6-((2-amino-2-oxo-1-phenylethyl)thio)-3,5-dicyano-4-cyclopropyl pyridin-2-yl)(methyl)amino)acetate

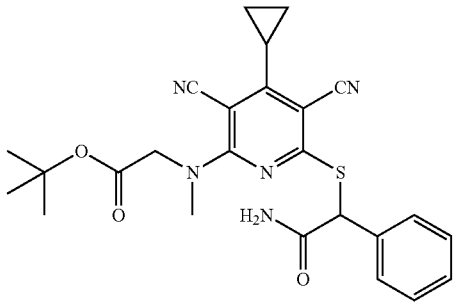 [SMILES: CN(CC(=O)OC(C)(C)C)c1nc(SC(C(N)=O)c2ccccc2)c(C#N)c(C2CC2)c1C#N]

To a solution of tert-butyl 2-((6-chloro-3,5-dicyano-4-cyclopropylpyridin-2-yl)(methyl) amino)acetate (5 g) in N,N-dimethylformamide (40 mL) was added potassium thioacetate (2.470 g, 21.19 mmol) at room temperature and the mixture was stirred for 2 hours at the same temperature. Then, potassium carbonate (2.99 g, 21.19 mmol) and 2-amino-2-oxo-1-phenylethyl methanesulfonate (synthesis described in example 3 step 5, 4.32 g) were added at room temperature and the mixture was stirred for 2 hours at room temperature. The reaction mixture was poured into ice cold water (100 mL) resulting in the formation of a precipitate. The solid was collected by filtration, washed with water (60 mL) and dried under vacuum. The crude material was purified by silica gel chromatography (100-200 mesh, eluted with 70% EtOAc in petroleum ether) to provide tert-butyl 2-((6-((2-amino-2-oxo-1-phenylethyl)thio)-3,5-dicyano-4-cyclopropylpyridin-2-yl)(methyl)amino)acetate (3.2 g) as an off-white solid. LCMS m/z=478.1 [M+H]$^+$.

Step 3: 2-((6-((2-Amino-2-oxo-1-phenylethyl)thio)-3,5-dicyano-4-cyclopropylpyridin-2-yl) (methyl)amino)acetic acid

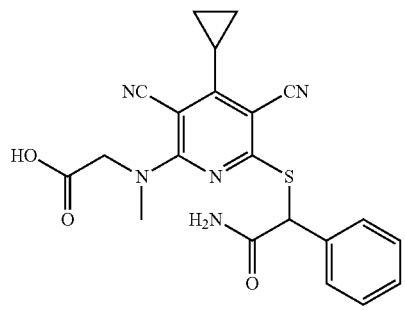 [SMILES: CN(CC(=O)O)c1nc(SC(C(N)=O)c2ccccc2)c(C#N)c(C2CC2)c1C#N]

To a solution of tert-butyl 2-((6-((2-amino-2-oxo-1-phenylethyl)thio)-3,5-dicyano-4-cyclopropyl pyridin-2-yl)(methyl)amino)acetate (2 g) in dichloromethane (20 mL) was added trifluoroacetic acid (0.5 ml, 6.49 mmol) at 0° C. and the reaction stirred for 2 hours at room temperature. The reaction mixture was concentrated under reduced pressure to give the crude product. The crude product was dissolved in dichloromethane (30 mL) and washed with saturated sodium bicarbonate solution (2×20 mL). The organic layer was dried over anhydrous sodium sulfate, filtered and concentrated to dryness under vacuum to afford 2-((6-((2-amino-2-oxo-1-phenylethyl)thio)-3,5-dicyano-4-cyclopropylpyridin-2-yl)(methyl)amino)acetic acid (1.6 g) as a brown solid. LCMS m/z=422.1 [M+H]⁺.

Step 4: 2-((3,5-Dicyano-4-cyclopropyl-6-((2-(3-hydroxyazetidin-1-yl)-2-oxoethyl) (methyl) amino) pyridin-2-yl)thio)-2-phenylacetamide

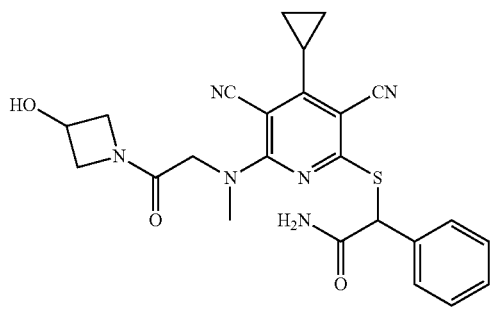 [SMILES: CN(CC(=O)N1CC(O)C1)c1nc(SC(C(N)=O)c2ccccc2)c(C#N)c(C2CC2)c1C#N]

To a solution of 2-((6-((2-amino-2-oxo-1-phenylethyl) thio)-3,5-dicyano-4-cyclopropylpyridin-2-yl)(methyl) amino)acetic acid, (500 mg) in N,N-dimethylformamide (5 mL) were added diisopropylethylamine (0.829 mL, 4.75 mmol) and HATU (677 mg, 1.779 mmol) at room temperature. After 15 minutes, azetidin-3-ol hydrochloride (130 mg, 1.186 mmol) was added at room temperature and the mixture was stirred for 16 hours. Water (10 mL) was added to the reaction mixture and the mixture extracted with ethyl acetate (10 mL). The organic layer was dried over anhydrous sodium sulfate, filtered and concentrated under reduced pressure. The crude material was purified by prep-HPLC to afford 2-((3,5-dicyano-4-cyclopropyl-6-((2-(3-hydroxyazetidin-1-yl)-2-oxoethyl)(methyl)amino)pyridin-2-yl)thio)-2-phenylacetamide (165 mg) as an off-white solid. LCMS m/z=477.1 [M+H]⁺. ¹H NMR (400 MHz, DMSO-d₆) δ ppm 7.83 (br d, J=9.65 Hz, 1H), 7.54-7.44 (m, 2H), 7.42-7.26 (m, 4H), 5.75 (d, J=5.48 Hz, 1H), 5.49 (d, J=9.21 Hz, 1H), 4.68-4.24 (m, 4H), 4.16-4.06 (m, 1H), 3.97-3.87 (m, 1H) 3.66 (dt, J=10.14, 4.91 Hz, 1H), 3.29 (s, 3H), 2.16-2.07 (m, 1H), 1.16-1.09 (m, 2H), 0.99-0.90 (m, 2H).

Example 393

2-((6-(4-((2-Amino-2-oxoethyl)amino)piperidin-1-yl)-3,5-dicyano-4-ethylpyridin-2-yl)thio)-2-phenylacetamide

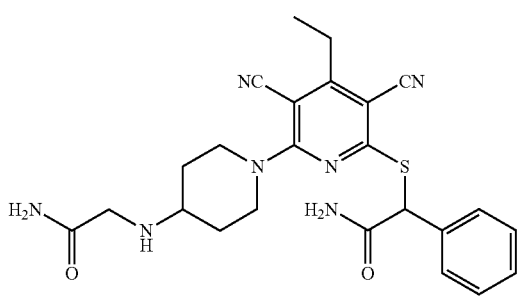 [SMILES: CCc1c(C#N)c(SC(C(N)=O)c2ccccc2)nc(N2CCC(NCC(N)=O)CC2)c1C#N]

To a stirred solution of 2-((6-(4-aminopiperidin-1-yl)-3,5-dicyano-4-ethylpyridin-2-yl)thio)-2-phenylacetamide, Hydrochloride (synthesis described in example 286 step 2, 500 mg) in dichloromethane (20 mL) was added triethylamine (0.273 mL, 1.962 mmol) followed by 2-bromoacetamide (135 mg, 0.981 mmol) at 0° C. The reaction was stirred at room temperature for 14 hours. The reaction was quenched with water (40 mL), the layers separated, and the aqueous layer was extracted with dichloromethane (2×50 mL). The combined organic layers were dried over anhydrous Na₂SO₄, filtered, and concentrated under reduced pressure. The crude material was purified by prep-HPLC to afford 2-((6-(4-((2-amino-2-oxoethyl)amino)piperidin-1-yl)-3,5-dicyano-4-ethylpyridin-2-yl)thio)-2-phenylacetamide (200 mg) as an off-white solid. LCMS m/z=478.1 [M+H]⁺. ¹H NMR (400 MHz, DMSO-d₆) δ ppm 7.89 (s, 1H), 7.55-7.48 (m, 2H), 7.42-7.25 (m, 5H), 7.04 (br s, 1H), 5.53 (s, 1H), 4.38 (d, J=13.81 Hz, 2H), 3.39-3.31 (m, 2H), 3.11 (s, 2H), 2.80-2.69 (m, 3H), 1.90 (d, J=12.50 Hz, 2H), 1.41-1.28 (m, 2H), 1.20 (t, J=7.56 Hz, 3H). One proton not observed.

Example 396

2-((6-((2-Amino-2-oxoethyl)(methyl)amino)-3,5-dicyano-4-cyclopropylpyridin-2-yl)thio)-2-phenylacetamide Step 1: 2-((6-Chloro-3,5-dicyano-4-cyclopropylpyridin-2-yl)(methyl)amino)acetamide

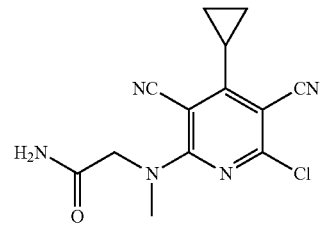 [SMILES: CN(CC(N)=O)c1nc(Cl)c(C#N)c(C2CC2)c1C#N]

To a stirred solution of 2-(methylamino)acetamide, hydrochloride (20.41 g, 164 mmol) in dichloromethane (1000 mL) was added triethylamine (54.6 mL, 378 mmol) followed by 2,6-dichloro-4-cyclopropylpyridine-3,5-dicarbonitrile (synthesis described in example 4 step 2, 30 g, 126 mmol). The reaction mixture was stirred at room temperature for 1 hour. Water (1000 mL) was added and the mixture extracted with DCM (2×1000 mL). The combined organic layers were dried over Na₂SO₄, filtered, and concentrated under reduced pressure to obtain the crude material. Purification of the crude material by silica gel chromatography (60-120 mesh; 10% MeOH/EtOAc as eluent) afforded 2-((6-chloro-3,5-dicyano-4-cyclopropylpyridin-2-yl)(methyl) amino)acetamide (32 g). LCMS m/z=290.4 [M+H]⁺.

Step 2: 2-((6-((2-Amino-2-oxoethyl)(methyl)amino)-3,5-dicyano-4-cyclopropylpyridin-2-yl)thio)-2-phenylacetamide

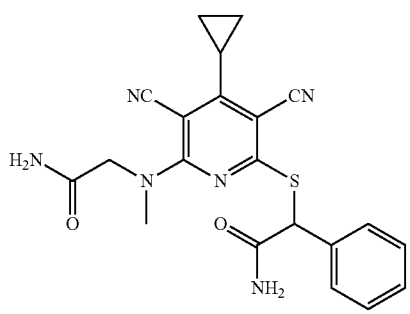 [SMILES: CN(CC(N)=O)c1nc(SC(C(N)=O)c2ccccc2)c(C#N)c(C2CC2)c1C#N]

To a stirred solution of 2-((6-chloro-3,5-dicyano-4-cyclopropylpyridin-2-yl)(methyl)amino)acetamide (32 g, 110 mmol) in N,N-dimethylformamide (800 mL) was added potassium thioacetate (18.92 g, 166 mmol) at 0° C. The reaction mixture was stirred at room temperature for 30 minutes, then $K_2CO_3$ (22.90 g, 166 mmol) and 2-amino-2-oxo-1-phenylethylmethanesulfonate (synthesis described in example 3 step 5, 25.3 g, 110 mmol) were added at 0° C. The reaction mixture was stirred at room temperature for 16 hours. Ice water (800 mL) was added and the mixture extracted with 5% methanol in ethyl acetate (2×1000 mL). The combined organic layers were dried over $Na_2SO_4$, filtered, and concentrated under reduced pressure to obtain the crude product. Purification of the crude material by chromatography using neutral alumina (10% MeOH/EtOAc as eluent) provided a residue. This residue was suspended in 10% ethanol in diethyl ether (1000 mL) for 6 hours, filtered, the collected solid washed with diethyl ether (500 mL), and dried. The solid was dissolved in ethanol (15 L in 3 batches), filtered, and the filtrate concentrated under reduced pressure to obtain the desired material. The material was suspended in ethanol (500 mL) for 2 hours, filtered, the collected solid washed with ethanol (300 mL), and dried to afford 2-((6-((2-amino-2-oxoethyl)(methyl)amino)-3,5-dicyano-4-cyclopropylpyridin-2-yl)thio)-2-phenylacetamide (22 g) as an off white solid. LCMS m/z=421.0 [M+H]⁺. ¹H NMR (400 MHz, DMSO-$d_6$) δ ppm 7.75 (s, 1H), 7.55 (br s, 1H), 7.48-7.51 (m, 2H), 7.24-7.41 (m, 5H), 5.57 (s, 1H), 4.49 (d, J=17.10 Hz, 1H), 4.26 (d, J=17.10 Hz, 1H), 3.31-3.40 (m, 3H), 2.11 (tt, J=8.74, 5.62 Hz, 1H), 1.07-1.22 (m, 2H), 0.89-1.01 (m, 2H).

Example 397

2-((6-((2-Amino-2-oxo-1-phenylethyl)thio-3,5-dicyano-4-cyclopropylpyridin-2-yl)methyl)amino)ethyl carbamate

Step 1: 2-Chloro-4-cyclopropyl-6-((2-hydroxyethyl)(methyl)amino)pyridine-3,5-dicarbonitrile

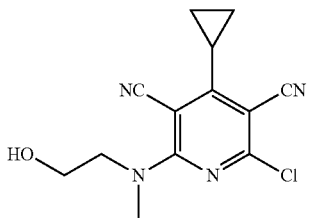 [SMILES: CN(CCO)c1nc(Cl)c(C#N)c(C2CC2)c1C#N]

To a stirred solution of 2-(methylamino)ethanol (0.303 g, 3.95 mmol) in dichloromethane (10 mL) was added triethylamine (0.842 mL, 5.92 mmol) followed by 2,6-dichloro-4-cyclopropylpyridine-3,5-dicarbonitrile (synthesis described in example 4 step 2, 1.0 g) at 0° C. and the reaction mixture was stirred for 1 hour at the same temperature. The reaction mixture was diluted with dichloromethane (100 mL) and washed with saturated sodium chloride solution (40 mL) and water (50 mL). The organic layer was dried over $Na_2SO_4$, filtered and concentrated under reduced pressure. The crude material was triturated with petroleum ether and a small amount of diethyl ether to obtain a precipitate. The precipitate was collected by filtration, washed with excess petroleum ether, and dried under vacuum to afford 2-chloro-4-cyclopropyl-6-((2-hydroxyethyl)(methyl)amino)pyridine-3,5-dicarbonitrile (1.0 g) as an off-white solid. LCMS m/z=277.1 [M+H]⁺.

Step 2: 2-((6-Chloro-3,5-dicyano-4-cyclopropylpyridin-2-yl)(methyl)amino)ethyl carbamate

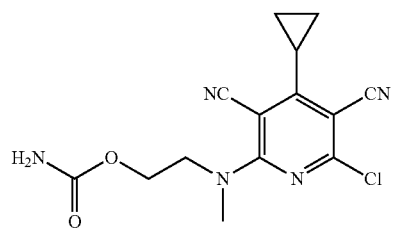 [SMILES: CN(CCOC(N)=O)c1nc(Cl)c(C#N)c(C2CC2)c1C#N]

To a stirred solution of 2-chloro-4-cyclopropyl-6-((2-hydroxyethyl)(methyl)amino)pyridine-3,5-dicarbonitrile (1.0 g) in toluene (20 mL) was added at 0° C. sodium cyanate (1.343 g, 13.01 mmol) followed by trifluoroacetic acid (1.002 mL, 13.01 mmol). The reaction mixture was stirred for 16 hours at room temperature. The reaction mixture was diluted with ethyl acetate (100 mL) and washed with saturated sodium bicarbonate solution (50 mL) and water (100 mL). The organic layer was dried over $Na_2SO_4$, filtered, and concentrated under reduced pressure. The crude material was triturated with petroleum ether and a small amount of diethyl ether to provide a precipitate. The precipitate was collected by filtration and dried under vacuum to afford 2-((6-chloro-3,5-dicyano-4-cyclopropylpyridin-2-yl)(methyl)amino)ethyl carbamate (0.8 g) as an off-white solid. LCMS m/z=320.1 [M+H]⁺.

Step 3: 2-((6-((2-Amino-2-oxo-1-phenylethyl)thio)-3,5-dicyano-4-cyclopropylpyridin-2-yl)(methyl)amino)ethyl carbamate

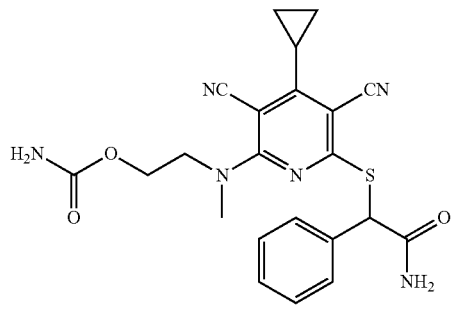 [SMILES: CN(CCOC(N)=O)c1nc(SC(C(N)=O)c2ccccc2)c(C#N)c(C2CC2)c1C#N]

To a stirred solution of 2-((6-chloro-3,5-dicyano-4-cyclopropylpyridin-2-yl)(methyl)amino)ethyl carbamate (0.800 g) in N,N-dimethylformamide (10 mL) was added potassium thioacetate (0.381 g, 3.27 mmol) at room temperature and the reaction was stirred for 2 hours at room temperature. To the reaction mixture were added potassium carbonate (0.460 g, 3.27 mmol) and 2-amino-2-oxo-1-phenylethyl methane sulfonate (synthesis described in example 3 step 5, 0.665 g) and the reaction was stirred for 1 hour at room temperature. The reaction mixture was poured into ice cold water (50 mL) and extracted with ethyl acetate (200 mL). The organic layer was washed with saturated brine solution (100 mL), water (300 mL), dried over anhydrous sodium sulfate, filtered and concentrated under reduced pressure. The crude material was washed with acetonitrile (20 mL) and dried under vacuum to afford 2-((6-((2-amino-2-oxo-1-phenylethyl)thio)-3,5-dicyano-4-cyclopropylpyridin-2-yl)(methyl)amino)ethyl carbamate (370 mg) as an off-white solid. LCMS m/z=451.1 [M+H]⁺. ¹H NMR (400 MHz, DMSO-$d_6$) δ ppm 7.81 (s, 1H), 7.53-7.47 (m, 2H), 7.42-7.29 (m, 4H), 6.57 (br s, 2H), 5.54 (s, 1H), 4.21-4.12 (m, 2H), 4.08-3.91 (m, 2H), 3.37 (s, 3H), 2.16-2.06 (m, 1H), 1.17-1.10 (m, 2H), 0.99-0.92 (m, 2H).

Example 398

(2R)-2-Amino-N-(1-(6-((2-amino-2-oxo-1-phenylethyl)thio)-3,5-dicyano-4-ethylpyridin-2-yl)piperidin-4-yl)-3-hydroxypropanamide Step 1: tert-Butyl ((2R)-1-((1-(6-((2-amino-2-oxo-1-phenylethyl)thio)-3,5-dicyano-4-ethylpyridin-2-yl)piperidin-4-yl)amino)-3-hydroxy-1-oxopropan-2-yl)carbamate

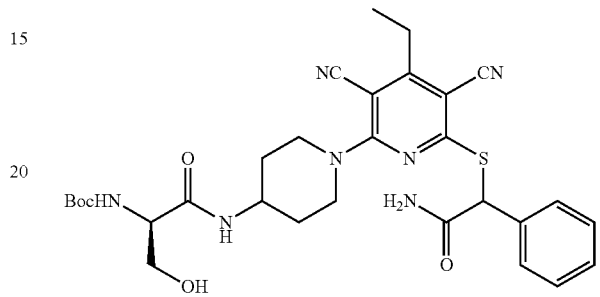

To a stirred solution of (R)-2-((tert-butoxycarbonyl)amino)-3-hydroxypropanoic acid (362 mg, 1.729 mmol) in N,N-dimethylformamide (15 mL) was added diisopropylethylamine (0.770 mL, 4.32 mmol) at room temperature. The reaction mixture was stirred at the same temperature for 5 minutes then HATU (671 mg, 1.729 mmol) and 2-((6-(4-aminopiperidin-1-yl)-3,5-dicyano-4-ethylpyridin-2-yl)thio)-2-phenylacetamide, Hydrochloride (synthesis described in example 286 step 2, 400 mg, 0.864 mmol) were added in one portion, and the resultant reaction mixture was stirred for 2 hours. The reaction mixture was diluted with cold water (100 mL) and stirred for 15 minutes to form a precipitate. The precipitate was collected by Buchner filtration, washed with excess water, and dried in vacuo. The crude solid was triturated with diethyl ether (30 mL) to afford tert-butyl ((2R)-1-((1-(6-((2-amino-2-oxo-1-phenylethyl)thio)-3,5-dicyano-4-ethylpyridin-2-yl)piperidin-4-yl)amino)-3-hydroxy-1-oxopropan-2-yl)carbamate (500 mg) as an off-white solid. LCMS m/z=608.2 [M+H]⁺.

Step 2: (2R)-2-Amino-N-(1-(6-((2-amino-2-oxo-1-phenylethyl)thio)-3,5-dicyano-4-ethylpyridin-2-yl)piperidin-4-yl)-3-hydroxypropanamide

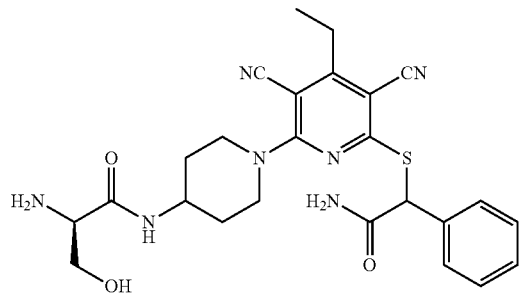 [SMILES: CCc1c(C#N)c(SC(C(N)=O)c2ccccc2)nc(N2CCC(NC(=O)[C@H](N)CO)CC2)c1C#N]

To a stirred solution of tert-butyl ((2R)-1-((1-(6-((2-amino-2-oxo-1-phenylethyl)thio)-3,5-dicyano-4-ethylpyridin-2-yl)piperidin-4-yl)amino)-3-hydroxy-1-oxopropan-2- yl)carbamate (500 mg) in 1,4-dioxane (10 mL) was added hydrochloric acid (4 M in 1,4-dioxane, 1.748 mL, 6.99 mmol) at 5° C. The resultant reaction mixture was stirred at room temperature for 5 hours. The reaction mixture was diluted with diethyl ether (50 mL) and stirred for 10 minutes at room temperature to afford a precipitate. The solid was collected by Buchner filtration, washed with excess diethyl ether, and dried in vacuo. The crude material was purified by prep-HPLC to afford (2R)-2-amino-N-(1-(6-((2-amino-2-oxo-1-phenylethyl)thio)-3,5-dicyano-4-ethylpyridin-2-yl) piperidin-4-yl)-3-hydroxypropanamide (140 mg) as an off-white solid. LCMS m/z=508.1 [M+H]$^+$. $^1$H NMR (400 MHz, DMSO-d$_6$) δ ppm 7.89 (s, 1H), 7.80 (d, J=7.67 Hz, 1H), 7.54-7.46 (m, 2H), 7.42-7.25 (m, 4H), 5.53 (s, 1H), 4.68 (t, J=5.48 Hz, 1H), 4.44 (br t, J=12.28 Hz, 2H), 3.91 (br s, 1H), 3.51 (dt, J=10.03, 4.96 Hz, 1H), 3.43-3.33 (m, 3H), 3.18 (t, J=5.59 Hz, 1H), 2.76 (q, J=7.60 Hz, 2H), 1.88-1.80 (m, 4H), 1.57-1.45 (m, 2H), 1.21 (t, J=7.56 Hz, 3H).

Example 399

(2S)-2-Amino-N-(1-(6-((2-amino-2-oxo-1-phenylethyl)thio-3,5-dicyano-4-ethylpyridin-2-yl) piperidin-4-yl)-3-hydroxypropanamide Step 1: tert-Butyl ((2S)-1-((1-(6-((2-amino-2-oxo-1-phenylethyl)thio)-3,5-dicyano-4-ethylpyridin-2-yl) piperidin-4-yl)amino)-3-hydroxy-1-oxopropan-2-yl) carbamate

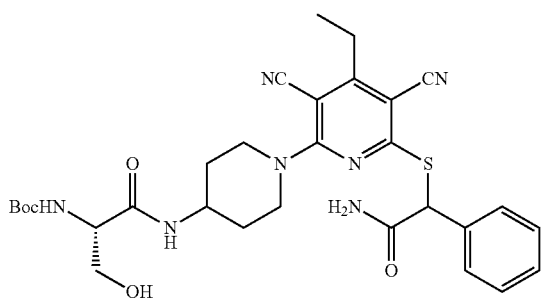 [SMILES: CCc1c(C#N)c(SC(C(N)=O)c2ccccc2)nc(N2CCC(NC(=O)[C@H](CO)NC(=O)OC(C)(C)C)CC2)c1C#N]

To a stirred solution of (S)-2-((tert-butoxycarbonyl) amino)-3-hydroxypropanoic acid (91 mg, 0.432 mmol) in N,N-dimethylformamide (15 mL) was added diisopropylethylamine (0.770 mL, 4.32 mmol) at room temperature. The reaction mixture was stirred at the same temperature for 5 minutes then HATU (671 mg, 1.729 mmol) and 2-((6-(4-aminopiperidin-1-yl)-3,5-dicyano-4-ethylpyridin-2-yl) thio)-2-phenylacetamide, Hydrochloride (synthesis described in example 286 step 2, 400 mg) were added in one portion, and the resultant reaction mixture was stirred for 2 hours. The reaction mixture was diluted with cold water (100 mL) and stirred for 15 minutes to afford a solid. The solid was collected by Buchner filtration, washed with excess water, and dried in vacuo. The solid was triturated with diethyl ether (30 mL) to afford tert-butyl((2S)-1-((1-(6-((2-amino-2-oxo-1-phenylethyl)thio)-3,5-dicyano-4-ethylpyridin-2-yl)piperidin-4-yl)amino)-3-hydroxy-1-oxopropan-2-yl)carbamate (520 mg) as an off-white solid. LCMS m/z=609.0 [M+H]$^+$.

Step 2: (2S)-2-Amino-N-(1-(6-((2-amino-2-oxo-1-phenylethyl)thio)-3,5-dicyano-4-ethylpyridin-2-yl) piperidin-4-yl)-3-hydroxypropanamide

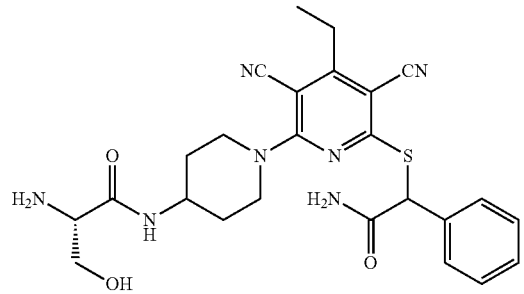 [SMILES: CCc1c(C#N)c(SC(C(N)=O)c2ccccc2)nc(N2CCC(NC(=O)[C@@H](N)CO)CC2)c1C#N]

To a stirred solution of tert-butyl ((2S)-1-((1-(6-((2-amino-2-oxo-1-phenylethyl)thio)-3,5-dicyano-4-ethylpyridin-2-yl)piperidin-4-yl)amino)-3-hydroxy-1-oxopropan-2-yl)carbamate (500 mg) in 1,4-dioxane (15 mL) was added hydrochloric acid (4 M in 1,4-dioxane 1.770 mL, 7.08 mmol) at 5° C. The resultant reaction mixture was stirred at room temperature for 5 hours. The reaction mixture was diluted with diethyl ether (50 mL) and stirred for 10 minutes at room temperature to afford a precipitate. The precipitated solid was collected by Buchner filtration, washed with excess diethyl ether, and dried in vacuo. The crude material was purified by prep-HPLC to afford (2S)-2-amino-N-(1-(6-((2-amino-2-oxo-1-phenylethyl)thio)-3,5-dicyano-4-ethylpyridin-2-yl)piperidin-4-yl)-3-hydroxypropanamide (260 mg) as an off-white solid. LCMS m/z=508.1 [M+H]$^+$. $^1$H NMR (400 MHz, DMSO-d$_6$) δ ppm 7.87 (s, 1H), 7.78 (d, J=7.89 Hz, 1H), 7.52-7.46 (m, 2H), 7.39-7.27 (m, 4H), 5.51 (s, 1H), 4.66 (t, J=5.48 Hz, 1H), 4.42 (br t, J=11.84 Hz, 2H), 3.84-3.96 (m, 1H), 3.49 (dt, J=10.25, 5.07 Hz, 1H), 3.40-3.30 (m, 3H), 3.19-3.13 (m, 1H), 2.74 (q, J=7.67 Hz, 2H), 1.91-1.75 (m, 4H), 1.56-1.41 (m, 2H), 1.19 (t, J=7.67 Hz, 3H).

Example 400

2-(4-(2-Amino-2-oxoethyl)phenyl)-2-(3,5-dicyano-4-ethyl-6-(4-methyl-1,4-diazepan-1-yl)pyridin-2-ylthio)acetamide Step 1: 2,2'-(1,4-Phenylene)diacetonitrile

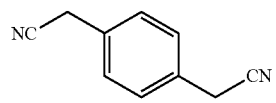 [SMILES: N#CCc1ccc(CC#N)cc1]

A mixture of 1,4-bis(bromomethyl)benzene (8.0 g, 30.3 mmol) and cyanopotassium (4.80 g, 73.6 mmol) in ethanol (80.0 mL) and water (40 mL) was stirred at 50-60° C. for 3 hours. Water (300 mL) was added into the mixture. The resulting mixture was extracted with DCM (3×200 mL). The combined organic layer was washed with water (200 mL) three times and brine (200 mL), then concentrated to afford 2,2'-(1,4-phenylene)diacetonitrile (4.3 g, 91% yield) as a white solid. $^1$H NMR (400 MHz, CDCl$_3$) δ 7.39 (s, 4H), 3.79 (s, 4H).

Step 2: 2-Bromo-2-(4-(cyanomethyl)phenyl)acetonitrile

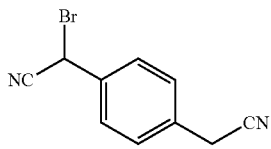 [SMILES: N#CCc1ccc(C(Br)C#N)cc1]

A mixture of 2,2'-(1,4-phenylene)diacetonitrile (2.3 g, 14.73 mmol) 1-bromopyrrolidine-2,5-dione (2.6 g, 14.73 mmol) benzoic peroxyanhydride (0.36 g, 1.47 mmol) in CCl$_4$ (30 mL) was stirred at 75-80° C. for 4 hours. A second reaction mixture of 2,2'-(1,4-phenylene)diacetonitrile (2.0 g, 12.81 mmol) 1-bromopyrrolidine-2,5-dione (2.279 g, 12.81 mmol) benzoic peroxyanhydride (0.310 g, 1.281 mmol) in CC14 (30 mL) was stirred at 75-80° C. for 4 hours. The mixtures were combined, then concentrated. The residue was purified by flash chromatography (eluted by petroleum ether:ethyl acetate=20:1-1:1) to afford 2-bromo-2-(4-(cyanomethyl)phenyl)acetonitrile (2.6 g, 11.1 mmol). $^1$H NMR (400 MHz, CDCl$_3$) δ ppm 7.32 (d, J=8.2 Hz, 2H), 7.17 (d, J=8.1 Hz, 2H), 5.23 (s, 1H), 3.51 (s, 2H).

Step 3: 2-(4-(2-Amino-2-oxoethyl)phenyl)-2-bromoacetamide

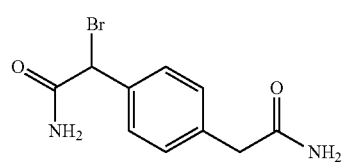 [SMILES: NC(=O)Cc1ccc(C(Br)C(N)=O)cc1]

A mixture of 2-bromo-2-(4-(cyanomethyl)phenyl)acetonitrile (1.5 g, 6.38 mmol) acetamide (3.8 g, 63.80 mmol) and palladium(II) chloride (0.11 g, 0.64 mmol) in tetrahydrofuran (15 mL) and water (5.00 mL) was degassed under vacuum, then stirred for 3 hours at 20-30° C. The mixture was concentrated. DCM (30 mL) and MeOH (10 mL) were added and the mixture was stirred for 1 hour. The mixture was filtered, then dried under vacuum to afford 2-(4-(2-amino-2-oxoethyl)phenyl)-2-bromoacetamide (670 mg, 39%). LCMS m/z=270.9 [M+H]$^+$.

Step 4: 2-(4-(2-Amino-2-oxoethyl)phenyl)-2-(3,5-dicyano-4-ethyl-6-(4-methyl-1,4-diazepan-1-yl)pyridin-2-ylthio)acetamide

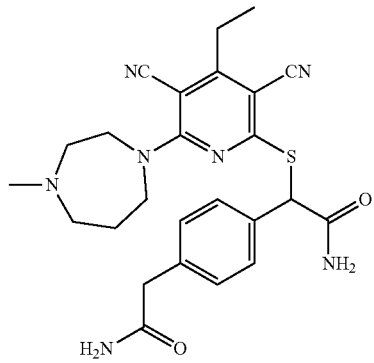 [SMILES: CCc1c(C#N)c(SC(C(N)=O)c2ccc(CC(N)=O)cc2)nc(N2CCCN(C)CC2)c1C#N]

A mixture of 4-ethyl-2-mercapto-6-(4-methyl-1,4-diazepan-1-yl)pyridine-3,5-dicarbonitrile (synthesis described in example 69 step 1, 267 mg, 0.89 mmol) 2-(4-(2-amino-2-oxoethyl)phenyl)-2-bromoacetamide (200 mg, 0.74 mmol) and triethylamine (112 mg, 1.11 mmol) in N,N-dimethylformamide (10 mL) was stirred for 2 hours at 20-30° C. The mixture was filtered and washed with water, then the cake was stirred with MeOH and water for 1 hour, then filtered. The cake was stirred with DMSO (30 mL) for 3 hours, then water (120 mL) was added dropwise. After stirring for 16 hours, the mixture was filtered and washed with water, then dried to afford 2-(4-(2-amino-2-oxoethyl)phenyl)-2-((3,5-dicyano-4-ethyl-6-(4-methyl-1,4-diazepan-1-yl)pyridin-2-yl)thio)acetamide (116 mg, 32% yield). LCMS m/z=492.1 [M+H]$^+$. $^1$H NMR (400 MHz, DMSO-d$_6$) δ ppm 7.90 (s, 1H), 7.48 (s, 1H), 7.42 (d, J=8.1 Hz, 2H), 7.33 (s, 1H), 7.26 (d, J=8.0 Hz, 2H), 6.88 (s, 1H), 5.50 (s, 1H), 4.01-3.92 (m, 2H), 3.91-3.85 (m, 2H), 3.37 (s, 2H), 2.77 (q, J=7.6 Hz, 2H), 2.72-2.63 (m, 2H), 2.55 (s, 2H), 2.28 (s, 3H), 2.00-1.90 (m, 2H), 1.21 (t, J=7.6 Hz, 3H).

Example 401

2-(4-(2-Amino-2-oxoethyl)phenyl)-2-(3,5-dicyano-6-(dimethylamino)-4-ethylpyridin-2-ylthio)acetamide

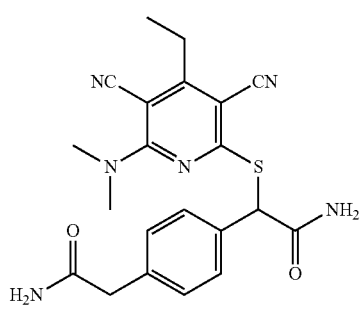 [SMILES: CCc1c(C#N)c(SC(C(N)=O)c2ccc(CC(N)=O)cc2)nc(N(C)C)c1C#N]

A mixture of 2-chloro-6-(dimethylamino)-4-ethylpyridine-3,5-dicarbonitrile (208 mg, 0.89 mmol) potassium ethanethioate (synthesis described in example 3 step 3, 101 mg, 0.89 mmol) triethylamine (187 mg, 1.84 mmol) in N,N- dimethylformamide (10 mL) was stirred for 1 hour at 20-30° C. 2-(4-(2-amino-2-oxoethyl)phenyl)-2-bromoacetamide (synthesis described in example 400 step 3, 200 mg, 0.74 mmol) was added, then the mixture was stirred for 16 hours at 20-30° C. Water (30 mL) was added and the mixture was stirred, then the mixture was stirred for 1 hour, filtered and washed with water. The cake was stirred for 1 hour with ethyl acetate (30 mL), then filtered and dried to afford 2-(4-(2-amino-2-oxoethyl)phenyl)-2-((3,5-dicyano-6-(dimethylamino)-4-ethylpyridin-2-yl)thio)acetamide (150 mg, 48% yield). LCMS m/z=423.1 [M+H]$^+$. $^1$H NMR (400 MHz, DMSO-d$_6$) δ ppm 7.89 (s, 1H), 7.48 (s, 1H), 7.44 (d, J=8.1 Hz, 2H), 7.31 (s, 1H), 7.25 (d, J=8.0 Hz, 2H), 6.89 (s, 1H), 5.57 (s, 1H), 3.36 (s, 2H), 3.35 (s, 6H), 2.75 (q, J=7.5 Hz, 2H), 1.20 (t, J=7.6 Hz, 3H).

Example 402

2-((3,5-Dicyano-6-(dimethylamino)-4-ethylpyridin-2-yl)thio)-2-(4-1N-methylsulfamoyl)phenyl)acetamide

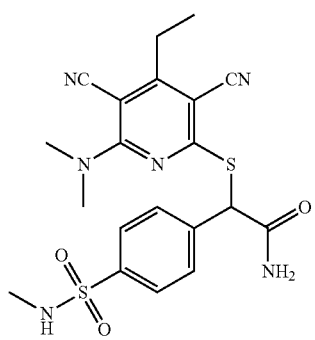 [SMILES: CCc1c(C#N)c(SC(C(N)=O)c2ccc(S(=O)(=O)NC)cc2)nc(N(C)C)c1C#N]

A mixture of 2-(dimethylamino)-4-ethyl-6-mercaptopyridine-3,5-dicarbonitrile (synthesis described in example 92 step 3, 200 mg, 0.86 mmol), 2-amino-1-(4-(N-methylsulfamoyl)phenyl)-2-oxoethyl methanesulfonate (synthesis described in example 378 step 4, 319 mg, 0.99 mmol) and triethylamine (0.360 mL, 2.58 mmol) in DMF (10 mL) was stirred at 55° C. for 16 hours. Then it was concentrated and the residue was extracted with DCM and washed with water. The organic layer was concentrated in vacuo to dryness and the residue was purified by column chromatography to afford 2-((3,5-dicyano-6-(dimethylamino)-4-ethylpyridin-2-yl)thio)-2-(4-(N-methylsulfamoyl)phenyl)acetamide (36 mg, 9% yield). LCMS m/z=459.1 [M+H]$^+$. $^1$H NMR (400 MHz, DMSO-d$_6$) δ ppm 8.04 (s, 1H), 7.77 (m, 4H), 7.53-7.38 (m, 2H), 5.72 (s, 1H), 3.31 (s, 6H), 2.75 (d, J=7.6 Hz, 2H), 2.43 (t, J=6.3 Hz, 3H), 1.20 (t, J=7.5 Hz, 3H).

Example 403

4-Ethyl-2-(4-methyl-1,4-diazepan-1-yl)-6-(4-(methylsulfonylmethyl)benzylthio)pyridine-3,5-dicarbonitrile Step 1: Methyl 4-(methylthiomethyl)benzoate

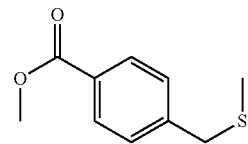

To a solution of sodium methanethiolate (0.734 g, 9.95 mmol) in methanol (30 mL) stirred at 0° C. was added methyl 4-(bromomethyl)benzoate (1.9 g, 8.29 mmol) in one charge. The reaction mixture was stirred at room temperature for 16 hours. The reaction mixture was diluted with water (250 mL), partitioned between ethyl acetate (100 mL) and water (250 mL). The organic phase was washed with water (10 mL), dried over sodium sulphate and concentrated. The residue was purified by silica gel column (eluted with hexane/EtOAc) to afford methyl 4-(methylthiomethyl)benzoate (1.5 g, 92% yield). LCMS m/z=197.0 [M+H]$^+$.

Step 2: Methyl 4-(methylsulfonylmethyl)benzoate

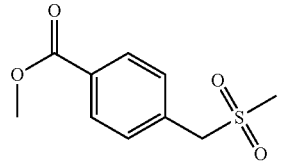

A mixture of methyl 4-((methylthio)methyl)benzoate (500 mg, 2.55 mmol) and H$_2$O$_2$ (5 mL, 16 mmol) was stirred in acetic acid (10 mL) at 120° C. for 2 hours. The reaction was concentrated in vacuo, then water (10 mL) was added dropwise to afford a white solid. The solid was filtered and dried in vacuo to afford methyl 4-((methylsulfonyl)methyl)benzoate (500 mg, 2.19 mmol, 86% yield) as a white solid. LCMS m/z=228.9 [M+H]$^+$.

Step 3: (4-(Methylsulfonylmethyl)phenyl)methanol

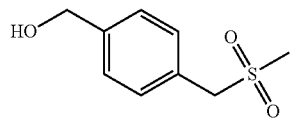

To a solution of methyl 4-((methylsulfonyl)methyl)benzoate (400 mg, 1.75 mmol) in tetrahydrofuran (30 mL) stirred at 0° C. was added solid aluminum(III) lithium hydride (133 mg, 3.50 mmol) portionwise. The reaction mixture was stirred at room temperature for 2 hours. water (0.15 mL) was added dropwise, then 10% NaOH (0.45 mL).

The mixture was filtered and the filtrate was concentrated to afford (4-(Methylsulfonylmethyl)phenyl)methanol. LCMS m/z=183 [M+H-18]⁺.

Step 4: tert-Butyl 1-(chloromethyl)-4-(methylsulfonylmethyl)benzene

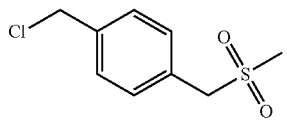

To a solution of (4-((methylsulfonyl)methyl)phenyl)methanol (269 mg, 1.34 mmol) in dichloromethane (30 mL) stirred in air at 0° C. was added thionyl chloride (0.392 mL, 5.37 mmol) dropwise. The reaction mixture was stirred at room temperature for 1 hour then concentrated to afford tert-butyl 1-(chloromethyl)-4-(methylsulfonylmethyl)benzene (294 mg, 100% yield). LCMS m/z=219 [M+H]⁺.

Step 5: 4-ethyl-2-(4-methyl-1,4-diazepan-1-yl)-6-(4-(methylsulfonylmethyl)benzylthio)pyridine-3,5-dicarbonitrile

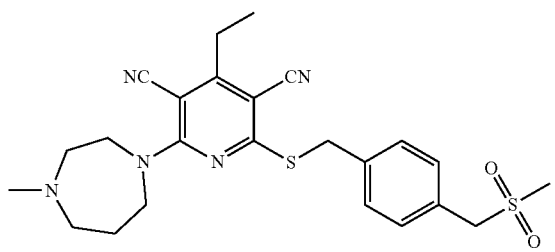

A mixture of 1-(chloromethyl)-4-((methylsulfonyl)methyl)benzene (400 mg, 1.83 mmol), triethylamine (0.765 mL, 5.49 mmol) and 4-ethyl-2-mercapto-6-(4-methyl-1,4-diazepan-1-yl)pyridine-3,5-dicarbonitrile (described in example 69 step 1, 551 mg, 1.83 mmol) was stirred in N,N-dimethylformamide (30 mL) at room temperature for 2 hours. The mixture was concentrated and the residue was purified by silica gel column (eluted with CH₂Cl₂/MeOH) to afford 4-ethyl-2-(4-methyl-1,4-diazepan-1-yl)-6-(4-(methylsulfonylmethyl)benzylthio)pyridine-3,5-dicarbonitrile (120 mg, 0.24 mmol, 13% yield). LCMS m/z=483.8 [M+H]⁺. ¹H NMR (400 MHz, MeOD) δ ppm 7.45 (q, J=8.3 Hz, 4H), 4.55 (s, 2H), 4.43 (s, 2H), 4.01-3.96 (m, 2H), 3.93 (t, J=6.1 Hz, 2H), 2.99-2.91 (m, 2H), 2.90 (s, 3H), 2.84-2.79 (m, 2H), 2.72-2.66 (m, 2H), 2.41 (s, 3H), 2.08-2.00 (m, 2H), 1.31 (t, 3H).

Example 404

2-((3,5-Dicyano-6-(dimethylamino-d₆)-4-ethylpyridin-2-yl)thio)-2-phenylacetamide Step 1: 2-Chloro-6-(dimethylamino-d₆)-4-ethylpyridine-3,5-dicarbonitrile

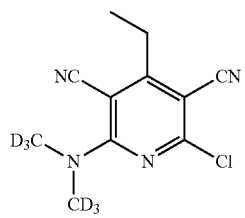 [SMILES: [2H]C([2H])([2H])N(c1nc(Cl)c(C#N)c(CC)c1C#N)C([2H])([2H])[2H]]

To a solution of 2,6-dichloro-4-ethylpyridine-3,5-dicarbonitrile (synthesis described in example 3, step 2, 2.5 g, 11.06 mmol), dimethylamine-d₆, hydrochloride (1.017 g, 11.61 mmol), in ethanol (30 mL) at 0° C. was added Et₃N (3.39 mL, 24.33 mmol) dropwise. The resulting mixture was stirred at 0° C. for 60 minutes, then for 2 hours at room temperature. 150 mL of water was added to the reaction, and the resulting mixture stirred for 30 minutes. The resulting precipitate was filtered, dried at the pump for two hours, then in a vacuum oven over the weekend to afford 2-chloro-6-(dimethylamino-d₆)-4-ethylpyridine-3,5-dicarbonitrile (950 mg, 3.95 mmol, 36% yield) as an off-white solid. LCMS m/z=241.0 [M+H]⁺.

Step 2: 2-((3,5-Dicyano-6-(dimethylamino-d₆)-4-ethylpyridin-2-yl)thio)-2-phenylacetamide

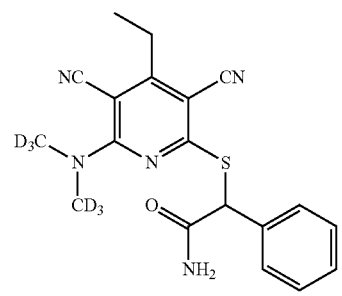 [SMILES: [2H]C([2H])([2H])N(c1nc(SC(C(N)=O)c2ccccc2)c(C#N)c(CC)c1C#N)C([2H])([2H])[2H]]

To 20-mL vial was added S-(2-amino-2-oxo-1-phenylethyl) ethanethioate (synthesis described in example 62, step 5, 191 mg, 0.914 mmol), ethanol (10 mL), and the mixture heated to reflux. Then NaBH₄ (47.1 mg, 1.246 mmol) was added portionwise. The reaction was stirred at reflux for 45 minutes, then cooled to room temperature, and solid 2-chloro-6-(dimethylamino-d₆)-4-ethylpyridine-3,5-dicarbonitrile (200 mg, 0.831 mmol) was added. The reaction mixture was stirred at room temperature for one hour. The resulting mixture was filtered, washed with ethanol and the residue was dried at the pump for an hour, then in a vacuum oven over the weekend to afford 2-((3,5-dicyano-6-(dimethylamino-d₆)-4-ethylpyridin-2-yl)thio)-2-phenylacetamide (270 mg, 0.727 mmol, 87% yield) as a white solid. LCMS m/z=372.2 [M+H]⁺. ¹H NMR (DMSO-d₆) δ ppm 7.94 (s, 1H), 7.48-7.57 (m, 2H), 7.25-7.43 (m, 4H), 5.60 (s, 1H), 2.75 (q, J=7.6 Hz, 2H), 1.20 (t, J=7.5 Hz, 3H).

Example 405

(R)-2-((3,5-Dicyano-4-ethyl-6-(4-(pyrrolidin-1-yl) piperidin-1-yl)pyridin-2-yl)thio)-2-phenylacetamide Step 1: 2-Chloro-4-ethyl-6-(4-(pyrrolidin-1-yl)piperidin-1-yl)pyridine-3,5-dicarbonitrile

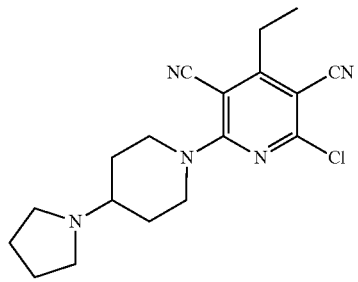 [SMILES: CCc1c(C#N)c(Cl)nc(N2CCC(N3CCCC3)CC2)c1C#N]

To a solution of 2,6-dichloro-4-ethylpyridine-3,5-dicarbonitrile (synthesis described in example 3, step 2, 300 mg, 1.327 mmol) in dichloromethane (40 mL) stirred at 0° C. was added a solution of 4-(pyrrolidin-1-yl)piperidine (205 mg, 1.327 mmol) and triethylamine (0.222 mL, 1.592 mmol) in DCM (20 mL) dropwise. The reaction mixture was stirred at room temperature for 2 hours. The reaction mixture was partitioned between dichloromethane (100 mL) and water (100 mL). The organic phase was washed with saturated brine (25 mL), dried over sodium sulphate and evaporated in vacuo to give the crude 2-chloro-4-ethyl-6-(4-(pyrrolidin-1-yl)piperidin-1-yl)pyridine-3,5-dicarbonitrile (508 mg, 100% yield, 90% purity) as a yellow solid. LCMS m/z=344.2 [M+H]$^+$.

Step 2: (R)-2-((3,5-Dicyano-4-ethyl-6-(4-(pyrrolidin-1-yl)piperidin-1-yl)pyridin-2-yl)thio)-2-phenylacetamide

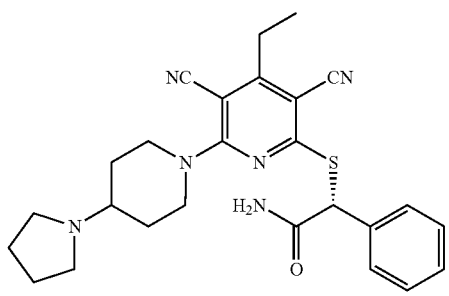 [SMILES: CCc1c(C#N)c(S[C@@H](C(N)=O)c2ccccc2)nc(N2CCC(N3CCCC3)CC2)c1C#N]

A mixture of 2-chloro-4-ethyl-6-(4-(pyrrolidin-1-yl)piperidin-1-yl)pyridine-3,5-dicarbonitrile (508 mg, 1.330 mmol, 90% purity) and potassium thioacetate (182 mg, 1.596 mmol) was stirred in N,N-dimethylformamide (20 mL) at 20° C. for 30 minutes. Then triethylamine (0.222 mL, 1.596 mmol) and (S)-2-amino-2-oxo-1-phenylethyl 4-methylbenzenesulfonate (synthesis described in example 418 step 3, 487 mg, 1.596 mmol) was added successively. The mixture was stirred at 20° C. overnight. The reaction mixture was partitioned between ethyl acetate (100 mL) and water (100 mL). The organic phase was washed with water (50 mL), saturated brine (50 mL), dried over sodium sulphate and evaporated in vacuo to give the crude product. The crude product was added to a silica gel (12 g) column and eluted by DCM:MeOH=10:1 to give (R)-2-((3,5-dicyano-4-ethyl-6-(4-(pyrrolidin-1-yl)piperidin-1-yl)pyridin-2-yl)thio)-2-phenylacetamide (80 mg, 0.163 mmol, 12% yield) as a white solid. LCMS m/z=475.3 [M+H]$^+$. $^1$H NMR (400 MHz, MeOD) δ 7.53-7.52 (m, 2H), 7.41-7.35 (m, 3H), 5.50 (s, 1H), 4.78-4.68 (m, 2H), 3.52-3.12 (m, 2H), 2.88 (q, J=7.6 Hz, 2H), 2.69-2.66 (m, 4H), 2.41-2.39 (m, 1H), 2.12-2.08 (m, 2H), 1.85-1.83 (m, 4H), 1.58-1.53 (m, 2H), 1.29 (t, J=7.6 Hz, 3H).

Example 406

(R)-2-((3,5-Dicyano-6-(4-(dimethylamino)piperidin-1-yl)-4-ethylpyridin-2-yl)thio)-2-phenylacetamide

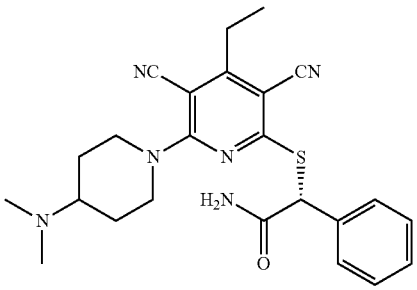 [SMILES: CCc1c(C#N)c(S[C@@H](C(N)=O)c2ccccc2)nc(N2CCC(N(C)C)CC2)c1C#N]

A mixture of 2-chloro-6-(4-(dimethylamino)piperidin-1-yl)-4-ethylpyridine-3,5-dicarbonitrile (synthesis described in example 207, step 1, 300 mg, 0.850 mmol, 90% purity) and potassium thioacetate (116 mg, 1.019 mmol) was stirred in N,N-dimethylformamide (20 mL) at 20° C. for 30 minutes. Then triethylamine (0.142 mL, 1.019 mmol) and (S)-2-amino-2-oxo-1-phenylethyl 4-methylbenzenesulfonate (synthesis described in example 418 step 3, 311 mg, 1.019 mmol) was added successively. The mixture was stirred at 20° C. overnight. The reaction mixture was partitioned between ethyl acetate (100 mL) and water (100 mL). The organic phase was washed with water (50 mL), saturated brine (50 mL), dried over sodium sulphate and evaporated in vacuo to give the crude product. The crude product was added to a silica gel (12 g) column and eluted by DCM:MeOH=5:1 to give (R)-2-((3,5-dicyano-6-(4-(dimethylamino)piperidin-1-yl)-4-ethylpyridin-2-yl)thio)-2-phenylacetamide (94 mg, 0.210 mmol, 25% yield) as a white solid. LCMS m/z=449.3 [M+H]$^+$. $^1$H NMR (400 MHz, DMSO) δ 7.93 (s, 1H), 7.54-7.52 (m, 2H), 7.39-7.35 (m, 4H), 5.54 (s, 1H), 4.58-4.55 (m, 2H), 3.18 (t, J=11.9 Hz, 2H), 2.83-2.64 (m, 2H), 2.42-2.35 (m, 1H), 2.19 (s, 6H), 1.88-1.85 (m, 2H), 1.41-1.36 (m, 2H), 1.20 (t, J=7.2 Hz, 3H).

Example 407

2-(3,5-dicyano-6-(dimethylamino)-4-ethylpyridin-2-ylthio)-2-(3-(2-(dimethylamino)ethoxy)phenyl)acetamide Step 1: 3-(2-(Dimethylamino)ethoxy)benzonitrile

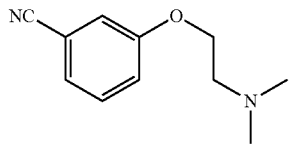

To a solution of 3-hydroxybenzonitrile (10 g, 84 mmol) in toluene (200 mL) was added a solution of sodium methanolate (4.54 g, 84 mmol) in methanol (40.0 mL) at room temperature. The methanol was distilled at 100° C. to give a white solid. To 2-chloro-N,N-dimethylethanamine hydrochloride (12.09 g, 84 mmol) in toluene (200 mL) was added saturated sodium carbonate solution (50 mL) at 0° C. and was stirred for 4 hours. The organic phase was separated and the above white solid was added to the organic layer of 2-chloro-N,N-dimethylethanamine. Then the reaction mixture was stirred at 65° C. for 12 hours. The reaction mixture was filtered, evaporated in vacuo to give the crude product as a white solid. The crude product was added to a silica gel column (150 g) and was eluted with $CH_2Cl_2$:MeOH (gradient: 30:1-10:1) to obtain 3-(2-(dimethylamino)ethoxy)benzonitrile (1.5 g, 7.88 mmol, 9% yield) as a yellow oil. LCMS m/z=191.0 $[M+H]^+$.

Step 2: 3-(2-(Dimethylamino)ethoxy)benzaldehyde

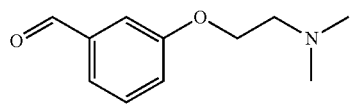

A suspension of 3-(2-(dimethylamino)ethoxy)benzonitrile (1.4 g, 7.36 mmol) and nickel (0.086 g, 1.472 mmol) in formic acid (10 mL) was stirred under nitrogen at 125° C. for 5 hours. The organic phase was filtered and evaporated in vacuo to give the crude product as a yellow solid. The crude product was added to a silica gel column (100 g) and was eluted with $CH_2Cl_2$:MeOH (gradient: 100:1-10:1) to give 3-(2-(dimethylamino)ethoxy)benzaldehyde (1 g) as yellow oil. LCMS m/z=194.2 $[M+H]^+$.

Step 3: 2-((3,5-Dicyano-6-(dimethylamino)-4-ethylpyridin-2-yl)thio)-2-(3-(2-(dimethylamino)ethoxy)phenyl)acetamide

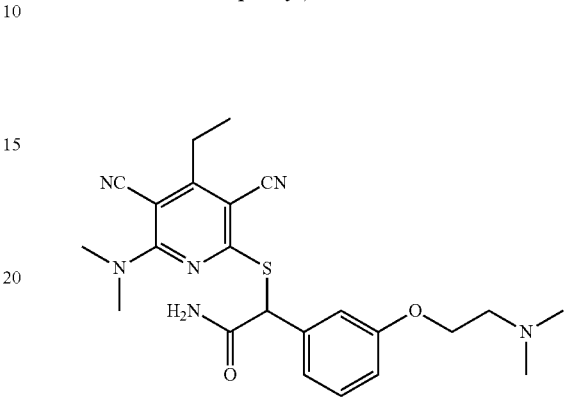

A solution of 3-(2-(dimethylamino)ethoxy)benzaldehyde (900 mg, 4.66 mmol) and potassium 1,3-dioxoisoindolin-2-ide (108 mg, 0.582 mmol) in trimethylsilanecarbonitrile (10 mL, 75.0 mmol) was stirred at at room temperature for overnight. The organic phase was evaporated in vacuo to give the crude as a yellow solid. A solution of the yellow solid (500 mg) was stirred in hydrogen chloride (10 mL, 120 mmol) for 12 hours. The reaction mixture was evaporated in vacuo to give the crude product as a brown solid. To this solid was added methanesulfonyl chloride (196 mg, 1.71 mmol) and triethylamine (0.949 mL, 6.81 mmol) in dichloromethane (20 mL) and the mixture was stirred at room temperature overnight. The organic phase was evaporated in vacuo to give 2-amino-1-(3-(2-(dimethylamino)ethoxy)phenyl)-2-oxoethyl methanesulfonate (700 mg) as a brown solid. A solution of 2-chloro-6-(dimethylamino)-4-ethylpyridine-3,5-dicarbonitrile (synthesis described in example 3 step 3, 519 mg, 2.21 mmol), triethylamine (672 mg, 6.64 mmol) and potassium ethanethioate (278 mg, 2.434 mmol) in N,N-dimethylformamide (30 mL) was stirred at room temperature for 2 hours. Then 2-amino-1-(3-(2-(dimethylamino)ethoxy)phenyl)-2-oxoethyl methanesulfonate (700 mg) was added and the mixture was stirred at 60° C. for 12 hours. The organic phase was evaporated in vacuo to give a brown liquid which was added to a silica gel column (50 g) and was eluted with $CH_2Cl_2$:MeOH (gradient:30:1-10:1) to afford 2-((3,5-dicyano-6-(dimethylamino)-4-ethylpyridin-2-yl)thio)-2-(3-(2-(dimethylamino)ethoxy)phenyl)acetamide (20.5 mg, 0.045 mmol) as a white solid. LCMS m/z=452.9 $[M+H]^+$. $^1$H NMR (400 MHz, $CDCl_3$) δ 7.34-7.29 (m, 1H), 7.13-7.05 (m, 2H), 6.91 (d, J=7.9 Hz, 1H), 6.76 (br. s, 1H), 5.61 (s, 1H), 5.43 (s, 1H), 4.34 (br. s, 2H), 3.43 (s, 6H), 3.20 (m, 2H), 2.94 (q, J=7.7 Hz, 2H), 2.70 (s, 6H), 1.34 (t, J=7.5 Hz, 3H).

Example 408

2-((3,5-Dicyano-4-ethyl-6-(4-(neopentylamino)piperidin-1-yl)pyridin-2-yl)thio)-2-(4-fluorophenyl)acetamide Step 1: 2-((3,5-Dicyano-4-ethyl-6-(4-oxopiperidin-1-yl)pyridin-2-yl)thio)-2-(4-fluorophenyl)acetamide

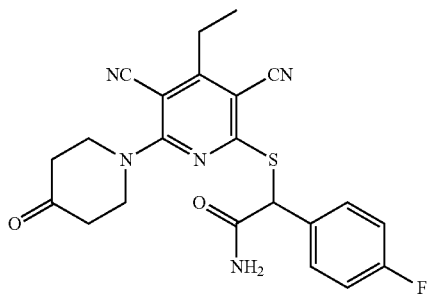 [SMILES: CCc1c(C#N)c(SC(C(N)=O)c2ccc(F)cc2)nc(N2CCC(=O)CC2)c1C#N]

To a suspension of 2,6-dichloro-4-ethylpyridine-3,5-dicarbonitrile (synthesis described in example 3 step 2, 360 mg, 1.592 mmol) and piperidin-4-one hydrochloride monohydrate (245 mg, 1.592 mmol) in ethanol (5 mL) at −20° C. was added a solution of triethylamine (0.444 mL, 3.18 mmol) in ethanol (5 mL). The reaction mixture was stirred at the same temperature for 2 h. To the reaction mixture were then added potassium ethanethioate (218 mg, 1.911 mmol) and Et$_3$N (0.555 mL, 3.98 mmol). The reaction mixture was warmed to 40° C. and stirred at the same temperature for 3 h. To the reaction mixture was added 2-amino-1-(4-fluorophenyl)-2-oxoethyl methanesulfonate (synthesis described in example 207 step 3, 591 mg, 2.389 mmol) and the reaction was stirred overnight at 40° C. The heterogenous mixture was cooled to room temperature and filtered. The collected solid was washed with ethanol, water, ethanol, and Et$_2$O, then dried to afford 2-((3,5-dicyano-4-ethyl-6-(4-oxopiperidin-1-yl)pyridin-2-yl)thio)-2-(4-fluorophenyl)acetamide (425 mg) as a white solid. LCMS m/z=438.0 [M+H]$^+$.

Step 2: 2-((3,5-dicyano-4-ethyl-6-(4-(neopentylamino)piperidin-1-yl)pyridin-2-yl)thio)-2-(4-fluorophenyl)acetamide

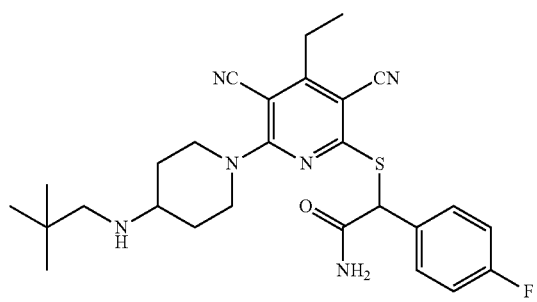 [SMILES: CCc1c(C#N)c(SC(C(N)=O)c2ccc(F)cc2)nc(N2CCC(NCC(C)(C)C)CC2)c1C#N]

To a suspension of 2-((3,5-dicyano-4-ethyl-6-(4-oxopiperidin-1-yl)pyridin-2-yl)thio)-2-(4-fluorophenyl)acetamide (75 mg, 0.171 mmol) in dichloromethane (DCM) (0.5 mL) and tetrahydrofuran (THF) (0.5 mL) at room temperature was added 2,2-dimethylpropan-1-amine (0.022 mL, 0.189 mmol). The reaction mixture was stirred at room temperature for 1 h then sodium triacetoxyborohydride (109 mg, 0.514 mmol) was added. After stirring at room temperature for 3 hours, the reaction mixture was concentrated. The resulting material was taken up in DMSO and methanol and purified by reverse phase HPLC (Gilson, 30 mm×50 mm Gemini Column, NH$_4$OH modifier) to afford 2-((3,5-dicyano-4-ethyl-6-(4-(neopentylamino)piperidin-1-yl)pyridin-2-yl)thio)-2-(4-fluorophenyl)acetamide (35 mg) as an off white solid. LCMS m/z=509.1 [M+H]$^+$. $^1$H NMR (400 MHz, DMSO-d$_6$) δ 7.96 (s, 1H), 7.56 (dd, J=5.4, 8.7 Hz, 2H), 7.38 (s, 1H), 7.22 (t, J=8.7 Hz, 2H), 5.56 (s, 1H), 4.44-4.32 (m, 2H), 3.33-3.28 (m, 2H), 2.75 (q, J=7.5 Hz, 2H), 2.68 (br. s., 1H), 2.31 (s, 2H), 1.92 (d, J=11.2 Hz, 2H), 1.41-1.26 (m, 2H), 1.24 (s, 1H), 1.20 (t, J=7.6 Hz, 3H), 0.87 (s, 9H).

Example 409

2-((3,5-dicyano-4-ethyl-6-(3-fluoro-4-A(neopentylamino)piperidin-1-yl)pyridin-2-yl)thio)-2-phenylacetamide Step 1: 2-((3,5-dicyano-4-ethyl-6-(3-fluoro-4-oxopiperidin-1-yl)pyridin-2-yl)thio)-2-phenylacetamide

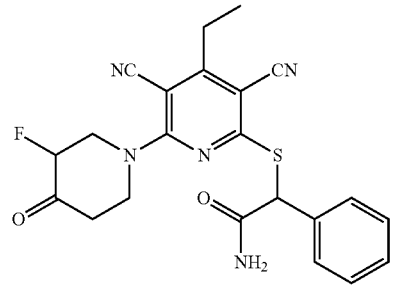 [SMILES: CCc1c(C#N)c(SC(C(N)=O)c2ccccc2)nc(N2CCC(=O)C(F)C2)c1C#N]

To a suspension of 2,6-dichloro-4-ethylpyridine-3,5-dicarbonitrile (synthesis described in example 3, step 2, 500 mg, 2.212 mmol) in ethanol (5 mL) at −20° C. was added a solution of 3-fluoropiperidin-4-one, hydrochloride (357 mg, 2.322 mmol) and triethylamine (0.617 mL, 4.42 mmol) in ethanol (5 mL). The reaction mixture was stirred at −20° C. for 2 h. To the reaction mixture were then added potassium ethanethioate (379 mg, 3.32 mmol) and Et$_3$N (0.771 mL, 5.53 mmol). The reaction mixture was warmed to 40° C. and stirred at the same temperature for 3 h. To the reaction mixture was added 2-amino-2-oxo-1-phenylethyl methanesulfonate (synthesis described in example 3, step 5, 1.02 g, 4.45 mmol). After stirring overnight at 40° C., the reaction mixture was cooled to room temperature and concentrated. The resulting material was partitioned between ethyl acetate and water. The organic layer was separated and the aqueous layer extracted with ethyl acetate (2×). The combined organic layers were washed with saturated brine, dried, and concentrated to provide the crude product. The crude product was purified by silica gel chromatography (ISCO CombiFlash®, 120 g SNAP ULTRA column, Hex/EtOAc 50-100%) to afford 2-((3,5-dicyano-4-ethyl-6-(3-fluoro-4-oxopiperidin-1-yl)pyridin-2-yl)thio)-2-phenylacetamide (497 mg) as a light brown solid. LCMS m/z=438.1 [M+H]$^+$.

Step 2: 2-((3,5-dicyano-4-ethyl-6-(3-fluoro-4-A (neopentylamino)piperidin-1-yl)pyridin-2-yl)thio)-2-phenylacetamide

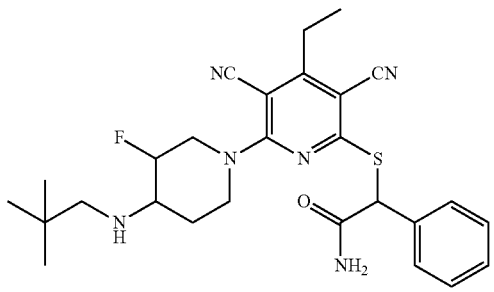 [SMILES: CCc1c(C#N)c(SC(C(N)=O)c2ccccc2)nc(N2CCC(NCC(C)(C)C)C(F)C2)c1C#N]

To a solution of 2-((3,5-dicyano-4-ethyl-6-(3-fluoro-4-oxopiperidin-1-yl)pyridin-2-yl)thio)-2-phenylacetamide (50 mg, 0.114 mmol) in a mixture of dichloromethane (DCM) (0.5 mL) and tetrahydrofuran (THF) (0.5 mL) at room temperature was added 2,2-dimethylpropan-1-amine (0.020 mL, 0.171 mmol). The reaction mixture was stirred at room temperature for 1 h at which time sodium triacetoxyborohydride (37 mg, 0.175 mmol) was added. After stirring at room temperature for 2 h, the reaction mixture was concentrated. The resulting material was taken up in a mixture of DMSO and MeOH, and purified by reverse phase HPLC (Gilson, 30 mm×50 mm Gemini Column, NH$_4$OH modifier) to afford 2-((3,5-dicyano-4-ethyl-6-(3-fluoro-4-A(neopentylamino)piperidin-1-yl)pyridin-2-yl)thio)-2-phenylacetamide (20 mg) as a white solid. LCMS m/z=509.2 [M+H]$^+$. $^1$H NMR (400 MHz, DMSO-d$_6$) δ 7.96 (s, 1H), 7.56-7.49 (m, 2H), 7.42-7.31 (m, 4H), 5.57-5.51 (m, 1H), 5.01-4.78 (m, 2H), 4.59-4.49 (m, 1H), 3.57-3.39 (m, 1H), 3.24-3.12 (m, 1H), 2.87-2.71 (m, 3H), 2.42-2.30 (m, 2H), 1.92-1.80 (m, 1H), 1.72-1.51 (m, 1H), 1.33 (q, J=8.3 Hz, 1H), 1.21 (t, J=7.6 Hz, 3H), 0.88 (s, 9H).

Example 410

2-((6-(4-aminopiperidin-1-yl)-3,5-dicyano-4-ethylpyridin-2-yl)thio)-2-(4-(trifluoromethyl)phenyl)acetamide Step 1: tert-butyl (1-(6-((2-amino-2-oxo-1-(4-(trifluoromethyl)phenyl)ethyl)thio)-3,5-dicyano-4-ethylpyridin-2-yl)piperidin-4-yl)carbamate

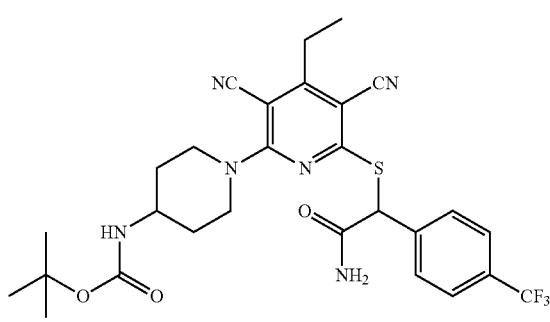 [SMILES: CCc1c(C#N)c(SC(C(N)=O)c2ccc(C(F)(F)F)cc2)nc(N2CCC(NC(=O)OC(C)(C)C)CC2)c1C#N]

To a suspension of 2,6-dichloro-4-ethylpyridine-3,5-dicarbonitrile (synthesis described in example 3, step 2, 50 mg, 0.221 mmol) in ethanol (1 mL) at −20° C. was added a solution of tert-butyl piperidin-4-ylcarbamate (46 mg, 0.230 mmol) and triethylamine (0.032 mL, 0.232 mmol) in ethanol (2 mL). The reaction mixture was stirred at the same temperature for 2 h. To the reaction mixture was then added potassium thioacetate (32 mg, 0.280 mmol) and Et$_3$N (0.077 mL, 0.553 mmol). The reaction mixture was warmed to 20° C. and stirred for 4 h, then heated at 40° C. for 3 h. To the reaction mixture was added 2-amino-2-oxo-1-(4-(trifluoromethyl)phenyl)ethyl methanesulfonate (synthesis described in example 233, step 2, 99 mg, 0.332 mmol). The reaction was heated at 40° C. overnight. After the heterogeneous reaction mixture cooled to room temperature, the solid that was present was collected by filtration, washed sequentially with ethanol, water, ethanol, Et$_2$O, and then dried to provide tert-butyl (1-(6-((2-amino-2-oxo-1-(4-(trifluoromethyl)phenyl)ethyl)thio)-3,5-dicyano-4-ethylpyridin-2-yl)piperidin-4-yl)carbamate (68 mg) as a white solid. LCMS m/z=589.2 [M+H]$^+$. The filtrate was concentrated and the remaining residue purified by reverse phase HPLC (Gilson, 30 mm×50 mm Gemini Column, NH$_4$OH modifier) to yield additional tert-butyl (1-(6-((2-amino-2-oxo-1-(4-(trifluoromethyl)phenyl)ethyl)thio)-3,5-dicyano-4-ethylpyridin-2-yl)piperidin-4-yl)carbamate (48 mg) as a white solid LCMS m/z=589.2 [M+H]$^+$.

Step 2: 2-((6-(4-aminopiperidin-1-yl)-3,5-dicyano-4-ethylpyridin-2-yl)thio)-2-(4-(trifluoromethyl)phenyl)acetamide

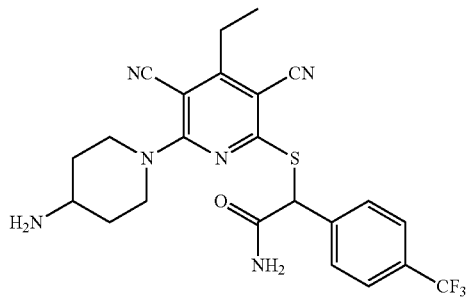 [SMILES: CCc1c(C#N)c(SC(C(N)=O)c2ccc(C(F)(F)F)cc2)nc(N2CCC(N)CC2)c1C#N]

Tert-butyl (1-(6-((2-amino-2-oxo-1-(4-(trifluoromethyl)phenyl)ethyl)thio)-3,5-dicyano-4-ethylpyridin-2-yl)piperidin-4-yl)carbamate (53 mg, 0.090 mmol) was suspended in a solution of 4 M HCl (1.000 mL, 4.0 mmol) in dioxane at room temperature. The reaction mixture was stirred at room temperature for 3 h then was concentrated. The resulting material was taken up in a mixture of DMSO and MeOH, and free based with isopropylamine. This mixture was purified by reverse phase HPLC (Gilson, 30 mm×50 mm Gemini Column, NH$_4$OH modifier) to yield 2-((6-(4-aminopiperidin-1-yl)-3,5-dicyano-4-ethylpyridin-2-yl)thio)-2-(4-(trifluoromethyl)phenyl)acetamide 11 mg as an off white solid. LCMS m/z=489.0 [M+H]$^+$. In a separate experiment, tert-butyl (1-(6-((2-amino-2-oxo-1-(4-(trifluoromethyl)phenyl)ethyl)thio)-3,5-dicyano-4-ethylpyridin-2-yl)piperidin-4-yl)carbamate (41 mg, 0.070 mmol) was suspended in a solution of 4M HCl (1.000 mL, 4.00 mmol) in dioxane at room temperature. The reaction mixture was stirred at room temperature for 3 h then was concentrated. The resulting material was taken up in a mixture of DMSO and MeOH, and free based with isopropylamine. This free based material was combined with the purified material described above (11

Example 411

2-((3,5-Dicyano-4-ethyl-6-(4-(pyrrolidin-1-yl)piperidin-1-yl)pyridin-2-yl)thio)-2-phenylacetamide

Step 1: 2-((3,5-Dicyano-4-ethyl-6-(4-oxopiperidin-1-yl)pyridin-2-yl)thio)-2-phenylacetamide

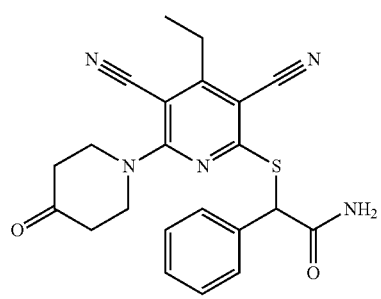 [SMILES: CCc1c(C#N)c(SC(C(N)=O)c2ccccc2)nc(N2CCC(=O)CC2)c1C#N]

To a slurry of 2,6-dichloro-4-ethylpyridine-3,5-dicarbonitrile (synthesis described in example 3 step 2, 0.653 g, 2.89 mmol) and piperidin-4-one, hydrochloride, monohydrate (0.444 g, 2.89 mmol) in Ethanol (20 mL) at 0° C. was added triethylamine (0.443 mL, 3.18 mmol) dropwise. The reaction was stirred for 5 h. To the reaction was sequentially added potassium thioacetate (0.495 g, 4.33 mmol) in one portion and triethylamine (1.007 mL, 7.22 mmol). After stirring at 20° C. overnight (~15 h), 2-amino-2-oxo-1-phenylethyl methanesulfonate (synthesis described in example 3 step 5, 1.324 g, 5.78 mmol) was added to the reaction in one portion and the reaction stirred for 5 h at 40° C. A solid was present. The reaction was allowed to cool to room temperature. The mixture was diluted with water (~25 mL) and filtered through a polyethylene fritted funnel (ChemGlass OP-6602). The collected solid was washed sequentially with water (2×20 mL), ethanol (2×20 mL), and diethyl ether (2×20 mL), and thoroughly dried in a vacuum oven at 60° C. overnight to afford 2-((3,5-dicyano-4-ethyl-6-(4-oxopiperidin-1-yl)pyridin-2-yl)thio)-2-phenylacetamide (0.66 g, 55%) as an off-white solid. LCMS m/z=420.0 [M+H]$^+$.

Step 2: 2-((3,5-Dicyano-4-ethyl-6-(4-(pyrrolidin-1-yl)piperidin-1-yl)pyridin-2-yl)thio)-2-phenylacetamide

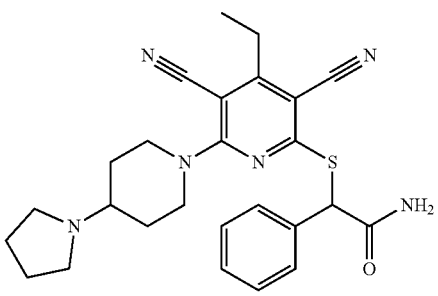 [SMILES: CCc1c(C#N)c(SC(C(N)=O)c2ccccc2)nc(N2CCC(N3CCCC3)CC2)c1C#N]

To a suspension of 2-((3,5-dicyano-4-ethyl-6-(4-oxopiperidin-1-yl)pyridin-2-yl)thio)-2-phenylacetamide (0.049 g, 0.117 mmol) in tetrahydrofuran (1 mL) and dichloromethane (1 mL) was added pyrrolidine (0.014 mL, 0.175 mmol). After stirring for 15 min at room temperature, sodium triacetoxyborohydride (0.037 g, 0.175 mmol) was added. The reaction was homogeneous after 6 h. Purification of the reaction solution using reverse phase HPLC (0.1% NH$_4$OH modifier, C18 50×30 mm Gemini column) gave 2-((3,5-dicyano-4-ethyl-6-(4-(pyrrolidin-1-yl)piperidin-1-yl)pyridin-2-yl)thio)-2-phenylacetamide (33 mg, 60%) as a white solid. LCMS m/z=475.1 [M+H]$^+$. 1H NMR (400 MHz, CHLOROFORM-d) δ ppm 7.51-7.32 (m, 5H), 6.63 (br. s., 1H), 5.84 (br. s, 1H), 5.35 (s, 1H), 4.63 (dd, J=3.4, 13.6 Hz, 2H), 3.36-3.16 (m, 2H), 2.92 (q, J=7.6 Hz, 2H), 2.72 (br. s., 4H), 2.44 (br. s, 1H), 2.15-2.03 (m, 2H), 1.95-1.67 (m, 6H), 1.33 (t, J=7.7 Hz, 3H).

Example 412

(R)-2-((6-(4-aminopiperidin-1-yl)-3,5-dicyano-4-ethylpyridin-2-yl)thio)-2-phenylacetamide, Hydrochloride

Step 1: (R)-tert-butyl (1-(6-((2-amino-2-oxo-1-phenylethyl)thio)-3,5-dicyano-4-ethylpyridin-2-yl)piperidin-4-yl)carbamate

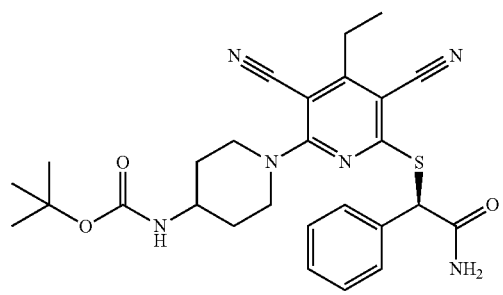 [SMILES: CCc1c(C#N)c(S[C@@H](C(N)=O)c2ccccc2)nc(N2CCC(NC(=O)OC(C)(C)C)CC2)c1C#N]

A mixture of tert-butyl (1-(6-chloro-3,5-dicyano-4-ethylpyridin-2-yl)piperidin-4-yl)carbamate (synthesis described in example example 81 step 1, 500 mg, 1.154 mmol) and potassium thioacetate (132 mg, 1.154 mmol) was stirred in N,N-dimethylformamide (20 mL) at 20° C. for 30 minutes. Then triethylamine (0.193 mL, 1.385 mmol) and

783

(S)-2-amino-2-oxo-1-phenylethyl 4-methylbenzenesulfonate (synthesis described in example 418, step 3, 352 mg, 1.154 mmol) was added successively. The mixture was stirred 20° C. overnight. The reaction mixture was partitioned between ethyl acetate 100 mL and water 100 mL. The organic phase was washed with water 50 mL, saturated brine 50 mL, dried over sodium sulphate and evaporated in vacuo to give the crude product. The crude product was added to a silica gel (12 g) column and was eluted with CH$_2$Cl$_2$/MeOH (50/1) to afford (R)-tert-butyl (1-(6-((2-amino-2-oxo-1-phenylethyl)thio)-3,5-dicyano-4-ethylpyridin-2-yl)piperidin-4-yl)carbamate (240 mg, 0.429 mmol, 37% yield) as a white solid. LCMS m/z=465.2 [M+H-t-Bu]$^+$.

Step 2: (R)-2-((6-(4-aminopiperidin-1-yl)-3,5-dicyano-4-ethylpyridin-2-yl)thio)-2-phenylacetamide, Hydrochloride

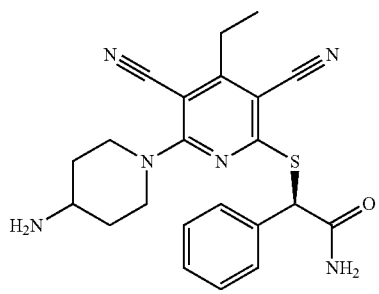 [SMILES: CCc1c(C#N)c(S[C@@H](C(N)=O)c2ccccc2)nc(N2CCC(N)CC2)c1C#N]

A suspension of (R)-tert-butyl (1-(6-((2-amino-2-oxo-1-phenylethyl)thio)-3,5-dicyano-4-ethylpyridin-2-yl)piperidin-4-yl)carbamate (50 mg, 0.096 mmol) in HCl (4 M in dioxane) (2 mL) was stirred at room temperature for 1 hour. The reaction was concentrated without heating to afford the crude product as a white solid. Purified by prep-HPLC (10-(95-A-CN (0.1% FA)-H$_2$O (0.1% TFA)). then concentrated (0° C.), treated with HCl in dioxane (2 mL), concentrated, then treated with HCl in dioxane (2 mL), concentrated then lyophilized to afford (R)-2-((6-(4-aminopiperidin-1-yl)-3,5-dicyano-4-ethylpyridin-2-yl)thio)-2-phenylacetamide, Hydrochloride (12 mg, 0.026 mmol, 27% yield) as a light gray solid. LCMS m/z=421.0 [M+H]$^+$. $^1$H NMR (DMSO-d$_6$) δ ppm $^1$H NMR (400 MHz, DMSO) δ 8.24-7.94 (m, 3H), 7.53 (d, J=7.7 Hz, 2H), 7.46-7.31 (m, 3H), 5.56 (s, 1H), 4.59 (d, J=13.8 Hz, 2H), 3.51-3.47 (m, 1H), 3.45-3.40 (m, 2H), 3.33-3.20 (m, 2H), 2.78 (q, J=7.5 Hz, 2H), 2.15-2.01 (m, 2H), 1.69-1.52 (m, 2H), 1.22 (t, J=7.6 Hz, 3H).

784

Example 413

2-((6-((2-amino-2-oxoethyl)(methyl)amino)-3,5-dicyano-4-ethylpyridin-2-yl)thio)-2-phenylacetamide (Single Enantiomer)

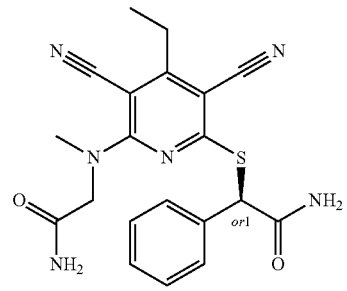 [SMILES: CCc1c(C#N)c(S[C@@H](C(N)=O)c2ccccc2)nc(N(C)CC(N)=O)c1C#N]

The racemic mixture of 2-((6-((2-amino-2-oxoethyl)(methyl)amino)-3,5-dicyano-4-ethylpyridin-2-yl)thio)-2-phenylacetamide (3.00 g) was dissolved in 200 mg portions in 360 volumes (72 mL) of boiling 1:1 methanol:ethanol and purified by chiral HPLC (Chiralpak AD-H, 5 microns (50 mm×250 mm), 100 mL/min. flow rate, 30:70 n-heptane:ethanol (isocratic, no modifier required)). Carried out a total of 60 chiral prep runs at 50 mg racemate per run. Collected a total of about 15 L of product solution for enantiomer 2. Concentrated the solution to near dryness to afford a white slurry. Filtered the white slurry to collect the product. Rinsed with ethanol. Dried the wet cake under high vacuum at 45° C. to a final constant weight to afford 2-((6-((2-amino-2-oxoethyl)(methyl)amino)-3,5-dicyano-4-ethylpyridin-2-yl)thio)-2-phenylacetamide (1.247 g) as a white solid. LCMS m/z=409.1 [M+H]$^+$. Optical Rotation: Alpha D=−318 degrees (DMSO, 23° C., C=0.20). $^1$H NMR (DMSO-d$_6$) δ 7.83 (s, 1H), 7.62 (s, 1H), 7.44-7.55 (m, 2H), 7.24-7.43 (m, 5H), 5.59 (s, 1H), 4.52 (d, J=17.2 Hz, 1H), 4.29 (d, J=17.2 Hz, 1H), 3.39 (s, 3H), 2.77 (q, J=7.5 Hz, 2H), 1.20 (t, J=7.6 Hz, 3H).

Example 414

2-{[3,5-dicyano-6-(dimethylamino)-4-ethylpyridin-2-yl]sulfanyl}-2-phenylacetamide

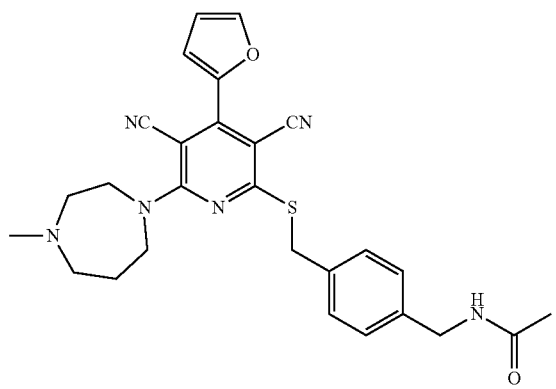 [SMILES: CC(=O)NCc1ccc(CSc2nc(N3CCCN(C)CC3)c(C#N)c(-c3ccco3)c2C#N)cc1]

To a solution of 2,6-dichloro-4-(furan-2-yl)pyridine-3,5-dicarbonitrile (synthesis described in example 135 step 2, 300 mg, 1.136 mmol) in N,N-dimethylformamide (3 mL) was added 1-methyl-1,4-diazepane (123 mg, 1.079 mmol), followed by TEA (115 mg, 1.14 mmol) dropwise. The reaction was stirred at room temperature for 1 hour. Potassium ethanethioate (130 mg, 1.136 mmol) was added to the mixture. The reaction was stirred at room temperature for 30 minutes then N-(4-(chloromethyl)benzyl)acetamide (synthesis described in example 336 step 3, 225 mg, 1.136 mmol) and TEA (230 mg, 2.28 mmol) were added to the solution. The mixture was stirred at room temperature overnight. The mixture was concentrated under vacuum. The crude product was purified by silica gel column chromatography (eluted by MeOH-DCM 0-10%) and triturated with Et$_2$O to give N-(4-(((3,5-dicyano-4-(furan-2-yl)-6-(4-methyl-1,4-diazepan-1-yl)pyridin-2-yl)thio)methyl)benzyl) acetamide (100 mg, 0.199 mmol, 18% yield) as a brown solid. LCMS m/z=500.8 [M+H]$^+$. $^1$H NMR (400 MHz, MeOD) δ 7.88 (d, J=1.5 Hz, 1H), 7.43-7.37 (m, 3H), 7.28 (d, J=8.1 Hz, 2H), 6.75 (dd, J=3.6, 1.8 Hz, 1H), 4.53 (s, 2H), 4.36 (s, 2H), 4.02-3.91 (m, 4H), 2.83-2.76 (m, 2H), 2.67-2.61 (m, 2H), 2.37 (s, 3H), 2.11-2.04 (m, 2H), 2.00 (s, 3H). One proton not observed.

Example 415

(3S)-1-(6-((2-amino-2-oxo-1-phenylethyl)thio-3,5-dicyano-4-ethylpyridin-2-yl) Pyrrolidin-3-yl dihydrogen phosphate Step1: (3S)-1-(6-((2-amino-2-oxo-1-phenylethyl) thio)-3,5-dicyano-4-ethylpyridin-2-yl) pyrrolidin-3-yl di-tert-butyl phosphate

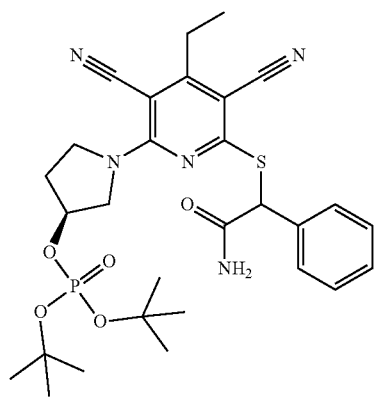 [SMILES: CCc1c(C#N)c(SC(C(N)=O)c2ccccc2)nc(N2CC[C@H](OP(=O)(OC(C)(C)C)OC(C)(C)C)C2)c1C#N]

To a stirred solution of (S)-di-tert-butyl (1-(6-chloro-3,5-dicyano-4-ethylpyridin-2-yl)pyrrolidin-3-yl) phosphate (synthesis described in example 418 step 2, 10.0 g, 21.33 mmol) in N,N-dimethylformamide (DMF) (200 mL) was added potassium thioacetate (3.65 g, 32.0 mmol) at room temperature and stirred for 16 hr at 50° C. The reaction mixture was cooled to room temperature, then K$_2$CO$_3$ (4.42 g, 32.0 mmol) and 2-amino-2-oxo-1-phenylethyl methanesulfonate (synthesis described in example 3 step 5, 4.89 g, 21.33 mmol) were added at room temperature. The resulting reaction mixture was stirred at room temperature for 18 hr. After the reaction mixture was diluted with ice cold water (1000 mL) and stirred for 10 min a precipitation occurred. The precipitated solid was filtered and dried to provide the crude material. The crude material was purified by neutral alumina column chromatography (Eluent: 80% EtOAc in petroleum ether) to afford (3S)-1-(6-((2-amino-2-oxo-1-phenylethyl)thio)-3,5-dicyano-4-ethylpyridin-2-yl) pyrrolidin-3-yl di-tert-butyl phosphate (4.5 g, 34%) as a pale brown solid. LCMS (m/z)=600.1 [M+H]$^+$.

Step 4: (3S)-1-(6-((2-amino-2-oxo-1-phenylethyl) thio)-3,5-dicyano-4-ethylpyridin-2-yl) Pyrrolidin-3-yl dihydrogen phosphate

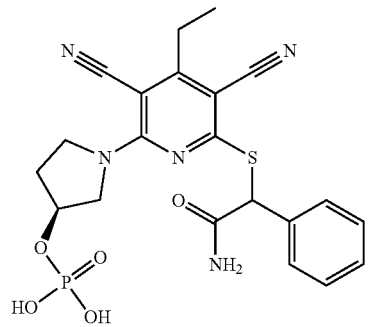 [SMILES: CCc1c(C#N)c(SC(C(N)=O)c2ccccc2)nc(N2CC[C@H](OP(=O)(O)O)C2)c1C#N]

To a stirred solution of (3S)-1-(6-((2-amino-2-oxo-1-phenylethyl)thio)-3,5-dicyano-4-ethylpyridin-2-yl)pyrrolidin-3-yl di-tert-butyl phosphate (3.0 g, 5.00 mmol) in ethanol (40 mL) was added 2.0 M hydrochloric acid (20 mL, 40.0 mmol) in diethyl ether at room temperature. The resulting reaction mixture was stirred at room temperature for 1 hr. The reaction mixture was concentrated under reduced pressure to give the crude material. The crude material was co-distilled with EtOH (50 mL) and diethyl ether (50 mL) (5 times), and triturated with diethyl ether to provide a precipitate. The precipitated solid was filtered and dried to afford (3S)-1-(6-((2-amino-2-oxo-1-phenylethyl)thio)-3,5-dicyano-4-ethylpyridin-2-yl) pyrrolidin-3-yl dihydrogen phosphate (2.180 g, 88%) as an off-white solid. LCMS (m/z): 487.8 [M+H]$^+$. $^1$H NMR (400 MHz, DMSO-d$_6$) δ ppm 11.30 (s, 1H), 7.90 (s, 1H), 7.52 (d, J=7.02 Hz, 2H), 7.41-7.21 (m, 4H), 5.61 (s, 1H), 4.94 (s., 1H), 4.10-3.78 (m, 4H), 2.75 (q, J=7.5 Hz, 2H), 2.29-2.08 (m, 2H), 1.20 (t, J=7.56 Hz, 3H).

Example 416

(3R)-1-(6-((2-amino-2-oxo-1-phenylethyl)thio)-3,5-dicyano-4-ethylpyridin-2-yl)pyrrolidin-3-yl dihydrogen phosphate

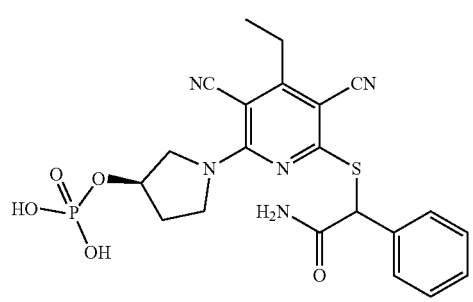 [SMILES: CCc1c(C#N)c(SC(C(N)=O)c2ccccc2)nc(N2CC[C@@H](OP(=O)(O)O)C2)c1C#N]

A mixture of 2-((3,5-dicyano-4-ethyl-6-((R)-3-hydroxy-pyrrolidin-1-yl)pyridin-2-yl)thio)-2-phenylacetamide (synthesis described in example 168 step 2, 0.5 g, 1.227 mmol) in polyphosphoric acid (5 mL) was stirred at 50° C. overnight. The mixture was treated with crushed ice and stirred at room temperature overnight. The resultant mixture was purified by prep-HPLC (0.1% TFA modifier) to provide (3R)-1-(6-((2-amino-2-oxo-1-phenylethyl)thio)-3,5-dicyano-4-ethylpyridin-2-yl)pyrrolidin-3-yl dihydrogen phosphate (200 mg, 33% yield) as a white solid. LCMS m/z=487.7 [M+H]$^+$. $^1$H NMR (400 MHz, DMSO) δ ppm 11.98-10.32 (br s, 2H), 7.93 (s, 1H), 7.53 (d, J=7.2 Hz, 2H), 7.42-7.26 (m, 4H), 5.61 (s, 1H), 4.95 (s, 1H), 4.09-3.81 (m, 4H), 2.76 (q, J=7.3 Hz, 2H), 2.28-2.09 (m, 2H), 1.21 (t, J=7.5 Hz, 3H).

Example 417

(S)-1-(6-(((S)-2-amino-2-oxo-1-phenylethyl)thio)-3,5-dicyano-4-ethylpyridin-2-yl)pyrrolidin-3-yl dihydroden phosphate Step 1: (R)-2-amino-2-oxo-1-phenylethyl 4-methylbenzenesulfonate

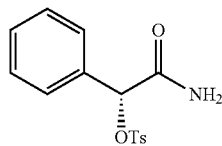 [SMILES: Cc1ccc(S(=O)(=O)O[C@@H](C(N)=O)c2ccccc2)cc1]

To a stirred solution of (R)-2-hydroxy-2-phenylacetamide (30 g, 198 mmol) in 1,4-dioxane (300 mL) were added DIPEA (104 mL, 595 mmol) and DMAP (2.425 g, 19.85 mmol) at room temperature. The reaction mixture was cooled to 0° C., then Ts-Cl (56.8 g, 298 mmol) was added portionwise to the reaction mixture and stirred at room temperature for 16 hr. The reaction mixture was poured into ice cold water (2000 mL), stirred for 10 min, and solid precipitated. The precipitated solid was filtered and dried to provide the crude compound. The crude material was triturated with diethyl ether (2×500 mL), filtered and dried to afford (R)-2-amino-2-oxo-1-phenylethyl 4-methylbenzenesulfonate (35 g, 56%) as an off-white solid. LCMS m/z=306.1 [M+H]$^+$.

Step 2: (S)-1-(6-(((S)-2-amino-2-oxo-1-phenylethyl)thio)-3,5-dicyano-4-ethylpyridin-2-yl)pyrrolidin-3-yl di-tert-butyl phosphate

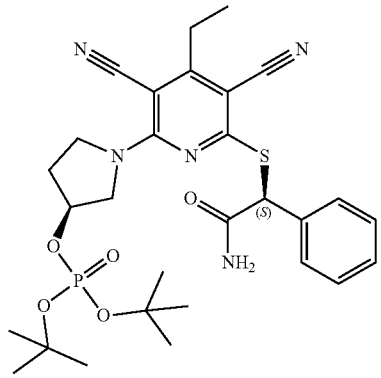

To a stirred solution of (S)-di-tert-butyl (1-(6-chloro-3,5-dicyano-4-ethylpyridin-2-yl)pyrrolidin-3-yl) phosphate (synthesis described in example 418 step 2, 40.0 g, 85 mmol) in N,N-dimethylformamide (DMF) (400 mL) was added potassium thioacetate (14.61 g, 128 mmol) at room temperature and stirred for 2 hr. TEA (17.83 mL, 128 mmol) and (R)-2-amino-2-oxo-1-phenylethyl 4-methylbenzenesulfonate (26.0 g, 85 mmol) were added to the reaction mixture at room temperature and stirred for 18 hr. The reaction mixture was diluted with ice cold water (2000 mL) and extracted with EtOAc (3×1500 mL). The combined organic layers were washed with ice cold water (3×2000 mL), brine solution (1000 mL), dried over anhydrous Na$_2$SO$_4$, filtered and concentrated under reduced pressure to give the crude material. The crude material was triturated with diethyl ether (200 mL) and n-pentane (500 mL), filtered and dried to provide a brown solid. The solid material was dissolved in EtOAc (1000 mL) and filtered through Celite®. The filtrate was concentrated under reduced pressure to afford (S)-1-(6-(((S)-2-amino-2-oxo-1-phenylethyl)thio)-3,5-dicyano-4-ethylpyridin-2-yl)pyrrolidin-3-yl di-tert-butyl phosphate (40.02 g, 66.3%) as a pale brown solid. LCMS m/z=600.3 [M+H]$^+$.

Step 3: (S)-1-(6-(((S)-2-amino-2-oxo-1-phenylethyl)thio)-3,5-dicyano-4-ethylpyridin-2-yl)pyrrolidin-3-yl dihydrogen phosphate

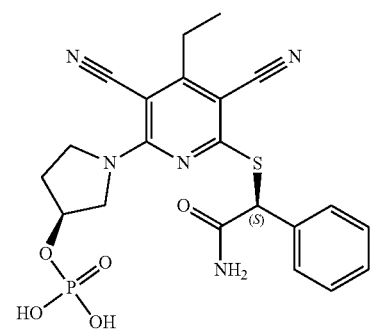

To a stirred solution of (S)-1-(6-(((S)-2-amino-2-oxo-1-phenylethyl)thio)-3,5-dicyano-4-ethylpyridin-2-yl)pyrrolidin-3-yl di-tert-butyl phosphate (40.0 g, 56.5 mmol) in diethyl ether (800 mL) and ethanol (400 mL) was added 2.0 M hydrochloric acid (400 mL, 800 mmol) in diethyl ether at 0° C. The reaction mixture was stirred at room temperature for 2 hr. The reaction mixture was concentrated under reduced pressure to give crude compound. The crude material was co-distilled with EtOH (400 mL) and diethyl ether (800 mL) (3 times), and thoroughly dried to afford a pale brown solid. The solid was triturated with a mixture of EtOH (400 mL) and diethyl ether (800 mL), filtered and dried to afford (S)-1-(6-(((S)-2-amino-2-oxo-1-phenylethyl)thio)-3,5-dicyano-4-ethylpyridin-2-yl)pyrrolidin-3-yl dihydrogen phosphate (19.0 g, 69%) as an off-white solid. LCMS m/z=488.0 [M+H]$^+$. Two batches of of (S)-1-(6-(((S)-2-a min o-2-oxo-1-ph enylethyl)thio)-3,5-dicyano-4-ethylpyridin-2-yl)pyrrolidin-3-yl dihydrogen phosphate (4.65 g and 19.0 g) were combined and dissolved in ethanol (4.0 L) The solution was evaporated under reduced pressure to provide an off-white solid. The solid was triturated with a mixture of EtOH and diethyl ether (300:600 mL), filtered and dried to give an off-white solid. The solid was thoroughly ground to afford (S)-1-(6-MS)-2-amino-2-oxo-1-phenylethyl)thio)-3,5-dicyano-4-ethylpyridin-2-yl)pyrrolidin-3-yl dihydrogen phosphate (21.1 g) as an off-white solid. LCMS m/z=488.0 [M+H]$^+$. $^1$H NMR (400 MHz, DMSO-d$_6$) δ 7.89 (s, 1H), 7.56-7.50 (m, 2H), 7.41-7.30 (m, 3H), 7.25 (s, 1H), 5.61 (s, 1H), 4.97-4.90 (m, 1H), 4.10-3.92 (m, 3H), 3.90-3.80 (m, 1H), 2.75 (q, J=7.5 Hz, 2H), 2.28-2.07 (m, 2H), 1.21 (t, J=7.6 Hz, 3H) (two phosphate protons not observed).

Example 418

(S)-1-(6-(((R-2-amino-2-oxo-1-phenylethyl)thio-3,5-dicyano-4-ethylpyridin-2-yl) pyrrolidin-3-yl dihydrogen phosphate Step1: (S)-2-chloro-4-ethyl-6-(3-hydroxypyrrolidin-1-yl) pyridine-3,5-dicarbonitrile

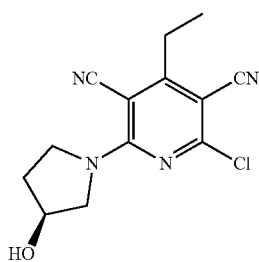 [SMILES: CCc1c(C#N)c(Cl)nc(N2CC[C@H](O)C2)c1C#N]

To a stirred solution of (S)-pyrrolidin-3-ol, hydrochloride (54.7 g, 442 mmol) in dichloromethane (DCM) (3000 mL) were added TEA (154 mL, 1106 mmol) and 2,6-dichloro-4-ethylpyridine-3,5-dicarbonitrile (synthesis described in example 3, step 2, 100 g, 442 mmol) at room temperature under Nitrogen atmosphere. The resulting reaction mixture was stirred at room temperature for 2 hr. The reaction mixture was diluted with water (2000 mL) and extracted with DCM (2×2000 mL). The combined organic layers were washed with water (2×2000 mL), brine solution (1000 mL), dried over anhydrous Na$_2$SO$_4$, filtered and concentrated under reduced pressure to provide the crude material. The crude material was triturated with diethyl ether (1000 mL), filtered and dried to afford (S)-2-chloro-4-ethyl-6-(3-hy-droxypyrrolidin-1-yl) pyridine-3,5-dicarbonitrile (110 g, 89%) as a pale brown solid. LCMS m/z=277.1 [M+H]$^+$.

Step 2: (S)-di-tert-butyl (1-(6-chloro-3,5-dicyano-4-ethylpyridin-2-yl)pyrrolidin-3-yl) phosphate

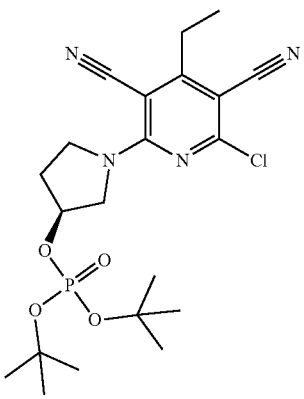 [SMILES: CCc1c(C#N)c(Cl)nc(N2CC[C@H](OP(=O)(OC(C)(C)C)OC(C)(C)C)C2)c1C#N]

To a stirred solution of (S)-2-chloro-4-ethyl-6-(3-hydroxypyrrolidin-1-yl)pyridine-3,5-dicarbonitrile (160 g, 578 mmol) in tetrahydrofuran (THF) (1500 mL) were added 1H-tetrazole (81 g, 1156 mmol) and di-tert-butyl diethylphosphoramidite (202 g, 809 mmol) at room temperature. The reaction mixture was stirred at room temperature for 1 hr. The resulting reaction mixture was cooled to 0° C., then 2-hydroperoxy-2-methylpropane (145 mL, 867 mmol) was added dropwise to the reaction mixture and stirred at room temperature for 1 hr. The reaction mixture was quenched with saturated sodium bisulfite solution (1.5 L) and extracted with ethyl acetate (3×1.5 L). The combined organic layers were washed with water (1.0 L), brine solution (1.0 L), dried over Na$_2$SO$_4$, filtered and concentrated under reduced pressure to provide the crude material. The crude material was purified by neutral alumina column chromatography (eluent: 20% EtOAc in hexane) to afford (S)-di-tert-butyl (1-(6-chloro-3,5-dicyano-4-ethylpyridin-2-yl) pyrrolidin-3-yl) phosphate (125 g, 46%) as an off white solid. LCMS m/z=469.2 [M+H]$^+$.

Step 3: (S)-2-amino-2-oxo-1-phenylethyl 4-methylbenzenesulfonate

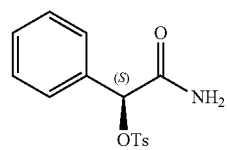

To a stirred solution of (S)-2-hydroxy-2-phenylacetamide (30 g, 198 mmol) in 1,4-dioxane (300 mL) were added DIPEA (104 mL, 595 mmol) and DMAP (2.425 g, 19.85 mmol) at room temperature. The reaction mixture was cooled to 0° C., then Ts-Cl (56.8 g, 298 mmol) was added portionwise to the reaction mixture and the reaction mixture was stirred at room temperature for 16 hr. The reaction mixture was poured into ice cold water (2000 mL), stirred for 10 min, and solid precipitated. The precipitated solid was collected by filtration and dried to give the crude compound.

The crude material was triturated with diethyl ether (2×500 mL) to afford (S)-2-amino-2-oxo-1-phenylethyl 4-methylbenzenesulfonate (38 g, 58%) as an off-white solid. LCMS m/z=306.1 [M+H]⁺.

Step 4: (S)-1-(6-(((R)-2-amino-2-oxo-1-phenylethyl)thio)-3,5-dicyano-4-ethylpyridin-2-yl) pyrrolidin-3-yl di-tert-butyl phosphate

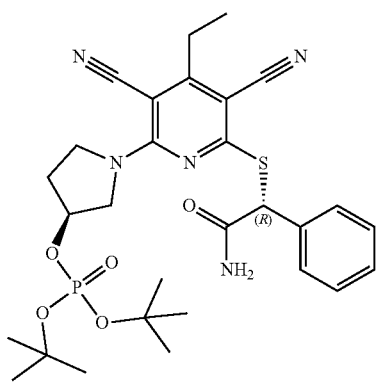

To a stirred solution of (S)-di-tert-butyl (1-(6-chloro-3,5-dicyano-4-ethylpyridin-2-yl)pyrrolidin-3-yl) phosphate (40.0 g, 84 mmol) in N,N-dimethylformamide (DMF) (400 mL) was added potassium thioacetate (14.46 g, 127 mmol) at room temperature and stirred for 2 hr at room temperature. TEA (17.65 mL, 127 mmol) and (S)-2-amino-2-oxo-1-phenylethyl 4-methylbenzenesulfonate (28.1 g, 84 mmol) were added to the reaction mixture at room temperature and stirred for 18 hr. The reaction mixture was diluted with ice cold water (2000 mL) and extracted with EtOAc (3×1500 mL). The combined organic layers were washed with ice cold water (3×2000 mL), brine solution (1000 mL), dried over anhydrous Na₂SO₄, filtered and concentrated under reduced pressure to provide the crude material. The crude material was triturated with diethyl ether (200 mL) and n-pentane (1000 mL), filtered and dried to afford a pale brown solid. The solid material was dissolved in EtOAc (500 mL) and filtered through Celite®. The filtrate was concentrated under reduced pressure to afford (S)-1-(6-(((R)-2-amino-2-oxo-1-phenylethyl)thio)-3,5-dicyano-4-ethylpyridin-2-yl) pyrrolidin-3-yl di-tert-butyl phosphate (38.0 g, 59%) as a pale brown solid. LCMS m/z=600.3 [M+H]⁺.

Step 5: (S)-1-(6-(((R)-2-amino-2-oxo-1-phenylethyl)thio)-3,5-dicyano-4-ethylpyridin-2-yl)pyrrolidin-3-yl dihydrogen phosphate

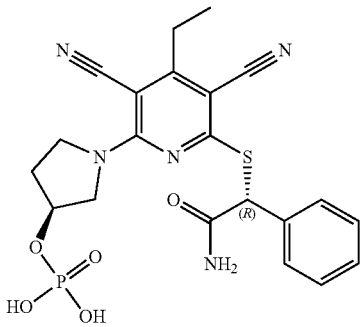

To a stirred solution of (S)-1-(6-(((R)-2-amino-2-oxo-1-phenylethyl)thio)-3,5-dicyano-4-ethylpyridin-2-yl)pyrrolidin-3-yl di-tert-butyl phosphate (38.0 g, 50.2 mmol) in ethanol (400 mL) and diethyl ether (800 mL) was added 2.0 M hydrochloric acid (400 mL, 800 mmol) in diethyl ether at 0° C. The reaction mixture was stirred at room temperature for 2 hr. The reaction mixture was concentrated under reduced pressure to provide the crude material. The crude material was co-distilled with EtOH (400 mL) and diethyl ether (800 mL) (3 times), and dried to afford a pale brown solid. The solid material was triturated with EtOH (400 mL) and diethyl ether (800 mL), filtered and dried to afford (S)-1-(6-(((R)-2-amino-2-oxo-1-phenylethyl)thio)-3,5-dicyano-4-ethylpyridin-2-yl)pyrrolidin-3-yl dihydrogen phosphate (18.5 g, 75%) as an off-white solid. LCMS (m/z): 488.0 [M+H]⁺.

Step 6: (S)-1-(6-(((R)-2-amino-2-oxo-1-phenylethyl)thio)-3,5-dicyano-4-ethylpyridin-2-yl)pyrrolidin-3-yl dihydrogen phosphate

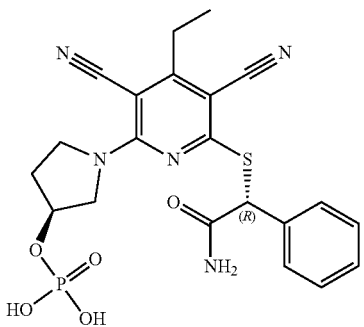

Two batches of (S)-1-(6-(((R)-2-amino-2-oxo-1-phenylethyl)thio)-3,5-dicyano-4-ethylpyridin-2-yl)pyrrolidin-3-yl dihydrogen phosphate (4.7 g and 18.5 g) were combined and dissolved in ethanol (4.0 L). The solution was evaporated under reduced pressure to give an off-white solid. The solid material was triturated with a mixture of EtOH and diethyl ether (200 mL:1000 mL), filtered and dried to provide an off-white solid. The solid was thoroughly ground in a mortar and pestle to afford (S)-1-(6-(((R)-2-amino-2-oxo-1-phenylethyl)thio)-3,5-dicyano-4-ethylpyridin-2-yl)pyrrolidin-3-yl dihydrogen phosphate (22.5 g, 98%) as an off-white solid.

LCMS (m/z)=488.0 [M+H]⁺. ¹H NMR (400 MHz, DMSO-d₆) δ 7.88 (s, 1H), 7.52-7.48 (m, 2H), 7.40-7.23 (m, 4H), 5.59 (s, 1H), 4.92 (s, 1H), 4.05-3.96 (m, 2H), 3.95-3.82 (m, 2H), 2.73 (q, J=7.5 Hz, 2H), 2.24-2.06 (m, 2H), 1.19 (t, J=7.6 Hz, 3H). Two phosphate protons not observed.

Example 419

2-((3,5-Dicyano-6-(dimethylamino)-4-ethylpyridin-2-yl)thio)-2-(3-(dimethylphosphoryl)phenyl)acetamide Step 1: 3-(Dimethylphosphoryl)benzonitrile

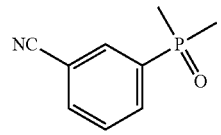

A mixture of 3-iodobenzonitrile (4.9 g, 21.40 mmol), dimethylphosphine oxide (2.00 g, 25.7 mmol), PdOAc₂ (0.240 g, 1.070 mmol), xantphos (0.62 g, 1.07 mmol) and potassium phosphate (5.45 g, 25.7 mmol) in N,N-dimethylformamide (100 mL) was stirred at 120° C. for 12 hours under nitrogen atmosphere. Then it was concentrated in vacuo to remove the solvent. The residue was purified by silica gel column (50 g), eluted with DCM:MeOH=20:1 to obtain 3-(dimethylphosphoryl)benzonitrile (3.1 g, 81% yield) as a white solid. LCMS m/z=180.1 [M+H]⁺.

Step 2: 3-(Dimethylphosphoryl)benzaldehyde

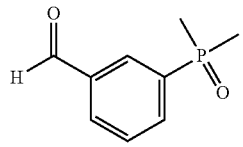

A mixture of 3-(dimethylphosphoryl)benzonitrile (3 g, 16.75 mmol) and nickel (0.491 g, 8.37 mmol) in 88% aqueous formic acid (100 mL) was stirred at 125° C. for 7 hours under nitrogen atmosphere. After cooling to room temperature, the reaction mixture was filtered with Celite® and the filtrate was concentrated in vacuo to dryness. The residue was added to a silica gel column (30 g) and was eluted with DCM:MeOH=40:1 to obtain 3-(dimethylphosphoryl)benzaldehyde (3.4 g, 100% yield, purity 90%) as a yellow oil. LCMS m/z=183.0 [M+H]⁺.

Step 3: 2-(3-(Dimethylphosphoryl)phenyl)-2-hydroxyacetamide

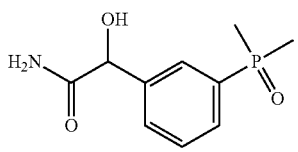

A mixture of 3-(dimethylphosphoryl)benzaldehyde (3.27 g, 17.95 mmol) and potassium 1,3-dioxoisoindolin-2-ide (0.665 g, 3.59 mmol) in trimethylsilanecarbonitrile (50 mL) was stirred at 20° C. for 14 hours. Then the reaction mixture was concentrated in vacuo to dryness. The residue was added to a silica gel column (30 g) and eluted with DCM:MeOH=40:1 to obtain a brown oil (2.8 g). A mixture of this brown oil (1.4 g), palladium(II) chloride (0.190 g, 1.071 mmol) and acetamide (3.16 g, 53.5 mmol) in tetrahydrofuran (30 mL) and water (10 mL) was stirred at 20° C. for 14 hours. Then it was concentrated in vacuo to dryness. The residue was added to a silica gel column (30 g) and eluted with DCM:MeOH=10:1 to obtain 2-(3-(dimethylphosphoryl)phenyl)-2-hydroxyacetamide (1.8 g) as a brown oil. LCMS m/z=228.1 [M+H]⁺.

Step 4: 2-Amino-1-(3-(dimethylphosphoryl)phenyl)-2-oxoethyl methanesulfonate

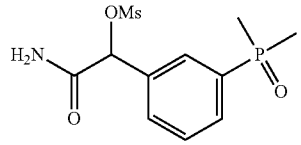 [SMILES: CP(C)(=O)c1cccc(C(OS(C)(=O)=O)C(N)=O)c1]

MsCl (0.274 mL, 3.52 mmol) was added dropwise to a stirred mixture of 2-(3-(dimethylphosph-oryl)phenyl)-2-hydroxyacetamide (800 mg, 3.52 mmol) and TEA (0.982 mL, 7.04 mmol) in dichloromethane (15 mL) and N,N-dimethylformamide (15 mL) at 0° C. The mixture was stirred at 0° C. for 3 hours. Then the reaction mixture was concentrated in vacuo to dryness. The residue was added to a silica gel column (30 g) and was eluted with CH₂Cl₂:MeOH=10:1 to obtain the 2-amino-1-(3-(dimethylphosphoryl)phenyl)-2-oxoethyl methanesulfonate (2.7 g, 76% yield, purity 30%) as a yellow oil. LCMS m/z=305.9 [M+H]⁺.

Step 5: 2-((3,5-dicyano-6-(dimethylamino)-4-ethylpyridin-2-yl)thio)-2-(3-(dimethylphosphoryl)phenyl)acetamide

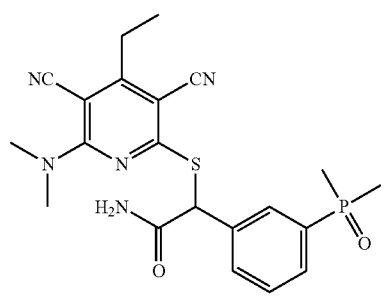

A mixture of 2-(dimethylamino)-4-ethyl-6-mercaptopyridine-3,5-dicarbonitrile (synthesis described in example 92, step 3, 260 mg, 1.119 mmol), 2-amino-1-(3-(dimethylphosphoryl)phenyl)-2-oxoethyl methanesulfonate (410 mg, 1.343 mmol) and TEA (0.468 mL, 3.36 mmol) in N,N-dimethylformamide (25 mL) was stirred at 45° C. for 14 hours. Then it was concentrated in vacuo to remove the solvent. The residue was added to a silica gel column (30 g) and was eluted with CH₂Cl₂:MeOH=15:1 to obtain the crude product and purified further by prep-TLC (CH₂Cl₂: MeOH=15:1) to obtain the 2-((3,5-dicyano-6-(dimethylamino)-4-ethylpyridin-2-yl)thio)-2-(3-(dimethylphosphoryl)phenyl)acetamide (126 mg, 25%) as a yellow solid. LCMS m/z=442.2 [M+H]⁺. ¹H NMR (400 MHz, CD₃OD) δ ppm 7.97 (d, J=12.3 Hz, 1H), 7.80-7.75 (m, 2H), 7.62-7.57 (m, 1H), 5.70 (s, 1H), 3.40 (s, 6H), 2.88 (q, J=7.6 Hz, 2H), 1.82 (s, 3H), 1.79 (s, 3H), 1.29 (t, J=7.6 Hz, 3H).

Example 420

2-((3,5-Dicyano-4-ethyl-6-((S)-3-hydroxypyrrolidin-1-yl)pyridin-2-yl)thio)-2-(3-(dimethylphosphoryl)phenyl)acetamide

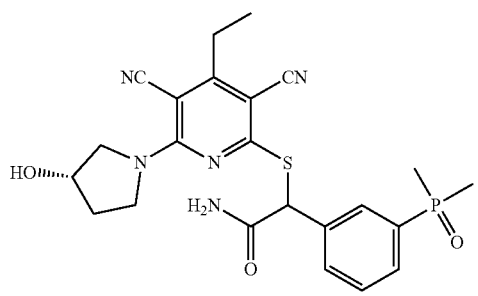 [SMILES: CCc1c(C#N)c(SC(C(N)=O)c2cccc(P(C)(C)=O)c2)nc(N2CC[C@H](O)C2)c1C#N]

A mixture of (S)-2-chloro-4-ethyl-6-(3-hydroxypyrrolidin-1-yl)pyridine-3,5-dicarbonitrile (synthesis described in example 418, step 1, 350 mg, 1.27 mmol) and potassium thioacetate (159 mg, 1.39 mmol) in N,N-dimethylformamide (30 mL) was stirred at 20° C. for 0.5 hour. Then 2-amino-1-(3-(dimethylphosphoryl)phenyl)-2-oxoethyl methanesulfonate (synthesis described in example 419 setp 4, 425 mg, 1.39 mmol) and TEA (0.529 mL, 3.79 mmol) were added, the mixture was stirred at 20° C. for 24 hours. Then it was concentrated in vacuo to remove the solvent. The residue was added to a silica gel column (30 g) and was eluted with CH₂Cl₂:MeOH=15:1 to obtain the crude product and purified further by prep-TLC (CH₂Cl₂/MeOH=15/1) to obtain the 2-((3,5-dicyano-4-ethyl-6-((S)-3-hydroxypyrrolidin-1-yl)pyridin-2-yl)thio)-2-(3-(dimethylphosphoryl)phenyl)acetamide (103 mg, 17% yield) as a gray solid. LCMS m/z=484.1 [M+H]⁺. ¹H NMR (400 MHz, CD₃OD) δ ppm 7.98 (d, J=12.2 Hz, 1H), 7.81-7.74 (m, 2H), 7.62-7.58 (m, 1H), 5.71 (s, 1H), 4.53 (m, 1H), 3.93-3.84 (m, 4H), 2.87 (q, J=7.6 Hz, 2H), 2.10-2.06 (m, 2H), 1.82 (s, 3H), 1.79 (s, 3H), 1.28 (t, J=7.6 Hz, 3H).

Example 421

(R)-2-((6-((2-amino-2-oxo-1-phenylethyl)thio)-3,5-dicyano-4-ethylpyridin-2-yl(methyl)amino)ethyl dihydroden phosphate Step 1: 2-((3,5-dicyano-4-ethyl-6-((2-hydroxyethyl)(methyl)amino)pyridin-2-yl)thio)-2-phenylacetamide To a solution of 2,6-dichloro-4-ethylpyridine-3,5-dicarbonitrile (synthesis describe in example 3, step 2, 75.0 g, 0.332 mol) and TEA (46 mL, 0.332 mol) in DCM (1.5 L) was added 2-(methylamino)ethanol (24.9 g, 0.332 mol) dropwise at 0° C. The resulting solution was stirred at rt for 1 h. Water was added, and the mixture was extracted with DCM (3×500 mL). The combined organic layers were dried over MgSO₄, filtered and concentrated in vacuo. The residue was purified by column chromatography (silica gel, PE/EA=3/1) to afford 2-chloro-4-ethyl-6-((2-hydroxyethyl)(methyl)amino)pyridine-3,5-dicarbonitrile (74.0 g, 84%) as a white solid. LCMS (m/z)=264.9 [M+H]⁺. A solution of 2-chloro-4-ethyl-6-((2-hydroxyethyl)(methyl)amino)pyridine-3,5-dicarbonitrile (71.3 g, 0.269 mol) and KSAc (35.9 g, 0.315 mol) in DMF (1 L) was stirred at rt for 1 h. Then 2-amino-2-oxo-1-phenylethyl methanesulfonate (synthesis describe in example 3, step 5, 72.1 g, 0.315 mol) and TEA (74.8 mL, 0.538 mol) were added. The resulting mixture was stirred at rt overnight and concentrated under reduced pressure. The residue was dissolved in EA (1 L) and washed with water (3×500 mL). The organic layer was dried and concentrated in vacuo. The residue was purified by column chromatography (silica gel, DCM/MeOH=50/1) to afford 2-(3,5-dicyano-4-ethyl-6-((2-hydroxyethyl)(methyl)amino)pyridin-2-ylthio)-2-phenylacetamide (32.0 g, 30%) as a white solid. LCMS (m/z)=396.1 [M+H]⁺.

Step 2: 2-((6-((2-amino-2-oxo-1-phenylethyl)thio)-3,5-dicyano-4-ethylpyridin-2-yl)(methyl)amino) ethyl dihydrogen phosphate

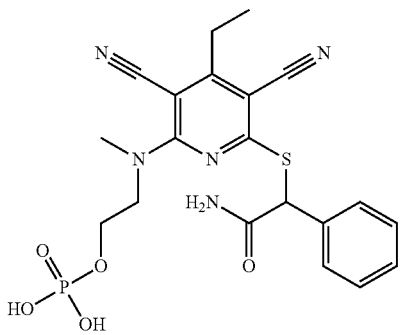

To a suspension of 2-(3,5-dicyano-4-ethyl-6-((2-hydroxyethyl)(methyl)amino)pyridin-2-ylthio)-2-phenylacetamide (12.45 g, 31.5 mmol) and TEA (13.2 mL, 94.6 mmol) in anhydrous THF (200 mL) at 0° C. was added $POCl_3$ (14.5 g, 94.6 mmol) dropwise. The resulting mixture was stirred at 0° C. for 1 h. Ice was added slowly to quench the reaction and the resulting mixture was extracted with EA (3×300 mL). The combined organic layers were dried, filtered and concentrated under reduced pressure. The residue was purified by column chromatography (silica gel, MeOH/DCM=1: 20) to afford the crude product. The crude product was dissolved in acetone and added dropwise into water. The precipitate was filtered, dried and recrystallized with Me-CN to afford 2-((6-(2-amino-2-oxo-1-phenylethylthio)-3,5-dicyano-4-ethylpyridin-2-yl)(methyl)amino)ethyl dihydrogen phosphate (8 g, 53%) as a yellow solid. LCMS (m/z)=475.9 [M+H]$^+$. $^1$H NMR (400 MHz, DMSO-d$_6$) δ ppm 8.27 (s, 1H), 7.57 (d, J=8.0 Hz, 2H), 7.39-7.30 (m, 4H), 5.67 (s, 1H), 4.05 (s, 2H), 4.00 (d, J=4 Hz, 2H), 3.43 (s, 3H), 2.76 (q, J=8 Hz, 2H), 1.20 (t, J=8 Hz, 3H), 2 phosphate protons not fully resolved.

Step 3: (R)-2-((6-((2-amino-2-oxo-1-phenylethyl)thio)-3,5-dicyano-4-ethylpyridin-2-yl)(methyl)amino)ethyl dihydrogen phosphate

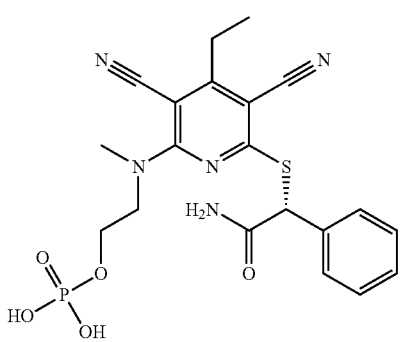 [SMILES: CCc1c(C#N)c(SC(C(N)=O)c2ccccc2)nc(N(C)CCOP(=O)(O)O)c1C#N]

2-((6-(2-amino-2-oxo-1-phenylethylthio)-3,5-dicyano-4-ethylpyridin-2-yl)(methyl)amino)ethyl dihydrogen phosphate (1.987 g) was dissolved in hot 1:1 heptane/EtOH with some drops of MSA for solubility, and subjected to normal-phase HPLC chiral separation using 75:25:0.1 Heptane mixture (95:5:0.1 Heptane:ethanol:methanesulfonic acid (MSA)); EtOH mixture (5:95:0.1 Heptane:EtOH:MSA); 0.1 MSA on a 30×250 mm AD-H column. After removing the solvent in vacuo, the residue was taken up in EtOAc, washed twice with water, dried over $Na_2SO_4$, filtered, and concentrated to afford 741.2 mg of peak 2. LCMS (m/z)=476.1 [M+H]$^+$. $^1$H NMR (400 MHz, METHANOL-d$_4$) δ ppm 7.51-7.61 (m, 2H), 7.31-7.46 (m, 3H), 5.55 (s, 1H), 4.22-4.30 (m, 2H), 4.07-4.22 (m, 2H), 3.56 (s, 3H), 2.92 (q, J=7.60 Hz, 2H), 1.32 (t, J=7.60 Hz, 3H). Comparing the observed VCD and IR spectra of the product with the calculated spectra of the modeled (S)-structure, the absolute configuration was assigned as (R)-2-((6-((2-amino-2-oxo-1-phenylethyl)thio)-3,5-dicyano-4-ethylpyridin-2-yl)(methyl)amino)ethyl dihydrogen phosphate.

Example 422

(R)-2-((3,5-dicyano-4-ethyl-6-((S)-3-hydroxypyrrolidin-1-yl)pyridin-2-yl)thio)-2-(4-methoxyphenyl) acetamide Step 1: Methyl 2-hydroxy-2-(4-methoxyphenyl)acetate

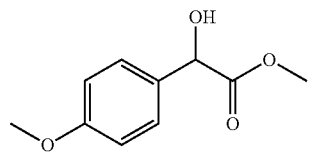

To a stirred solution of 2-hydroxy-2-(4-methoxyphenyl) acetic acid (5 g, 27.4 mmol) in methanol (50 mL) was added acetyl chloride (5.85 mL, 82 mmol) at 0° C. The resulting reaction mixture was stirred at room temperature for 16 h. The reaction was concentrated under reduced pressure to obtain crude methyl 2-hydroxy-2-(4-methoxyphenyl)acetate (5.1 g, 14.63 mmol, 53.3% yield) as an off white solid. The crude was used without further purification. LCMS (m/z)=195.02 [M–H]$^-$.

Step 2: 2-hydroxy-2-(4-methoxyphenyl)acetamide

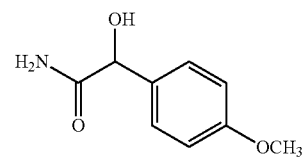 [SMILES: COc1ccc(C(O)C(N)=O)cc1]

To a stirred solution of methyl 2-hydroxy-2-(4-methoxyphenyl)acetate (5.1 g, 26.0 mmol) in methanol (50 mL) was added ammonium hydroxide (25 mL, 173 mmol) at RT and stirred at RT for 16 h. The reaction mixture was concentrated under reduced pressure to obtain crude compound. The solid material was triturated with diethyl ether (200 mL) to afford 2-hydroxy-2-(4-methoxyphenyl)acetamide (4.5 g, 16.44 mmol, 63.2% yield) as an off-white solid. LCMS (m/z)=182.07 [M+H]$^+$.

Step 3: 2-amino-1-(4-methoxyphenyl)-2-oxoethyl methanesulfonate

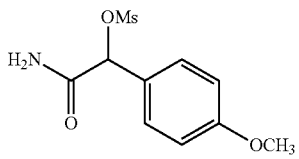

To a stirred solution of 2-hydroxy-2-(4-methoxyphenyl) acetamide (2 g, 11.04 mmol) in dichloromethane (DCM) (40 mL) was added TEA (4.62 mL, 33.1 mmol) at room temperature. The reaction mixture was cooled to 0° C., then methanesulphonyl chloride (1.290 mL, 16.56 mmol) was added portionwise to the reaction mixture. The reaction mixture was stirred at room temperature for 1 h. Reaction mixture was quenched with water (100 mL) and extracted with DCM (2×100 mL). The combined organic layer was dried over anhydrous sodium sulphate, filtered and evaporated under reduced pressure to get crude 2-amino-1-(4-methoxyphenyl)-2-oxoethyl methanesulfonate (1.8 g, 6.60 mmol, 59.7% yield) as a pale yellow solid. $^1$H NMR (400 MHz, DMSO-$d_6$): δ ppm 7.41 (s, 1H), 7.29 (d, J=8.55 Hz, 2H), 7.17 (s, 1H), 6.90 (d, J=8.77 Hz, 2H), 4.47 (s, 1H), 3.74 (s, 3H), 3.24 (s, 3H).

Step 4: 2-((3,5-dicyano-4-ethyl-6-((S)-3-hydroxypyrrolidin-1-yl)pyridin-2-yl)thio)-2-(4-methoxyphenyl)acetamide

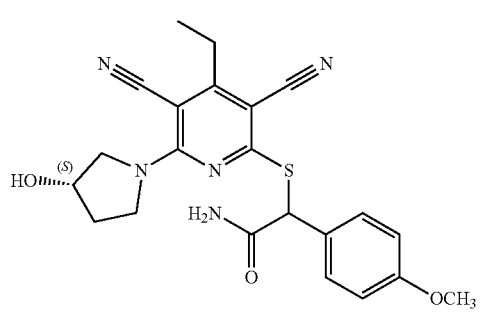

To a stirred solution of (S)-2-chloro-4-ethyl-6-(3-hydroxypyrrolidin-1-yl)pyridine-3,5-dicarbonitrile (synthesis described in example 418 step 1, 1.5 g, 5.30 mmol) in N,N-dimethylformamide (DMF) (30 mL) was added potassium thioacetate (1.210 g, 10.60 mmol) at room temperature. The reaction stirred at room temperature for 2 h. Then TEA (1.477 mL, 10.60 mmol) and 2-amino-1-(4-methoxphenyl)-2-oxoethyl methanesulfonate (1.880 g, 6.89 mmol) were added to the reaction mixture at room temperature and stirred for 3 h. The reaction mixture was diluted with water (100 mL) and extracted with EtOAc (3×100 mL). The combined organic layer was dried over anhydrous sodium sulfate, filtered, concentrated under reduced pressure. The crude material was purified by normal phase chromatography (silicagel, 40 µm, flow rate 40 ml/min) using a Grace Reveleris purification instrument by eluting 4% MeOH in DCM to afford 2-((3,5-dicyano-4-ethyl-6-((S)-3-hydroxypyrrolidin-1-yl)pyridin-2-yl)thio)-2-(4-methoxyphenyl)acetamide (1.6 g, 3.64 mmol, 68.6% yield) as an off-white solid. LCMS (m/z)=438.1[M+H]$^+$.

Step 5: (R)-2-((3,5-dicyano-4-ethyl-6-((S)-3-hydroxypyrrolidin-1-yl)pyridin-2-yl)thio)-2-(4-methoxyphenyl)acetamide

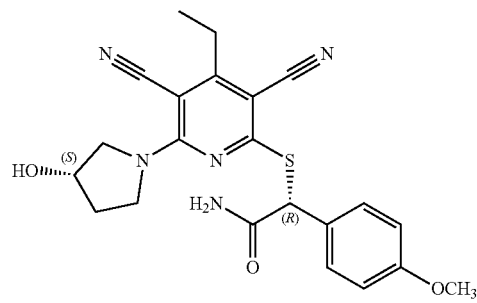

The diastereomeric mixture of 2-((3,5-dicyano-4-ethyl-6-((S)-3-hydroxypyrrolidin-1-yl)pyridin-2-yl)thio)-2-(4-methoxyphenyl)acetamide (1.6 g, 3.66 mmol) was separated by chiral SFC Prep-HPLC (Chiralcel OJ-H (30×250 mm)) to afford peak-1 (R)-2-((3,5-dicyano-4-ethyl-6-((S)-3-hydroxypyrrolidin-1-yl)pyridin-2-yl)thio)-2-(4-methoxyphenyl)acetamide (220 mg, 0.502 mmol, 13.72% yield) as an off-white solid. LCMS of peak-1: m/z=438.08 [M+H]$^+$. $^1$H NMR (400 MHz, DMSO-$d_6$): δ ppm 7.80 (s, 1H), 7.42 (d, J=8.77 Hz, 2H), 7.22 (s, 1H), 6.93 (d, J=8.77 Hz, 2H), 5.54 (s, 1H), 5.13 (d, J=3.51 Hz, 1H), 4.48-4.38 (m, 1H), 3.98-3.79 (m, 4H), 3.74 (s, 3H), 2.75 (q, J=7.67 Hz, 2H), 2.07-1.86 (m, 2H), 1.20 (t, J=7.67 Hz, 3H). Comparing the measured VCD difference spectrum of (R)-2-((3,5-dicyano-4-ethyl-6-((S)-3-hydroxypyrrolidin-1-yl)pyridin-2-yl)thio)-2-(4-methoxyphenyl)acetamide minus (S)-2-((3,5-dicyano-4-ethyl-6-((S)-3-hydroxypyrrolidin-1-yl)pyridin-2-yl)thio)-2-(4-methoxyphenyl)acetamide with the calculated VCD difference spectrum of (R)-minus (S)-, the absolute configuration of peak 1 was assigned as (R)-2-((3,5-dicyano-4-ethyl-6-((S)-3-hydroxypyrrolidin-1-yl)pyridin-2-yl)thio)-2-(4-methoxyphenyl)acetamide

Example 423

(R)-2-((6-((R)-3-(aminomethyl)-3-hydroxypyrrolidin-1-yl)-3,5-dicyano-4-ethylpyridin-2-yl)thio)-2-phenylacetamide hydrochloride Step 1: tert-butyl((1-(6-chloro-3,5-dicyano-4-ethylpyridin-2-yl)-3-hydroxypyrrolidin-3-yl)methyl)carbamate

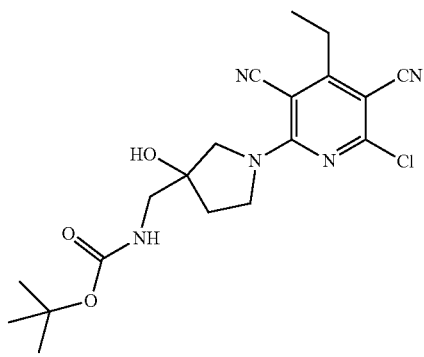 [SMILES: CCc1c(C#N)c(Cl)nc(N2CCC(O)(CNC(=O)OC(C)(C)C)C2)c1C#N]

To a stirred solution of tert-butyl((3-hydroxypyrrolidin-3-yl)methyl)carbamate (2.39 g, 11.06 mmol) in dichloromethane (DCM) (50 mL) was added TEA (4.62 mL, 33.2 mmol) and stirred at 26° C. Then 2,6-dichloro-4-ethylpyridine-3,5-dicarbonitrile (2.5 g, 11.06 mmol) was added to the reaction mixture at same temperature. The reaction mixture was stirred at 26° C. for 16 h. The reaction mixture was partitioned between water (500 mL) and DCM (2×200 mL). The combined organic layer was dried over anhydrous sodium sulphate, filtered and filtrate was evaporated to afford crude material. The crude material was washed with pentane and diethyl ether (1:1) to afford tert-butyl ((1-(6-chloro-3,5-dicyano-4-ethylpyridin-2-yl)-3-hydroxypyrrolidin-3-yl)methyl)carbamate (4.0 g, 88%) as an off white solid. LCMS (m/z): 406.11 [M+H]$^+$.

Step 2: tert-butyl((1-(6-chloro-3,5-dicyano-4-ethylpyridin-2-yl)-3-hydroxypyrrolidin-3-yl)methyl)carbamate, Single Stereoisomer

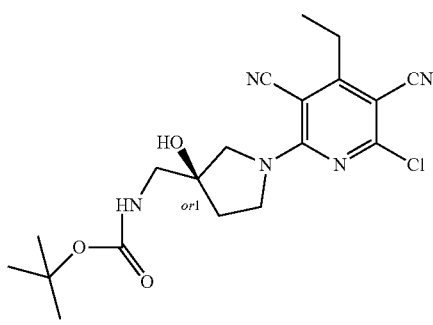

Peak-1 tert-butyl((1-(6-chloro-3,5-dicyano-4-ethylpyridin-2-yl)-3-hydroxypyrrolidin-3-yl)methyl)carbamate was submitted to chiral SFC Purification (Column: Lux Cellulose-2 (4.6× 250 mm)) and resulting fractions were concentrated under reduced pressure individually to afford tert-butyl((1-(6-chloro-3,5-dicyano-4-ethylpyridin-2-yl)-3-hydroxypyrrolidin-3-yl)methyl)carbamate (1.4 g, 34.5%, Peak-1) as an off white solid, single unknown stereoisomer. LCMS (m/z): 406.20 [M+H]$^+$.

Step 3: tert-butyl((1-(6-((2-amino-2-oxo-1-phenylethyl)thio)-3,5-dicyano-4-ethylpyridin-2-yl)-3-hydroxypyrrolidin-3-yl)methyl)carbamate

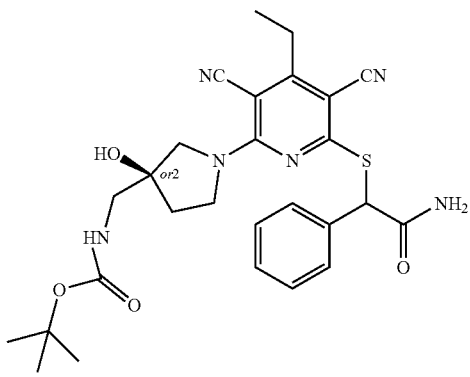 [SMILES: CCc1c(C#N)c(SC(C(N)=O)c2ccccc2)nc(N2CC[C@](O)(CNC(=O)OC(C)(C)C)C2)c1C#N]

To a stirred solution of tert-butyl ((1-(6-chloro-3,5-dicyano-4-ethylpyridin-2-yl)-3-hydroxypyrrolidin-3-yl)methyl)carbamate (1.35 g, 3.23 mmol, Peak-1 from previous step) in N,N dimethylformamide (DMF) (20 mL) was added potassium thioacetate (0.553 g, 4.84 mmol) at 0° C. under nitrogen atmosphere. The reaction mixture was stirred at 0° C. for 1 h, then K$_2$CO$_3$ (0.669 g, 4.84 mmol) and 2-amino-2-oxo-1-phenylethyl methanesulfonate (0.814 g, 3.55 mmol) were added at 0° C. The reaction stirred at 26° C. for 16 h. The reaction mixture was poured into ice cold water (200 mL) and extracted with EtOAc (2×150 mL). The combined organic layer was dried over anhydrous sodium sulphate, filtered and concentrated under reduced pressure to afford crude material. The crude material was washed with diethyl ether and pentane (1:1) to afford tert-butyl ((1-(6-((2-amino-2-oxo-1-phenylethyl)thio)-3,5-dicyano-4-ethylpyridin-2-yl)-3-hydroxypyrrolidin-3-yl)methyl)carbamate (1.4 g, 74.0%) as a pale yellow solid, a mixture of 2 diastereomers. LCMS (m/z): 537.05 [M+H]$^+$.

Step 4: tert-butyl((1-(6-((2-amino-2-oxo-1-phenylethyl)thio)-3,5-dicyano-4-ethylpyridin-2-yl)-3-hydroxypyrrolidin-3-yl)methyl)carbamate, Single Diastereomer

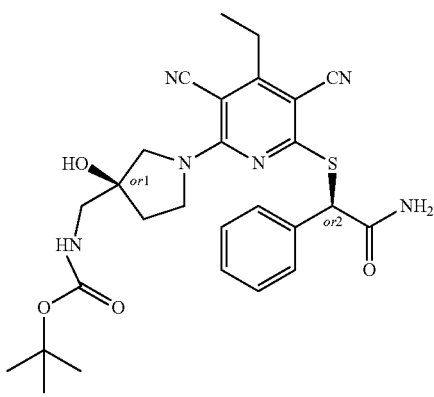 [SMILES: CCc1c(C#N)c(S[C@@H](C(N)=O)c2ccccc2)nc(N2CC[C@](O)(CNC(=O)OC(C)(C)C)C2)c1C#N]

tert-butyl ((1-(6-((2-amino-2-oxo-1-phenylethyl)thio)-3,5-dicyano-4-ethylpyridin-2-yl)-3-hydroxypyrrolidin-3-yl)methyl)carbamate (1.4 g, from the previous step) was submitted to chiral SFC purification (Chiralpak AD-H (30×250 mm), acetonitrile/IPA). The resulting fractions of peak 2 were concentrated under reduced pressure to afford tert-butyl ((1-(6-((2-amino-2-oxo-1-phenylethyl)thio)-3,5-dicyano-4-ethylpyridin-2-yl)-3-hydroxypyrrolidin-3-yl)methyl)carbamate (310 mg, 23.65%, a single diastereomer) as an off-white solid. LCMS (m/z): 537.25 [M+H]$^+$.

Step 5: (R)-2-((6-((R)-3-(aminomethyl)-3-hydroxypyrrolidin-1-yl)-3,5-dicyano-4-ethylpyridin-2-yl)thio)-2-phenylacetamide hydrochloride

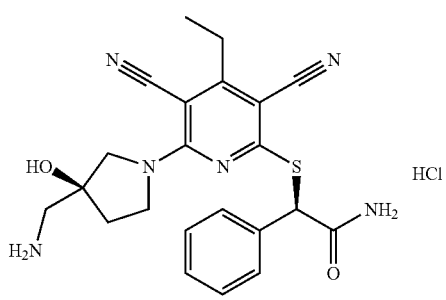 [SMILES: CCc1c(C#N)c(S[C@@H](C(N)=O)c2ccccc2)nc(N2CC[C@](O)(CN)C2)c1C#N ; Cl]

To a stirred solution of tert-butyl ((1-(6-((2-amino-2-oxo-1-phenylethyl)thio)-3,5-dicyano-4-ethylpyridin-2-yl)-3-hydroxypyrrolidin-3-yl)methyl)carbamate (280 mg, 0.510 mmol, peak 2 from previous step) in dichloromethane (DCM) (10 mL) was added TFA (0.196 mL, 2.55 mmol) dropwise at 0° C. The resulting reaction mixture was stirred for 1 h at 0° C. The progress of the reaction was monitored by TLC. The reaction mixture was evaporated under reduced pressure to get crude material. The crude material was washed with diethyl ether and pentane (1:1) to get crude compound as a TFA salt. The crude material was dissolved in ethanol (15 mL) and 5 mL of 2M HCl in diethyl ether solution was added. The resulting solution was concentrated in vacuo at 40° C. The process was repeated 2 times. The crude material was washed with n-heptane (30 mL) followed by diethyl ether (20 mL) to afford (R)-2-((6-((R)-3-(aminomethyl)-3-hydroxypyrrolidin-1-yl)-3,5-dicyano-4-ethylpyridin-2-yl)thio)-2-phenylacetamide hydrochloride (214 mg, 85%) as a pale yellow solid. Absolute configuration of the chiral center adjacent to sulfur was was confirmed by VCD analysis LCMS (m/z): 437.14 [M+H]$^+$. $^1$H NMR (400 MHz, DMSO-d$_6$): δ ppm 8.45-7.88 (m, 4H), 7.58 (d, J=7.02 Hz, 2H), 7.47-7.18 (m, 4H), 5.87-5.64 (m, 2H), 4.16-3.83 (m, 4H), 3.2-3.05 (m, 2H), 2.75 (q, J=7.38 Hz, 2H), 2.06 (d, J=6.14 Hz, 2H), 1.28 (t, J=7.5 Hz, 3H).

Example 424

(R)-2-(4-chlorophenyl)-2-((3,5-dicyano-4-ethyl-6-((S)-3-hydroxypyrrolidin-1-yl)pyridin-2-yl)thio) acetamide

Step 1: Methyl 2-(4-chlorophenyl)-2-hydroxyacetate

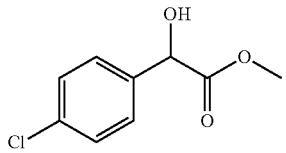

To a stirred solution of 2-(4-chlorophenyl)-2-hydroxyacetic acid (5 g, 26.8 mmol) in methanol (50 mL) was added acetyl chloride (5.72 mL, 80 mmol) at 0° C. The reaction mixture was stirred at rt for 5 h. The reaction progress was monitored by TLC and the reaction mixture was concentrated under reduced pressure to remove all volatiles. Cold ethanol (15 ml) was added to crude compound, stirred for 5 minutes, and filtered to afford methyl 2-(4-chlorophenyl)-2-hydroxyacetate (4.8 g, 23.93 mmol, 89% yield) as an off white solid. $^1$H NMR (400 MHz, DMSO-d$_6$): δ ppm 7.48-7.39 (m, 4H), 6.00-5.32 (m, 1H), 5.18 (s, 1H), 3.67 (s, 3H).

Step 2: (S)-2-(4-chlorophenyl)-2-hydroxyacetamide

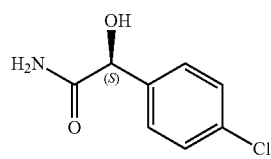

To a stirred solution of methyl 2-(4-chlorophenyl)-2-hydroxyacetate (4.7 g, 23.43 mmol) in methanol (50 mL) was added ammonium hydroxide (3.65 mL, 23.43 mmol) at 0° C. The reaction mixture was stirred at rt for 16 h. The reaction progress was monitored by TLC. The reaction mixture was concentrated under reduced pressure to remove all volatiles. The crude was dissolved in water and extracted with ethyl acetate (2×50 mL). The combined organic layer was washed with saturated NaHCO$_3$ solution, brine solution, dried over anhydrous sodium sulphate, filtered and concentrated to afford 2-(4-chlorophenyl)-2-hydroxyacetamide (2.9 g) as an off-white solid (Chiral-HPLC: 49.14%, rt=2.79, 50.88%, rt=3.4). 2-(4-chlorophenyl)-2-hydroxyacetamide (2.8 g, 14.98 mmol) was further purified by chiral SFC Prep-HPLC (chiralpak AD-H (30×250 mm) column, MeOH), to afford peak-2 (S)-2-(4-chlorophenyl)-2-hydroxyacetamide (1.1 g, 5.63 mmol, 37.6% yield) as an off-white solid. LCMS (m/z): 184.0 [M−H]⁻. Peak-2: $RA^D$ at 28° C.=+86.13 (c 2, acetone), >98% ee.

Step 3: (S)-2-amino-1-(4-chlorophenyl)-2-oxoethyl 4-methylbenzenesulfonate

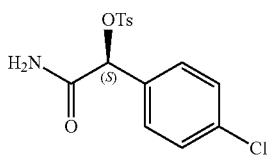

To a stirring suspension of (S)-2-(4-chlorophenyl)-2-hydroxyacetamide (0.400 g, 2.150 mmol) in 1,4-dioxane (10 mL) was added DIPEA (1.127 mL, 6.45 mmol), DMAP (0.263 g, 2.150 mmol) and p-toluenesulphonyl chloride (0.615 g, 3.23 mmol) under nitrogen at 0° C. The reaction mixture was stirred at rt for 16 h. The reaction progress was monitored by TLC. The reaction mixture was poured into ice cold water (20 mL) and stirred for 10 minutes. The precipitated solid was filtered and dried. The crude was washed with diethyl ether (2×20 mL) to afford (S)-2-amino-1-(4-chlorophenyl)-2-oxoethyl 4-methylbenzenesulfonate (0.330 g, 44.6% yield) as an off-white solid. LCMS (m/z): 339.99 [M+H]⁺.

Step 4: (R)-2-(4-chlorophenyl)-2-((3,5-dicyano-4-ethyl-6-((S)-3-hydroxypyrrolidin-1-yl)pyridin-2-yl)thio)acetamide

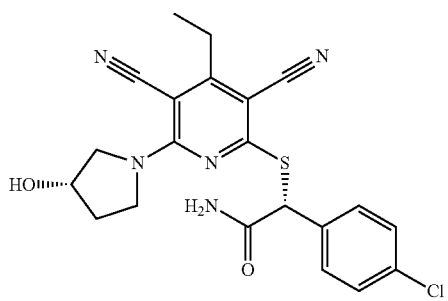 [SMILES: CCc1c(C#N)c(S[C@@H](C(N)=O)c2ccc(Cl)cc2)nc(N2CC[C@H](O)C2)c1C#N]

To a solution of (S)-2-chloro-4-ethyl-6-(3-hydroxypyrrolidin-1-yl)pyridine-3,5-dicarbonitrile (synthesis described in example 418 step 1, 0.250 g, 0.872 mmol) in N,N-dimethylformamide (DMF) (10 mL) was added potassium thioacetate (0.199 g, 1.743 mmol) at rt. The mixture was stirred for 2 h at the same temperature. The reaction progress was monitored by TLC (50% ethylacetate:pet ether, rf: 0.5, UV active). Triethylamine (0.243 mL, 1.743 mmol) and (S)-2-amino-1-(4-chlorophenyl)-2-oxoethyl 4-methylbenzenesulfonate (0.300 g, 0.872 mmol) were added at rt and stirred for 4 h at rt. The reaction progress was monitored by TLC (50% EtOAc/Pet ether, Rf: 0.4, UV active). The reaction mixture was poured into ice water (30 ml) and extracted with ethylacetate (3×40 ml). The combined organic layer was washed with brine solution and cold water. The organic layer was dried over anhydrous $Na_2SO_4$, filtered and concentrated under reduced pressure. The crude compound was washed with pentane (2×30 ml) and diethyl ether (2×20 ml) to afford (R)-2-(4-chlorophenyl)-2-((3,5-dicyano-4-ethyl-6-((S)-3-hydroxypyrrolidin-1-yl)pyridin-2-yl) thio)acetamide (0.160 g, 0.356 mmol, 40.8% yield) as a pale brown solid. Comparing the observed VCD and IR spectra of the product with the calculated spectra of the modeled two possible structures, the absolute configuration of the chiral center adjacent to sulfur was confirmed to be (R)-. LCMS (m/z): 440.08 [M−H]⁻. ¹H NMR (400 MHz, DMSO-d₆): δ ppm 7.93 (s, 1H), 7.54 (d, J=8.10 Hz, 2H), 7.44 (d, J=8.55 Hz, 2H), 7.33 (s, 1H), 5.63 (s, 1H), 5.13 (d, J=3.6 Hz, 1H), 4.48-4.38 (m, 1H), 3.99-3.64 (m, 4H), 2.74 (q, J=7.5 Hz, 2H), 2.05-1.87 (m, 2H), 1.20 (t, J=7.6 Hz, 3H).

Example 425

(R)-2-((3,5-dicyano-4-ethyl-6-((S)-3-hydroxypyrrolidin-1-yl)pyridin-2-yl)thio)-2-(4-fluoro phenylacetamide Step 1: 2-(4-fluorophenyl)-2-hydroxyacetamide, Single Stereoisomer

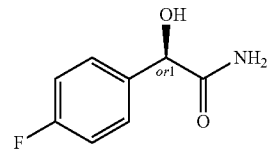 [SMILES: NC(=O)[C@H](O)c1ccc(F)cc1]

2-(4-fluorophenyl)-2-hydroxyacetamide (synthesis described in example 207, step 2, 4.0 g, 23.41 mmol) was subjected to chiral SFC HPLC (Chiralpak-AS-H ((30×250 mm) column). The pure fractions were concentrated under reduced pressure to afford 2-(4-fluorophenyl)-2-hydroxyacetamide (peak 2, 1.56 g, 9.14 mmol, 39.0% yield) as a white solid LCMS m/z=167.99 [M−H]⁻.

Step 2: 2-amino-1-(4-fluorophenyl)-2-oxoethyl methanesulfonate, Single Stereoisomer

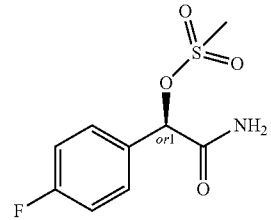 [SMILES: CS(=O)(=O)O[C@@H](C(N)=O)c1ccc(F)cc1]

To a stirred solution of chiral pure 2-(4-fluorophenyl)-2-hydroxyacetamide (1.0 g, 5.85 mmol, peak 2 from previous step) in DCM (10 mL) was added TEA (2.44 mL, 17.56 mmol) and methanesulfonyl chloride (0.9 mL, 11.71 mmol) at 0° C. The mixture stirred at room temperature for 1 h. The reaction mixture was diluted with water (100 mL) and extracted with DCM (3×100 mL). The combined organic layer was washed with water (100 mL), brine solution (100 mL) and dried over anhydrous $Na_2SO_4$, filtered and concentrated under reduced pressure. The crude material was triturated with n-pentane (100 mL), filtered and dried under vacuum to afford 2-amino-1-(4-fluorophenyl)-2-oxoethyl Step 3: (R)-2-((3,5-dicyano-4-ethyl-6-((S)-3-hydroxypyrrolidin-1-yl)pyridin-2-yl)thio)-2-(4-fluorophenyl)acetamide methanesulfonate, single stereoisomer (0.95 g, 61.6%) as an off-white solid. LCMS (m/z)=248.00 [M+H]$^+$.

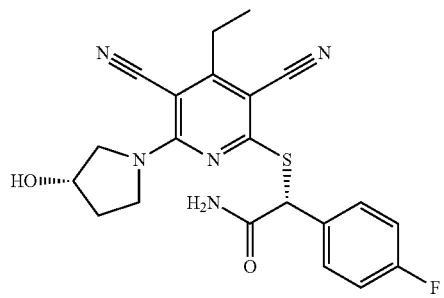 [SMILES: CCc1c(C#N)c(S[C@@H](C(N)=O)c2ccc(F)cc2)nc(N2CC[C@H](O)C2)c1C#N]

To a stirred solution of (S)-2-chloro-4-ethyl-6-(3-hydroxypyrrolidin-1-yl)pyridine-3,5-dicarbonitrile (synthesis described in example 418, step 1, 650 mg, 2.29 mmol) in N,N-dimethylformamide (DMF) (30 mL) was added potassium thioacetate (294 mg, 2.52 mmol) at room temperature. The mixture stirred for 2 h at room temperature. TEA (0.65 mL, 4.58 mmol) and 2-amino-1-(4-fluorophenyl)-2-oxoethyl methanesulfonate from the previous step (0.694 g, 2.63 mmol) were added. The reaction mixture at room temperature and stirred for 16 h. Reaction mixture was diluted with ice cold water (150 mL) and stirred for 10 min. The precipitated solid was filtered and dried under vacuum. The crude material was triturated with diethyl ether:acetonitrile (10:1 (2×30 mL)), filtered and dried under vacuum to afford (R)-2-((3,5-dicyano-4-ethyl-6-((S)-3-hydroxypyrrolidin-1-yl)pyridin-2-yl)thio)-2-(4-fluorophenyl)acetamide (420 mg, 42.3 mmol) as an off white solid. LCMS (m/z)=426.13 [M+H]$^+$. $^1$H NMR (400 MHz, DMSO-d$_6$): δ 7.90 (s, 1H), 7.67-7.48 (m, 2H), 7.30 (s, 1H), 7.27-7.03 (m, 2H), 5.62 (s, 1H), 5.13 (d, J=3.5 Hz, 1H), 4.44-4.38 (m, 1H), 3.89-3.67 (m, 4H), 2.74 (q, J=7.5 Hz, 2H), 2.16-1.86 (m, 2H), 1.20 (t, J=7.6 Hz, 3H). Comparing the observed VCD difference between (S)-2-((3,5-dicyano-4-ethyl-6-((S)-3-hydroxypyrrolidin-1-yl)pyridin-2-yl)thio)-2-(4-fluorophenyl)acetamide and (R)-2-((3,5-dicyano-4-ethyl-6-((S)-3-hydroxypyrrolidin-1-yl)pyridin-2-yl)thio)-2-(4-fluorophenyl)acetamide with the VCD difference between two previously analyzed reference compounds, the absolute configuration of this material was assigned as (R)-2-((3,5-dicyano-4-ethyl-6-((S)-3-hydroxypyrrolidin-1-yl)pyridin-2-yl)thio)-2-(4-fluorophenyl)acetamide.

Example 426

(S)-1-(6-(((R)-2-amino-1-(4-fluorophenyl)-2-oxoethyl)thio)-3,5-dicyano-4-ethylpyridin-2-yl)pyrrolidin-3-yl dihydrogen phosphate Step 1: (S)-1-(6-(((R)-2-amino-1-(4-fluorophenyl)-2-oxoethyl)thio)-3,5-dicyano-4-ethylpyridin-2-yl)pyrrolidin-3-yl di-tert-butyl phosphate

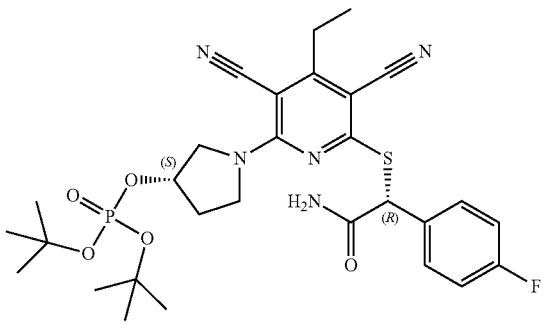

To a stirred solution of (S)-di-tert-butyl (1-(6-chloro-3,5-dicyano-4-ethylpyridin-2-yl)pyrrolidin-3-yl) phosphate (synthesis described in example 418, step 2, 0.6 g, 1.26 mmol) in N,N-dimethylformamide (DMF) (25 mL) was added potassium thioacetate (148 mg, 1.26 mmol) at room temperature. The reaction was stirred for 2 h. Then TEA (0.27 mL, 1.9 mmol) and 2-amino-1-(4-fluorophenyl)-2-oxoethyl methanesulfonate (synthesis described in example 425, step 2, 348 mg, 1.39 mmol) were added to the reaction mixture at room temperature and stirred for 16 h. The reaction mixture was diluted with ice cold water (100 mL) and stirred for 30 min. The solid was filtered, washed with water (300 mL), and dried under vacuum to afford (S)-1-(6-(((R)-2-amino-1-(4-fluorophenyl)-2-oxoethyl)thio)-3,5-dicyano-4-ethylpyridin-2-yl)pyrrolidin-3-yl di-tert-butyl phosphate (0.86 g, 85%) LCMS (m/z)=618.26 [M+H]$^+$.

Step 4: (S)-1-(6-(((R)-2-amino-1-(4-fluorophenyl)-2-oxoethyl)thio)-3,5-dicyano-4-ethyl pyridin-2-yl)pyrrolidin-3-yl dihydrogen phosphate

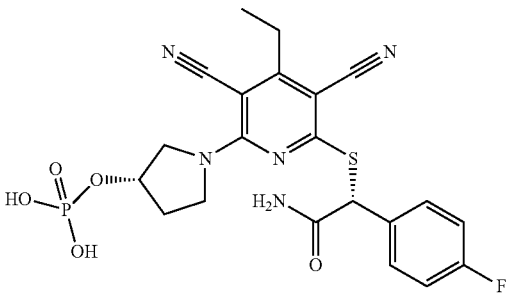 [SMILES: CCc1c(C#N)c(S[C@@H](C(N)=O)c2ccc(F)cc2)nc(N2CC[C@H](OP(=O)(O)O)C2)c1C#N]

To a stirred solution of (S)-1-(6-(((R)-2-amino-1-(4-fluorophenyl)-2-oxoethyl)thio)-3,5-dicyano-4-ethylpyridin-2-yl)pyrrolidin-3-yl di-tert-butyl phosphate (0.850 g, 1.05 mmol) in ethanol (5 mL) was added 2.0 M hydrochloric acid (10.59 mL, 20.23 mmol) in diethyl ether at 0° C. The reaction mixture was stirred at room temperature for 2 h and then was concentrated under reduced pressure. The crude material was triturated with a mixture of EtOH (10 mL) and diethyl ether (30 mL). The solid was filtered, washed with excess diethyl ether (200 mL), and dried under vacuum to afford (S)-1-(6-(((R)-2-amino-1-(4-fluorophenyl)-2-oxoethyl)thio)-3,5-dicyano-4-ethylpyridin-2-yl)pyrrolidin-3-yl dihydrogen phosphate (290 mg, 53.2%) as an orange solid. LCMS (m/z)=506.21 [M+H]$^+$. $^1$H NMR (400 MHz, DMSO-d$_6$): δ ppm 8.01 (s, 1H), 7.60-7.53 (m, 2H), 7.28 (s, 1H), 7.20 (t, J=8.77 Hz, 2H), 5.64 (s, 1H), 4.96-4.90 (m, 1H), 3.87-4.10 (m, 4H), 2.74 (q, J=7.67 Hz, 2H), 2.26-2.07 (m, 2H), 1.19 (t, J=7.56 Hz, 3H), 2 protons not fully resolved. Based on the VCD difference between (S)-2-((3,5-dicyano-4-ethyl-6-((S)-3-hydroxypyrrolidin-1-yl)pyridin-2-yl)thio)-2-(4-fluorophenyl)acetamide and (R)-2-((3,5-dicyano-4-ethyl-6-((S)-3-hydroxypyrrolidin-1-yl)pyridin-2-yl)thio)-2-(4-fluorophenyl)acetamide, two previously analyzed reference compounds, the absolute configuration of this material was assigned as (S)-1-(6-(((R)-2-amino-1-(4-fluorophenyl)-2-oxoethyl)thio)-3,5-dicyano-4-ethylpyridin-2-yl)pyrrolidin-3-yl dihydrogen phosphate.

Example 427

2-((3,5-dicyano-4-ethyl-6-((S)-3-hydroxypyrrolidin-1-yl) pyridin-2-yl) thio)-2-(4-fluorophenyl) acetamide

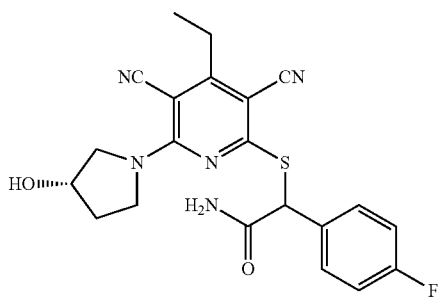 [SMILES: CCc1c(C#N)c(SC(C(N)=O)c2ccc(F)cc2)nc(N2CC[C@H](O)C2)c1C#N]

To a stirred solution of (S)-2-chloro-4-ethyl-6-(3-hydroxypyrrolidin-1-yl)pyridine-3,5-dicarbonitrile (synthesis described in example 418 step 1, 550 mg, 1.789 mmol) in N,N-dimethylformamide (DMF) (10 mL), was added potassium thioacetate (204 mg, 1.789 mmol) at room temperature. The reaction mixture was stirred for 2 h at the same temperature. Then potassium carbonate (247 mg, 1.789 mmol) was added followed by 2-amino-1-(4-fluorophenyl)-2-oxoethylmethanesulfonate (synthesis described in example 207 step 3, 750 mg, 2.022 mmol) at room temperature. The reaction mixture was stirred for 2 h. The reaction mixture was quenched with cold water (50 mL) and the obtained solid was filtered, washed with diethyl ether (2×20 mL), and dried under vacuum to obtain crude material. The crude material was triturated with 10% methanol in diethyl ether (30 mL) followed by n-pentane (30 mL) to obtain crude material. The crude compound was purified by silica gel column chromatography (100-200 mesh, eluted with 4% MeOH in DCM) to afford 2-((3,5-dicyano-4-ethyl-6-((S)-3-hydroxypyrrolidin-1-yl) pyridin-2-yl)thio)-2-(4-fluorophenyl)acetamide (300 mg, 38.7%) as an off white solid. LCMS (m/z)=426.00 [M+H]$^+$. $^1$H NMR (400 MHz, DMSO-d$_6$): δ ppm 7.90 (s, 1H), 7.58-7.52 (m, 2H), 7.30 (s, 1H), 7.21 (t, J=8.77 Hz, 2H), 5.65-5.62 (m, 1H), 5.14-5.11 (m, 1H), 4.43-4.40 (m, 1H), 4.02-3.65 (m, 4H), 2.74 (q, J=7.67 Hz, 2H), 2.07-1.85 (m, 2H), 1.20 (t, J=7.56 Hz, 3H).

Example 428

2-((3,5-dicyano-4-ethyl-6-((S-3-hydroxypyrrolidin-1-yl) pyridin-2-yl) thio-2-(2,6-difluorophenyl) acetamide Step 1: 2-(2,6-difluorophenyl)-2-hydroxyacetonitrile

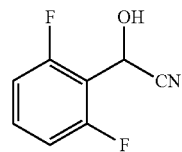 [SMILES: N#CC(O)c1c(F)cccc1F]

To a stirred solution of 2,6-difluorobenzaldehyde (2.0 g, 13.79 mmol) in DCM (40 mL) was added TMS-CN (3.77 mL, 27.6 mmol) followed by zinc iodide (0.889 g, 2.76 mmol) at room temperature. The reaction mixture was stirred at room temperature for 1 h. The reaction mixture was diluted with DCM (200 mL) and washed with water (50 mL), dried over anhydrous sodium sulfate, filtered, and concentrated under reduced pressure to afford crude 2-(2,6-difluorophenyl)-2-((trimethylsilyl) oxy) acetonitrile (2.5 g, 75%) as a crude yellow liquid. Used without further purification. To a stirred solution of 2-(2,6-difluorophenyl)-2-((trimethylsilyl)oxy)acetonitrile (2.3 g, 9.53 mmol) in DCM (30 mL) was added hydrochloric acid (14.30 mL, 28.6 mmol) in water (2M solution) at room temperature. The reaction mixture was stirred at room temperature for 30 min. Reaction progress was monitored by TLC. The reaction mixture was diluted with DCM (100 mL) and washed with water (50 mL), dried over anhydrous sodium sulfate, filtered and concentrated under reduced pressure. The crude material was triturated with the mixture of diethyl ether (10 mL) in pet ether (30 mL) to afford 2-(2,6-difluorophenyl)-2-hydroxyacetonitrile (1.5 g, 93%) as a yellow solid. $^1$H NMR (400 MHz, DMSO-d$_6$): δ ppm 7.77-7.41 (m, 1H), 7.29-7.08 (m, 3H), 5.93 (d, J=5.26 Hz, 1H).

Step 2: 2-(2,6-difluorophenyl)-2-hydroxyacetamide

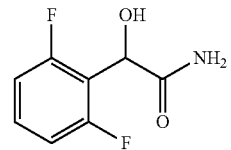 [SMILES: NC(=O)C(O)c1c(F)cccc1F]

To a stirred suspension of 2-(2,6-difluorophenyl)-2-hydroxyacetonitrile (1.4 g, 8.28 mmol) in dichloromethane (DCM) (20 mL) was added H$_2$SO$_4$ (0.882 mL, 16.56 mmol) at 0° C. under nitrogen atmosphere. The reaction mixture was stirred at 0° C. for 1.5 h. The reaction mixture was quenched with aq NaHCO$_3$ (70 mL) solution and extracted with ethyl acetate (3×200 mL). The combined organic layer was washed with brine (100 mL) solution, dried over anhydrous sodium sulfate, filtered and concentrated under reduced pressure. The crude material was triturated with diethyl ether (20 mL), filtered, and dried under vacuum to afford 2-(2,6-difluorophenyl)-2-hydroxyacetamide (800 mg, 51.6%) as an off white solid. ¹H NMR (400 MHz, DMSO-d$_6$): δ ppm 7.58-7.32 (m, 3H), 7.05 (t, J=8.44 Hz, 2H), 6.37 (d, J=5.48 Hz, 1H), 5.16 (d, J=5.26 Hz, 1H).

Step 3: 2-amino-1-(2,6-difluorophenyl)-2-oxoethyl methanesulfonate

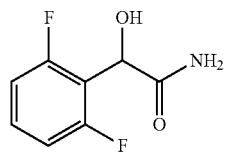 [SMILES: NC(=O)C(O)c1c(F)cccc1F]

To a stirred suspension of 2-(2,6-difluorophenyl)-2-hydroxyacetamide (800 mg, 4.27 mmol) in dichloromethane (DCM) (15 mL) was added triethylamine (1.216 mL, 8.55 mmol) and methane sulfonyl chloride (0.408 mL, 5.13 mmol) under nitrogen atmosphere at 0° C. The reaction was stirred at room temperature for 1 h. The reaction mixture was diluted with water (50 mL). The aqueous layer was extracted with ethyl acetate (3×100 mL). The combined organic layer (ethyl acetate only) was dried over anhydrous sodium sulfate, filtered and concentrated under reduced pressure to afford 2-amino-1-(2,6-difluorophenyl)-2-oxoethyl methanesulfonate (0.98 g, 77% yield) as a light pink solid. LCMS (m/z)=266.06 [M+H]⁺.

Step 4: 2-((3,5-dicyano-4-ethyl-6-((S)-3-hydroxy-pyrrolidin-1-yl) pyridin-2-yl)thio)-2-(2,6-difluorophenyl)acetamide

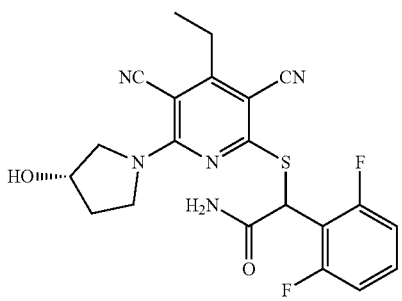 [SMILES: CCc1c(C#N)c(SC(C(N)=O)c2c(F)cccc2F)nc(N2CC[C@H](O)C2)c1C#N]

To a stirred solution of (S)-2-chloro-4-ethyl-6-(3-hydroxypyrrolidin-1-yl)pyridine-3,5-dicarbonitrile (synthesis described in example 418 step 1, 0.90 g, 2.93 mmol) in N,N-Dimethylformamide (DMF) (10 mL) was added potassium thioacetate (0.512 g, 4.39 mmol) at room temperature and the reaction mixture was stirred at the same temperature for 2 h. To the reaction mixture, potassium carbonate (0.619 g, 4.39 mmol) and 2-amino-1-(2,6-difluorophenyl)-2-oxoethylmethanesulfonate (0.872 g, 2.93 mmol) were added and stirred for 3 h at room temperature. The reaction mixture was poured into ice cold water (70 mL) and extracted with ethyl acetate (2×200 mL). The combined organic layer was washed with water (100 mL), brine solution (100 mL), dried over anhydrous sodium sulfate, filtered and concentrated under reduced. This crude material was purified by silica gel column chromatography (100-200 mesh, eluted with 4% MeOH in DCM) to obtain a pale brown solid. The pale brown solid was triturated with a mixture of methanol (1 mL) in diethyl ether (15 mL) to afford 2-((3,5-dicyano-4-ethyl-6-((S)-3-hydroxypyrrolidin-1-yl)pyridin-2-yl)thio)-2-(2,6-difluorophenyl)acetamide (148 mg, 11.38%) as an off-white solid. LCMS (m/z)=444.07 [M+H]⁺. ¹H NMR (400 MHz, DMSO-d$_6$): δ ppm 7.59 (s, 1H), 7.55-7.41 (m, 2H), 7.16 (t, J=8.44 Hz, 2H), 6.25-6.23 (m, 1H), 5.18-5.15 (m, 1H), 4.47-4.41 (m, 1H), 3.69-4.02 (m, 4H), 2.78 (q, J=7.53 Hz, 2H), 1.87-2.12 (m, 2H), 1.22 (t, J=7.34 Hz, 3H).

Example 429

2-((3,5-dicyano-4-ethyl-6-((S-3-hydroxypyrrolidin-1-yl) pyridin-2-yl) thio-2-(2,3-difluorophenyl) acetamide Step 1: 2-(2,3-difluorophenyl)-2-((trimethylsilyl)oxy) acetonitrile

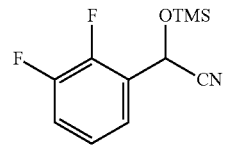

To a stirred solution of 2,3-difluorobenzaldehyde (5 g, 35.2 mmol) in dichloromethane (DCM) (60 mL) was added zinc iodide (2.246 g, 7.04 mmol) and TMS-CN (5.66 mL, 42.2 mmol) at room temperature. The reaction mixture was stirred at room temperature for 3 h. The reaction mixture was diluted with dichloromethane (50 mL) and washed with water (50 mL), dried over anhydrous sodium sulfate, filtered, and concentrated under reduced pressure to afford 2-(2,3-difluorophenyl)-2-((trimethylsilyl)oxy)acetonitrile (5.1 g, 54%). The crude material was used in the next step without purification. GC-MS (m/z)=241.1 [M]⁺.

Step 2: 2-(2,3-difluorophenyl)-2-hydroxyacetamide

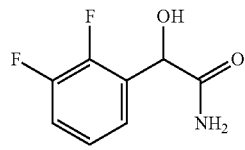

To a stirred solution of 2-(2,3-difluorophenyl)-2-((trimethylsilyl)oxy)acetonitrile (6 g, 24.86 mmol) in dichloromethane (DCM) (60 mL) was added sulfuric acid (5.325 mL, 100 mmol) at 0° C. The mixture stirred at room temperature for 2 h. Then ammonium hydroxide (10 mL, 257 mmol) was added at 0° C. and the resulting mixture was stirred at room temperature for 2 h. The reaction mixture was diluted with dichloromethane (100 mL) and washed with water (50 mL), dried over anhydrous sodium sulfate, filtered and concentrated under reduced pressure. The crude material was washed with n-pentane (3×20 mL) to afford 2-(2,3-difluorophenyl)-2-hydroxyacetamide (1.1 g, 21%) as an off-white solid. LCMS (m/z)=188.04 [M+H]⁺.

Step 3: 2-amino-1-(2,3-difluorophenyl)-2-oxoethyl methanesulfonate

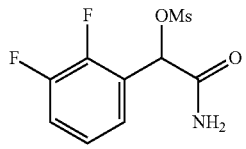

To a stirred suspension of 2-(2,3-difluorophenyl)-2-hydroxyacetamide (1 g, 5.34 mmol), TEA (2.234 mL, 16.03 mmol) in dichloromethane (DCM) (15 mL) was added methane sulfonyl chloride (0.833 mL, 10.69 mmol) at 0° C. under nitrogen atmosphere. The resulting mixture was stirred at 0° C. for 3 h. The reaction mixture was concentrated under reduced pressure, diluted with water (30 mL), and extracted with dichloromethane (2×100 mL). The combined organic layer was dried over anhydrous sodium sulfate, filtered, and concentrated under reduced pressure. The crude material was triturated with diethyl ether (3×20 mL), filtered and dried under vacuum to afford 2-amino-1-(2,3-difluorophenyl)-2-oxoethylmethanesulfonate (600 mg, 21%) as an off-white solid. LCMS (m/z)=266.25 [M+H]$^+$.

Step 4: 2-((3,5-dicyano-4-ethyl-6-((S)-3-hydroxypyrrolidin-1-yl) pyridin-2-yl)thio)-2-(2,3-difluorophenyl)acetamide

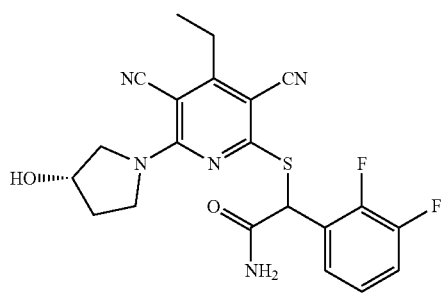 [SMILES: CCc1c(C#N)c(SC(C(N)=O)c2cccc(F)c2F)nc(N2CC[C@H](O)C2)c1C#N]

To a stirred solution of (S)-2-chloro-4-ethyl-6-(3-hydroxpyrrolidin-1-yl)pyridine-3,5-dicarbonitrile (synthesis described in example 418 step 1, 600 mg, 1.930 mmol) in N,N-dimethylformamide (DMF) (15 mL), potassium thioacetate (331 mg, 2.89 mmol) was added at room temperature and stirred for 2 h at room temperature. To the reaction mixture, potassium carbonate (533 mg, 3.86 mmol) and 2-amino-1-(2,3-difluorophenyl)-2-oxoethyl methanesulfonate (563 mg, 2.123 mmol) were added. After the reaction mixture stirred for 16 h at room temperature, it was diluted with water (20 mL) and extracted with ethyl acetate (2×200 mL). The combined organic layer was dried over anhydrous sodium sulfate, filtered and concentrated under reduced pressure. This crude material was purified by silica gel column chromatography (100-200 mesh, eluent, 60% ethyl acetate in pet ether) to afford 2-((3,5-dicyano-4-ethyl-6-((S)-3-hydroxypyrrolidin-1-yl)pyridin-2-yl)thio)-2-(2,3-difluorophenyl)acetamide (286 mg, 33.4%) as an off-white solid. LCMS (m/z)=444.13 [M+H]$^+$. $^1$H NMR (400 MHz, DMSO-d$_6$): δ ppm 7.91 (s, 1H), 7.52-7.39 (m, 2H), 7.37-7.30 (m, 1H), 7.29-7.19 (m, 1H), 5.92-5.90 (m, 1H), 5.19-5.09 (m, 1H), 4.43-4.38 (m, 1H), 3.98-3.63 (m, 4H), 2.76 (q, J=7.60 Hz, 2H), 2.05-1.86 (m, 2H), 1.21 (t, J=7.56 Hz, 3H).

Example 430

2-((3,5-dicyano-4-ethyl-6-((S-3-hydroxypyrrolidin-1-yl) pyridin-2-yl)thio-2-(2,4-difluorophenyl)acetamide

Step 1: 2-(2,4-difluorophenyl)-2-hydroxyacetamide

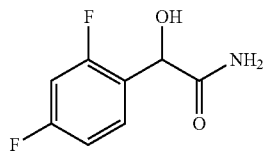 [SMILES: NC(=O)C(O)c1ccc(F)cc1F]

To a stirred solution of 2-(2,4-difluorophenyl)-2-hydroxyacetic acid (1 g, 5.21 mmol) in methanol (50 mL) was added acetyl chloride (1.17 mL, 15.63 mmol) at 0° C. The resulting reaction mixture was stirred at room temperature for 5 h. The reaction mixture was concentrated under reduced pressure. The crude material was dissolved in methanol (50 mL), and aq. ammonia (7.24 mL, 52.1 mmol) was added. The reaction mixture stirred at room temperature for 16 h. The reaction mixture was evaporated under reduced pressure, then cold ethanol (15 ml) was added and stirred for 5 minutes. The mixture was filtered to afford 2-(2,4-difluorophenyl)-2-hydroxyacetamide (800 mg, 74.7% yield) as an off-white solid. LCMS (m/z)=188.04 [M+H]$^+$. Used without further purification.

Step 2: 2-amino-1-(2,4-difluorophenyl)-2-oxoethyl methanesulfonate

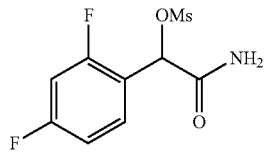

To a stirred solution of 2-(2,4-difluorophenyl)-2-hydroxyacetamide (0.800 g, 3.89 mmol) in dichloromethane (20 mL) was added triethylamine (3.39 mL, 12.57 mmol) and methanesulfonyl chloride (0.631 mL, 6.28 mmol) under nitrogen at 0° C. The reaction mixture was stirred at room temperature for 1 h. The reaction mixture was poured into ice cold water (15 mL) and extracted with dichloromethane (3×15 mL). The combined organic layer was dried over anhydrous sodium sulfate, filtered and evaporated under reduced pressure. The crude was triturated with diethyl ether (3×10 mL), filtered and dried under vacuum to afford 2-amino-1-(2,4-difluorophenyl)-2-oxoethyl methanesulfonate (1.3 g, 84% yield) as an off-white solid. LCMS (m/z)=266.10 [M+H]$^+$.

Step 3: 2-((3,5-dicyano-4-ethyl-6-((S)-3-hydroxy-pyrrolidin-1-yl) pyridin-2-yl) thio)-2-(2,4-difluorophenyl)acetamide

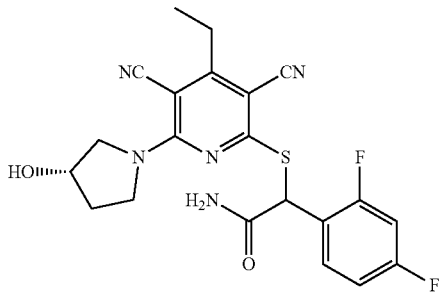 [SMILES: CCc1c(C#N)c(SC(C(N)=O)c2ccc(F)cc2F)nc(N2CC[C@H](O)C2)c1C#N]

To a solution of (S)-2-chloro-4-ethyl-6-(3-hydroxpyrrolidin-1-yl) pyridine-3,5-dicarbonitrile (synthesis described in example 418, step 1, 1.0 g, 3.25 mmol) in N,N-dimethylformamide (30 mL) was added potassium thioacetate (0.379 g, 3.25 mmol). The mixture was stirred at room temperature for 2 h, then treated with $K_2CO_3$ (1.198 g, 3.25 mmol) and 2-amino-1-(2,4-difluorophenyl)-2-oxoethyl methanesulfonate (1.198 g, 3.25 mmol). The mixture was stirred at room temperature for 16 h. The reaction mixture was poured in to ice-cold water (100 mL) and stirred for 30 min. Then it was extracted with DCM (3×20 mL). The combined organic layer was washed with brine solution (20 mL), dried over anhydrous sodium sulfate, filtered, and concentrated under reduced pressure. The crude compound was triturated with acetonitrile to afford 2-((3,5-dicyano-4-ethyl-6-((S)-3-hydroxypyrrolidin-1-yl) pyridin-2-yl)thio)-2-(2,4-difluorophenyl) acetamide (0.485 g, 33.3% yield) as an off-white solid. LCMS (m/z)=444.00 [M+H]$^+$. $^1$H NMR (400 MHz, DMSO-$d_6$): δ ppm 7.88 (s, 1H), 7.62-7.51 (m, 1H), 7.43 (s, 1H), 7.37-7.27 (m, 1H), 7.13 (t, J=8.55 Hz, 1H), 5.83 (s, 1H), 5.16-5.09 (m, 1H), 4.43-4.35 (m, 1H), 3.94-3.58 (m, 4H), 2.76 (q, J=7.31 Hz, 2H), 2.04-1.84 (m, 2H), 1.21 (t, J=7.56 Hz, 3H).

Example 431

(R)-2-((3,5-dicyano-4-ethyl-6-((2-hydroxyethyl)(methyl)amino)pyridin-2-yl)thio)-2-phenylacetamide

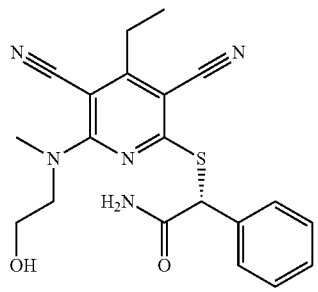

Peak 2

2-((3,5-dicyano-4-ethyl-6-((2-hydroxyethyl)(methyl)amino)pyridin-2-yl)thio)-2-phenylacetamide (500 mg, synthesis described in example 147) was dissolved in 30 mL of hot EtOH, and subjected to to normal-phase HPLC chiral separation using 60:30 n-heptane:ethanol solvent system (no modifier) on a Chiralpak AD-H, 5 microns column. The solvent was removed under reduced pressure to afford 230 mg of the second eluting peak. 2-((3,5-dicyano-4-ethyl-6-((2-hydroxyethyl)(methyl)amino)pyridin-2-yl)thio)-2-phenylacetamide. Comparing the observed VCD and IR spectra of the product with the calculated spectra of the modeled (R)-structure, the absolute configuration was assigned as (R)-. LCMS (m/z)=396.2 [M+H]$^+$. $^1$H NMR (400 MHz, DMSO-$d_6$) δ ppm 7.90 (s, 1H), 7.45-7.54 (m, 2H), 7.27-7.43 (m, 4H), 5.53 (s, 1H), 4.85 (t, J=5.45 Hz, 1H), 3.97-3.79 (m, 2H), 3.70-3.58 (m, 2H), 3.40 (s, 3H), 2.76 (q, J=7.52 Hz, 2H), 1.21 (t, J=7.60 Hz, 3H).

Example 432

2-((3,5-Dicyano-6-(4-(cyclobutyl(methyl)amino)piperidin-1-yl)-4-ethylpyridin-2-yl)thio)-2-(4-fluorophenyl)acetamide

Step 1: tert-Butyl 4-(cyclobutyl(methyl)amino)piperidine-1-carboxylate

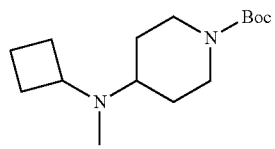 [SMILES: CN(C1CCC1)C1CCN(C(=O)OC(C)(C)C)CC1]

A mixture of N-methylcyclobutanamine (550 mg, 6.46 mmol) and tert-butyl 4-oxopiperidine-1-carboxylate (1287 mg, 6.46 mmol) was stirred in dichloromethane (20 mL) at room temperature for 20 minutes. Then AcOH (0.037 mL, 0.646 mmol) and sodium cyanoborohydride (609 mg, 9.69 mmol) was added. The mixture was stirred at room temperature for 16 hours. The reaction mixture was quenched with water, partitioned between dichloromethane 25 mL and water 25 mL. The organic phase was washed with water 10 mL for 3 times, dried over sodium sulphate and evaporated in vacuo to give tert-butyl 4-(cyclobutyl(methyl)amino)piperidine-1-carboxylate (600 mg) as a colourless oil. LCMS (m/z)=269.3 [M+H]$^+$.

Step 2: N-Cyclobutyl-N-methylpiperidin-4-amine

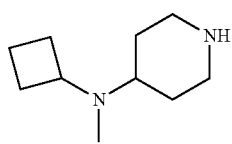

tert-Butyl 4-(cyclobutyl(methyl)amino)piperidine-1-carboxylate (580 mg, 2.161 mmol) was desolved in dichloromethane (15 mL). TFA (5 mL, 64.9 mmol) was added dropwise. The mixture was stirred at room temperature overninght. Solvent was removed in vacuo to afford N-cyclobutyl-N-methylpiperidin-4-amine (300 mg). LCMS (m/z)=169.3 [M+H]$^+$.

Step 3: 2-Chloro-6-(4-(cyclobutyl(methyl)amino)piperidin-1-yl)-4-ethylpyridine-3,5-dicarbonitrile

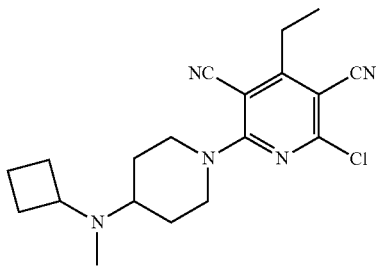 [SMILES: CCc1c(C#N)c(Cl)nc(N2CCC(N(C)C3CCC3)CC2)c1C#N]

N-Cyclobutyl-N-methylpiperidin-4-amine (150 mg, 0.891 mmol) and triethylamine (0.248 mL, 1.783 mmol) in DMF (10 mL) was added to 2,6-dichloro-4-ethylpyridine-3,5-dicarbonitrile (synthesis described in example 3, step 2, 202 mg, 0.891 mmol) in DMF (10 mL) dropwise at 0° C. The mixture was stirred at room temperature overninght. The reaction mixture was quenched with water, partitioned between ethyl acetate 50 mL and water 50 mL. The organic phase was washed with water 25 mL and saturated brine 25 mL, dried over sodium sulphate and evaporated in vacuo to give the crude product as a brown oil. The crude product was added to a silica gel column (4 g) and was eluted with CH$_2$Cl$_2$/MeOH (100/1) to afford 2-chloro-6-(4-(cyclobutyl(methyl)amino)piperidin-1-yl)-4-ethylpyridine-3,5-dicarbonitrile (160 mg). LCMS (m/z)=358.2 [M+H]$^+$.

Step 4: 2-((3,5-Dicyano-6-(4-(cyclobutyl(methyl)amino)piperidin-1-yl)-4-ethylpyridin-2-yl)thio)-2-(4-fluorophenyl)acetamide

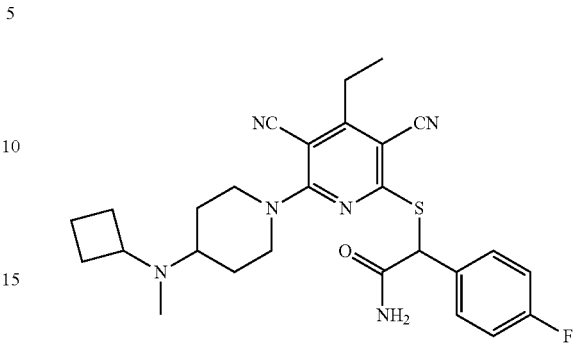

2-Chloro-6-(4-(cyclobutyl(methyl)amino)piperidin-1-yl)-4-ethylpyridine-3,5-dicarbonitrile (160 mg, 0.447 mmol) and potassium thioacetate (51.1 mg, 0.447 mmol) in N,N-dimethylformamide (20 mL) was stirred at room temperature for 30 minutes. Then 2-amino-1-(4-fluorophenyl)-2-oxoethyl methanesulfonate (synthesis described in example 207, step 3, 111 mg, 0.447 mmol) and triethylamine (0.125 mL, 0.894 mmol) was added. The mixture was stirred at room temperature overninght. The reaction mixture was quenched with water, partitioned between ethyl acetate 50 mL and water 50 mL. The organic phase was washed with water 25 mL, saturated brine 25 mL, dried over sodium sulphate and evaporated in vacuo to give the crude product as a brown oil. The crude product was added to a silica gel column (12 g) and was eluted with CH$_2$Cl$_2$/MeOH. The solvent was evaporated in vacuo to give 2-((3,5-dicyano-6-(4-(cyclobutyl(methyl)amino)piperidin-1-yl)-4-ethylpyridin-2-yl)thio)-2-(4-fluorophenyl)acetamide (45 mg) as a light brown solid. LCMS (m/z)=507.3 [M+H]$^+$. $^1$H NMR (400 MHz, MeOD) δ 7.59 (dd, J=8.4, 5.3 Hz, 2H), 7.17 (t, J=8.6 Hz, 2H), 5.54 (s, 1H), 4.89-4.79 (m, 2H), 3.91-3.80 (m, 1H), 3.59-3.48 (m, 1H), 3.24 (dd, J=26.5, 13.4 Hz, 2H), 2.93 (q, J=7.5 Hz, 2H), 2.62 (s, 3H), 2.41-2.20 (m, 4H), 2.13-2.01 (m, 2H), 1.97-1.76 (m, 4H), 1.32 (t, J=7.5 Hz, 3H).

The compounds in Table 1 below (Examples 441 to 696) were made generally according to the above procedures and are readily made by those of skill in the art. As used in the table below and throughout the specification, stereocenters marked with "or1" indicate a single unidentified stereocenter.

| Example | Structure/Name | LCMS m/z | 1H NMR |
|---|---|---|---|
| 441 | | 505.3 [M + H]$^+$ | $^1$H NMR (400 MHz, CDCl$_3$) δ 7.54-7.45 (m, 2H), 7.45-7.34 (m, 3H), 6.64-6.47 (m, 1H), 5.97-5.66 (m, 1H), 5.42-5.34 (m, 1H), 4.79-4.66 (m, 2H), 3.77-3.54 (m, 1H), 3.48-3.35 (m, 1H), 3.26-3.05 (m, 11.2 Hz, 4H), 2.94 (q, J = 7.6 Hz, 3H), 2.73-2.58 (m, 1H), 2.14-1.98 (m, 2H), 1.98-1.62 (m, 7H), 1.35 (t, J = 7.6 Hz, 3H). |

| Example | Structure/Name | LCMS m/z | 1H NMR |
|---|---|---|---|
| | 2-((3,5-dicyano-4-ethyl-6-(4-((S)-2-(hydroxymethyl)pyrrolidin-1-yl)piperidin-1-yl)pyridin-2-yl)thio)-2-phenylacetamide | | |
| 443 | 2-((3,5-dicyano-4-ethyl-6-(4-((2-hydroxyethyl)(methyl)amino)piperidin-1-yl)pyridin-2-yl)thio)-2-phenylacetamide | 479.3 [M + H]+ | $^1$H NMR (400 MHz, CDCl$_3$) δ 7.51-7.45 (m, 2H), 7.44-7.35 (m, 3H), 6.57 (s, 1H), 5.90 (s, 1H), 5.40 (s, 1H), 4.76 (d, J = 13.3 Hz, 2H), 3.65 (t, J = 5.2 Hz, 2H), 3.12 (dd, J = 22.3, 11.5 Hz, 2H), 2.94 (q, J = 7.6 Hz, 2H), 2.88-2.61 (m, 4H), 2.38 (s, 3H), 2.01 (d, J = 12.0 Hz, 2H), 1.75-1.57 (m, 2H), 1.35 (t, J = 7.6 Hz, 3H). |
| 444 | 2-((3,5-dicyano-4-ethyl-6-(4-((2-hydroxy-2-methylpropyl)(methyl)amino)piperidin-1-yl)pyridin-2-yl)thio)-2-phenylacetamide | 507.0 [M + H]+ | $^1$H NMR (400 MHz, CDCl$_3$) δ 7.54-7.45 (m, 2H), 7.45-7.34 (m, 3H), 6.64 (s, 1H), 6.35 (s, 1H), 5.40 (s, 1H), 4.77 (d, J = 13.0 Hz, 2H), 3.23-3.11 (m, 1H), 3.11-2.98 (m, 2H), 2.93 (q, J = 7.5 Hz, 2H), 2.82-2.50 (m, 5H), 2.21-2.01 (m, 3H), 1.90-1.76 (m, 1H), 1.76-1.61 (m, 1H), 1.39-1.23 (m, 9H). |
| 445 | 2-((3,5-dicyano-4-ethyl-6-(4-(pyrrolidin-1-ylmethyl)piperidin-1-yl)pyridin-2-yl)thio)-2-phenylacetamide | 488.8 [M + H]+ | $^1$H NMR (400 MHz, CDCl$_3$) δ 7.52-7.46 (m, 2H), 7.43-7.35 (m, 3H), 6.76 (s, 1H), 5.86 (s, 1H), 5.43 (s, 1H), 4.68 (d, J = 13.4 Hz, 2H), 3.16 (t, J = 13.0 Hz, 2H), 2.91 (q, J = 7.6 Hz, 2H), 2.79-2.48 (m, 6H), 2.01-1.89 (m, 7H), 1.43-1.29 (m, 5H). |

| Example | Structure/Name | LCMS m/z | 1H NMR |
|---|---|---|---|
| 446 | 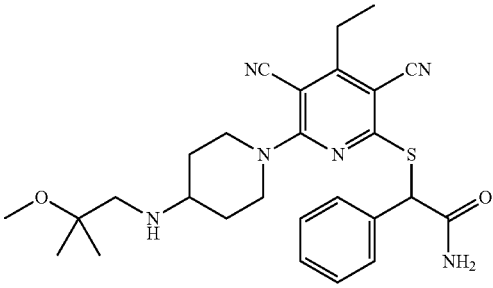<br>2-((3,5-dicyano-4-ethyl-6-(4-((2-methoxy-2-methylpropyl)amino)piperidin-1-yl)pyridin-2-yl)thio)-2-phenylacetamide | 506.8 [M + H]⁺ | $^1$H NMR (400 MHz, DMSO) δ 8.52 (br. s, 1H), 8.03 (br. s, 1H), 7.54 (d, J = 7.3 Hz, 2H), 7.45-7.31 (m, 4H), 5.59 (s, 1H), 4.66 (s, 2H), 3.17 (s, 6H), 3.05 (s, 2H), 2.78 (q, J = 7.5 Hz, 2H), 2.21 (m, 2H), 1.68 (br. s, 2H), 1.22 (m, 9H). |
| 447 | 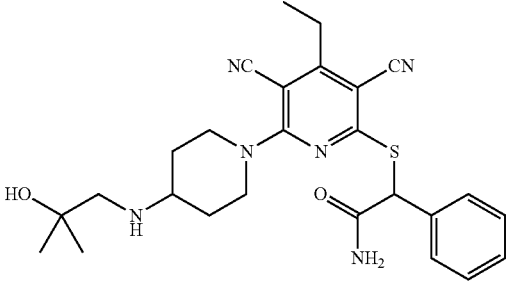<br>2-((3,5-dicyano-4-ethyl-6-(4-((2-hydroxy-2-methylpropyl)amino)piperidin-1-yl)pyridin-2-yl)thio)-2-phenylacetamide | 492.9 [M + H]⁺ | $^1$H NMR (400 MHz, MeOD) δ 7.55 (d, J = 6.7 Hz, 2H), 7.47-7.35 (m, 3H), 5.52 (s, 1H), 4.69 (t, J = 12.0 Hz, 2H), 3.27-3.24 (m, 2H), 2.94-2.89 (m, 3H), 2.72 (s, 2H), 2.13-2.10 (m, 2H), 1.57-1.53 (m, 2H), 1.37-1.23 (m, 9H). |
| 448 | 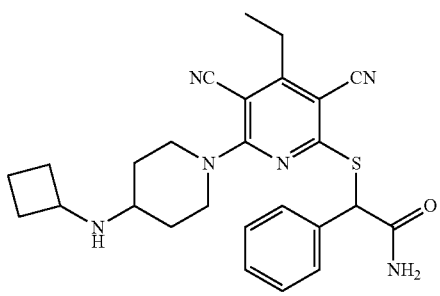<br>2-((3,5-dicyano-6-(4-(cyclobutylamino)piperidin-1-yl)-4-ethylpyridin-2-yl)thio)-2-phenylacetamide | 475.0 [M + H]⁺ | $^1$H NMR (400 MHz, DMSO-d₆) δ 7.94 (s, 1H), 7.53-7.51 (m, 2H), 7.41-7.32 (m, 4H), 5.53 (s, 1H), 4.44-4.40 (m, 2H), 3.34-3.26 (m, 3H), 2.76 (s, 1H), 2.73 (q, J = 7.4 Hz, 2H), 2.14 (m, 2H), 1.89-1.64 (m, 6H), 1.35 (m, 2H), 1.22 (t, J = 7.6 Hz, 3H). |

| Example | Structure/Name | LCMS m/z | 1H NMR |
|---|---|---|---|
| 449 | 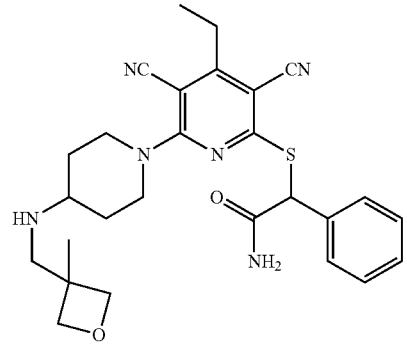 [SMILES: CCc1c(C#N)c(SC(C(N)=O)c2ccccc2)nc(N2CCC(NCC3(C)COC3)CC2)c1C#N]<br>2-((3,5-dicyano-4-ethyl-6-(4-(((3-methyloxetan-3-yl)methyl)amino)piperidin-1-yl)pyridin-2-yl)thio)-2-phenylacetamide | 504.8 [M + H]+ | $^1$H NMR (400 MHz, CDCl$_3$) δ 7.51-7.44 (m, 2H), 7.45-7.35 (m, 3H), 6.58 (br. s, 1H), 5.75 (br. s, 1H), 5.39 (s, 1H), 4.59-4.49 (m, 2H), 4.47 (d, J = 5.8 Hz, 2H), 4.40 (d, J = 5.8 Hz, 2H), 3.41-3.35 (m, 2H), 2.99-2.84 (m, 5H), 2.10 (br. s, 2H), 1.62-1.47 (m, 2H), 1.38-1.30 (m, 6H). |
| 450 | 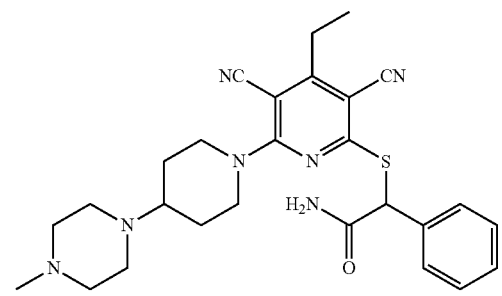 [SMILES: CCc1c(C#N)c(SC(C(N)=O)c2ccccc2)nc(N2CCC(N3CCN(C)CC3)CC2)c1C#N]<br>2-((3,5-dicyano-4-ethyl-6-(4-(4-methylpiperazin-1-yl)piperidin-1-yl)pyridin-2-yl)thio)-2-phenylacetamide | 503.9 [M + H]+ | $^1$H NMR (400 MHz, CDCl$_3$) δ 7.48 (d, J = 6.9 Hz, 2H), 7.42-7.30 (m, 3H), 6.54 (br. s, 1H), 5.67 (br. s, 1H), 5.40 (s, 1H), 4.71 (d, J = 13.7 Hz, 2H), 3.18 (dd, J = 23.0, 11.3 Hz, 2H), 2.93 (q, J = 7.3 Hz, 2H), 2.86-2.56 (m, 9H), 2.41 (s, 3H), 2.19-2.02 (m, 2H), 1.73-1.60 (m, 2H), 1.34 (t, J = 7.6 Hz, 3H). |
| 451 | 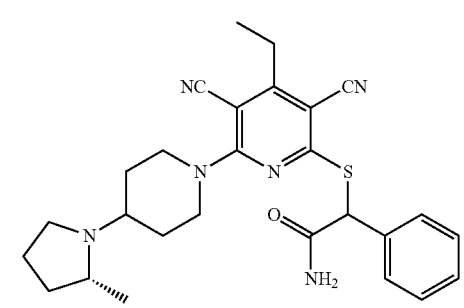 [SMILES: CCc1c(C#N)c(SC(C(N)=O)c2ccccc2)nc(N2CCC(N3CCC[C@H]3C)CC2)c1C#N]<br>2-((3,5-dicyano-4-ethyl-6-(4-((R)-2-methylpyrrolidin-1-yl)piperidin-1-yl)pyridin-2-yl)thio)-2-phenylacetamide | 489.0 [M + H]+ | $^1$H NMR (400 MHz, MeOD) δ 7.56 (d, J = 7.2 Hz, 2H), 7.47-7.37 (m, 3H), 5.53 (s, 1H), 4.90-4.80 (m, 2H), 3.92-3.79 (s, 1H), 3.69-3.59 (m, 1H), 3.54-3.42 (m, 1H), 3.31-3.13 (m, 3H), 2.93 (q, J = 7.5 Hz, 2H), 2.36-2.16 (m, 3H), 2.15-2.02 (m, 2H), 1.88-1.72 (m, 3H), 1.45 (d, J = 5.9 Hz, 3H), 1.32 (t, J = 7.6 Hz, 3H). |
| 452 | 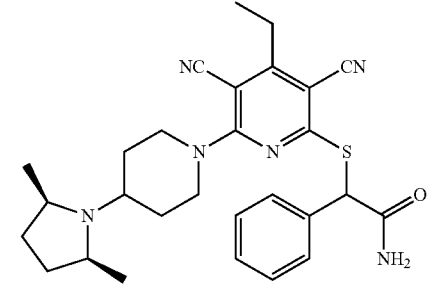 [SMILES: CCc1c(C#N)c(SC(C(N)=O)c2ccccc2)nc(N2CCC(N3[C@H](C)CC[C@@H]3C)CC2)c1C#N] | 502.9 [M + H]+ | $^1$H NMR (400 MHz, DMSO) δ 7.95 (s, 1H), 7.53 (d, J = 7.2 Hz, 2H), 7.44-7.29 (m, 4H), 5.56 (s, 1H), 4.77-4.59 (m, 2H), 3.18-2.82 (m, 5H), 2.75 (q, J = 7.4 Hz, 2H), 1.90-1.64 (m, 4H), 1.50-1.30 (m, 4H), 1.21 (t, J = 7.6 Hz, 3H), 1.01 (s, 6H). |

| Example | Structure/Name | LCMS m/z | 1H NMR |
|---|---|---|---|
| 453 | 2-((3,5-dicyano-6-(4-((2R,5S)-2,5-dimethylpyrrolidin-1-yl)piperidin-1-yl)-4-ethylpyridin-2-yl)thio)-2-phenylacetamide | 489.2 [M + H]+ | 1H NMR (400 MHz, MeOD) δ 7.56 (d, J = 6.9 Hz, 2H), 7.47-7.39 (m, 3H), 5.52 (s, 1H), 4.89-4.77 (m, 2H), 3.84-3.74 (m, 1H), 3.64-3.54 (m, 1H), 3.49-3.38 (m, 1H), 3.29-3.16 (m, 3H), 2.92 (q, J = 7.6 Hz, 2H), 2.31-2.16 (m, 3H), 2.10-2.01 (m, 2H), 1.85-1.72 (m, 3H), 1.42 (s, 3H), 1.32 (t, J = 7.6 Hz, 3H). |
| 454 | 2-((3,5-dicyano-4-ethyl-6-(4-((S)-2-methylpyrrolidin-1-yl)piperidin-1-yl)pyridin-2-yl)thio)-2-phenylacetamide | 489.0 [M + H]+ | 1H NMR (400 MHz, MeOD) δ 7.56 (d, J = 7.1 Hz, 2H), 7.46-7.39 (m, 3H), 5.52 (s, 1H), 4.90-4.85 (m, 2H), 3.95-3.91 (m, 1H), 3.65-3.61 (m, 1H), 3.24-3.19 (m, 2H), 2.91 (q, J = 7.6 Hz, 2H), 2.68 (s, 3H), 2.38-2.29 (m, 4H), 1.95-1.87 (m, 2H), 1.85-1.75 (m, 4H), 1.31 (t, J = 7.6 Hz, 3H). |
| 455 | 2-((3,5-dicyano-6-(4-(cyclobutyl(methyl)amino)piperidin-1-yl)-4-ethylpyridin-2-yl)thio)-2-phenylacetamide | 510.8 [M + H]+ | 1H NMR (400 MHz, DMSO) δ 7.92 (s, 1H), 7.52 (d, J = 7.2 Hz, 2H), 7.49-7.09 (m, 10H), 5.54 (s, 1H), 4.41 (d, J = 10.8 Hz, 2H), 3.80 (s, 2H), 3.37 (m, 1H), 3.30 (m, 1H), 2.79-2.73 (m, 3H), 2.04-1.92 (m, 2H), 1.50-1.32 (m, 2H), 1.21 (t, J = 7.6 Hz, 3H). |

2-(6-(4-(benzylamino)piperidin-1-yl)-3,5-dicyano-4-ethylpyridin-2-ylthio)-2-phenylacetamide

| Example | Structure/Name | LCMS m/z | 1H NMR |
|---|---|---|---|
| 456 | 2-((3,5-dicyano-4-ethyl-6-(4-(((6-methoxypyridin-2-yl)methyl)amino)piperidin-1-yl)pyridin-2-yl)thio)-2-phenylacetamide | 542.3 [M + H]+ | $^1$H NMR (400 MHz, DMSO) δ 7.93 (s, 1H), 7.69 (t, J = 7.8 Hz, 1H), 7.52 (d, J = 7.2 Hz, 2H), 7.43-7.30 (m, 4H), 7.06 (d, J = 7.2 Hz, 1H), 6.69 (d, J = 8.0 Hz, 1H), 5.54 (s, 1H), 4.49-4.36 (m, 2H), 3.97-3.73 (m, 5H), 3.33-3.26 (m, 3H), 2.94-2.81 (m, 1H), 2.76 (q, J = 7.5 Hz, 2H), 2.06-1.93 (m, 2H), 1.51-1.36 (m, 2H), 1.21 (t, J = 7.6 Hz, 3H). |
| 457 | 2-((3,5-dicyano-4-ethyl-6-(4-((S)-3-fluoropyrrolidin-1-yl)piperidin-1-yl)pyridin-2-yl)thio)-2-phenylacetamide | 492.9 [M + H]+ | $^1$H NMR (400 MHz, MeOD) δ 7.55 (d, J = 6.7 Hz, 2H), 7.47-7.34 (m, 3H), 5.53 (s, 1H), 5.30 (m, 0.5H), 5.15 (m, 0.5H), 4.75-4.65 (m, 2H), 3.24 (t, J = 12.9 Hz, 2H), 3.17-3.00 (m, 2H), 2.91 (q, J = 7.6 Hz, 2H), 2.80 (ddd, J = 32.1, 12.0, 5.0 Hz, 1H), 2.61-2.45 (m, 2H), 2.23 (dtd, J = 20.7, 14.6, 6.3 Hz, 1H), 2.15-1.98 (m, 3H), 1.67-1.53 (m, 2H), 1.31 (t, J = 7.6 Hz, 3H). |
| 458 | N-(4-(((3,5-dicyano-4-ethyl-6-(methyl(2-(neopentylamino)ethyl)amino)pyridin-2-yl)thio)methyl)phenyl)-N-methylmethanesulfonamide | 529.3 [M + H]+ | $^1$H NMR (400 MHz, MeOD) δ 7.47 (d, J = 8.6 Hz, 2H), 7.41 (d, J = 8.6 Hz, 2H), 4.57 (s, 2H), 3.93 (t, J= 7.0 Hz, 2H), 3.43 (s, 3H), 3.31 (s, 3H), 2.99-2.86 (m, 7H), 2.36 (s, 2H), 1.32 (t, J = 7.6 Hz, 3H), 0.88 (s, 9H). |

| Example | Structure/Name | LCMS m/z | 1H NMR |
|---|---|---|---|
| 459 | 2-((3,5-dicyano-4-ethyl-6-(methyl(2-((R)-2-methylpyrrolidin-1-yl)ethyl)amino)pyridin-2-yl)thio)-2-phenylacetamide | 463.3 [M + H]+ | $^1$H NMR (400 MHz, MeOD) δ 7.55 (t, J = 5.7 Hz, 2H), 7.47-7.34 (m, 3H), 5.53-5.57 (m, 1H), 4.31-3.99 (m, 2H), 3.98-3.86 (m, 1H), 3.64-3.35 (m, 5H), 3.13-2.66 (m, 4H), 2.28-2.08 (m, 1H), 2.05-1.83 (m, 2H), 1.60 (s, 1H), 1.32 (t, J = 7.5 Hz, 6H). |
| 460 | 2-((3,5-dicyano-4-ethyl-6-(4-((R)-3-fluoropyrrolidin-1-yl)piperidin-1-yl)pyridin-2-yl)thio)-2-phenylacetamide | 493.3 [M + H]+ | $^1$H NMR (400 MHz, CDCl$_3$) δ 7.50-7.44 (m, 2H), 7.44-7.35 (m, 3H), 6.60 (s, 1H), 5.62 (br. s, 1H), 5.38 (s, 1H), 5.29-5.15 (m, 1H), 4.69-4.51 (m, 2H), 3.35 (t, J = 11.4 Hz, 2H), 3.13-2.70 (m, 5H), 2.65-2.38 (m, 2H), 2.25-1.98 (m, 4H), 1.80-1.61 (m, 2H), 1.35 (t, J = 7.6 Hz, 3H). |
| 461 | N-(4-(((3,5-dicyano-4-ethyl-6-methoxyethyl)(methyl)amino)ethyl)(methyl)amino)pyridin-2-yl)thio)methyl)phenyl)-N-methylmethanesulfonamide | 531.3 [M + H]+ | $^1$H NMR (400 MHz, MeOD) δ 7.46 (d, J = 8.6 Hz, 2H), 7.41 (d, J = 8.6 Hz, 2H), 4.57 (s, 2H), 3.93 (t, J = 7.2 Hz, 2H), 3.47-3.42 (m, 5H), 3.31 (s, 3H), 3.29 (s, 3H), 2.95-2.87 (m, 5H), 2.76 (t, J = 7.1 Hz, 2H), 2.62 (t, J = 5.5 Hz, 2H), 2.32 (s, 3H), 1.32 (t, J = 7.6 Hz, 3H). |
| 462 | | 503.0 [M + H]+ | $^1$H NMR (400 MHz, MeOD) δ 7.55 (d, J = 7.6 Hz, 2H), 7.45-7.35 (m, 3H), 5.53 (s, 1H), 4.84-4.70 (m, 2H), 3.64-3.40 (m, 2H), 3.24-3.05 (m, , 3H), 2.91 (q, J = 7.6 Hz, 2H), 2.24-2.07 (m, 4H), 1.76-1.47 (m, 4H), 1.32 (t, J = 7.6 Hz, 3H), 1.19 (s, 6H). |

| Example | Structure/Name | LCMS m/z | 1H NMR |
|---|---|---|---|
| 463 | 2-((3,5-dicyano-6-(4-((2S,5S)-2,5-dimethylpyrrolidin-1-yl)piperidin-1-yl)-4-ethylpyridin-2-yl)thio)-2-phenylacetamide | 463.3 [M + H]⁺ | ¹H NMR (400 MHz, MeOD) δ 7.57 (t, J = 6.6 Hz, 2H), 7.53-7.25 (m, 3H), 5.52-5.47 (m, 1H), 4.36-3.93 (m, 2H), 3.86-3.56 (m, 3H), 3.56-3.48 (m, 3H), 3.42-3.16 (m, 2H), 2.96 (q, J = 7.6 Hz, 2H), 2.44-2.29 (m, 1H), 2.24-2.03 (m, 2H), 1.89-1.67 (m, 1H), 1.51 (s, 3H), 1.33 (t, J = 7.6 Hz, 3H). |
| 464 | 2-((3,5-dicyano-4-ethyl-6-(methyl(2-((S)-2-methylpyrrolidin-1-yl)ethyl)amino)pyridin-2-yl)thio)-2-phenylacetamide | 505.3 [M + H]⁺ | ¹H NMR (400 MHz, CDCl₃) δ 7.48 (d, J = 6.5 Hz, 2H), 7.45-7.35 (m, 3H), 6.64-6.53 (m, 1H), 5.90-5.75 (m, 1H), 5.42-5.35 (m, 1H), 4.80-4.67 (m, 2H), 3.76-3.38 (m, 3H), 3.22-3.06 (m, 4H), 3.00-2.83 (m, 3H), 2.67-2.62 (m, 1H), 2.11-1.99 (m, 2H), 1.92-1.68 (m, 6H), 1.35 (t, J = 7.6 Hz, 3H). |
| 465 | ISOMER 1 2-((3,5-dicyano-4-ethyl-6-(4-((R)-2-(hydroxymethyl)pyrrolidin-1-yl)piperidin-1-yl)pyridin-2-yl)thio)-2-phenylacetamide | 467.1 [M + H]⁺ | ¹H NMR (DMSO-d₆) δ 9.94 (br. s., 1H), 7.99 (br. s., 1H), 7.57 (dd, J = 8.4, 5.6 Hz, 2H), 7.43 (br. s., 1H), 7.26 (t, J = 8.7 Hz, 2H), 5.58 (s, 1H), 4.73 (d, J = 11.2 Hz, 2H), 3.51 (br. s., 1H), 3.08-3.22 (m, 2H), 2.77 (d, J = 4.6 Hz, 8H), 2.38-2.49 (m, 1H), 2.14 (d, J = 10.6 Hz, 2H), 1.53-1.77 (m, 2H), 1.22 (t, J = 7.5 Hz, 3H) |
|  | 2-((3,5-dicyano-6-(4-(dimethylamino)piperidin-1-yl)-4-ethylpyridin-2-yl)thio)-2-(4-fluorophenyl)acetamide, Formic acid salt |  |  |

| Example | Structure/Name | LCMS m/z | 1H NMR |
|---|---|---|---|
| 466 | 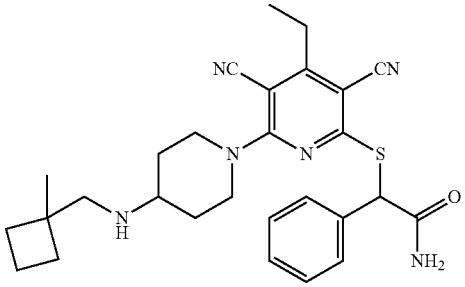 [SMILES: CCc1c(C#N)c(SC(C(N)=O)c2ccccc2)nc(N2CCC(NCC3(C)CCC3)CC2)c1C#N]<br>2-((3,5-dicyano-4-ethyl-6-(4-(((1-methylcyclobutyl)methyl)amino)piperidin-1-yl)pyridin-2-yl)thio)-2-phenylacetamide | 502.7 [M + H]$^+$ | $^1$H NMR (400 MHz, MeOD) δ 7.56 (d, J = 7.1 Hz, 2H), 7.48-7.37 (m, 3H), 5.51 (s, 1H), 4.83 (t, J = 15.8 Hz, 2H), 3.51-3.36 (m, 1H), 3.23 (t, J = 13.2 Hz, 2H), 3.12 (s, 2H), 2.94 (q, J = 7.6 Hz, 2H), 2.33-2.26 (m, 2H), 2.11-1.95 (m, 4H), 1.91-1.82 (m, 2H), 1.79-1.68 (m, 2H), 1.36-1.27 (m, 6H). |
| 467 | 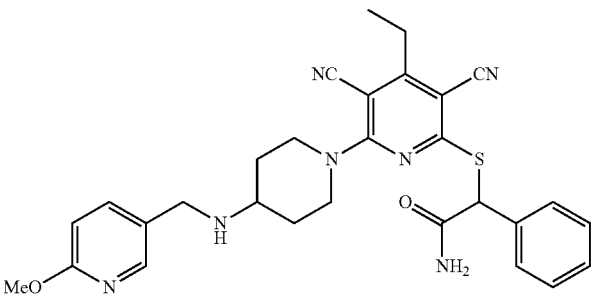 [SMILES: CCc1c(C#N)c(SC(C(N)=O)c2ccccc2)nc(N2CCC(NCc3ccc(OC)nc3)CC2)c1C#N]<br>2-((3,5-dicyano-4-ethyl-6-(4-(((6-methoxypyridin-3-yl)methyl)amino)piperidin-1-yl)pyridin-2-yl)thio)-2-phenylacetamide | 542.3 [M + H]$^+$ | $^1$H NMR (400 MHz, MeOD) δ 8.22 (s, 1H), 7.80 (d, J = 8.5 Hz, 1H), 7.55 (d, J = 6.8 Hz, 2H), 7.48-7.32 (m, 3H), 6.87 (d, J = 8.6 Hz, 1H), 5.52 (s, 1H), 4.75 (t, J = 13.3 Hz, 2H), 4.04 (s, 2H), 3.94 (s, 3H), 3.29-3.14 (m, 3H), 2.92 (q, J = 7.6 Hz, 2H), 2.23 (d, J = 12.5 Hz, 2H), 1.67-1.57 (m, 2H), 1.32 (t, J = 7.6 Hz, 3H). |
| 468 | 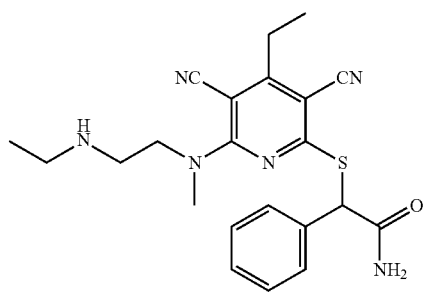 [SMILES: CCNCCN(C)c1nc(SC(C(N)=O)c2ccccc2)c(C#N)c(CC)c1C#N]<br>2-(3,5-dicyano-4-ethyl-6-((2-(ethylamino)ethyl)(methyl)amino)pyridin-2-ylthio)-2-phenylacetamide | 422.9 [M + H]$^+$ | $^1$H NMR (400 MHz, CDCl$_3$) δ ppm 7.50-7.45 (m, 2H), 7.44-7.37 (m, 3H), 7.23 (s, 1H), 5.86 (s, 1H), 5.38 (s, 1H), 4.02-3.94 (m, 1H), 3.92-3.84 (m, 1H), 3.51 (S, 3H), 3.05-2.97 (m, 2H), 2.97-2.91 (m, 2H), 2.79 (q, J = 7.0 Hz, 2H), 1.34 (t, J = 7.6 Hz, 3H), 1.18 (t, J = 7.1 Hz, 3H). |

| Example | Structure/Name | LCMS m/z | 1H NMR |
|---|---|---|---|
| 469 | 2-((3,5-dicyano-4-ethyl-6-(4-((4-methylpiperazin-1-yl)methyl)piperidin-1-yl)pyridin-2-yl)thio)-2-phenylacetamide | 517.9 [M + H]+ | $^1$H NMR (400 MHz, CDCl$_3$) δ 7.49-7.47 (m, 2H), 7.44-7.38 (m, 3H), 6.54 (s, 1H), 5.55 (s, 1H), 5.41 (s, 1H), 4.68 (d, J = 13.4 Hz, 2H), 3.20-3.09 (m, 2H), 2.93 (q, J = 7.6 Hz, 2H), 2.67-2.46 (m, 7H), 2.39 (s, 3H), 2.28 (d, J = 7.0 Hz, 2H), 2.04-1.79 (m, 4H), 1.36-1.27 (m, 5H). |
| 470 | 2-((3,5-dicyano-4-ethyl-6-(methyl(2-(methylamino)ethyl)amino)pyridin-2-yl)thio)-2-phenylacetamide | 409.3 [M + H]+ | $^1$H NMR (400 MHz, CDCl$_3$) δ ppm 7.50-7.45 (m, 2H), 7.44-7.37 (m, 3H), 7.25 (s, 1H), 6.21 (br. s, 1H), 5.41 (s, 1H), 3.98 (dt, J = 14.0, 6.9 Hz, 1H), 3.83 (dt, J = 14.1, 7.2 Hz, 1H), 3.48? (s, 3H), 2.99-2.86 (m, 4H), 2.54-2.44 (m, 4H), 1.34 (t, J = 7.6 Hz, 3H). |
| 471 | N-(4-(((3,5-dicyano-4-ethyl-6-(methyl(2-(methylamino)ethyl)amino)pyridin-2-yl)thio)methyl)phenyl)-N-methylmethanesulfonamide | 473.2 [M + H]+ | $^1$H NMR (400 MHz, MeOD) δ 7.49 (d, J = 8.6 Hz, 2H), 7.43 (d, J = 8.6 Hz, 2H), 4.58 (s, 2H), 4.04 (t, J = 6.6 Hz, 2H), 3.50 (s, 3H), 3.32 (s, 3H), 3.24 (t, J = 6.6 Hz, 2H), 2.99-2.90 (m, 5H), 2.67 (s, 3H), 1.33 (t, J = 7.6 Hz, 3H). |
| 472 | | 502.7 [M + H]+ | $^1$H NMR (400 MHz, MeOD) δ 7.55 (d, J = 7.5 Hz, 2H), 7.46-7.36 (m, 3H), 5.53 (s, 1H), 4.82-4.69 (m, 2H), 3.51-3.38 (m, 2H), 3.23-3.12 (m, 2H), 3.08-2.98 (m, 1H), 2.91 (q, J = 7.6 Hz, 2H), 2.28-2.08 (m, 4H), 1.76-1.62 (m, 2H), 1.55-1.44 (m, 2H), 1.32 (t, J = 7.6 Hz, 3H), 1.15 (d, J = 5.8 Hz, 6H). |

| Example | Structure/Name | LCMS m/z | 1H NMR |
|---|---|---|---|
| | 2-((3,5-dicyano-6-(4-((2R,5R)-2,5-dimethylpyrrolidin-1-yl)piperidin-1-yl)-4-ethylpyridin-2-yl)thio)-2-phenylacetamide | | |
| 473 | 2-((3,5-dicyano-4-ethyl-6-(4-(((1-methylcyclopropyl)methyl)amino)piperidin-1-yl)pyridin-2-yl)thio)-2-phenylacetamide | 489.3 [M + H]⁺ | ¹H NMR (400 MHz, MeOD) δ 7.56 (d, J = 6.7 Hz, 2H), 7.49-7.34 (m, 3H), 5.52 (s, 1H), 4.81 (t, J = 13.9 Hz, 2H), 3.51-3.37 (m, 1H), 3.29-3.12 (m, 2H), 3.05-2.84 (m, 4H), 2.27 (d, J = 12.3 Hz, 2H), 1.81-1.64 (m, 2H), 1.32 (t, J = 7.6 Hz, 3H), 1.25 (s, 3H), 0.66 (t, J = 5.1 Hz, 2H), 0.56 (t, J = 5.2 Hz, 2H). |
| 474 | 2-((3,5-dicyano-4-ethyl-6-(4-((4-fluorobenzyl)amino)piperidin-1-yl)pyridin-2-yl)thio)-2-phenylacetamide | 528.8 [M + H]⁺ | ¹H NMR (400 MHz, DMSO) δ 9.30 (s, 1H), 8.00 (s, 1H), 7.72-7.63 (m, 2H), 7.54 (d, J = 7.3 Hz, 2H), 7.39-7.29 (m, 6H), 5.58 (s, 1H), 4.65 (d, J = 13.2 Hz, 2H), 4.22 (s, 2H), 3.49-3.39 (m, 1H), 3.22 (t, J = 12.8 Hz, 2H), 2.78 (q, J = 7.6 Hz, 2H), 2.27-2.24 (m, 2H), 1.73-1.66 (m, 2H), 1.22 (t, J = 7.6 Hz, 3H). |
| 475 | 2-((3,5-dicyano-4-ethyl-6-((2-((S)-2-(hydroxymethyl)pyrrolidin-1-yl)ethyl)(methyl)amino)pyridin-2-yl)thio)-2-phenylacetamide | 478.8 [M + H]⁺ | ¹H NMR (400 MHz, MeOD) δ 7.55 (d, J = 7.1 Hz, 2H), 7.41-7.37 (m, 3H), 5.63-5.59 (m, 1H), 4.23-3.89 (m, 2H), 3.54-3.50 (m, 2H), 3.45-3.43 (m, 3H), 3.27-3.15 (m, 2H), 2.91 (q, J = 7.6 Hz, 2H), 2.65 (s, 2H), 2.44-2.33 (m, 1H), 1.98-1.90 (m, 1H), 1.83-1.70 (m, 2H), 1.66-1.58 (m, 1H), 1.31 (t, J = 7.6 Hz, 3H). |

| Example | Structure/Name | LCMS m/z | 1H NMR |
|---|---|---|---|
| 476 | 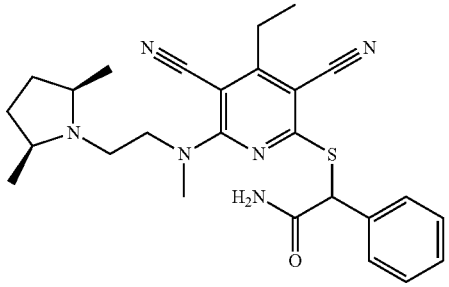 [SMILES: CCc1c(C#N)c(SC(C(N)=O)c2ccccc2)nc(N(C)CCN2[C@H](C)CC[C@@H]2C)c1C#N]<br>2-(3,5-dicyano-6-((2-((2S,5R)-2,5-dimethylpyrrolidin-1-yl)ethyl)(methyl)amino)-4-ethylpyridin-2-ylthio)-2-phenylacetamide | 477.3 [M + H]$^+$ | $^1$H NMR (400 MHz, DMSO) δ 7.90 (s, 1H), 7.50 (d, J = 7.3 Hz, 2H), 7.45-7.27 (m, 4H), 5.55 (s, 1H), 3.95-3.76 (m, 2H), 3.38 (s, 3H), 2.85-2.71 (m, 4H), 2.62-2.55 (m, 2H), 1.83-1.70 (m, 2H), 1.28-1.16 (m, 5H), 0.97 (t, J = 5.9 Hz, 6H). |
| 477 | 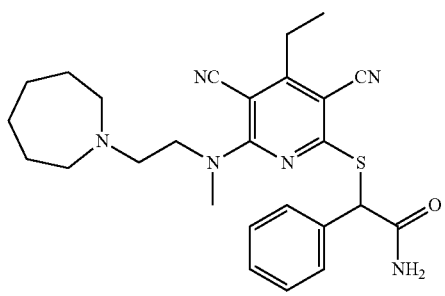 [SMILES: CCc1c(C#N)c(SC(C(N)=O)c2ccccc2)nc(N(C)CCN2CCCCCC2)c1C#N]<br>2-((6-((2-(azepan-1-yl)ethyl)(methyl)amino)-3,5-dicyano-4-ethylpyridin-2-yl)thio)-2-phenylacetamide | 476.9 [M + H]$^+$ | $^1$H NMR (400 MHz, CDCl$_3$) δ 7.58 (d, J = 7.0 Hz, 2H), 7.47 (s, 1H), 7.45-7.33 (m, 3H), 6.22 (s, 1H), 5.61 (s, 1H), 4.60-4.48 (m, 1H), 4.11 (s, 1H), 3.49 (s, 3H), 3.31 (s, 6H), 2.94 (q, J = 7.5 Hz, 2H), 2.10-1.86 (m, 4H), 1.82-1.62 (m, 4H), 1.34 (t, J = 7.6 Hz, 3H). |
| 478 | 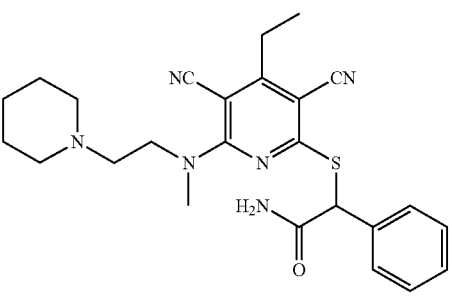 [SMILES: CCc1c(C#N)c(SC(C(N)=O)c2ccccc2)nc(N(C)CCN2CCCCC2)c1C#N]<br>2-((3,5-dicyano-4-ethyl-6-(methyl(2-(piperidin-1-yl)ethyl)amino)pyridin-2-yl)thio)-2-phenylacetamide | 462.8 [M + H]$^+$ | $^1$H NMR (400 MHz, CDCl$_3$) δ 7.55 (d, J = 7.0 Hz, 2H), 7.45-7.29 (m, 4H), 6.05 (br. s, 1H), 5.55 (s, 1H), 4.55-4.45 (m, 1H), 4.07 (br. s, 1H), 3.51 (s, 3H), 3.44-2.52 (m, 8H), 2.05-1.55 (m, 6H), 1.34 (t, J = 7.6 Hz, 3H). |
| 479 | 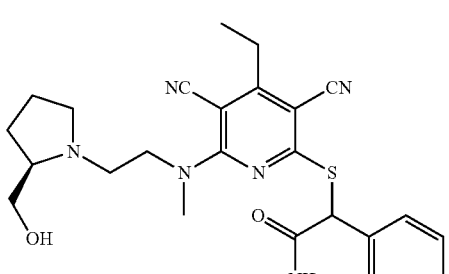 | 478.8 [M + H]$^+$ | $^1$H NMR (400 MHz, MeOD) δ 7.55 (d, J = 7.0 Hz, 2H), 7.43-7.37 (m, 3H), 5.61 (s, 1H), 4.24-3.85 (m, 2H), 3.58-3.48 (m, 2H), 3.47-3.40 (m, 3H), 3.27-3.22 (m, 2H), 2.91 (q, J = 7.6 Hz, 2H), 2.71 (br. s, 2H), 2.45 (br. s, 1H), 1.98-1.90 (m, 1H), 1.81-1.72 (m, 2H), 1.68-1.58 (m, 1H), 1.31 (t, J = 7.6 Hz, 3H). |

| Example | Structure/Name | LCMS m/z | 1H NMR |
|---|---|---|---|
| | 2-((3,5-dicyano-4-ethyl-6-((2-((R)-2-(hydroxymethyl)pyrrolidin-1-yl)ethyl)(methyl)amino)pyridin-2-yl)thio)-2-phenylacetamide | | |
| 480 | N-(4-(((3,5-dicyano-4-ethyl-6-((2-(methoxyethyl)amino)ethyl)(methyl)amino)pyridin-2-yl)thio)methyl)phenyl)-N-methylmethanesulfonamide | 517.3 [M + H]+ | 1H NMR (400 MHz, CDCl3) δ 7.41 (d, J = 8.5 Hz, 2H), 7.35 (d, J = 8.5 Hz, 2H), 4.44 (s, 2H), 3.86 (t, J = 6.9 Hz, 2H), 3.49 (t, J = 10.0, 5.0 Hz, 2H), 3.42 (s, 3H), 3.36 (s, 3H), 3.33 (s, 3H), 2.99-2.90 (m, 4H), 2.86 (s, 3H), 2.83-2.78 (m, 2H), 1.74 (br. s, 1H), 1.34 (t, J = 7.6 Hz, 3H). |
| 481 | N-(4-(((3,5-dicyano-4-ethyl-6-(methyl(2-((1-methylcyclopropyl)amino)ethyl)amino)pyridin-2-yl)thio)methyl)phenyl)-N-methylmethanesulfonamide | 513.3 [M + H]+ | 1H NMR (400 MHz, CDCl3) δ 7.42 (d, J = 8.4 Hz, 2H), 7.35 (d, J = 8.5 Hz, 2H), 4.46 (s, 2H), 3.92 (s, 2H), 3.42 (s, 3H), 3.34 (br. s, 3H), 3.10 (t, J = 6.9 Hz, 2H), 2.94 (q, J = 7.6 Hz, 2H), 2.87 (s, 3H), 1.38-1.27 (m, 6H), 0.77-0.62 (m, 2H), 0.46 (s, 2H). |
| 482 | N-(4-(((3,5-dicyano-6-((2-(dimethylamino)ethyl)(methyl)amino)-4-ethylpyridin-2-yl)thio)methyl)phenyl)-N-methylmethanesulfonamide | 487.3 [M + H]+ | 1H NMR (400 MHz, CDCl3) δ 7.40 (d, J = 8.6 Hz, 2H), 7.35 (d, J = 8.6 Hz, 2H), 4.45 (s, 2H), 3.88 (t, J = 6.6 Hz, 2H), 3.44 (s, 3H), 3.33 (s, 3H), 2.92 (q, J = 7.6 Hz, 2H), 2.86 (s, 3H), 2.62 (t, J = 6.6 Hz, 2H), 2.28 (s, 6H), 1.34 (t, J = 7.6 Hz, 3H). |

| Example | Structure/Name | LCMS m/z | 1H NMR |
|---|---|---|---|
| 483 | 2-(3,5-dicyano-4-ethyl-6-((2-(ethyl(methyl)amino)ethyl)(methyl)amino)pyridin-2-ylthio)-2-phenylacetamide | 437.3 [M + H]⁺ | ¹H NMR (400 MHz, DMSO) δ ppm 7.96 (s, 1H), 7.53-7.48 (m, 2H), 7.41-7.30 (m, 4H), 5.55 (s, 1H), 4.00-3.91 (m, 1H), 3.86-3.77 (m, 1H), 3.33 (s, 3H), 2.76 (q, J = 7.4 Hz, 2H), 2.56 (t, J = 6.3 Hz, 2H), 2.39-2.32 (m, 2H), 2.16 (s, 3H), 1.20 (t, J = 7.6 Hz, 3H), 0.89 (t, J = 7.1 Hz, 3H). |
| 484 | N-(4-(((6-((2-aminoethyl)(methyl)amino)-3,5-dicyano-4-ethylpyridin-2-yl)thio)methyl)phenyl)-N-methylmethanesulfonamide | 459.2 [M + H]⁺ | ¹H NMR (400 MHz, MeOD) δ 7.49 (d, J = 8.5 Hz, 2H), 7.43 (d, J = 8.5 Hz, 2H), 4.56 (s, 2H), 4.01 (t, J = 6.7 Hz, 2H), 3.49 (s, 3H), 3.32 (s, 3H), 3.19 (t, J = 6.7 Hz, 2H), 2.99-2.90 (m, 5H), 1.33 (t, J = 7.6 Hz, 3H). |
| 485 | 2-((3,5-dicyano-6-((2-((2R,5R)-2,5-dimethylpyrrolidin-1-yl)ethyl)(methyl)amino)-4-ethylpyridin-2-yl)thio)-2-phenylacetamide | 476.8 [M + H]⁺ | ¹H NMR (400 MHz, DMSO) δ 7.93 (s, 1H), 7.50 (d, J = 5.4 Hz, 2H), 7.45-7.26 (m, 4H), 5.62-5.51 (m, 1H), 3.99-3.76 (m, 2H), 3.32 (s, 3H), 2.96 (s, 2H), 2.87-2.65 (m, 4H), 1.93-1.67 (m, 2H), 1.32-1.13 (m, 5H), 0.85 (t, J = 6.5 Hz, 6H). |
| 486 | | 464.8 [M + H]⁺ | ¹H NMR (400 MHz, MeOD) δ 7.54 (d, J = 7.1 Hz, 2H), 7.48-7.30 (m, 3H), 5.67-5.59 (m, 1H), 4.37 (br. s, 1H), 4.20-4.10 (m, 1H), 3.93-3.79 (m, 1H), 3.46 (s, 3H), 2.98-2.77 (m, 6H), 2.69-2.56 (m, 2H), 2.19, 2.09 (m, 1H), 1.80-1.64 (m, 1H), 1.31 (t, J = 7.6 Hz, 3H). |

| Example | Structure/Name | LCMS m/z | 1H NMR |
|---|---|---|---|
| | 2-(3,5-dicyano-4-ethyl-6-((2-((S)-3-hydroxypyrrolidin-1-yl)ethyl)(methyl)amino)pyridin-2-ylthio)-2-phenylacetamide | | |
| 487 | methyl 2-((1-(6-((2-amino-2-oxo-1-phenylethyl)thio)-3,5-dicyano-4-ethylpyridin-2-yl)piperidin-4-yl)amino)-2-methylpropanoate | 521.3 [M + H]⁺ | ¹H NMR (400 MHz, MeOD) δ 7.54 (d, J = 7.2 Hz, 2H), 7.45-7.35 (m, 3H), 5.52 (s, 1H), 4.67-4.54 (m, 2H), 3.74 (s, 3H), 3.28-3.17 (m, 2H), 2.90 (q, J = 7.6 Hz, 2H), 2.84-2.75 (m, 1H), 1.98 (d, J = 12.4 Hz, 2H), 1.49 (q, J = 24.5, 13.1 Hz, 2H), 1.37 (s, 6H), 1.31 (t, J = 7.6 Hz, 3H). |
| 488 | 2-((3,5-dicyano-4-ethyl-6-(methyl(2-(neopentylamino)ethyl)amino)pyridin-2-yl)thio)-2-phenylacetamide | 465.3 [M + H]⁺ | ¹H NMR (400 MHz, CDCl₃) δ 7.47 (dd, J = 7.5, 1.9 Hz, 2H), 7.43-7.36 (m, 3H), 7.04 (s, 1H), 5.35 (s, 1H), 4.07-3.76 (m, 2H), 3.50 (s, 3H), 3.06-2.87 (m, 4H), 2.47 (s, 2H), 1.34 (t, J = 7.6 Hz, 3H), 0.91 (s, 9H). |
| 489 | 2-(3,5-dicyano-4-ethyl-6-(methyl(2-(1-methylcyclopropylamino)ethyl)amino)pyridin-2-ylthio)-2-phenylacetamide | 449.3 [M + H]⁺ | ¹H NMR (400 MHz, CDCl₃) δ 7.47 (dd, J = 6.5, 2.9 Hz, 2H), 7.43-7.36 (m, 3H), 7.21 (s, 1H), 5.25 (s, 1H), 4.30 (br. s, 1H), 4.01-3.91 (m, 1H), 3.55 (s, 3H), 3.29-3.14 (m, 2H), 2.96 (q, J = 7.6 Hz, 2H), 1.50 (s, 3H), 1.36 (t, J = 7.6 Hz, 3H), 1.16 (br. s, 2H), 0.68 (br. s, 2H). |

| Example | Structure/Name | LCMS m/z | 1H NMR |
|---|---|---|---|
| 490 | 2-((3,5-dicyano-6-((2-((2S,5S)-2,5-dimethylpyrrolidin-1-yl)ethyl)(methyl)amino)-4-ethylpyridin-2-yl)thio)-2-phenylacetamide | 477.3 [M + H]⁺ | ¹H NMR (400 MHz, DMSO) δ 7.93 (s, 1H), 7.51 (d, J = 7.3 Hz, 2H), 7.46-7.20 (m, 4H), 5.61-5.52 (m, 1H), 4.00-3.74 (m, 2H), 3.34 (s, 1.5H), 3.33 (s, 1.5H), 2.97 (s, 2H), 2.86-2.62 (m, 4H), 1.91-1.73 (m, 2H), 1.30-1.09 (m, 5H), 0.85 (t, J = 6.3 Hz, 6H). |
| 491 | 2-((3,5-dicyano-4-ethyl-6-((2-((2-methoxyethyl)amino)ethyl)(methyl)amino)pyridin-2-yl)thio)-2-phenylacetamide | 453.3 [M + H]⁺ | ¹H NMR (400 MHz, CDCl₃) δ 7.53-7.46 (m, 2H), 7.45-7.34 (m, 4H), 7.22 (s, 1H), 5.26 (s, 1H), 4.61-4.51 (m, 1H), 3.92-3.79 (m, 2H), 3.79-3.71 (m, 1H), 3.56 (s, 3H), 3.37 (s, 3H), 3.33-3.13 (m, 4H), 2.96 (q, J = 7.6 Hz, 2H), 1.35 (t, J = 7.6 Hz, 3H). |
| 492 | 2-((3,5-dicyano-4-ethyl-6-(4-((2-methoxy-2-methylpropyl)(methyl)amino)piperidin-1-yl)pyridin-2-yl)thio)-2-phenylacetamide | 521.3 [M + H]⁺ | ¹H NMR (400 MHz, MeOD) δ 7.55 (d, J = 6.8 Hz, 2H), 7.48-7.35 (m, 3H), 5.54 (s, 1H), 4.85-4.74 (m, 2H), 3.25 (S, 3H), 3.13 (t, J = 12.7 Hz, 2H), 2.91 (q, J = 7.5 Hz, 2H), 2.80-2.26 (m, 6H), 2.09-1.88 (m, 2H), 1.71-1.54 (m, 2H), 1.31 (t, J = 7.6 Hz, 3H), 1.22 (s, 6H). |
| 493 | | 422.9 [M + H]⁺ | ¹H NMR (400 MHz, CDCl₃) δ 7.57 (d, J = 6.2 Hz, 2H), 7.51 (br. s, 1H), 7.45-7.34 (m, 3H), 5.93 (br. s, 1H), 5.61 (s, 1H), 4.58-4.44 (m, 1H), 4.12 (br. s, 1H), 3.53 (s, 3H), 3.26-3.15 (m, 2H), 2.95 (q, J = 7.5 Hz, 2H), 2.90-2.72 (m, 6H), 1.34 (t, J = 7.6 Hz, 3H). |

| Example | Structure/Name | LCMS m/z | 1H NMR |
|---|---|---|---|
| | 2-((3,5-dicyano-6-((2-(dimethylamino)ethyl)(methyl)amino)-4-ethylpyridin-2-yl)thio)-2-phenylacetamide | | |
| 494 | 2-(3,5-dicyano-4-ethyl-6-((2-((R)-3-hydroxypyrrolidin-1-yl)ethyl)(methyl)amino)pyridin-2-ylthio)-2-phenylacetamide | 465.3 [M + H]⁺ | ¹H NMR (400 MHz, MeOD) δ 7.54 (d, J = 7.2 Hz, 2H), 7.46-7.34 (m, 3H), 5.66-5.59 (m, 1H), 4.36 (br. s, 1H), 4.24-4.07 (m, 1H), 3.90-3.80 (m, 1H), 3.46 (s, 3H), 2.97-2.76 (m, 6H), 2.69-2.56 (m, 2H), 2.14 (td, J = 14.3, 7.4 Hz, 1H), 1.81-1.66 (m, 1H), 1.31 (t, J = 7.6 Hz, 3H). |
| 495 | 2-((3,5-dicyano-4-ethyl-6-((2-((2-fluoroethyl)amino)ethyl)(methyl)amino)pyridin-2-yl)thio)-2-phenylacetamide | 440.7 [M + H]⁺ | ¹H NMR (400 MHz, MeOD) δ 7.61-7.50 (m, 2H), 7.50-7.39 (m, 3H), 5.44 (s, 1H), 4.78 (t, J = 4.6 Hz, 1H), 4.66 (t, J = 4.6 Hz, 1H), 4.18-3.91 (m, 4H), 3.54 (s, 3H), 3.38 (m, 1H), 3.23 (m, 1H), 2.95 (q, J = 7.6 Hz, 2H), 1.33 (t, J = 7.7 Hz, 3H). |
| 496 | 2-((3,5-dicyano-6-(4-(3,3-difluoropyrrolidin-1-yl)piperidin-1-yl)-4-ethylpyridin-2-yl)thio)-2-phenylacetamide | 510.8 [M + H]⁺ | ¹H NMR (400 MHz, DMSO) δ 7.92 (s, 1H), 7.53 (d, J = 7.6 Hz, 2H), 7.39-7.34 (m, 4H), 5.53 (s, 1H), 4.43 (br. s, 2H), 3.32-3.16 (m, 2H), 2.98 (t, J = 13.8 Hz, 2H), 2.79-2.72 (m, 4H), 2.47 (m, 1H), 2.29-2.20 (m, 2H), 1.92 (d, J = 11.7 Hz, 2H), 1.45-1.39 (m, 2H), 1.21 (t, J = 7.6 Hz, 3H). |

-continued

| Example | Structure/Name | LCMS m/z | 1H NMR |
|---|---|---|---|
| 497 | 2-((1-(6-((2-amino-2-oxo-1-phenylethyl)thio)-3,5-dicyano-4-ethylpyridin-2-yl)piperidin-4-yl)amino)acetic acid | 478.7 [M + H]⁺ | ¹H NMR (400 MHz, DMSO) δ 7.98 (s, 1H), 7.52 (d, J = 7.3 Hz, 2H), 7.46-7.28 (m, 4H), 5.55 (s, 1H), 4.58 (d, J = 13.4 Hz, 2H), 3.46-3.34 (m, 2H), 3.52 (q, J = 27.4, 14.3 Hz, 5H), 2.83-2.72 (m, 2H), 2.14-2.04 (m, 2H), 1.62-1.47 (m, 2H), 1.21 (t, J = 7.5 Hz, 3H). |
| 498 | 2-((6-((3-aminocyclobutyl)(methyl)amino)-3,5-dicyano-4-ethylpyridin-2-yl)thio)-2-phenylacetamide | 421.2 [M + H]⁺ | ¹H NMR (400 MHz, DMSO) δ 8.19 (s, 1H), 8.03 (br. s, 2H), 7.60 (d, J = 7.2 Hz, 2H), 7.52-7.24 (m, 4H), 5.77 (s, 1H), 5.60-5.40 (m, 1H), 3.74 (br. s, 1H), 3.28 (s, 3H), 2.84-2.66 (m, 4H), 2.48-2.39 (m, 2H), 1.22 (t, J = 7.3 Hz, 3H). |
| 499 | 2-(4-aminopiperidin-1-yl)-4-ethyl-6-((4-((methylsulfonyl)methyl)benzyl)thio)pyridine-3,5-dicarbonitrile | 470.2 [M + H]⁺ | ¹H NMR (400 MHz, DMSO) δ 7.45 (d, J = 8.1 Hz, 2H), 7.38 (d, J = 8.1 Hz, 2H), 4.53 (s, 2H), 4.51-4.41 (m, 4H), 3.32-3.15 (m, 5H), 2.90 (s, 3H), 2.78 (q, J = 7.6 Hz, 2H), 2.02-1.91 (m, 2H), 1.60-1.40 (m, 2H), 1.22 (t, J = 7.6 Hz, 3H). |
| 500 | | 504.9 [M + H]⁺ | ¹H NMR (400 MHz, MeOD) δ 7.50-7.41 (m, 4H), 4.64-4.53 (m, 3H), 4.52-4.44 (m, 1H), 3.92 (t, J = 7.0 Hz, 2H), 3.45 (s, 3H), 3.31 (s, 3H), 3.03-2.87 (m, 9H), 1.34-1.30 (m, 3H). |

-continued

| Example | Structure/Name | LCMS m/z | 1H NMR |
|---|---|---|---|
| | N-(4-(((3,5-dicyano-4-ethyl-6-fluoroethyl)amino)ethyl)(methyl)amino)pyridin-2-yl)thio)methyl)phenyl)-N-methylmethanesulfonamide | | |
| 501 | 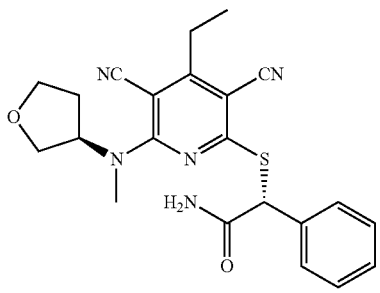 [SMILES: CCc1c(C#N)c(S[C@@H](C(N)=O)c2ccccc2)nc(N(C)[C@@H]2CCOC2)c1C#N]<br>(R)-2-(3,5-dicyano-4-ethyl-6-(methyl((R)-tetrahydrofuran-3-yl)amino)pyridin-2-ylthio)-2-phenylacetamide | 422.2 [M + H]⁺ | ¹H NMR (400 MHz, CDCl3) δ ppm 7.50-7.45 (m, 2H), 7.45-7.38 (m, 3H), 6.58 (br. s, 1H), 5.51-5.41 (m, 3H), 4.20-4.14 (m, 1H), 3.98-3.89 (m, 2H), 3.74 (dd, J = 16.7, 8.8 Hz, 1H), 3.34 (s, 3H), 2.96 (q, J = 7.6 Hz, 2H), 2.55-2.46 (m, 1H), 2.05-1.95 (m, 1H), 1.36 (t, J = 7.6 Hz, 3H). |
| 502 | 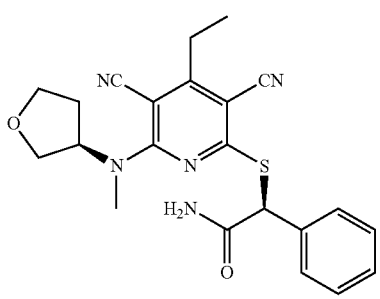 [SMILES: CCc1c(C#N)c(S[C@H](C(N)=O)c2ccccc2)nc(N(C)[C@@H]2CCOC2)c1C#N]<br>(S)-2-(3,5-dicyano-4-ethyl-6-(methyl((R)-tetrahydrofuran-3-yl)amino)pyridin-2-ylthio)-2-phenylacetamide | 422.2 [M + H]⁺ | ¹H NMR (400 MHz, CDCl₃) δ ppm 7.52-7.46 (m, 2H), 7.45-7.38 (m, 3H), 6.57 (br. s, 1H), 5.52 (br. s, 1H), 5.41-5.36 (m, 2H), 4.20-4.14 (m, 1H), 4.00-3.95 (m, 1H), 3.89-3.83 (m, 1H), 3.76-3.68 (m, 1H), 3.35 (s, 3H), 2.96 (q, J = 7.6 Hz, 2H), 2.62-2.51 (m, 1H), 2.03-1.93 (m, 1H), 1.36 (t, J = 7.6 Hz, 3H). |
| 503 | 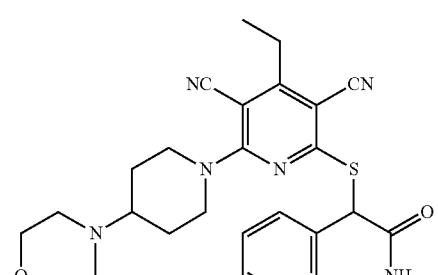<br>2-((3,5-dicyano-4-ethyl-6-(4-morpholinopiperidin-1-yl)pyridin-2-yl)thio)-2-phenylacetamide | 490.8 [M + H]⁺ | ¹H NMR (400 MHz, CDCl₃) δ 7.51-7.45 (m, 2H), 7.43-7.39 (m, 3H), 6.56 (br. s, 1H), 5.70 (br. s, 1H), 5.39 (s, 1H), 4.70 (d, J = 13.7 Hz, 2H), 3.77 (s, 4H), 3.20 (t, J = 12.8 Hz, 2H), 2.93 (q, J = 7.5 Hz, 2H), 2.57-2.48 (m, 5H), 2.07 (d, J = 12.4 Hz, 2H), 1.67-1.53 (m, 2H), 1.34 (t, J = 7.6 Hz, 3H). |

| Example | Structure/Name | LCMS m/z | 1H NMR |
|---|---|---|---|
| 504 | 2-((3,5-dicyano-4-ethyl-6-(4-(2-hydroxyethyl)-3-oxopiperazin-1-yl)pyridin-2-yl)thio)-2-phenylacetamide | 465.1 [M + H]+ | ¹H NMR (400 MHz, CDCl₃) δ 7.54-7.46 (m, 2H), 7.43-7.33 (m, 3H), 6.90 (s, 1H), 6.17 (s, 1H), 5.42 (s, 1H), 4.53 (dd, J = 39.2, 17.5 Hz, 2H), 4.27-4.17 (m, 1H), 4.14-4.04 (m, 1H), 3.89-3.77 (m, 2H), 3.74-3.52 (m, 4H), 2.95 (q, J = 7.5 Hz, 2H), 1.35 (t, J = 7.6 Hz, 3H) |
| 505 | 2-((3,5-dicyano-4-ethyl-6-(4-(pyrrolidin-1-yl)piperidin-1-yl)pyridin-2-yl)thio)-2-(4-fluorophenyl)acetamide | 493.1 [M + H]+ | ¹H NMR (400 MHz, DMSO-d₆) δ ppm 7.95 (s, 1H), 7.59-7.53 (m, 2H), 7.39 (s, 1H), 7.27-7.20 (m, 2H), 5.55 (s, 1H), 4.47-4.35 (m, 2H), 3.33-3.26 (m, 2H), 2.75 (q, J = 7.4 Hz, 2H), 2.58-2.53 (m, 1H, partially obscured by residual solvent signal), 2.40-2.20 (m, 1H), 1.94 (d, 4H), 1.55-1.35 (m, 2H), 1.20 (t, J = 7.6 Hz, 3H) |
| 506 | (R)-2-((6-((3S,4R)-4-amino-3-fluoropiperidin-1-yl)-3,5-dicyano-4-ethylpyridin-2-yl)thio)-2-phenylacetamide 2,2,2-trifluoroacetate | 439.2 [M + H]+ | ¹H NMR (400 MHz, DMSO-d₆) δ ppm 8.35-8.25 (m, 3H), 7.97 (s, 1H), 7.56-7.50 (m, 2H), 7.45-7.33 (m, 4H), 5.55 (s, 1H), 5.17-4.90 (m, 2H), 4.64 (d, J = 11.4 Hz, 1H), 3.80-3.66 (m, 1H), 3.57 (dd, J = 15.0, 39.4 Hz, 1H), 3.31-3.21 (m, 1H), 2.79 (q, J = 7.6 Hz, 2H), 2.04-1.84 (m, 2H), 1.22 (t, J = 7.6 Hz, 3H). |
| 507 |  | 453.1 [M + H]+ | ¹H NMR (400 MHz, DMSO-d₆) δ ppm 7.96 (br. s., 1H), 7.56-7.49 (m, 2H), 7.44-7.29 (m, 4H), 5.56-5.52 (m, 1H), 5.01-4.78 (m, 2H), 4.60-4.45 (m, 1H), 3.59-3.39 (m, 1H), 2.83-2.64 (m, 3H), 2.38-2.32 (m, 3H), 1.94-1.83 (m, 1H), 1.69-1.50 (m, 1H), 1.31-1.08 (m, 5H) |

| Example | Structure/Name | LCMS m/z | 1H NMR |
|---|---|---|---|
| | 2((3,5-dicyano-4-ethyl-6-(3-fluoro-4-(methylamino)piperidin-1-yl)pyridin-2-yl)thio)-2-phenylacetamide | | |
| 508 | rel-2-((6-(trans)-4-amino-3-fluoropiperidin-1-yl)-3,5-dicyano-4-ethylpyridin-2-yl)thio)-2-phenylacetamide | 439.1 [M + H]⁺ | ¹H NMR (400 MHz, DMSO-d₆) δ ppm 7.97 (s, 1H), 7.57-7.50 (m, 2H), 7.42-7.31 (m, 4H), 5.58-5.54 (m, 1H), 4.46-4.21 (m, 2H), 4.16-4.03 (m, 1H), 3.80-3.66 (m, 1H), 3.64-3.55 (m, 1H), 3.09-2.98 (m, 1H), 2.77 (q, J = 7.6 Hz, 2H), 2.02-1.88 (m, 1H), 1.84 (br. s., 2H), 1.50-1.39 (m, 1H), 1.21 (t, J = 7.6 Hz, 3H). |
| 509 | (R)-2-((6-((3R,4S)-4-amino-3-fluoropiperidin-1-yl)-3,5-dicyano-4-ethylpyridin-2-yl)thio)-2-phenylacetamide • (0.67)2,2,2-trifluoroacetate • (0.33)methanesulfonate | 439.1 [M + H]⁺ | ¹H NMR (400 MHz, DMSO-d₆) δ ppm 8.33 (br s, 3H), 7.97 (s, 1H), 7.57-7.46 (m, 2H), 7.44-7.30 (m, 4H), 5.55 (s, 1H), 5.17-4.97 (m, 2H), 4.64 (d, J = 11.9 Hz, 1H), 3.81-3.62 (m, 1H), 3.51 (dd, J = 15.0, 39.2 Hz, 1H), 3.27 (t, J = 11.8 Hz, 1H), 2.79 (q, J = 7.6 Hz, 2H), 2.06-1.84 (m, 2H), 1.21 (t, J = 7.6 Hz, 3H). |
| 510 | 2((3,5-dicyano-4-ethyl-6-(3-fluoro-4-((2-methoxyethyl)amino)piperidin-1-yl)pyridin-2-yl)thio)-2-phenylacetamide | 497.1 [M + H]⁺ | ¹H NMR (400 MHz, DMSO-d₆) δ ppm 7.96 (br. s., 1H), 7.57-7.48 (m, 2H), 7.43-7.29 (m, 4H), 5.56-5.51 (m, 1H), 5.00-4.77 (m, 2H), 4.59-4.46 (m, 1H), 3.58-3.43 (m, 1H), 3.41 (t, J = 5.4 Hz, 2H), 3.26 (s, 3H), 2.96-2.69 (m, 5H), 1.95-1.80 (m, 1H), 1.70-1.50 (m, 1H), 1.25-1.18 (m, 5H). |

| Example | Structure/Name | LCMS m/z | 1H NMR |
|---|---|---|---|
| 511 | 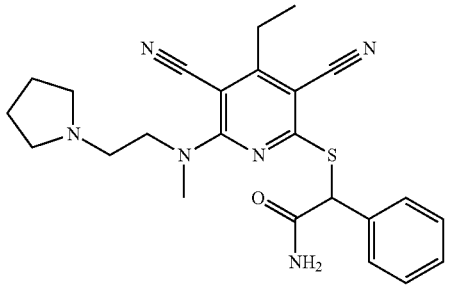 [SMILES: CCc1c(C#N)c(SC(C(N)=O)c2ccccc2)nc(N(C)CCN2CCCC2)c1C#N]<br>2-((3,5-dicyano-4-ethyl-6-(methyl(2-(pyrrolidin-1-yl)ethyl)amino)pyridin-2-yl)thio)-2-phenylacetamide | 449.1 [M + H]+ | $^1$H NMR (400 MHz, DMSO-d$_6$) δ ppm 7.97 (s, 1H), 7.52-7.47 (m, 2H), 7.40-7.30 (m, 4H), 5.55 (s, 1H), 4.03-3.94 (m, 1H), 3.79 (td, J = 6.8, 14.2 Hz, 1H), 2.75 (q, J = 7.6 Hz, 2H), 2.69 (t, J = 6.3 Hz, 2H), 2.48-2.41 (m, 4H), 1.68-1.60 (m, 4H), 1.20 (t, J = 7.6 Hz, 3H) (3H obscured). |
| 512 | 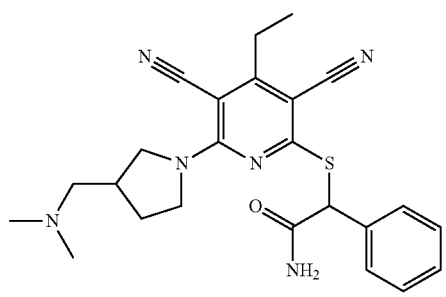 [SMILES: CCc1c(C#N)c(SC(C(N)=O)c2ccccc2)nc(N2CCC(CN(C)C)C2)c1C#N]<br>2-((3,5-dicyano-6-(3-((dimethylamino)methyl)pyrrolidin-1-yl)-4-ethylpyridin-2-yl)thio)-2-phenylacetamide | 449.2 [M + H]+ | $^1$H NMR (400 MHz, DMSO-d$_6$) δ ppm 7.94-7.87 (m, 1H), 7.51 (dt, J = 2.3, 4.1 Hz, 2H), 7.41-7.25 (m, 4H), 5.62-5.54 (m, 1H), 4.04-3.87 (m, 2H), 3.87-3.67 (m, 1H), 3.57-3.46 (m, 1H), 2.73 (q, J = 7.5 Hz, 2H), 2.34-2.20 (m, 2H), 2.19 (s, 6H), 2.10-1.98 (m, 1H), 1.75-1.59 (m, 1H), 1.19 (t, J = 7.6 Hz, 3H) (1H obscured by DMSO). |
| 513 | 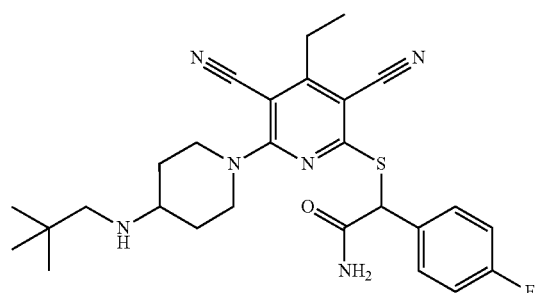<br>2-((3,5-dicyano-4-ethyl-6-(4-((2-hydroxy-2-methylpropyl)amino)piperidin-1-yl)pyridin-2-yl)thio)-2-(4-fluorophenyl)acetamide | 511.2 [M + H]+ | $^1$H NMR (400 MHz, DMSO-d$_6$) δ ppm 7.95 (s, 1H), 7.59-7.51 (m, 2H), 7.38 (s, 1H), 7.26-7.17 (m, 2H), 5.55 (s, 1H), 4.43-4.32 (m, 2H), 4.20 (s, 1H), 2.80-2.65 (m, 3H), 2.44 (s, 3H), 1.98-1.84 (m, 2H), 1.54 (br. s., 1H), 1.40-1.23 (m, 2H), 1.20 (t, J = 7.6 Hz, 3H), 1.09 (s, 6H) (1H obscured by residual water peak). |
| 514 | 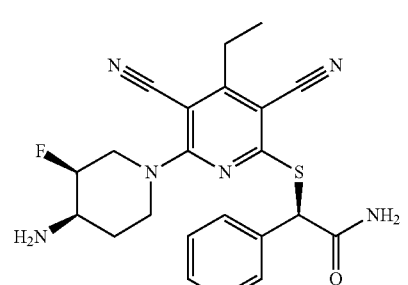 | 437.1 [M + H]+ | $^1$H NMR (400 MHz, DMSO-d$_6$) δ ppm 7.98 (s, 1H), 7.90 (br. s., 3H), 7.54-7.50 (m, 2H), 7.43-7.34 (m, 4H), 5.68 (d, J = 4.1 Hz, 1H), 5.52 (s, 1H), 4.62 (d, J = 12.7 Hz, 2H), 3.98 (br. s., 1H), 3.56 (d, J = 13.4 Hz, 1H), 3.19 (t, J = 11.5 Hz, 1H), 2.82-2.72 (m, 2H), 2.46 (br. s., 1H), 1.94-1.75 (m, 2H), 1.22 (t, J = 7.6 Hz, 3H) |

| Example | Structure/Name | LCMS m/z | 1H NMR |
|---|---|---|---|
| | (R)-2-((6-((3S,4R)-4-amino-3-hydroxypiperidin-1-yl)-3,5-dicyano-4-ethylpyridin-2-yl)thio)-2-phenylacetamide, Trifluoroacetic acid salt | | |
| 515 | 2-((3,5-dicyano-6-((2-(diethylamino)ethyl)(methyl)amino)-4-ethylpyridin-2-yl)thio)-2-phenylacetamide | 451.1 [M + H]+ | 1H NMR (400 MHz, DMSO-d6) δ ppm 7.94 (s, 1H), 7.51-7.48 (m, 2H), 7.40-7.30 (m, 4H), 5.54 (s, 1H), 3.97-3.88 (m, 1H), 3.85-3.76 (m, 1H), 3.34 (s, 3H), 2.75 (q, J = 7.6 Hz, 2H), 2.62-2.53 (m, 2H), 2.44-2.37 (m, 4H), 1.19 (t, J = 7.6 Hz, 3H), 0.84 (t, J = 7.1 Hz, 6H). |
| 516 | 2-((3,5-dicyano-6-((2-((R)-3-(dimethylamino)pyrrolidin-1-yl)ethyl)(methyl)amino)-4-ethylpyridin-2-yl)thio)-2-phenylacetamide | 492.2 [M + H]+ | 1H NMR (400 MHz, DMSO-d6) δ ppm 7.95 (s, 1H), 7.50 (d, J = 7.4 Hz, 2H), 7.41-7.30 (m, 4H), 5.54 (s, 1H), 4.00-3.90 (m, 1H), 3.80 (dd, J = 6.3, 14.2 Hz, 1H), 2.80-2.52 (m, 8H), 2.40-2.31 (m, 1H), 2.05 (s, 6H), 1.83-1.72 (m, 1H), 1.59-1.48 (m, 1H), 1.20 (t, J = 7.6 Hz, 3H) |
| 517 | 2-((3,5-dicyano-6-((2-((S)-3-(dimethylamino)pyrrolidin-1-yl)ethyl)(methyl)amino)-4-ethylpyridin-2-yl)thio)-2-phenylacetamide | 492.2 [M + H]+ | 1H NMR (400 MHz, DMSO-d6) δ ppm 7.96 (s, 1H), 7.52-7.48 (m, 2H), 7.41-7.30 (m, 4H), 5.54 (s, 1H), 4.01-3.91 (m, 1H), 3.85-3.75 (m, 1H), 3.34 (br. s., 3H), 2.79-2.52 (m, 8H), 2.39-2.29 (m, 1H), 2.07-2.02 (m, 6H), 1.83-1.72 (m, 1H), 1.59-1.48 (m, 1H), 1.20 (t, J = 7.6 Hz, 3H). |

| Example | Structure/Name | LCMS m/z | 1H NMR |
|---|---|---|---|
| 518 | 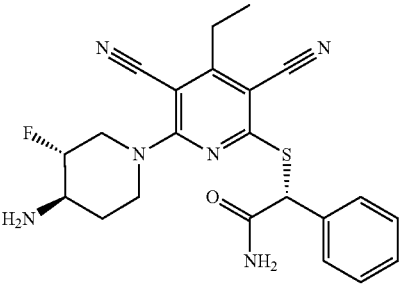<br>(R)-2-((6-((3R,4R)-4-amino-3-fluoropiperidin-1-yl)-3,5-dicyano-4-ethylpyridin-2-yl)thio)-2-phenylacetamide, Trifluoroacetic acid salt | 439.1 [M + H]+ | $^1$H NMR (400 MHz, DMSO-$d_6$) δ ppm 8.32 (br s, 3H), 7.98 (s, 1H), 7.56-7.50 (m, 2H), 7.43-7.32 (m, 4H), 5.55 (s, 1H), 4.87-4.71 (m, 2H), 4.65 (dt, J = 5.2, 9.6 Hz, 1H), 4.50 (d, J = 14.2 Hz, 1H), 3.41-3.23 (m, 2H), 2.79 (q, J = 7.6 Hz, 2H), 2.21-2.11 (m, 1H), 1.73-1.58 (m, 1H), 1.22 (t, J = 7.6 Hz, 3H). |
| 519 | 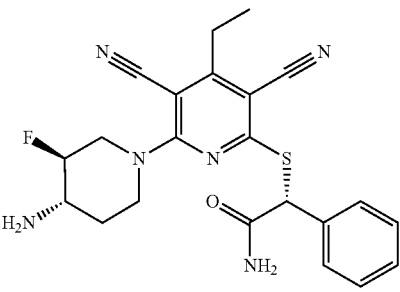 [SMILES: CCc1c(C#N)c(S[C@@H](C(N)=O)c2ccccc2)nc(N2CC[C@H](N)[C@@H](F)C2)c1C#N]<br>(R)-2-((6-((3S,4S)-4-amino-3-fluoropiperidin-1-yl)-3,5-dicyano-4-ethylpyridin-2-yl)thio)-2-phenylacetamide, Trifluoroacetic acid salt | 439.1 [M + H]+ | $^1$H NMR (400 MHz, DMSO-$d_6$) δ ppm 8.32 (br. s., 3H), 7.98 (s, 1H), 7.56-7.50 (m, 2H), 7.43-7.32 (m, 4H), 5.55 (s, 1H), 4.87-4.71 (m, 2H), 4.65 (dt, J = 5.2, 9.6 Hz, 1H), 4.50 (d, J = 14.2 Hz, 1H), 3.41-3.23 (m, 2H), 2.79 (q, J = 7.6 Hz, 2H), 2.21-2.11 (m, 1H), 1.73-1.58 (m, 1H), 1.22 (t, J = 7.6 Hz, 3H). |
| 520 | 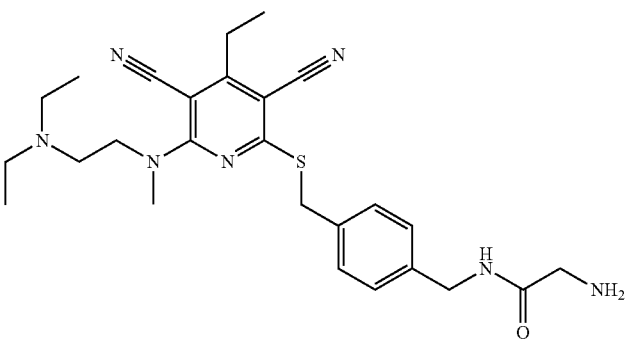 [SMILES: CCc1c(C#N)c(SCc2ccc(CNC(=O)CN)cc2)nc(N(C)CCN(CC)CC)c1C#N]<br>2-amino-N-(4-(((3,5-dicyano-6-((2-(diethylamino)ethyl)(methyl)amino)-4-ethylpyridin-2-yl)thio)methyl)benzyl)acetamide | 494.2 [M + H]+ | $^1$H NMR (400 MHz, DMSO-$d_6$) δ ppm 8.31 (br. s., 1H), 7.33 (d, J = 7.9 Hz, 2H), 7.22 (d, J = 7.9 Hz, 2H), 4.48 (s, 2H), 4.31-4.21 (m, 2H), 3.84 (t, J = 6.5 Hz, 2H), 3.36 (s, 3H), 2.76 (q, J = 7.6 Hz, 2H), 2.60 (t, J = 6.5 Hz, 2H), 2.42 (q, J = 7.1 Hz, 4H), 1.26-1.14 (m, 3H), 0.86 (t, J = 7.1 Hz, 6H) |

| Example | Structure/Name | LCMS m/z | 1H NMR |
|---|---|---|---|
| 521 | 2-((3,5-dicyano-4-ethyl-6-(3-(methylamino)pyrrolidin-1-yl)pyridin-2-yl)thio)-2-phenylacetamide | 421.1 [M + H]+ | ¹H NMR (400 MHz, DMSO-d₆) δ ppm 7.97-7.88 (m, 1H), 7.56-7.48 (m, 2H), 7.42-7.27 (m, 4H), 5.62-5.56 (m, 1H), 3.98-3.54 (m, 4H), 3.25 (br. s., 1H), 2.78-2.70 (m, 2H), 2.32-2.28 (m, 3H), 2.08-1.96 (m, 1H), 1.96-1.79 (m, 1H), 1.25-1.13 (m, 3H) |
| 522 | 2-((6-(4-aminopiperidin-1-yl)-3,5-dicyano-4-ethylpyridin-2-yl)thio)-2-(4-fluorophenyl)acetamide hydrochloride | 439.1 [M + H]+ | ¹H NMR (400 MHz, DMSO-d₆) δ ppm 8.09 (br. s., 3H), 8.04 (s, 1H), 7.60-7.54 (m, 2H), 7.39 (s, 1H), 7.26-7.19 (m, 2H), 5.60 (s, 1H), 4.58 (d, J = 13.4 Hz, 2H), 3.43-3.37 (m, 1H), 3.25 (dt, J = 6.1, 11.8 Hz, 2H), 2.76 (q, J = 7.6 Hz, 2H), 2.13-2.03 (m, 2H), 1.67-1.50 (m, 2H), 1.20 (t, J = 7.6 Hz, 3H) |
| 523 | (R)-2-((6-((3R,4R)-4-amino-3-hydroxypiperidin-1-yl)-3,5-dicyano-4-ethylpyridin-2-yl)thio)-2-phenylacetamide 2,2,2-trifluoroacetate* | 437.1 [M + H]+ | ¹H NMR (400 MHz, DMSO-d₆) δ ppm 8.04 (br. s., 3H), 7.99-7.88 (m, 1H), 7.54-7.50 (m, 2H), 7.44-7.32 (m, 4H), 5.94 (br. s., 1H), 5.55-5.52 (m, 1H), 4.69-4.52 (m, 2H), 3.23-3.13 (m, 2H), 3.11-3.01 (m, 1H), 2.78 (q, J = 7.6 Hz, 2H), 2.47-2.39 (m, 1H), 2.12-1.99 (m, 1H), 1.63-1.49 (m, 1H), 1.22 (t, J = 7.6 Hz, 3H) |
| 524 | | 407.0 [M + H]+ | ¹H NMR (400 MHz, DMSO-d₆) δ ppm 7.92 (br. s., 1H), 7.54-7.49 (m, 2H), 7.41-7.29 (m, 4H), 5.61-5.58 (m, 1H), 4.02-3.82 (m, 2H), 3.76 (br. s., 1H), 3.62-3.46 (m, 2H), 2.74 (q, J = 7.5 Hz, 2H), 2.05-1.88 (m, 1H), 1.77 (br. s., 3H), 1.20 (t, J = 7.5 Hz, 3H) |

| Example | Structure/Name | LCMS m/z | 1H NMR |
|---|---|---|---|
| | 2-((6-((R)-3-aminopyrrolidin-1-yl)-3,5-dicyano-4-ethylpyridin-2-yl)thio)-2-phenylacetamide | | |
| 525 | 2-((6-(3-(aminomethyl)pyrrolidin-1-yl)-3,5-dicyano-4-ethylpyridin-2-yl)thio)-2-phenylacetamide | 421.1 [M + H]⁺ | ¹H NMR (400 MHz, DMSO-d₆) δ ppm 7.91 (br. s., 1H), 7.54-7.49 (m, 2H), 7.41-7.31 (m, 4H), 5.61-5.56 (m, 1H), 4.00-3.69 (m, 3H), 3.62-3.42 (m, 1H), 2.74 (q, J = 7.5 Hz, 2H), 2.64-2.58 (m, 2H), 2.32-2.22 (m, 1H), 2.12-2.00 (m, 1H), 1.80-1.64 (m, 1H), 1.20 (t, J = 7.6 Hz, 3H) |
| 526 | 2-((3,5-dicyano-4-ethyl-6-(4-(methylamino)piperidin-1-yl)pyridin-2-yl)thio)-2-(4-fluorophenyl)acetamide | 453.2 [M + H]⁺ | ¹H NMR (400 MHz, DMSO-d₆) δ ppm 7.95 (s, 1H), 7.59-7.51 (m, 2H), 7.37 (s, 1H), 7.26-7.18 (m, 2H), 5.55 (s, 1H), 4.41-4.29 (m, 2H), 3.41-3.35 (m, 1H), 2.74 (q, J = 7.4 Hz, 2H), 2.65-2.56 (m, 1H), 2.30 (s, 3H), 1.94-1.86 (m, 2H), 1.38-1.24 (m, 2H), 1.19 (t, J = 7.6 Hz, 3H) |
| 527 | 2-((3,5-dicyano-6-(4-(cyclopropylamino)-3-fluoropiperidin-1-yl)-4-ethylpyridin-2-yl)thio)-2-phenylacetamide | 479.1 [M + H]⁺ | ¹H NMR (400 MHz, DMSO-d₆) δ ppm 7.95 (br. s., 1H), 7.56-7.50 (m, 2H), 7.43-7.31 (m, 4H), 5.57-5.52 (m, 1H), 5.04-4.82 (m, 2H), 4.62-4.50 (m, 1H), 3.60-3.38 (m, 1H), 3.25-3.13 (m, 1H), 3.01-2.85 (m, 1H), 2.77 (q, J = 7.6 Hz, 2H), 2.35-2.14 (m, 2H), 1.93-1.79 (m, 1H), 1.73-1.52 (m, 1H), 1.21 (t, J = 7.6 Hz, 3H), 0.46-0.37 (m, 2H), 0.29-0.23 (m, 2H) |

| Example | Structure/Name | LCMS m/z | 1H NMR |
|---|---|---|---|
| 528 | 2-((6-((S)-3-aminopyrrolidin-1-yl)-3,5-dicyano-4-ethylpyridin-2-yl)thio)-2-phenylacetamide | 407.1 [M + H]⁺ | ¹H NMR (400 MHz, DMSO-d₆) δ ppm 7.92 (br. s., 1H), 7.52 (d, J = 8.1 Hz, 2H), 7.41-7.29 (m, 4H), 5.61-5.58 (m, 1H), 4.02-3.70 (m, 3H), 3.65-3.46 (m, 3H), 2.74 (d, J = 7.6 Hz, 2H), 2.06-1.95 (m, 1H), 1.84-1.67 (m, 2H), 1.20 (t, J = 7.5 Hz, 3H) |
| 529 | 2-((6-((2-((R)-3-aminopyrrolidin-1-yl)ethyl)(methyl)amino)-3,5-dicyano-4-ethylpyridin-2-yl)thio)-2-phenylacetamide | 464.1 [M + H]⁺ | ¹H NMR (400 MHz, DMSO-d₆) δ ppm 7.98 (s, 1H), 7.54-7.47 (m, 2H), 7.43-7.29 (m, 4H), 5.55 (s, 1H), 3.95 (td, J = 6.8, 13.8 Hz, 1H), 3.84-3.73 (m, 1H), 3.30-3.23 (m, 1H), 2.76 (q, J = 7.6 Hz, 2H), 2.72-2.54 (m, 4H), 2.48-2.41 (m, 1H), 2.18 (dt, J = 4.8, 9.1 Hz, 1H), 1.99-1.89 (m, 1H), 1.58 (br. s., 2H), 1.35-1.26 (m, 1H), 1.21 (t, J = 7.6 Hz, 3H) (3H obscured) |
| 530 | 2-((3,5-dicyano-6-((R)-3-(dimethylamino)pyrrolidin-1-yl)-4-ethylpyridin-2-yl)thio)-2-(4-fluorophenyl)acetamide | 453.1 [M + H]⁺ | ¹H NMR (400 MHz, DMSO-d₆) δ ppm 7.94 (br. s., 1H), 7.56 (dd, J = 5.6, 7.9 Hz, 2H), 7.38 (br. s., 1H), 7.26-7.17 (m, 2H), 5.60 (s, 1H), 4.09-3.86 (m, 2H), 3.84-3.51 (m, 2H), 2.79-2.69 (m, 3H), 2.23 (br. s., 6H), 2.19-2.12 (m, 1H), 1.87-1.74 (m, 1H), 1.20 (t, J = 7.5 Hz, 3H) |
| 531 | | 439.1 [M + H]⁺ | ¹H NMR (400 MHz, DMSO-d₆) δ ppm 8.32 (br. s., 3H), 7.97 (s, 1H), 7.59-7.47 (m, 2H), 7.45-7.31 (m, 4H), 5.55 (s, 1H), 5.19-4.96 (m, 2H), 4.64 (d, J = 11.9 Hz, 1H), 3.81-3.63 (m, 1H), 3.51 (dd, J = 14.7, 38.8 Hz, 1H), 3.27 (t, J = 11.8 Hz, 1H), 2.79 (q, J = 7.5 Hz, 2H), 2.07-1.84 (m, 2H), 1.21 (t, J = 7.6 Hz, 3H) |

| Example | Structure/Name | LCMS m/z | 1H NMR |
|---|---|---|---|
| | (S)-2-((6-((3S,4R)-4-amino-3-fluoropiperidin-1-yl)-3,5-dicyano-4-ethylpyridin-2-yl)thio)-2-phenylacetamide • (0.67)2,2,2-trifluoroacetate • (0.33)methanesulfonate | | |
| 532 | 2-((3,5-dicyano-4-ethyl-6-(4-(neopentylamino)piperidin-1-yl)pyridin-2-yl)thio)-2-(4-(trifluoromethyl)phenyl)acetamide | 559.3 [M + H]+ | $^1$H NMR (400 MHz, DMSO-$d_6$) δ ppm 8.08 (s, 1H), 7.77 (s, 4H), 7.49 (s, 1H), 5.68 (s, 1H), 4.42-4.29 (m, 2H), 3.32-3.24 (m, 2H), 2.75 (q, J = 7.6 Hz, 2H), 2.70-2.62 (m, 1H), 2.30 (s, 2H), 1.93-1.86 (m, 2H), 1.39-1.28 (m, 2H), 1.20 (t, J = 7.6 Hz, 3H), 0.87 (s, 9H) |
| 533 | tert-butyl ((3S,4R)-1-(6-(((R)-2-amino-2-oxo-1-phenylethyl)thio)-3,5-dicyano-4-ethylpyridin-2-yl)-3-hydroxypiperidin-4-yl)carbamate | 537.2 [M + H]+ | $^1$H NMR (400 MHz, DMSO-$d_6$) δ ppm 7.92 (s, 1H), 7.52 (d, J = 7.1 Hz, 2H), 7.43-7.31 (m, 4H), 6.42 (d, J = 7.9 Hz, 1H), 5.51 (s, 1H), 4.92 (d, J = 3.8 Hz, 1H), 4.53 (d, J = 13.4 Hz, 2H), 3.82 (br. s., 1H), 3.73-3.61 (m, 1H), 3.53 (d, J = 13.4 Hz, 1H), 3.21 (t, J = 11.8 Hz, 1H), 2.80-2.69 (m, 2H), 1.84-1.72 (m, 1H), 1 66-1 59 (m, 1H), 1.41 (s, 9H), 1.20 (t, J = 7.6 Hz, 3H) |
| 534 | rel-tert-butyl (cis)-1-(6-((2-amino-2-oxo-1-phenylethyl)thio)-3,5-dicyano-4-ethylpyridin-2-yl)-3-fluoropiperidin-4-yl)carbamate | 539.1 [M + H]+ | $^1$H NMR (400 MHz, DMSO-$d_6$) δ ppm 7.93 (s, 1H), 7.54-7.48 (m, 2H), 7.43-7.30 (m, 4H), 7.17-7.08 (m, 1H), 5.54-5.51 (m, 1H), 4.92-4.75 (m, 2H), 4.63-4.52 (m, 1H), 3.91-3.72 (m, 1H), 3.59-3.39 (m, 1H), 3.31-3.21 (m, 1H), 2.77 (q, J = 7.6 Hz, 2H), 1.92-1.70 (m, 2H), 1.41 (s, 9H), 1.20 (t, J = 7.6 Hz, 3H) |

| Example | Structure/Name | LCMS m/z | 1H NMR |
|---|---|---|---|
| 535 | 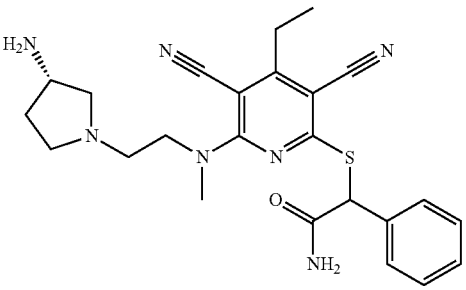 [SMILES: CCc1c(C#N)c(SC(C(N)=O)c2ccccc2)nc(N(C)CCN2CC[C@H](N)C2)c1C#N]<br>2-((6-((2-((S)-3-aminopyrrolidin-1-yl)ethyl)(methyl)amino)-3,5-dicyano-4-ethylpyridin-2-yl)thio)-2-phenylacetamide | 464.1 [M + H]+ | $^1$H NMR (400 MHz, DMSO-d$_6$) δ ppm 7.98 (s, 1H), 7.53-7.48 (m, 2H), 7.41-7.31 (m, 4H), 5.55 (s, 1H), 4.00-3.91 (m, 1H), 3.83-3.74 (m, 1H), 3.30-3.23 (m, 1H), 2.76 (q, J = 7.4 Hz, 2H), 2.72-2.54 (m, 4H), 2.48-2.41 (m, 1H), 2.18 (dt, J = 4.8, 9.0 Hz, 1H), 1.99-1.89 (m, 1H), 1.60 (br. s., 2H), 1.35-1.26 (m, 1H), 1.21 (t, J = 7.5 Hz, 3H) |
| 536 | 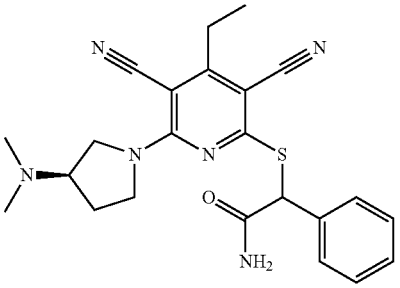 [SMILES: CCc1c(C#N)c(SC(C(N)=O)c2ccccc2)nc(N2CC[C@@H](N(C)C)C2)c1C#N]<br>2-((3,5-dicyano-6-((R)-3-(dimethylamino)pyrrolidin-1-yl)-4-ethylpyridin-2-yl)thio)-2-phenylacetamide | 435.1 [M + H]+ | $^1$H NMR (400 MHz, DMSO-d$_6$) δ ppm 7.93 (br. s., 1H), 7.55-7.47 (m, 2H), 7.40-7.27 (m, 4H), 5.57 (s, 1H), 4.07-3.86 (m, 2H), 3.85-3.51 (m, 2H), 2.80-2.65 (m, 3H), 2.26-2.10 (m, 7H), 1.87-1.72 (m, 1H), 1.19 (t, J = 7.5 Hz, 3H) |
| 537 | 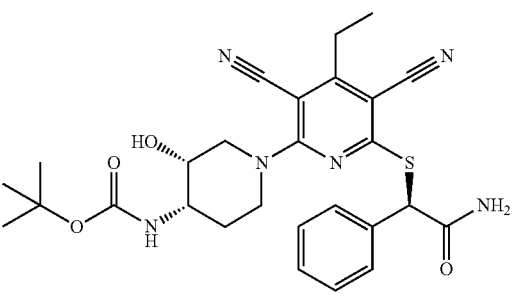 [SMILES: CCc1c(C#N)c(S[C@@H](C(N)=O)c2ccccc2)nc(N2CC[C@H](NC(=O)OC(C)(C)C)[C@H](O)C2)c1C#N]<br>tert-butyl ((3R,4S)-1-(6-(((R)-2-amino-2-oxo-1-phenylethyl)thio)-3,5-dicyano-4-ethylpyridin-2-yl)-3-hydroxypiperidin-4-yl)carbamate | 537.3 [M + H]+ | $^1$H NMR (400 MHz, DMSO-d$_6$) δ ppm 7.91 (s, 1H), 7.54-7.48 (m, 2H), 7.42-7.31 (m, 4H), 6.37 (d, J = 8.1 Hz, 1H), 5.49 (s, 1H), 4.95 (d, J = 3.8 Hz, 1H), 4.56 (d, J = 13.9 Hz, 1H), 4.48-4.40 (m, 1H), 3.82 (br. s., 1H), 3.72-3.62 (m, 1H), 3.51-3.45 (m, 1H), 3.22-3.13 (m, 1H), 2.79-2.71 (m, 2H), 1.92-1.80 (m, 1H), 1.67-1.58 (m, 1H), 1.40 (s, 9H), 1.20 (t, J = 7.6 Hz, 3H) |

| Example | Structure/Name | LCMS m/z | 1H NMR |
|---|---|---|---|
| 538 | 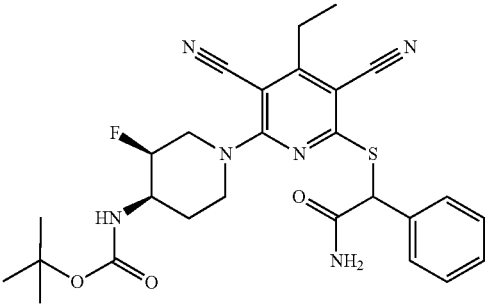 [SMILES: CCc1c(C#N)c(SC(C(N)=O)c2ccccc2)nc(N2CC[C@@H](NC(=O)OC(C)(C)C)[C@@H](F)C2)c1C#N]<br>rel-tert-butyl (cis)-1-(6-((2-amino-2-oxo-1-phenylethyl)thio)-3,5-dicyano-4-ethylpyridin-2-yl)-3-fluoropiperidin-4-yl)carbamate | 539.3 [M + H]+ | $^{1}$H NMR (400 MHz, DMSO-d$_6$) δ ppm 7.93 (s, 1H), 7.54-7.49 (m, 2H), 7.43-7.31 (m, 4H), 7.19-7.08 (m, 1H), 5.54-5.51 (m, 1H), 4.93-4.74 (m, 2H), 4.63-4.53 (m, 1H), 3.91-3.74 (m, 1H), 3.59-3.41 (m, 1H), 3.31-3.22 (m, 1H), 2.81-2.73 (m, 2H), 1.91-1.70 (m, 2H), 1.42 (s, 9H), 1.20 (t, J = 7.6 Hz, 3H) |
| 539 | 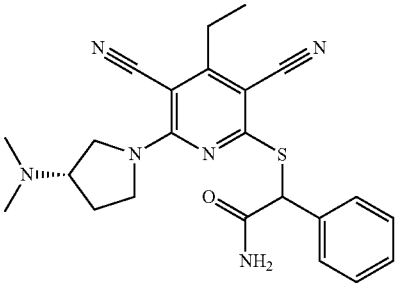 [SMILES: CCc1c(C#N)c(SC(C(N)=O)c2ccccc2)nc(N2CC[C@H](N(C)C)C2)c1C#N]<br>2-((3,5-dicyano-6-((S)-3-(dimethylamino)pyrrolidin-1-yl)-4-ethylpyridin-2-yl)thio)-2-phenylacetamide | 435.1 [M + H]+ | $^{1}$H NMR (400 MHz, DMSO-d$_6$) δ ppm 7.94 (s, 1H), 7.54-7.50 (m, 2H), 7.41-7.31 (m, 4H), 5.58 (s, 1H), 4.10-3.86 (m, 2H), 3.86-3.69 (m, 1H), 3.62-3.40 (m, 1H), 2.80-2.66 (m, 3H), 2.23 (br. s., 6H), 2.19-2.11 (m, 1H), 1.88-1.75 (m, 1H), 1.20 (t, J = 7.6 Hz, 3H) |
| 540 | 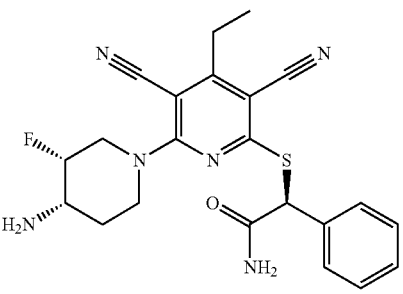 [SMILES: CCc1c(C#N)c(S[C@H](C(N)=O)c2ccccc2)nc(N2CC[C@H](N)[C@H](F)C2)c1C#N]<br>(S)-2-((6-((3R,4S)-4-amino-3-fluoropiperidin-1-yl)-3,5-dicyano-4-ethylpyridin-2-yl)thio)-2-phenylacetamide 2,2,2-trifluoroacetate | 439.2 [M + H]+ | $^{1}$H NMR (400 MHz, DMSO-d$_6$) δ ppm 8.39-8.25 (m, 3H), 7.97 (s, 1H), 7.57-7.50 (m, 2H), 7.45-7.33 (m, 4H), 5.55 (s, 1H), 5.19-4.90 (m, 2H), 4.64 (d, J = 11.4 Hz, 1H), 3.81-3.66 (m, 1H), 3.57 (dd, J = 15.0, 39.2 Hz, 1H), 3.25 (t, J = 12.0 Hz, 1H), 2.79 (q, J = 7.6 Hz, 2H), 2.05-1.83 (m, 2H), 1.22 (t, J = 7.6 Hz, 3H) |
| 541 | 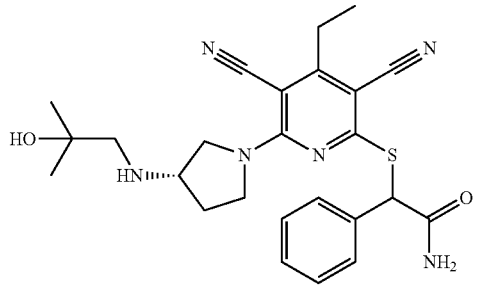 [SMILES: CCc1c(C#N)c(SC(C(N)=O)c2ccccc2)nc(N2CC[C@H](NCC(C)(C)O)C2)c1C#N] | 479.1 [M + H]+ | $^{1}$H NMR (400 MHz, DMSO-d$_6$) δ ppm 7.92 (br. s., 1H), 7.55-7.49 (m, 2H), 7.40-7.29 (m, 4H), 5.62-5.59 (m, 1H), 4.25-4.22 (m, 1H), 4.05-3.71 (m, 3H), 3.69-3.48 (m, 1H), 2.73 (q, J = 7.5 Hz, 2H), 2.47-2.39 (m, 2H), 2.04 (dt, J = 4.9, 12.2 Hz, 1H), 1.94-1.69 (m, 2H), 1.19 (t, J = 7.6 Hz, 3H), 1.12-1.05 (m, 6H) |

| Example | Structure/Name | LCMS m/z | 1H NMR |
|---|---|---|---|
| | 2-((3,5-dicyano-4-ethyl-6-((S)-3-((2-hydroxy-2-methylpropyl)amino)pyrrolidin-1-yl)pyridin-2-yl)thio)-2-phenylacetamide | | |
| 542 | tert-butyl((3R,4R)-1-(6-(((R)-2-amino-2-oxo-1-phenylethyl)thio)-3,5-dicyano-4-ethylpyridin-2-yl)-3-hydroxypiperidin-4-yl)carbamate* | 537.2 [M + H]⁺ | ¹H NMR (400 MHz, DMSO-d₆) δ ppm 7.93 (s, 1H), 7.51 (d, J = 6.8 Hz, 2H), 7.43-7.29 (m, 4H), 6.88 (d, J = 6.6 Hz, 1H), 5.51 (s, 1H), 5.15 (d, J = 4.1 Hz, 1H), 4.34 (d, J = 12.4 Hz, 1H), 4.22 (d, J = 13.7 Hz, 1H), 3.49-3.25 (m, 4H), 2.75 (q, J = 7.4 Hz, 2H), 2.02-1.92 (m, 1H), 1.47-1.33 (m, 10H), 1.20 (t, J = 7.5 Hz, 3H) |
| 543 | 4-(((3,5-dicyano-4-ethyl-6-(4-methyl-1,4-diazepan-1-yl)pyridin-2-yl)thio)methyl)-N-(1H-pyrazol-4-yl)benzamide | 501.1 [M + H]⁺ | ¹H NMR (400 MHz, DMSO-d₆) δ ppm 12.64 (br. s., 1H), 10.41 (s, 1H), 8.01 (br. s., 1H), 7.92 (d, J = 8.4 Hz, 2H), 7.73-7.61 (m, 1H), 7.54 (d, J = 8.4 Hz, 2H), 4.58 (s, 2H), 3.92-3.73 (m, 4H), 2.79 (q, J = 7.6 Hz, 2H), 2.63-2.57 (m, 2H), 2.49-2.45 (m, 2H), 2.22 (s, 3H), 1.96-1.87 (m, 2H), 1.23 (t, J = 7.6 Hz, 3H) |
| 544 | 2-((3,5-dicyano-6-((S)-3-(dimethylamino)pyrrolidin-1-yl)-4-ethylpyridin-2-yl)thio)-2-(4-fluorophenyl)acetamide | 453.1 [M + H]⁺ | ¹H NMR (400 MHz, DMSO-d₆) δ ppm 7.95 (s, 1H), 7.59-7.53 (m, 2H), 7.38 (br. s., 1H), 7.26-7.19 (m, 2H), 5.62-5.58 (m, 1H), 4.08-3.87 (m, 2H), 3.85-3.65 (m, 1H), 3.62-3.38 (m, 1H), 2.80-2.66 (m, 3H), 2.30-2.10 (m, 7H), 1.87-1.74 (m, 1H), 1.20 (t. J = 7.6 Hz, 3H) |

| Example | Structure/Name | LCMS m/z | 1H NMR |
|---|---|---|---|
| 545 | 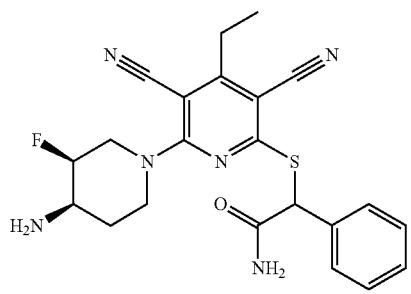 [SMILES: CCc1c(C#N)c(SC(C(N)=O)c2ccccc2)nc(N2CC[C@@H](N)[C@@H](F)C2)c1C#N]<br>rel-2-(((6-cis-4-amino-3-fluoropiperidin-1-yl)-3,5-dicyano-4-ethylpyridin-2-yl)thio)-2-phenylacetamide | 439.4 [M + H]⁺ | ¹H NMR (400 MHz, DMSO-d₆) δ ppm 7.96 (s, 1H), 7.55-7.49 (m, 2H), 7.41-7.30 (m, 4H), 5.56-5.51 (m, 1H), 4.80-4.60 (m, 2H), 4.51-4.39 (m, 1H), 3.61-3.38 (m, 1H), 3.28-3.15 (m, 1H), 3.04-2.90 (m, 1H), 2.76 (q, J = 7.6 Hz, 2H), 1.79-1.69 (m, 1H), 1.69-1.56 (m, 3H), 1.20 (t, J = 7.6 Hz, 3H) |
| 546 | 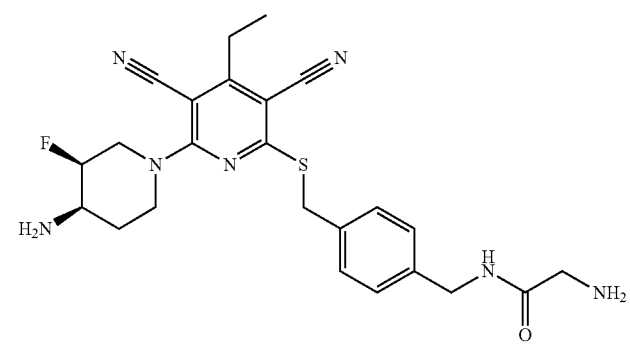 [SMILES: CCc1c(C#N)c(SCc2ccc(CNC(=O)CN)cc2)nc(N2CC[C@@H](N)[C@@H](F)C2)c1C#N]<br>rel-2-amino-N-(4-(((6-(cis-4-amino-3-fluoropiperidin-1-yl)-3,5-dicyano-4-ethylpyridin-2-yl)thio)methyl)benzyl)acetamide | 482.4 [M + H]⁺ | ¹H NMR (400 MHz, DMSO-d₆) δ ppm 8.30 (t, J = 6.0 Hz, 1H), 7.35 (d, J = 8.1 Hz, 2H), 7.22 (d, J = 8.1 Hz, 2H), 4.83-4.63 (m, 2H), 4.54-4.38 (m, 3H), 4.26 (d, J = 6.1 Hz, 2H), 3.63-3.45 (m, 2H), 3.30-3.21 (m, 2H), 3.11 (s, 2H), 3.02-2.87 (m, 1H), 2.76 (q, J = 7.6 Hz, 2H), 1.78-1.54 (m, 4H), 1.20 (t, J = 7.6 Hz, 3H) |
| 547 | 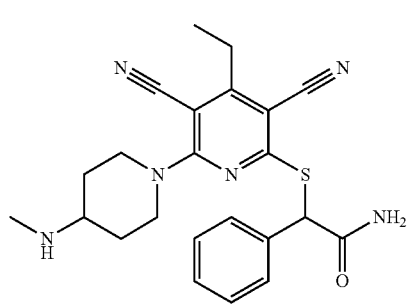 [SMILES: CCc1c(C#N)c(SC(C(N)=O)c2ccccc2)nc(N2CCC(NC)CC2)c1C#N]<br>2-((3,5-dicyano-4-ethyl-6-(4-(methylamino)piperidin-1-yl)pyridin-2-yl)thio)-2-phenylacetamide | 435.1 [M + H]⁺ | ¹H NMR (400 MHz, DMSO-d₆) δ ppm 7.94 (s, 1H), 7.57-7.47 (m, 2H), 7.44-7.27 (m, 4H), 5.54 (s, 1H), 4.36 (d, J = 13.4 Hz, 2H), 3.42-3.29 (m, 2H), 2.75 (q, J = 7.5 Hz, 2H), 2.66-2.55 (m, 1H), 2.30 (s, 3H), 1.91 (d, J = 11.4 Hz, 2H), 1.69 (br. s., 1H), 1.40-1.25 (m, 2H), 1.20 (t, J = 7.6 Hz, 3H) |

| Example | Structure/Name | LCMS m/z | 1H NMR |
|---|---|---|---|
| 548 | 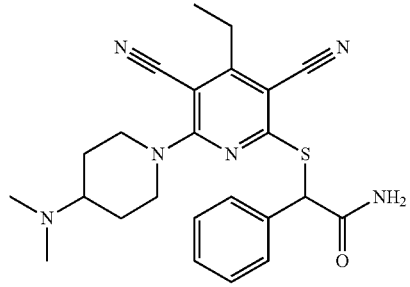 [SMILES: CCc1c(C#N)c(SC(C(N)=O)c2ccccc2)nc(N2CCC(N(C)C)CC2)c1C#N]<br>2-((3,5-dicyano-6-(4-(dimethylamino)piperidin-1-yl)-4-ethylpyridin-2-yl)thio)-2-phenylacetamide | 449.1 [M + H]+ | ¹H NMR (400 MHz, DMSO-d₆) δ ppm 7.93 (s, 1H), 7.56-7.46 (m, 2H), 7.43-7.25 (m, 4H), 5.53 (s, 1H), 4.56 (d, J = 12.9 Hz, 2H), 3.23-3.10 (m, 2H), 2.74 (q, J = 7.6 Hz, 2H), 2.46-2.35 (m, 1H), 2.22-2.11 (m, 6H), 1.86 (d, J = 12.2 Hz, 2H), 1.49-1.28 (m, 2H), 1.20 (t, J = 7.6 Hz, 3H) |
| 549 | 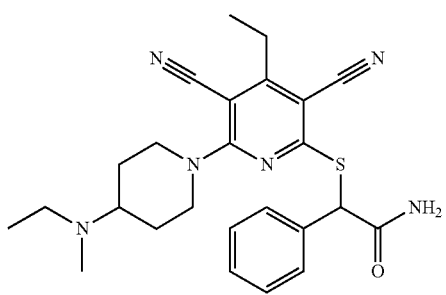 [SMILES: CCc1c(C#N)c(SC(C(N)=O)c2ccccc2)nc(N2CCC(N(C)CC)CC2)c1C#N]<br>2-((3,5-dicyano-4-ethyl-6-(4-(ethyl(methyl)amino)piperidin-1-yl)pyridin-2-yl)thio)-2-phenylacetamide | 463.1 [M + H]+ | ¹H NMR (400 MHz, DMSO-d₆) δ ppm 7.95 (s, 1H), 7.57-7.46 (m, 2H), 7.43-7.26 (m, 4H), 5.54 (s, 1H), 4.60 (d, J = 12.7 Hz, 2H), 3.21-3.07 (m, 2H), 2.82-2.61 (m, 3H), 2.47 (q, J = 7.2 Hz, 2H), 2.15 (s, 3H), 1.81 (d, J = 12.2 Hz, 2H), 1.54-1.30 (m, 2H), 1.21 (t, J = 7.6 Hz, 3H), 0.99 (t, J = 7.1 Hz, 3H) |
| 550 | 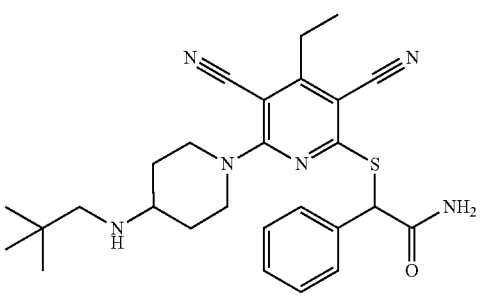 [SMILES: CCc1c(C#N)c(SC(C(N)=O)c2ccccc2)nc(N2CCC(NCC(C)(C)C)CC2)c1C#N]<br>2-((3,5-dicyano-4-ethyl-6-(4-(neopentylamino)piperidin-1-yl)pyridin-2-yl)thio)-2-phenylacetamide | 491.1 [M + H]+ | ¹H NMR (400 MHz, DMSO-d₆) δ ppm 7.94 (s, 1H), 7.59-7.49 (m, 2H), 7.44-7.29 (m, 4H), 5.54 (s, 1H), 4.48-4.33 (m, 2H), 3.44-3.27 (m, 2H) 2.75 (q, J = 7.6 Hz, 2H), 2.73-2.62 (m, 1H), 2.32 (br. s., 2H), 2.00-1.85 (m, 2H), 1.51-1.26 (m, 3H), 1.21 (t, J = 7.6 Hz, 3H), 0.88 (s, 9H) |
| 551 | 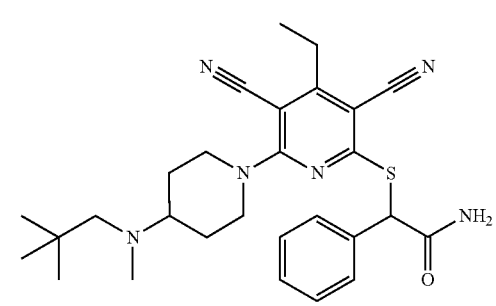 [SMILES: CCc1c(C#N)c(SC(C(N)=O)c2ccccc2)nc(N2CCC(N(C)CC(C)(C)C)CC2)c1C#N] | 505.2 [M + H]+ | ¹H NMR (400 MHz, DMSO-d₆) δ ppm 7.94 (s, 1H), 7.58-7.48 (m, 2H), 7.44-7.25 (m, 4H), 5.55 (s, 1H), 4.67 (d, J = 13.4 Hz, 2H), 3.15-2.98 (m, 2H), 2.75 (q, J = 7.6 Hz, 2H), 2.69-2.57 (m, 1H), 2.25 (s, 3H), 2.16 (s, 2H), 1.80 (d, J = 12.2 Hz, 2H), 1.55-1.34 (m, 2H), 1.21 (t, J = 7.6 Hz, 3H), 0.86 (s, 9H) |

| Example | Structure/Name | LCMS m/z | 1H NMR |
|---|---|---|---|
| | 2-((3,5-dicyano-4-ethyl-6-(4-(methyl(neopentyl)amino)piperidin-1-yl)pyridin-2-yl)thio)-2-phenylacetamide | | |
| 552 | 2-((3,5-dicyano-6-(4-(cyclopropylamino)piperidin-1-yl)-4-ethylpyridin-2-yl)thio)-2-phenylacetamide | 461.1 [M + H]⁺ | ¹H NMR (400 MHz, DMSO-d₆) δ ppm 7.94 (s, 1H), 7.56-7.49 (m, 2H), 7.43-7.29 (m, 4H), 5.54 (s, 1H), 4.43-4.32 (m, 2H), 3.39-3.29 (m., 2H), 2.84 (br. s., 1H), 2.75 (q, J = 7.6 Hz, 2H), 2.27 (br. s., 1H), 2.11 (tt, J = 3.5, 6.5 Hz, 1H), 2.00-1.90 (m, 2H), 1.43-126 (m, 2H), 1.20 (t, J = 7.6 Hz, 3H), 0.44-0.36 (m, 2H), 0.25-0.18 (m, 2H) |
| 553 | 2-((3,5-dicyano-4-ethyl-6-(4-((2-methoxyethyl)amino)piperidin-1-yl)pyridin-2-yl)thio)-2-phenylacetamide | 479.4 [M + H]⁺ | ¹H NMR (400 MHz, DMSO-d₆) δ ppm 7.94 (s, 1H), 7.57-7.47 (m, 2H), 7.45-7.28 (m, 4H), 5.53 (s, 1H), 4.46-4.31 (m, 2H), 3.40 (t, J = 5.7 Hz, 2H), 3.33-3.27 (m, 2H), 3.26 (s, 3H), 2.82-2.66 (m, 5H), 1.92 (d, J = 12.9 Hz, 2H), 1.63 (br. s., 1H), 1.39-1.25 (m, 2H), 1.20 (t, J = 7.6 Hz, 3H) |
| 554 | 2-((3,5-dicyano-6-(4-((2,2-difluoroethyl)amino)piperidin-1-yl)-4-ethylpyridin-2-yl)thio)-2-phenylacetamide | 485.3 [M + H]⁺ | ¹H NMR (400 MHz, DMSO-d₆) δ ppm 7.94 (s, 1H), 7.57-7.47 (m, 2H), 7.44-7.28 (m, 4H), 5.98 (tt, J = 4.6, 56.0 Hz, 1H), 5.53 (s, 1H), 4.49-4.35 (m, 2H), 3.33-3.24 (m, 2H), 2.94 (t, J = 14.6 Hz, 2H), 2.84-2.70 (m, 3H), 2.08 (br. s., 1H), 1.94 (d, J = 10.9 Hz, 2H), 1.41-1.24 (m, 2H), 1.21 (t, J = 7.6 Hz, 3H) |

| Example | Structure/Name | LCMS m/z | 1H NMR |
|---|---|---|---|
| 555 | 2-((3,5-dicyano-4-ethyl-6-(((R)-2-((neopentylamino)methyl)morpholino)pyridin-2-yl)thio)-2-phenylacetamide | 507.4 [M + H]+ | $^1$H NMR (400 MHz, DMSO-$d_6$) δ ppm 7.91 (s, 1 H), 7.52 (d, J = 7.1 Hz, 2 H), 7.30-7.43 (m, 4 H), 5.48- 5.55 (m, 1 H), 4.45-4.62 (m, 2 H), 3.89-4.00 (m, 1 H), 3.44-3.62 (m, 2 H), 3.20-3.29 (m, 1 H), 3.06-3.16 (m, 1 H), 2.77 (q, J = 7.5 Hz, 2 H), 2.66 (br. s., 2 H), 2.29 (br. s., 2 H), 1.37-1.52 (m, 1 H), 1.21 (t, J = 7.6 Hz, 3 H), 0.81-0.90 (m, 9 H) |
| 556 | N-(4-(((3,5-dicyano-4-ethyl-6-(4-(isopropylamino)piperidin-1-yl)pyridin-2-yl)thio)methyl)phenyl)-N-methylmethanesulfonamide | 527.1 [M + H]+ | $^1$H NMR (400 MHz, DMSO-$d_6$) δ ppm 7.42-7.47 (m, 2 H), 7.35-7.40 (m, 2 H), 4.50 (s, 2 H), 4.35-444 (m, 2 H), 3.25-3.33 (m, 4 H), 3.22 (s, 3 H), 2.93 (s, 3 H), 2.73-2.80 (m, 2 H), 1.85-1.95 (m, 2 H), 1.18-1.38 (m, 6 H), 0.97 (d, J = 6.1 Hz, 6 H) |
| 557 | N-(4-(((3,5-dicyano-4-ethyl-6-(4-((2-methoxyethyl)amino)piperidin-1-yl)pyridin-2-yl)thio)methyl)phenyl)-N-methylmethanesulfonamide | 543.1 [M + H]+ | $^1$H NMR (400 MHz, DMSO-$d_6$) δ ppm 7.42-7.48 (m, 2 H), 7.34-7.40 (m, 2 H), 4.50 (s, 2 H), 4.30-4.40 (m, 2 H), 3.28-3 41 (m, 4 H), 3.24 (s, 3 H), 3.22 (s, 3 H), 2.93 (s, 3 H), 2.67-2.80 (m, 5 H), 1.84-1.95 (m, 2 H), 1.60 (br. s., 1 H), 1.24-1.34 (m, 2 H), 1.21 (t, J = 7.6 Hz, 3H) |

| Example | Structure/Name | LCMS m/z | 1H NMR |
|---|---|---|---|
| 558 | 2-((3,5-dicyano-6-(2-((dimethylamino)methyl)morpholino)-4-ethylpyridin-2-yl)thio)-2-phenylacetamide | 465.3 [M + H]+ | $^1$H NMR (400 MHz, DMSO-$d_6$) δ ppm 7.86-7.96 (m, 1 H), 7.48-7.54 (m, 2 H), 7.31-7.43 (m, 4 H), 5.49-5.55 (m, 1 H), 4.41-4.57 (m, 2 H), 3.89-3.98 (m, 1 H), 3.45-3.69 (m, 2 H), 3.18-3.29 (m, 1 H), 3.00-3.09 (m, 1 H), 2.77 (q, J = 1.4 Hz, 2 H), 2.30-2.44 (m, 2 H), 2.19 (d, J = 4.3 Hz, 6 H), 1.21 (t, J = 7.6 Hz, 3 H) |
| 559 | 2-((3,5-dicyano-6-(2-((diethylamino)methyl)morpholino)-4-ethylpyridin-2-yl)thio)-2-phenylacetamide | 493.1 [M + H]+ | $^1$H NMR (400 MHz, DMSO-$d_6$) δ ppm 7.90 (br. s., 1 H), 7.48-7.55 (m, 2 H), 7.31-7.43 (m, 4 H), 5.49-5.56 (m, 1 H), 4.46-4.59 (m, 2 H), 3.88-3.98 (m, 1 H), 3.41-3.63 (m, 2 H), 3.15-3.25 (m, 1 H), 3.03-3.13 (m, 1 H), 2.77 (q, J = 7.5 Hz, 2 H), 2.40-2.57 (m, 6 H), 1.21 (t, J = 7.6 Hz, 3H), 0.91-0.97 (m, 6 H) |
| 560 | 2-((3,5-dicyano-4-ethyl-6-(2-(pyrrolidin-1-ylmethyl)morpholino)pyridin-2-yl)thio)-2-phenylacetamide | 491.1 [M + H]+ | $^1$H NMR (400 MHz, DMSO-$d_6$) δ ppm 7.93 (br. s., 1 H), 7.48-7.55 (m, 2 H), 7.31-7.43 (m, 4 H), 5.49-5.56 (m, 1 H), 4.52-4.63 (m, 1 H), 4.40-4.51 (m, 1 H), 3.90-3.98 (m, 1 H), 3.62-3.73 (m, 1 H), 3.46-3.62 (m, 1 H), 3.18-3.30 (m, 2 H), 2.99-3.10 (m, 1 H), 2.77 (q, J = 7.6 Hz, 2 H), 2.55 (s, 5 H), 1.55-1.77 (m, 4 H), 1.21 (t, J = 7.6 Hz, 3 H) |

| Example | Structure/Name | LCMS m/z | 1H NMR |
|---|---|---|---|
| 561 | (R)-2-((6-((R)-2-(aminomethyl)morpholino)-3,5-dicyano-4-ethylpyridin-2-yl)thio)-2-phenylacetamide, Hydrochloride | 437.1 [M + H]⁺ | ¹H NMR (400 MHz, DMSO-d₆) δ ppm 8.01-8.17 (m, 4 H), 7.52-7.58 (m, 2 H), 7.34-7.47 (m, 4 H), 5.56 (s, 1 H), 4 56 (d, J = 13.2 Hz, 1 H), 4.43 (d, J = 11.9 Hz, 1 H), 4.04 (d, J = 10.9 Hz, 1 H), 3.73-3.81 (m, 1 H), 3.51-3.59 (m, 1 H), 3.38-3.44 (m, 1 H), 3.15 (br. s., 1 H), 3.09 (dd, J = 13.4, 10.4 Hz, 1 H), 2.91 (br. s., 1 H), 2.79 (q, J = 7.4 Hz, 2 H), 1.23 (t, J = 7.6 Hz, 3 H) |
| 562 | 2-((6-(2-(aminomethyl)morpholino)-3,5-dicyano-4-ethylpyridin-2-yl)thio)-2-phenylacetamide | 437.0 [M + H]⁺ | ¹H NMR (400 MHz, DMSO-d₆) δ ppm 7.93-8.08 (m, 1 H), 7.48-7.56 (m, 2 H), 7.30-7.44 (m, 4 H), 5.48-5.56 (m, 1 H), 4.50-4.66 (m, 1 H), 4.39-4.49 (m, 1 H), 3.89-4.01 (m, 1 H), 3.45-3.59 (m, 1 H), 3.36-3.43 (m, 1 H), 3.22-3.33 (m, 1 H), 2.95-3.07 (m, 1 H), 2.77 (q, J = 7.6 Hz, 2 H), 2.61-2.71 (m, 2 H), 1.46-1.68 (m, 2 H), 1.22 (t, J = 7.6 Hz, 3 H) |
| 563 | 2-((3,5-dicyano-4-ethyl-6-(2-((methylamino)methyl)morpholino)pyridin-2-yl)thio)-2-phenylacetamide | 451.1 [M + H]⁺ | ¹H NMR (400 MHz, DMSO-d₆) δ ppm 7.90-8.06 (m, 1 H), 7.48-7.56 (m, 2 H), 7.31-7.44 (m, 4 H), 5.46-5.56 (m, 1 H), 4.40-4.64 (m, 2 H), 3.90-3.98 (m, 1 H), 3.44-3.61 (m, 2 H), 3.23-3.32 (m, 1 H), 3.14-3.20 (m, 1 H), 3.00-3.12 (m, 1 H), 2.77 (q, J = 7.7 Hz, 2 H), 2.57-2.62 (m, 2 H), 2.27-2.32 (m, 3 H), 1.21 (t, J = 7.6 Hz, 3 H) |

| Example | Structure/Name | LCMS m/z | 1H NMR |
|---|---|---|---|
| 564 | 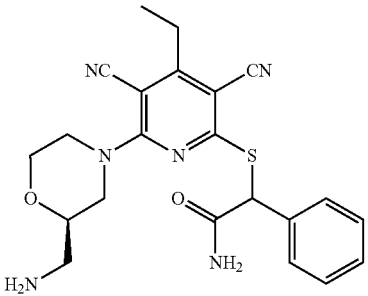 [SMILES: CCc1c(C#N)c(SC(C(N)=O)c2ccccc2)nc(N2CCO[C@H](CN)C2)c1C#N]<br>2-((6-((R)-2-(aminomethyl)morpholino)-3,5-dicyano-4-ethylpyridin-2-yl)thio)-2-phenylacetamide | 437.1 [M + H]⁺ | ¹H NMR (400 MHz, DMSO-d₆) δ ppm 7.91-8.09 (m, 1 H), 7.52 (d, J = 5.3 Hz, 2 H), 7.31-7.46 (m, 4 H), 5.47-5.58 (m, 1 H), 4.51-4.67 (m, 1 H), 4.39-4.49 (m, 1 H), 3.87-4.03 (m, 1 H), 3.45-3.61 (m, 1 H), 3.37-3.44 (m, 1 H), 3.21-3.29 (m, 1 H), 2.95-3.07 (m, 1 H), 2.72-2.83 (m, 2 H), 2.60-2.72 (m, 2 H), 1.74 (br. s., 2 H), 1.21 (t, J = 7.4 Hz, 3 H) |
| 565 | 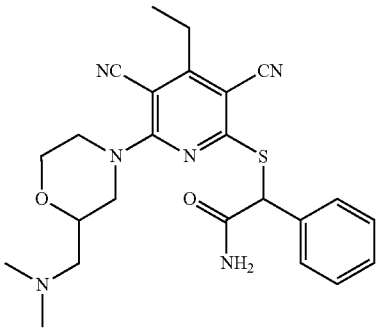 [SMILES: CCc1c(C#N)c(SC(C(N)=O)c2ccccc2)nc(N2CCOC(CN(C)C)C2)c1C#N]<br>2-((3,5-dicyano-6-(3-((dimethylamino)methyl)piperidin-1-yl)-4-ethylpyridin-2-yl)thio)-2-phenylacetamide | 463.1 [M + H]⁺ | ¹H NMR (400 MHz, DMSO-d₆) δ ppm 7.86-8.04 (m, 1 H), 7.48-7.56 (m, 2 H), 7.30-7.42 (m, 4 H), 5.50-5.56 (m, 1 H), 4.29-4.55 (m, 2 H), 3.15-3.26 (m, 1 H), 2.94-3.12 (m, 1 H), 2.76 (q, J = 7.6 Hz, 2 H), 1.97-2.20 (m, 8 H), 1.72-1.89 (m, 3 H), 1.41-1.62 (m, 1 H), 1.23-1.30 (m, 1 H), 1.20 (t, J = 7.5 Hz, 3 H) |
| 566 | 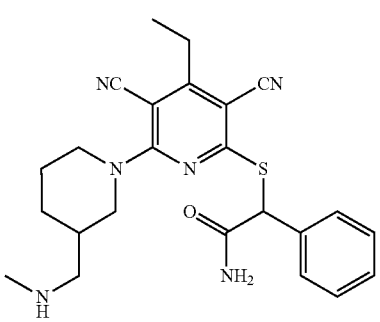 [SMILES: CCc1c(C#N)c(SC(C(N)=O)c2ccccc2)nc(N2CCCC(CNC)C2)c1C#N]<br>2-((3,5-dicyano-4-ethyl-6-(3-((methylamino)methyl)piperidin-1-yl)pyridin-2-yl)thio)-2-phenylacetamide | 449.4 [M + H]⁺ | ¹H NMR (400 MHz, DMSO-d₆) δ ppm 7.90-8.33 (m, 1H), 7.49-7.57 (m, 2 H), 7.30-7.42 (m, 4 H), 5.49-5.59 (m, 1 H), 4.38-4.76 (m, 2 H), 3.16-3.27 (m, 1 H), 2.83-3.04 (m, 1 H), 2.76 (q, J = 7.4 Hz, 2 H), 2.31-2.46 (m, 2 H), 2.23-2.30 (m, 3 H), 1.69-1.88 (m, 3 H), 1.40-1.62 (m, 1 H), 1.25-1.34 (m, 1 H), 1.21 (t, J = 7.6 Hz, 3 H) |

| Example | Structure/Name | LCMS m/z | 1H NMR |
|---|---|---|---|
| 567 | 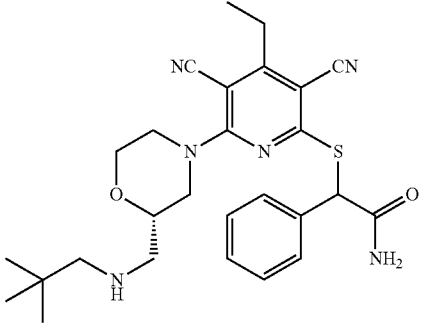 [SMILES: CCc1c(C#N)c(SC(C(N)=O)c2ccccc2)nc(N2CCO[C@@H](CNCC(C)(C)C)C2)c1C#N]<br>2-((3,5-dicyano-4-ethyl-6-((S)-2-((neopentylamino)methyl)morpholino)pyridin-2-yl)thio)-2-phenylacetamide | 507.2 [M + H]+ | $^1$H NMR (400 MHz, DMSO-$d_6$) δ ppm 7.91 (s, 1 H), 7.48-7.55 (m, 2 H), 7.31-7.43 (m, 4 H), 5.48-5.55 (m, 1 H), 4.43-4.62 (m, 2 H), 3.90-4.01 (m, 1 H), 3.44-3.61 (m, 2 H), 3.20-3.30 (m, 1 H), 3.05-3.16 (m, 1 H), 2.77 (q, J = 7.6 Hz, 2 H), 2.66 (br. s., 2 H), 2.29 (br. s., 2 H), 1.45 (br. s., 1 H), 1.21 (t, J = 7.6 Hz, 3 H), 0.83-0.89 (m, 9 H) |
| 568 | 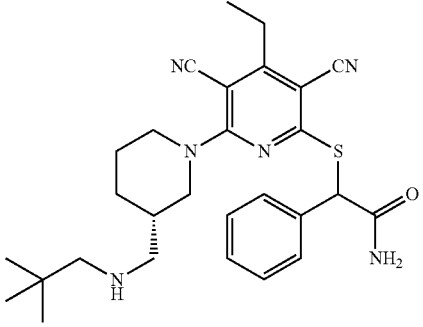 [SMILES: CCc1c(C#N)c(SC(C(N)=O)c2ccccc2)nc(N2CCC[C@@H](CNCC(C)(C)C)C2)c1C#N]<br>2-((3,5-dicyano-4-ethyl-6-((S)-3-((neopentylamino)methyl)piperidin-1-yl)pyridin-2-yl)thio)-2-phenylacetamide | 505.2 [M + H]+ | $^1$H NMR (400 MHz, DMSO-$d_6$) δ ppm 7.90-8.00 (m, 1H), 7.48-7.56 (m, 2 H), 7.30-7.42 (m, 4 H), 5.48-5.56 (m, 1 H), 4.37-4.59 (m, 2 H), 3.02-3.23 (m, 2 H), 2.75 (q, J = 7.4 Hz, 2 H), 2.39-2.47 (m, 2 H), 2.15-2.29 (m, 2 H), 1.81-1.92 (m, 1 H), 1.67-1.81 (m, 2 H), 1.25-1.61 (m, 3 H), 1.20 (t, J = 7.6 Hz, 3 H), 0.84 (s, 9 H) |
| 569 | 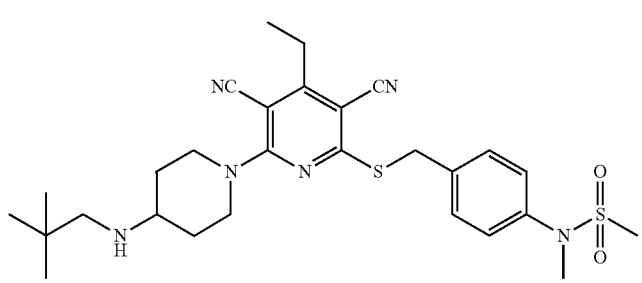 [SMILES: CCc1c(C#N)c(SCc2ccc(N(C)S(C)(=O)=O)cc2)nc(N2CCC(NCC(C)(C)C)CC2)c1C#N]<br>N-(4-(((3,5-dicyano-4-ethyl-6-(4-(neopentylamino)piperidin-1-yl)pyridin-2-yl)thio)methyl)phenyl)-N-methylmethanesulfonamide | 555.1 [M + H]+ | $^1$H NMR (400 MHz, DMSO-$d_6$) δ ppm 7.42-7.48 (m, 2 H), 7.34-7.40 (m, 2 H), 4.51 (s, 2 H), 4.29-4.41 (m, 2 H), 3.29-3.38 (m, 2 H), 3.22 (s, 3 H), 2.93 (s, 3 H), 2.77 (q, J = 7.6 Hz, 2 H), 2.58-2.71 (m, 1 H), 2.29 (s, 2 H), 1.86-1.97 (m, 2 H), 1.27-1.43 (m, 3 H), 1.21 (t, J = 7.6 Hz, 3 H), 0.86 (s, 9 H) |

| Example | Structure/Name | LCMS m/z | 1H NMR |
|---|---|---|---|
| 570 | 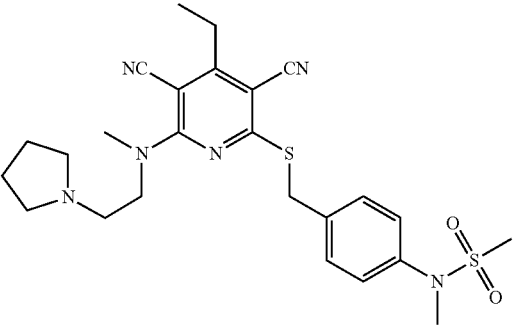 [SMILES: CCc1c(C#N)c(SCc2ccc(N(C)S(C)(=O)=O)cc2)nc(N(C)CCN2CCCC2)c1C#N]<br>N-(4-(((3,5-dicyano-4-ethyl-6-(methyl(2-(pyrrolidin-1-yl)ethyl)amino)pyridin-2-yl)thio)methyl)phenyl)-N-methylmethanesulfonamide | 513.0 [M + H]+ | $^1$H NMR (400 MHz, DMSO-$d_6$) δ ppm 7.41-7.46 (m, 2 H), 7.34-7.40 (m, 2 H), 4.54 (s, 2 H), 3.86 (t, J = 6.8 Hz, 2 H), 3.38 (s, 3 H), 3.22 (s, 3 H), 2.93 (s, 3H), 2.78 (q, J = 7.6 Hz, 2 H), 2.67 (t, J = 6.8 Hz, 2 H), 2.38-2.46 (m, 4 H), 1.57-1.66 (m, 4 H), 1.22 (t, J = 7.6 Hz, 3 H) |
| 571 | 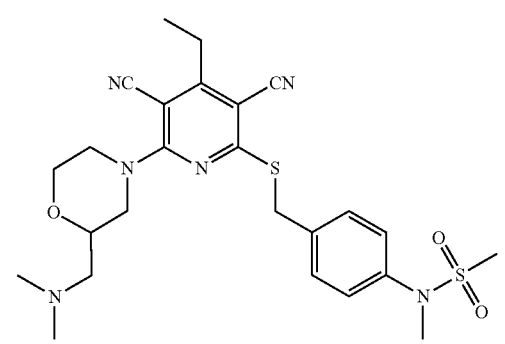<br>N-(4-(((3,5-dicyano-6-(2-((dimethylamino)methyl)morpholino)-4-ethylpyridin-2-yl)thio)methyl)phenyl)-N-methylmethanesulfonamide | 529.3 [M + H]+ | $^1$H NMR (400 MHz, DMSO-$d_6$) δ ppm 7.42-7.49 (m, 2 H), 7.33-7.41 (m, 2 H), 4.55-4.63 (m, 1 H), 4.52 (s, 2 H), 4.33-4.43 (m, 1 H), 3.88-3.98 (m, 1 H), 3.59-3.70 (m, 1 H), 3.48-3.58 (m, 1 H), 3.24-3.33 (m, 1 H), 3.22 (s, 3 H), 2.97-3.06 (m, 1 H), 2.93 (s, 3 H), 2.78 (q, J = 7.6 Hz, 2 H), 2.28-2.39 (m, 2 H), 2.16 (s, 6 H), 1.22 (t, J = 7.6 Hz, 3 H) |
| 572 | 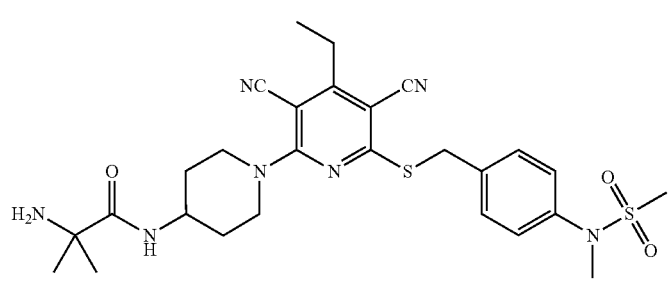 [SMILES: CCc1c(C#N)c(SCc2ccc(N(C)S(C)(=O)=O)cc2)nc(N2CCC(NC(=O)C(C)(C)N)CC2)c1C#N]<br>2-amino-N-(1-(3,5-dicyano-4-ethyl-6-((4-(N-methylmethylsulfonamido)benzyl)thio)pyridin-2-yl)piperidin-4-yl)-2-methylpropanamide | 570.2 [M + H]+ | $^1$H NMR (400 MHz, DMSO-$d_6$) δ ppm 7.69-7.78 (m, 1 H), 7.42-7.49 (m, 2 H), 7.34-7.40 (m, 2 H), 4.51 (s, 2 H), 4.40-4.48 (m, 2 H), 3.76-3.95 (m, 1 H), 3.27-3.33 (m, 2 H), 3.22 (s, 3 H), 2.93 (s, 3 H), 2.78 (q, J = 7.6 Hz, 2 H), 1.79-1.93 (m, 4 H), 1.45-1.60 (m, 2 H), 1.22 (t, J = 7.6 Hz, 3 H), 1.17 (s, 6 H) |

-continued

| Example | Structure/Name | LCMS m/z | 1H NMR |
|---|---|---|---|
| 573 | N-(4-(((3,5-dicyano-6-(4-(cyclopropylamino)piperidin-1-yl)-4-ethylpyridin-2-yl)thio)methyl)phenyl)-N-methylmethanesulfonamide | 525.1 [M + H]⁺ | ¹H NMR (400 MHz, DMSO-d₆) δ ppm 7.42-7.48 (m, 2 H), 7.33-7.40 (m, 2 H), 4.51 (s, 2 H), 4.28-4.41 (m, 2 H), 3.29-3.40 (m, 2 H), 3.22 (s, 3 H), 2.93 (s, 3 H), 2.70-2.87 (m, 3 H), 2.24 (br. s., 1 H), 2.04-2.13 (m, 1 H), 1.86-2.00 (m, 2 H), 1.27-1.40 (m, 2 H), 1.21 (t, J = 7.6 Hz, 3 H), 0.34-0.42 (m, 2 H), 0.17-0.25 (m, 2 H) |
| 574 | N-(4-(((3,5-dicyano-4-ethyl-6-(2-(pyrrolidin-1-ylmethyl)morpholino)pyridin-2-yl)thio)methyl)phenyl)-N-methylmethanesulfonamide | 555.1 [M + H]⁺ | ¹H NMR (400 MHz, DMSO-d₆) δ ppm 7.42-7.48 (m, 2 H), 7.33-7.40 (m, 2 H), 4.61-4.74 (m, 1 H), 4.51 (s, 2 H), 4.33-4.43 (m, 1 H), 3.87-3.98 (m, 1 H), 3.61-3.71 (m, 1 H), 3.48-3.59 (m, 1 H), 3.26-3.33 (m, 1 H), 3.22 (s, 3 H), 2.97-3.06 (m, 1 H), 2.93 (s, 3 H), 2.78 (q, J = 7.4 Hz, 2 H), 2.55-2.69 (m, 1 H), 2.33-2.50 (m, 5 H), 1.50-1.70 (m, 4 H), 1.22 (t, J = 7.6 Hz, 3 H) |
| 575 | 2-amino-N-(((2S)-4-(6-((2-amino-2-oxo-1-phenylethyl)thio)-3,5-dicyano-4-ethylpyridin-2-yl)morpholin-2-yl)methyl)-2-methylpropanamide | 522.2 [M + H]⁺ | ¹H NMR (400 MHz, DMSO-d₆) δ ppm 8.08-8.20 (m, 1 H), 7.88-8.04 (m, 1 H), 7.49-7.59 (m, 2 H), 7.29-7.47 (m, 4 H), 5.50-5.57 (m, 1 H), 4.34-4.53 (m, 2 H), 3.91-4.03 (m, 1 H), 3.47-3.63 (m, 2 H), 3.13-3.31 (m, 3 H), 2.96-3.09 (m, 1 H), 2.77 (q, J = 7.6 Hz, 2 H), 1.95 (br. s., 2 H), 1.14-1.25 (m, 9H) |

| Example | Structure/Name | LCMS m/z | 1H NMR |
|---|---|---|---|
| 576 | 2-((6-((S)-3-(aminomethyl)piperidin-1-yl)-3,5-dicyano-4-ethylpyridin-2-yl)thio)-2-phenylacetamide | 435.1 [M + H]⁺ | ¹H NMR (400 MHz, DMSO-d₆) δ ppm 8.11-8.39 (m, 1H), 7.49-7.63 (m, 2 H), 7.29-7.43 (m, 4 H), 5.53-5.62 (m, 1 H), 4.40-4.80 (m, 2 H), 3.14-3.26 (m, 2 H), 2.80-3.00 (m, 1 H), 2.76 (q, J = 7.5 Hz, 2 H), 2.52-2.60 (m, 1 H), 2.35-2.47 (m, 1 H), 1.88-2.22 (m, 1 H), 1.73-1.87 (m, 2 H), 1.39-1.66 (m, 2 H), 1.16-1.31 (m, 4 H) |
| 577 | N-(4-(((3,5-dicyano-4-ethyl-6-(methyl(2-(piperidin-1-yl)ethyl)amino)pyridin-2-yl)thio)methyl)phenyl)-N-methylmethanesulfonamide | 527.1 [M + H]⁺ | ¹H NMR (400 MHz, DMSO-d₆) δ ppm 7.40-7.45 (m, 2H), 7.33-7.39 (m, 2H), 4.53 (s, 2H), 3.84 (t, J = 6.6 Hz, 2H), 3.34 (s, 3H), 3.21 (s, 3H), 2.92 (s, 3H), 2.77 (q, J = 7.6 Hz, 2H), 2.45-2.49 (m, 2H), 2.22-2.36 (m, 4H), 1.26-1 41 (m, 6H), 1.21 (t, J = 7.6 Hz, 3H) |
| 578 | 2-((3,5-dicyano-6-((R)-2-((diethylamino)methyl)morpholino)-4-ethylpyridin-2-yl)thio)-2-phenylacetamide | 493.4 [M + H]⁺ | ¹H NMR (400 MHz, DMSO-d₆) δ ppm 7.83-7.95 (m, 1H), 7.48-7.55 (m, 2 H), 7.31-7.44 (m, 4 H), 5.47-5.56 (m, 1 H), 4.47-4.59 (m, 2 H), 3.87-3.98 (m, 1 H), 3.41-3.63 (m, 2 H), 3.14-3.26 (m, 1 H), 3.02-3.14 (m, 1 H), 2.77 (q, J = 7.4 Hz, 2 H), 2.39-2.59 (m, 6 H), 1.21 (t, J = 7.6 Hz, 3 H), 0.90-0.98 (m, 6 H) |

| Example | Structure/Name | LCMS m/z | 1H NMR |
|---|---|---|---|
| 579 | 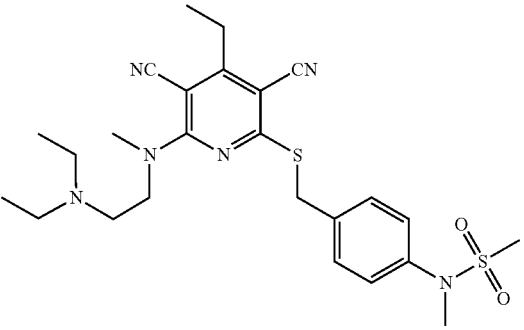 [SMILES: CCc1c(C#N)c(SCc2ccc(N(C)S(C)(=O)=O)cc2)nc(N(C)CCN(CC)CC)c1C#N]<br>N-(4-(((3,5-dicyano-6-((2-(diethylamino)ethyl)(methyl)amino)-4-ethylpyridin-2-yl)thio)methyl)phenyl)-N-methylmethanesulfonamide | 515.1 [M + H]+ | $^1$H NMR (400 MHz, DMSO-d$_6$) δ ppm 7.41-7.47 (m, 2H), 7.31-7.40 (m, 2 H), 4.53 (s, 2 H), 3.84 (t, J = 6.5 Hz, 2 H), 3.36 (s, 3 H), 3.22 (s, 3 H), 2.93 (s, 3 H), 2.78 (q, J = 7.5 Hz, 2 H), 2.59 (t, J = 6.5 Hz, 2 H), 2.42 (q, J = 7.1 Hz, 4 H), 1.22 (t, J = 7.6 Hz, 3 H), 0.86 (t, J = 7.1 Hz, 6 H) |
| 580 | 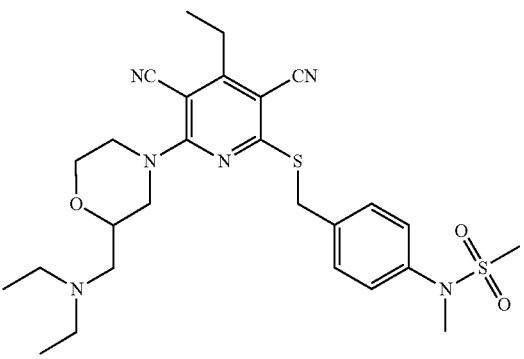 [SMILES: CCc1c(C#N)c(SCc2ccc(N(C)S(C)(=O)=O)cc2)nc(N2CCOC(CN(CC)CC)C2)c1C#N]<br>N-(4-(((3,5-dicyano-6-(2-((diethylamino)methyl)morpholino)-4-ethylpyridin-2-yl)thio)methyl)phenyl)-N-methylmethanesulfonamide | 557.2 [M + H]+ | $^1$H NMR (400 MHz, DMSO-d$_6$) δ ppm 7.41-7.47 (m, 2 H), 7.34-7.40 (m, 2 H), 4.63-4.73 (m, 1 H), 4.52 (s, 2 H), 4.37-4.45 (m, 1 H), 3.88-3.98 (m, 1 H), 3.47-3.65 (m, 2 H), 3.25-3.33 (m, 1 H), 3.22 (s, 3 H), 3.02 (dd, J = 10.4, 13.4 Hz, 1H), 2.93 (s, 3 H), 2.78 (q, J = 7.4 Hz, 2H), 2.36-2.49 (m, 6 H), 1.22 (t, J = 7.6 Hz, 3 H), 0.90 (t, J = 7.1 Hz, 6 H) |
| 581 | 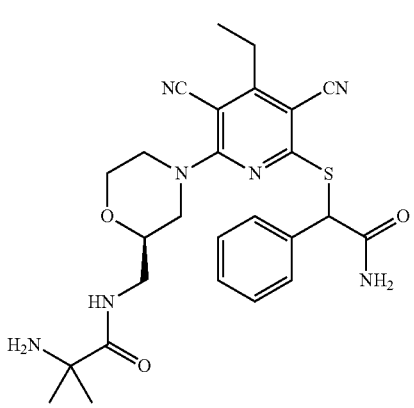 [SMILES: CCc1c(C#N)c(SC(C(N)=O)c2ccccc2)nc(N2CCO[C@H](CNC(=O)C(C)(C)N)C2)c1C#N]<br>2-amino-N-(((2R)-4-(6-((2-amino-2-oxo-1-phenylethyl)thio)-3,5-dicyano-4-ethylpyridin-2-yl)morpholin-2-yl)methyl)-2-methylpropanamide | 522.1 [M + H]+ | $^1$H NMR (400 MHz, DMSO-d$_6$) δ ppm 8.08-8.21 (m, 1 H), 7.91-8.04 (m, 1 H), 7.50-7.57 (m, 2 H), 7.30-7.46 (m, 4 H), 5.49-5.57 (m, 1 H), 4.35-4.51 (m, 2 H), 3.91-4.02 (m, 1 H), 3.46-3.63 (m, 2 H), 3.12-3.33 (m, 3 H), 2.95-3.09 (m, 1 H), 2.77 (q, J = 7.6 Hz, 2 H), 1.94 (s, 2H), 1.13-1.24 (m, 9 H) |

-continued

| Example | Structure/Name | LCMS m/z | 1H NMR |
|---|---|---|---|
| 582 | N-(4-(((3,5-dicyano-4-ethyl-6-(4-(pyrrolidin-1-yl)piperidin-1-yl)pyridin-2-yl)thio)methyl)phenyl)-N-methylmethanesulfonamide | 539.2 [M + H]+ | $^1$H NMR (400 MHz, CHLOROFORM-d) δ ppm 7.39-7.44 (m, 2 H), 7.33-7.38 (m, 2 H), 4.49-4.60 (m, 2 H), 4.42 (s, 2 H), 3.32-3.35 (m, 3 H), 3.20-3.31 (m, 2 H), 2.92 (q, J = 7.4 Hz, 2 H), 2.85-2.88 (m, 3 H), 2.53-2.72 (m, 4 H), 2.24-2 46 (m, 1 H), 2.05 (d, J = 12.9 Hz, 2 H), 1.76-1.94 (m, 4 H), 1.61-1.75 (m, 2 H, 1.34 (t, J = 7.6 Hz, 3 H) |
| 583 | 2-((6-(4-aminopiperidin-1-yl)-3,5-dicyano-4-ethylpyridin-2-yl)thio)-2-(3-fluoropyridin-2-yl)acetamide | 440.1 [M + H]+ | $^1$H NMR (400 MHz, DMSO-d$_6$) δ ppm 8.39-8.45 (m, 1 H), 7.77-7.84 (m, 1 H), 7.74 (s, 1 H), 7.46-7.53 (m, 2 H), 5.98 (s, 1 H), 4.29-4.40 (m, 2 H), 3.24-3.32 (m, 2 H), 2.85-2.96 (m, 1 H), 2.78 (q, J = 7.6 Hz, 2H), 1.67-1.86 (m, 4 H), 1.18-1.35 (m, 5 H) |
| 584 | (R)-2-amino-N-(1-(3,5-dicyano-4-ethyl-6-((4-(N-methylmethylsulfonamido)benzyl)thio)pyridin-2-yl)piperidin-4-yl)propanamide | 556.1 [M + H]+ | $^1$H NMR (400 MHz, DMSO-d$_6$) δ ppm 7.76 (d, J = 7.9 Hz, 1 H), 7.41-7.48 (m, 2 H), 7.32-7.41 (m, 2 H), 4.51 (s, 2 H), 4.36-4.46 (m, 2 H), 3.82-3.97 (m, 1 H), 3.40-3.28 (m, 2 H), 3.17-3.25 (m, 4 H), 2.93 (s, 3 H), 2.77 (q, J = 7.6 Hz, 2 H), 1.71-1.91 (m, 4 H), 1.41-1.57 (m, 2 H), 1.22 (t, J = 7.6 Hz, 3 H), 1.11 (d, J = 6.8 Hz, 3 H) |
| 585 | (S)-2-amino-N-(1-(3,5-dicyano-4-ethyl-6-((4-(N-methylmethylsulfonamido) | 556.2 [M + H]+ | $^1$H NMR (400 MHz, DMSO-d$_6$) δ ppm 7.76 (d, J = 8.1 Hz, 1 H), 7.42-7.48 (m, 2 H), 7.33-7.41 (m, 2 H), 4 51 (s, 2 H), 4.34-4.47 (m, 2 H), 3.80-3.97 (m, 1 H), 3.41-3.27 (m, 2 H), 3.14-3.26 (m, 4 H), 2.93 (s, 3 H), 2.77 (q, J = 7.6 Hz, 2 H), 1.70-1 90 (m, 4 H), 1 41-1.56 (m, 2 H), 1.22 (t, J = 7.6 Hz, 3 H), 1.11 (d, J = 6.8 Hz, 3 H) |

-continued

| Example | Structure/Name | LCMS m/z | 1H NMR |
|---|---|---|---|
| | benzyl)thio)pyridin-2-yl)piperidin-4-yl)propanamide | | |
| 586 | 2-((6-((S)-2-(aminomethyl)morpholino)-3,5-dicyano-4-ethylpyridin-2-yl)thio)-2-phenylacetamide | 437.1 [M + H]+ | $^1$H NMR (400 MHz, DMSO-d$_6$) δ ppm 7.89-8.09 (m, 1 H), 7.49-7.56 (m, 2 H), 7.31-7.44 (m, 4 H), 5.49-5.55 (m, 1 H), 4.51-4.66 (m, 1 H), 4.38-4.49 (m, 1 H), 3.90-4.01 (m, 1 H), 3.45-3.60 (m, 1 H), 3.39-3.44 (m, 1 H), 3.18-3.29 (m, 1 H), 2.97-3.06 (m, 1 H), 2.77 (q, J = 7.6 Hz, 2 H), 2.60-2.72 (m, 2 H), 1.49-1.90 (m, 2 H), 1.21 (t, J = 7.6 Hz, 3 H) |
| 587 | N-(4-(((6-(4-aminopiperidin-1-yl)-3,5-dicyano-4-ethylpyridin-2-yl)thio)methyl)phenyl)-N-methylmethanesulfonamide | 485.3 [M + H]+ | $^1$H NMR (400 MHz, DMSO-d$_6$) δ ppm 7.42-7.49 (m, 2 H), 7.32-7.40 (m, 2 H), 4.51 (s, 2 H), 4.32-4.43 (m, 2 H), 3.25-3.32 (m, 2 H), 3.22 (s, 3 H), 2.84-2.96 (m, 4 H), 2.76 (q, J = 7.4 Hz, 2 H), 1.72-1.96 (m, 4 H), 1.16-1.35 (m, 5H) |
| 588 | 2-amino-N-(((3S)-1-(6-((2-amino-2-oxo-1-phenylethyl)thio)-3,5-dicyano-4-ethylpyridin-2-yl)piperidin-3-yl)methyl)-2-methylpropanamide | 520.2 [M + H]+ | $^1$H NMR (400 MHz, DMSO-d$_6$) δ ppm 7.90-8.10 (m, 2 H), 7.50-7.57 (m, 2 H), 7.31-7.49 (m, 4 H), 5.48-5.58 (m, 1 H), 4.32-4.47 (m, 2 H), 3.04-3.19 (m, 2 H), 2.87-3.04 (m, 2 H), 2.75 (q, J = 7.4 Hz, 2 H), 1.88-2.06 (m, 2 H), 1.72-1.86 (m, 3 H), 1.25-1.61 (m, 2 H), 1.14-1.23 (m, 9 H) |

| Example | Structure/Name | LCMS m/z | 1H NMR |
|---|---|---|---|
| 589 | 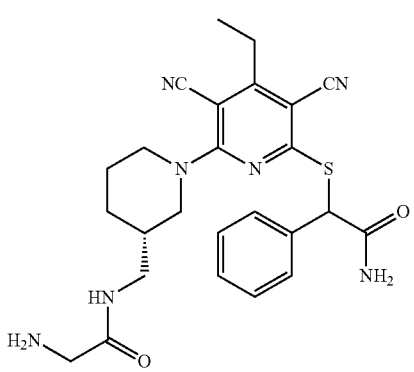 [SMILES: CCc1c(C#N)c(SC(C(N)=O)c2ccccc2)nc(N2CCC[C@@H](CNC(=O)CN)C2)c1C#N]<br>2-amino-N-(((3S)-1-(6-((2-amino-2-oxo-1-phenylethyl)thio)-3,5-dicyano-4-ethylpyridin-2-yl)piperidin-3-yl)methyl)acetamide | 492.1 [M + H]$^+$ | $^1$H NMR (400 MHz, DMSO-d$_6$) δ ppm 7.91-8.08 (m, 2 H), 7.49-7.57 (m, 2 H), 7.28-7.46 (m, 4 H), 5.49-5.58 (m, 1 H), 4.35-4.53 (m, 2 H), 3.08-3.19 (m, 4 H), 2.89-3.08 (m, 2 H), 2.75 (q, J = 7.4 Hz, 2 H), 2.19-2.40 (m, 2 H), 1.71-1.88 (m, 3 H), 1.25-1.64 (m, 2 H), 1.20 (t, J = 7.5 Hz, 3 H) |
| 590 | 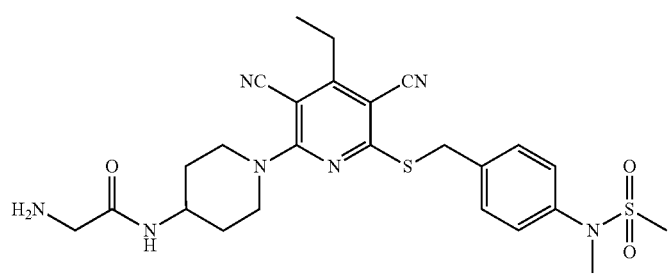 [SMILES: CCc1c(C#N)c(SCc2ccc(N(C)S(C)(=O)=O)cc2)nc(N2CCC(NC(=O)CN)CC2)c1C#N]<br>2-amino-N-(1-(3,5-dicyano-4-ethyl-6-((4-(N-methylmethylsulfonamido)benzyl)thio)pyridin-2-yl)piperidin-4-yl)acetamide | 542.1 [M + H]$^+$ | $^1$H NMR (400 MHz, DMSO-d$_6$) δ ppm 7.70-7.87 (m, 1H), 7.42-7.49 (m, 2 H), 7.33-7.42 (m, 2 H), 4.51 (s, 2 H), 4.36-4.47 (m, 2 H), 3.86-4.03 (m, 1 H), 3.28-3.39 (m, 2 H), 3.22 (s, 3 H), 3.06 (br. s., 2 H), 2.93 (s, 3 H), 2.77 (q, J = 7.6 Hz, 2 H), 1.66-1.92 (m, 4 H), 1.41-1.56 (m, 2 H), 1.22 (t, J = 7.6 Hz, 3 H) |
| 591 | 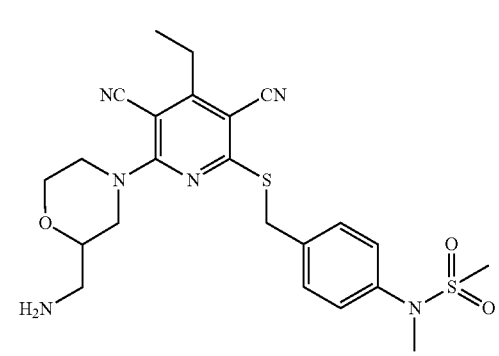 [SMILES: CCc1c(C#N)c(SCc2ccc(N(C)S(C)(=O)=O)cc2)nc(N2CCOC(CN)C2)c1C#N]<br>N-(4-(((6-(2-(aminomethyl)morpholino)-3,5-dicyano-4-ethylpyridin-2-yl)thio)methyl)phenyl)-N-methylmethanesulfonamide | 501.1 [M + H]$^+$ | $^1$H NMR (400 MHz, DMSO-d$_6$) δ ppm 7.42-7.49 (m, 2 H), 7.34-7.41 (m, 2 H), 4.47-4.61 (m, 3 H), 4.35-4.44 (m, 1 H), 3.89-4.00 (m, 1 H), 3.45-3.57 (m, 1 H), 3.26-3.43 (m, 2 H), 3.22 (s, 3 H), 2.98-3.08 (m, 1 H), 2.93 (s, 3 H), 2.78 (q, J = 7.6 Hz, 2 H), 2.54-2.69 (m, 2 H), 1.39-1.76 (m, 2 H), 1.22 (t, J = 7.6 Hz, 3 H) |

| Example | Structure/Name | LCMS m/z | 1H NMR |
|---|---|---|---|
| 592 | 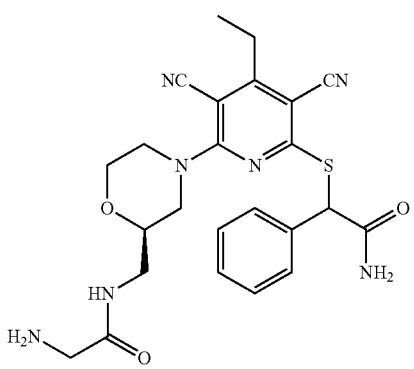 [SMILES: CCc1c(C#N)c(SC(C(N)=O)c2ccccc2)nc(N2CCO[C@H](CNC(=O)CN)C2)c1C#N]<br>2-amino-N-(((2R)-4-(6-((2-amino-2-oxo-1-phenylethyl)thio)-3,5-dicyano-4-ethylpyridin-2-yl)morpholin-2-yl)methyl)acetamide | 494.0 [M + H]+ | $^1$H NMR (400 MHz, DMSO-d$_6$) δ ppm 8.03-8.12 (m, 1 H), 7.92-8.02 (m, 1 H), 7.50-7.57 (m, 2 H), 7.31-7.45 (m, 4 H), 5.50-5.57 (m, 1 H), 4.47-4.56 (m, 1 H), 4.34-4.47 (m, 1 H), 3.93-4.03 (m, 1 H), 3.47-3.64 (m, 2 H), 3.17-3.42 (m, 3 H), 3.11 (s, 2 H), 2.95-3.08 (m, 1 H), 2.77 (q, J = 7.4 Hz, 2 H), 1.88 (br. s., 2H), 1.21 (t, J = 7.6 Hz, 3 H) |
| 593 | 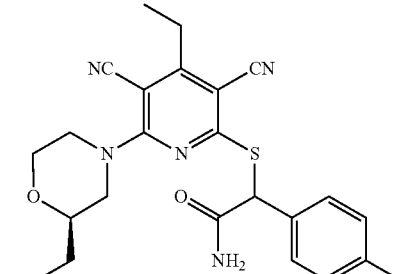<br>2-((6-((R)-3-(aminomethyl)piperidin-1-yl)-3,5-dicyano-4-ethylpyridin-2-yl)thio)-2-(4-fluorophenyl)acetamide | 453.1 [M + H]+ | $^1$H NMR (400 MHz, DMSO-d$_6$) δ ppm 8.09-8.36 (m, 1H), 7.55-7.64 (m, 2 H), 7.35-7.47 (m, 1 H), 7.23 (t, J = 8.7 Hz, 2 H), 5.55-5.61 (m, 1 H), 4.38-4.73 (m, 2 H), 3.03-3.25 (m, 3 H), 2.83-3.00 (m, 1 H), 2.76 (q, J = 7.6 Hz, 2 H), 2.44-2.62 (m, 2 H), 1.75-1.90 (m, 2 H), 1.72-1.59 (m, 1 H), 1.41-1.57 (m, 1 H), 1.24-1.34 (m, 1 H), 1.21 (t, J = 7.5 Hz, 3 H) |
| 594 | 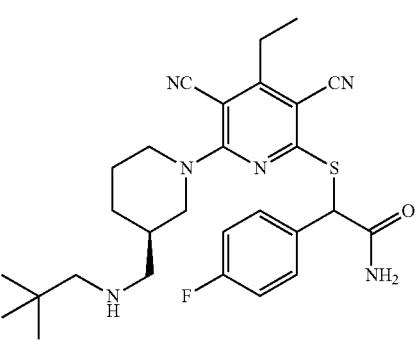 [SMILES: CCc1c(C#N)c(SC(C(N)=O)c2ccc(F)cc2)nc(N2CCC[C@H](CNCC(C)(C)C)C2)c1C#N]<br>2-((3,5-dicyano-4-ethyl-6-((R)-3-((neopentylamino)methyl)piperidin-1-yl)pyridin-2-yl)thio)-2-(4-fluorophenyl)acetamide | 523.3 [M + H]+ | $^1$H NMR (400 MHz, DMSO-d$_6$) δ ppm 7.98 (br. s., 1 H), 7.53-7.61 (m, 2 H), 7.40 (br. s., 1 H), 7.22 (t, J = 8.9 Hz, 2 H), 5.53-5.58 (m, 1 H), 4.36-4.57 (m, 2 H), 3.02-3.23 (m, 2 H), 2.75 (q, J = 7.6 Hz, 2 H), 2.39-2.47 (m, 2 H), 2.14-2.30 (m, 2 H), 1.81-1.93 (m, 1 H), 1.68-1.81 (m, 2 H), 1.25-1.64 (m, 3 H), 1.20 (t, J = 7.6 Hz, 3 H), 0.80-0.86 (m, 9 H) |

| Example | Structure/Name | LCMS m/z | 1H NMR |
|---|---|---|---|
| 595 | N-(4-(((3,5-dicyano-4-ethyl-6-(4-methyl-1,4-diazepan-1-yl)pyridin-2-yl)thio)methyl)phenyl)-1-fluoro-N-methylmethanesulfonamide | 517.0 [M + H]+ | $^1$H NMR (400 MHz, DMSO-d$_6$) δ ppm 7.41-7.48 (m, 2 H), 7.33-7.40 (m, 2 H), 5.63 (d, J = 45.9 Hz, 2 H), 4.52 (s, 2 H), 3.80-3.94 (m, 4 H), 3.30 (s, 3 H), 2.78 (q, J = 7.6 Hz, 2 H), 2.59-2.70 (m, 2 H), 2.45-2.49 (m, 2 H), 2.23 (s, 3 H), 1.83-1.96 (m, 2 H), 1.22 (t, J = 7.6 Hz, 3 H) |
| 596 | N-(4-(((3,5-dicyano-4-ethyl-6-(2-((methylamino)methyl)morpholino)pyridin-2-yl)thio)methyl)phenyl)-N-methylmethanesulfonamide | 515.1 [M + H]+ | $^1$H NMR (400 MHz, DMSO-d$_6$) δ ppm 7.42-7.49 (m, 2 H), 7.35-7.41 (m, 2 H), 4.48-4.57 (m, 3 H), 4.35-4.44 (m, 1 H), 3.90-4.00 (m, 1 H), 3.54-3.64 (m, 1 H), 3.47-3.54 (m, 1 H), 3.25-3.32 (m, 2 H), 3.19-3.24 (m, 3 H), 3.02-3.12 (m, 1 H), 2.90-2.96 (m, 3 H), 2.78 (q, J = 7.6 Hz, 2 H), 2.55-2.69 (m, 2 H), 2.17-2.35 (m, 3 H), 1.19-1.25 (m, 3 H) |
| 597 | N-(4-(((3,5-dicyano-6-(3-((dimethylamino)methyl)piperidin-1-yl)-4-ethylpyridin-2-yl)thio)methyl)phenyl)-N-methylmethanesulfonamide | 527.1 [M + H]+ | $^1$H NMR (400 MHz, DMSO-d$_6$) δ ppm 7.43-7.49 (m, 2 H), 7.33-7.40 (m, 2 H), 4.49-4.60 (m, 3 H), 4.28-4.39 (m, 1 H), 3.23-3.32 (m, 1 H), 3.22 (s, 3 H), 2.98-3.07 (m, 1 H), 2.93 (s, 3 H), 2.77 (q, J = 7.6 Hz, 2 H), 2.05-2.16 (m, 7 H), 1.97-2.04 (m, 1 H), 1.68-1.89 (m, 3 H), 1.44-1.59 (m, 1 H), 1.16-1.29 (m, 4 H) |

| Example | Structure/Name | LCMS m/z | 1H NMR |
|---|---|---|---|
| 598 | 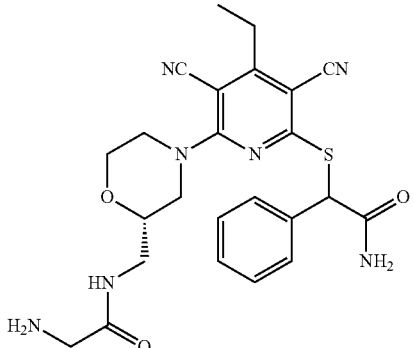<br>2-amino-N-(((2S)-4-(6-((2-amino-2-oxo-1-phenylethyl)thio)-3,5-dicyano-4-ethylpyridin-2-yl)morpholin-2-yl)methyl)acetamide | 494.1 [M + H]+ | 1H NMR (400 MHz, DMSO-d6) δ ppm 8.03-8.12 (m, 1 H), 7.91-8.02 (m, 1 H), 7.50-7.57 (m, 2 H), 7.31-7.45 (m, 4 H), 5.51-5.57 (m, 1 H), 4.47-4.57 (m, 1 H), 4.36-4.47 (m, 1 H), 3.92-4.03 (m, 1 H), 3.47-3.62 (m, 2 H), 3.36-3.43 (m, 1 H), 3.18-3.31 (m, 2 H), 3.11 (s, 2 H), 2.95-3.07 (m, 1 H), 2.77 (q, J = 7.4 Hz, 2 H), 1.85 (br. s., 2 H), 1.21 (t, J = 7.6 Hz, 3 H) |
| 599 | 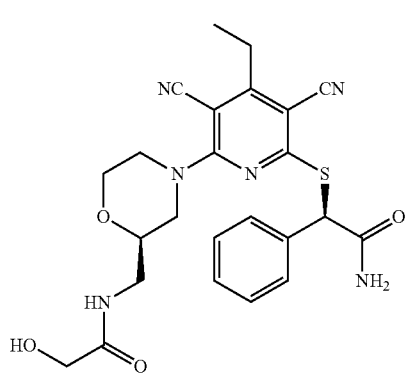 [SMILES: CCc1c(C#N)c(S[C@@H](C(N)=O)c2ccccc2)nc(N2CCO[C@H](CNC(=O)CO)C2)c1C#N]<br>N-(((R)-4-(6-(((R)-2-amino-2-oxo-1-phenylethyl)thio)-3,5-dicyano-4-ethylpyridin-2-yl)morpholin-2-yl)methyl)-2-hydroxyacetamide | 495.0 [M + H]+ | 1H NMR (400 MHz, DMSO-d6) δ ppm 7.96 (s, 1 H), 7.87 (t, J = 5.8 Hz, 1 H), 7.50-7.55 (m, 2 H), 7.32-7.44 (m, 4 H), 5.54 (s, 1 H), 4.46-4.56 (m, 1 H), 4.39 (d, J = 11.7 Hz, 1 H), 3.97 (d, J = 11.7 Hz, 1 H), 3.84 (s, 2 H), 3.46-3.62 (m, 4 H), 3.21-3.36 (m, 2 H), 3.01 (dd, J = 13.4, 10.4 Hz, 1 H), 2.72-2.82 (m, 2 H), 1.21 (t, J = 7.6 Hz, 3 H) |
| 600 | 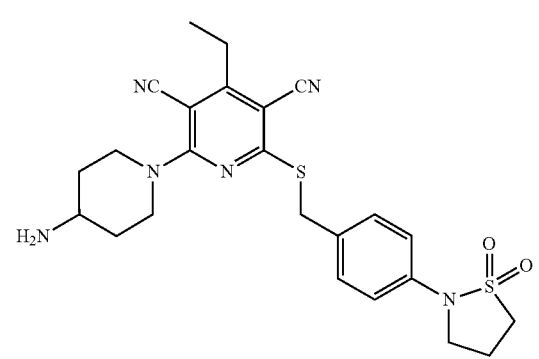 [SMILES: CCc1c(C#N)c(SCc2ccc(N3CCCS3(=O)=O)cc2)nc(N2CCC(N)CC2)c1C#N]<br>2-(4-aminopiperidin-1-yl)-6-((4-(1,1-dioxidoisothiazolidin-2-yl)benzyl)thio)-4-ethylpyridine-3,5-dicarbonitrile | 497.1 [M + H]+ | 1H NMR (400 MHz, DMSO-d6) δ ppm 7.37-7.44 (m, 2 H), 7.13-7.20 (m, 2 H), 4.47 (s, 2 H), 4.35-4.44 (m, 2 H), 3.72 (t, J = 6.5 Hz, 2 H), 3.51 (t, J = 7.5 Hz, 2 H), 3.27-3.33 (m, 2 H), 2.84-2.95 (m, 1 H), 2.76 (q, J = 7.6 Hz, 2 H), 2.40 (quin, J = 7.0 Hz, 2 H), 1.79-1.90 (m, 2 H), 1.64 (br. s., 2 H), 1.25-1.36 (m, 2 H), 1.21 (t, J = 7.6 Hz, 3 H) |

| Example | Structure/Name | LCMS m/z | 1H NMR |
|---|---|---|---|
| 601 | 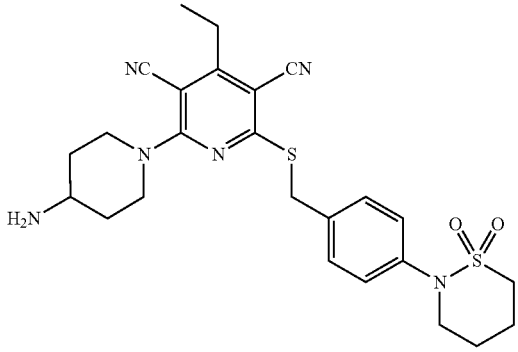 [SMILES: CCc1c(C#N)c(SCc2ccc(N3CCCCS3(=O)=O)cc2)nc(N2CCC(N)CC2)c1C#N]<br>2-(4-aminopiperidin-1-yl)-6-((4-(1,1-dioxido-1,2-thiazinan-2-yl)benzyl)thio)-4-ethylpyridine-3,5-dicarbonitrile | 511.1 [M + H]⁺ | ¹H NMR (400 MHz, DMSO-d₆) δ ppm 7.38-7.46 (m, 2 H), 7.23-7.33 (m, 2 H), 4.50 (s, 2 H), 4.30-4.43 (m, 2 H), 3.60-3.67 (m, 2 H), 3.25-3.31 (m, 4 H), 2.84-2.94 (m, 1 H), 2.76 (q, J = 7.4 Hz, 2 H), 2.07-2.20 (m, 2 H), 1.75-1.89 (m, 4 H), 1.60 (br. s., 2 H), 1.16-1.33 (m, 5H) |
| 602 | 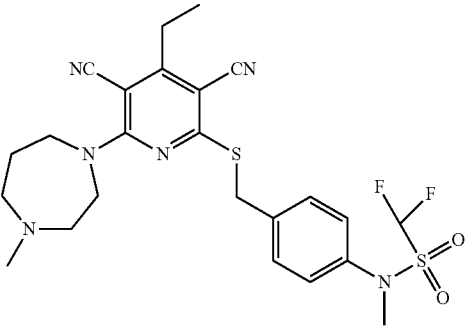 [SMILES: CCc1c(C#N)c(SCc2ccc(N(C)S(=O)(=O)C(F)F)cc2)nc(N2CCCN(C)CC2)c1C#N]<br>N-(4-(((3,5-dicyano-4-ethyl-6-(4-methyl-1,4-diazepan-1-yl)pyridin-2-yl)thio)methyl)phenyl)-1,1-difluoro-N-methylmethanesulfonamide | 535.0 [M + H]⁺ | ¹H NMR (400 MHz, DMSO-d₆) δ ppm 7.44-7.50 (m, 2 H), 7.36-7.42 (m, 2 H), 7.26 (t, J = 52.5 Hz, 1 H), 4.53 (s, 2 H), 3.80-3.93 (m, 4 H), 3.36 (s, 3 H), 2.78 (q, J = 7.6 Hz, 2 H), 2.60-2.67 (m, 2 H), 2.44-2.48 (m, 2 H), 2.23 (s, 3 H), 1.83-1.95 (m, 2 H), 1.22 (t, J = 7.6 Hz, 3 H) |
| 603 | 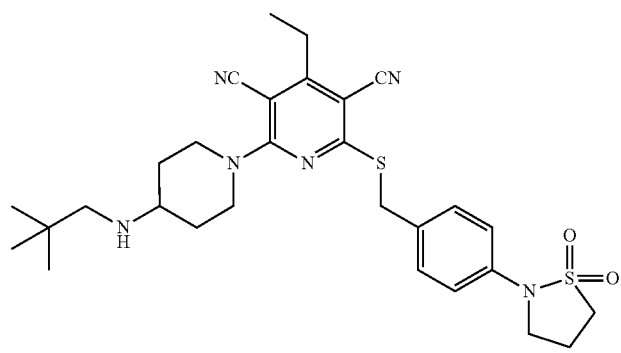 [SMILES: CCc1c(C#N)c(SCc2ccc(N3CCCS3(=O)=O)cc2)nc(N2CCC(NCC(C)(C)C)CC2)c1C#N]<br>2-((4-(1,1-dioxidoisothiazolidin-2-yl)benzyl)thio)-4-ethyl-6-(4-(neopentylamino)piperidin-1-yl)pyridine-3,5-dicarbonitrile | 567.3 [M + H]⁺ | ¹H NMR (400 MHz, DMSO-d₆) δ ppm 7.41 (d, J = 8.6 Hz, 2 H), 7.16 (d, J = 8.6 Hz, 2 H), 4.47 (s, 2 H), 4.39 (d, J = 13.4 Hz, 2 H), 3.72 (t, J = 6.5 Hz, 2 H), 3.51 (t, J = 7.4 Hz, 2 H), 3.27-3.40 (m, 2 H), 2.76 (q, J = 7.6 Hz, 2 H), 2.62-2.71 (m, 1 H), 2.40 (quin, J = 6.9 Hz, 2 H), 2.30 (br. s., 2 H), 1.86-1.99 (m, 2 H), 1.28-1.42 (m, 3 H), 1.21 (t, J = 7.6 Hz, 3 H), 0.86 (s, 9 H) |

| Example | Structure/Name | LCMS m/z | 1H NMR |
|---|---|---|---|
| 604 | 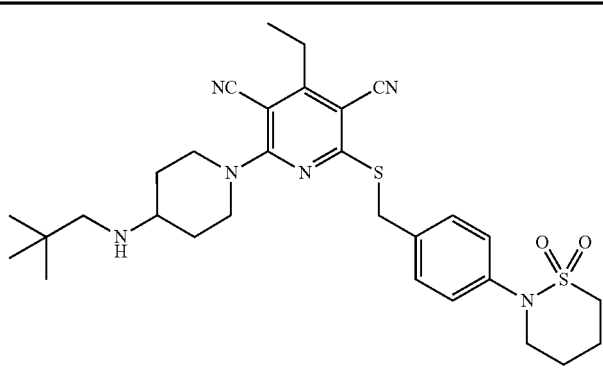<br>2-((4-(1,1-dioxido-1,2-thiazinan-2-yl)benzyl)thio)-4-ethyl-6-(4-(neopentylamino)piperidin-1-yl)pyridine-3,5-dicarbonitrile | 581.3 [M + H]+ | $^1$H NMR (400 MHz, DMSO-d$_6$) δ ppm 7.42 (d, J = 8.4 Hz, 2 H), 7.27 (d, J = 8.4 Hz, 2 H), 4.50 (s, 2 H), 4.37 (d, J = 13.4 Hz, 2 H), 3.59-3.66 (m, 2 H), 3.22-3.40 (m, 4 H), 2.76 (q, J = 7.6 Hz, 2 H), 2.59-2.71 (m, 1 H), 2.29 (br. s., 2 H), 2.09-2.19 (m, 2 H), 1.86-1.97 (m, 2 H), 1.74-1.84 (m, 2 H), 1.26-1.42 (m, 3 H), 1.21 (t, J = 7.6 Hz, 3 H), 0.86 (s, 9 H) |
| 605 | 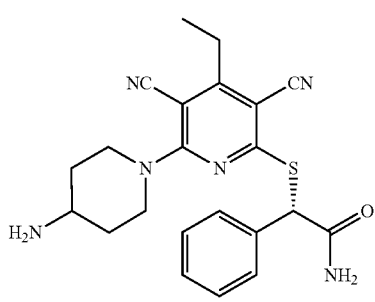<br>(S)-2-((6-(4-aminopiperidin-1-yl)-3,5-dicyano-4-ethylpyridin-2-yl)thio)-2-phenylacetamide, Hydrochloride | 421.1 [M + H]+ | $^1$H NMR (400 MHz, DMSO-d$_6$) δ ppm 8.07 (br. s., 3H), 7.98 (s, 1H), 7.56-7.48 (m, 2H), 7.44-7.30 (m, 4H), 5.55 (s, 1H), 4.59 (d, J = 13.9 Hz, 2H), 3.46-3.33 (m, 1H), 3.31-3.17 (m, 2H), 2.77 (q, J = 7.6 Hz, 2H), 2.12-2.00 (m, 2H), 1.66-1.49 (m, 2H), 1.21 (t, J = 7.6 Hz, 3H) |
| 606 | 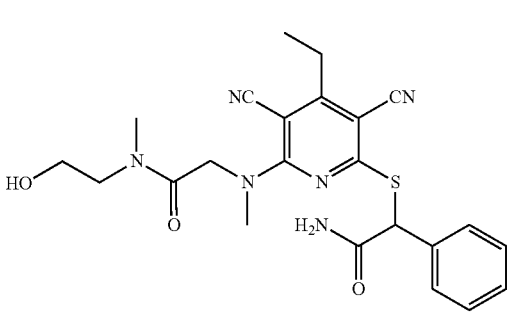 [SMILES: CCc1c(C#N)c(SC(C(N)=O)c2ccccc2)nc(N(C)CC(=O)N(C)CCO)c1C#N]<br>2-((6-((2-amino-2-oxo-1-phenylethyl)thio)-3,5-dicyano-4-ethylpyridin-2-yl)(methyl)amino)-N-(2-hydroxyethyl)-N-methylacetamide | 467.11 [M + H]+ | $^1$H NMR (400 MHz, DMSO-d$_6$) δ ppm 7.52-7.25 (m, 7 H), 5.51 (br s, 1 H), 4.61-4.93 (m, 3 H), 3.58 (br s, 2 H), 3.39 (br s, 2 H), 3.31 (s, 3 H), 2.90 (br s, 3 H), 2.78 (q, J = 7.53 Hz, 2 H), 1.22 (t, J = 7.56 Hz, 3 H). |

-continued

| Example | Structure/Name | LCMS m/z | 1H NMR |
|---|---|---|---|
| 607 | 2-((3,5-dicyano-4-ethyl-6-((S)-3-(methylamino)piperidin-1-yl)pyridin-2-yl)thio)-2-phenylacetamide | 435.19 [M + H]+ | ¹H NMR (400 MHz, DMSO-d₆) δ ppm 7.94 (s, 1 H), 7.53 (dd, J = 7.23, 1.53 Hz, 2 H), 7.41-7.30 (m, 4 H), 5.56 (d, J = 4.17 Hz, 1 H), 4.46-4.38 (m, 1 H), 4.28-4.18 (m, 1 H), 3.42-3.31 (m, 2 H), 2.82-2.67 (m, 3 H), 2.37 (d, J = 7.02 Hz, 3 H), 2.02-1.95 (m, 1 H), 1.87-1.78 (m, 1 H), 1.38-1.58 (m, 2 H), 1.21 (t, J = 7.56 Hz, 3 H). |
| 608 | 2-((6-(4-amino-4-methylpiperidin-1-yl)-3,5-dicyano-4-ethylpyridin-2-yl)thio)-2-phenylacetamide | 435.13 [M + H]+ | ¹H NMR (400 MHz, DMSO-d₆) δ ppm 7.89 (s, 1 H), 7.54-7.49 (m, 2 H), 7.39-7.30 (m, 4 H), 5.53 (s, 1 H), 4.12-4.05 (m, 2 H), 3.76-3.68 (m, 2 H), 2.75 (q, J = 7.67 Hz, 2 H), 1.66-1.47 (m, 6 H), 1.20 (t, J = 7.56 Hz, 3 H), 1.11 (s, 3H). |
| 609 | 2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)-N-methylacetamide | 507.16 [M + H]+ | ¹H NMR (400 MHz, DMSO-d₆) δ ppm 7.85 (br d, J = 10.96 Hz, 1 H), 7.48 (t, J = 7.02 Hz, 2 H), 7.41-7.31 (m, 4 H), 5.49 (d, J = 12.50 Hz, 1 H), 5.07-4.87 (m, 2 H), 4.68 (br d, J = 18.20 Hz, 0.5 H), 4.35 (t, J = 5.92 Hz, 0.5 H), 3.41-3.33 (m, 2 H), 3.29-3.15 (m, 5 H), 3.05-2.85 (m, 3 H), 2.76 (q, J = 7.31 Hz, 2 H), 1.20 (t, J = 7.56 Hz, 3 H), 0.49-0.36 (m, 4 H) |
| 610 |  | 462.07 [M + H]+ | ¹H NMR (400 MHz, DMSO-d₆) δ ppm 8.55 (br s, 1 H), 7.83 (s, 1 H), 7.52-7.47 (m, 2 H), 7.40-7.31 (m, 3 H), 7.23 (s, 1 H), 5.54 (s, 1 H), 4.66 (br s, 3 H), 4.31 (br s, 2 H), 3.13 (s, 2 H), 2.12-2.04 (m, 1 H), 1.83 (br s, 2 H), 1.17-1.09 (m, 2 H), 0.98-0.92 (m, 2 H). |

| Example | Structure/Name | LCMS m/z | 1H NMR |
|---|---|---|---|
| | 2-amino-N-(1-(6-((2-amino-2-oxo-1-phenylethyl)thio)-3,5-dicyano-4-cyclopropylpyridin-2-yl)azetidin-3-yl)acetamide | | |
| 611 | (2S)-2-amino-N-(1-(6-((2-amino-2-oxo-1-phenylethyl)thio)-3,5-dicyano-4-cyclopropylpyridin-2-yl)azetidin-3-yl)-3-hydroxypropanamide | 492.04 [M + H]$^+$ | $^1$H NMR (400 MHz, DMSO-d$_6$) δ ppm 8.57 (br s, 1 H), 7.85 (s, 1 H), 7.52-7.46 (m, 2 H), 7.39-7.31 (m, 3 H), 7 22 (s, 1 H), 5.54 (s, 1 H), 4.78-4.61 (m, 4 H), 4.32 (br s, 2H), 3.55-3.43 (m, 2 H), 3.22 (t, J = 5.48 Hz, 1 H), 2.11-2.03 (m, 1 H), 1.86 (br s, 2 H), 1.14-1.08 (m, 2 H), 0.98-0.92 (m, 2 H) |
| 612 | 2-((6-((S)-3-aminopiperidin-1-yl)-3,5-dicyano-4-ethylpyridin-2-yl)thio)-2-phenylacetamide | 421.2 [M + H]$^+$ | $^1$H NMR (400 MHz, DMSO-d$_6$) δ ppm 7.90 (s, 1 H) 7.50-7.56 (m, 2 H) 7.30-7.42 (m, 4 H) 5.51 (s, 1 H) 4.25-4.44 (m, 2 H) 3.18-3.27 (m, 1 H) 2.98 (dd, J = 12.72, 9.21 Hz, 1 H) 2.75 (q, J = 7.45 Hz, 3 H) 1.94-2.09 (br, 2 H) 1.76-1.93 (m, 2 H) 1.42-1.54 (m, 1 H) 1.27-1.37 (m, 1 H) 1.21 (t, J = 7.67 Hz, 3 H). |
| 613 | 2-((3,5-dicyano-4-ethyl-6-((2-((R)-3-hydroxypyrrolidin-1-yl)-2-oxoethyl)(methyl)amino)pyridin-2-yl)thio)-2-phenylacetamide | 479.27 [M + H]$^+$ | $^1$H NMR (400 MHz, DMSO-d$_6$) δ ppm 7.88-7.77 (m, 1 H) 7.61-7.44 (m, 2 H) 7.42-7.14 (m, 4 H) 5.51-5.43 (m, 1 H) 5.13-4.94 (m, 1 H) 4.84-4.51 (m, 2 H) 4.38-4.25 (m, 1 H) 3.79-3.30 (m, 7 H) 2.81-2.65 (m, 2 H) 2.00-1.73 (m, 2 H) 1.20 (t, J = 7.56 Hz, 3 H). |

| Example | Structure/Name | LCMS m/z | 1H NMR |
|---|---|---|---|
| 614 | 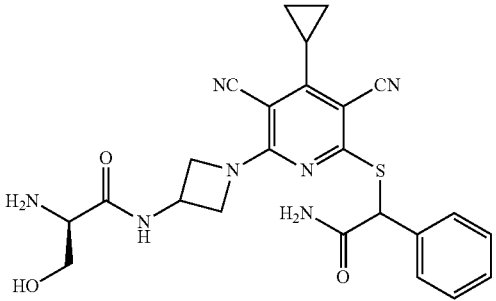 [SMILES: N#Cc1c(SC(C(N)=O)c2ccccc2)nc(N2CC(NC(=O)[C@H](N)CO)C2)c(C#N)c1C1CC1]<br>(2R)-2-amino-N-(1-(6-((2-amino-2-oxo-1-phenylethyl)thio)-3,5-dicyano-4-cyclopropylpyridin-2-yl)azetidin-3-yl)-3-hydroxypropanamide | 492.04 [M + H]+ | 1H NMR (400 MHz, DMSO-d6) δ ppm 8.58 (br s, 1 H), 7.85 (s, 1 H), 7.50 (d, J = 6.80 Hz 2 H), 7.42-7.28 (m, 3 H), 7.23 (s, 1 H), 5.54 (s, 1 H), 4.80-4.57 (m, 4 H), 4.32 (br s, 2 H), 3.57-3.43 (m, 2 H), 3.21 (t, J = 5.37 Hz, 1 H), 2.11-2.04 (m, 1 H), 1.90-1.70 (m, 2 H), 1.18-1.07 (m, 2 H), 0.98-0.91 (m, 2 H) |
| 615 | 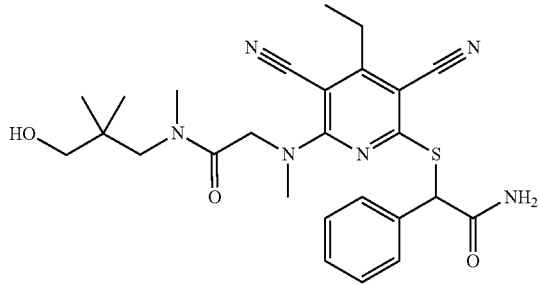 [SMILES: CCc1c(C#N)c(SC(C(N)=O)c2ccccc2)nc(N(C)CC(=O)N(C)CC(C)(C)CO)c1C#N]<br>2-((6-((2-amino-2-oxo-1-phenylethyl)thio)-3,5-dicyano-4-ethylpyridin-2-yl)(methyl)amino)-N-(3-hydroxy-2,2-dimethylpropyl)-N-methylacetamide | 509.11 [M + H]+ | 1H NMR (400 MHz, CHLOROFORM-d) δ ppm 7.50-7.37 (m, 5 H), 6.72 (br s, 1 H), 5.55 (br s, 1 H), 5.24 (s, 1 H), 4.78 (d, J = 17.10 Hz, 1 H), 4.51 (d, J = 17.32 Hz, 1 H), 4.20 (m, 1 H), 3.47 (s, 3 H), 3.34 (s, 1 H), 3.22-3.04 (m, 6H), 2.94 (q, J = 7.53 Hz, 2 H), 1.34 (t, J = 7.56 Hz, 3 H), 0.95 (s, 3 H), 0.90 (s, 3 H). |
| 616 | 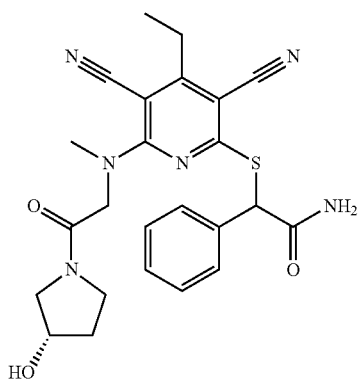 [SMILES: CCc1c(C#N)c(SC(C(N)=O)c2ccccc2)nc(N(C)CC(=O)N2CC[C@H](O)C2)c1C#N]<br>2-((3,5-dicyano-4-ethyl-6-((2-((S)-3-hydroxypyrrolidin-1-yl)-2-oxoethyl)(methyl)amino)pyridin-2-yl)thio)-2-phenylacetamide | 479.2 [M + H]+ | 1H NMR (400 MHz, DMSO-d6) δ ppm 7.89-7.77 (m, 1H), 7.54-7.42 (m, 2H), 7.42-7.27 (m, 4H), 5.51-5.46 (m, 1H), 5.09 (d, J = 3.73 Hz, 1H), 4.86-4.42 (m, 2H), 4.39-4.23 (m, 1H), 3.33 (d, J = 2.41 Hz, 7H), 2.78 (q, J = 7.23 Hz, 2H), 2.08-1.66 (m, 2H), 1.20 (t, J = 7.56 Hz, 3H). |

-continued

| Example | Structure/Name | LCMS m/z | 1H NMR |
|---|---|---|---|
| 617 | 2-((6-(4-amino-4-methylpiperidin-1-yl)-3,5-dicyano-4-ethylpyridin-2-yl)thio)-2-phenylacetamide | 435.13 [M + H]+ | ¹H NMR (400 MHz, DMSO-d₆) δ ppm 7.89 (s, 1H), 7.51 (d, J = 7.02 Hz, 2H), 7.45-7.17 (m, 4H), 5.53 (s, 1H), 4.09 ( d, J = 13.81 Hz, 2H), 3.79-3.61 (m, 2H), 2.78 (q, J = 7.23 Hz, 2H), 1.64-1.41 (m, 6H), 1.20 (t, J = 7.67 Hz, 3H), 1.10 (s, 3H). |
| 618 | 2-((6-(4-(aminomethyl)-4-fluoropiperidin-1-yl)-3,5-dicyano-4-ethylpyridin-2-yl)thio)-2-phenylacetamide hydrochloride | 453.33 [M + H]+ | ¹H NMR (400 MHz, DMSO-d₆) δ ppm 8.19-7.92 (m, 4H), 7.54 (d, J = 7.23 Hz, 2H), 7.43-7.28 (m, 4H), 5.58 (s, 1H), 4.44 (d, J = 14.25 Hz, 2H), 3.47-3.33 (m, 2H), 3.19-3.09 (m, 2H) 2.78 (q, J = 7.23 Hz, 2H), 2 08-1.73 (m, 4H), 1.24-1.12 (m, 3H). |
| 619 | 2-((6-((2-amino-2-oxo-1-phenylethyl)thio)-3,5-dicyano-4-cyclopropylpyridin-2-yl)(methyl)amino)-N-(2-aminoethyl)acetamide hydrochloride | 464.09 [M + H]+ | ¹H NMR (400 MHz, DMSO-d₆) δ ppm 8.39 (t, J = 5.92 Hz, 1H), 7.98 (s, 1H), 7.91 (s, 3H), 7.54-7.48 (m, 2H), 7.42-7.31 (m, 4H), 5.57 (s, 1H), 4.56-4.40 (m, 2H), 3.37 (s, 2H), 3.35 (s, 3H), 2.89 (t, J = 6.03 Hz, 2H), 2.15-2 06 (m, 1H), 1.17-1.11 (m, 2H), 0.98-0.92 (m, 2H). |
| 620 |  | 463.14 [M + H]+ | ¹H NMR (400 MHz, DMSO-d₆) δ ppm 7.86 (s, 1H), 7.54-7.43 (m, 2H), 7.43-7.27 (m, 4H), 5.49 (s, 1H), 4.75 (m, 1H), 4.55 (m, 1H), 3.50-3.42 (m, 4H), 3.42-3.25 (s, 3H), 2.76 (q, J = 7.45 Hz, 2H), 1.89 (m, 2H), 1 77 (m, 2H), 1 20 (t, J = 7.67 Hz, 3H). |

| Example | Structure/Name | LCMS m/z | 1H NMR |
|---|---|---|---|
| | 2-((3,5-dicyano-4-ethyl-6-(methyl(2-oxo-2-(pyrrolidin-1-yl)ethyl)amino)pyridin-2-yl)thio)-2-phenylacetamide | | |
| 621 | 2-((3,5-dicyano-4-ethyl-6-((2-(4-hydroxypiperidin-1-yl)-2-oxoethyl)(methyl)amino)pyridin-2-yl)thio)-2-phenylacetamide | 493.18 [M + H]$^+$ | $^1$H NMR (400 MHz, DMSO-d$_6$) δ ppm 7.85 (s, 1H), 7.52-7.46 (m, 2H), 7.42-7.30 (m, 4H), 5.51 (s, 1H), 4.90-4.85 (m, 1H), 4.74-4.64 (m, 2H), 3.89-3.82 (m, 1H), 3.75-3.66 (m, 1H), 3.63-3.56 (m, 1H), 3.28 (s, 3H), 3.20-3.05 (m, 2H), 2.75 (q, J = 7.67 Hz, 2H), 1.82-1.66 (m, 2H), 1.52-1.42 (m, 1H), 1.36-1.25 (m, 1H), 1.19 (t, J = 7.56 Hz, 3H). |
| 622 | 2-((3,5-dicyano-4-ethyl-6-(methyl(2-oxo-2-(piperazin-1-yl)ethyl)amino)pyridin-2-yl)thio)-2-phenylacetamide | 478.06 [M + H]$^+$ | $^1$H NMR (400 MHz, DMSO-d$_6$) δ ppm 7.85 (s, 1H), 7.52-7.46 (m, 2H), 7.42-7.29 (m, 4H), 5.51 (s, 1H), 4.87 (m, 1H), 4.66 (m, 1H), 3.38 (d, J = 4.60 Hz, 4H), 3.29 (s, 3H), 2.79-2.69 (m, 4H), 2.66-2.62 (m, 2H), 1.19 (t, J = 7.56 Hz, 3H). |
| 623 | 2-((3,5-dicyano-4-ethyl-6-(methyl(2-morpholino-2-oxoethyl)amino)pyridin-2-yl)thio)-2-phenylacetamide | 479.07 [M + H]$^+$ | $^1$H NMR (400 MHz, DMSO-d$_6$) δ ppm 7.86 (s, 1H), 7.51-7.47 (m, 2H), 7.42-7.31 (m, 4H), 5.49 (s, 1H), 4.89 (m, 1H), 4.69 (m, 1H), 3.65-3.54 (m, 4H), 3.44 (m, 4H), 3.31 (s, 3H), 2.76 (q, J = 7.60 Hz, 2H), 1.20 (t, J = 7.56 Hz, 3H). |

| Example | Structure/Name | LCMS m/z | 1H NMR |
|---|---|---|---|
| 624 | (R)-2-((6-((S)-3-(amino methyl)-3-hydroxypyrrolidin-1-yl)-3,5-dicyano-4-ethylpyridin-2-yl)thio)-2-phenylacetamide | 437.19 [M + H]⁺ | ¹H NMR (400 MHz, DMSO-d₆) δ ppm 8.15 (s, 4H), 7.57 (d, J = 7.02 Hz, 2H), 7.41-7.29 (m, 3H), 7.22 (s, 1H), 5.72 (d, J = 8.33 Hz, 2H), 4.08-3.91 (m, 3H), 3.87 (s, 1H), 3.12-3.07 (m, 2H), 2.75 (q, J = 7.45 Hz, 2H), 2.06 (d, J = 5.70 Hz, 2H), 1.21 (t, J = 7.45 Hz, 3H). |
| 625 | 2-((3,5-dicyano-4-ethyl-6-((S)-3-(guanidinooxy)pyrrolidin-1-yl)pyridin-2-yl)thio)-2-phenylacetamide | 465.09 [M + H]⁺ | ¹H NMR (400 MHz, DMSO-d₆) δ ppm 7.89 (s, 1H), 7.62-7.45 (m, 2H), 7.42-7.31 (m, 3H), 7.30-7.24 (s, 1H), 5.61 (d, J = 4.38 Hz, 1H), 5.06 (s, 2H), 4.41 (d, J = 8.33 Hz, 3H), 4.09-3.70 (m, 4H), 2.76 (q, J = 7.47 Hz, 2H), 2.18 (m, 1H), 2.03-1.91 (m, 1H), 1.20 (t, J = 7.45 Hz, 3H) |
| 626 | 4-(((6-(4-aminopiperidin-1-yl)-3,5-dicyano-4-ethylpyridin-2-yl)thio)methyl)phenyl methanesulfonate 2,2,2-trifluoroacetate | 471.7 [M + H]⁺ | ¹H NMR (400 MHz, DMSO) δ 8.03 (s, 3H), 7.54 (d, J = 8.5 Hz, 2H), 7.33 (d, J = 8.5 Hz, 2H), 4.53 (d, J = 19.8 Hz, 4H), 3.39 (s, 4H), 3.26 (t, J = 12.6 Hz, 2H), 2.79 (q, J = 7.4 Hz, 2H), 2.05 (d, J = 11.4 Hz, 2H), 1.58 (d, J = 11.7 Hz, 2H), 1.23 (t, J = 7.6 Hz, 3H). |
| 627 | | 480.14 [M + H]⁺ | ¹H NMR (400 MHz, DMSO-d₆) δ ppm 8.17 (s, 1H), 7.99 (s, 1H), 7.54-7.50 (m, 2H), 7.40-7.30 (m, 4H), 4.82-4.76 (m, 1H), 3.99-3.92 (m, 1H), 3.81-3.72 (m, 1H), 3.43-3.34 (m, 5H), 2.75 (q, J = 7.53 Hz, 2H), 2.53-2.47 (m, 2H), 1.20 (t, J = 7.45 Hz, 3H), 1.14-1.06 (m, 6H). |

| Example | Structure/Name | LCMS m/z | 1H NMR |
|---|---|---|---|
| | 2-amino-N-(2-((6-((2-amino-2-oxo-1-phenylethyl)thio)-3,5-dicyano-4-ethylpyridin-2-yl)(methyl)amino)ethyl)-2-methylpropanamide | | |
| 628 | 2-((6-((2-(2-aminoethoxy)ethyl)(methyl)amino)-3,5-dicyano-4-ethylpyridin-2-yl)thio)-2-phenylacetamide | 439.15 [M + H]+ | ¹H NMR (400 MHz, DMSO-d₆) δ ppm 8.35 (s, 1H), 7.95 (s, 1H), 7.52-7.48 (m, 2H), 7.41-7.32 (m, 4H), 5.52 (s, 1H), 4.00-3.96 (m, 2H), 3.64 (t, J 5.04 Hz, 2H), 3.48 (t, J = 5.37 Hz, 2H), 3.40 (s, 3H), 2.82 (s, 2H), 2.74 (q, J = 7.50 Hz, 2H), 1.21 (t, J = 7.56 Hz, 3H). |
| 629 | 4-amino-N-(1-(6-((2-amino-2-oxo-1-phenylethyl)thio)-3,5-dicyano-4-ethylpyridin-2-yl)piperidin-4-yl)butanamide formate | 506.32 [M + H]+ | ¹H NMR (400 MHz, DMSO-d₆) δ ppm 8.41 (s, 1H), 8.00 (d, J = 7.45 Hz, 1H), 7.95 (s, 1H), 7.54-7.48 (m, 2H), 7.42-7.26 (m, 4H), 5.54 (s, 1H), 4.41 (m, 2H), 3.94-3.90 (m, 1H), 3.30-3.41 (m, 2H), 2.80-2.66 (m, 4H), 2.17 (t, J = 7.34 Hz, 2H), 1.89 (m, 2H), 1.73 (m, 2H), 1.52-1.37 (m, 2H), 1.21 (t, J = 7.56 Hz, 3H). |
| 630 | 2-((6-((2-amino-2-oxo-1-phenylethyl)thio)-3,5-dicyano-4-ethylpyridin-2-yl)(methyl)amino)-N-(2-aminoethyl)acetamide hydrochloride | 452.19 [M + H]+ | 1H NMR (400 MHz, DMSO-d₆) δ ppm 8.40-8.37 (t, J = 5.59 Hz, 1H), 8.04-7.80 (m, 4H), 7.52-7.51 (d, J = 6.80 Hz, 2H), 7.45-7.26 (m, 4H), 5.59 (s, 1H), 4.58-4.38 (m, 2H), 3.45-3.32 (m, 5H), 2.89 (s, 2H), 2.78-2.74 (q, J = 7.53 Hz, 2H), 1.23-1.19 (t, J = 7.56 Hz, 3H). |

-continued

| Example | Structure/Name | LCMS m/z | 1H NMR |
|---|---|---|---|
| 631 | 2-((6-((2-(azetidin-1-yl)-2-oxoethyl)(methyl)amino)-3,5-dicyano-4-ethylpyridin-2-yl)thio)-2-phenylacetamide | 449.10 [M + H]+ | $^1$H NMR (400 MHz, DMSO-d$_6$) δ ppm 7.86 (s, 1H), 7.52-7.47 (m, 2H), 7.41-7.30 (m, 4H), 5.53 (s, 1H), 4.59 (m, 1H), 4.40 (m, 1H), 4.22-4.07 (m, 2H), 3.96-3.86 (m, 2H), 3.31 (s, 3H), 2.77 (q, J = 7.53 Hz, 2H), 2.24 (m, 2H), 1.20 (t, J = 7.67 Hz, 3H). |
| 632 | 2-((6-((R)-3-(aminomethyl)-3-fluoropyrrolidin-1-yl)-3,5-dicyano-4-ethylpyridin-2-yl)thio)-2-phenylacetamide | 439.14 [M + H]+ | $^1$H NMR (400 MHz, DMSO-d$_6$) δ 7.88 (s, 1H), 7.60-7.53 (m, 2H), 7.45-7.19 (m, 4H), 5.60 (s, 1H), 4.23-3.79 (m, 4H), 3.05-2.86 (d, J = 5.7 Hz, 2H), 2.75 (q, J = 7.7 Hz, 2H), 2.31-1.97 (m, 2H), 1.73 (s, 1H), 1.20 (t, J = 7.5 Hz, 3H). |
| 633 | 2-((3,5-dicyano-4-ethyl-6-((2-(3-hydroxyazetidin-1-yl)-2-oxoethyl)(methyl)amino)pyridin-2-yl)thio)-2-phenylacetamide | 465.09 [M + H]+ | $^1$H NMR (400 MHz, DMSO-d$_6$) δ ppm 7.85 (d, J = 8.55 Hz, 1H), 7.54-7.46 (m, 2H), 7.42-7.32 (m, 4H), 5.75 (d, J = 5.70 Hz, 1H), 5.51 (d, J = 8.11 Hz, 1H), 4.68-4.56 (m, 1H), 4.53-4.45 (m, 1H), 4.44-4.34 (m, 1H), 4.29 (t, J = 7.45 Hz, 1H), 4.16-4.07 (m, 1H), 3.99-3.86 (m, 1H), 3.69-3.57 (m, 1H), 3.31 (d, J = 2.41 Hz, 3H), 2.77 (q, J = 7.23 Hz, 2H), 1.20 (t, J = 7.56 Hz, 3H). |
| 634 | | 479.13 [M + H]+ | $^1$H NMR (400 MHz, DMSO-d$_6$) δ ppm 7.90 (s, 1H), 7.55-7.47 (m, 2H), 7.42-7.27 (m, 4H), 5.53 (s, 1H), 5.07 (s, 2H), 4.34 (s, 2H), 4.14-3.96 (m, 2H), 3.92-3.84 (m, 1H), 3.83-3.74 (m, 2H), 2.75 (q, J = 7.60 Hz, 2H), 1.93-1.80 (m, 2H), 1.78-1.66 (m, 2H), 1.20 (t, J = 7.56 Hz, 3H). |

| Example | Structure/Name | LCMS m/z | 1H NMR |
|---|---|---|---|
| | 2-((3,5-dicyano-4-ethyl-6-(4-(guanidinooxy)piperidin-1-yl)pyridin-2-yl)thio)-2-phenylacetamide | | |
| 635 | 2-((6-(3-aminoazetidin-1-yl)-3,5-dicyano-4-ethylpyridin-2-yl)thio)-2-phenylacetamide (single stereoisomer) | 393.24 [M + H]+ | ¹H NMR (400 MHz, TFA-d) δ ppm 7.48 (s, 5H), 5.69 (s, 1H), 5.09-4.97 (m, 2H), 4.94-4.88 (m, 2H), 4.64 (s, 1H), 3.01 (d, J = 7.23 Hz, 2H), 1.42 (t, J = 7.45 Hz, 3H). |
| 636 | 2-((3,5-dicyano-4-ethyl-6-((R)-3-(methylamino)piperidin-1-yl)pyridin-2-yl)thio)-2-phenylacetamide | 435.19 [M + H]+ | ¹H NMR (400 MHz, DMSO-d₆) δ ppm 8.09 (s, 2H), 7.62-7.54 (m, 2H), 7.42-7.29 (m, 4H), 5.70 (d, J = 10.30 Hz, 1H), 4.54-4.69 (m, 1H), 4.28-4.13 (m, 1H), 3.55-3.34 (m, 2H), 3.07 (s, 1H), 2.78 (q, J = 7.60 Hz, 2H), 2.53 (d, J = 2.19 Hz, 3H), 2.15-2.05 (m, 1H), 1.94-1.82 (m, 1H), 168-1.54 (m, 2H), 1.21 (t, J = 7.56 Hz, 3H). |
| 637 | 2-((3,5-dicyano-4-ethyl-6-((2-((3R,4S)-3-hydroxy-4-(hydroxymethyl)pyrrolidin-1-yl)-2-oxoethyl)(methyl)amino)pyridin-2-yl)thio)-2-phenylacetamide | 509.14 [M + H]+ | ¹H NMR (400 MHz, DMSO-d₆) δ ppm 7.90-7.74 (m, 1H), 7.60-7.42 (m, 2H), 7.42-7.00 (m, 4H), 5.50-5.40 (m, 1H), 5.05-4.90 (m, 1H), 4.76-4.38 (m, 3H), 4.32-4.16 (m, 1H), 3.70-3.30 (m, 8H), 3.18-3.05 (m, 1H), 2.76 (q, J = 7.38 Hz, 2H), 2.34-2.13 (m, 1H), 1.20 (t, J = 7.67 Hz, 3H). |

| Example | Structure/Name | LCMS m/z | 1H NMR |
|---|---|---|---|
| 638 | 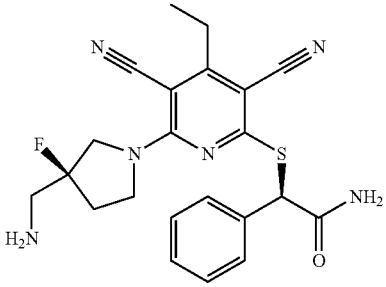 [SMILES: CCc1c(C#N)c(S[C@@H](C(N)=O)c2ccccc2)nc(N2CC[C@](F)(CN)C2)c1C#N]<br>(R)-2-((6-((S)-3-(aminomethyl)-3-fluoropyrrolidin-1-yl)-3,5-dicyano-4-ethylpyridin-2-yl)thio)-2-phenylacetamide | 439.17 [M + H]⁺ | ¹H NMR (400 MHz, DMSO-d₆) δ ppm 8.47 (s, 3H), 8.16 (s, 1H), 7.58 (d, J = 7.02 Hz, 2H), 7.43-7.32 (m, 3H), 7.27 (s, 1H), 5.76 (s, 1H), 4.40-3.90 (m, 4H), 3.57-3.33 (m, 2H), 2.77 (q, J = 7.38 Hz, 2H), 2.45-2.16 (m, 2H), 1.21 (t, J = 7.56 Hz, 3H). |
| 639 | 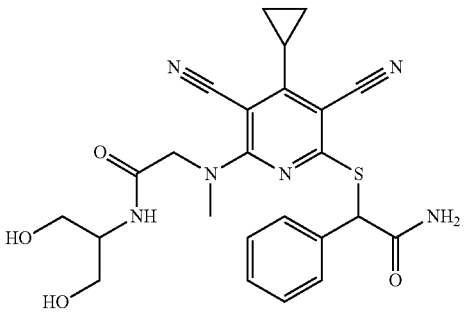 [SMILES: CN(CC(=O)NC(CO)CO)c1nc(SC(C(N)=O)c2ccccc2)c(C#N)c(C2CC2)c1C#N]<br>2-((6-((2-amino-2-oxo-1-phenylethyl)thio)-3,5-dicyano-4-cyclopropylpyridin-2-yl)(methyl)amino)-N-(1,3-dihydroxypropan-2-yl)acetamide | 495.07 [M + H]⁺ | ¹H NMR (400 MHz, DMSO-d₆) δ ppm 7.83-7.73 (m, 2H), 7.55-7.45 (m, 2H), 7.42-7.27 (m, 4H), 5.52-5.45 (m, 1H), 4.67-4.63 (m, 2H), 4.54-4.45 (m, 1H), 4.42-4.31 (m, 1H), 3.89-3.73 (m, 1H), 3.51-3.39 (m, 4H), 3.33 (s, 3H), 2.05-2.16 (m, 1H), 1.18-1.08 (m, 2H), 1.00-0.90 (m, 2H). |
| 640 | 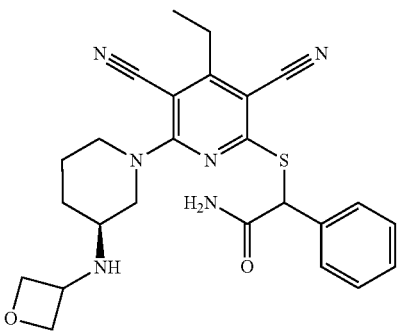 [SMILES: CCc1c(C#N)c(SC(C(N)=O)c2ccccc2)nc(N2CCC[C@H](NC3COC3)C2)c1C#N]<br>2-((3,5-dicyano-4-ethyl-6-((S)-3-(oxetan-3-ylamino)piperidin-1-yl)pyridin-2-yl)thio)-2-phenylacetamide | 477.16 [M + H]⁺ | ¹H NMR (400 MHz, DMSO-d₆) δ ppm 7.89 (s, 1H), 7.51 (d, J = 7.02 Hz, 2H), 7.40-7.28 (m, 4H), 5.52 (d, J = 5.04 Hz, 1H), 4.66-4.57 (m, 2H), 4.43-4.32 (m, 1H), 4.32-4.20 (m, 3H), 4.04-3.95 (m, 1H), 3.16-3.08 (m, 1H), 3.06-2.95 (m, 1H), 2.76 (q, J = 7.60 Hz, 2H), 2.62-2.51 (m, 2H), 1.93-1.76 (m, 2H), 1.53-1.30 (m, 2H), 1.21 (t, J = 7.56 Hz, 3H). |

| Example | Structure/Name | LCMS m/z | 1H NMR |
|---|---|---|---|
| 641 | 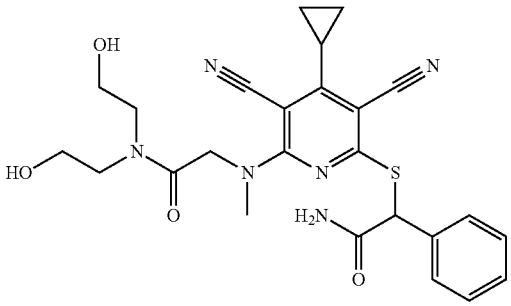 [SMILES: CN(CC(=O)N(CCO)CCO)c1nc(SC(C(N)=O)c2ccccc2)c(C#N)c(C2CC2)c1C#N]<br>2-((6-((2-amino-2-oxo-1-phenylethyl)thio)-3,5-dicyano-4-cyclopropylpyridin-2-yl)(methyl)amino)-N,N-bis(2-hydroxyethyl)acetamide | 509.17 [M + H]+ | ¹H NMR (400 MHz, DMSO-d₆) δ ppm 7.79 (s, 1H), 7.50-7.45 (m, 2H), 7.40-7.29 (m, 4H), 5.43 (s, 1H), 5.03 (t, J = 5.26 Hz, 1H), 4.91-4.84 (m, 1H), 4.77-4.68 (m, 2H), 3.60 (q, J = 5.33 Hz, 2H), 3.53 (q, J = 5.92 Hz, 2H), 3.45-3.33 (m, 4H), 3.26 (s, 3H), 2.14-2.05 (m, 1H), 1.16-1.07 (m, 2H), 0.97-0.91 (m, 2H). |
| 642 | 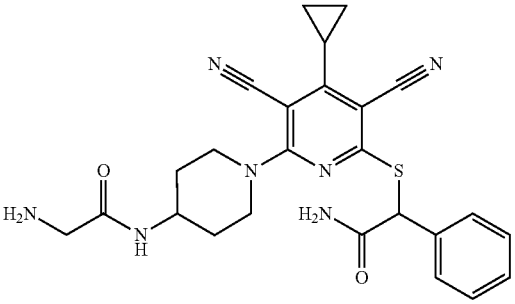 [SMILES: N#Cc1c(SC(C(N)=O)c2ccccc2)nc(N2CCC(NC(=O)CN)CC2)c(C#N)c1C1CC1]<br>2-amino-N-(1-(6-((2-amino-2-oxo-1-phenylethyl)thio)-3,5-dicyano-4-cyclopropylpyridin-2-yl)piperidin-4-yl)acetamide formate | 490.03 [M + H]+ | ¹H NMR (400 MHz, DMSO-d₆) δ ppm 8.27 (s, 1H), 7.96 (d, J = 7.67 Hz, 1H), 7.89 (s, 1H), 7.52-7.45 (m, 2H), 7.41-7.27 (m, 4H), 5.52 (s, 1H), 4.43-4.32 (m, 2H), 3.93 (s, 1H), 3.39-3.27 (m, 2H), 3.21 (s, 2H), 2.19-2.04 (m, 1H), 1.93-1.82 (m, 2H), 1.58-1.40 (m, 2H), 1.21-1.11 (m, 2H), 1.00-0.88 (m, 2H). |
| 643 | 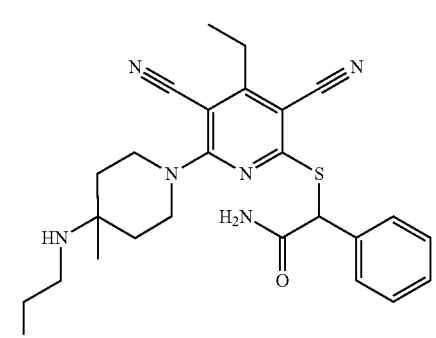<br>2-((3,5-dicyano-4-ethyl-6-(4-((2-hydroxyethyl)amino)-4-methylpiperidin-1-yl)pyridin-2-yl)thio)-2-phenylacetamide | 479.13 [M + H]+ | ¹H NMR (400 MHz, DMSO-d₆) δ ppm 7.89 (s, 1H), 7.54-7.48 (m, 2H), 7.40-7.30 (m, 4H), 5.53 (s, 1H), 4.46 (s, 1H), 4.08-3.99 (m, 2H), 3.77-3.67 (m, 2H), 3.47 (s, 2H), 2.75 (q, J = 7.45 Hz, 2H), 2.55 (t, J = 5.81 Hz, 2H), 1.67-1.61 (m, 3H), 1.53-1.43 (m, 2H), 1.20 (t, J = 7.56 Hz, 3H), 1.08 (s, 3H). |

-continued

| Example | Structure/Name | LCMS m/z | 1H NMR |
|---|---|---|---|
| 644 | 2-((3,5-dicyano-4-ethyl-6-((2-(guanidinooxy)ethyl)(methyl)amino)pyridin-2-yl)thio)-2-phenylacetamide | 453.13 [M + H]+ | $^1$H NMR (400 MHz, DMSO-$d_6$) δ ppm 7.91 (s, 1H), 7.53-7.47 (m, 2H), 7.40-7.27 (m, 4H), 5.58 (s, 1H), 5.00 (s, 2H), 4.33 (s, 2H), 4.13-3.89 (m, 2H), 3.87-3.82 (m, 2H), 3.38 (s, 3H), 2.74 (q, J = 7.50 Hz, 2H), 1.20 (t, J = 7.56 Hz, 3H). |
| 645 | 2-((6-(4-((2-aminoethyl)amino)piperidin-1-yl)-3,5-dicyano-4-ethylpyridin-2-yl)thio)-2-phenylacetamide dihydrochloride | 464.2 [M + H]+ | $^1$H NMR (400 MHz, DMSO-$d_6$) δ ppm 9.69 (s, 2H), 8.32 (s, 3H), 7.98 (s, 1H), 7.55-7.51 (m, 2H), 7.43-7.32 (m, 4H), 5.58 (s, 1H), 4.63 (s, 2H), 3.49 (s, 1H), 3.27-3.18 (m, 6H), 2.77 (q, J = 7.31 Hz, 2H), 2.27-2.18 (m, 2H), 1.75-1.62 (m, 2H) 1.22 (t, J = 7.67 Hz, 3H). |
| 646 | 2-((3,5-dicyano-4-ethyl-6-((2-((S)-2-(hydroxymethyl)morpholino)-2-oxoethyl)(methyl)amino)pyridin-2-yl)thio)-2-phenylacetamide | 507.16 [M − H]− | $^1$H NMR (400 MHz, 90° C., DMSO-$d_6$) δ ppm 7.48 (d, J = 7.23 Hz, 2H), 7.40-6.98 (m, 5H), 5.52 (s, 1H), 4.90-4.60 (m, 2H), 4.42 (s, 1H), 4.04-3.68 (m, 3H), 3.64-3.35 (m, 5H), 3.32 (s, 3H), 3.02-3.00 (m, 1H), 2.79 (q, J = 7.67 Hz, 2H), 1.22 (t, J = 7.56 Hz, 3H). |
| 647 | | 495.26 [M + H]+ | $^1$H NMR (400 MHz, 90° C., DMSO-$d_6$) δ ppm 7.50-7.44 (m, 2H), 7.42-7.26 (m, 5H), 5.49 (d, J = 7.23 Hz, 1H), 4.70-4.49 (m, 4H), 4.18-3.99 (m, 2H), 3.72-3.61 (m, 1H), 3.48 (s, 1H), 3.33 (s, 5H), 2.79 (q, J = 7.60 Hz, 2H), 1.22 (t, J = 7.78 Hz, 3H). |

| Example | Structure/Name | LCMS m/z | 1H NMR |
|---|---|---|---|
| | 2-((3,5-dicyano-6-((2-((cis)-3,4-dihydroxypyrrolidin-1-yl)-2-oxoethyl)(methyl)amino)-4-ethylpyridin-2-yl)thio)-2-phenylacetamide | | |
| 648 | 2-((3,5-dicyano-4-ethyl-6-((2-(((S)-3-(hydroxymethyl)pyrrolidin-1-yl)-2-oxoethyl)(methyl)amino)pyridin-2-yl)thio)-2-phenylacetamide | 493.2 [M + H]⁺ | ¹H NMR (400 MHz, DMSO-d₆) δ ppm 7.86 (s, 1H), 7.48 (d, J = 7.89 Hz, 2H), 7.42-7.23 (m, 4H), 5.52-5.42 (m, 1H), 4.82-4.47 (m, 3H), 3.64-3.31 (m, 8H), 3.25-3.08 (m, 1H), 2.75 (q, J = 7.45 Hz, 2H), 2.42-2.21 (m, 1H), 1.99-1.55 (m, 2H), 1.19 (t, J = 7.67 Hz, 3H). |
| 649 | ((3S,4S)-3-hydroxy-4-(hydroxymethyl)pyrrolidin-1-yl)-2-oxoethyl)(methyl)amino)pyridin-2-yl)thio)-2-phenylacetamide | 509.2 [M + H]⁺ | ¹H NMR (400 MHz, DMSO-d₆) δ ppm 7.84 (d, J = 11.84 Hz, 1H), 7.52-7.44 (m, 2H), 7.43-7.27 (m, 4H), 5.52-5.43 (m, 1H,), 5.19-5.04 (m, 1H), 4.77-4.49 (m, 3H), 4.16-3.99 (m, 1H), 3.75-3.59 (m, 1H), 3.55-3.31 (m, 6H), 3.28-3.17 (m, 2H), 2.75 (q, J = 7.45 Hz, 2H), 2.25-2.06 (m, 1H), 1.20 (t, J = 7.56 Hz, 3H). |
| 650 | (R)-2-amino-N-((1-(3,5-dicyano-4-ethyl-6-((4-(N-methylmethylsulfonamido)benzyl)thio)pyridin-2-yl)pyrrolidin-3-yl)methyl)acetamide | 542.18 [M + H]⁺ | ¹H NMR (400 MHz, DMSO-d₆) δ ppm 8.00 (t, J = 5.92 Hz, 1H), 7.47-7.42 (m, 2H), 7.39-7.33 (m, 2H), 4.52 (s, 2H), 3.95-3.74 (m, 3H), 3.55 (s, 1H), 3.24-3.14 (m, 5H), 3.08 (s, 2H), 2.93 (s, 3H), 2.75 (q, J = 7.45 Hz, 2H), 2.47-2.42 (m, 1H), 2.07-1.98 (m, 1H), 1.90-1.67 (m, 3H), 1.21 (t, J = 7.56 Hz, 3H). |

-continued

| Example | Structure/Name | LCMS m/z | 1H NMR |
|---|---|---|---|
| 651 | 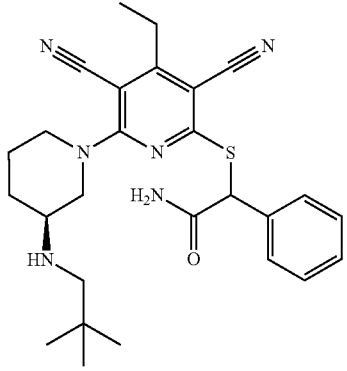 [SMILES: CCc1c(C#N)c(SC(C(N)=O)c2ccccc2)nc(N2CCC[C@H](NCC(C)(C)C)C2)c1C#N]<br>2-((3,5-dicyano-4-ethyl-6-((S)-3-(neopentylamino)piperidin-1-yl)pyridin-2-yl)thio)-2-phenylacetamide | 491.23 [M + H]+ | $^{1}$H NMR (400 MHz, DMSO-d$_6$) δ 7.88 (s, 1H), 7.72-7.48 (m, 2H), 7.45-7.20 (m, 4H), 5.53 (s, 1H), 4.56-4.04 (m, 2H), 3.34-3.29 (m, 1H), 3.28-3.20 (m, 1H), 2.75 (q, J = 7.5 Hz, 2H), 2.60 (s, 1H), 2.41-2.28 (m, 2H), 1.99-1.90 (m, 1H), 1.87-1.77 (m, 1H) 1.60-1.27 (m, 3H), 1.27-1.10 (t, J = 7.6 Hz, 3H), 0.85 (s, 9H). |
| 652 | 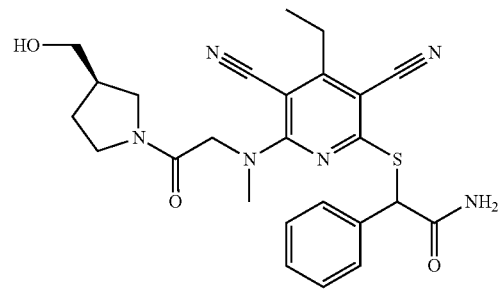 [SMILES: CCc1c(C#N)c(SC(C(N)=O)c2ccccc2)nc(N(C)CC(=O)N2CC[C@@H](CO)C2)c1C#N]<br>2-((3,5-dicyano-4-ethyl-6-((2-((R)-3-(hydroxymethyl)pyrrolidin-1-yl)-2-oxoethyl)(methyl)amino)pyridin-2-yl)thio)-2-phenylacetamide | 491.1 [M + H]+ | $^{1}$H NMR (400 MHz, DMSO-d$_6$) δ 7.86 (s, 1H), 7.48 (d, J = 7.0 Hz, 2H), 7.44-7.18 (m, 4H), 5.59-5.43 (m, 1H), 4.82-4.35 (m, 3H), 3.64-3.32 (m, 5H), 3.29 (s, 3H), 3.15 (m, 1H), 2.76 (q, J = 7.7 Hz, 2H), 2.42-2.19 (m, 1H), 2.02-1.81 (m, 1H), 1.77-1.53 (m, 1H), 1.19 (t, J = 7.6 Hz, 3H). |
| 653 | 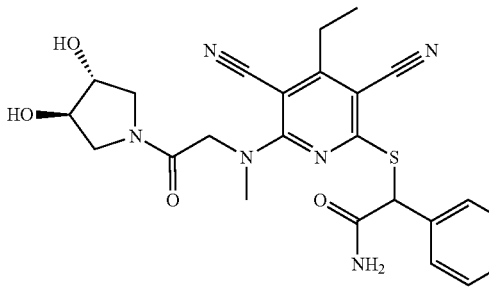<br>2-((3,5-dicyano-6-((2-((3R,4R)-3,4-dihydroxypyrrolidin-1-yl)-2-oxoethyl)(methyl)amino)-4-ethylpyridin-2-yl)thio)-2-phenylacetamide | 495.13 [M + H]+ | $^{1}$H NMR (400 MHz, DMSO-d$_6$) δ 7.76 (s, 1H), 7.54-7.43 (m, 2H), 7.41-7.32 (m, 4H), 7.28 (s, 1H), 5.41 (d, J = 10.3 Hz, 1H), 5.27 (m, 1H), 5.19 (m, 1H), 4.81-4.78 (m, 1H), 4.76-4.73 (m, 1H), 4.06-3.91 (m, 2H), 3.79-3.64 (m, 1H), 3.34 (s, 3H), 3.49-3.30 (m, 2H), 2.77 (q, J = 7.7 Hz, 2H), 1.21 (t, J = 7.6 Hz, 3H). |

| Example | Structure/Name | LCMS m/z | 1H NMR |
|---|---|---|---|
| 654 | 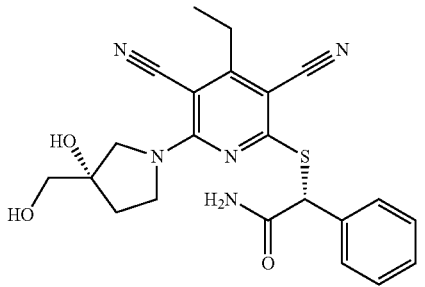 [SMILES: CCc1c(C#N)c(S[C@@H](C(N)=O)c2ccccc2)nc(N2CC[C@@](O)(CO)C2)c1C#N]<br>(R)-2-((3,5-dicyano-4-ethyl-6-((S)-3-hydroxy-3-(hydroxymethyl)pyrrolidin-1-yl)pyridin-2-yl)thio)-2-phenylacetamide | 438.14 [M + H]⁺ | ¹H NMR (400 MHz, DMSO-d₆) δ ppm 7.91-7.84 (brs, 1H), 7.51 (dt, J = 6.2, 1.5 Hz, 2H), 7.44-7.32 (m, 3H), 7.26 (brs, 1H), 5.59 (s, 1H), 4.95 (s, 2H), 3.92 (brs, 3H), 3.68 (brs, 1H), 3.55-3.39 (m, 2H), 2.74 (q, J = 7.5 Hz, 2H), 2.04 (m, 1H), 1.78 (brs, 1H), 1.20 (t, J = 7.5 Hz, 3H). |
| 655 | 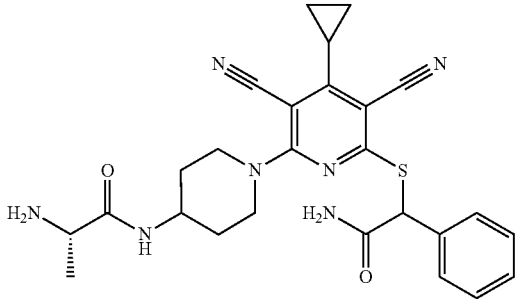 [SMILES: C[C@H](N)C(=O)NC1CCN(c2nc(SC(C(N)=O)c3ccccc3)c(C#N)c(C3CC3)c2C#N)CC1]<br>(2S)-2-amino-N-(1-(6-((2-amino-2-oxo-1-phenylethyl)thio)-3,5-dicyano-4-cyclopropylpyridin-2-yl)piperidin-4-yl)propanamide | 504.07 [M + H]⁺ | ¹H NMR (400 MHz, DMSO-d₆) δ ppm 7.88 (s, 1 H), 7.74 (br d, J = 7.89 Hz, 1 H), 7.49-7.53 (m, 2 H), 7.27-7.39 (m, 4 H), 5.52 (s, 1 H), 4.39 (br t, J = 12.83 Hz, 2 H), 3.89 (m, 1 H), 3.33 (br s, 2 H), 3.19-3.24 (m, 1 H), 2.08-2.14 (m, 1 H), 1.87 (m, 2 H), 1.75 (br s, 2 H), 1.43-1.51 (m, 2 H), 1.09-1.14 (m, 5 H), 0.95-1.00 (m, 2 H). |
| 656 | 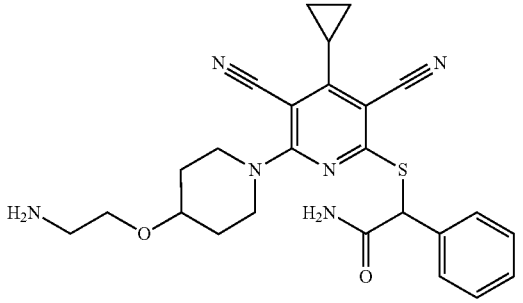 [SMILES: N#Cc1c(SC(C(N)=O)c2ccccc2)nc(N2CCC(OCCN)CC2)c(C#N)c1C1CC1]<br>2-((6-(4-(2-aminoethoxy)piperidin-1-yl)-3,5-dicyano-4-cyclopropylpyridin-2-yl)thio)-2-phenylacetamide | 477.12 [M + H]⁺ | ¹H NMR (400 MHz, DMSO-d₆) δ ppm 7.89 (s, 1 H), 7.54-7.48 (m, 2 H), 7.41-7.23 (m, 4 H), 5.52 (s, 1 H), 4.12-4.00 (m, 2 H), 3.67-3.50 (m, 4 H), 3.43 (t, J = 5.70 Hz, 3 H), 2.69 (t, J = 5.81 Hz, 2 H), 2.15-2.05 (m, 1 H), 1.98-1.85 (m, 2 H), 1.63-1.48 (m, 2 H), 1.17-1.08 (m, 2 H), 1.00-0.92 (m, 2 H). |

| Example | Structure/Name | LCMS m/z | 1H NMR |
|---|---|---|---|
| 657 | 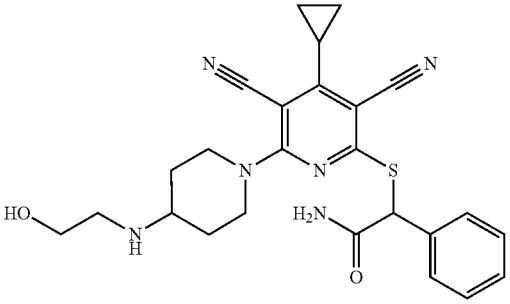 [SMILES: N#Cc1c(SC(C(N)=O)c2ccccc2)nc(N2CCC(NCCO)CC2)c(C#N)c1C1CC1]<br>2-((3,5-dicyano-4-cyclopropyl-6-(4-((2-hydroxyethyl)amino)piperidin-1-yl)pyridin-2-yl)thio)-2-phenylacetamide | 477.12 [M + H]⁺ | ¹H NMR (400 MHz, DMSO-d₆) δ ppm 7.88 (s, 1 H), 7.58-7.43 (m, 2 H), 7.23-7.40 (m, 4 H), 5.52 (s, 1 H), 4.48-4.42 (m 1 H), 4.37-4.24 (m, 2 H), 3.48-3.43 (m, 2 H), 3.25-3.38 (m, 2 H), 2.79-2.72 (m, 1 H), 2.63 (t, J = 5.81 Hz, 2H), 2.15-2.00 (m, 1 H), 1.95-1.86 (m, 2 H), 1.75 (s, 1 H), 1.38-1.23 (m, 2 H), 1.18-1.07 (m, 2 H), 0.98-0.87 (m, 2 H). |
| 658 | 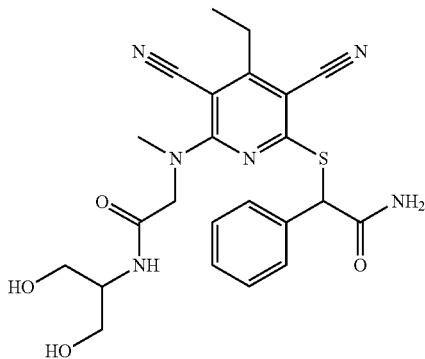 [SMILES: CCc1c(C#N)c(SC(C(N)=O)c2ccccc2)nc(N(C)CC(=O)NC(CO)CO)c1C#N]<br>2-((6-((2-amino-2-oxo-1-phenylethyl)thio)-3,5-dicyano-4-ethylpyridin-2-yl)(methyl)amino)-N-(1,3-dihydroxypropan-2-yl)acetamide | 481.15 [M − H]⁻ | ¹H NMR (400 MHz, DMSO-d₆) δ ppm 7.85-7.76 (m, 2H), 7.54-7.47 (m, 2 H), 7.43-7.27 (m, 4 H), 5.51 (s, 1 H), 4.65 (td, J = 5.48, 1.97 Hz, 2 H), 4.55-4.48 (m, 1 H), 4.41-4.34 (m, 1 H), 3.84-3.74 (m, 1 H), 3.49-3.42 (m, 3 H), 3.35 (s, 3 H), 2.77 (q, J = 7.67 Hz, 2 H), 1.20 (t, J = 7.56 Hz, 3 H). |
| 659 | 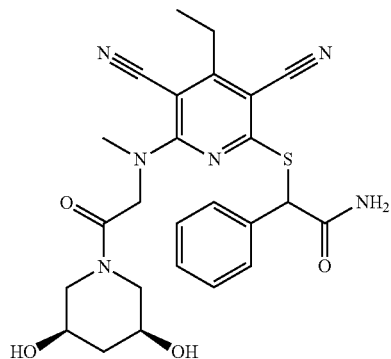 [SMILES: CCc1c(C#N)c(SC(C(N)=O)c2ccccc2)nc(N(C)CC(=O)N2C[C@H](O)C[C@H](O)C2)c1C#N]<br>2-((3,5-dicyano-6-((2-((3R,5S)-3,5-dihydroxypiperidin-1-yl)-2-oxoethyl)(methyl)amino)-4-ethylpyridin-2-yl)thio)-2-phenylacetamide | 507.09 [M − H]⁻ | ¹H NMR (400 MHz, DMSO-d₆) δ ppm 7.86 (s, 1 H), 7.49-7.26 (m, 2 H), 7.41-7.29 (m, 4 H), 5.52 (d, J = 5.04 Hz, 1 H), 5.09-4.95 (m, 2 H), 4.91-4.81 (m, 1 H), 4.75-4.63 (m, 1 H), 4.37-4.23 (m, 1 H), 3.71-3.56 (m, 2 H), 3.46-3.36 (m, 1 H), 3.27 (d, J = 5.70 Hz, 3 H), 2.80-2.62 (m, 3 H), 2.36-2.25 (m, 1 H), 2.23-2.10 (m, 1 H), 1.30-1.14 (m, 4 H). |

| Example | Structure/Name | LCMS m/z | 1H NMR |
|---|---|---|---|
| 660 | 2-((3,5-dicyano-6-((2-((3S,4S)-3,4-dihydroxypyrrolidin-1-yl)-2-oxoethyl)(methyl)amino)-4-ethylpyridin-2-yl)thio)-2-phenylacetamide | 495.13 [M + H]+ | $^1$H NMR (400 MHz, DMSO-d$_6$) δ ppm 7.76 (br s, 1H), 7.51-7.44 (m, 2H), 7.41-7.32 (m, 3H), 7.31-7.27 (m, 1H), 5.41 (d, J = 10.1 Hz, 1H), 5.27 (dd, J = 1.9, 3.4 Hz, 1H), 5.19 (dd, J = 3.3, 7.9 Hz, 1H), 4.77 (br dd, J = 3.4, 17.4 Hz, 1H), 4.56 (br d, J = 17.3 Hz, 1H), 4.05-3.87 (m, 2H), 3.79-3.60 (m, 1H), 3.53-3.32 (m, 6H), 2.77 (q, J = 7.4 Hz, 2H), 1.27-1.15 (m, 3H). |
| 661 | 2-((3,5-dicyano-4-ethyl-6-(4-((2-hydroxyethyl)amino)-4-(hydroxymethyl)piperidin-1-yl)pyridin-2-yl)thio)-2-phenylacetamide | 495.18 [M + H]+ | $^1$H NMR (400 MHz, DMSO-d$_6$) δ ppm 7.89 (br s, 1 H), 7.51 (br d, J = 7.02 Hz, 2 H), 7.41-7.29 (m, 4 H), 5.53 (s, 1 H), 4.54 (br s, 1 H), 4.46 (br t, J = 4.82 Hz, 1 H), 4.18 (br d, J = 12.93 Hz, 2 H), 3.65-3.55 (m, 2 H), 3.46 (q, J = 4.97 Hz, 2 H), 3.27 (br d, J = 4.38 Hz, 2 H), 2.75 (q, J = 7.53 Hz, 2 H), 2.60-2.51 (m, 2 H), 1.65-1.50 (m, 5 H), 1.26-1.18 (m, 3 H). |
| 662 | 2-((3,5-dicyano-4-ethyl-6-((2-((R)-2-(hydroxymethyl)morpholino)-2-oxoethyl)(methyl)amino)pyridin-2-yl)thio)-2-phenylacetamide | 509.17 [M + H]+ | $^1$H NMR (400 MHz, DMSO-d$_6$, 90° C.) δ ppm: 7.48 (d, J = 7.02 Hz, 2 H), 7.39-7.26 (m, 4 H), 7.26-7.11 (m, 1 H), 5.52 (s, 1 H), 4.81 (br s, 1 H), 4.69 (br s, 1 H), 4.43 (br s, 1 H), 4.24-4.06 (m, 1 H), 3.84 (br d, J = 11.62 Hz, 2 H), 3.55-3.28 (m, 8 H), 2.99-2.97 (m, 1 H), 2.79 (q, J = 7.31 Hz, 2 H), 1.22 (t, J = 7.45 Hz, 3 H). |
| 663 | | 439.09 [M + H]+ | $^1$H NMR (400 MHz, DMSO-d$_6$) δ ppm 11.34 (s, 1 H), 7.79 (s, 1 H), 7.50 (d, J = 7.02 Hz, 2 H), 7.41-7.31 (m, 4 H), 5.56 (s, 1 H), 4.49 (br d, J = 17.32 Hz, 1 H), 4.30 (br d, J = 16.88 Hz, 1 H), 3.78-3.60 (m, 3 H), 3.39-3.32 (m, 3 H), 2.78 (q, J = 7.45 Hz, 2 H), 1.21 (br t, J = 7.56 Hz, 3 H). |

| Example | Structure/Name | LCMS m/z | 1H NMR |
|---|---|---|---|
| | 2-((6-((2-amino-2-oxo-1-phenylethyl)thio)-3,5-dicyano-4-ethylpyridin-2-yl)(methyl)amino)-N-methoxyacetamide | | |
| 664 | 2-((3,5-dicyano-4-ethyl-6-((2-((3R,4R)-3-hydroxy-4-(hydroxymethyl)pyrrolidin-1-yl)-2-oxoethyl)(methyl)amino)pyridin-2-yl)thio)-2-phenylacetamide | 509.14 [M + H]+ | ¹H NMR (400 MHz, DMSO-d₆) δ ppm 7.84 (br d, J = 12.28 Hz, 1 H), 7.48 (td, J = 4.38, 2.41 Hz, 2 H), 7.27-7.43 (m, 4 H), 5.43-5.53 (m, 1 H), 5.04-5.20 (m, 1 H), 4.45-4.81 (m, 3 H), 3.99-4.16 (m, 1 H), 3.31-3.76 (m, 7 H), 3.15-3.28 (m, 2 H), 2.76 (q, J = 7.31 Hz, 2 H), 2.06-2.26 (m, 1 H), 1.20 (t, J = 7.56 Hz, 3 H). |
| 665 | 2-((6-((2-amino-2-oxo-1-phenylethyl)thio)-3,5-dicyano-4-ethylpyridin-2-yl)(methyl)amino)-N-(3-hydroxypropyl)-N-methylacetamide | 481.09 [M + H]+ | ¹H NMR (400 MHz, DMSO-d₆) δ ppm 7.86 (s, 1H), 7.44-7.55 (m, 2H), 7.27-7.54 (m, 4H), 5.54-5.49 (m, 1H), 4.79-4.97 (m, 1H), 4.59-4.75 (m, 1H), 4.38 (t, J = 5.2 Hz, 1H), 3.31-3.49 (m, 4H), 3.29 (s, 3H), 2.97 (s, 2H), 2.83 (s, 1H), 2.75 (q, J = 7.60 Hz, 2H), 1.58-1.79 (m, 2H), 1.19 (t, J = 7.56 Hz, 3H). |
| 666 | 2-((6-((2-amino-2-oxo-1-phenylethyl)thio)-3,5-dicyano-4-ethylpyridin-2-yl)(methyl)amino)-N-((R)-2,3-dihydroxypropyl)acetamide | 483.2 [M + H]+ | ¹H NMR (400 MHz, DMSO-d₆) δ ppm 8.02 (br t, J = 5.81 Hz, 1 H), 7.82 (s, 1 H), 7.49 (br d, J = 7.23 Hz, 2 H), 7.29-7.41 (m, 4 H), 5.53 (s, 1 H), 4.74 (dd, J = 5.04, 2.63 Hz, 1H), 4.47-4.58 (m, 2 H), 4.36 (br d, J = 17.10 Hz, 1 H), 3.54 (dt, J = 10.36, 5.23 Hz, 1 H), 3.33-3.39 (m, 3 H), 3.34-3.22 (m, 3 H), 3.00-3.10 (m, 1 H), 2.77 (q, J = 7.53 Hz, 2 H), 1.20 (t, J = 7.56 Hz, 3 H). |

-continued

| Example | Structure/Name | LCMS m/z | 1H NMR |
|---|---|---|---|
| 667 | 2-((6-(4-((2-amino-2-oxoethyl)amino)piperidin-1-yl)-3,5-dicyano-4-cyclopropylpyridin-2-yl)thio)-2-phenylacetamide | 490.15 [M + H]⁺ | ¹H NMR (400 MHz, DMSO-d₆): δ ppm 7.88 (s, 1 H), 7.55-7.48 (m, 2 H), 7.41-7.18 (m, 5 H), 7.03 (s, 1 H), 5.52 (s, 1 H), 4.32 (d, J = 13.15 Hz, 2 H), 3.26-3.21 (m, 2 H), 3.10 (s, 2 H), 2.75-2.64 (m, 1 H), 2.22 (s, 1 H), 2.15-2.04 (m, 1 H), 1.94-1.83 (m, 2 H), 1.41-1.27 (m, 2 H), 1.16-1.08 (m, 2 H), 1.00-0.93 (m, 2 H). |
| 668 | 2-((6-((2-amino-2-oxo-1-phenylethyl)thio)-3,5-dicyano-4-ethylpyridin-2-yl)(methyl)amino)-N,N-bis(2-hydroxyethyl)acetamide | 497.14 [M + H]⁺ | ¹H NMR (400 MHz, DMSO-d₆) δ ppm 7.81 (s, 1 H), 7.51-7.47 (m, 2 H), 7.40-7.32 (m, 4 H), 5.45 (s, 1 H), 5.03 (t, J = 5.15 Hz, 1 H), 4.93-4.86 (m, 1 H), 4.80-4.71 (m, 2 H), 3.61 (q, J = 5.33 Hz, 2 H), 3.56-3.50 (m, 2 H), 3.45-3.36 (m, 4 H), 3.28 (s, 3 H), 2.76 (q, J = 7.67 Hz, 2 H), 1.20 (t, J = 7.56 Hz, 3 H). |
| 669 | 2-((6-((2-amino-2-oxo-1-phenylethyl)thio)-3,5-dicyano-4-ethylpyridin-2-yl)(methyl)amino)-N-(2-hydroxyethyl)acetamide | 453.13 [M + H]⁺ | ¹H NMR (400 MHz, DMSO-d₆): δ ppm 8.06 (t, J = 5.26 Hz, 1 H), 7.81 (s, 1 H), 7.52-7.45 (m, 2 H), 7.40-7.30 (m, 4 H), 5.54 (s, 1 H), 4.69 (t, J = 5.48 Hz, 1 H), 4.57-4.46 (m, 1 H), 4.39-4.28 (m, 1 H), 3.43 (q, J = 5.99 Hz, 2 H), 3.36 (s, 3 H), 3.19 (q, J = 5.70 Hz, 2 H), 2.77 (q, J = 7.38 Hz, 2 H), 1.20 (t, J = 7.67 Hz, 3 H). |
| 670 | | 409.19 [M + H]⁺ | ¹H NMR (400 MHz, DMSO-d₆) δ ppm 8.05 (s, 1 H), 7.93 (br s, 2 H), 7.51-7.57 (m, 2 H), 7.34-7.42 (m, 4 H), 5.53 (s, 1 H), 3.71-3.87 (m, 2 H), 3.36 (s, 3 H), 2.74-2.89 (m, 4 H), 1.90-1.98 (m, 2 H), 1.17-1.28 (m, 4 H). |

| Example | Structure/Name | LCMS m/z | 1H NMR |
|---|---|---|---|
| | 2-((6-((3-aminopropyl)(methyl)amino)-3,5-dicyano-4-ethylpyridin-2-yl)thio)-2-phenylacetamide hydrochloride | | |
| 671 | 2-((6-(3-(aminomethyl)azetidin-1-yl)-3,5-dicyano-4-ethylpyridin-2-yl)thio)-2-phenylacetamide | 407.12 [M + H]⁺ | ¹H NMR (400 MHz, DMSO-d₆) δ ppm 7.82 (s, 1 H), 7.54-7.46 (m, 2 H), 7.40-7.30 (m, 3 H), 7.25 (s, 1 H), 5.55 (s, 1 H), 4.44 (s, 2 H), 4.14 (s, 2 H), 2.80-2.78 (q, J = 7.60 Hz, 2 H), 2.72-2.65 (m, 3 H), 2.0 (s, 2 H), 1.18 (t, J = 7.56 Hz, 3H). |
| 672 | (S)-2-amino-N-((1-(3,5-dicyano-4-ethyl-6-((4-(N-methylmethylsulfonamido)benzyl)thio)pyridin-2-yl)pyrrolidin-3-yl)methyl)acetamide | 542.05 [M + H]⁺ | ¹H NMR (400 MHz, DMSO-d₆) δ ppm 8.01 (t, J = 5.70 Hz, 1 H), 7.48-7.43 (m, 2 H), 7.38-7.32 (m, 2 H), 4.53 (s, 2 H), 4.01-3.67 (m, 3 H), 3.58-3.51 (m, 1 H), 3.26-3.14 (m, 5 H), 3.09 (s, 2 H), 2.93 (s, 3 H), 2.80-2.69 (m, 2 H), 2.49-2.41 (m, 1 H), 2.10-1.93 (m, 2 H), 1.73 (dd, J = 12.39, 7.13 Hz, 1 H), 1.25-1.18 (m, 4 H). |
| 673 | 2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)acetamide | 493.11 [M + H]⁺ | ¹H NMR (400 MHz, DMSO-d₆) δ ppm 8.03 (t, J = 5.70 Hz, 1 H), 7.81 (s, 1 H), 7.49 (d, J = 6.80 Hz, 2 H), 7.41-7.29 (m, 4 H), 5.55 (s, 1 H), 4.57 (d, J = 17.10 Hz, 1 H), 4.46 (t, J = 5.70 Hz, 1 H), 4.37 (d, J = 17.10 Hz, 1 H), 3.35 (s, 3H), 3.26 (dd, J = 5.70, 1.97 Hz, 2H), 3.16 (d, J = 5.70 Hz, 2 H), 2.77 (q, J = 7.38 Hz, 2 H), 1.20 (t, J = 7.56 Hz, 3 H), 0.41-0.22 (m, 4 H). |

| Example | Structure/Name | LCMS m/z | 1H NMR |
|---|---|---|---|
| 674 | 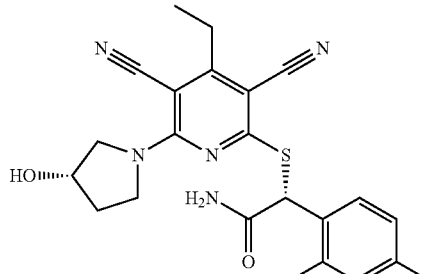<br>(R)-2-((3,5-dicyano-4-ethyl-6-((S)-3-hydroxypyrrolidin-1-yl)pyridin-2-yl)thio)-2-(2,4-difluorophenyl)acetamide | 444.08 [M + H]⁺ | ¹H NMR (400 MHz, DMSO-d₆) δ ppm 7.88 (s, 1H), 7.56 (td, J = 8.7, 6.4 Hz, 1H), 7.42 (s, 1H), 7.31 (ddd, J = 10.5, 9.2, 2.7 Hz, 1H), 7.13 (td, J = 8.5, 2.6 Hz, 1H), 5.83 (s, 1H), 5.12 (d, J = 3.6 Hz, 1H), 4.40 (s, 1H), 3.79-3.53 (m, 4H), 2.76 (q, J = 7.5 Hz, 2H), 2.10-1.81 (m, 2H), 1.21 (t, J = 7.6 Hz, 3H). |
| 675 | 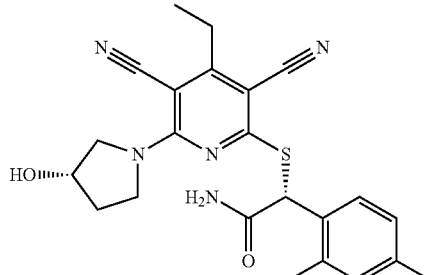<br>2-((6-((2-amino-2-oxo-1-phenylethyl)thio)-3,5-dicyano-4-ethylpyridin-2-yl)(methyl)amino)-N-(3-(hydroxymethyl)oxetan-3-yl)acetamide | 495.10 [M + H]⁺ | ¹H NMR (400 MHz, DMSO-d₆) δ ppm 8.55 (s, 1 H), 7.81 (s, 1 H), 7.49-7.54 (m, 2 H), 7.31-7.43 (m, 4 H), 5.54 (s, 1 H), 5.11 (t, J = 5.92 Hz, 1 H), 4.44-4.57 (m, 5 H), 4.36 (d, J = 17.32 Hz, 1 H), 3.67 (d, J = 5.92 Hz, 2 H), 3.35 (s, 3 H), 2.77 (q, J = 7.45 Hz, 2H), 1.21 (t, J = 7.56 Hz, 3 H). |
| 676 | 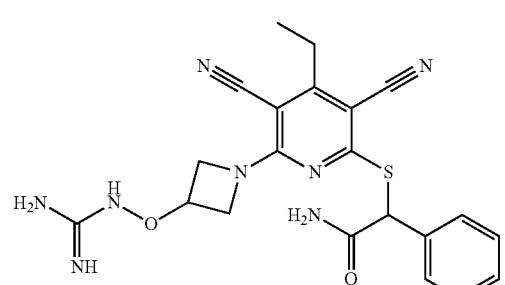<br>2-((3,5-dicyano-4-ethyl-6-(3-(guanidinooxy)azetidin-1-yl)pyridin-2-yl)thio)-2-phenylacetamide | 451.12 [M + H]⁺ | ¹H NMR (400 MHz, DMSO-d₆) δ ppm 7.88 (s, 1 H), 7.54-7.48 (m, 2 H), 7.41-7.29 (m, 3 H), 7.25 (s, 1 H), 5.57 (s, 1 H), 5.24 (s, 2 H), 4.69-4.22 (m, 7H), 2.69 (q, J = 7.38 Hz, 2 H), 1.18 (t, J = 7.67 Hz, 3 H). |
| 677 | 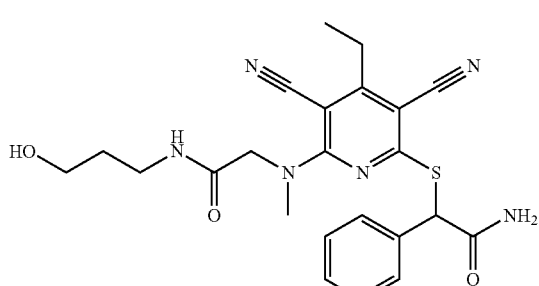 | 467.11 [M + H]⁺ | ¹H NMR (400 MHz, DMSO-d₆) δ ppm 8.03 (br t, J = 5.59 Hz, 1 H), 7.81 (s, 1 H), 7.45-7.52 (m, 2 H), 7.29-7.42 (m, 4 H), 5.55 (s, 1 H), 4.52 (d, J = 17.10 Hz, 1 H), 4.39 (t, J = 5.26 Hz, 1 H), 4.31 (d, J = 17.10 Hz, 1 H), 3.38-3.44 (m, 2 H), 3.36 (s, 3 H), 3.12-3.20 (m, 2 H), 2.77 (q, J = 7.67 Hz, 2 H), 1.57 (quin, J = 6.63 Hz, 2 H), 1.20 (t, J = 7.67 Hz, 3 H). |

| Example | Structure/Name | LCMS m/z | 1H NMR |
|---|---|---|---|
| | 2-((6-((2-amino-2-oxo-1-phenylethyl)thio)-3,5-dicyano-4-ethylpyridin-2-yl)(methyl)amino)-N-(3-hydroxypropyl)acetamide | | |
| 678 | 2-((3,5-dicyano-6-(4-(2,3-dihydroxypropyl)-1,4-diazepan-1-yl)-4-ethylpyridin-2-yl)thio)-2-phenylacetamide | 495.07 [M + H]⁺ | ¹H NMR (400 MHz, DMSO-d₆) δ ppm 8.20 (s, 1 H), 7.89 (s, 1 H), 7.54-7.42 (m, 2 H), 7.40-7.10 (m, 4 H), 5.51 (s, 1 H), 3.97-3.80 (m, 4 H), 3.62-3.55 (m, 2 H), 3.34-3.27 (m, 2 H), 2.89-2.68 (m, 4 H), 2.68-2.61 (m, 2 H), 2.57-2.52 (m, 1 H), 2.39-2.32 (m, 1 H), 1.90 (m, 2 H), 1.21 (t, J = 7.56 Hz, 3 H). |
| 679 | 2-((6-((2-amino-2-oxo-1-phenylethyl)thio)-3,5-dicyano-4-ethylpyridin-2-yl)(methyl)amino)-N-hydroxyacetamide | 425 [M + H]⁺ | ¹H NMR (400 MHz, DMSO-d₆, 90° C.) δ ppm 10.26 (br s, 1 H), 8.76 (br s, 2 H), 7.51 (br d, J = 6.80 Hz, 2 H), 7.42-7.20 (m, 3 H), 7.15 (br s, 1 H), 5.58 (s, 1 H), 4.59-4.25 (m, 2 H), 3.38 (s, 3 H), 2.80 (q, J = 7.23 Hz, 2 H), 1.23 (t, J = 7.56 Hz, 3 H). |
| 680 | 3-amino-N-(1-(6-((2-amino-2-oxo-1-phenylethyl)thio)-3,5-dicyano-4-cyclopropylpyridin-2-yl)azetidin-3-yl)oxetane-3-carboxamide | 504.07 [M + H]⁺ | ¹H NMR (400 MHz, DMSO-d₆) δ ppm 8.73 (s, 1 H), 7.83 (s, 1 H), 7.53-7.44 (m, 2 H), 7.42-7.24 (m, 3 H), 7.23 (s, 1 H), 5.54 (s, 1 H), 4.88-4.60 (m, 5 H), 4.39 (d, J = 6.14 Hz, 5 H), 2.08 (t, J = 8.69, 5.67 Hz, 1 H), 1.19-1.06 (m, 2 H), 1.01-0.90 (m, 2 H). |

| Example | Structure/Name | LCMS m/z | 1H NMR |
|---|---|---|---|
| 681 | 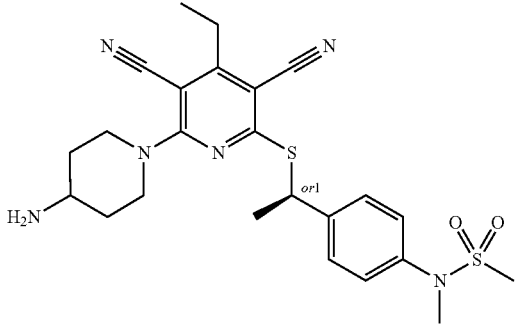 [SMILES: CCc1c(C#N)c(S[C@H](C)c2ccc(N(C)S(C)(=O)=O)cc2)nc(N2CCC(N)CC2)c1C#N]<br>ISOMER 2<br>N-(4-(1-(((6-(4-aminopiperidin-1-yl)-3,5-dicyano-4-ethylpyridin-2-yl)thio)ethyl)phenyl)-N-methylmethanesulfonamide | 499.18 [M + H]+ | ¹H NMR (400 MHz, DMSO-d₆) δ ppm 8.15 (s, 3H), 7.56-7.48 (m, 2H), 7.43-7.36 (m, 2H), 5.15 (q, J = 7.0 Hz, 1H), 4.51 (d, J = 13.7 Hz, 2H), 3.39 (s, 1H), 3.23 (s, 5H), 2.95 (s, 3H), 2.77 (q, J = 7.5 Hz, 2H), 2.15-2.04 (m, 2H), 1.73 (d, J = 7.1 Hz, 3H), 1.68-1.58 (m, 2H), 1.21 (t, J = 7.6 Hz, 3H). |
| 682 | 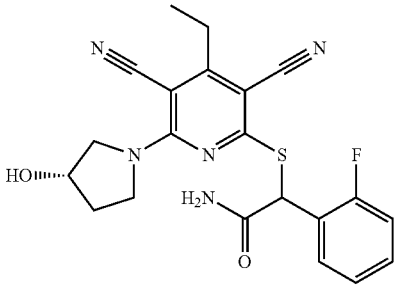 [SMILES: CCc1c(C#N)c(SC(C(N)=O)c2ccccc2F)nc(N2CC[C@H](O)C2)c1C#N]<br>2-((3,5-dicyano-4-ethyl-6-((S)-3-hydroxypyrrolidin-1-yl)pyridin-2-yl)thio)-2-(2-fluorophenyl)acetamide | 426.12 [M + H]+ | ¹H NMR (400 MHz, DMSO-d₆) δ ppm 7.86 (br s, 1 H), 7.52 (br t, J = 7.56 Hz, 1 H), 7.36-7.45 (m, 2 H), 7.19-7.30 (m, 2 H), 5.86 (s, 1 H), 5.12 (br s, 1 H), 4.40 (br s, 1 H), 3.68-3.98 (m, 4 H), 2.76 (q, J = 7.53 Hz, 2 H), 1.87-2.05 (m, 2 H), 1.21 (brt, J = 7.45 Hz, 3 H). |
| 683 | 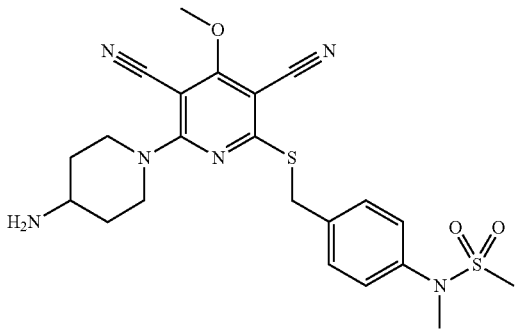 [SMILES: COc1c(C#N)c(SCc2ccc(N(C)S(C)(=O)=O)cc2)nc(N2CCC(N)CC2)c1C#N]<br>N-(4-(((6-(4-aminopiperidin-1-yl)-3,5-dicyano-4-methoxypyridin-2-yl)thio)methyl)phenyl)-N-methylmethanesulfonamide hydrochloride | 487.07 [M + H]+ | ¹H NMR (400 MHz, DMSO-d₆) δ ppm 8.13 (br s, 3 H), 7.47-7.42 (m, 2 H), 7.41-7.35 (m, 2 H), 4.51 (s, 3 H), 4.46 (br s, 1 H), 4.27 (s, 3 H), 3.41-3.34 (m, 1H), 3.26 (s, 2H), 3.22 (s, 3H), 2.93 (s, 3 H), 2.10-2.02 (m, 2 H), 1.65-1.54 (m, 2 H). |

| Example | Structure/Name | LCMS m/z | 1H NMR |
|---|---|---|---|
| 684 | 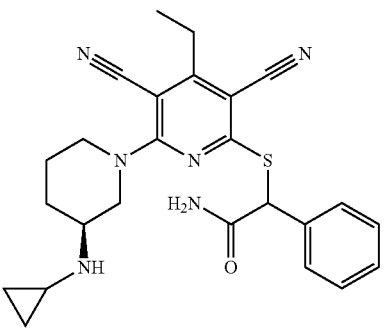 [SMILES: CCc1c(C#N)c(SC(C(N)=O)c2ccccc2)nc(N2CCC[C@H](NC3CC3)C2)c1C#N]<br>2-((3,5-dicyano-6-((S)-3-(cyclopropylamino)piperidin-1-yl)-4-ethylpyridin-2-yl)thio)-2-phenylacetamide | 461.19 [M + H]⁺ | $^1$H NMR (400 MHz, DMSO-d$_6$) δ ppm 7.88 (s, 1H), 7.53-7.49 (m, 2H), 7.40-7.29 (m, 4H), 5.53 (d, J = 4.6 Hz, 1H), 4.52-4.44 (m, 1H), 4.36-4.28 (m, 1H), 3.27-3.02 (m, 2H), 2.78-2.74 (m, 3H), 2.12-2.08 (m, 1H), 2.02-1.98 (m, 1H), 1.81-1.77 (m, 1H), 1.47-1.43 (m, 2H), 1.20 (t, J = 7.6 Hz, 3H), 0.40-0.35 (m, 2H), 0.22-0.14 (m, 2H). |
| 685 | 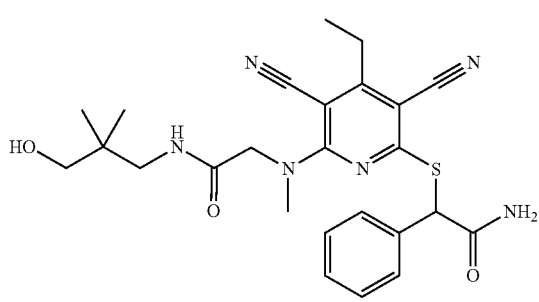 [SMILES: CCc1c(C#N)c(SC(C(N)=O)c2ccccc2)nc(N(C)CC(=O)NCC(C)(C)CO)c1C#N]<br>2-((6-((2-amino-2-oxo-1-phenylethyl)thio)-3,5-dicyano-4-ethylpyridin-2-yl)(methyl)amino)-N-(3-hydroxy-2,2-dimethylpropyl)acetamide | 495.13 [M + H]⁺ | $^1$H NMR (400 MHz, DMSO-d$_6$) δ ppm 7.97 (t, J = 6.03 Hz, 1 H), 7.83 (s, 1 H), 7.54-7.44 (m, 2 H), 7.42-7.28 (m, 4 H), 5.56 (s, 1 H), 4.63-4.48 (m, 1 H), 4.54-4.41 (m, 1 H), 4.43-4.38 (m, 1 H), 3.34 (s, 3 H), 3.10 (d, J = 5.92 Hz, 2 H), 3.00 (d, J = 6.14 Hz, 2 H), 2.65-2.83 (m, 2 H), 1.20 (t, J = 7.67 Hz, 3 H), 0.77 (s, 6 H) |
| 686 | 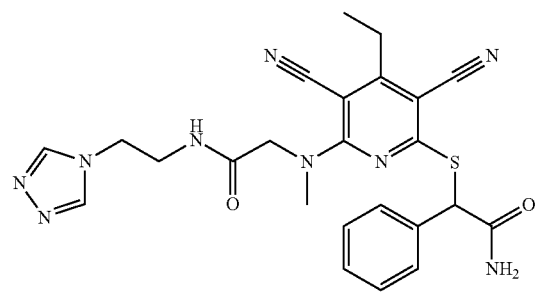 [SMILES: CCc1c(C#N)c(SC(C(N)=O)c2ccccc2)nc(N(C)CC(=O)NCCn2cnnc2)c1C#N]<br>N-(2-(4H-1,2,4-triazol-4-yl)ethyl)-2-((6-((2-amino-2-oxo-1-phenylethyl)thio)-3,5-dicyano-4-ethylpyridin-2-yl)(methyl)amino)acetamide | 504.07 [M + H]⁺ | $^1$H NMR (400 MHz, DMSO-d$_6$) δ ppm 8.47 (s, 2 H), 8.23 (br t, J = 5.70 Hz, 1 H), 7.86 (s, 1 H), 7.44-7.54 (m, 2 H), 7.28-7.42 (m, 4 H), 5.54 (s, 1 H), 4.49 (d, J = 17.32 Hz, 1 H), 4.33-4.43 (m, 1 H), 4.12 (t, J = 5.70 Hz, 2 H), 3.40-3.49 (m, 2 H), 3.29 (s, 3 H), 2.77 (q, J = 7.60 Hz, 2 H), 1.20 (t, J = 7.56 Hz, 3 H). |

| Example | Structure/Name | LCMS m/z | 1H NMR |
|---|---|---|---|
| 687 | 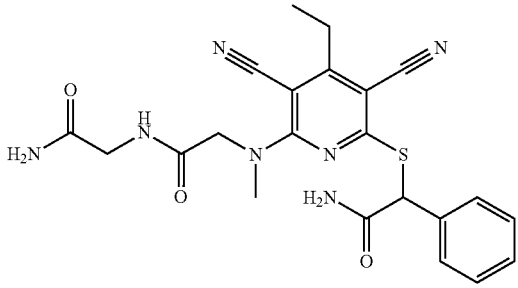 [SMILES: CCc1c(C#N)c(SC(C(N)=O)c2ccccc2)nc(N(C)CC(=O)NCC(N)=O)c1C#N]<br>N1-(2-((6-((2-amino-2-oxo-1-phenylethyl)thio)-3,5-dicyano-4-ethylpyridin-2-yl)(methyl)amino)ethyl) oxalamide | 466.11 [M + H]+ | $^1$H NMR (400 MHz, DMSO-d$_6$) δ ppm 8.88 (br t, J = 5.92 Hz, 1 H), 8.01 (br s, 1 H), 7.89-7.74 (m, 2 H), 7.63 (br s, 1 H), 7.53 (br d, J = 7.23 Hz, 2 H), 7.46-7.23 (m, 4 H), 5.56 (s, 1 H), 4.05-3.94 (m, 1 H), 3.85-3.75 (m, 1 H), 3.48 (br dd, J = 13.26, 6.47 Hz, 1 H), 3.39 (s, 4 H), 2.76 (q, J = 7.38 Hz, 2 H), 1.21 (brt, J = 7.45 Hz, 3 H). |
| 688 | 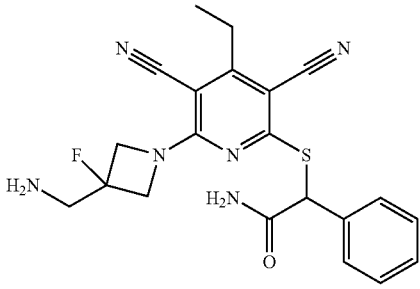 [SMILES: CCc1c(C#N)c(SC(C(N)=O)c2ccccc2)nc(N2CC(F)(CN)C2)c1C#N]<br>2-((6-(3-(aminomethyl)-3-fluoroazetidin-1-yl)-3,5-dicyano-4-ethylpyridin-2-yl)thio)-2-phenylacetamide | 425.12 [M + H]+ | $^1$H NMR (400 MHz, DMSO-d$_6$) δ ppm 7.82 (s, 1 H), 7.54-7.49 (m, 2 H), 7.42-7.33 (m, 3 H), 7.27 (s, 1 H), 5.56 (s, 1 H), 4.66-4.53 (m, 2 H), 4.49-4.37 (m, 2 H), 3.03-2.95 (m, 2 H), 2.71 (q, J = 7.45 Hz, 2 H), 1.81 (br s, 2 H), 1.24-1.17 (m, 3 H). |
| 689 | 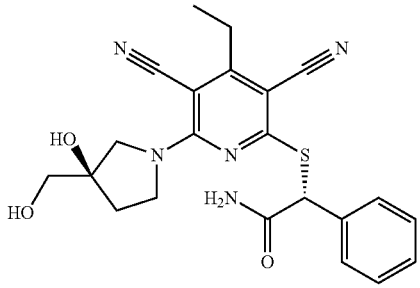 [SMILES: CCc1c(C#N)c(S[C@@H](C(N)=O)c2ccccc2)nc(N2CC[C@](O)(CO)C2)c1C#N]<br>(R)-2-((3,5-dicyano-4-ethyl-6-((R)-3-hydroxy-3-(hydroxymethyl)pyrrolidin-1-yl)pyridin-2-yl)thio)-2-phenylacetamide | 438.14 [M + H]+ | $^1$H NMR (400 MHz, DMSO-d$_6$) δ ppm 7.88 (s, 1 H), 7.52 (d, J = 7.02 Hz, 2 H), 7.40-7.29 (m, 3 H), 7.26 (br s, 1 H), 5.61 (s, 1 H), 5.02-4.90 (m, 2 H), 4.10-3.67 (m, 4 H), 3.53-3.42 (m, 2 H), 2.82-2.69 (m, 2 H), 2.13-1.93 (m, 1 H), 1.78 (s, 1 H), 1.20 (t, J = 7.45 Hz, 3 H). |

| Example | Structure/Name | LCMS m/z | 1H NMR |
|---|---|---|---|
| 690 | 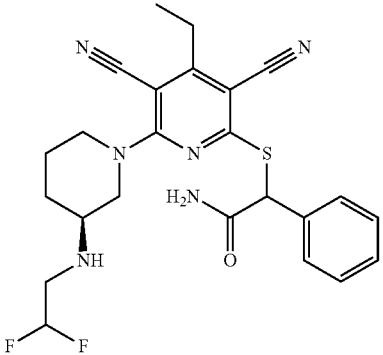 [SMILES: CCc1c(C#N)c(SC(C(N)=O)c2ccccc2)nc(N2CCC[C@H](NCC(F)F)C2)c1C#N]<br>2-((3,5-dicyano-6-((S)-3-((2,2-difluoroethyl)amino)piperidin-1-yl)-4-ethylpyridin-2-yl)thio)-2-phenylacetamide | 485.2 [M + H]+ | $^1$H NMR (400 MHz, DMSO-d$_6$) δ ppm 7.88 (s, 1 H), 7.51 (d, J = 7.45 Hz, 2 H), 7.43-7.30 (m, 4 H), 6.09-5.89 (m, 1 H), 5.58-5.52 (m, 1 H), 4.47-4.31 (m, 2 H), 3.22-2.94 (m, 4 H), 2.80-2.65 (m, 3 H), 2.11-1.91 (m, 2 H), 1.83-1.76 (m, 1 H), 1.58-1.37 (m, 2 H), 1.21 (t, J = 7.67 Hz, 3 H). |
| 691 | 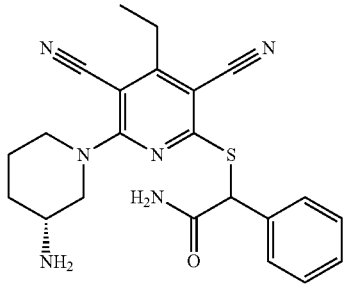 [SMILES: CCc1c(C#N)c(SC(C(N)=O)c2ccccc2)nc(N2CCC[C@@H](N)C2)c1C#N]<br>2-((6-((R)-3-aminopiperidin-1-yl)-3,5-dicyano-4-ethylpyridin-2-yl)thio)-2-phenylacetamide | 421.2 [M + H]+ | $^1$H NMR (400 MHz, DMSO-d$_6$) δ ppm 7.91 (br s, 1 H), 7.52 (br d, J = 7.02 Hz, 2 H), 7.28-7.44 (m, 4 H), 5.52 (s, 1 H), 4.24-4.44 (m, 2 H), 3.18-3.25 (m, 2 H), 3.01 (br dd, J = 13.15, 9.65 Hz, 1H), 2.71-2.84 (m, 4 H), 1.75-1.95 (m, 2 H), 1.43-1.60 (m, 1 H), 1.30-1.41 (m, 1 H), 1.21 (br t, J = 7.56 Hz, 3 H). |
| 692 | 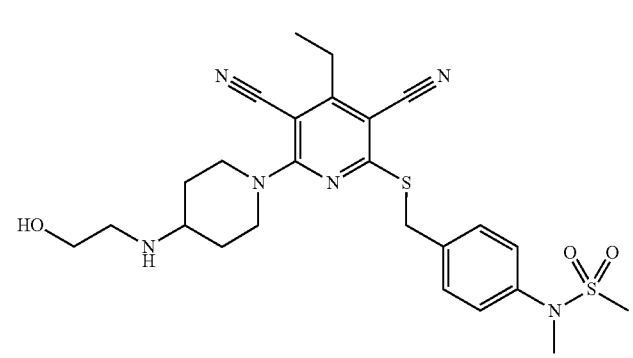 [SMILES: CCc1c(C#N)c(SCc2ccc(N(C)S(C)(=O)=O)cc2)nc(N2CCC(NCCO)CC2)c1C#N]<br>N-(4-(((3,5-dicyano-4-ethyl-6-(4-((2-hydroxyethyl)amino)piperidin-1-yl)pyridin-2-yl)thio)methyl)phenyl)-N-methylmethanesulfonamide | 528.8 [M + H]+ | $^1$H NMR (400 MHz, DMSO-d$_6$) δ ppm 8.18 (s, 1H), 7.45 (d, J = 8.5 Hz, 2H), 7.38 (d, J = 8.5 Hz, 2H), 4.52 (s, 2H), 4.44-4.40 (m, 2H), 3.52-3.50 (m, 2H), 3.31-3.26 (m, 3H), 3.22 (s, 3H), 2.94 (s, 3H), 2.93-2.91 (m, 1H), 2.82-2.70 (m, 4H), 1.97 (m, 2H), 1.41 (m, 2H), 1.22 (t, J = 7.5 Hz, 3H). |

-continued

| Example | Structure/Name | LCMS m/z | 1H NMR |
|---|---|---|---|
| 693 | 2-((6-(4-aminopiperidin-1-yl)-3,5-dicyano-4-methoxypyridin-2-yl)thio)-2-phenylacetamide 2,2,2-trifluoroacetate | 422.8 [M + H]$^+$ | $^1$H NMR (400 MHz, DMSO-d$_6$) δ ppm 8.15-8.00 (br, 3H), 7.98-7.92 (br, 1H), 7.52 (d, J = 7.2 Hz, 2H), 7.42-7.32 (m, 4H), 5.54 (s, 1H), 4.55 (m, 2H), 4.27 (s, 3H), 3.46-3.35 (m, 1H), 3.29-3.19 (m, 2H), 2.09-2.01 (m, 2H), 1.62-1.49 (m, 2H). |
| 694 | ISOMER 2 2-((3,5-dicyano-4-ethyl-6-((S)-4-hydroxyisoxazolidin-2-yl)pyridin-2-yl)thio)-2-phenylacetamide | 409.8 [M + H]$^+$ | $^1$H NMR (400 MHz, DMSO-d$_6$) δ ppm 7.94 (s, 1H), 7.53 (d, J = 7.5 Hz, 2H), 7.41-7.35 (m, 4H), 5.64 (br, 1H), 5.57 (s, 1H), 4.73 (br, 1H), 4.15-4.03 (m, 3H), 4.00 (d, J = 11.9 Hz, 1H), 2.80-2.76 (m, 2H), 1.22-1.18 (m, 3H). |
| 695 | (R)-2-((3,5-dicyano-4-ethyl-6-((3-hydroxypropyl)(methyl)amino)pyridin-2-yl)thio)-2-phenylacetamide | 409.8 [M + H]$^+$ | $^1$H NMR (400 MHz, DMSO-d$_6$) δ ppm 7.88 (s, 1H), 7.51 (d, J = 7.1 Hz, 2H), 7.43-7.30 (m, 4H), 5.61 (s, 1H), 4.77 (br, 1H), 3.92 (dt, J = 14.6, 7.2 Hz, 1H), 3.76 (dt, J = 14.3, 7.2 Hz, 1H), 3.49 (m, 2H), 3.34 (s, 3H), 2.76 (q, J = 7.5 Hz, 2H), 1.81 (m, 2H), 1.21 (t, J = 7.6 Hz, 3H). |
| 696 | 2-((3,5-dicyano-6-((S)-3-hydroxypyrrolidin-1-yl)-4- | 409.8 [M + H]$^+$ | $^1$H NMR (400 MHz, DMSO-d$_6$) δ ppm 7.92 (s, 1H), 7.54-7.48 (m, 2H), 7.41-7.30 (m, 4H), 5.60 (s, 1H), 5.23-5.07 (br, 1H), 4.44-4.37 (m, 1H), 4.23 (s, 3H), 3.93-3.64 (m, 4H), 2.02-1.87 (m, 2H). |

| Example | Structure/Name | LCMS m/z | 1H NMR |
|---|---|---|---|
| | methoxypyridin-2-yl)thio)-2-phenylacetamide | | |
| 697 | 2-((3,5-dicyano-4-ethyl-6-(4-(3-methoxyazetidin-1-yl)piperidin-1-yl)pyridin-2-yl)thio)-2-phenylacetamide | 491.1 [M + H]+ | 1H NMR (400 MHz, DMSO-d6) δ 7.92 (s, 1H), 7.54-7.48 (m, 2H), 7.41-7.30 (m, 4H), 5.52 (s, 1H), 4.23-4.15 (m, 2H), 3.99-3.92 (m, 1H), 3.53-3.44 (m, 4H), 3.17 (s, 3H), 2.83-2.71 (m, 4H), 2.37-2.29 (m, 1H), 1.78-1.66 (m, 2H), 1.34-1.22 (m, 2H), 1.20 (t, J = 7.6 Hz, 3H) |
| 698 | 2-((3,5-dicyano-4-ethyl-6-(4-(3-methoxyazetidin-1-yl)piperidin-1-yl)pyridin-2-yl)thio)-2-(4-fluorophenyl)acetamide | 509.1 [M + H]+ | 1H NMR (400 MHz, DMSO-d6) δ 7.94 (s, 1H), 7.59-7.51 (m, 2H), 7.38 (s, 1H), 7.27-7.18 (m, 2H), 5.54 (s, 1H), 4.24-4.10 (m, 2H), 3.99-3.91 (m, 1H), 3.53-3.44 (m, 4H), 3.17 (s, 3H), 2.82-2.71 (m, 4H), 2.37-2.30 (m, 1H), 1.78-1.69 (m, 2H), 1.33-1.23 (m, 2H), 1.20 (t, J = 7.6 Hz, 3H) |
| 699 | 2-((3,5-dicyano-4-ethyl-6-(methyl(1-methylpyrrolidin-3-yl)amino)pyridin-2-yl)thio)-2-phenylacetamide | 435.1 [M + H]+ | 1H NMR (400 MHz, DMSO-d6) δ = 8.36-8.27 (m, 1H), 8.06-7.92 (m, 1H), 7.53-7.48 (m, 2H), 7.43-7.30 (m, 4H), 5.56-5.45 (m, 1H), 3.65-3.38 (m, 2H), 2.74-2.61 (m, 3H), 2.48-2.28 (m, 4H), 2.27-2.24 (m, 3H), 1.98-1.85 (m, 1H), 1.55-1.41 (m, 1H), 1.19 (t, J = 7.6 Hz, 3H) |

*Examples 523 and 542 are deemed to be 3:1 mixtures of diastereomers with the major component as drawn.

Example 700

DNMT1 Assays—In Vitro

Compounds of the invention are assayed for DNMT1 selective activity in one or more of the following DNMT1 assays and may be assayed in one or more of the following DNMT3 assays.

DNMT1 Breaklight Assay

DNMT1 breaklight in vitro assays were conducted in a total volume of 50 µl in a standard 384 well format, using black non-binding surface microplates (Corning 3575). Five µl of human full length DNMT1 (produced internally), used at a final concentration of 40 nM, was added to 5 µl of substrate mixture containing final concentrations of 125 nM hemi methylated oligonucleotide (synthesized at ATD Bio; 5'-FAM-ATCTAGCG5ATCAGTTTTCTGATG5G5TAGAT-3' where 5=methyl deoxycitidine) and 2 µM ultrapure SAM (Cisbio #62SAHZLD). Negative control wells used 5 µl of DNMT1 and 5 µl of oligonucleotide but 0 µM SAM. All reagents were made up in 1× assay buffer (20 mM Tris pH 6.8, 25 mM NaCl, 0.5 mM $MgCl_2$, 0.01% Triton X100 and 1 mM DTT). The reaction was incubated at 26° C. for 45 min and then stopped with the addition of 40 µl detection reagent. Detection reagent, made up in 1× Gla assay buffer (20 mM Tris pH 8.0, 80 mM NaCl, 0.75 mM $MgCl_2$, 0.01% Triton X100 and 1 mM DTT) has a final concentration of 100 µM SAH (Sigma #A9384) and 0.0008 units/µl Gla1 restriction endonuclease (Sibenzyme #E494). Following addition of the detection reagent the plate was incubated in the dark at room temperature for 5 hr. Fluorescence intensity was then measured on the PHERAstar FS (BMG Labtech) at Ex 485 nm and Em 520 nm, with a gain of 400 and an integration time of 100 ms.

Gla1 Breaklight Counter-Screen Assay

Gla1 breaklight in vitro counter-screen assays were conducted in a total volume of 50 µl in a standard 384 well format, using black non-binding surface microplates (Corning #3575). Ten µl of substrate mixture containing final concentrations of 100 nM hemi methylated oligonucleotide (synthesized at ATD Bio; 5'-FAM-ATCTAGCG5ATCAGTTTTCTGATG5G5TAGAT-3' where 5=methyl deoxycitidine sequence) and 25 nM fully methylated oligonucleotide (synthesized at ATD Bio; 5'-FAM-ATCTAG5G5ATCAGTTTTCTGATG5G5TAGAT-3' where 5=methyl deoxycitidine) was added to test wells. Negative control wells used 10 µl 125 nM hemi methylated oligonucleotide. Oligonucleotides were made up in 1× assay buffer (20 mM Tris pH 6.8, 25 mM NaCl, 0.5 mM $MgCl_2$, 0.01% Triton X100 and 1 mM DTT). 40 µl Gla1 detection reagent was added immediately, made up in 1× Gla assay buffer (20 mM Tris pH 8.0, 80 mM NaCl, 0.75 mM $MgCl_2$, 0.01% Triton X100 and 1 mM DTT) with a final concentration of 100 µM SAH (Sigma #A9384) and 0.0008 units/µl Gla1 restriction endonuclease (Sibenzyme #E494). Following addition of the detection reagent the plate was incubated in the dark at room temperature for 5 hr. Fluorescence intensity was then measured on the PHERAstar FS (BMG Labtech) at Ex 485 nm and Em 520 nm, with a gain of 400 and an integration time of 100 ms.

DNMT3a/3l Breakliqht Assay

DNMT3a/3l breaklight in vitro assays were conducted in a total volume of 50 µl in a standard 384 well format, using black non-binding surface microplates (Corning #3575). Five µl of human DNMT3a/3l (produced internally), used at a final concentration of 600 nM, was added to 5 µl of substrate mixture containing final concentrations of 125 nM hemi methylated oligonucleotide (synthesized at ATD Bio; 5'-FAM-ATCTAGCG5ATCAGTTTTCTGATG5G5TAGAT-3' where 5=methyl deoxycitidine) and 2 µM ultrapure SAM (Cisbio #62SAHZLD). Negative control wells used 5 µl of DNMT3a/3l and 5 µl of oligonucleotide but also included 200 µM SAH. All reagents were made up in 1× assay buffer (20 mM Tris pH 7.4, 100 mM NaCl, 1.5 mM EDTA, 0.1 mM $MgCl_2$, 1 mM CHAPS and 1 mM DTT). The reaction was incubated at 37° C. for 90 min and then stopped with the addition of 40 µl detection reagent. Detection reagent, made up in 1× Gla assay buffer (20 mM Tris pH 8.0, 80 mM NaCl, 0.75 mM $MgCl_2$, 0.01% Triton X100 and 1 mM DTT) has a final concentration of 200 µM SAH (Sigma #A9384) and 0.0008 units/µl Gla1 restriction endonuclease (Sibenzyme #E494). Following addition of the detection reagent the plate was incubated in the dark at room temperature for 5 hr. Fluorescence intensity was then measured on the PHERAstar FS (BMG Labtech) at Ex 485 nm and Em 520 nm, with a gain of 400 and an integration time of 100 ms.

DNMT1 SPA Assay Methods:

Biochemical activity of DNMT1 analyzed using SPA technology. Plates (Griener 784075) were pre-stamped with 100 nL/well of compound (11-point, 3-fold serial dilution). Reaction was initiated upon the addition of 5 µL of 2× enzyme mix to wells containing 5 µL of 2× substrate mix. Low control wells contained 5 µL of buffer instead of enzyme. Following a 40 minute incubation, the reaction was quenched upon the addition of 10 µL of stop mixture containing 1 mM SAM (Sigma A7007) and 2 mg/mL PEI beads (Perkin Elmer RPNQ0098). Plates were sealed, centrifuged for 1 min and then read on a Viewlux (Perkin Elmer) using the 613 nm emission filter/300 s read time following a 30 minute dark adapt. Assay conditions prior to quench consisted of 40 nM DNMT1 (601-1600, produced internally), 100 nM 3H-SAM (American Radiolabeled Chemicals ART 0288), 900 nM SAM (New England BioLabs B9003S) and 200 nM hemi methylated DNA oligonucleotide (synthesized at Integrated DNA Technologies, 5'-CCTCTTCTAACTGCCATSGATCCTGA-TAGCAGGTGCATGC-3') in 50 mM HEPES (pH 8.0), 2 mM MgCl2, 1 mM DTT, 0.01% NP-40 and 0.01% BSA.

Example 701

Effects on Erythroid Progenitor Cells (EPCs)—In Vitro

Day 7 EPCs were cultured in duplicate plates with serially diluted Compound A for 5 days at 37° C. Wells were then analyzed for either induction of fetal hemoglobin (HbF,HbF ELISA) or cell growth (Cell Titer-Glo). In both cases, signal was normalized to vehicle-control treated cells. Compound A induced an increase in HbF with an average pEC50=6.5, and inhibited cell growth by 50% with an average pGI50=5.9. Representative curves for each assay are indicated in FIG. 1A.

To assay the effect of Compound A on DNA methylation, EPCs treated for 3 days with Compound A were harvested and genomic DNA was bisulfite sequenced. Methylation of nine CpG sites in or near the promoter regions of HBG1 and HBG2 gene loci were selected and analyzed based on their previous characterization as sites of DNMT1 methylation during erythropoiesis (Mabaera et al. Blood: 110 (4). 2007).

Figure 1B:
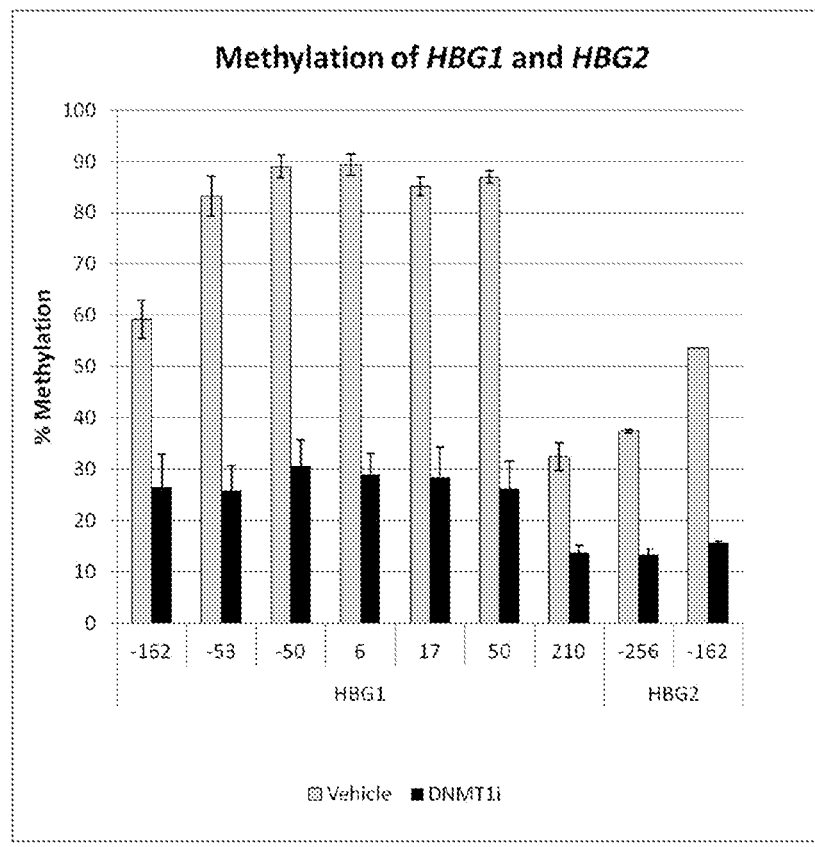
FIG. 1B depicts the effect of Compound A on HBG1 and HBG2 DNA methylation. Erythroid progenitor cells (EPCs) were treated for 3 days with vehicle (gray bars) or 5 µM Compound A (black bars), genomic DNA was extracted and bisulfite sequenced for nine loci in the promoter regions of HBG1 and HBG2 that were previously described to be sites of DNMT1 cytosine methylation. Sites of methylation are labeled as positions relative to respective start sites

As indicated in FIG. 1B, all nine sites showed reduction in methylation, averaging 65±5% decrease compared with vehicle treated cells Methods Culture, Expansion, and Characterization of Day 7 Erythroid Progenitor Cells (EPC)s All donors provided written informed consent for use of their samples, and the collection and use of the samples received institutional review board approval. All cryopreserved human bone marrow CD34+ cells used here were obtained from AllCells (Emeryville, Calif.) and were generally from different donors. The CD34+ cells were cultured to generate EPCs at day 7. Briefly, 1 million cells were cultured in 5% CO2, 5% O2 at 37° C. in H3000 Stemspan media (StemCell Technologies Vancouver, BC, Canada) supplemented with 2 mM L-glutamine, 40 µg/mL human low-density lipoproteins (StemCell Technologies), 10 ng/mL recombinant human (rh) interleukin IL-3 (R&D Systems, Minneapolis, Minn.), 100 ng/mL rh stem cell factor (R&D Systems), and 0.5 U/mL rh erythropoietin (Invitrogen, Grand Island, N.Y.). Cells were split and refed on day 4 with complete culture media described above and harvested on day 7 for evaluation of erythroid marker expression and assessment of γ-globin induction. Day 7 EPCs were then frozen in liquid nitrogen at 5 to 10 million cells/mL in 95% fetal bovine serum (FBS; Invitrogen) with 5% DMSO for subsequent use.

At the time of compound treatment, frozen day 7 EPCs prepared as described above were thawed, washed once and re-suspended in complete culture media as described above with the exception of an increase of rhEPO to 3 U/mL. Cells were counted and diluted to $3.3 \times 10^3$ cell/mL for plating into assay plates. Cells were then dispensed, at 30 µL per well with Multidrop™ Combi Reagent Dispenser (Thermo Scientific), into 384-well cell culture plates into which test compounds were pre-dispensed at 100 nL/well. Black Clear Bottom (Greiner Bio-One; 781090) and White (Greiner Bio-One; 781080) plates were used for ELISA and Cell Titer-Glo assays, respectively. The final cell density in the assays is 1,000 cells per well, with final compound concentrations between 33 nM (highest) and 6.6 nM (lowest) for the 22-points serial dilution.

To monitor cell health and cell growth, cell growth assays were performed at the time of cell plating (day 0) using Cell Titer-Glo (detailed below). For compound treatment, the cell culture plates were incubated for 5 days at 37° C. with 5% CO$_2$.

Fetal Hemoglobin (HbF) ELISA

Coating anti-HbF Ab (Bethyl Lab; cat. A80-136A) was diluted by 100-fold in the coating buffer (0.05 M carbonate-bicarbonate, pH 9.6), and then 20 µL/well was added to a 384-well MaxiSorp ELISA plate (Thermo Fisher; cat. 464718). After 1 hour incubation at room temperature, the plates were washed twice with ELISA washing buffer (50 mM Tris, 0.05% Tween 20, pH 8.0) with an EL406 plate washer (BioTek, Winooski, Vt.). Then, 40 µL/well of blocking buffer consisting of 50 mM Tris and 1% BSA (pH 8.0) was added to the plate and stored at 4° C. with cover sheet overnight, or until time of the assay. The coated ELISA plates were stable for up to 30 days at 4° C. On the day of assay, the plates were washed twice with ELISA washing buffer prior to addition of cell lysate.

After 5 days at 37° C. with 5% CO$_2$ cell culture plates for ELISA assay were put into −80° C. freezer for a minimum of 2 hours. After thawing at room temperature, 30 µL of cell lysis buffer (Invitrogen; cat. FNN0011, supplemented with 1× protease inhibitor) was added to each well and the resulting cell lysate was mixed eight times with a Cybi-Well (Jena, Germany) pipettor. Following the mixing procedure, 20 µL/well of lysate was transferred to the coated ELISA plates described above followed by a 1 hour incubation at room temperature. The ELISA assay plates were washed three times with ELISA wash buffer. 20 µL per well of 1:75,000 to 100,000 diluted horseradish peroxidase (HRP) conjugate detection antiHbF Ab (Bethyl Labs; cat. A80-136P, diluted in 50 mM Tris [pH 8.0], 1% BSA, 0.05% Tween-20) was then added. After another 1 hour incubation at room temperature, the plates was washed four times, and then 20 µL per well of tetra methyl benzidine ELISA substrate (Thermo Scientific; cat. 34028) was added. After 3-10 min incubation at room temperature in the dark, 20 µL/well of stop solution (0.2 M sulfuric acid) was added. The plates were then read at absorbance 450 nm (OD450) with an EnVision plate reader (PerkinElmer, Waltham, Mass.). Average reading of the control wells (16 wells in column 6 of each assay plate) containing DMSO only were used as the basal level for normalization. The γ-globin level of each compound treated well was calculated as a percentage of the basal level (100%).

The normalized responses of the 22 concentrations of each test compound were subjected to curve fitting using a customized statistical computing tool based on R (R Foundation for Statistical Computing). An EC50 value (compound concentration at ½ Max %) and the corresponding Max % was determined from fitted curve of each active compounds.

Cell Growth Analysis in Day 7 EPCs

Cell growth assays were performed on cell culture plates after 5 days incubation at 37° C. with 5% CO$_2$. 15 µL per well of Cell Titer-Glo (Promega, Madison, Wis.) assay reagent was added to the assay plates. The plates were then incubated at room temperature for 10 min prior to reading on ViewLux 1430 (Perkin Elmer) using a luminescence protocol. Average reading of control wells (16 wells in column 6 of each assay plate) containing DMSO only were used as the basal level for normalization. The Cell Titer-Glo signal of each test well was calculated as a percentage of the basal level (100%). The normalized responses of the 22 concentrations of each test compound were subjected to curve fitting using a customized statistical computing tool based on R (R Foundation for Statistical Computing).

To monitor cell health and cell growth, the Cell Titer-Glo signal of DMSO control wells were compared to signal obtained on day 0 (see above). For healthy cell growth, increase of appromixally 20-folds was typically observed at day 5 over day 0.

Bisulfite Sequence Analysis

Genomic DNA was extracted in duplicate from Day 7 EPCs cultured at 37° C. with 5% CO2 and 5% O2 for 3 days in the presence of compound using a ZYMO gDNA kit (Zymo Research, Irvine, Calif.). The isolated DNA was bisulfite converted using a Zymo EZ DNA Methylation Kit. Primer sets for Bisulfite treated regions within the HBG1 and HBG2 were designed using ABI Methyl Primer Express Software. Analyzed regions included 9 previously described sites of DNMT1-dependent DNA methylation (Mabaera et al. *Blood:* 110 (4). 2007). DNA was further amplified on the fluidigm and QC'd using the Agilent bio-analyzer. MiSeq was performed using the Illumina system and the output was Analyzed using ArrayStudio v8 and CLC-GWB v8.1.

Example 702

MV-4-11 Anti-Proliferative Activity (pEC$_{50}$ Category)

Cell proliferation assay. Optimal cell seeding density was determined empirically for MV-4-11 AML cells by examining the growth of a wide range of seeding densities in a 384-well format to identify conditions that permitted maximal and continued proliferation for 6 days. MV-4-11 cells were plated in duplicate plates 24 hours before treatment with a 20-point two-fold dilution series of compound or 0.15% DMSO. Plates were incubated for 6 days at 37° C. in 5% $CO_2$. Cells were then lysed with CellTiter-Glo (CTG) (Promega) and chemiluminescent signal was detected with an appropriate microplate reader. In addition, an untreated plate of cells was harvested at the time of compound addition (T$_0$) to quantify the initial cell density. CTG values obtained after 6 days of treatment were expressed as a percent of the T$_0$ value and plotted against compound concentration. Data were fit with a four parameter equation to generate a concentration response curve from which growth IC$_{50}$ values were calculated.

Example 703

Sickle Cell Assays—In Vivo

A mouse model of sickle cell disease was utilized to measure the in vivo efficacy of Compound A previously shown to have potent in vitro activity in human primary erythroid progenitor cells derived from normal bone marrow or sickle cell patient peripheral blood mononuclear cells.

Methods

Experimental Preparation

The in vivo activity of Compound A was investigated in the the sickle cell mouse model in accordance with US/UK standards of animal care.

Male and female human hemoglobin transgenic mice [B6; 129-Hbatm1(HBA)Tow/Hbbtm2(HBG1,HBB*)Tow/J Mice (Jackson Laboratories, Me.)] were approximately 6-8 weeks old and weighed approximately 15-25 grams at the initiation of the studies. To the extent possible, groups were gender balanced and comprised of 6 mice.

Experimental Protocol

Mice were administered vehicle (10% DMA/90% PEG400), 10 or 50 mg/kg Compound A twice daily (BID) by oral route five days per week, over a two week period.

At the end of the dosing period, mice were euthanized by CO2 asphyxiation and blood from the vena cava was collected into EDTA tubes for fetal hemoglobin analysis. % HbF protein was determined by high performance liquid chromatography and % F cells (HbF expressing erythrocytes) were determined by flow cytometry. The mouse monoclonal anti-human HbF antibody conjugated to APC (Life Technologies, Grand Island, N.Y.) was used to identify HbF expressing erythroid cells. The nuclear dye, syto16, (Life Technologies) was used to separate the reticulocyte and RBC populations. Protein and cellular data were collected on the Bio-Rad D10 analyzer (Bio-Rad, Benicia, Calif.) and the FACs Canto I (BD BioSciences, San Jose, Calif.) respectively. Flow cytometry data was analyzed with Flowjo v7 software (Treestar, Inc Ashland. Oreg.). Group mean and standard deviation were determined for the control and treatment groups. Data were graphed and analyzed using 1-Way ANOVA with Tukey post test (Graphpad Prism v5 [La Jolla, Calif.]).

Results

Figure 2A:
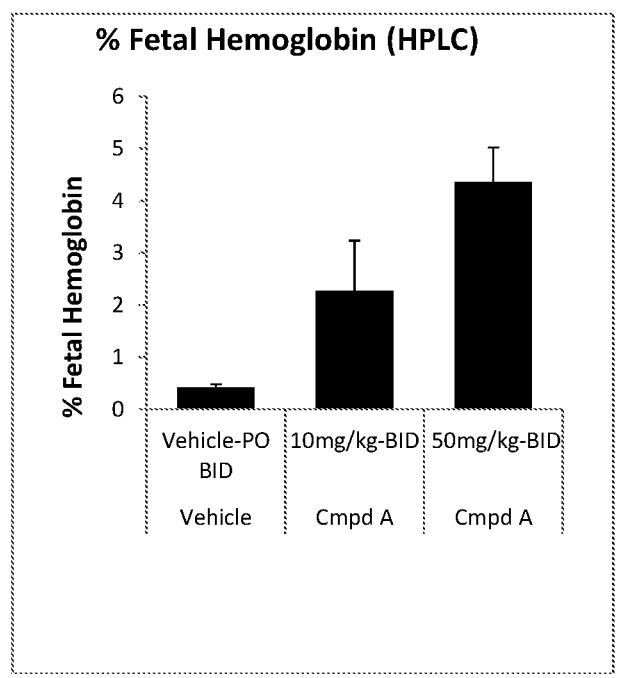
FIG. 2A depicts the effect of Compound A on fetal hemoglobin in the transgenic mouse model. Compound A administered orally to sickle cell disease (SCD) model transgenic mice at 10 or 50 mg/kg, BID daily caused dose dependent increases in % HbF protein, measured by HPLC.

Compound A administered orally at 10 or 50 mg/kg, BID daily (5 days dosed, 2 days holiday, 4 days dosed) caused an increase in % HbF protein that was dose dependent and statistically significant (5.4-fold, p<0.05; 10.3-fold, p<0.001, respectively) [FIG. 2A].

Figure 2B:
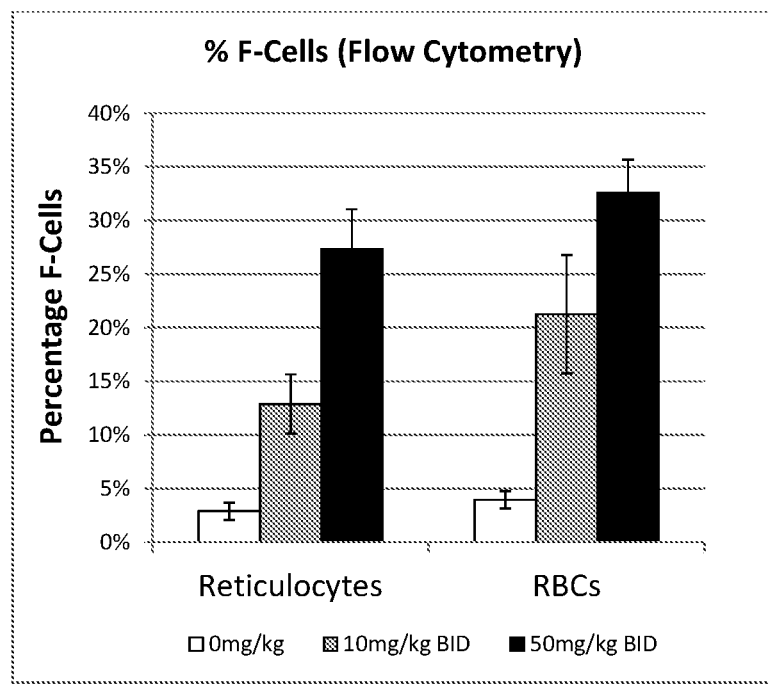
FIG. 2B depicts the effect of Compound A on fetal hemoglobin in the transgenic mouse model. Compound A administered orally to SCD transgenic mice at 10 or 50 mg/kg, BID daily caused dose dependent increases in % F-reticulocytes and % F-RBCs, measured by flow cytometry.

Compound A treatment caused increases in % F reticulocytes and % F RBCs following oral adminstration of 10 or 50 mg/kg BID in a 2 week dose period. Dose dependent and statistically significant increases in % F reticulocytes (4-fold and 9-fold, respectively; p<0.001) and % F RBCs (6-fold and 8-fold, respectively; p<0.001) were observed [FIG. 2B].

Example 704

Capsule Composition

An oral dosage form for administering the present invention is produced by filing a standard two piece hard gelatin capsule with the ingredients in the proportions shown in Table 2, below.

TABLE 2

| INGREDIENTS | AMOUNTS |
|---|---|
| 2-((3,5-dicyano-4-cyclopropyl-6-(1,4-diazepan-1-yl)pyridin-2-yl)thio)-2-phenylacetamide (Compound of Example 4) | 7 mg |
| Lactose | 53 mg |
| Talc | 16 mg |
| Magnesium Stearate | 4 mg |

Example 705

Injectable Parenteral Composition

An injectable form for administering the present invention is produced by stirring 1.7% by weight of 2-((3,5-Dicyano-4-ethyl-6-(1,7-diazaspiro[3.5]nonan-1-yl)pyridin-2-yl)thio)-2-phenylacetamide trifluoroacetate (Compound of Example 38) in 10% by volume propylene glycol in water.

Example 706

Tablet Composition

The sucrose, calcium sulfate dihydrate and an inhibitor of the activity of DNMT1 as shown in Table 3 below, are mixed and granulated in the proportions shown with a 10% gelatin solution. The wet granules are screened, dried, mixed with the starch, talc and stearic acid; screened and compressed into a tablet.

TABLE 3

| INGREDIENTS | AMOUNTS |
|---|---|
| N-(4-((3,5-Dicyano-4-ethyl-6-(4-(pyrrolidin-1-yl)piperidin-1-yl)pyridin-2-ylthio)methyl)benzyl)acetamide trifluoroacetate (Compound of Example 66) | 12 mg |
| calcium sulfate dehydrate | 30 mg |
| Sucrose | 4 mg |
| Starch | 2 mg |
| Talc | 1 mg |
| stearic acid | 0.5 mg |

BIOLOGICAL ACTIVITY

Those of skill in the art will recognise that the above assays are subject to experimental variability. Accordingly, it is to be understood that the values given below are exemplary only.

Compounds of the invention are tested for activity against DNMT1 generally according to the above breaklight assay and/or SPA assay.

DNMT1 data table:

| Example# | DNMT1 BioChemical ($pIC_{50}$ category) | EPC ELISA ($pEC_{50}$ category) | MV4-11 Anti-proliferative activity ($EC_{50}$ category) | DNMT3A Breaklight $IC_{50}$ (micromolar) | DNMT3B Breaklight $IC_{50}$ (micromolar) |
|---|---|---|---|---|---|
| 1 | B | A | | 417 | >500 |
| 2 | C | A | | >500 | >500 |
| 3 | D | C | | >500 | >500 |
| 4 | D | D | B | | |
| 5 | D | D | | | |
| 6 | D | D | | >500 | >500 |
| 7 | D | D | | >500 | >500 |
| 8 | C | B | B | >500 | >500 |
| 9 | C | A | | >500 | >500 |
| 10 | C | A | | | |
| 11 | C | C | | | |
| 12 | C | C | | | |
| 13 | C | C | | | |
| 14 | D | C | | | |
| 15 | C | B | | | |
| 16 | D | D | | | |
| 17 | D | D | | | |
| 18 | D | D | B | | |
| 19 | C | D | | | |
| 20 | D | D | | | |
| 21 | C | B | | | |
| 22 | C | D | | | |
| 23 | D | B | | | |
| 24 | D | D | | | |
| 25 | D | D | | | |
| 26 | C | A | | | |
| 27 | D | A | | | |
| 28 | D | D | | | |
| 29 | D | D | | | |
| 30 | C | A | | | |
| 31 | C | A | B | | |
| 32 | D | B | | | |
| 33 | C | C | | | |
| 34 | C | B | B | | |
| 35 | C | B | | >500 | >500 |
| 36 | D | B | | | |
| 37 | C | B | | | |
| 38 | C | C | B | | |
| 39 | D | D | | | |
| 40 | D | D | C | | |
| 41 | C | B | | >500 | >500 |
| 42 | D | D | C | | |
| 43 | D | C | | | |
| 44 | D | B | B | | |
| 46 | C | A | B | >500 | >500 |
| 47 | C | C | | >500 | >500 |
| 48 | C | B | | >500 | >500 |
| 49 | D | C | | >500 | >500 |
| 50 | C | D | | >500 | >500 |
| 51 | C | A | | >500 | >500 |
| 52 | C | B | | >500 | >500 |
| 53 | B | B | | >500 | >500 |
| 54 | C | B | | | |
| 55 | C | D | B | >500 | 272 |
| 56 | D | D | B | >500 | >500 |
| 57 | C | C | C | >500 | >500 |
| 58 | D | B | | | |
| 59 | C | C | | >500 | >500 |
| 60 | D | | | | |
| 61 | D | D | | | |
| 62 | C | C | | | |

-continued

DNMT1 data table:

| Example# | DNMT1 BioChemical (pIC$_{50}$ category) | EPC ELISA (pEC$_{50}$ category) | MV4-11 Antiproliferative activity (EC$_{50}$ category) | DNMT3A Breaklight IC$_{50}$ (micromolar) | DNMT3B Breaklight IC$_{50}$ (micromolar) |
|---|---|---|---|---|---|
| 63 | C | C | B | | |
| 64 | D | D | C | >500 | >500 |
| 65 | C | B | | | |
| 66 | D | D | | | |
| 67 | D | D | | | |
| 68 | C | A | | | |
| 69 | B | A | | | |
| 70 | C | C | | | |
| 71 | D | A | | | |
| 72 | B | A | | | |
| 73 | C | A | | | |
| 74 | B | B | | | >250 |
| 75 | C | A | | | |
| 76 | D | C | | | >250 |
| 77 | D | D | | | >250 |
| 78 | C | A | | | |
| 79 | D | C | | | |
| 80 | D | C | | | |
| 81 | C | A | | | >250 |
| 82 | C | B | | | |
| 83 | D | D | | | >250 |
| 84 | D | D | | | >250 |
| 85 | C | B | | | |
| 86 | D | D | | | >250 |
| 87 | D | C | | | |
| 88 | C | A | | | |
| 89 | C | A | | | |
| 90 | C | A | | | |
| 91 | C | B | | | |
| 92 | C | B | | | |
| 93 | C | A | | | |
| 94 | C | A | | | |
| 95 | C | B | | | |
| 96 | D | A | | | |
| 97 | D | A | | | |
| 98 | D | A | | | |
| 99 | C | B | | | |
| 100 | C | A | | | |
| 101 | D | C | | | |
| 102 | B | A | | | |
| 103 | B | B | | | |
| 104 | D | D | | | 254 |
| 105 | D | B | | | |
| 106 | D | D | | >500 | >500 |
| 107 | D | D | | >500 | >500 |
| 108 | B | C | | | |
| 109 | C | D | | | |
| 110 | C | B | | | |
| 111 | C | D | | | |
| 112 | D | D | | >500 | >500 |
| 113 | C | | | | |
| 114 | C | B | B | | |
| 115 | D | D | | | |
| 116 | D | D | | | |
| 117 | C | D | | | |
| 118 | D | D | | >500 | 124 |
| 119 | C | D | | | |
| 120 | C | D | | | |
| 121 | D | C | | | |
| 122 | D | D | C | | |
| 123 | D | D | B | | |
| 124 | C | B | | | |
| 125 | D | D | C | 322 | 75 |
| 126 | C | D | | >500 | >500 |
| 127 | D | C | | >500 | >500 |
| 128 | C | C | | >500 | >500 |
| 129 | C | B | | >500 | >500 |
| 130 | C | | B | >500 | >500 |
| 131 | C | | | | |
| 132 | C | | | | |
| 133 | B | B | | | |

| | | | DNMT1 data table: | | |
|---|---|---|---|---|---|
| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
| 134 | C | B | | | |
| 135 | C | B | | | |
| 136 | D | D | | >500 | 379 |
| 137 | D | C | | | |
| 138 | D | D | | | 167 |
| 139 | D | C | | | |
| 140 | D | D | | | |
| 141 | D | D | | | |
| 142 | D | C | | | |
| 143 | D | D | | | |
| 144 | D | D | | | |
| 145 | D | D | D | | |
| 146 | D | C | | | |
| 147 | C | C | | | |
| 148 | D | D | | | |
| 149 | D | D | | | |
| 150 | B | A | | | |
| 151 | B | A | | | |
| 152 | B | B | | | |
| 153 | D | C | | | |
| 154 | B | B | | | |
| 155 | B | A | | | |
| 156 | D | C | | | |
| 157 | B | B | | | |
| 158 | C | D | | | |
| 159 | B | C | | | |
| 160 | B | B | | | |
| 161 | C | B | | | |
| 162 | B | B | | | |
| 163 | B | A | | | |
| 164 | C | C | B | | |
| 165 | C | A | | | |
| 166 | C | D | | | |
| 167 | D | D | | | |
| 168 | D | C | | | |
| 170 | D | B | | | |
| 171 | C | A | | | |
| 172 | B | D | | | |
| 173 | C | C | | | |
| 174 | C | C | | | |
| 175 | C | A | | | |
| 176 | C | C | | | |
| 177 | C | B | | | |
| 178 | D | B | | | |
| 181 | C | B | | | |
| 182 | C | C | | | |
| 183 | C | B | | | |
| 184 | C | C | | | |
| 185 | C | C | | | |
| 186 | D | B | | | |
| 187 | C | B | | | |
| 188 | C | B | | | |
| 189 | C | C | | | |
| 190 | C | B | | | |
| 191 | D | C | | | |
| 192 | D | B | | | |
| 193 | D | C | | | |
| 194 | C | D | | | |
| 195 | C | C | | | |
| 196 | D | D | | | |
| 197 | C | C | | | |
| 198 | D | C | | | |
| 199 | D | A | | | |
| 200 | C | B | | | |
| 201 | C | C | | | |
| 202 | C | C | | | |
| 203 | C | A | | | |
| 204 | C | B | | | |
| 205 | D | D | | | |
| 206 | C | A | | | |
| 207 | C | D | | | |

-continued

| | | | DNMT1 data table: | | |
|---|---|---|---|---|---|
| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
| 208 | C | C | | | |
| 209 | C | C | | | |
| 210 | D | D | | | |
| 211 | C | D | | | |
| 212 | C | B | | | |
| 213 | C | B | | | |
| 214 | B | A | | | |
| 215 | D | D | | | |
| 216 | B | D | | | |
| 217 | C | B | | | |
| 218 | C | D | | | |
| 219 | C | B | | | |
| 220 | C | D | | | |
| 221 | C | D | | | |
| 222 | B | C | | | |
| 223 | C | B | | | |
| 224 | C | C | | | |
| 225 | B | C | | | |
| 228 | B | C | | | |
| 230 | C | B | | | |
| 231 | C | C | | | |
| 232 | C | C | | | |
| 233 | C | D | | | |
| 234 | C | B | | | |
| 235 | C | C | | | |
| 236 | D | A | | | |
| 237 | C | B | | | |
| 238 | D | B | | | |
| 239 | B | A | | | |
| 240 | C | B | | | |
| 241 | C | B | | | |
| 242 | D | D | | | |
| 243 | D | C | | | |
| 244 | C | D | | | |
| 245 | C | C | | | |
| 246 | C | A | | | |
| 247 | B | C | | | |
| 248 | C | A | | | |
| 249 | B | A | | | |
| 250 | C | B | | | |
| 251 | B | B | | | |
| 252 | D | D | | | |
| 254 | D | C | | | |
| 255 | B | C | | | |
| 256 | C | B | | | |
| 258 | C | B | | | |
| 259 | D | C | | | |
| 260 | C | B | | | |
| 261 | C | B | | | |
| 262 | D | B | | | |
| 263 | C | C | | | |
| 264 | B | A | | | |
| 266 | B | C | | | |
| 267 | B | B | | | |
| 268 | B | B | | | |
| 269 | B | B | | | |
| 270 | D | B | | | |
| 272 | B | A | | | |
| 273 | C | B | | | |
| 274 | D | D | | | |
| 275 | C | C | | | |
| 276 | C | A | | | |
| 277 | D | B | | | |
| 278 | D | B | | | |
| 279 | C | A | | | |
| 281 | D | C | | | |
| 282 | D | B | | | |
| 283 | C | B | | | |
| 284 | C | A | | | |
| 285 | C | B | | | |
| 286 | D | B | | | |

-continued

| | | | MV4-11 | | |
|---|---|---|---|---|---|
| | DNMT1 | | Anti- | DNMT3A | DNMT3B |
| | BioChemical | EPC ELISA | proliferative | Breaklight | Breaklight |
| | (pIC$_{50}$ | (pEC$_{50}$ | activity (EC$_{50}$ | IC$_{50}$ | IC$_{50}$ |
| Example# | category) | category) | category) | (micromolar) | (micromolar) |
| 287 | C | B | | | |
| 288 | D | B | | | |
| 289 | C | B | | | |
| 290 | C | B | | | |
| 291 | C | B | | | |
| 292 | C | B | | | |
| 293 | C | A | | | |
| 294 | C | A | | | |
| 295 | C | A | | | |
| 296 | C | A | | | |
| 297 | C | A | | | |
| 298 | D | D | | | |
| 299 | D | C | | | |
| 300 | C | B | | | |
| 301 | D | C | | | |
| 302 | C | A | | | |
| 303 | C | C | | | |
| 304 | C | | | | |
| 305 | D | C | | | |
| 308 | D | C | | | |
| 310 | B | D | | | |
| 318 | D | D | C | | |
| 319 | B | C | | | |
| 320 | B | C | | | |
| 321 | D | D | | | |
| 322 | D | C | | | |
| 324 | C | A | | | |
| 328 | B | C | | | |
| 329 | C | B | | | |
| 330 | D | B | | | |
| 331 | C | A | | | |
| 332 | B | C | | | |
| 333 | D | B | | | |
| 335 | C | A | | | |
| 336 | C | B | | | |
| 337 | C | A | | | |
| 338 | C | A | | | |
| 339 | D | B | | | |
| 340 | D | B | | | |
| 341 | D | D | | | |
| 342 | C | A | | | |
| 343 | D | C | | | |
| 344 | C | B | | | |
| 345 | D | B | | | |
| 346 | C | A | | | |
| 347 | C | B | | | |
| 348 | C | A | | | |
| 349 | C | B | | | |
| 350 | C | A | | | |
| 351 | C | A | | | |
| 352 | C | B | | | |
| 354 | C | B | | | |
| 355 | D | D | | | |
| 356 | D | C | | | |
| 357 | C | A | | | |
| 358 | D | A | | | |
| 359 | C | B | | | |
| 360 | C | B | | | |
| 361 | C | B | | | |
| 362 | C | A | | | |
| 363 | C | B | | | |
| 364 | D | D | | | |
| 365 | C | B | | | |
| 366 | D | D | | | |
| 367 | C | B | | | |
| 368 | D | A | | | |
| 369 | D | B | | | |
| 370 | C | B | | | |
| 371 | C | B | | | |
| 372 | D | C | | | |
| 373 | D | C | | | |

-continued

| | DNMT1 data table: | | | | |
|---|---|---|---|---|---|
| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
| 374 | D | C | | | |
| 375 | D | B | | | |
| 376 | C | C | | | |
| 377 | B | A | | | |
| 378 | C | B | | | |
| 379 | C | C | | | |
| 380 | C | B | | | |
| 381 | C | B | | | |
| 382 | D | D | | | |
| 383 | D | C | | | |
| 384 | C | A | | | |
| 385 | C | A | | | |
| 386 | C | B | | | |
| 387 | D | B | | | |
| 388 | C | B | | | |
| 390 | C | C | | | |
| 391 | D | B | | | |
| 392 | D | C | | | |
| 393 | D | C | | | |
| 396 | C | B | | | |
| 397 | C | B | | | |
| 398 | D | B | | | |
| 399 | D | B | | | |
| 400 | D | B | | | |
| 401 | D | B | | | |
| 402 | D | B | | | |
| 403 | C | C | | | |
| 404 | D | C | | | |
| 405 | D | D | | | |
| 406 | D | D | | | |
| 407 | D | B | | | |
| 408 | D | D | | | |
| 409 | D | D | | | |
| 410 | D | C | | | |
| 411 | D | D | | | |
| 412 | D | D | | | |
| 413 | D | D | | | |
| 414 | C | B | | | |
| 415 | B | B | | | |
| 416 | B | B | | | |
| 417 | A | A | | | |
| 418 | B | A | | | |
| 419 | C | B | | | |
| 420 | C | B | | | |
| 421 | B | | | | |
| 422 | D | D | | | |
| 423 | D | C | | | |
| 424 | D | C | | | |
| 425 | D | C | | | |
| 426 | B | A | | | |
| 427 | D | C | | | |
| 428 | C | C | | | |
| 429 | C | C | | | |
| 430 | D | C | | | |
| 431 | D | D | | | |
| 432 | D | | | | |
| 441 | D | D | | | |
| 443 | D | D | | | |
| 444 | D | D | | | |
| 445 | D | D | | | |
| 446 | D | D | | | |
| 447 | D | D | | | |
| 448 | D | D | | | |
| 449 | D | D | | | |
| 450 | D | D | | | |
| 451 | D | D | | | |
| 452 | D | D | | | |
| 453 | D | D | | | |
| 454 | D | D | | | |
| 455 | D | D | | | |
| 456 | D | D | | | |

-continued

| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
|---|---|---|---|---|---|
| 457 | D | D | | | |
| 458 | D | D | | | |
| 459 | D | D | | | |
| 460 | D | D | | | |
| 461 | D | D | | | |
| 462 | D | D | | | |
| 463 | D | D | | | |
| 464 | D | D | | | |
| 465 | D | D | | | |
| 466 | D | D | | | |
| 467 | D | D | | | |
| 468 | D | D | | | |
| 469 | D | D | | | |
| 470 | D | D | | | |
| 471 | D | D | | | |
| 472 | D | | | | |
| 473 | D | | | | |
| 474 | D | D | | | |
| 475 | D | D | | | |
| 476 | D | D | | | |
| 477 | D | D | | | |
| 478 | D | D | | | |
| 479 | D | D | | | |
| 480 | D | C | | | |
| 481 | D | D | | | |
| 482 | D | D | | | |
| 483 | D | D | | | |
| 484 | D | D | | | |
| 485 | D | D | | | |
| 486 | D | D | | | |
| 487 | D | D | | | |
| 488 | D | D | | | |
| 489 | D | D | | | |
| 490 | D | C | | | |
| 491 | D | D | | | |
| 492 | D | D | | | |
| 493 | D | C | | | |
| 494 | D | D | | | |
| 495 | D | B | | | |
| 496 | C | D | | | |
| 497 | D | B | | | |
| 498 | D | C | | | |
| 499 | D | D | | | |
| 500 | D | B | | | |
| 501 | D | | | | |
| 502 | D | | | | |
| 503 | D | C | | | |
| 504 | D | B | | | |
| 505 | D | D | | | |
| 506 | D | D | | | |
| 507 | D | D | | | |
| 508 | D | D | | | |
| 509 | D | D | | | |
| 510 | D | D | | | |
| 511 | D | D | | | |
| 512 | D | D | | | |
| 513 | D | D | | | |
| 514 | D | | | | |
| 515 | D | D | | | |
| 516 | D | D | | | |
| 517 | D | D | | | |
| 518 | D | D | | | |
| 519 | D | D | | | |
| 520 | D | D | | | |
| 521 | D | D | | | |
| 522 | D | D | | | |
| 523 | D | D | | | |
| 524 | D | D | | | |
| 525 | D | D | | | |
| 526 | D | D | | | |
| 527 | D | D | | | |

-continued

| | DNMT1 data table: | | | | |
|---|---|---|---|---|---|
| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
| 528 | D | D | | | |
| 529 | D | C | | | |
| 530 | D | B | | | |
| 531 | B | D | | | |
| 532 | D | D | | | |
| 533 | D | D | | | |
| 534 | D | D | | | |
| 535 | D | C | | | |
| 536 | D | C | | | |
| 537 | D | C | | | |
| 538 | D | D | | | |
| 539 | D | B | | | |
| 540 | B | D | | | |
| 541 | D | D | | | |
| 542 | D | C | | | |
| 543 | D | A | | | |
| 544 | D | B | | | |
| 545 | D | D | | | |
| 546 | C | D | | | |
| 547 | D | D | | | |
| 548 | D | D | | | |
| 549 | D | D | | | |
| 550 | D | D | | | |
| 551 | D | D | | | |
| 552 | D | D | | | |
| 553 | D | | | | |
| 554 | D | D | | | |
| 555 | D | D | | | |
| 556 | D | D | | | |
| 557 | D | D | | | |
| 558 | D | D | | | |
| 559 | D | D | | | |
| 560 | D | D | | | |
| 561 | D | D | | | |
| 562 | D | D | | | |
| 563 | D | D | | | |
| 564 | D | D | | | |
| 565 | D | D | | | |
| 566 | D | D | | | |
| 567 | D | D | | | |
| 568 | D | D | | | |
| 569 | D | D | | | |
| 570 | D | D | | | |
| 571 | D | D | | | |
| 572 | D | D | | | |
| 573 | D | D | | | |
| 574 | D | D | | | |
| 575 | D | D | | | |
| 576 | D | D | | | |
| 577 | D | D | | | |
| 578 | D | D | | | |
| 579 | D | D | | | |
| 580 | D | D | | | |
| 581 | D | D | | | |
| 582 | D | D | | | |
| 583 | D | D | | | |
| 584 | D | D | | | |
| 585 | D | D | | | |
| 586 | D | D | | | |
| 587 | D | D | | | |
| 588 | D | D | | | |
| 589 | D | C | | | |
| 590 | D | B | | | |
| 591 | D | D | | | |
| 592 | D | D | | | |
| 593 | D | D | | | |
| 594 | D | D | | | |
| 595 | D | D | | | |
| 596 | D | C | | | |
| 597 | D | D | | | |
| 598 | D | B | | | |

-continued

DNMT1 data table:

| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
|---|---|---|---|---|---|
| 599 | D | B | | | |
| 600 | D | A | | | |
| 601 | D | A | | | |
| 602 | C | D | | | |
| 603 | D | A | | | |
| 604 | D | A | | | |
| 605 | C | D | | | |
| 606 | D | D | | | |
| 607 | D | D | | | |
| 608 | D | D | | | |
| 609 | D | D | | | |
| 610 | D | B | | | |
| 611 | D | B | | | |
| 612 | D | D | | | |
| 613 | D | D | | | |
| 614 | D | B | | | |
| 615 | D | D | | | |
| 616 | D | D | | | |
| 617 | B | D | | | |
| 618 | D | D | | | |
| 619 | D | B | | | |
| 620 | D | D | | | |
| 621 | D | D | | | |
| 622 | D | D | | | |
| 623 | D | D | | | |
| 624 | D | B | | | |
| 625 | D | D | | | |
| 626 | D | D | | | |
| 627 | D | D | | | |
| 628 | D | D | | | |
| 629 | D | B | | | |
| 630 | D | D | | | |
| 631 | D | D | | | |
| 632 | D | B | | | |
| 633 | D | D | | | |
| 634 | D | B | | | |
| 635 | D | C | | | |
| 636 | D | D | | | |
| 637 | D | B | | | |
| 638 | D | C | | | |
| 639 | D | B | | | |
| 640 | D | D | | | |
| 641 | D | B | | | |
| 642 | D | B | | | |
| 643 | D | D | | | |
| 644 | D | B | | | |
| 645 | D | C | | | |
| 646 | D | D | | | |
| 647 | D | C | | | |
| 648 | D | D | | | |
| 649 | D | B | | | |
| 650 | D | B | | | |
| 651 | D | D | | | |
| 652 | D | D | | | |
| 653 | D | B | | | |
| 654 | D | B | | | |
| 655 | D | C | | | |
| 656 | D | B | | | |
| 657 | D | B | | | |
| 658 | D | B | | | |
| 659 | D | D | | | |
| 660 | D | B | | | |
| 661 | D | B | | | |
| 662 | D | D | | | |
| 663 | D | D | | | |
| 664 | D | B | | | |
| 665 | D | D | | | |
| 666 | D | B | | | |
| 667 | D | B | | | |
| 668 | D | C | | | |
| 669 | D | D | | | |

-continued

DNMT1 data table:

| Example# | DNMT1 BioChemical (pIC$_{50}$ category) | EPC ELISA (pEC$_{50}$ category) | MV4-11 Anti-proliferative activity (EC$_{50}$ category) | DNMT3A Breaklight IC$_{50}$ (micromolar) | DNMT3B Breaklight IC$_{50}$ (micromolar) |
|---|---|---|---|---|---|
| 670 | D | D | | | |
| 671 | D | D | | | |
| 672 | D | | | | |
| 673 | D | D | | | |
| 674 | D | B | | | |
| 675 | D | C | | | |
| 676 | D | B | | | |
| 677 | D | C | | | |
| 678 | D | | | | |
| 679 | D | C | | | |
| 680 | D | B | | | |
| 681 | D | B | | | |
| 682 | D | B | | | |
| 683 | D | D | | | |
| 684 | D | D | | | |
| 685 | D | C | | | |
| 686 | D | B | | | |
| 687 | D | C | | | |
| 688 | D | B | | | |
| 689 | D | B | | | |
| 690 | D | B | | | |
| 691 | D | B | | | |
| 692 | D | D | | | |
| 693 | D | D | | | |
| 694 | D | B | | | |
| 695 | D | B | | | |
| 696 | D | | | | |
| 697 | D | D | | | |
| 698 | D | D | | | |
| 699 | C | B | | | |

Binning category (pXC$_{50}$):
Category A: <4.5
Category B: 4.5 ≤ x < 6.0
Category C: 6.0 ≤ x < 6.5
Category D: ≥6.5

Comments
1. The compounds show the indicated binned activity in either the breaklight or the spa assay described above.
2. Where a field is empty, the compound was not tested in that assay.

The compounds of Examples 1 to 67 were tested generally according to the above DNMT1 breaklight assay and in repeated experimental runs exhibited an average IC50mcM value from 0.12 to 4.78 against DNMT1.

The compounds of Examples 5, 12, 20, 25, 28, 37, 40, 43, 56 and 61 were tested generally according to the above DNMT1 breaklight assay and in repeated experimental runs exhibited an average IC50mcM value to 0.50.

The compounds of Examples 10, 13, 26, 30, 32, 33, 34, 49, 55 and 59 were tested generally according to the above DNMT1 breaklight assay and in repeated experimental runs exhibited an average IC50mcM value >0.50 and <0.75.

The compounds of Examples 8, 9, 21, 22, 35, 36, 38, 41, 58 and 63 were tested generally according to the above DNMT1 breaklight assay and in repeated experimental runs exhibited an average IC50mcM value >0.75.

The compounds of Examples 68 to 149 were tested generally according to the above DNMT1 breaklight assay and/or SPA assay and in repeated experimental runs exhibited an average pIC50 value from 4.8 to 7.3 against DNMT1.

The compounds of Examples 69, 72, 74, 78, 81, 92, 102, 103, 108, 109, 129, 133, 216, 247, 266, 279, 310, 377, 531, 540, and 617 were tested generally according to the above DNMT1 breaklight assay and/or SPA assay and in repeated experimental runs exhibited an average pIC50 value to 6.0.

The compounds of Examples 70, 82, 85, 99, 110, 117, 119, 120, 126, 130, 131, 132, 165, 237, 283, 286, 303, 324, 379, 496, 546, 602, 683, and 685 were tested generally according to the above DNMT1 breaklight assay and/or SPA assay and in repeated experimental runs exhibited an average pIC50 value >6.0 and ≤6.5.

The compounds of Examples 76, 77, 80, 83, 86, 115, 121, 122, 125, 136, 137, 138, 143, 148, 149, 168, 409, 425, 477, 523, 562, 592, 626, and 649 were tested generally according to the above DNMT1 breaklight assay and/or SPA assay and in repeated experimental runs exhibited an average pIC50 value >6.5.

The compound of Example 15 was tested generally according to the above DNMT1 breaklight assay and in repeated experimental runs exhibited an average IC50mcM value of 0.44.

The compound of Example 11 was tested generally according to the above DNMT1 breaklight assay and in repeated experimental runs exhibited an average IC50mcM value of 0.58.

The compound of Example 48 was tested generally according to the above DNMT1 breaklight assay and in repeated experimental runs exhibited an average IC50mcM value of 0.89.

The compound of Example 72 was tested generally according to the above DNMT1 breaklight assay and/or SPA assay and in repeated experimental runs exhibited an average pIC50 value of 5.7.

The compound of Example 79 was tested generally according to the above DNMT1 breaklight assay and/or SPA assay and in repeated experimental runs exhibited an average pIC50 value of 6.5.

The compound of Example 86 was tested generally according to the above DNMT1 breaklight assay and/or SPA assay and in repeated experimental runs exhibited an average pIC50 value of 6.7.

The compound of Example 115 was tested generally according to the above DNMT1 breaklight assay and/or SPA assay and in repeated experimental runs exhibited an average pIC50 value of 6.7.

The compound of Example 119 was tested generally according to the above DNMT1 breaklight assay and/or SPA assay and in repeated experimental runs exhibited an average pIC50 value of 6.4.

The compound of Example 138 was tested generally according to the above DNMT1 breaklight assay and/or SPA assay and in repeated experimental runs exhibited an average pIC50 value of 7.0.

The compound of Example 337 was tested generally according to the above DNMT1 breaklight assay and/or SPA assay and in repeated experimental runs exhibited an average pIC50 value of 5.5.

The compound of Example 540 was tested generally according to the above DNMT1 breaklight assay and/or SPA assay and in repeated experimental runs exhibited an average pIC50 value of 5.5.

The compound of Example 617 was tested generally according to the above DNMT1 breaklight assay and/or SPA assay and in repeated experimental runs exhibited an average pIC50 value of 5.6.

The compound of Example 266 was tested generally according to the above DNMT1 breaklight assay and/or SPA assay and in repeated experimental runs exhibited an average pIC50 value of 5.7.

The compound of Example 310 was tested generally according to the above DNMT1 breaklight assay and/or SPA assay and in repeated experimental runs exhibited an average pIC50 value of 5.7.

The compound of Example 216 was tested generally according to the above DNMT1 breaklight assay and/or SPA assay and in repeated experimental runs exhibited an average pIC50 value of 5.8.

The compound of Example 247 was tested generally according to the above DNMT1 breaklight assay and/or SPA assay and in repeated experimental runs exhibited an average pIC50 value of 5.8.

The compound of Example 531 was tested generally according to the above DNMT1 breaklight assay and/or SPA assay and in repeated experimental runs exhibited an average pIC50 value of 5.8.

The compound of Example 279 was tested generally according to the above DNMT1 breaklight assay and/or SPA assay and in repeated experimental runs exhibited an average pIC50 value of 6.

The compound of Example 379 was tested generally according to the above DNMT1 breaklight assay and/or SPA assay and in repeated experimental runs exhibited an average pIC50 value of 6.1.

The compound of Example 165 was tested generally according to the above DNMT1 breaklight assay and/or SPA assay and in repeated experimental runs exhibited an average pIC50 value of 6.2.

The compound of Example 283 was tested generally according to the above DNMT1 breaklight assay and/or SPA assay and in repeated experimental runs exhibited an average pIC50 value of 6.2.

The compound of Example 303 was tested generally according to the above DNMT1 breaklight assay and/or SPA assay and in repeated experimental runs exhibited an average pIC50 value of 6.2.

The compound of Example 324 was tested generally according to the above DNMT1 breaklight assay and/or SPA assay and in repeated experimental runs exhibited an average pIC50 value of 6.2.

The compound of Example 602 was tested generally according to the above DNMT1 breaklight assay and/or SPA assay and in repeated experimental runs exhibited an average pIC50 value of 6.3.

The compound of Example 237 was tested generally according to the above DNMT1 breaklight assay and/or SPA assay and in repeated experimental runs exhibited an average pIC50 value of 6.4.

The compound of Example 496 was tested generally according to the above DNMT1 breaklight assay and/or SPA assay and in repeated experimental runs exhibited an average pIC50 value of 6.4.

The compound of Example 546 was tested generally according to the above DNMT1 breaklight assay and/or SPA assay and in repeated experimental runs exhibited an average pIC50 value of 6.4.

The compound of Example 286 was tested generally according to the above DNMT1 breaklight assay and/or SPA assay and in repeated experimental runs exhibited an average pIC50 value of 6.5.

The compound of Example 683 was tested generally according to the above DNMT1 breaklight assay and/or SPA assay and in repeated experimental runs exhibited an average pIC50 value of 6.5.

The compound of Example 685 was tested generally according to the above DNMT1 breaklight assay and/or SPA assay and in repeated experimental runs exhibited an average pIC50 value of 6.5.

The compound of Example 626 was tested generally according to the above DNMT1 breaklight assay and/or SPA assay and in repeated experimental runs exhibited an average pIC50 value of 6.7.

The compound of Example 168 was tested generally according to the above DNMT1 breaklight assay and/or SPA assay and in repeated experimental runs exhibited an average pIC50 value of 6.7.

The compound of Example 409 was tested generally according to the above DNMT1 breaklight assay and/or SPA assay and in repeated experimental runs exhibited an average pIC50 value of 6.8.

The compound of Example 592 was tested generally according to the above DNMT1 breaklight assay and/or SPA assay and in repeated experimental runs exhibited an average pIC50 value of 6.8.

The compound of Example 425 was tested generally according to the above DNMT1 breaklight assay and/or SPA assay and in repeated experimental runs exhibited an average pIC50 value of 6.8.

The compound of Example 649 was tested generally according to the above DNMT1 breaklight assay and/or SPA assay and in repeated experimental runs exhibited an average pIC50 value of 6.9.

The compound of Example 477 was tested generally according to the above DNMT1 breaklight assay and/or SPA assay and in repeated experimental runs exhibited an average pIC50 value of 7.

The compound of Example 523 was tested generally according to the above DNMT1 breaklight assay and/or SPA assay and in repeated experimental runs exhibited an average pIC50 value of 7.1.

The compound of Example 562 was tested generally according to the above DNMT1 breaklight assay and/or SPA assay and in repeated experimental runs exhibited an average pIC50 value of 7.1.

The compounds of Examples 3, 6, 7, 8, 9, 35, 41, 47, 52 and 56 were tested generally according to the above DNMT3A and DNMT3B breaklight assays and in repeated experimental runs exhibited an average IC50mcM value greater than 500 mcM.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound according to Formula (IVbbr):

(IVbbr)

[Chemical structure showing a pyridine with substituents $R^{41bbr}$, $X^{41bbr}$, $X^{42bbr}$, $R^{43bbr}$, $R^{44bbr}$, $R^{45bbr}$, $Y^{4bbr}$, and $NH_2$ group connected via C(=O)]

wherein:
$X^{41bbr}$ and $X^{42bbr}$ are independently selected from: —CN, methyl, fluoro, chloro, bromo and iodo;
$Y^{4bbr}$ is selected from: S and NH;
$R^{41bbr}$ is selected from:
$C_{1-6}$alkyl,
$C_{1-6}$alkyl substituted with from 1 to 9 substituents independently selected from: fluoro, chloro, bromo, iodo, oxo, $C_{1-4}$alkyloxy, —OH, —COOH, —NH$_2$ —N(H)$C_{1-4}$alkyl, —N($C_{1-4}$alkyl)$_2$ and —CN,
$C_{1-4}$alkyloxy,
$C_{1-4}$alkyloxy substituted from 1 to 4 times by fluoro,
—N(H)$C_{1-4}$alkyl,
—N($C_{1-4}$alkyl)$_2$,
S$C_{1-4}$alkyl,
aryl,
aryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and CN,
$C_{1-4}$alkoxy,
—CN,
oxo,
—OH,
—NO$_2$, and
—NH$_2$,
heteroaryl,
heteroaryl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN,
$C_{1-4}$alkoxy,
—CN,
oxo,
—OH,
—NO$_2$, and
—NH$_2$,
cycloalkyl,
cycloalkyl substituted with from 1 to 4 substituents independently selected from:
fluoro,
chloro,
bromo,
iodo,
$C_{1-6}$alkyl,
$C_{1-6}$alkyl substituted with from 1 to 9 substituents independently selected from: fluoro, chloro, bromo, iodo, oxo, —OH, —NH$_2$ and —CN,
$C_{1-4}$alkoxy,
—CN,
oxo,
—OH,
—NO$_2$, and
—NH$_2$;
$R^{43bbr}$ is selected from:
$C_{1-4}$alkyl,
phenyl,
phenyl substituted with 1 or 2 substituents independently selected from: fluoro, —CH$_3$, —CF$_3$, chloro, —C(O)phenyl, pyrrolidinyl, —P(O)(CH$_3$)$_2$, —C(O)NH$_2$, —S(O)$_2$NHCH$_3$, —OCH$_2$CH$_2$N(CH$_3$)$_2$ and —CH$_2$C(O)NH$_2$,
thienyl,
piperidinyl,
pyridine, and
pyridine substituted with 1 or 2 substituents independently selected from: fluoro, —CH$_3$, —CF$_3$, and —OCH$_3$;
$R^{44bbr}$ and $R^{45bbr}$ are independently selected from:
hydrogen,
$C_{1-6}$alkyl,
$C_{1-6}$alkyl substituted with from 1 to 9 substituents independently selected from: phenyl, morpholino, triazolyl, imidazolyl, pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)C(CH$_3$)$_2$CH$_2$OH, —NHCH$_2$CH$_3$, —NHCH$_2$CH$_2$OCH$_3$, —N(CH$_3$)

CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
   where said phenyl, morpholino, triazolyl, imidazolyl, azepinyl, azetidinyl, pyrrolidinyl, piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cycloalkyl,
cycloalkyl substituted with from one to five substituents independently selected from:
   fluoro,
   chloro,
   —OH,
   C$_{1-6}$alkyl, and
   C$_{1-6}$alkyl substituted with from 1 to 9 substituents independently selected from: fluoro and chloro;
heterocycloalkyl, and
heterocycloalkyl substituted with from 1 to 5 substituents independently selected from:
   fluoro,
   chloro,
   bromo,
   iodo,
   C$_{1-6}$alkyl,
   C$_{1-6}$alkyl substituted with from 1 to 9 substituents independently selected from: fluoro, chloro, bromo, iodo, oxo, —OH, —NH$_2$ and —CN,
   aryl,
   C$_{1-4}$alkoxy,
   C$_{1-4}$alkoxy substituted with from 1 to 4 substituents independently selected from: fluoro, oxo, —OH, —COOH, —NH$_2$, and —CN,
   —CN,
   oxo,
   —OH,
   —COOH,
   —NO$_2$,
   —NH$_2$, and
   SO$_2$NH$_2$, or
R$^{44bbr}$ and R$^{45bbr}$ are taken together with the nitrogen to which they are
attached, and optionally from 1 to 3 additional heteroatoms independently
selected from O, N, and S, to form a heterocycloalkyl, which is optionally
substituted with from 1 to 5 substituents independently selected from:
   fluoro,
   chloro,
   bromo,
   iodo,
   C$_{1-6}$alkyl,
   C$_{1-6}$alkyl substituted with from 1 to 9 substituents independently selected from: fluoro, chloro, C$_{1-4}$alkoxy, oxo, phenyl, cycloalkyl, heterocycloalkyl, methylheterocycloalkyl-, —OH, —NH$_2$, —N(H)C$_{1-5}$alkyl, aminoheterocycloalkyl-, —N(C$_{1-5}$alkyl)$_2$, —CN, —N(C$_{1-4}$alkyl)(CH$_2$OCH$_3$), and —NHC$_{1-4}$alkyl substituted by one or two substituents independently selected from oxo, NH$_2$, and —OH,
   aryl,
   cycloalkyl,
   heterocycloalkyl,
   heterocycloalkyl substituted with from 1 to 9 substituents independently selected from: C$_{1-6}$alkyl, —C$_{1-6}$alkylOH, fluoro, —C$_{1-6}$alkylNH$_2$, chloro, bromo, iodo, oxo, —OH, —NH$_2$ and —CN,
   C$_{1-4}$alkoxy,
   C$_{1-4}$alkoxy substituted with from 1 to 4 substituents independently selected from: fluoro, oxo, —OH, —COOH, —NH$_2$, and —CN,
   —CN,
   oxo,
   —OH,
   —OP(O)(OH)$_2$,
   —COOH,
   —CONH$_2$,
   —NO$_2$,
   —NH$_2$,
   —N(H)C$_{1-5}$alkyl,
   —N(H)C$_{1-6}$alkyl substituted with from 1 to 9 substituents independently selected from: fluoro, chloro, bromo, iodo, C$_{1-4}$alkoxy, oxo, phenyl, cycloalkyl, aminoC$_{1-4}$alkoxy, heterocycloalkyl, methylheterocycloalkyl-, —OH, —NH$_2$, —N(H)C$_{1-4}$alkyl, —N(C$_{1-4}$alkyl)$_2$, and —CN,
   —Ooxetanyl,
   —ONHC(NH)NH$_2$,
   —NHcyclopropyl,
   —NHoxetanyl,
   —N(C$_{1-5}$alkyl)$_2$,
   —S(O)$_2$CH$_2$CH$_3$,
   S(O)$_2$CH$_2$CH$_2$CH$_3$,
   —S(O)$_2$CH$_3$,
   —SO$_2$NH$_2$,
   —S(O)$_2$phenyl,
   benzoyl,
   benzylamino,
   -propylpyrrolidinyl,
   -methylcyclopropyl,
   cyclobutylamino,
   cyclobutyl-N(CH$_3$)—,
   piperidinyl,
   imidazolyl,
   morpholinyl,
   morpholinylmethyl,
   methylpiperazinylmethyl,
   methylpiperazinyl,
   pyrrolidinyl,
   pyrrolidinylmethyl,
   (methoxypyridinylmethyl)amino,
   methylpyrrolidinyl,
   difluoropyrrolidinyl,
   dimethylpyrrolidinyl,
   (methylcyclopropylmethyl)amino,
   hydroxymethylpyrrolidinyl,
   fluoropyrrolidinyl,
   fluorophenylmethylamino,
   piperazinlymethyl,
   oxazolidinyl,
   (methyloxetanmethyl)amino, (methylcyclobutylmethyl)amino,
oxoimidazolidinyl, and
2-hydroxyethylpiperidinyl;
provided that:
$X^{41bbr}$ and $X^{42bbr}$ are not both hydrogen, and
$R^{44bbr}$ and $R^{45bbr}$ are not both hydrogen;
or a pharmaceutically acceptable salt or prodrug thereof.

2. A compound according to claim 1 represented by the following Formula (VIbbr):

(VIbbr)

wherein:
$R^{60bbr}$ is selected from:
$C_{1-3}$alkyl,
$C_{1-3}$alkyl substituted with from 1 to 6 substituents independently selected from: fluoro and chloro,
—N(H)$C_{1-3}$alkyl,
—N($C_{1-3}$alkyl)$_2$,
$SC_{1-4}$alkyl,
$C_{1-3}$alkyloxy,
aryl,
aryl substituted with from one to 3 substituents independently selected from:
fluoro,
chloro,
—OH, and
$C_{1-3}$alkyl,
heteroaryl,
heteroaryl substituted with from one to 3 substituents independently selected from:
fluoro,
chloro,
—OH, and
$C_{1-3}$alkyl,
cycloalkyl,
cycloalkyl substituted with from one to three substituents independently selected from:
fluoro,
chloro,
—OH, and
$C_{1-3}$alkyl;
$R^{61bbr}$ is selected from:
—$CH_3$,
phenyl,
phenyl substituted with 1 or 2 substituents independently selected from: fluoro, —$CH_3$, —$CF_3$, chloro, —C(O)phenyl, pyrrolidinyl, —C(O)$NH_2$, —S(O)$_2$NHCH$_3$, —OCH$_2$CH$_2$N(CH$_3$)$_2$ and —CH$_2$C(O)NH$_2$,
thienyl,
piperidinyl,
pyridine, and
pyridine substituted with 1 or 2 substituents independently selected from: fluoro, —$CH_3$, —$CF_3$, and —OCH$_3$;

$R^{63bbr}$ and $R^{64bbr}$ are independently selected from:
hydrogen,
$C_{1-4}$alkyl,
$C_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cycloalkyl,
cycloalkyl substituted with from 1 to 5 substituents independently selected from:
fluoro,
chloro,
—OH, and
$C_{1-6}$alkyl,
heterocycloalkyl, and
heterocycloalkyl substituted with from 1 to 5 substituents independently selected from:
fluoro,
chloro,
—OH, and
$C_{1-6}$alkyl, or
$R^{63bbr}$ and $R^{64bbr}$ are taken together with the nitrogen to which they are attached, and optionally from 1 to 3 additional heteroatoms
independently selected from O, N, and S, to form a heterocycloalkyl, to form a heterocycloalkyl, which is optionally substituted with from 1 to 5 substituents independently selected from:
fluoro,
chloro,
—OH,
—OP(O)(OH)$_2$,
—CN,
$C_{1-6}$alkyl,
$C_{1-6}$alkyl substituted with from 1 to 9 substituents independently selected from: fluoro, chloro, $C_{1-4}$alkoxy, oxo, phenyl, cycloalkyl, heterocycloalkyl, methylheterocycloalkyl, —OH, —NH$_2$, —N(H)$C_{1-5}$alkyl, aminoheterocycloalkyl, —N($C_{1-5}$alkyl)$_2$, —CN, —N($C_{1-4}$alkyl)(CH$_2$OCH$_3$), and —NHC$_{1-4}$alkyl substituted by one or two substituents independently selected from oxo, NH$_2$, and —OH, heterocycloalkyl,
heterocycloalkyl substituted with from 1 to 9 substituents independently selected from: $C_{1-6}$alkyl, —$C_{1-6}$alkylOH, fluoro, chloro, oxo and —OH,
$C_{1-4}$alkoxy,
$C_{1-4}$alkoxy substituted with from 1 to 4 substituents independently selected from: fluoro, oxo, —OH, —COOH, —NH$_2$, and —CN,
oxo,
—NH$_2$,
—N(H)$C_{1-6}$alkyl,
—N(H)$C_{1-6}$alkyl substituted with from 1 to 9 substituents independently selected from: fluoro, chloro, $C_{1-4}$alkoxy, oxo, phenyl, cycloalkyl, aminoC$_{1-4}$alkoxy, heterocycloalkyl, methylheterocycloalkyl, —OH, —NH$_2$, —N(H)C$_{1-4}$alkyl, —N(C$_{1-4}$alkyl)$_2$, and —CN,
—ONHC(NH)NH$_2$,
Ooxetanyl,
—ONHC(NH)NH$_2$,
—NHcyclopropyl,
—NHoxetanyl,
—N(C$_{1-4}$alkyl)$_2$,
—S(O)$_2$CH$_2$CH$_3$,
S(O)$_2$CH$_2$CH$_2$CH$_3$,
—S(O)$_2$CH$_3$,
—S(O)$_2$phenyl,
benzoyl,
benzylamino,
propylpyrrolidinyl,
-methylcyclopropyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
(methoxypyridinylmethyl)amino,
methylpyrrolidinyl,
difluoropyrrolidinyl,
dimethylpyrrolidinyl,
(methylcyclopropylmethyl)amino,
hydroxymethylpyrrolidinyl,
fluoropyrrolidinyl,
(fluorophenylmethyl)amino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;
provided that:
$R^{63bbr}$ and $R^{64bbr}$ are not both hydrogen;
or a pharmaceutically acceptable salt or prodrug thereof.

3. A compound according to claim 1 represented by the following Formula (Qb):

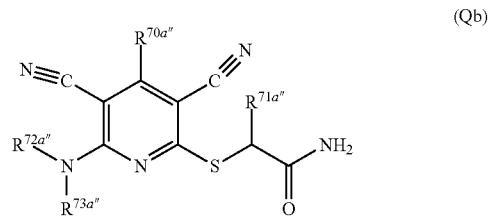

wherein:
$R^{70a''}$ is selected from:
ethyl,
—OCH$_3$,
—CH$_2$CF$_3$, and
cyclopropyl;
$R^{71a''}$ is selected from:
phenyl,
phenyl substituted with 1 or 2 substituents independently selected from: fluoro, —CH$_3$, —CF$_3$, and chloro,
pyridine, and
pyridine substituted with 1 or 2 substituents independently selected from: fluoro, —CH$_3$, —CF$_3$, and —OCH$_3$; and
$R^{72a''}$ and $R^{73a''}$ are independently selected from:
hydrogen,
$C_{1-4}$alkyl,
$C_{1-4}$alkyl substituted with from 1 to 4 substituents independently selected from: phenyl, morpholino, triazolyl, imidazolyl, —CH$_2$CH$_2$pyrrolidinyl, —OC(O)NH$_2$, —OCH$_2$CH$_2$NH$_2$, —ONHC(NH$_2$)NH$_2$, —NHCH$_2$C(CH$_3$)$_3$, —NOCH$_3$, —NHOH, —NHCH$_2$CH$_2$F, —N(CH$_3$)CH$_2$CH$_2$OCH$_3$, —N(CH$_2$CH$_3$)$_2$, —NCH(CH$_2$OH)$_2$, —N(CH$_2$CH$_2$OH)$_2$, —NHCH$_2$CH$_2$OH, —NHCH$_2$CH$_2$NH$_2$, —N(CH$_3$)CH$_2$(CH$_3$)$_2$CH$_2$OH, —NHCH$_2$CH$_3$, —NHCH$_2$CH$_2$OCH$_3$, —N(CH$_3$)CH$_2$CH$_2$OH, —NHC(O)C(O)NH$_2$, —N(CH$_3$)CH$_2$CH$_2$CH$_2$OH, —N(CH$_3$)CH$_2$CH(OH)CH$_2$OH, —N(CH$_3$)CH$_2$CH$_2$NH$_2$, oxo, —NHCH$_2$C(CH$_3$)$_2$CH$_2$OH, —OH, —NH$_2$, —NHCH$_3$, —NHCH$_2$CH$_2$CH$_2$OH, —N(CH$_3$)$_2$, —N(CH$_3$)CH$_2$CH$_3$, —NHOC(CH$_3$)$_2$NH$_2$, —N(CH$_3$)CH$_2$cyclopropyl, —NHCH$_2$cyclopropyl, —NHoxetanyl, —NCH$_2$CH$_2$triazole, piperazinyl, piperidinyl, pyrazolyl, azepinyl, azetidinyl, methoxy, and cyclopropylamino,
where said phenyl, morpholino, triazolyl, imidazolyl, azepinyl, azetidinyl, pyrrolidinyl piperazinyl, piperidinyl, oxetanyl, cyclopropyl, and pyrazolyl are optionally substituted with from 1 to 4 substituents independently selected from: methyl, fluoro, —NH$_2$, —N(CH$_3$)$_2$, hydroxymethyl, oxo, —OH, and —CH$_2$NH$_2$,
cyclobutyl,
aminocyclobutyl,
tetrahydrofuran,
5-oxa-2azaspiro[3.4]octan, and
8-azabicyclo[3.2.1]octan, or
$R^{72a''}$ and $R^{73a''}$ are taken together with the nitrogen to which they are attached, and optionally from 1 to 3 additional heteroatoms independently selected from O, N, and S, to form a heterocycloalkyl selected from:
pyrrolidinyl,
pyrrolo[3,4-c]pyrazolyl,
piperidinyl,
1,4diazepanyl,
piperazinyl,
6,7-dihydro-triazolo[4,5-c]pyridinyl,
2,9-diazaspiro [5.5] undecanyl,
2,8-diazaspiro[4.5]decanyl,
octahydro-1H-pyrrolo[1,2a][1,4]diazepinyl,
oxa-diazaspiro[4.5]decanyl,
oxazolyl,
morpholinyl,
1-oxa-6-azaspiro [3.4]octanyl,
2-oxa-6-azaspiro [3.4]octanyl,
1,7-diazaspiro[3.5]nonanyl,
2,7-diazaspiro[3.5]nonanyl,
2,6-diazaspiro[3.4]octanyl,
azetidinyl,
hexahydropyrrolo[3,4-b]oxazinyl,
dihydronaphthyridinyl,
diazabicycloheptanyl,
1,8-diazaspiro[4.5]decanyl, and
5-oxa-2-azaspiro[3.4]octanyl,
all of which are optionally substituted with from 1 to 5 substituents independently selected from:
fluoro,
chloro,
oxo,
—OH,
—OP(O)(OH)$_2$,
—CN,
—CH$_3$,
—CH$_2$OH,
methoxy,
—CH$_2$CH$_3$,
—C(O)CH$_3$,
—C(O)NH$_2$,
—OCH$_2$CH$_2$OH,
—OCH$_2$CH$_2$NH$_2$,
—ONHC(NH)NH$_2$,
—OC(O)NH$_2$,
—Ooxetanyl,
—CH$_2$CH$_2$OH,
—CH$_2$CH$_2$CH$_2$OH,
—CH$_2$CH$_2$CH$_3$,
—CH$_2$CH$_2$OCH$_3$,
—CH$_2$CH(OH)CH$_3$,
—CH$_2$CH(OH)CH$_2$OH,
—CH$_2$C(O)OCH$_3$,
—CH$_2$C(O)NH$_2$,
—C(O)CH(CH$_3$)$_2$,
—CH$_2$CH$_2$N(CH$_3$)$_2$,
—CH$_2$CH$_2$NHCH$_2$CH$_3$,
—CH$_2$CH$_2$CH$_2$N(CH$_3$)$_2$,
—CH$_2$CH$_2$NHCH$_2$C(CH$_3$)$_3$,
—CH$_2$CH$_2$N(CH$_3$)CH$_2$OCH$_3$,
—C(CH$_3$)$_2$CH$_2$OH,
—CH$_2$C(CH$_3$)$_{20}$H,
—CH$_2$C(CH$_3$)$_{20}$CH$_3$,
—C(O)CH$_2$OH,
—CH$_2$isothiazolyl,
—CH$_2$thiazolyl,
—CH$_2$pyrazolyl,
—CH$_2$imidazolyl,
—CH$_2$pyridinyl,
—CH$_2$oxazolyl,
—CH$_2$pyrrolyl,
—CH$_2$isoxazoly,
—CH$_2$furanyl,
—CH$_2$CH$_{2morpholinyl}$,
—CH$_2$CH$_2$pyrrolidinyl,
—CH$_2$CH$_2$pyrrolidinylCH$_3$,
—CH$_2$CH$_2$CH$_2$pyrrolidinyl,
—C(O)phenyl,
—C(O)C(tetrahydropyranyl)NH$_2$,
—NH$_2$,
—NHCH$_3$,
—N(CH$_3$)$_2$,
—NHC(O)CH$_3$,
—NHCH$_2$CHF$_2$,
—NHCH$_2$C(CH$_3$)$_3$,
—NHCH$_2$CH(CH$_3$)$_2$,
—NHCH$_2$CH$_2$OCH$_3$,
—NHCH$_2$CH$_2$OH,
—NHCH$_2$CH$_2$NH$_2$,
—NHCH$_2$C(O)OH,
—NHC(O)CH$_2$NH$_2$,
—NHC(O)CH$_2$CH$_2$CH$_2$NH$_2$,
—NHCH$_2$C(O)NH$_2$,
—NHCH$_2$C(OH)(CH$_3$)$_2$,
—NHC(O)CH(CH$_3$)NH$_2$,
—NHC(O)$_0$CH(CH$_3$)NH$_2$,
—NHC(O)CH(CH$_3$)$_2$,
—NHC(O)C(CH$_3$)$_2$NH$_2$,
—NHC(O)CH$_2$OH,
—NHC(O)CH(CH$_2$OH)NH$_2$,
—NHC(O)(oxetanyl)NH$_2$,
—NHC(O)OC(CH$_3$)$_3$,
—NHC(CH$_3$)$_2$C(O)OCH$_3$,
—NHcyclopropyl,
—NHoxetanyl,
—CH$_2$NH$_2$,
—CH$_2$CH$_2$NH$_2$,
—CH$_2$CH$_2$CH$_2$NH$_2$,
—CH$_2$NHCH$_2$C(CH$_3$)$_3$,
—CH$_2$NHC(O)C(CH$_3$)$_3$,
—CH$_2$NHC(O)CH$_2$NH$_2$,
—CH$_2$NHC(O)CH$_2$OH,
—CH$_2$N(CH$_3$)$_2$,
—CH$_2$NHCH$_3$,
—CH$_2$N(CH$_2$CH$_3$)$_2$,
—CH$_2$CH$_2$N(CH$_3$)$_2$,
—S(O)$_2$CH$_2$CH$_3$,
—S(O)$_2$CH$_2$CH$_2$CH$_3$,
—S(O)$_2$phenyl,
—S(O)$_2$CH$_3$,
benzoyl,
benzylamino,
-propylpyrrolidinyl,
-methylcyclopropyl,
cyclobutylamino,
cyclobutyl-N(CH$_3$)—,
piperidinyl,
imidazolyl,
morpholinyl,
morpholinylmethyl,
methylpiperazinylmethyl,
methylpiperazinyl,
pyrrolidinyl,
pyrrolidinylmethyl,
(methoxypyridinylmethyl)amino,
methylpyrrolidinyl, difluoropyrrolidinyl,
dimethylpyrrolidinyl,
(methylcyclopropylmethyl)amino,
hydroxymethylpyrrolidinyl,
fluoropyrrolidinyl,
(fluorophenylmethyl)amino,
piperazinylmethyl,
oxazolidinyl,
(methyloxetanylmethyl)amino,
(methylcyclobutylmethyl)amino,
oxoimidazolidinyl, and
2-hydroxyethylpiperidinyl;

provided that:
$R^{72a''}$ and $R^{73a''}$ are not both hydrogen;
or a pharmaceutically acceptable salt or prodrug thereof.

4. A compound of claim 1 selected from:
2-{[3,5-dicyano-6-(dimethylamino)-4-ethylpyridin-2-yl]sulfanyl}-2-phenylacetamide;
2-((3,5-dicyano-4-cyclopropyl-6-(1,4-diazepan-1-yl)pyridin-2-yl)thio)-2-phenylacetamide;
2-{[3,5-dicyano-4-cyclopropyl-6-(4-ethyl-1,4-diazepan-1-yl)pyridin-2-yl]sulfanyl}-2-phenylacetamide;
2-((3,5-dicyano-4-ethyl-6-(4-propyl-1,4-diazepan-1-yl)pyridin-2-yl)thio)-2-phenylacetamide;
2-{[3,5-dicyano-4-ethyl-6-(4-ethyl-1,4-diazepan-1-yl)pyridin-2-yl]sulfanyl}-2-phenylacetamide;
2-{[3,5-dicyano-4-ethyl-6-(5-oxo-1,4-diazepan-1-yl)pyridin-2-yl]sulfanyl}-2-phenylacetamide;
2-((3,5-dicyano-4-cyclopropyl-6-morpholinopyridin-2-yl)thio)-2-(pyridin-4-yl)acetamide;
2-{[3,5-dicyano-4-ethyl-6-(4-methyl-3-oxopiperazin-1-yl)pyridin-2-yl]sulfanyl}-2-(pyridin-4-yl)acetamide;
2-[(3,5-dicyano-4-ethyl-6-{methyl[2-(morpholin-4-yl)ethyl]amino}pyridin-2-yl)sulfanyl]-2-phenylacetamide;
2-{[3,5-dicyano-4-ethyl-6-(4-propylpiperazin-1-yl)pyridin-2-yl]sulfanyl}-2-phenylacetamide;
2-({3,5-dicyano-4-ethyl-6-[4-(piperidin-4-yl)piperazin-1-yl]pyridin-2-yl}sulfanyl)-2-phenylacetamide;
2-({3,5-dicyano-4-cyclopropyl-6-[3-(hydroxymethyl)piperazin-1-yl]pyridin-2-yl}sulfanyl)-2-phenylacetamide;
2-{[3,5-dicyano-4-cyclopropyl-6-(3-oxopiperazin-1-yl)pyridin-2-yl]sulfanyl}-2-phenylacetamide;
2-({3,5-dicyano-4-cyclopropyl-6-[4-(morpholin-4-yl)piperidin-1-yl]pyridin-2-yl}sulfanyl)-2-phenylacetamide;
2-((3,5-dicyano-4-ethyl-6-(2,8-diazaspiro[4.5]decan-8-yl)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((3,5-Dicyano-4-cyclopropyl-6-(3-methylpiperazin-1-yl)pyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
2-((3,5-Dicyano-4-cyclopropyl-6-(2,6-dimethylmorpholino)pyridin-2-yl)thio)-2-phenylacetamide;
2-((3,5-Dicyano-4-cyclopropyl-6-(3-(dimethylamino)piperidin-1-yl)pyridin-2-yl)thio)-2-phenylacetamide;
2-((6-(4-(Aminomethyl)-4-hydroxypiperidin-1-yl)-3,5-dicyano-4-cyclopropylpyridin-2-yl)thio)-2-phenylacetamide;
2-((3,5-dicyano-4-cyclopropyl-6-(3-(methylamino)piperidin-1-yl)pyridin-2-yl)thio)-2-phenylacetamide;
2-((6-(3-aminopiperidin-1-yl)-3,5-dicyano-4-cyclopropylpyridin-2-yl)thio)-2-phenylacetamide;
2-((3,5-dicyano-4-cyclopropyl-6-(dimethylamino)pyridin-2-yl)thio)-2-(pyridin-4-yl)acetamide;
2-((3,5-dicyano-6-(dimethylamino)-4-ethylpyridin-2-yl)thio)-2-(pyridin-4-yl)acetamide;
2-((6-(4-aminopiperidin-1-yl)-3,5-dicyano-4-cyclopropylpyridin-2-yl)thio)-2-phenylacetamide;
2-((3,5-dicyano-4-cyclopropyl-6-(4-(dimethylamino)piperidin-1-yl)pyridin-2-yl)thio)-2-phenylacetamide;
2-((3,5-dicyano-4-cyclopropyl-6-(piperazin-1-yl)pyridin-2-yl)thio)-2-(pyridin-4-yl)acetamide;
2-((3,5-dicyano-4-cyclopropyl-6-(1,4-diazepan-1-yl)pyridin-2-yl)thio)-2-(pyridin-4-yl)acetamide;
2-((3,5-dicyano-4-cyclopropyl-6-((R)-3-hydroxypiperidin-1-yl)pyridin-2-yl)thio)-2-phenylacetamide;
2-(3,5-dicyano-4-cyclopropyl-6-((S)-3-hydroxypiperidin-1-yl)pyridin-2-ylthio)-2-phenylacetamide;
2-((3,5-dicyano-4-cyclopropyl-6-((S)-3-hydroxypyrrolidin-1-yl)pyridin-2-yl)thio)-2-(pyridin-4-yl)acetamide;
2-((3,5-dicyano-4-ethyl-6-(4-ethylpiperazin-1-yl)pyridin-2-yl)thio)-2-phenylacetamide;
2-((3,5-Dicyano-4-ethyl-6-(1-oxa-6-azaspiro[3.4]octan-6-yl)pyridin-2-yl)thio)-2-phenylacetamide;
2-((6-(4-(3-aminopropyl)piperazin-1-yl)-3,5-dicyano-4-ethylpyridin-2-yl)thio)-2-phenylacetamide;
2-((3,5-Dicyano-4-ethyl-6-(1,7-diazaspiro[3.5]nonan-1-yl)pyridin-2-yl)thio)-2-phenylacetamide;
2-((3,5-Dicyano-4-cyclopropyl-6-(4-(pyrrolidin-1-ylmethyl)piperidin-1-yl)pyridin-2-yl)thio)-2-phenylacetamide;
2-((3,5-Dicyano-4-cyclopropyl-6-(4-(4-methylpiperazin-1-yl)piperidin-1-yl)pyridin-2-yl)thio)-2-phenylacetamide;
(R)-2-((3,5-dicyano-6-(1,4-diazepan-1-yl)-4-ethylpyridin-2-yl)amino)-2-phenylacetamide;
2-((3,5-Dicyano-4-cyclopropyl-6-(4-(pyrrolidin-1-yl)piperidin-1-yl)pyridin-2-yl)thio)-2-phenylacetamide;
2-((3,5-Dicyano-4-ethyl-6-(2,7-diazaspiro[3.5]nonan-7-yl)pyridin-2-yl)thio)-2-phenylacetamide;
2-((3,5-Dicyano-4-ethyl-6-(2,6-diazaspiro[3.4]octan-6-yl)pyridin-2-yl)thio)-2-phenylacetamide;
2-((3,5-dicyano-4-cyclopropyl-6-(1,4-diazepan-1-yl)pyridin-2-yl)thio)propanamide;
2-((3,5-Dicyano-4-ethyl-6-(4-(2-oxoimidazolidin-1-yl)piperidin-1-yl)pyridin-2-yl)thio)-2-phenylacetamide;
2-((3,5-Dicyano-4-ethyl-6-(4-hydroxypiperidin-1-yl)pyridin-2-yl)thio)-2-phenylacetamide;
2-((3,5-Dicyano-4-ethyl-6-((S)-3-hydroxypyrrolidin-1-yl)pyridin-2-yl)thio)-2-phenylacetamide;
2-((3,5-Dicyano-4-ethyl-6-(3-oxopiperazin-1-yl)pyridin-2-yl)thio)-2-phenylacetamide;
2-((3,5-Dicyano-4-ethyl-6-(2-methoxyethyl)(methyl)amino)pyridin-2-yl)thio)-2-phenylacetamide;
2-((3,5-Dicyano-4-ethyl-6-(3-methoxyazetidin-1-yl)pyridin-2-yl)thio)-2-phenylacetamide;
2-((3,5-Dicyano-4-ethyl-6-(piperazin-1-yl)pyridin-2-yl)thio)-2-phenylacetamide;
2-((3,5-Dicyano-4-ethyl-6-(4-methyl-1,4-diazepan-1-yl)pyridin-2-yl)thio)-2-phenylacetamide;
2-((3,5-Dicyano-4-ethyl-6-morpholinopyridin-2-yl)thio)-2-phenylacetamide;
2-[[6-(azetidin-1-yl)-3,5-dicyano-4-ethyl-2-pyridyl]sulfanyl]-2-phenyl-acetamide;
2-((3,5-dicyano-4-ethyl-6-(4-oxopiperidin-1-yl)pyridin-2-yl)thio)-2-phenylacetamide;
2-((3,5-dicyano-4-ethyl-6-(1'-(2-hydroxyethyl)-[4,4'-bipiperidin]-1-yl)pyridin-2-yl)thio)-2-phenylacetamide;

2-((3,5-Dicyano-6-((3S,5R)-3,5-dimethylpiperazin-1-yl)-4-ethylpyridin-2-yl)thio)-2-phenylacetamide;
2-((6-(8-azabicyclo[3.2.1]octan-3-yl(methyl)amino)-3,5-dicyano-4-ethylpyridin-2-yl)thio)-2-phenylacetamide;
2-((3,5-Dicyano-4-cyclopropyl-6-(2-(hydroxymethyl)morpholino)pyridin-2-yl)thio)-2-phenylacetamide;
(R)-2-((3,5-dicyano-6-(dimethylamino)-4-ethylpyridin-2-yl)thio)-2-phenylacetamide;
(R)-2-[(3,5-Dicyano-4-ethyl-6-morpholino-2-pyridyl)sulfanyl]-2-phenyl-acetamide;
2-{[3,5-dicyano-4-ethyl-6-(5-methyl-1,4-diazepan-1 sulfanyl}-2-phenylacetamide;
2-(({3,5-Dicyano-4-ethyl-6-[4-(2-methoxyethyl)-1,4-diazepan-1-yl]pyridin-2-yl}sulfanyl)-2-phenylacetamide;
2-((3,5-dicyano-4-ethyl-6-(4-(2-hydroxypropyl)-1,4-diazepan-1-yl)pyridin-2-yl)thio)-2-phenylacetamide;
Methyl 2-[4-(6-{[carbamoyl(phenyl)methyl]sulfanyl}-3,5-dicyano-4-ethylpyridin-2-yl)-1,4-diazepan-1-yl]acetate;
2-{[3,5-Dicyano-4-cyclopropyl-6-(4-methyl-5-oxo-1,4-diazepan-1-yl)pyridin-2-yl]sulfanyl}-2-phenylacetamide;
2-{[3,5-Dicyano-4-cyclopropyl-6-(5-oxo-1,4-diazepan-1-yl)pyridin-2-yl]sulfanyl}-2-phenylacetamide;
2-{[3,5-Dicyano-4-ethyl-6-(4-methyl-5-oxo-1,4-diazepan-1-yl)pyridin-2-yl]sulfanyl}-2-phenylacetamide;
2-{[3,5-Dicyano-6-(1,4-diazepan-1-yl)-4-ethylpyridin-2-yl]sulfanyl}-2-phenylacetamide;
2-(({3,5-Dicyano-6-[4-(2-hydroxyethyl)-1,4-diazepan-1-yl]-4-(2,2,2-trifluoroethyl)pyridin-2-yl}sulfanyl)-2-phenylacetamide;
(2R)-2-(({3,5-Dicyano-4-ethyl-6-[4-(2-hydroxyethyl)-1,4-diazepan-1-yl]pyridin-2-yl}amino)-2-phenylacetamide;
2-({6-[(3S)-3-Aminopyrrolidin-1-yl]-3,5-dicyano-4-cyclopropylpyridin-2-yl}sulfanyl)-2-phenylacetamide;
2-((3,5-Dicyano-4-ethyl-6-(2,9-diazaspiro[5.5]undecan-9-yl)pyridin-2-yl)thio)-2-phenylacetamide;
2-((3,5-Dicyano-4-ethyl-6-(hexahydro-1H-pyrrolo[1,2-a][1,4]diazepin-2(3H)-yl)pyridin-2-yl)thio)-2-phenylacetamide;
2-((3,5-Dicyano-4-ethyl-6-(2-methyl-2,9-diazaspiro[5.5]undecan-9-yl)pyridin-2-yl)thio)-2-phenylacetamide;
2-((3,5-Dicyano-6-(2-(cyclopropylmethyl)-2,9-diazaspiro[5.5]undecan-9-yl)-4-ethylpyridin-2-yl)thio)-2-phenylacetamide;
2-((3,5-Dicyano-6-(4-(3-(dimethylamino)propyl)piperazin-1-yl)-4-ethylpyridin-2-yl)thio)-2-phenylacetamide;
2-((3,5-Dicyano-4-ethyl-6-(4-(pyrrolidin-3-yl)piperidin-1-yl)pyridin-2-yl)thio)-2-phenylacetamide;
2-((6-([4,4'-Bipiperidin]-1-yl)-3,5-dicyano-4-ethylpyridin-2-yl)thio)-2-phenylacetamide;
2-((6-(4-(2-Aminoethyl)piperazin-1-yl)-3,5-dicyano-4-ethylpyridin-2-yl)thio)-2-phenylacetamide;
2-((6-(4-(3-Aminopropyl)piperazin-1-yl)-3,5-dicyano-4-cyclopropylpyridin-2-yl)thio)-2-phenylacetamide;
2-((3,5-Dicyano-4-cyclopropyl-6-(4-((4-methyl piperazin-1-yl)methyl)piperidin-1-yl)pyridin-2-yl)thio)-2-phenylacetamide;
2-((6-(4-Acetylpiperazin-1-yl)-3,5-dicyano-4-ethylpyridin-2-yl)thio)-2-phenylacetamide;
2-((3,5-Dicyano-4-cyclopropyl-6-(dimethylamino)pyridin-2-yl)thio)-2-phenylacetamide;
2-(4-Chlorophenyl)-2-((3,5-dicyano-6-(dimethylamino)-4-ethylpyridin-2-yl)thio)acetamide;
2-((3,5-Dicyano-4-ethyl-6-(4-(2-hydroxyethyl)piperazin-1-yl)pyridin-2-yl)thio)-2-phenylacetamide;
2-[(3,5-Dicyano-4-cyclopropyl-6-morpholino-2-pyridyl)sulfanyl]-2-phenyl-acetamide;
2-((6-(4-Benzoylpiperazin-1-yl)-3,5-dicyano-4-ethylpyridin-2-yl)thio)-2-phenylacetamide;
2-((3,5-Dicyano-4-ethyl-6-((5S,6S)-6-hydroxy-1-(methylsulfonyl)-1,8-diazaspiro[4.5]decan-8-yl)pyridin-2-yl)thio)-2-phenylacetamide;
2-((3,5-Dicyano-6-(4,4-difluoropiperidin-1-yl)-4-ethylpyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide;
2-((3,5-dicyano-4-(furan-2-yl)-6-(4-methyl-1,4-diazepan-1-yl)pyridin-2-yl)thio)-2-phenylacetamide;
2-((6-(4-Amino-4-methylpiperidin-1-yl)-3,5-dicyano-4-ethylpyridin-2-yl)thio)-2-phenylacetamide;
2-Amino-N-(1-(6-((2-amino-2-oxo-1-phenylethyl)thio)-3,5-dicyano-4-ethylpyridin-2-yl)piperidin-4-yl)acetamide;
(2S)-2-Amino-N-(1-(6-((2-amino-2-oxo-1-phenylethyl)thio)-3,5-dicyano-4-ethylpyridin-2-yl)piperidin-4-yl)propanamide;
2-((6-(4-(3-Aminooxetane-3-carbonyl)piperazin-1-yl)-3,5-dicyano-4-ethylpyridin-2-yl)thio)-2-phenylacetamide;
4-Amino-N-(1-(6-((2-amino-2-oxo-1-phenylethyl)thio)-3,5-dicyano-4-ethylpyridin-2-yl)piperidin-4-yl)tetrahydro-2H-pyran-4-carboxamide;
2-((6-(4-(4-Aminotetrahydro-2H-pyran-4-carbonyl)piperazin-1-yl)-3,5-dicyano-4-ethylpyridin-2-yl)thio)-2-phenylacetamide;
2-((3,5-Dicyano-6-(4-(2-hydroxyethyl)-1,4-diazepan-1-yl)-4-methoxypyridin-2-yl)thio)-2-phenylacetamide;
2-((6-(4-Aminopiperidin-1-yl)-3,5-dicyano-4-ethylpyridin-2-yl)thio)-2-phenylacetamide;
2-((6-((2-Aminoethyl)(methyl)amino)-3,5-dicyano-4-ethylpyridin-2-yl)thio)-2-phenylacetamide;
2-((6-((2-Amino-2-oxoethyl)(methyl)amino)-3,5-dicyano-4-ethylpyridin-2-yl)thio)-2-phenylacetamide;
2-((3,5-Dicyano-4-ethyl-6-(3-hydroxyazetidin-1-yl)pyridin-2-yl)thio)-2-phenylacetamide;
2-(3,5-Dicyano-4-ethyl-6-((2-hydroxyethyl)(methyl)amino)pyridin-2-ylthio)-2-phenylacetamide;
2-Amino-N-(1-(6-((2-amino-2-oxo-1-phenylethyl)thio)-3,5-dicyano-4-ethylpyridin-2-yl)piperidin-4-yl)-2-methylpropanamide;
2-((6-(4-(2-Aminoethoxy)piperidin-1-yl)-3,5-dicyano-4-ethylpyridin-2-yl)thio)-2-phenylacetamide;
1-(6-((2-Amino-2-oxo-1-phenylethyl)thio)-3,5-dicyano-4-ethylpyridin-2-yl)pyrrolidin-3-yl dihydrogen phosphate;
2-((6-((2-Amino-2-oxo-1-phenylethyl)thio)-3,5-dicyano-4-ethylpyridin-2-yl)(methyl)amino)ethyl dihydrogen phosphate;
1-(6-((2-Amino-2-oxo-1-phenylethyl)thio)-3,5-dicyano-4-ethylpyridin-2-yl)azetidin-3-yl dihydrogen phosphate;
(2S)-2-((1-(6-((2-Amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-Amino-2-oxo-1-phenylethyl)thio)-3,5-dicyano-4-ethylpyridin-2-yl)piperidin-4-yl)oxy)ethyl dihydrogen phosphate;
1-(6-((2-Amino-2-oxo-1-phenylethyl)thio)-3,5-dicyano-4-ethylpyridin-2-yl)piperidin-4-yl dihydrogen phosphate;

2-((3,5-Dicyano-6-(dimethylamino)-4-ethylpyridin-2-yl) thio)-2-(piperidin-4-yl)acetamide;
2-((3,5-Dicyano-4-ethyl-6-(4-(propylsulfonyl)piperazin-1-yl)pyridin-2-yl)thio)-2-phenylacetamide;
2-((3,5-Dicyano-4-ethyl-6-(4-(phenylsulfonyl)piperazin-1-yl)pyridin-2-yl)thio)-2-phenylacetamide;
2-((3,5-Dicyano-4-ethyl-6-((R)-3-hydroxypyrrolidin-1-yl)pyridin-2-yl)thio)-2-phenylacetamide;
2-((3,5-Dicyano-4-ethyl-6-(2-oxa-6-azaspiro[3.4]octan-6-yl)pyridin-2-yl)thio)-2-phenylacetamide;
(R)-2-((3,5-Dicyano-4-ethyl-6-(4-ethyl-1,4-diazepan-1-yl)pyridin-2-yl)amino)-2-phenylacetamide;
(R)-2-((3,5-Dicyano-4-ethyl-6-(4-(3-(pyrrolidin-1-yl) propyl)-1,4-diazepan-1-yl)pyridin-2-yl)amino)-2-phenylacetamide;
2-(3,5-Dicyano-4-cyclopropyl-6-(3-hydroxypiperidin-1-yl)pyridin-2-ylthio)-2-phenylacetamide;
2-((3,5-Dichloro-4-ethyl-6-(4-methyl-1,4-diazepan-1-yl) pyridin-2-yl)thio)-2-phenylacetamide;
2-((3,5-Dicyano-6-(1,1-dioxidothiomorpholino)-4-ethylpyridin-2-yl)thio)-2-phenylacetamide;
2-((3,5-Dicyano-4-ethyl-6-(methyl(2-(piperazin-1-yl) ethyl)amino)pyridin-2-yl)thio)-2-phenylacetamide;
(R)-2-((3,5-Dicyano-4-ethyl-6-((S)-3-hydroxypyrrolidin-1-yl)pyridin-2-yl)thio)-2-phenylacetamide;
2-((6-((2-(4-(Aminomethyl)-4-hydroxypiperidin-1-yl) ethyl)(methyl)amino)-3,5-dicyano-4-ethylpyridin-2-yl)thio)-2-phenylacetamide;
2-((4-Cyano-3-(1,4-diazepan-1-yl)-6,7-dihydro-5H-cyclopenta[c]pyridin-1-yl)thio)-2-phenylacetamide;
2-((6-(4-(1H-Imidazol-1-yl)piperidin-1-yl)-3,5-dicyano-4-ethylpyridin-2-yl)thio)-2-phenylacetamide;
2-((3,5-Dicyano-4-ethyl-6-(4-(pyridin-4-ylmethyl)piperazin-1-yl)pyridin-2-yl)thio)-2-phenylacetamide;
2-((3,5-Dicyano-6-(2-(dimethylamino)ethoxy)-4-ethylpyridin-2-yl)thio)-2-phenylacetamide;
2-((1-(6-((2-Amino-2-oxo-1-phenylethyl)thio)-3,5-dicyano-4-cyclopropylpyridin-2-yl)piperidin-3-yl) amino)acetic acid;
2-((3,5-Dicyano-4-ethyl-6-(4-(oxazol-2-ylmethyl)piperazin-1-yl)pyridin-2-yl)thio)-2-phenylacetamide;
2-((6-(4-((1H-Pyrrol-2-yl) methyl) piperazin-1-yl)-3,5-dicyano-4-ethylpyridin-2-yl)thio)-2-phenylacetamide;
2-((3,5-Dicyano-6-(3,4-dihydro-2,7-naphthyridin-2 (1H)-yl)-4-ethylpyridin-2-yl)thio)-2-phenylacetamide;
2-((3,5-Dicyano-4-ethyl-6-((S)-3-hydroxypyrrolidin-1-yl)pyridin-2-yl)thio)-2-(pyridin-3-yl)acetamide;
2-((6-(4-((1H-Pyrrol-3-yl)methyl)piperazin-1-yl)-3,5-dicyano-4-ethylpyridin-2-yl)thio)-2-phenylacetamide;
2-((3,5-Dicyano-4-ethyl-6-(4-(isoxazol-3-ylmethyl)piperazin-1-yl)pyridin-2-yl)thio)-2-phenylacetamide;
2-((3,5-Dicyano-4-ethyl-6-(4-(oxazol-5-ylmethyl)piperazin-1-yl)pyridin-2-yl)thio)-2-phenylacetamide;
2-((3,5-Dicyano-4-ethyl-6-(4-(isoxazol-4-ylmethyl)piperazin-1-yl)pyridin-2-yl)thio)-2-phenylacetamide;
3-Amino-N-(1-(6-((2-amino-2-oxo-1-phenylethyl)thio)-3,5-dicyano-4-ethylpyridin-2-yl)piperidin-4-yl)oxetane-3-carboxamide;
2-((6-(4-((1H-Pyrazol-4-yl)methyl)piperazin-1-yl)-3,5-dicyano-4-ethylpyridin-2-yl)thio)-2-phenylacetamide;
2-((6-(4-((1H-Imidazol-5-yl)methyl)piperazin-1-yl)-3,5-dicyano-4-ethylpyridin-2-yl)thio)-2-phenylacetamide;
2-((3,5-Dicyano-4-ethyl-6-(4-(1-hydroxy-2-methylpropan-2-yl)piperazin-1-yl)pyridin-2-yl)thio)-2-phenylacetamide;
2-((6-(4-((1H-Imidazol-2-yl)methyl)piperazin-1-yl)-3,5-dicyano-4-ethylpyridin-2-yl)thio)-2-phenylacetamide;
2-((3,5-Dicyano-6-(dimethylamino)-4-methoxypyridin-2-yl)thio)-2-phenylacetamide;
2-((3,5-Dicyano-6-(dimethylamino)-4-ethoxypyridin-2-yl)thio)-2-phenylacetamide;
2-((3,5-Dicyano-4-ethoxy-6-(4-(2-hydroxyethyl)-1,4-diazepan-1-yl) pyridin-2-yl)thio)-2-phenylacetamide;
2-((3,5-Dicyano-4-ethyl-6-(4-(2-hydroxy-2-methylpropyl)-1,4-diazepan-1-yl)pyridin-2-yl)thio)-2-phenylacetamide;
2-((3,5-Dicyano-4-ethyl-6-(4-(thiazol-5-ylmethyl)piperazin-1-yl)pyridin-2-yl)thio)-2-phenylacetamide;
2-((3,5-Dicyano-4-ethyl-6-(piperazin-1-yl)pyridin-2-yl) thio)-2-(4-fluorophenyl)acetamide;
2-((3,5-Dicyano-4-ethyl-6-(4-(isothiazol-4-ylmethyl)piperazin-1-yl)pyridin-2-yl)thio)-2-phenylacetamide;
2-((3,5-Dicyano-6-(dimethylamino)-4-ethylpyridin-2-yl) thio)-2-(4-fluorophenyl)acetamide;
2-((3,5-Dicyano-6-(dimethylamino)-4-ethylpyridin-2-yl) thio)-2-(5-fluoropyridin-2-yl)acetamide;
2-((3,5-Dicyano-4-ethyl-6-(4-(furan-3-ylmethyl)piperazin-1-yl)pyridin-2-yl)thio)-2-phenylacetamide;
2-((3,5-Dicyano-4-ethyl-6-((2-morpholinoethyl)thio) pyridin-2-yl)thio)-2-phenylacetamide;
2-((3,5-Dicyano-6-(4-methyl-1,4-diazepan-1-yl)-4-(methylthio)pyridin-2-yl)thio)-2-phenylacetamide;
2-((3,5-Dichloro-4-ethyl-6-(4-(2-hydroxyethyl)-1,4-diazepan-1-yl)pyridin-2-yl)thio)-2-phenylacetamide;
2-((3,5-Dicyano-4-ethyl-6-(hexahydropyrrolo[3,4-b][1,4] oxazin-6(2H)-yl)pyridin-2-yl)thio)-2-phenylacetamide;
2-((3,5-Dicyano-4-ethyl-6-(4-methyl-1,4-diazepan-1-yl) pyridin-2-yl)thio)-2-(5-methylpyridin-2-yl)acetamide;
2-((3,5-Dicyano-4-ethyl-6-(4-methyl-1,4-diazepan-1-yl) pyridin-2-yl)thio)-2-(6-fluoropyridin-2-yl)acetamide;
2-((3,5-Dicyano-6-(4-(dimethylamino)piperidin-1-yl)-4-ethylpyridin-2-yl)thio)-2-(4-fluorophenyl)acetamide;
2-((3,5-Dicyano-4-ethyl-6-(4-methyl-1,4-diazepan-1-yl) pyridin-2-yl) thio)-2-(4-methylpyridin-2-yl) acetamide;
2-((3,5-Dicyano-4-ethyl-6-(4-methyl-1,4-diazepan-1-yl) pyridin-2-yl)thio)-2-(3-methoxypyridin-2-yl)acetamide;
2-((3,5-Dicyano-6-(4-(dimethylamino)piperidin-1-yl)-4-ethylpyridin-2-yl)thio)-2-(2,4-difluorophenyl)acetamide;
2-((3,5-Dicyano-4-ethyl-6-(4-(pyrrolidin-1-yl)piperidin-1-yl)pyridin-2-yl)thio)-2-(5-fluoropyridin-2-yl)acetamide;
2-((3,5-Dicyano-4-ethoxy-6-(4-(2-hydroxyethyl)-1,4-diazepan-1-yl)pyridin-2-yl)thio)propanamide;
2-((3,5-Dicyano-6-(4-(2-hydroxyethyl)-1,4-diazepan-1-yl)-4-propoxypyridin-2-yl)thio)-2-phenylacetamide;
2-((3,5-Dicyano-4-ethyl-6-(4-methyl-1,4-diazepan-1-yl) pyridin-2-yl)thio)-2-(4-methoxypyridin-2-yl)acetamide;
2-((3,5-Dicyano-4-ethyl-6-(2-methyl-2,8-diazaspiro[4.5] decan-8-yl)pyridin-2-yl)thio)-2-phenylacetamide;
2-((3,5-Dicyano-6-(4-(dimethylamino)piperidin-1-yl)-4-ethylpyridin-2-yl)thio)-2-(3,4-difluorophenyl)acetamide;
1-(6-((2-Amino-2-oxo-1-phenylethyl)thio)-3,5-dicyano-4-ethylpyridin-2-yl)piperidine-4-carboxamide;
2-((3,5-Dicyano-6-((2-(dimethylamino)ethyl)thio)-4-ethylpyridin-2-yl)thio)-2-phenylacetamide;
2-((3,5-Dicyano-6-((3S,4R)-3,4-dihydroxypyrrolidin-1-yl)-4-ethylpyridin-2-yl)thio)-2-phenylacetamide;

2-((3,5-Dicyano-4-ethyl-6-(4-methyl-1,4-diazepan-1-yl) pyridin-2-yl)thio)-2-(3-fluoropyridin-2-yl) acetamide;

2-((3,5-Dicyano-4-ethyl-6-(4-methyl-1,4-diazepan-1-yl) pyridin-2-yl)thio)-2-(5-methoxypyridin-2-yl)acetamide;

2-((3,5-Dicyano-4-ethyl-6-(4-(1-hydroxy-2-methylpropan-2-yl)piperazin-1-yl)pyridin-2-yl)thio)-2-(4-fluorophenyl)acetamide;

2-((3,5-Dicyano-4-ethyl-6-(4-methyl-1,4-diazepan-1-yl) pyridin-2-yl)thio)-2-(3-(trifluoromethyl)phenyl)acetamide;

2-((3,5-Dicyano-4-ethyl-6-(4-(2-hydroxyethoxy)piperidin-1-yl)pyridin-2-yl)thio)-2-phenylacetamide;

2-((3,5-Dicyano-4-ethyl-6-(4-methyl-1,4-diazepan-1-yl) pyridin-2-yl)thio)-2-(2-fluoropyridin-3-yl)acetamide;

2-((3,5-Dicyano-4-ethyl-6-(4-methyl-1,4-diazepan-1-yl) pyridin-2-yl)thio)-2-(6-fluoropyridin-3-yl)acetamide;

3-((6-(2-Amino-2-oxo-1-phenylethylthio)-3,5-dicyano-4-ethylpyridin-2-yl)(methyl)amino)propanamide;

2-((3,5-Dicyano-4-ethyl-6-(4-(oxetan-3-yloxy)piperidin-1-yl)pyridin-2-yl)thio)-2-phenylacetamide;

2-((3,5-Dicyano-6-(4-((2,2-difluoroethyl) amino)-4-methylpiperidin-1-yl)-4-ethylpyridin-2-yl) thio)-2-phenylacetamide;

2-((3,5-Dicyano-4-ethyl-6-(4-methyl-1,4-diazepan-1-yl) pyridin-2-yl)thio)-2-(4-(trifluoromethyl)phenyl)acetamide;

2-((6-(4-Aminopiperazin-1-yl)-3,5-dicyano-4-ethylpyridin-2-yl)thio)-2-phenylacetamide;

2-((6-((2-Amino-2-oxoethyl)thio)-3,5-dicyano-4-ethylpyridin-2-yl)thio)-2-phenylacetamide;

2-((3,5-Dicyano-4-ethyl-6-(pyrrolo[3,4-c]pyrazol-5 (1H,4H,6H)-yl)pyridin-2-yl)thio)-2-phenylacetamide;

2-((3,5-Dicyano-6-(dimethylamino)-4-ethylpyridin-2-yl) thio)-2-(5-methoxypyridin-2-yl)acetamide;

2-((3,5-Dicyano-6-(dimethylamino)-4-ethylpyridin-2-yl) thio)-2-(5-methylpyridin-2-yl)acetamide;

2-((3,5-Dicyano-4-ethyl-6-(4-methyl-1,4-diazepan-1-yl) pyridin-2-yl)thio)-2-(2-fluoropyridin-4-yl)acetamide;

2-((3,5-Dicyano-4-ethyl-6-(4-hydroxy-4-(hydroxymethyl)piperidin-1-yl)pyridin-2-yl)thio)-2-phenylacetamide;

2-((3,5-Dicyano-4-ethyl-6-(2-oxo-3-oxa-1,8-diazaspiro[4.5]decan-8-yl)pyridin-2-yl)thio)-2-phenylacetamide;

2-((6-(4-Amino-4-(hydroxymethyl)piperidin-1-yl)-3,5-dicyano-4-ethylpyridin-2-yl)thio)-2-phenylacetamide;

2-((6-(4-(Aminomethyl)-4-hydroxypiperidin-1-yl)-3,5-dicyano-4-ethylpyridin-2-yl)thio)-2-phenylacetamide;

2-(3-Benzoylphenyl)-2-((3,5-dicyano-4-ethyl-6-(4-(2-hydroxyethyl)-1,4-diazepan-1-yl)pyridin-2-yl)thio)acetamide;

2-(4-Benzoylphenyl)-2-((3,5-dicyano-4-ethyl-6-(4-(2-hydroxyethyl)-1,4-diazepan-1-yl)pyridin-2-yl)thio)acetamide;

2-((3,5-Dicyano-4-ethyl-6-(4-methyl-1,4-diazepan-1-yl) pyridin-2-yl)thio)-2-(2-methylpyridin-4-yl)acetamide;

2-((3,5-Dicyano-4-ethyl-6-(4-methyl-1,4-diazepan-1-yl) pyridin-2-yl)thio)-2-(3-(pyrrolidin-1-yl)phenyl)acetamide;

2-((3,5-Dicyano-4-ethyl-6-(4-methyl-1,4-diazepan-1-yl) pyridin-2-yl)thio)-2-(3-fluoropyridin-4-yl)acetamide;

2-((3,5-Dicyano-4-ethyl-6-(4-methyl-1,4-diazepan-1-yl) pyridin-2-yl)thio)-2-(2,5-difluoropyridin-4-yl)acetamide;

2-((3,5-Dicyano-6-(4-(2,5-dioxoimidazolidin-1-yl)piperidin-1-yl)-4-ethylpyridin-2-yl)thio)-2-phenylacetamide;

4-Amino-1-(6-((2-amino-2-oxo-1-phenylethyl) thio)-3,5-dicyano-4-ethylpyridin-2-yl) piperidine-4-carboxamide;

2-((3,5-Dicyano-6-(4-(2,5-dioxopyrrolidin-1-yl)piperidin-1-yl)-4-ethylpyridin-2-yl)thio)-2-phenylacetamide;

2-((3,5-dicyano-4-ethyl-6-(4-methyl-1,4-diazepan-1-yl) pyridin-2-yl)thio)-2-phenylacetamide (isomer 1);

2-((3,5-dicyano-4-ethyl-6-(4-methyl-1,4-diazepan-1-yl) pyridin-2-yl)thio)-2-phenylacetamide (Isomer 2);

2-((3,5-Dicyano-4-ethyl-6-(2-oxo-1-oxa-3,8-diazaspiro [4.5]decan-8-yl)pyridin-2-yl)thio)-2-phenylacetamide;

1-(6-((2-Amino-2-oxo-1-phenylethyl)thio)-3,5-dicyano-4-ethylpyridin-2-yl)-4-hydroxy piperidine-4-carboxamide;

1-(6-((2-Amino-2-oxo-1-phenylethyl)thio)-3,5-dicyano-4-ethylpyridin-2-yl)azetidin-3-yl carbamate;

2-((3,5-Dicyano-6-(4-(2,4-dioxooxazolidin-3-yl)piperidin-1-yl)-4-ethylpyridin-2-yl)thio)-2-phenylacetamide;

3-((6-((2-Amino-2-oxo-1-phenylethyl)thio)-3,5-dicyano-4-ethylpyridin-2-yl)(methyl)amino)-2-hydroxy-2-methylpropanamide;

2-((3,5-Dicyano-4-ethyl-6-(3-(hydroxymethyl)azetidin-1-yl)pyridin-2-yl)thio)-2-phenylacetamide;

2-(3,5-Dicyano-4-ethyl-6-(piperazin-1-yl)pyridin-2-yl-thio)-2-(thiophen-3-yl)acetamide;

2-((3,5-Dicyano-4-ethyl-6-(4-methyl-1,4-diazepan-1-yl) pyridin-2-yl) thio)-2-(5-methylpyridin-3-yl) acetamide;

2-((6-(4-(3-Amino-2-oxopyrrolidin-1-yl)piperidin-1-yl)-3,5-dicyano-4-ethylpyridin-2-yl)thio)-2-phenylacetamide;

1-(6-((2-Amino-2-oxo-1-phenylethyl)thio)-3,5-dicyano-4-ethylpyridin-2-yl)piperidin-4-yl (2S)-2-amino-3-methylbutanoate;

2-((6-((2-Amino-2-oxo-1-phenylethyl)thio)-3,5-dicyano-4-ethylpyridin-2-yl) (methyl) amino)ethyl (2S)-2-amino-3-methylbutanoate;

2,2'-((3,5-Dicyano-4-ethylpyridine-2,6-diyl)bis(sulfanediyl))bis(2-phenylacetamide);

(2S)-(1-(6-((2-Amino-2-oxo-1-phenylethyl)thio)-3,5-dicyano-4-ethylpyridin-2-yl)azetidin-3-yl)methyl 2-amino-3-methylbutanoate;

2-((6-(3-Aminoazetidin-1-yl)-3,5-dicyano-4-ethylpyridin-2-yl)thio)-2-phenylacetamide;

2-((3,5-Dicyano-4-ethyl-6-methylpyridin-2-yl)thio)-2-phenylacetamide;

N-(1-(6-((2-Amino-2-oxo-1-phenylethyl)thio)-3,5-dicyano-4-ethylpyridin-2-yl)piperidin-4-yl)-2-hydroxyacetamide;

N-(1-(6-((2-Amino-2-oxo-1-phenylethyl)thio)-3,5-dicyano-4-ethylpyridin-2-yl)azetidin-3-yl)-2-hydroxyacetamide;

2-((3-Cyano-4-ethyl-5-methyl-6-(piperazin-1-yl)pyridin-2-yl)thio)-2-phenylacetamide;

2-((3,5-Dicyano-4-ethyl-6-(5-methyl-2,5-diazabicyclo [2.2.1]heptan-2-yl)pyridin-2-yl)thio)-2-phenylacetamide;

2-((3,5-Dicyano-4-ethyl-6-(4-(2-(pyrrolidin-1-yl)ethyl) piperazin-1-yl)pyridin-2-yl)thio)-2-phenylacetamide;

2-((3,5-Dicyano-6-(dimethylamino)-4-ethylpyridin-2-yl) thio)-2-phenylacetamide-2-d;

(R)-2-((3,5-Dicyano-6-(dimethylamino)-4-ethylpyridin-2-yl)thio)-2-phenylacetamide-2-d;

2-((6-(4-(4-Bromobenzoyl)piperazin-1-yl)-3,5-dicyano-4-ethylpyridin-2-yl)thio)-2-phenylacetamide;

2-((3,5-Dicyano-4-ethyl-6-(4-(2-hydroxyethyl)-1,4-diazepan-1-yl)pyridin-2-yl)thio)-2-phenylacetamide;

2-((3,5-Dicyano-6-(4-cyanopiperidin-1-yl)-4-ethylpyridin-2-yl)thio)-2-phenylacetamide;
(S)-2-((3,5-Dicyano-4-ethyl-6-((S)-3-hydroxypyrrolidin-1-yl)pyridin-2-yl)thio)-2-phenylacetamide;
2-((6-(4-Amino-4-methylpiperidin-1-yl)-3,5-dicyano-4-cyclopropylpyridin-2-yl)thio)-2-phenylacetamide;
2-((3,5-Dicyano-4-ethyl-6-((S)-3-hydroxypyrrolidin-1-yl)pyridin-2-yl)thio)-2-(pyridin-2-yl)acetamide;
2-((3,5-Dichloro-4-ethyl-6-(piperazin-1-yl)pyridin-2-yl)thio)-2-phenylacetamide;
tert-Butyl (1-(6-((2-amino-2-oxo-1-phenylethyl)thio)-3,5-dicyano-4-ethylpyridin-2-yl)piperidin-4-yl)carbamate;
2-((6-(3-(2-Amino-2-oxoethyl)azetidin-1-yl)-3,5-dicyano-4-ethylpyridin-2-yl)thio)-2-phenylacetamide;
(2R)-1-(6-((2-Amino-2-oxo-1-phenylethyl)thio)-3,5-dicyano-4-ethylpyridin-2-yl)azetidin-3-yl 2-amino-3-methylbutanoate;
2-((3,5-Dicyano-4-ethyl-6-(methyl((5-oxo-4,5-dihydro-1H-1,2,4-triazol-3-yl)methyl)amino)pyridin-2-yl)thio)-2-phenylacetamide;
2-((6-(((4H-1,2,4-Triazol-3-yl)methyl)(methyl)amino)-3,5-dicyano-4-ethylpyridin-2-yl)thio)-2-phenylacetamide;
2-((3,5-Dicyano-4-ethoxy-6-methylpyridin-2-yl)thio)-2-phenylacetamide;
2-((3,5-Dicyano-4,6-diethylpyridin-2-yl)thio)-2-phenylacetamide;
2-((6-((2-(4H-1,2,4-Triazol-4-yl)ethyl)(methyl)amino)-3,5-dicyano-4-ethylpyridin-2-yl)thio)-2-phenylacetamide;
2-((6-(((1H-Pyrazol-3-yl)methyl)(methyl)amino)-3,5-dicyano-4-ethylpyridin-2-yl)thio)-2-phenylacetamide;
2-((3,5-Dicyano-6-(6,7-dihydro-1H-[1,2,3]triazolo[4,5-c]pyridin-5(4H)-yl)-4-ethylpyridin-2-yl)thio)-2-phenylacetamide;
2-((6-(((1H-Imidazol-2-yl)methyl)(methyl)amino)-3,5-dicyano-4-ethylpyridin-2-yl)thio)-2-phenylacetamide;
2-((6-(((1H-Imidazol-5-yl)methyl)(methyl)amino)-3,5-dicyano-4-ethylpyridin-2-yl)thio)-2-phenylacetamide;
(2R)-2-Amino-N-(1-(6-((2-amino-2-oxo-1-phenylethyl)thio)-3,5-dicyano-4-ethylpyridin-2-yl)piperidin-4-yl)propanamide;
4-(2-Amino-1-((3,5-dicyano-4-ethyl-6-(4-methyl-1,4-diazepan-1-yl)pyridin-2-yl)thio)-2-oxoethyl)benzamide;
2-((3,5-Dicyano-4-cyclopropyl-6-(3-hydroxypyrrolidin-1-yl)pyridin-2-yl)thio)-2-phenylacetamide;
2-((3,5-Dicyano-4-ethyl-6-(3-hydroxypyrrolidin-1-yl)pyridin-2-yl)thio)-2-phenylacetamide;
(2R)-2-Amino-N-(1-(6-((2-amino-2-oxo-1-phenylethyl)thio)-3,5-dicyano-4-cyclopropyl pyridin-2-yl)piperidin-4-yl)propanamide;
2-((6-((2-Aminoethyl)(methyl)amino)-3,5-dicyano-4-cyclopropylpyridin-2-yl)thio)-2-phenylacetamide;
2-Amino-N-(1-(6-((2-amino-2-oxo-1-phenylethyl) thio)-3,5-dicyano-4-cyclopropylpyridin-2-yl)piperidin-4-yl)-2-methylpropanamide;
4-(2-Amino-1-((3,5-dicyano-6-(dimethylamino)-4-ethylpyridin-2-yl)thio)-2-oxoethyl)benzamide;
2-(6-(4-Aminopiperidin-1-yl)-3-cyano-4-ethyl-5-methylpyridin-2-ylthio)-2-phenylacetamide;
2-((3,5-Dicyano-4-ethyl-6-(4-methyl-1,4-diazepan-1-yl)pyridin-2-yl)thio)-2-(4-(N-methylsulfamoyl)phenyl)acetamide;
2-((3,5-Dicyano-4-ethyl-6-(6-fluoro-1,4-diazepan-1-yl)pyridin-2-yl)thio)-2-phenylacetamide;
2-((6-(4-Amino-3,3-difluoropiperidin-1-yl)-3,5-dicyano-4-ethylpyridin-2-yl)thio)-2-phenylacetamide;
tert-Butyl (1-(6-((2-amino-2-oxo-1-phenylethyl) thio)-3,5-dicyano-4-ethylpyridin-2-yl)-3,3-difluoropiperidin-4-yl) carbamate;
2-((3,5-Dicyano-4-cyclopropyl-6-((2-hydroxyethyl)(methyl)amino)pyridin-2-yl)thio)-2-phenylacetamide;
2-((3,5-Dicyano-4-cyclopropyl-6-(3-hydroxyazetidin-1-yl)pyridin-2-yl)thio)-2-phenylacetamide;
1-(6-((2-Amino-2-oxo-1-phenylethyl)thio)-3,5-dicyano-4-ethylpyridin-2-yl)pyrrolidine-3-carboxamide;
2-((6-((3-Aminopropyl) (methyl) amino)-3,5-dicyano-4-cyclopropylpyridin-2-yl) thio)-2-phenylacetamide;
2-((3,5-Dicyano-4-cyclopropyl-6-((2-(3-hydroxyazetidin-1-yl)-2-oxoethyl)(methyl)amino) pyridin-2-yl)thio)-2-phenylacetamide;
2-((6-(4-((2-Amino-2-oxoethyl)amino)piperidin-1-yl)-3,5-dicyano-4-ethylpyridin-2-yl)thio)-2-phenylacetamide;
2-((6-((2-Amino-2-oxoethyl)(methyl)amino)-3,5-dicyano-4-cyclopropylpyridin-2-yl)thio)-2-phenylacetamide;
2-((6-((2-Amino-2-oxo-1-phenylethyl) thio)-3,5-dicyano-4-cyclopropylpyridin-2-yl)(methyl)amino)ethyl carbamate;
(2R)-2-Amino-N-(1-(6-((2-amino-2-oxo-1-phenylethyl)thio)-3,5-dicyano-4-ethylpyridin-2-yl)piperidin-4-yl)-3-hydroxypropanamide;
(2S)-2-Amino-N-(1-(6-((2-amino-2-oxo-1-phenylethyl)thio)-3,5-dicyano-4-ethylpyridin-2-yl) piperidin-4-yl)-3-hydroxypropanamide;
2-(4-(2-Amino-2-oxoethyl)phenyl)-2-(3,5-dicyano-4-ethyl-6-(4-methyl-1,4-diazepan-1-yl)pyridin-2-ylthio) acetamide;
2-(4-(2-Amino-2-oxoethyl)phenyl)-2-(3,5-dicyano-6-(dimethylamino)-4-ethylpyridin-2-ylthio)acetamide;
2-((3,5-Dicyano-6-(dimethylamino)-4-ethylpyridin-2-yl)thio)-2-(4-(N-methylsulfamoyl)phenyl)acetamide;
2-((3,5-Dicyano-6-(dimethylamino-$d_6$)-4-ethylpyridin-2-yl)thio)-2-phenylacetamide;
(R)-2-((3,5-Dicyano-4-ethyl-6-(4-(pyrrolidin-1-yl)piperidin-1-yl)pyridin-2-yl)thio)-2-phenylacetamide;
(R)-2-((3,5-Dicyano-6-(4-(dimethylamino)piperidin-1-yl)-4-ethylpyridin-2-yl)thio)-2-phenylacetamide;
2-(3,5-dicyano-6-(dimethylamino)-4-ethylpyridin-2-ylthio)-2-(3-(2-(dimethylamino)ethoxy)phenyl)acetamide;
2-((3,5-Dicyano-4-ethyl-6-(4-(neopentylamino)piperidin-1-yl)pyridin-2-yl)thio)-2-(4-fluorophenyl)acetamide;
2-((3,5-dicyano-4-ethyl-6-(3-fluoro-4-A(neopentylamino)piperidin-1-yl)pyridin-2-yl)thio)-2-phenylacetamide;
2-((6-(4-aminopiperidin-1-yl)-3,5-dicyano-4-ethylpyridin-2-yl)thio)-2-(4-(trifluoromethyl)phenyl)acetamide;
2-((3,5-Dicyano-4-ethyl-6-(4-(pyrrolidin-1-yl)piperidin-1-yl)pyridin-2-yl)thio)-2-phenylacetamide;
(R)-2-((6-(4-aminopiperidin-1-yl)-3,5-dicyano-4-ethylpyridin-2-yl)thio)-2-phenylacetamide;
2-((6-((2-amino-2-oxoethyl)(methyl)amino)-3,5-dicyano-4-ethylpyridin-2-yl)thio)-2-phenylacetamide; (single enantiomer)
(3S)-1-(6-((2-amino-2-oxo-1-phenylethyl) thio)-3,5-dicyano-4-ethylpyridin-2-yl) Pyrrolidin-3-yl dihydrogen phosphate;

(3R)-1-(6-((2-amino-2-oxo-1-phenylethyl)thio)-3,5-dicyano-4-ethylpyridin-2-yl)pyrrolidin-3-yl dihydrogen phosphate;

(S)-1-(6-(((S)-2-amino-2-oxo-1-phenylethyl)thio)-3,5-dicyano-4-ethylpyridin-2-yl)pyrrolidin-3-yl dihydrogen phosphate;

(S)-1-(6-(((R)-2-amino-2-oxo-1-phenylethyl) thio)-3,5-dicyano-4-ethylpyridin-2-yl) pyrrolidin-3-yl dihydrogen phosphate;

2-((3,5-Dicyano-6-(dimethylamino)-4-ethylpyridin-2-yl)thio)-2-(3-(dimethylphosphoryl)phenyl)acetamide;

2-((3,5-Dicyano-4-ethyl-6-((S)-3-hydroxypyrrolidin-1-yl)pyridin-2-yl)thio)-2-(3-(dimethylphosphoryl)phenyl)acetamide;

(R)-2-((6-((2-amino-2-oxo-1-phenylethyl)thio)-3,5-dicyano-4-ethylpyridin-2-yl)(methyl)amino)ethyl dihydrogen phosphate;

(R)-2-((3,5-dicyano-4-ethyl-6-((S)-3-hydroxypyrrolidin-1-yl)pyridin-2-yl)thio)-2-(4-methoxyphenyl)acetamide;

(R)-2-(4-chlorophenyl)-2-((3,5-dicyano-4-ethyl-6-((S)-3-hydroxypyrrolidin-1-yl)pyridin-2-yl)thio)acetamide;

(R)-2-((3,5-dicyano-4-ethyl-6-((S)-3-hydroxypyrrolidin-1-yl)pyridin-2-yl)thio)-2-(4-fluoro phenyl)acetamide;

(S)-1-(6-(((R)-2-amino-1-(4-fluorophenyl)-2-oxoethyl)thio)-3,5-dicyano-4-ethylpyridin-2-yl)pyrrolidin-3-yl dihydrogen phosphate;

2-((3,5-dicyano-4-ethyl-6-((S)-3-hydroxypyrrolidin-1-yl)pyridin-2-yl) thio)-2-(4-fluorophenyl) acetamide;

2-((3,5-dicyano-4-ethyl-6-((S)-3-hydroxypyrrolidin-1-yl)pyridin-2-yl) thio)-2-(2,6-difluorophenyl) acetamide;

2-((3,5-dicyano-4-ethyl-6-((S)-3-hydroxypyrrolidin-1-yl)pyridin-2-yl) thio)-2-(2,3-difluorophenyl) acetamide;

2-((3,5-dicyano-4-ethyl-6-((S)-3-hydroxypyrrolidin-1-yl)pyridin-2-yl) thio)-2-(2,4-difluorophenyl) acetamide;

2-((3,5-dicyano-4-ethyl-6-(4-((S)-2-(hydroxymethyl)pyrrolidin-1-yl)piperidin-1-yl)pyridin-2-yl)thio)-2-phenylacetamide;

2-((3,5-dicyano-4-ethyl-6-(4-((2-hydroxyethyl)(methyl)amino)piperidin-1-yl)pyridin-2-yl)thio)-2-phenylacetamide;

2-((3,5-dicyano-4-ethyl-6-(4-((2-hydroxy-2-methylpropyl)(methyl)amino)piperidin-1-yl)pyridin-2-yl)thio)-2-phenylacetamide;

2-((3,5-dicyano-4-ethyl-6-(4-(pyrrolidin-1-ylmethyl)piperidin-1-yl)pyridin-2-yl)thio)-2-phenylacetamide;

2-((3,5-dicyano-4-ethyl-6-(4-((2-methoxy-2-methylpropyl)amino)piperidin-1-yl)pyridin-2-yl)thio)-2-phenylacetamide;

2-((3,5-dicyano-4-ethyl-6-(4-((2-hydroxy-2-methylpropyl)amino)piperidin-1-yl)pyridin-2-yl)thio)-2-phenylacetamide;

2-((3,5-dicyano-6-(4-(cyclobutylamino)piperidin-1-yl)-4-ethylpyridin-2-yl)thio)-2-phenylacetamide;

2-((3,5-dicyano-4-ethyl-6-(4-(((3-methyloxetan-3-yl)methyl)amino)piperidin-1-yl)pyridin-2-yl)thio)-2-phenylacetamide;

2-((3,5-dicyano-4-ethyl-6-(4-(4-methylpiperazin-1-yl)piperidin-1-yl)pyridin-2-yl)thio)-2-phenylacetamide;

2-((3,5-dicyano-4-ethyl-6-(4-((R)-2-methylpyrrolidin-1-yl)piperidin-1-yl)pyridin-2-yl)thio)-2-phenylacetamide;

2-((3,5-dicyano-6-(4-((2R,5S)-2,5-dimethylpyrrolidin-1-yl)piperidin-1-yl)-4-ethylpyridin-2-yl)thio)-2-phenylacetamide;

2-((3,5-dicyano-4-ethyl-6-(4-((S)-2-methylpyrrolidin-1-yl)piperidin-1-yl)pyridin-2-yl)thio)-2-phenylacetamide;

2-((3,5-dicyano-6-(4-(cyclobutyl(methyl)amino)piperidin-1-yl)-4-ethylpyridin-2-yl)thio)-2-phenylacetamide;

2-(6-(4-(benzylamino)piperidin-1-yl)-3,5-dicyano-4-ethylpyridin-2-ylthio)-2-phenylacetamide;

2-((3,5-dicyano-4-ethyl-6-(4-(((6-methoxypyridin-2-yl)methyl)amino)piperidin-1-yl)pyridin-2-yl)thio)-2-phenylacetamide;

2-((3,5-dicyano-4-ethyl-6-(4-((S)-3-fluoropyrrolidin-1-yl)piperidin-1-yl)pyridin-2-yl)thio)-2-phenylacetamide;

2-((3,5-dicyano-4-ethyl-6-(methyl(2-((R)-2-methylpyrrolidin-1-yl)ethyl)amino)pyridin-2-yl)thio)-2-phenylacetamide;

2-((3,5-dicyano-4-ethyl-6-(4-((R)-3-fluoropyrrolidin-1-yl)piperidin-1-yl)pyridin-2-yl)thio)-2-phenylacetamide;

2-((3,5-dicyano-6-(4-((2S,5S)-2,5-dimethylpyrrolidin-1-yl)piperidin-1-yl)-4-ethylpyridin-2-yl)thio)-2-phenylacetamide;

2-((3,5-dicyano-4-ethyl-6-(methyl(2-((S)-2-methylpyrrolidin-1-yl)ethyl)amino)pyridin-2-yl)thio)-2-phenylacetamide;

2-((3,5-dicyano-4-ethyl-6-(4-((R)-2-(hydroxymethyl)pyrrolidin-1-yl)piperidin-1-yl)pyridin-2-yl)thio)-2-phenylacetamide;

2-((3,5-Dicyano-6-(4-(dimethylamino)piperidin-1-yl)-4-ethylpyridin-2-yl)thio)-2-(4-fluorophenyl)acetamide;

2-((3,5-dicyano-4-ethyl-6-(4-(((1-methylcyclobutyl)methyl)amino)piperidin-1-yl)pyridin-2-yl)thio)-2-phenylacetamide;

2-((3,5-dicyano-4-ethyl-6-(4-(((6-methoxypyridin-3-yl)methyl)amino)piperidin-1-yl)pyridin-2-yl)thio)-2-phenylacetamide;

2-(3,5-dicyano-4-ethyl-6-((2-(ethylamino)ethyl)(methyl)amino)pyridin-2-ylthio)-2-phenylacetamide;

2-((3,5-dicyano-4-ethyl-6-(4-((4-methylpiperazin-1-yl)methyl)piperidin-1-yl)pyridin-2-yl)thio)-2-phenylacetamide;

2-((3,5-dicyano-4-ethyl-6-(methyl(2-(methylamino)ethyl)amino)pyridin-2-yl)thio)-2-phenylacetamide;

2-((3,5-dicyano-6-(4-((2R,5R)-2,5-dimethylpyrrolidin-1-yl)piperidin-1-yl)-4-ethylpyridin-2-yl)thio)-2-phenylacetamide;

2-((3,5-dicyano-4-ethyl-6-(4-(((1-methylcyclopropyl)methyl)amino)piperidin-1-yl)pyridin-2-yl)thio)-2-phenylacetamide;

2-((3,5-dicyano-4-ethyl-6-(4-((4-fluorobenzyl)amino)piperidin-1-yl)pyridin-2-yl)thio)-2-phenylacetamide;

2-((3,5-dicyano-4-ethyl-6-((2-((S)-2-(hydroxymethyl)pyrrolidin-1-yl)ethyl)(methyl)amino)pyridin-2-yl)thio)-2-phenylacetamide;

2-(3,5-dicyano-6-((2-((2S,5R)-2,5-dimethylpyrrolidin-1-yl)ethyl)(methyl)amino)-4-ethylpyridin-2-ylthio)-2-phenylacetamide;

2-((6-((2-(azepan-1-yl)ethyl)(methyl)amino)-3,5-dicyano-4-ethylpyridin-2-yl)thio)-2-phenylacetamide;

2-((3,5-dicyano-4-ethyl-6-(methyl(2-(piperidin-1-yl)ethyl)amino)pyridin-2-yl)thio)-2-phenylacetamide;

2-((3,5-dicyano-4-ethyl-6-((2-((R)-2-(hydroxymethyl)pyrrolidin-1-yl)ethyl)(methyl)amino)pyridin-2-yl)thio)-2-phenylacetamide;

2-(3,5-dicyano-4-ethyl-6-((2-(ethyl(methyl)amino)ethyl)(methyl)amino)pyridin-2-ylthio)-2-phenylacetamide;

2-((3,5-dicyano-6-((2-((2R,5R)-2,5-dimethylpyrrolidin-1-yl)ethyl)(methyl)amino)-4-ethylpyridin-2-yl)thio)-2-phenylacetamide;
2-(3,5-dicyano-4-ethyl-6-((2-((S)-3-hydroxypyrrolidin-1-yl)ethyl)(methyl)amino)pyridin-2-ylthio)-2-phenylacetamide;
methyl 2-((1-(6-((2-amino-2-oxo-1-phenylethyl)thio)-3,5-dicyano-4-ethylpyridin-2-yl)piperidin-4-yl)amino)-2-methylpropanoate;
2-(3,5-dicyano-4-ethyl-6-(methyl(2-(neopentylamino)ethyl)amino)pyridin-2-yl)thio)-2-phenylacetamide;
2-(3,5-dicyano-4-ethyl-6-(methyl(2-(1-methylcyclopropylamino)ethyl)amino)pyridin-2-ylthio)-2-phenylacetamide;
2-((3,5-dicyano-6-((2-((2S,5S)-2,5-dimethylpyrrolidin-1-yl)ethyl)(methyl)amino)-4-ethylpyridin-2-yl)thio)-2-phenylacetamide;
2-((3,5-dicyano-4-ethyl-6-((2-((2-methoxyethyl)amino)ethyl)(methyl)amino)pyridin-2-yl)thio)-2-phenylacetamide;
2-((3,5-dicyano-4-ethyl-6-(4-(2-methoxy-2-methylpropyl)(methyl)amino)piperidin-1-yl)pyridin-2-yl)thio)-2-phenylacetamide;
2-((3,5-dicyano-6-((2-(dimethylamino)ethyl)(methyl)amino)-4-ethylpyridin-2-yl)thio)-2-phenylacetamide;
2-(3,5-dicyano-4-ethyl-6-((2-((R)-3-hydroxypyrrolidin-1-yl)ethyl)(methyl)amino)pyridin-2-ylthio)-2-phenylacetamide;
2-((3,5-dicyano-4-ethyl-6-((2-((2-fluoroethyl)amino)ethyl)(methyl)amino)pyridin-2-yl)thio)-2-phenylacetamide;
2-((3,5-dicyano-6-(4-(3,3-difluoropyrrolidin-1-yl)piperidin-1-yl)-4-ethylpyridin-2-yl)thio)-2-phenylacetamide;
2-((1-(6-((2-amino-2-oxo-1-phenylethyl)thio)-3,5-dicyano-4-ethylpyridin-2-yl)piperidin-4-yl)amino)acetic acid;
2-((6-((3-aminocyclobutyl)(methyl)amino)-3,5-dicyano-4-ethylpyridin-2-yl)thio)-2-phenylacetamide;
(R)-2-(3,5-dicyano-4-ethyl-6-(methyl((R)-tetrahydrofuran-3-yl)amino)pyridin-2-ylthio)-2-phenylacetamide;
(S)-2-(3,5-dicyano-4-ethyl-6-(methyl((R)-tetrahydrofuran-3-yl)amino)pyridin-2-ylthio)-2-phenylacetamide;
2-((3,5-dicyano-4-ethyl-6-(4-morpholinopiperidin-1-yl)pyridin-2-yl)thio)-2-phenylacetamide;
2-((3,5-dicyano-4-ethyl-6-(4-(2-hydroxyethyl)-3-oxopiperazin-1-yl)pyridin-2-yl)thio)-2-phenylacetamide;
2-((3,5-dicyano-4-ethyl-6-(4-(pyrrolidin-1-yl)piperidin-1-yl)pyridin-2-yl)thio)-2-(4-fluorophenyl)acetamide;
(R)-2-((6-((3S,4R)-4-amino-3-fluoropiperidin-1-yl)-3,5-dicyano-4-ethylpyridin-2-yl)thio)-2-phenylacetamide;
2-((3,5-dicyano-4-ethyl-6-(3-fluoro-4-(methylamino)piperidin-1-yl)pyridin-2-yl)thio)-2-phenylacetamide;
rel-2-((6-(trans)-4-amino-3-fluoropiperidin-1-yl)-3,5-dicyano-4-ethylpyridin-2-yl)thio)-2-phenylacetamide;
(R)-2-((6-((3R,4S)-4-amino-3-fluoropiperidin-1-yl)-3,5-dicyano-4-ethylpyridin-2-yl)thio)-2-phenylacetamide;
2-((3,5-dicyano-4-ethyl-6-(3-fluoro-4-((2-methoxyethyl)amino)piperidin-1-yl)pyridin-2-yl)thio)-2-phenylacetamide;
2-((3,5-dicyano-4-ethyl-6-(methyl(2-(pyrrolidin-1-yl)ethyl)amino)pyridin-2-yl)thio)-2-phenylacetamide;
2-((3,5-dicyano-6-(3-((dimethylamino)methyl)pyrrolidin-1-yl)-4-ethylpyridin-2-yl)thio)-2-phenylacetamide;
2-((3,5-dicyano-4-ethyl-6-(4-((2-hydroxy-2-methylpropyl)amino)piperidin-1-yl)pyridin-2-yl)thio)-2-(4-fluorophenyl)acetamide;
(R)-2-((6-((3S,4R)-4-amino-3-hydroxypiperidin-1-yl)-3,5-dicyano-4-ethylpyridin-2-yl)thio)-2-phenylacetamide;
2-((3,5-dicyano-6-((2-(diethylamino)ethyl)(methyl)amino)-4-ethylpyridin-2-yl)thio)-2-phenylacetamide;
2-((3,5-dicyano-6-((2-((R)-3-(dimethylamino)pyrrolidin-1-yl)ethyl)(methyl)amino)-4-ethylpyridin-2-yl)thio)-2-phenylacetamide;
2-((3,5-dicyano-6-((2-((S)-3-(dimethylamino)pyrrolidin-1-yl)ethyl)(methyl)amino)-4-ethylpyridin-2-yl)thio)-2-phenylacetamide;
(R)-2-((6-((3R,4R)-4-amino-3-fluoropiperidin-1-yl)-3,5-dicyano-4-ethylpyridin-2-yl)thio)-2-phenylacetamide;
(R)-2-((6-((3S,4S)-4-amino-3-fluoropiperidin-1-yl)-3,5-dicyano-4-ethylpyridin-2-yl)thio)-2-phenylacetamide;
2-((3,5-dicyano-4-ethyl-6-(3-(methylamino)pyrrolidin-1-yl)pyridin-2-yl)thio)-2-phenylacetamide;
2-((6-(4-aminopiperidin-1-yl)-3,5-dicyano-4-ethylpyridin-2-yl)thio)-2-(4-fluorophenyl)acetamide;
(R)-2-((6-((3R,4R)-4-amino-3-hydroxypiperidin-1-yl)-3,5-dicyano-4-ethylpyridin-2-yl)thio)-2-phenylacetamide;
2-((6-((R)-3-aminopyrrolidin-1-yl)-3,5-dicyano-4-ethylpyridin-2-yl)thio)-2-phenylacetamide;
2-((6-(3-(aminomethyl)pyrrolidin-1-yl)-3,5-dicyano-4-ethylpyridin-2-yl)thio)-2-phenylacetamide;
2-((3,5-dicyano-4-ethyl-6-(4-(methylamino)piperidin-1-yl)pyridin-2-yl)thio)-2-(4-fluorophenyl)acetamide;
2-((3,5-dicyano-6-(4-(cyclopropylamino)-3-fluoropiperidin-1-yl)-4-ethylpyridin-2-yl)thio)-2-phenylacetamide;
2-((6-((S)-3-aminopyrrolidin-1-yl)-3,5-dicyano-4-ethylpyridin-2-yl)thio)-2-phenylacetamide;
2-((6-((2-((R)-3-aminopyrrolidin-1-yl)ethyl)(methyl)amino)-3,5-dicyano-4-ethylpyridin-2-yl)thio)-2-phenylacetamide;
3,5-dicyano-6-((R)-3-(dimethylamino)pyrrolidin-1-yl)-4-ethylpyridin-2-yl)thio)-2-(4-fluorophenyl)acetamide;
(S)-2-((6-((3S,4R)-4-amino-3-fluoropiperidin-1-yl)-3,5-dicyano-4-ethylpyridin-2-yl)thio)-2-phenylacetamide;
2-((3,5-dicyano-4-ethyl-6-(4-(neopentylamino)piperidin-1-yl)pyridin-2-yl)thio)-2-(4-(trifluoromethyl)phenyl)acetamide;
tert-butyl ((3S,4R)-1-(6-(((R)-2-amino-2-oxo-1-phenylethyl)thio)-3,5-dicyano-4-ethylpyridin-2-yl)-3-hydroxypiperidin-4-yl)carbamate;
rel-tert-butyl (cis)-1-(6-((2-amino-2-oxo-1-phenylethyl)thio)-3,5-dicyano-4-ethylpyridin-2-yl)-3-fluoropiperidin-4-yl)carbamate;
2-((6-((2-((S)-3-aminopyrrolidin-1-yl)ethyl)(methyl)amino)-3,5-dicyano-4-ethylpyridin-2-yl)thio)-2-phenylacetamide;
2-((3,5-dicyano-6-((R)-3-(dimethylamino)pyrrolidin-1-yl)-4-ethylpyridin-2-yl)thio)-2-phenylacetamide;
tert-butyl ((3R,4S)-1-(6-(((R)-2-amino-2-oxo-1-phenylethyl)thio)-3,5-dicyano-4-ethylpyridin-2-yl)-3-hydroxypiperidin-4-yl)carbamate;
rel-tert-butyl (cis)-1-(6-((2-amino-2-oxo-1-phenylethyl)thio)-3,5-dicyano-4-ethylpyridin-2-yl)-3-fluoropiperidin-4-yl)carbamate;
2-((3,5-dicyano-6-((S)-3-(dimethylamino)pyrrolidin-1-yl)-4-ethylpyridin-2-yl)thio)-2-phenylacetamide;
(S)-2-((6-((3R,4S)-4-amino-3-fluoropiperidin-1-yl)-3,5-dicyano-4-ethylpyridin-2-yl)thio)-2-phenylacetamide;

2-((3,5-dicyano-4-ethyl-6-((S)-3-((2-hydroxy-2-methyl-propyl)amino)pyrrolidin-1-yl)pyridin-2-yl)thio)-2-phenylacetamide;

tert-butyl ((3R,4R)-1-(6-(((R)-2-amino-2-oxo-1-phenyl-ethyl)thio)-3,5-dicyano-4-ethylpyridin-2-yl)-3-hydroxypiperidin-4-yl)carbamate;

2-((3,5-dicyano-6-((S)-3-(dimethylamino)pyrrolidin-1-yl)-4-ethylpyridin-2-yl)thio)-2-(4-fluorophenyl)acetamide;

rel-2-((6-cis-4-amino-3-fluoropiperidin-1-yl)-3,5-dicyano-4-ethylpyridin-2-yl)thio)-2-phenylacetamide;

2-((3,5-dicyano-4-ethyl-6-(4-(methylamino)piperidin-1-yl)pyridin-2-yl)thio)-2-phenylacetamide;

2-((3,5-dicyano-6-(4-(dimethylamino)piperidin-1-yl)-4-ethylpyridin-2-yl)thio)-2-phenylacetamide;

2-((3,5-dicyano-4-ethyl-6-(4-(ethyl(methyl)amino)piperidin-1-yl)pyridin-2-yl)thio)-2-phenylacetamide;

2-((3,5-dicyano-4-ethyl-6-(4-(neopentylamino)piperidin-1-yl)pyridin-2-yl)thio)-2-phenylacetamide;

2-((3,5-dicyano-4-ethyl-6-(4-(methyl(neopentyl)amino)piperidin-1-yl)pyridin-2-yl)thio)-2-phenylacetamide;

2-((3,5-dicyano-6-(4-(cyclopropylamino)piperidin-1-yl)-4-ethylpyridin-2-yl)thio)-2-phenylacetamide;

2-((3,5-dicyano-4-ethyl-6-(4-((2-methoxyethyl)amino)piperidin-1-yl)pyridin-2-yl)thio)-2-phenylacetamide;

2-((3,5-dicyano-6-(4-((2,2-difluoroethyl)amino)piperidin-1-yl)-4-ethylpyridin-2-yl)thio)-2-phenylacetamide;

2-((3,5-dicyano-4-ethyl-6-((R)-2-((neopentylamino)methyl)morpholino)pyridin-2-yl)thio)-2-phenylacetamide;

2-((3,5-dicyano-6-(2-((dimethylamino)methyl)morpholino)-4-ethylpyridin-2-yl)thio)-2-phenylacetamide;

2-((3,5-dicyano-6-(2-((diethylamino)methyl)morpholino)-4-ethylpyridin-2-yl)thio)-2-phenylacetamide;

2-((3,5-dicyano-4-ethyl-6-(2-(pyrrolidin-1-ylmethyl)morpholino)pyridin-2-yl)thio)-2-phenylacetamide;

(R)-2-((6-((R)-2-(aminomethyl)morpholino)-3,5-dicyano-4-ethylpyridin-2-yl)thio)-2-phenylacetamide;

2-((6-(2-(aminomethyl)morpholino)-3,5-dicyano-4-ethylpyridin-2-yl)thio)-2-phenylacetamide;

2-((3,5-dicyano-4-ethyl-6-(2-((methylamino)methyl)morpholino)pyridin-2-yl)thio)-2-phenylacetamide;

2-((6-((R)-2-(aminomethyl)morpholino)-3,5-dicyano-4-ethylpyridin-2-yl)thio)-2-phenylacetamide;

2-((3,5-dicyano-6-(3-((dimethylamino)methyl)piperidin-1-yl)-4-ethylpyridin-2-yl)thio)-2-phenylacetamide;

2-((3,5-dicyano-4-ethyl-6-(3-((methylamino)methyl)piperidin-1-yl)pyridin-2-yl)thio)-2-phenylacetamide;

2-((3,5-dicyano-4-ethyl-6-((S)-2-((neopentylamino)methyl)morpholino)pyridin-2-yl)thio)-2-phenylacetamide;

2-((3,5-dicyano-4-ethyl-6-((S)-3-((neopentylamino)methyl)piperidin-1-yl)pyridin-2-yl)thio)-2-phenylacetamide;

2-amino-N-(((2S)-4-(6-((2-amino-2-oxo-1-phenylethyl)thio)-3,5-dicyano-4-ethylpyridin-2-yl)morpholin-2-yl)methyl)-2-methylpropanamide;

2-((6-((S)-3-(aminomethyl)piperidin-1-yl)-3,5-dicyano-4-ethylpyridin-2-yl)thio)-2-phenylacetamide;

2-((3,5-dicyano-6-((R)-2-((diethylamino)methyl)morpholino)-4-ethylpyridin-2-yl)thio)-2-phenylacetamide;

2-amino-N-(((2R)-4-(6-((2-amino-2-oxo-1-phenylethyl)thio)-3,5-dicyano-4-ethylpyridin-2-yl)morpholin-2-yl)methyl)-2-methylpropanamide;

2-((6-(4-aminopiperidin-1-yl)-3,5-dicyano-4-ethylpyridin-2-yl)thio)-2-(3-fluoropyridin-2-yl)acetamide;

2-((6-((S)-2-(aminomethyl)morpholino)-3,5-dicyano-4-ethylpyridin-2-yl)thio)-2-phenylacetamide;

2-amino-N-(((3S)-1-(6-((2-amino-2-oxo-1-phenylethyl)thio)-3,5-dicyano-4-ethylpyridin-2-yl)piperidin-3-yl)methyl)-2-methylpropanamide;

2-amino-N-(((3S)-1-(6-((2-amino-2-oxo-1-phenylethyl)thio)-3,5-dicyano-4-ethylpyridin-2-yl)piperidin-3-yl)methyl)acetamide;

2-amino-N-(((2R)-4-(6-((2-amino-2-oxo-1-phenylethyl)thio)-3,5-dicyano-4-ethylpyridin-2-yl)morpholin-2-yl)methyl)acetamide;

2-((6-((R)-3-(aminomethyl)piperidin-1-yl)-3,5-dicyano-4-ethylpyridin-2-yl)thio)-2-(4-fluorophenyl)acetamide;

2-((3,5-dicyano-4-ethyl-6-((R)-3-((neopentylamino)methyl)piperidin-1-yl)pyridin-2-yl)thio)-2-(4-fluorophenyl)acetamide;

2-amino-N-(((2S)-4-(6-((2-amino-2-oxo-1-phenylethyl)thio)-3,5-dicyano-4-ethylpyridin-2-yl)morpholin-2-yl)methyl)acetamide;

N-(((R)-4-(6-(((R)-2-amino-2-oxo-1-phenylethyl)thio)-3,5-dicyano-4-ethylpyridin-2-yl)morpholin-2-yl)methyl)-2-hydroxyacetamide;

(S)-2-((6-(4-aminopiperidin-1-yl)-3,5-dicyano-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(2-hydroxyethyl)-N-methyl acetamide;

2-((3,5-dicyano-4-ethyl-6-((S)-3-(methylamino)piperidin-1-yl)pyridin-2-yl)thio)-2-phenylacetamide;

2-((6-(4-amino-4-methylpiperidin-1-yl)-3,5-dicyano-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)-N-methylacetamide;

2-amino-N-(1-(6-((2-amino-2-oxo-1-phenylethyl)thio)-3,5-dicyano-4-cyclopropylpyridin-2-yl)azetidin-3-yl)acetamide;

(2S)-2-amino-N-(1-(6-((2-amino-2-oxo-1-phenylethyl)thio)-3,5-dicyano-4-cyclopropylpyridin-2-yl)azetidin-3-yl)-3-hydroxypropanamide;

2-((6-((S)-3-aminopiperidin-1-yl)-3,5-dicyano-4-ethylpyridin-2-yl)thio)-2-phenylacetamide;

2-((3,5-dicyano-4-ethyl-6-((2-((R)-3-hydroxypyrrolidin-1-yl)-2-oxoethyl)(methyl)amino)pyridin-2-yl)thio)-2-phenylacetamide;

(2R)-2-amino-N-(1-(6-((2-amino-2-oxo-1-phenylethyl)thio)-3,5-dicyano-4-cyclopropylpyridin-2-yl)azetidin-3-yl)-3-hydroxypropanamide;

2-((6-((2-amino-2-oxo-1-phenylethyl)thio)-3,5-dicyano-4-ethylpyridin-2-yl)(methyl)amino)-N-(3-hydroxy-2,2-dimethylpropyl)-N-methylacetamide;

2-((3,5-dicyano-4-ethyl-6-((2-((S)-3-hydroxypyrrolidin-1-yl)-2-oxoethyl)(methyl)amino)pyridin-2-yl)thio)-2-phenylacetamide;

2-((6-(4-amino-4-methylpiperidin-1-yl)-3,5-dicyano-4-ethylpyridin-2-yl)thio)-2-phenylacetamide;

2-((6-(4-(aminomethyl)-4-fluoropiperidin-1-yl)-3,5-dicyano-4-ethylpyridin-2-yl)thio)-2-phenylacetamide hydrochloride;

2-((6-((2-amino-2-oxo-1-phenylethyl)thio)-3,5-dicyano-4-cyclopropylpyridin-2-yl)(methyl)amino)-N-(2-aminoethyl)acetamide hydrochloride;

2-((3,5-dicyano-4-ethyl-6-(methyl(2-oxo-2-(pyrrolidin-1-yl)ethyl)amino)pyridin-2-yl)thio)-2-phenylacetamide;

2-((3,5-dicyano-4-ethyl-6-((2-(4-hydroxypiperidin-1-yl)-2-oxoethyl)(methyl)amino)pyridin-2-yl)thio)-2-phenylacetamide;

2-((3,5-dicyano-4-ethyl-6-(methyl(2-oxo-2-(piperazin-1-yl)ethyl)amino)pyridin-2-yl)thio)-2-phenylacetamide;

2-((3,5-dicyano-4-ethyl-6-(methyl(2-morpholino-2-oxoethyl)amino)pyridin-2-yl)thio)-2-phenylacetamide;

(R)-2-((6-((S)-3-(aminomethyl)-3-hydroxypyrrolidin-1-yl)-3,5-dicyano-4-ethylpyridin-2-yl)thio)-2-phenylacetamide;

2-((3,5-dicyano-4-ethyl-6-((S)-3-(guanidinooxy)pyrrolidin-1-yl)pyridin-2-yl)thio)-2-phenylacetamide;

2-amino-N-(2-((6-((2-amino-2-oxo-1-phenylethyl)thio)-3,5-dicyano-4-ethylpyridin-2-yl)(methyl)amino)ethyl)-2-methylpropanamide;

2-((6-((2-(2-aminoethoxy)ethyl)(methyl)amino)-3,5-dicyano-4-ethylpyridin-2-yl)thio)-2-phenylacetamide;

4-amino-N-(1-(6-((2-amino-2-oxo-1-phenylethyl)thio)-3,5-dicyano-4-ethylpyridin-2-yl)piperidin-4-yl)butanamide;

2-((6-((2-amino-2-oxo-1-phenylethyl)thio)-3,5-dicyano-4-ethylpyridin-2-yl)(methyl)amino)-N-(2-aminoethyl)acetamide;

2-((6-((2-(azetidin-1-yl)-2-oxoethyl)(methyl)amino)-3,5-dicyano-4-ethylpyridin-2-yl)thio)-2-phenylacetamide;

2-((6-((R)-3-(aminomethyl)-3-fluoropyrrolidin-1-yl)-3,5-dicyano-4-ethylpyridin-2-yl)thio)-2-phenylacetamide;

2-((3,5-dicyano-4-ethyl-6-((2-(3-hydroxyazetidin-1-yl)-2-oxoethyl)(methyl)amino)pyridin-2-yl)thio)-2-phenylacetamide;

2-((3,5-dicyano-4-ethyl-6-(4-(guanidinooxy)piperidin-1-yl)pyridin-2-yl)thio)-2-phenylacetamide;

2-((6-(3-aminoazetidin-1-yl)-3,5-dicyano-4-ethylpyridin-2-yl)thio)-2-phenylacetamide; (single stereoisomer)

2-((3,5-dicyano-4-ethyl-6-((R)-3-(methylamino)piperidin-1-yl)pyridin-2-yl)thio)-2-phenylacetamide;

2-((3,5-dicyano-4-ethyl-6-((2-((3R,4S)-3-hydroxy-4-(hydroxymethyl)pyrrolidin-1-yl)-2-oxoethyl)(methyl)amino)pyridin-2-yl)thio)-2-phenylacetamide;

(R)-2-((6-((S)-3-(aminomethyl)-3-fluoropyrrolidin-1-yl)-3,5-dicyano-4-ethylpyridin-2-yl)thio)-2-phenylacetamide;

2-((6-((2-amino-2-oxo-1-phenylethyl)thio)-3,5-dicyano-4-cyclopropylpyridin-2-yl)(methyl)amino)-N-(1,3-dihydroxypropan-2-yl)acetamide;

2-((3,5-dicyano-4-ethyl-6-((S)-3-(oxetan-3-ylamino)piperidin-1-yl)pyridin-2-yl)thio)-2-phenylacetamide;

2-((6-((2-amino-2-oxo-1-phenylethyl)thio)-3,5-dicyano-4-cyclopropylpyridin-2-yl)(methyl)amino)-N,N-bis(2-hydroxyethyl)acetamide;

2-amino-N-(1-(6-((2-amino-2-oxo-1-phenylethyl)thio)-3,5-dicyano-4-cyclopropylpyridin-2-yl)piperidin-4-yl)acetamide;

2-((3,5-dicyano-4-ethyl-6-(4-((2-hydroxyethyl)amino)-4-methylpiperidin-1-yl)pyridin-2-yl)thio)-2-phenylacetamide;

2-((3,5-dicyano-4-ethyl-6-((2-(guanidinooxy)ethyl)(methyl)amino)pyridin-2-yl)thio)-2-phenylacetamide;

2-((6-(4-((2-aminoethyl)amino)piperidin-1-yl)-3,5-dicyano-4-ethylpyridin-2-yl)thio)-2-phenylacetamide;

2-((3,5-dicyano-4-ethyl-6-((2-((S)-2-(hydroxymethyl)morpholino)-2-oxoethyl)(methyl)amino)pyridin-2-yl)thio)-2-phenylacetamide;

2-((3,5-dicyano-6-((2-((cis)-3,4-dihydroxypyrrolidin-1-yl)-2-oxoethyl)(methyl)amino)-4-ethylpyridin-2-yl)thio)-2-phenylacetamide;

2-((3,5-dicyano-4-ethyl-6-((2-((S)-3-(hydroxymethyl)pyrrolidin-1-yl)-2-oxoethyl)(methyl)amino)pyridin-2-yl)thio)-2-phenylacetamide;

2-((3,5-dicyano-4-ethyl-6-((2-((3S,4S)-3-hydroxy-4-(hydroxymethyl)pyrrolidin-1-yl)-2-oxoethyl)(methyl)amino)pyridin-2-yl)thio)-2-phenylacetamide;

2-((3,5-dicyano-4-ethyl-6-((S)-3-(neopentylamino)piperidin-1-yl)pyridin-2-yl)thio)-2-phenylacetamide;

2-((3,5-dicyano-4-ethyl-6-((2-((R)-3-(hydroxymethyl)pyrrolidin-1-yl)-2-oxoethyl)(methyl)amino)pyridin-2-yl)thio)-2-phenylacetamide;

2-((3,5-dicyano-6-((2-((3R,4R)-3,4-dihydroxypyrrolidin-1-yl)-2-oxoethyl)(methyl)amino)-4-ethylpyridin-2-yl)thio)-2-phenylacetamide;

(R)-2-((3,5-dicyano-4-ethyl-6-((S)-3-hydroxy-3-(hydroxymethyl)pyrrolidin-1-yl)pyridin-2-yl)thio)-2-phenylacetamide;

(2S)-2-amino-N-(1-(6-((2-amino-2-oxo-1-phenylethyl)thio)-3,5-dicyano-4-cyclopropylpyridin-2-yl)piperidin-4-yl)propanamide;

2-((6-(4-(2-aminoethoxy)piperidin-1-yl)-3,5-dicyano-4-cyclopropylpyridin-2-yl)thio)-2-phenylacetamide;

2-((3,5-dicyano-4-cyclopropyl-6-(4-((2-hydroxyethyl)amino)piperidin-1-yl)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(1,3-dihydroxypropan-2-yl)acetamide;

2-((3,5-dicyano-6-((2-((3R,5S)-3,5-dihydroxypiperidin-1-yl)-2-oxoethyl)(methyl)amino)-4-ethylpyridin-2-yl)thio)-2-phenylacetamide;

2-((3,5-dicyano-6-((2-((3S,4S)-3,4-dihydroxypyrrolidin-1-yl)-2-oxoethyl)(methyl)amino)-4-ethylpyridin-2-yl)thio)-2-phenylacetamide;

2-((3,5-dicyano-4-ethyl-6-(4-((2-hydroxyethyl)amino)-4-(hydroxymethyl)piperidin-1-yl)pyridin-2-yl)thio)-2-phenylacetamide;

2-((3,5-dicyano-4-ethyl-6-((2-((R)-2-(hydroxymethyl)morpholino)-2-oxoethyl)(methyl)amino)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-methoxyacetamide;

2-((3,5-dicyano-4-ethyl-6-((2-((3R,4R)-3-hydroxy-4-(hydroxymethyl)pyrrolidin-1-yl)-2-oxoethyl)(methyl)amino)pyridin-2-yl)thio)-2-phenylacetamide;

2-((6-((2-amino-2-oxo-1-phenylethyl)thio)-3,5-dicyano-4-ethylpyridin-2-yl)(methyl)amino)-N-(3-hydroxypropyl)-N-methyl acetamide;

2-((6-((2-amino-2-oxo-1-phenylethyl)thio)-3,5-dicyano-4-ethylpyridin-2-yl)(methyl)amino)-N-((R)-2,3-dihydroxypropyl)acetamide;

2-((6-(4-((2-amino-2-oxoethyl)amino)piperidin-1-yl)-3,5-dicyano-4-cyclopropylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N,N-bis(2-hydroxyethyl)acetamide;

2-((6-((2-amino-2-oxo-1-phenylethyl)thio)-3,5-dicyano-4-ethylpyridin-2-yl)(methyl)amino)-N-(2-hydroxyethyl)acetamide;

2-((6-((3-aminopropyl)(methyl)amino)-3,5-dicyano-4-ethylpyridin-2-yl)thio)-2-phenylacetamide;

2-((6-(3-(aminomethyl)azetidin-1-yl)-3,5-dicyano-4-ethylpyridin-2-yl)thio)-2-phenylacetamide;

2-((6-((2-amino-2-oxo-1-phenylethyl)thio)-3,5-dicyano-4-ethylpyridin-2-yl)(methyl)amino)-N-((1-(hydroxymethyl)cyclopropyl)methyl)acetamide;
(R)-2-((3,5-dicyano-4-ethyl-6-((S)-3-hydroxypyrrolidin-1-yl)pyridin-2-yl)thio)-2-(2,4-difluorophenyl)acetamide;
2-((6-((2-amino-2-oxo-1-phenylethyl)thio)-3,5-dicyano-4-ethylpyridin-2-yl)(methyl)amino)-N-(3-(hydroxymethyl)oxetan-3-yl)acetamide;
2-((3,5-dicyano-4-ethyl-6-(3-(guanidinooxy)azetidin-1-yl)pyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(3-hydroxypropyl)acetamide;
2-((3,5-dicyano-6-(4-(2,3-dihydroxypropyl)-1,4-diazepan-1-yl)-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-hydroxyacetamide;
3-amino-N-(1-(6-((2-amino-2-oxo-1-phenylethyl)thio)-3,5-dicyano-4-cyclopropylpyridin-2-yl)azetidin-3-yl)oxetane-3-carboxamide;
2-((3,5-dicyano-4-ethyl-6-((S)-3-hydroxypyrrolidin-1-yl)pyridin-2-yl)thio)-2-(2-fluorophenyl)acetamide;
2-((3,5-dicyano-6-((S)-3-(cyclopropylamino)piperidin-1-yl)-4-ethylpyridin-2-yl)thio)-2-phenylacetamide;
2-((6-((2-amino-2-oxo-1-phenylethyl)thio)-3,5-dicyano-4-ethylpyridin-2-yl)(methyl)amino)-N-(3-hydroxy-2,2-dimethylpropyl)acetamide;
N-(2-(4H-1,2,4-triazol-4-yl)ethyl)-2-((6-((2-amino-2-oxo-1-phenylethyl)thio)-3,5-dicyano-4-ethylpyridin-2-yl)(methyl)amino)acetamide;
N1-(2-((6-((2-amino-2-oxo-1-phenylethyl)thio)-3,5-dicyano-4-ethylpyridin-2-yl)(methyl)amino)ethyl)oxalamide;
2-((6-(3-(aminomethyl)-3-fluoroazetidin-1-yl)-3,5-dicyano-4-ethylpyridin-2-yl)thio)-2-phenylacetamide;
(R)-2-((3,5-dicyano-4-ethyl-6-((R)-3-hydroxy-3-(hydroxymethyl)pyrrolidin-1-yl)pyridin-2-yl)thio)-2-phenylacetamide;
2-((3,5-dicyano-6-((S)-3-((2,2-difluoroethyl)amino)piperidin-1-yl)-4-ethylpyridin-2-yl)thio)-2-phenylacetamide;
2-((6-((R)-3-aminopiperidin-1-yl)-3,5-dicyano-4-ethylpyridin-2-yl)thio)-2-phenylacetamide;
2-((6-(4-aminopiperidin-1-yl)-3,5-dicyano-4-methoxypyridin-2-yl)thio)-2-phenylacetamide;
2-((3,5-dicyano-4-ethyl-6-((S)-4-hydroxyisoxazolidin-2-yl)pyridin-2-yl)thio)-2-phenylacetamide;
(R)-2-((3,5-dicyano-4-ethyl-6-((3-hydroxypropyl)(methyl)amino)pyridin-2-yl)thio)-2-phenylacetamide;
2-((3,5-dicyano-6-((S)-3-hydroxypyrrolidin-1-yl)-4-methoxypyridin-2-yl)thio)-2-phenylacetamide;
2-((3,5-dicyano-4-ethyl-6-(4-(3-methoxyazetidin-1-yl)piperidin-1-yl)pyridin-2-yl)thio)-2-phenylacetamide;
2-((3,5-dicyano-4-ethyl-6-(4-(3-methoxyazetidin-1-yl)piperidin-1-yl)pyridin-2-yl)thio)-2-(4-fluorophenyl)acetamide;
(R)-2-((3,5-dicyano-4-ethyl-6-((2-hydroxyethyl)(methyl)amino)pyridin-2-yl)thio)-2-phenylacetamide;
(R)-2-((3,5-dicyano-4-ethyl-6-((S)-3-hydroxypyrrolidin-1-yl)pyridin-2-yl)thio)-2-(4-fluorophenyl)acetamide;
(R)-2-((6-((R)-3-(aminomethyl)-3-hydroxypyrrolidin-1-yl)-3,5-dicyano-4-ethylpyridin-2-yl)thio)-2-phenylacetamide;
2-((3,5-Dicyano-6-(4-(cyclobutyl(methyl)amino)piperidin-1-yl)-4-ethylpyridin-2-yl)thio)-2-(4-fluorophenyl)acetamide; and
2-((3,5-dicyano-4-ethyl-6-(methyl(1-methylpyrrolidin-3-yl)amino)pyridin-2-yl)thio)-2-phenylacetamide;
or a pharmaceutically acceptable salt or prodrug thereof.

5. A pharmaceutical composition comprising a compound according to claim 1 or a pharmaceutically acceptable salt or prodrug thereof and a pharmaceutically acceptable excipient.

6. A method of treating a disease selected from: cancer, pre-cancerous syndromes, beta haemoglobinopathy disordes, sickle cell disease, sickle cell anemia, and beta thalassemia, in a human in need thereof, which comprises administering to such human a therapeutically effective amount of a compound of claim 1 or a pharmaceutically acceptable salt or prodrug thereof.

7. A method of inhibiting DNMT1 activity in a human in need thereof, which comprises administering to such human a therapeutically effective amount of a compound as described in claim 1 or a pharmaceutically acceptable salt or prodrug thereof.

8. A method of treating cancer in a human in need thereof, which comprises: administering to such human a therapeutically effective amount of
   a) a compound of as described in claim 1 or a pharmaceutically acceptable salt or prodrug thereof; and
   b) at least one anti-neoplastic agent.

9. The method according to claim 8, wherein the at least one anti-neoplastic agent is selected from the group consisting of: anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis, inhibitors, immunotherapeutic agents, proapoptotic agents, cell cycle signaling inhibitors, proteasome inhibitors, inhibitors of cancer metabolism, anti-PD-L1 agents, PD-1 antagonist, immuno-modulators, STING modulating compounds, CD39 inhibitors, A2a and A2a adenosine antagonists, TLR4 antagonists, antibodies to ICOS, and antibodies to OX40.

10. A pharmaceutical combination comprising:
    a) a compound as described in claim 1 or a pharmaceutically acceptable salt or prodrug thereof; and
    b) at least one anti-neoplastic agent.

11. The method according to claim 6 wherein said cancer is selected from: breast cancer, inflammatory breast cancer, ductal carcinoma, lobular carcinoma, colon cancer, pancreatic cancer, insulinomas, adenocarcinoma, ductal adenocarcinoma, adenosquamous carcinoma, acinar cell carcinoma, glucagonoma, skin cancer, melanoma, metastatic melanoma, lung cancer, small cell lung cancer, non-small cell lung cancer, squamous cell carcinoma, adenocarcinoma, large cell carcinoma, brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid,
   lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), neuroendocrine cancers and testicular cancer.

12. The method according to claim 6 wherein said pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

13. A prodrug of a compound of claim 4 selected from:
1-(6-((2-amino-2-oxo-1-phenylethyl)thio)-3,5-dicyano-4-ethylpyridin-2-yl)pyrrolidin-3-yl dihydrogen phosphate;
1-(6-((2-amino-1-(4-fluorophenyl)-2-oxoethyl)thio)-3,5-dicyano-4-ethylpyridin-2-yl)pyrrolidin-3-yl dihydrogen phosphate;
2-((6-((2-amino-2-oxo-1-phenylethyl)thio)-3,5-dicyano-4-ethylpyridin-2-yl)(methyl)amino)ethyl dihydrogen phosphate;
1-(6-((2-amino-2-oxo-1-phenylethyl)thio)-3,5-dicyano-4-ethylpyridin-2-yl)azetidin-3-yl dihydrogen phosphate;
(2S)-2-((1-(6-((2-amino-2-oxo-1-phenylethyl)thio)-3,5-dicyano-4-ethylpyridin-2-yl)piperidin-4-yl)oxy)ethyl 2-amino-3-methylbutanoate;
2-((1-(6-((2-amino-2-oxo-1-phenylethyl)thio)-3,5-dicyano-4-ethylpyridin-2-yl)piperidin-4-yl)oxy)ethyl dihydrogen phosphate; and
1-(6-((2-amino-2-oxo-1-phenylethyl)thio)-3,5-dicyano-4-ethylpyridin-2-yl)piperidin-4-yl dihydrogen phosphate;
or a pharmaceutically acceptable salt thereof.

14. The compound of claim 1 which is: 2-((3,5-dicyano-4-(furan-2-yl)-6-(4-methyl-1,4-diazepan-1-yl)pyridin-2-yl)thio)-2-phenylacetamide;
or a pharmaceutically acceptable salt or prodrug thereof.

15. A method of treating a disease selected from: diabetic nephropathy, diabetes, podocyte injury, atherosclerosis, psoriasis, idiopathic pulmonary fibrosis, scleroderma, liver cirrhosis, rheumatoid arthritis, and Alzheimer's disease, in a human in need thereof, which comprises administering to such human a therapeutically effective amount of a compound as described in claim 1 or a pharmaceutically acceptable salt or prodrug thereof.

16. A prodrug of a compound of claim 4 selected from:
1-(6-((2-Amino-2-oxo-1-phenylethyl)thio)-3,5-dicyano-4-ethylpyridin-2-yl)pyrrolidin-3-yl dihydrogen phosphate;
(3R)-1-(6-((2-amino-2-oxo-1-phenylethyl)thio)-3,5-dicyano-4-ethylpyridin-2-yl)pyrrolidin-3-yl dihydrogen phosphate;
(S)-1-(6-(((S)-2-amino-2-oxo-1-phenylethyl)thio)-3,5-dicyano-4-ethylpyridin-2-yl)pyrrolidin-3-yl dihydrogen phosphate; and
(S)-1-(6-(((R)-2-amino-2-oxo-1-phenylethyl)thio)-3,5-dicyano-4-ethylpyridin-2-yl) pyrrolidin-3-yl dihydrogen phosphate;
or a pharmaceutically acceptable salt thereof.

17. A compound of claim 1 selected from:
2-((3,5-Dicyano-4-ethyl-6-(3-hydroxypyrrolidin-1-yl)pyridin-2-yl)thio)-2-phenylacetamide;
2-((3,5-Dicyano-4-ethyl-6-((S)-3-hydroxypyrrolidin-1-yl)pyridin-2-yl)thio)-2-phenylacetamide;
2-((3,5-Dicyano-4-ethyl-6-((R)-3-hydroxypyrrolidin-1-yl)pyridin-2-yl)thio)-2-phenylacetamide;
(R)-2-((3,5-Dicyano-4-ethyl-6-((S)-3-hydroxypyrrolidin-1-yl)pyridin-2-yl)thio)-2-phenylacetamide;
(R)-2-((3,5-Dicyano-4-ethyl-6-((R)-3-hydroxypyrrolidin-1-yl)pyridin-2-yl)thio)-2-phenylacetamide; and
(S)-2-((3,5-Dicyano-4-ethyl-6-((S)-3-hydroxypyrrolidin-1-yl)pyridin-2-yl)thio)-2-phenylacetamide;
or a pharmaceutically acceptable salt or prodrug thereof.

18. A compound which is

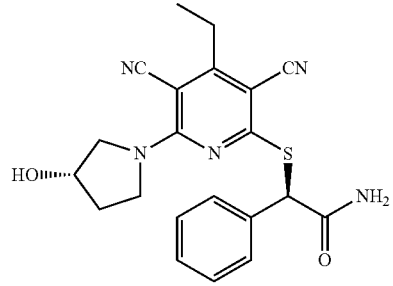 [SMILES: CCc1c(C#N)c(S[C@@H](C(N)=O)c2ccccc2)nc(N2CC[C@H](O)C2)c1C#N]

or a pharmaceutically acceptable salt or prodrug thereof.

19. A method of treating a disease selected from: cancer, pre-cancerous syndromes, beta haemoglobinopathy disorders, sickle cell disease, sickle cell anemia, and beta thalassemia, in a human in need thereof, which comprises administering to such human a therapeutically effective amount of a compound of claim 18 or a pharmaceutically acceptable salt or prodrug thereof.

20. A compound which is

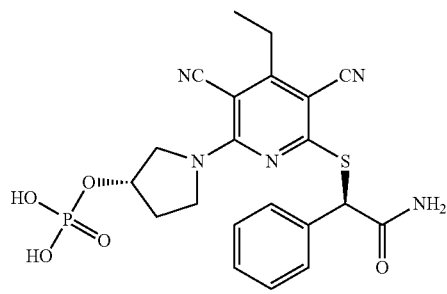 [SMILES: CCc1c(C#N)c(S[C@@H](C(N)=O)c2ccccc2)nc(N2CC[C@H](OP(=O)(O)O)C2)c1C#N]

or a pharmaceutically acceptable salt thereof.

21. A method of treating a disease selected from: cancer, pre-cancerous syndromes, beta haemoglobinopathy disorders, sickle cell disease, sickle cell anemia, and beta thalassemia, in a human in need thereof, which comprises administering to such human a therapeutically effective amount of a compound of claim 20 or a pharmaceutically acceptable salt thereof.

* * * * *